(12) United States Patent
Goldberg et al.

(10) Patent No.: US 10,975,068 B2
(45) Date of Patent: Apr. 13, 2021

(54) 6-AMINOPYRIDIN-3-YL THIAZOLES AS MODULATORS OF RORγT

(71) Applicant: Janssen Pharmaceutica NV, Beerse (BE)

(72) Inventors: Steven Goldberg, Carlsbad, CA (US); Kelly McClure, Ramona, CA (US); Virginia M. Tanis, Vista, CA (US); Elizabeth G. Fennema, La Mesa, CA (US); Alec D. Lebsack, Ladera Ranch, CA (US); Connor L. Martin, San Diego, CA (US); Hariharan Venkatesan, San Diego, CA (US); Xiaohua Xue, San Diego, CA (US); Craig R. Woods, San Diego, CA (US)

(73) Assignee: Janssen Pharmaceutica NV, Beerse (BE)

( * ) Notice: Subject to any disclaimer, the term of this patent is extended or adjusted under 35 U.S.C. 154(b) by 0 days.

(21) Appl. No.: 15/497,565

(22) Filed: Apr. 26, 2017

(65) Prior Publication Data
US 2017/0313691 A1 Nov. 2, 2017

Related U.S. Application Data

(60) Provisional application No. 62/328,074, filed on Apr. 27, 2016.

(51) Int. Cl.
| | |
|---|---|
| *C07D 417/14* | (2006.01) |
| *A61K 31/427* | (2006.01) |
| *C07D 417/04* | (2006.01) |
| *C07B 59/00* | (2006.01) |
| *C07D 487/08* | (2006.01) |
| *C07D 491/08* | (2006.01) |
| *C07D 491/107* | (2006.01) |
| *C07D 498/08* | (2006.01) |

(52) U.S. Cl.
CPC .......... *C07D 417/14* (2013.01); *C07B 59/002* (2013.01); *C07D 417/04* (2013.01); *C07D 487/08* (2013.01); *C07D 491/08* (2013.01); *C07D 491/107* (2013.01); *C07D 498/08* (2013.01); *C07B 2200/05* (2013.01)

(58) Field of Classification Search
CPC .......................... C07D 417/14; A61K 31/427
USPC ........................................ 546/270.4; 514/342
See application file for complete search history.

(56) References Cited

U.S. PATENT DOCUMENTS

| | | | |
|---|---|---|---|
| 5,342,835 | A | 8/1994 | Pepin et al. |
| 8,809,547 | B2 | 8/2014 | Bretschneider et al. |
| 9,850,236 | B2* | 12/2017 | Goldberg ............. C07D 417/06 |
| 10,369,146 | B2 | 8/2019 | Leonard et al. |
| 2005/0014805 | A1 | 1/2005 | Zhang et al. |
| 2012/0245137 | A1 | 9/2012 | Pajouhesh |
| 2014/0163001 | A1 | 6/2014 | Yamamoto |
| 2015/0038350 | A1 | 2/2015 | Nishinaga et al. |
| 2015/0072890 | A1 | 3/2015 | James |
| 2015/0111870 | A1 | 4/2015 | Leonard |
| 2015/0266824 | A1 | 9/2015 | Beck |
| 2016/0120850 | A1 | 5/2016 | Goldberg et al. |
| 2016/0122326 | A1 | 5/2016 | Goldberg et al. |
| 2016/0122335 | A1 | 5/2016 | Goldberg et al. |
| 2016/0122336 | A1 | 5/2016 | Goldberg et al. |
| 2016/0304476 | A1 | 10/2016 | Aicher |
| 2016/0304505 | A1 | 10/2016 | Aicher |
| 2017/0253591 | A1 | 9/2017 | Yamamoto |
| 2017/0313691 | A1 | 11/2017 | Goldberg |
| 2019/0269134 | A1 | 9/2019 | Fublein et al. |
| 2019/0382349 | A1 | 12/2019 | Goldberg et al. |

(Continued)

FOREIGN PATENT DOCUMENTS

| | | |
|---|---|---|
| CL | 201102650 | 10/2011 |
| CL | 201200534 | 2/2012 |

(Continued)

OTHER PUBLICATIONS

Yang et al., ":Targeting Th17, etc.," Trends in Pharmacological Sciences, 35(10), 493-500. (Year: 2014).*

(Continued)

*Primary Examiner* — Patricia L Morris
(74) *Attorney, Agent, or Firm* — Yuriy P. Stercho

(57) ABSTRACT

The present invention comprises compounds of Formula I.

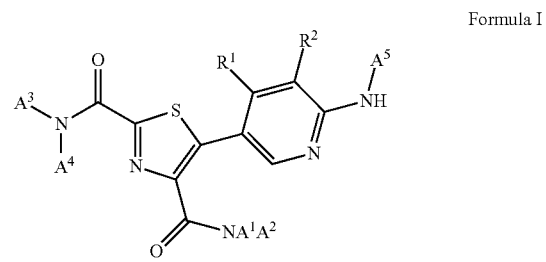

Formula I wherein:
$A^1$, $A^2$, $A^3$, $A^4$, $A^5$, $R^1$, and $R^2$ are defined in the specification.

The invention also comprises a method of treating or ameliorating a syndrome, disorder or disease, wherein the syndrome, disorder or disease is rheumatoid arthritis or psoriasis. The invention also comprises a method of modulating RORγt activity in a mammal by administration of a therapeutically effective amount of at least one compound of Formula I.

45 Claims, No Drawings

Specification includes a Sequence Listing.

(56) References Cited

U.S. PATENT DOCUMENTS

| | | |
|---|---|---|
| 2019/0382350 A1 | 12/2019 | Goldberg et al. |
| 2019/0382354 A1 | 12/2019 | Goldberg et al. |
| 2019/0382373 A1 | 12/2019 | Goldberg et al. |

FOREIGN PATENT DOCUMENTS

| | | |
|---|---|---|
| CL | 201803050 | 10/2018 |
| CL | 201901343 | 5/2019 |
| CN | 103833672 | 6/2014 |
| EP | 360701 A1 | 3/1990 |
| EP | 2433938 | 3/2012 |
| EP | 2474543 | 7/2012 |
| EP | 2738170 | 6/2014 |
| JP | 2005507932 | 3/2005 |
| WO | WO 1996003392 A1 | 2/1996 |
| WO | WO 2002083111 A2 | 10/2002 |
| WO | WO 2003015776 A1 | 2/2003 |
| WO | WO 2006087355 | 8/2006 |
| WO | WO 2006124687 A1 | 11/2006 |
| WO | WO 2007087427 A2 | 8/2007 |
| WO | WO 2008064317 A1 | 5/2008 |
| WO | WO 2008064318 A2 | 5/2008 |
| WO | WO 2009011850 | 1/2009 |
| WO | WO 2010006713 | 1/2010 |
| WO | WO 2011053948 A1 | 5/2011 |
| WO | WO 2011112263 A1 | 9/2011 |
| WO | WO 2011112264 A1 | 9/2011 |
| WO | WO 2011115892 A1 | 9/2011 |
| WO | WO 2012027965 | 3/2012 |
| WO | WO 2012074547 A2 | 6/2012 |
| WO | WO 2012129491 | 9/2012 |
| WO | WO 2012158784 A2 | 11/2012 |
| WO | WO 2012174362 | 12/2012 |
| WO | WO 2013029338 | 3/2013 |
| WO | WO 2013036912 A2 | 3/2013 |
| WO | WO 2013079223 A | 6/2013 |
| WO | WO 2013092939 A1 | 6/2013 |
| WO | WO 2013171729 | 11/2013 |
| WO | WO 2013/178362 | 12/2013 |
| WO | WO 2013178362 A1 | 12/2013 |
| WO | WO 2014/023367 | 2/2014 |
| WO | WO 2014/093191 | 6/2014 |
| WO | WO 2015035278 A1 | 3/2015 |
| WO | WO 2015042212 A1 | 3/2015 |
| WO | WO 2015082533 A1 | 6/2015 |
| WO | WO 2015103507 A1 | 7/2015 |
| WO | WO 2015103508 A1 | 7/2015 |
| WO | WO 2015103509 A1 | 7/2015 |
| WO | WO 2015103510 A1 | 7/2015 |
| WO | WO 2015145371 A1 | 10/2015 |
| WO | WO 2016/069974 | 5/2016 |
| WO | WO 2017/189823 | 11/2017 |
| WO | WO 2017/189829 | 11/2017 |
| WO | WO 2018123918 | 7/2018 |
| WO | WO 2018185236 | 10/2018 |

OTHER PUBLICATIONS

Chang M, "Pharmacologic Repression of Retinoic Acid Receptor—Related Orphan Nuclear Receptor ☐ Is Therapeutic in the Collagen-Induced Arthritis Experimental Model", Arthritis & Rheumatology (2014), 66(3), 579-588.

Fauber et al., J. Med. Chem. 2014, 57, 5871-5892.

Kumar N, "The Benzenesulfoamide T0901317 [N-(2,2,2-Trifluoroethyl)-N-[4-[2,2,2-trifluoro-1-hydroxy-1-(trifluoromethyl)ethyl]phenyl]-benzenesulfonamide] Is a Novel Retinoic Acid Receptor-Related Orphan Receptor-☐/☐ Inverse Agonist", Molecular Pharmacology (2010), 77(2), 228-236.

Liegault, et al., "Establishment of Broadly Applicable reaction condisions for the Palladium-Catalyzed Direct Arylation of Heteroatom-Containing Aromatic Compounds", The Journal of Organic Chemistry, (2009), vol. 74, No. 5, 6, pp. 1826-1834.

Yang et al., Trends in Pharmacological Sciences, Oct. 2014, vol. 35, No. 10, 493-500.

Yao, et al, "Preparation Method of N-butyl-5-phenylthiazole-4-Formamide Derivative Via Coupling Reaction Under Catalysis of Copper Catalyst", Database accession No. 2014:924023.

Zhang, et al., "Decarboxylative Cross-Coupling of Azoyl Carboxylic Acids with Aryl Halides", Organic Letters, (2010) vol. 12, No. 21, pp. 4745-47457.

PCT/US2015/058193, Written Opinion dated Jan. 26, 2016.
PCT/US2015/058198, Written Opinion dated Jan. 21, 2016.
PCT/US2015/058200, Written Opinion dated Jan. 27, 2016.
PCT/US2015/058193, International Search Report, dated Jan. 26, 2016.
PCT/US2015/058198, International Search Report, dated Jan. 21, 2016.
PCT/US2015/058200, International Search Report, dated Jan. 27, 2016.

Barczyk, a., W. Pierzchala, et al. (2003). "Interleukin-17 in sputum correlates with airway hyperresponsiveness to methacholine." Respir Med 97(6): 726-33.

Beurel, E., Harrington, L. E., Jope, R. S. (2013) "Inflammatory T helper 17 cells promote depression-like behavior in mice." Biol Psychiatry 73(7): 622-30.

Bowes, J. and A. Barton "The genetics of psoriatic arthritis: lessons from genome-wide association studies." Discov Med 10(52): 177-83 (2010).

Chang, M. R. et al. (2015) "Antiobesity Effect of a Small Molecule Repressor of RORγ." Mol Pharmacol. 88(1): 48-56.

Chen, Y., et al. (2011). "Emerging tendency towards autoimmune process in major depressive patients: A novel insight from Th17 cells." Psychiatry Research 188(2): 224-230.

Cua, D. J., J. Sherlock, et al. (2003). "Interleukin-23 rather than interleukin-12 is the critical cytokine for autoimmune inflammation of the brain." Nature 421(6924): 744-8.

Dong, C. (2006). "Diversification of T-helper-cell lineages: finding the family root of IL-17-producing cells." Nat Rev Immunol 6(4): 329-33.

Fujino, S., A. Andoh, et al. (2003). "Increased expression of interleukin 17 in inflammatory bowel disease." Gut 52(1): 65-70.

Garber K. (2011). "Psoriasis: from bed to bench and back" Nat Biotech 29, 563-566.

Gazouli, M., I. Pachoula, et al. "NOD2/CARD15, ATG16L1 and IL23R gene polymorphisms and childhood-onset of Crohn's disease." World J Gastroenterol 16(14): 1753-8 (2010).

Hueber, W., Patel, D.D., Dryja, T., Wright, A.M., Koroleva, I., Bruin, G., Antoni, C., Draelos, Z., Gold, M.H., Durez, P., Tak, P.P., Gomez-Reino, J.J., Foster, C.S., Kim, R.Y., Samson, C.M., Falk, N.S., Chu, D.S., Callanan, D., Nguyen, Q.D., Rose, K., Haider, A., Di Padova, F. (2010) Effects of AIN457, a fully human antibody to interleukin-17A, on psoriasis, rheumatoid arthritis, and uveitis. Sci Transl Med 2, 5272.

Ivanov, II, B. S. McKenzie, et al. (2006). "The orphan nuclear receptor RORgammat directs the differentiation program of proinflammatory IL-17+ T helper cells." Cell 126(6): 1121-33.

Kochi, Y., Y. Okada, et al. (2010) "A regulatory variant in CCR6 is associated with rheumatoid arthritis susceptibility." Nat Genet 42(6): 515-9.

Kolls, J. K. and A. Linden (2004). "Interleukin-17 family members and inflammation." Immunity 21(4): 467-76.

Korn, T., E. Bettelli, et al. (2009). "IL-17 and Th17 Cells." Annu Rev Immunol 27: 485-517.

Krueger, J. G., S. Fretzin, et al. "IL-17A is essential for cell activation and inflammatory gene circuits in subjects with psoriasis." J Allergy Clin Immunol 130(1): 145-154 e9 (2012).

Langrish, C. L., Y. Chen, et al. (2005). "IL-23 drives a pathogenic T cell population that induces autoimmune inflammation." J Exp Med 201(2): 233-40.

Leonardi, C., R. Matheson, et al. "Anti-interleukin-17 monoclonal antibody ixekizumab in chronic plaque psoriasis." N Engl J Med 366(13): 1190-9 (2012).

Lock, C., G. Hermans, et al. (2002). "Gene-microarray analysis of multiple sclerosis lesions yields new targets validated in autoimmune encephalomyelitis." Nat Med 8(5): 500-8.

(56) References Cited

OTHER PUBLICATIONS

Matulis, D., Kranz, J. K., Salemme, F. R., and Todd, M. J. (2005) Thermodynamic stability of carbonic anhydrase: measurements of binding affinity and stoichiometry using ThermoFluor. *Biochemistry* 44, 5258-66.
McKenzie, B. S., R. A. Kastelein, et al. (2006). "Understanding the IL-23-IL-17 immune pathway." Trends Immunol 27(1): 17-23.
Meissburger, B. et al. (2011) "Adipogenesis and insulin sensitivity in obesity are regulated by retinoid-related orphan receptor gamma." EMBO Mol Med. 3(11): 637-651.
Nunez, C., B. Dema, et al. (2008). "IL23R: a susceptibility locus for celiac disease and multiple sclerosis?" Genes Immun 9(4): 289-93.
Pantoliano, M. W., Petrella, E. C., Kwasnoski, J. D., Lobanov, V. S., Myslik, J., Graf, E., Carver, T., Asel, E., Springer, B. A., Lane, P., and Salemme, F. R. (2001) High-density miniaturized thermal shift assays as a general strategy for drug discovegy. *J Biomol Screen 6*, 429-40.
Papp, K. A., "Brodalumab, an anti-interleukin-17-receptor antibody for psoriasis." N Engl J Med 2012 366(13): 1181-9.
Stamp, L. K., M. J. James, et al. (2004). "Interleukin-17: the missing link between T-cell accumulation and effector cell actions in rheumatoid arthritis" Immunol Cell Biol 82(1): 1-9.
Tonel, G., C. Conrad, et al. "Cutting edge: A critical functional role for IL-23 in psoriasis." J Immunol 185(10): 5688-91 (2010).
Yen, D., J. Cheung, et al. (2006). "IL-23 is essential for T cell-mediated colitis and promotes inflammation via IL-17 and IL-6." J Clin Invest 116(5): 1310-6.
De Wit et al., ,RORγt inhibitors suppress TH17 responses in inflammatory arthritis and inflammatory bowel disease. Journal of Allergy and Clinical Immunology, vol. 137 , Issue 3, (2016), 960-963.
Bimekizumab demonstrates impressive joint and skin responses for psoriatic arthritis patients. Dec. 20, 2017. https://www.ucb.com/stories-media/Press-Releases/article/Bimekizumab-demonstrates-impressive-joint-and-skin-responses-for-psoriatic-arthritis-patients-nbsp.
Cheng, Chia-Chung et al., The Friedlander synthesis of quinolines, Organic Reactions, 1982, 28, pp. 37-201.
Dolff S et al., Disturbed Th1, Th2, Th17 and T-reg balance in patients with systemic lupus erythematosus, Clinical Immunology 141(2):197-204 Aug. 2011.
Feagan BG, et al. Ustekinumab as induction and maintenance therapy for Crohn's disease. N Engl J Med. 2016;375(20):1946-60.
Fitzpatrick, Leo Robert. Ror-gamma T inhibition as a Pharmacological Approach for Inflammatory Bowel Disease. Medical Research Archives, [S.l.], v. 2, n. 2, Aug. 2015.
Hodgson et al., Ustekinumab for Treating Moderately to Severely Active Crohn's Disease after Prior Therapy: An Evidence Review Group Perspective of a NICE Single Technology Appraisal. PharmacoEconomics (2018) 36:4, 387-398.
Innovimmune: ROR Gamma Inhibitor (INV-17) Tested in Lupus Model. 2015 EULAR Congress News. https://static1.squarespace.com/static/577aff0015d5db17f97d2d57/t/584f44f9725e254d6b032644/1481590043630/150611_INV-17+Lupus+Thursday_EULAR_2015+small+size.pdf.

Jethwa H at al., The interleukin (IL)-23/IL-17 axis in ankylosing spondylitis: new advances and potentials for treatment, Clinical and Experimental Immunology, 2015, 183: 30-36.
McGinley et al., (2018) Th17 cells, γδ T cells and their interplay in EAE and multiple sclerosis. *Journal of Autoimmunity* 87, 97-108.
Mease, P. J. et al. Brodalumab, an anti-IL17RA monoclonal antibody, in psoriatic arthritis, The New England Journal of Medicine 370, 2295-2306 (2014).
Poddhubnyy et al., Ann Rheum Dis 2014;0:1-7.
Qian et al., Clin. Invest. (2012) 2(4), 417-421.
Registry(STN)[online], [Search Date: May 13, 2019]CAS Registration No. 791058-42-9,263386-02-3.
Sandborn WJ et al. Ustekinumab Induction and Maintenance Therapy in Refractory Crohn's Disease N Engl J Med 2012; 367:1519-1528.
Silva MJ et al, Glucocorticoid Resistant Asthma: The Potential Contribution of IL-17. Biomark J. 2016, 1:6.
Wang X, Wei Y, Xiao H, et al. A novel IL-23p19/Ebi3 (IL-39) cytokine mediates inflammation in Lupus-like mice. Eur J Immunol. 2016;46(6):1343-1350.
Weitz JE et al., Ustekinumab: Targeting the IL-17 Pathway to Improve Outcomes in Psoriatic Arthritis. Expert Opin Biol Ther 2104 14, 515-526.
Withers DR, et al. Transient inhibition of ROR-γt therapeutically limits intestinal inflammation by reducing TH17 cells and preserving group 3 innate lymphoid cells Nature Medicine 2016, 22, 319.
Yang X et al. Does IL-17 Respond to the Disordered Lung Microbiome and Contribute to the Neutrophilic Phenotype in Asthma? Mediators of Inflammation. vol. 2016 (2016), Article ID 6470364, pp. 1-7.
PCT/US2017/029531, International Search Report, dated Sep. 15, 2017.
PCT/US2017/029531, International Preliminary Report on Patentability, dated Oct. 30, 2018.
PCT/IB2019/055043, International Search Report, dated Sep. 30, 2019.
PCT/IB2019/055043, Written Opinion, dated Sep. 30, 2019.
PCT/IB2019/055045, International Search Report, dated Sep. 30, 2019.
PCT/IB2019/055045, Written Opinion, dated Sep. 30, 2019.
PCT/IB2019/055046, International Search Report, dated Oct. 4, 2019.
PCT/IB2019/055046, Written Opinion, dated Oct. 4, 2019.
PCT/IB2019/055048, International Search Report, dated Sep. 27, 2019.
PCT/IB2019/055048, Written Opinion, dated Sep. 27, 2019.
Angew. Chem. Int. Ed. Engl. 1982, 21, 567-583.
Pure & Appl. Chem. 45, 1976, 11-30.
Eastman; Oncotarget. 2017, 8, 8854-8866. DOI: 10.18632/oncotarget.12673 (Year: 2017).
Guendisch; PLoS One 2017, 12, e0188391. DOI: 10.1371/journal.pone.0188391 (Year: 2017).
Huh; Eur. J. Immunol. 2012. 42, 2232-2237. DOI: 10.1002/eji.201242740 (Year: 2012).
Isono; Drug Discovery Today, 2014, 19, 1205-1211. DOI: 10.1016/j.drudis.2014.04.012 (Year: 2014).
Kiaei; Basic Clin Neurosci. 2013, 4, 3-4. URL: http://bcn.iums.ac.ir/article-1-307-en.html (Year: 2013).
Xue; Scientific Reports 2016, 6, Article No. 37977. DOI: 10.1038/srep37977 (Year: 2016).

\* cited by examiner

6-AMINOPYRIDIN-3-YL THIAZOLES AS MODULATORS OF RORγT

CROSS-REFERENCE TO RELATED APPLICATIONS

This application claims priority from U.S. Application No. 62/328,074, filed on Apr. 27, 2016, which is incorporated herein by reference.

SEQUENCE LISTING

The instant application contains a Sequence Listing which has been filed electronically in ASCII format and is hereby incorporated by reference in its entirety. Said ASCII copy, created on Apr. 11, 2017, is named PRD3409USNP.txt and is 8,313 bytes in size.

FIELD OF THE INVENTION

The invention is directed to substituted thiazole compounds, which are modulators of the nuclear receptor RORγt, pharmaceutical compositions, and methods for use thereof. More particularly, the RORγt modulators are useful for preventing, treating or ameliorating an RORγt mediated inflammatory syndrome, disorder or disease.

BACKGROUND OF THE INVENTION

Retinoic acid-related nuclear receptor gamma t (RORγt) is a nuclear receptor, exclusively expressed in cells of the immune system, and a key transcription factor driving Th17 cell differentiation. Th17 cells are a subset of CD4+ T cells, expressing CCR6 on their surface to mediate their migration to sites of inflammation, and dependent on IL-23 stimulation, through the IL-23 receptor, for their maintenance and expansion. Th17 cells produce several proinflammatory cytokines including IL-17A, IL-17F, IL-21, and IL-22 (Korn, T., E. Bettelli, et al. (2009). "IL-17 and Th17 Cells." Annu Rev Immunol 27: 485-517.), which stimulate tissue cells to produce a panel of inflammatory chemokines, cytokines and metalloproteases, and promote recruitment of granulocytes (Kolls, J. K. and A. Linden (2004). "Interleukin-17 family members and inflammation." Immunity 21(4): 467-76; Stamp, L. K., M. J. James, et al. (2004). "Interleukin-17: the missing link between T-cell accumulation and effector cell actions in rheumatoid arthritis" Immunol Cell Biol 82(1): 1-9). Th17 cells have been shown to be the major pathogenic population in several models of autoimmune inflammation, including collagen-induced arthritis (CIA) and experimental autoimmune encephalomyelitis (EAE) (Dong, C. (2006). "Diversification of T-helper-cell lineages: finding the family root of IL-17-producing cells." Nat Rev Immunol 6(4): 329-33; McKenzie, B. S., R. A. Kastelein, et al. (2006). "Understanding the IL-23-IL-17 immune pathway." Trends Immunol 27(1): 17-23.). RORγt-deficient mice are healthy and reproduce normally, but have shown impaired Th17 cell differentiation in vitro, a significantly reduced Th17 cell population in vivo, and decreased susceptibility to EAE (Ivanov, II, B. S. McKenzie, et al. (2006). "The orphan nuclear receptor RORgammat directs the differentiation program of proinflammatory IL-17+ T helper cells." Cell 126(6): 1121-33.). Mice deficient for IL-23, a cytokine required for Th17 cell survival, fail to produce Th17 cells and are resistant to EAE, CIA, and inflammatory bowel disease (IBD) (Cua, D. J., J. Sherlock, et al. (2003). "Interleukin-23 rather than interleukin-12 is the critical cytokine for autoimmune inflammation of the brain." Nature 421(6924): 744-8; Langrish, C. L., Y. Chen, et al. (2005). "IL-23 drives a pathogenic T cell population that induces autoimmune inflammation." J Exp Med 201(2): 233-40; Yen, D., J. Cheung, et al. (2006). "IL-23 is essential for T cell-mediated colitis and promotes inflammation via IL-17 and IL-6." J Clin Invest 116(5): 1310-6.). Consistent with these findings, an anti-IL23-specific monoclonal antibody blocks development of psoriasis-like inflammation in a murine disease model (Tonel, G., C. Conrad, et al. "Cutting edge: A critical functional role for IL-23 in psoriasis." J Immunol 185(10): 5688-91).

RORγT deficient mice exhibited resistance to learned helplessness. Treatment with the RORγT inhibitor SR1001, or anti-interleukin-17A antibodies reduced Th17-dependent learned helplessness (Beurel, E., Harrington, L. E., Jope, R. S. (2013) "Inflammatory T helper 17 cells promote depression-like behavior in mice." Biol Psychiatry 73(7): 622-30). In human patients with major depressive disorder, both peripheral blood lymphocyte RORγT mRNA expression and peripheral Th17 cells were found to be elevated relative to the control group (Chen, Y., et al. (2011). "Emerging tendency towards autoimmune process in major depressive patients: A novel insight from Th17 cells." Psychiatry Research 188(2): 224-230).

Administration of RORγ inverse agonist SR1555 to obese diabetic mice resulted in a modest reduction in food intake accompanied with significant reduction in fat mass, resulting in reduced body weight and improved insulin sensitivity (Chang, M. R. et al. (2015) "Antiobesity Effect of a Small Molecule Repressor of RORγ." Mol Pharmacol. 88(1): 48-56). In addition, Rorγ−/− mice are protected from hyperglycemia and insulin resistance in the state of obesity (Meissburger, B. et al. (2011) "Adipogenesis and insulin sensitivity in obesity are regulated by retinoid-related orphan receptor gamma." EMBO Mol Med. 3(11): 637-651).

In humans, a number of observations support the role of the IL-23/Th17 pathway in the pathogenesis of inflammatory diseases. IL-17, the key cytokine produced by Th17 cells, is expressed at elevated levels in a variety of allergic and autoimmune diseases (Barczyk, A., W. Pierzchala, et al. (2003). "Interleukin-17 in sputum correlates with airway hyperresponsiveness to methacholine." Respir Med 97(6): 726-33.; Fujino, S., A. Andoh, et al. (2003). "Increased expression of interleukin 17 in inflammatory bowel disease." Gut 52(1): 65-70.; Lock, C., G. Hermans, et al. (2002). "Gene-microarray analysis of multiple sclerosis lesions yields new targets validated in autoimmune encephalomyelitis." Nat Med 8(5): 500-8.; Krueger, J. G., S. Fretzin, et al. "IL-17A is essential for cell activation and inflammatory gene circuits in subjects with psoriasis." J Allergy Clin Immunol 130(1): 145-154 e9.). Furthermore, human genetic studies have shown association of polymorphisms in the genes for Th17 cell-surface receptors, IL-23R and CCR6, with susceptibility to IBD, multiple sclerosis (MS), rheumatoid arthritis (RA) and psoriasis (Gazouli, M., I. Pachoula, et al. "NOD2/CARD15, ATG16L1 and IL23R gene polymorphisms and childhood-onset of Crohn's disease." World J Gastroenterol 16(14): 1753-8., Nunez, C., B. Dema, et al. (2008). "IL23R: a susceptibility locus for celiac disease and multiple sclerosis?" Genes Immun 9(4): 289-93.; Bowes, J. and A. Barton "The genetics of psoriatic arthritis: lessons from genome-wide association studies." Discov Med 10(52): 177-83; Kochi, Y., Y. Okada, et al. "A regulatory variant in CCR6 is associated with rheumatoid arthritis susceptibility." Nat Genet 42(6): 515-9.).

Ustekinumab (Stelara®), an anti-p40 monoclonal antibody blocking both IL-12 and IL-23, is approved for the treatment of adult patients (18 years or older), with moderate to severe plaque psoriasis, who are candidates for phototherapy or systemic therapy. Currently, monoclonal antibodies specifically targeting only IL-23, to more selectively inhibit the Th17 subset, are also in clinical development for psoriasis (Garber K. (2011). "Psoriasis: from bed to bench and back" Nat Biotech 29, 563-566), further implicating the important role of the IL-23- and RORγt-driven Th17 pathway in this disease. Results from recent phase II clinical studies strongly support this hypothesis, as anti-IL-17 receptor and anti-IL-17 therapeutic antibodies both demonstrated high levels of efficacy in patients with chronic psoriasis (Papp, K. A., "Brodalumab, an anti-interleukin-17-receptor antibody for psoriasis." N Engl J Med 2012 366(13): 1181-9.; Leonardi, C., R. Matheson, et al. "Anti-interleukin-17 monoclonal antibody ixekizumab in chronic plaque psoriasis." N Engl J Med 366(13): 1190-9.). Anti-IL-17 antibodies have also demonstrated clinically relevant responses in early trials in RA and uveitis (Hueber, W., Patel, D. D., Dryja, T., Wright, A. M., Koroleva, I., Bruin, G., Antoni, C., Draelos, Z., Gold, M. H., Durez, P., Tak, P. P., Gomez-Reino, J. J., Foster, C. S., Kim, R. Y., Samson, C. M., Falk, N. S., Chu, D. S., Callanan, D., Nguyen, Q. D., Rose, K., Haider, A., Di Padova, F. (2010) Effects of AIN457, a fully human antibody to interleukin-17A, on psoriasis, rheumatoid arthritis, and uveitis. Sci Transl Med 2, 5272.).

All the above evidence supports inhibition of the Th17 pathway by modulating RORγt activity as an effective strategy for the treatment of immune-mediated inflammatory diseases.

SUMMARY OF THE INVENTION

The present invention comprises a compound of Formula I:

Formula I

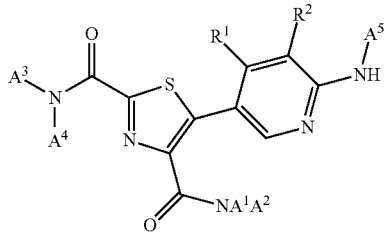

wherein $R^1$ is H, —$C_{(1-3)}$alkyl, —$CHF_2$, —$CF_3$, —CN, —$OCH_3$, —$OCH_2CH_3$, cyclopropyl, $OCF_3$, or $OCHF_2$;

$R^2$ is H, F, —$CHF_2$, —$CF_3$, —CN, —$OCH_3$, —$OCHF_2$, or $OCF_3$; provided that $R^2$ may not be H if $R^1$ is H;

$A^1$ and $A^2$ are taken together with their attached nitrogen to form a ring selected from the group consisting of

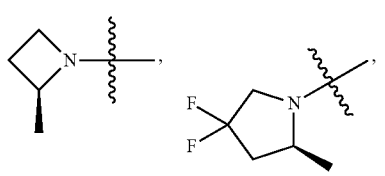

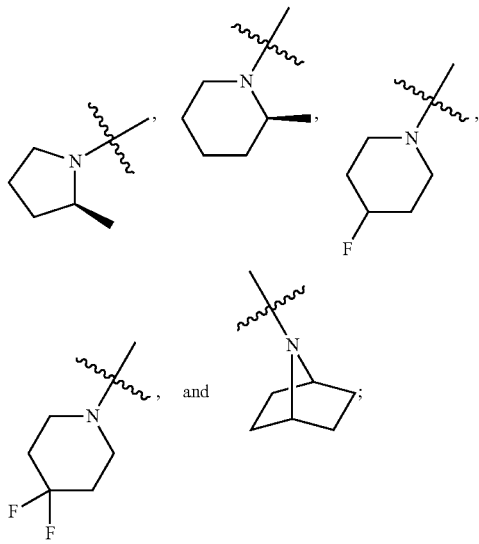

$A^3$ is H, —$C_{(1-6)}$alkyl,

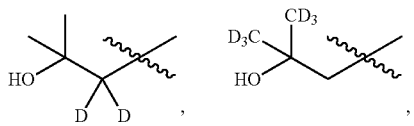

—$SO_2CH(CH_3)_2$, —$SO_2CH_3$,

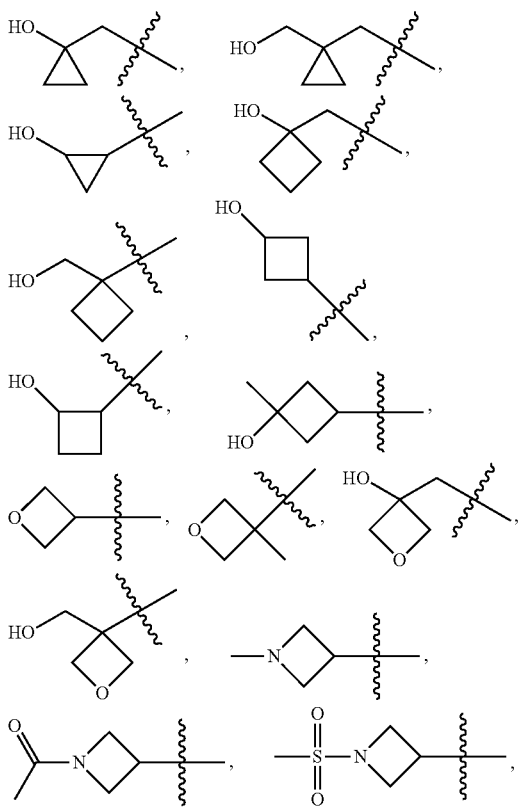

-continued

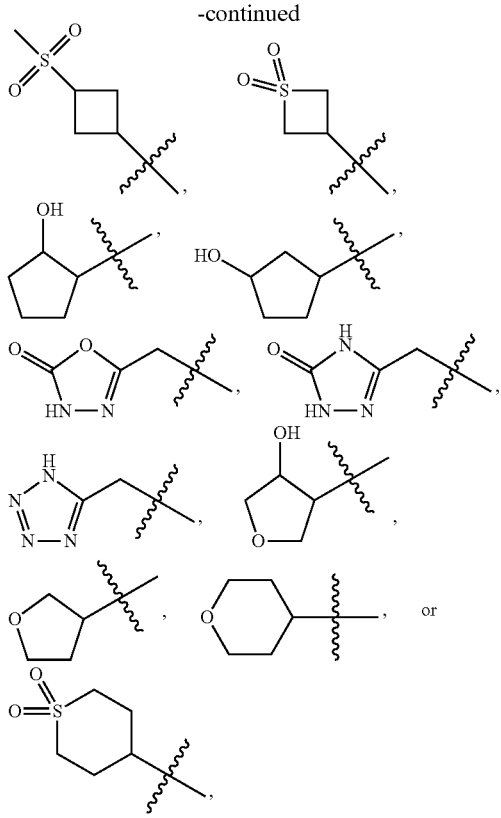

wherein said —C$_{(1-6)}$alkyl is optionally substituted with one —NH$_2$ group, one or two —OH groups, and may be additionally substituted with up to six fluorine atoms;

A$^4$ is —H, or —CH$_3$;

or A$^3$ and A$^4$ may be taken together with their attached nitrogen to form a ring selected from the group consisting of

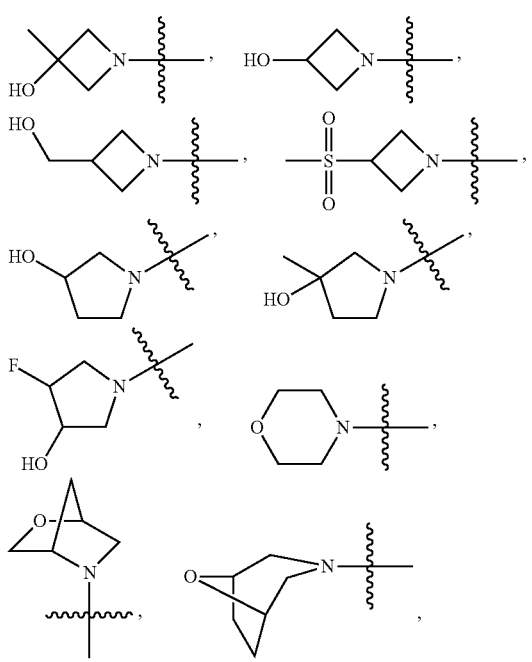

-continued

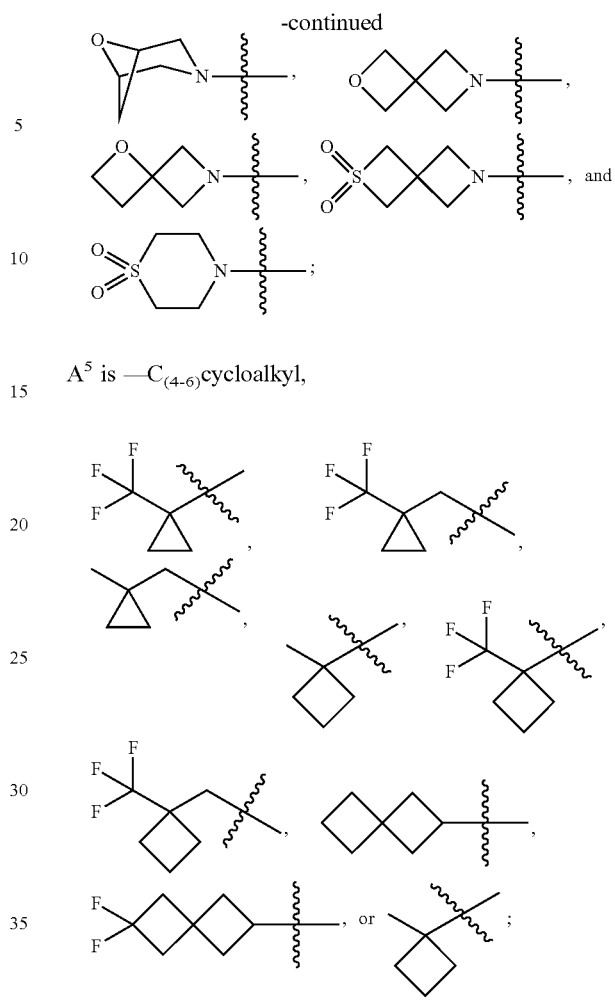

A$^5$ is —C$_{(4-6)}$cycloalkyl,

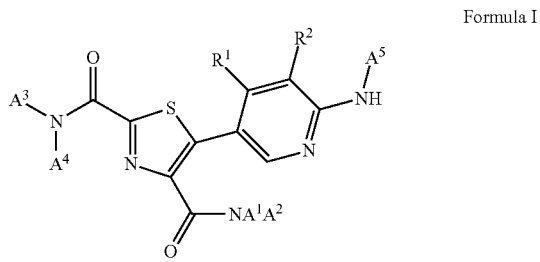

wherein said —C$_{(1-6)}$alkyl and —C$_{(4-6)}$cycloalkyl are optionally substituted with up to three fluorine atoms; and said —C$_{(1-6)}$alkyl is independently optionally substituted with one cyclobutyl, or up to two cyclopropyl groups; and pharmaceutically acceptable salts thereof.

DETAILED DESCRIPTION OF THE INVENTION

The present invention comprises a compound of Formula I:

Formula I wherein
R$^1$ is H, —C$_{(1-3)}$alkyl, —CHF$_2$, —CF$_3$, —CN, —OCH$_3$, —OCH$_2$CH$_3$, cyclopropyl, OCF$_3$, or OCHF$_2$;

R² is H, F, —CHF₂, —CF₃, —CN, —OCH₃, —OCHF₂, or OCF₃; provided that R² may not be H if R¹ is H;

A¹ and A² are taken together with their attached nitrogen to form a ring selected from the group consisting of

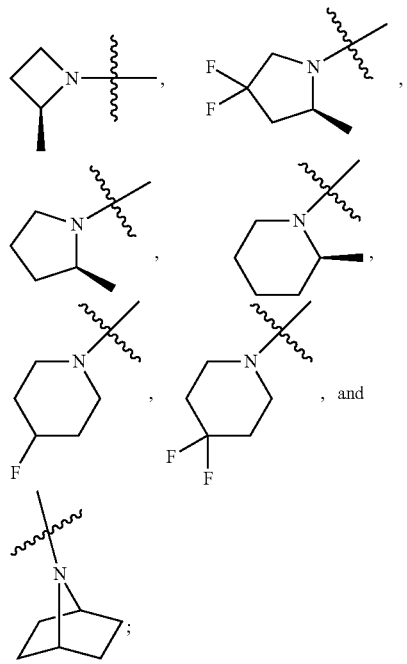

A³ is H, —C$_{(1-6)}$alkyl,

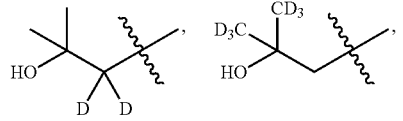

—SO₂CH(CH₃)₂, —SO₂CH₃,

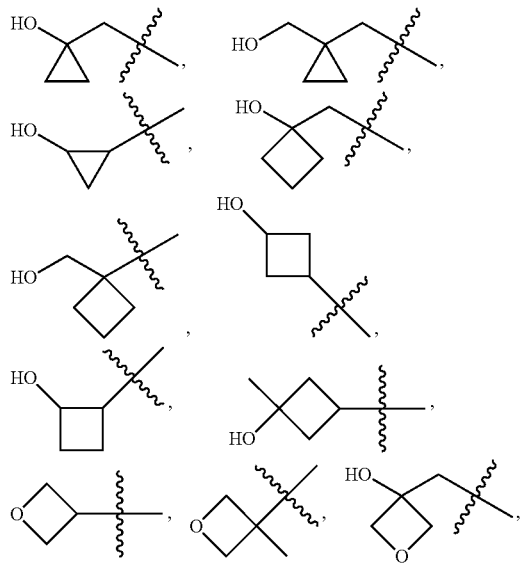

-continued

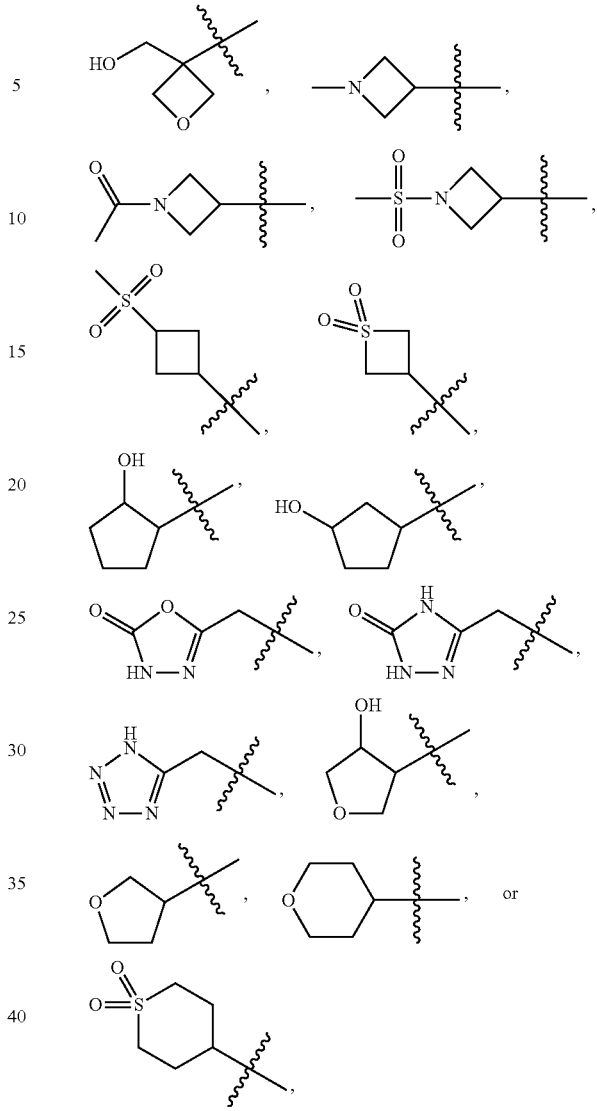

wherein said —C$_{(1-6)}$alkyl is optionally substituted with one —NH₂ group, one or two —OH groups, and may be additionally substituted with up to six fluorine atoms;

A⁴ is —H, or —CH₃;

or A³ and A⁴ may be taken together with their attached nitrogen to form a ring selected from the group consisting of

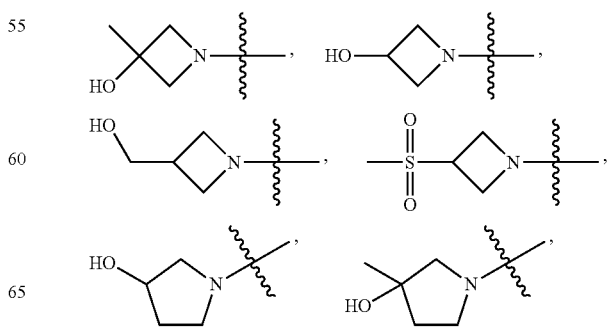

-continued

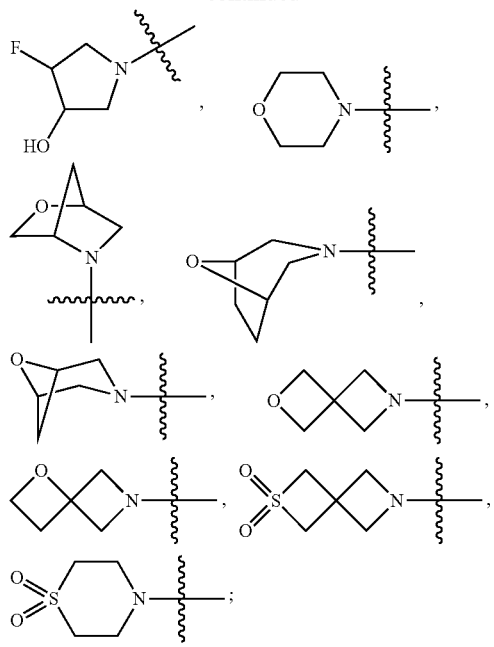

A⁵ is —C$_{(4-6)}$cycloalkyl, —C$_{(1-6)}$alkyl,

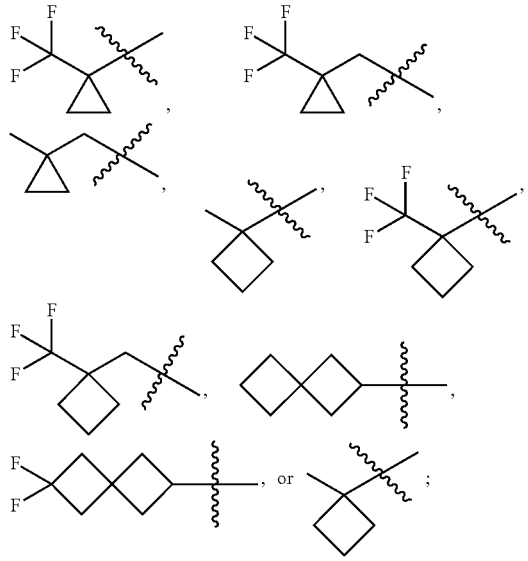

wherein said —C$_{(1-6)}$alkyl and —C$_{(4-6)}$cycloalkyl are optionally substituted with up to three fluorine atoms; and said —C$_{(1-6)}$alkyl is independently optionally substituted with one cyclobutyl, or up to two cyclopropyl groups;

and pharmaceutically acceptable salts thereof.

In another embodiment of the invention:

R¹ is H, —CHF$_2$, —CF$_3$, —CN, —OCH$_3$, —OCH$_2$CH$_3$, cyclopropyl, OCF$_3$, or OCHF$_2$;

R² is H, F, —CHF$_2$, —CF$_3$, —CN, —OCH$_3$, —OCHF$_2$, or OCF$_3$; provided that R² may not be H if R¹ is H;

A¹ and A² are taken together with their attached nitrogen to form a ring selected from the group consisting of

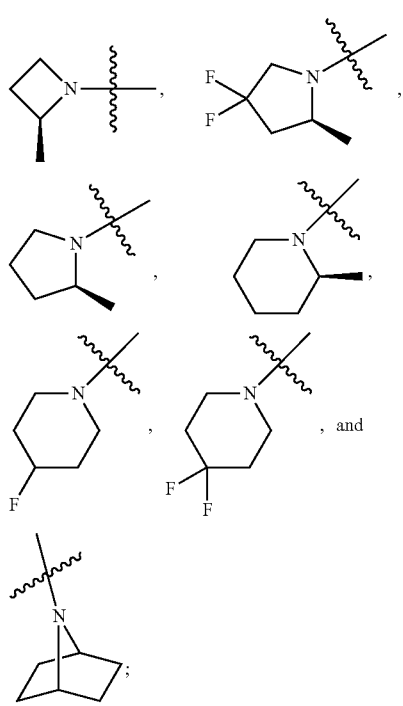

A³ is H, —C$_{(1-6)}$alkyl,

—SO$_2$CH(CH$_3$)$_2$, —SO$_2$CH$_3$,

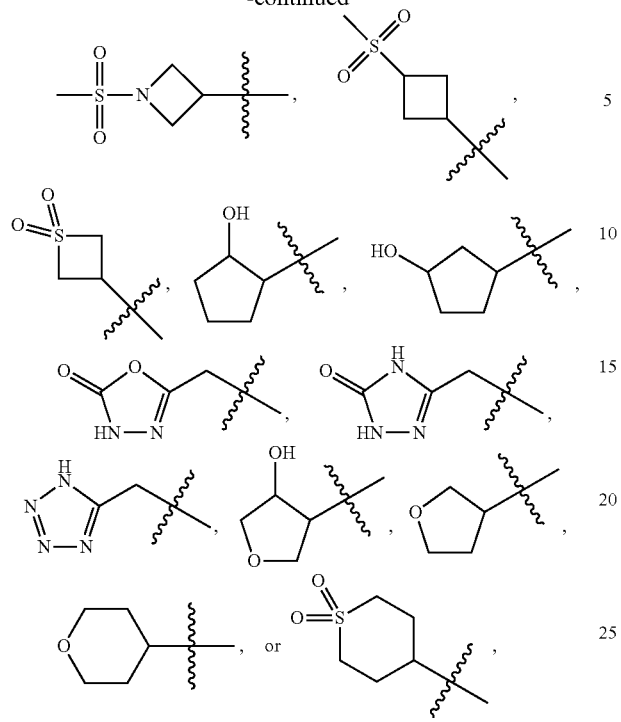

wherein said —C$_{(1-6)}$alkyl is optionally substituted with one —NH$_2$ group, one or two —OH groups, and may be additionally substituted with up to six fluorine atoms;

A$^4$ is —H, or —CH$_3$;

or A$^3$ and A$^4$ may be taken together with their attached nitrogen to form a ring selected from the group consisting of

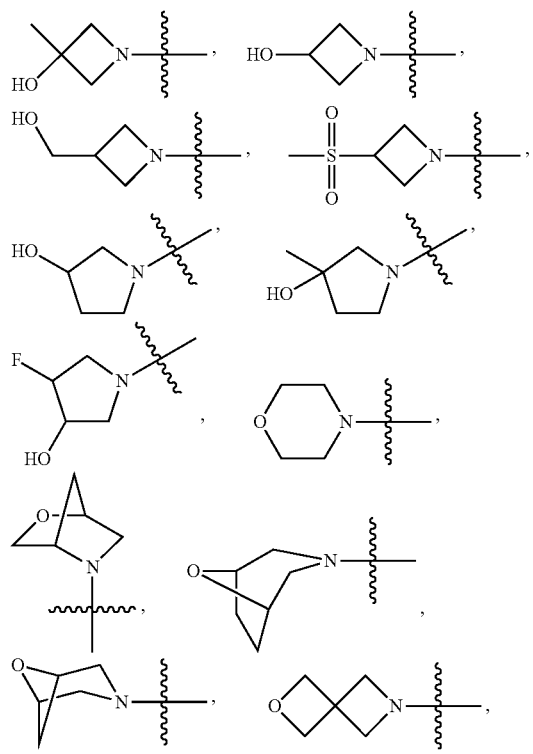

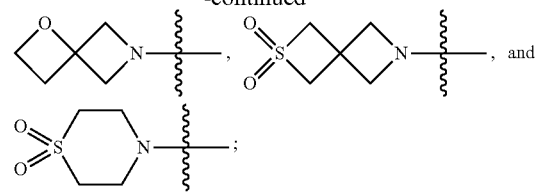

A$^5$ is —C$_{(1-6)}$cycloalkyl, —C$_{(3-6)}$alkyl,

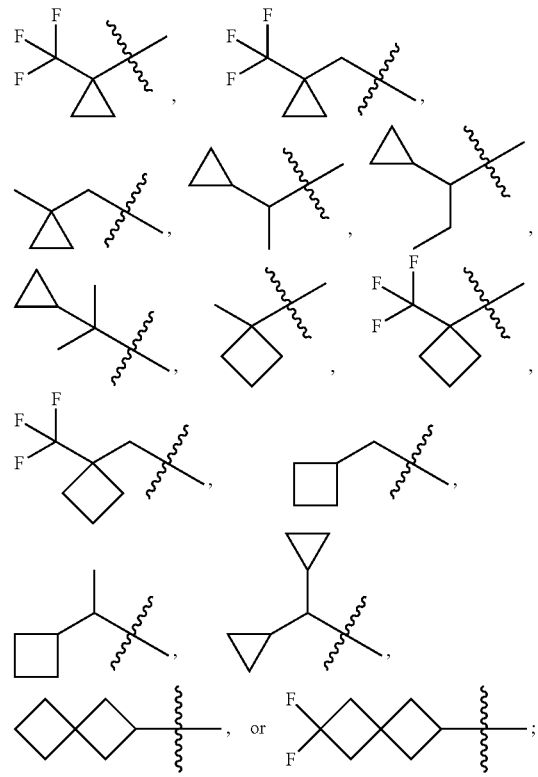

wherein said —C$_{(3-6)}$alkyl and —C$_{(4-6)}$cycloalkyl are optionally substituted with up to three fluorine atoms;

and pharmaceutically acceptable salts thereof.

In another embodiment of the invention:

R$^1$ is H, —CHF$_2$, —CF$_3$, —CN, —OCH$_3$, —OCH$_2$CH$_3$, or cyclopropyl;

R$^2$ is H, F, —CHF$_2$, —CF$_3$, —CN, —OCH$_3$, or —OCHF$_2$; provided that R$^2$ may not be H if R$^1$ is H;

A$^1$ and A$^2$ are taken together with their attached nitrogen to form a ring selected from the group consisting of

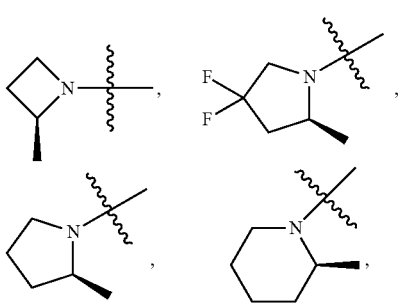

-continued
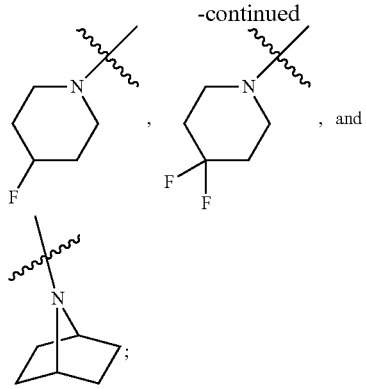
$A^3$ is H, —$C_{(1-6)}$alkyl,
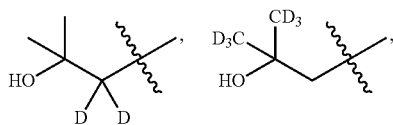
—SO₂CH(CH₃)₂, —SO₂CH₃,
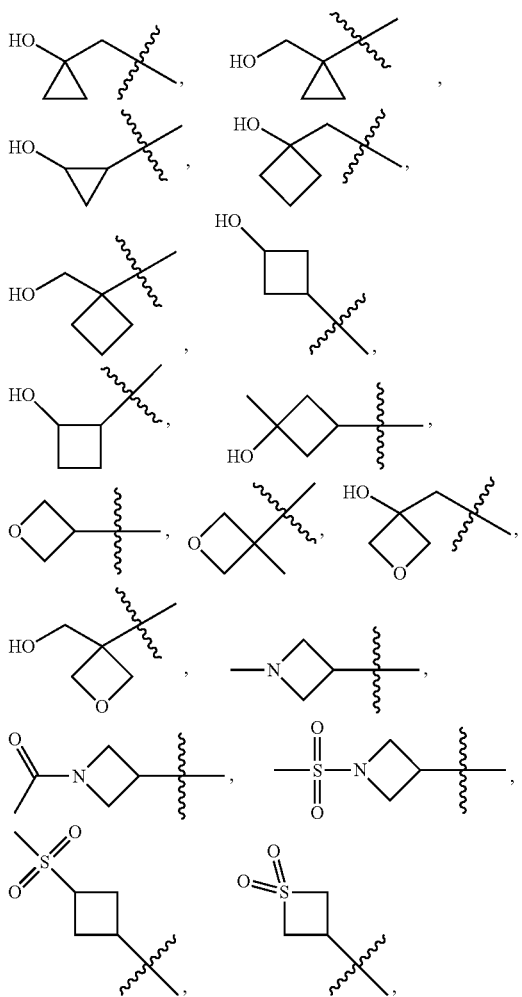
-continued
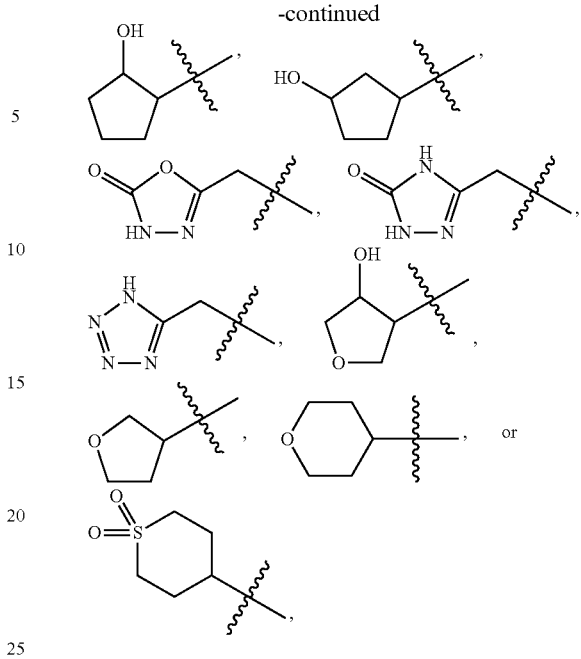
wherein said —$C_{(1-6)}$alkyl is optionally substituted with one —NH₂ group, one or two —OH groups, and may be additionally substituted with up to six fluorine atoms;
$A^4$ is —H, or —CH₃;
or $A^3$ and $A^4$ may be taken together with their attached nitrogen to form a ring selected from the group consisting of
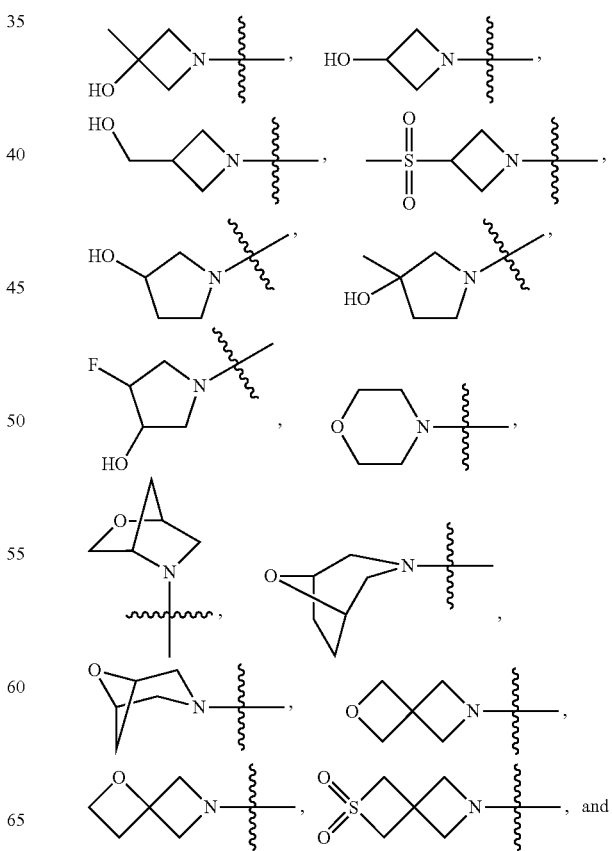
and -continued

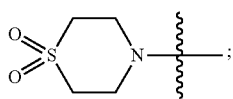

$A^5$ is —$C_{(1-6)}$cycloalkyl, —$C_{(3-6)}$alkyl,

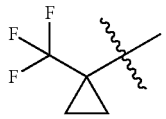


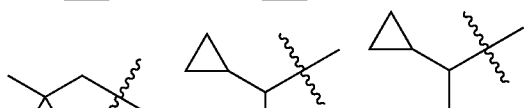

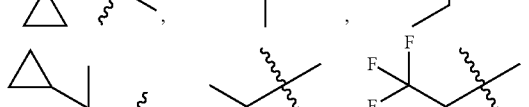


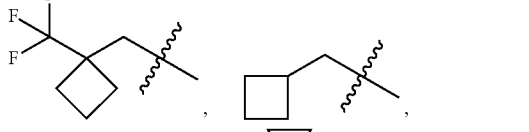


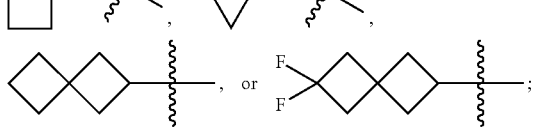

wherein said —$C_{(3-6)}$alkyl and —$C_{(4-6)}$cycloalkyl are optionally substituted with up to three fluorine atoms;

and pharmaceutically acceptable salts thereof.

In another embodiment of the invention:

$R^1$ is H, —$CHF_2$, —$CF_3$, —CN, —$OCH_3$, —$OCH_2CH_3$, or cyclopropyl;

$R^2$ is H, F, —$CHF_2$, —$CF_3$, —CN, —$OCH_3$, or —$OCHF_2$; provided that $R^2$ may not be H if $R^1$ is H;

$A^1$ and $A^2$ are taken together with their attached nitrogen to form a ring selected from the group consisting of

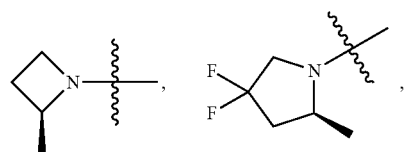

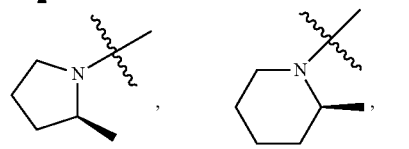

-continued

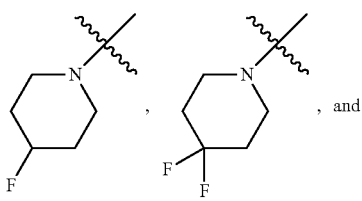

, and

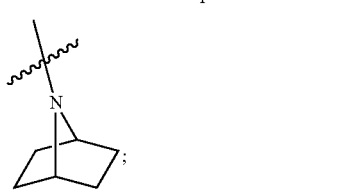

$A^3$ is H, —$C_{(1-6)}$alkyl,

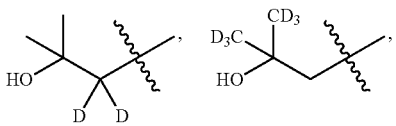

—$SO_2CH(CH_3)_2$, —$SO_2CH_3$,

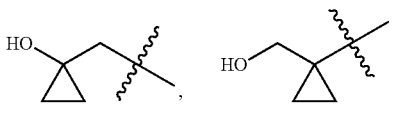

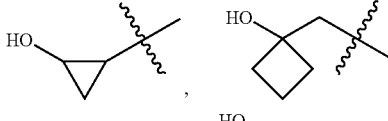

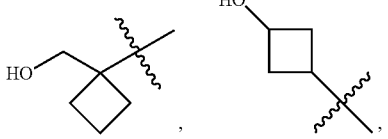


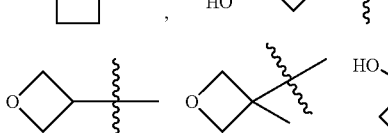

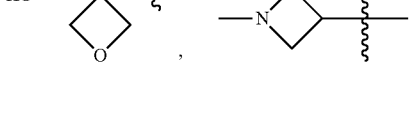

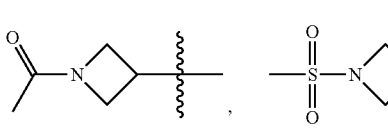

17

-continued

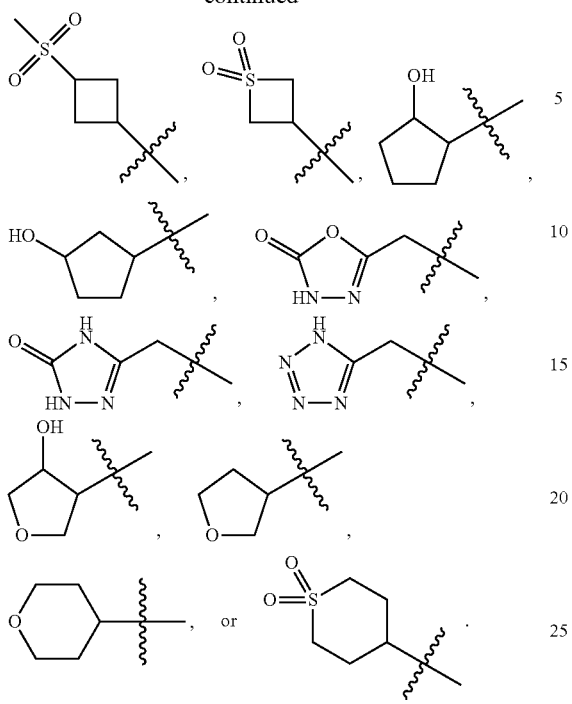

wherein said —C$_{(1-6)}$alkyl is optionally substituted with one —NH$_2$ group, one or two —OH groups, and may be additionally substituted with up to six fluorine atoms;

A$^4$ is H, or —CH$_3$;

or A$^3$ and A$^4$ may be taken together with their attached nitrogen to form a ring selected from the group consisting of

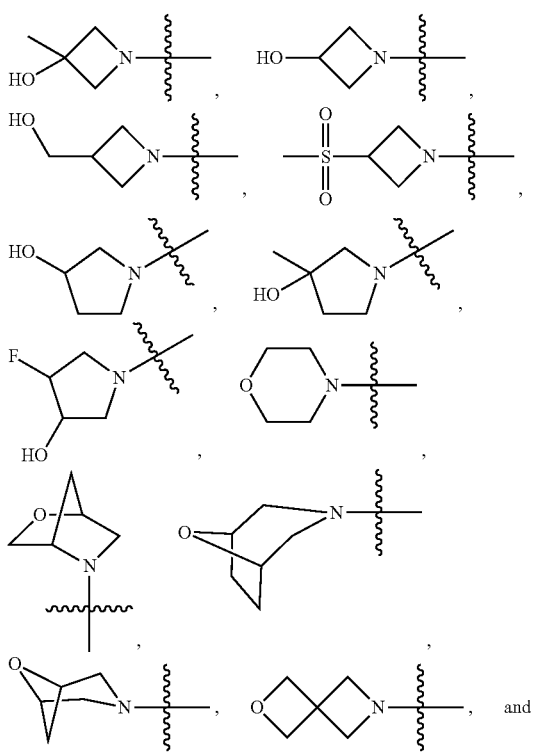

and

18

-continued

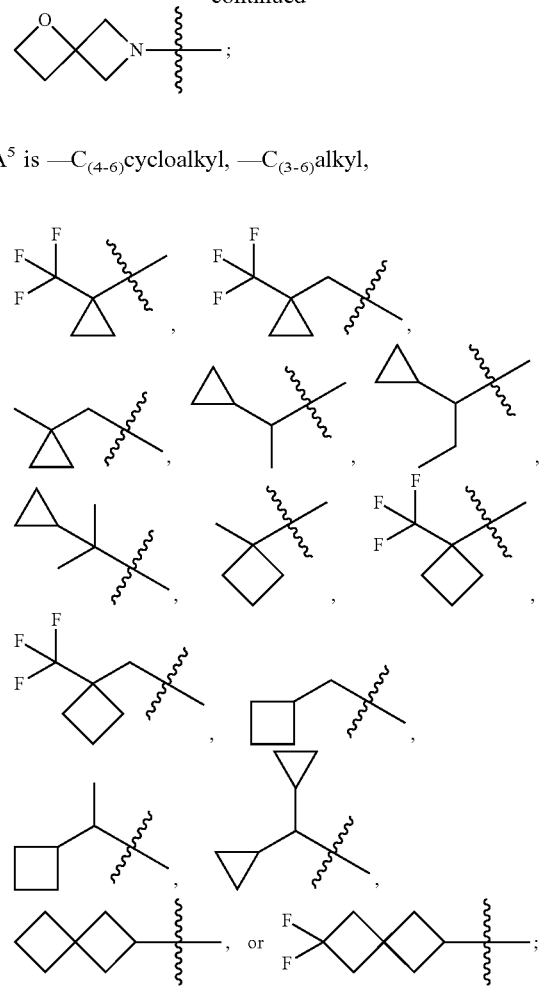

A$^5$ is —C$_{(4-6)}$cycloalkyl, —C$_{(3-6)}$alkyl, wherein said —C$_{(3-6)}$alkyl and —C$_{(4-6)}$cycloalkyl are optionally substituted with up to three fluorine atoms;

and pharmaceutically acceptable salts thereof.

In another embodiment of the invention:

R$^1$ is H, —CHF$_2$, —CF$_3$, —CN, —OCH$_3$, —OCH$_2$CH$_3$, or cyclopropyl;

R$^2$ is H, F, —CHF$_2$, —CF$_3$, —CN, —OCH$_3$, or —OCHF$_2$; provided that R$^2$ may not be H if R$^1$ is H;

A$^1$ and A$^2$ are taken together with their attached nitrogen to form a ring selected from the group consisting of

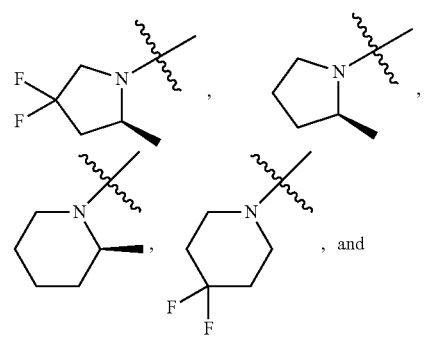

, and

-continued

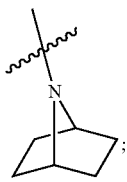

A³ is H, —C₍₁₋₆₎alkyl,

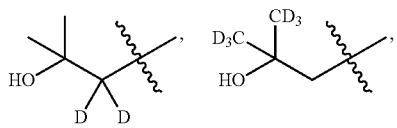

—SO₂CH(CH₃)₂, —SO₂CH₃,

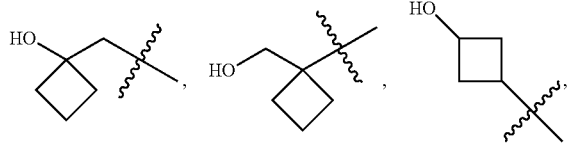

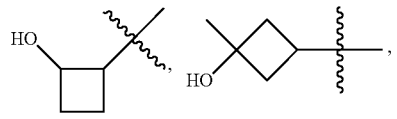

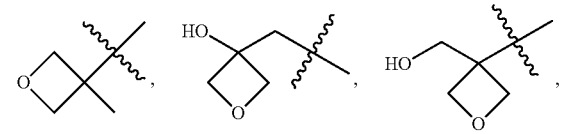

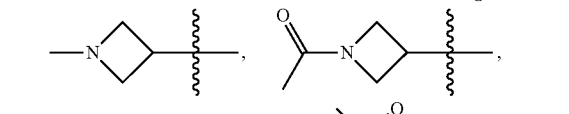

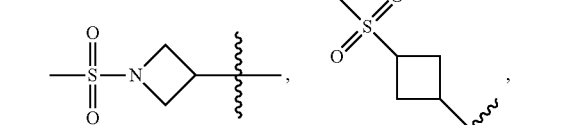

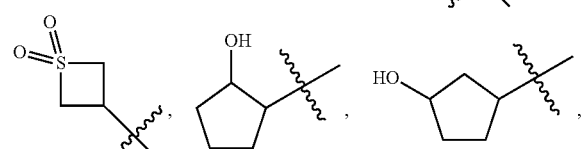

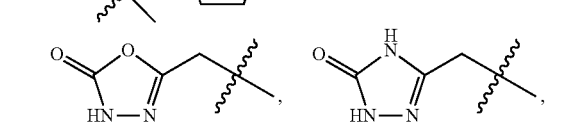

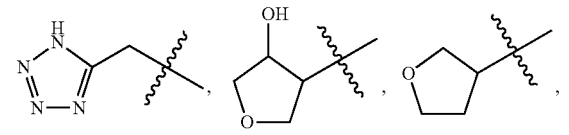

-continued

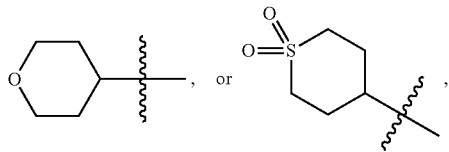, or wherein said —C₍₁₋₆₎alkyl is optionally substituted with one —NH₂ group, one or two —OH groups, and may be additionally substituted with up to six fluorine atoms;

A⁴ is H, or —CH₃;

or A³ and A⁴ may be taken together with their attached nitrogen to form a ring selected from the group consisting of

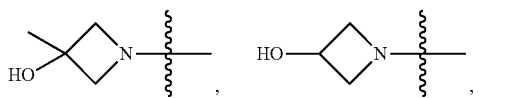

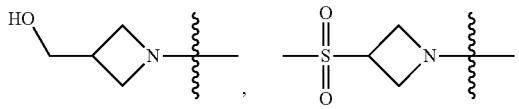

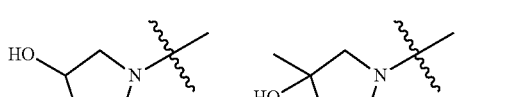

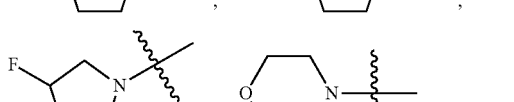

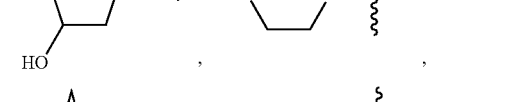

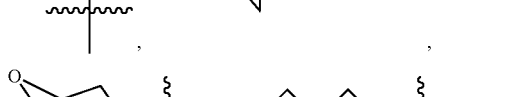

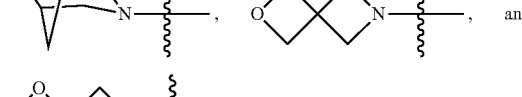, and

;

A⁵ is —C₍₁₋₆₎cycloalkyl, —C₍₃₋₆₎alkyl,

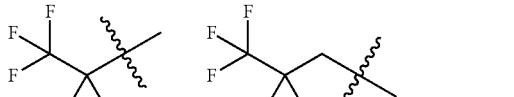

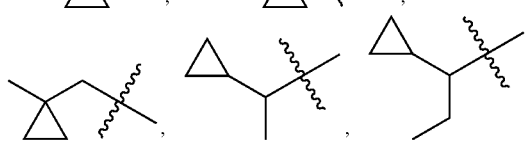

-continued

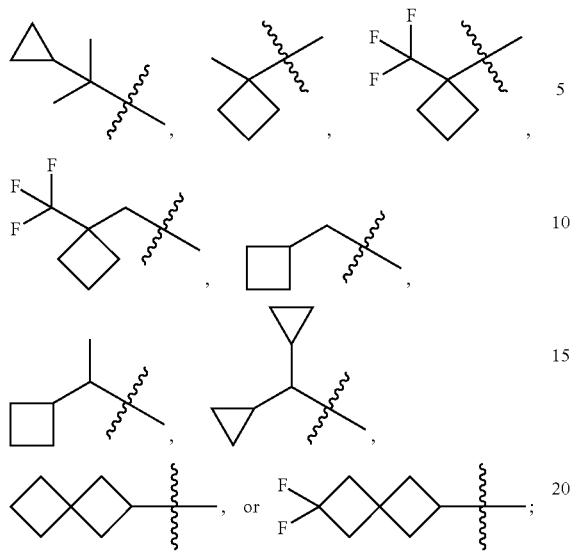

wherein said —C$_{(3-6)}$alkyl and —C$_{(1-6)}$cycloalkyl are optionally substituted with up to three fluorine atoms;

and pharmaceutically acceptable salts thereof.

In another embodiment of the invention:

R$^1$ is H, —CHF$_2$, —CF$_3$, —CN, —OCH$_3$, —OCH$_2$CH$_3$, cyclopropyl, OCF$_3$, or OCHF$_2$;

R$^2$ is H, F, —CHF$_2$, —CF$_3$, —CN, —OCH$_3$, —OCHF$_2$, or OCF$_3$; provided that R$^2$ may not be H if R$^1$ is H;

A$^1$ and A$^2$ are taken together with their attached nitrogen to form a ring selected from the group consisting of

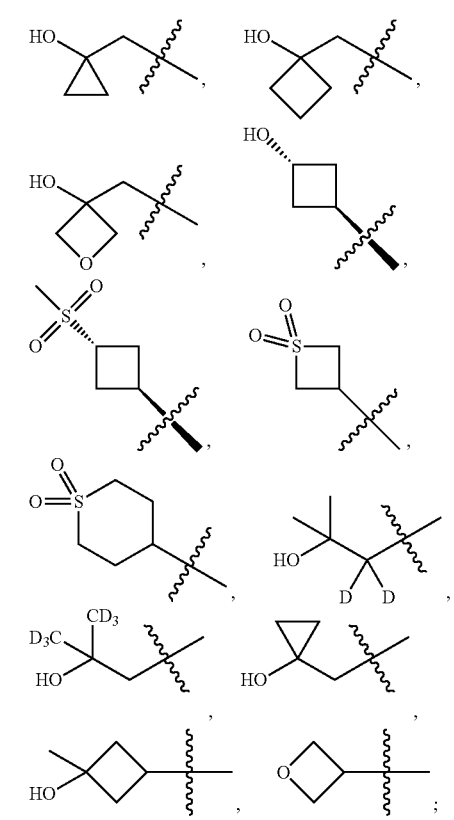

A$^3$ is C$_{(4-6)}$alkyl,

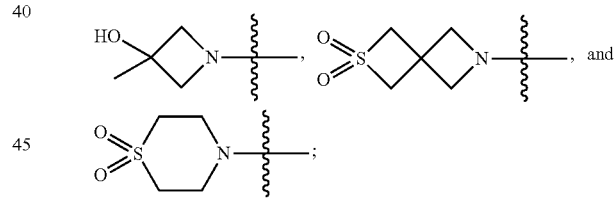

wherein said C$_{(4-6)}$alkyl is optionally substituted with one —OH group;

A$^4$ is —H, or —CH$_3$;

or A$^3$ and A$^4$ may be taken together with their attached nitrogen to form a ring selected from the group consisting of

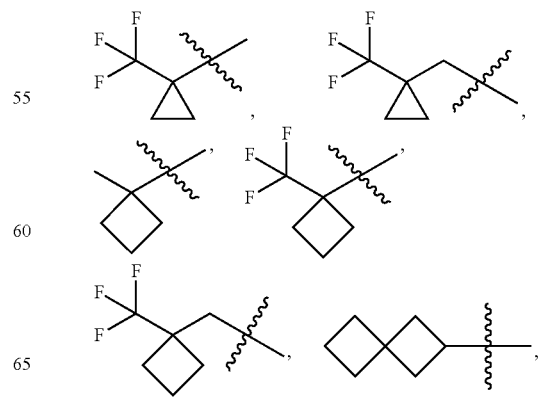

A$^5$ is —C$_{(4-6)}$cycloalkyl, —C$_{(2-5)}$alkyl,

-continued

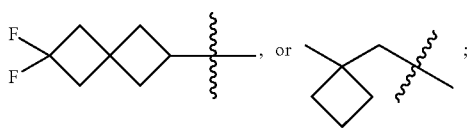

wherein said —C$_{(2-5)}$alkyl and —C$_{(4-6)}$cycloalkyl are optionally substituted with up to three fluorine atoms; and said —C$_{(2-5)}$alkyl is independently optionally substituted with up to two cyclopropyl groups;

and pharmaceutically acceptable salts thereof.

In another embodiment of the invention:

R$^1$ is H, —C$_{(1-3)}$alkyl, —CHF$_2$, —CF$_3$, —CN, —OCH$_3$, —OCH$_2$CH$_3$, cyclopropyl, OCF$_3$, or OCHF$_2$;

R$^2$ is H, F, —CHF$_2$, —CF$_3$, —CN, —OCH$_3$, —OCHF$_2$, or OCF$_3$; provided that R$^2$ may not be H if R$^1$ is H;

A$^1$ and A$^2$ are taken together with their attached nitrogen to form a ring selected from the group consisting of

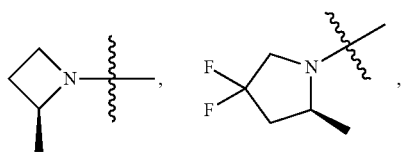
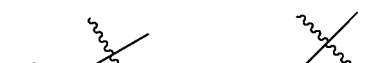
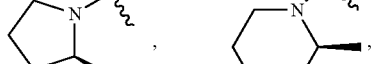

A$^3$ is C$_{(4-5)}$alkyl,

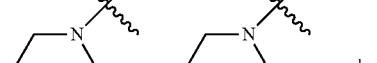
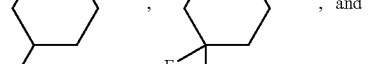
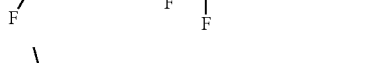

-continued

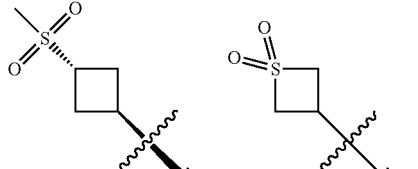
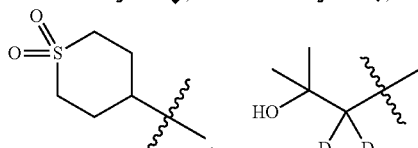
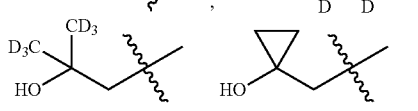
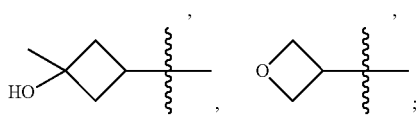

wherein said C$_{(4-5)}$alkyl is optionally substituted with one —OH group;

A$^4$ is —H, or —CH$_3$;

or A$^3$ and A$^4$ may be taken together with their attached nitrogen to form a ring selected from the group consisting of

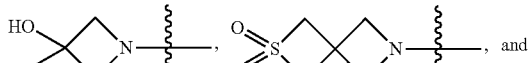
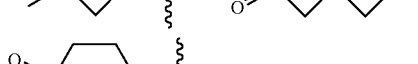
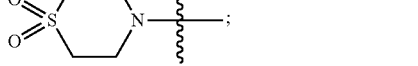

A$^5$ is —C$_{(4-6)}$cycloalkyl, —C$_{(3-5)}$alkyl,

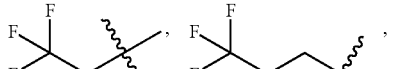
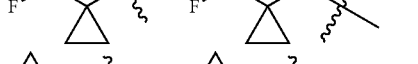
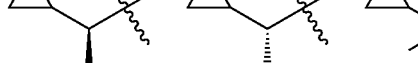
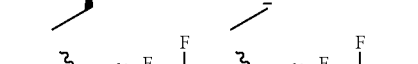
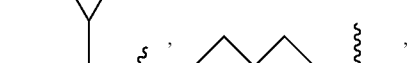

-continued

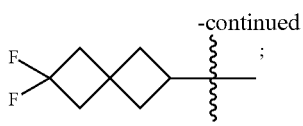

wherein said —C$_{(3-5)}$alkyl and —C$_{(4-6)}$cycloalkyl are optionally substituted with up to three fluorine atoms;

and pharmaceutically acceptable salts thereof.

In another embodiment of the invention:

R$^1$ is H, —C$_{(1-3)}$alkyl, —CHF$_2$, —CF$_3$, —CN, —OCH$_3$, —OCH$_2$CH$_3$, cyclopropyl, OCF$_3$, or OCHF$_2$;

R$^2$ is H, F, —CHF$_2$, —CF$_3$, —CN, —OCH$_3$, —OCHF$_2$, or OCF$_3$; provided that R$^2$ may not be H if R$^1$ is H;

A$^1$ and A$^2$ are taken together with their attached nitrogen to form a ring selected from the group consisting of

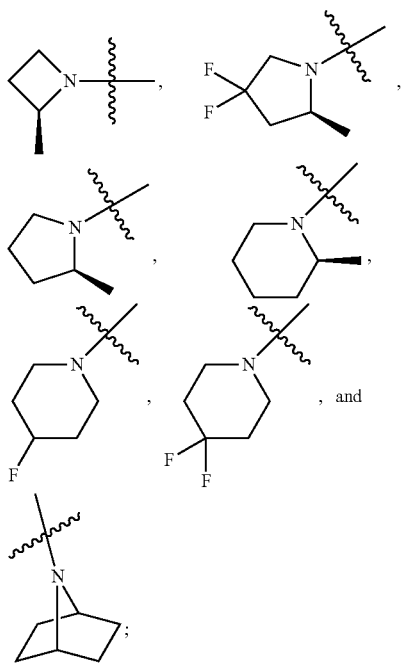

A$^3$ is —CH$_2$C(CH$_3$)$_2$OH, —CH$_2$CH$_2$C(CH$_3$)$_2$OH,

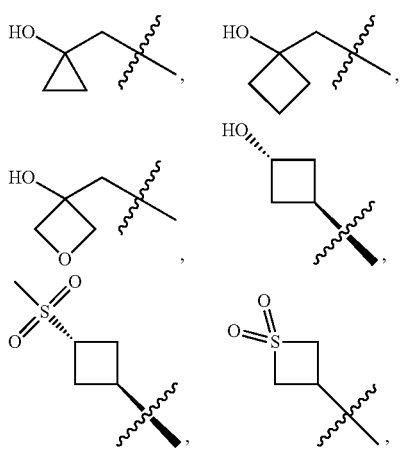

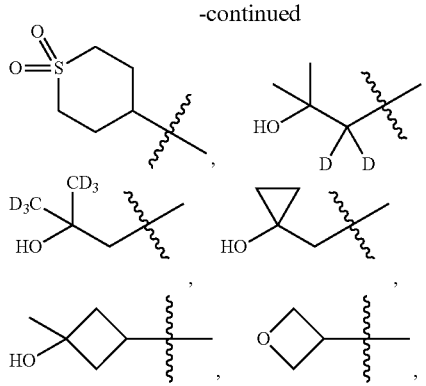

—CH(CH$_3$)C(CH$_3$)$_2$OH, or —C(CH$_3$)$_2$CH$_2$OH;

A$^4$ is —H, or —CH$_3$;

or A$^3$ and A$^4$ may be taken together with their attached nitrogen to form a ring selected from the group consisting of

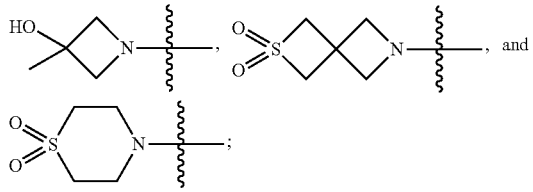

A$^5$ is —C$_{(4-6)}$cycloalkyl, —C$_{(3-5)}$alkyl,

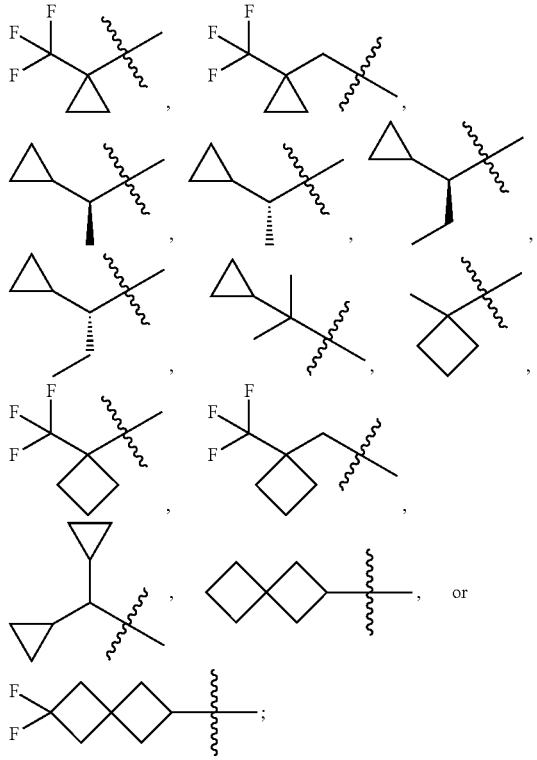

wherein said —C$_{(3-5)}$alkyl and —C$_{(4-6)}$cycloalkyl are optionally substituted with up to three fluorine atoms;

and pharmaceutically acceptable salts thereof.

In another embodiment of the invention:

R[1] is H, —CHF$_2$, —CF$_3$, —CN, —OCH$_3$, —OCH$_2$CH$_3$, or cyclopropyl;

R[2] is H, F, —CHF$_2$, —CF$_3$, —CN, —OCH$_3$, or —OCHF$_2$; provided that R[2] may not be H if R[1] is H;

A[1] and A[2] are taken together with their attached nitrogen to form a ring selected from the group consisting of

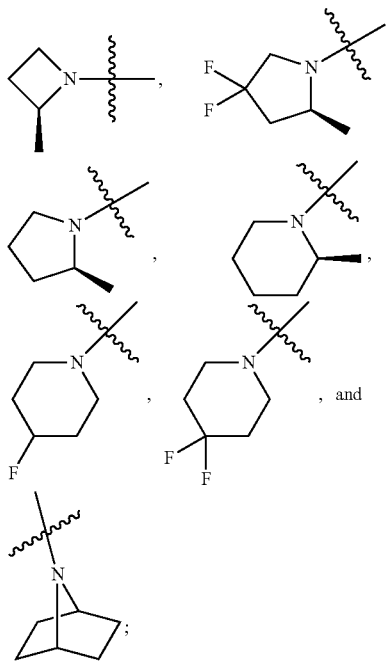

A[3] is —CH$_2$C(CH$_3$)$_2$OH, —CH$_2$CH$_2$C(CH$_3$)$_2$OH,

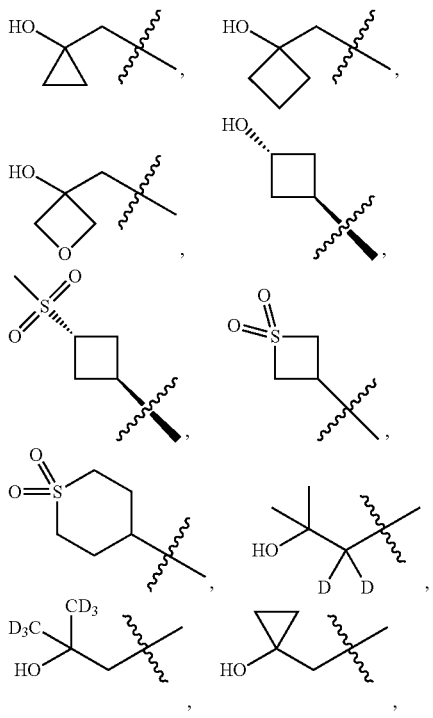

-continued

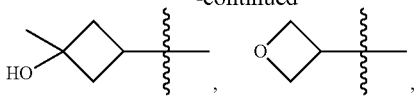

—CH(CH$_3$)C(CH$_3$)$_2$OH, or —C(CH$_3$)$_2$CH$_2$OH;

A[4] is —H, or —CH$_3$;

or A[3] and A[4] may be taken together with their attached nitrogen to form a ring selected from the group consisting of

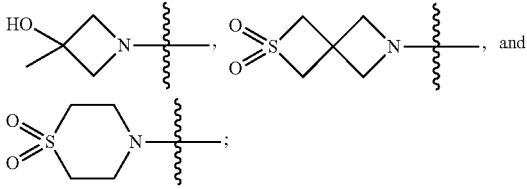

A[5] is —C$_{(4-6)}$cycloalkyl, —C$_{(3-5)}$alkyl,

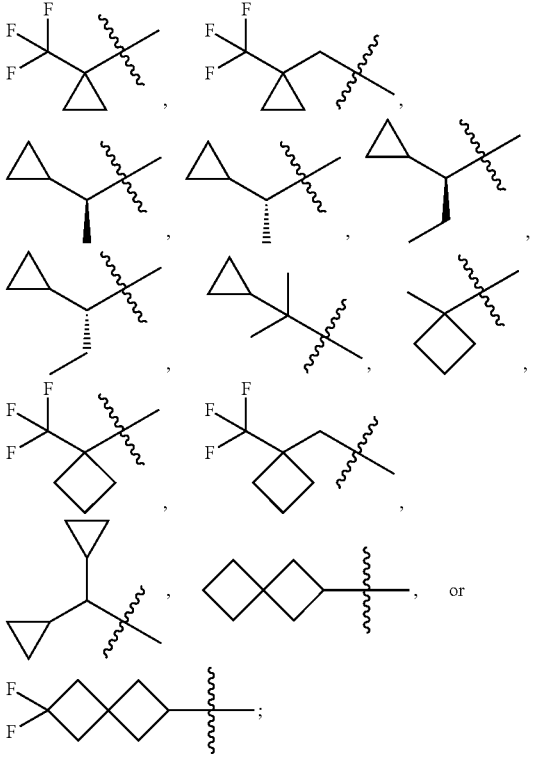

wherein said —C$_{(3-5)}$alkyl and —C$_{(4-6)}$cycloalkyl are optionally substituted with up to three fluorine atoms;

and pharmaceutically acceptable salts thereof.

In another embodiment of the invention:

R[1] is H, —CHF$_2$, —CF$_3$, —CN, —OCH$_3$, —OCH$_2$CH$_3$, or cyclopropyl;

R[2] is H, F, —CHF$_2$, —CF$_3$, —CN, —OCH$_3$, or —OCHF$_2$; provided that R[2] may not be H if R[1] is H;

A[1] and A[2] are taken together with their attached nitrogen to form a ring selected from the group consisting of

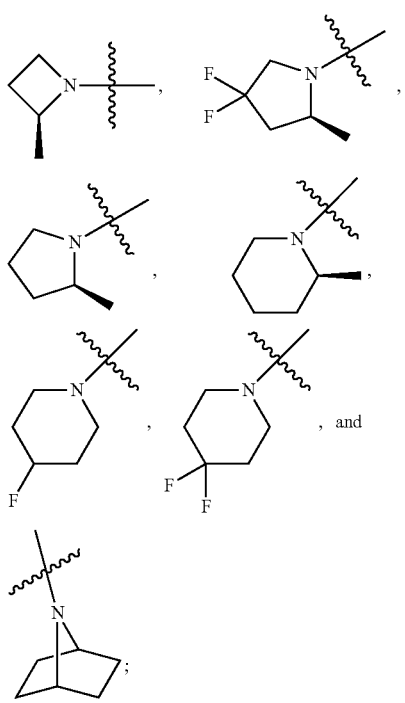

A³ is —CH₂C(CH₃)₂OH, —CH₂CH₂C(CH₃)₂)H,

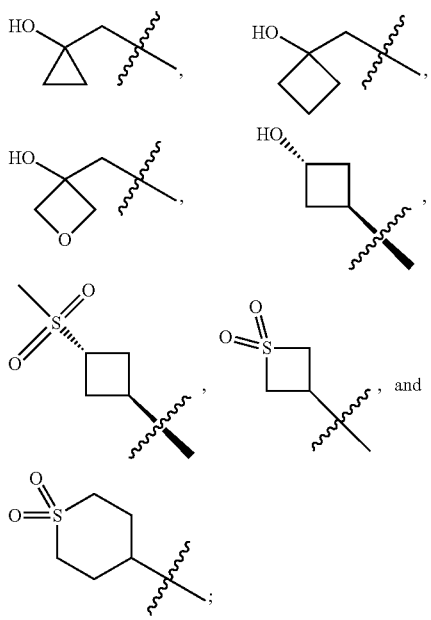

A⁴ is H;
A⁵ is —C₍₄₋₆₎cycloalkyl, —C₍₃₋₅₎alkyl,

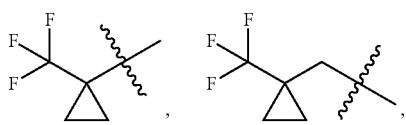

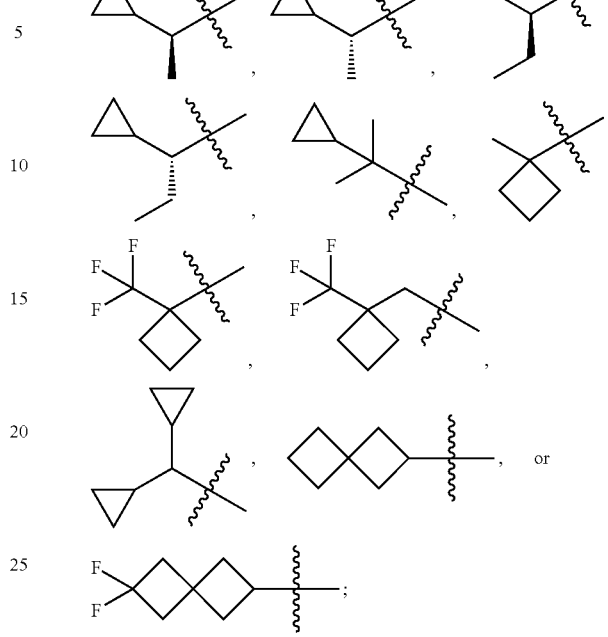

wherein said —C₍₃₋₅₎alkyl and —C₍₄₋₆₎cycloalkyl are optionally substituted with up to three fluorine atoms;

and pharmaceutically acceptable salts thereof.

In another embodiment of the invention:

R¹ is H, —CHF₂, —CF₃, —CN, —OCH₃, —OCH₂CH₃, or cyclopropyl;

R² is H, F, —CHF₂, —CF₃, —CN, —OCH₃, or —OCHF₂; provided that R² may not be H if R¹ is H;

A¹ and A² are taken together with their attached nitrogen to form a ring selected from the group consisting of

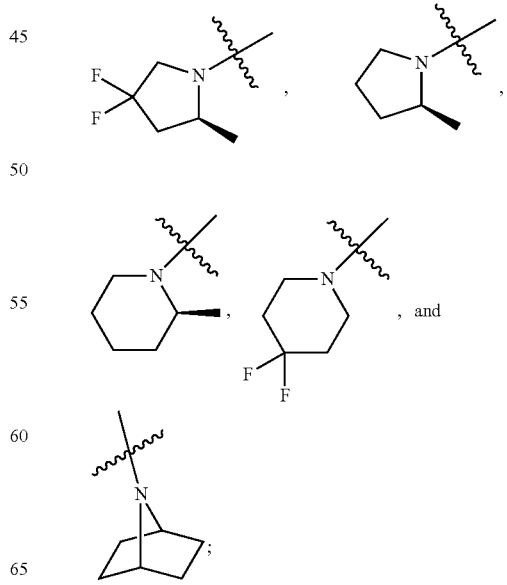

$A^3$ is —CH$_2$C(CH$_3$)$_2$OH, —CH$_2$CH$_2$C(CH$_3$)$_2$OH,

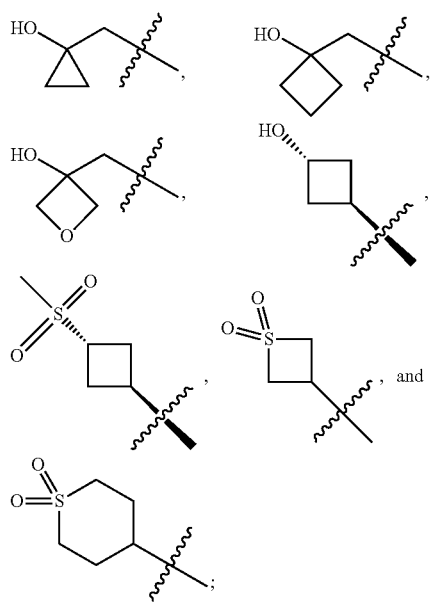

$A^4$ is H;
$A^5$ is —C$_{(4-6)}$cycloalkyl, —C$_{(3-5)}$alkyl,

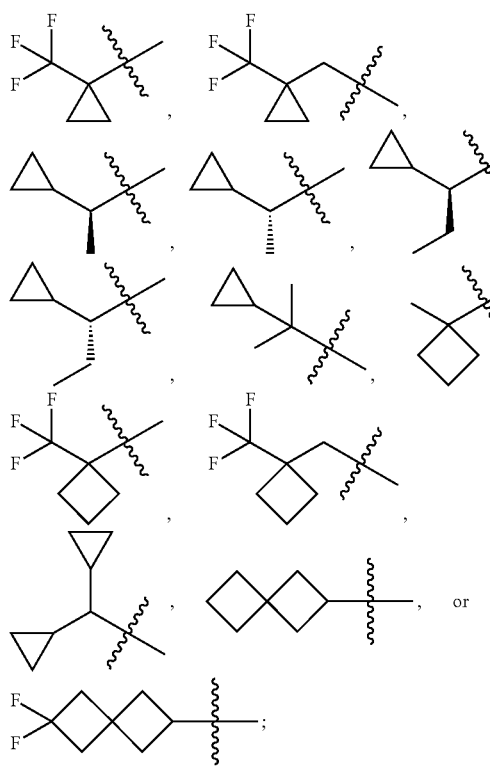

wherein said —C$_{(3-5)}$alkyl and —C$_{(4-6)}$cycloalkyl are optionally substituted with up to three fluorine atoms; and pharmaceutically acceptable salts thereof.

In another embodiment of the invention:
$R^1$ is H, —CHF$_2$, —CF$_3$, —CN, —OCH$_3$, —OCH$_2$CH$_3$, or cyclopropyl;
$R^2$ is H, F, —CHF$_2$, —CF$_3$, —CN, —OCH$_3$, or —OCHF$_2$; provided that $R^2$ may not be H if $R^1$ is H;

$A^1$ and $A^2$ are taken together with their attached nitrogen to form a ring which is

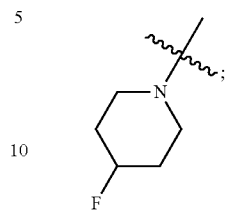

$A^3$ is —CH$_2$C(CH$_3$)$_2$OH, —CH$_2$CH$_2$C(CH$_3$)$_2$OH,

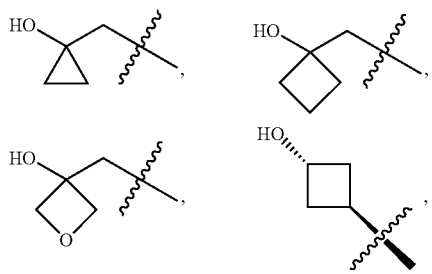

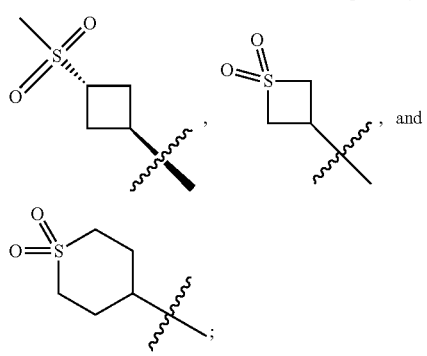

$A^4$ is H;
$A^5$ is —C$_{(4-6)}$cycloalkyl, —C$_{(3-5)}$alkyl,

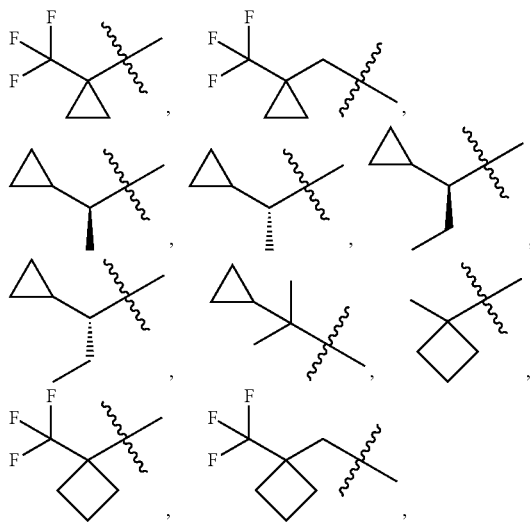

-continued
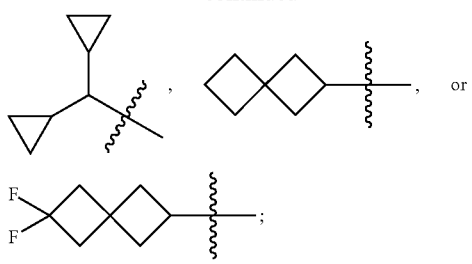
wherein said —C$_{(3-5)}$alkyl and —C$_{(4-6)}$cycloalkyl are optionally substituted with up to three fluorine atoms;
and pharmaceutically acceptable salts thereof.
Another embodiment of the invention is a compound selected from the group consisting of:
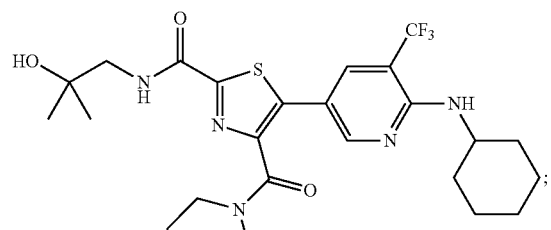
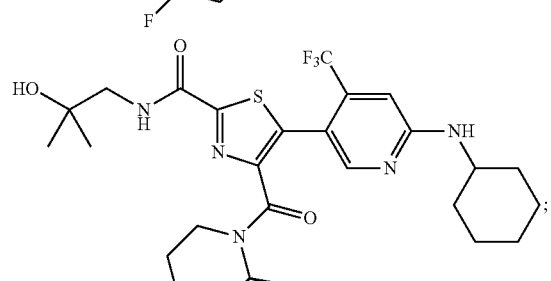
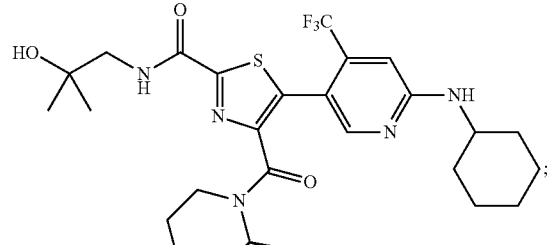
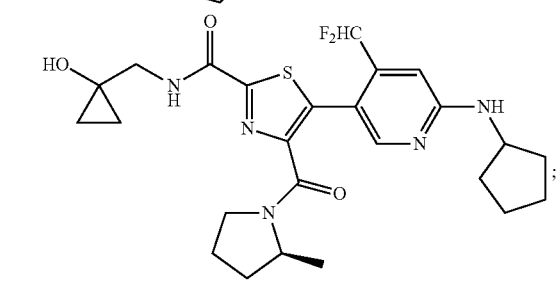
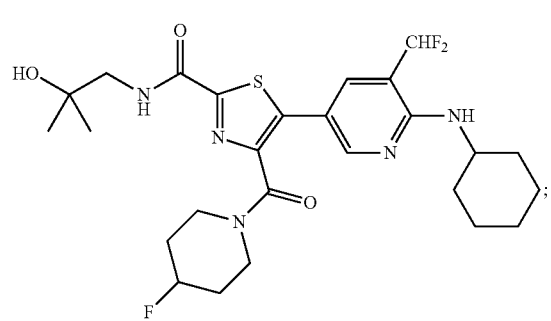
-continued
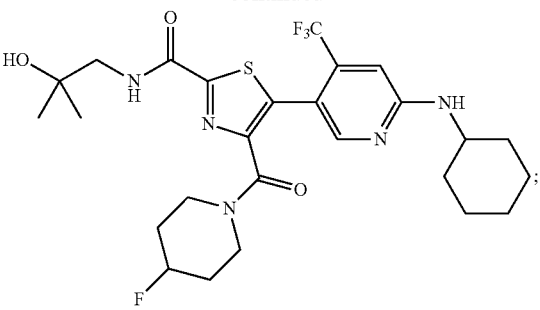
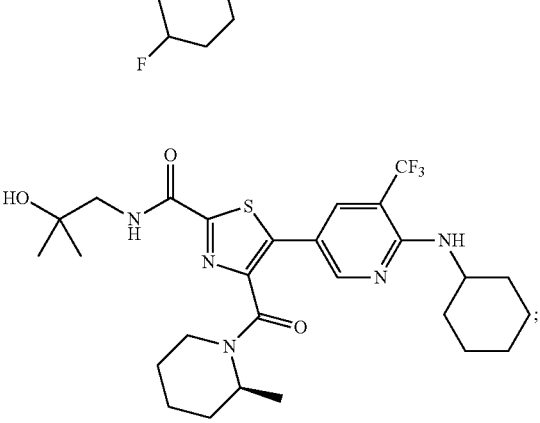
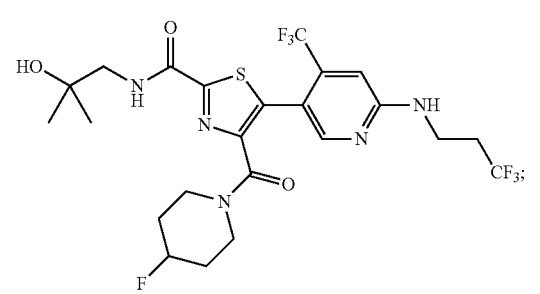
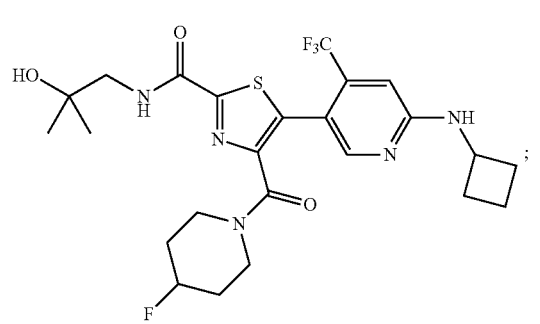

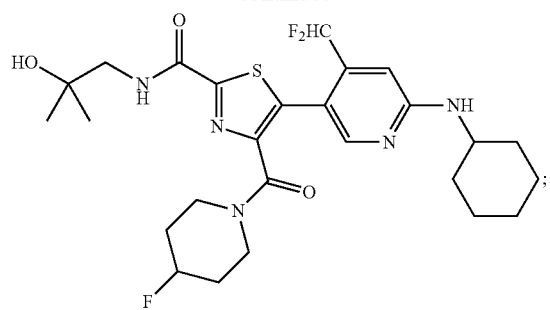
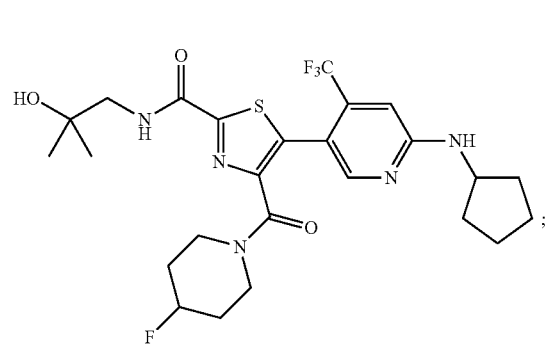
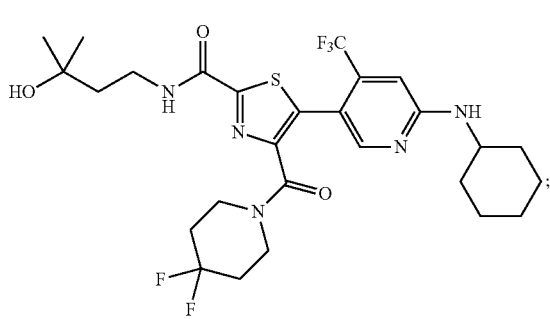
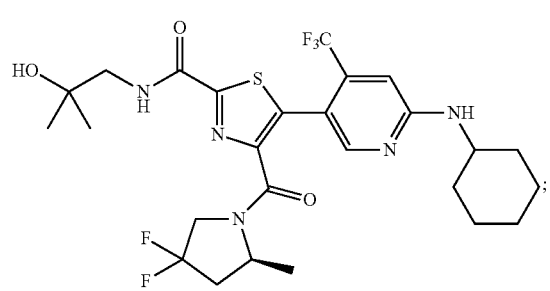
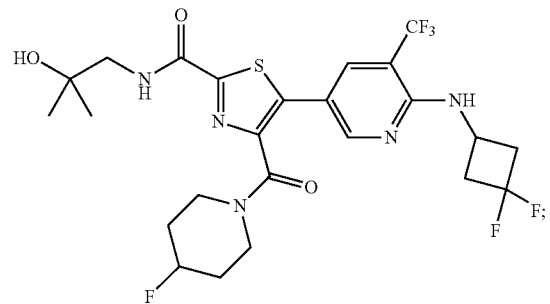
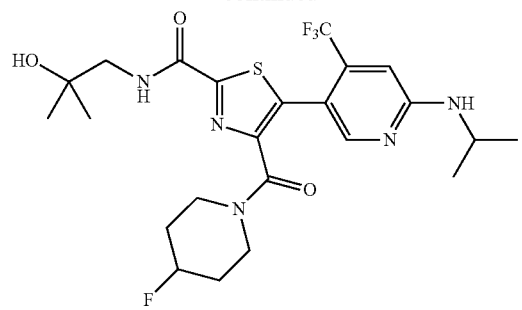
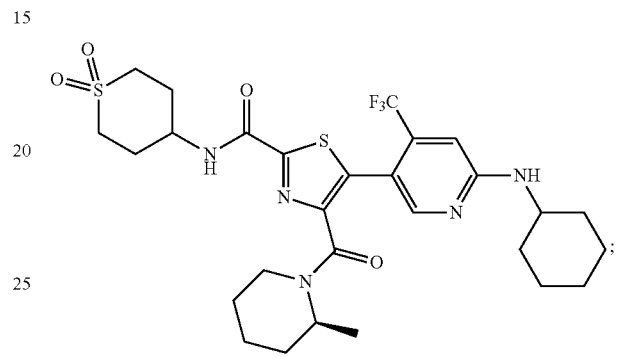
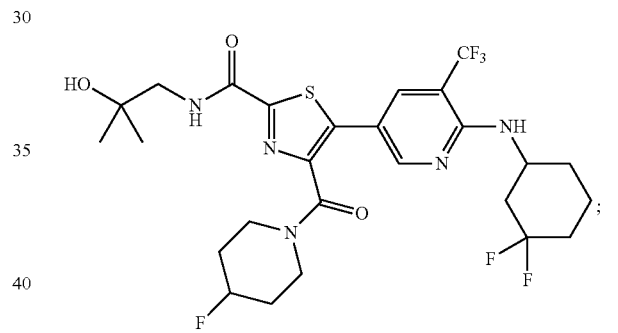
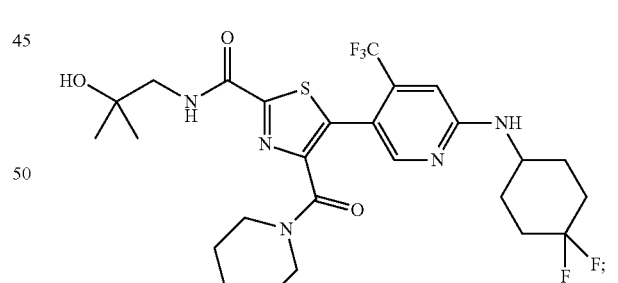
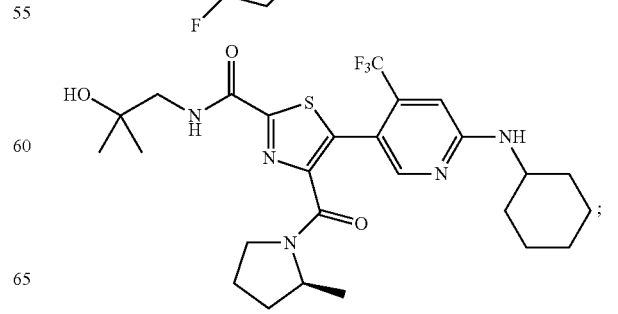

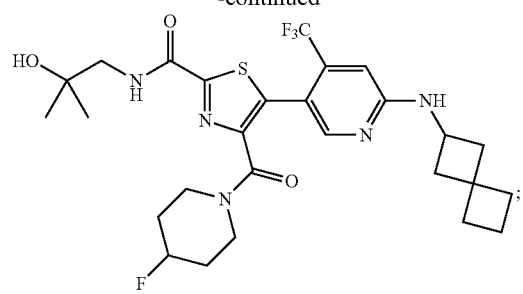
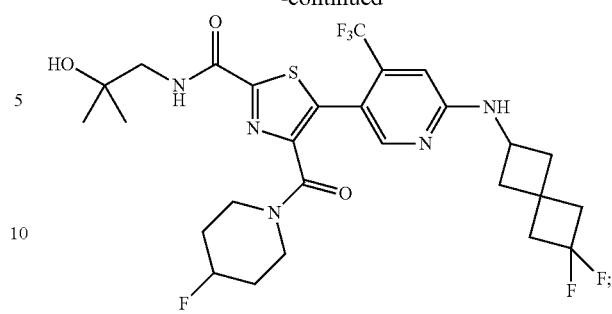
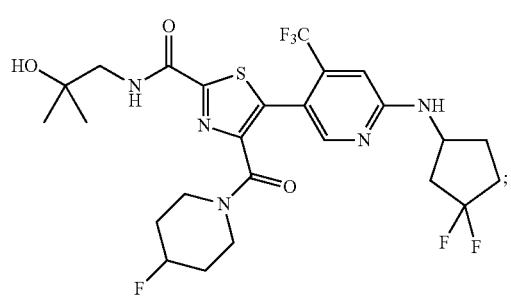
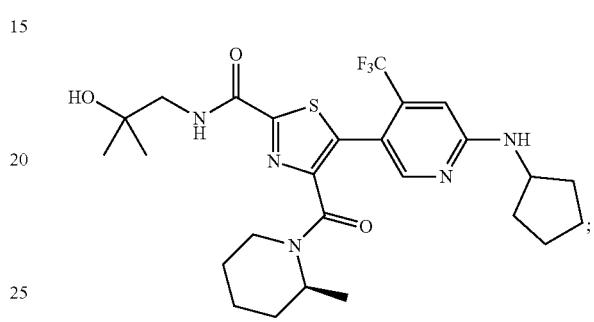
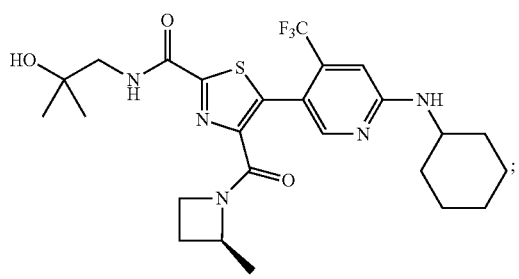
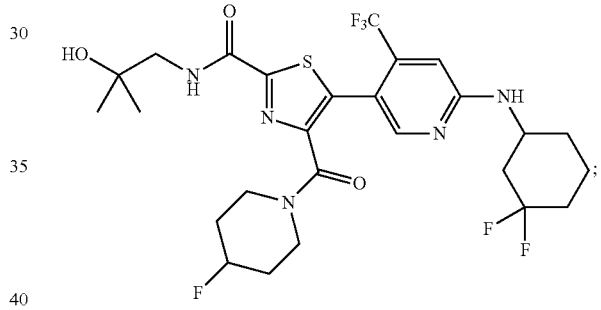
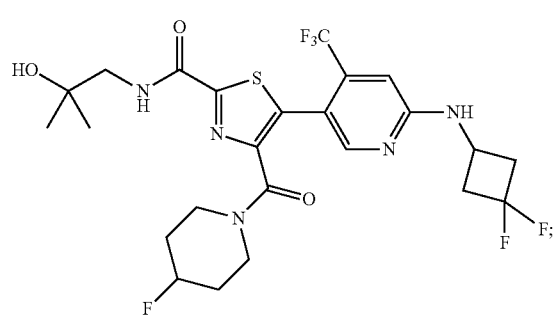
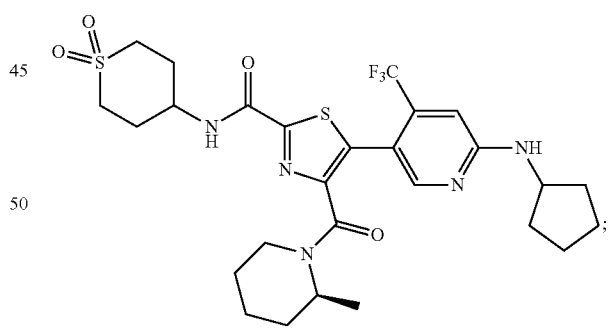
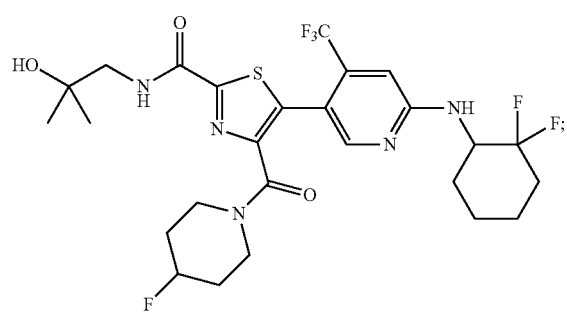
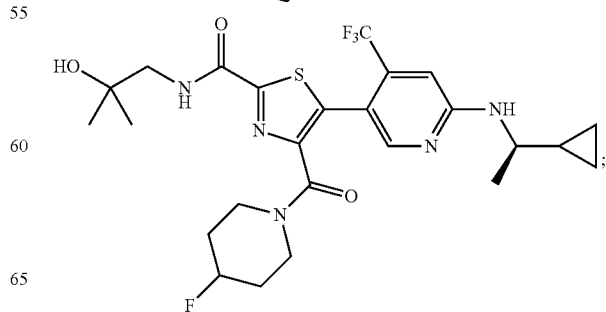

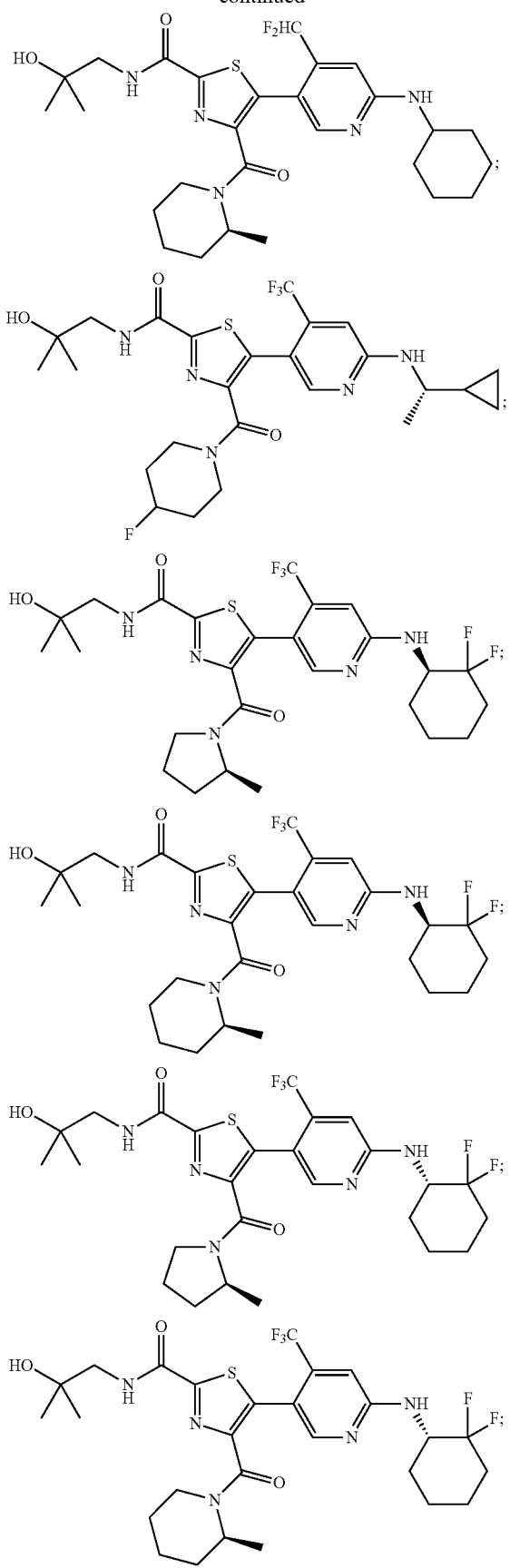
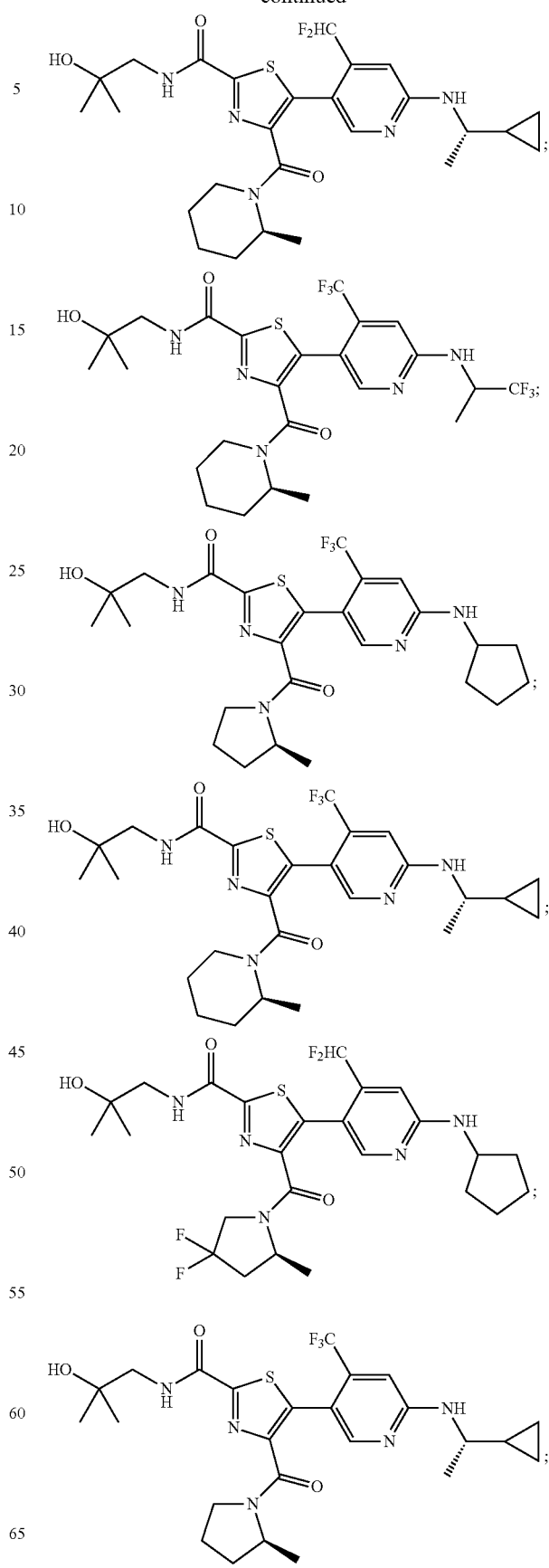

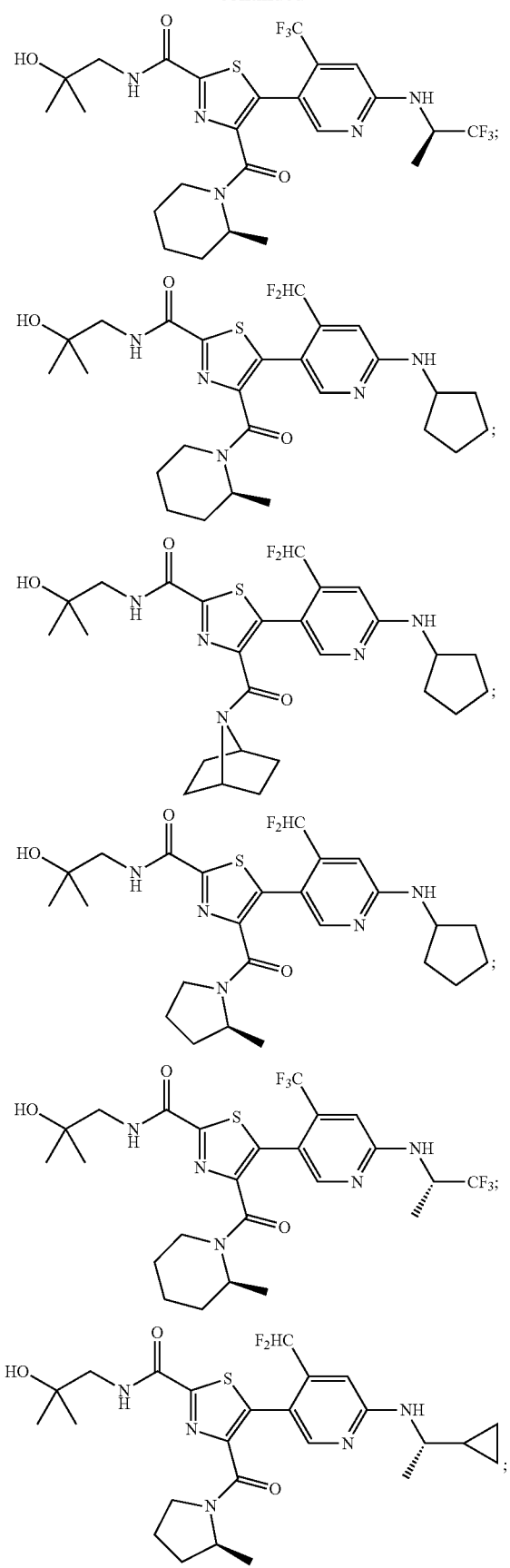
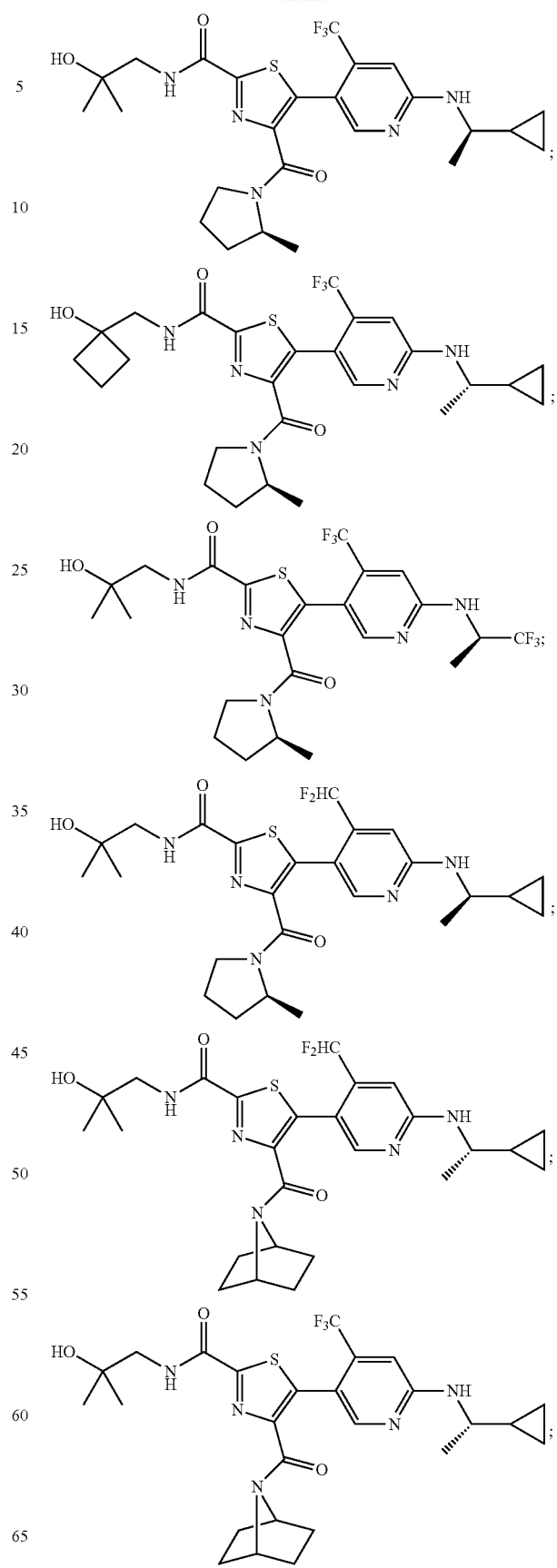

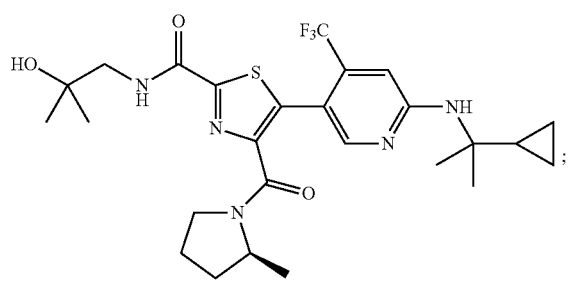
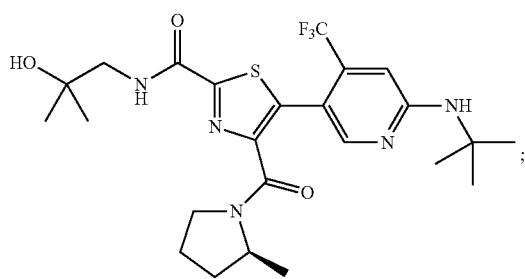
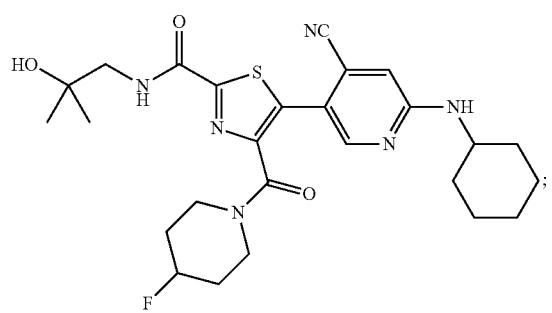
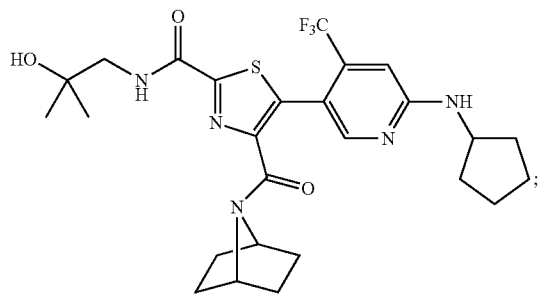
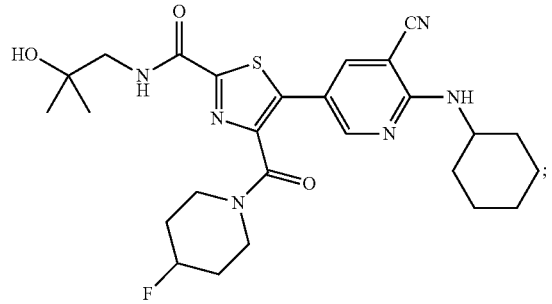 [SMILES: Cc1c(-c2sc(C(=O)NCC(C)(C)O)nc2C(=O)N2CCC(F)CC2)cnc(NC2CCCCC2)c1C#N]
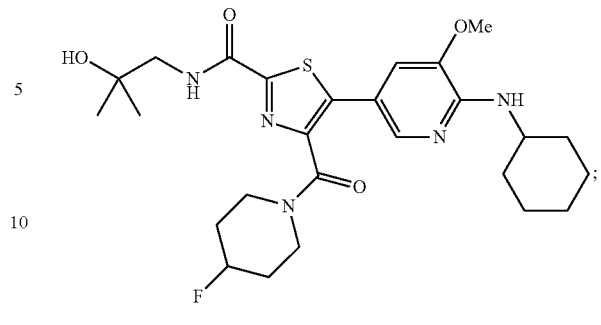
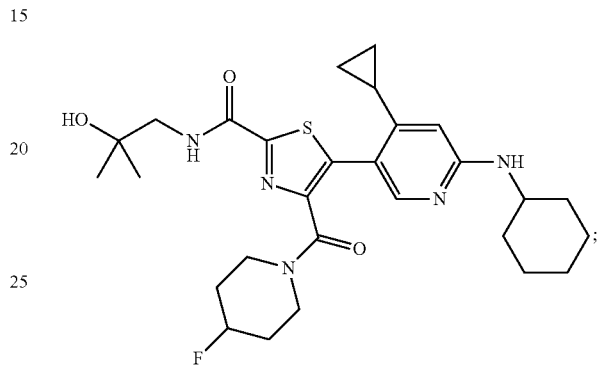
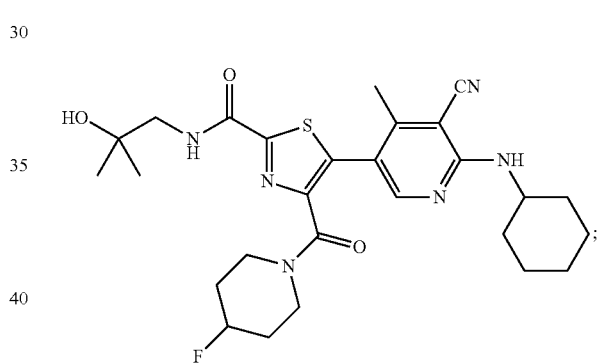
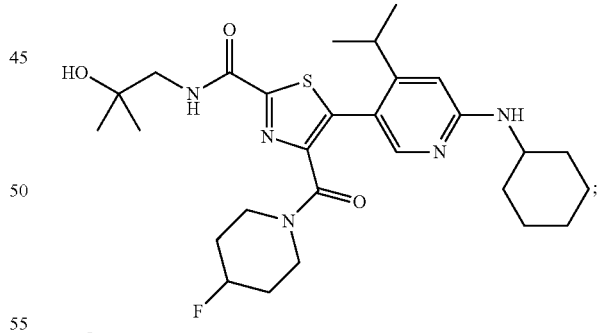
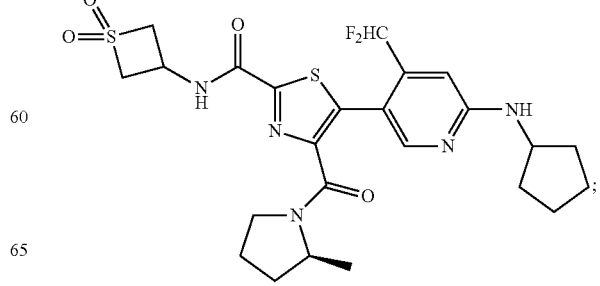

-continued

47
-continued
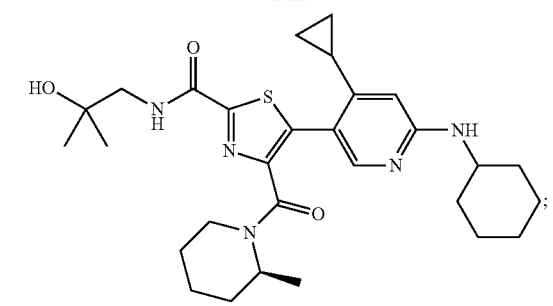
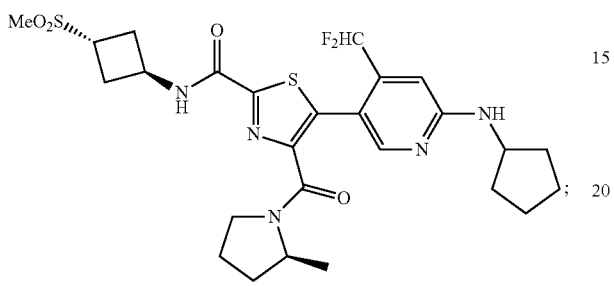
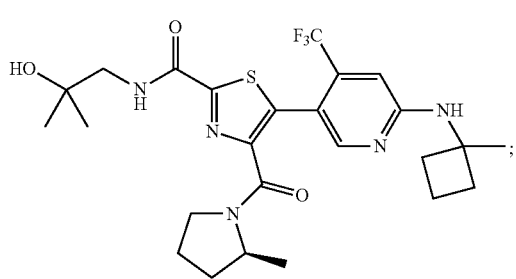
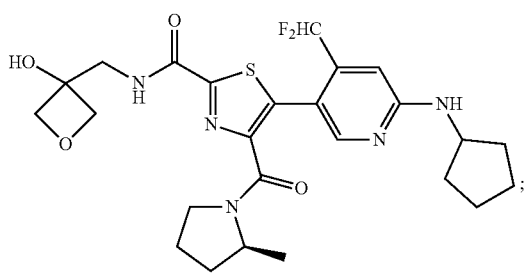
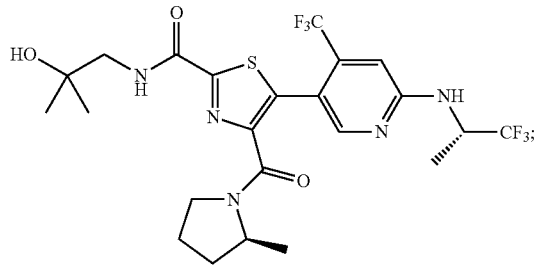
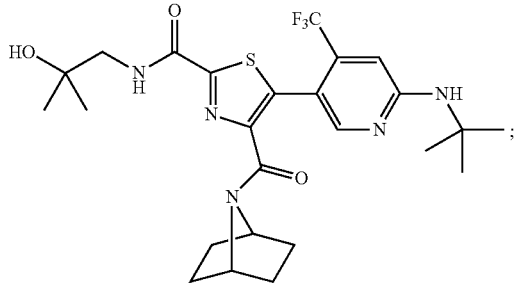
48
-continued
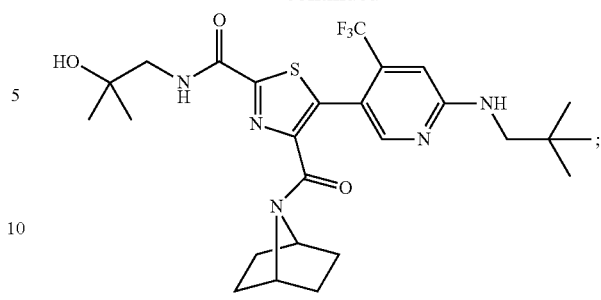
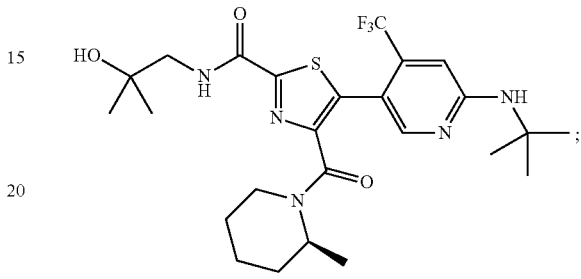
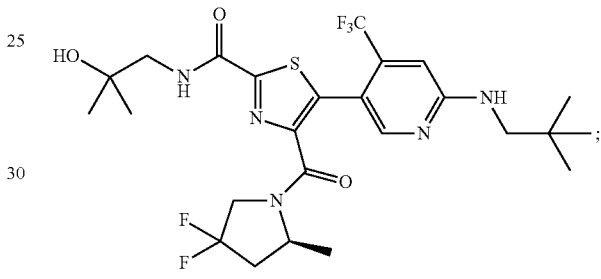
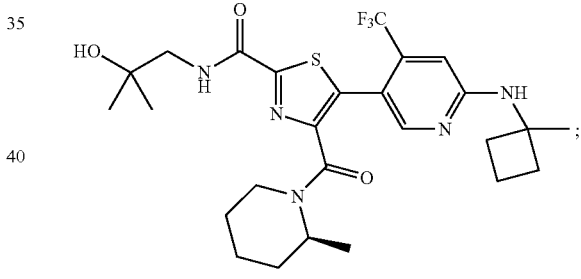

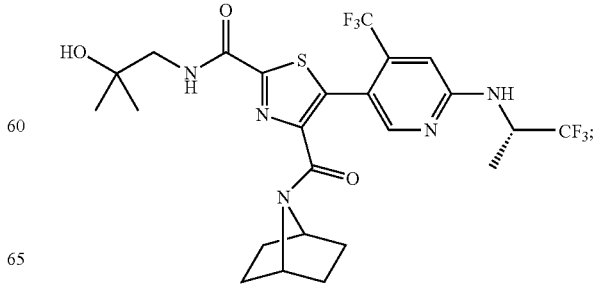

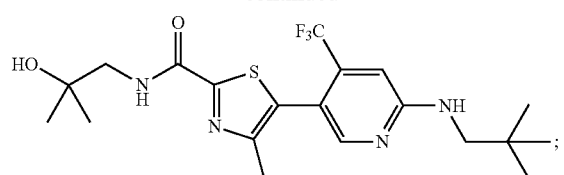
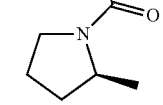
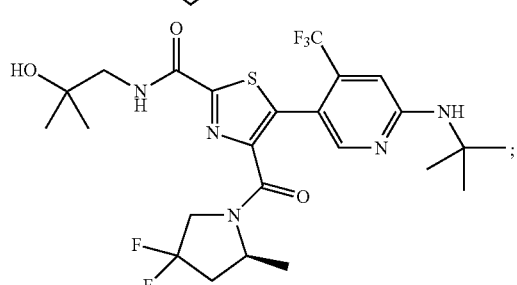
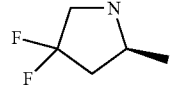
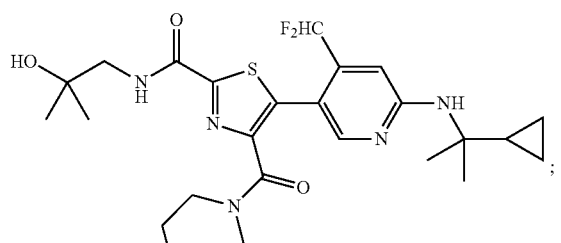
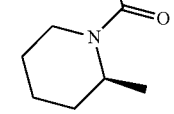
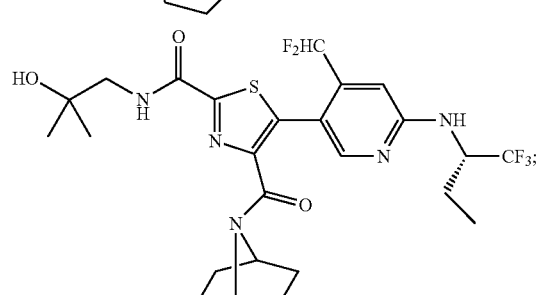
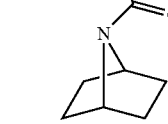
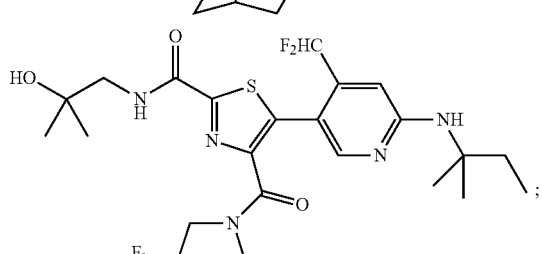
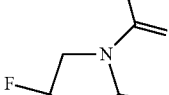
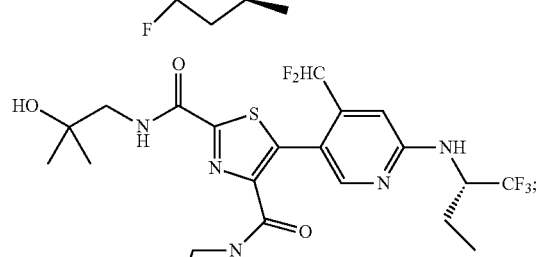
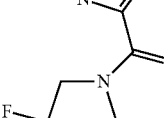
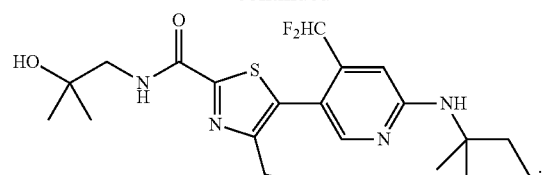
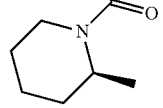
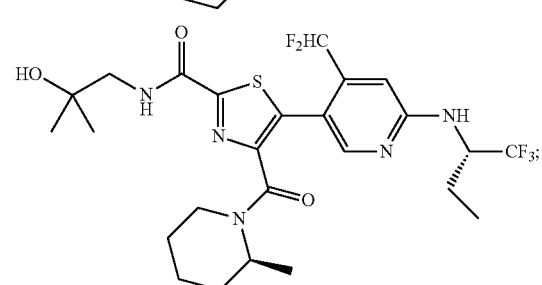
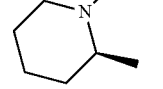
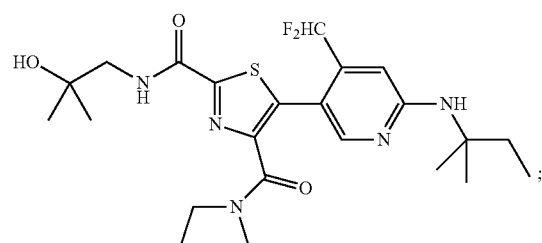
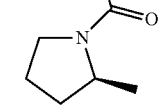
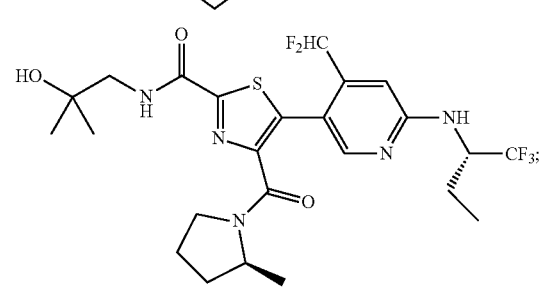
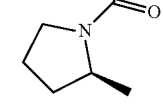
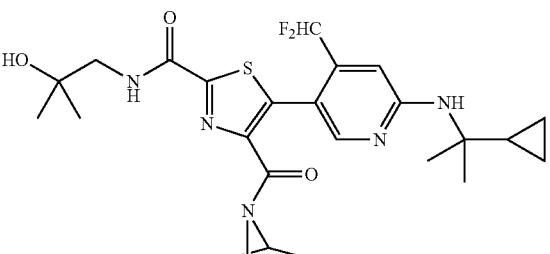
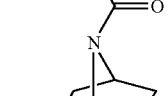
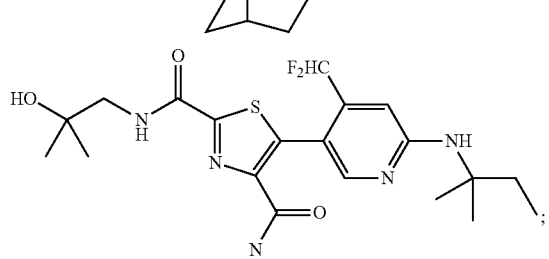
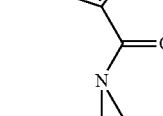

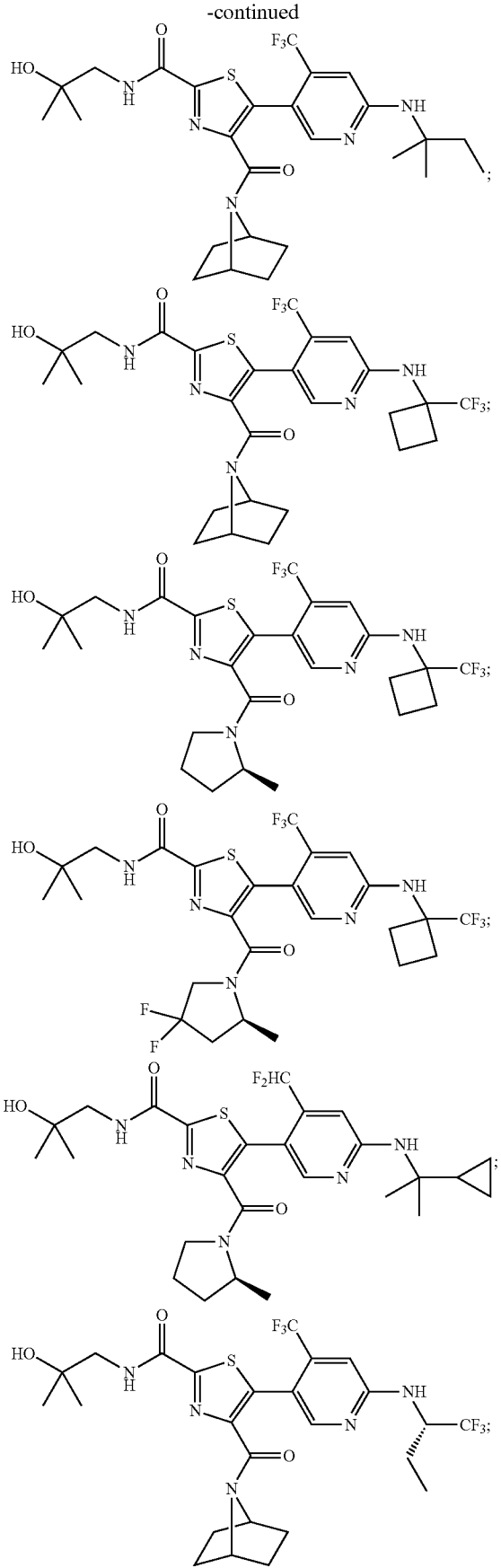
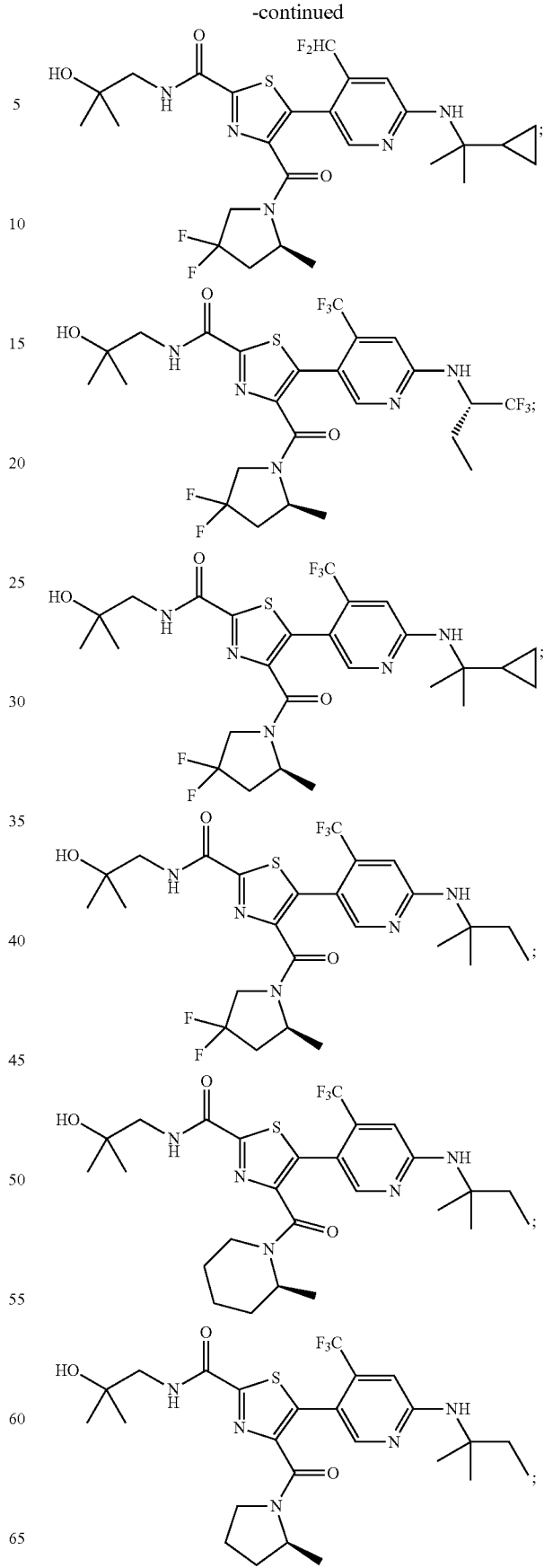

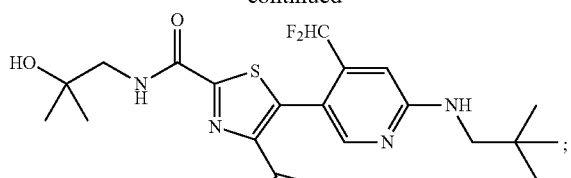

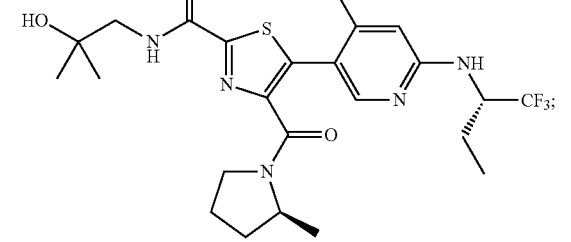
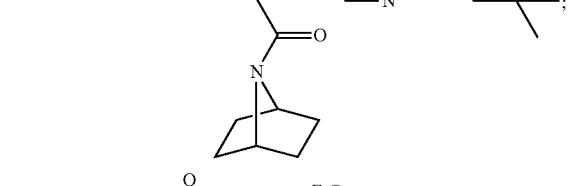
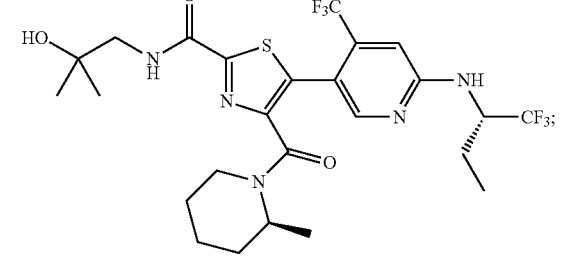
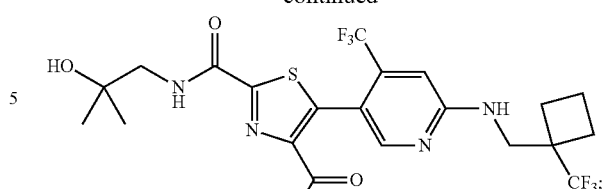

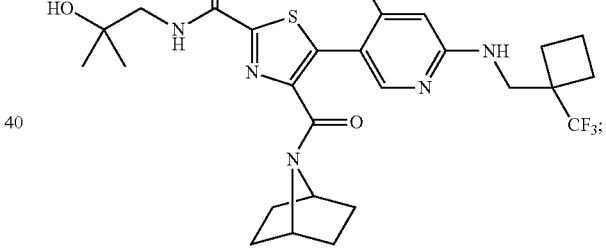
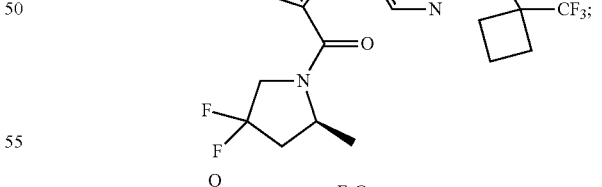
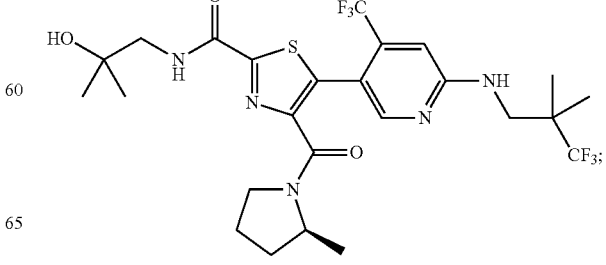

55
-continued
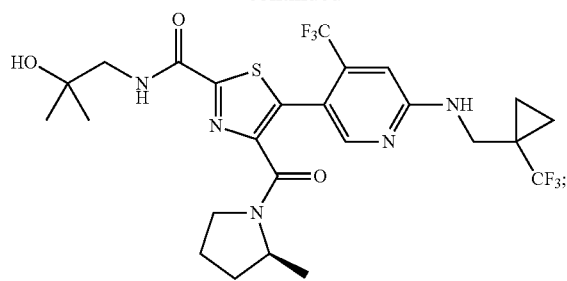
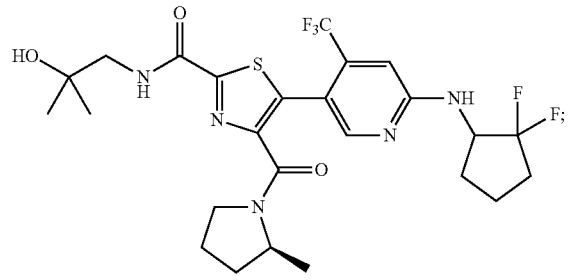
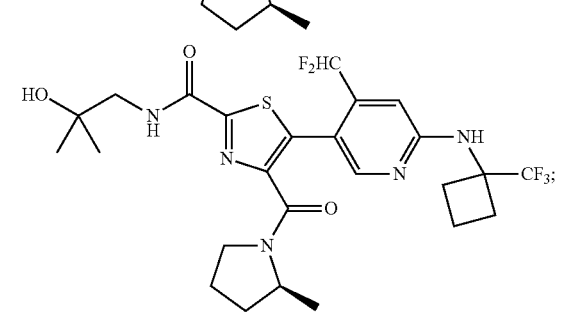
56
-continued
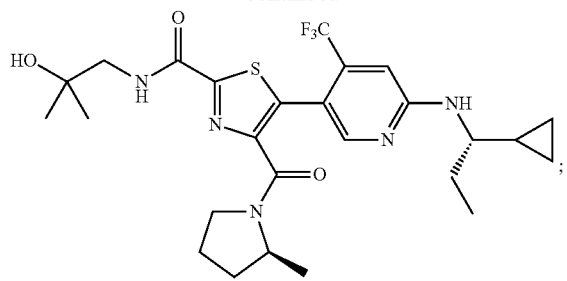
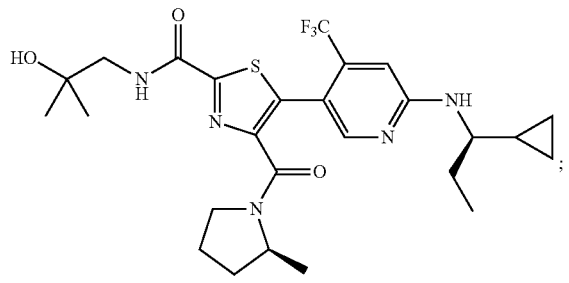
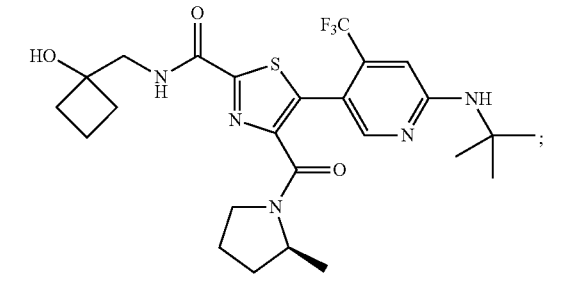
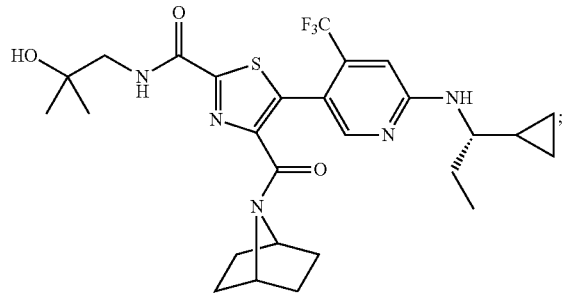
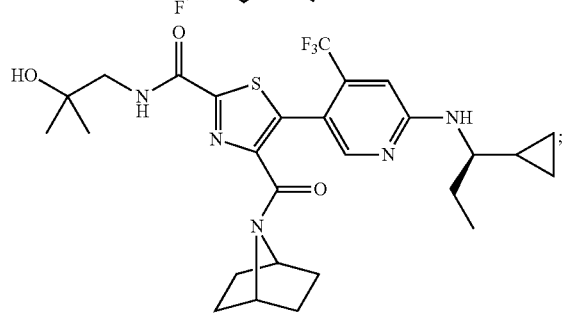

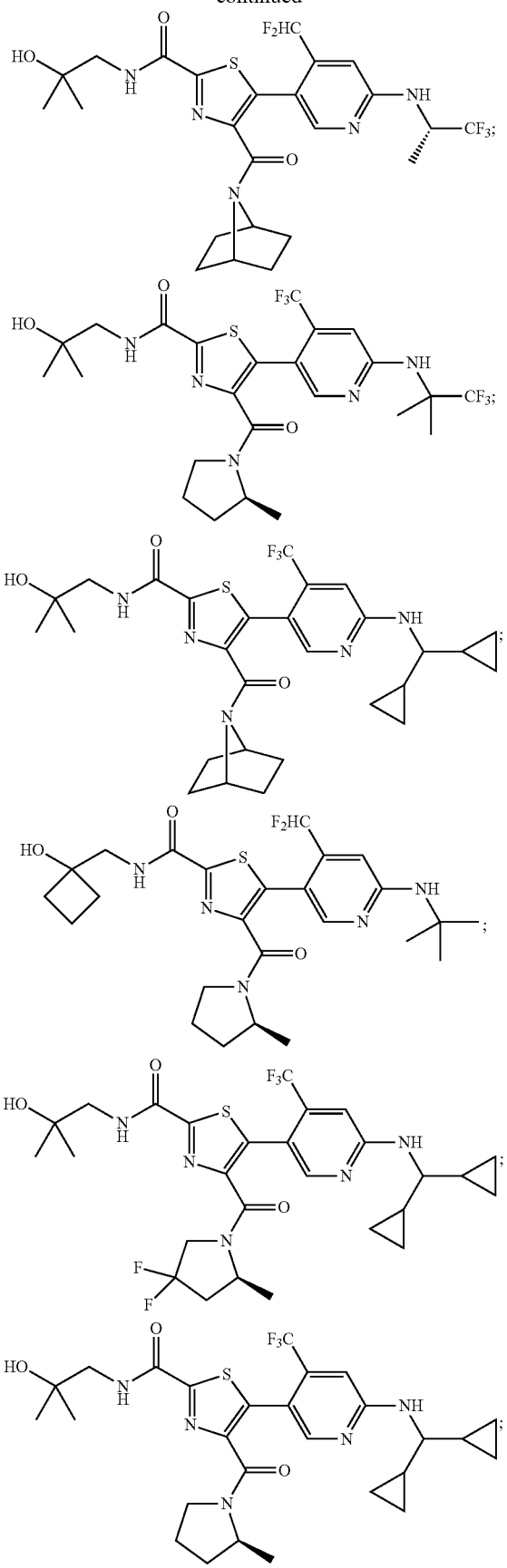
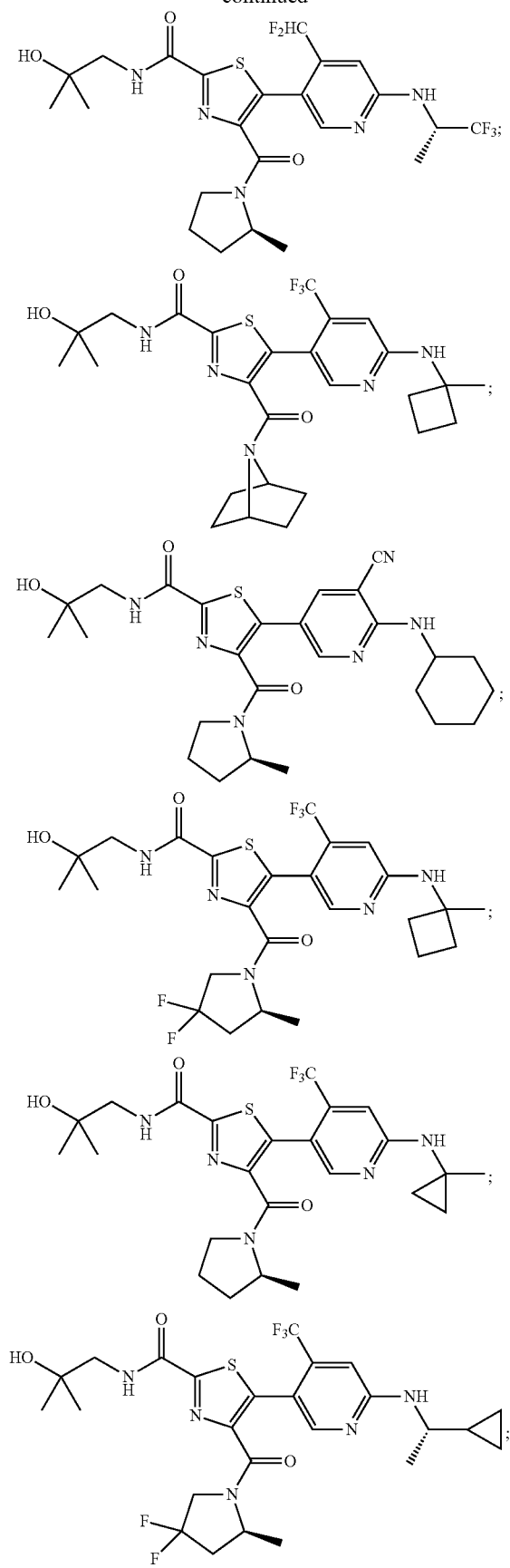

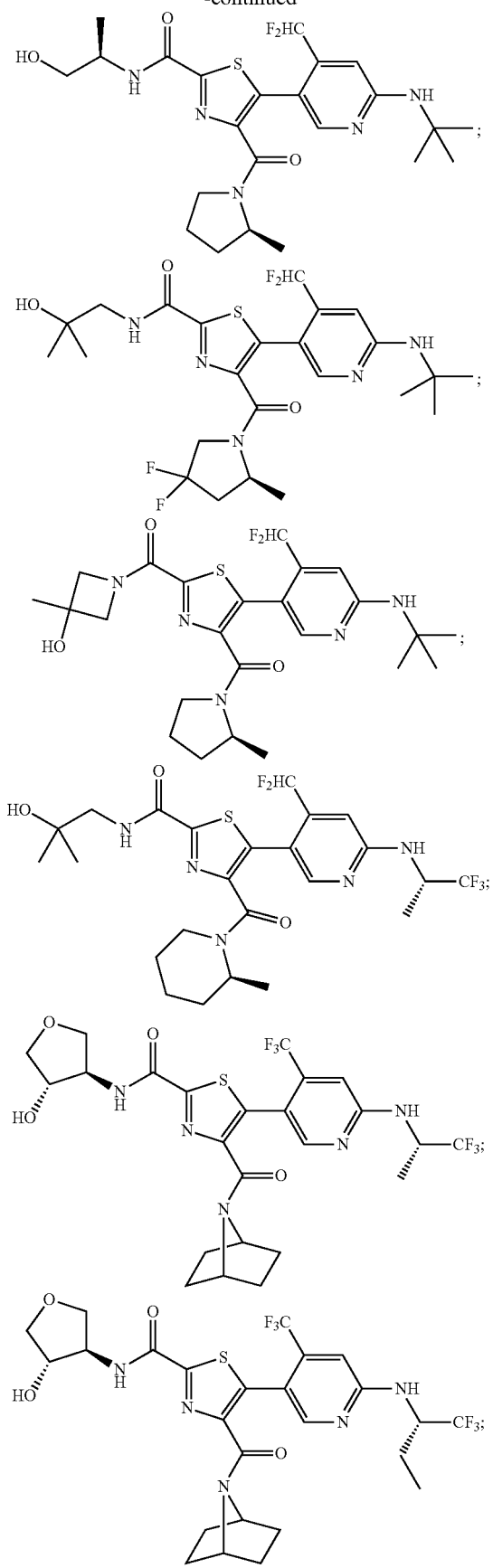
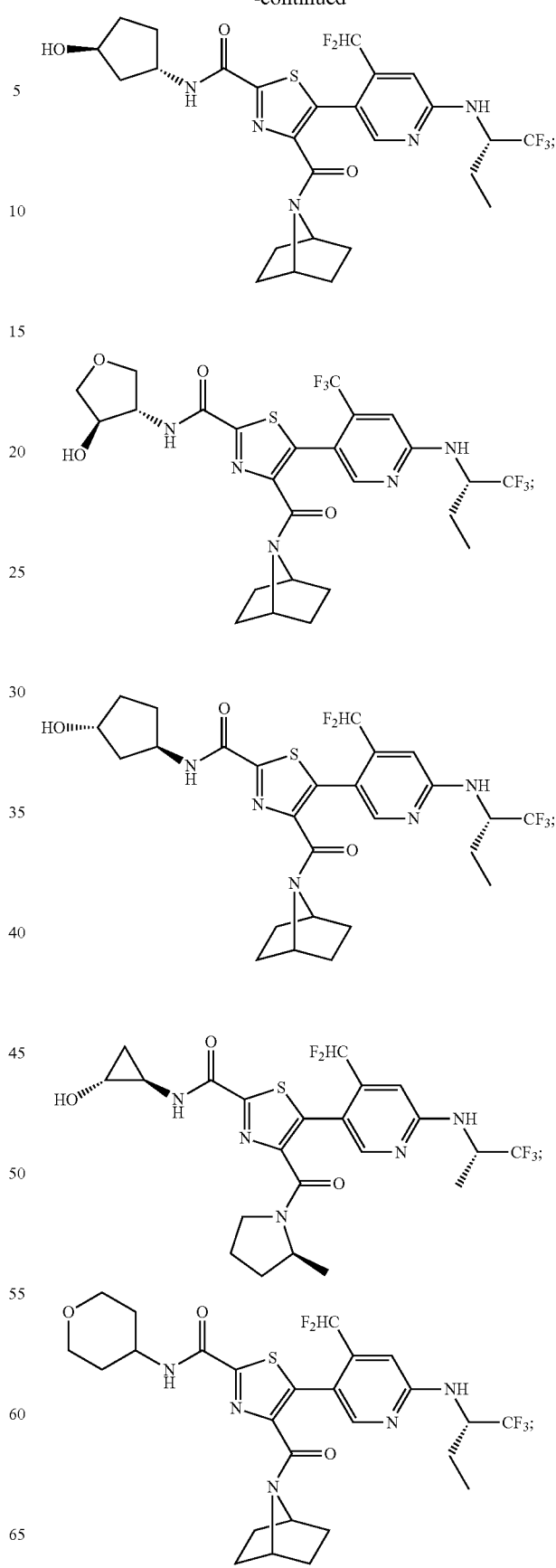

61
-continued
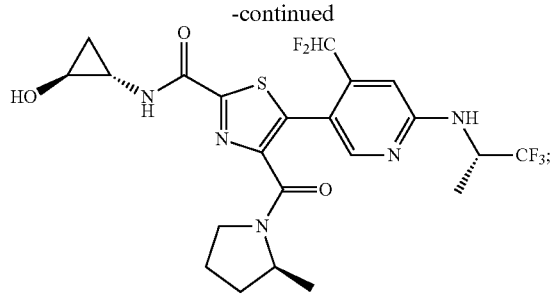
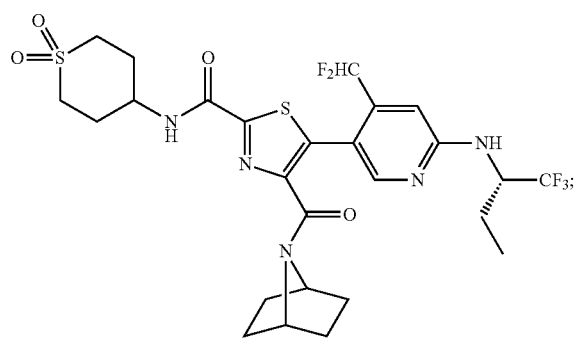
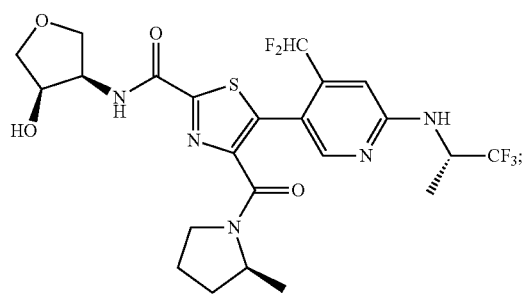
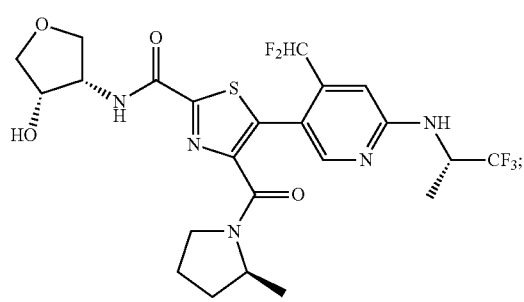
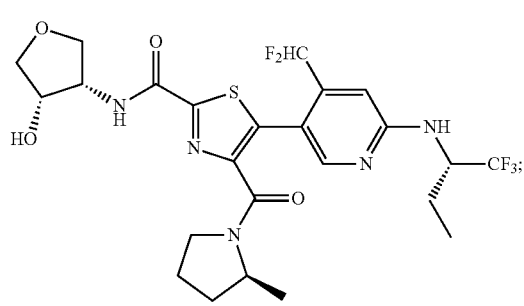
62
-continued
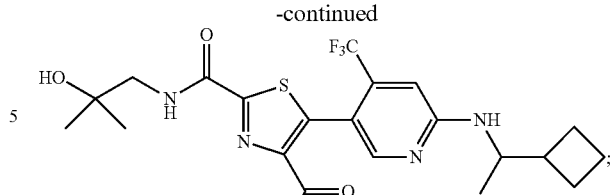
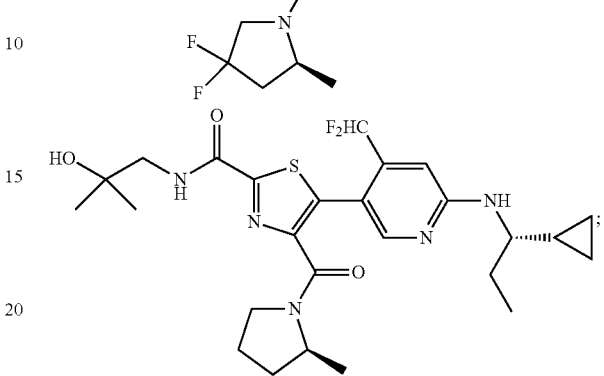
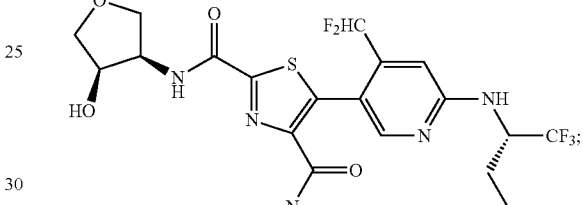
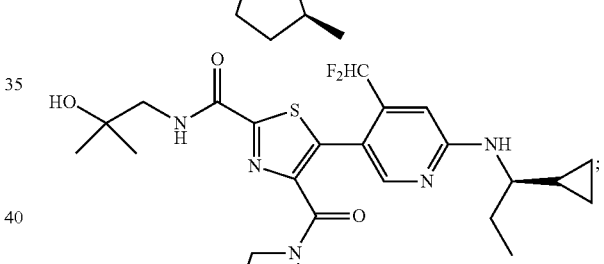
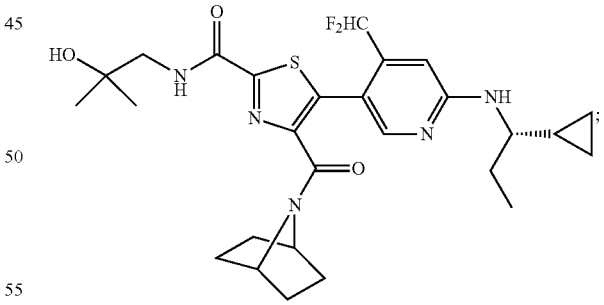
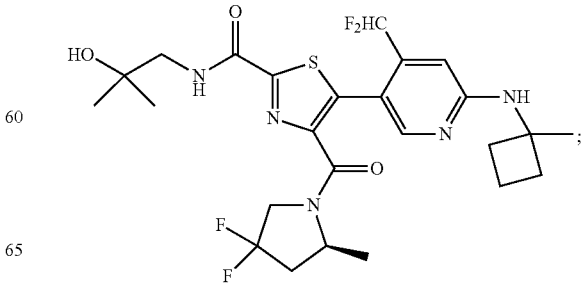

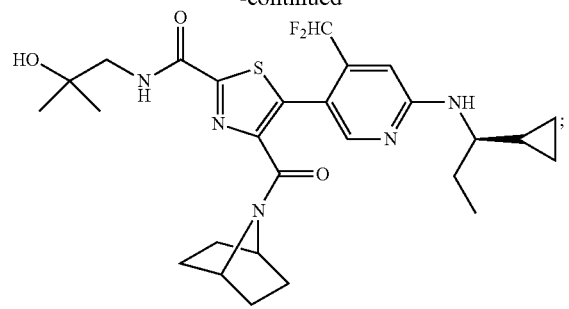
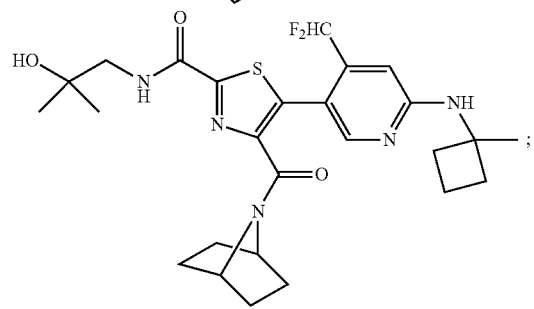
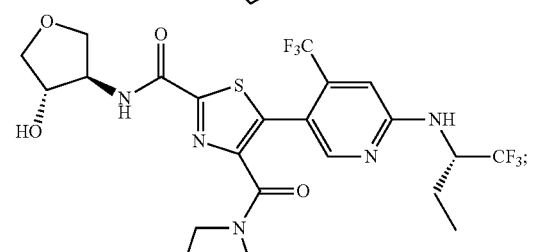
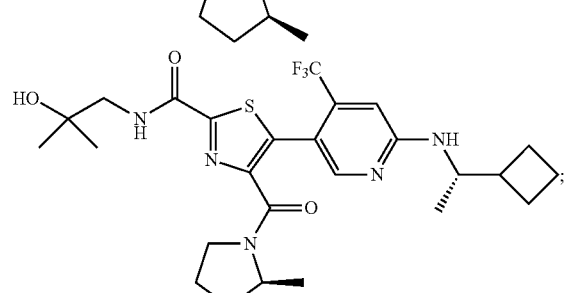
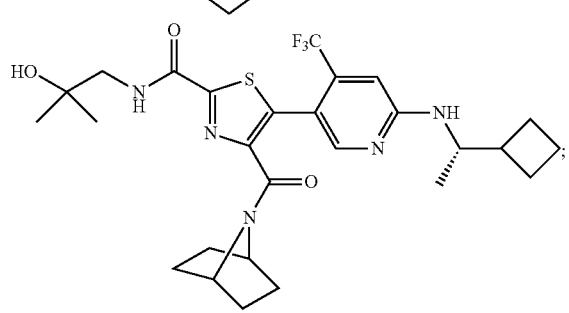
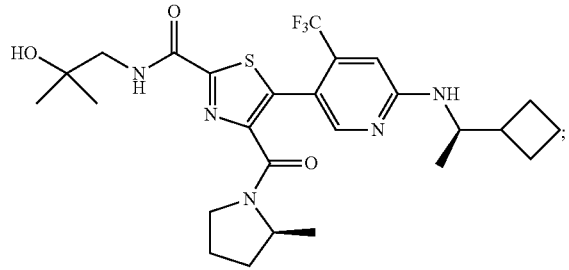
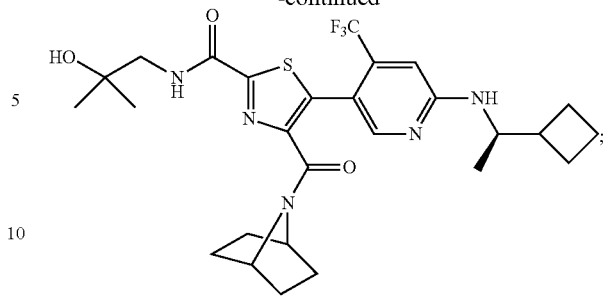
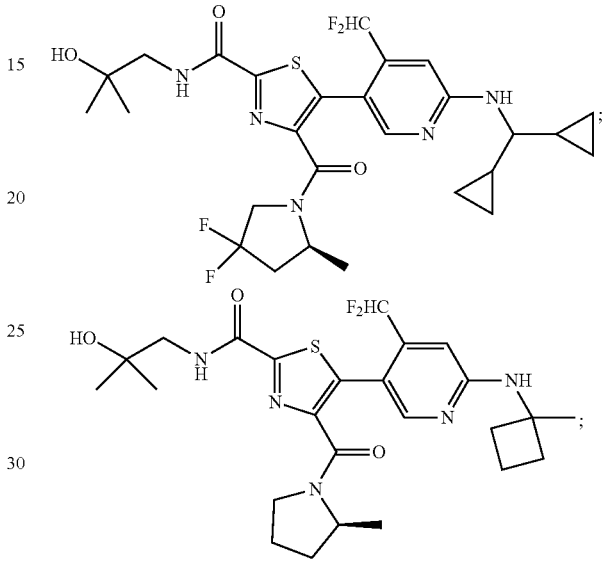
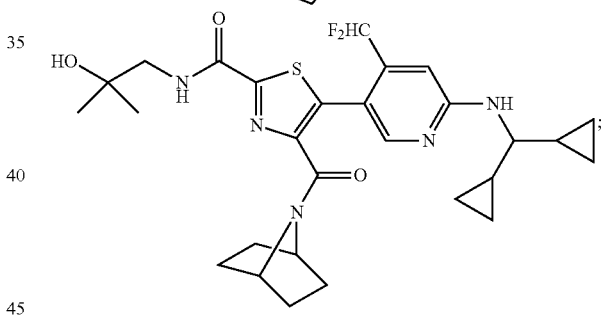
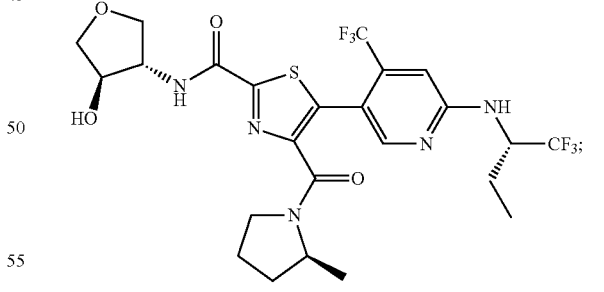
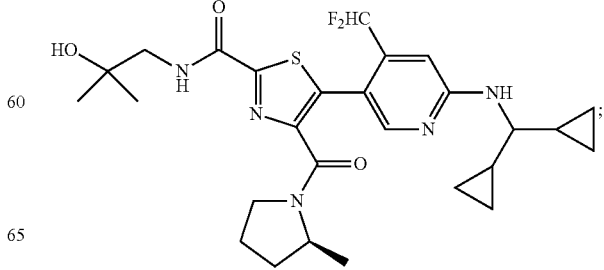

65
-continued
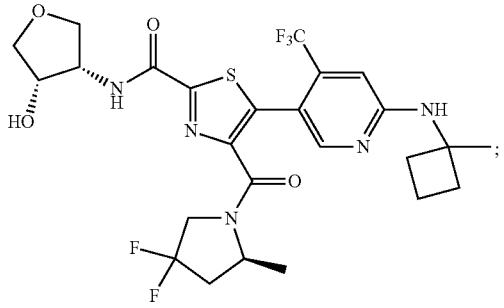
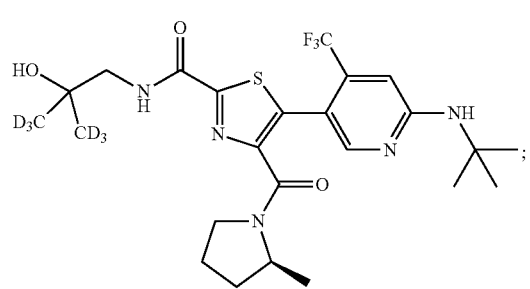
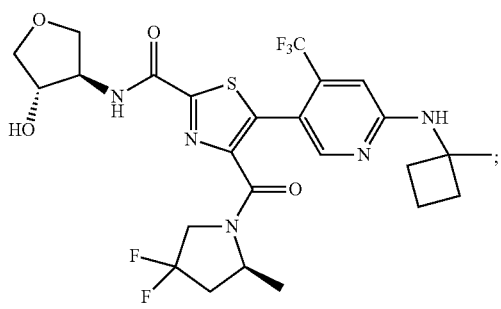
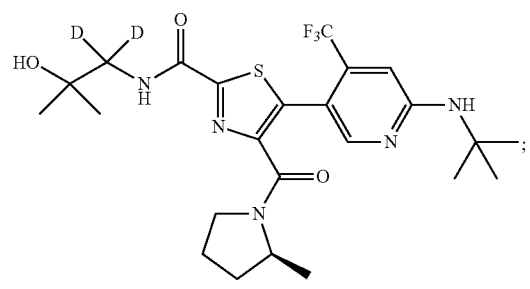
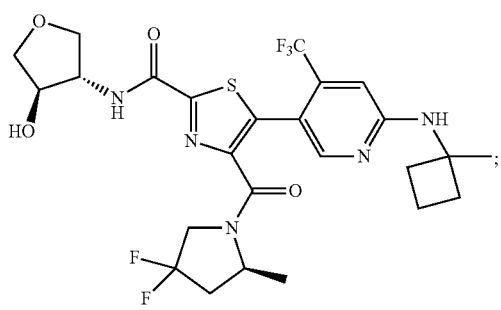
66
-continued
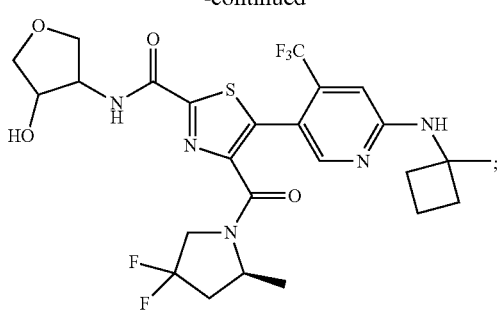
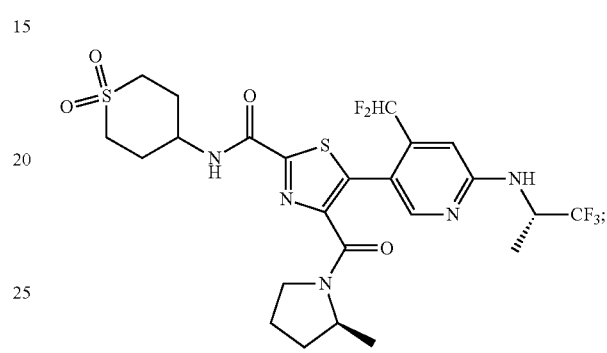
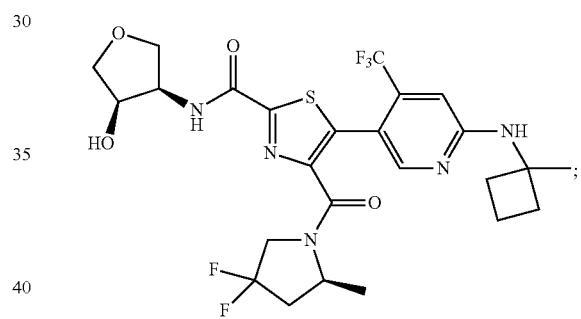
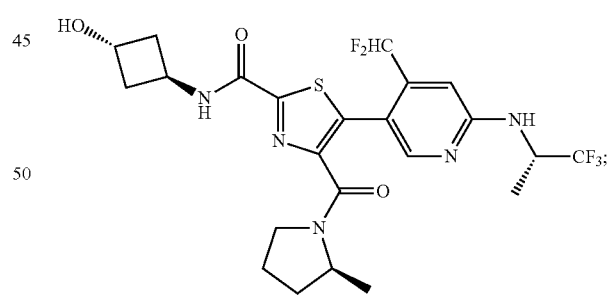
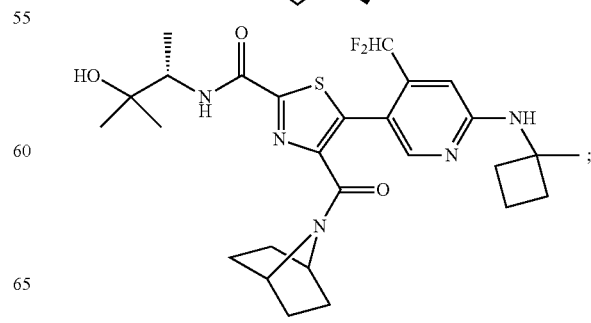

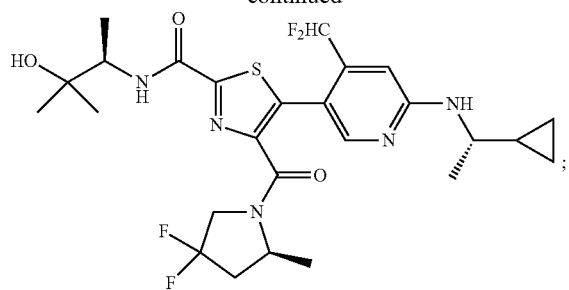
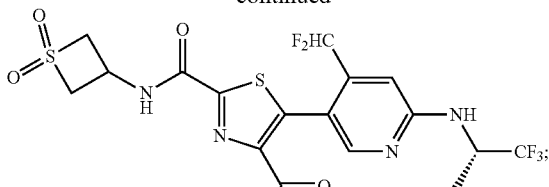
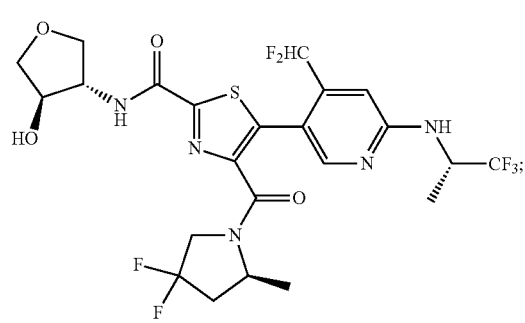
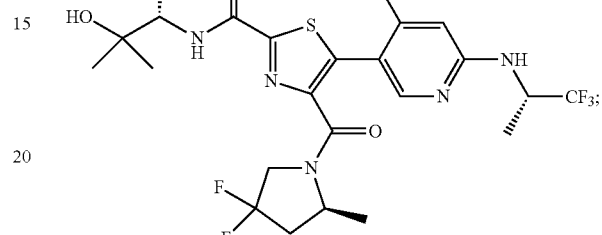
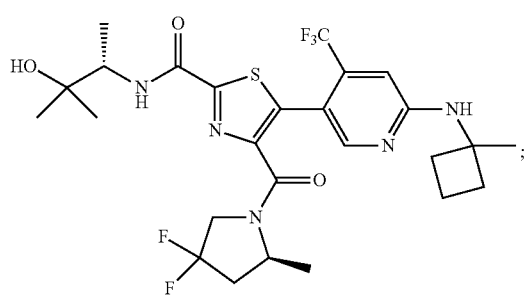
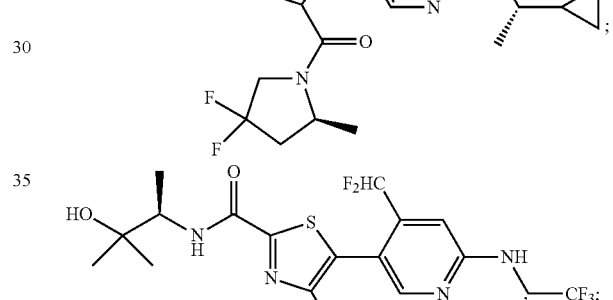
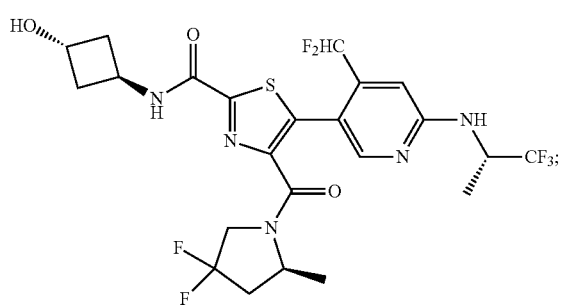
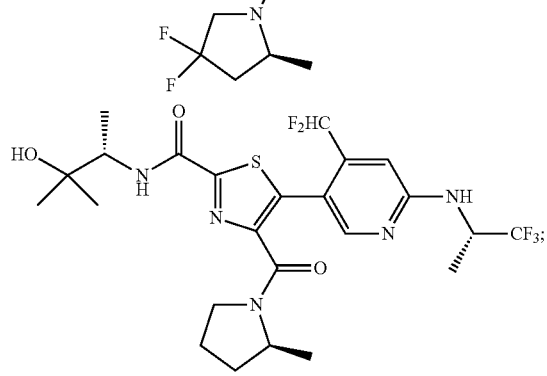
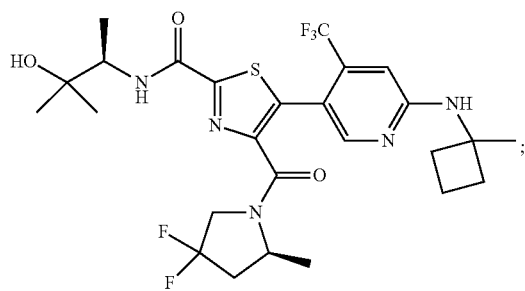
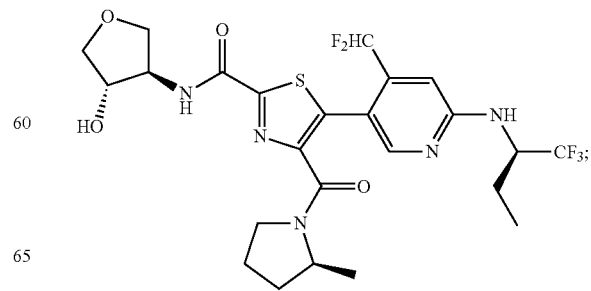

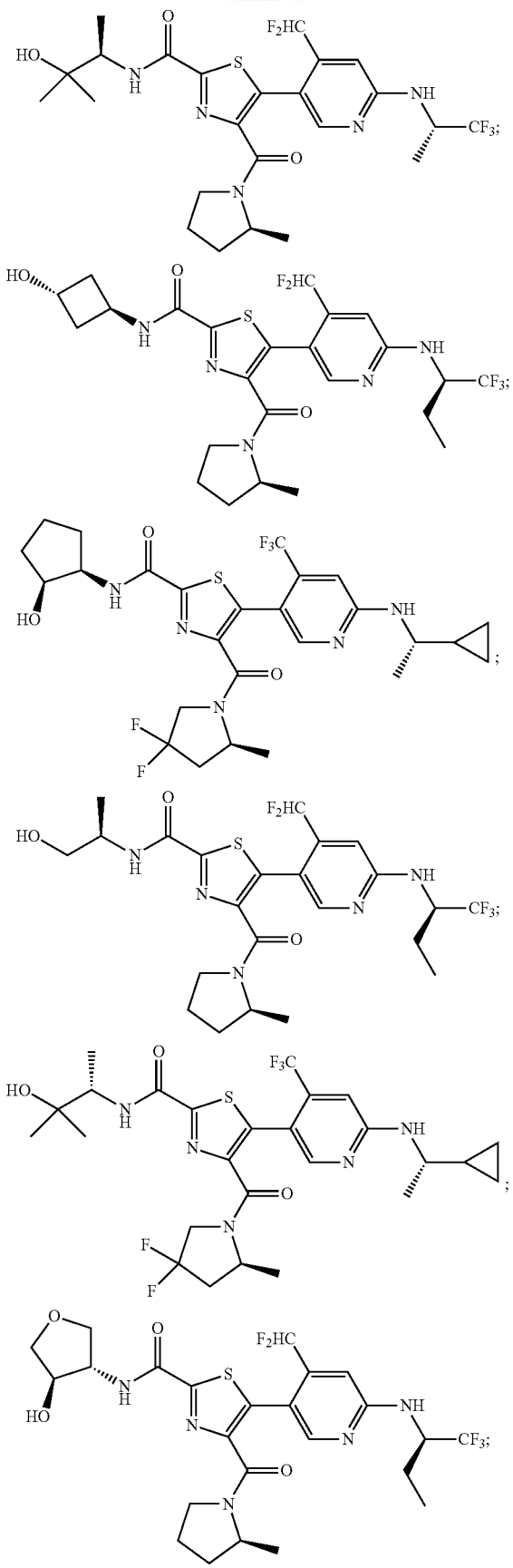
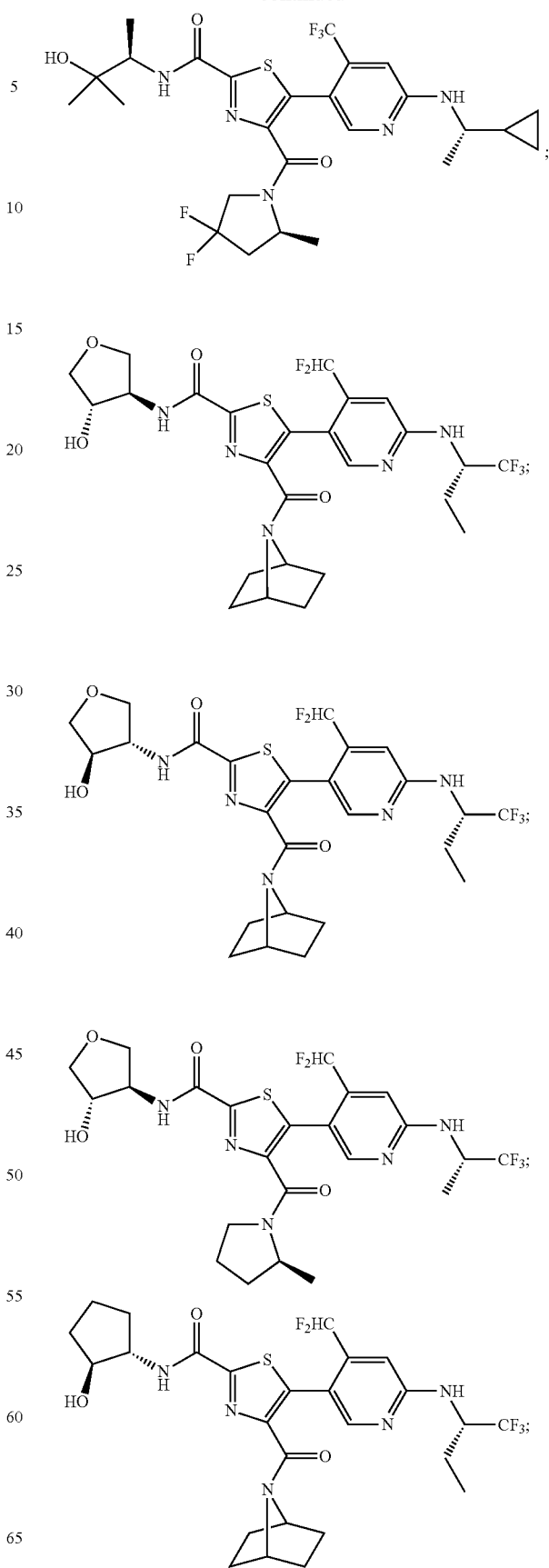

71
-continued
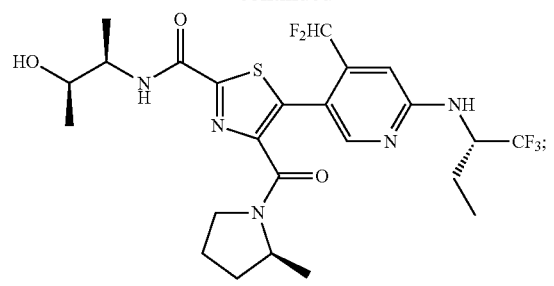
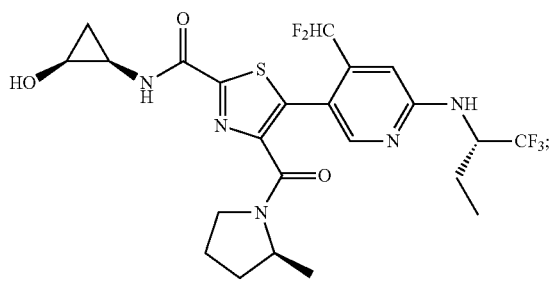
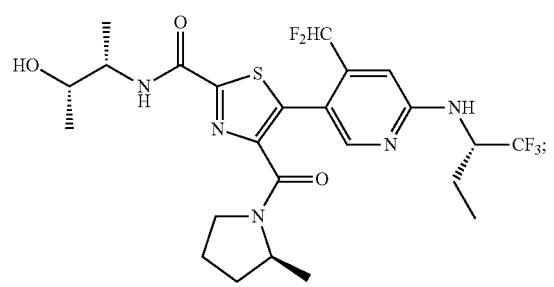
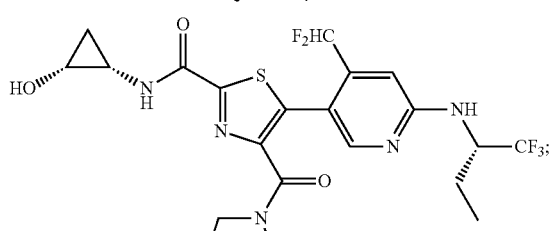
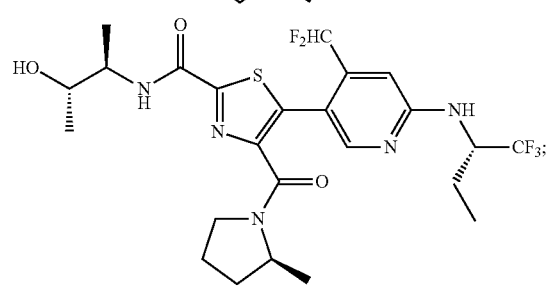
72
-continued
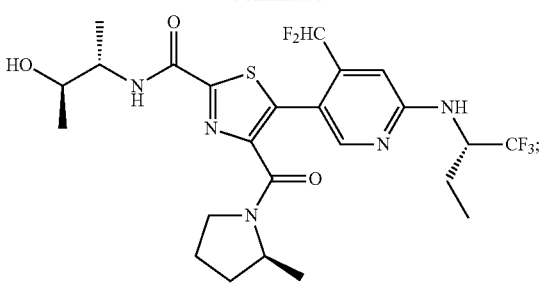
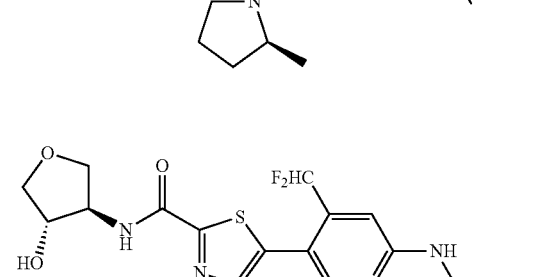
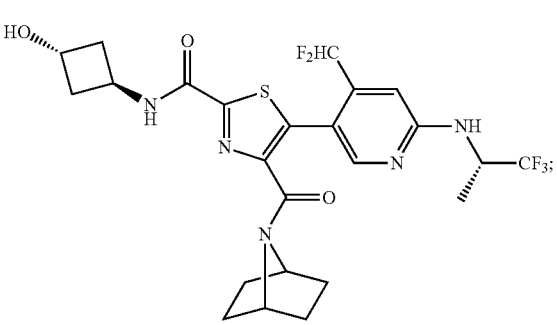
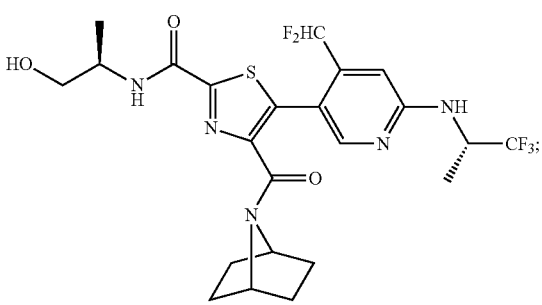

73
-continued
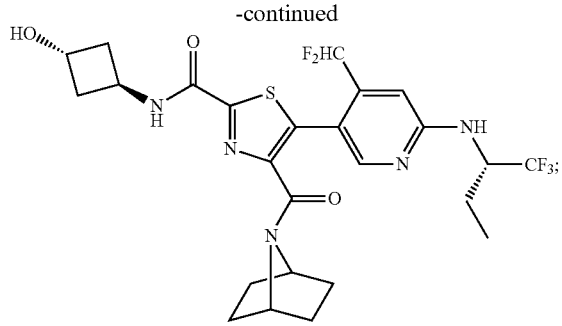
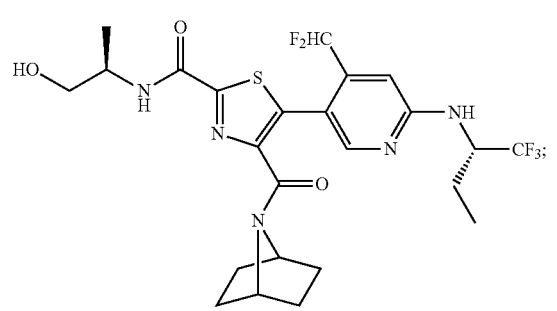
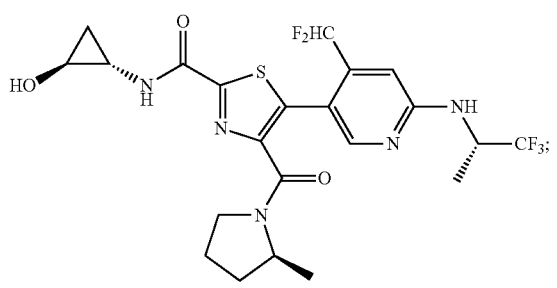
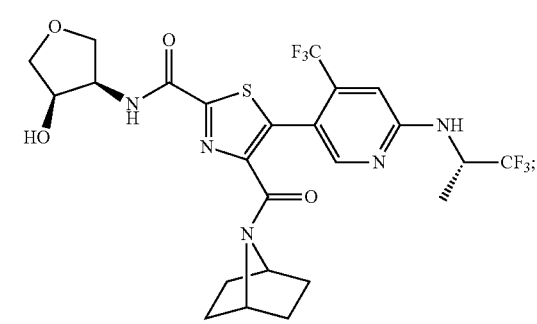
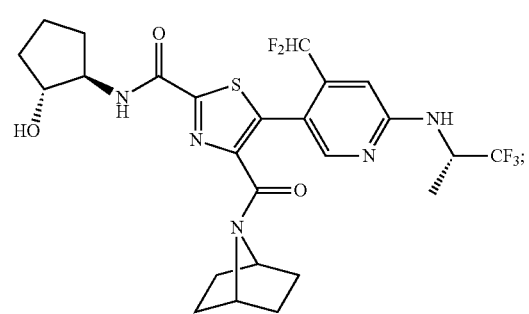
74
-continued
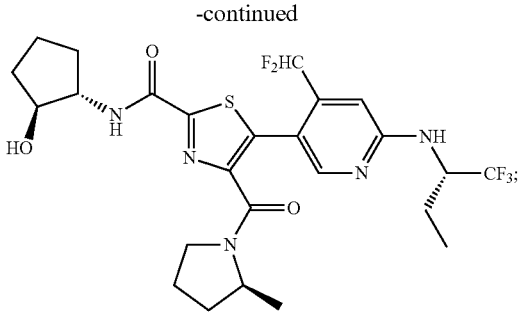
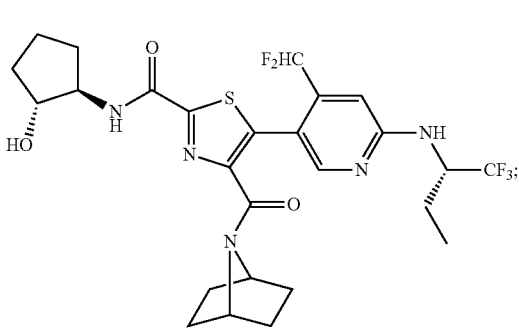
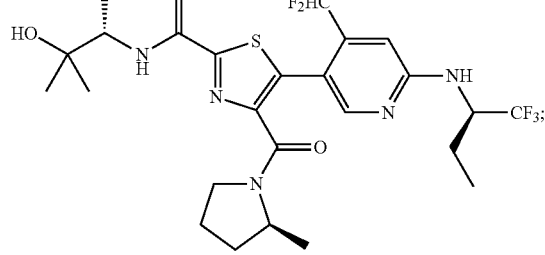
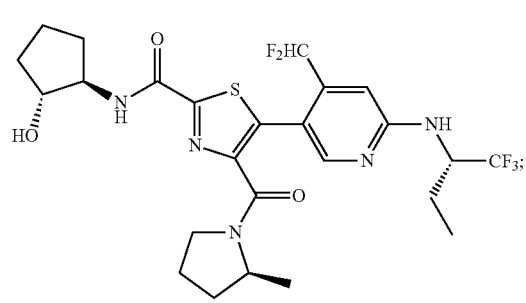
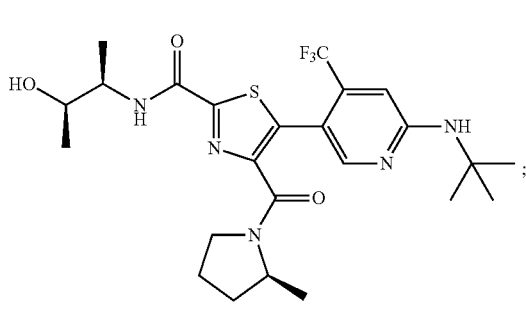

75
-continued
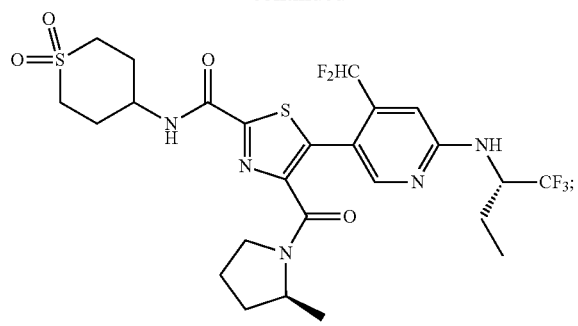
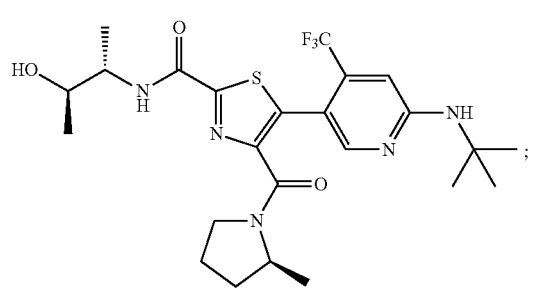
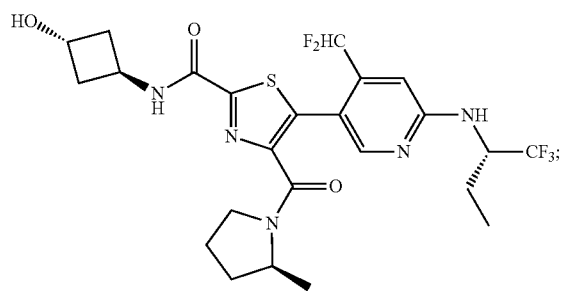
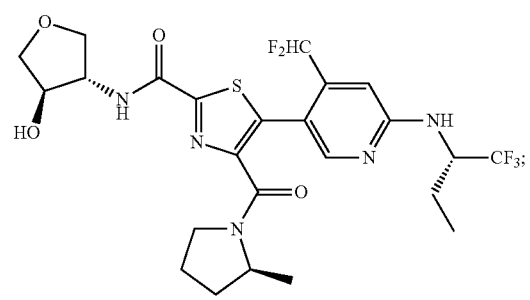
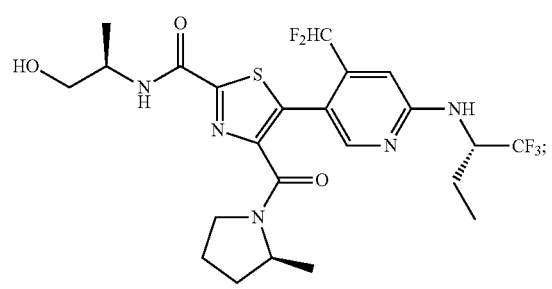
76
-continued
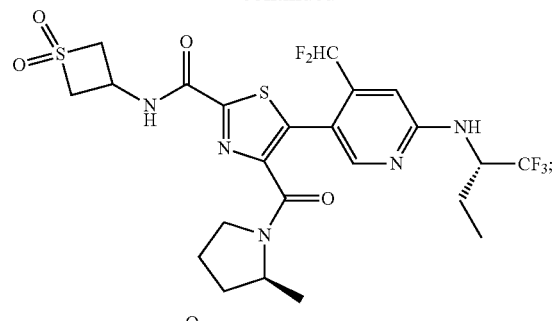
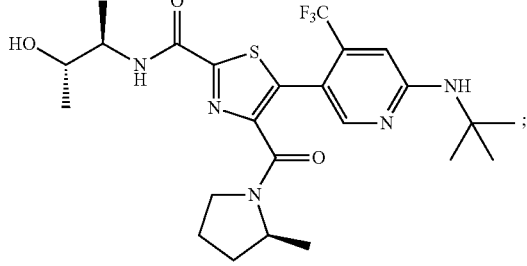
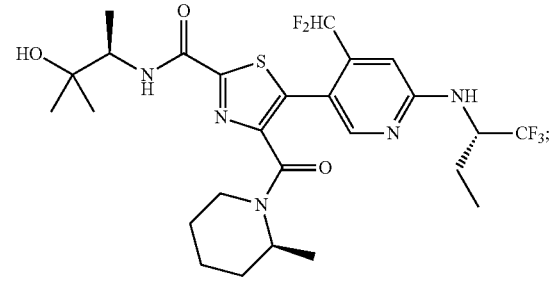
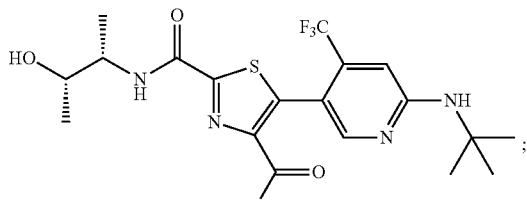
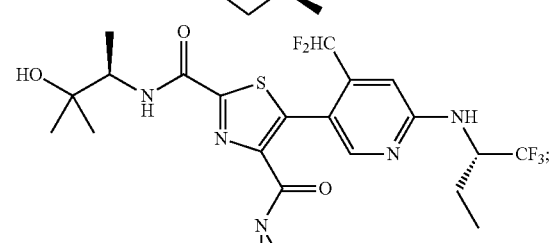
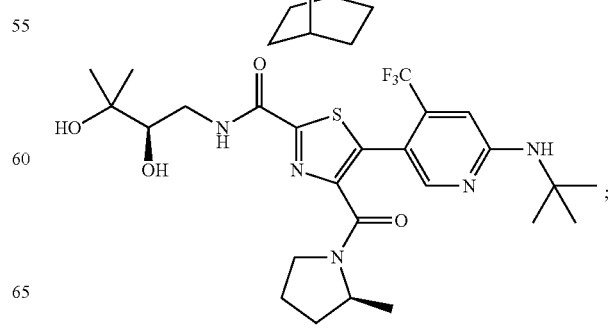

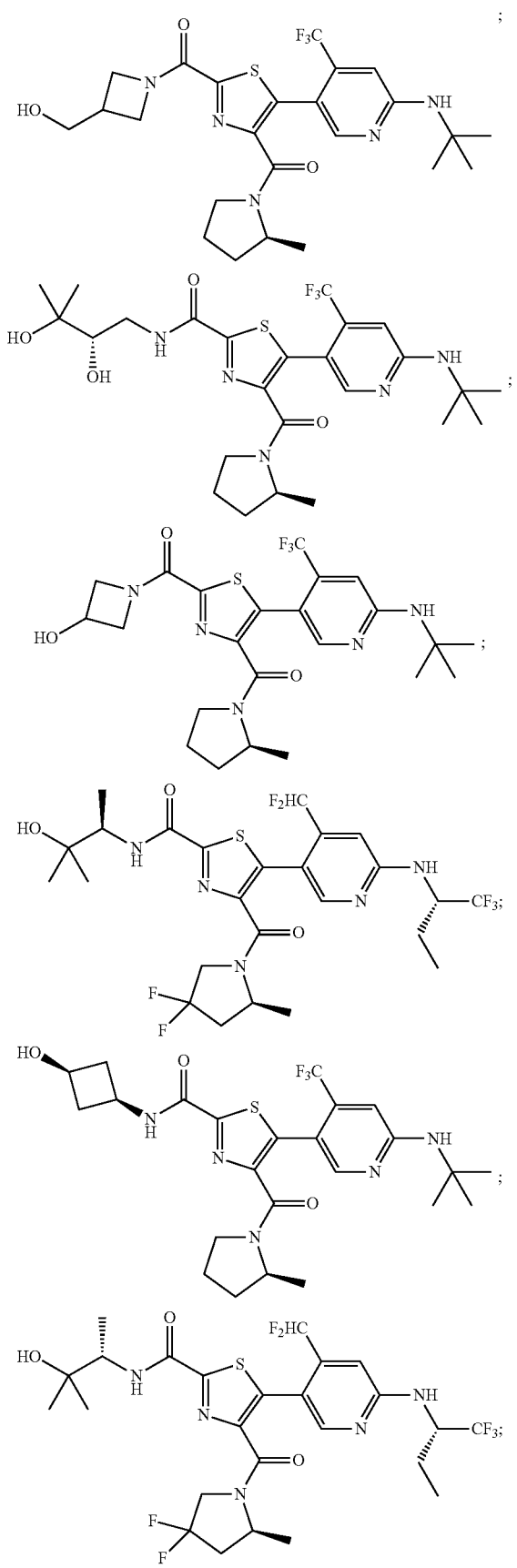
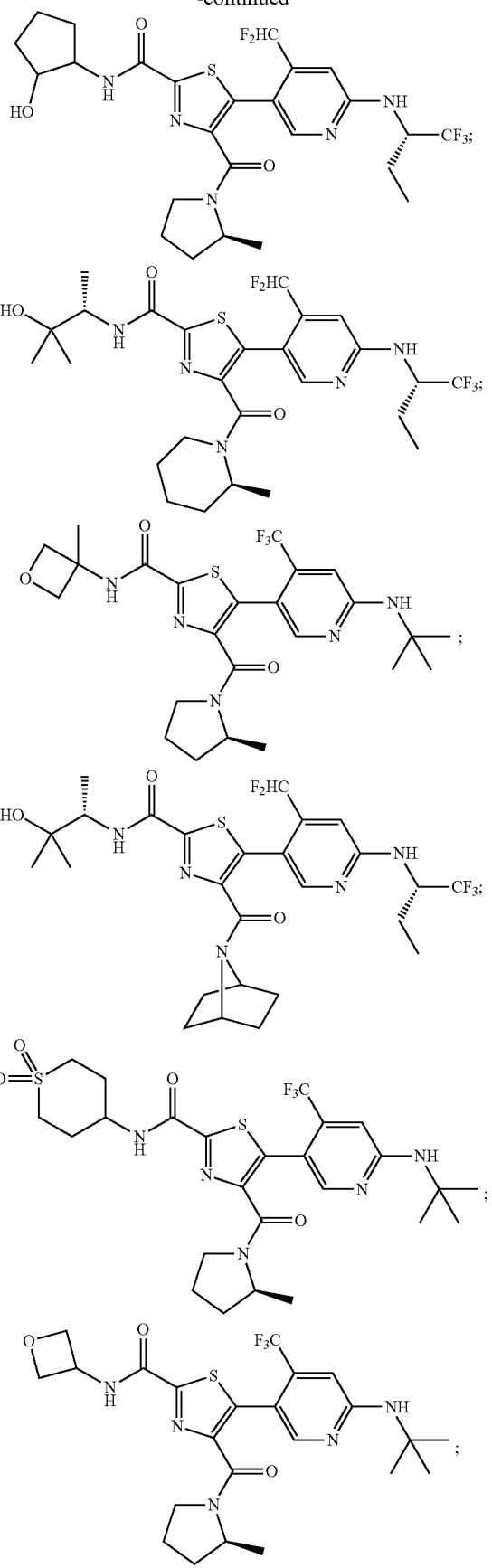

79
-continued
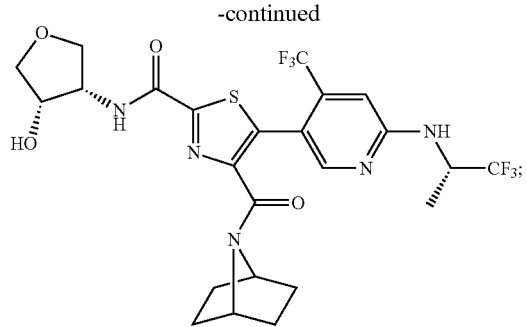
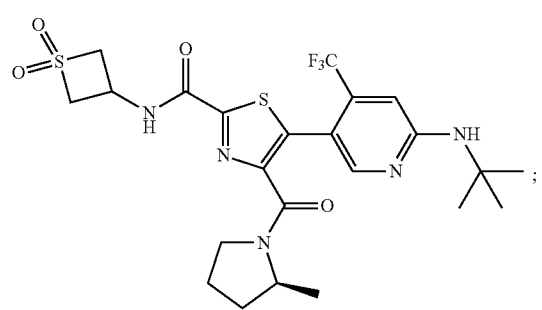
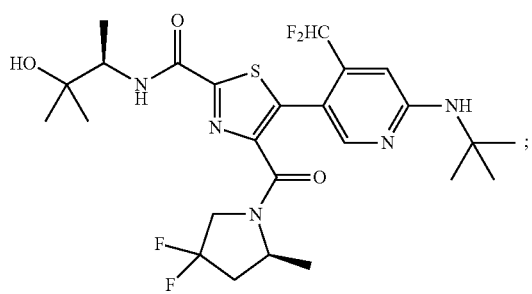
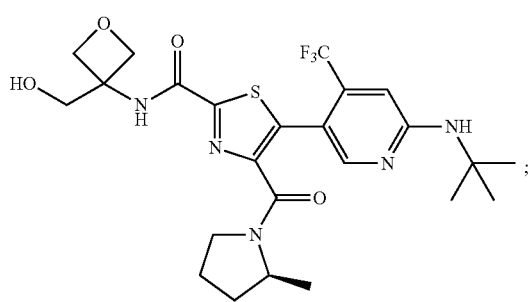
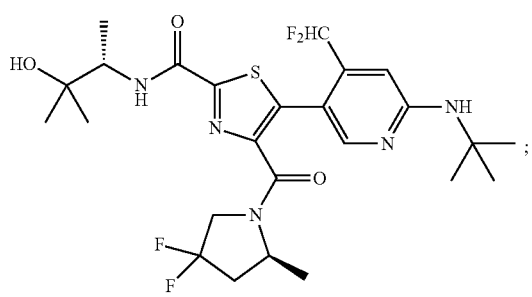
80
-continued
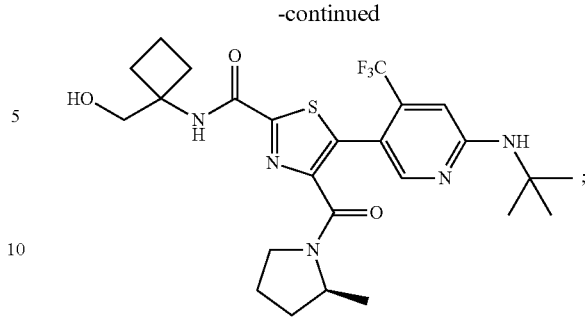
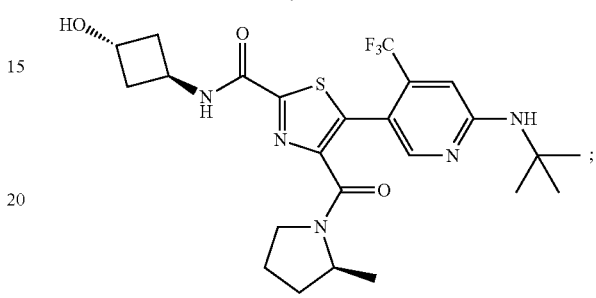
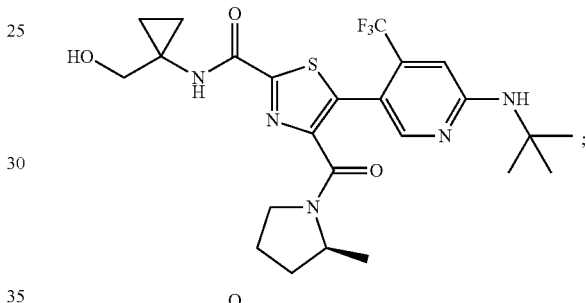
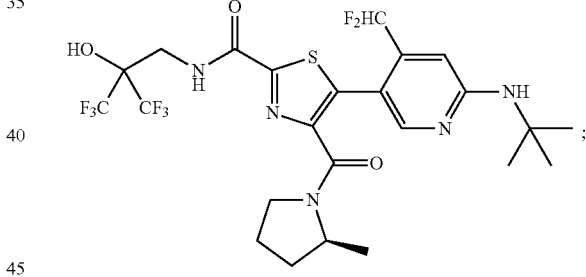
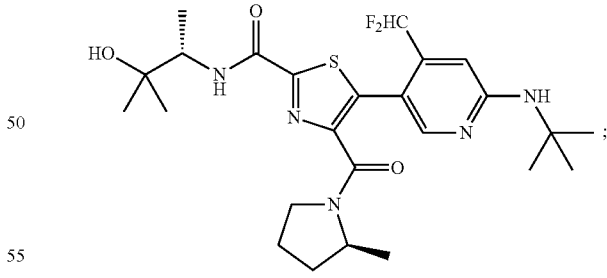
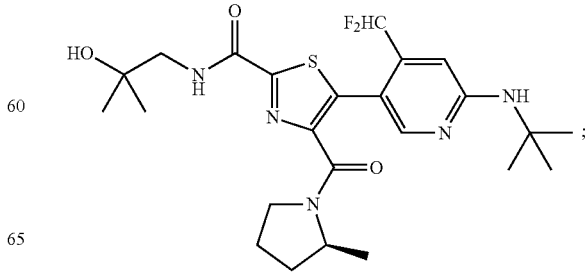

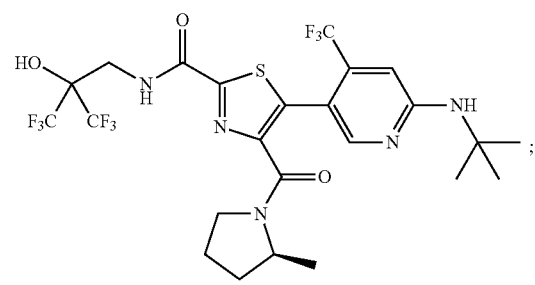
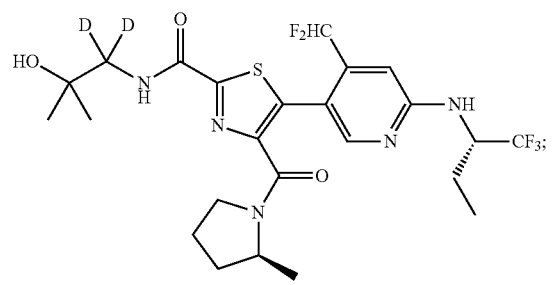
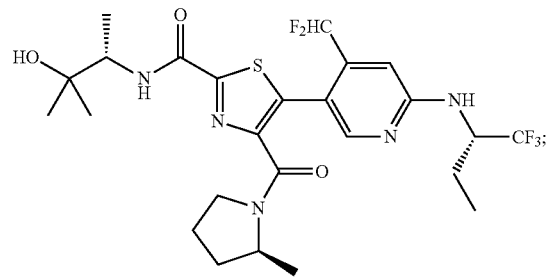
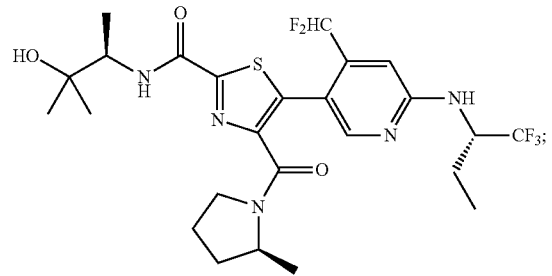
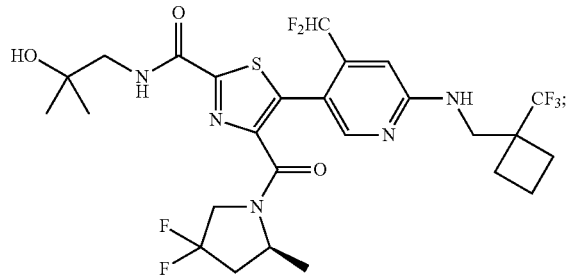
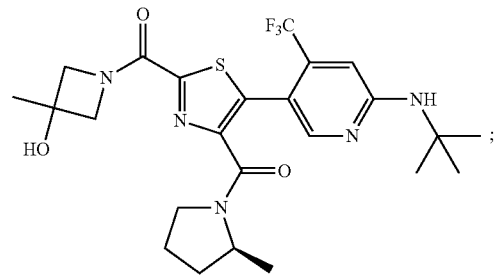
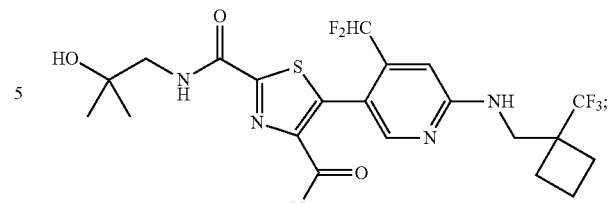
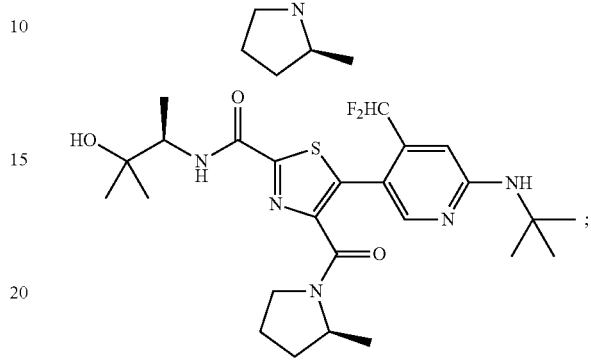
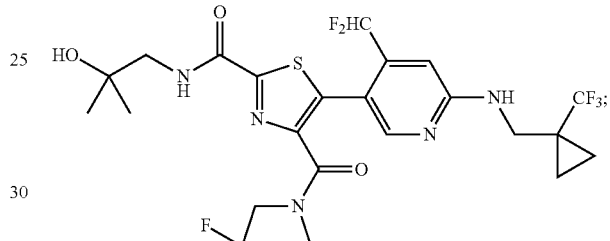
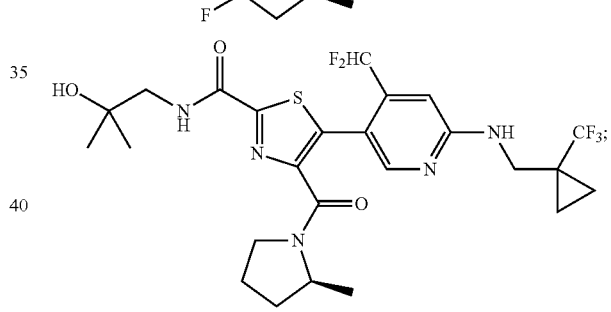
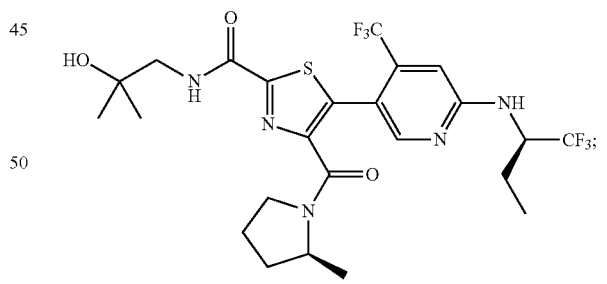
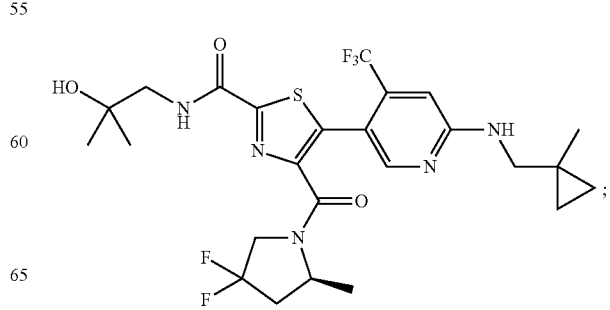

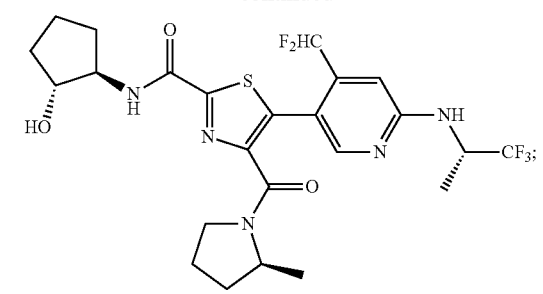
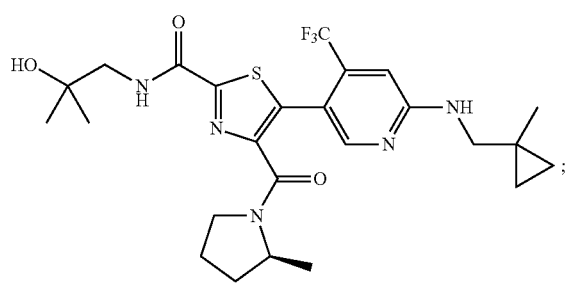
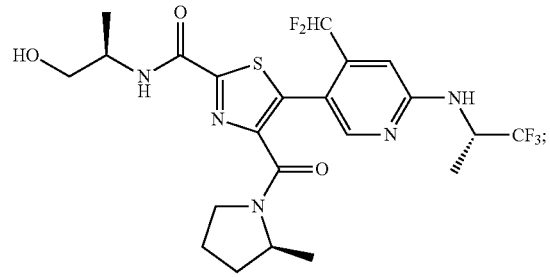
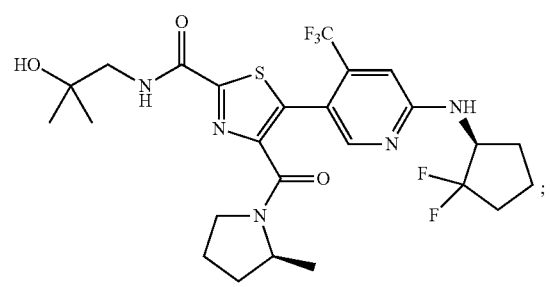
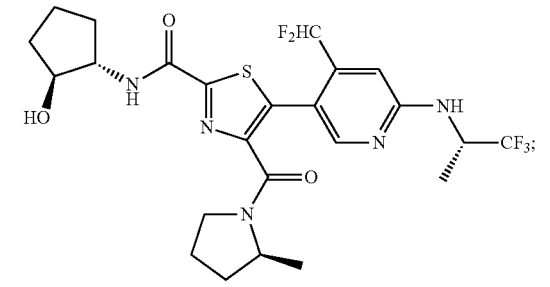
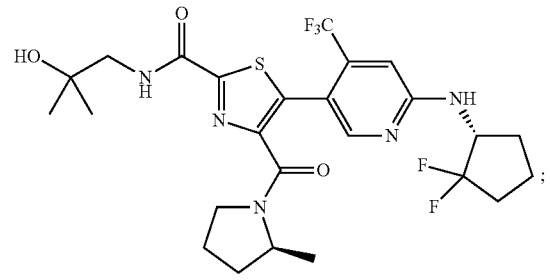
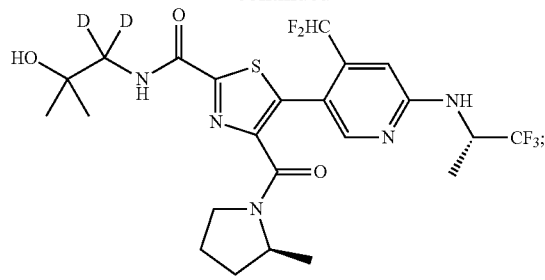
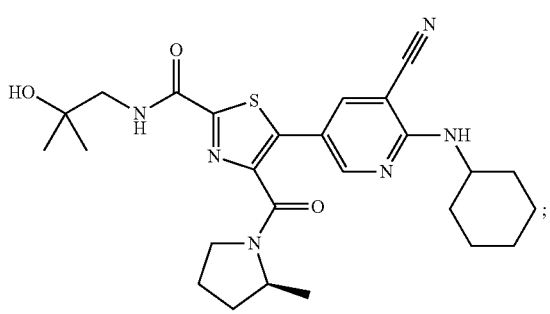
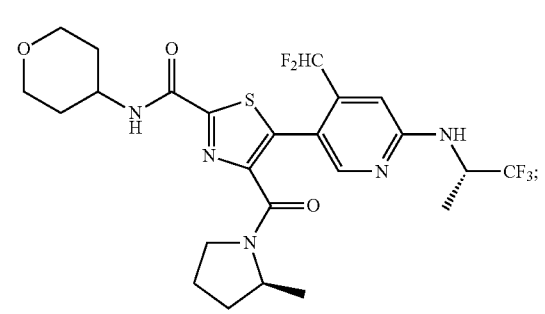
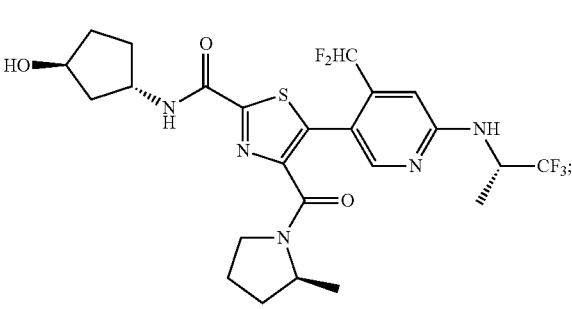
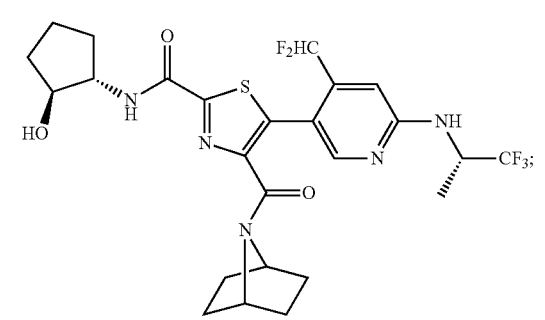

85
-continued
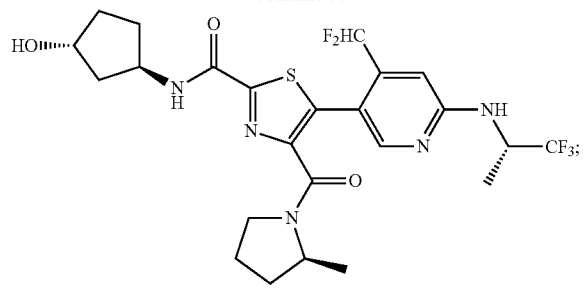
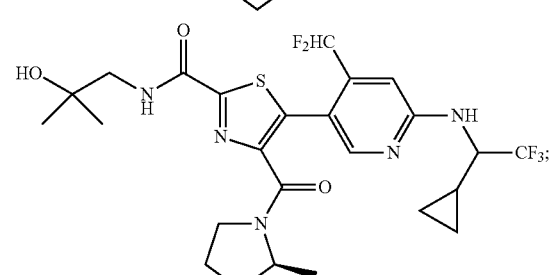
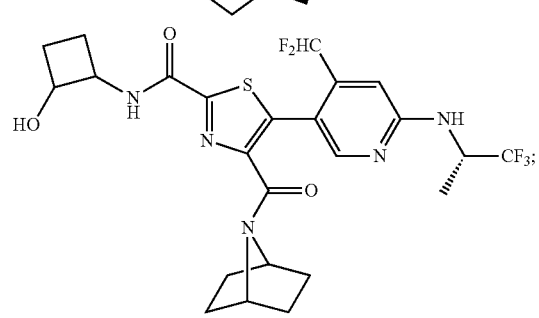
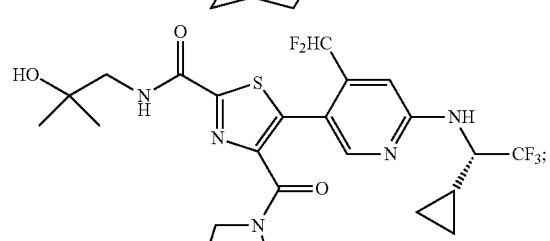
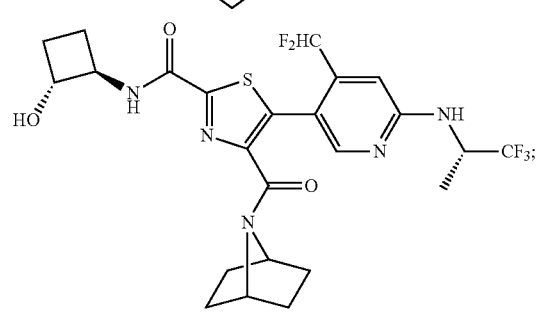
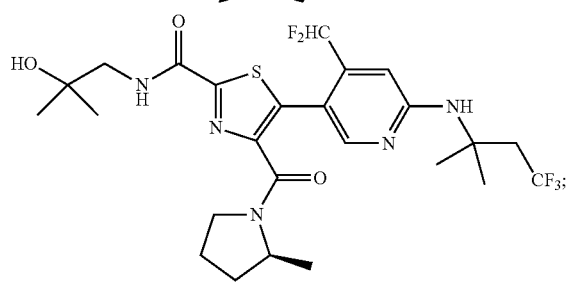
86
-continued
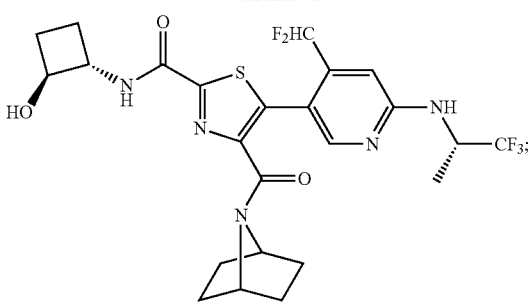
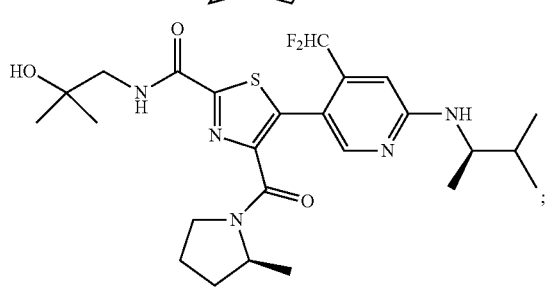
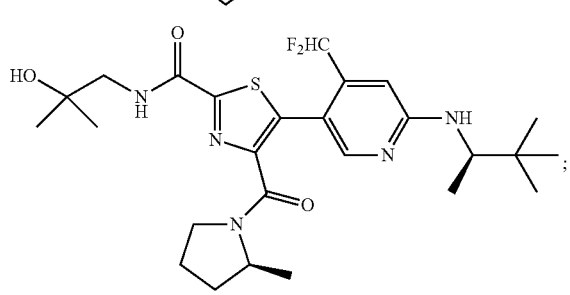
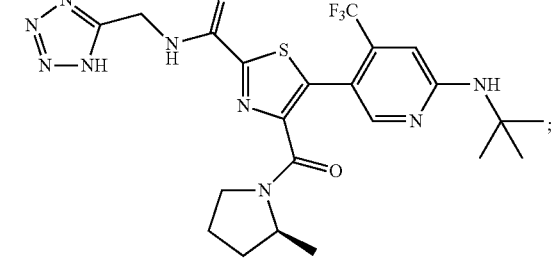
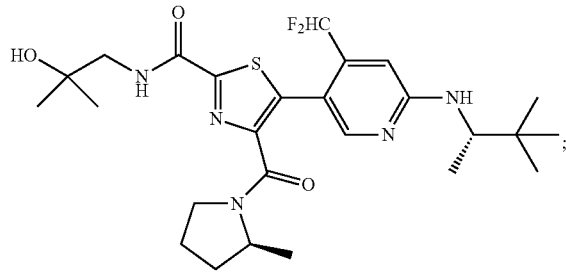
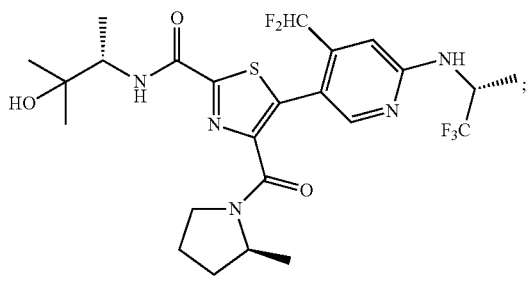

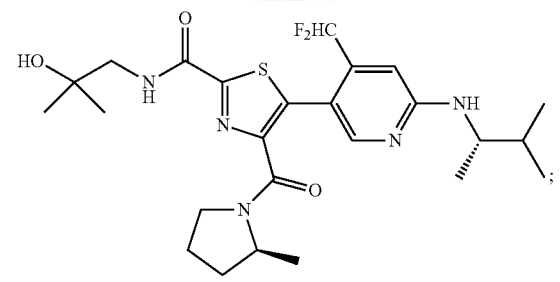
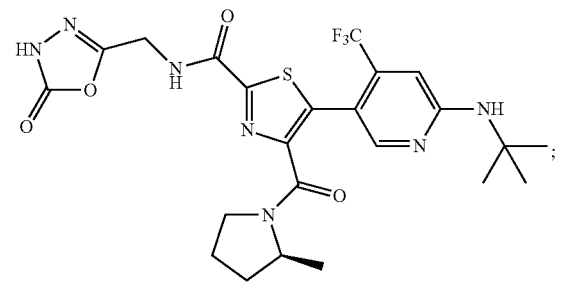
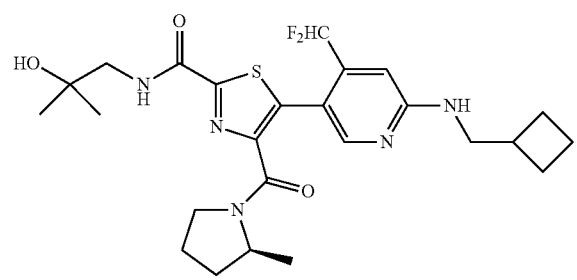
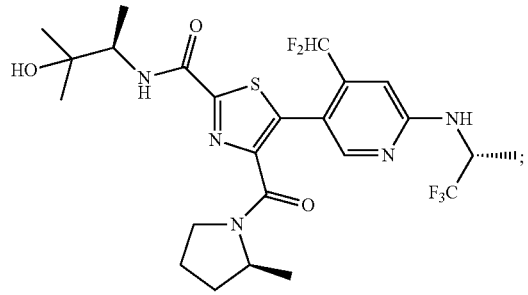
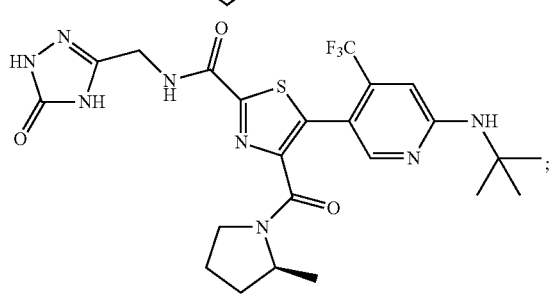
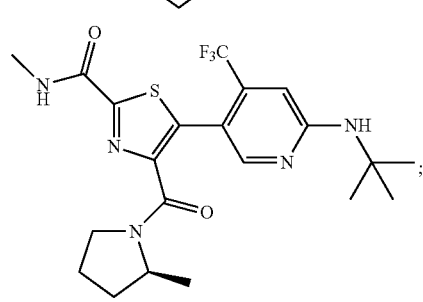
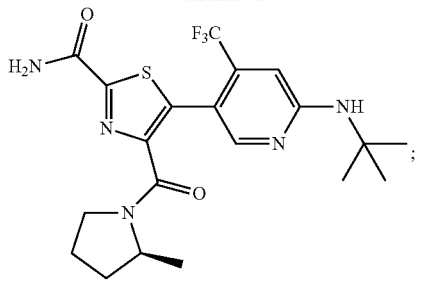
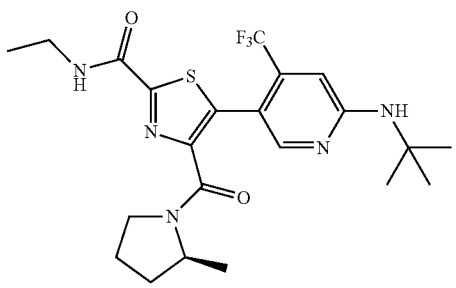
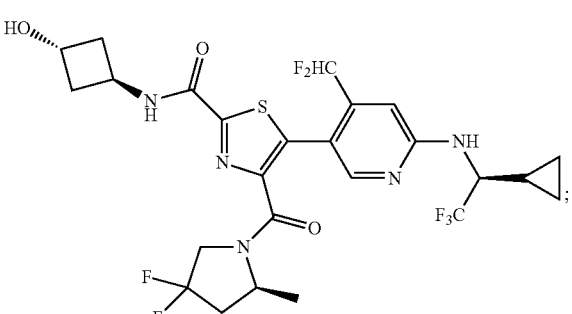
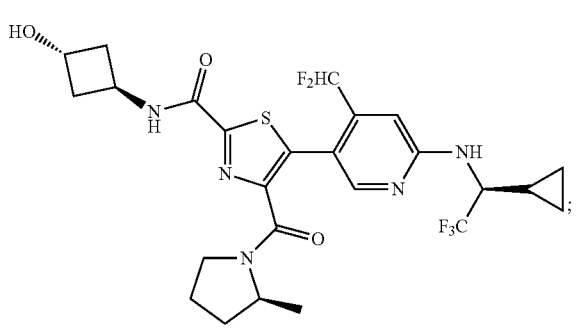
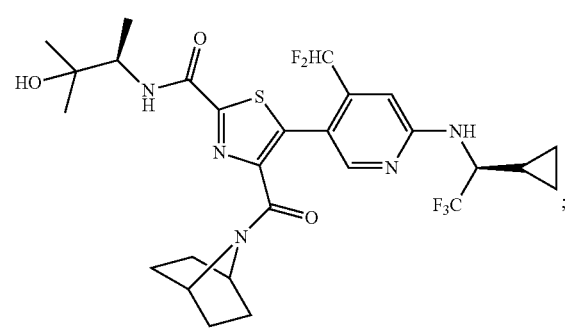

89
-continued
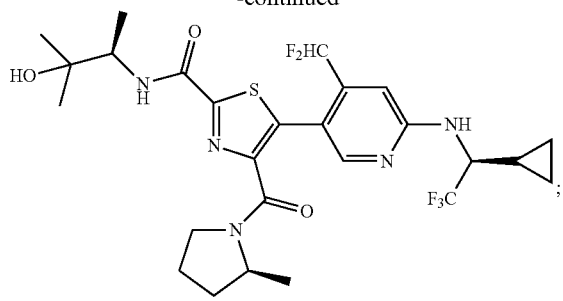
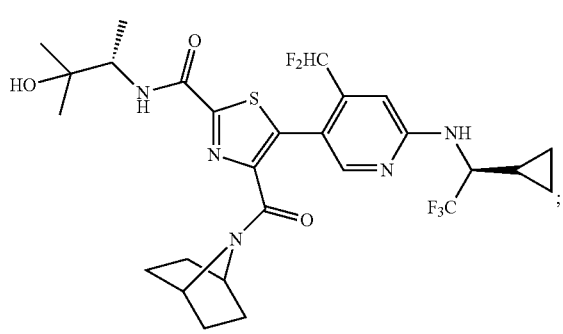
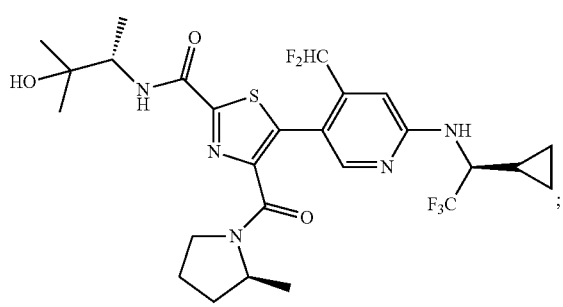
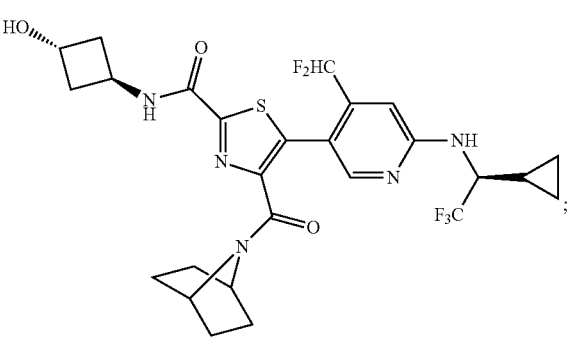
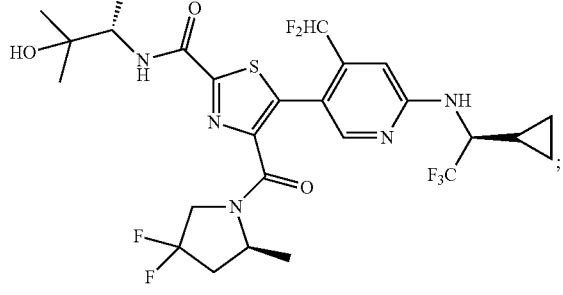
90
-continued
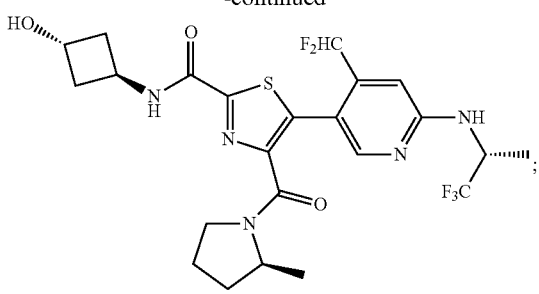
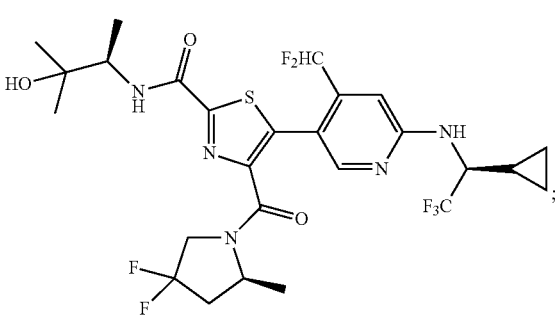
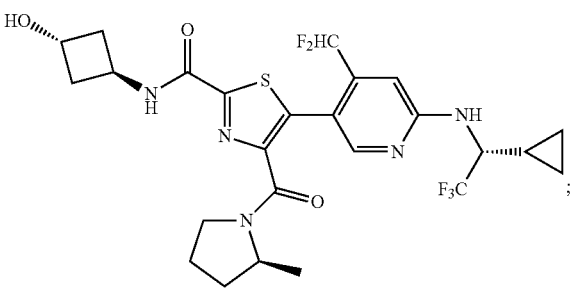
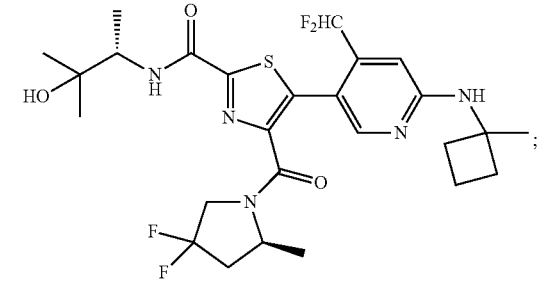
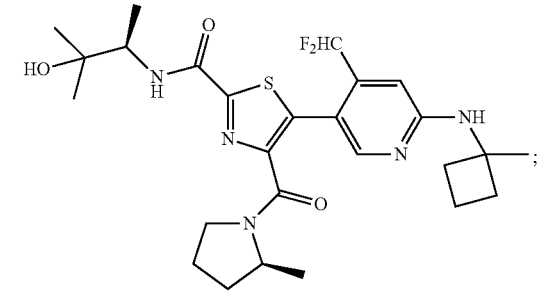

91
-continued
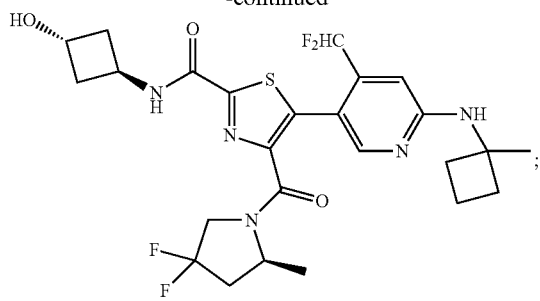
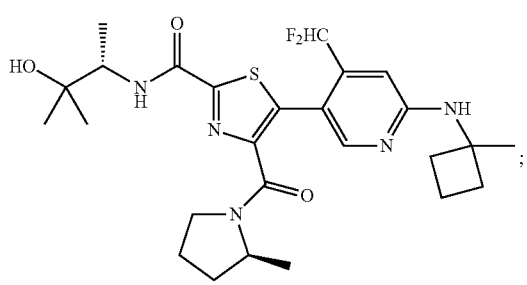
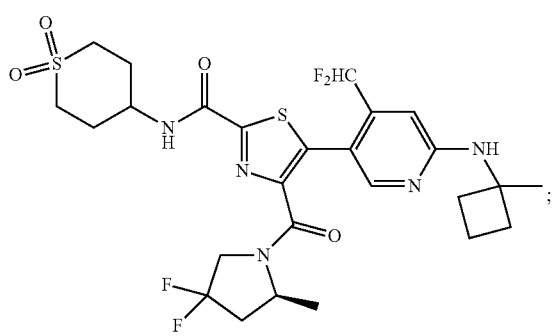
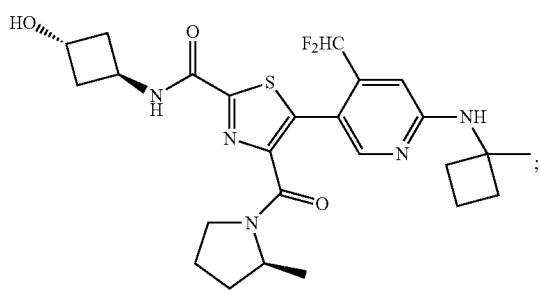
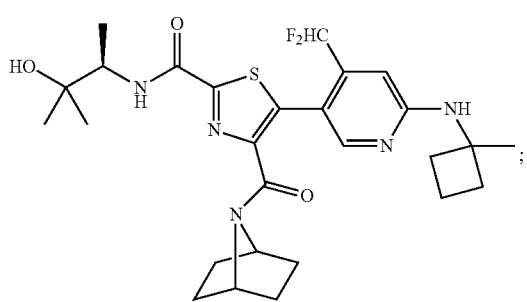
92
-continued
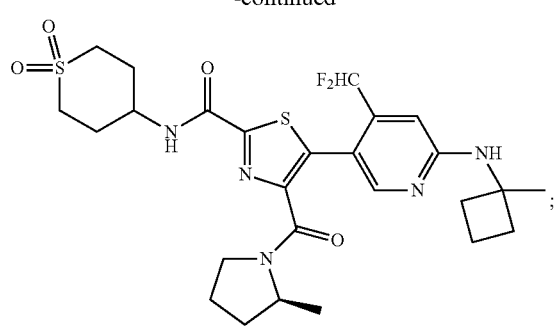
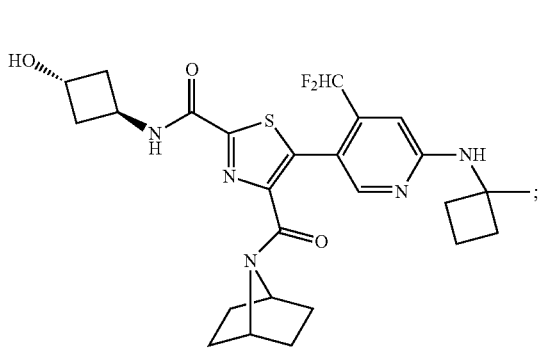
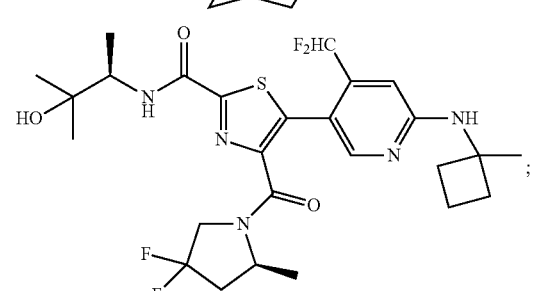
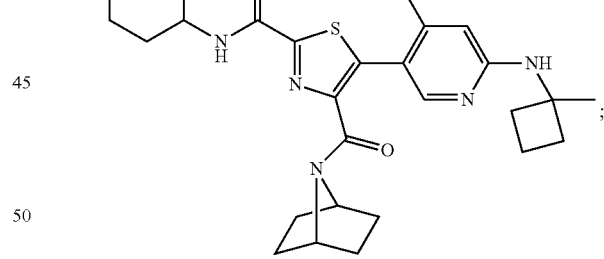
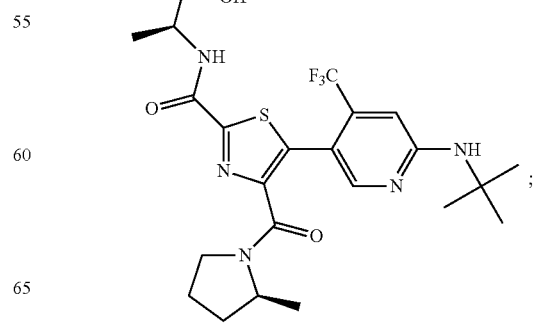

93
-continued
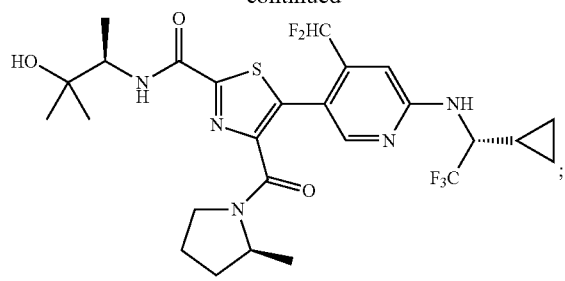
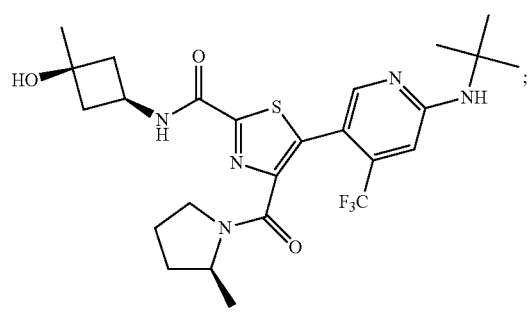
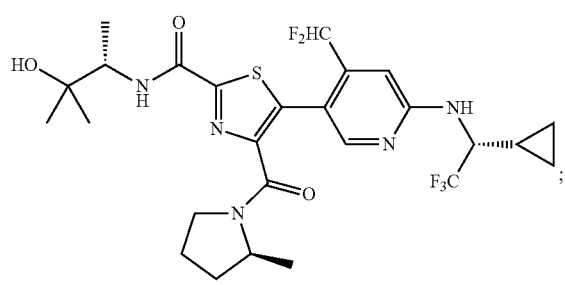
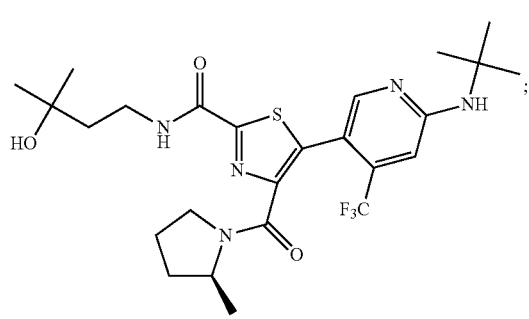
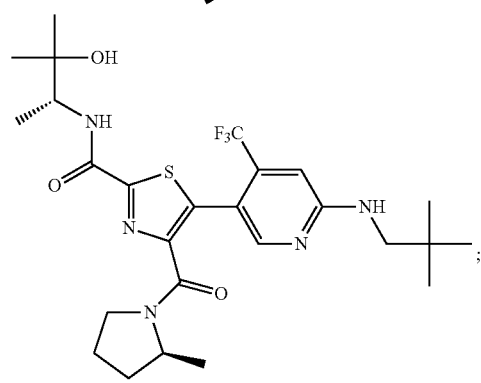
94
-continued
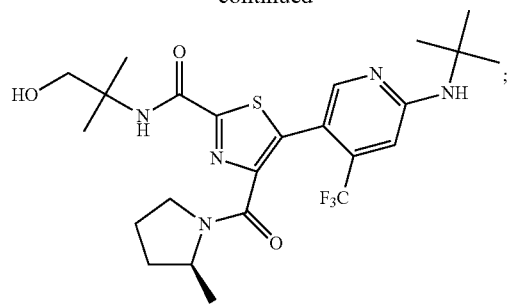
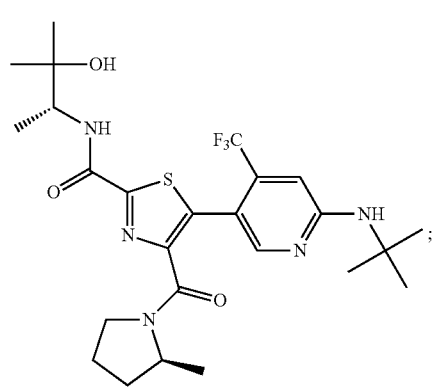
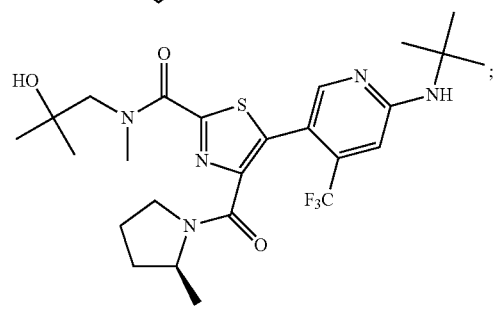
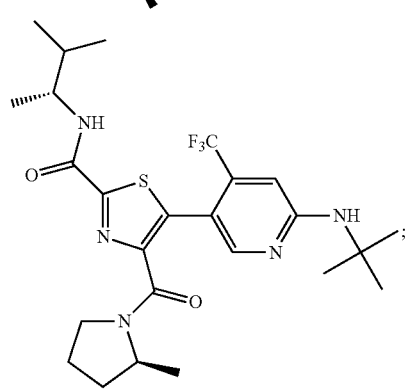
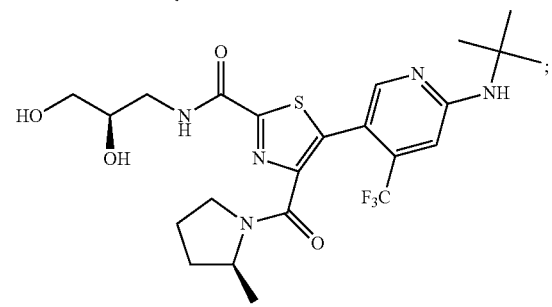

95
-continued
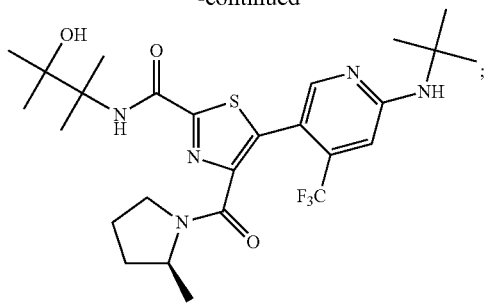
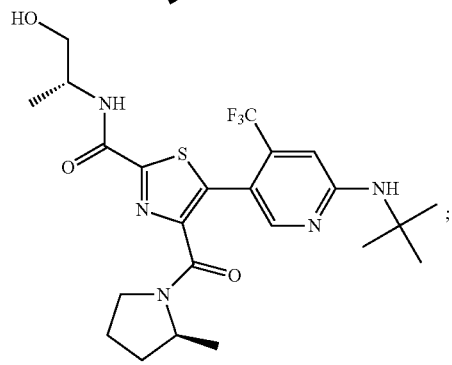
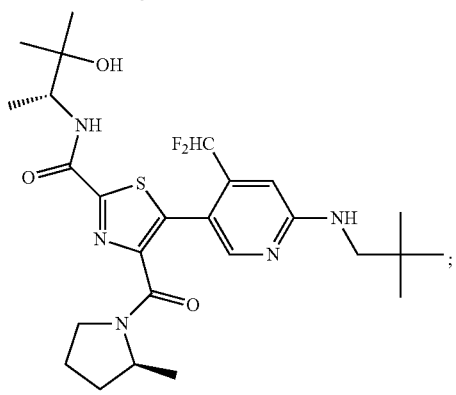
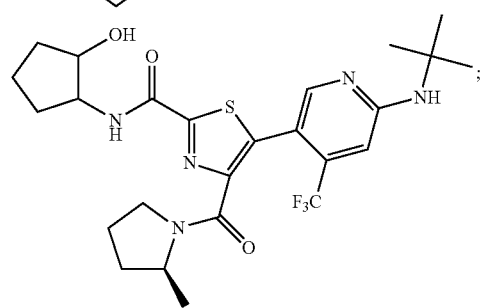
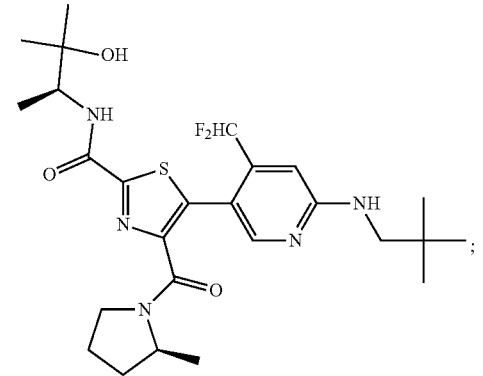
96
-continued
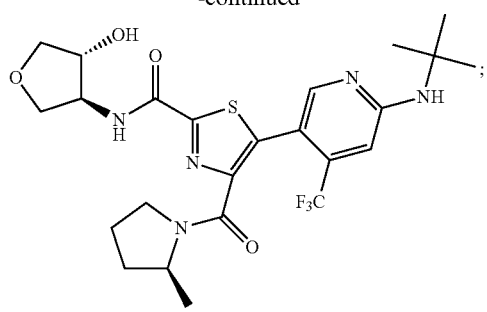
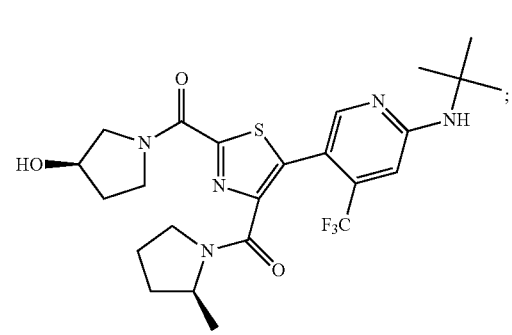
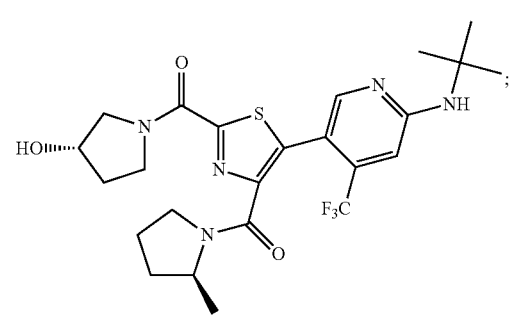
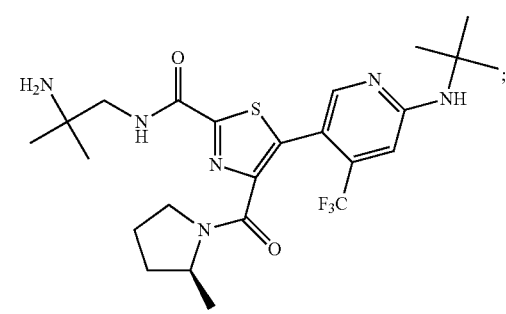
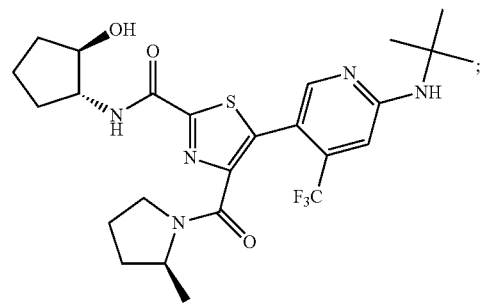

97
-continued
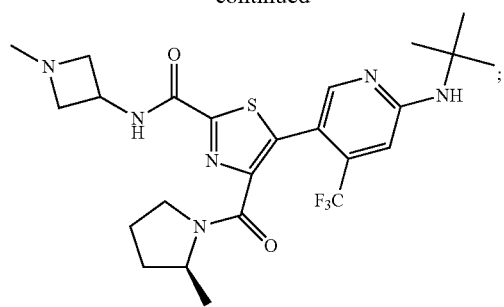
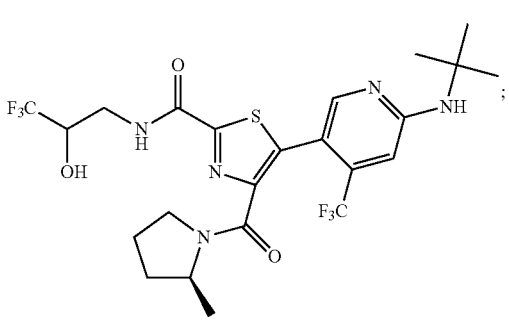
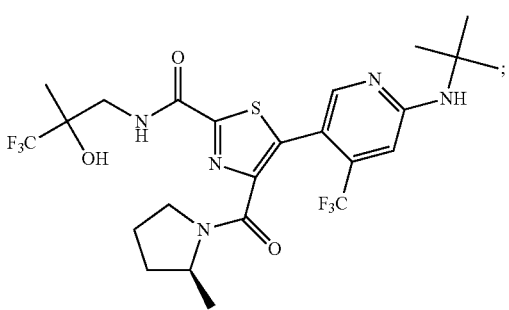
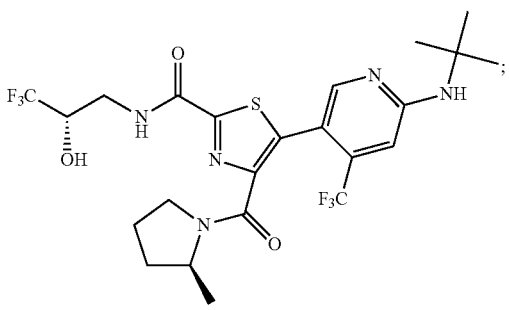
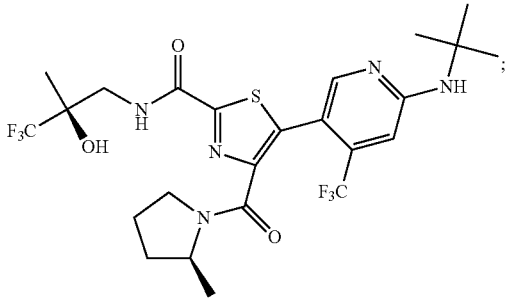
98
-continued
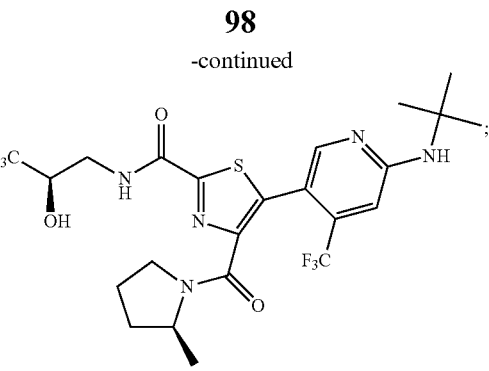
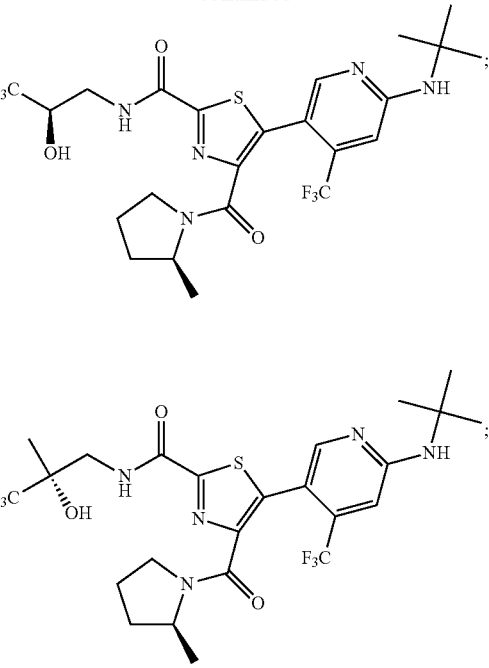
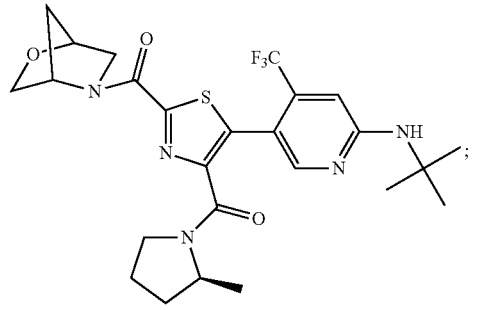
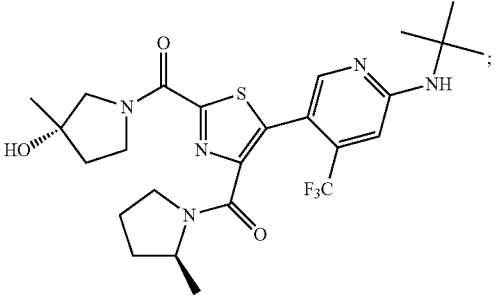
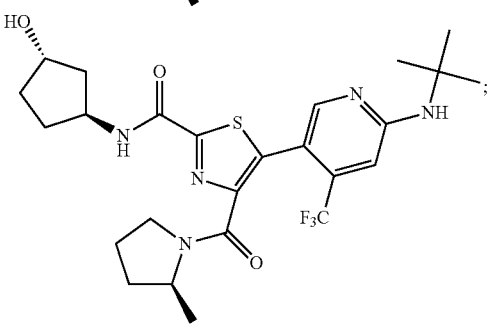

99
-continued
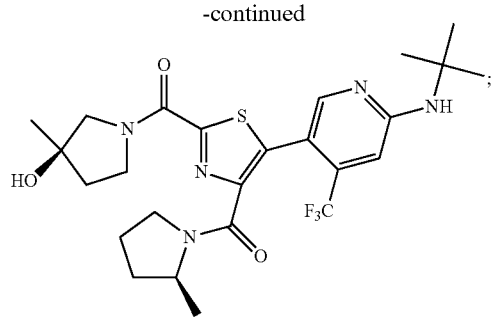
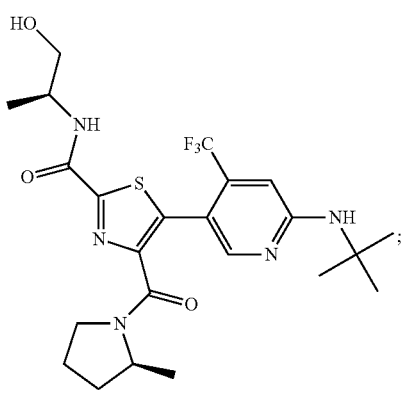
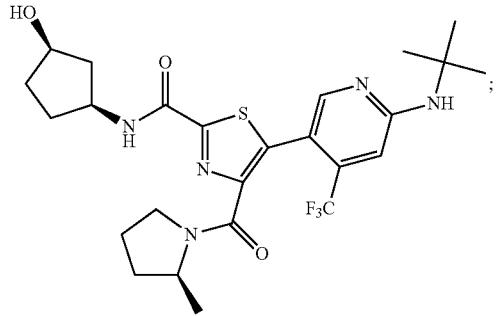
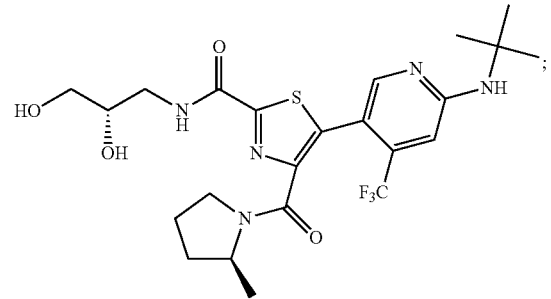
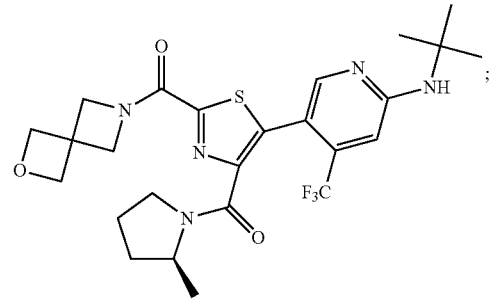
100
-continued
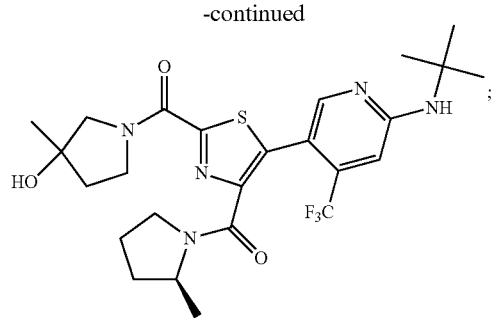
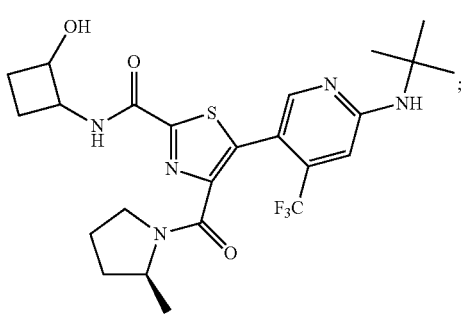
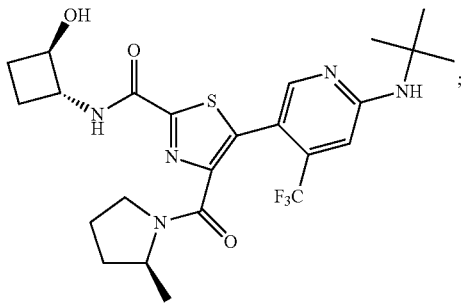
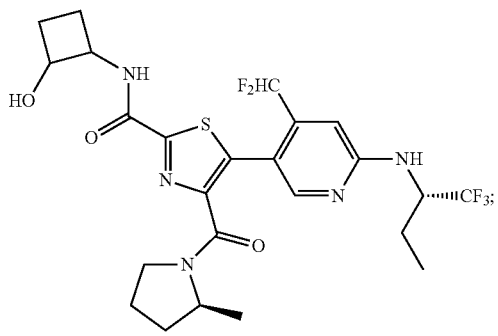
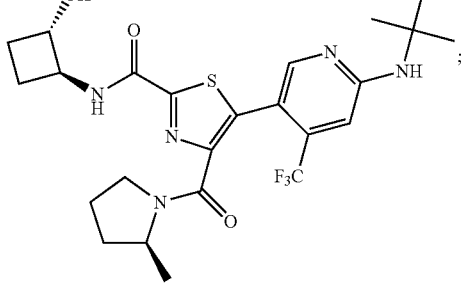

101
-continued
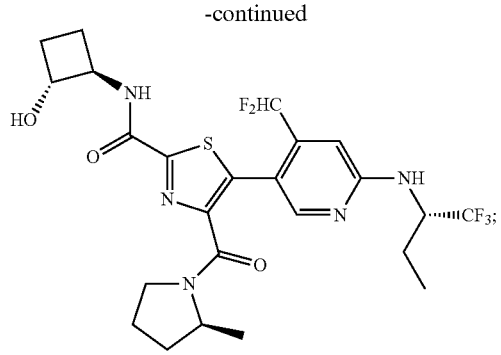
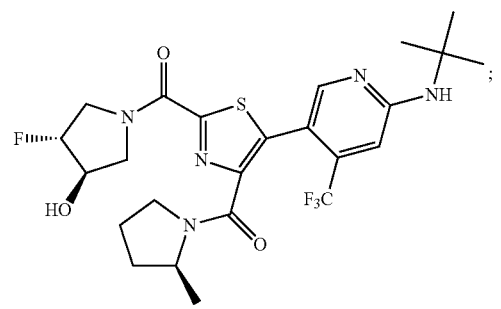
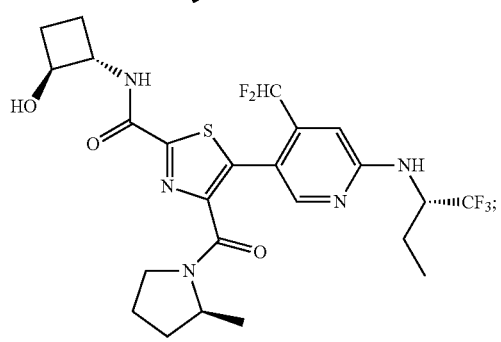
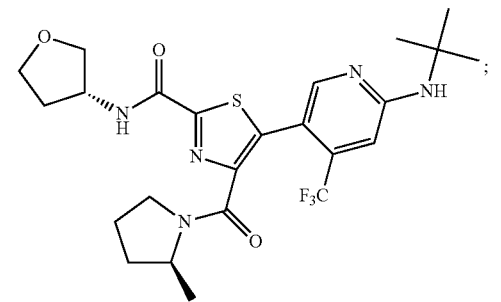
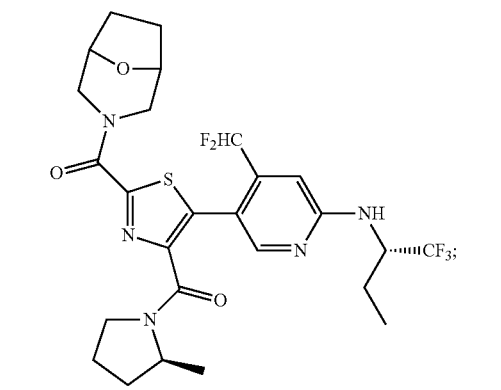
102
-continued
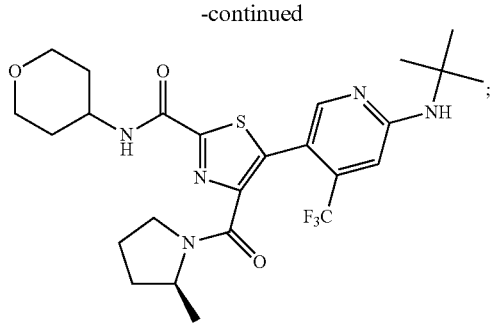
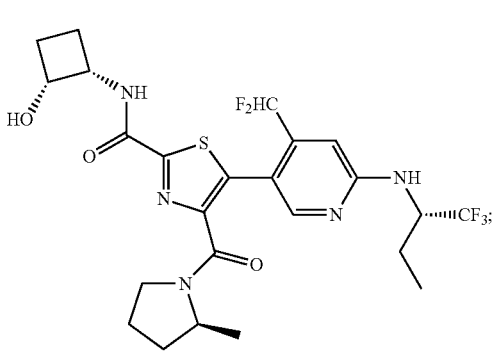
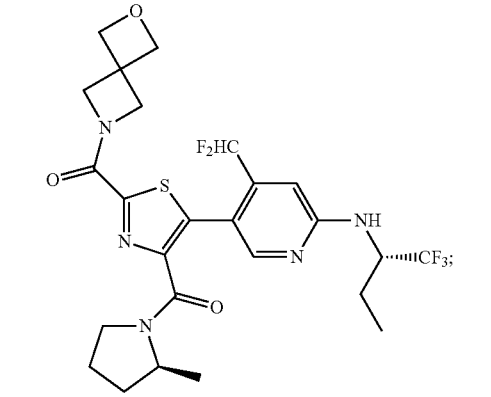
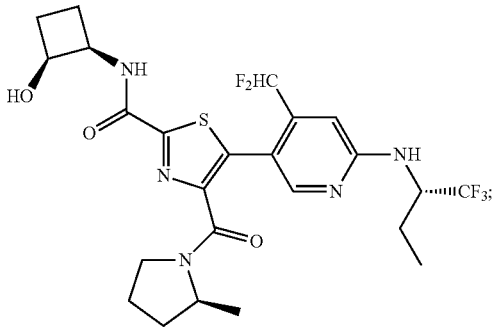

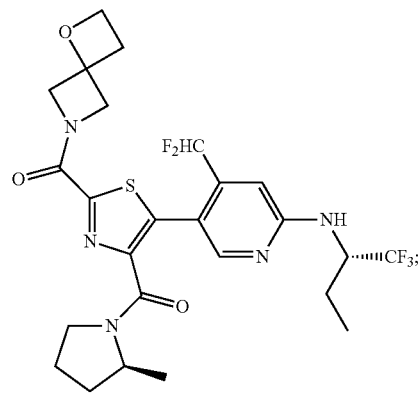
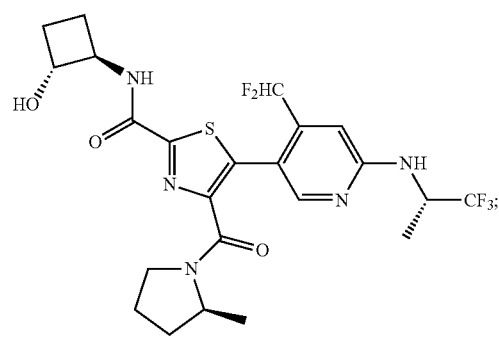
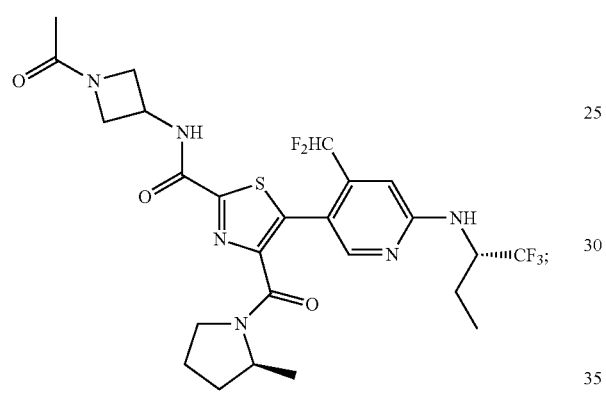
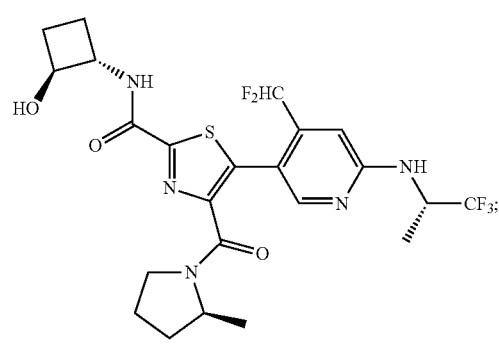
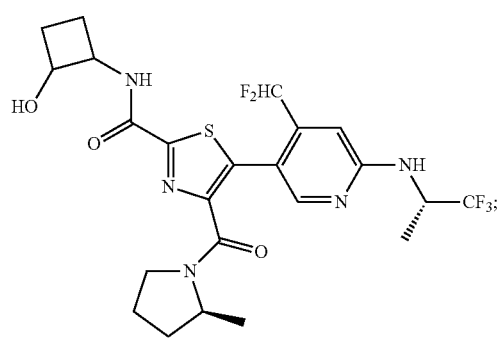
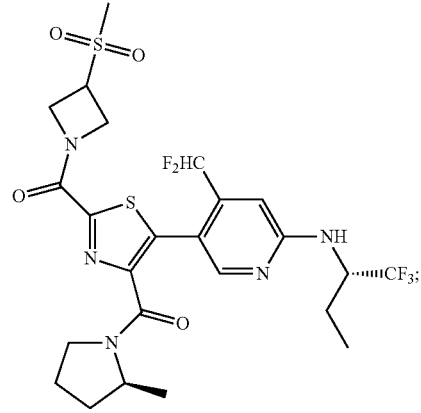
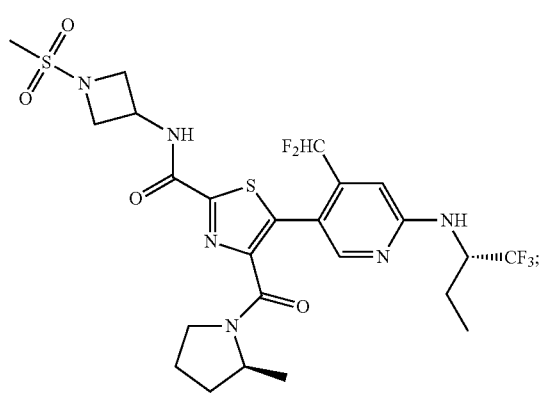
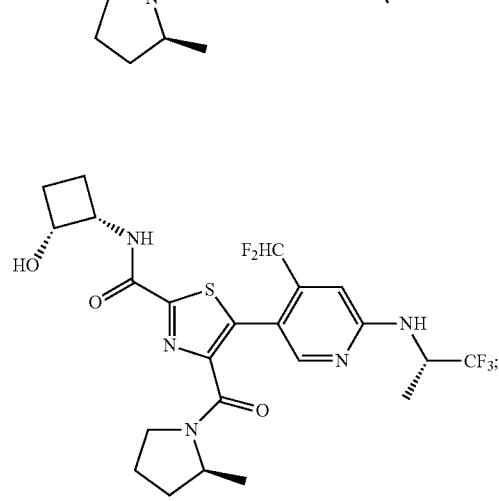

105
-continued
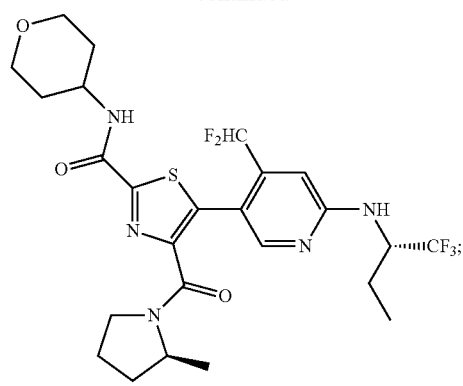
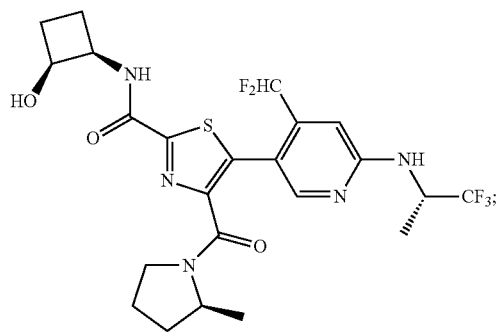
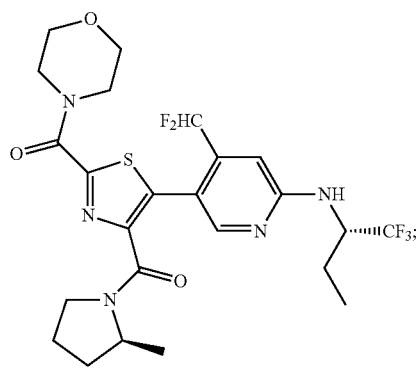
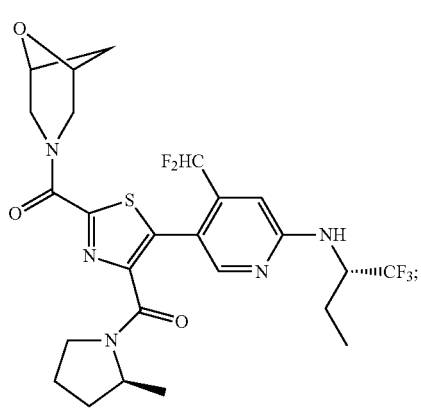
106
-continued
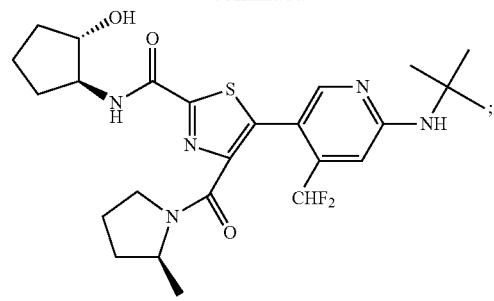
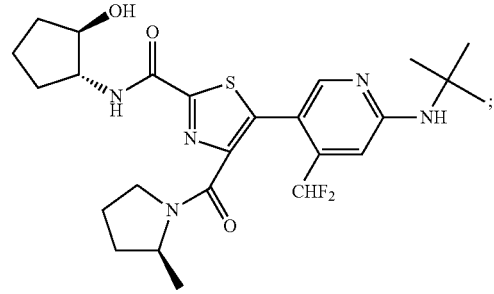
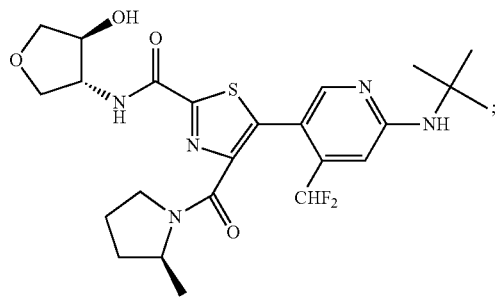
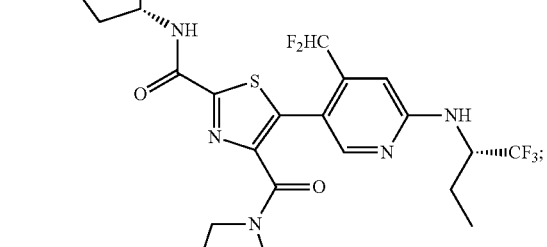
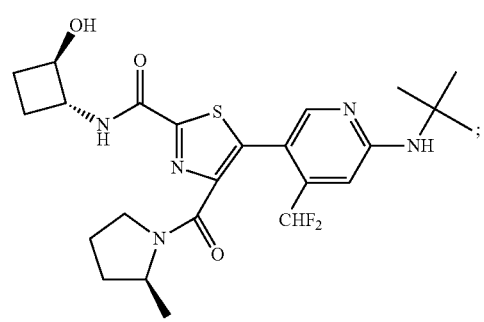

107
-continued
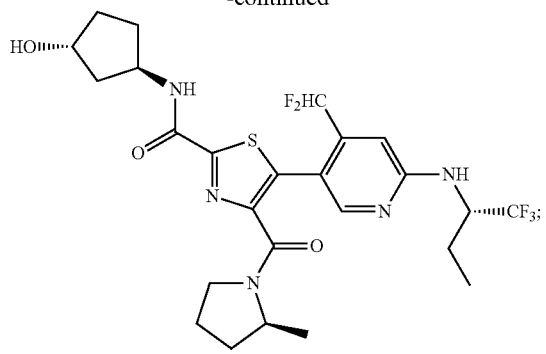
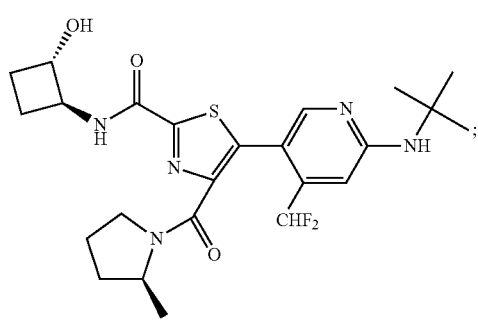
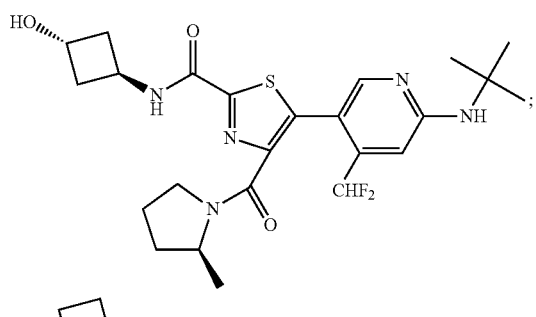
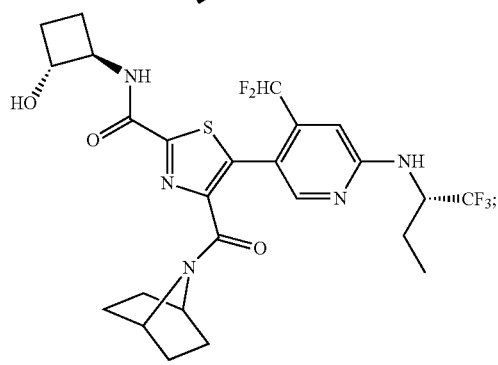
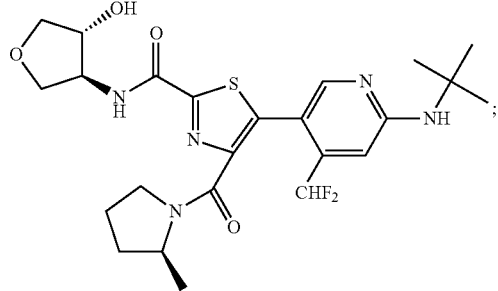
108
-continued
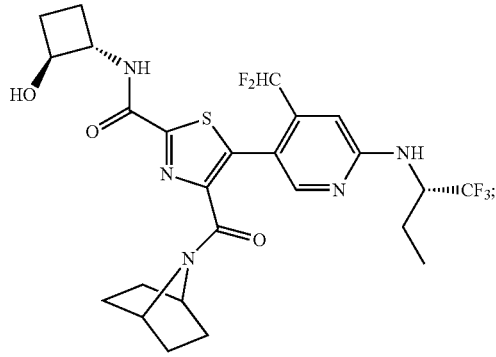
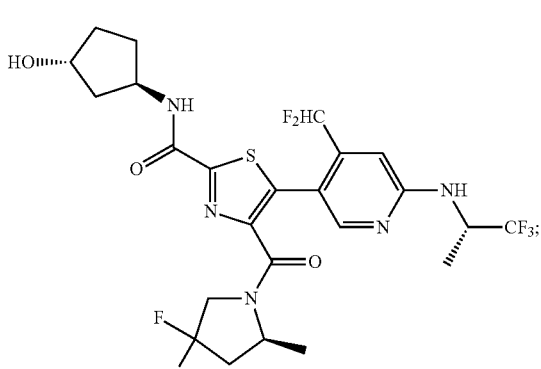
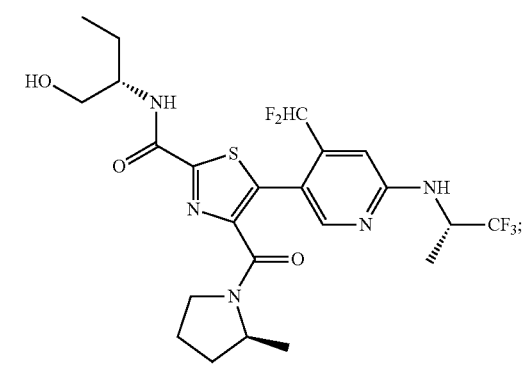
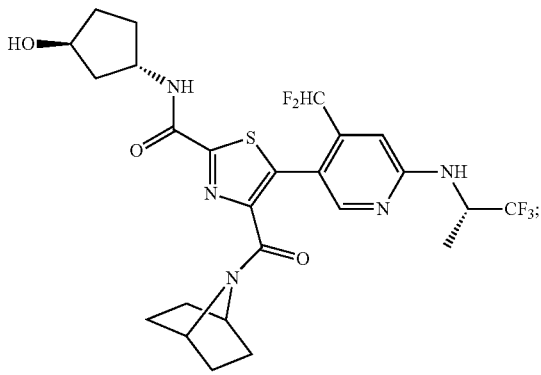

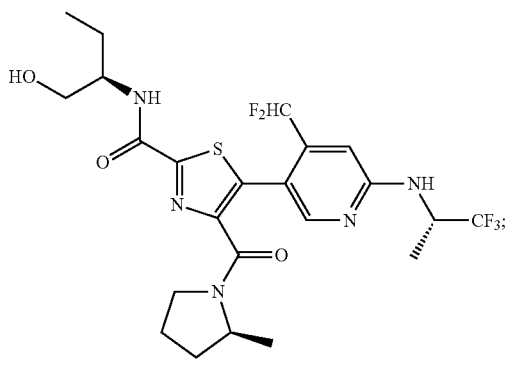
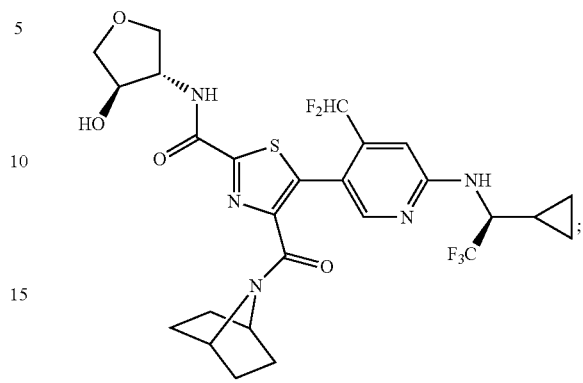
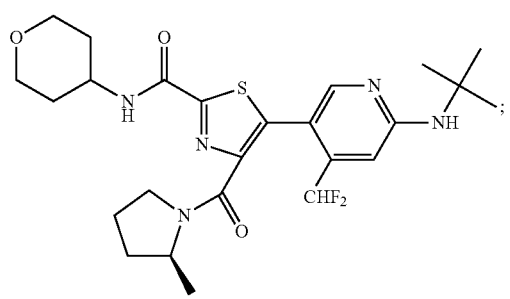
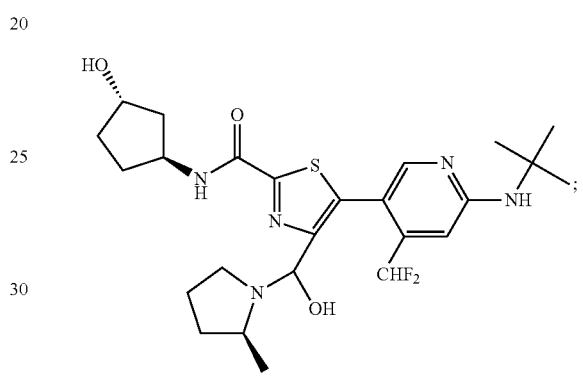
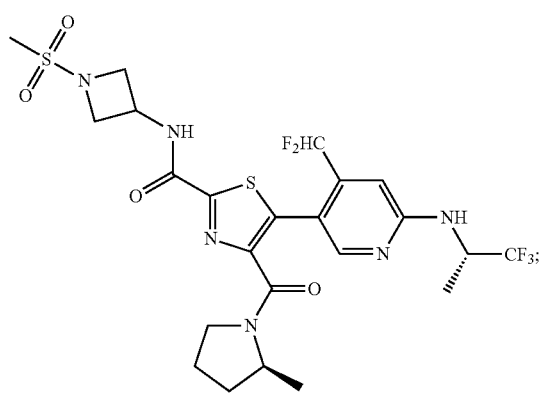
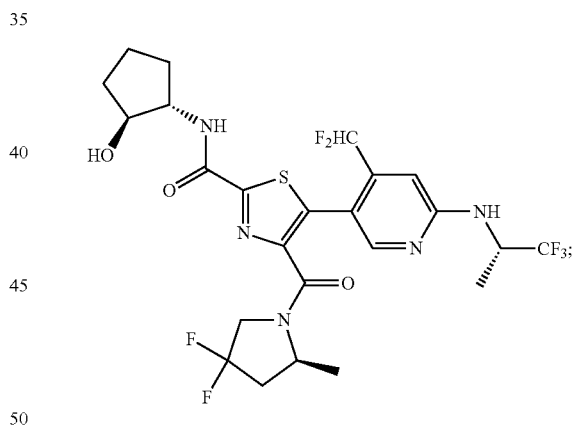
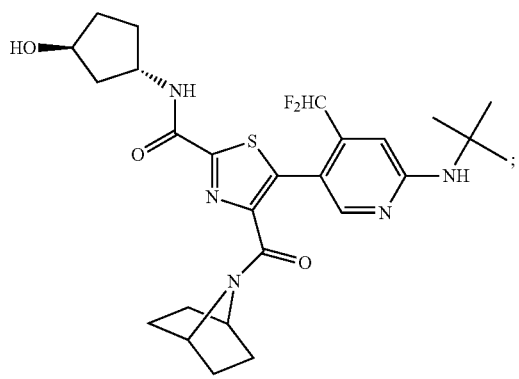
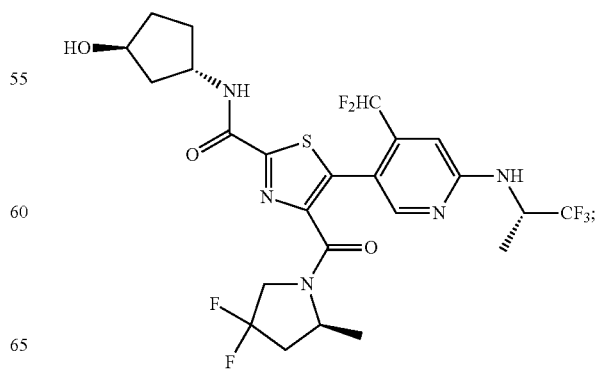

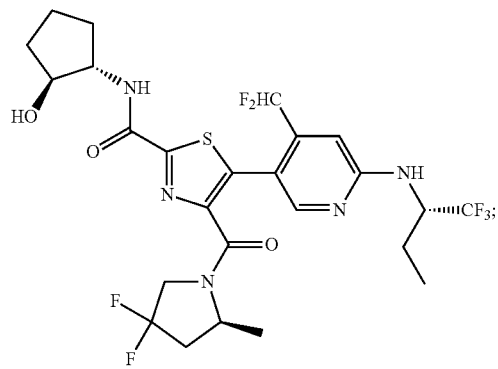
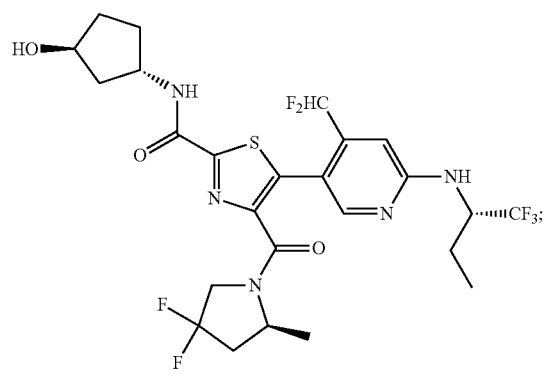
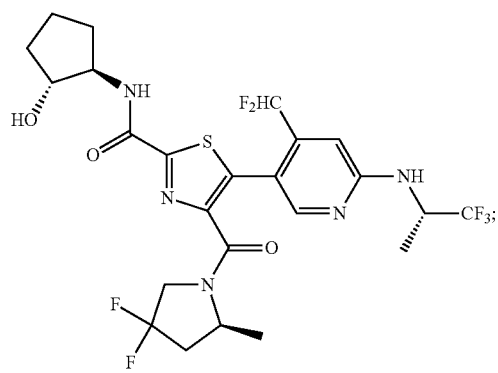
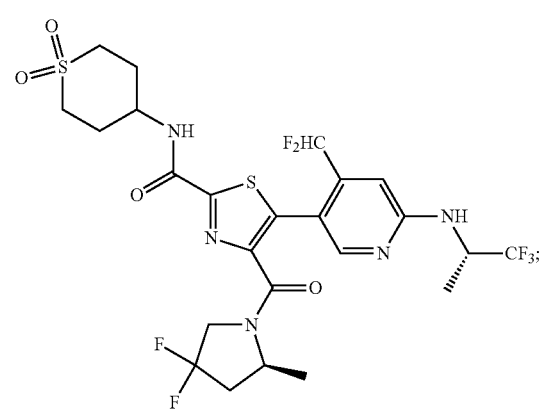
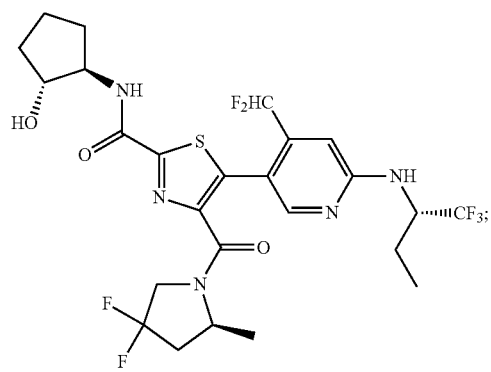
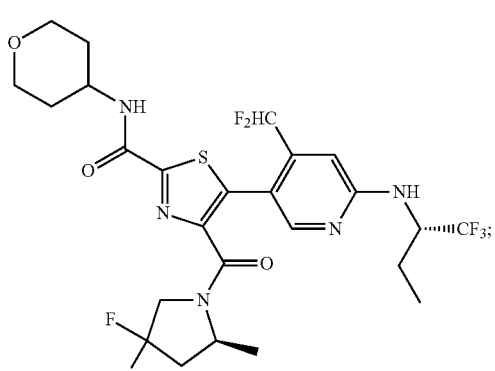
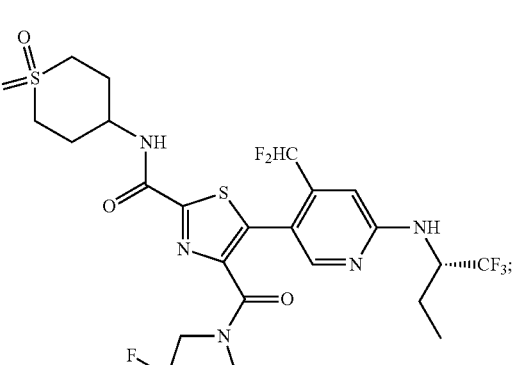
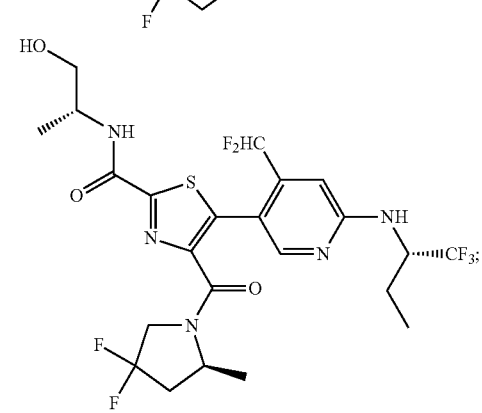

113
-continued
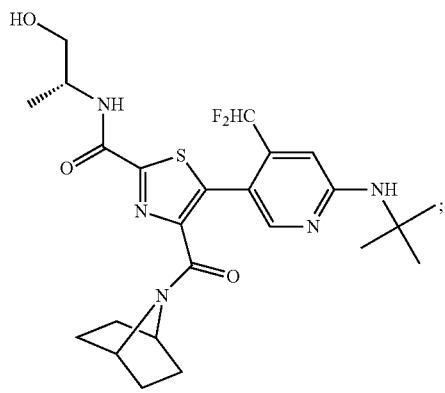
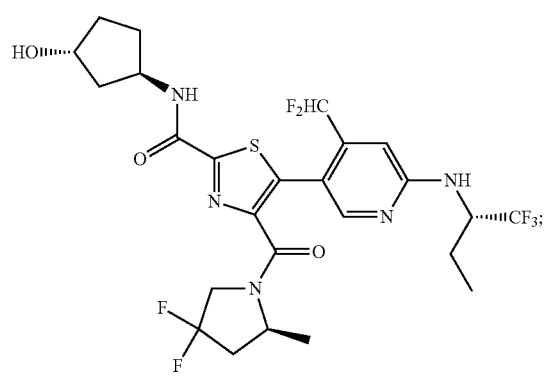
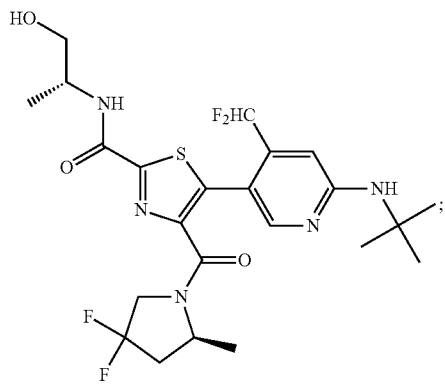
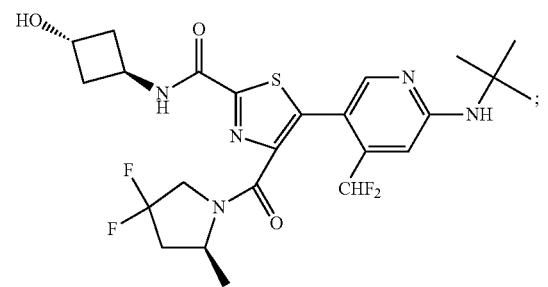
114
-continued
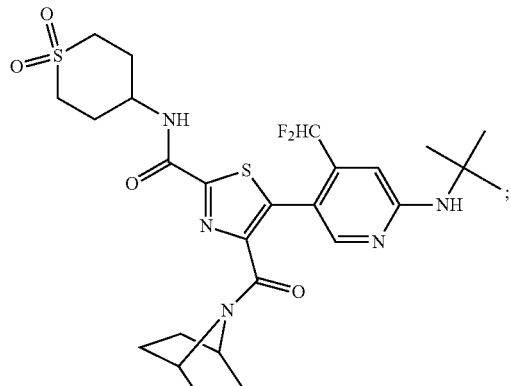
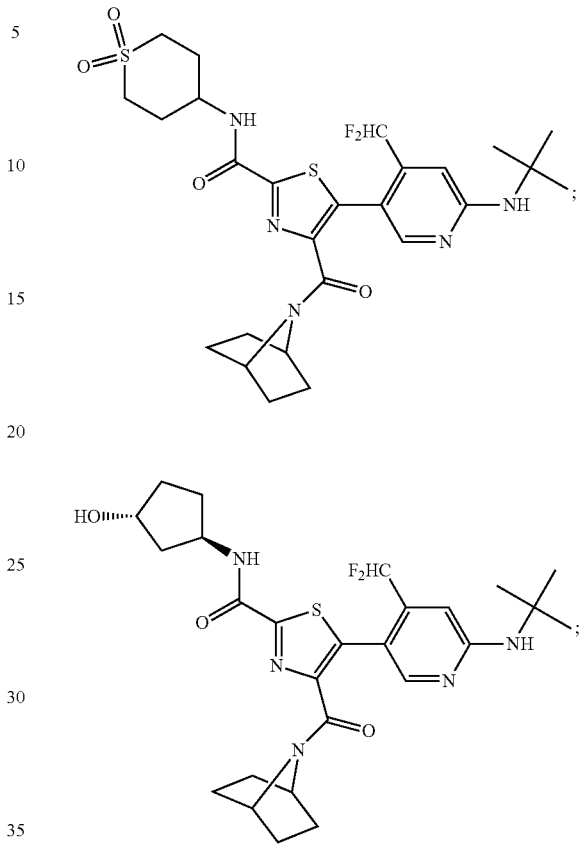
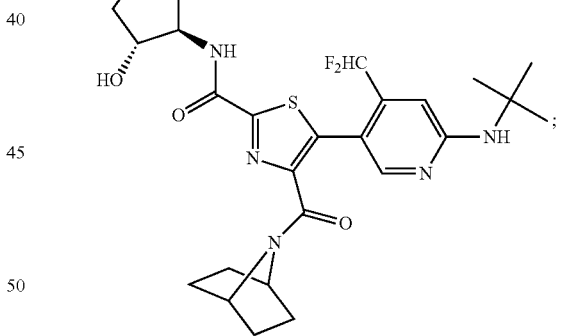
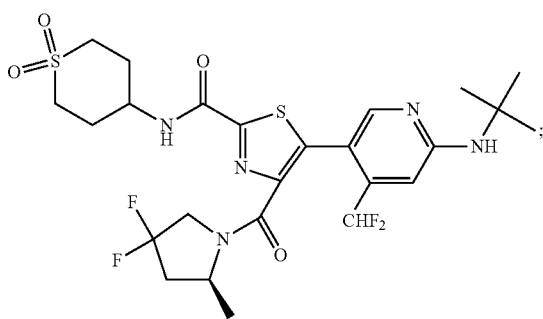

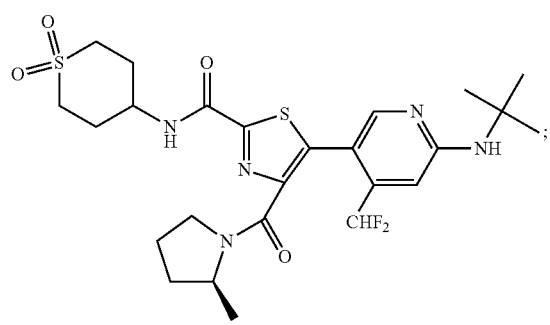
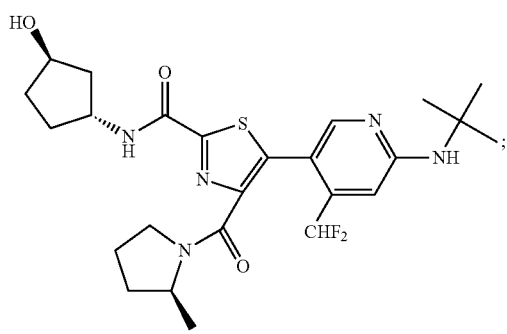
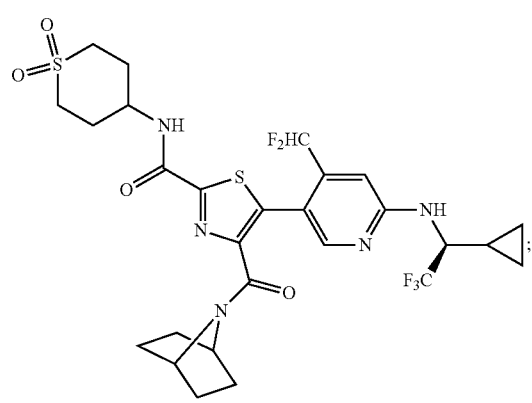
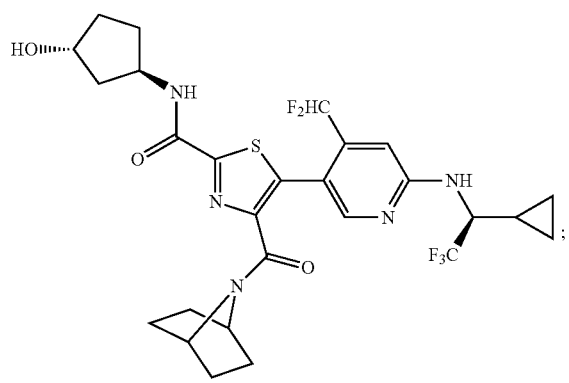
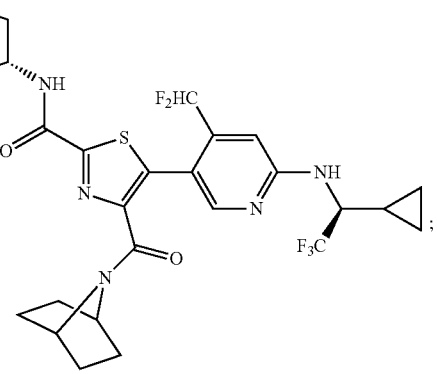
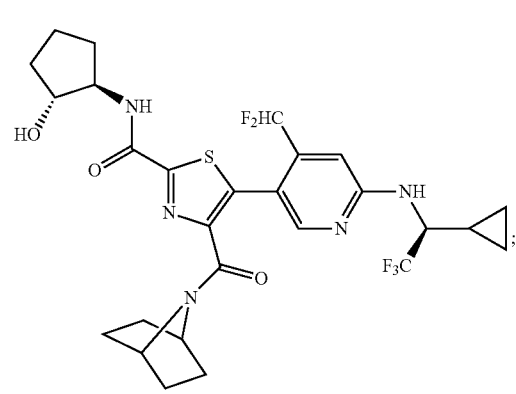

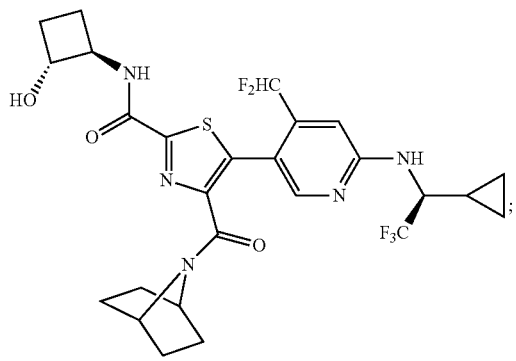
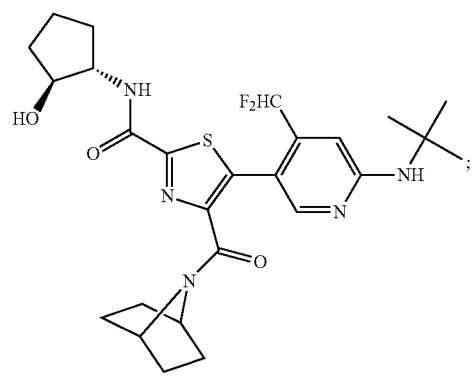
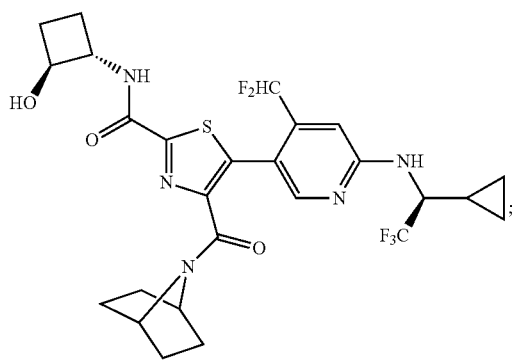
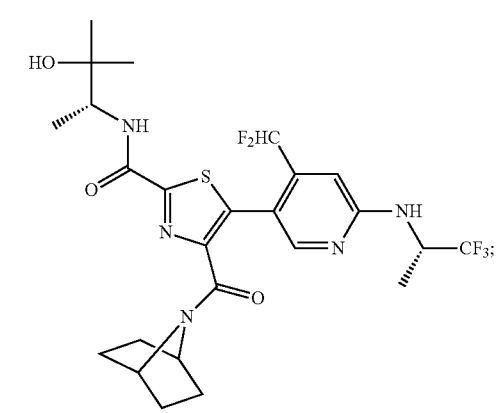
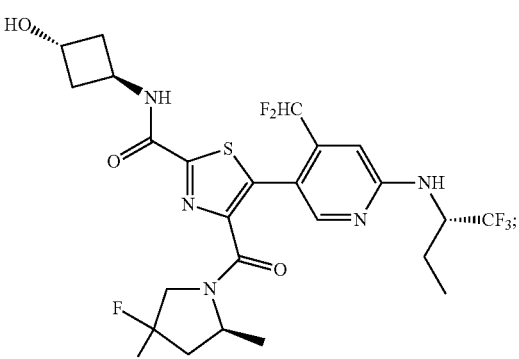
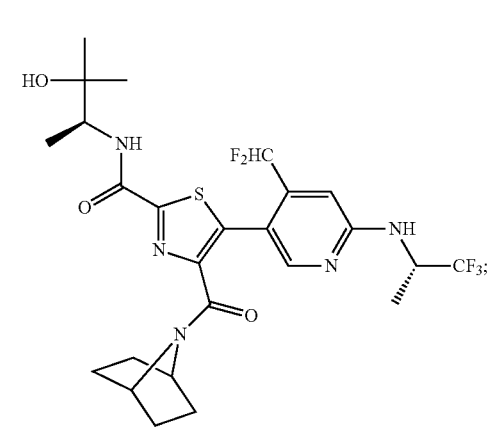
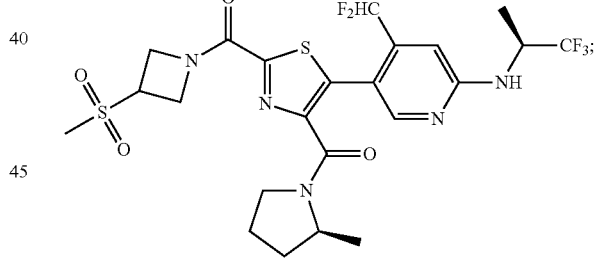
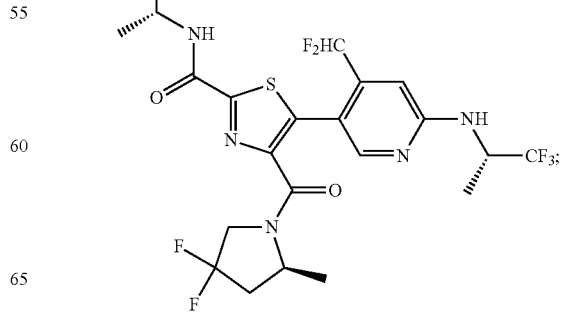

119
-continued
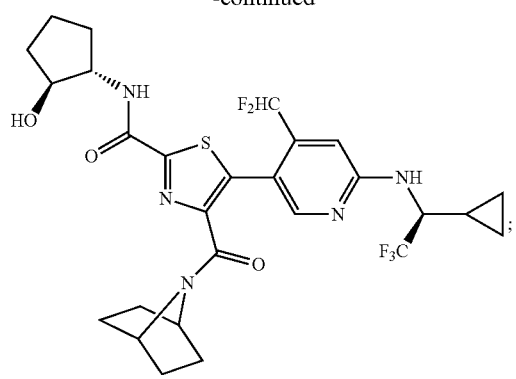
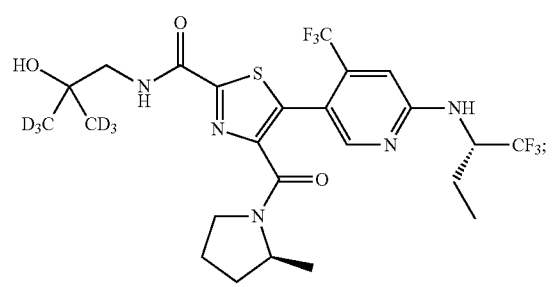
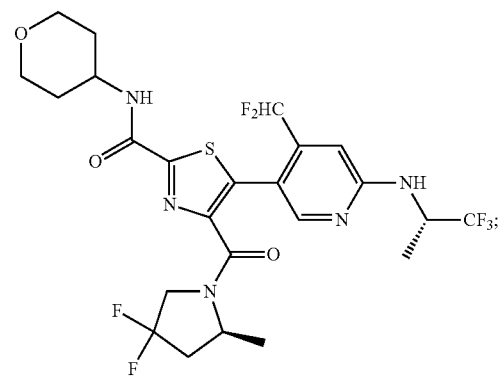
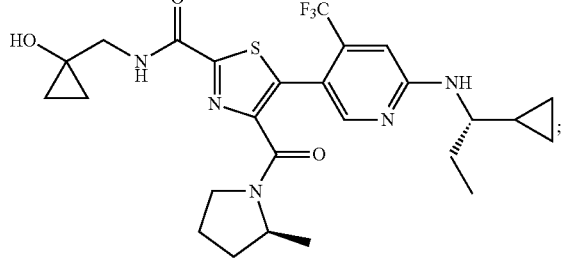
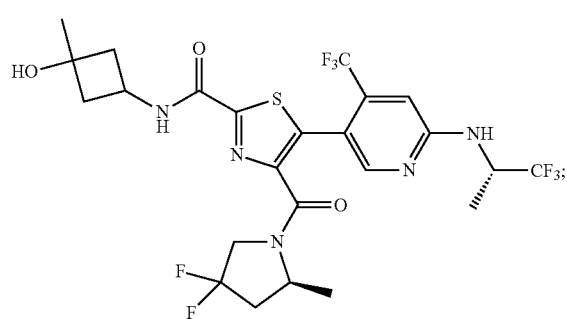
120
-continued
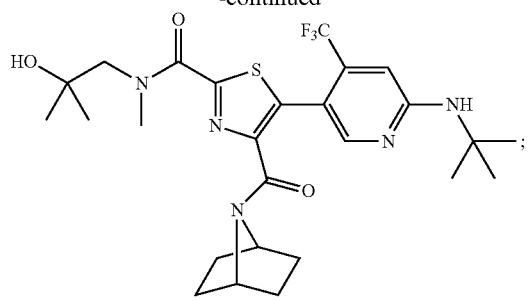
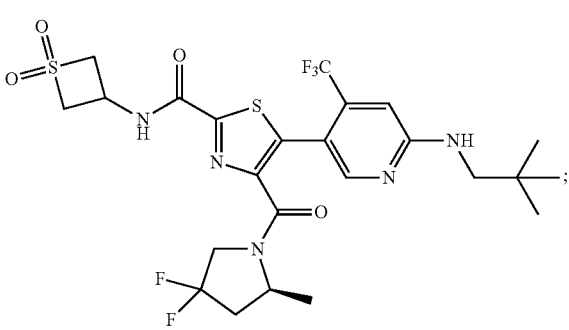
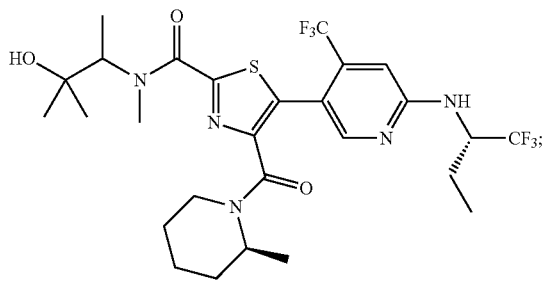
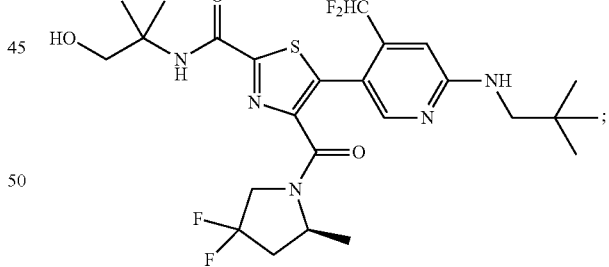
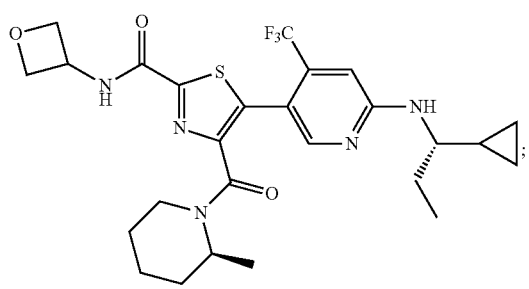

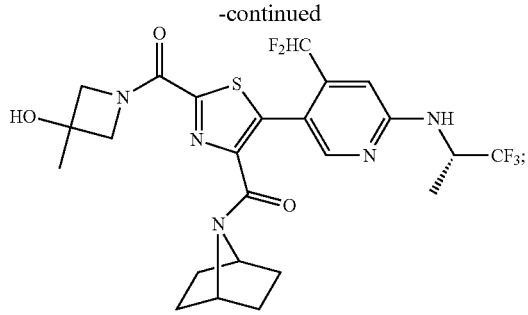
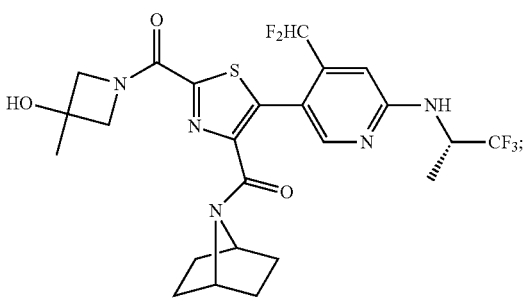
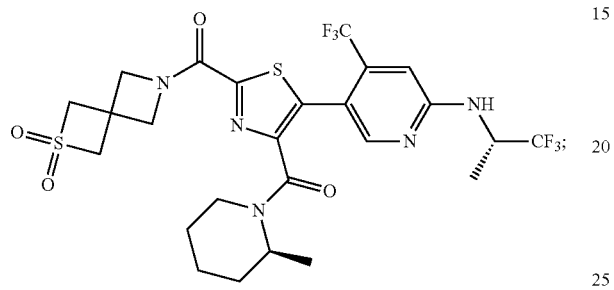
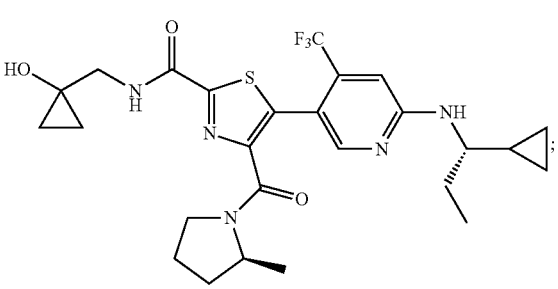
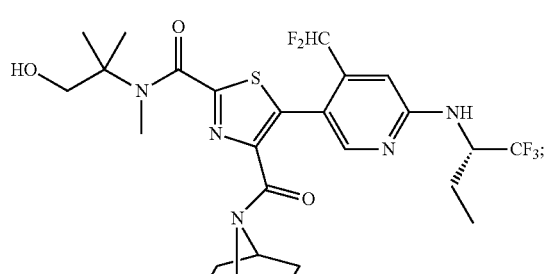
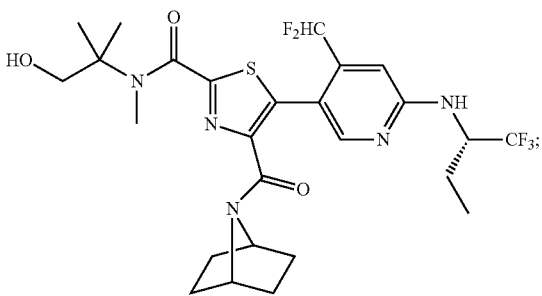
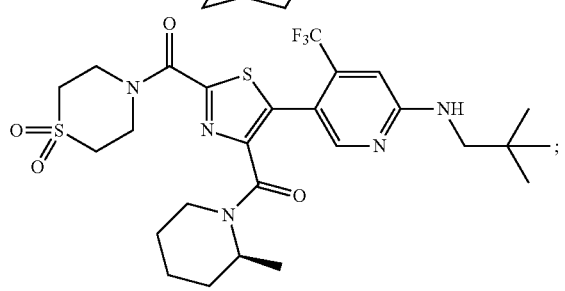
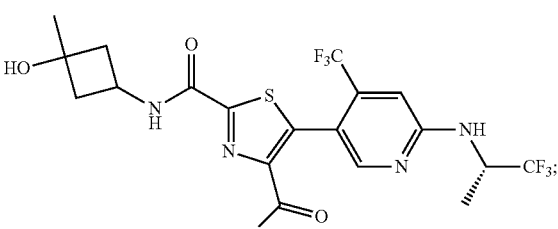
and pharmaceutically acceptable salts thereof.
Another embodiment of the invention is a compound selected from the group consisting of:
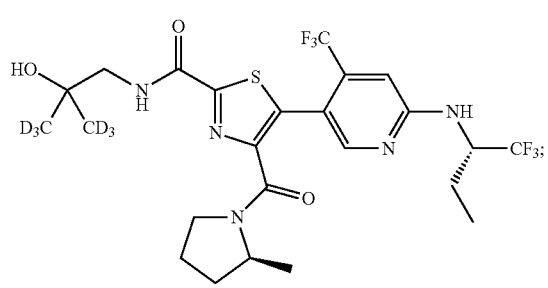
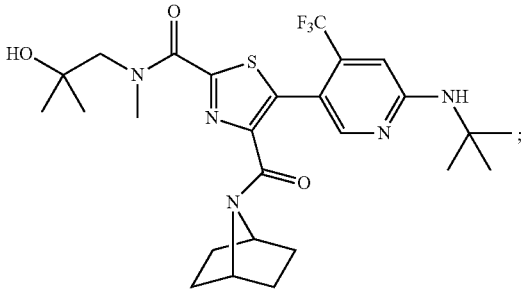

-continued
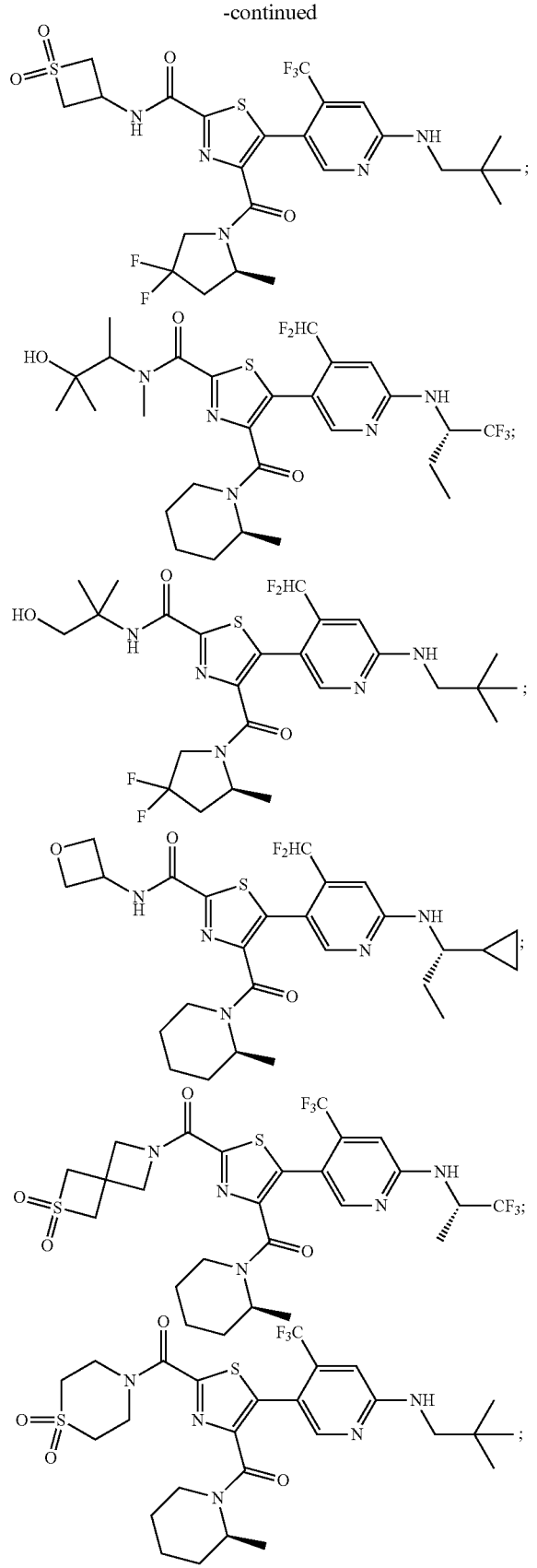
and pharmaceutically acceptable salts thereof.
Another embodiment of the invention is a compound selected from the group consisting of:
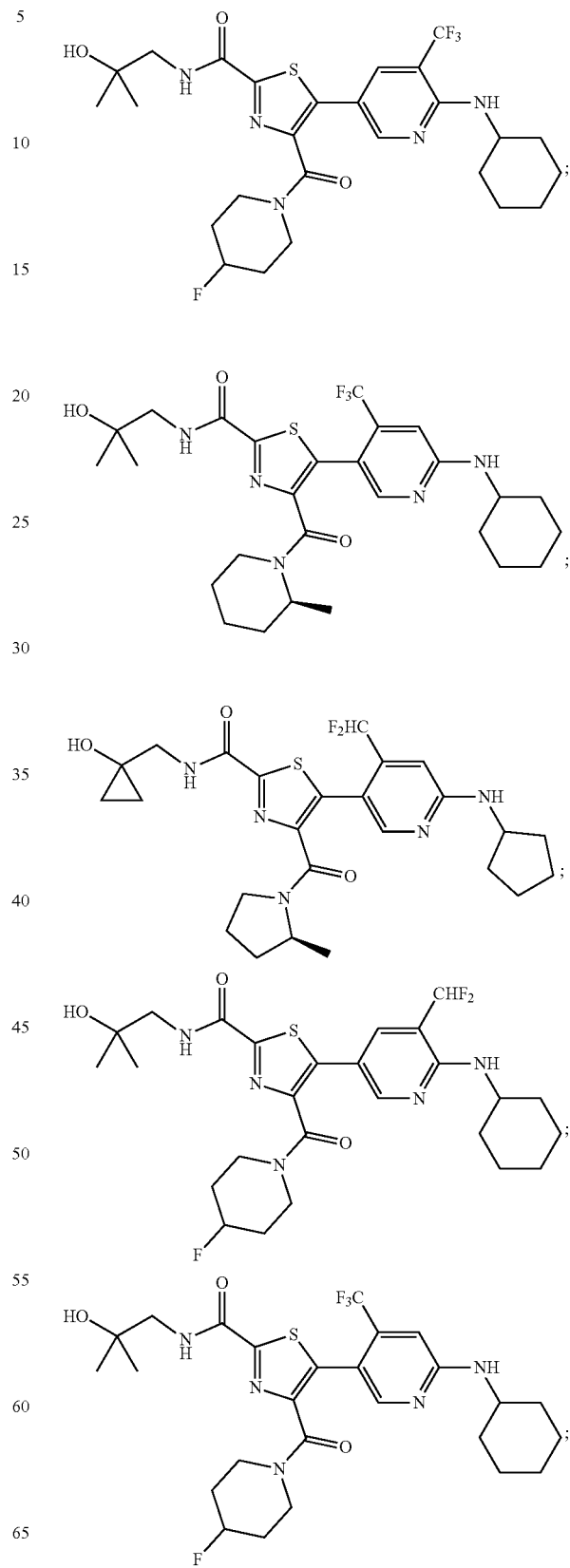

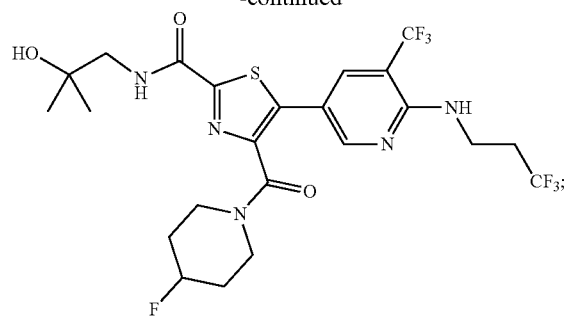
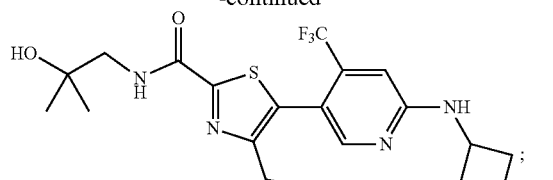

127
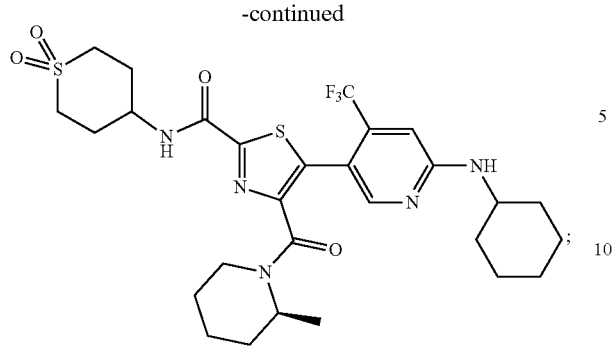
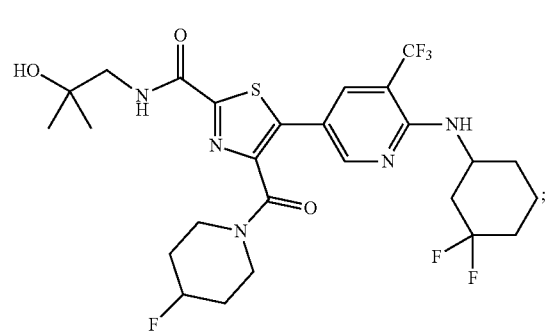
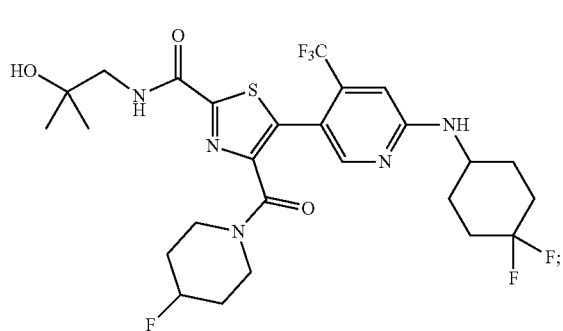
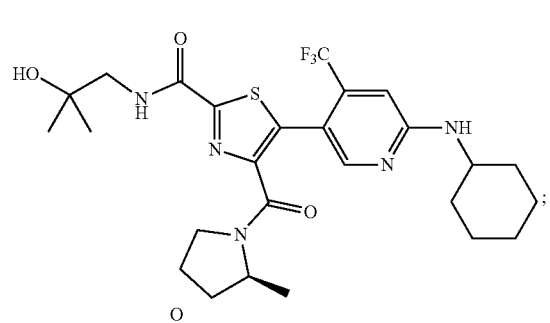
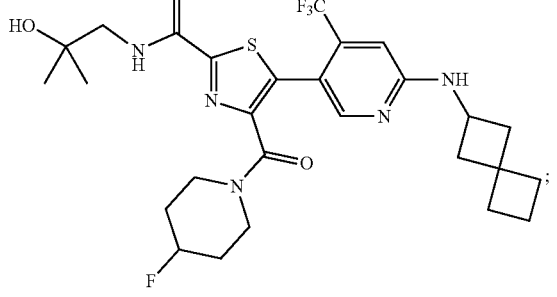
128
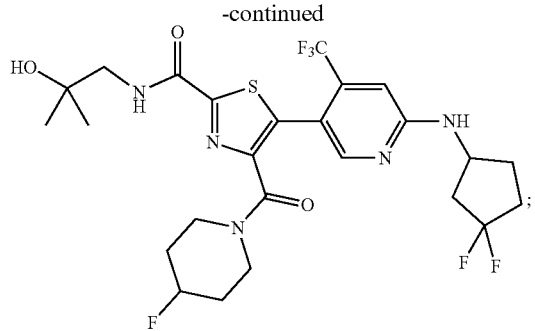
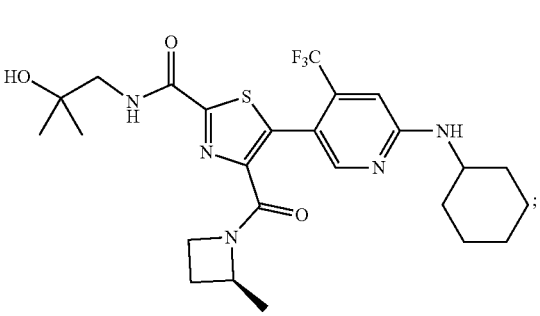
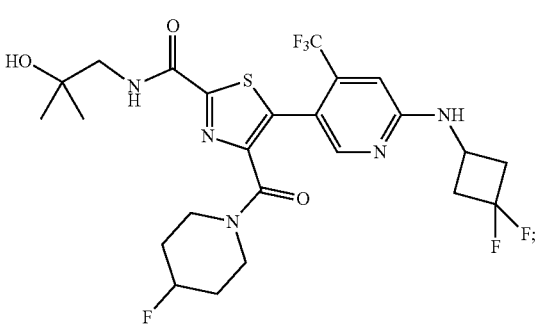
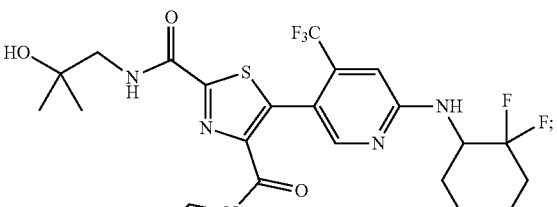
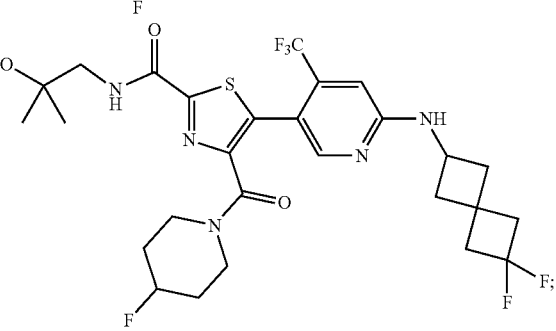

129
-continued
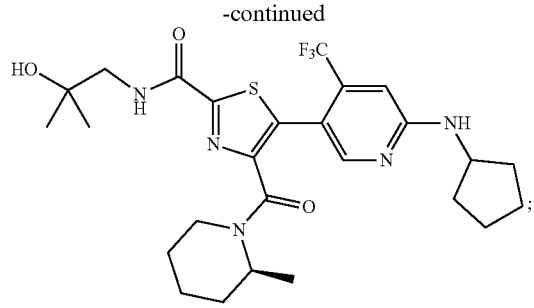
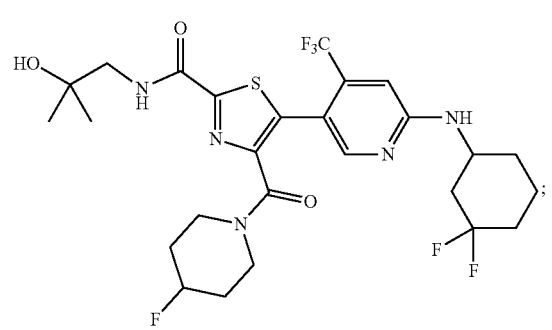
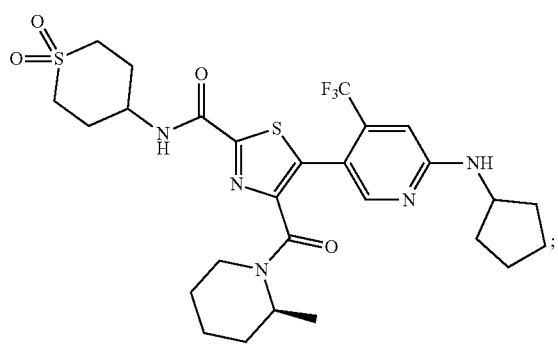
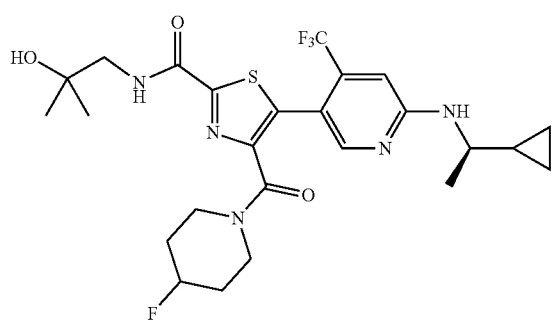
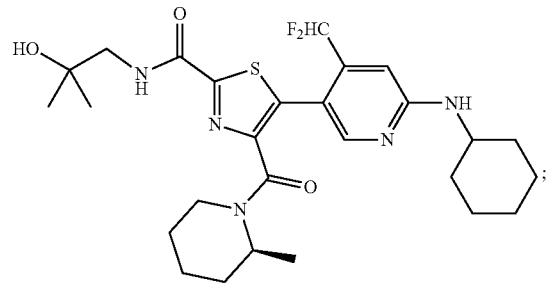
130
-continued
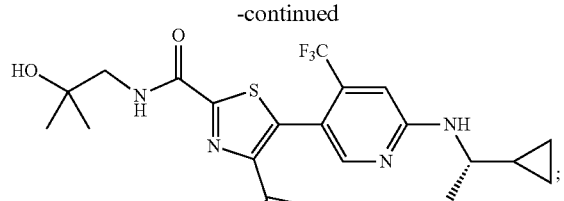

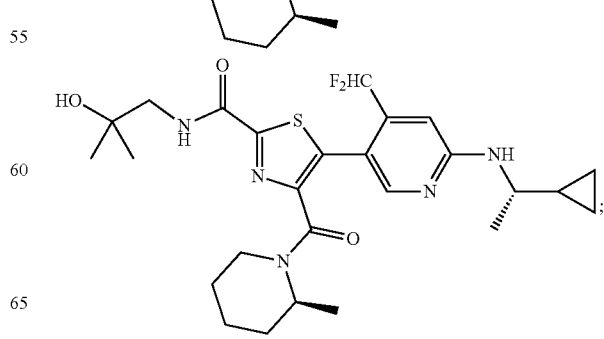

131
-continued
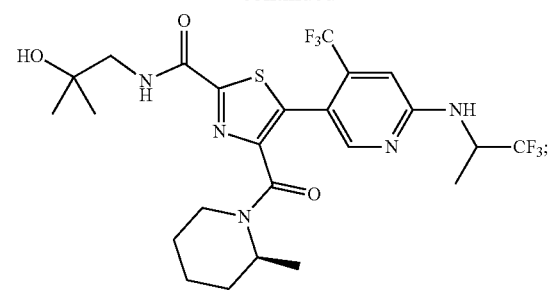
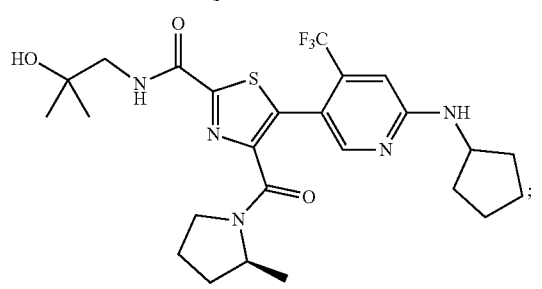
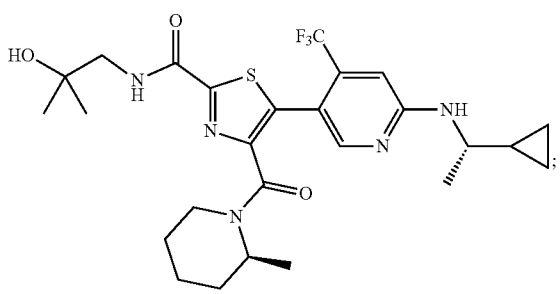
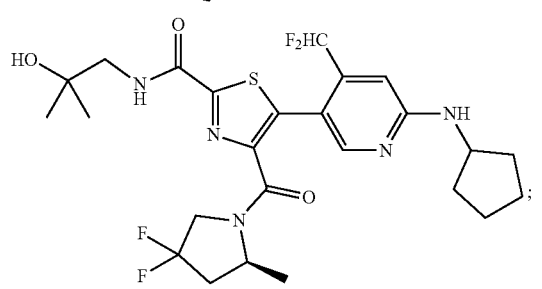
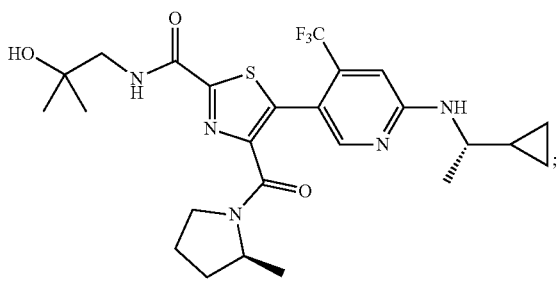
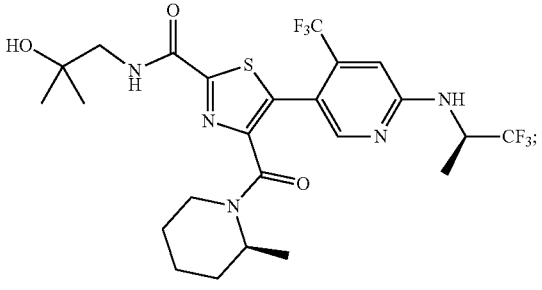
132
-continued
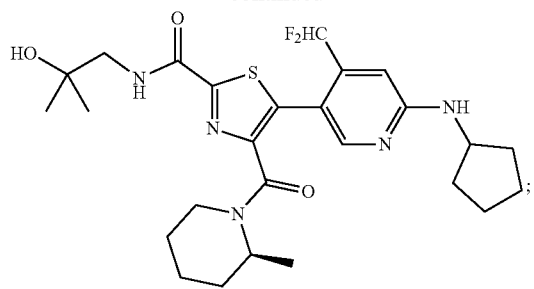
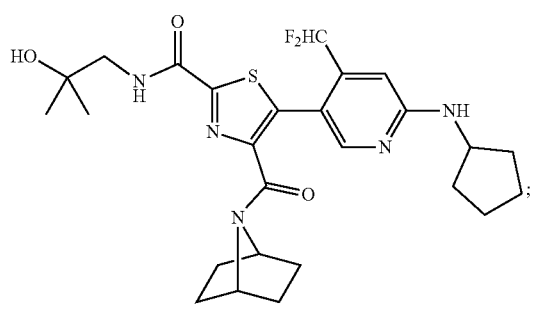
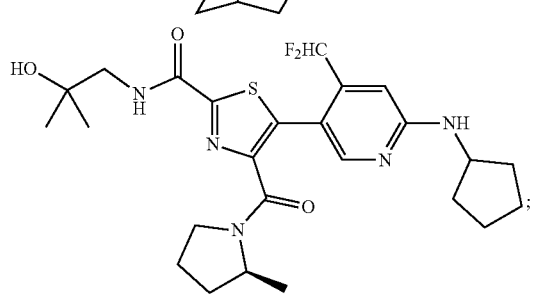
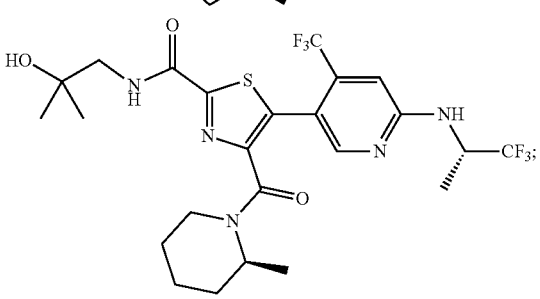
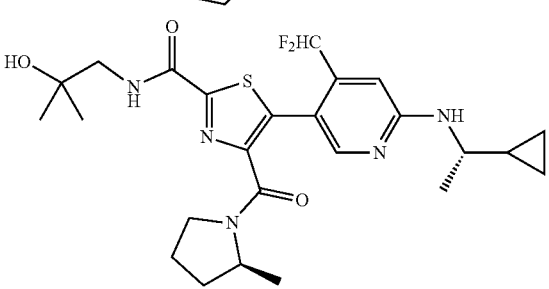
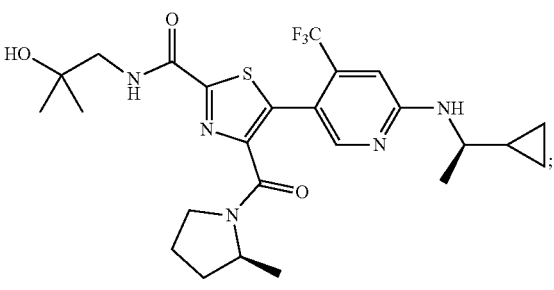

133
-continued
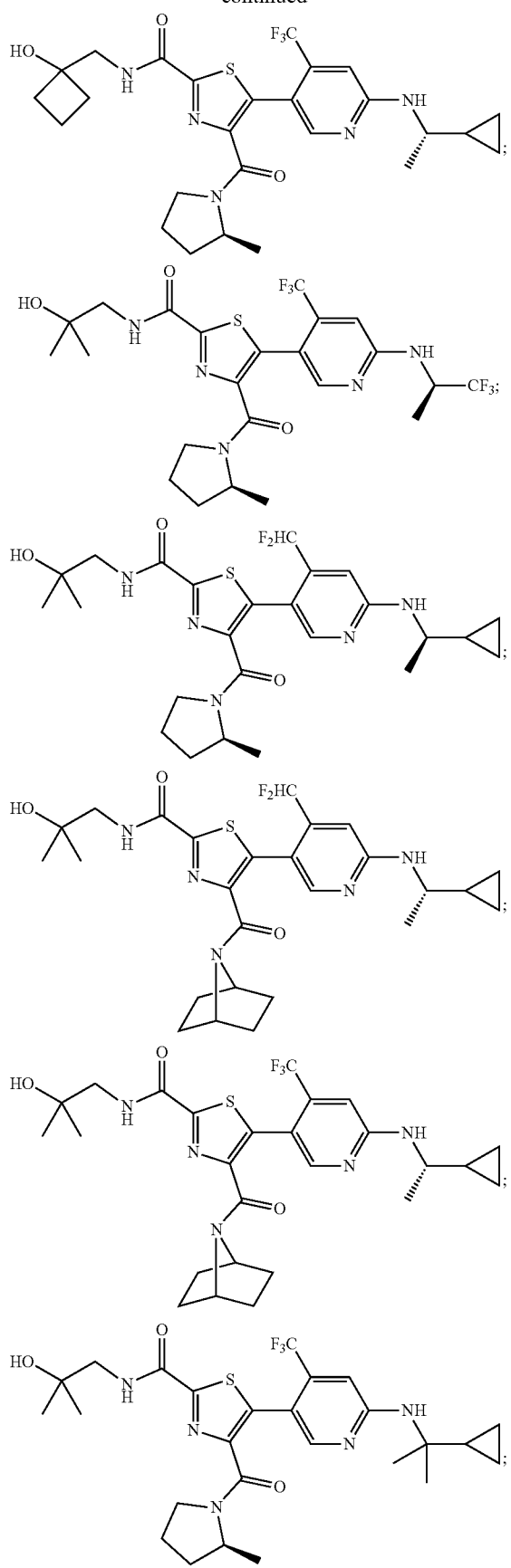
134
-continued
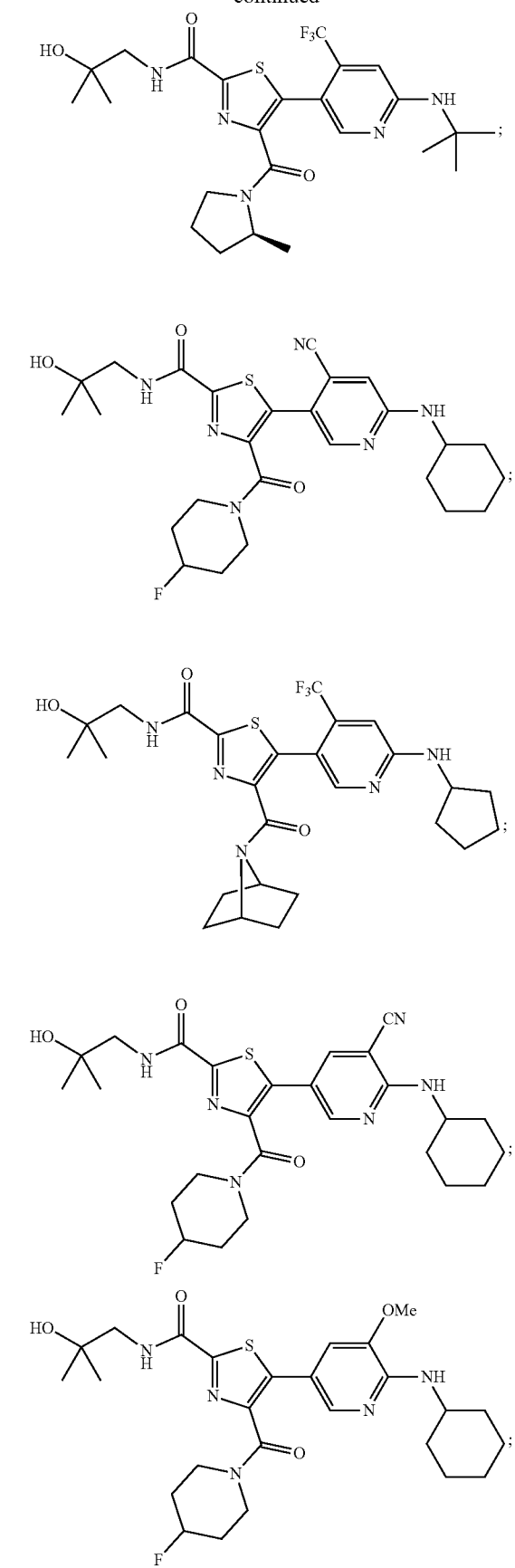

135
-continued
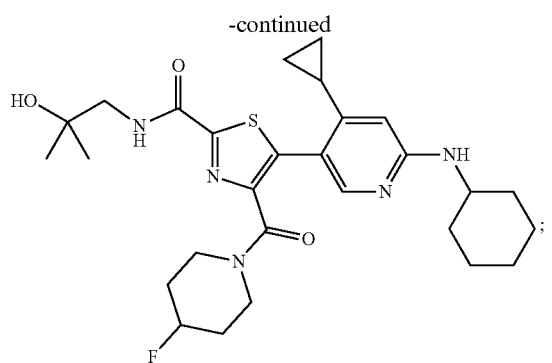
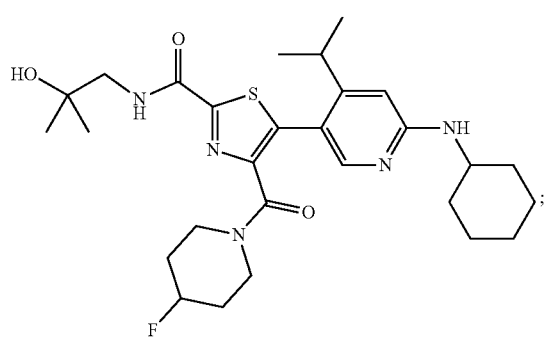
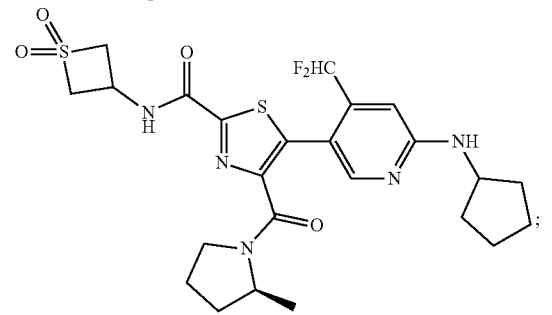
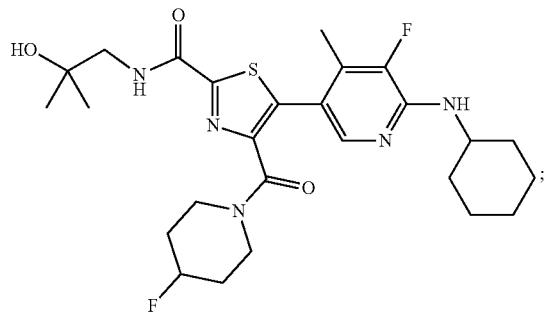
136
-continued
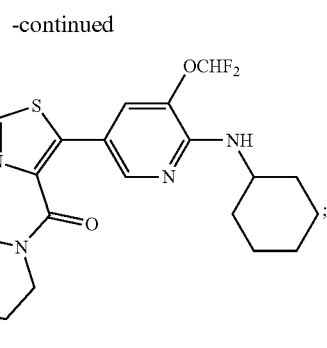
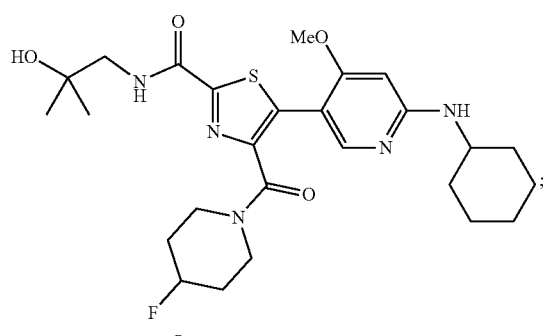
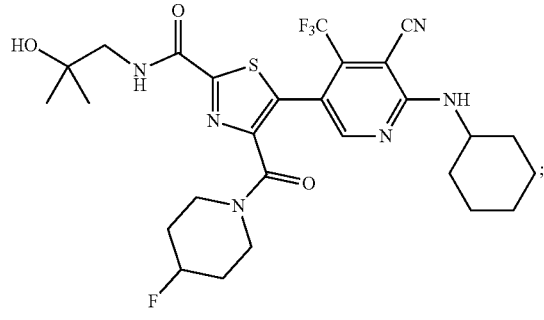
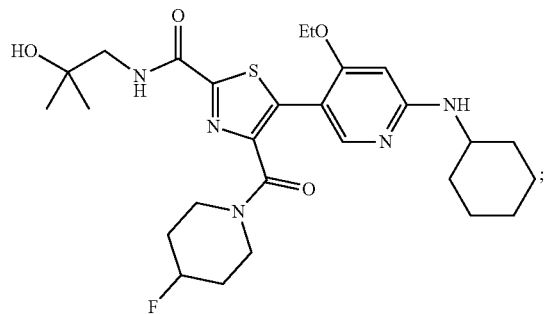

137
-continued
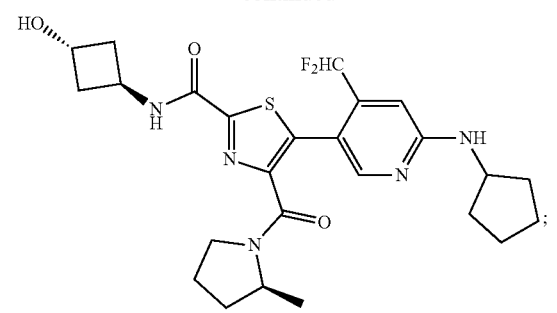
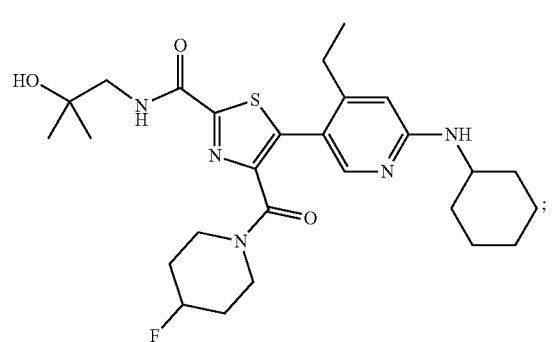
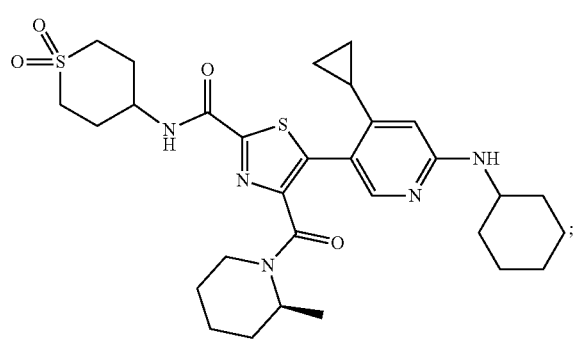
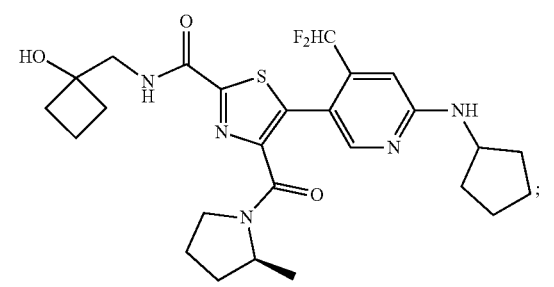
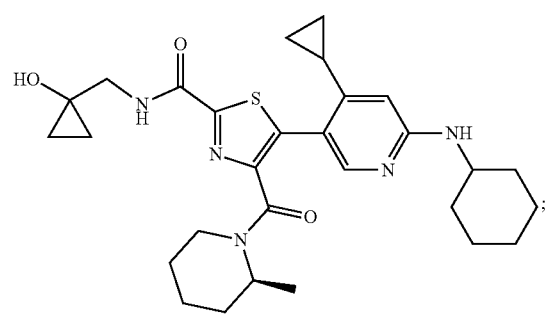
138
-continued
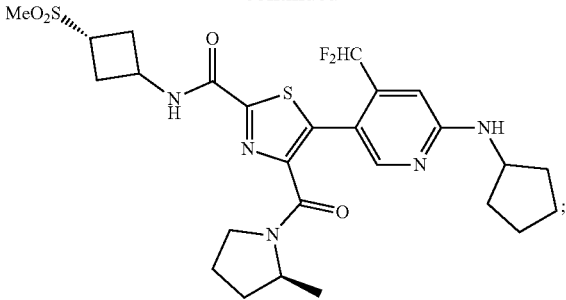
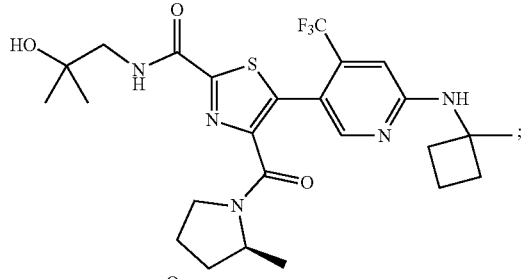
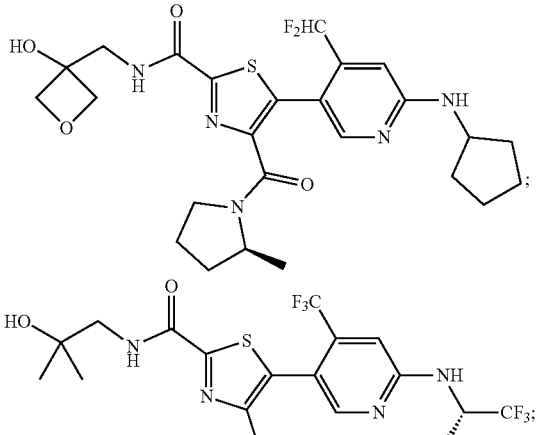
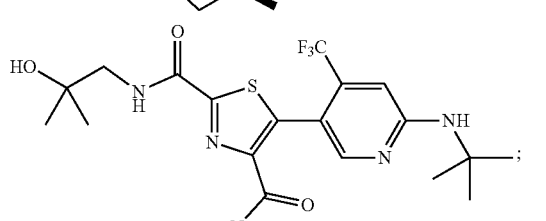
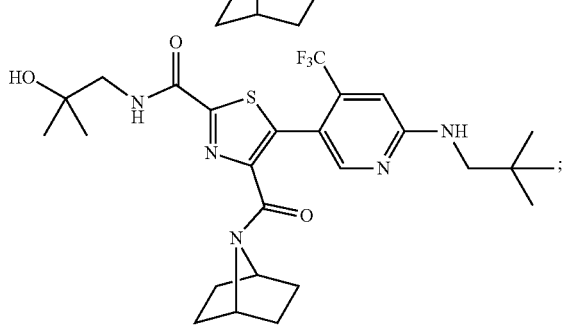

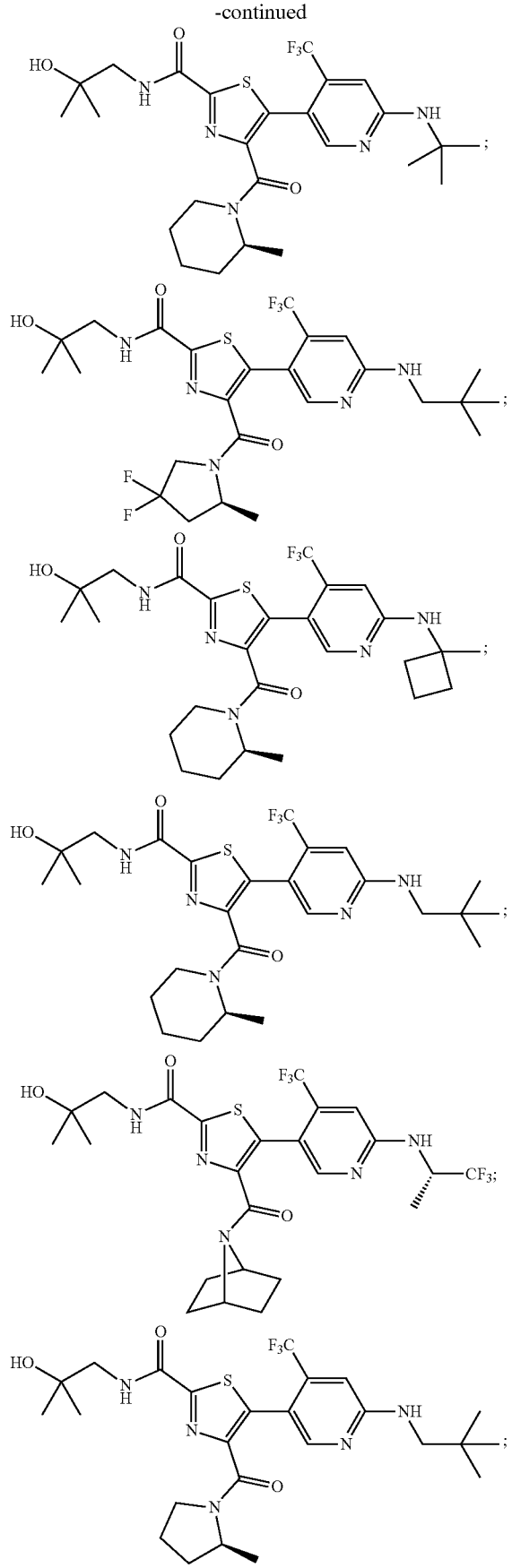
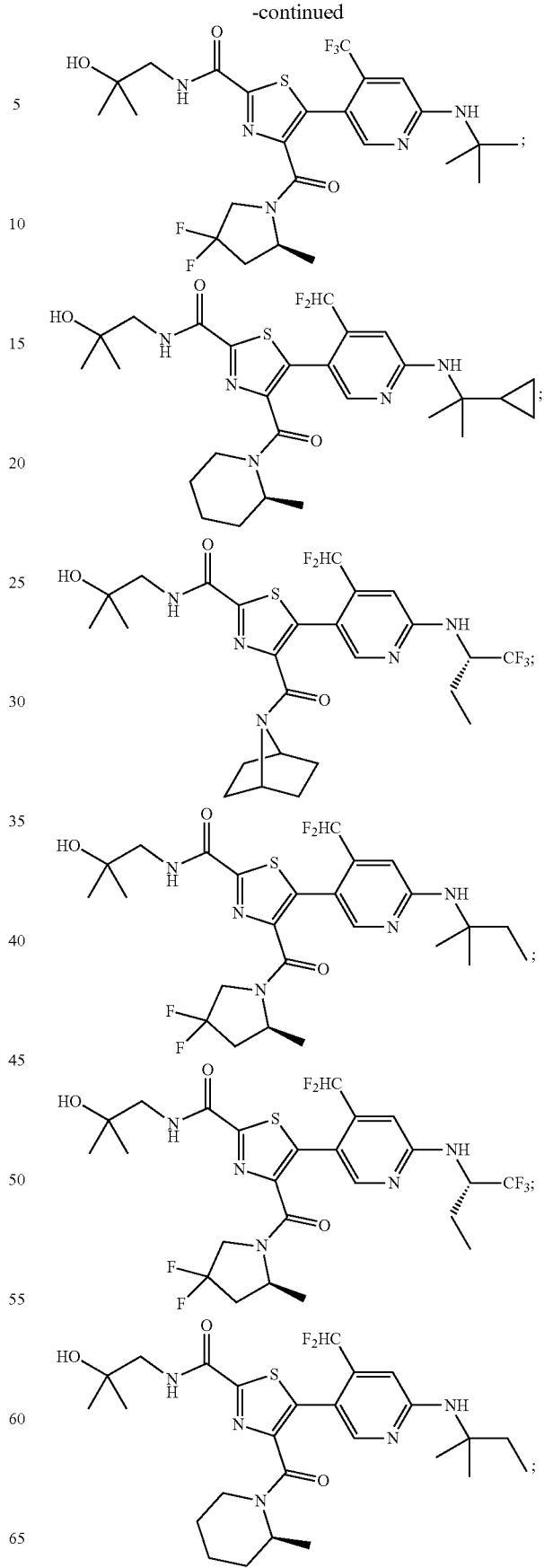

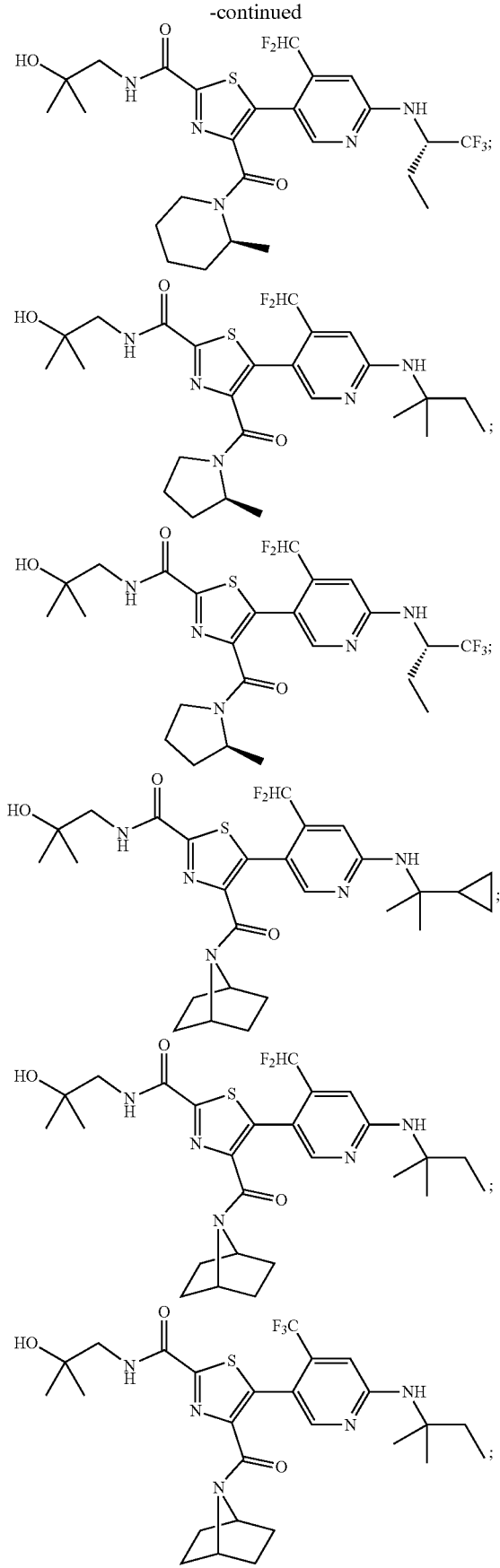
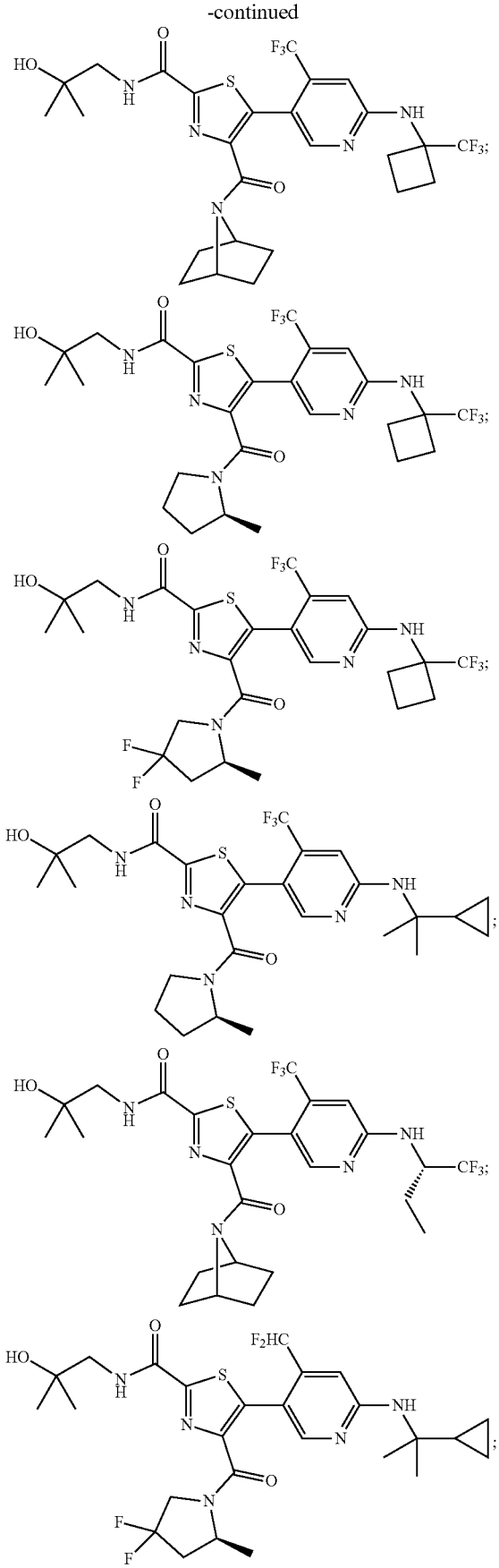

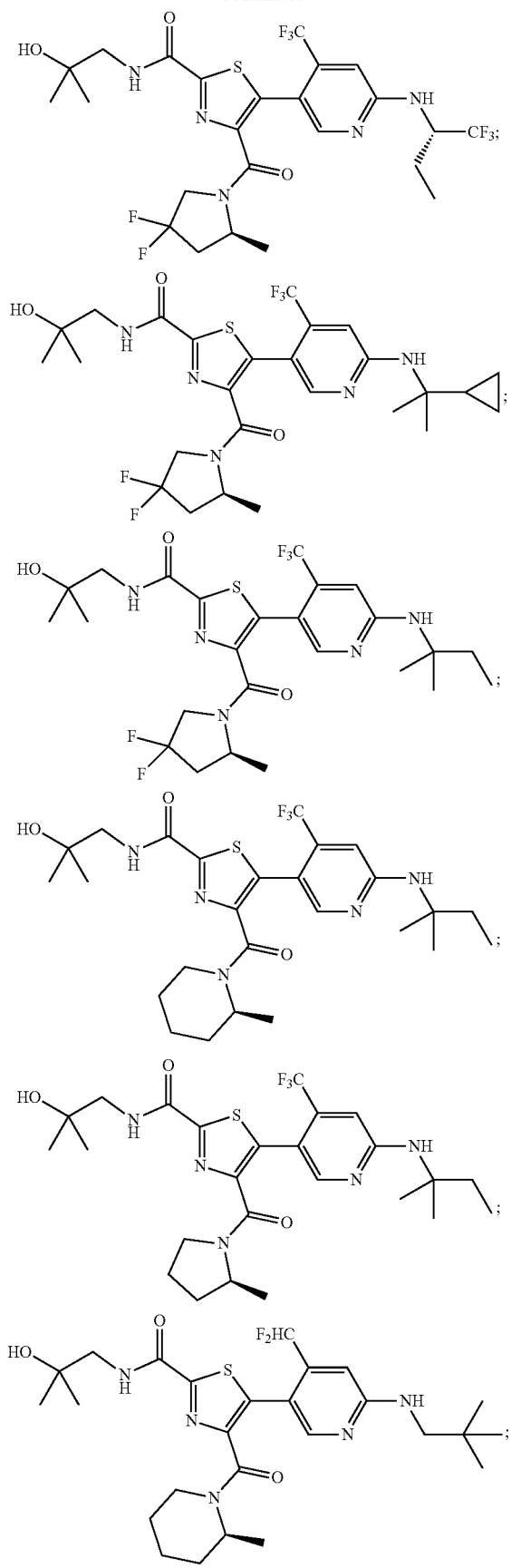
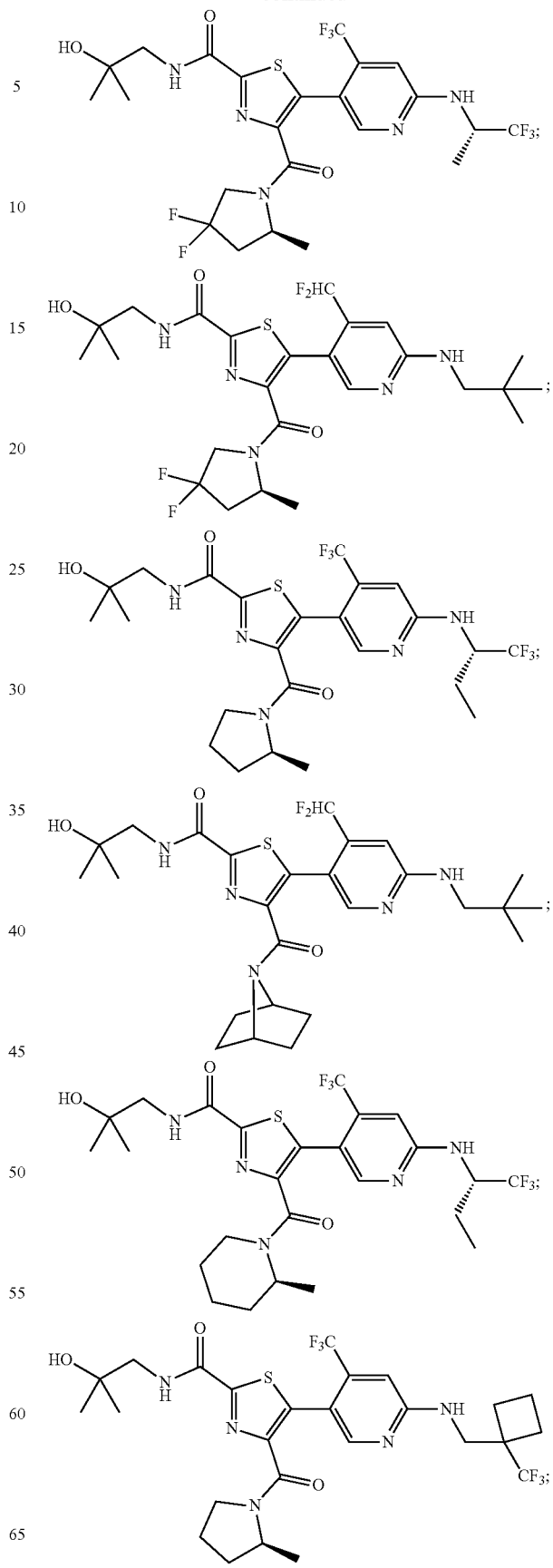

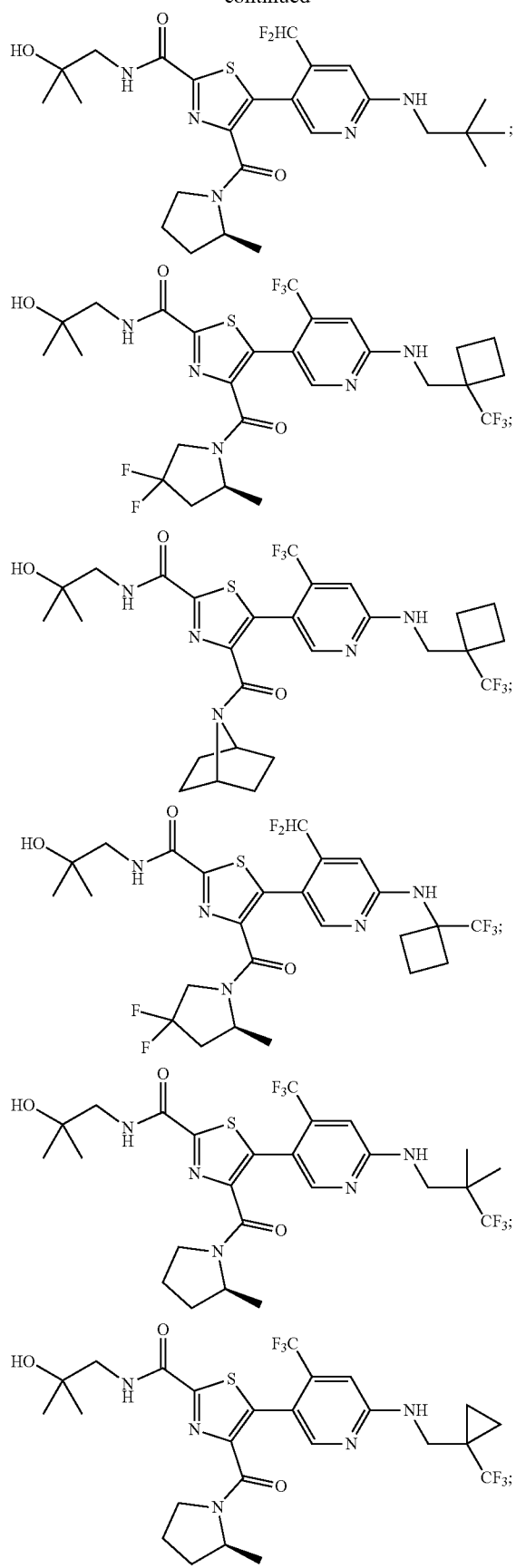
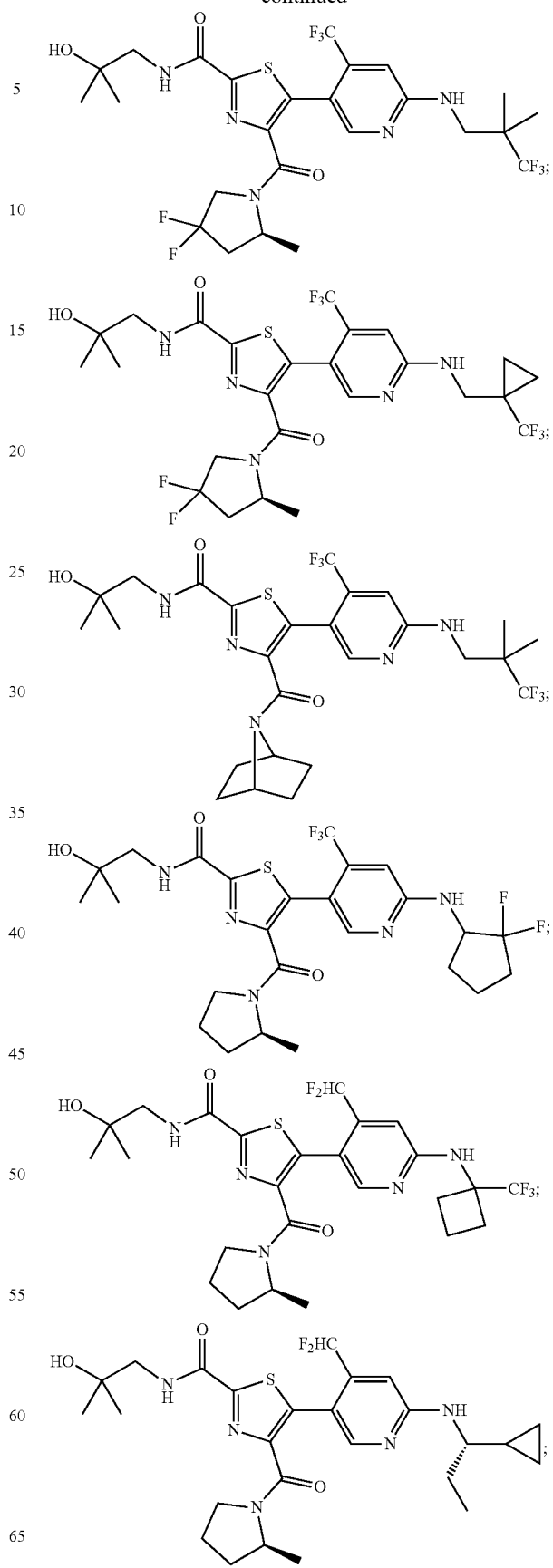

147
-continued
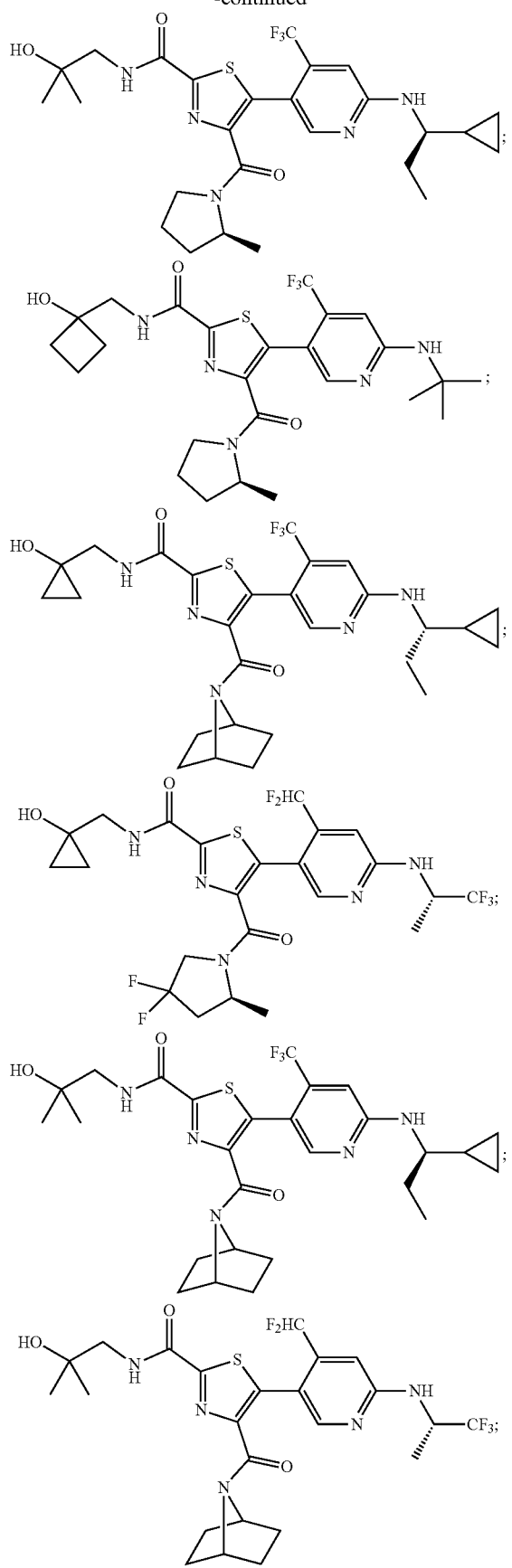
148
-continued
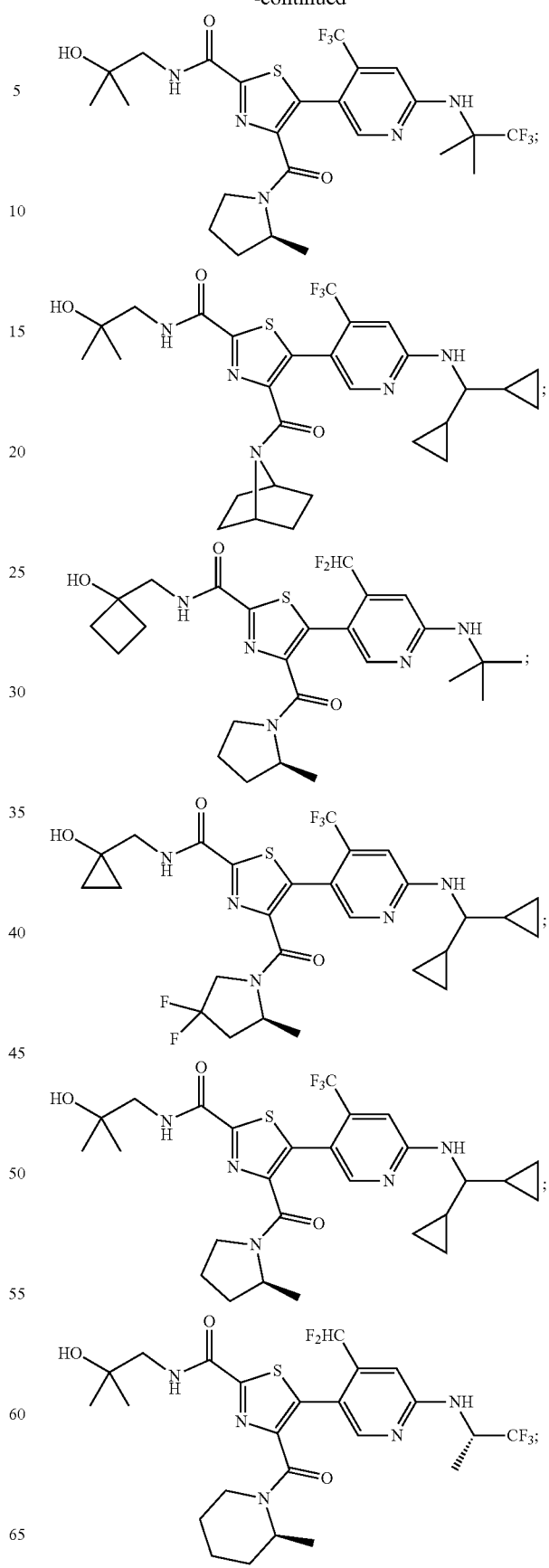

-continued
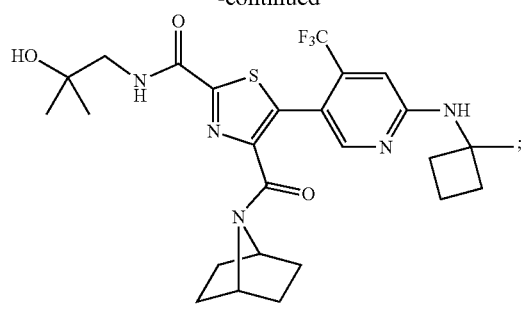
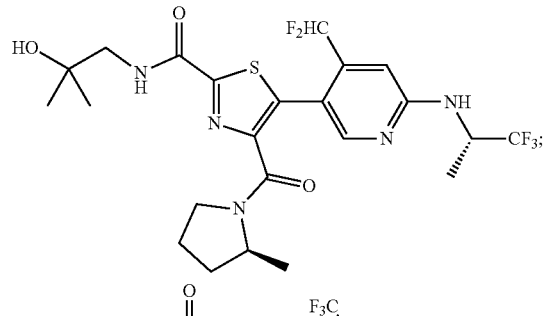
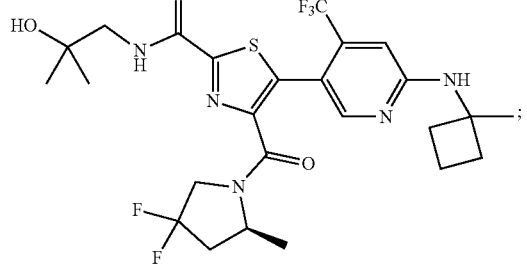
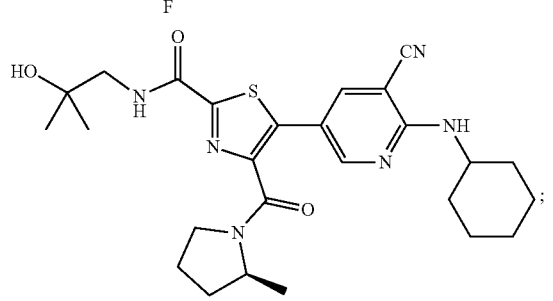
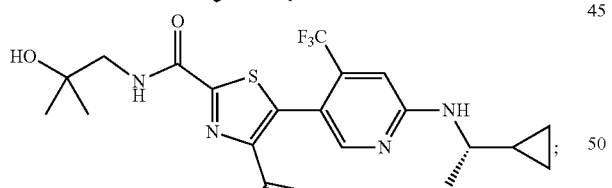
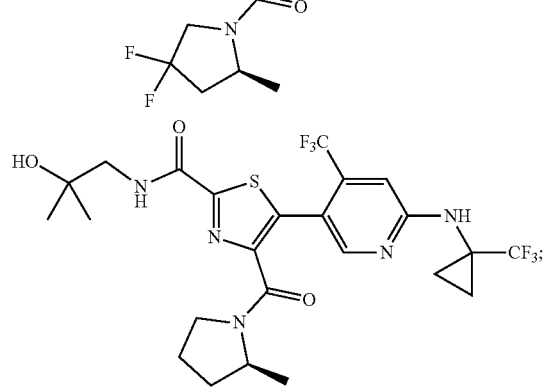
-continued
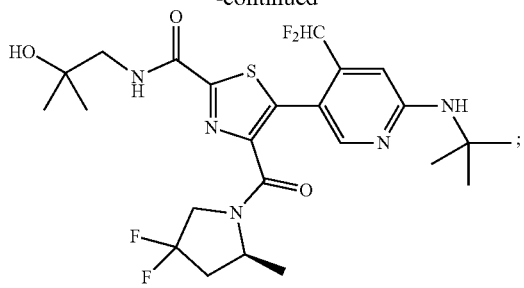
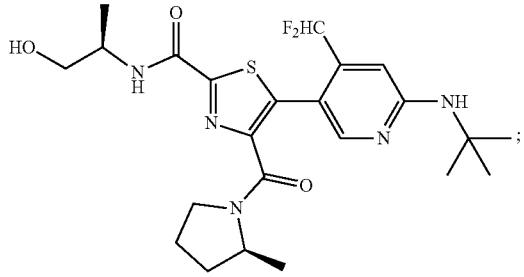
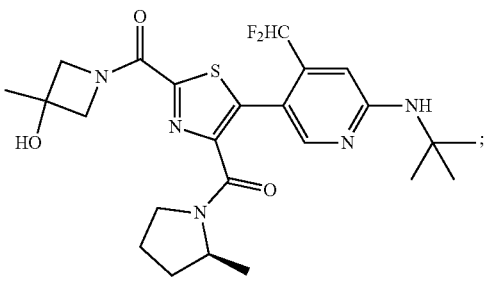
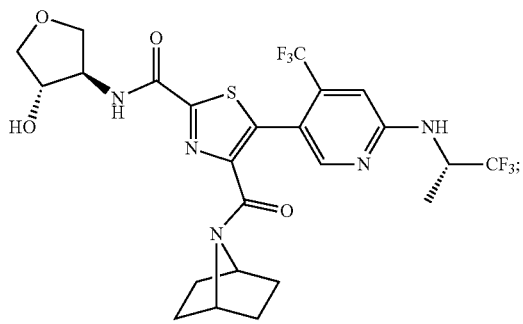
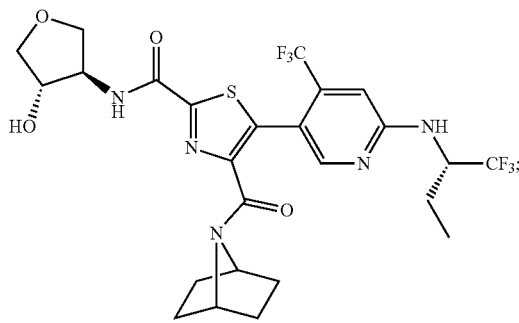

151
-continued
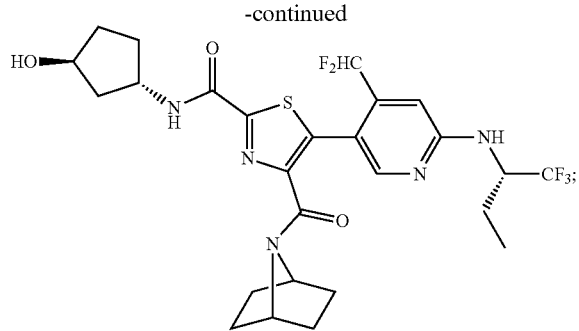
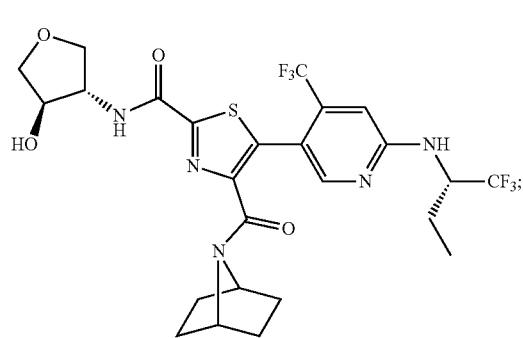
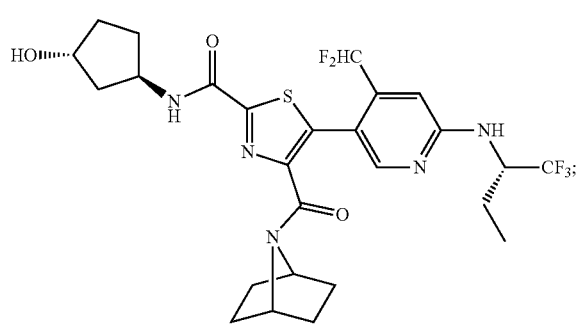
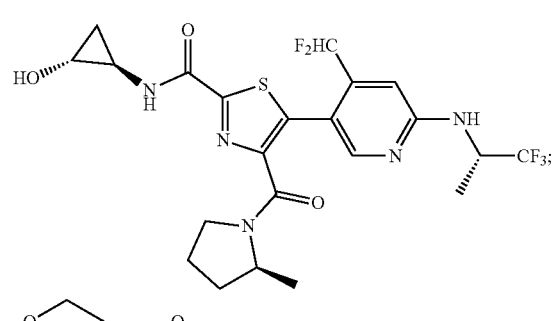
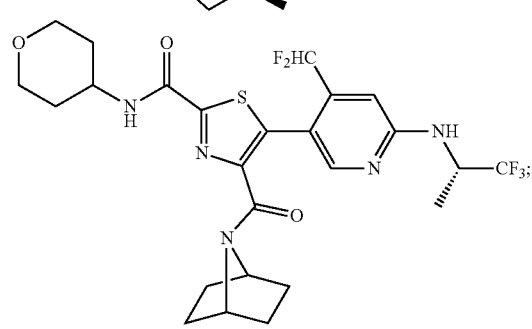
152
-continued
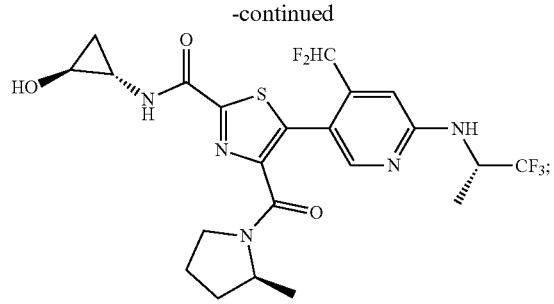
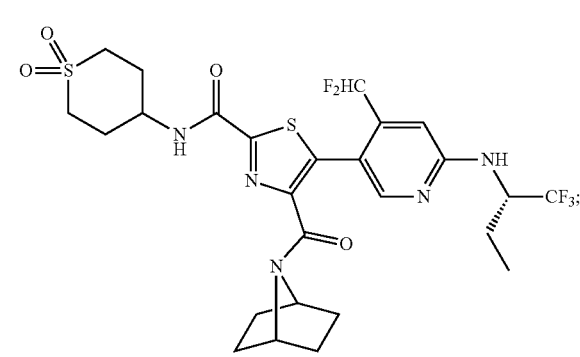
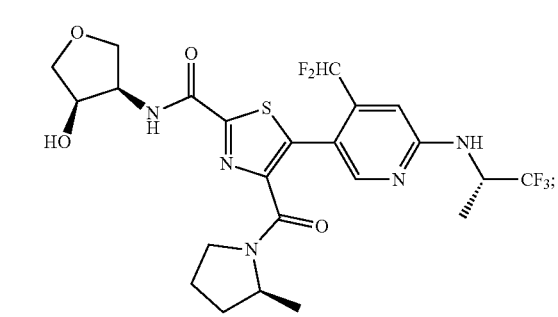
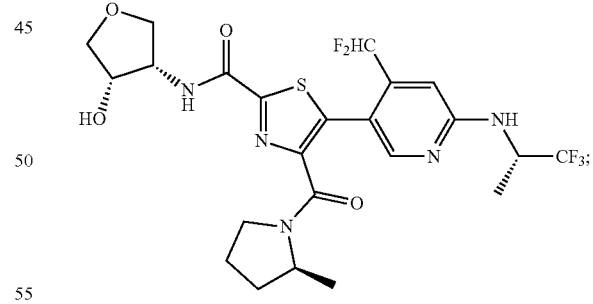
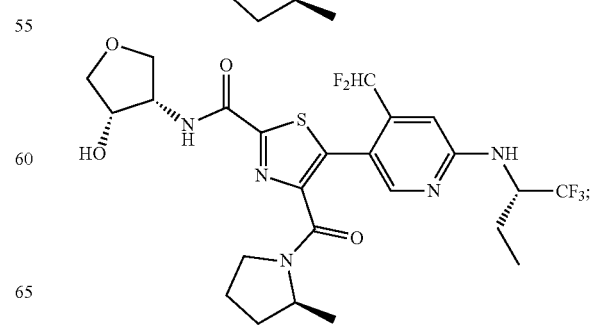

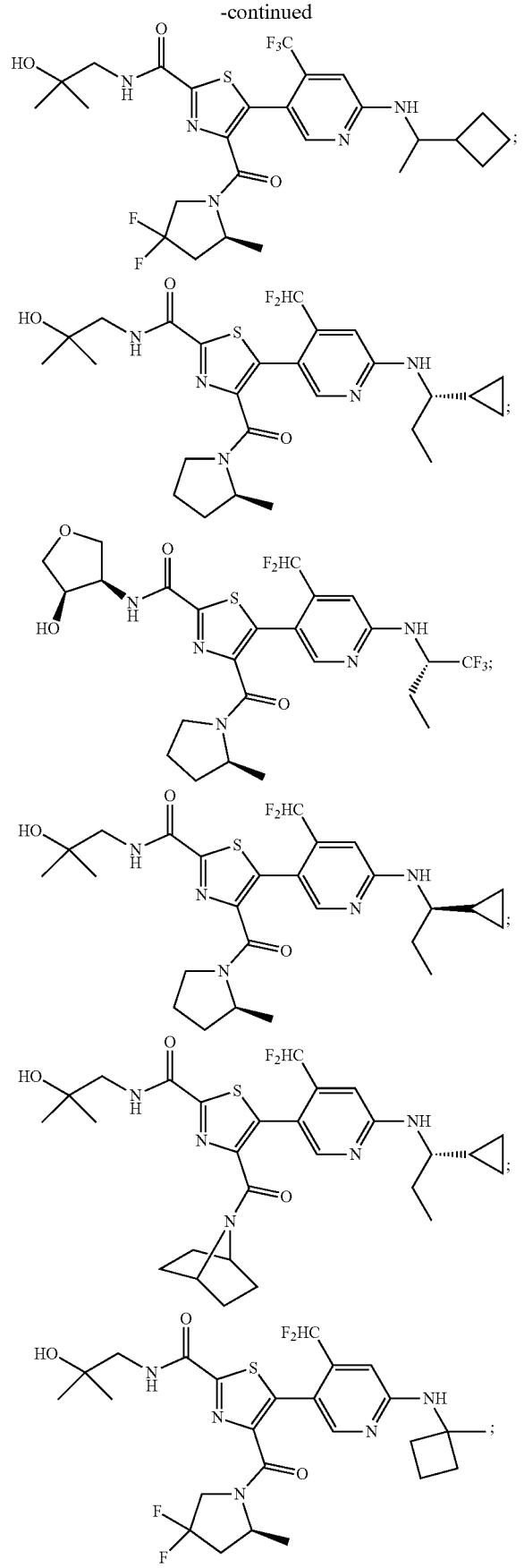
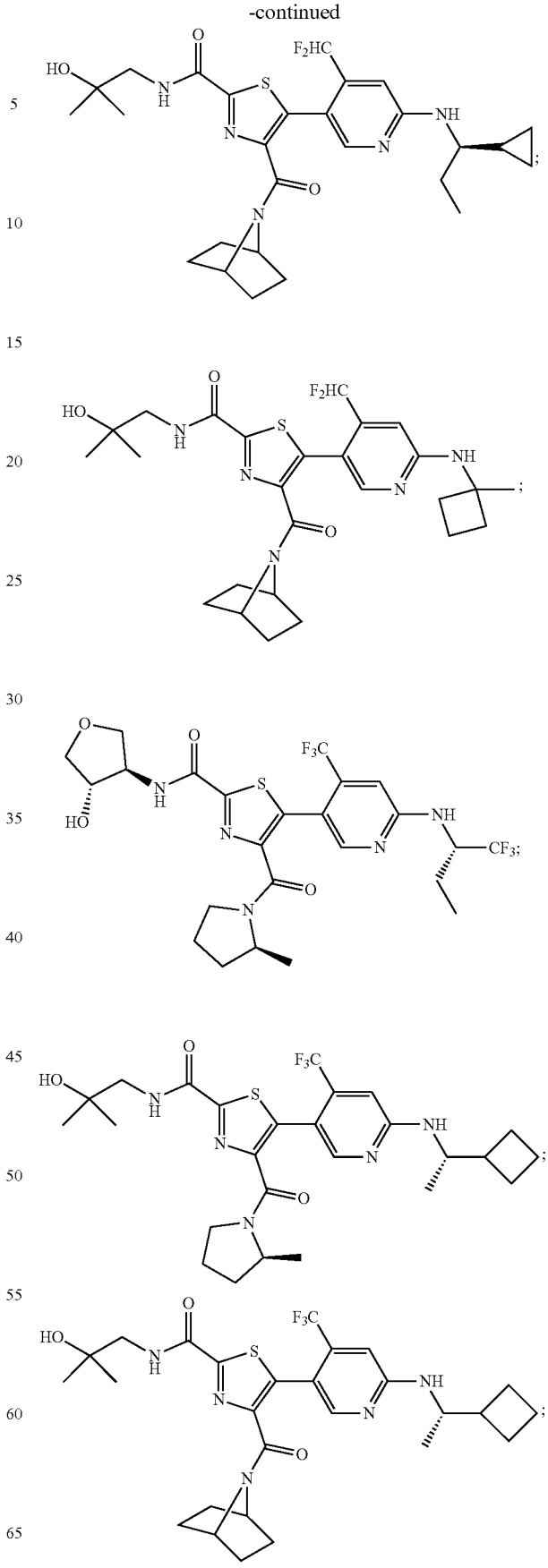

-continued
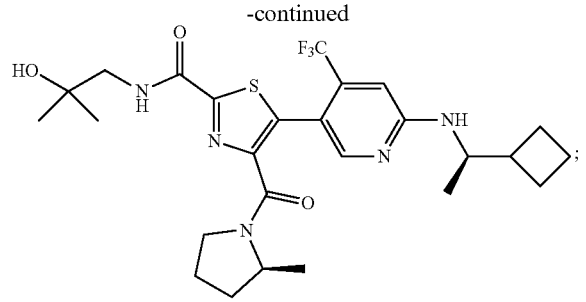
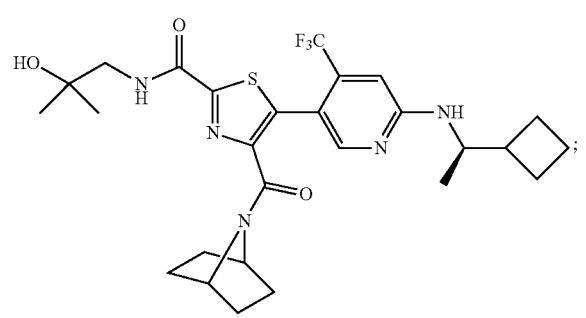
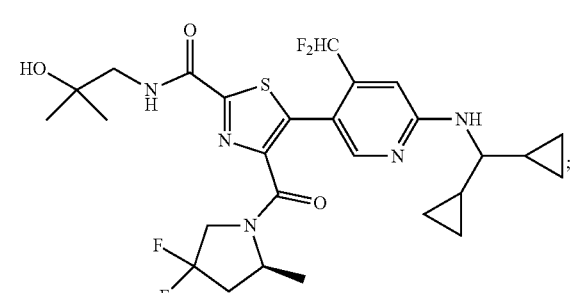
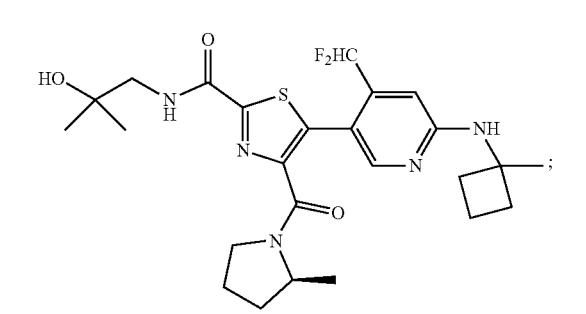
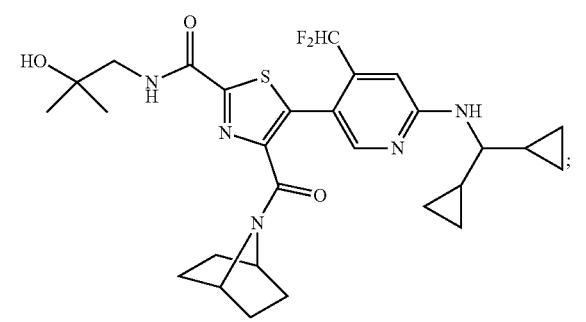
-continued
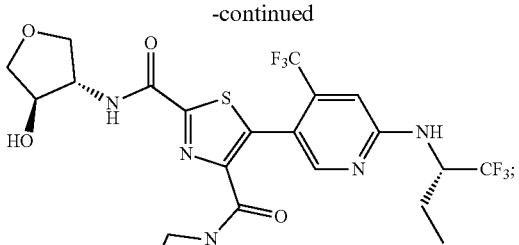
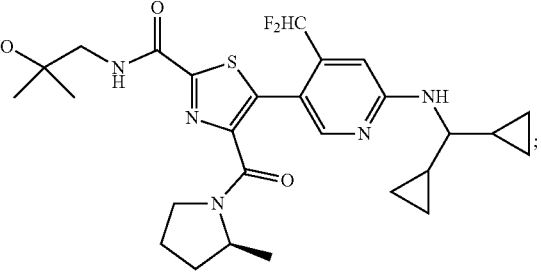
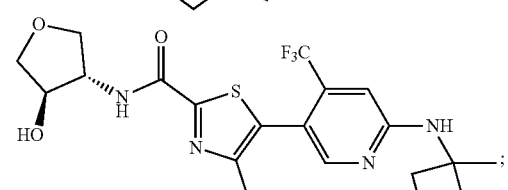
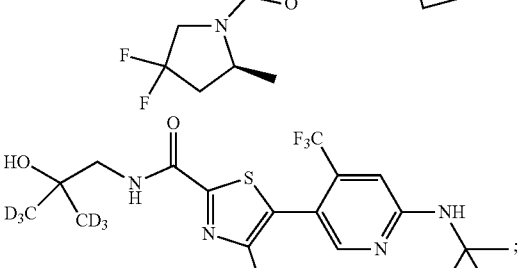
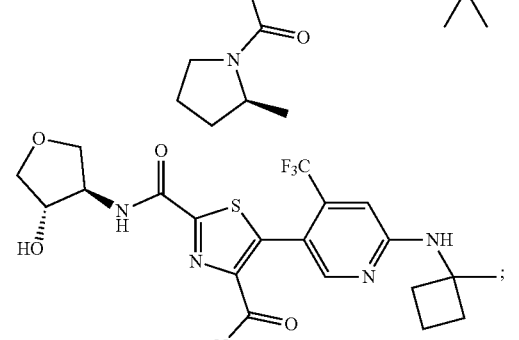
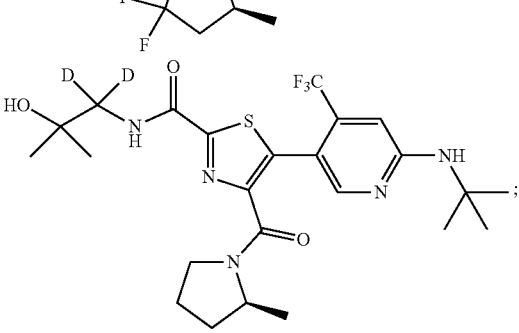

157
-continued
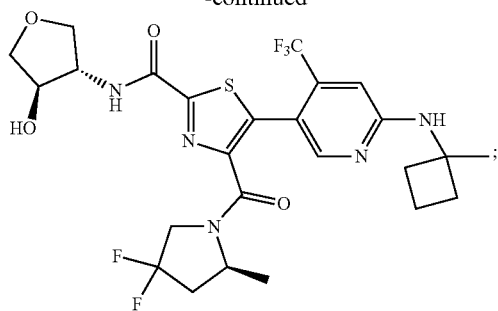
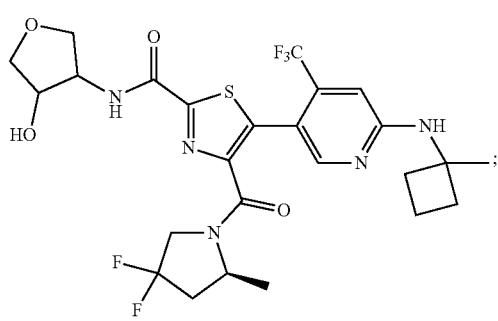
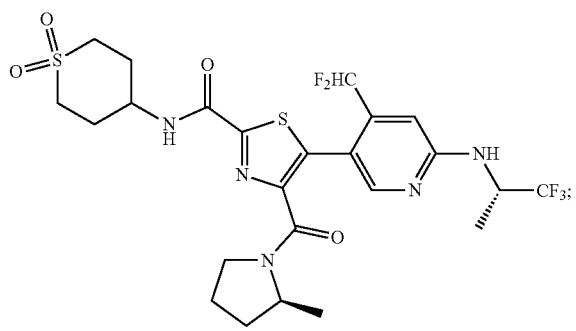
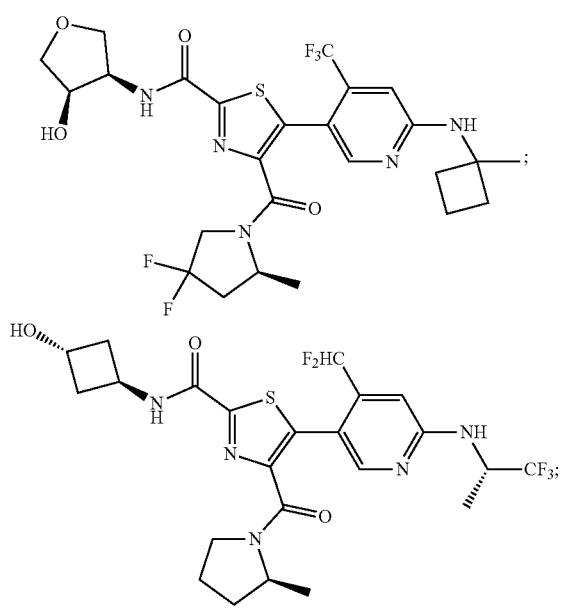
158
-continued
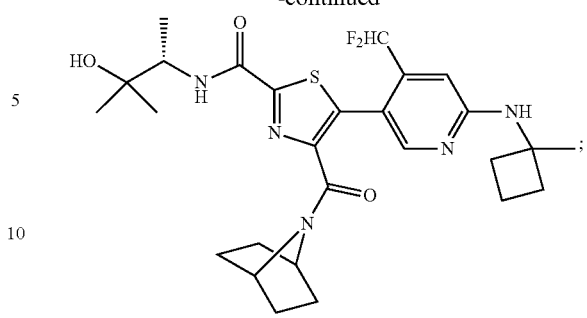
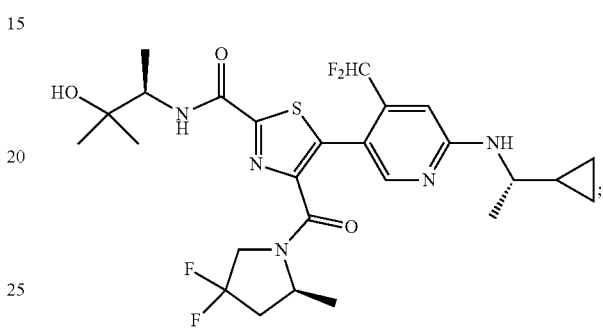
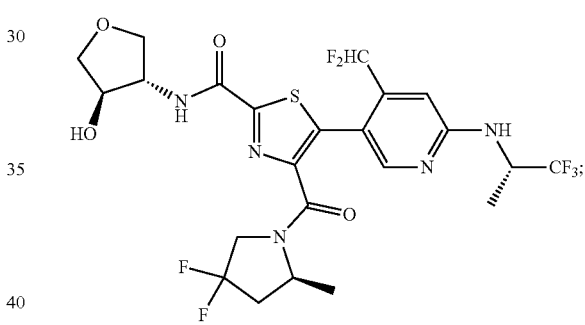
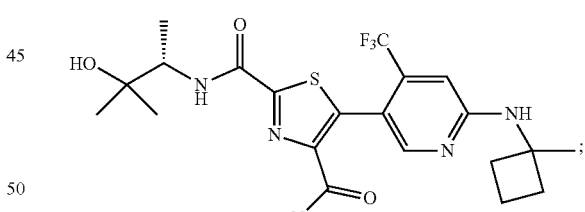
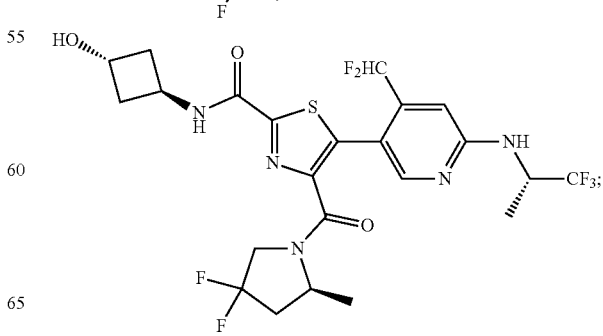

159
-continued
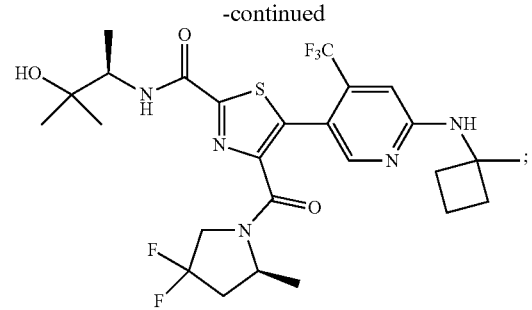
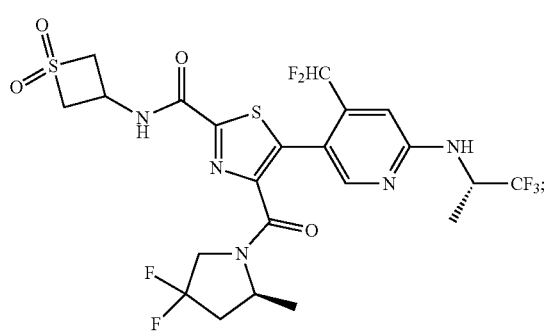
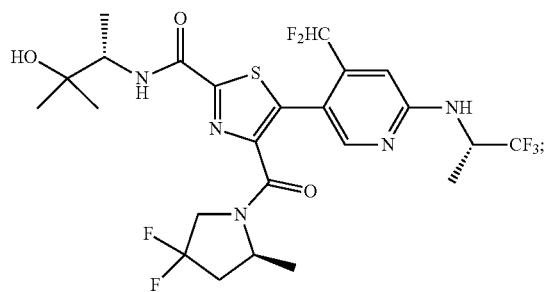
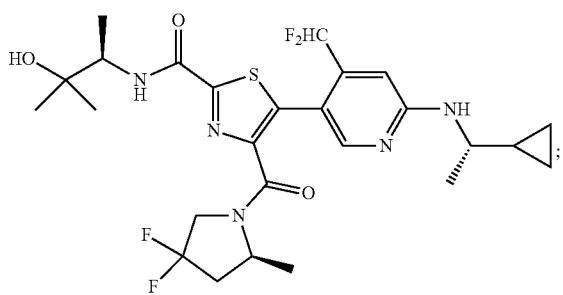
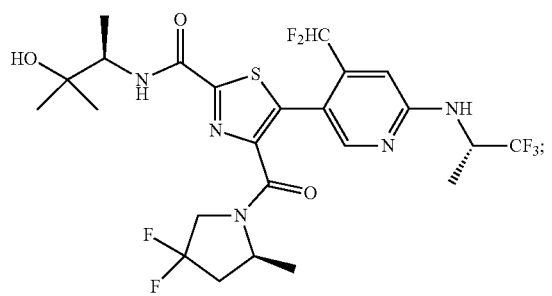
160
-continued
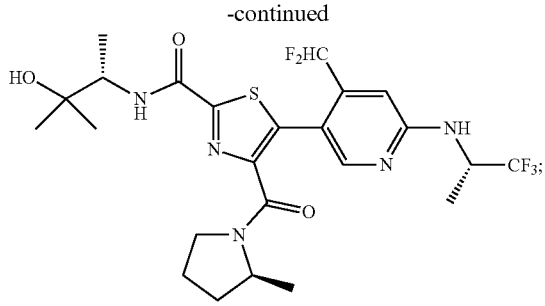
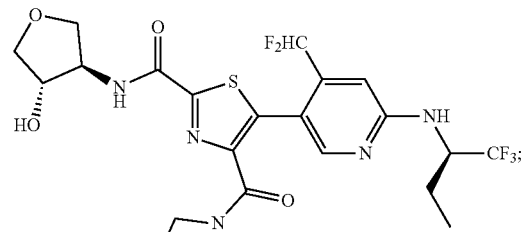
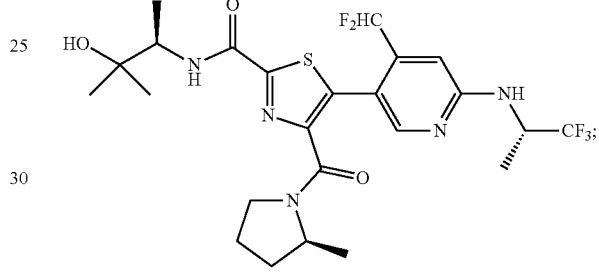
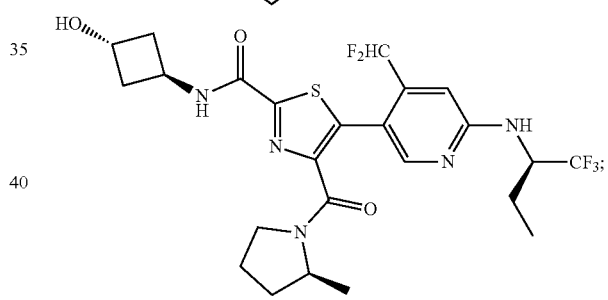
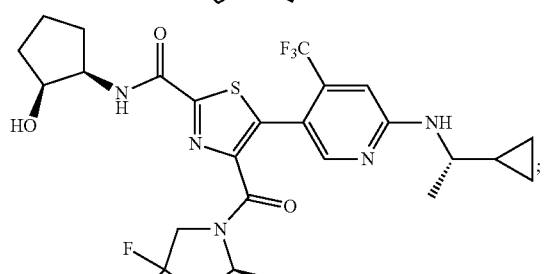
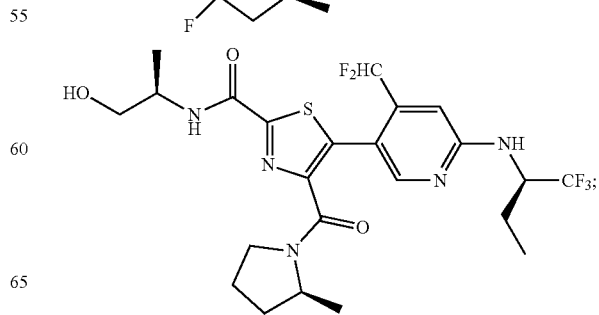

161
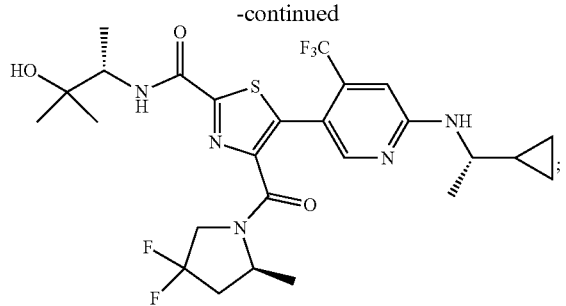
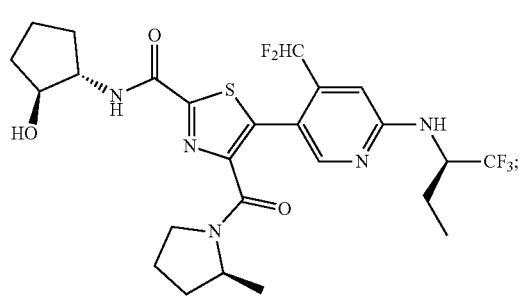
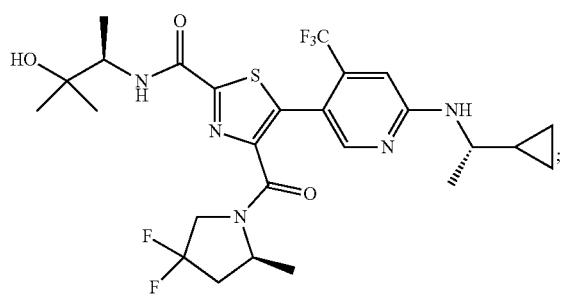
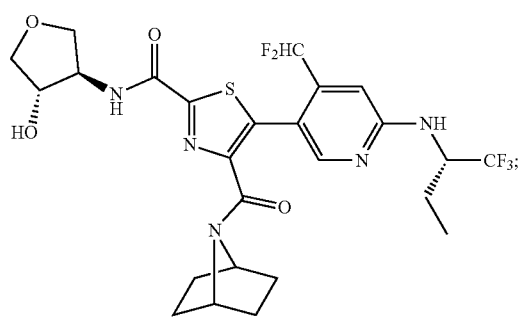
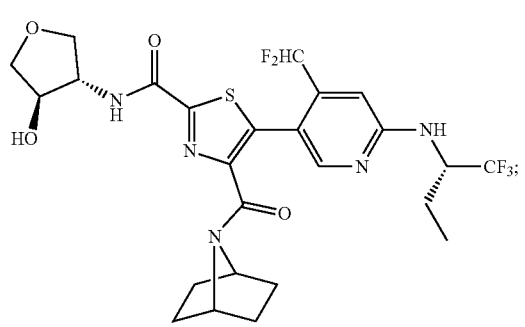
162
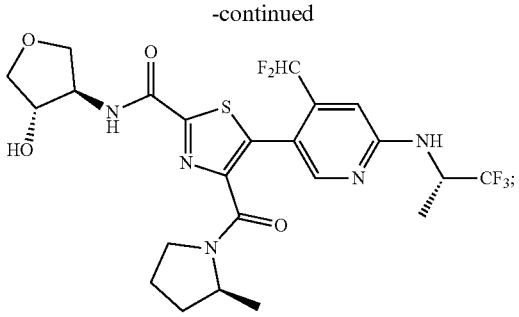
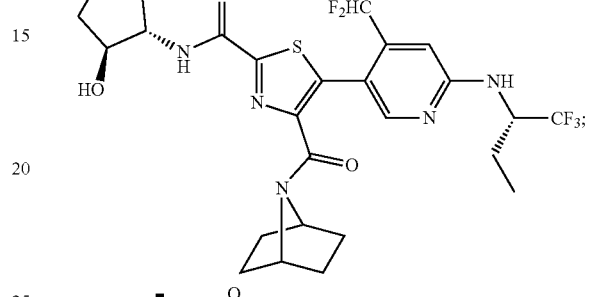
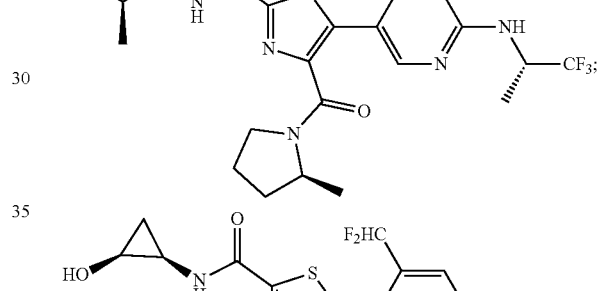
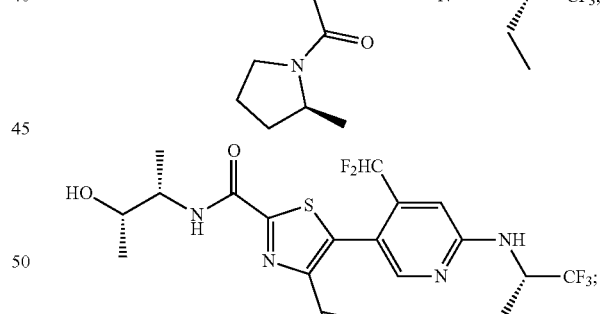
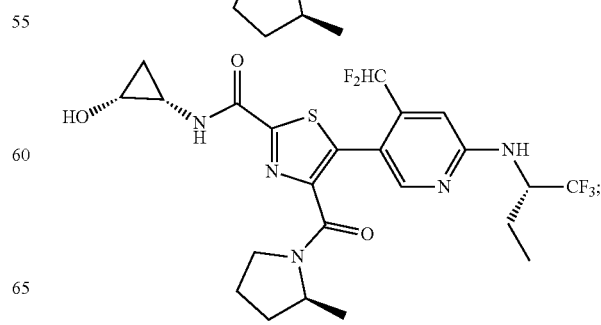

163
-continued
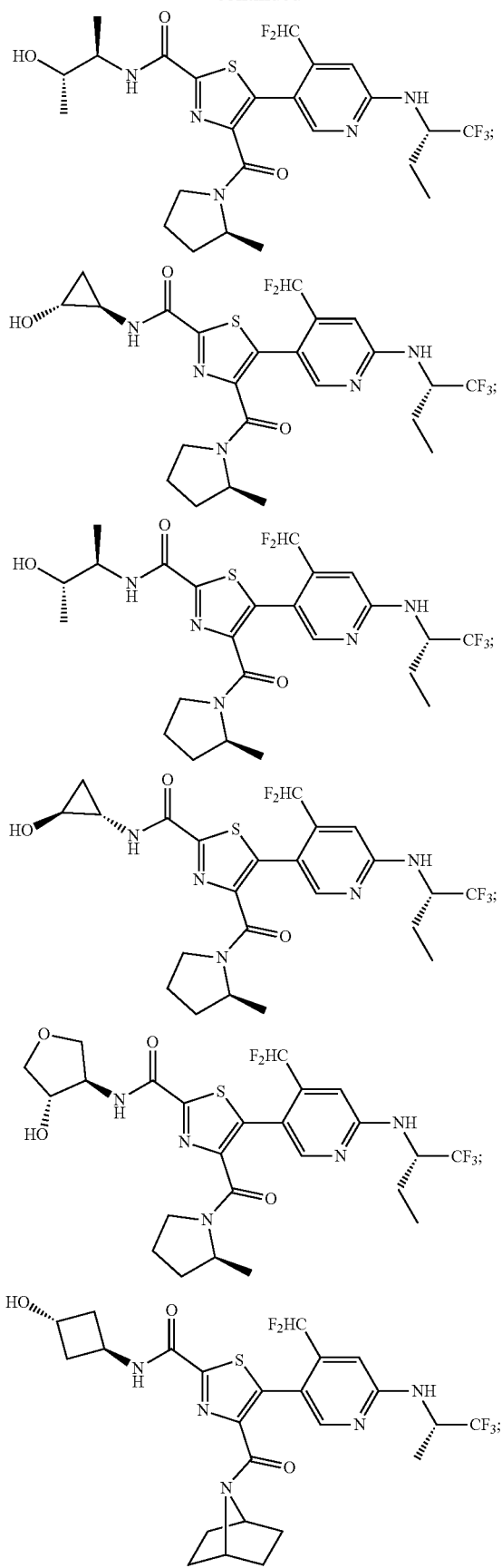
164
-continued
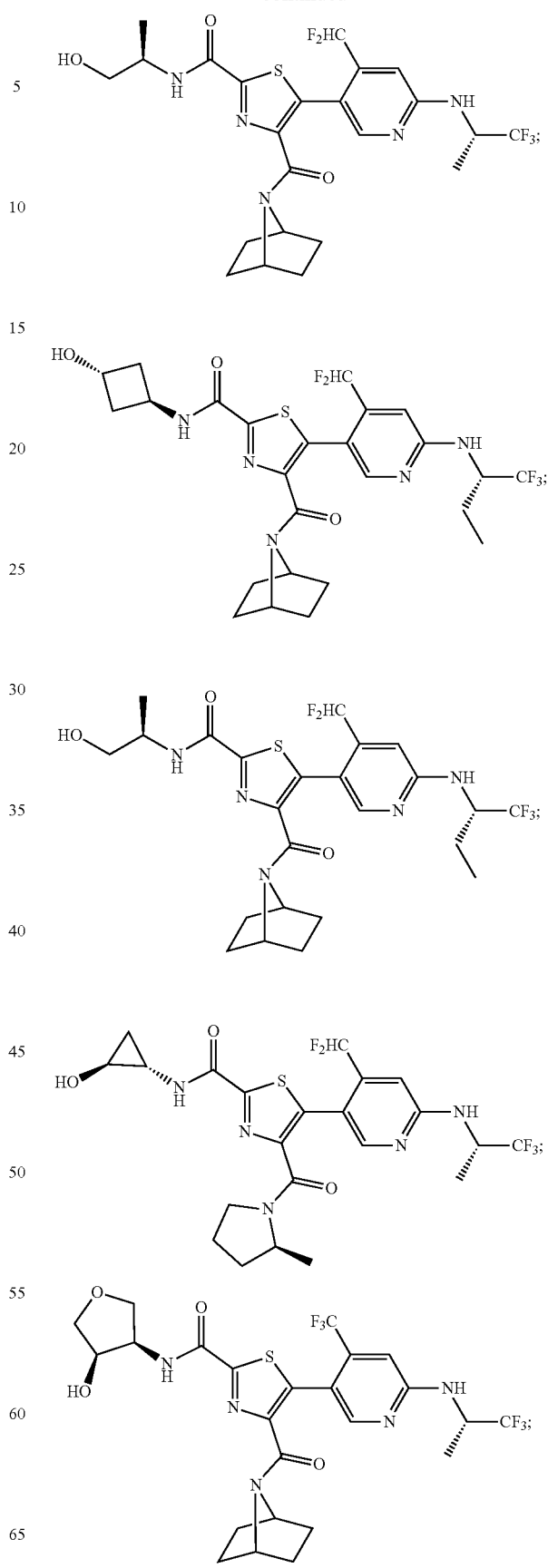

-continued
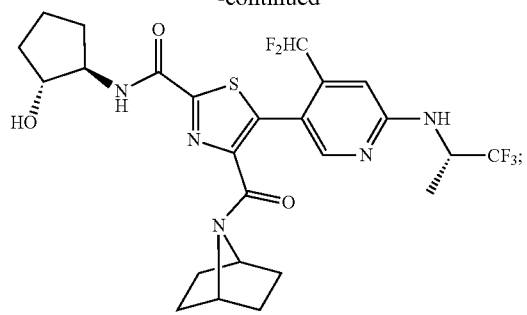
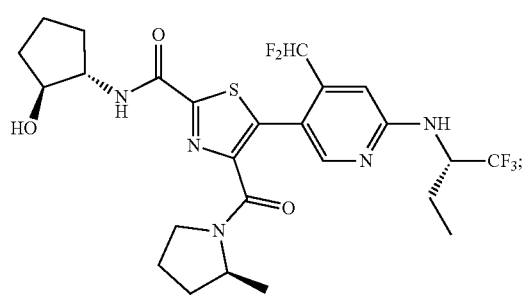
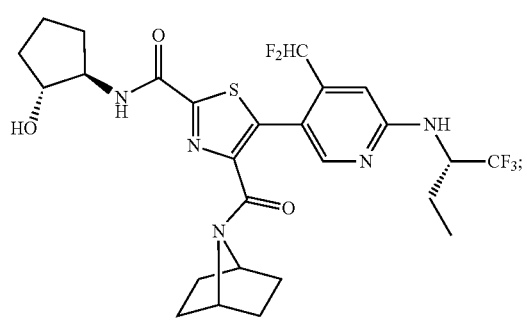
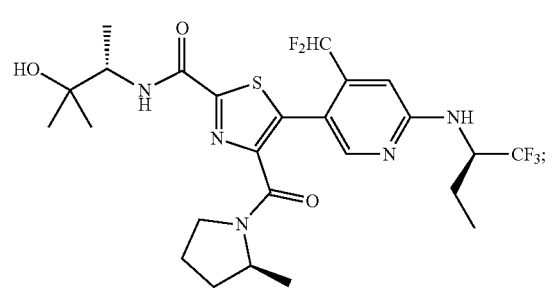
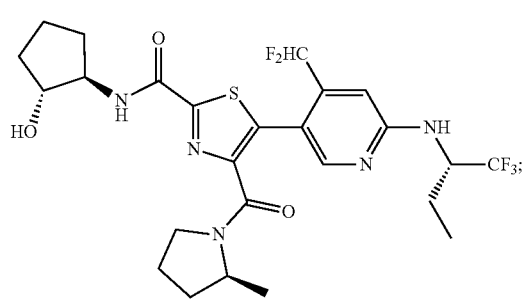
-continued
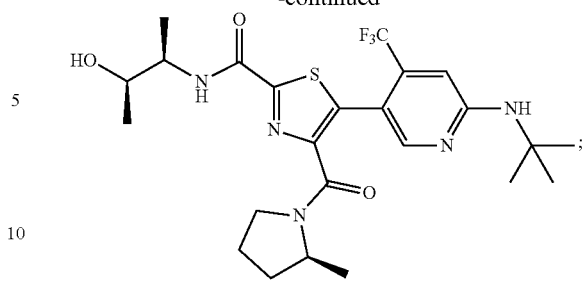
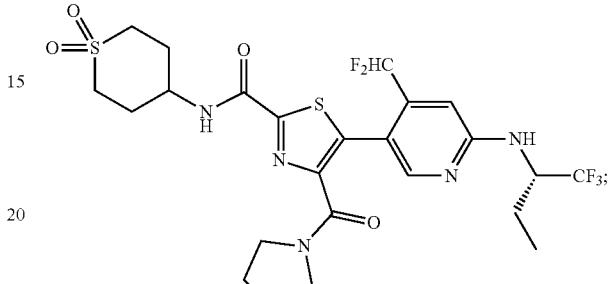
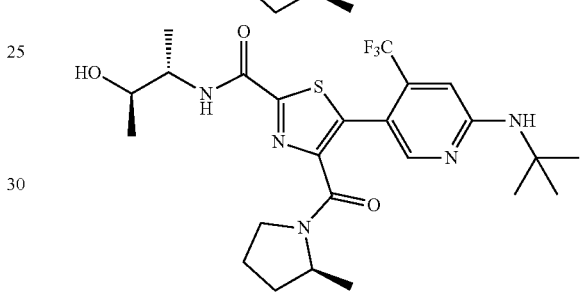
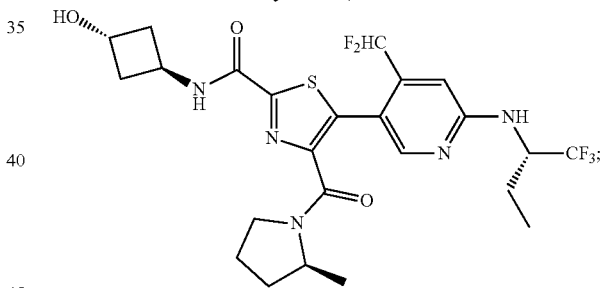
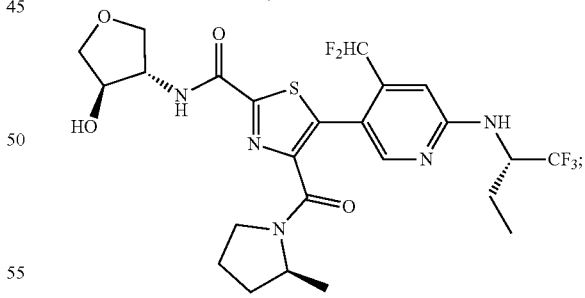
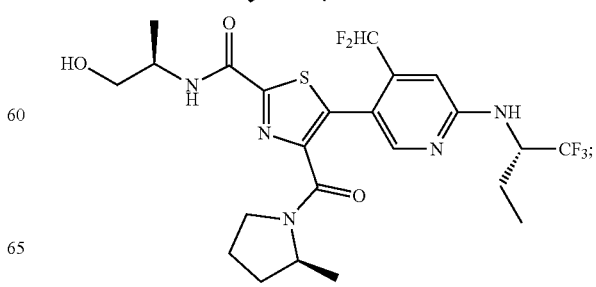

167
-continued
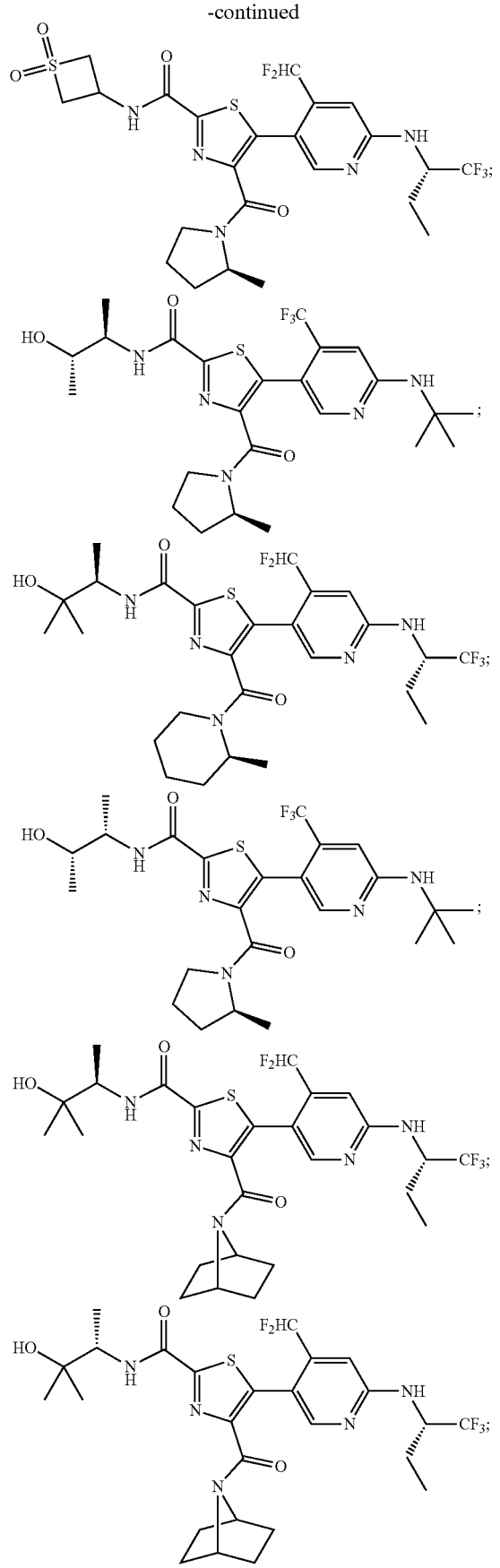
168
-continued
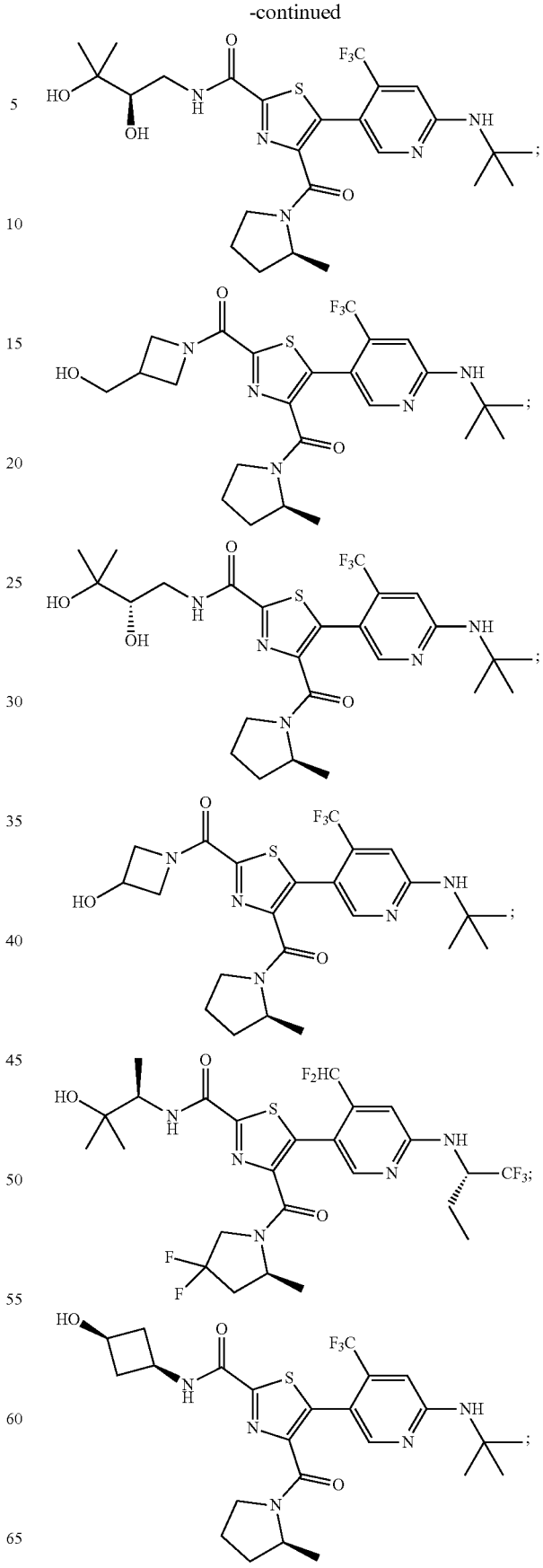

169
-continued
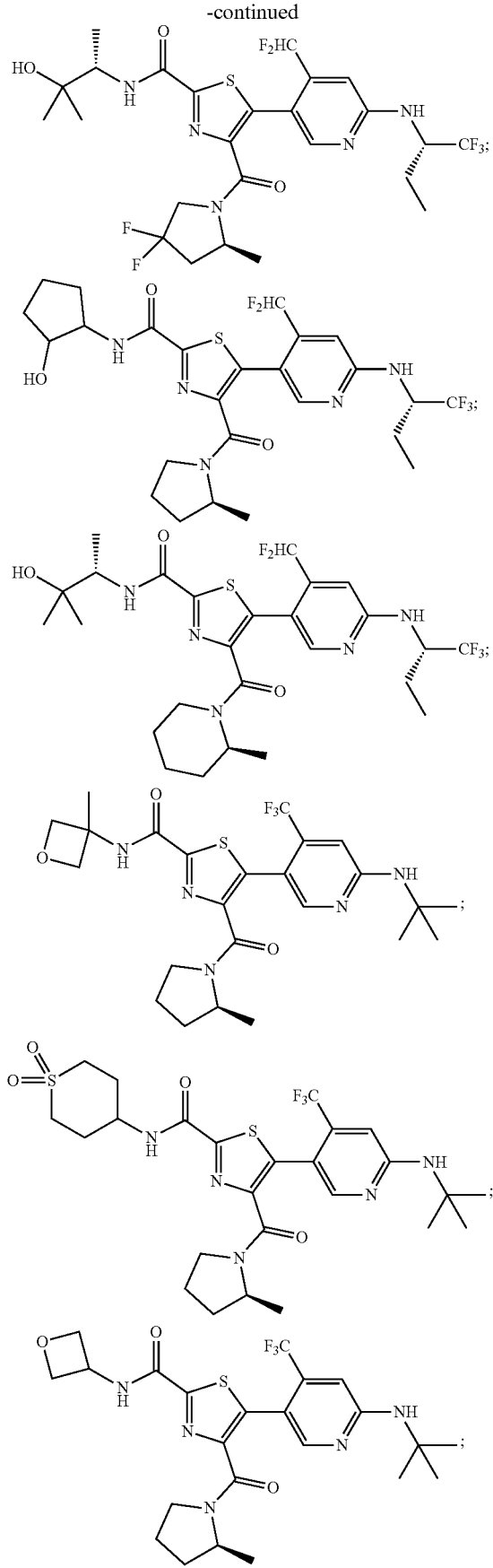
170
-continued
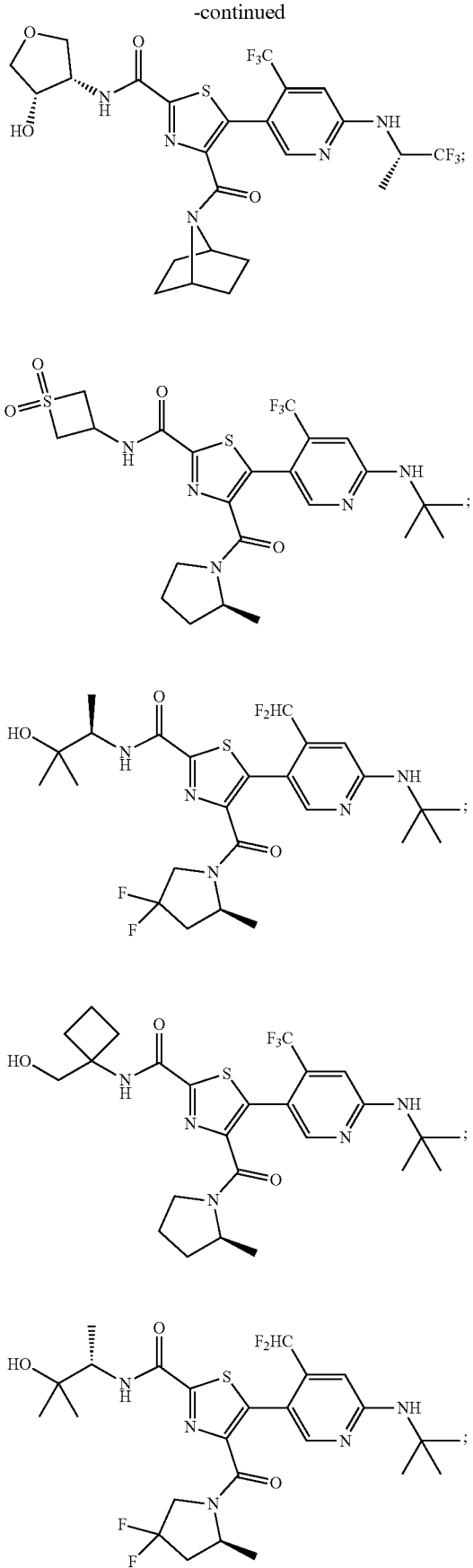

171
-continued
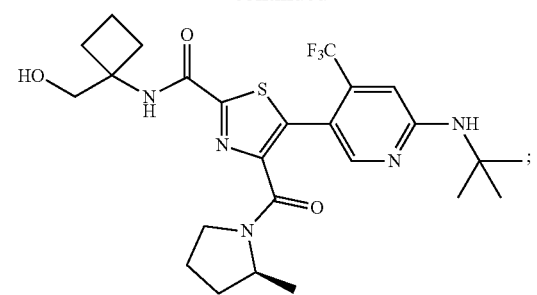
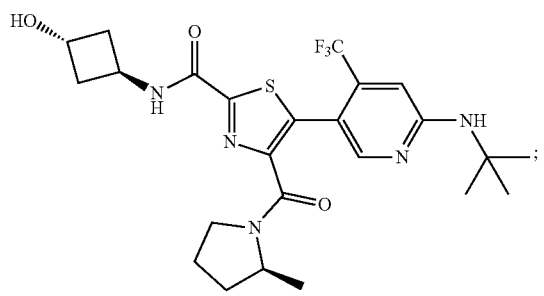
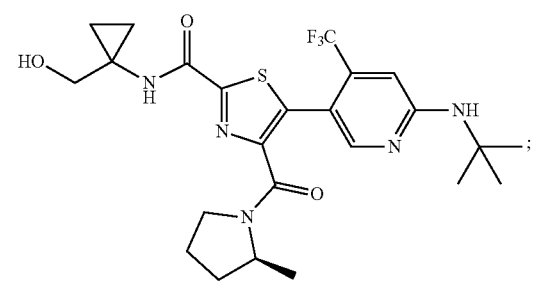
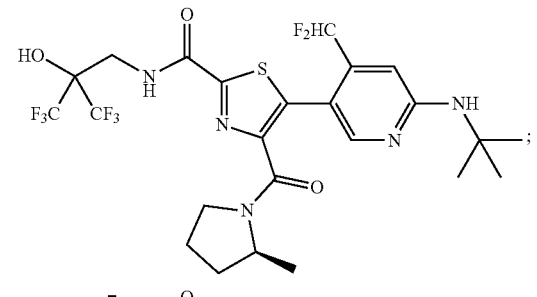
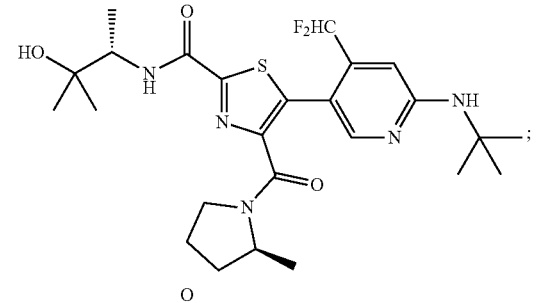
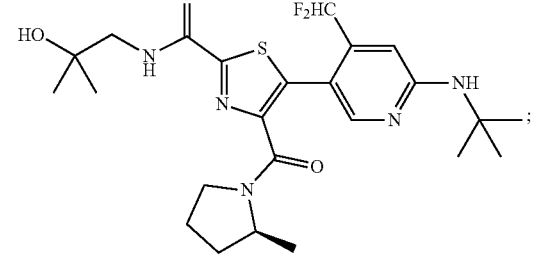
172
-continued
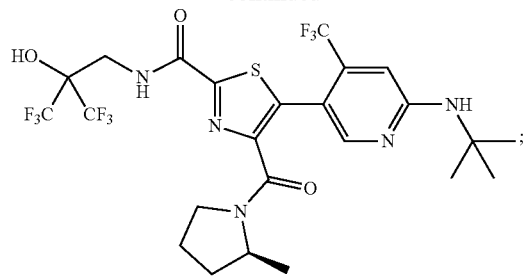
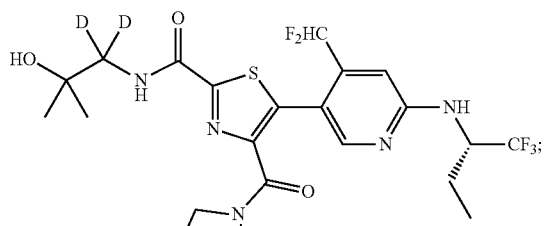
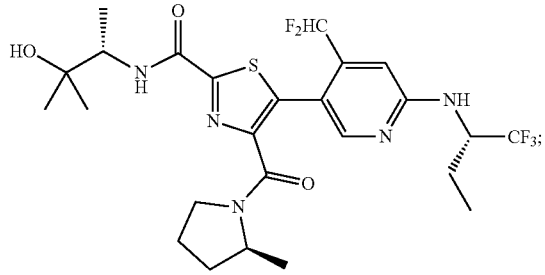
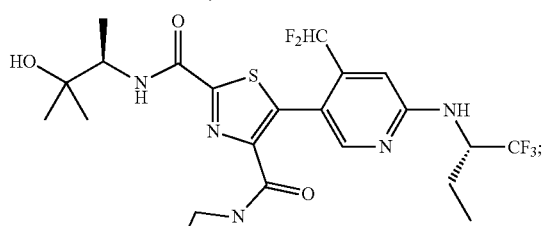
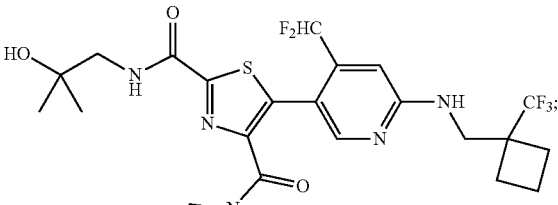
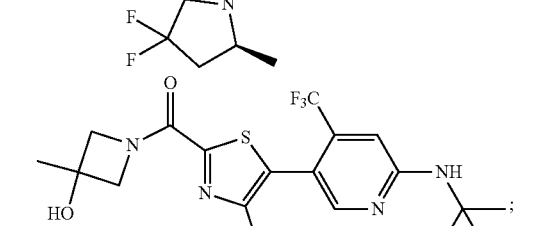
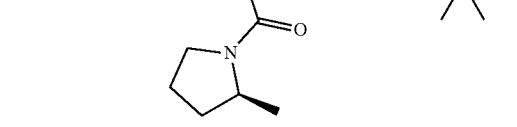

173
-continued
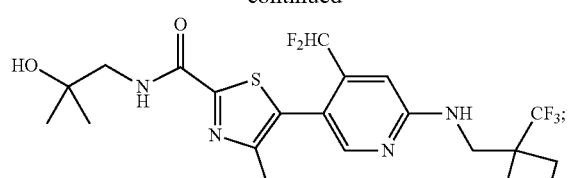
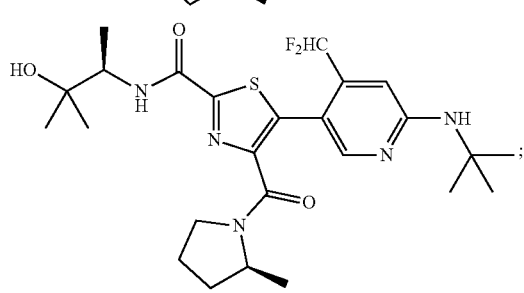
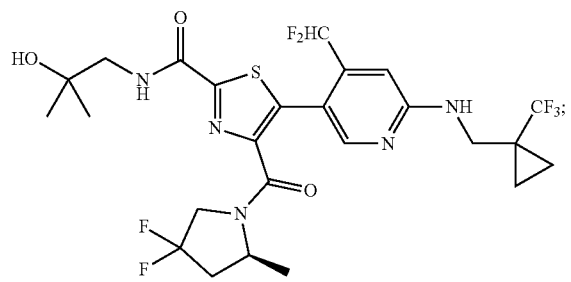
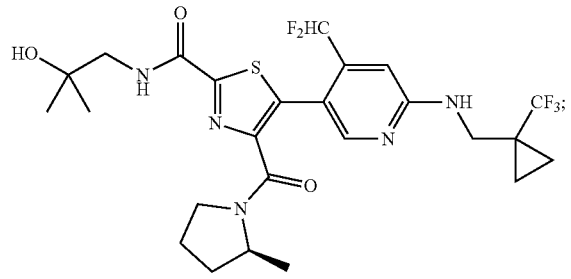
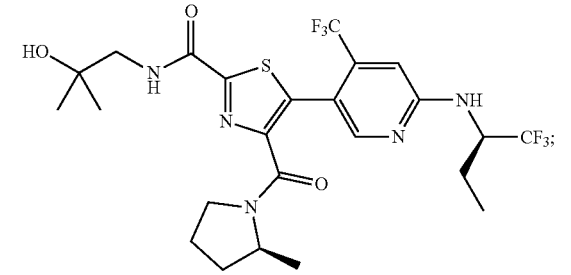
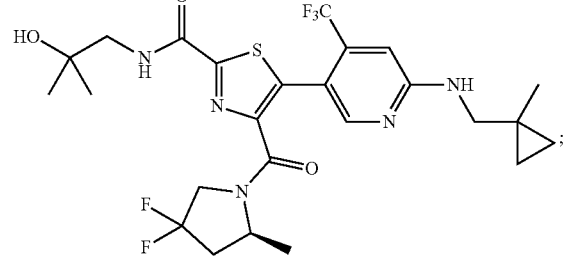
174
-continued
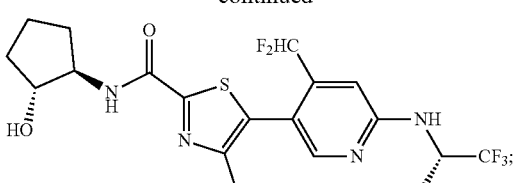
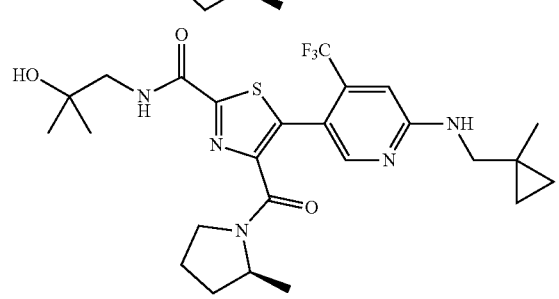
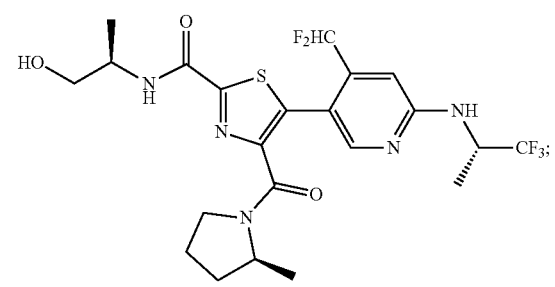
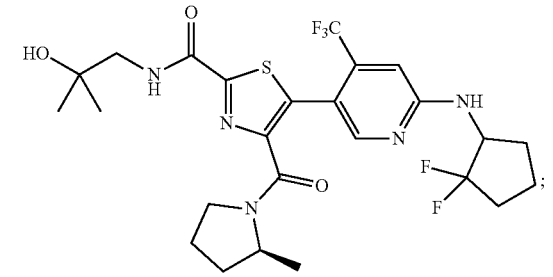
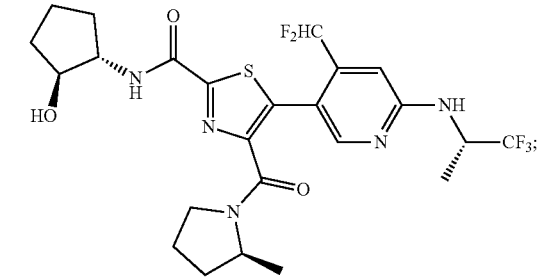
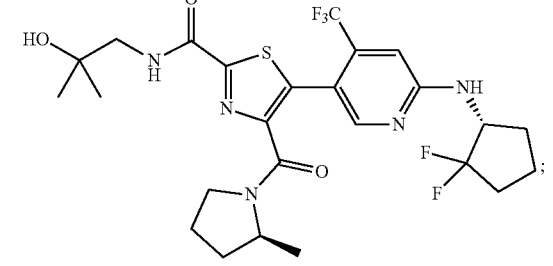

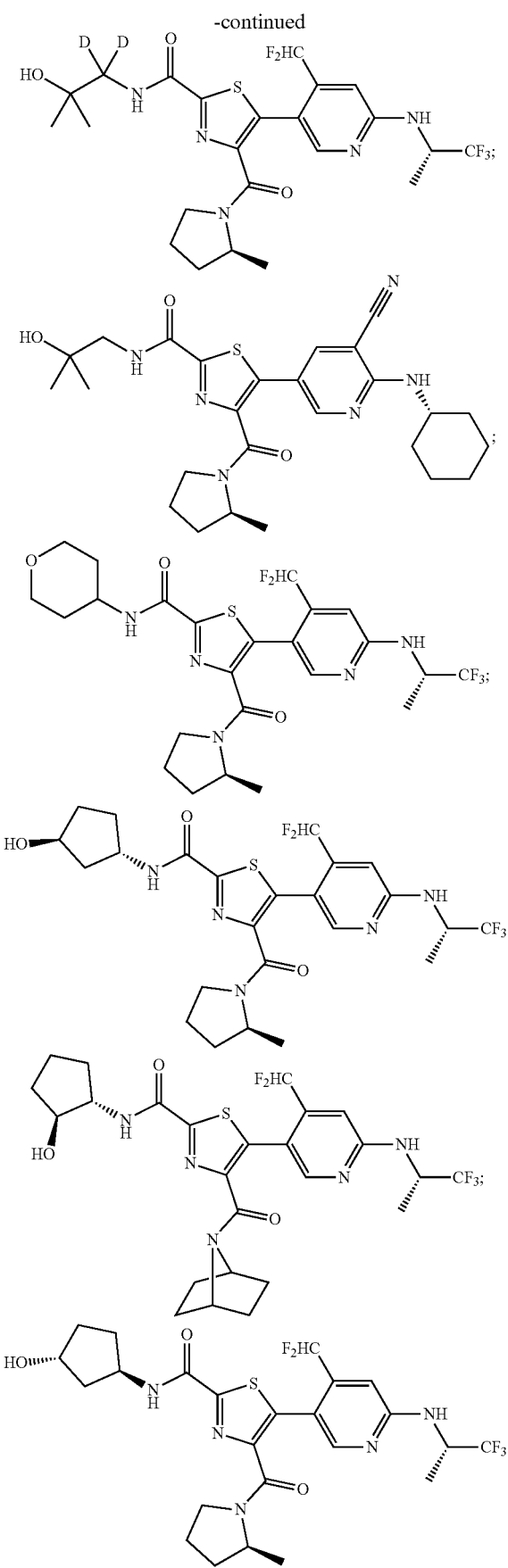
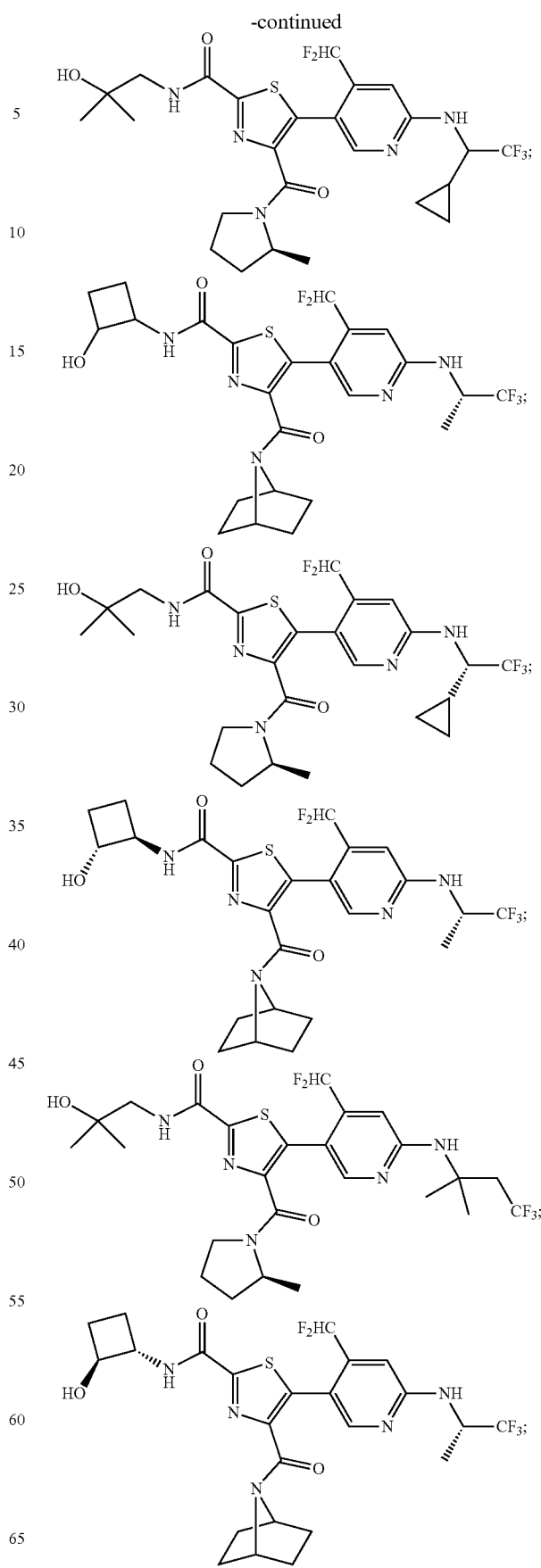

177
-continued
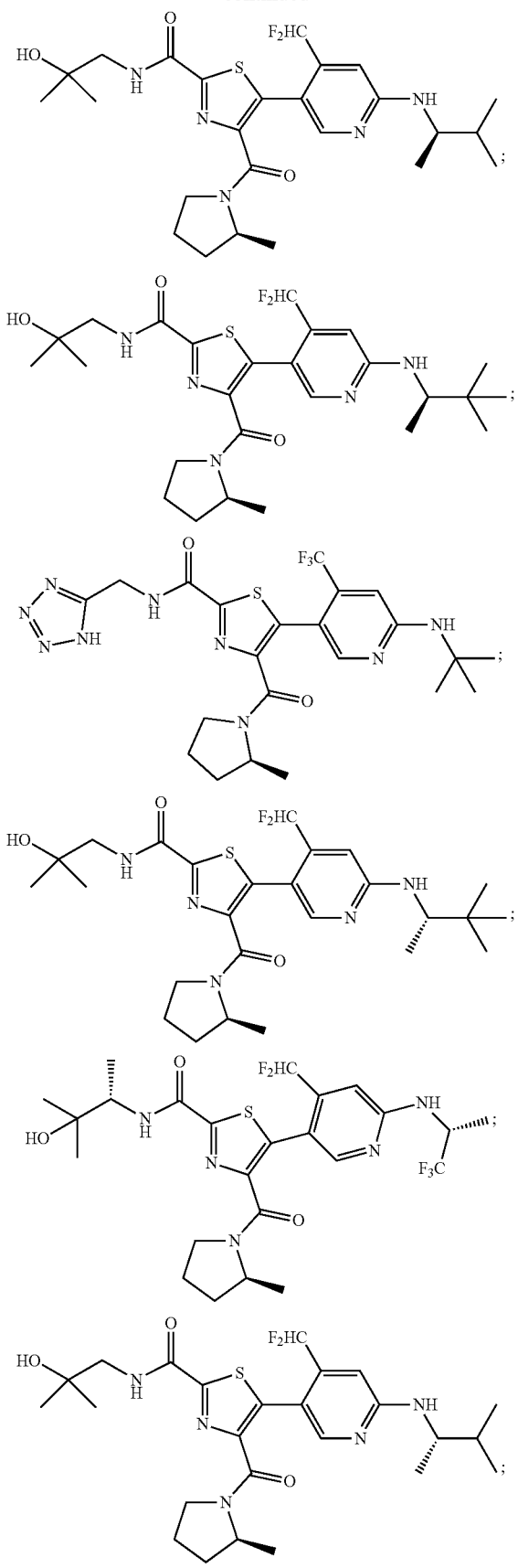
178
-continued
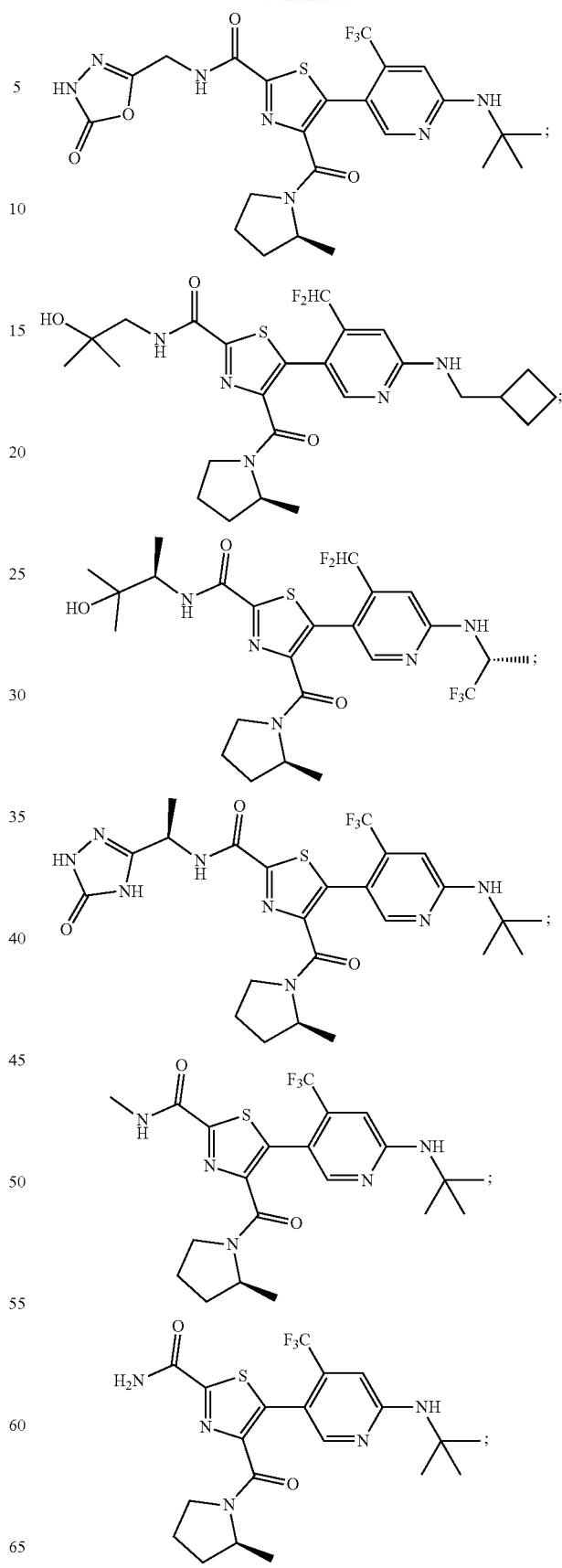

179
-continued
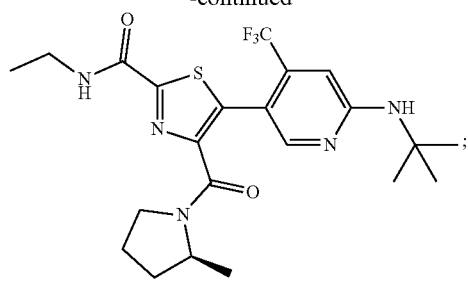
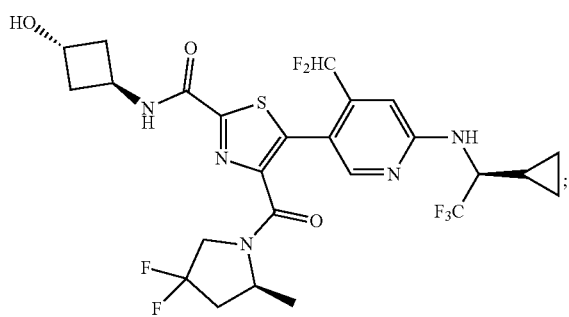
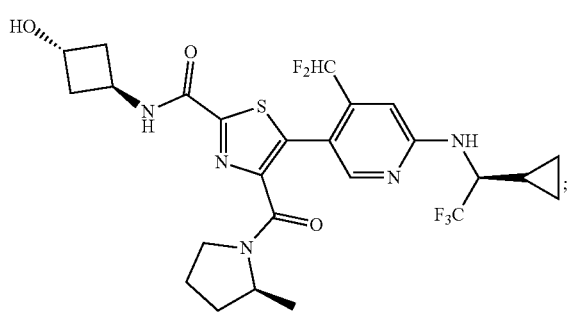
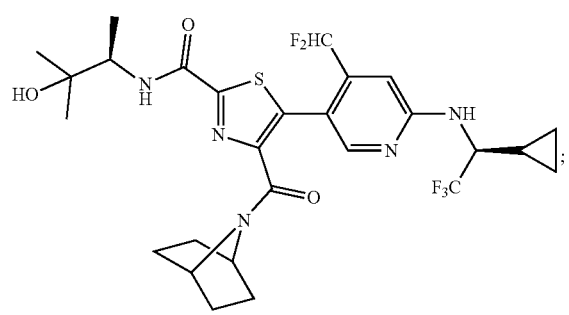
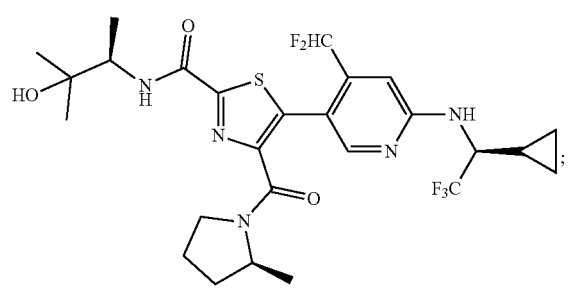
180
-continued
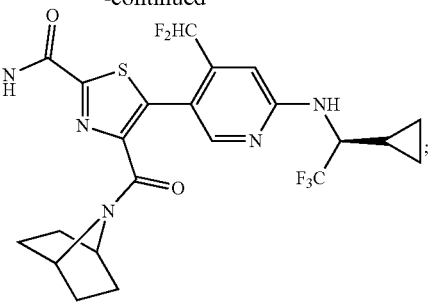
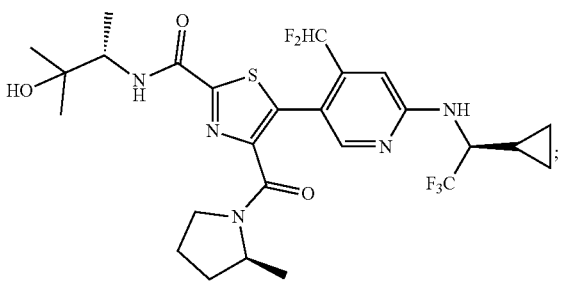
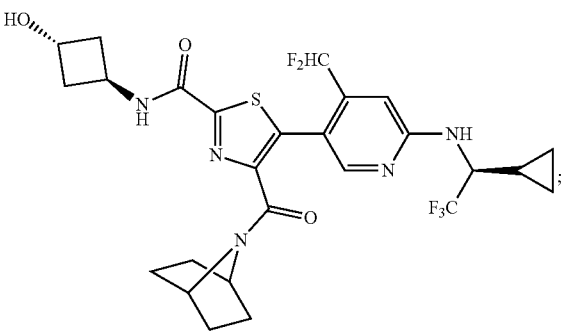
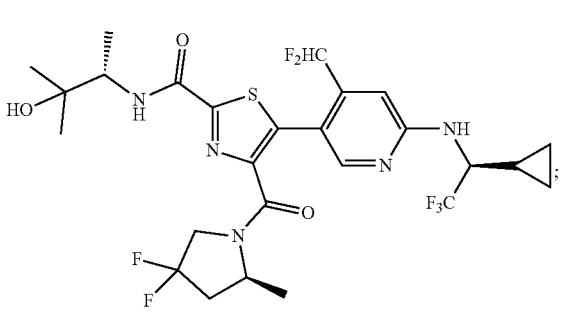
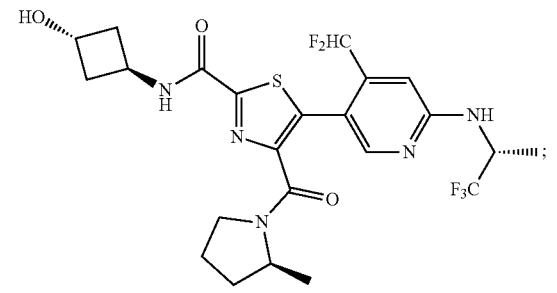

181
-continued
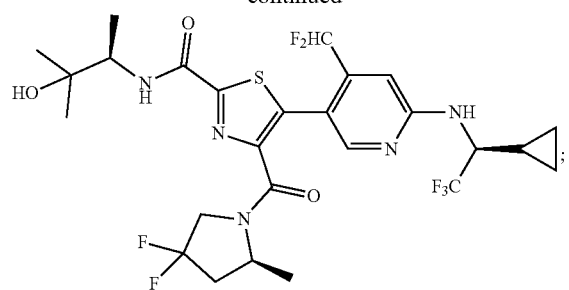
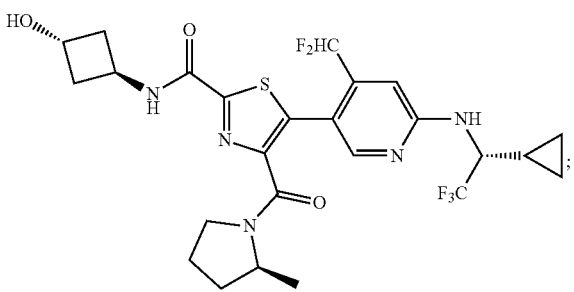
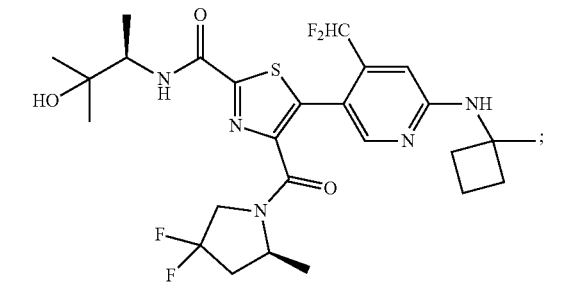
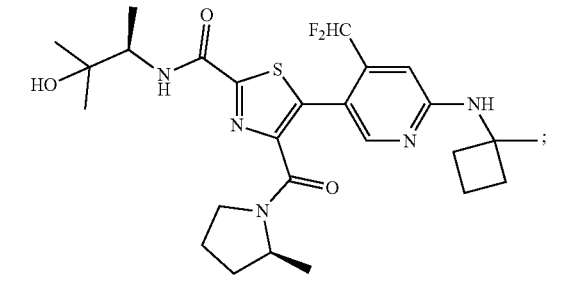
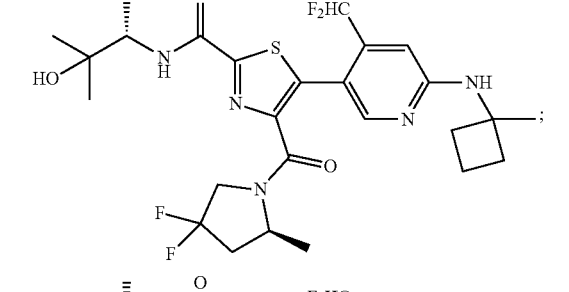
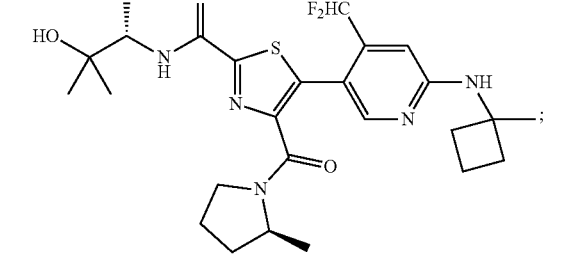
182
-continued
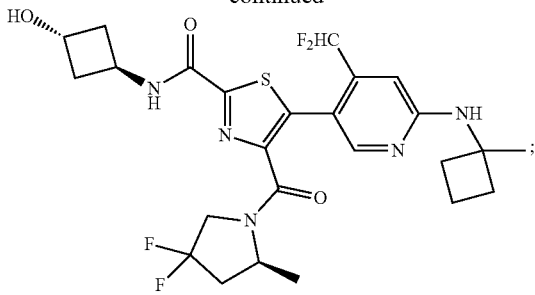
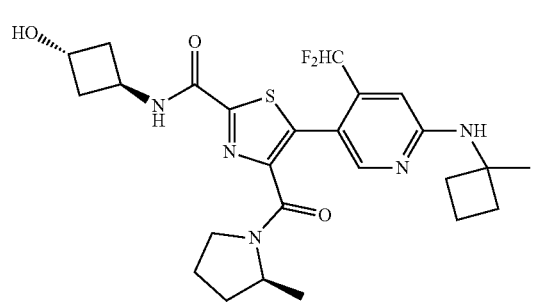
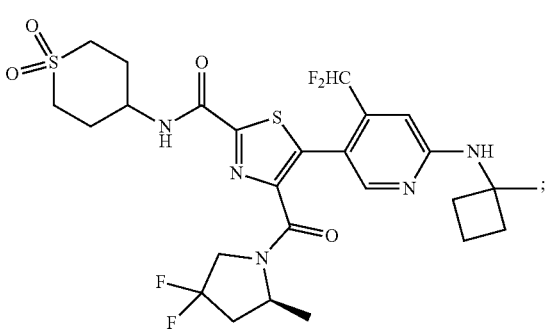
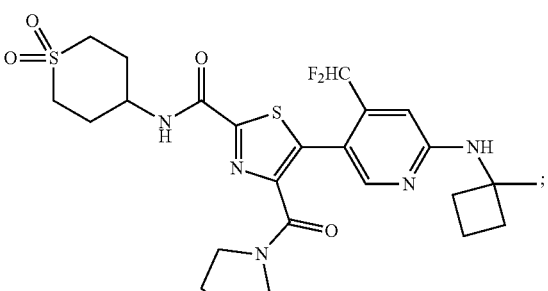
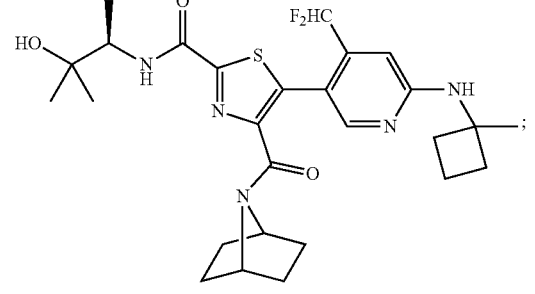

-continued
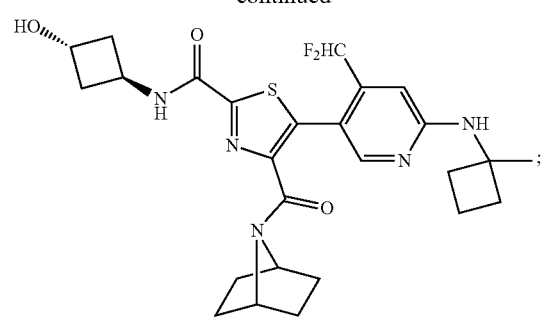
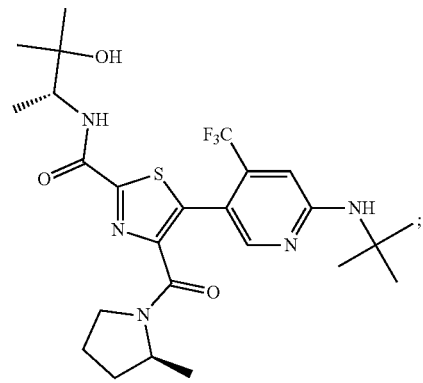
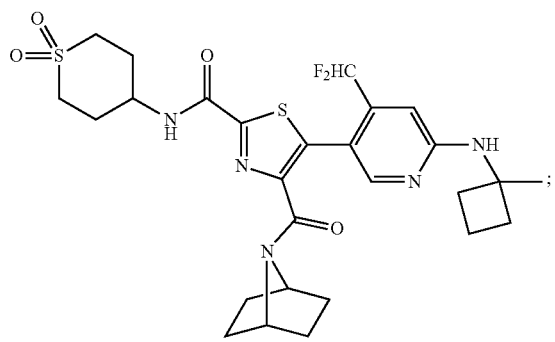
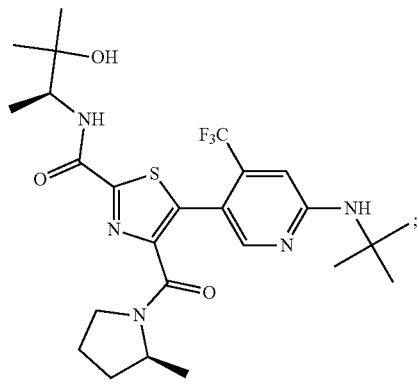
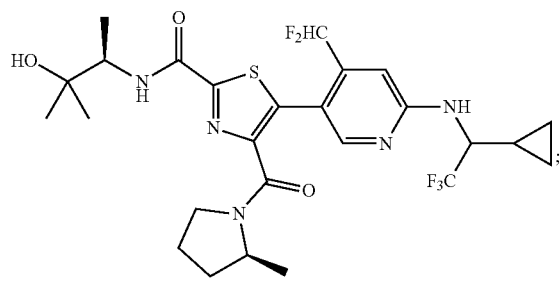
-continued
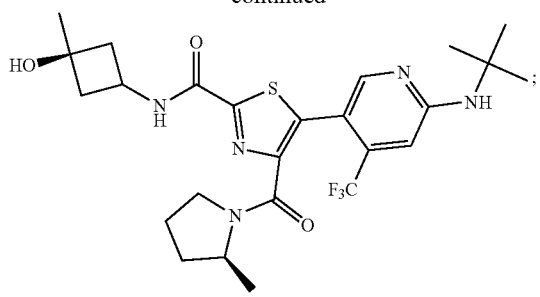
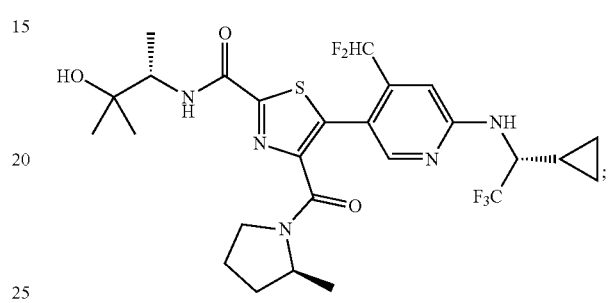
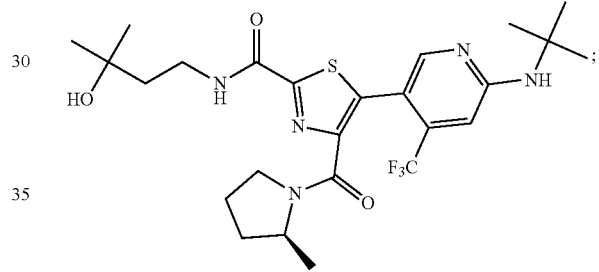
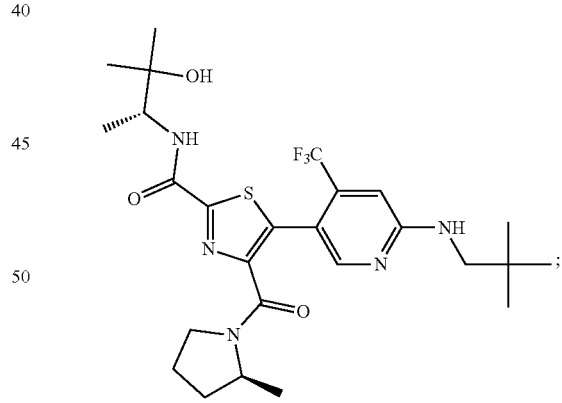
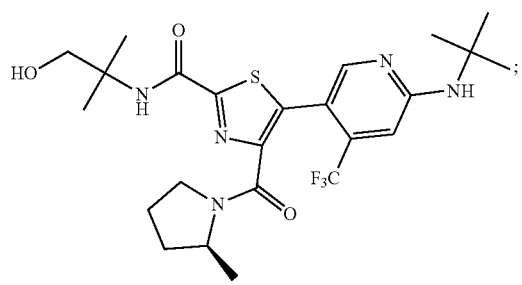

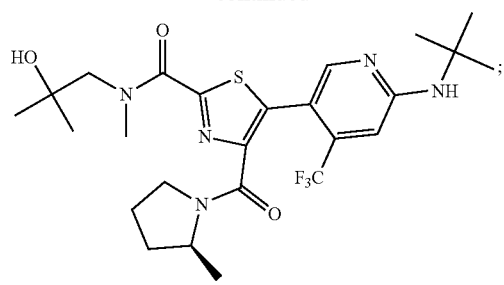
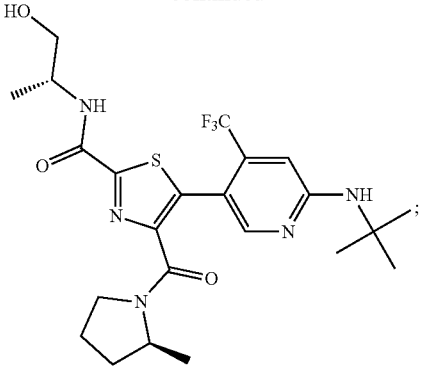
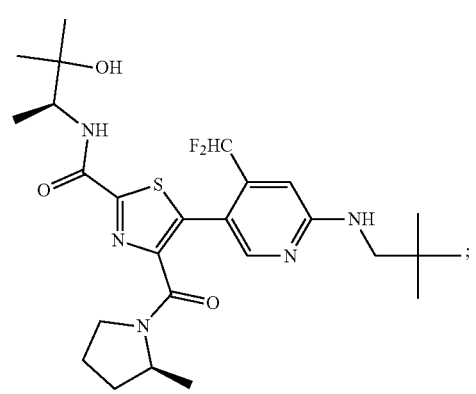
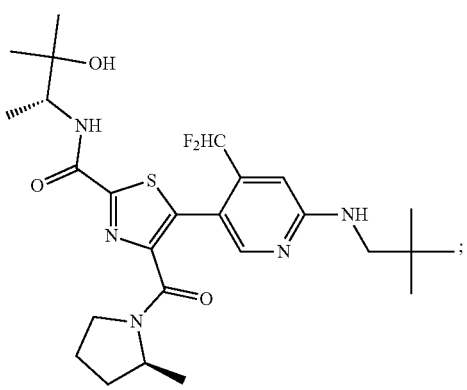
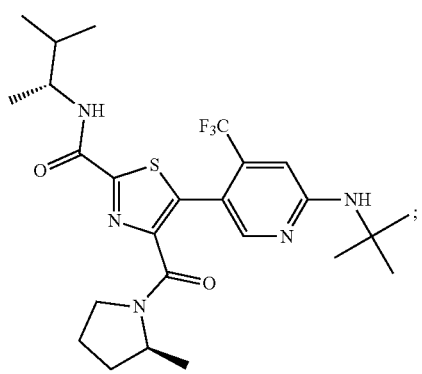
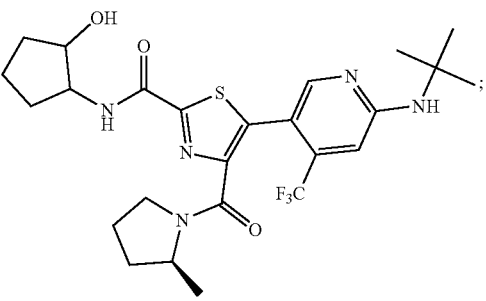
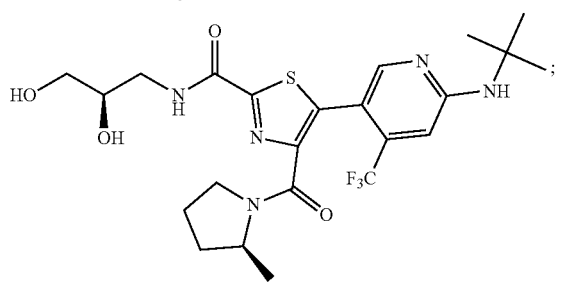
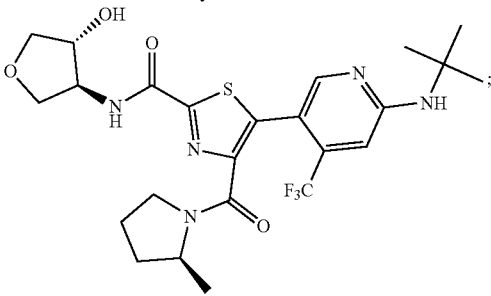
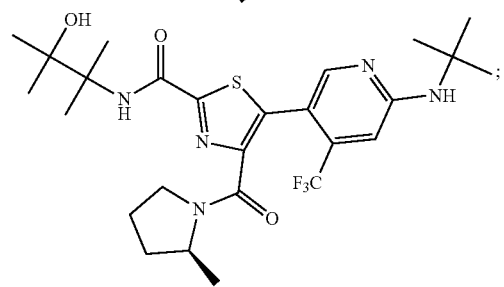
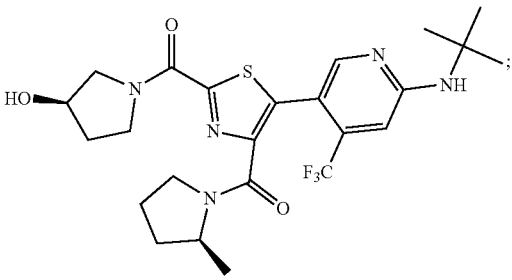

187
-continued
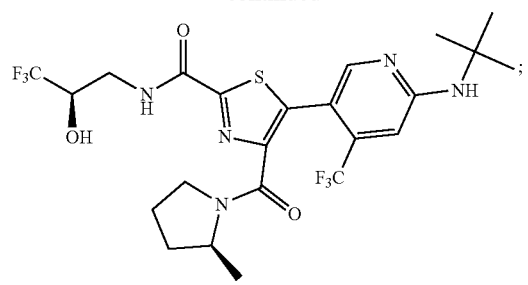
188
-continued
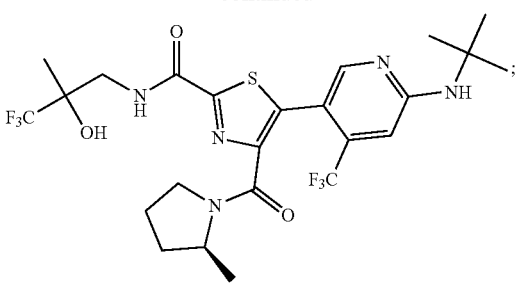
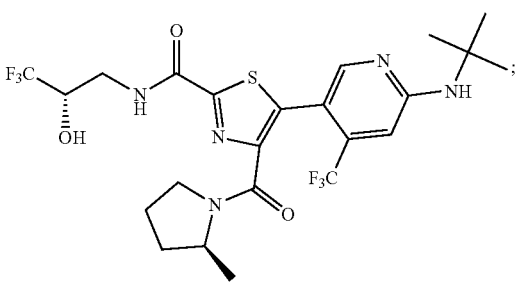
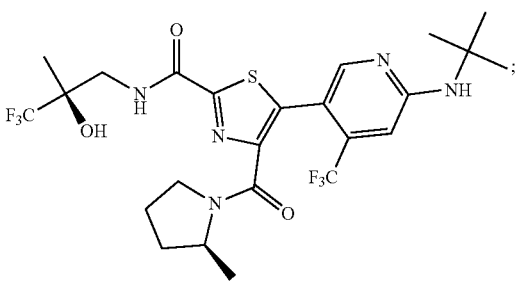
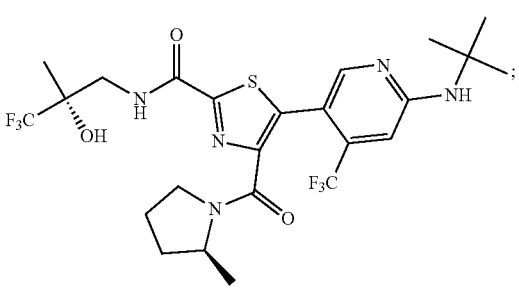
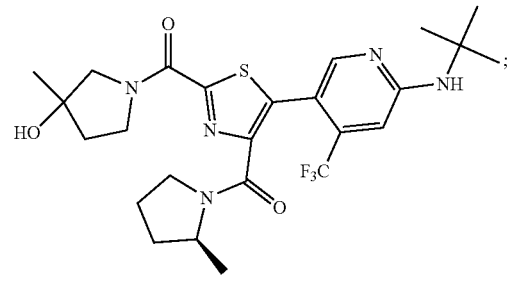
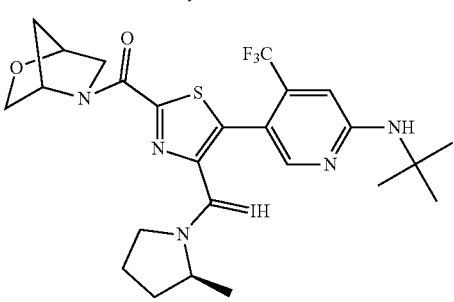

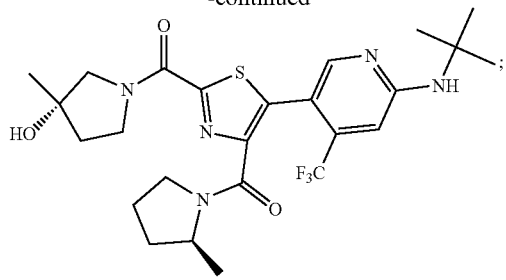
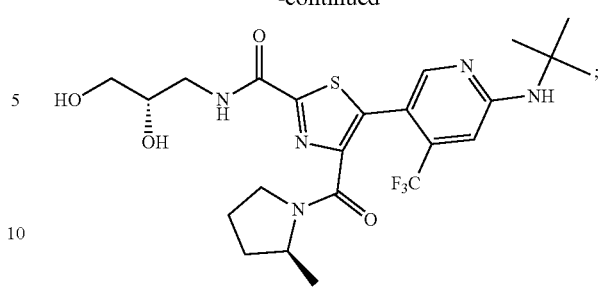
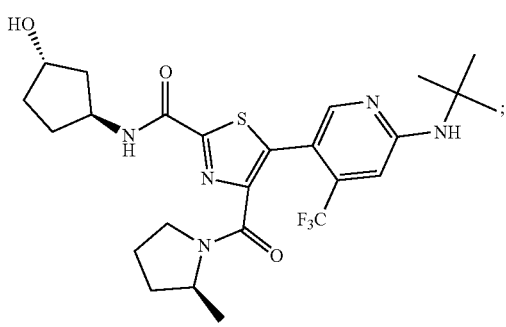
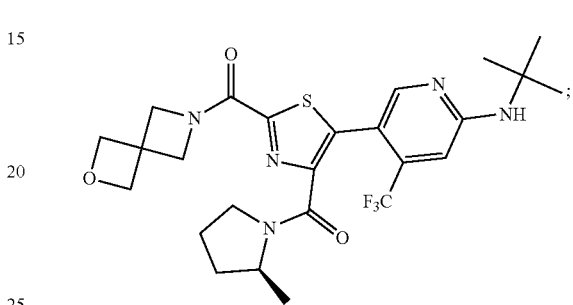
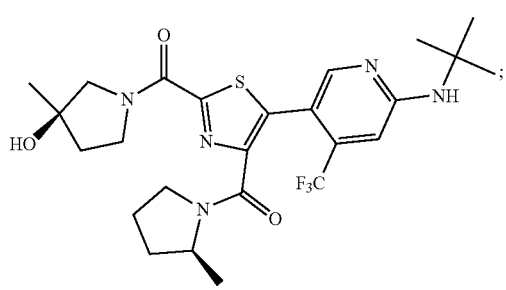
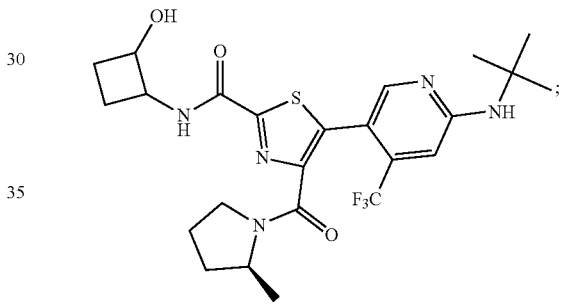
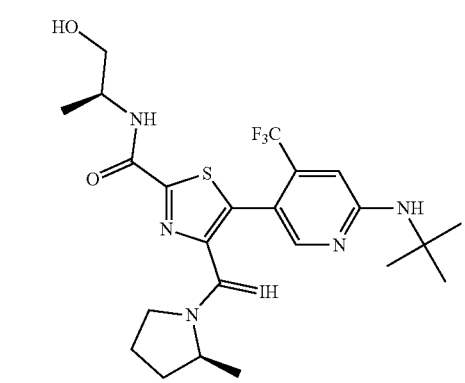
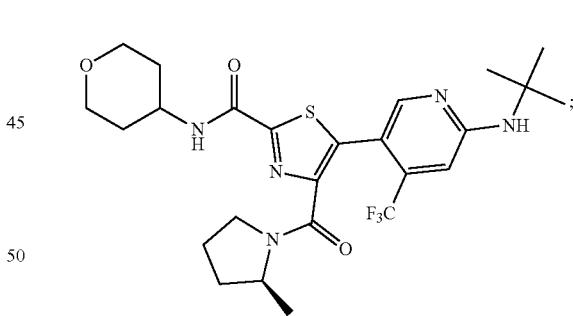
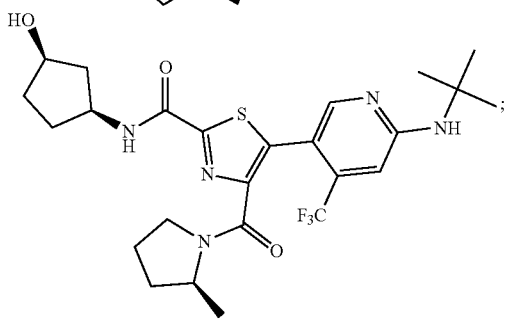
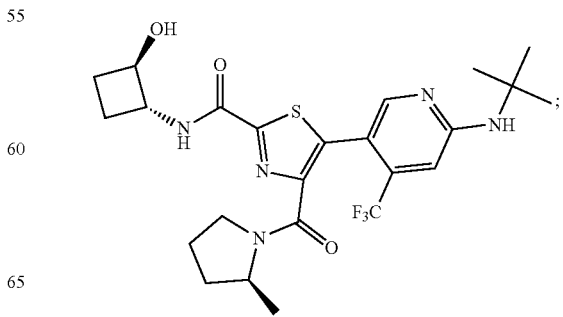

191
-continued
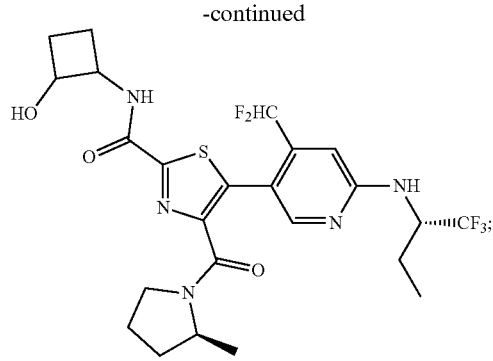
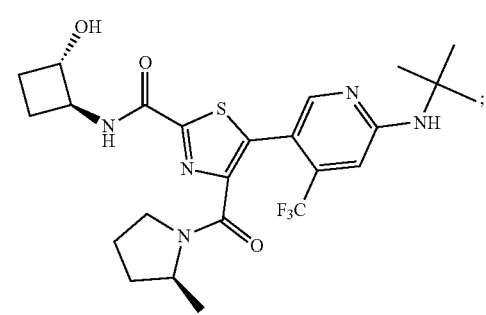
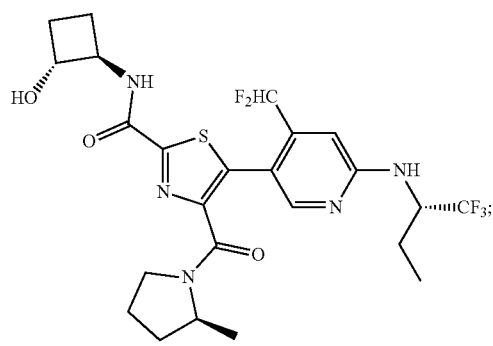
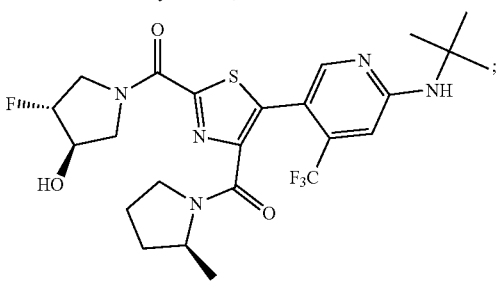
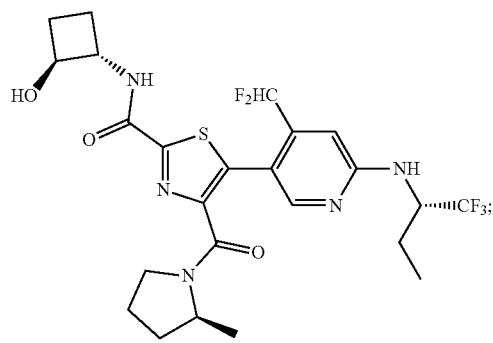
192
-continued
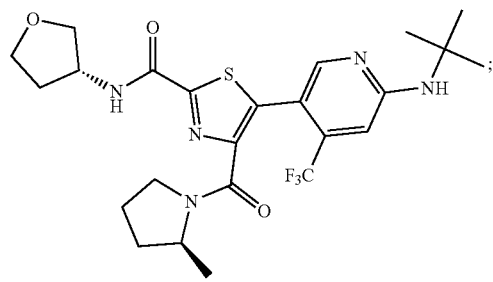
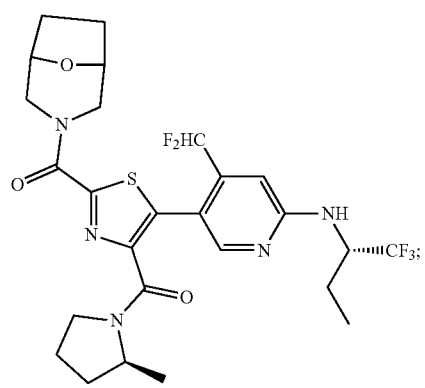
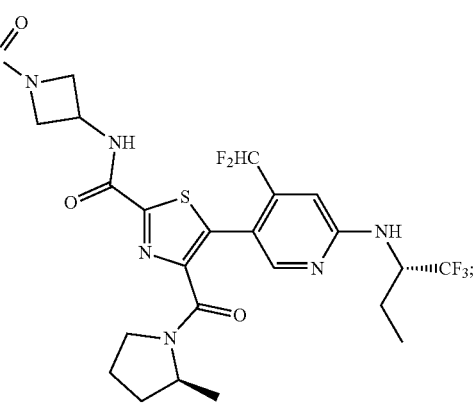
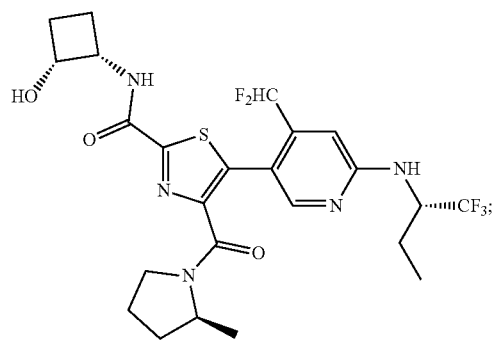

193
-continued
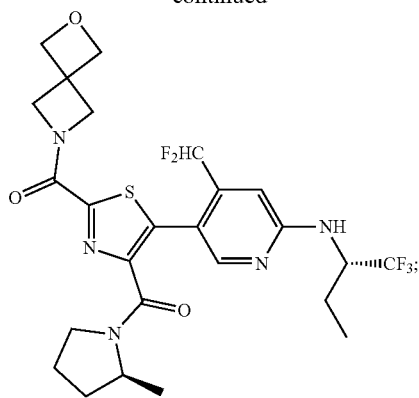
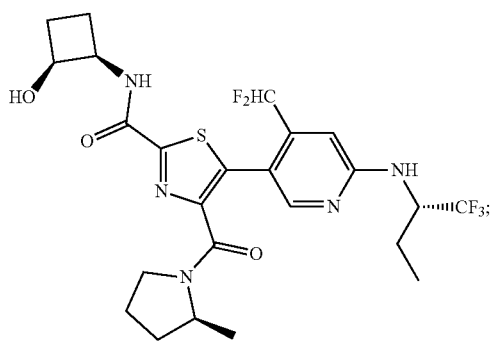
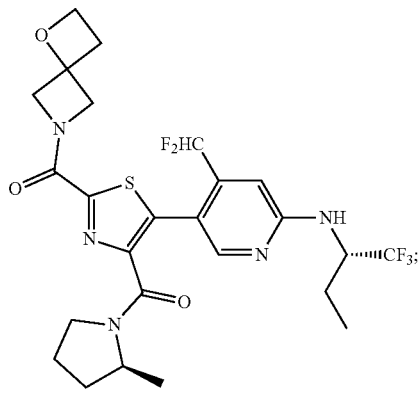
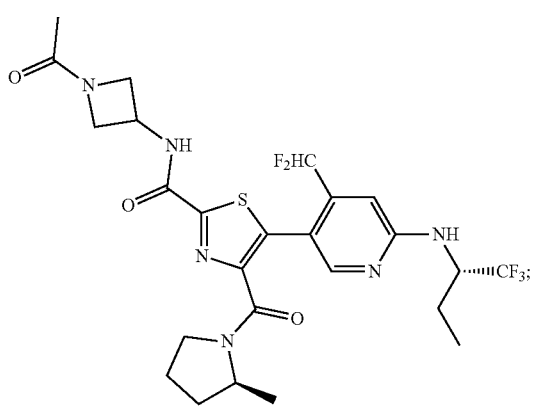
194
-continued
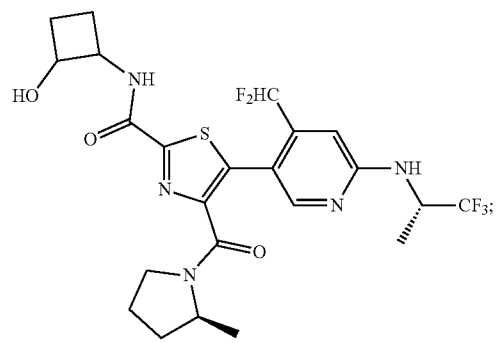
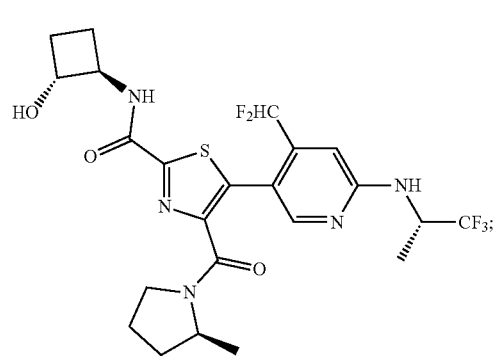
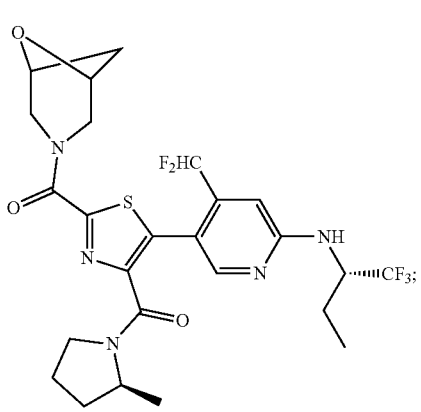
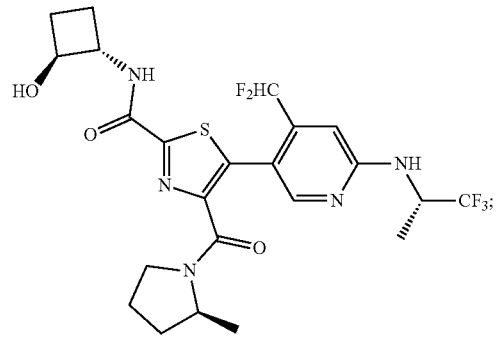

195
-continued
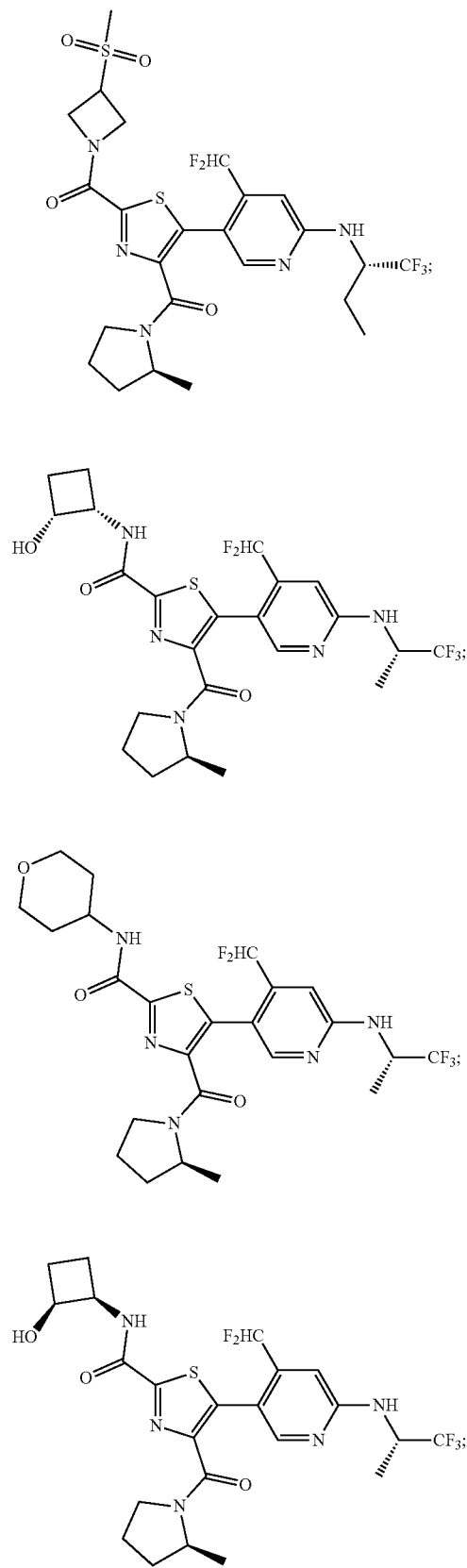
196
-continued
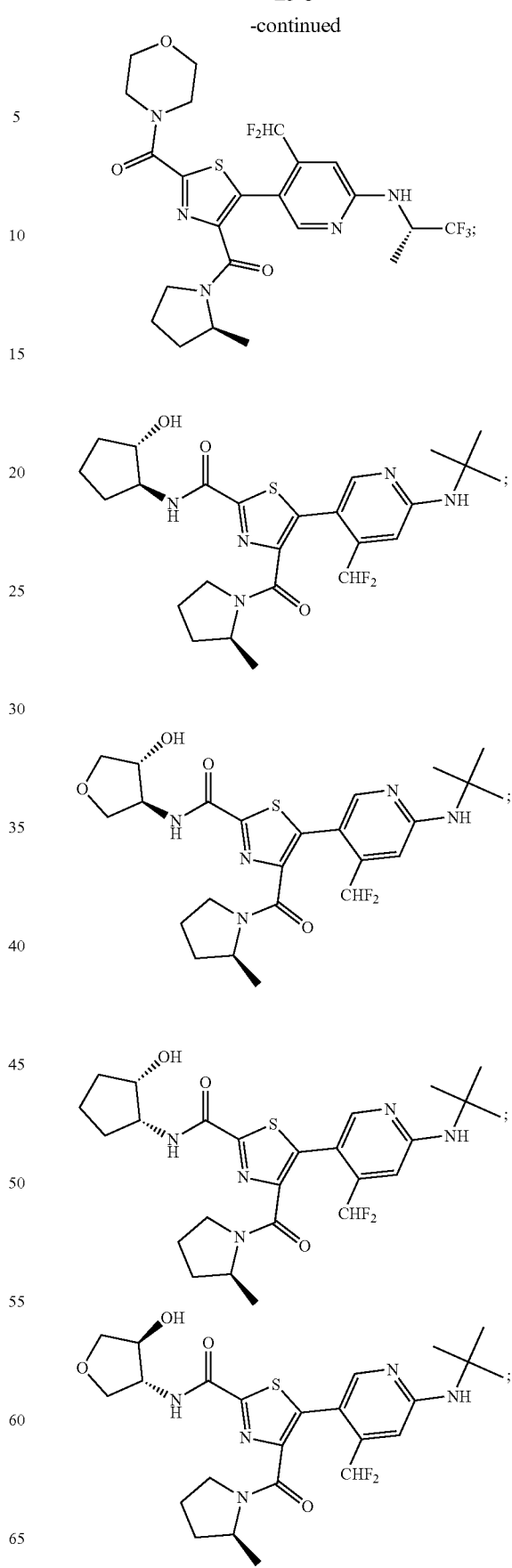

197
-continued
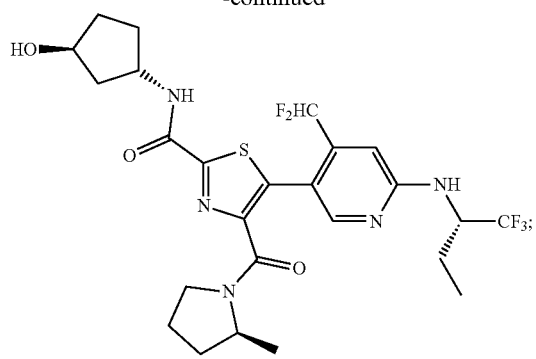
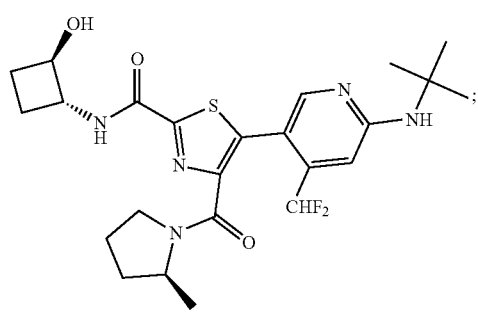
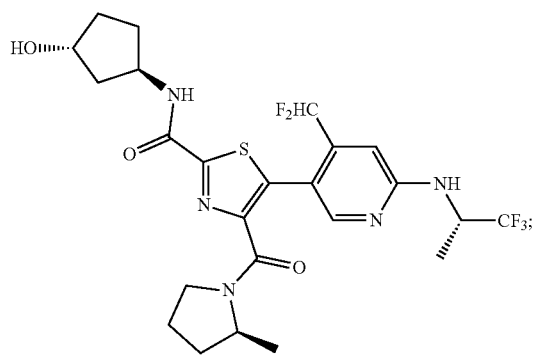
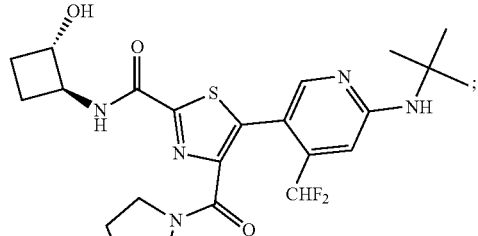
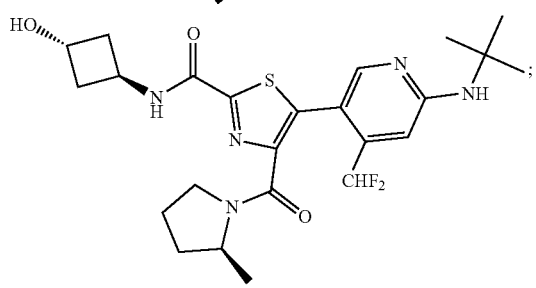
198
-continued
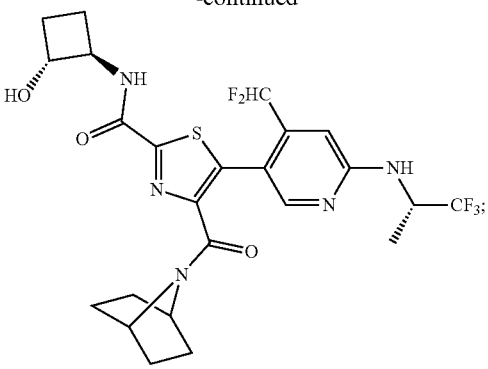
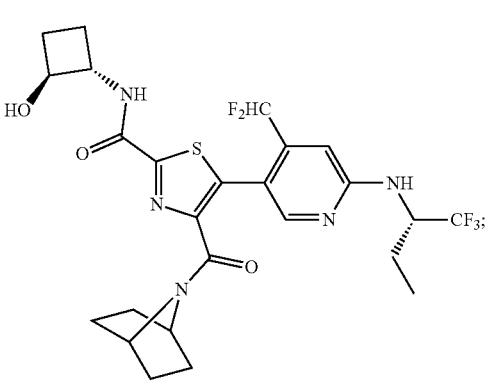
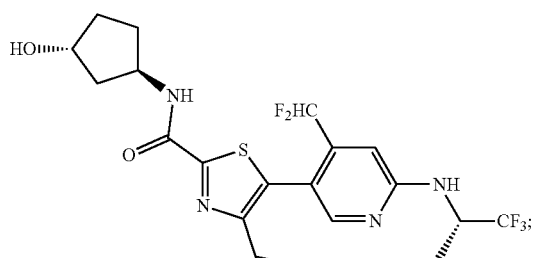
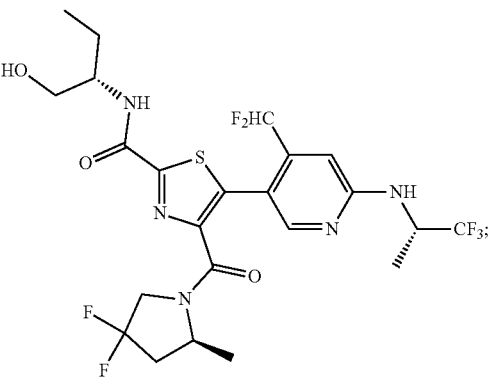

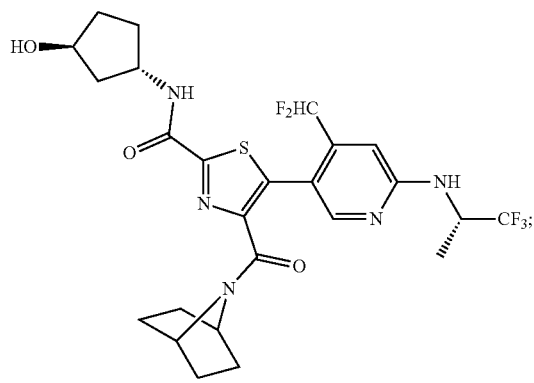
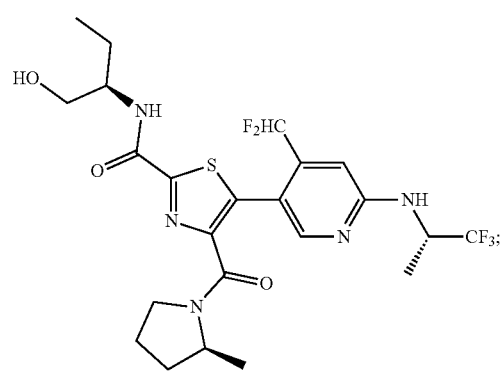
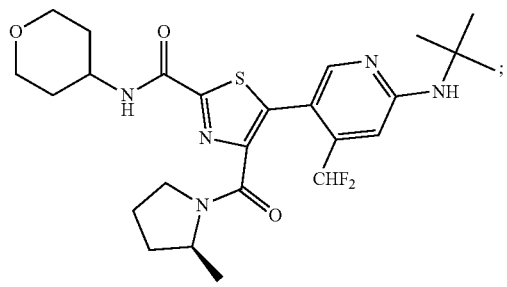
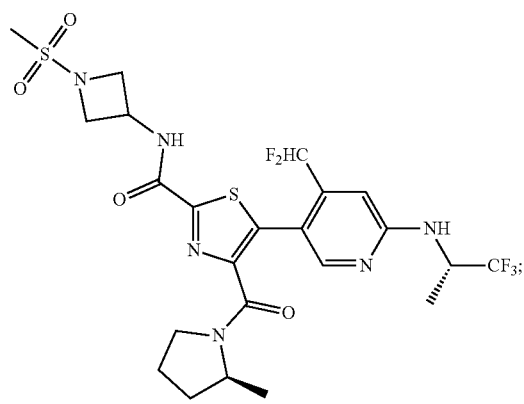
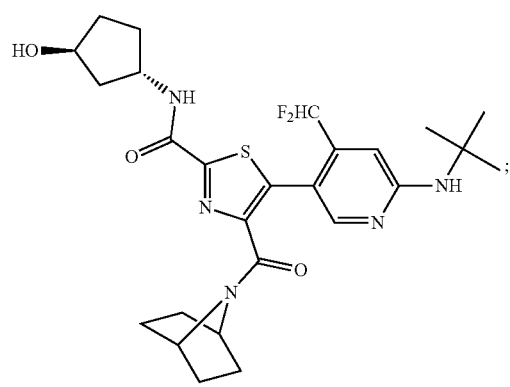
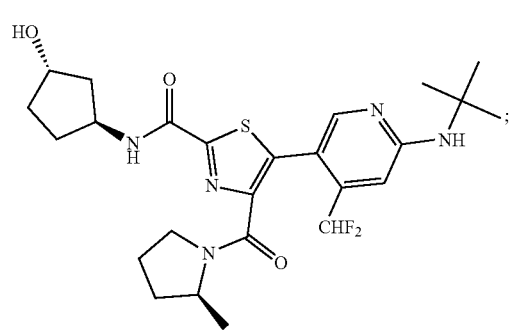
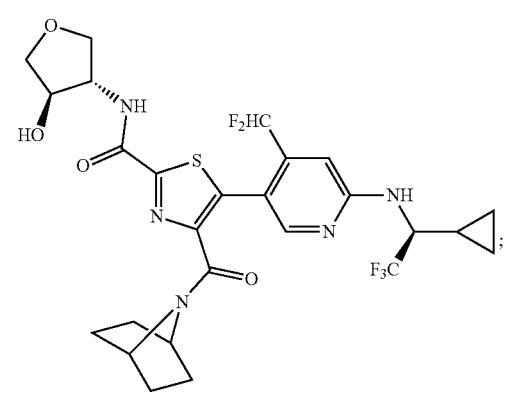
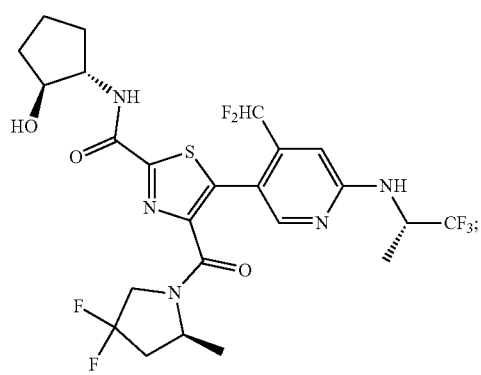

201
-continued
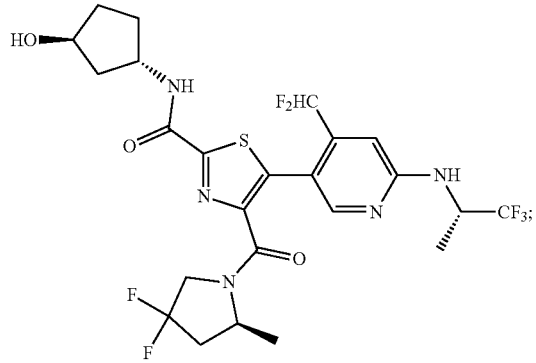
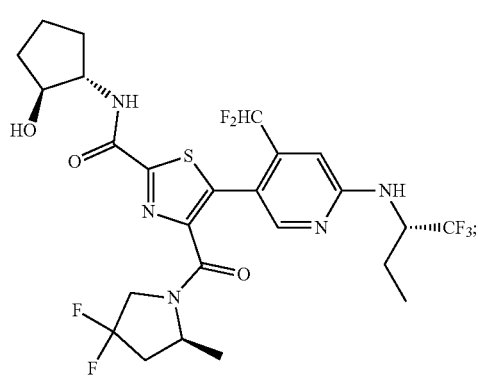
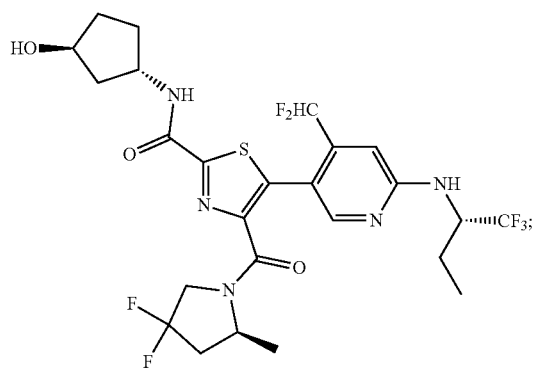
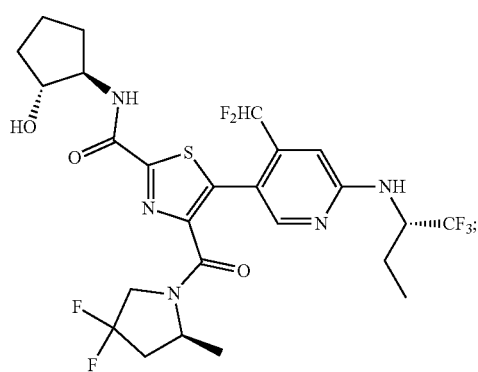
202
-continued
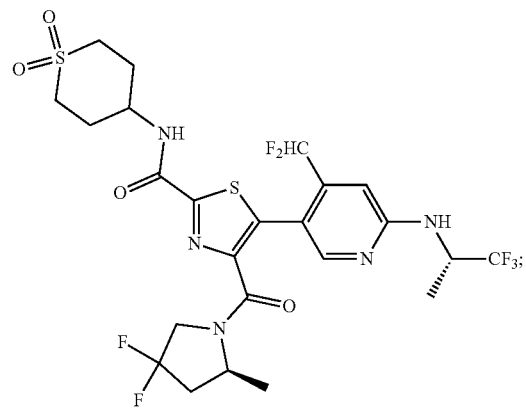
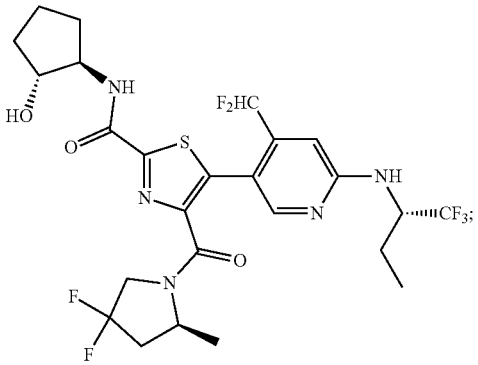
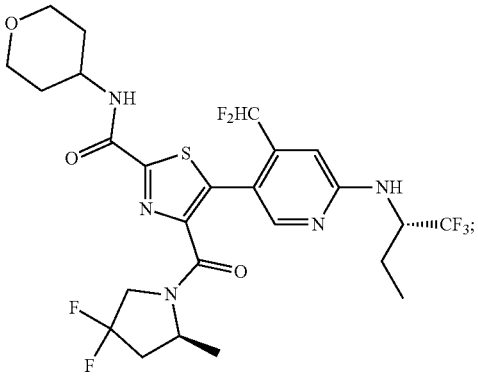
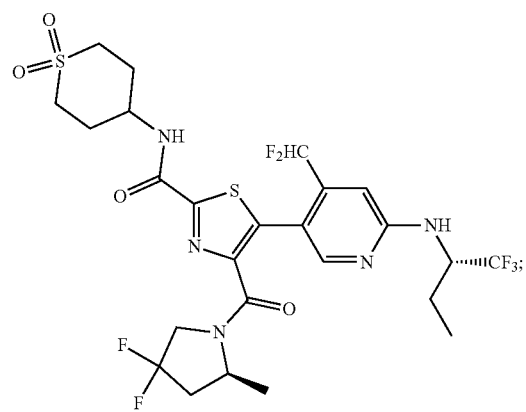

203
-continued
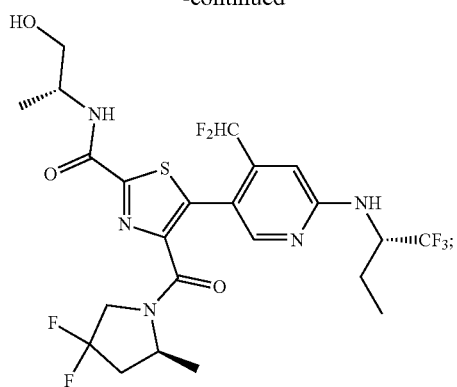
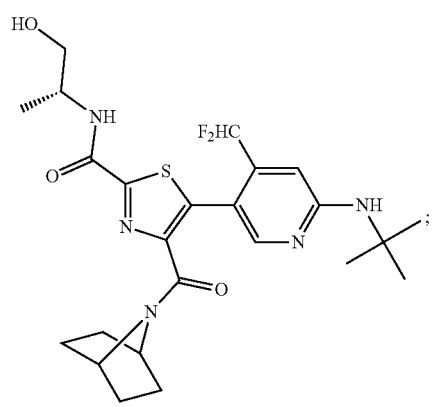
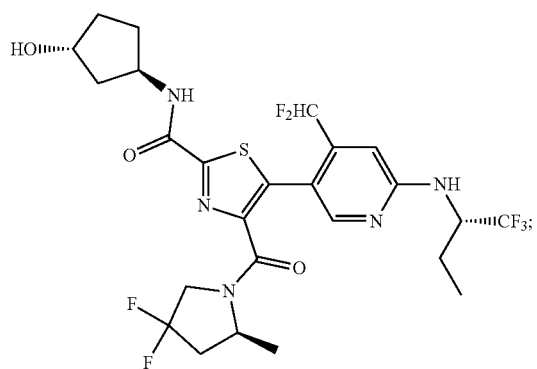
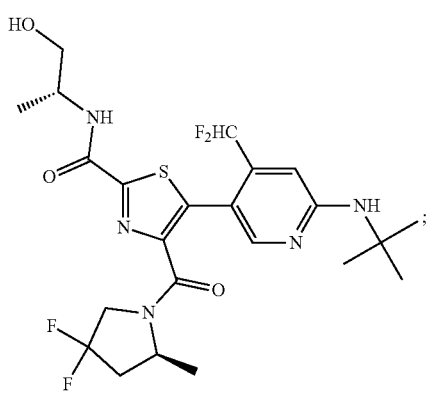
204
-continued
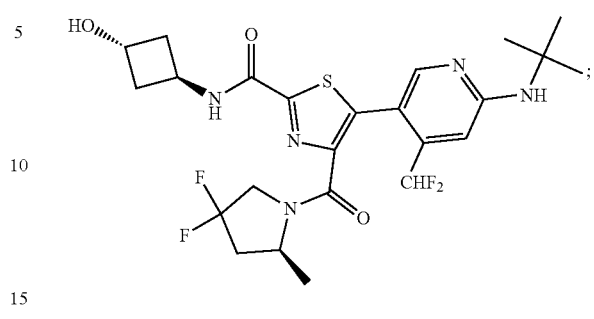
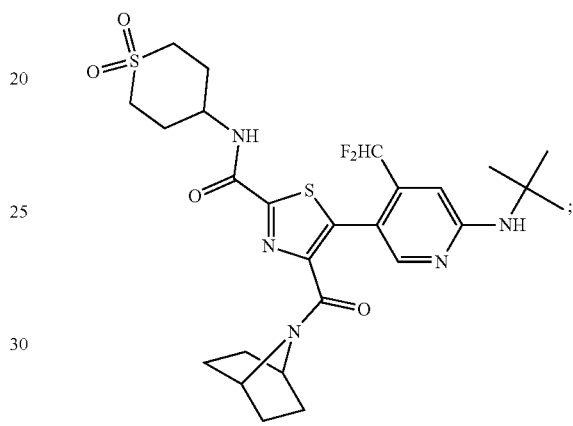
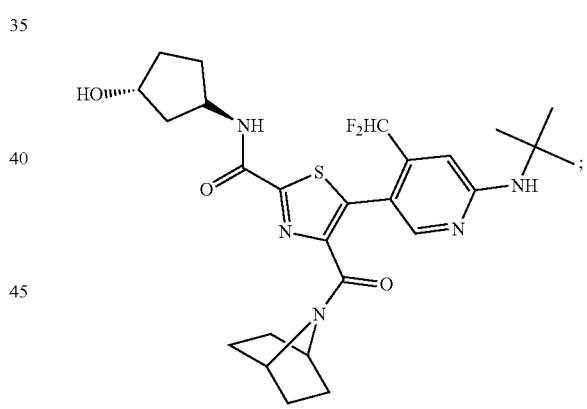
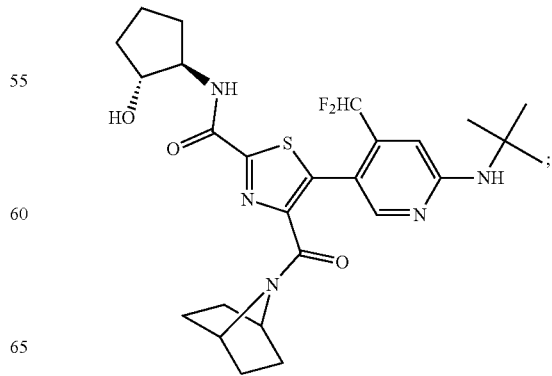

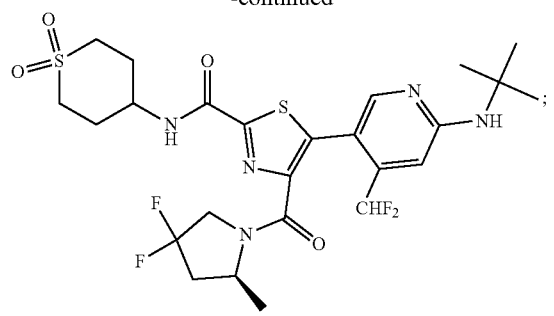
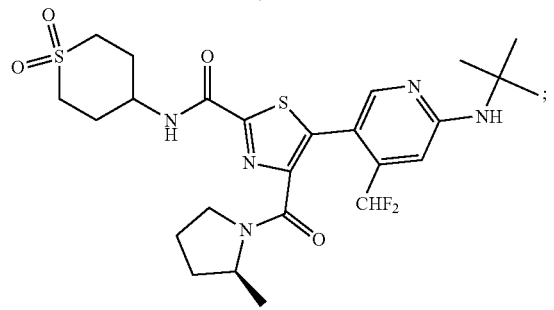
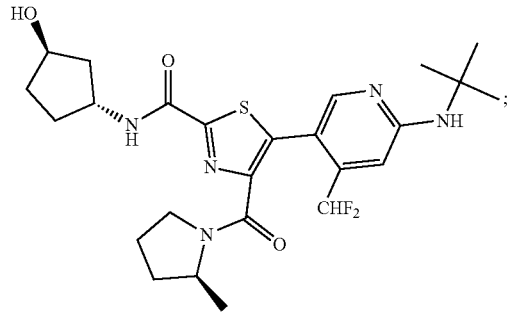
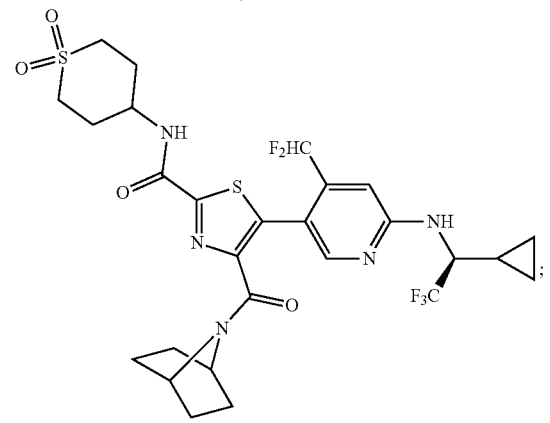
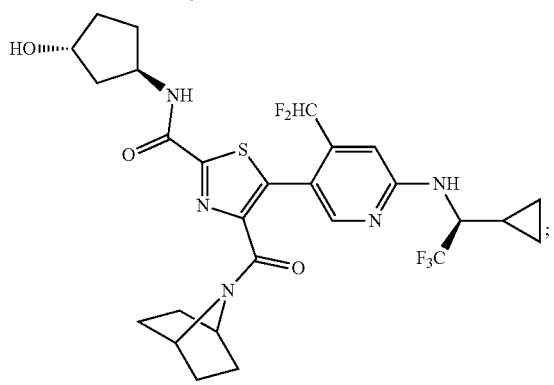
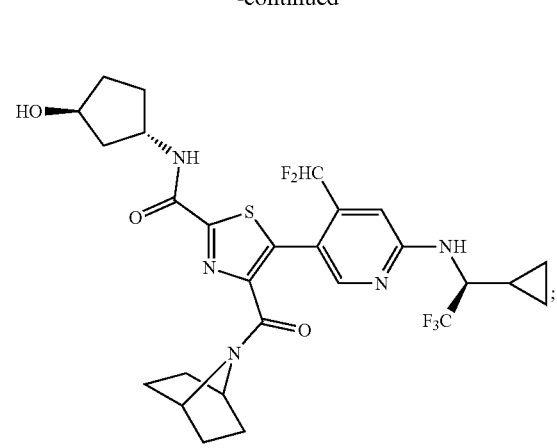
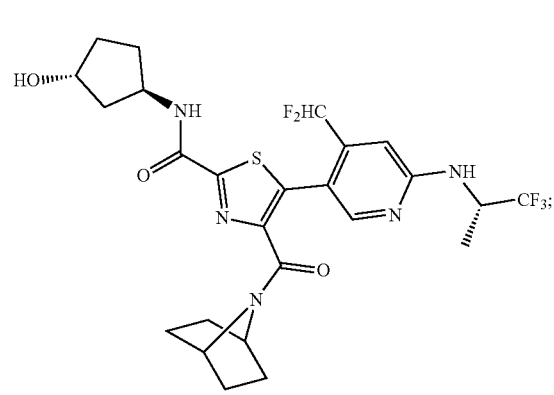
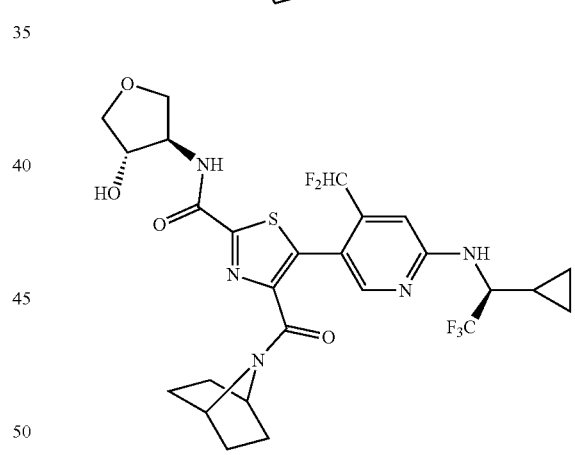
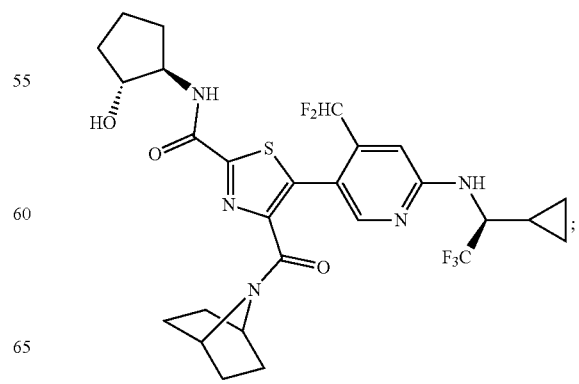

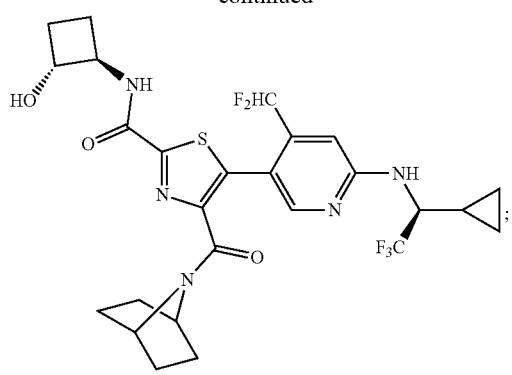
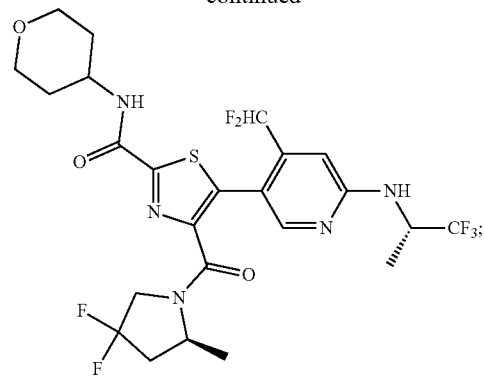
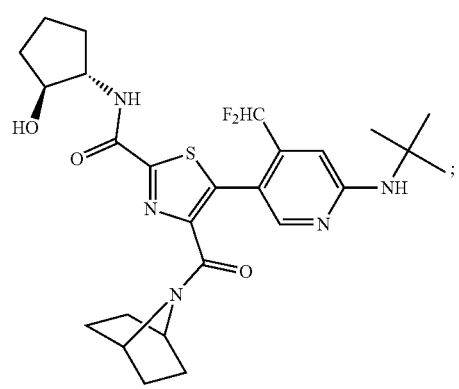
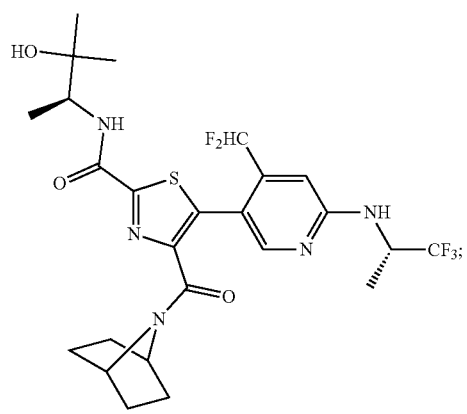
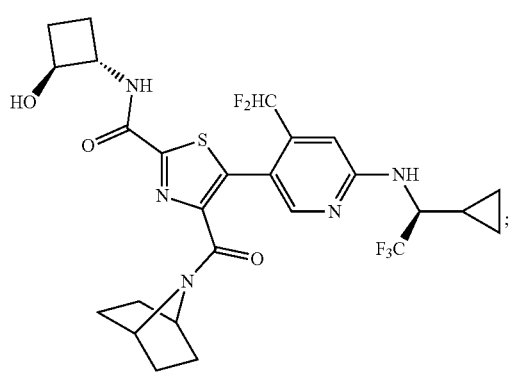
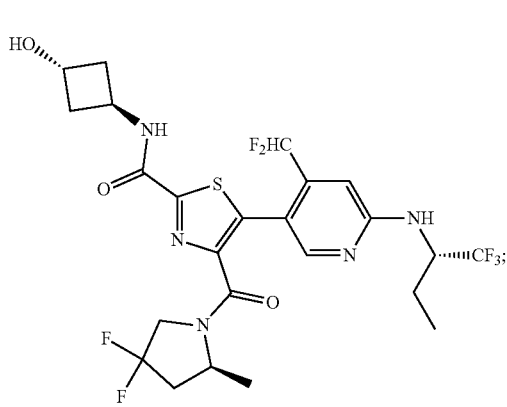
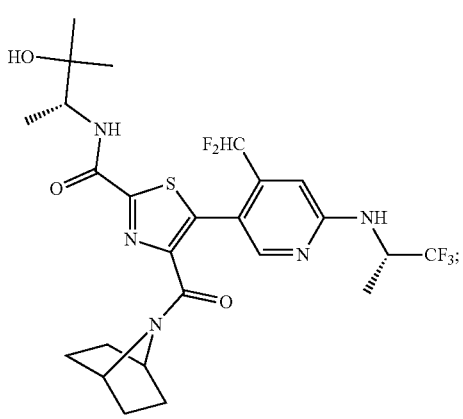
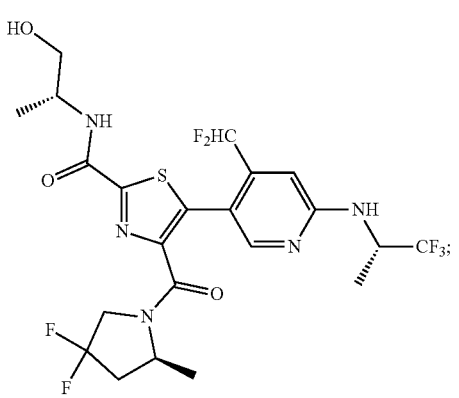

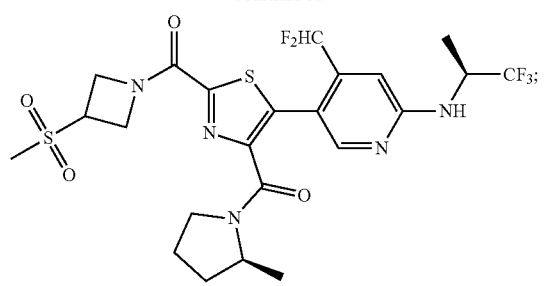
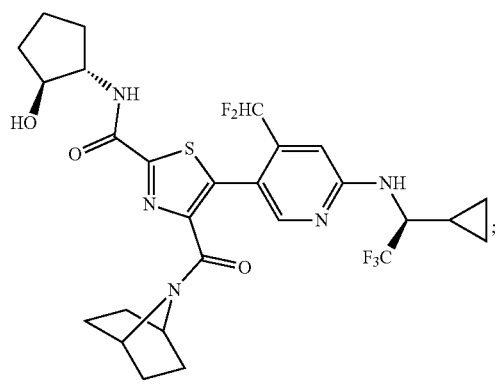
and pharmaceutically acceptable salts thereof.
Another embodiment of the invention is a compound selected from the group consisting of:
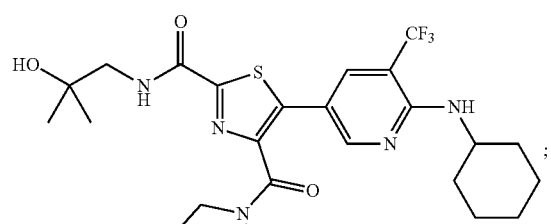
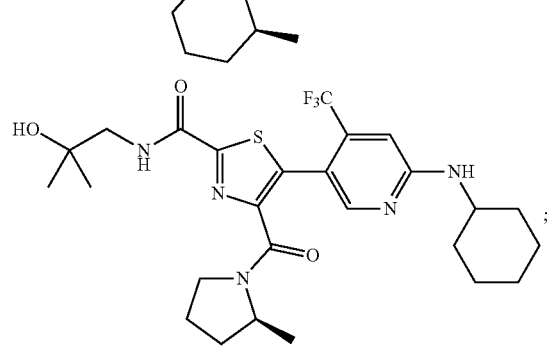
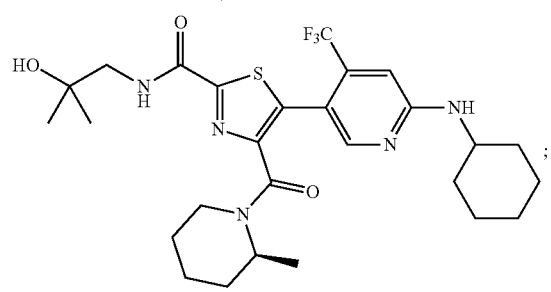
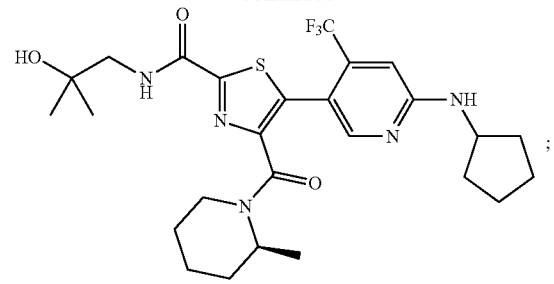
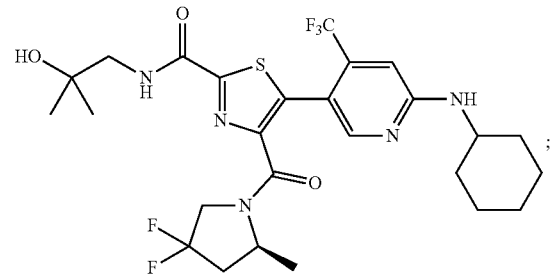
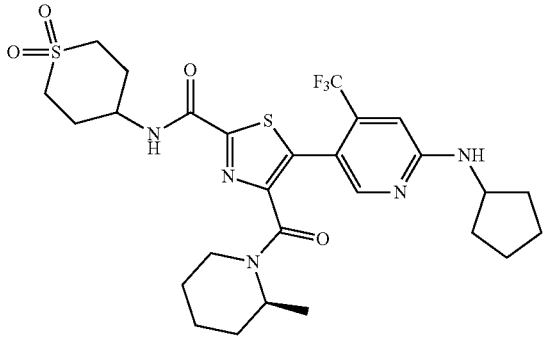
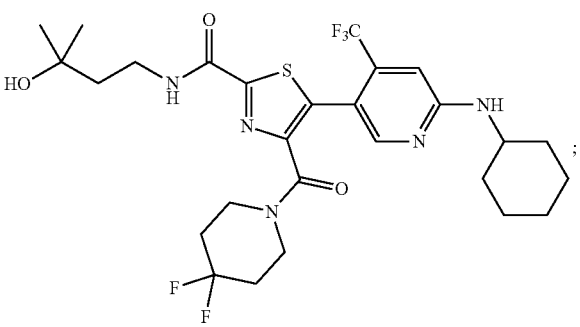
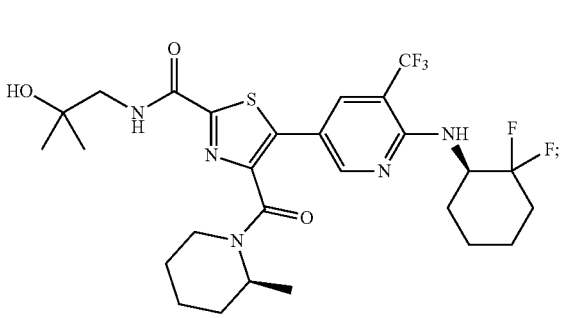

211
-continued
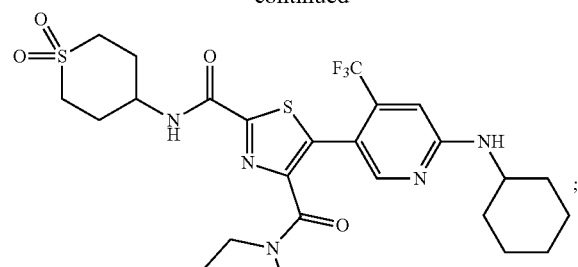
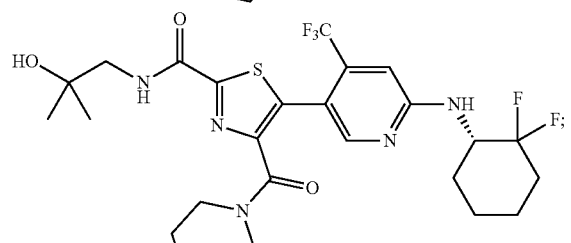
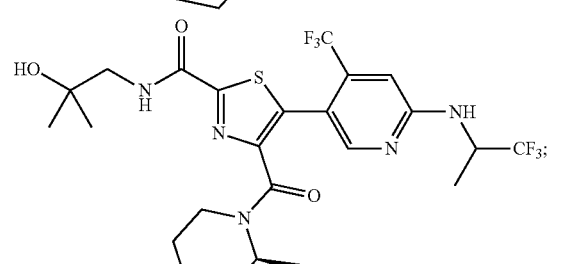
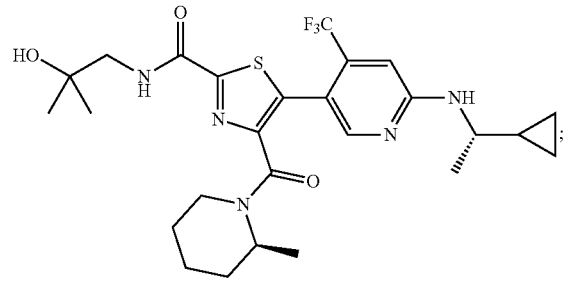
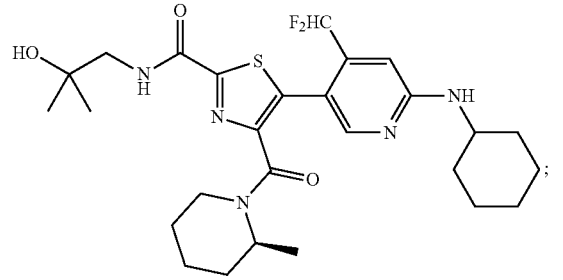
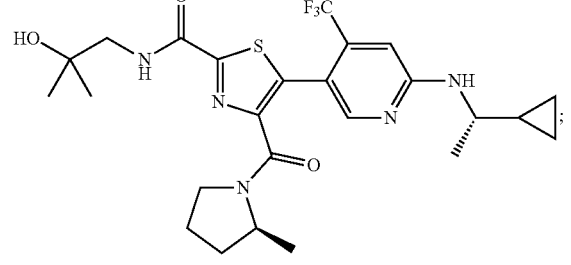
212
-continued
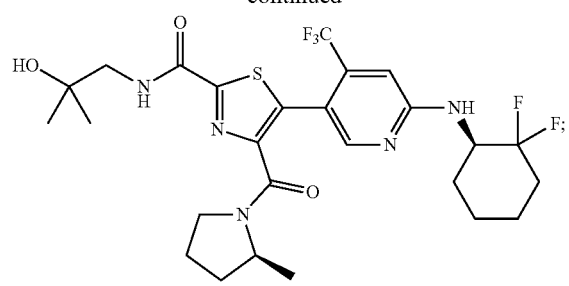
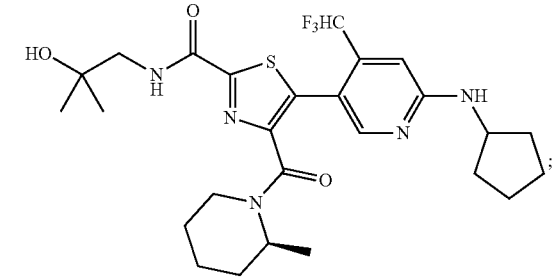
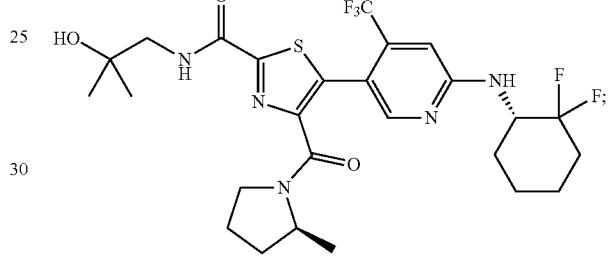
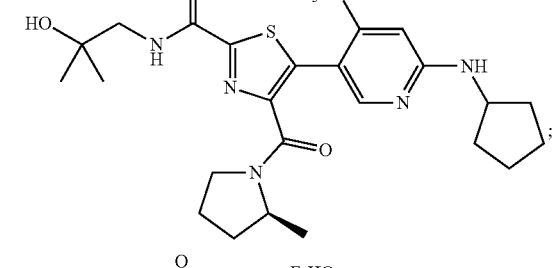
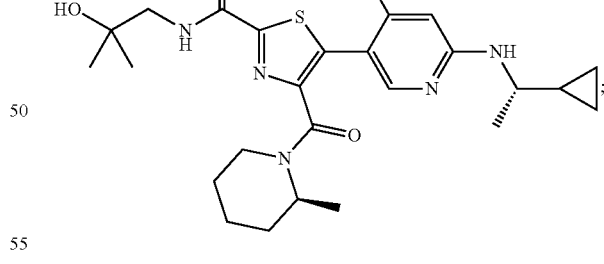
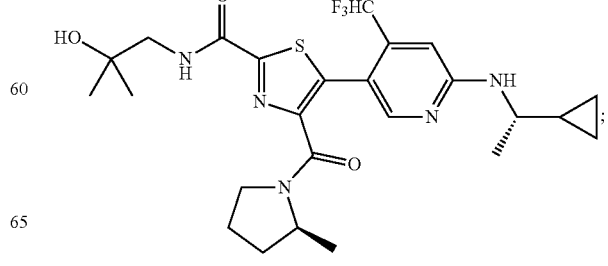

213
-continued
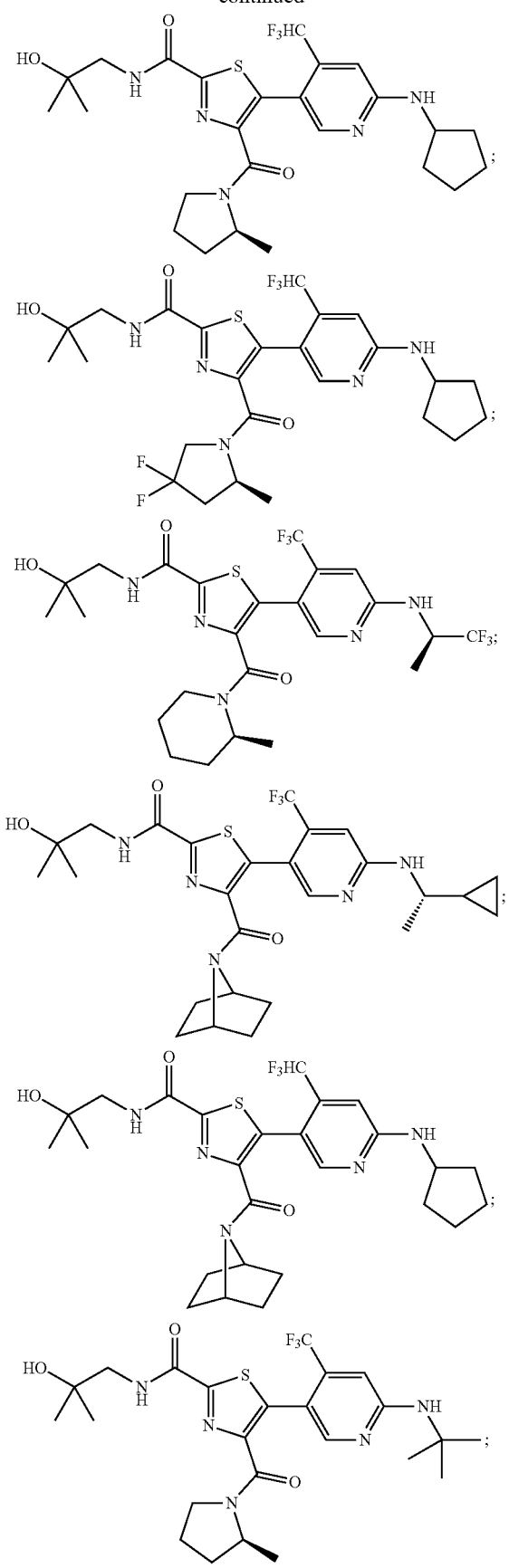
214
-continued
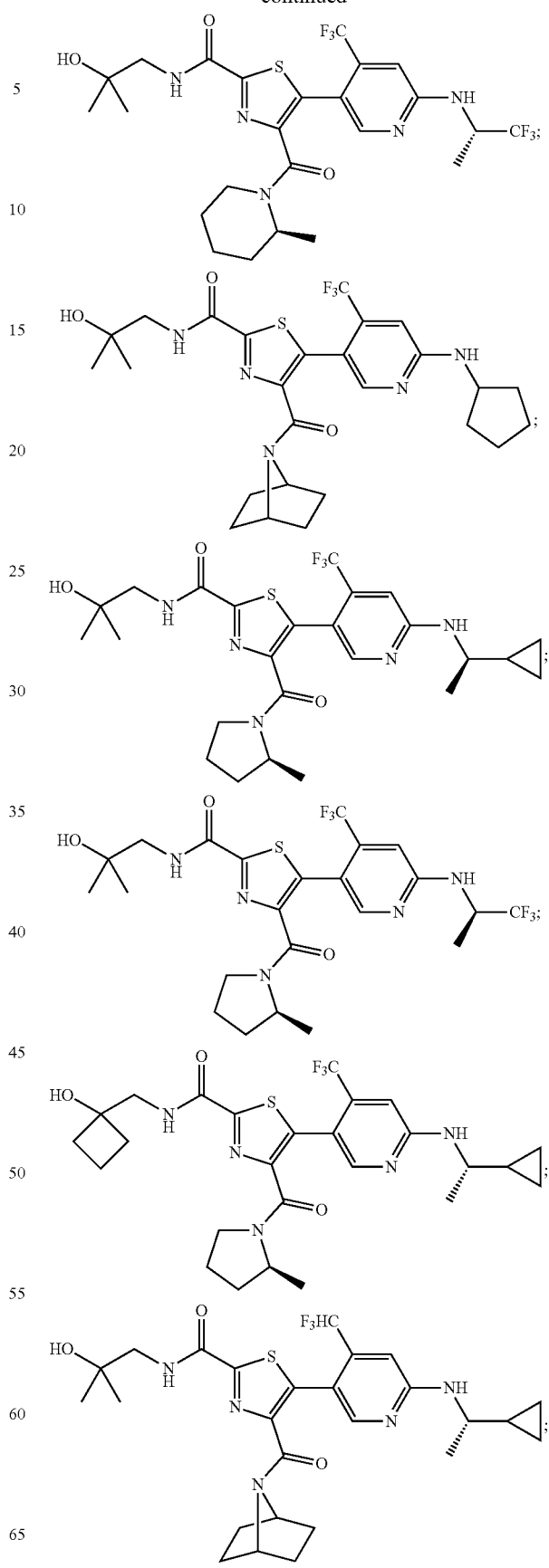

215
-continued
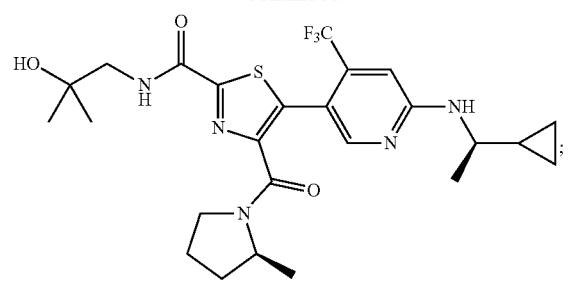
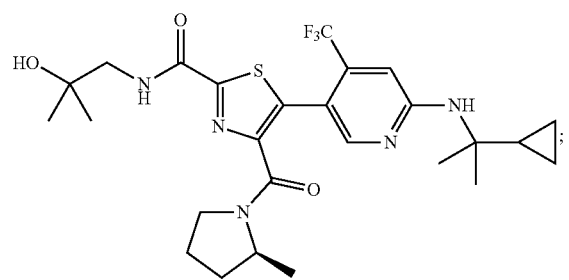
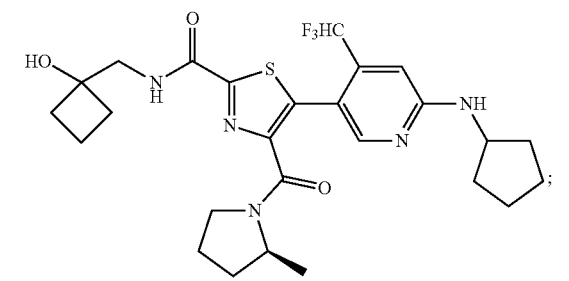
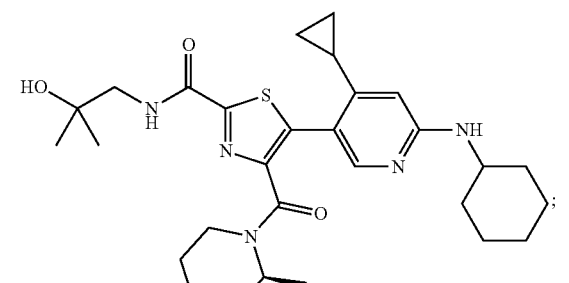
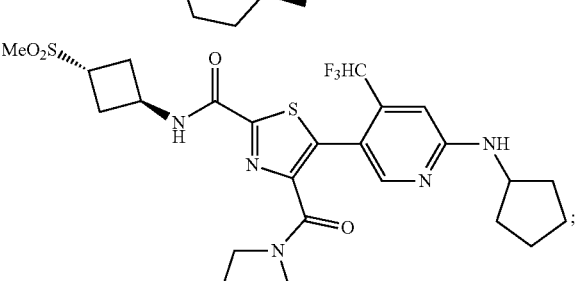
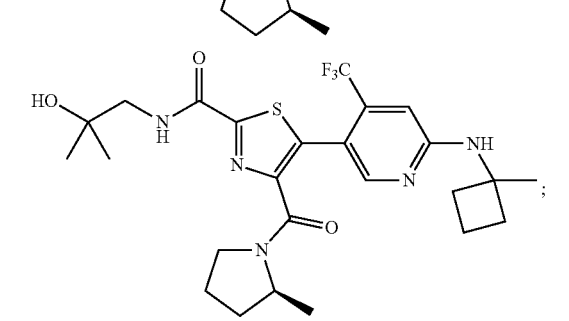
216
-continued
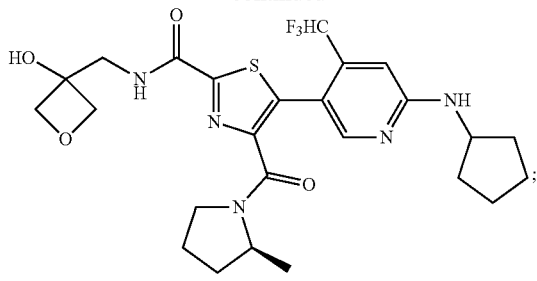
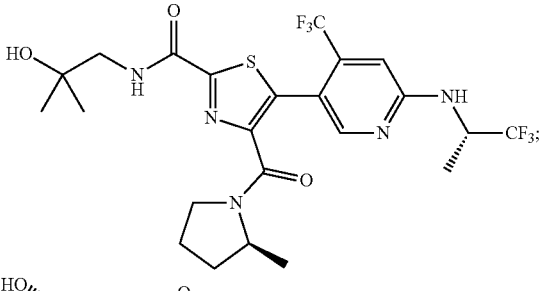
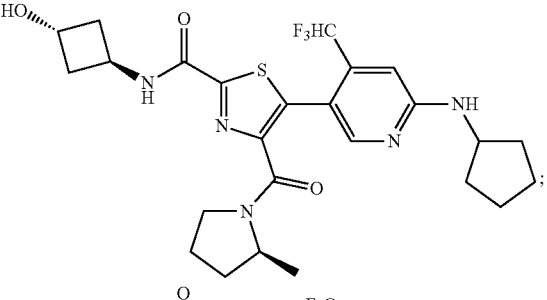
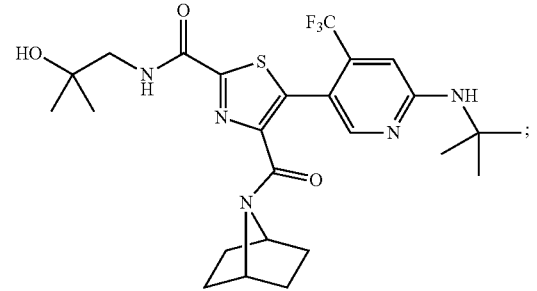
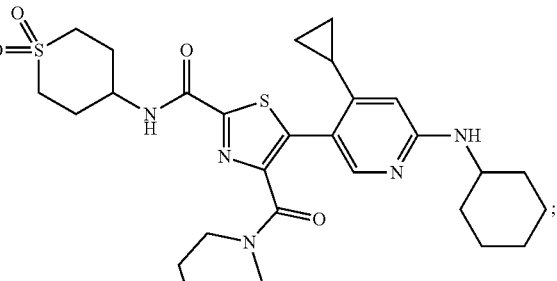
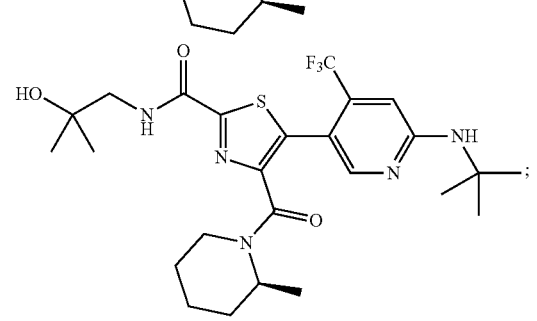

217
-continued
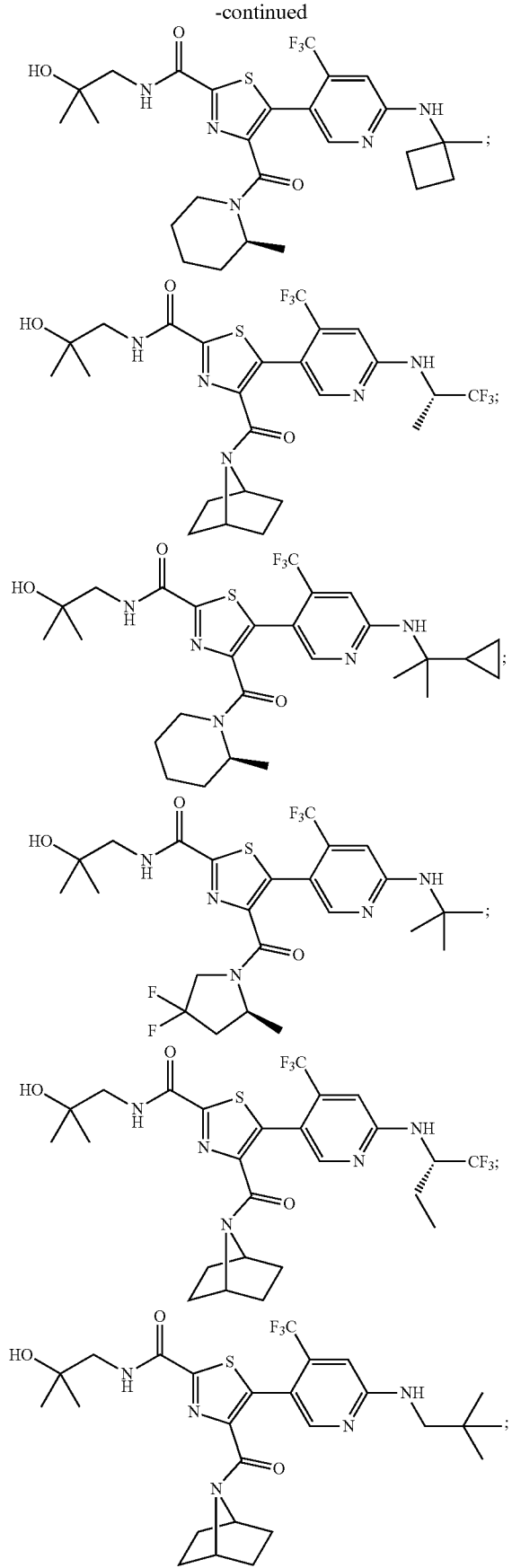
218
-continued
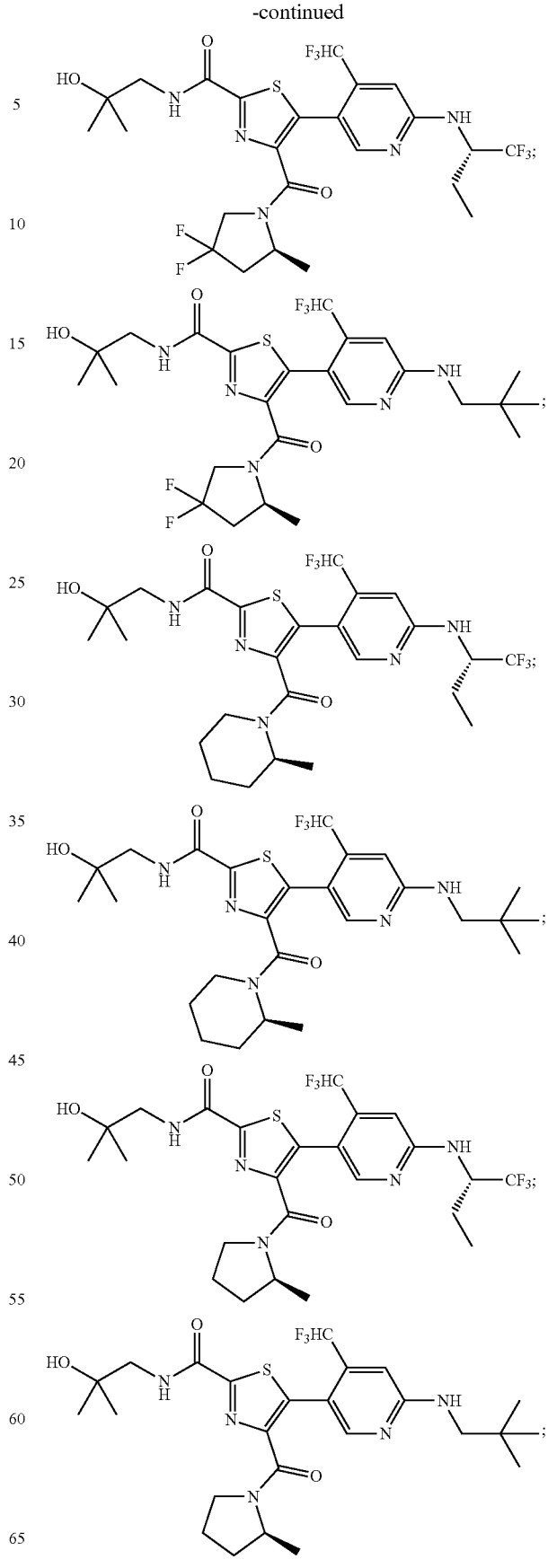

-continued

221
-continued
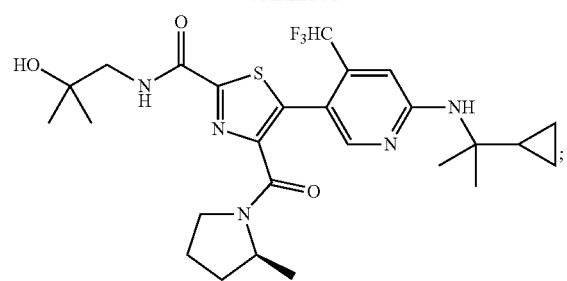
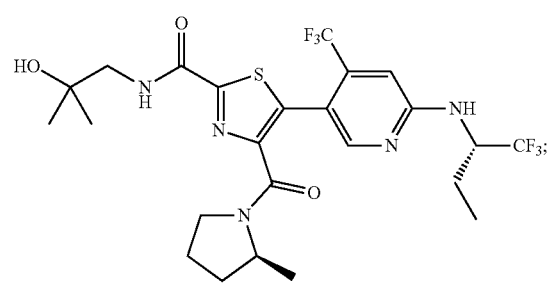
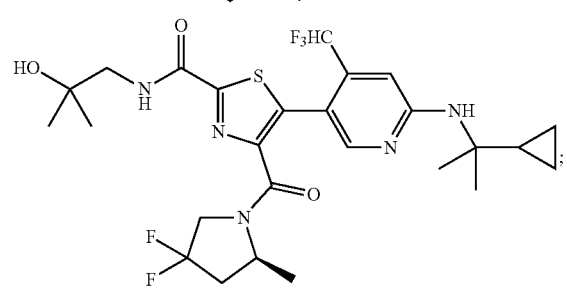
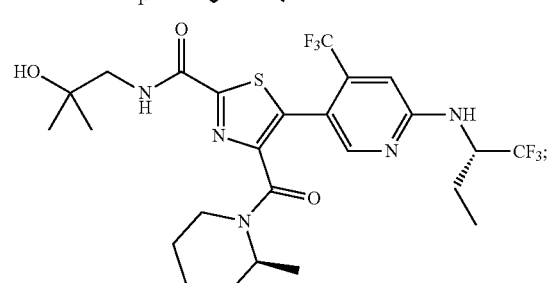
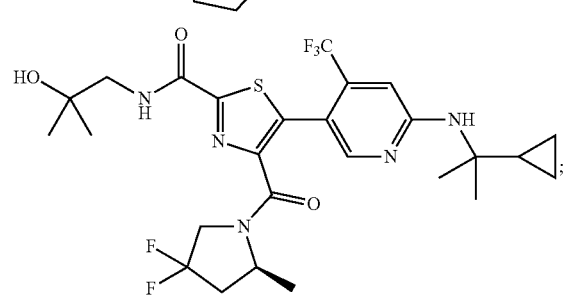
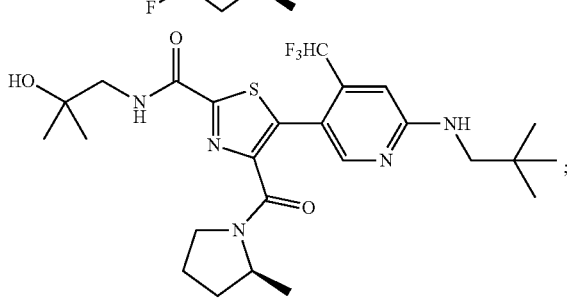
222
-continued
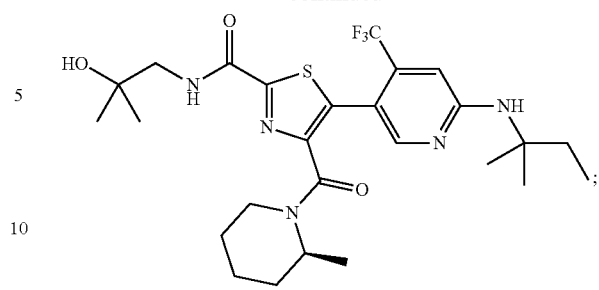
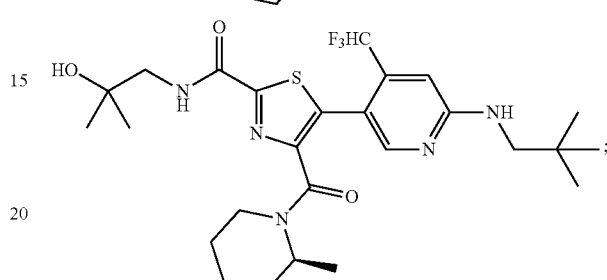
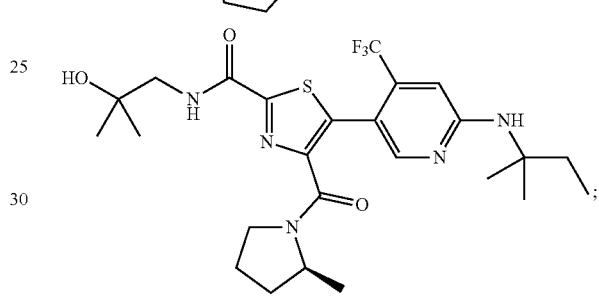
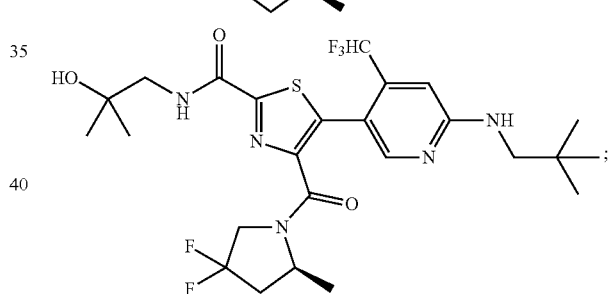
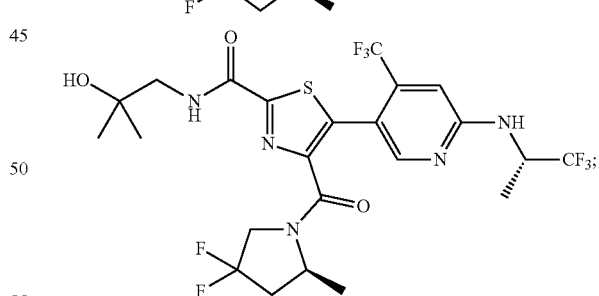
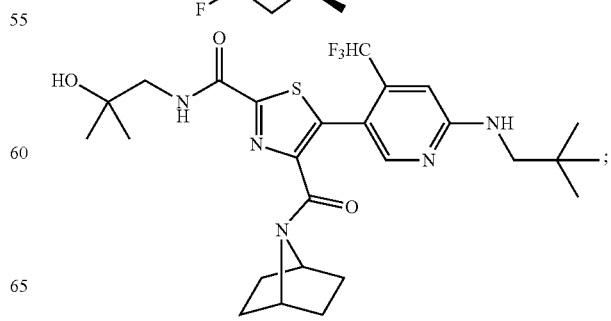

223
-continued
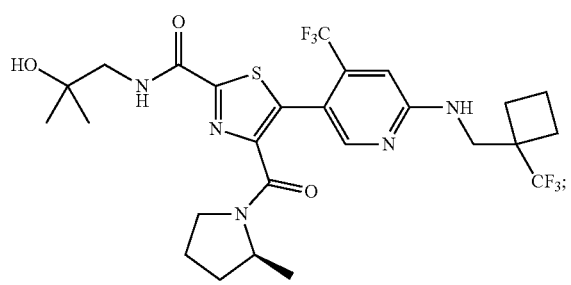
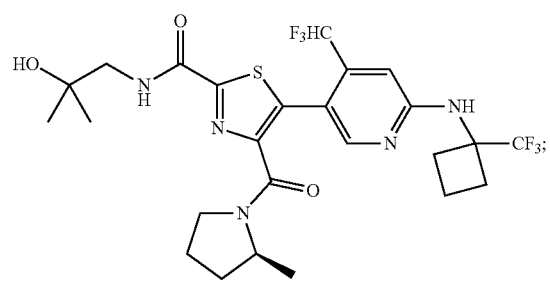
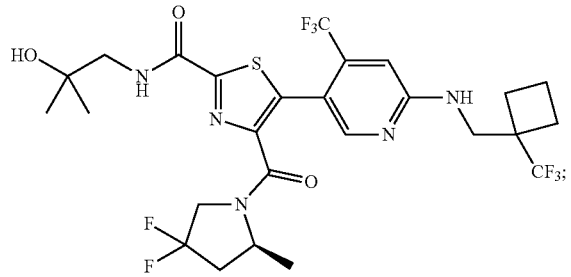
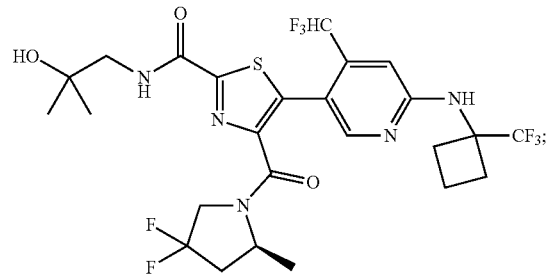
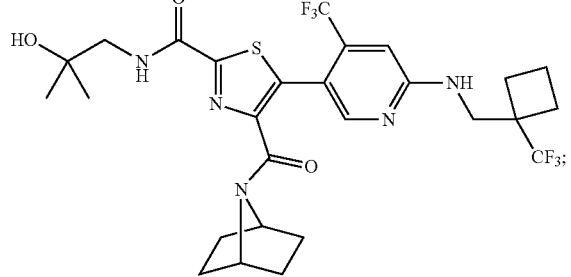
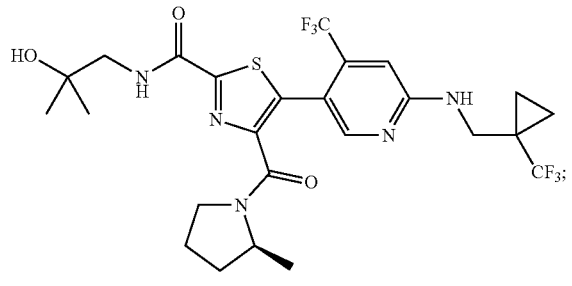
224
-continued
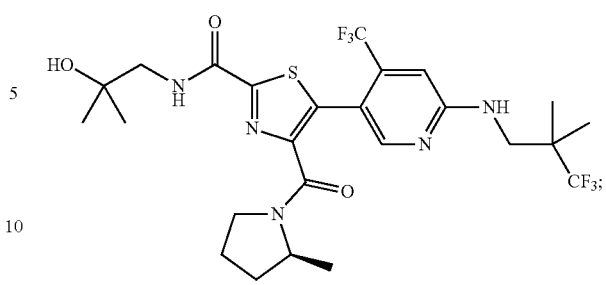
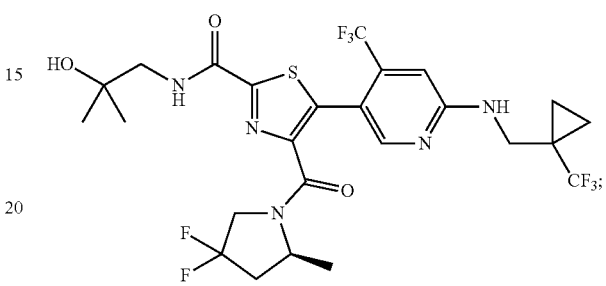

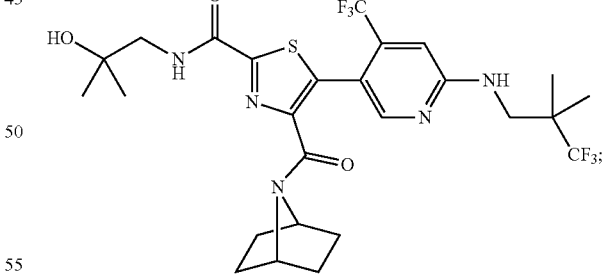
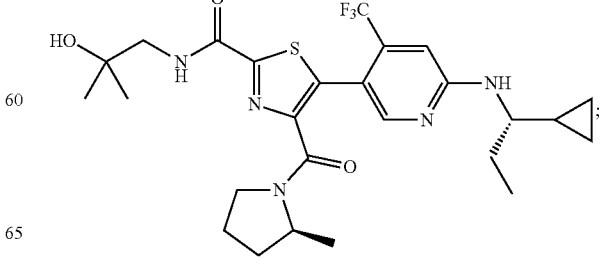

225
-continued
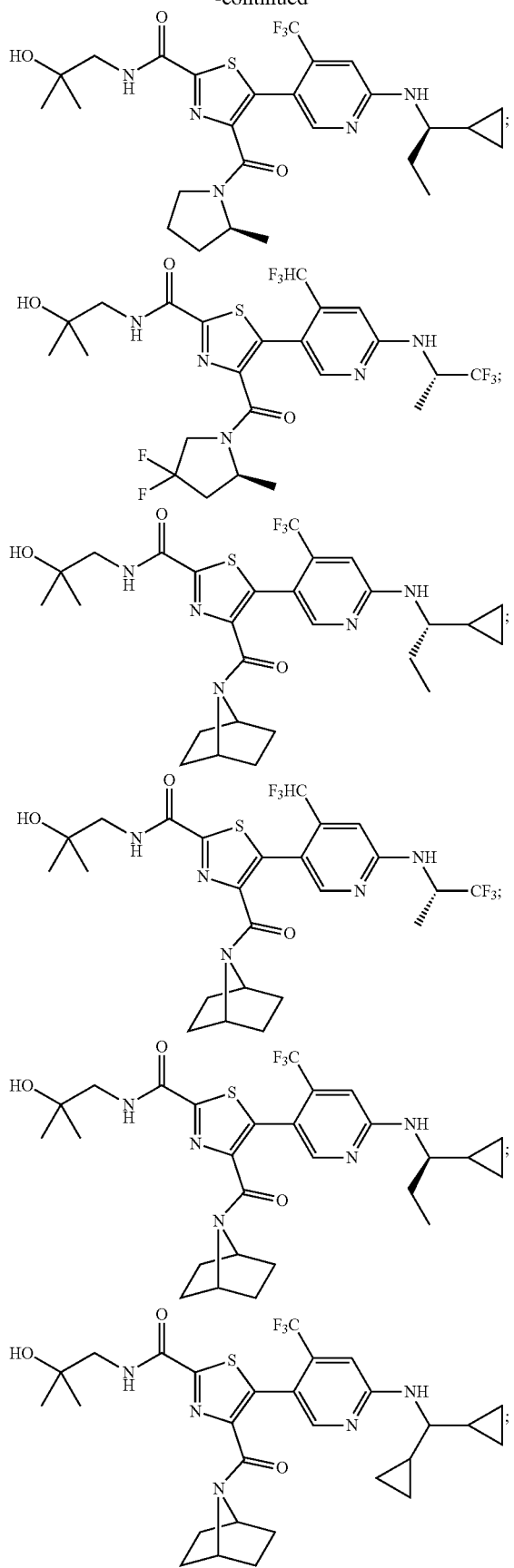
226
-continued
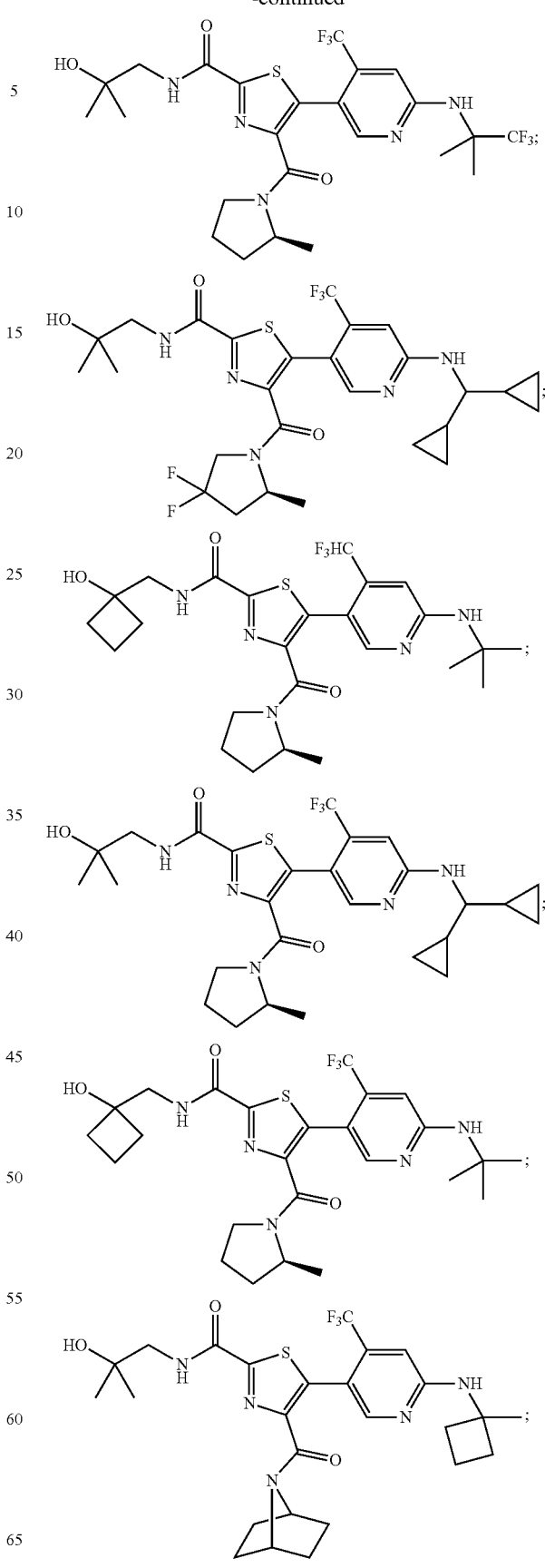

227
-continued
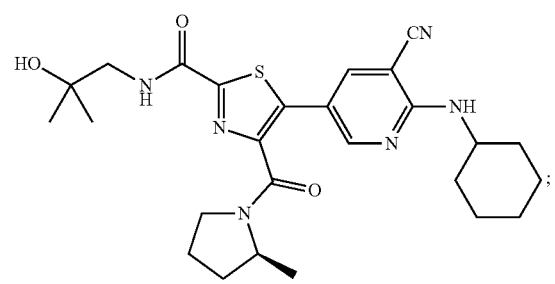
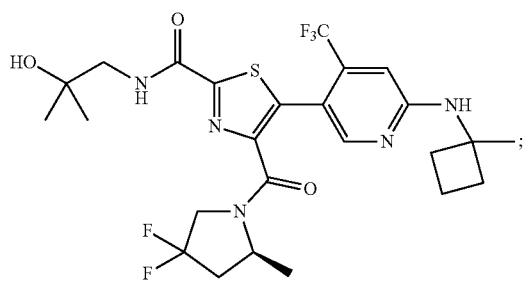
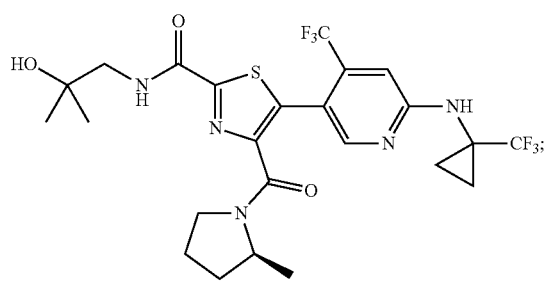
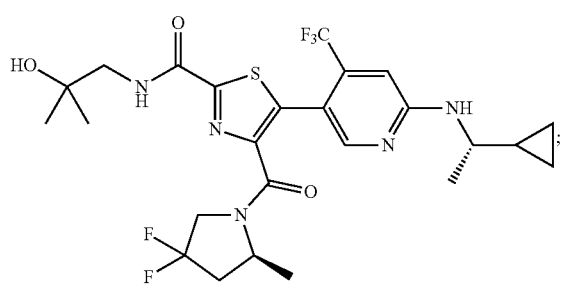
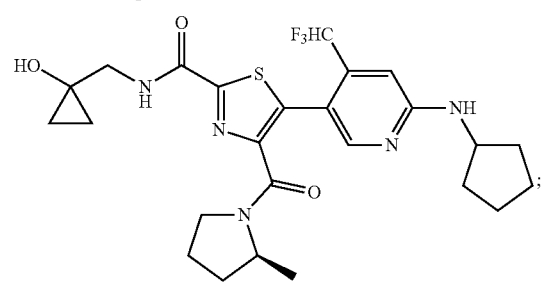
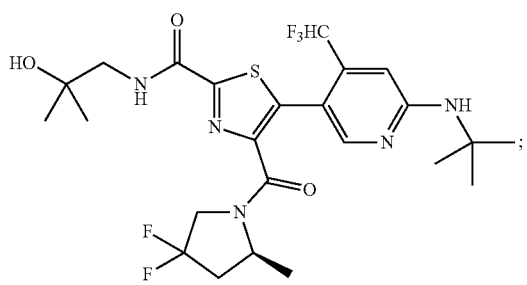
228
-continued
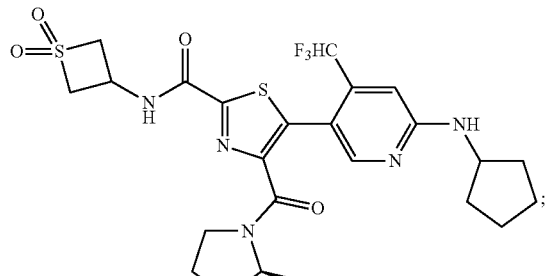
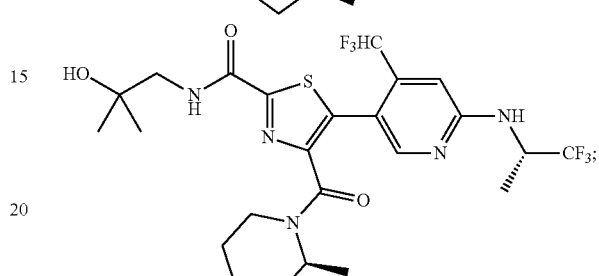
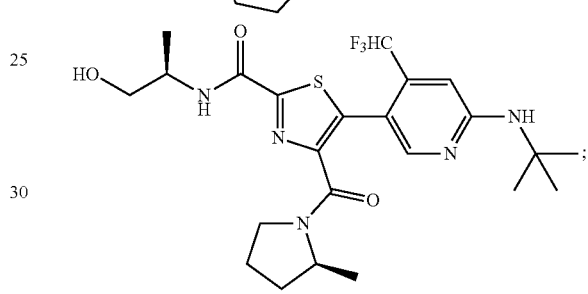
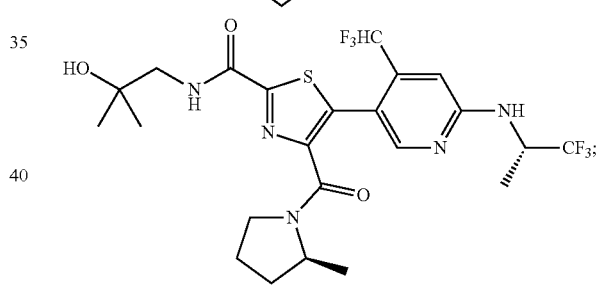
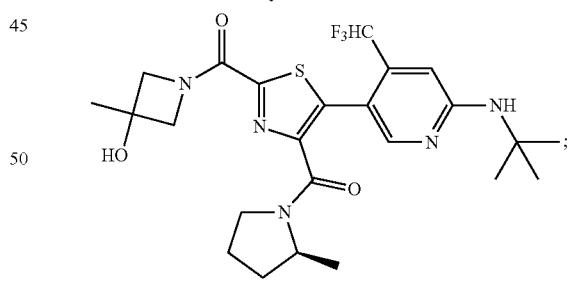
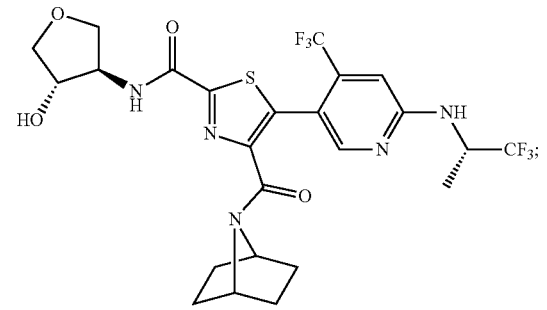

229
-continued
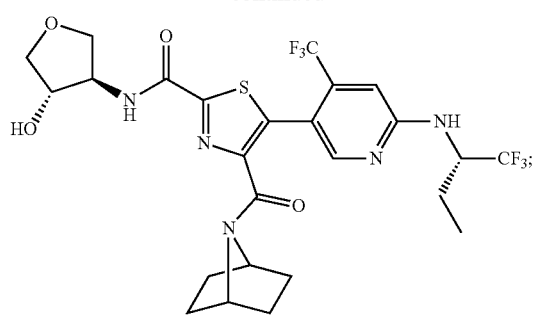
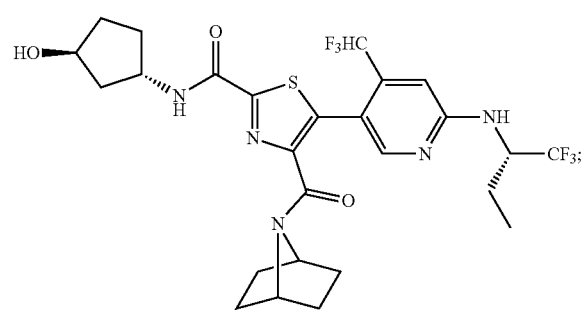
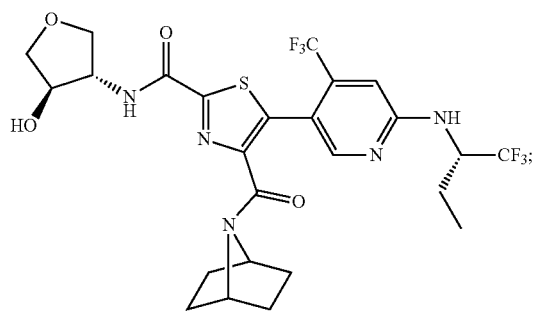
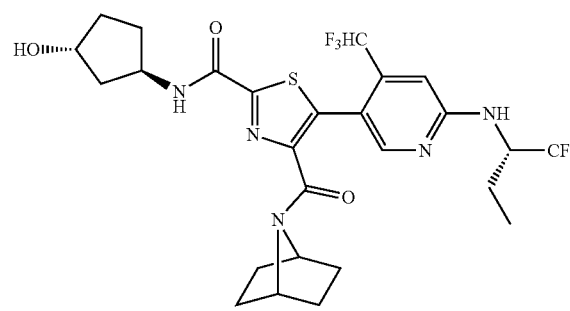
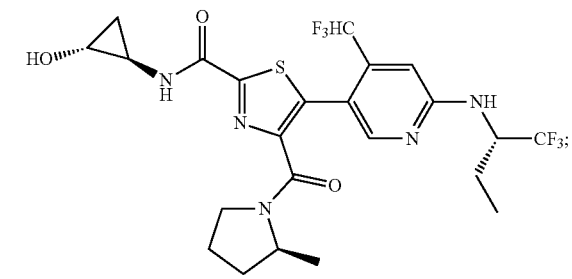
230
-continued
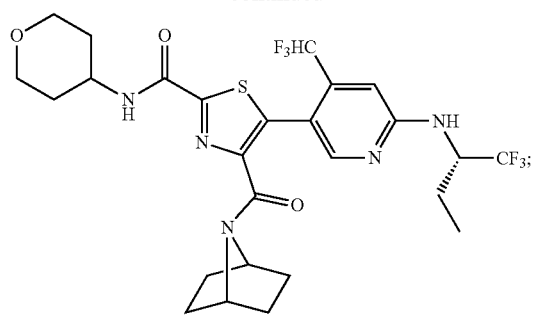
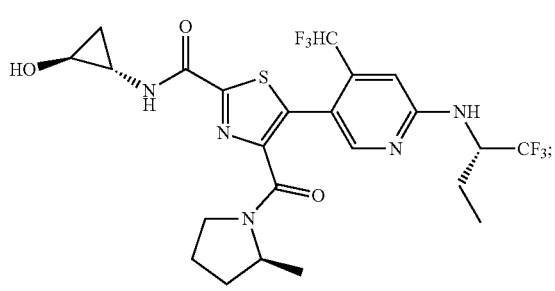
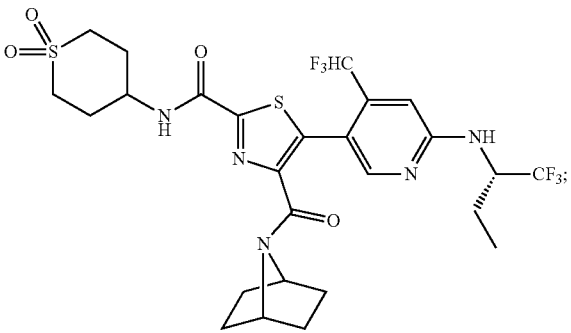
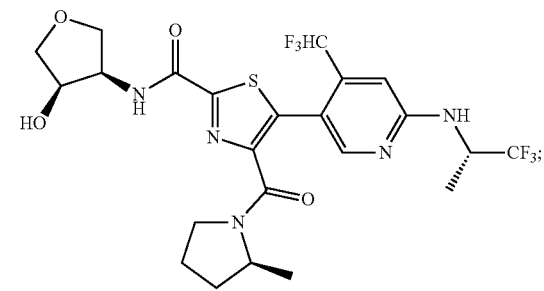
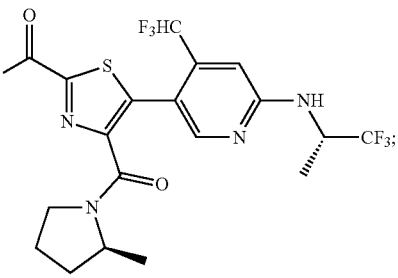

231
-continued
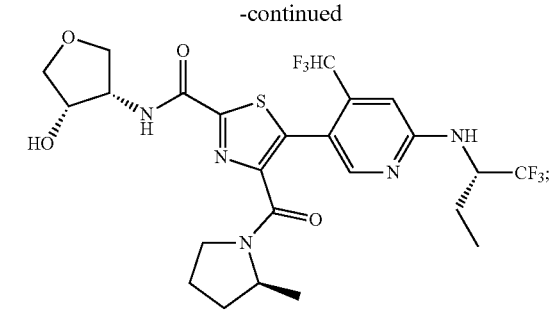
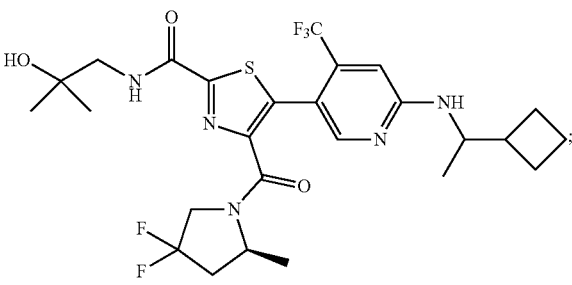
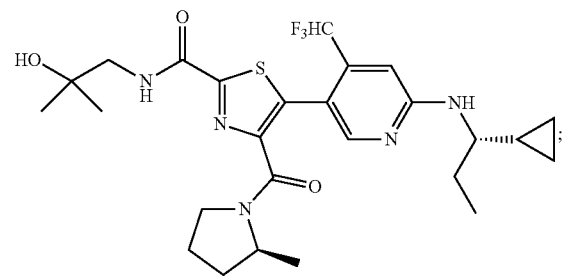
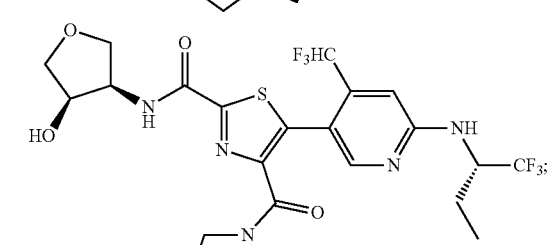
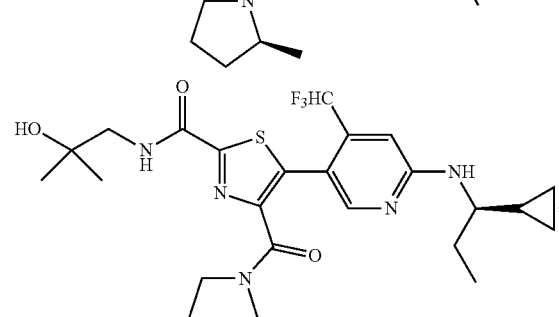
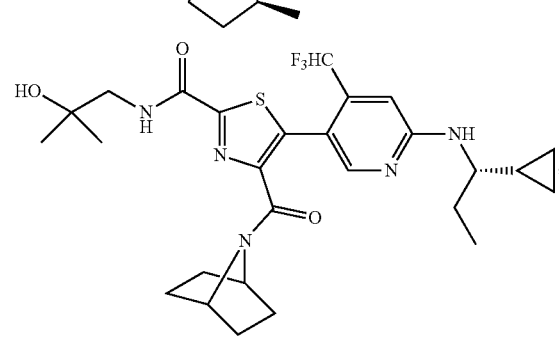
232
-continued
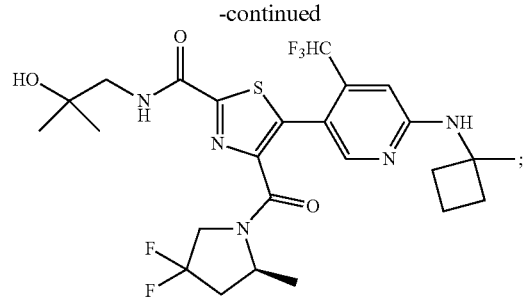
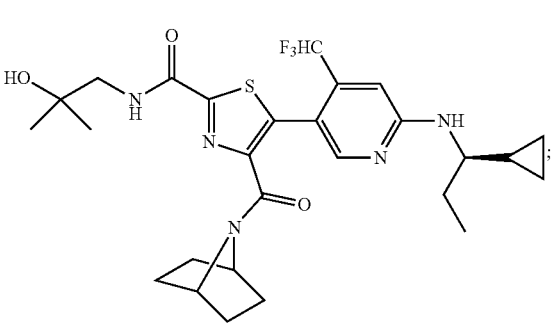
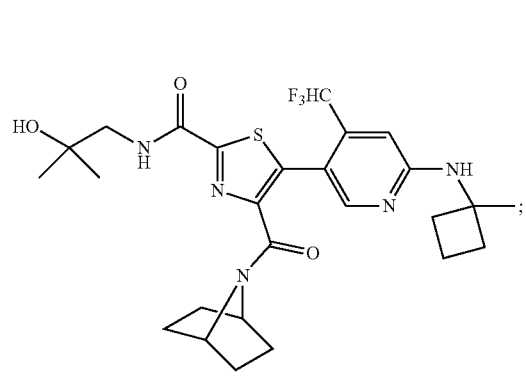
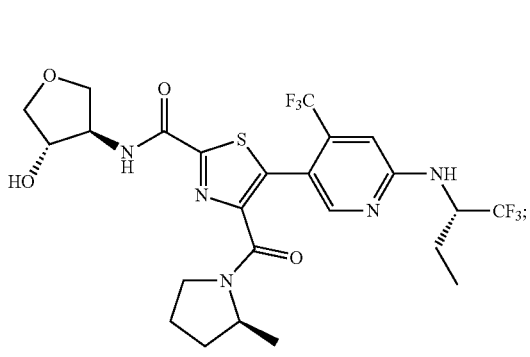
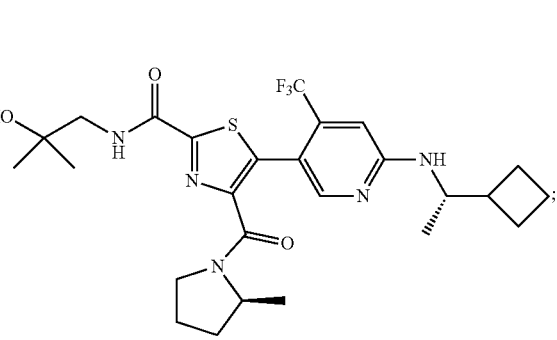

233
-continued
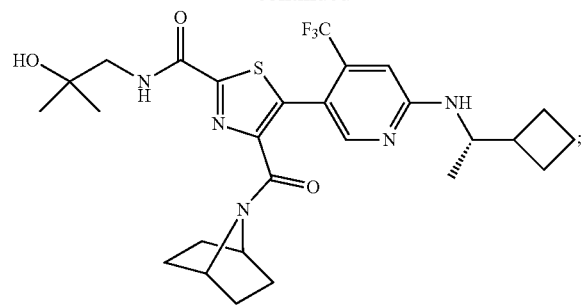
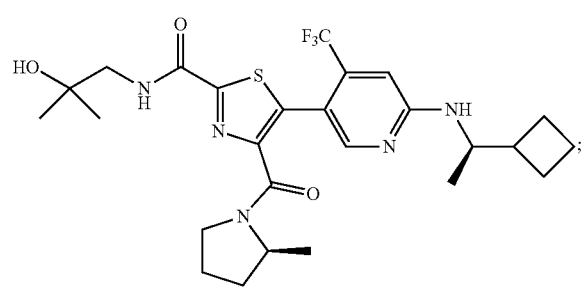
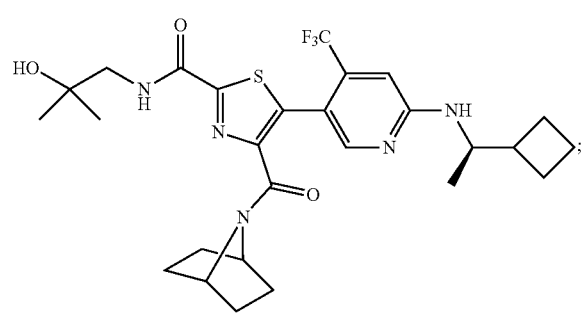
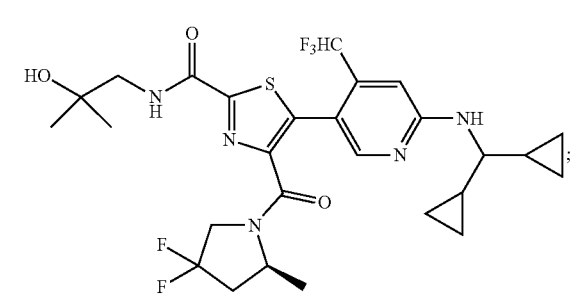
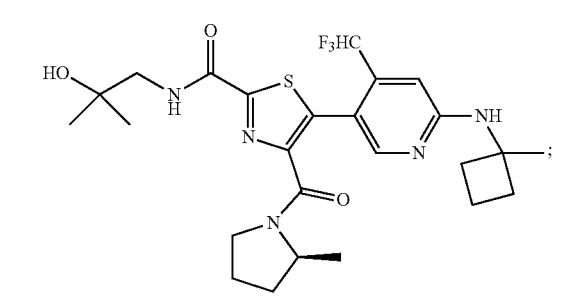
234
-continued
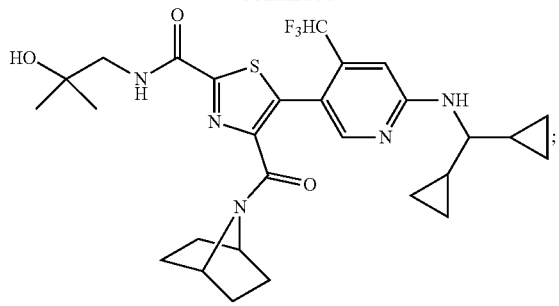
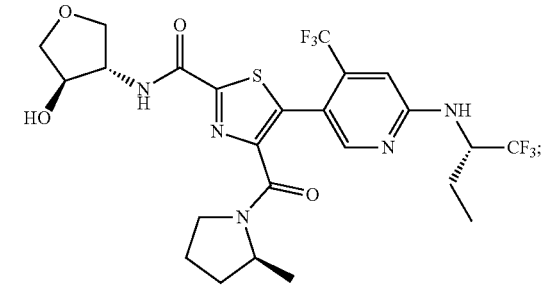
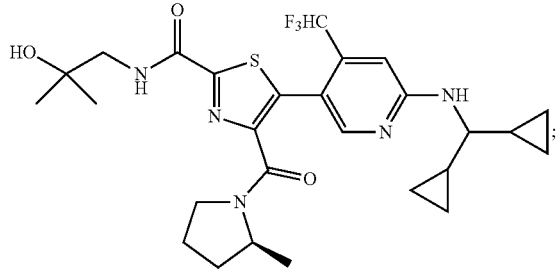
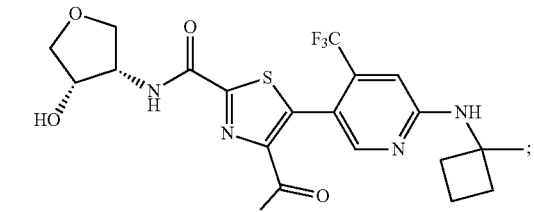
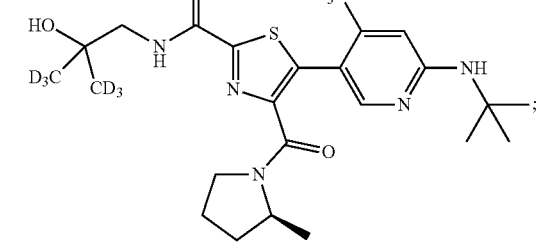
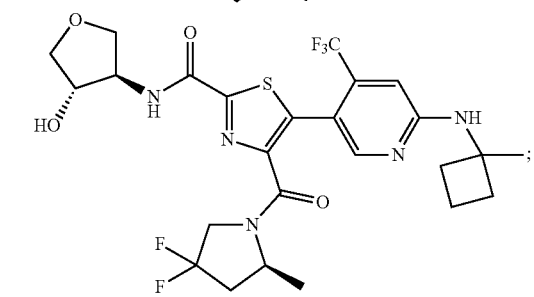

235
-continued
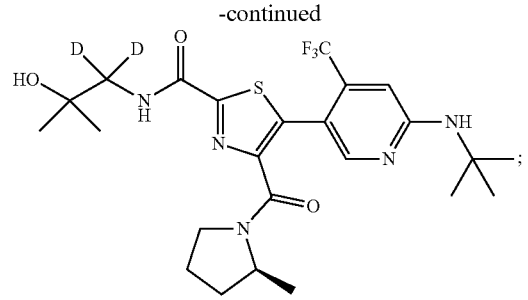
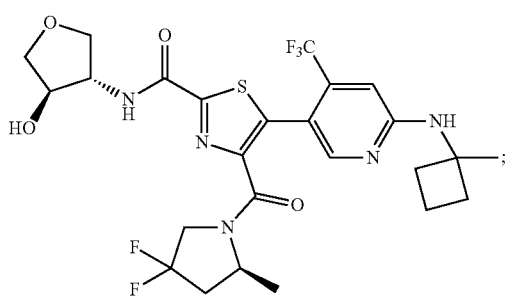
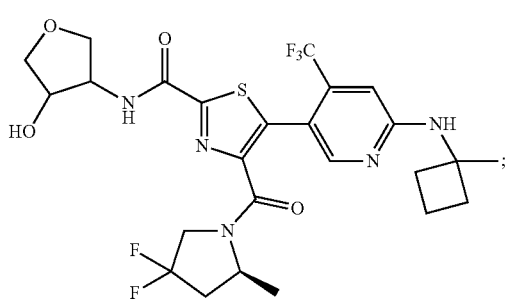
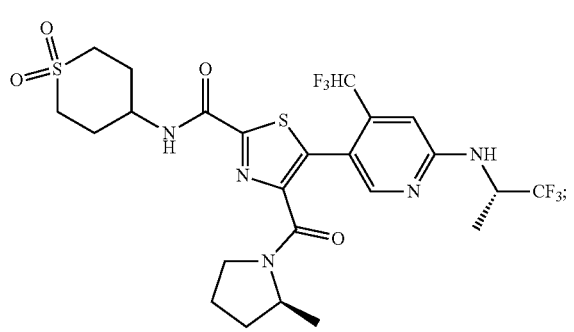
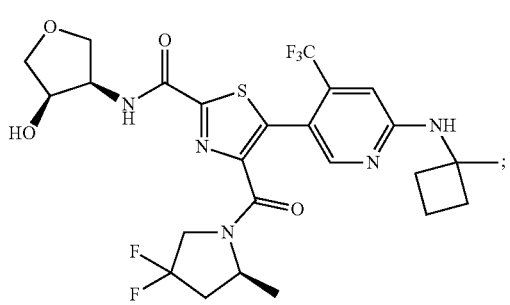
236
-continued
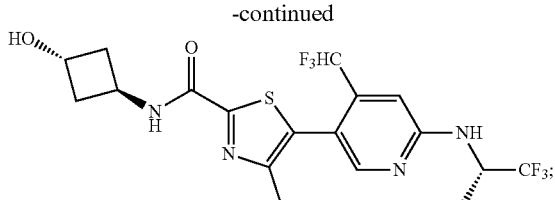
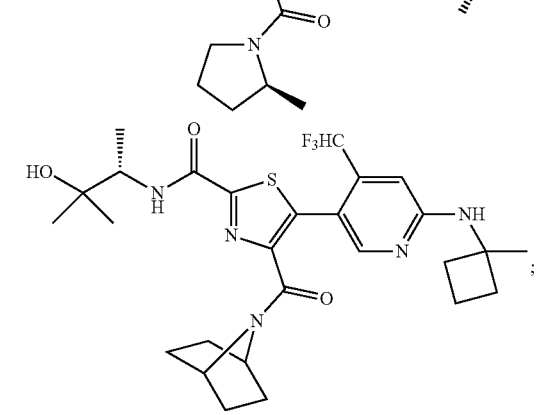
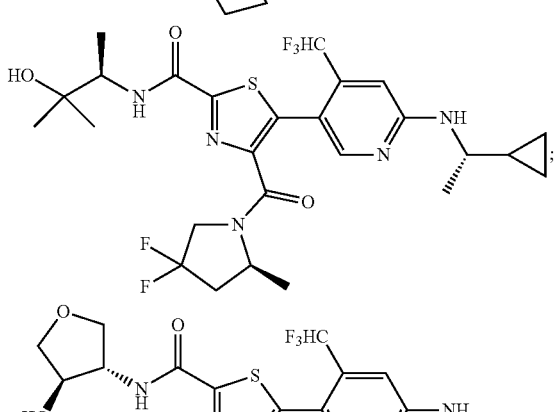
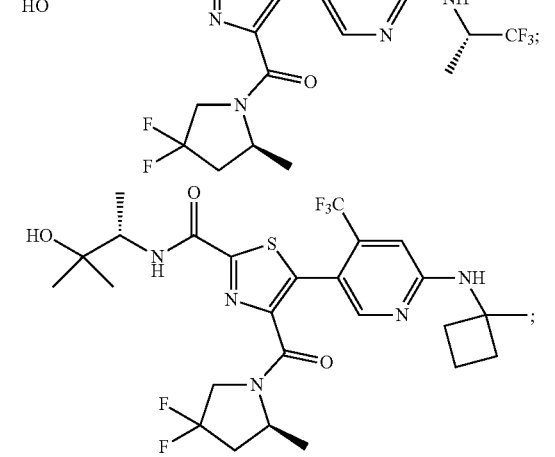
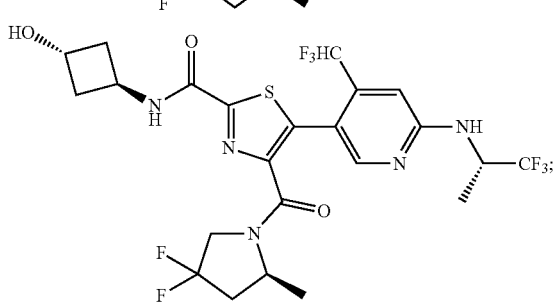

237
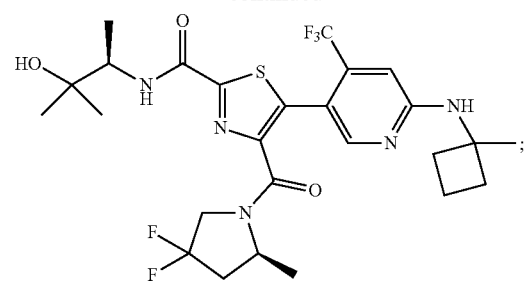
238
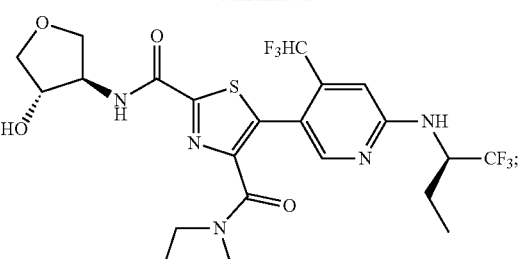
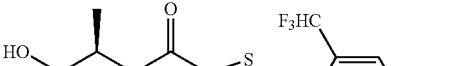
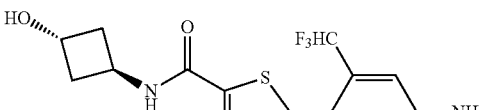

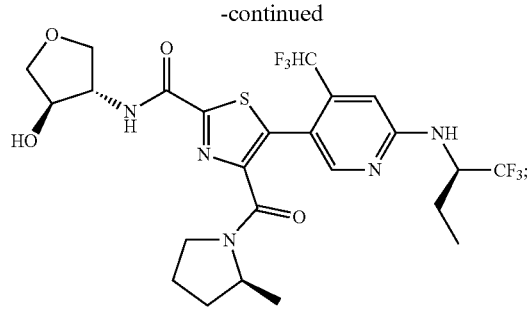
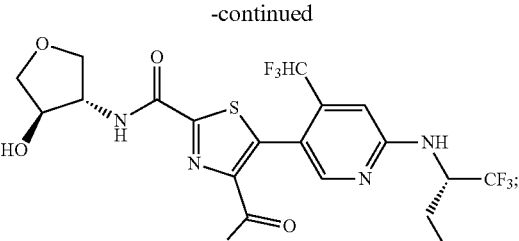
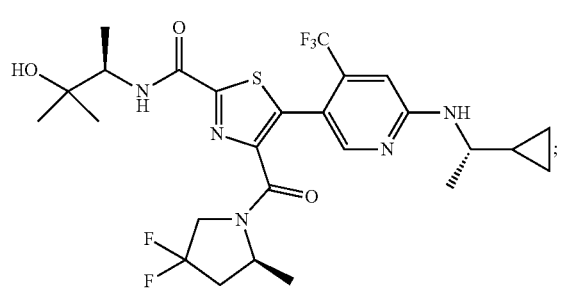
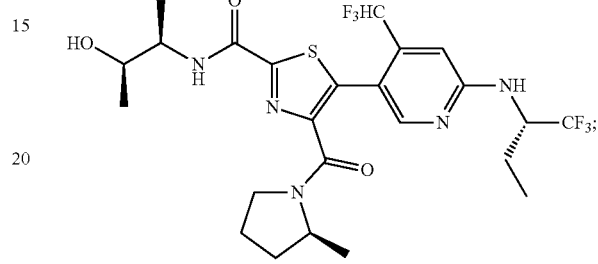
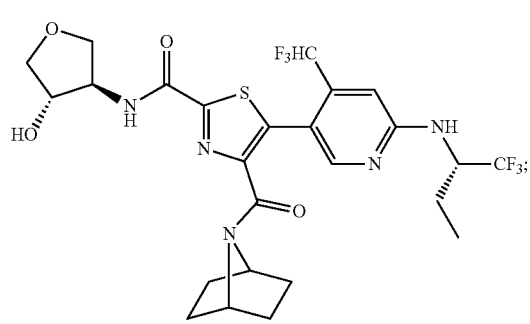
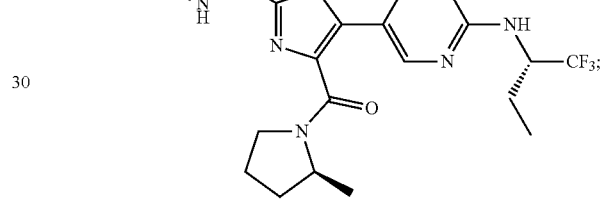
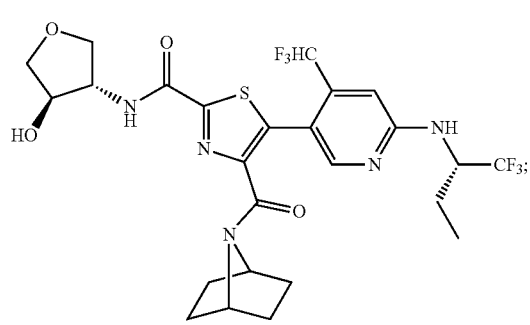
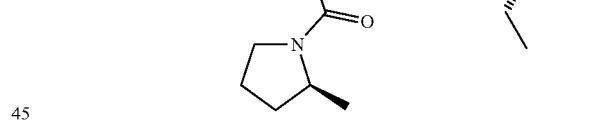
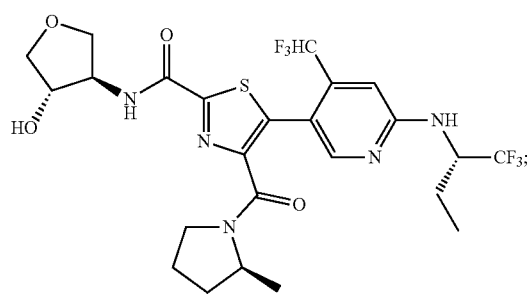
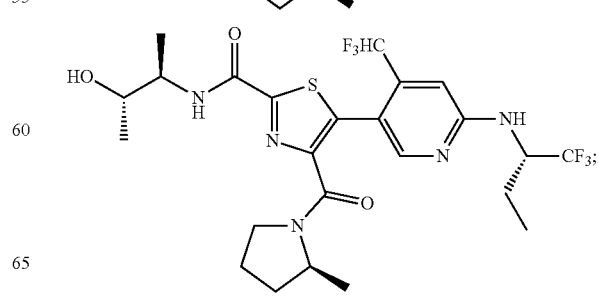

241
-continued
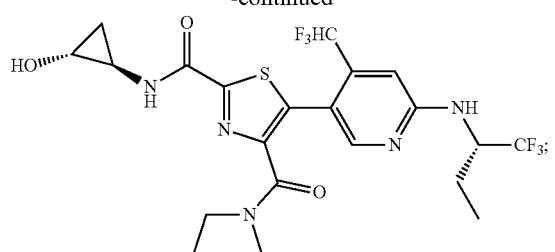
242
-continued
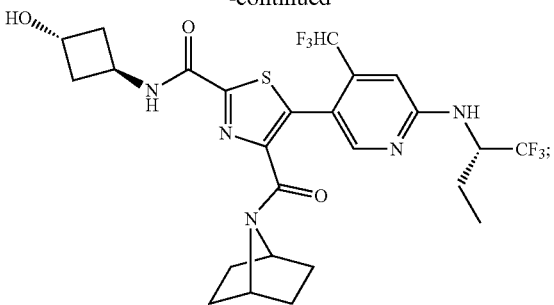
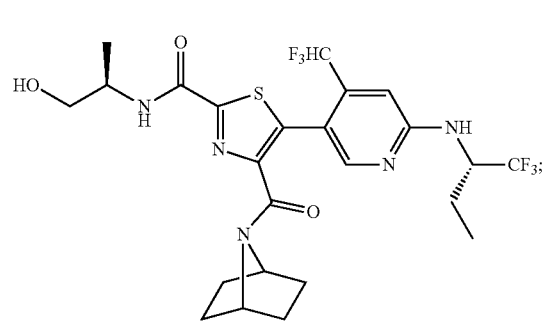
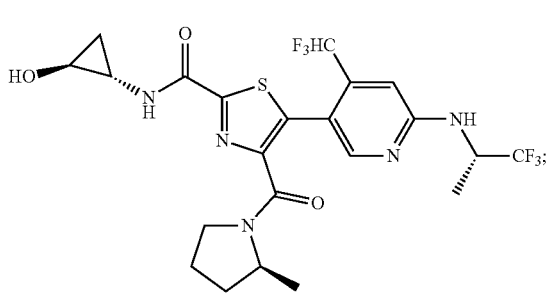
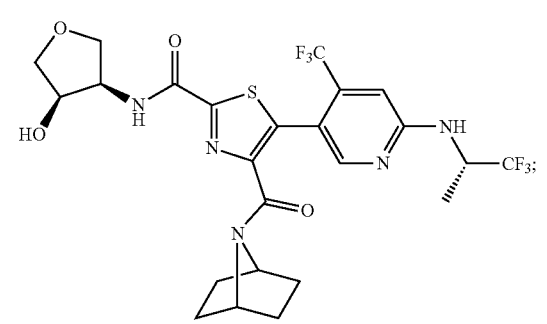
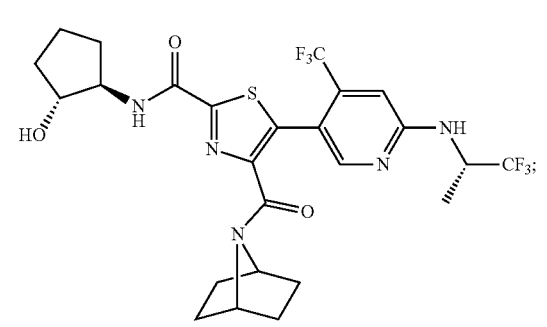

-continued
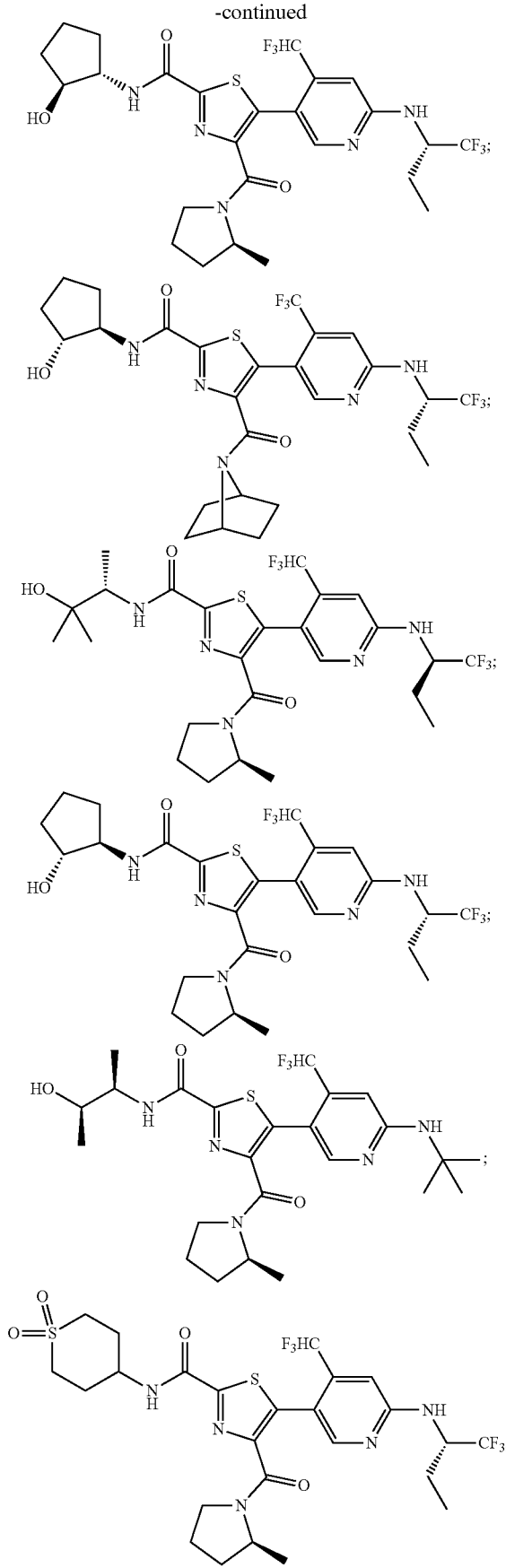
-continued
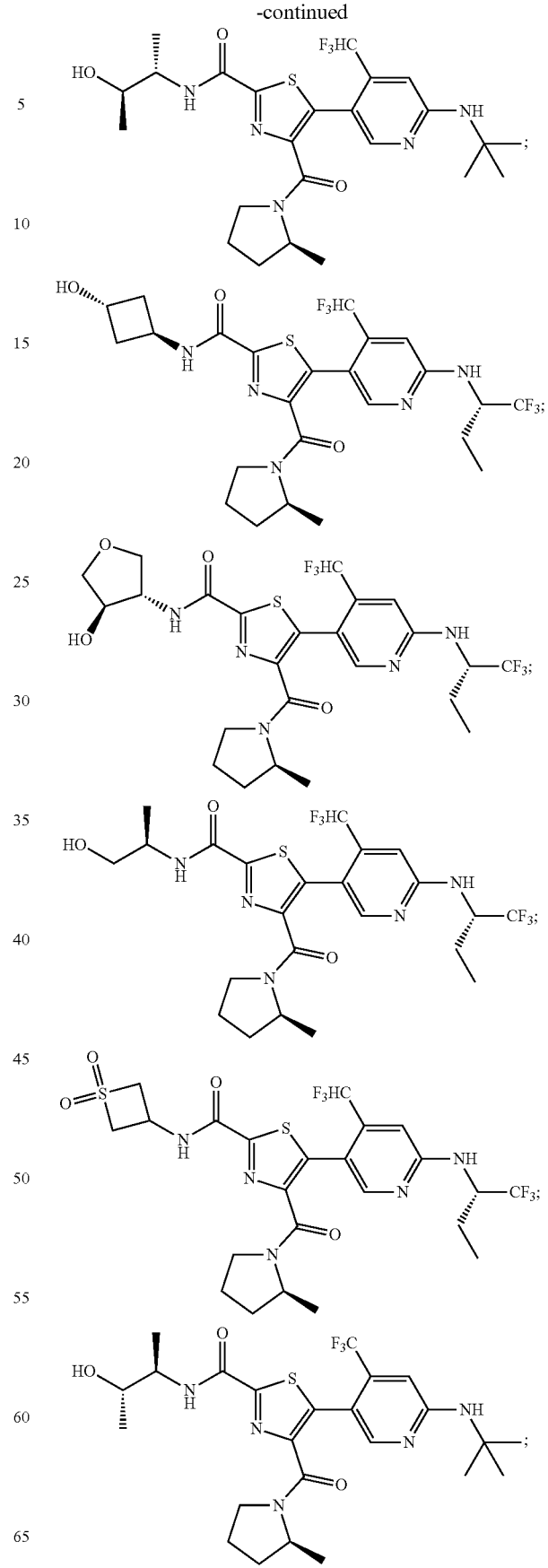

245
-continued
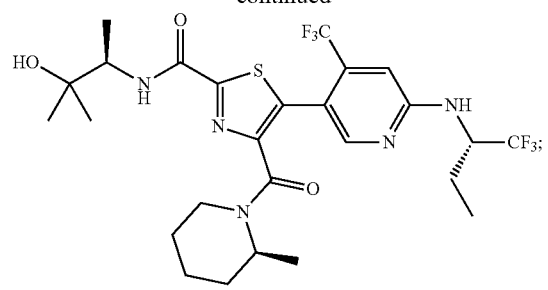
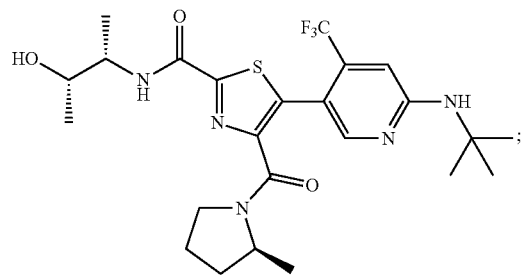
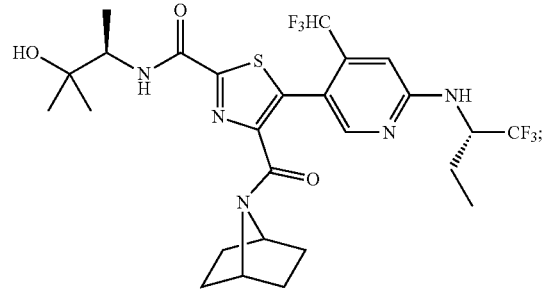
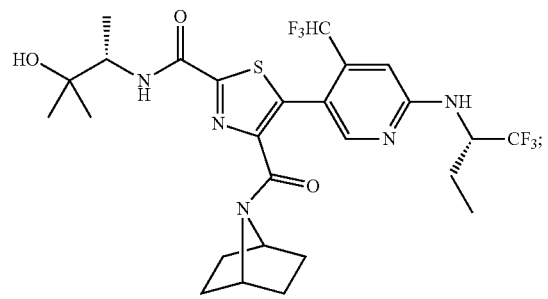
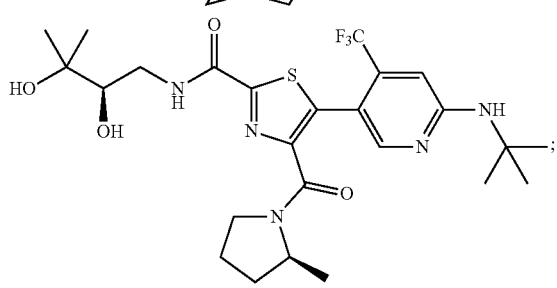
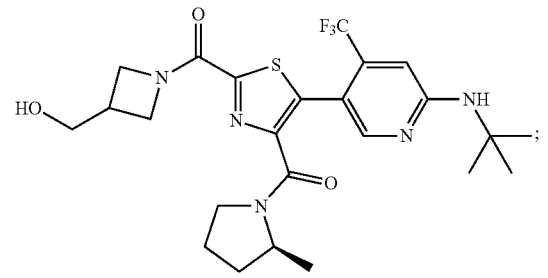
246
-continued
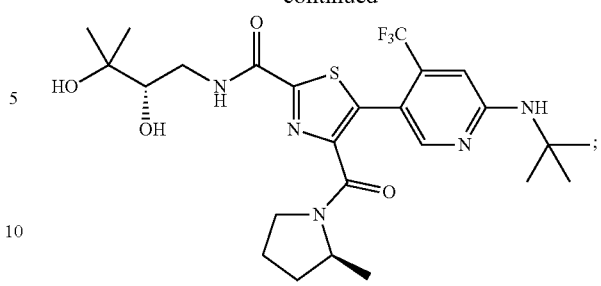
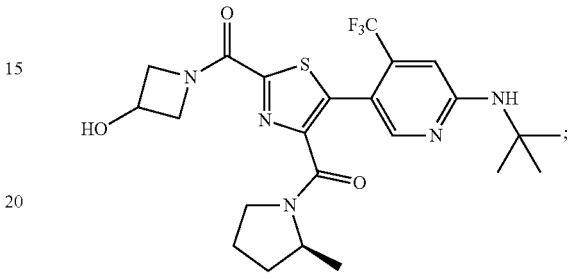

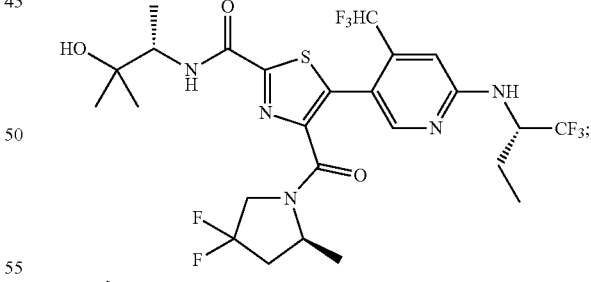
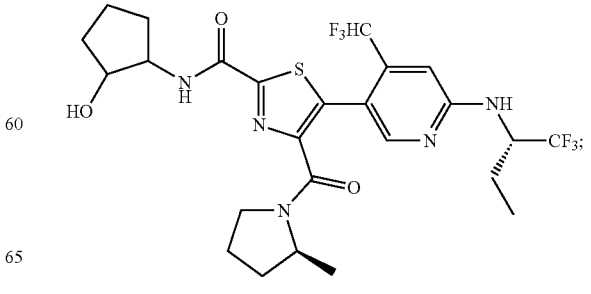

247
-continued
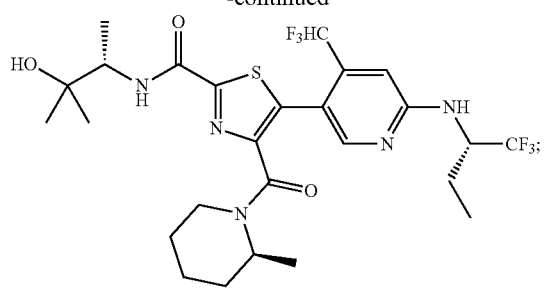
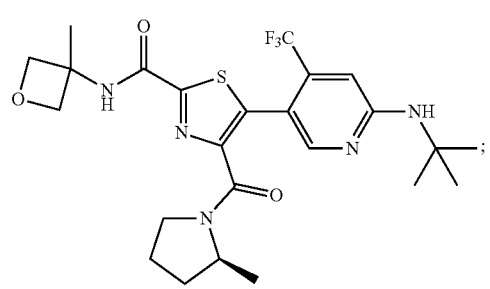
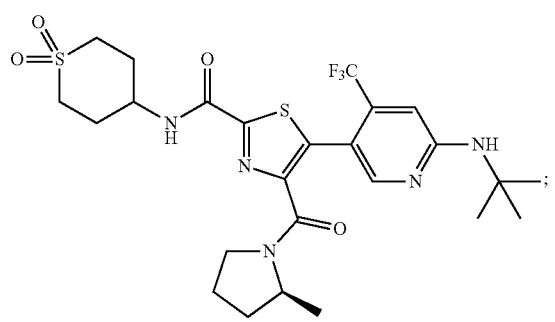
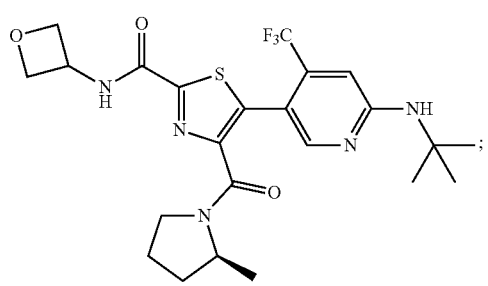
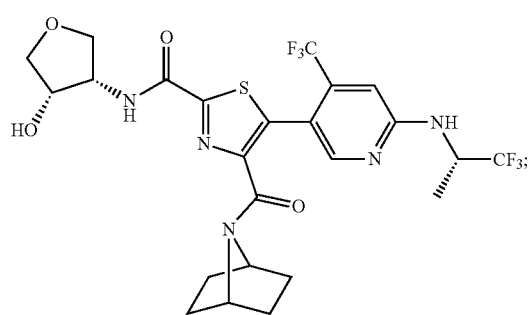
248
-continued
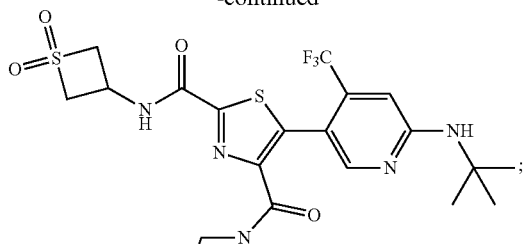
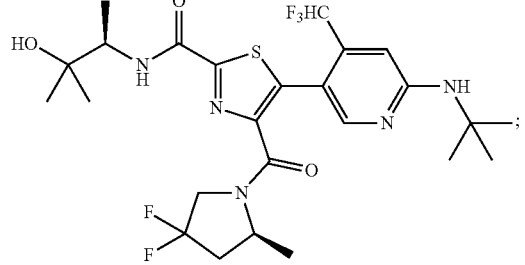
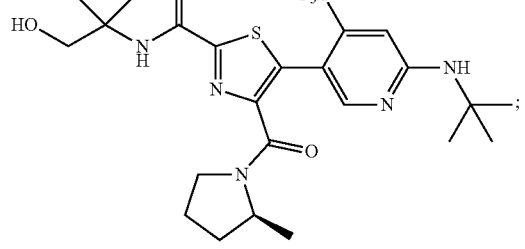
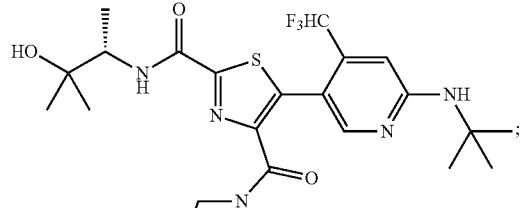
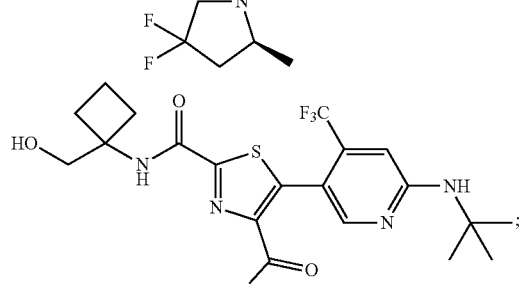
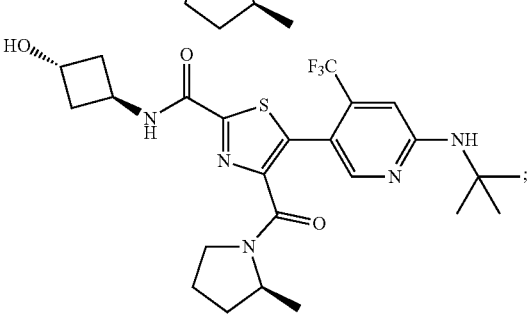

-continued
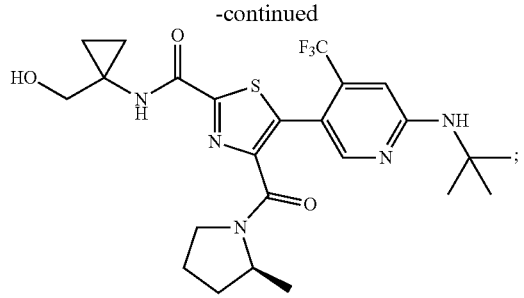
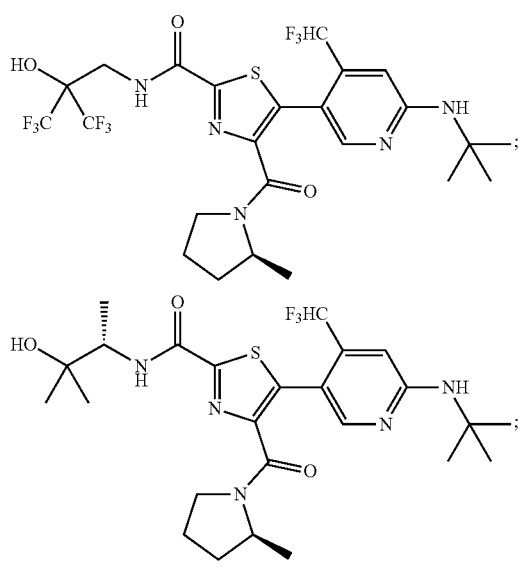
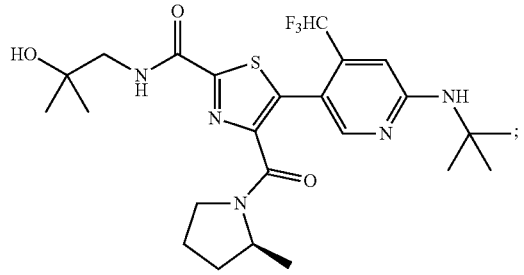
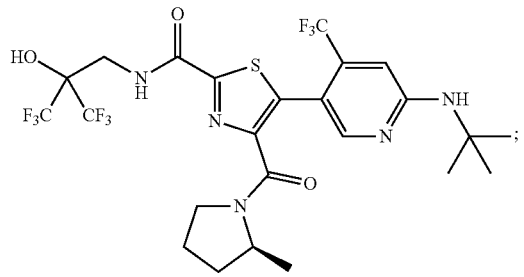
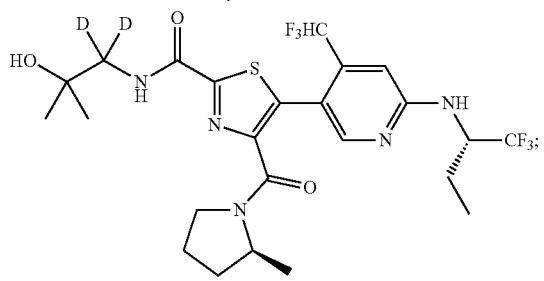
-continued
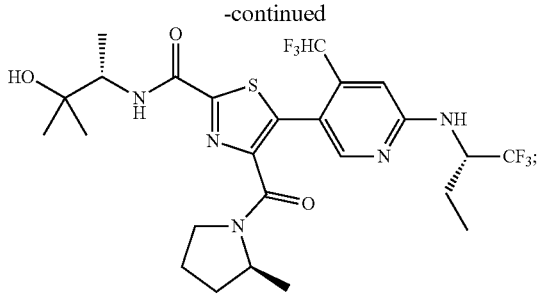
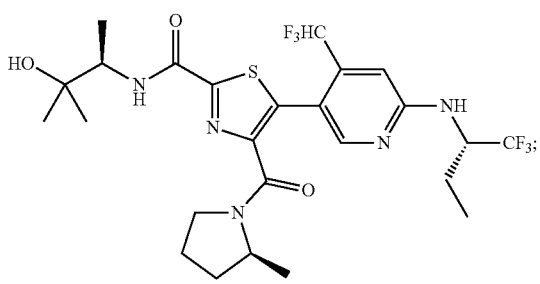
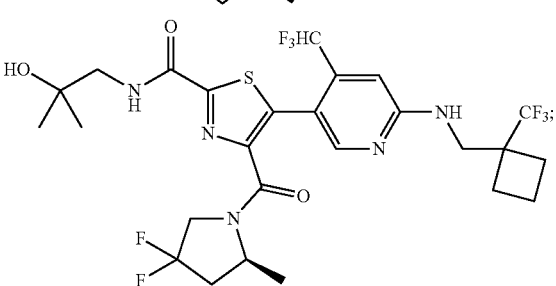
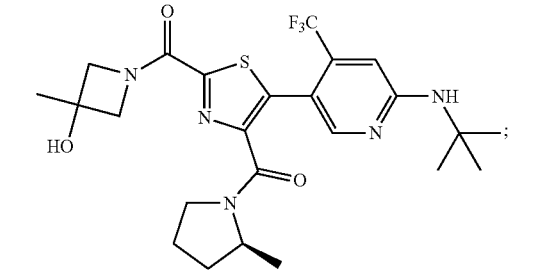
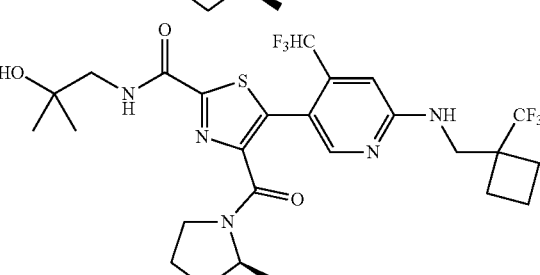
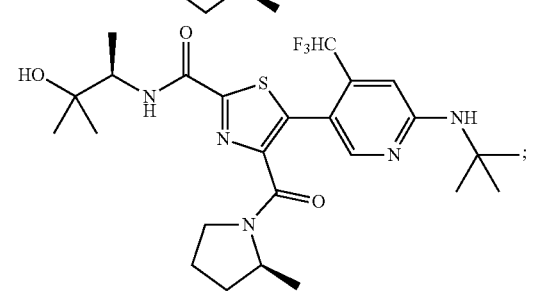

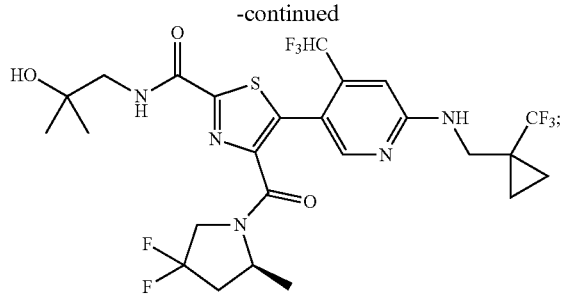
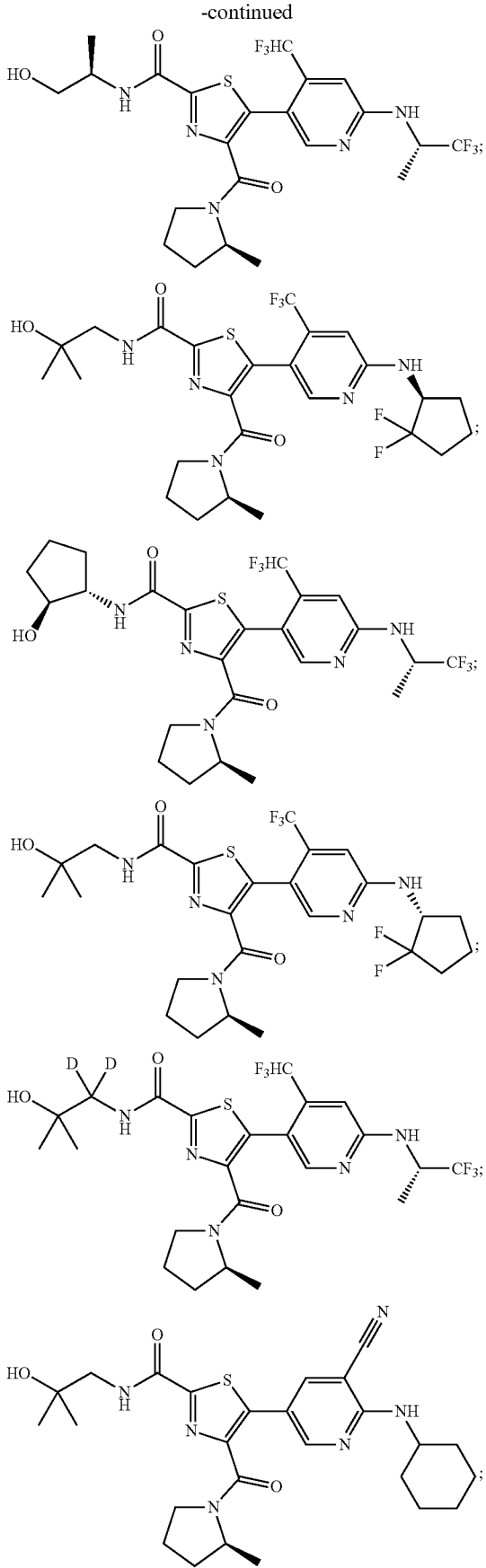

253
-continued
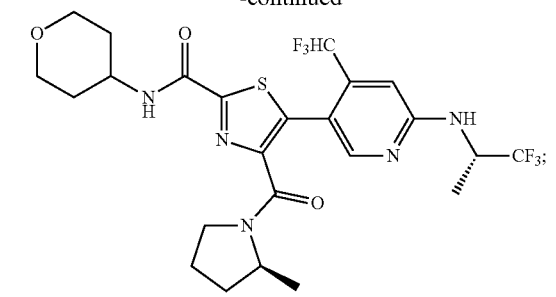
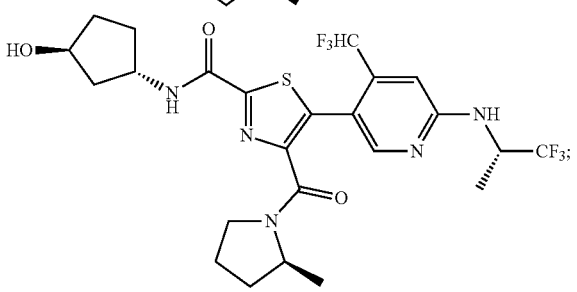
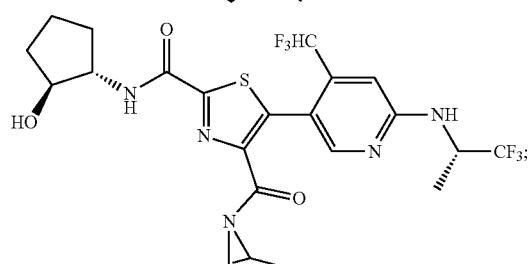
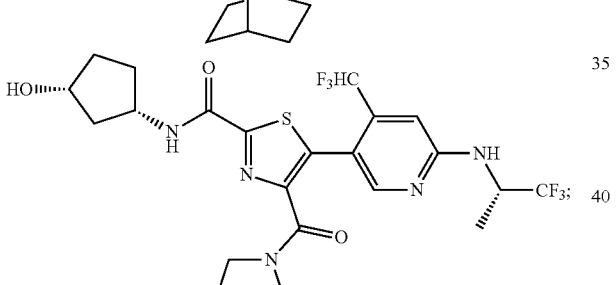
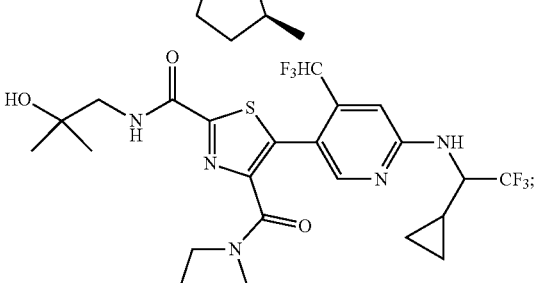
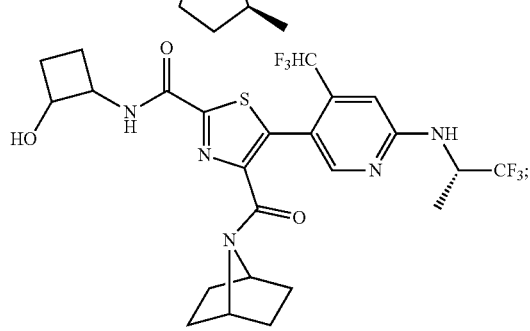
254
-continued
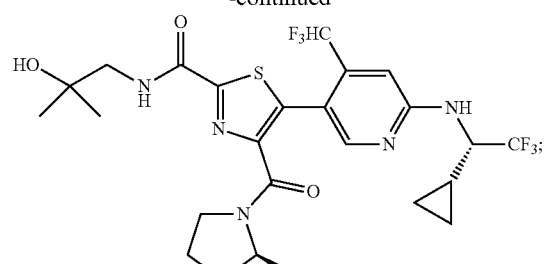
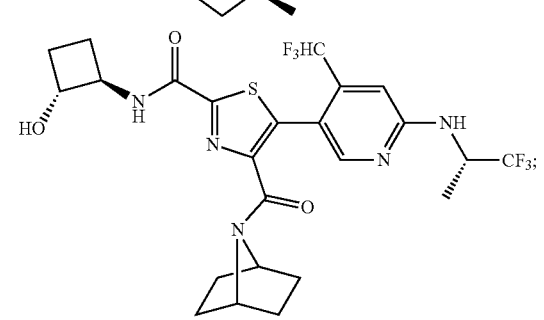
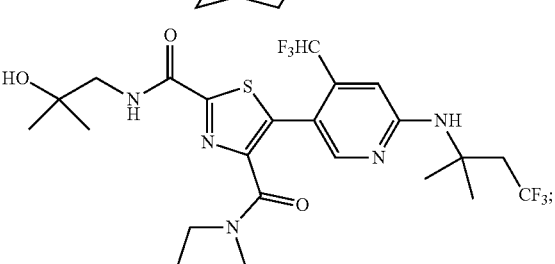
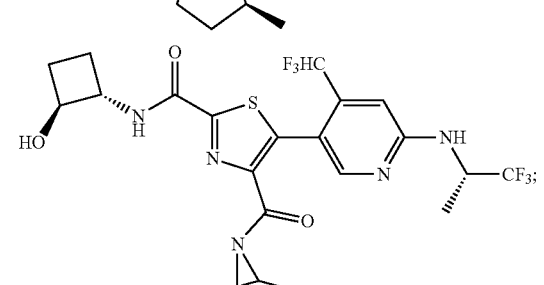
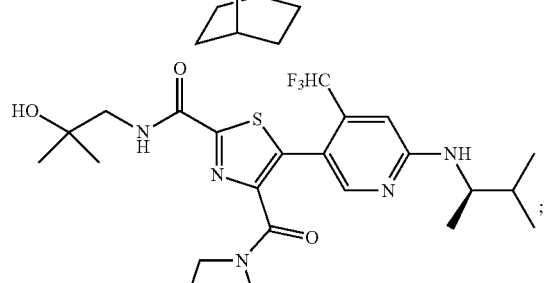
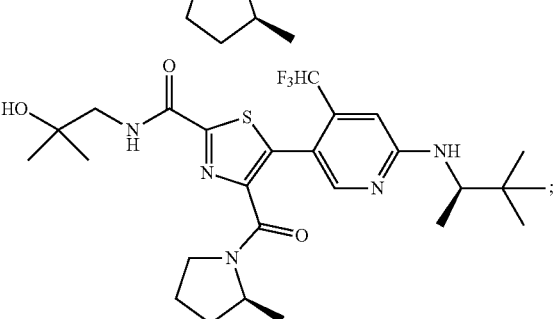

255
-continued
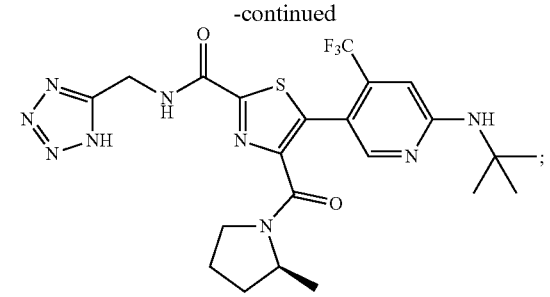
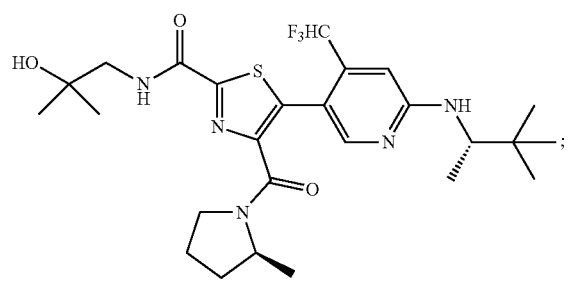
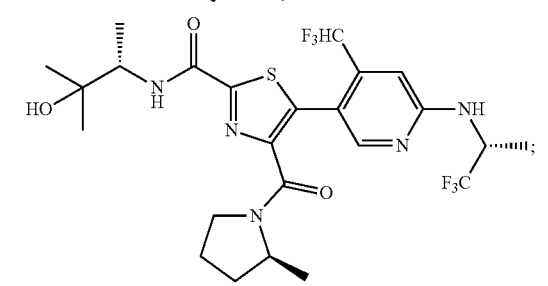
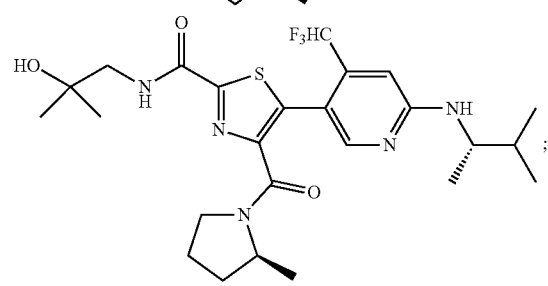
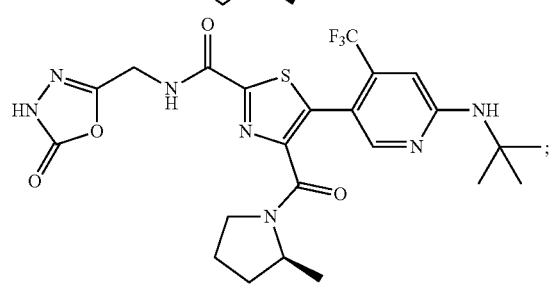
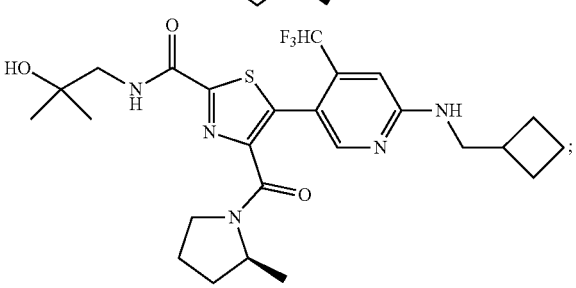
256
-continued
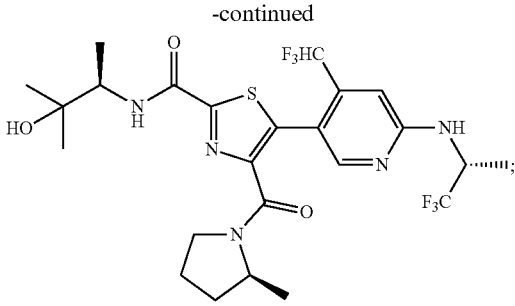
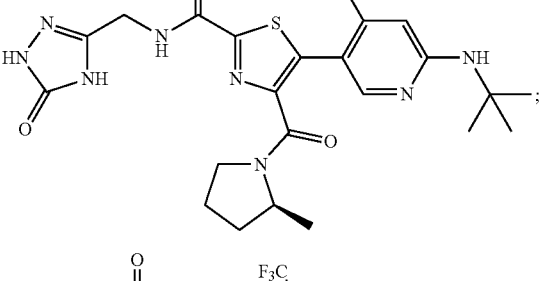
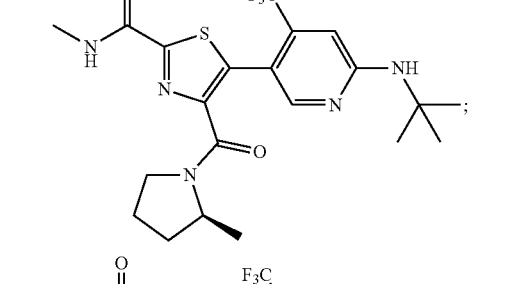
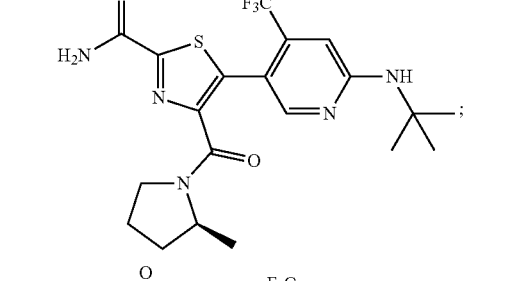
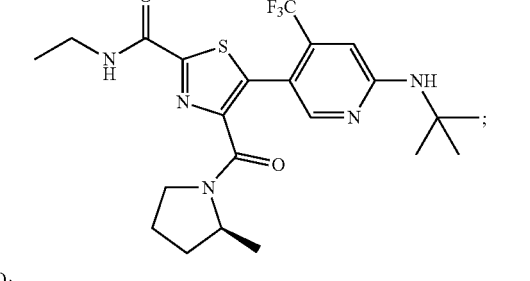
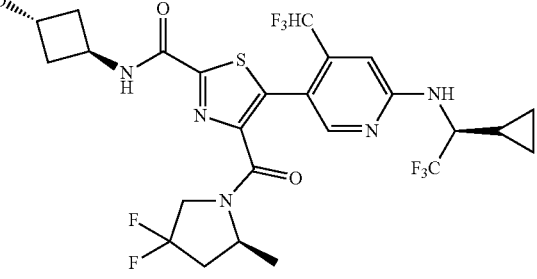

-continued
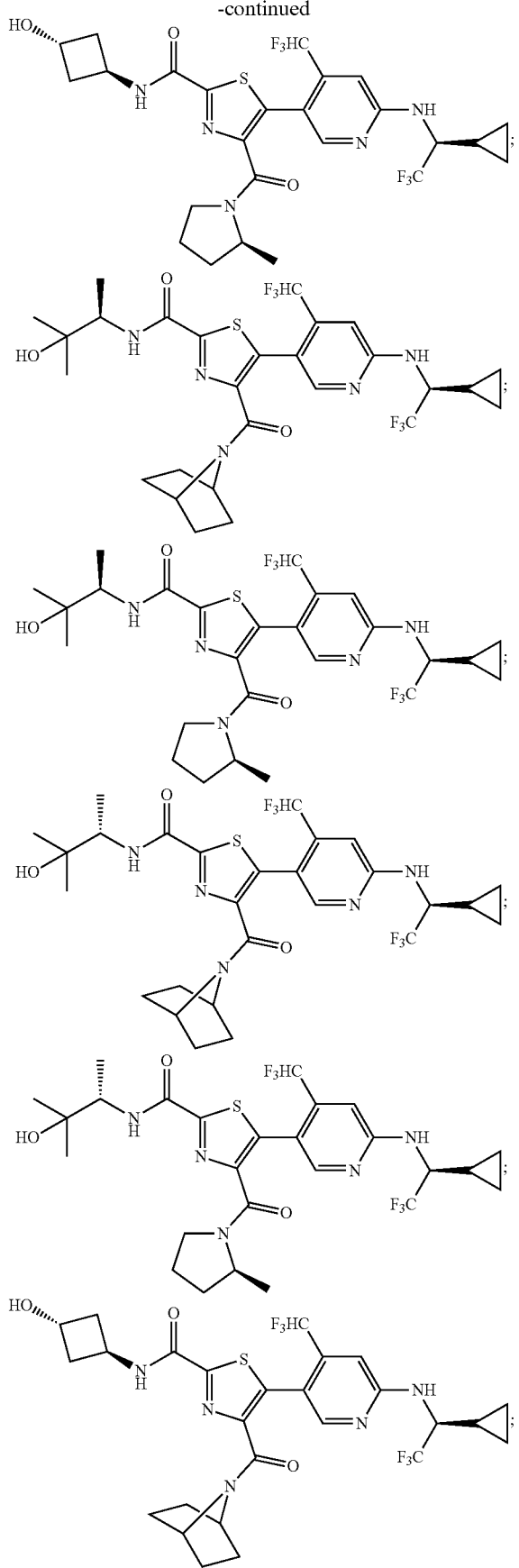
-continued
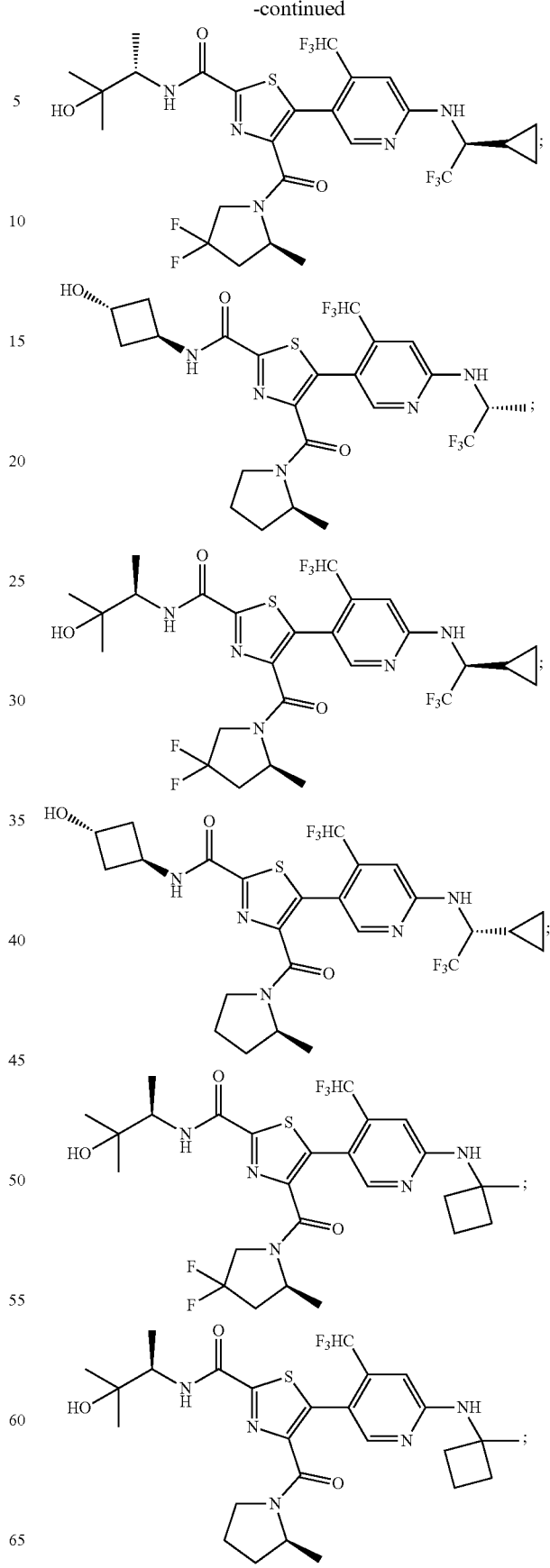

259
-continued
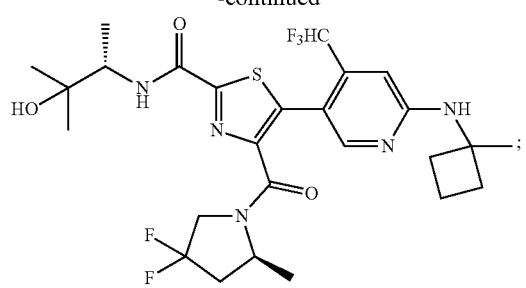
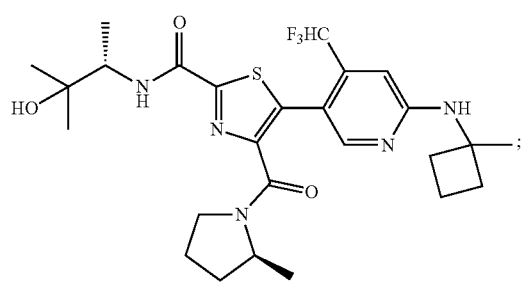
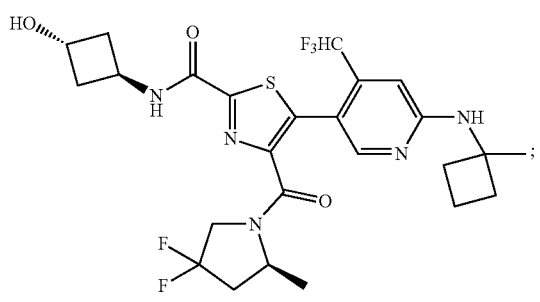
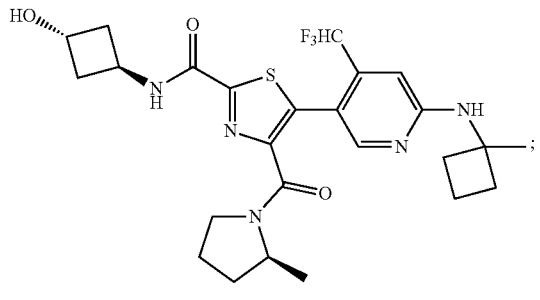
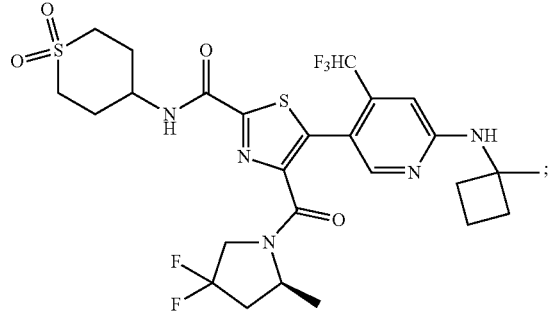
260
-continued
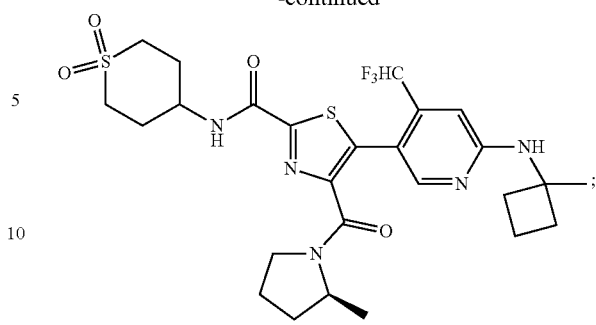
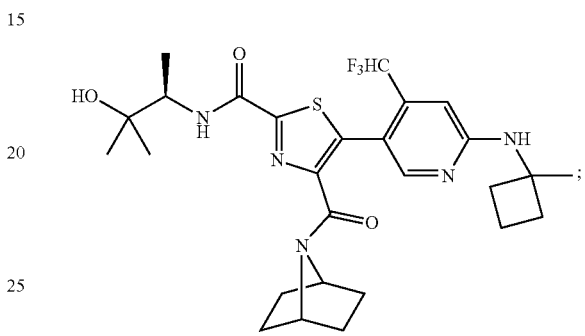
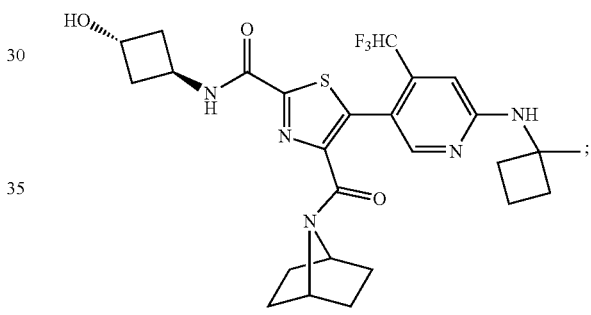
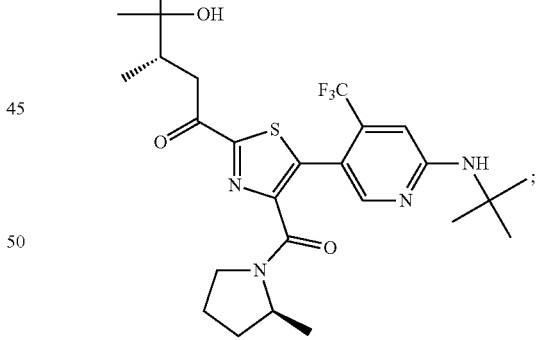
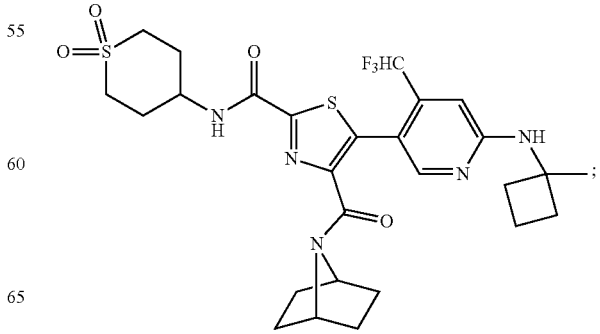

261
-continued
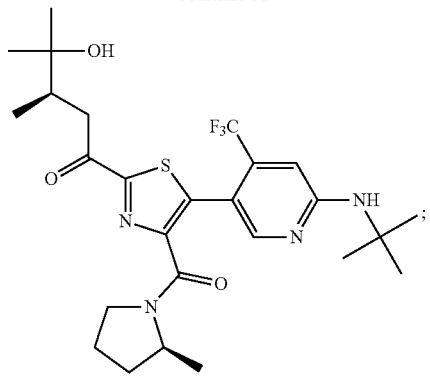
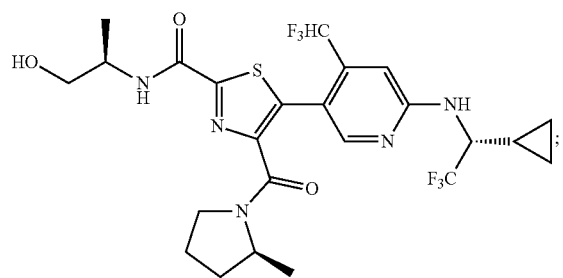
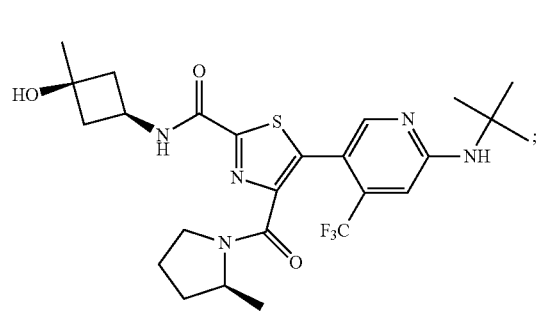
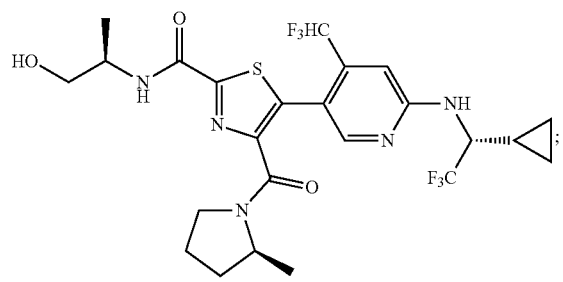
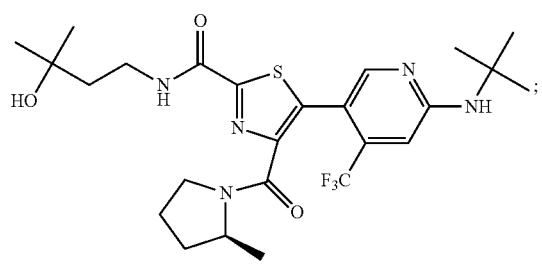
262
-continued
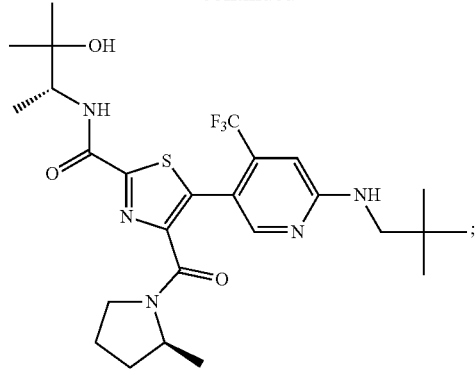
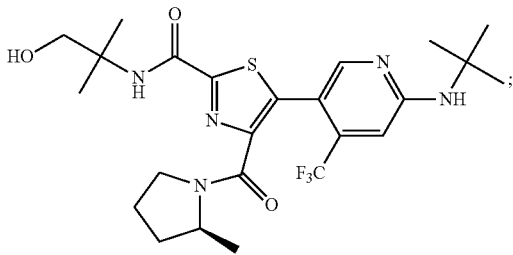
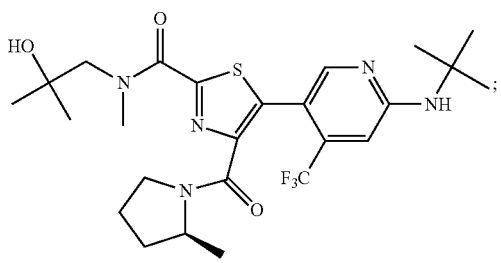
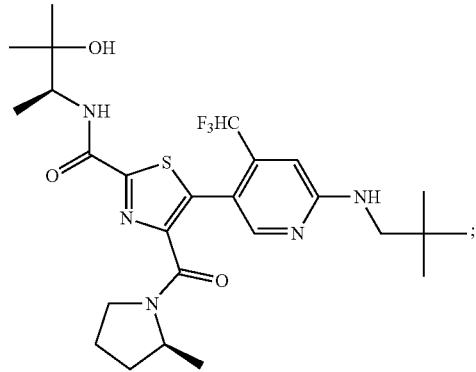
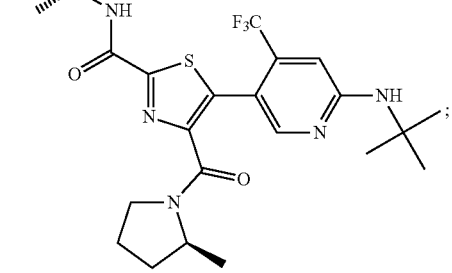

263
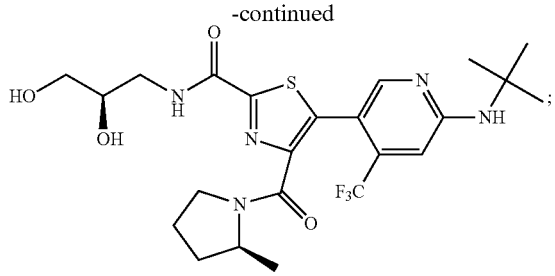
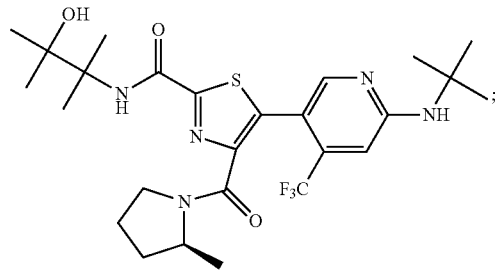
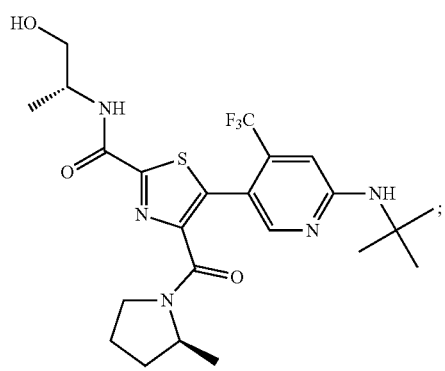
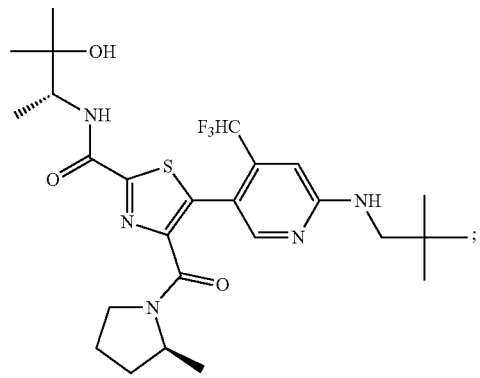
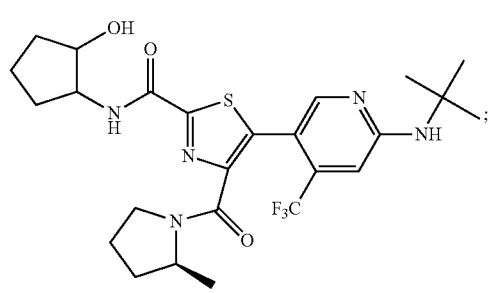
264
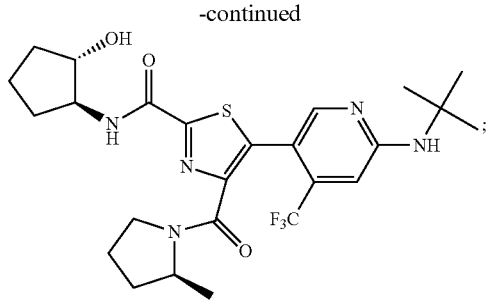
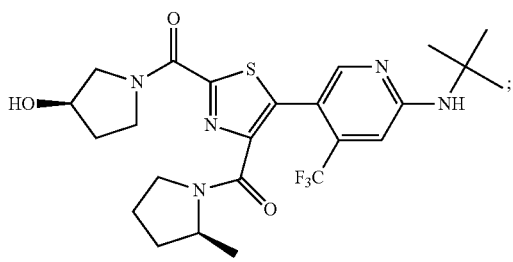
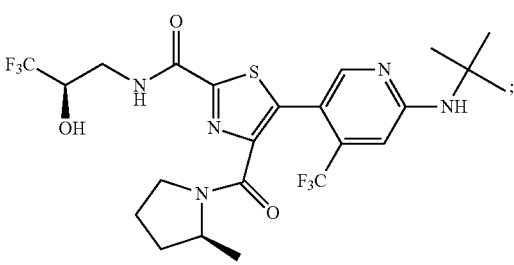
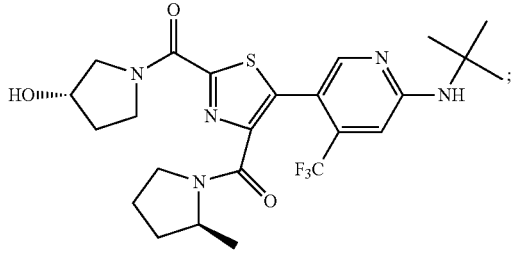
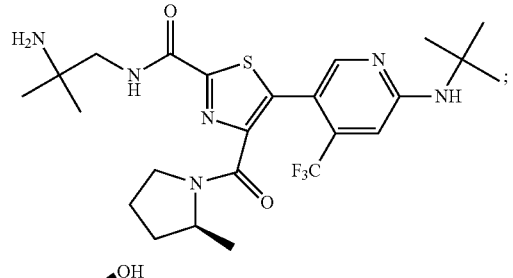
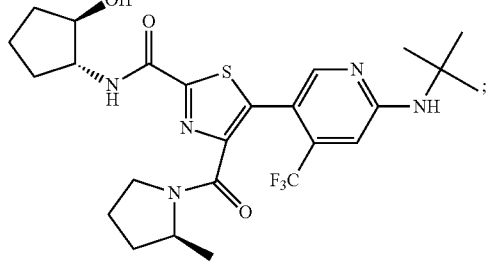

265
-continued
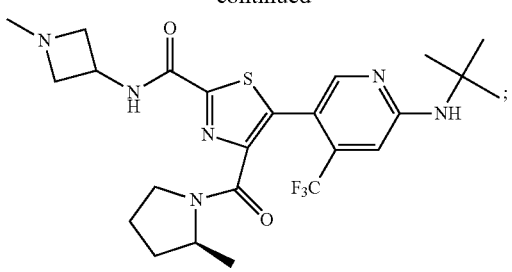
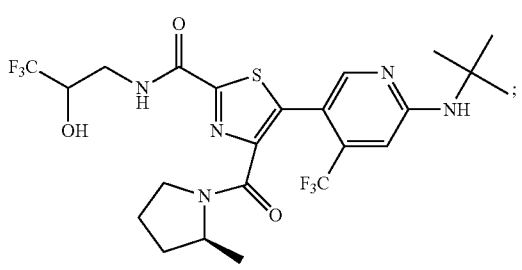
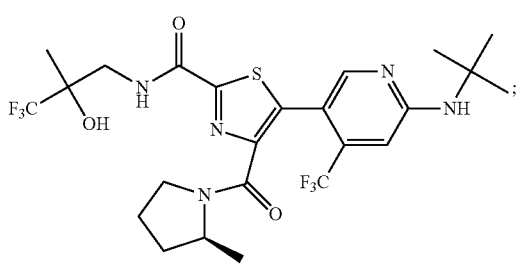
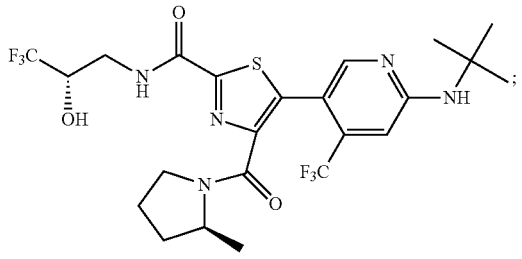
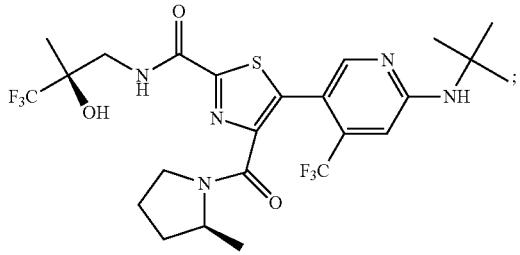
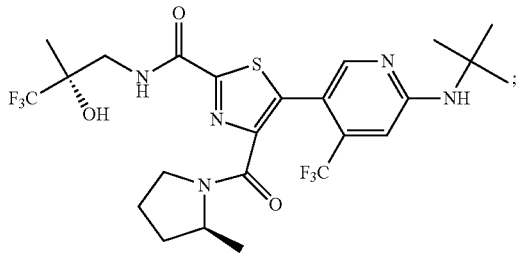
266
-continued
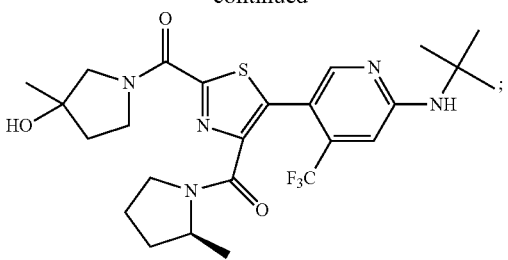
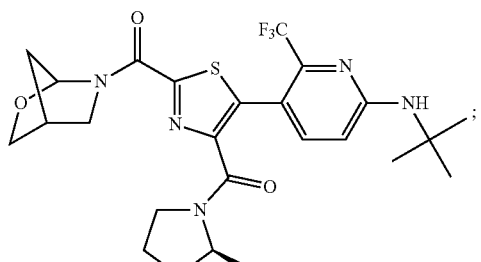
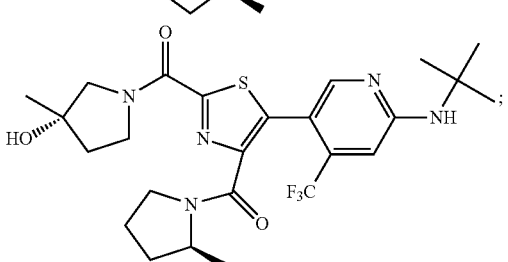
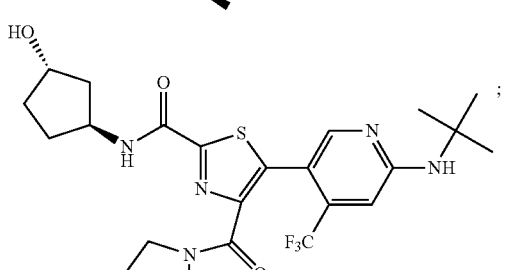
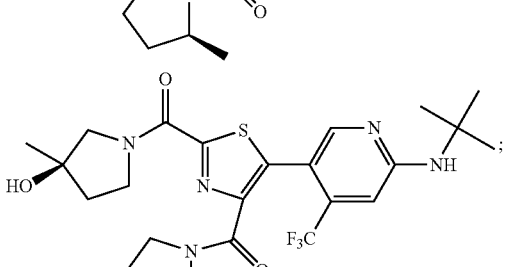
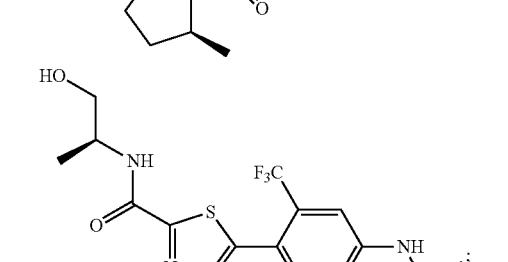

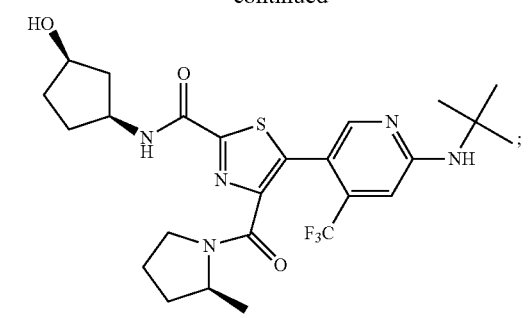
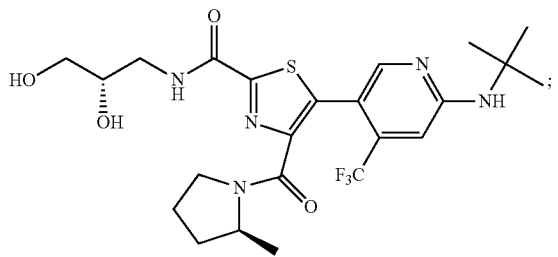
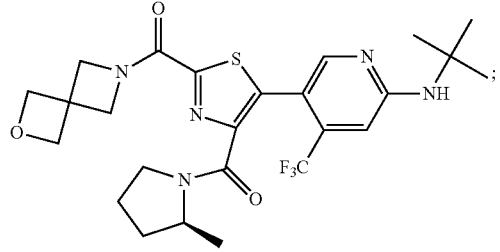
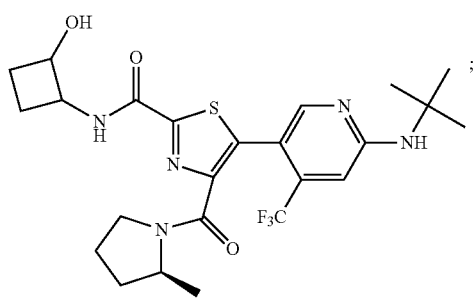
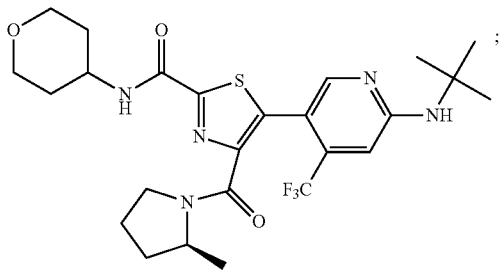
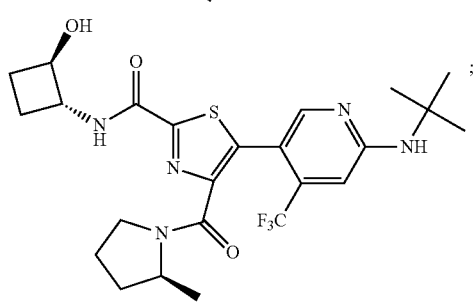
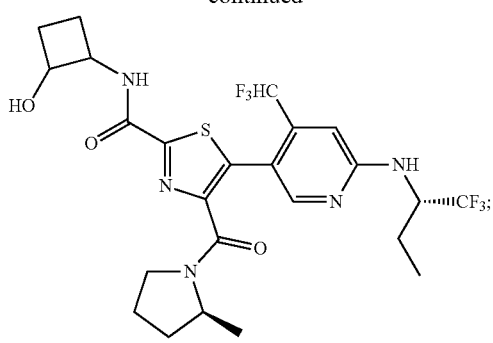
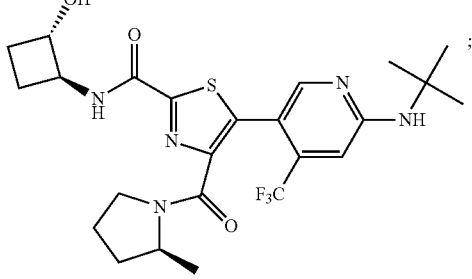
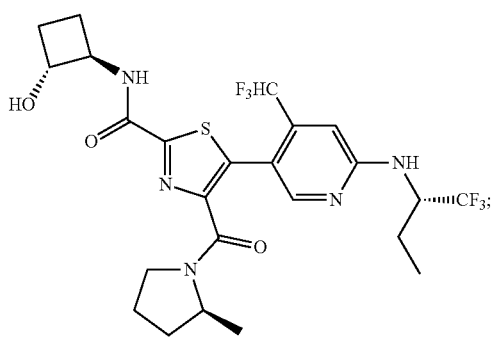
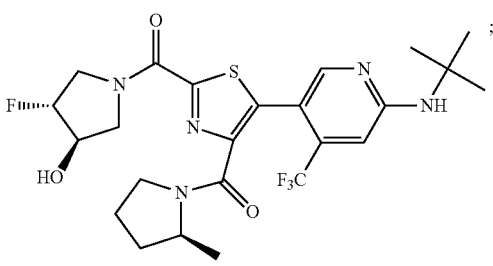
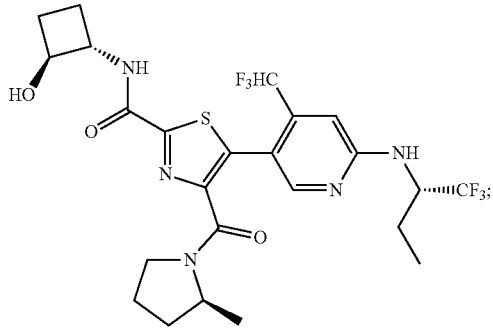

269
-continued
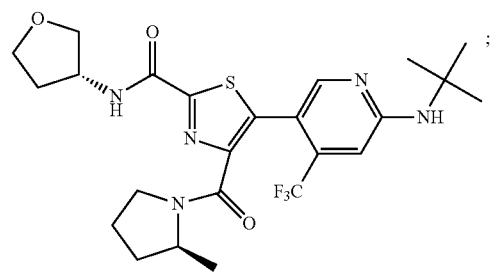
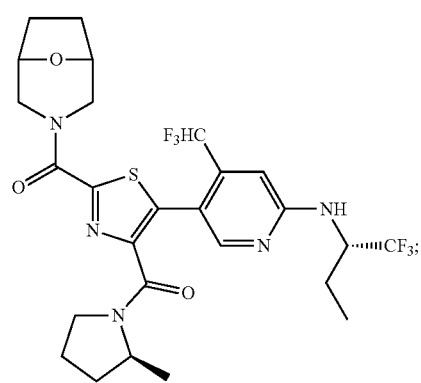
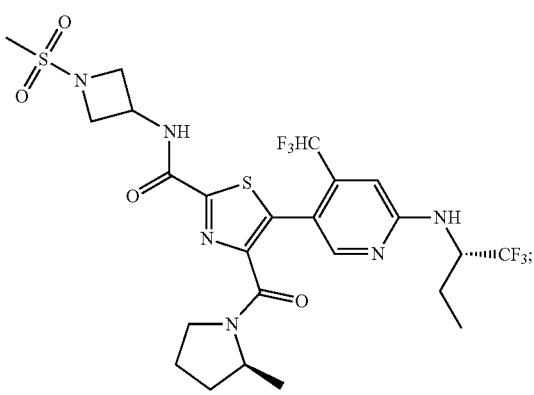
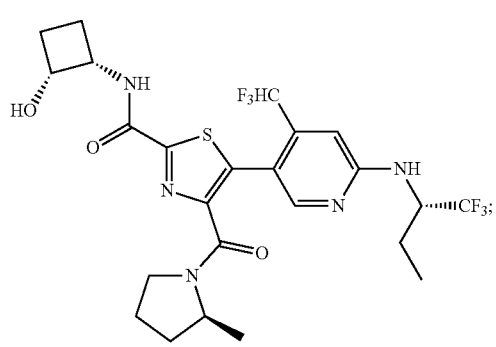
270
-continued
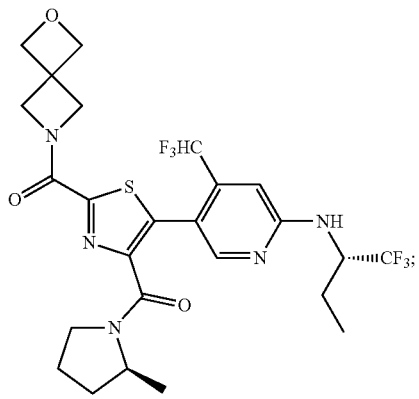
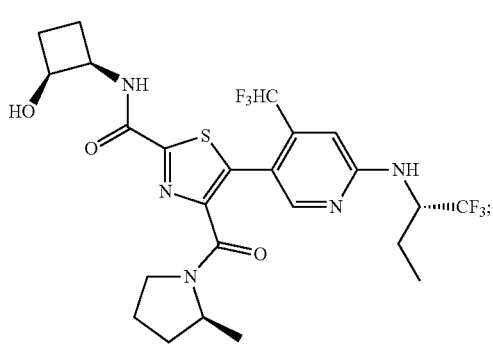
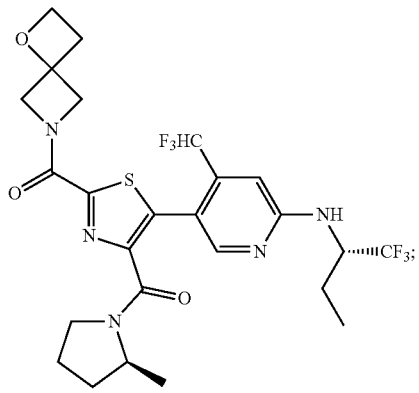
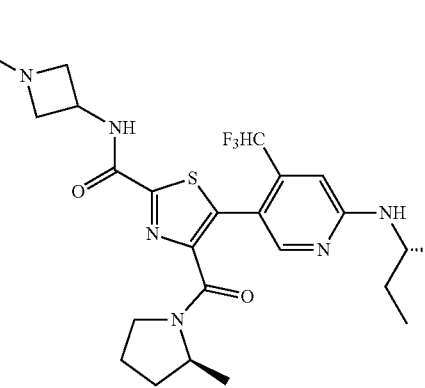

271
-continued
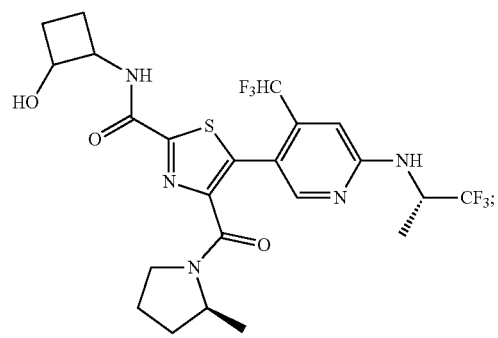
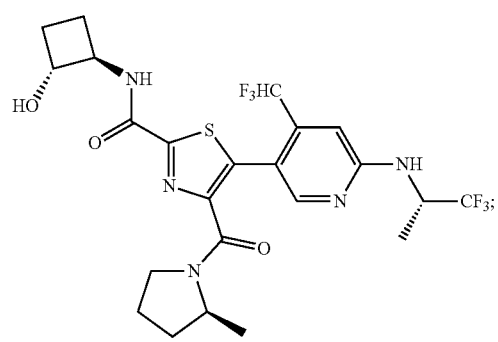
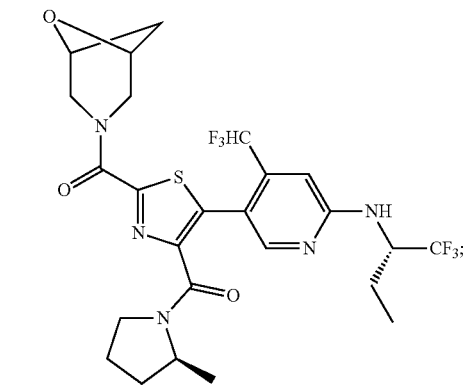
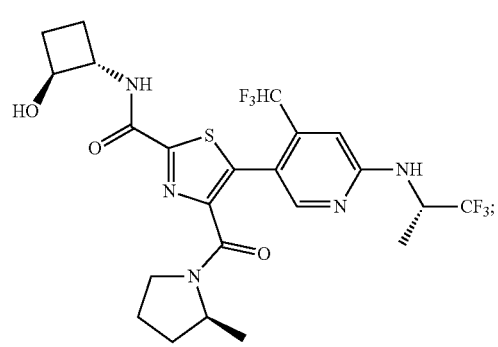
272
-continued
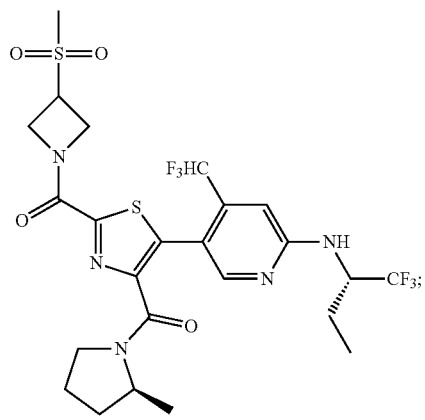
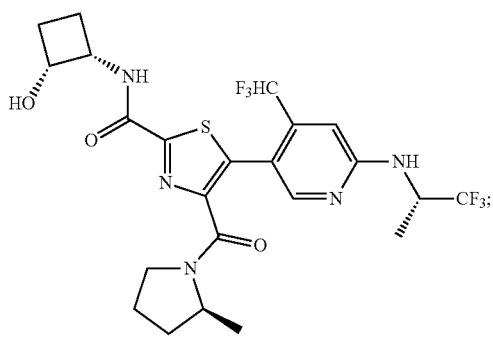
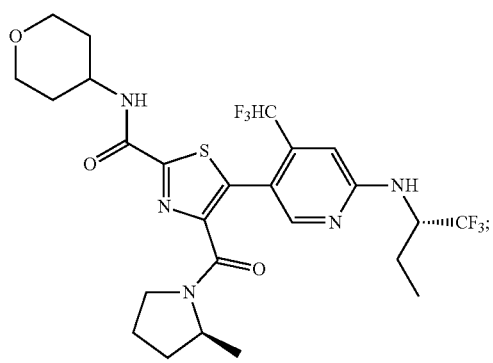
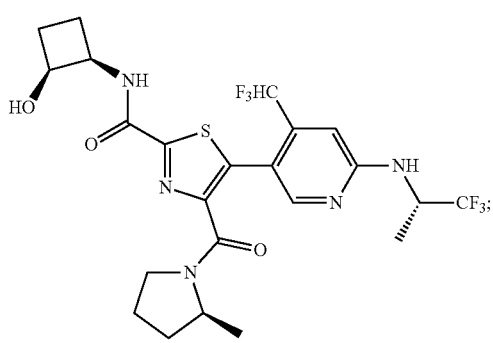

273
-continued
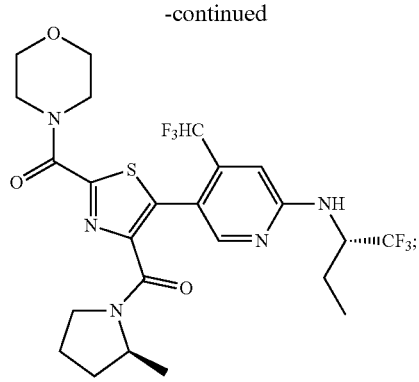
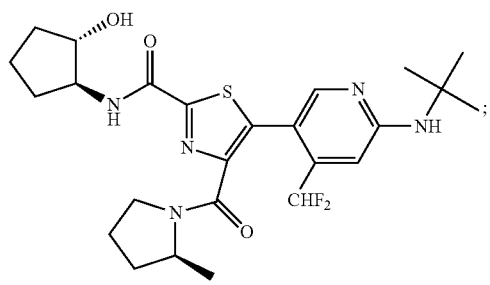
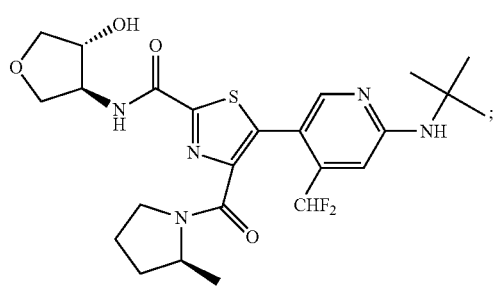
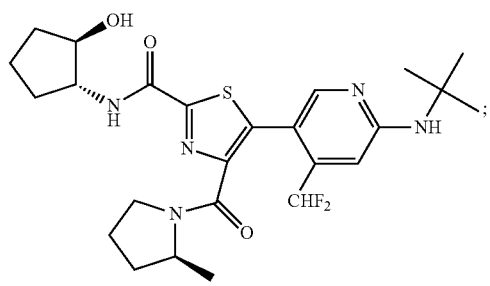
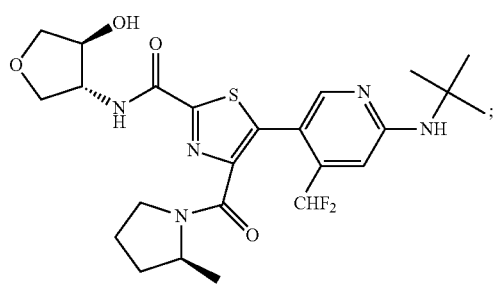
274
-continued
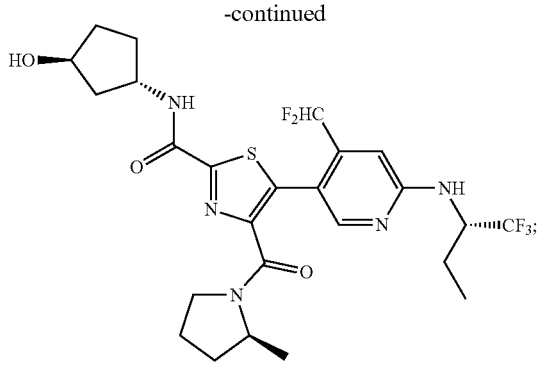
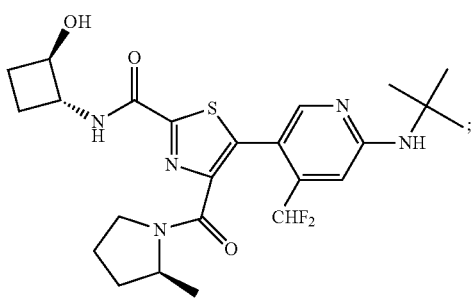
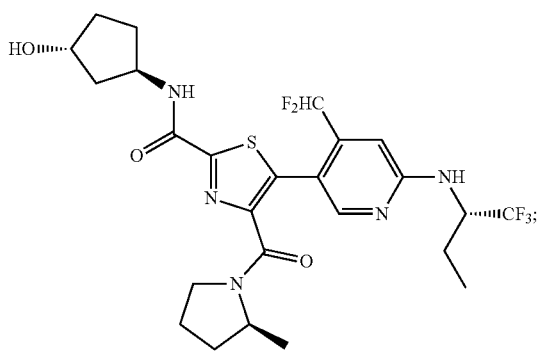
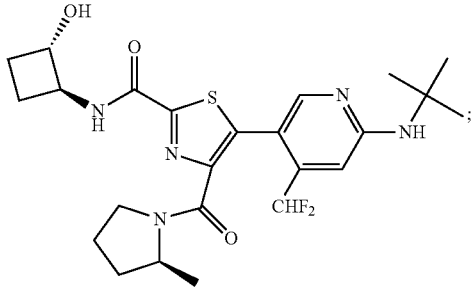
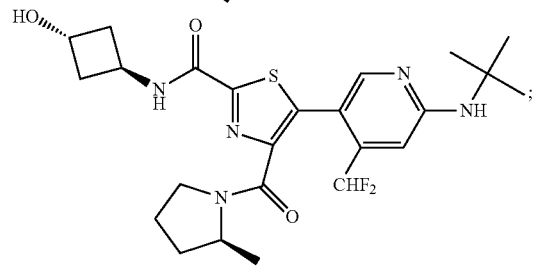

275
-continued
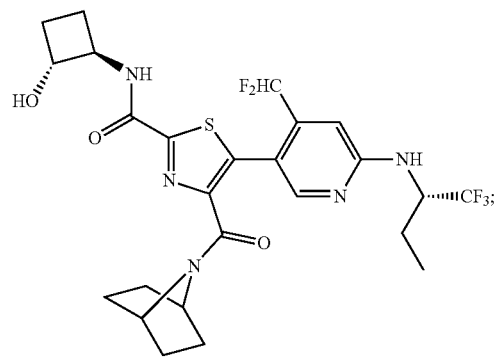
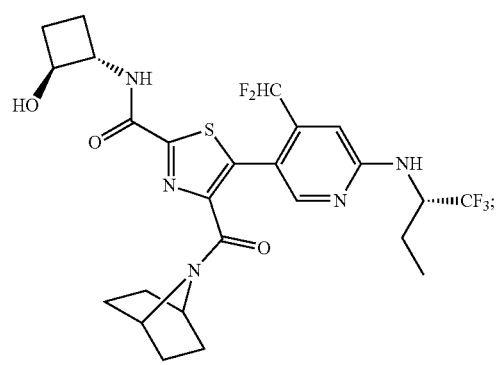
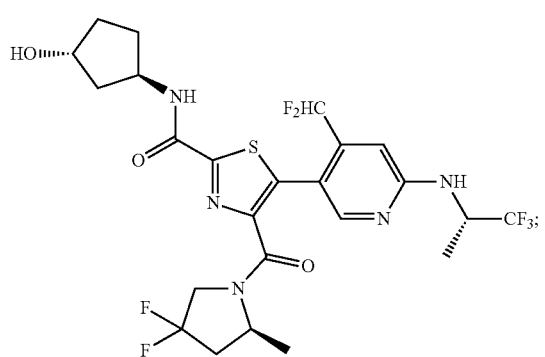
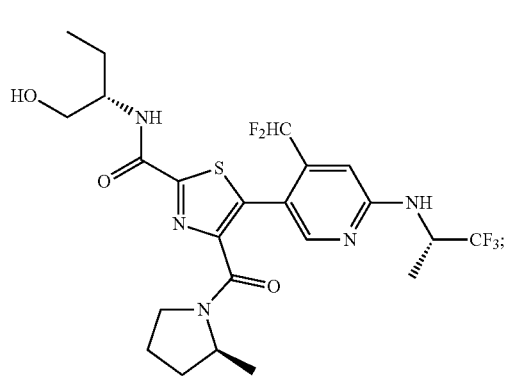
276
-continued
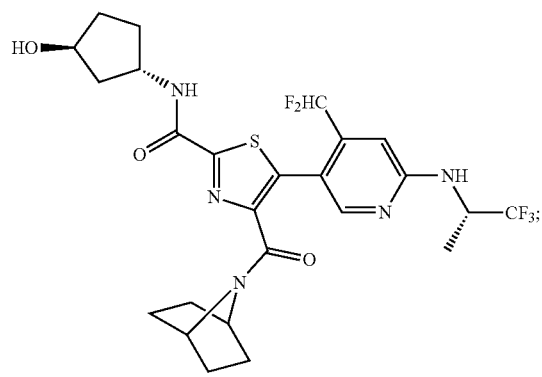
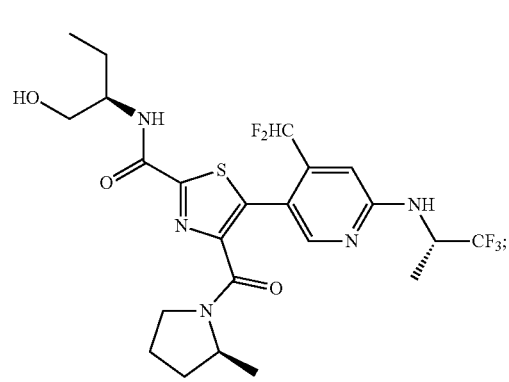
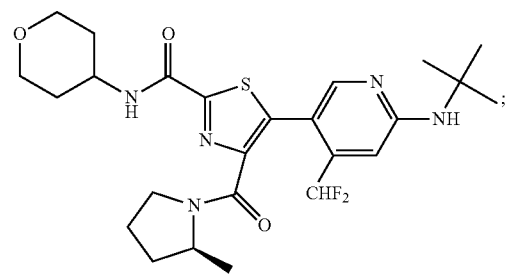
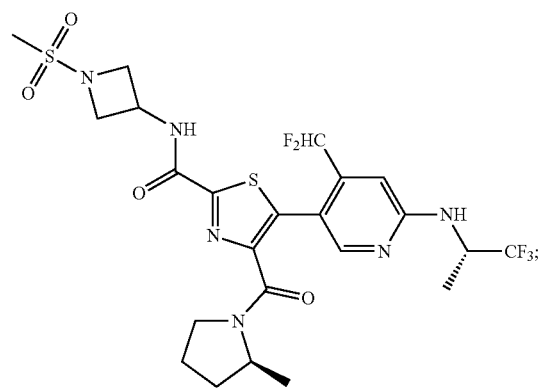

277
-continued
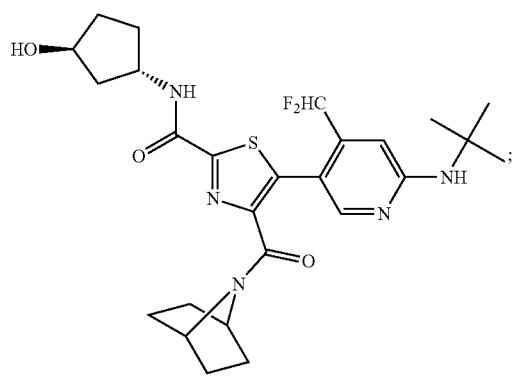
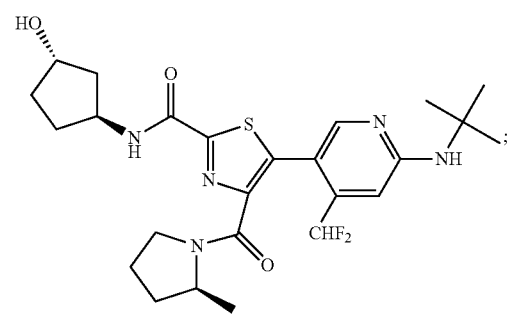
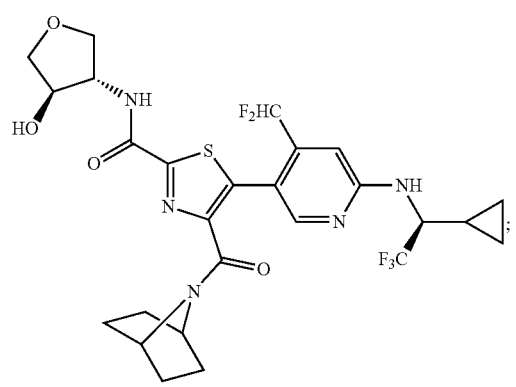
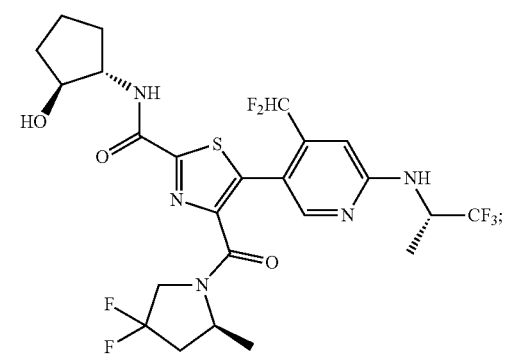
278
-continued
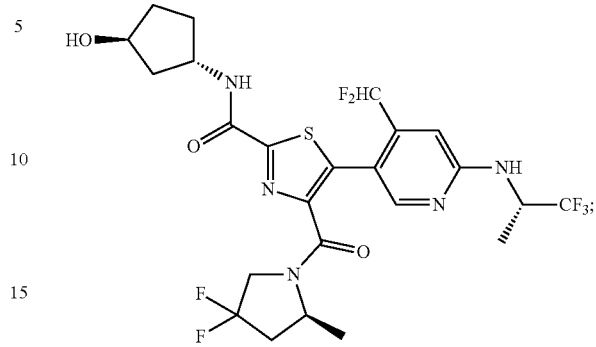
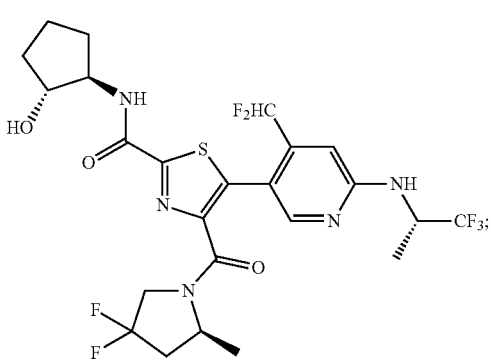

279
-continued
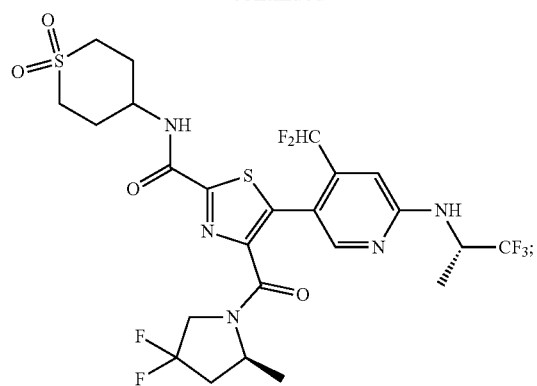
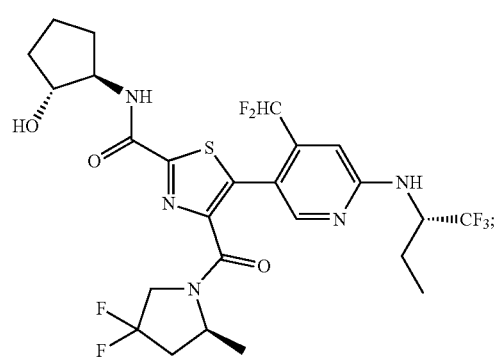
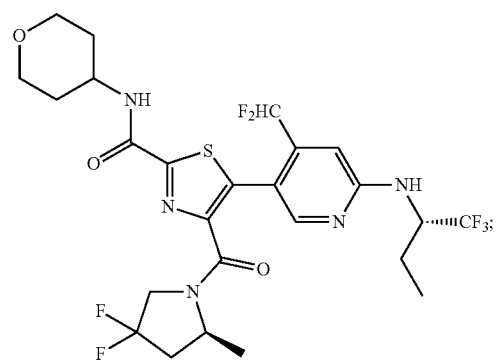
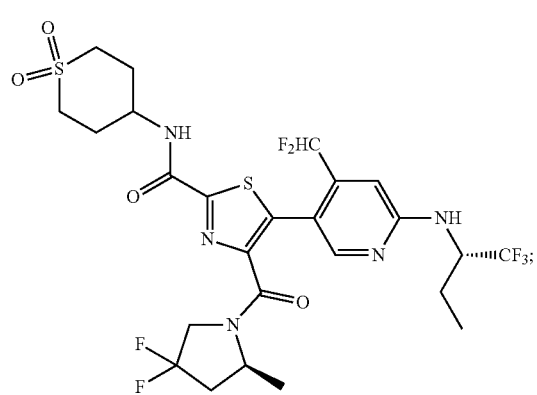
280
-continued
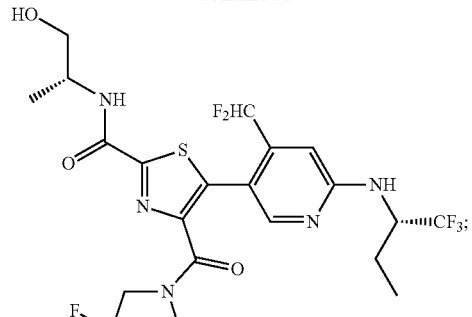
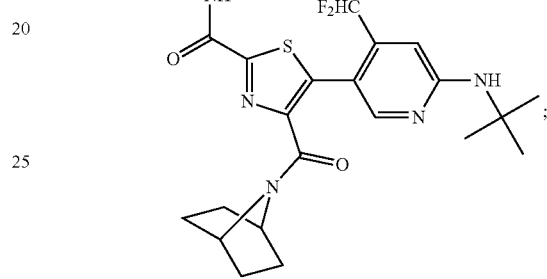
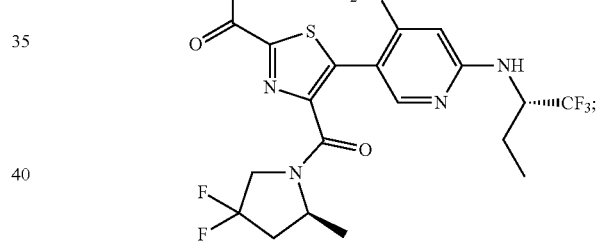
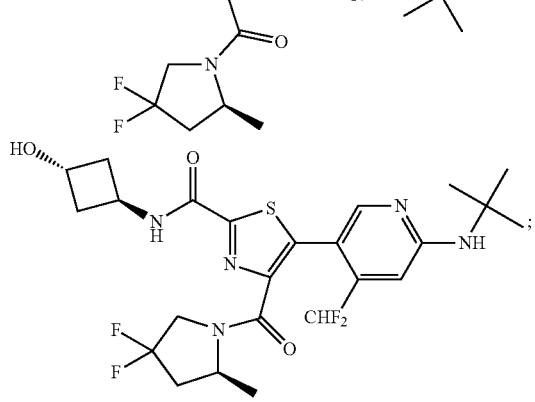

281
-continued
282
-continued
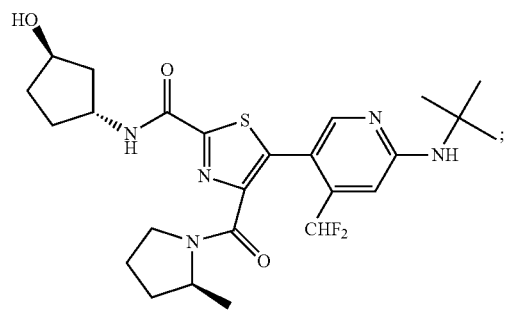
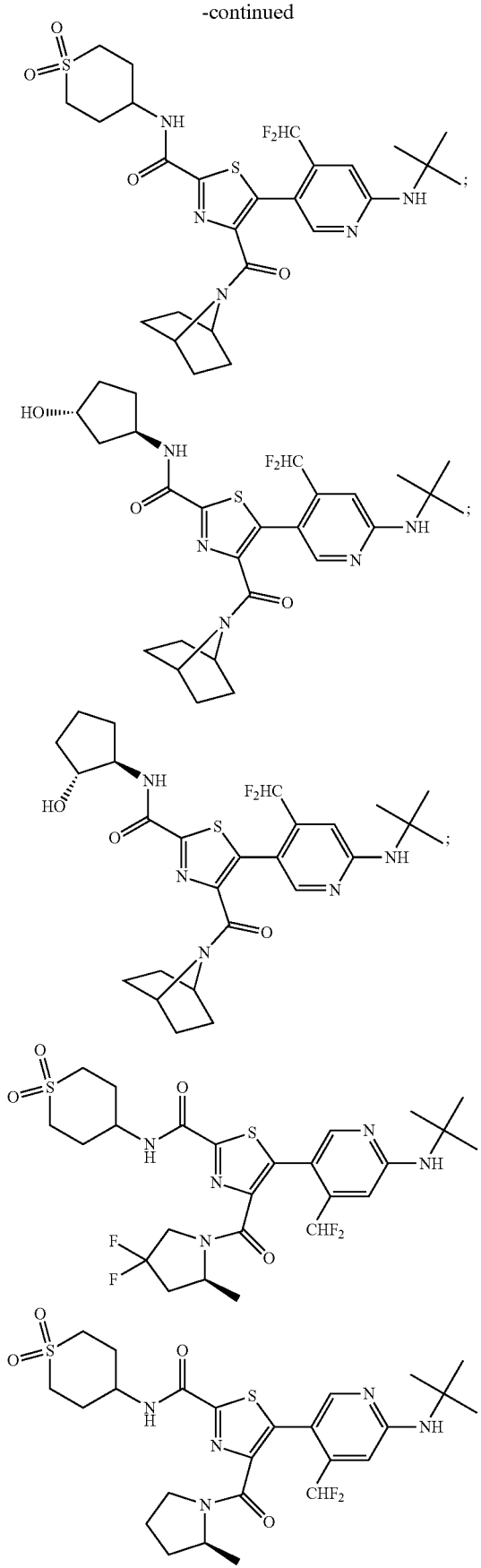

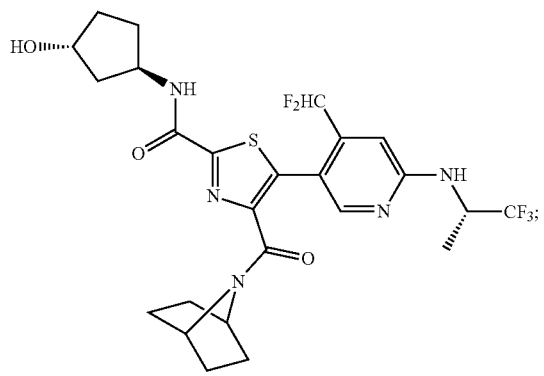
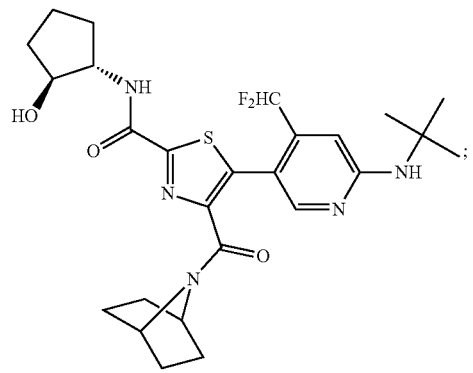
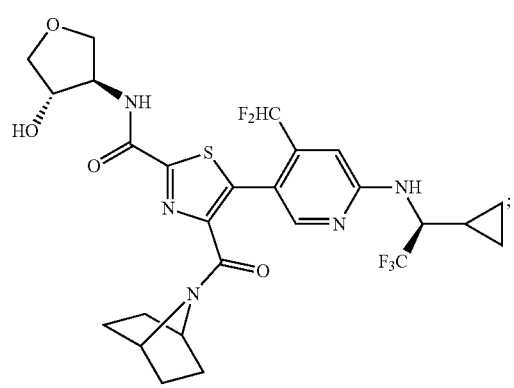
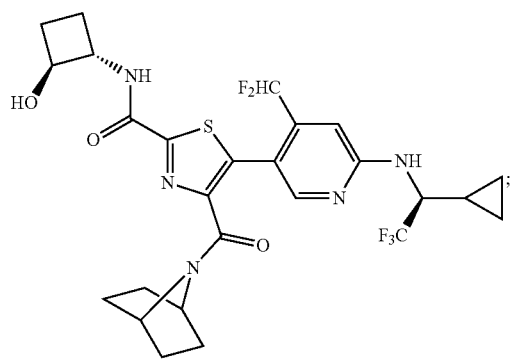
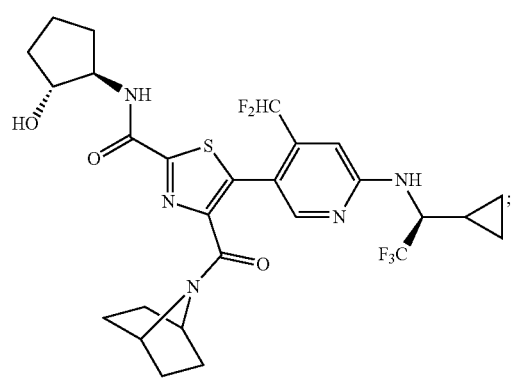
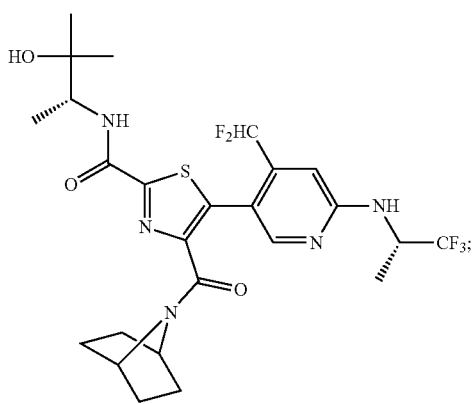
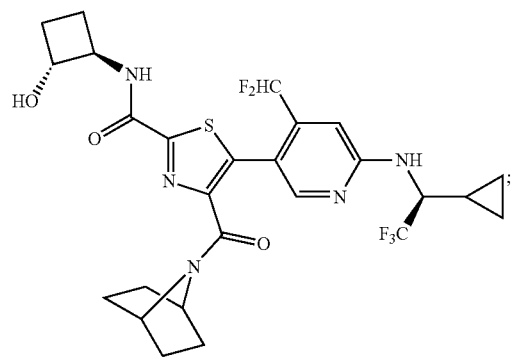
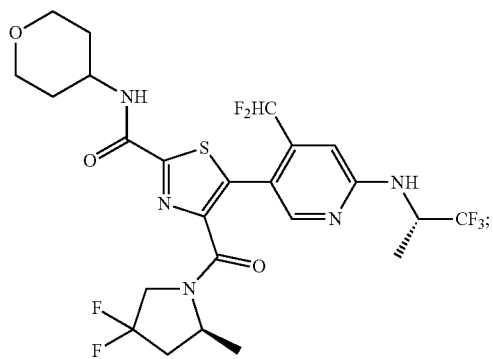

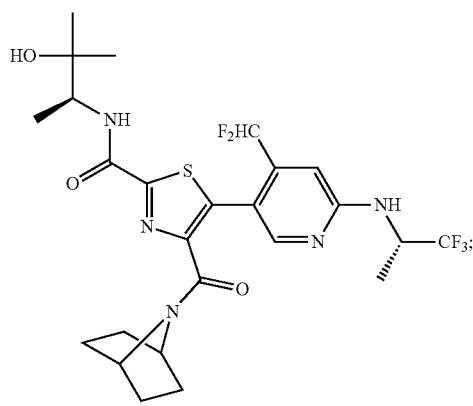
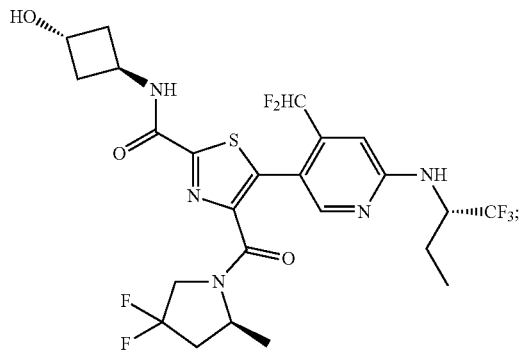
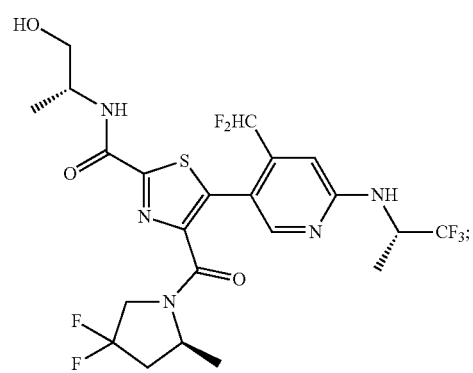
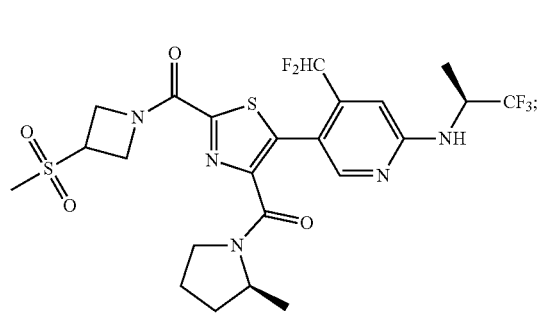
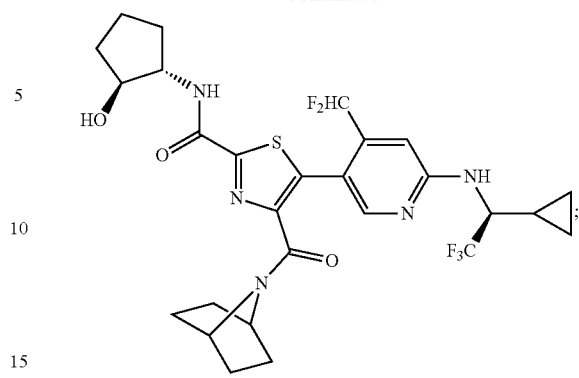
and pharmaceutically acceptable salts thereof.
Another embodiment of the invention is a compound selected from the group consisting of:
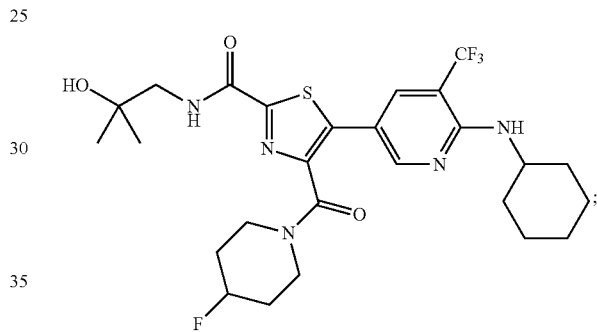
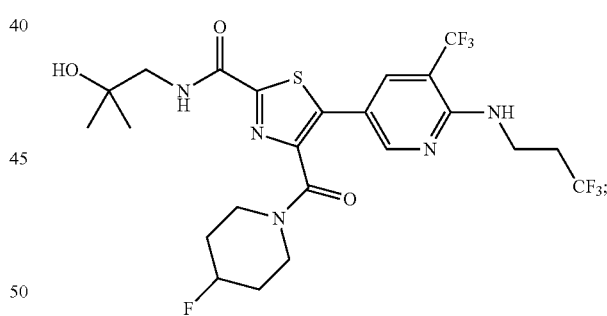
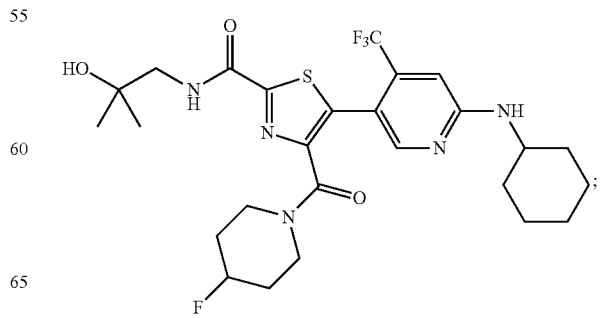

287
-continued
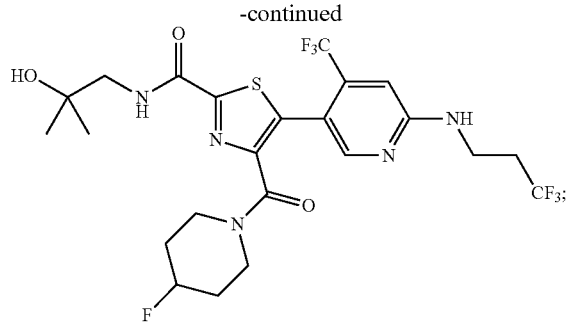
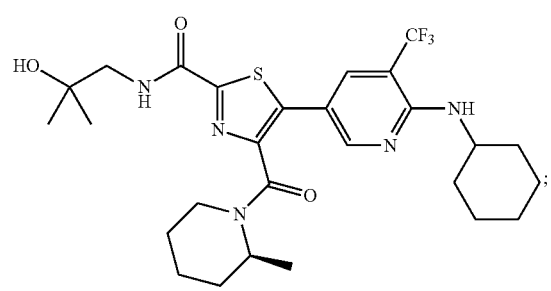
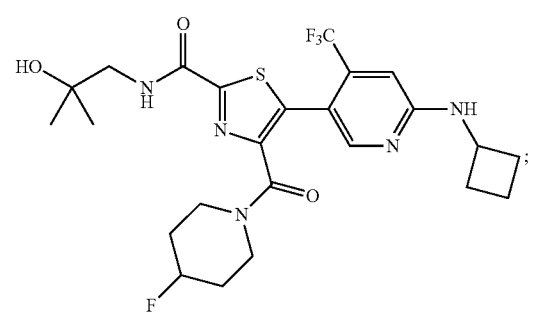
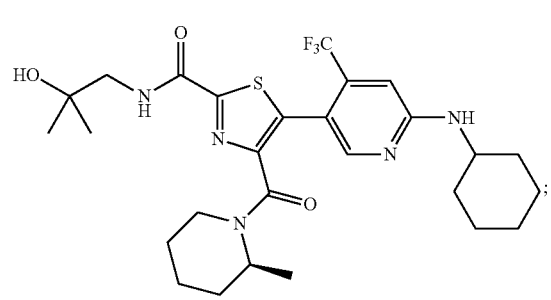
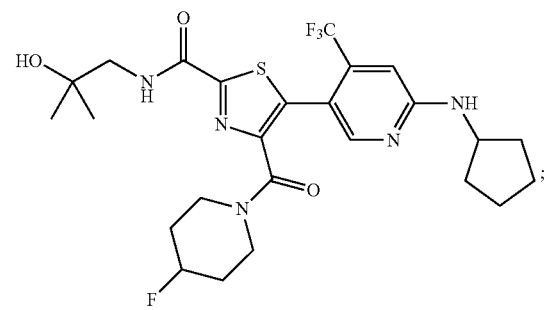
288
-continued
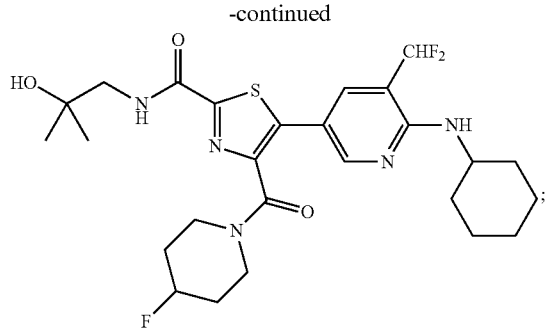
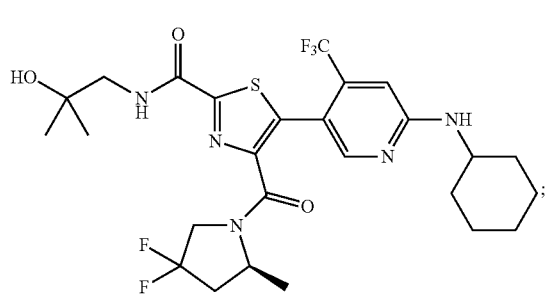
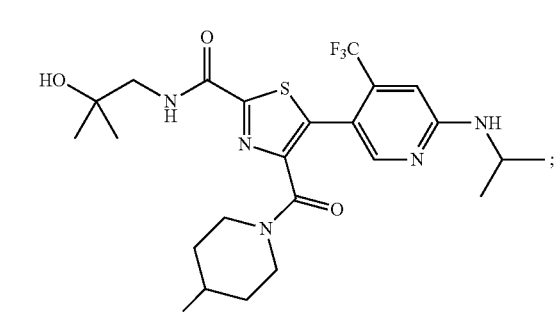
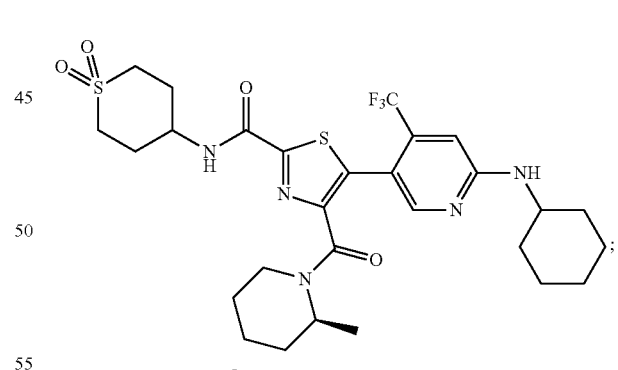
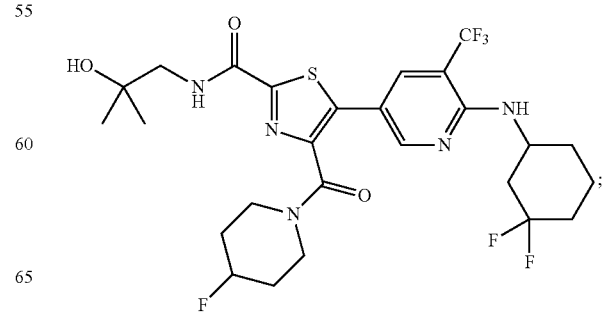

289
-continued
290
-continued
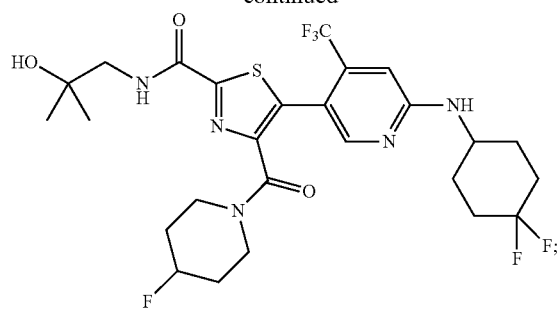
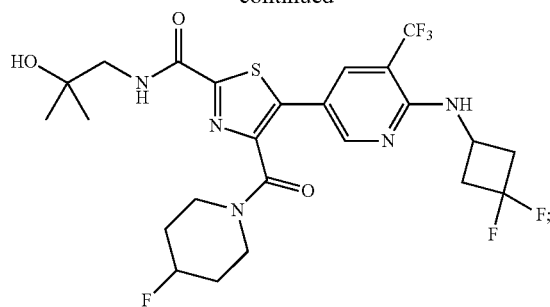

291
-continued
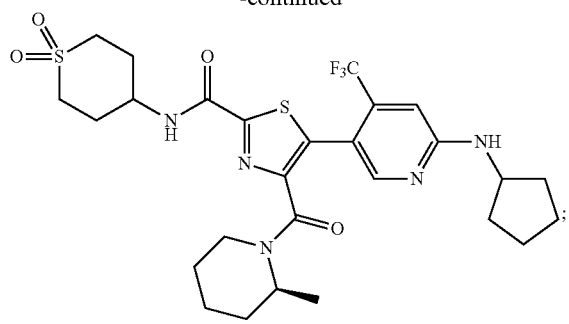
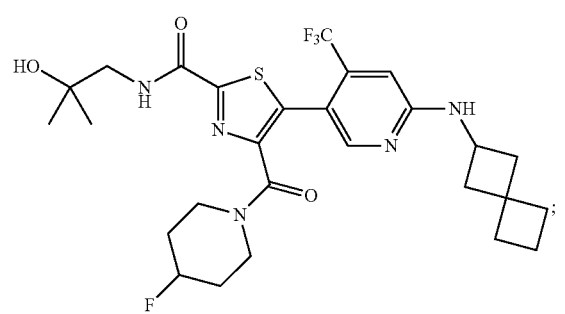
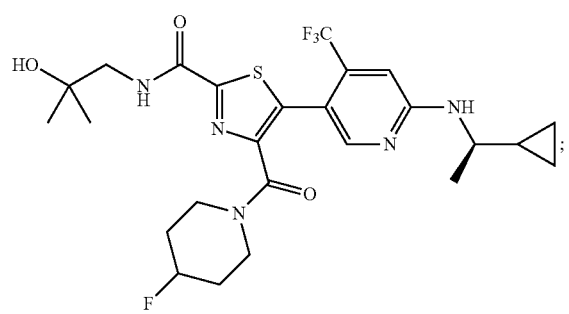
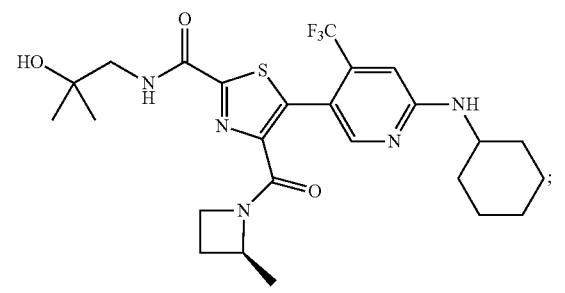
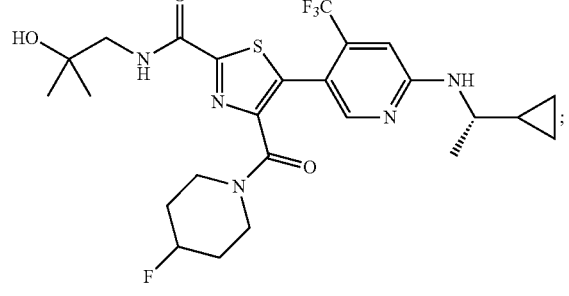
292
-continued
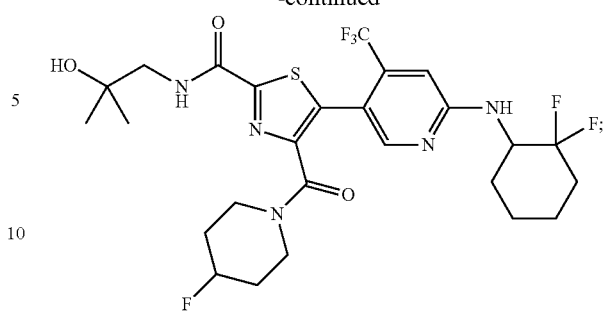
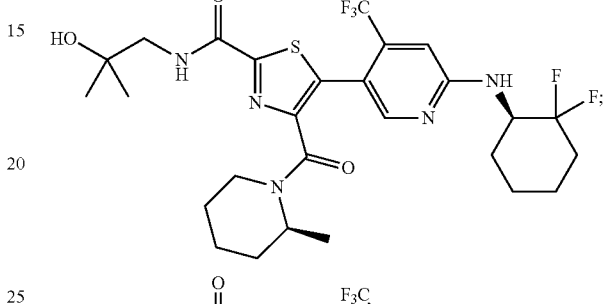
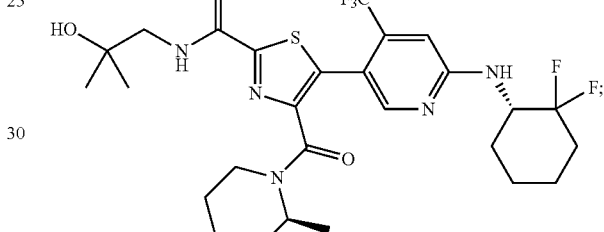
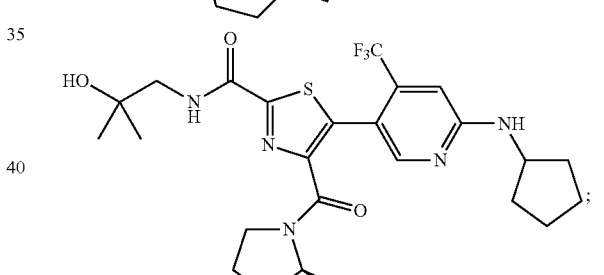
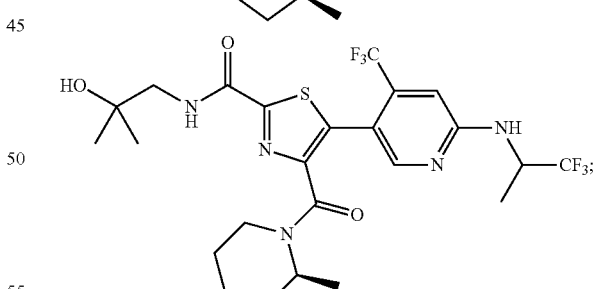
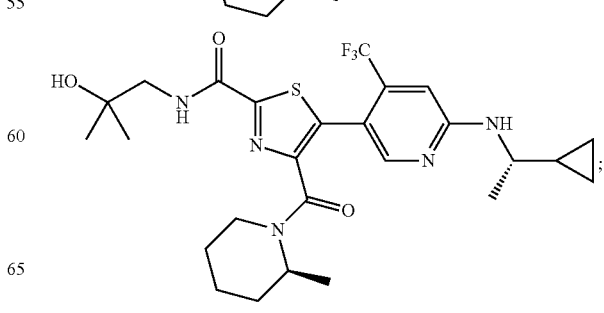

293
-continued
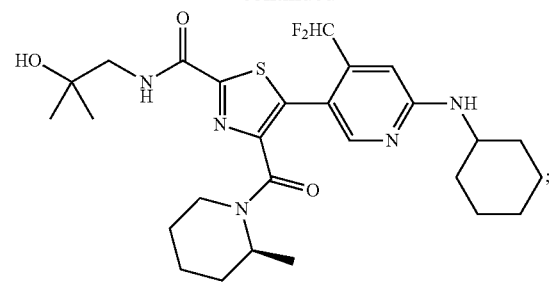
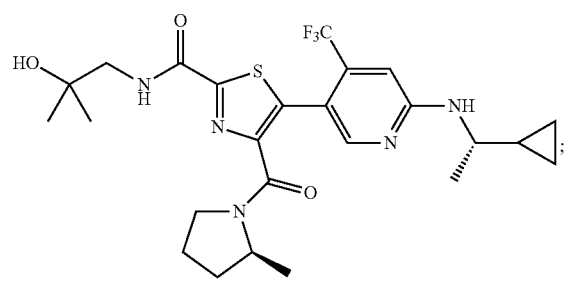
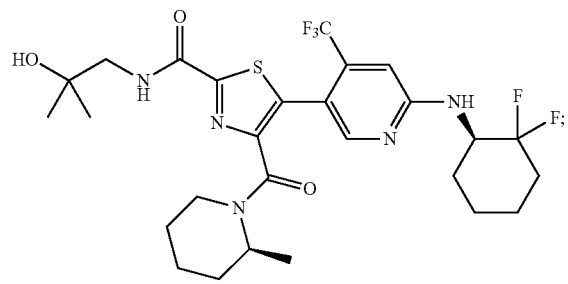
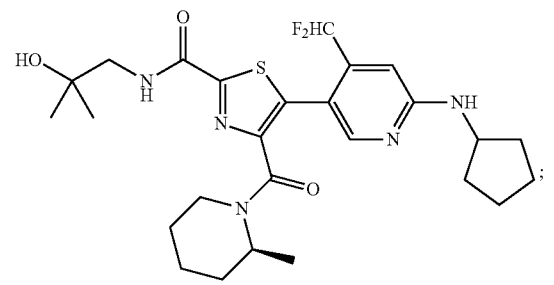
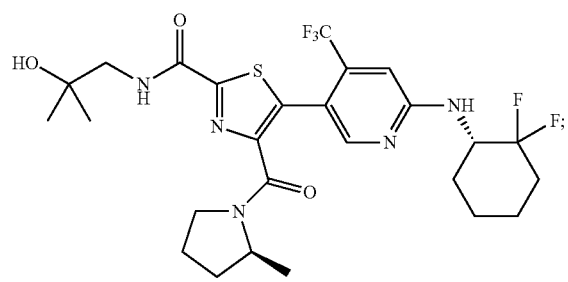
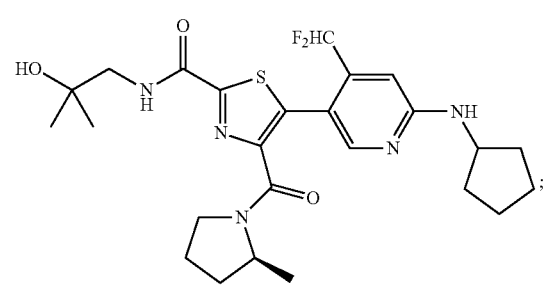
294
-continued
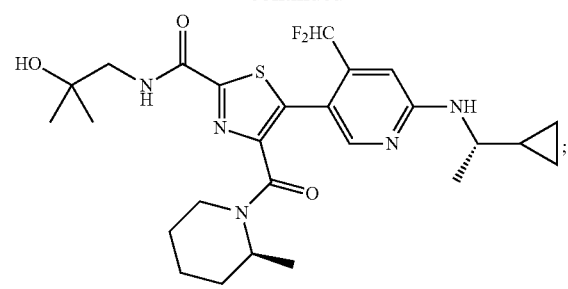
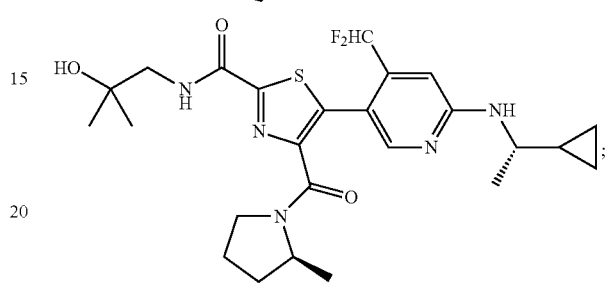
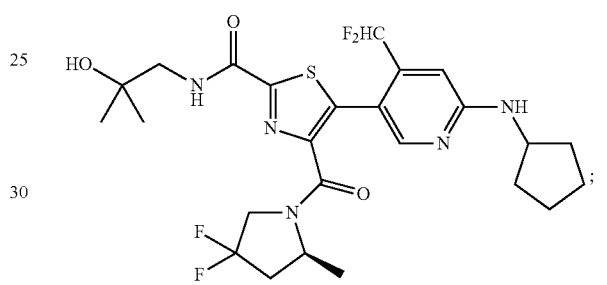
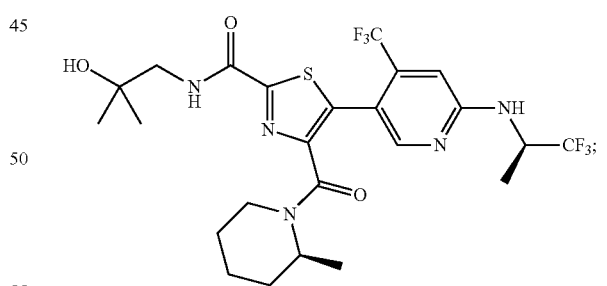
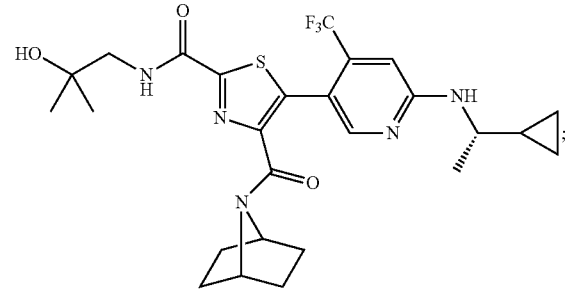

295
-continued
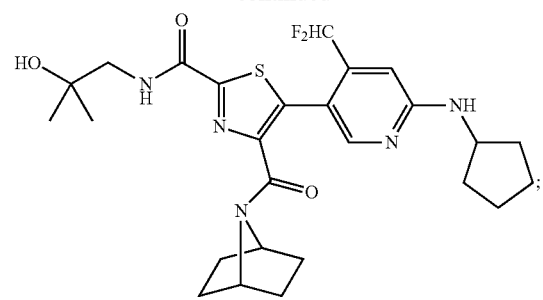
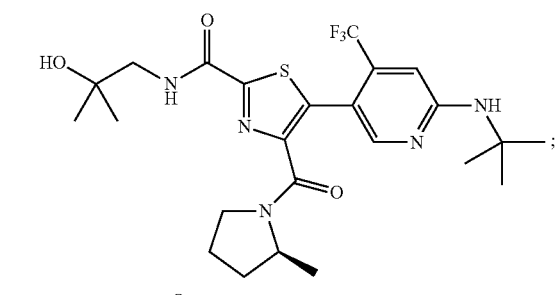
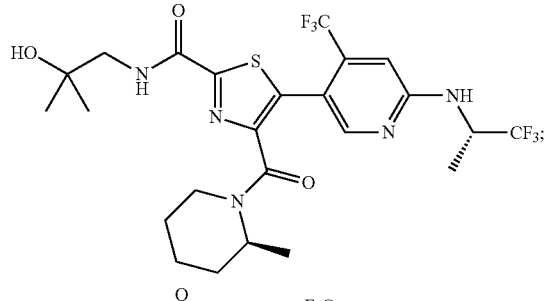
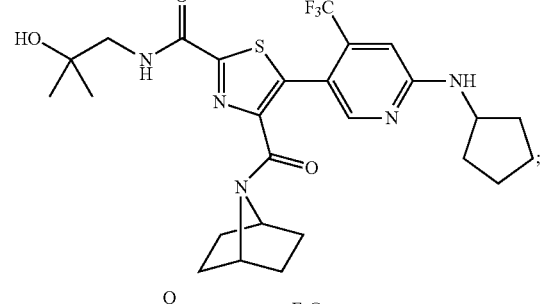
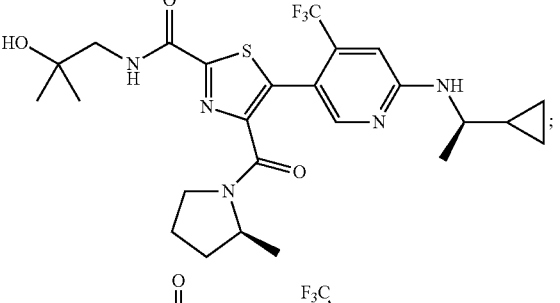
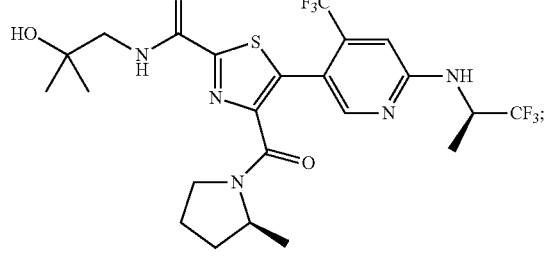
296
-continued
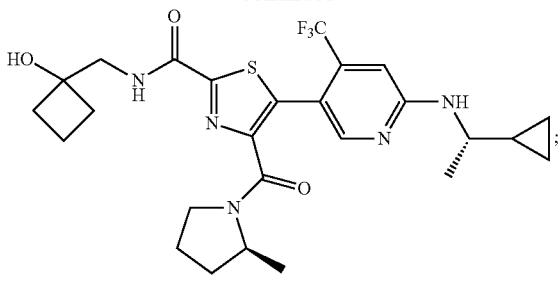
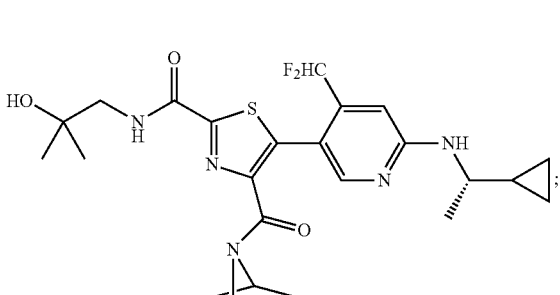
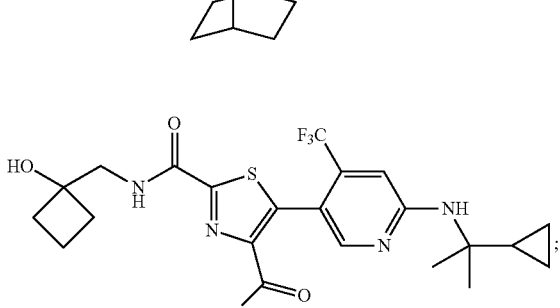
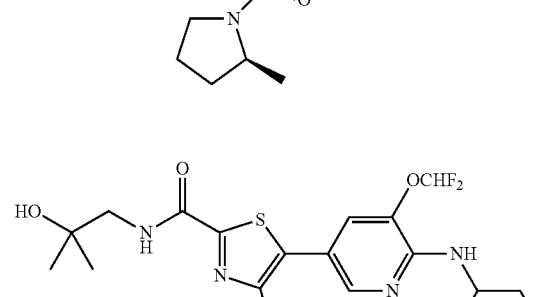
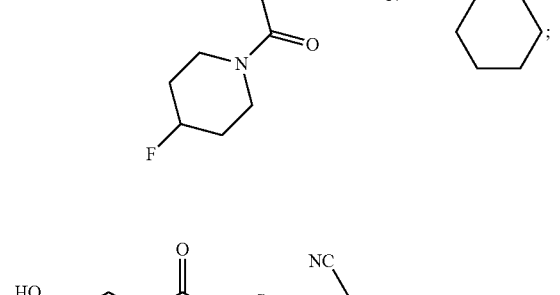
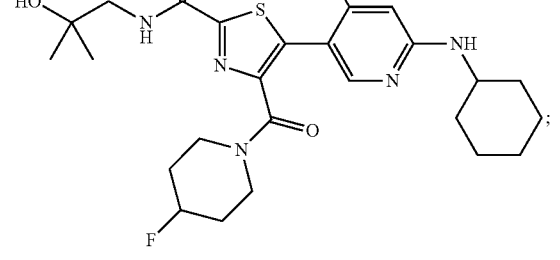

297
-continued
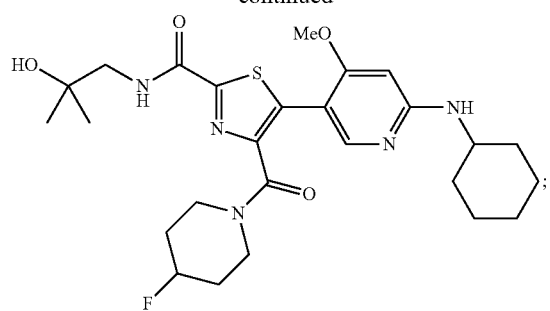
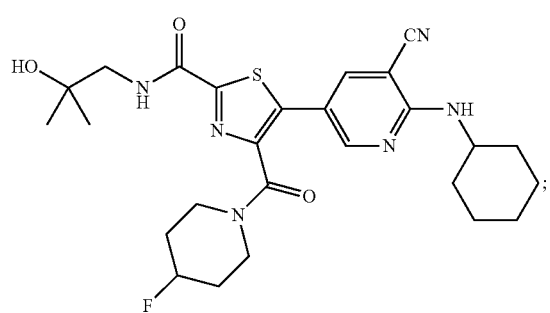
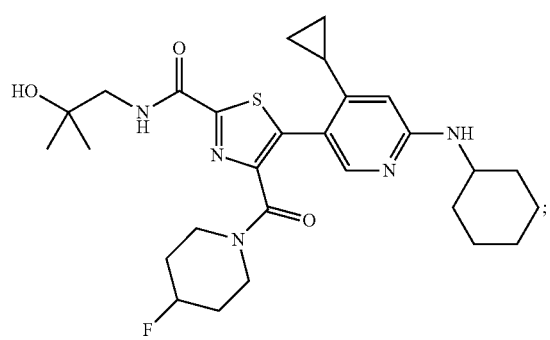
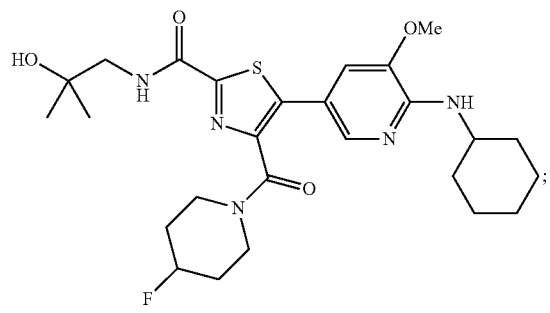
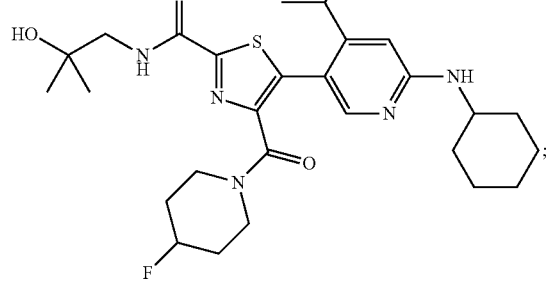
298
-continued
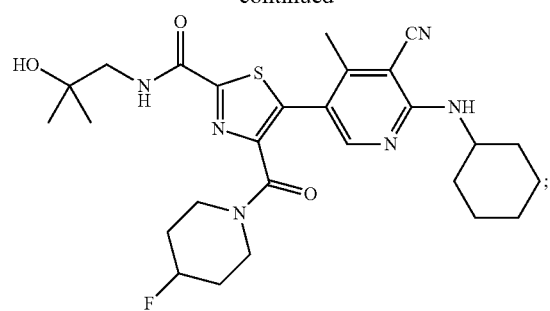
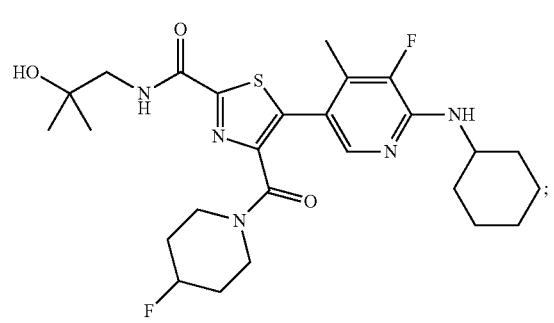 [SMILES: Cc1c(-c2sc(C(=O)NCC(C)(C)O)nc2C(=O)N2CCC(F)CC2)cnc(NC2CCCCC2)c1C#N]
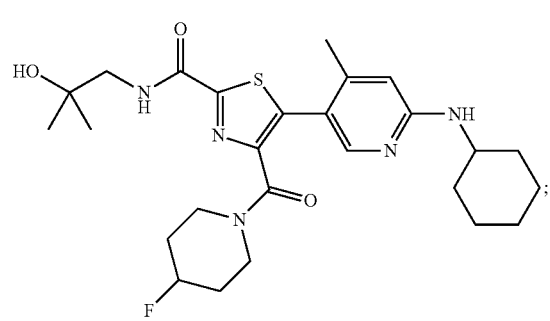
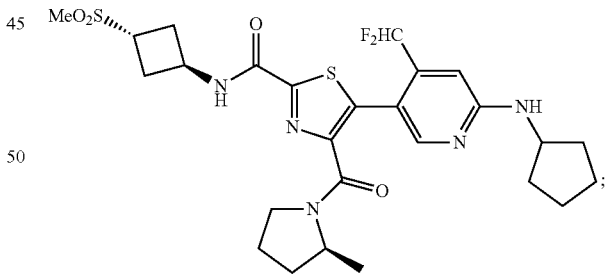
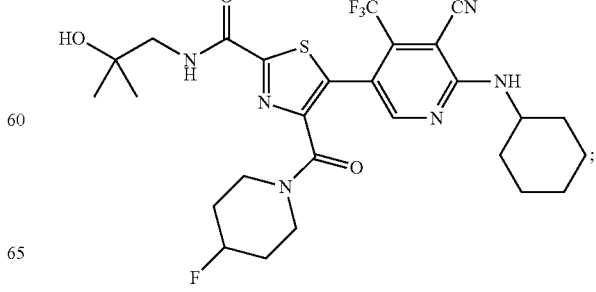

299
-continued
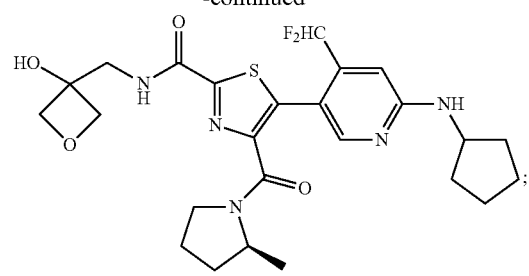
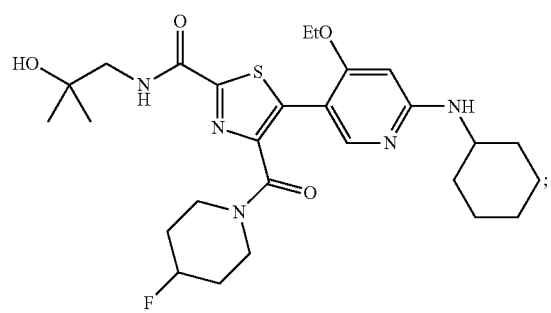
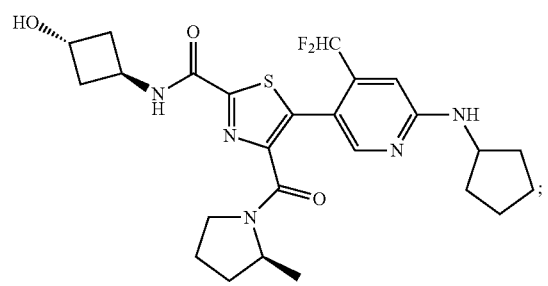
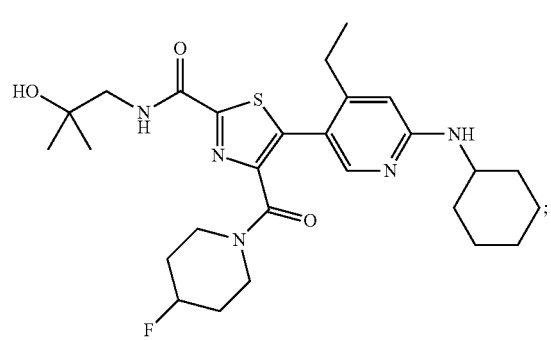
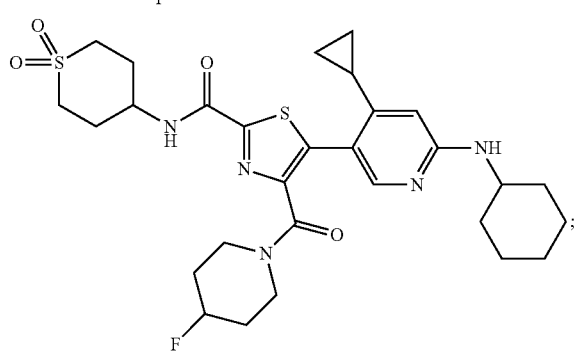
300
-continued
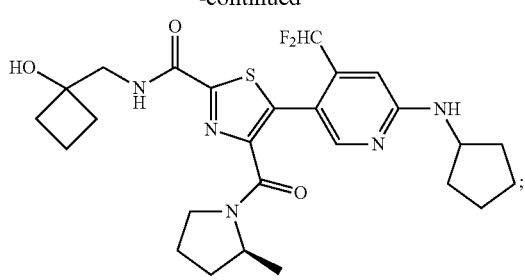
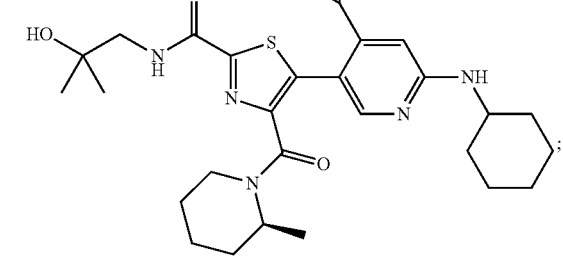
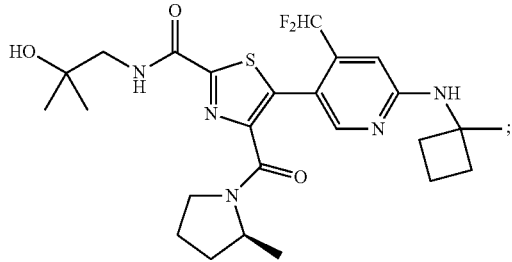
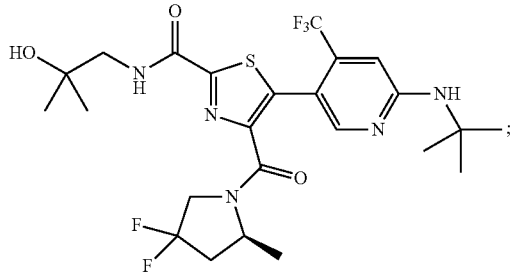
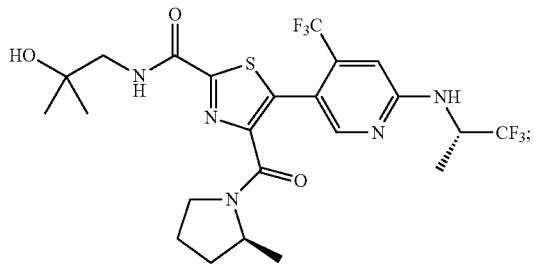
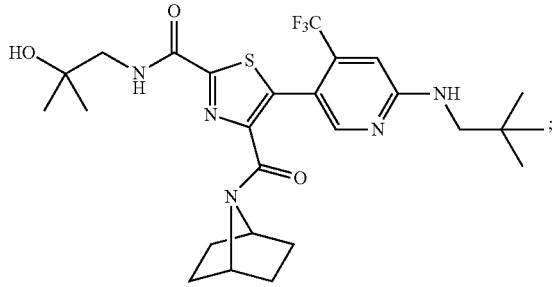

301
-continued
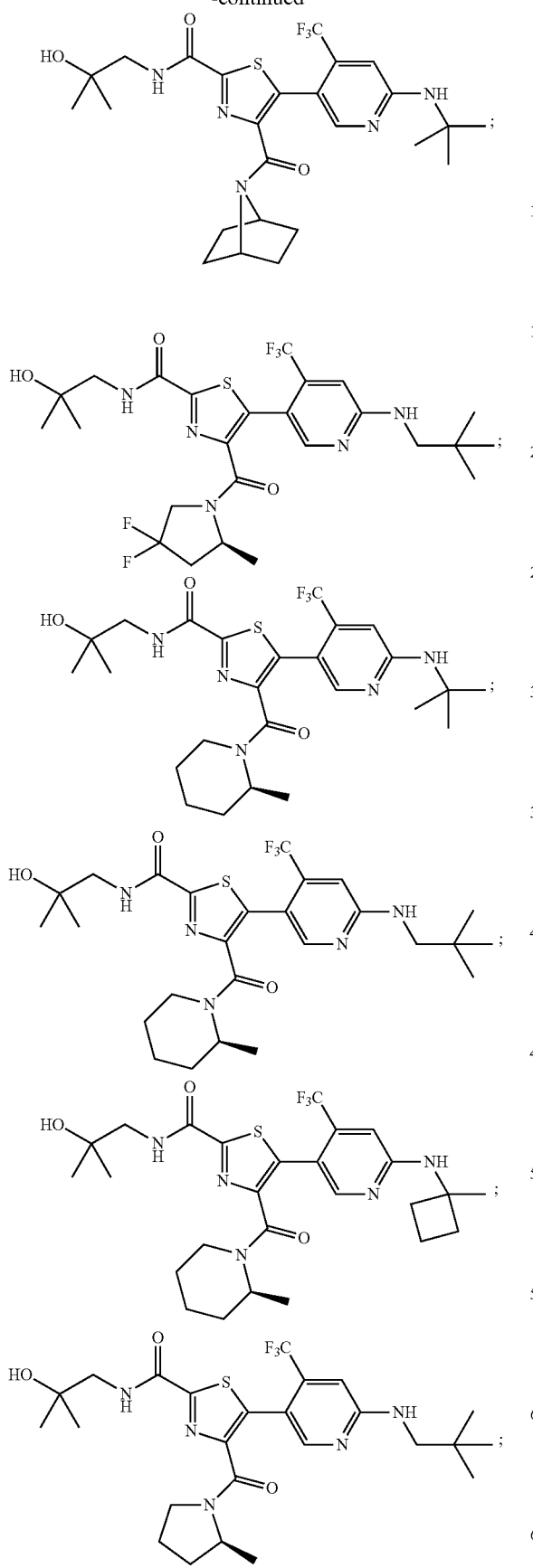
302
-continued
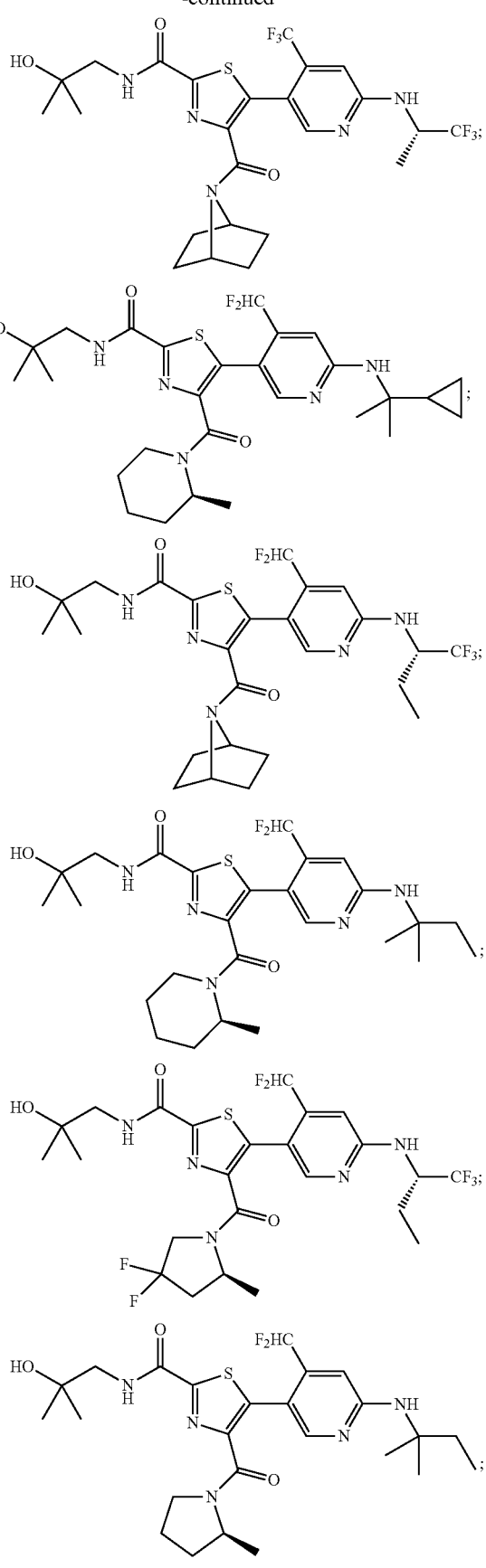

303
-continued
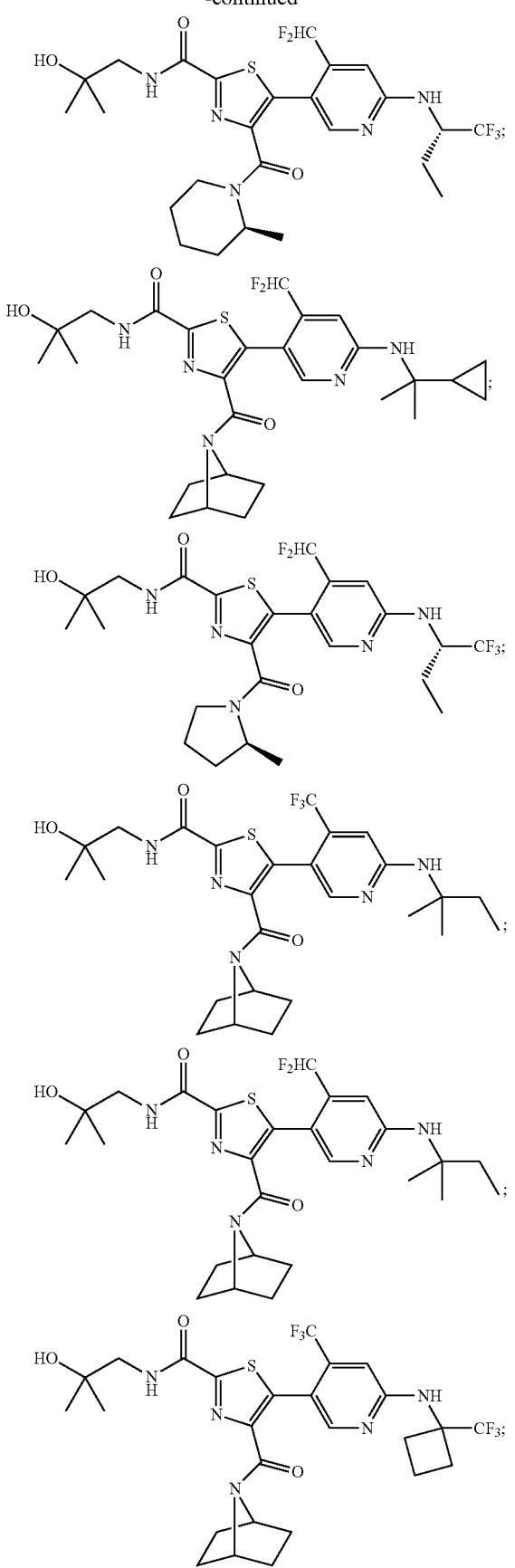
304
-continued
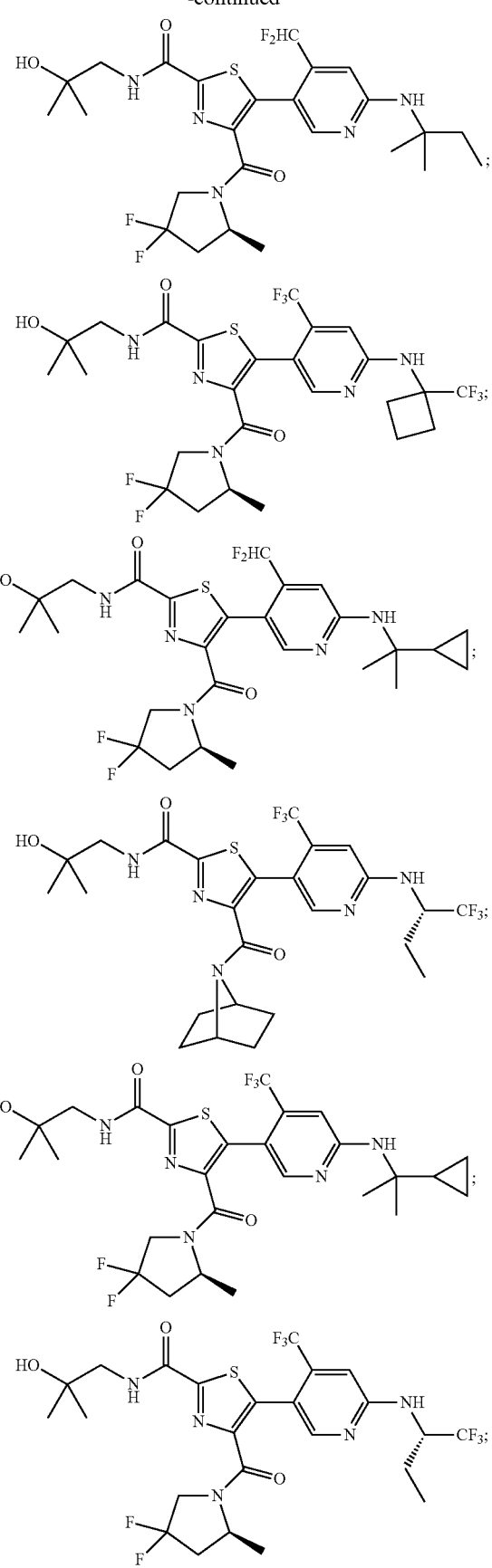

305
-continued
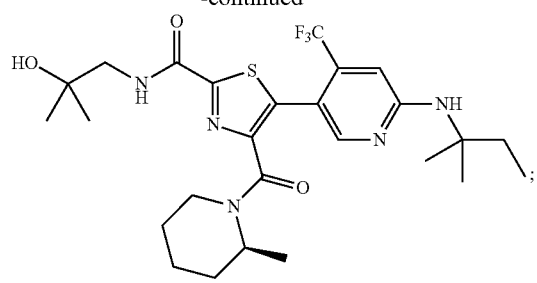
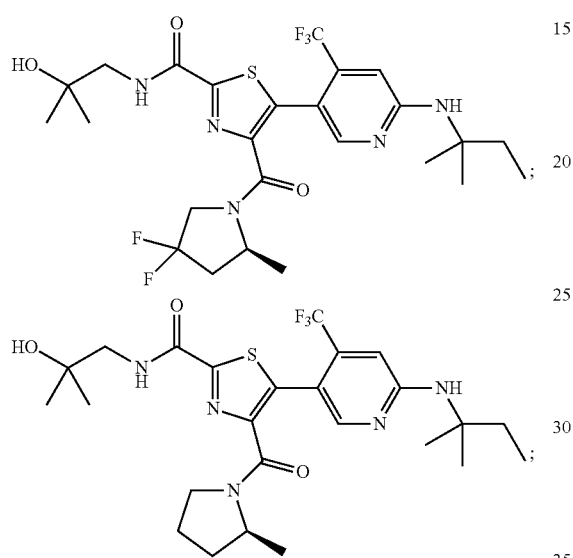
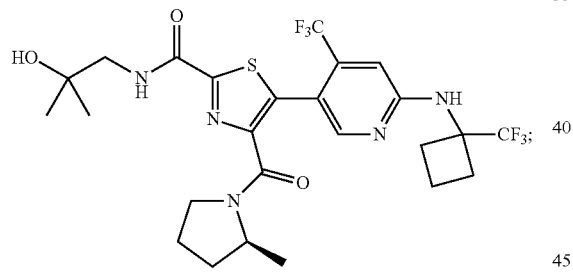
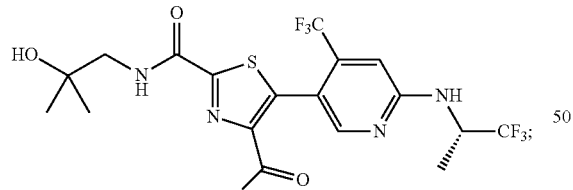
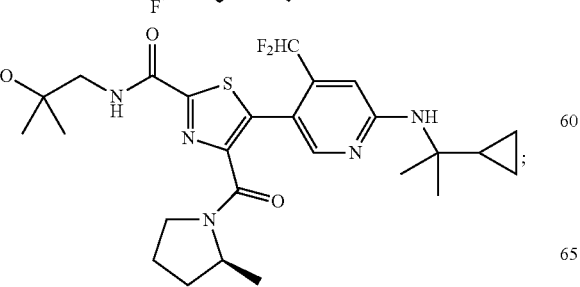
306
-continued
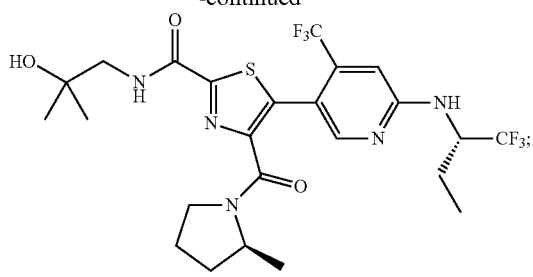
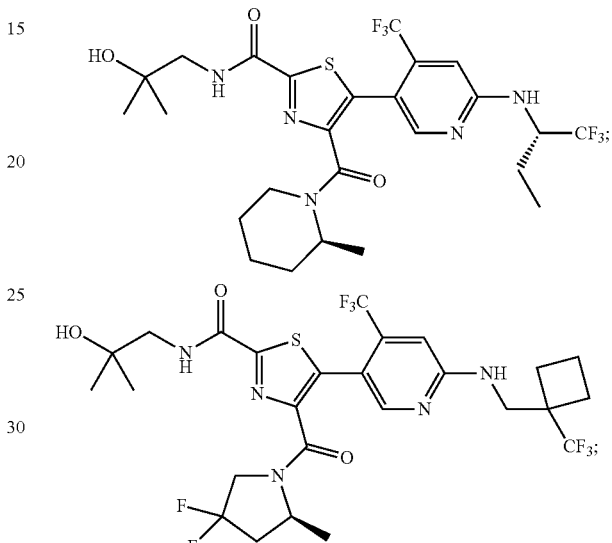
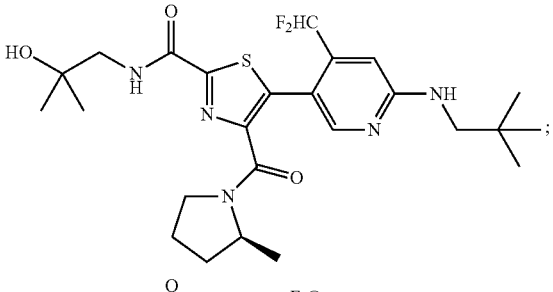
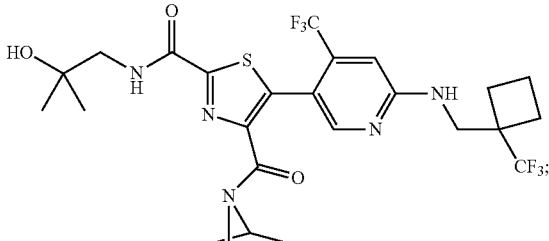
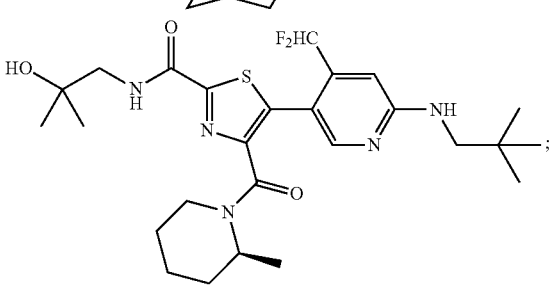

307
-continued
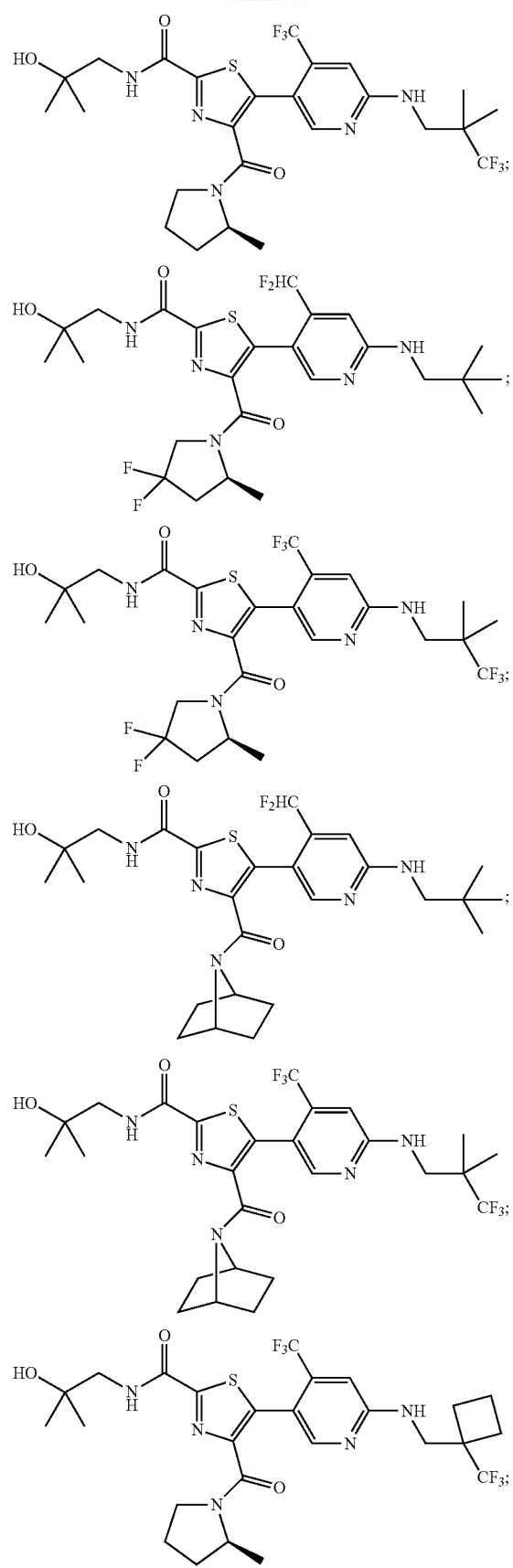
308
-continued
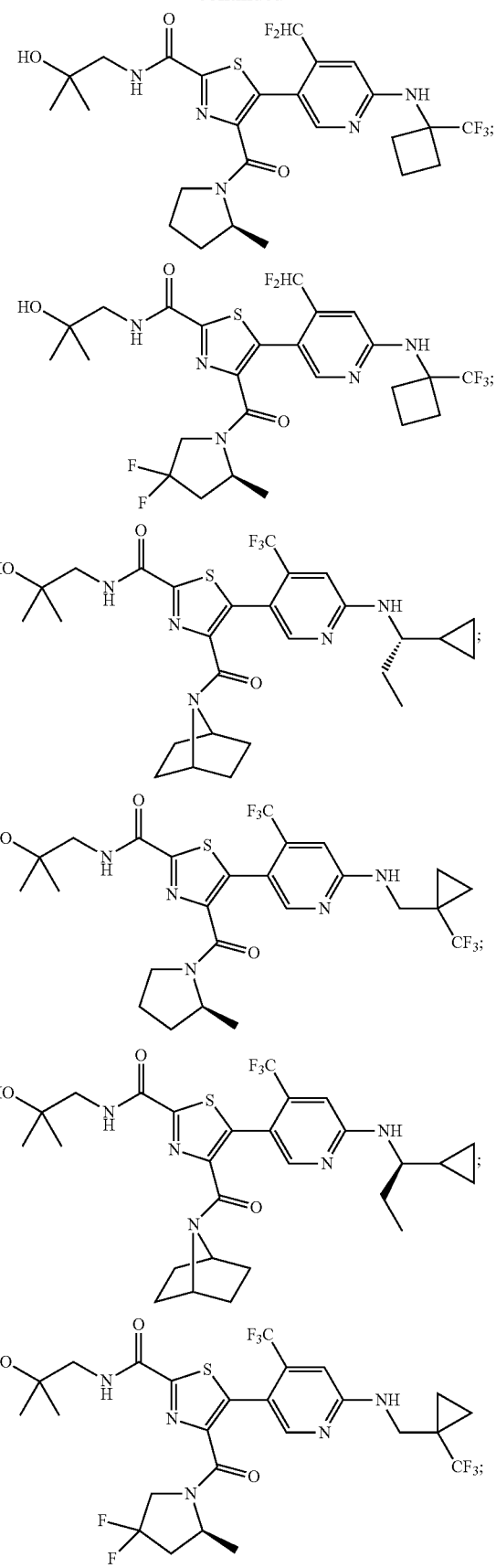

309
-continued
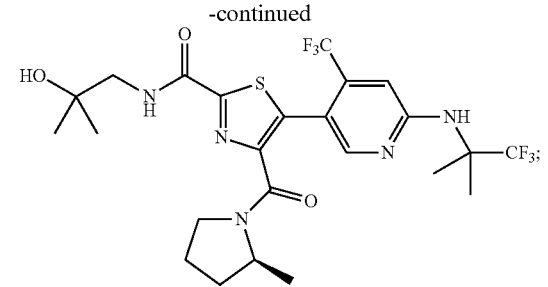
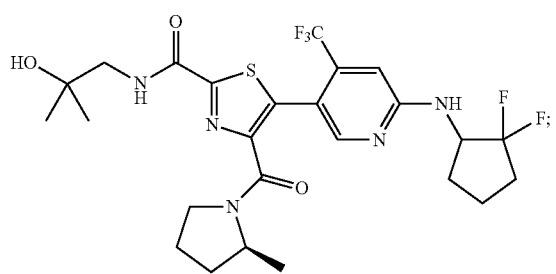
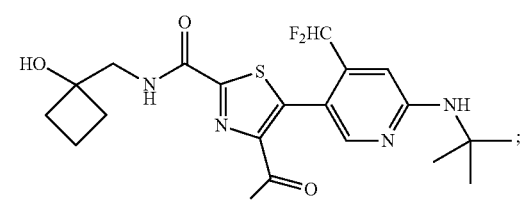
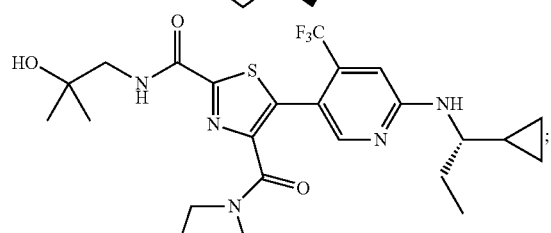
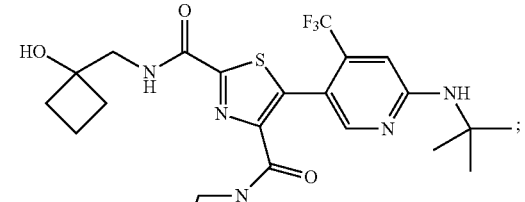
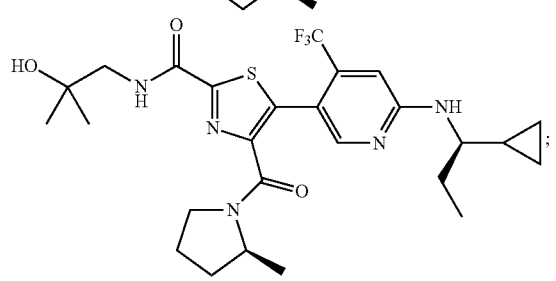
310
-continued
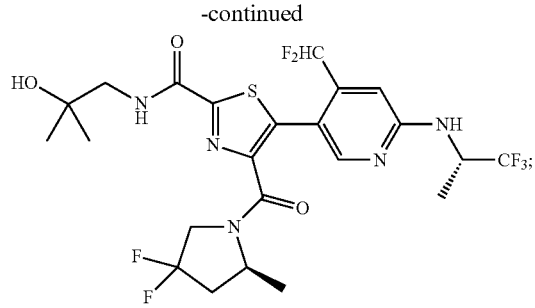
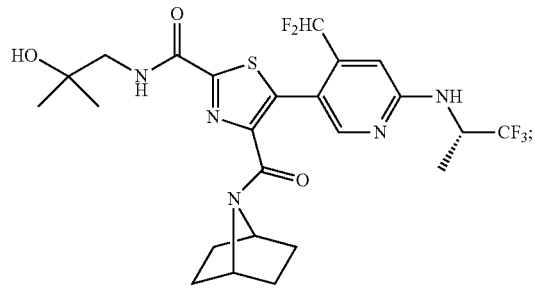
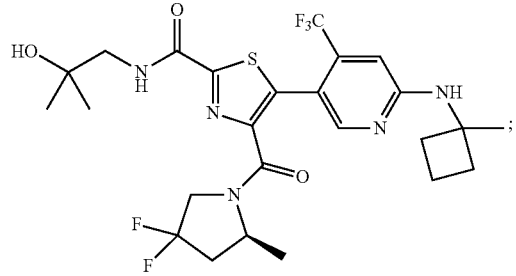
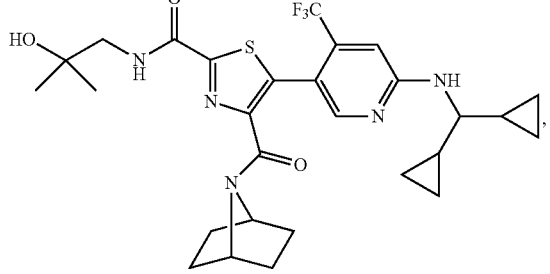
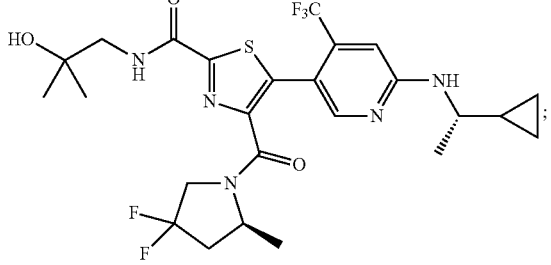
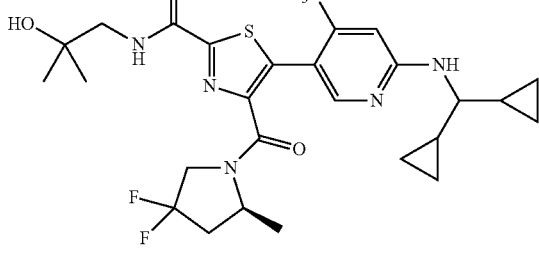

311
-continued
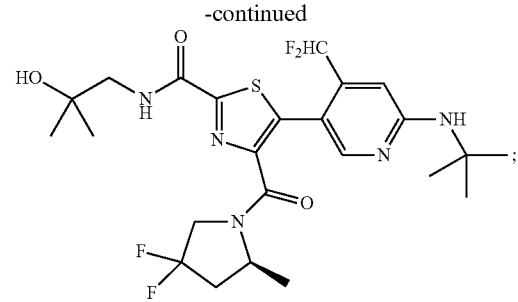
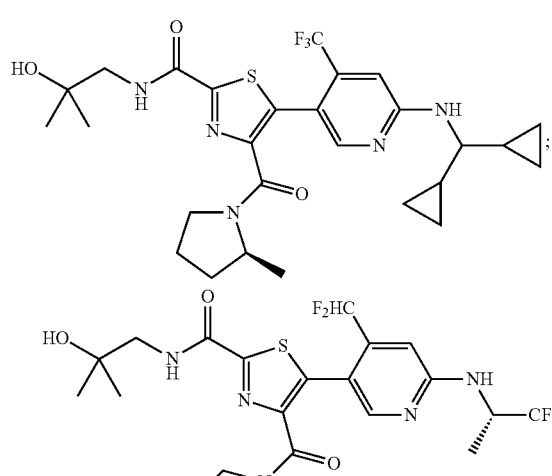
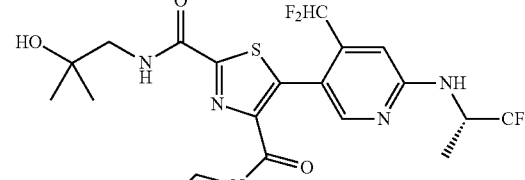
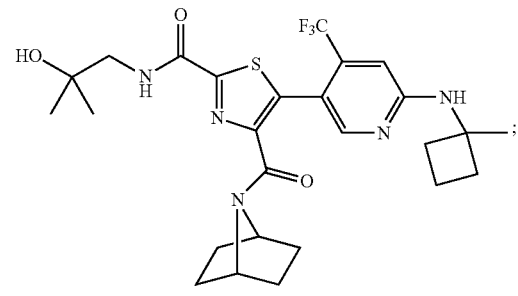
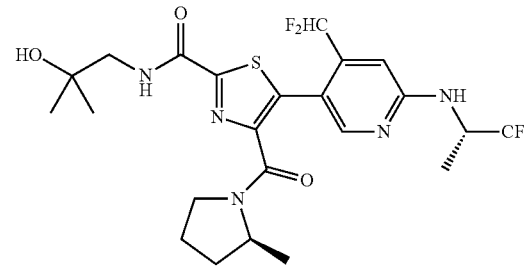
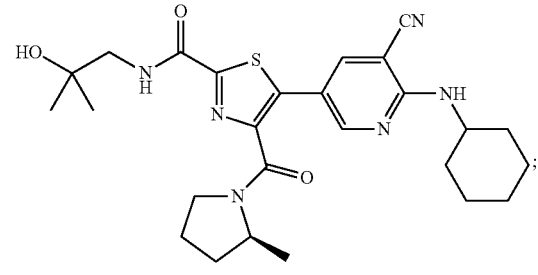
312
-continued
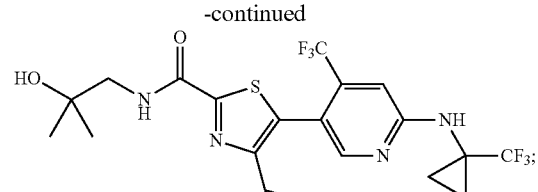
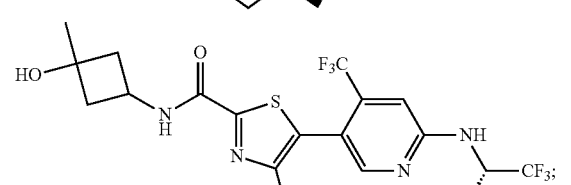
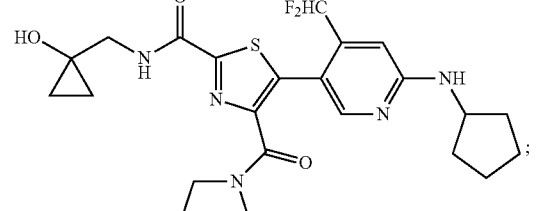
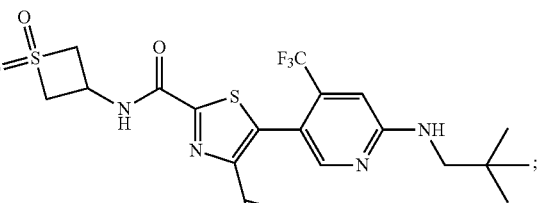
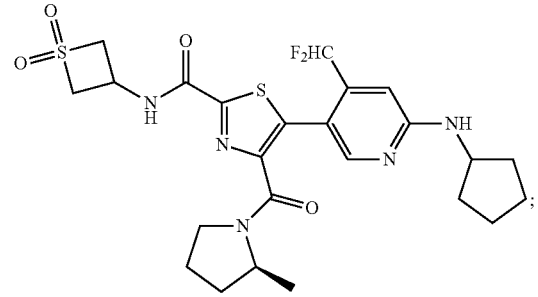
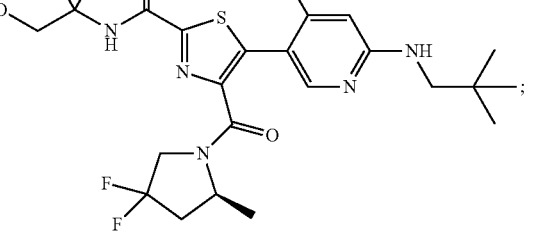

-continued
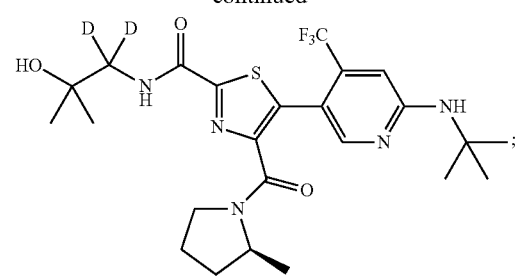
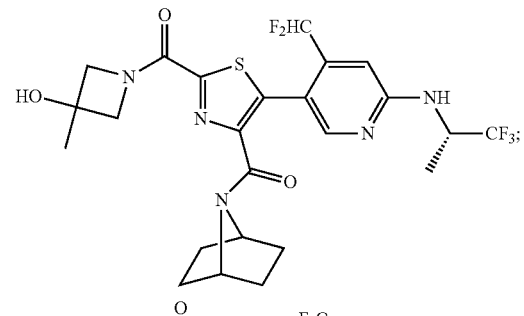
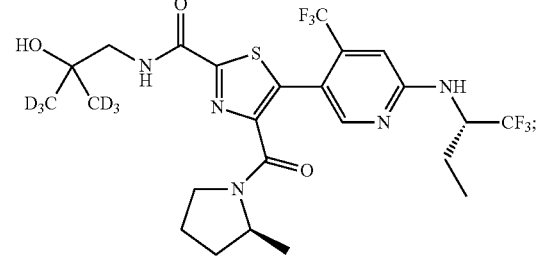
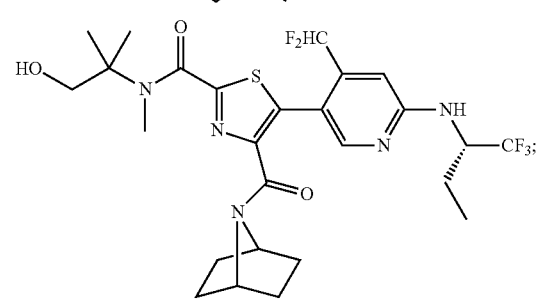
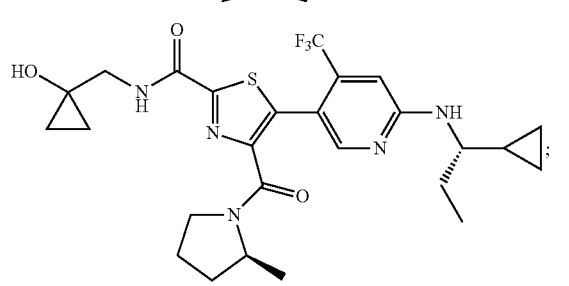
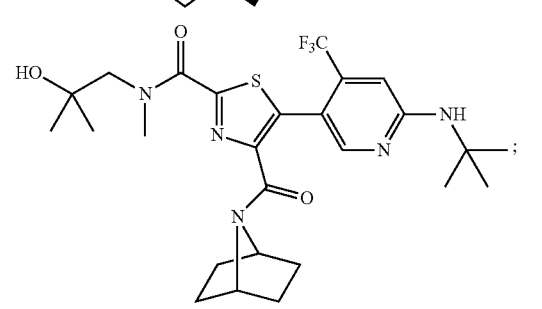
-continued
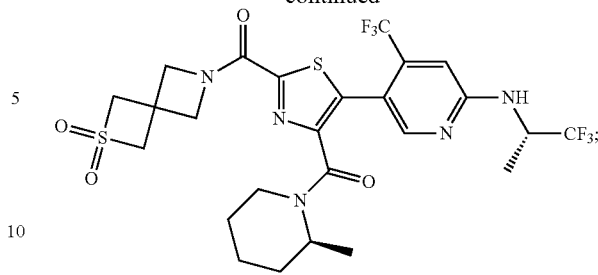
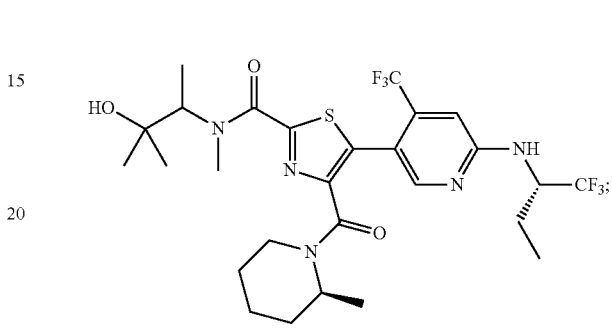
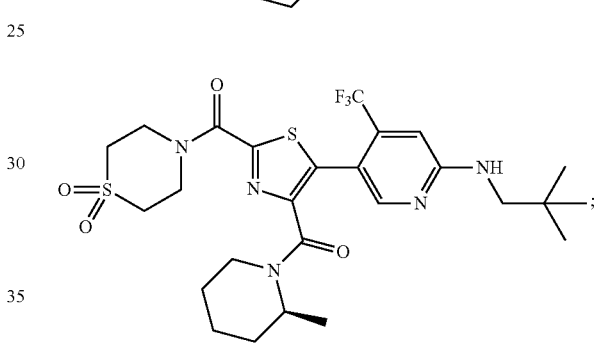
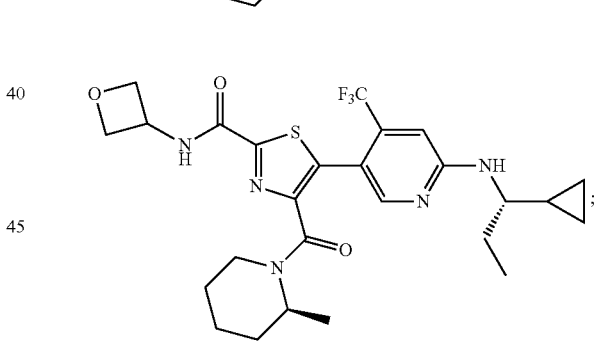
and pharmaceutically acceptable salts thereof.
Another embodiment of the invention is a compound selected from the group consisting of:
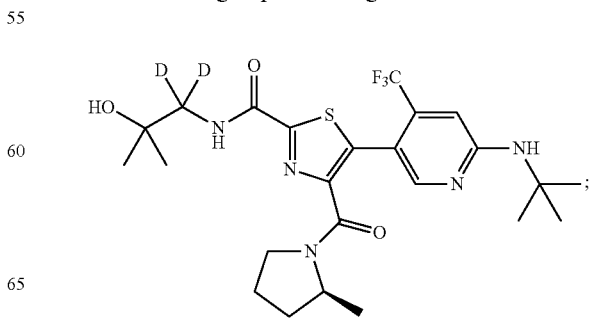

315
-continued
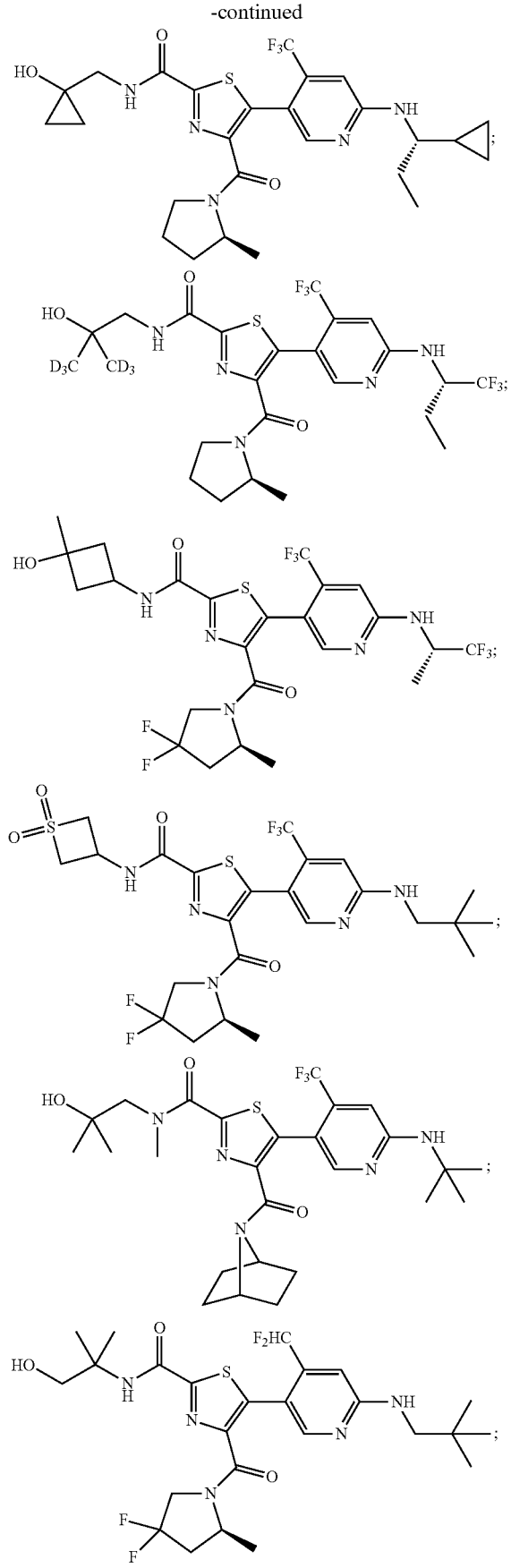
316
-continued
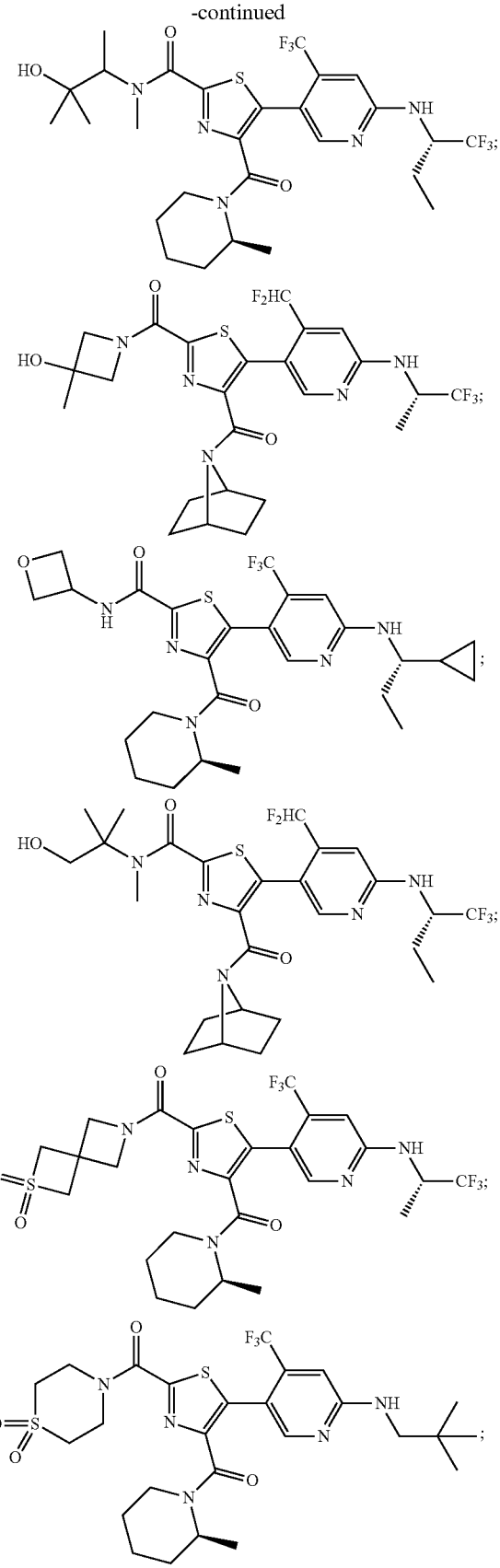
and pharmaceutically acceptable salts thereof.

Another embodiment of the invention is a compound selected from the group consisting of:
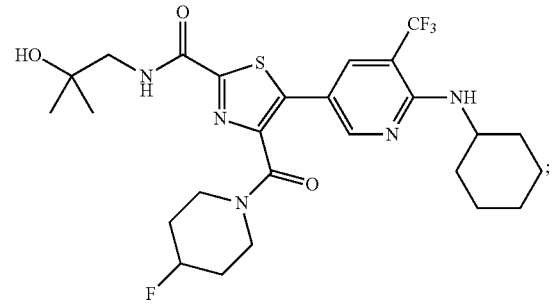
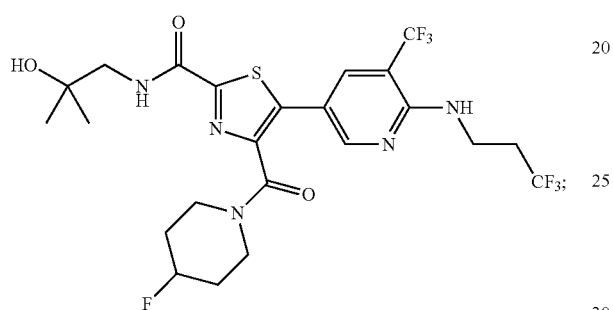
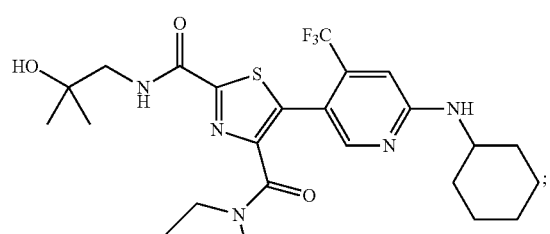
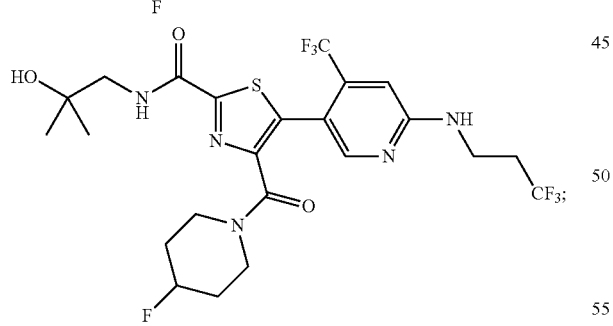
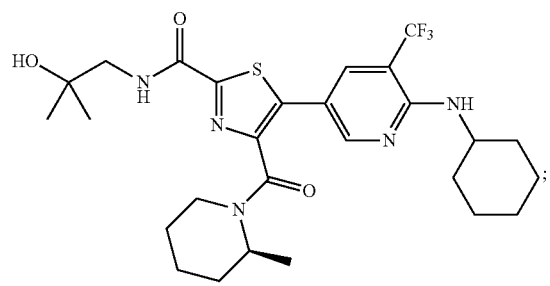
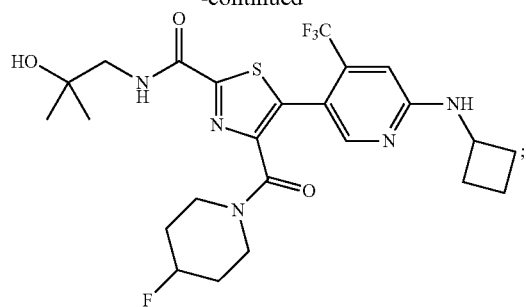
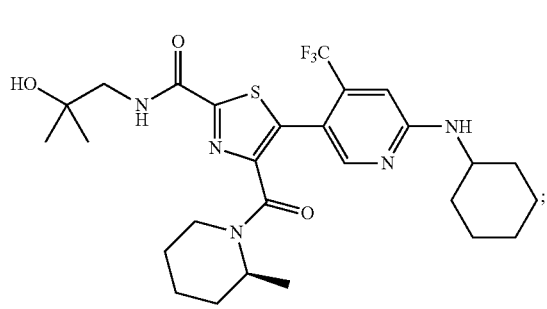
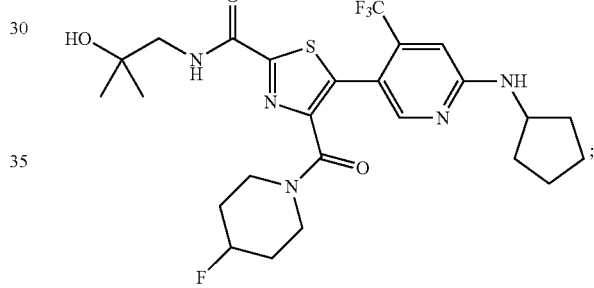
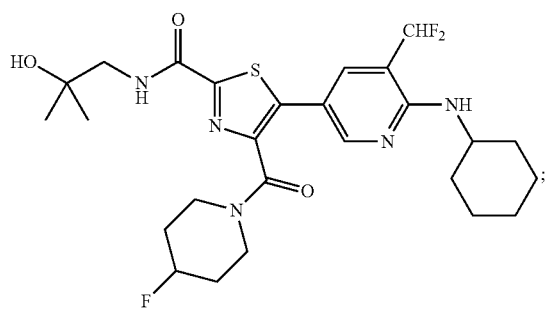
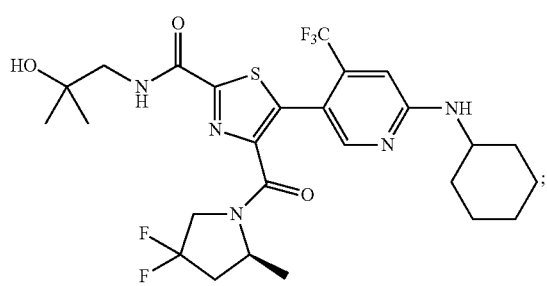

319
-continued
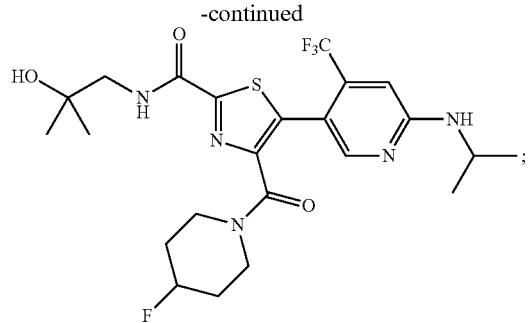
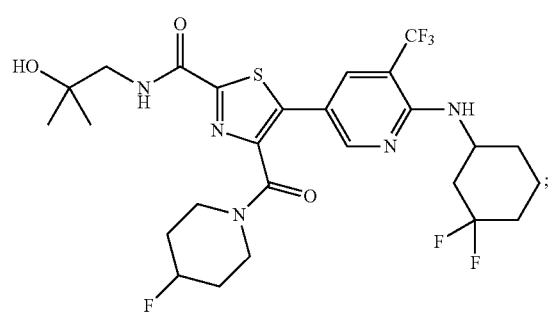
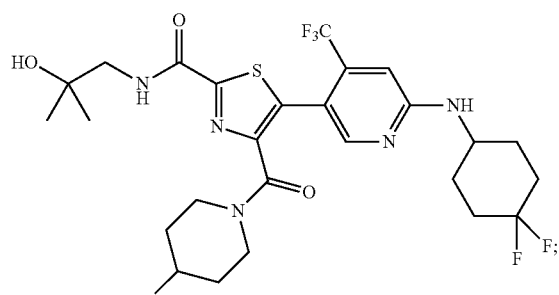
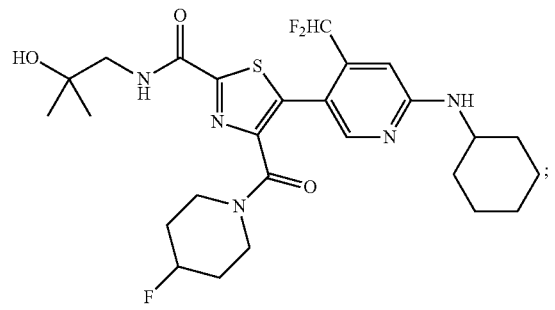
320
-continued
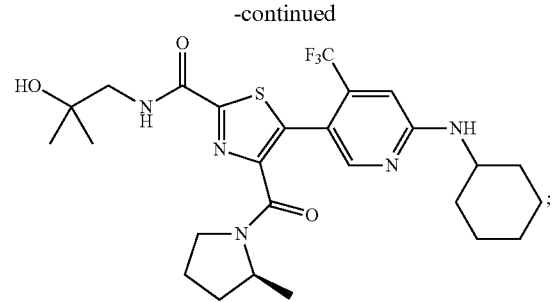
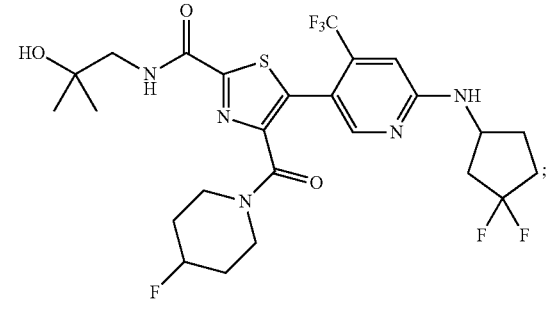
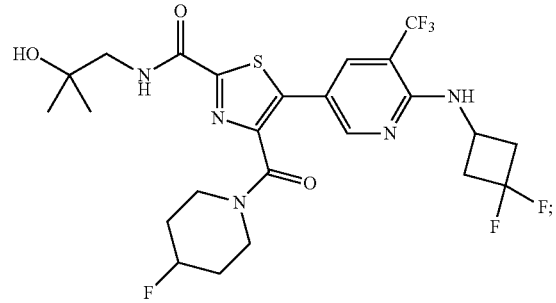
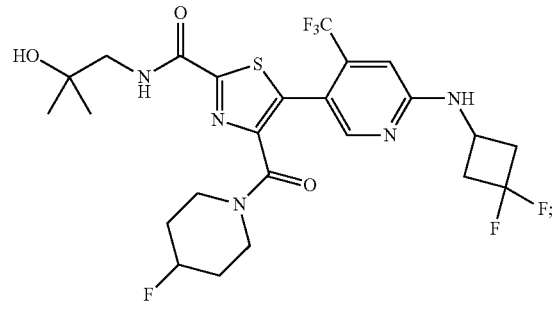

321
-continued
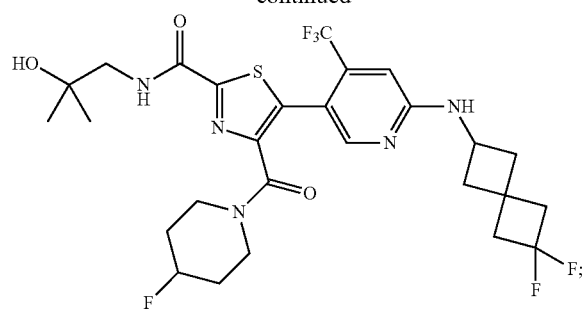
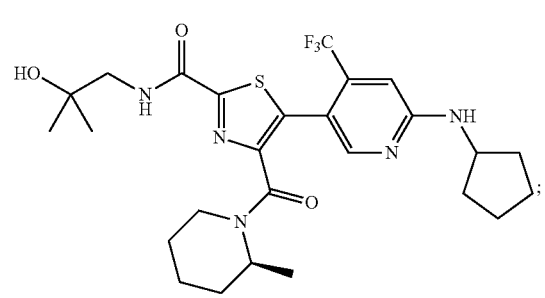
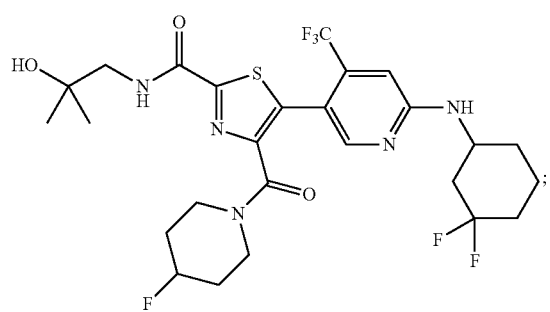
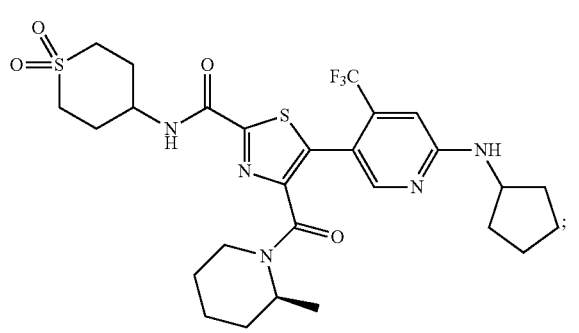
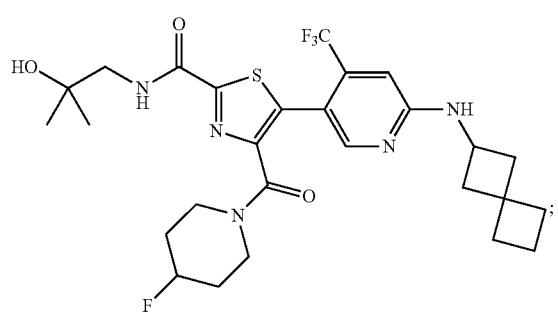
322
-continued
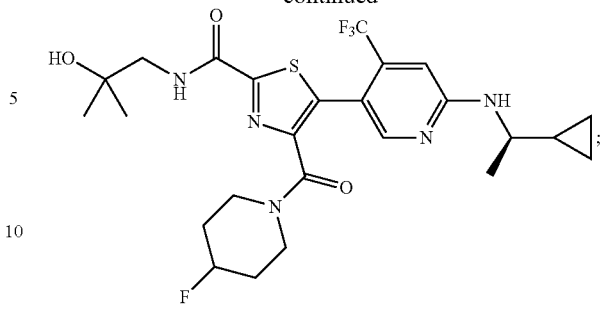
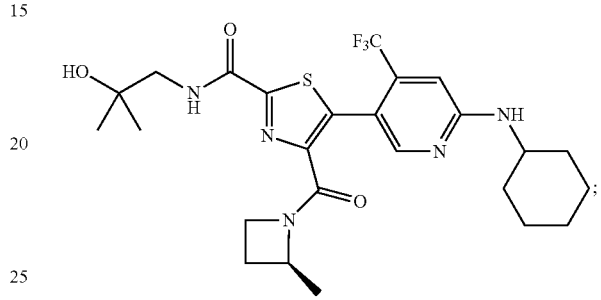
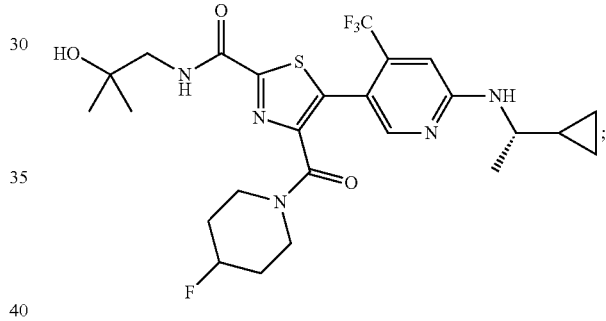
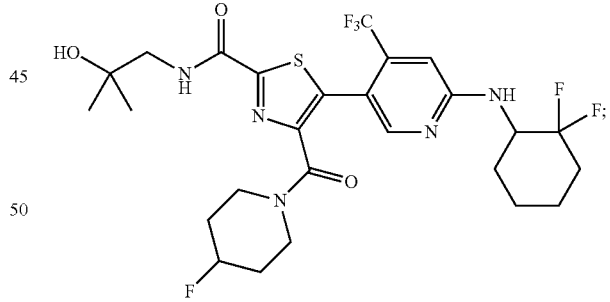
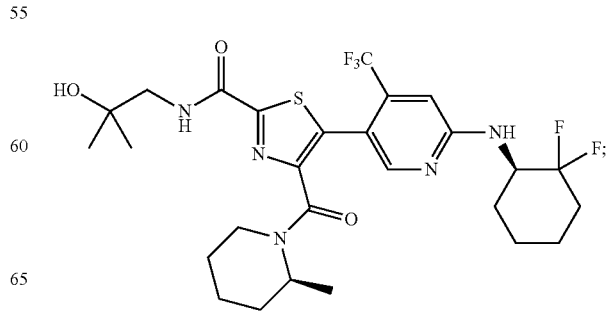

323
-continued
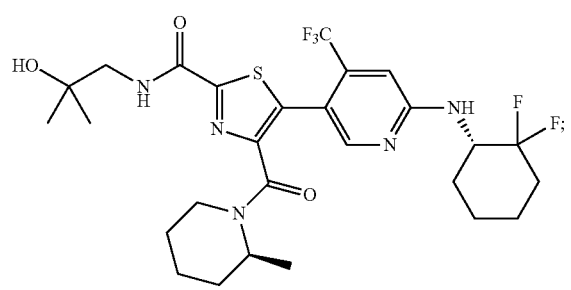
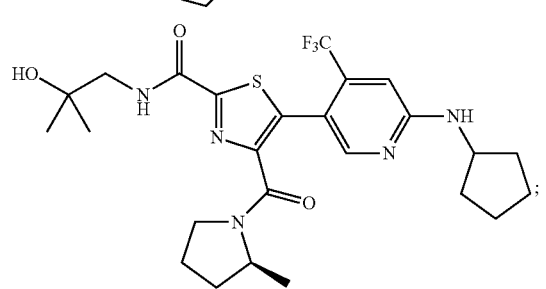
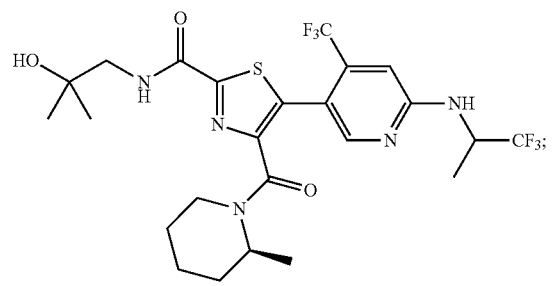
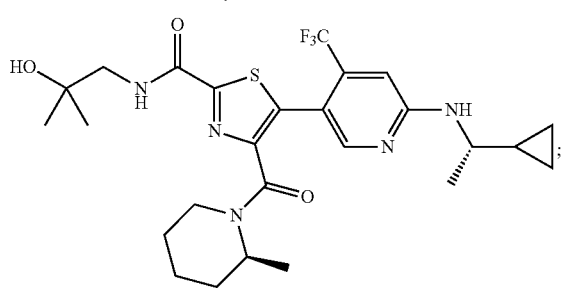
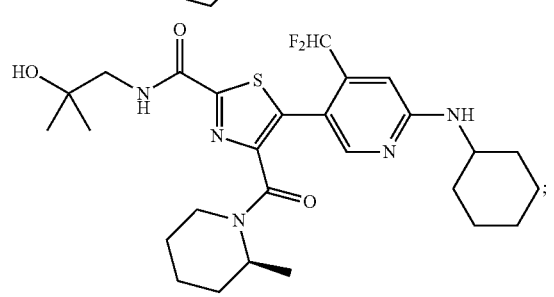
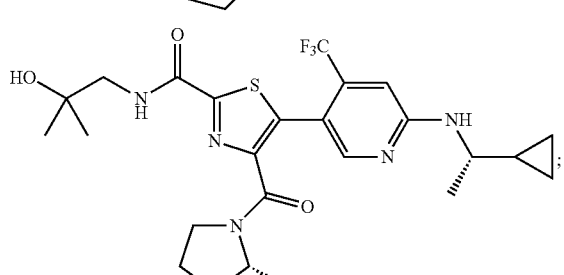
324
-continued
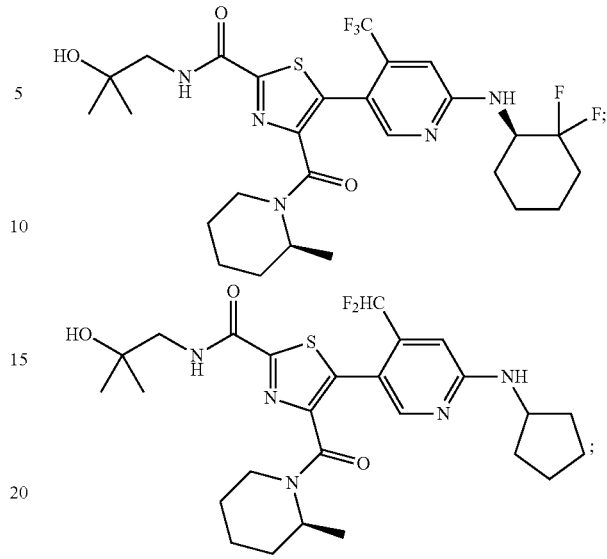
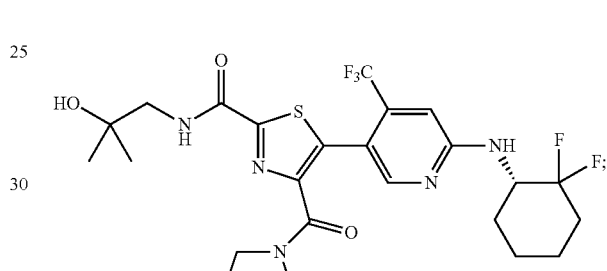
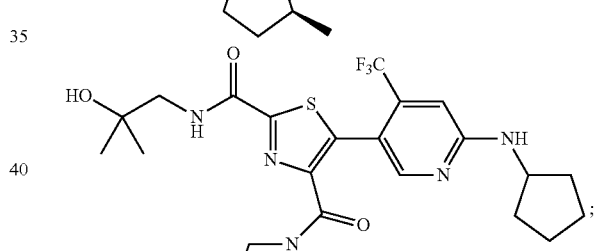
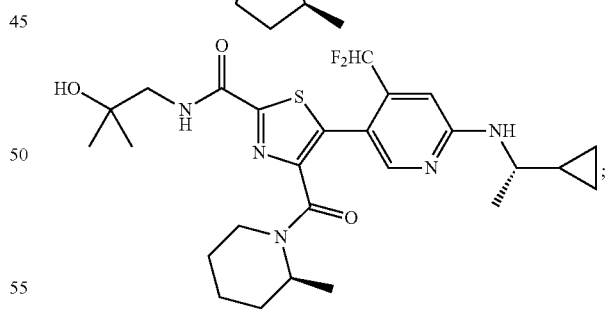
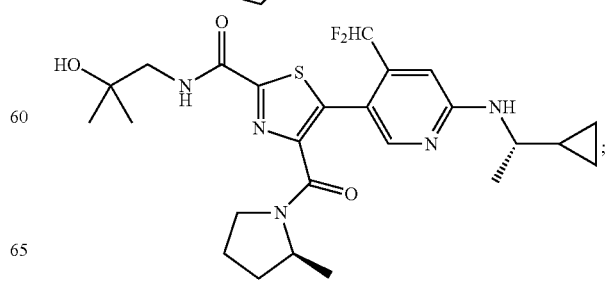

325
-continued
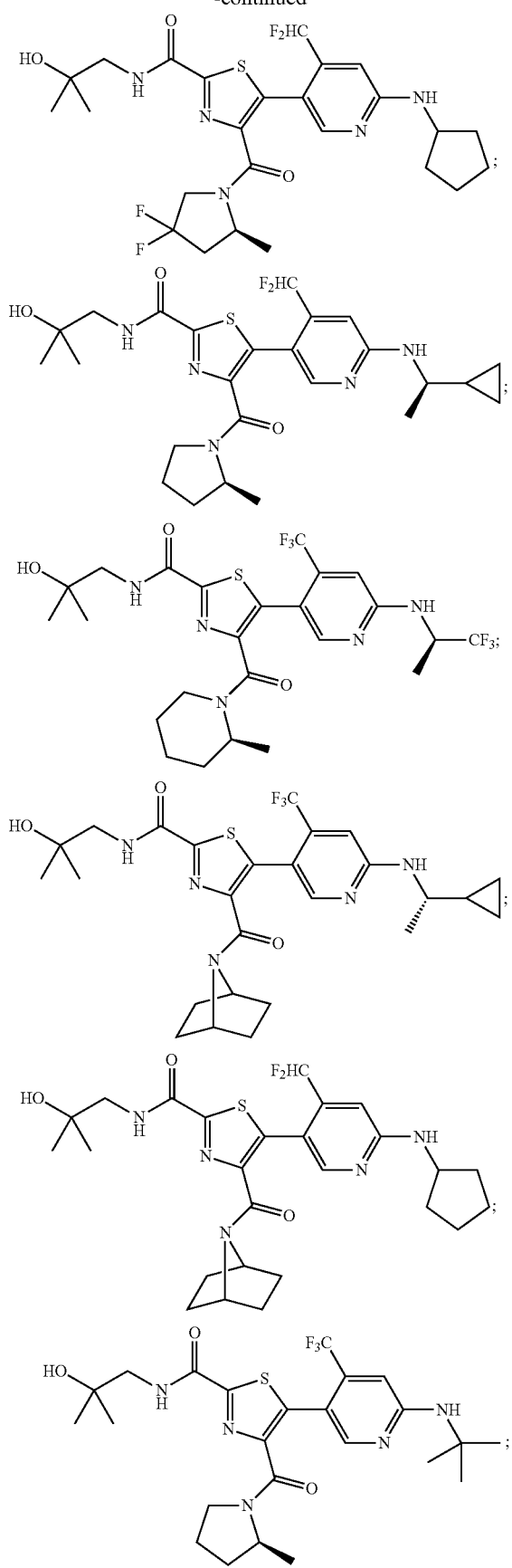
326
-continued
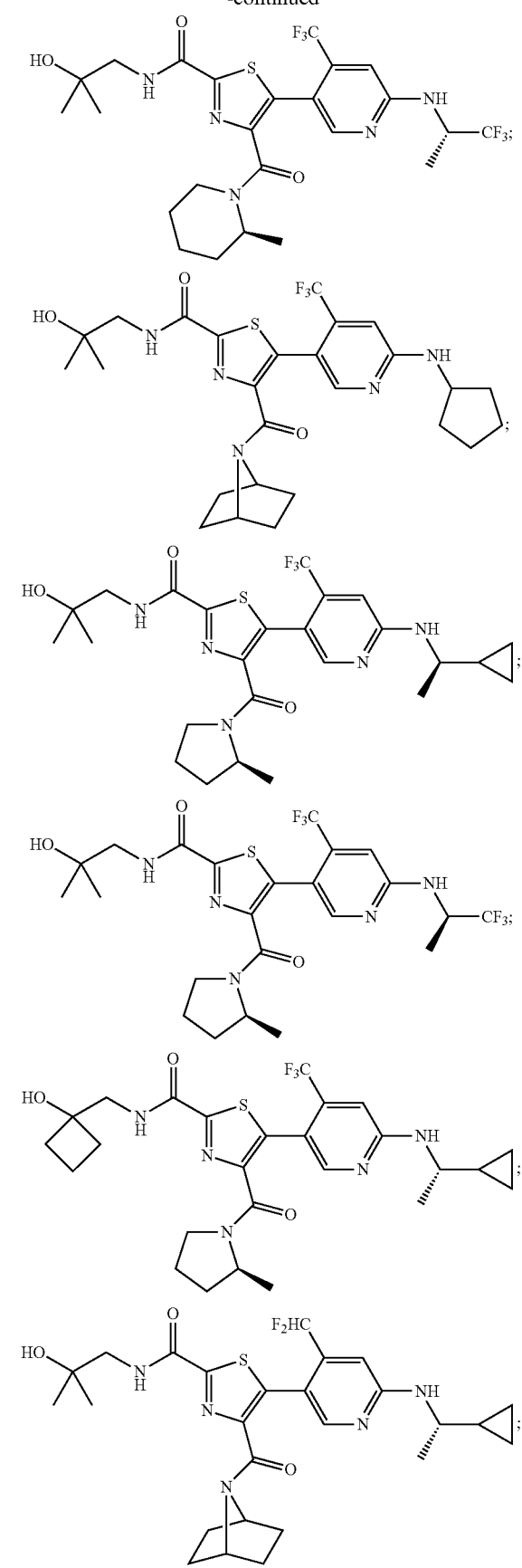

327
-continued
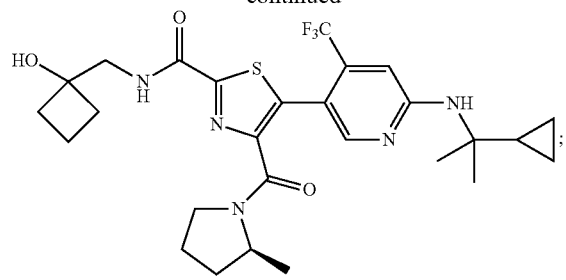
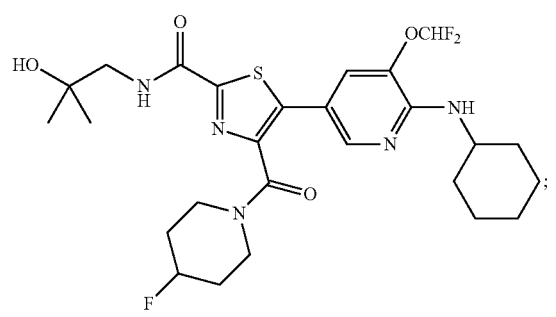
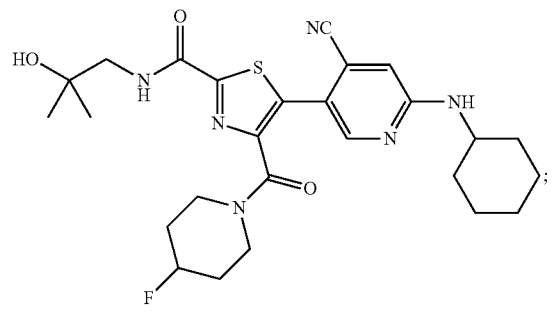
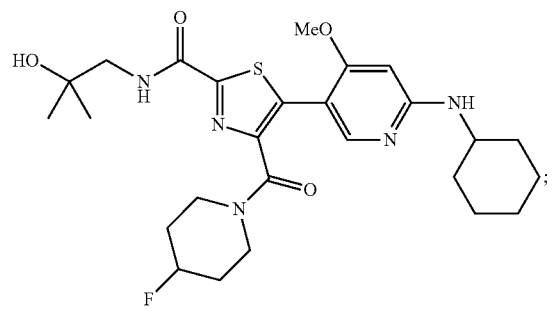
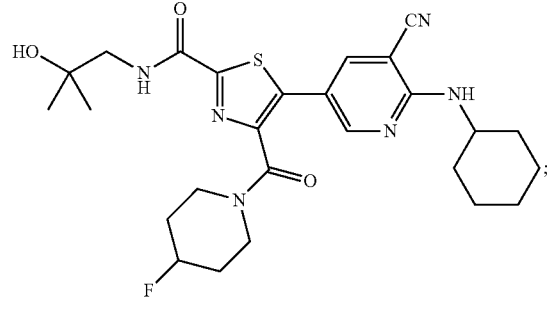
328
-continued
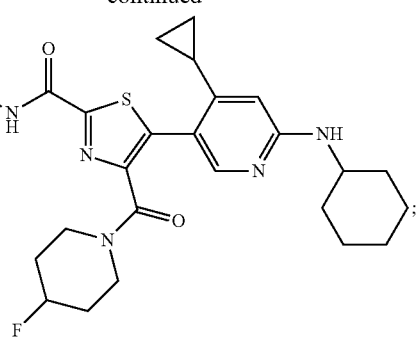
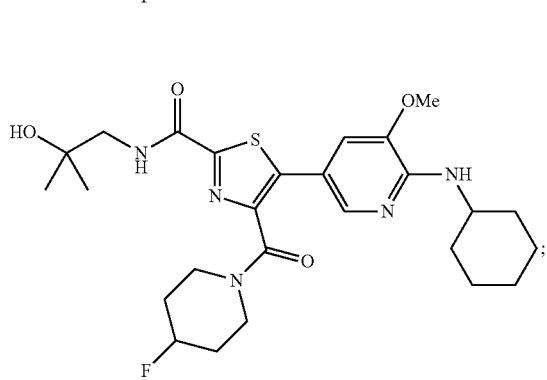
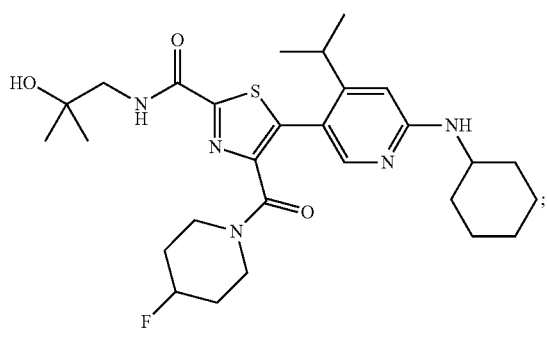
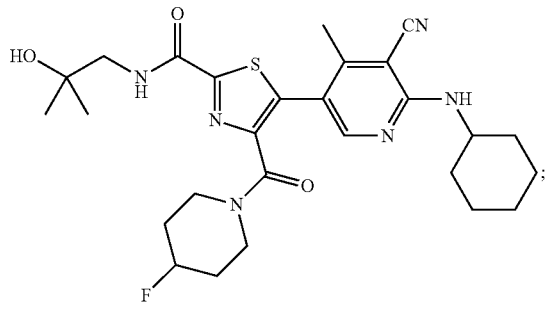
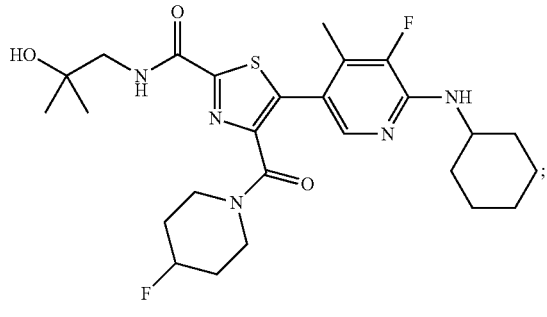

329
-continued
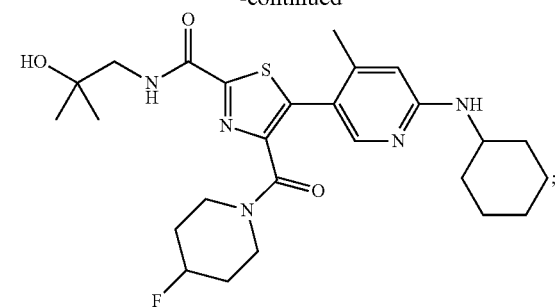
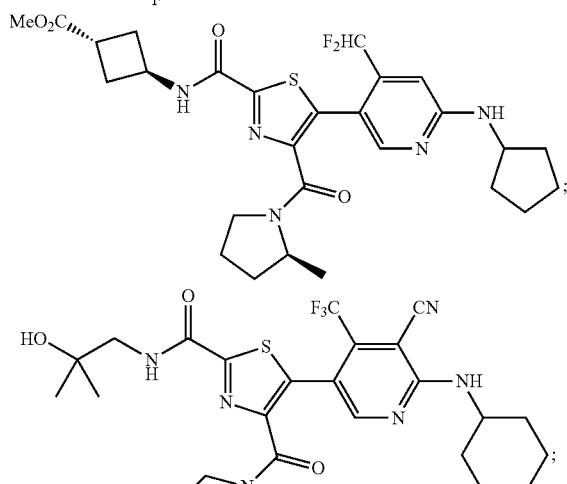
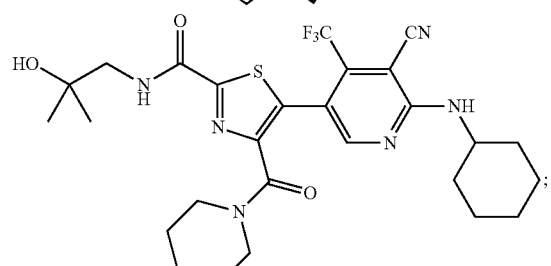
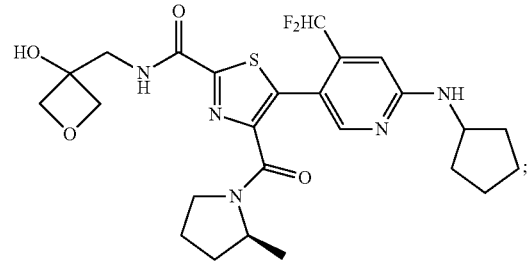
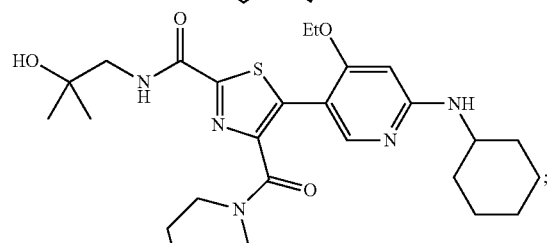
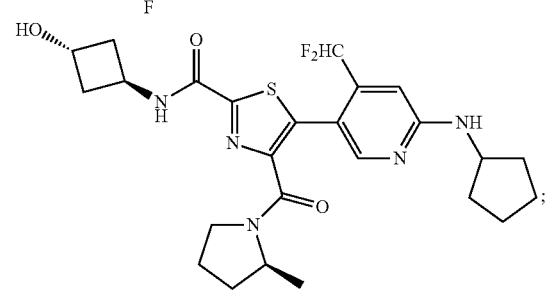
330
-continued
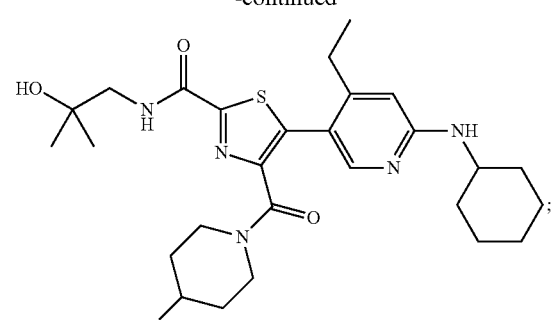
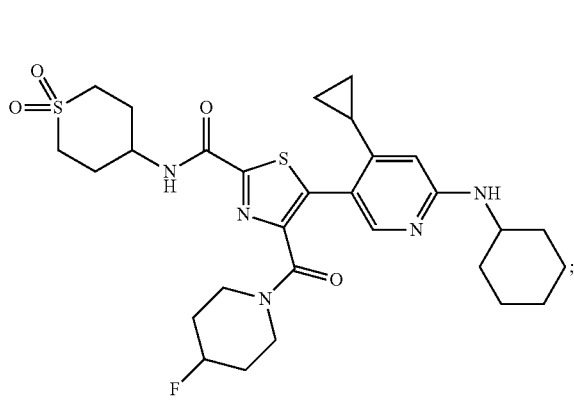
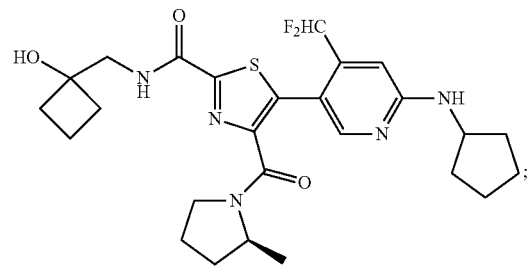
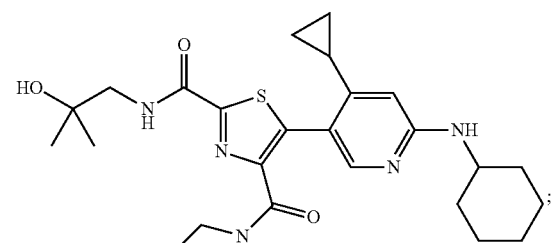
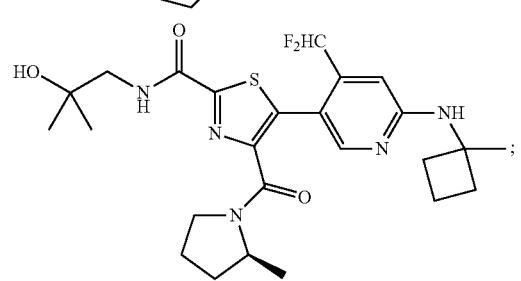

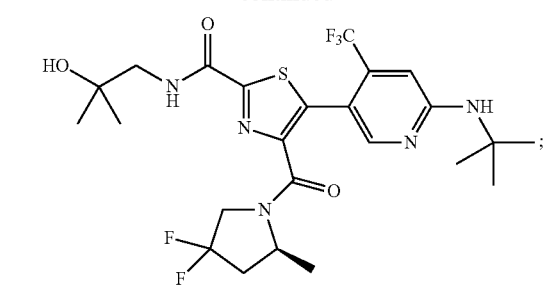
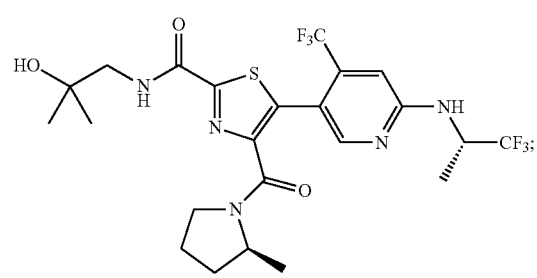
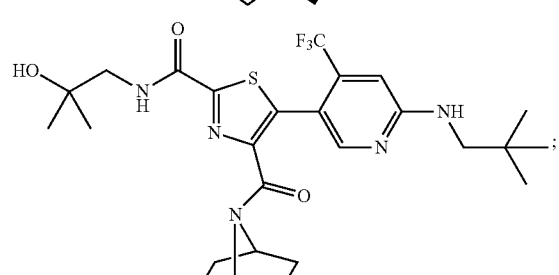
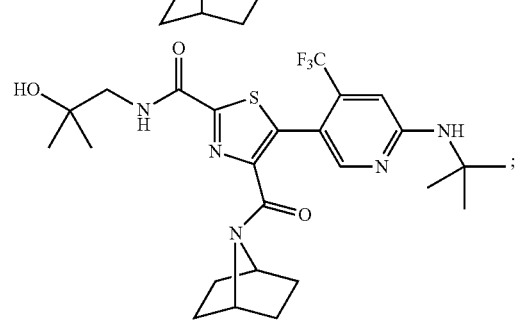
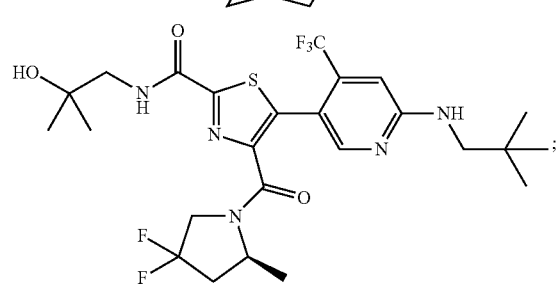
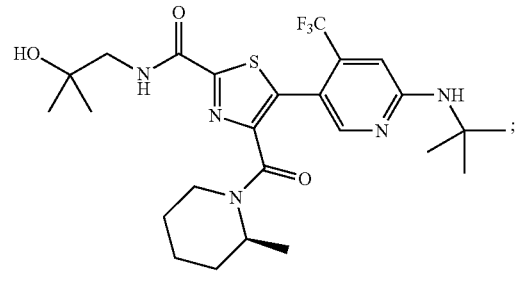
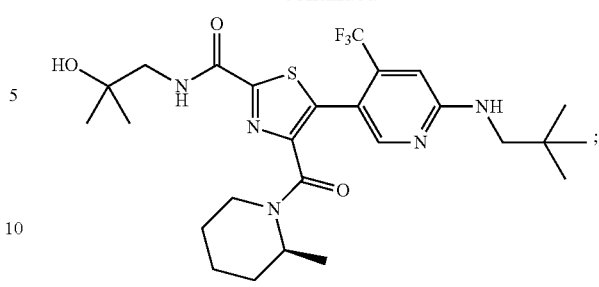
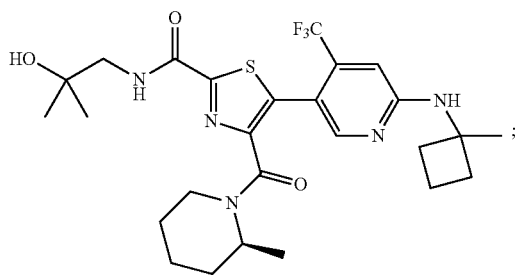
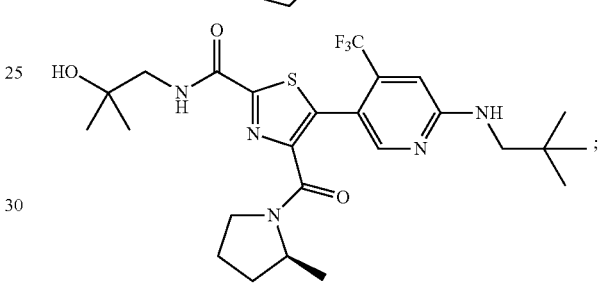
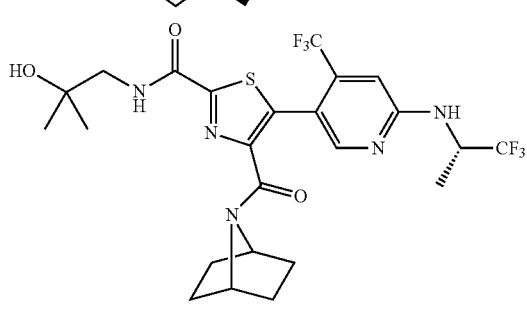
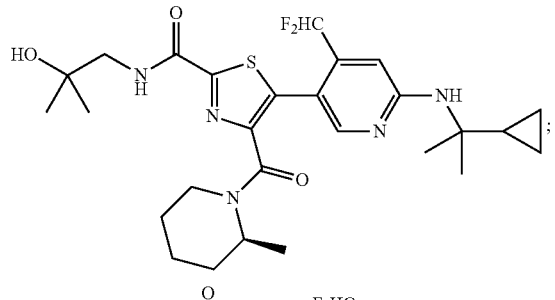
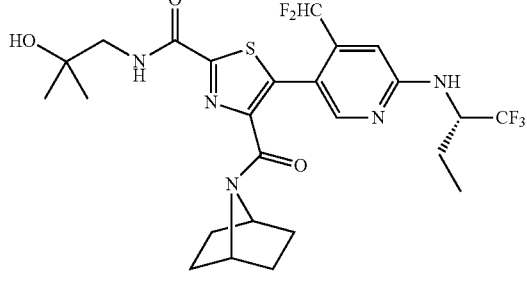

333
-continued
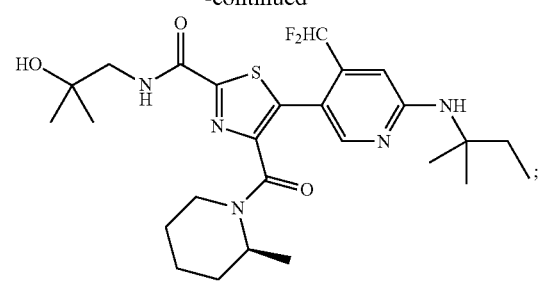
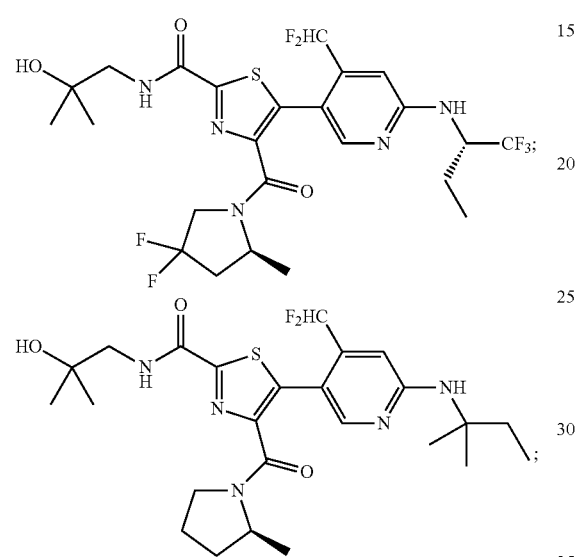
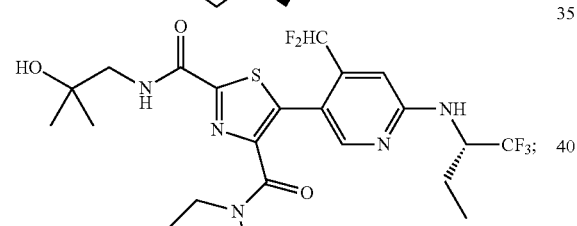
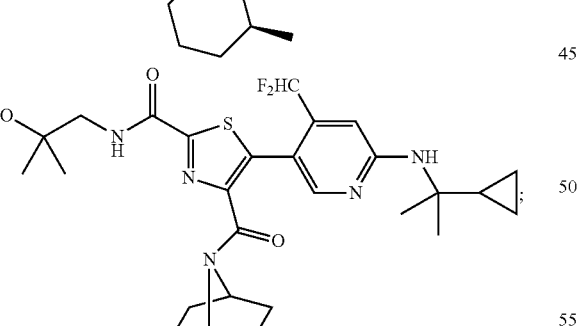
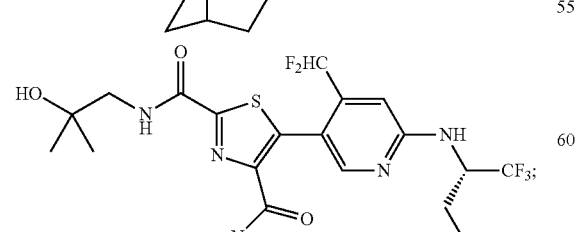
334
-continued
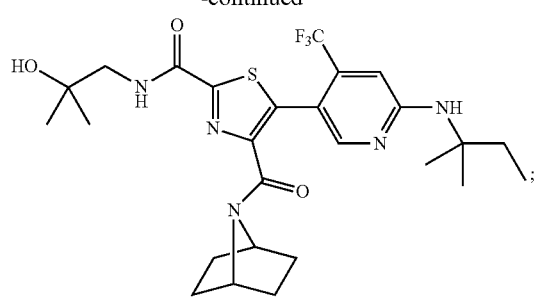
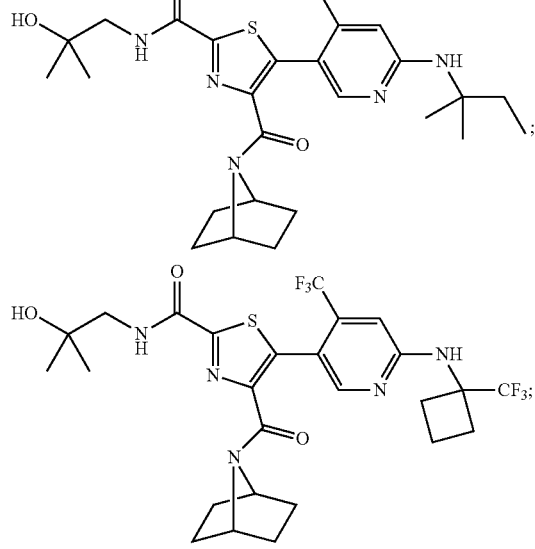
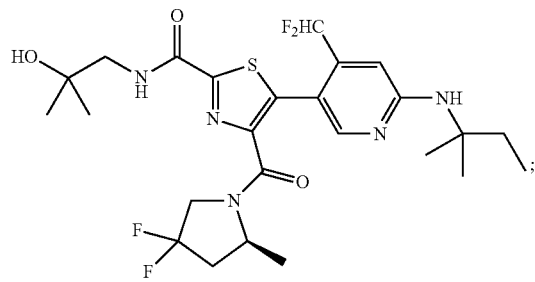
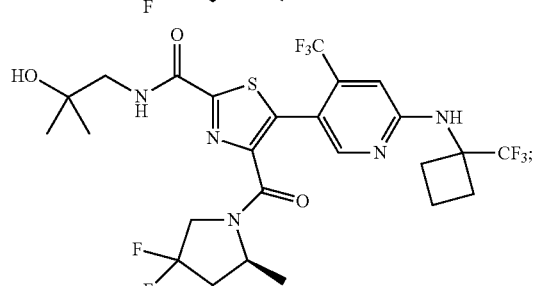
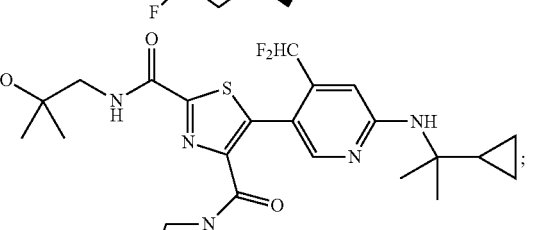
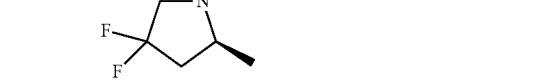

335
-continued
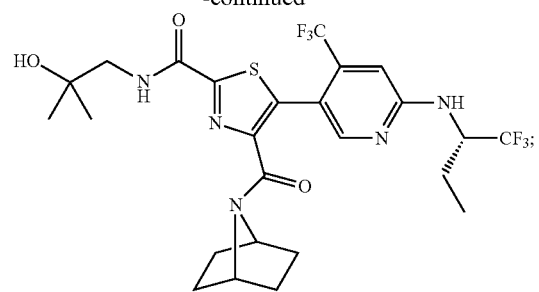
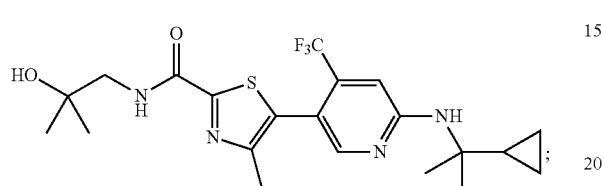
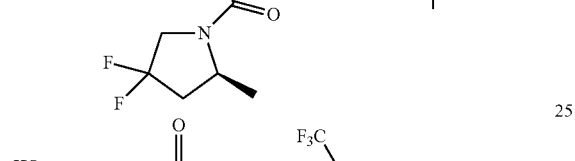
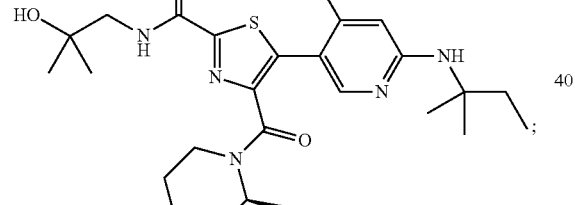
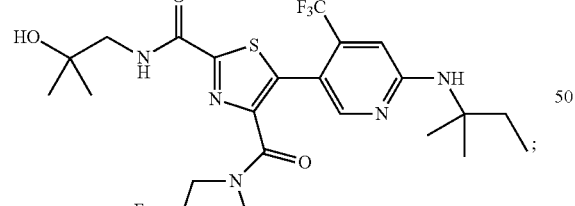
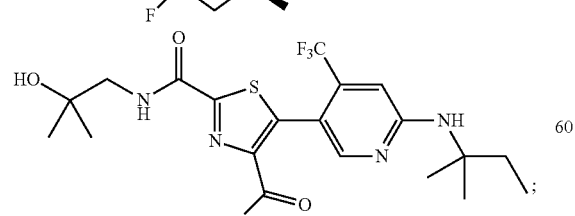
336
-continued
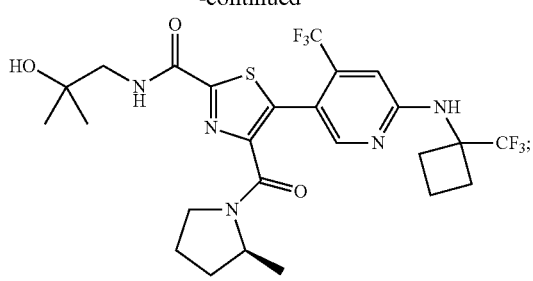
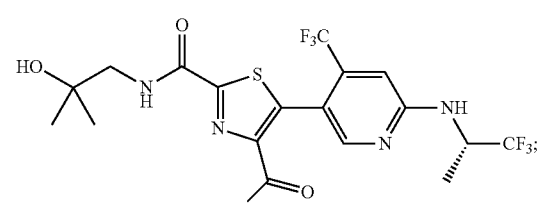
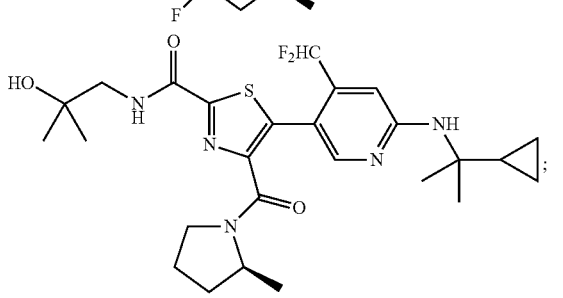

-continued
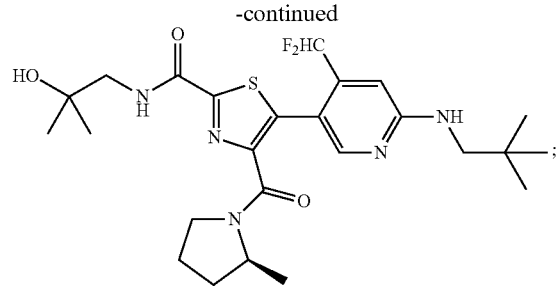
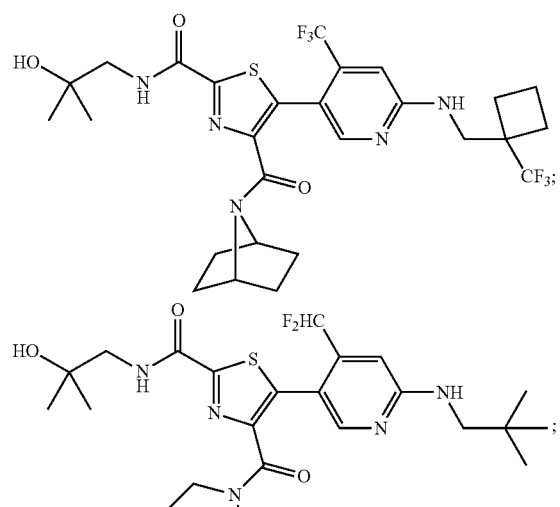
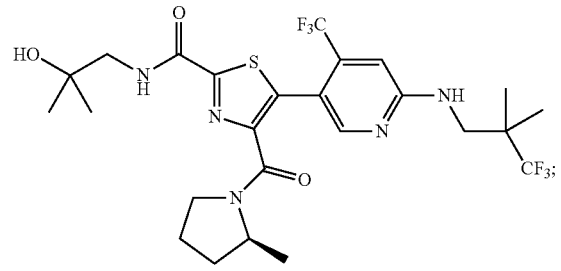
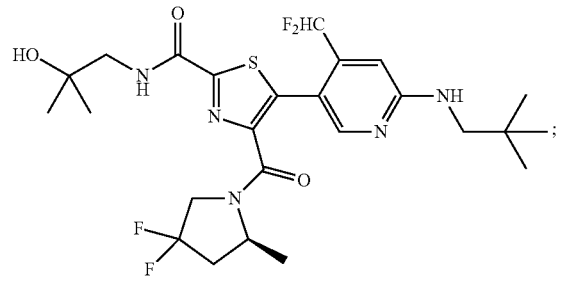
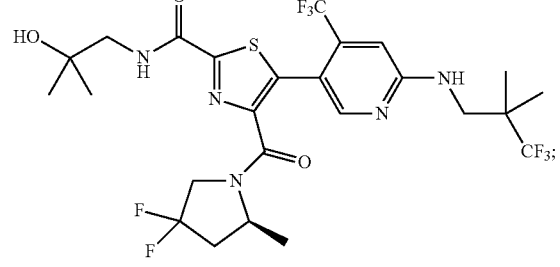
-continued
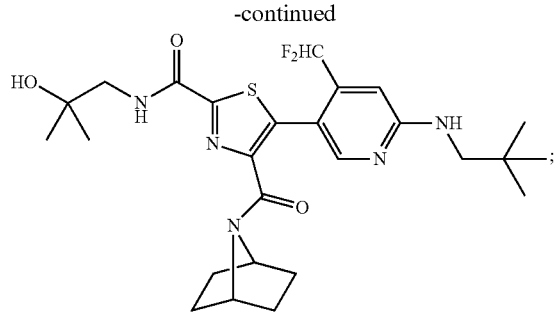
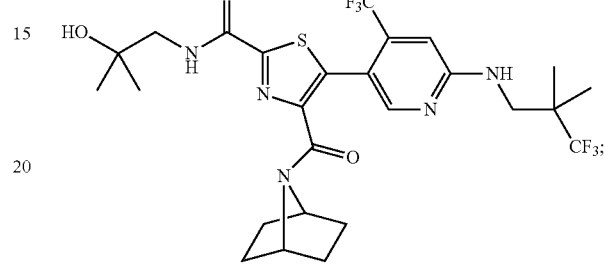
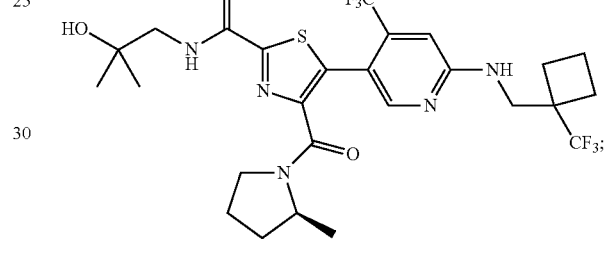

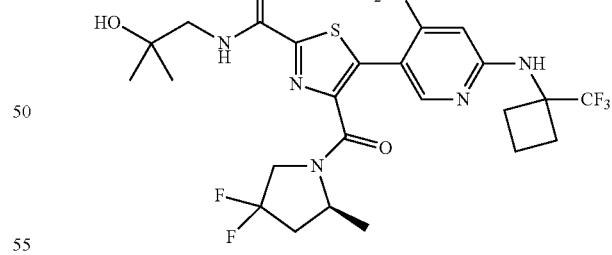
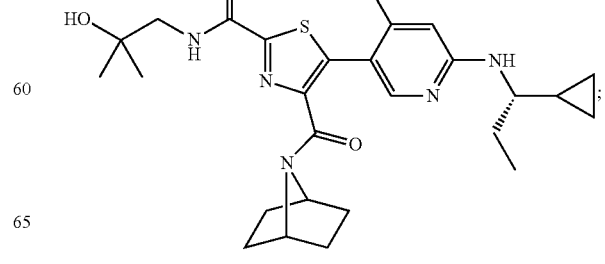

339
-continued
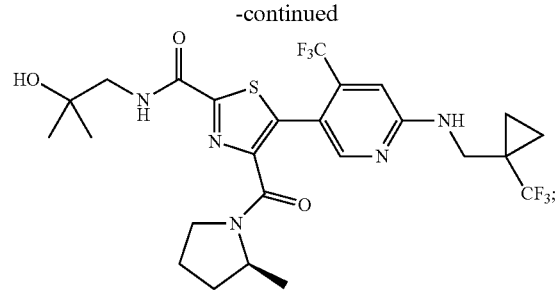
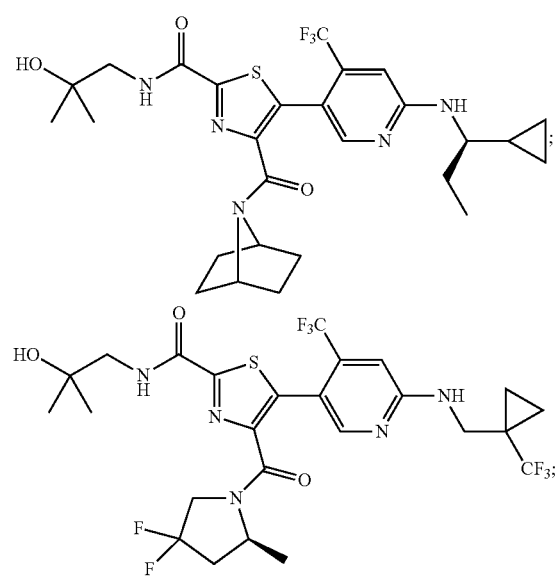
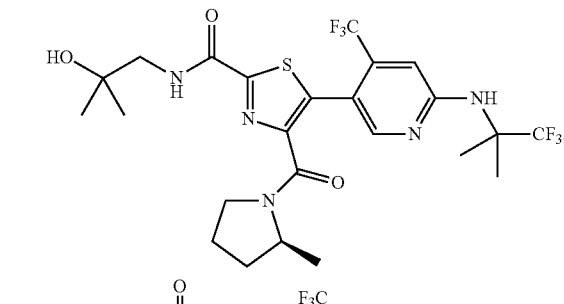
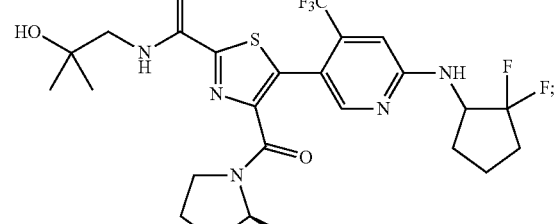
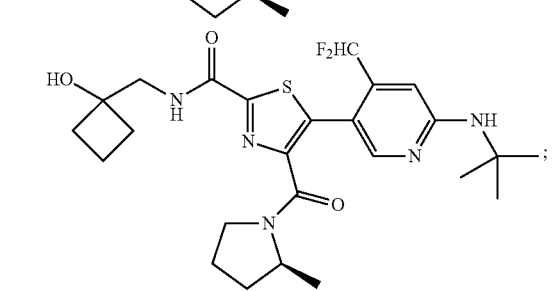
340
-continued
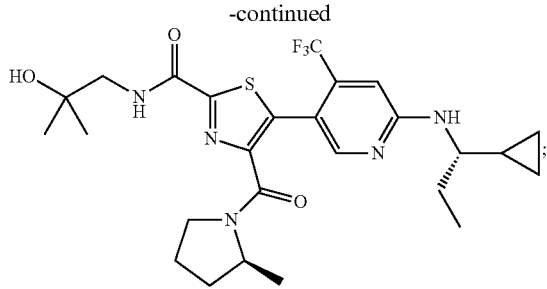
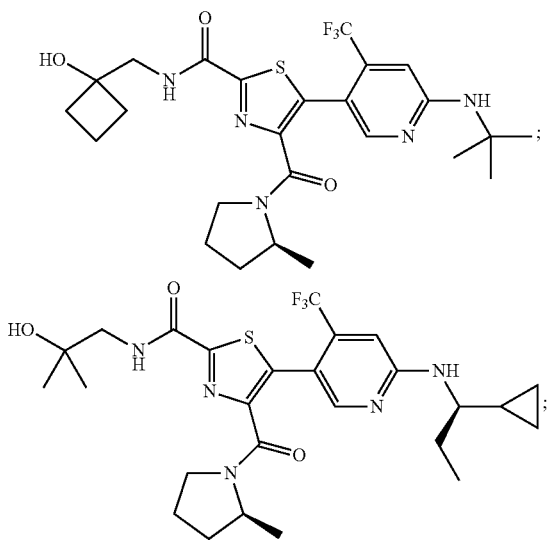
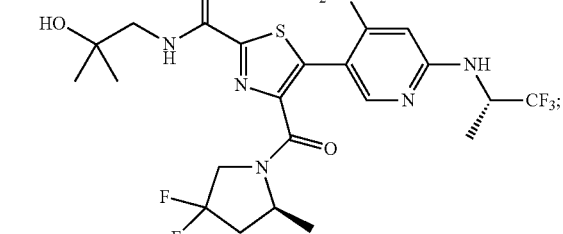
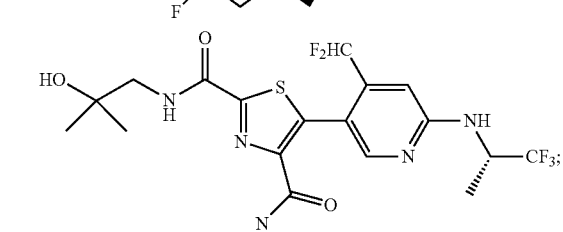
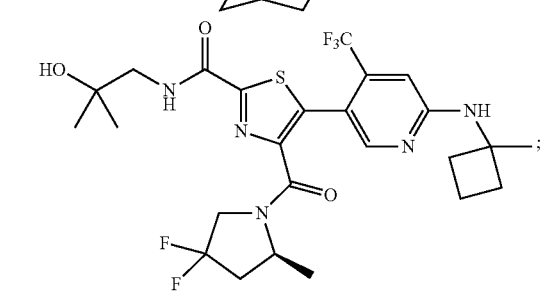

341
-continued
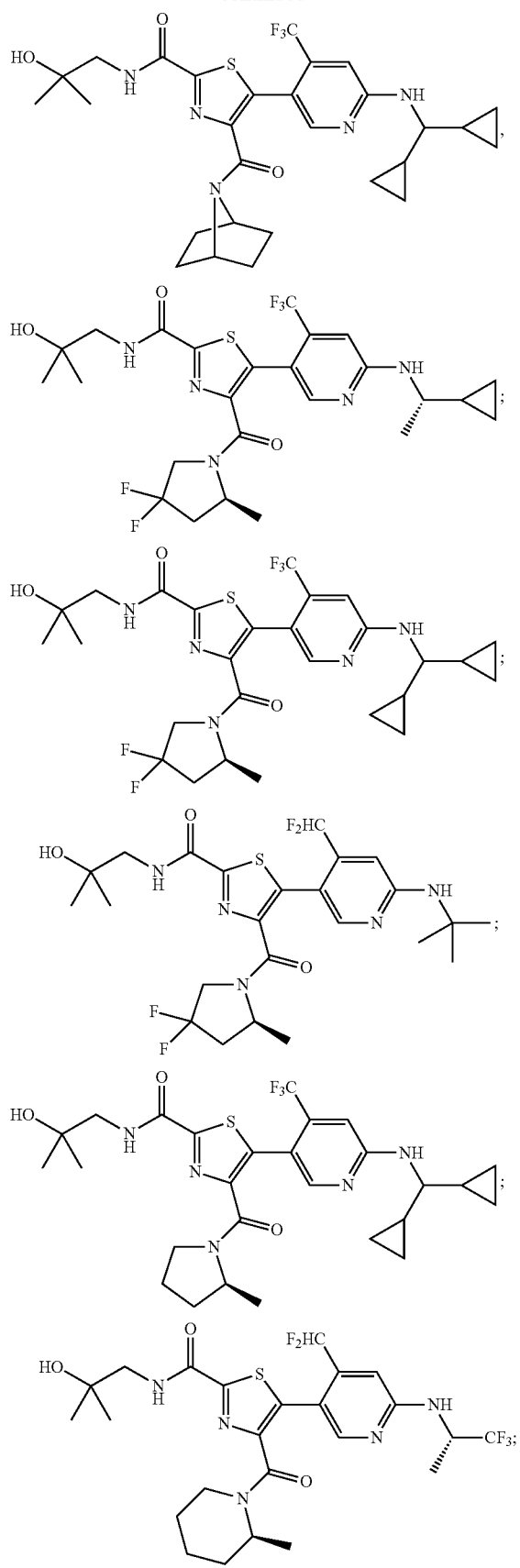
342
-continued
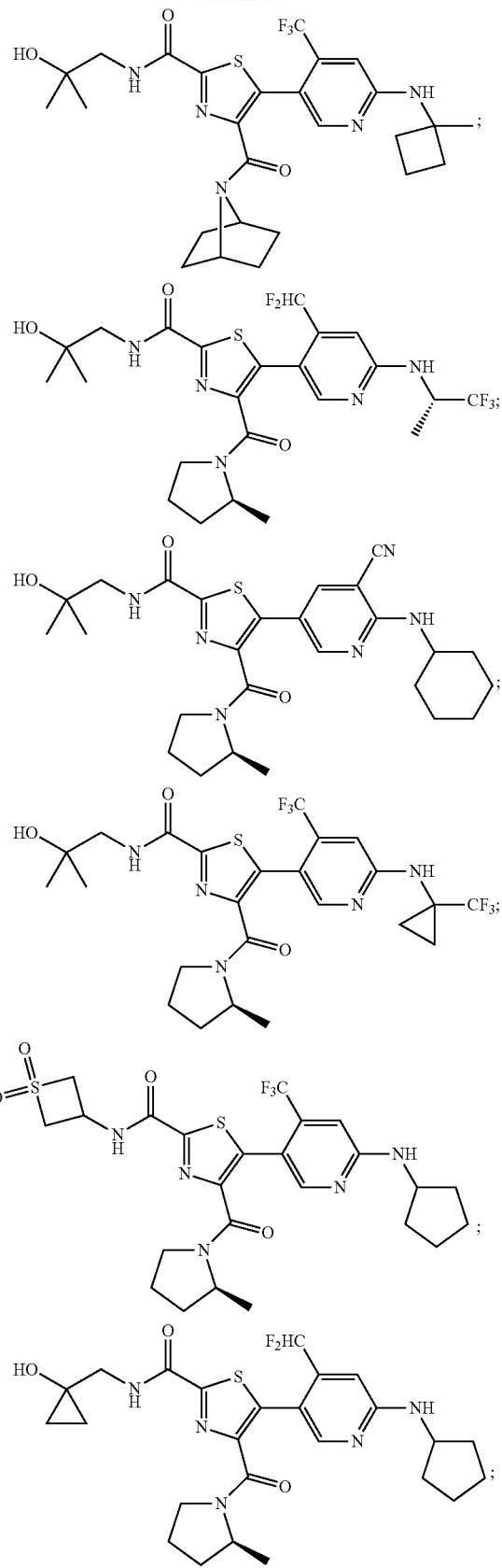
and pharmaceutically acceptable salts thereof.

Another embodiment of the invention is a compound selected from the group consisting of:
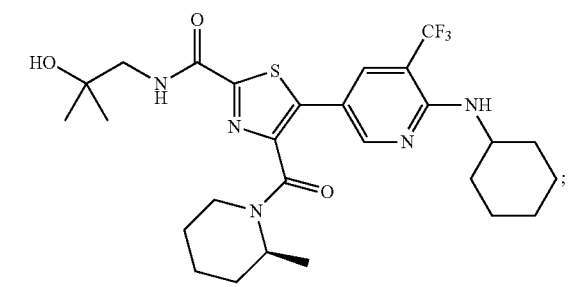;
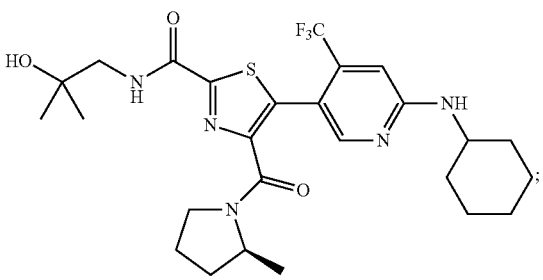;
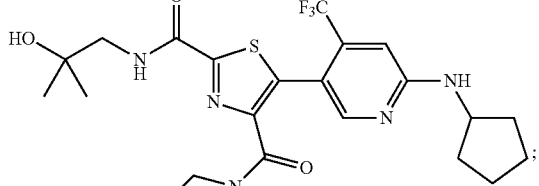;
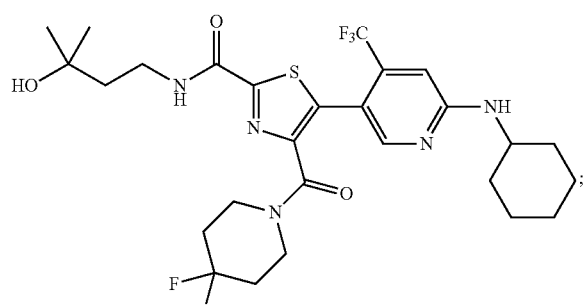;
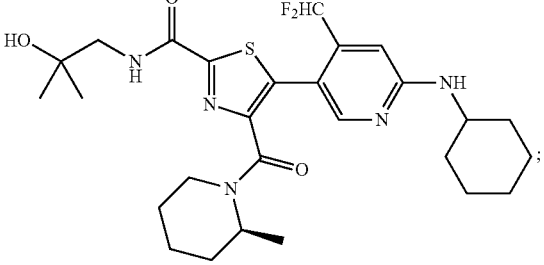;
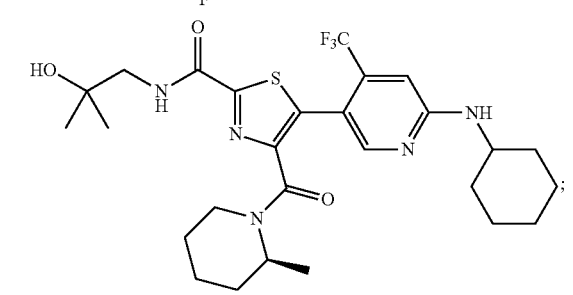;
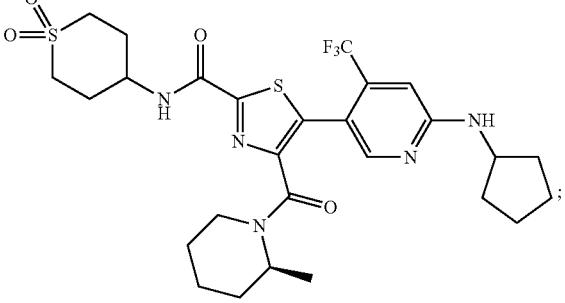;
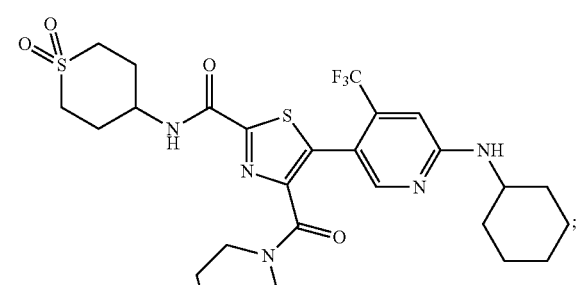;
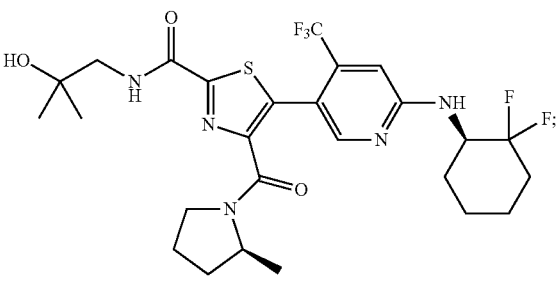;
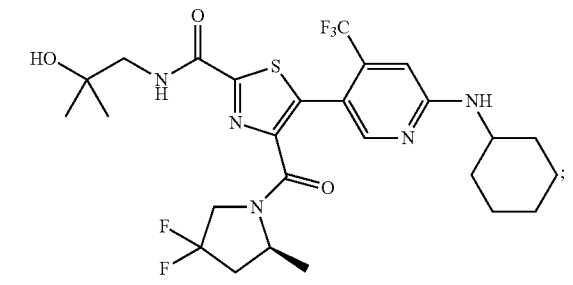;

345
-continued
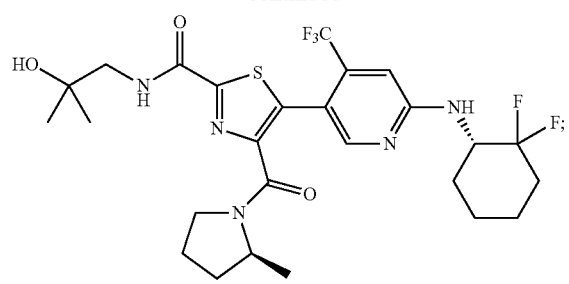
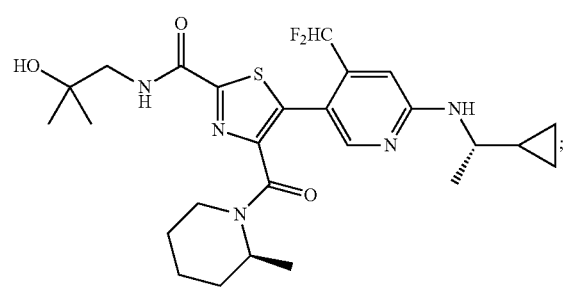
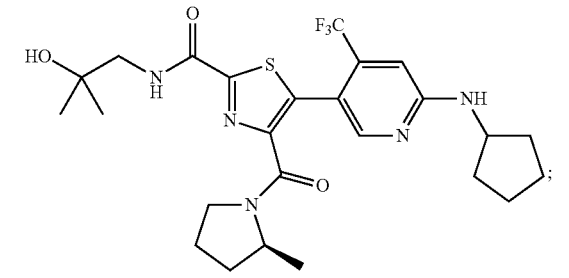
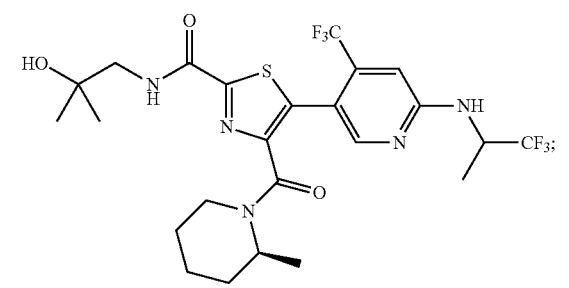
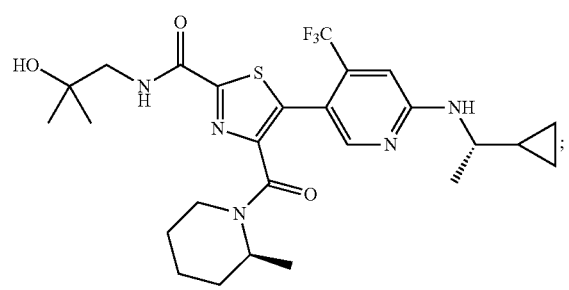
346
-continued
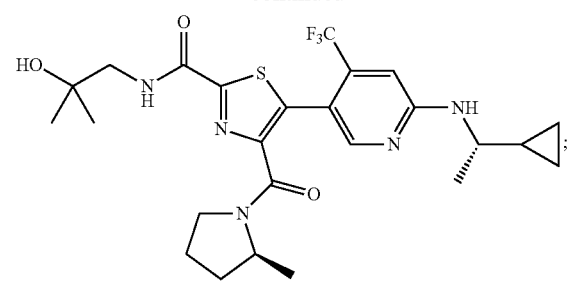
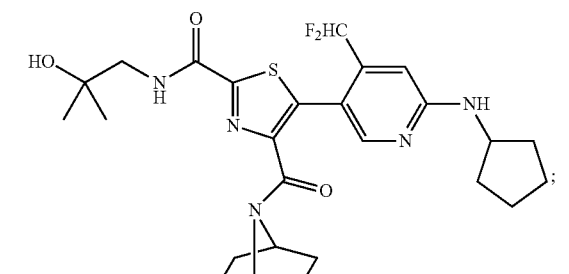
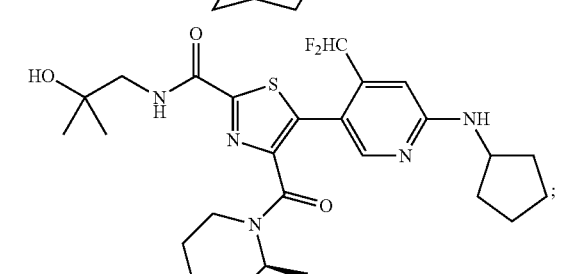
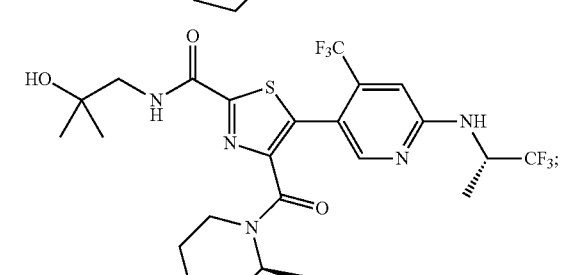
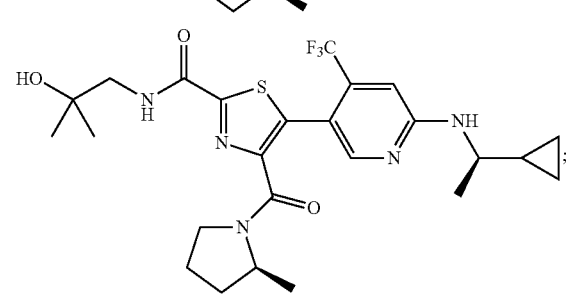

347
-continued
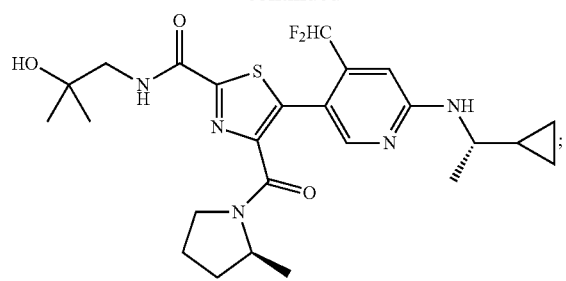
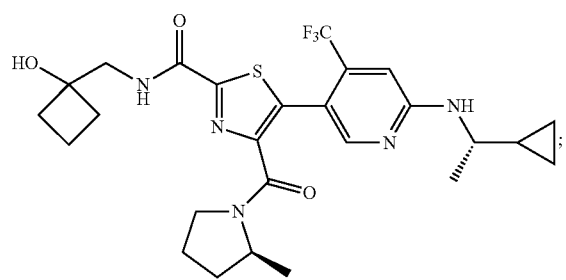
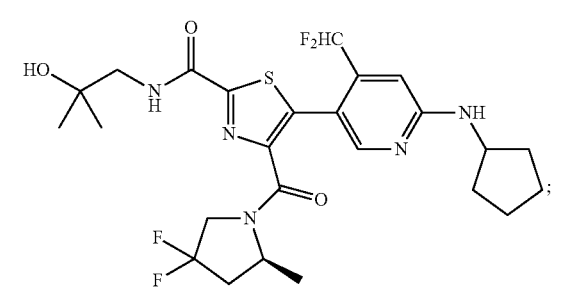
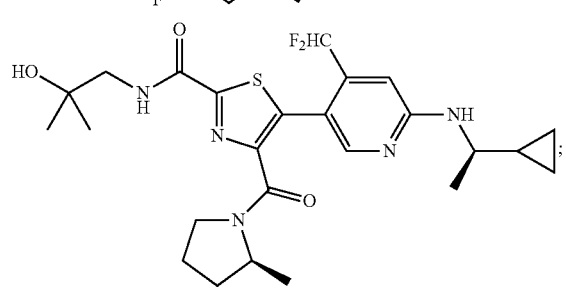
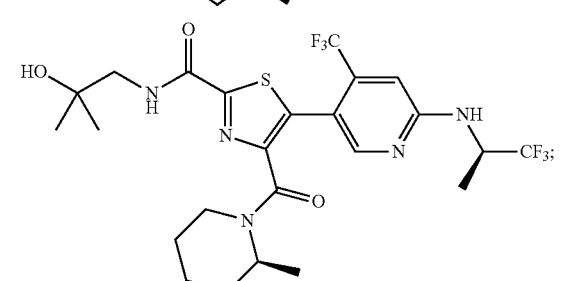
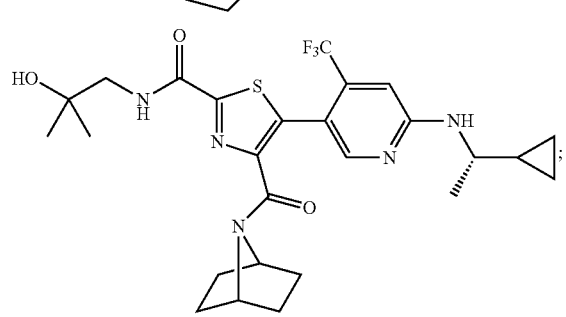
348
-continued
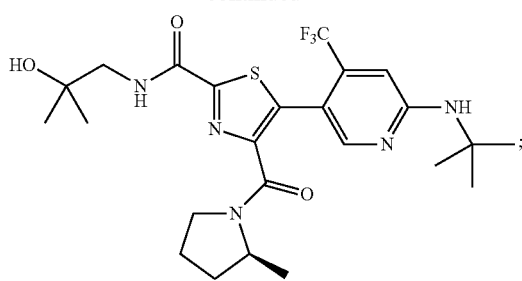
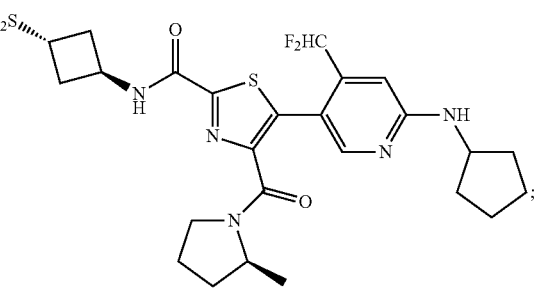
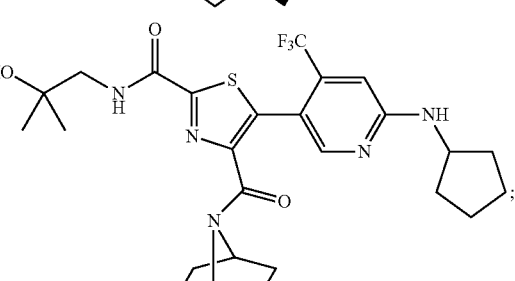
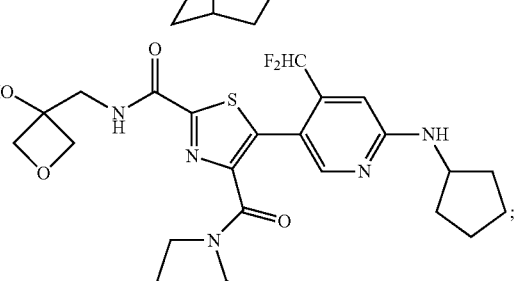
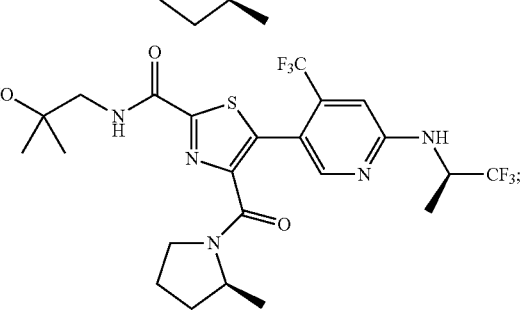
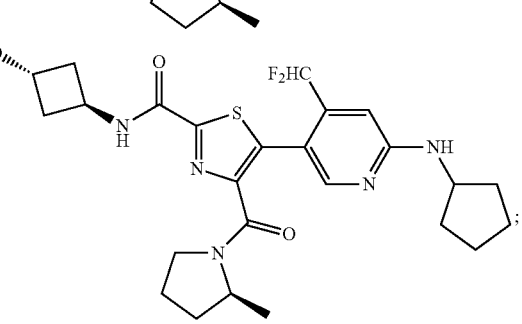

349
-continued
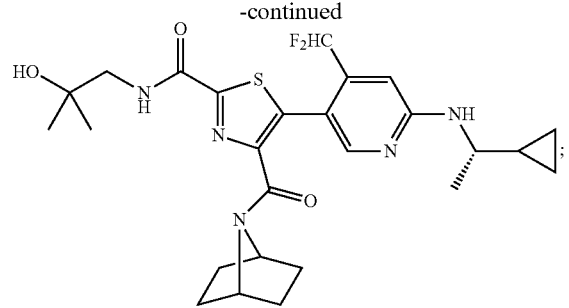
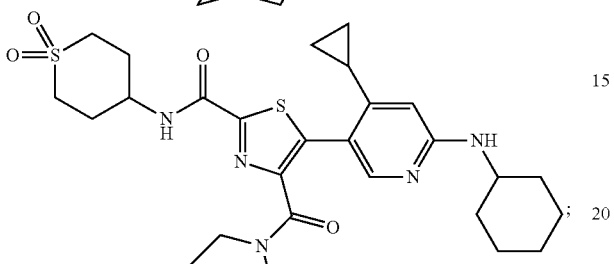
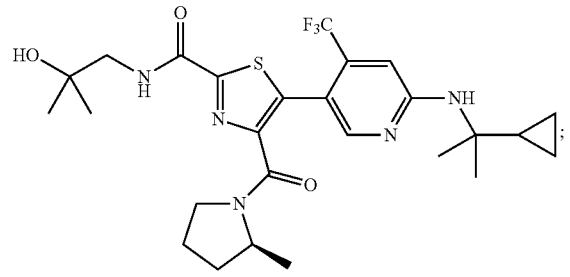
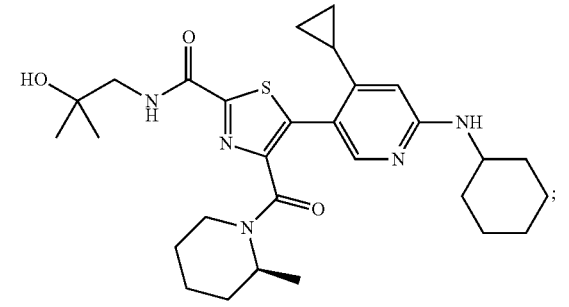
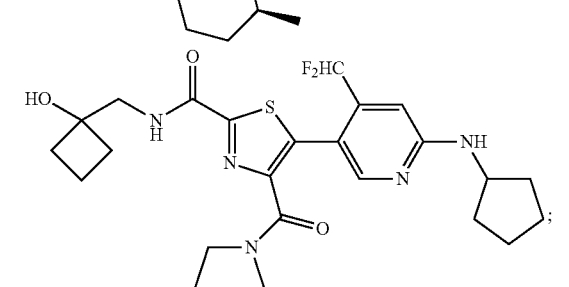
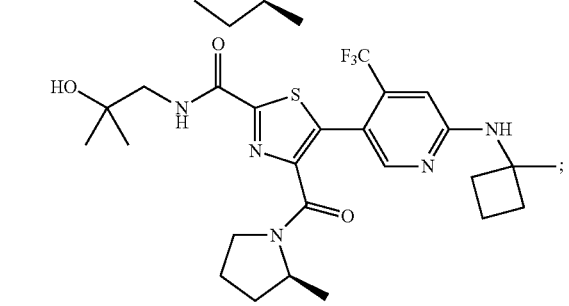
350
-continued
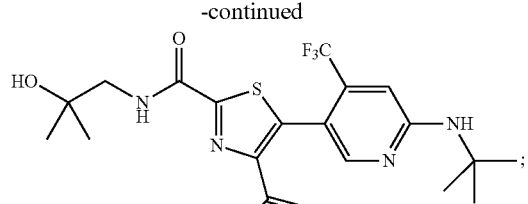
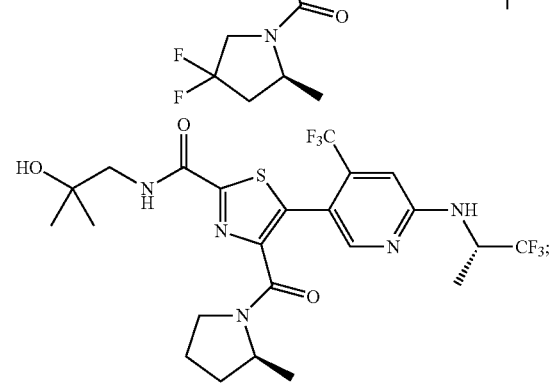

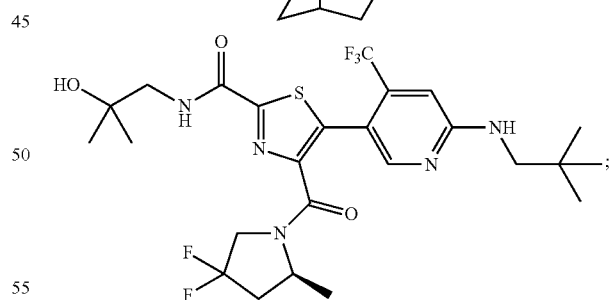
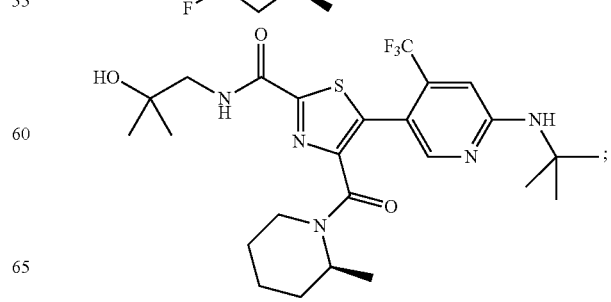

351
-continued
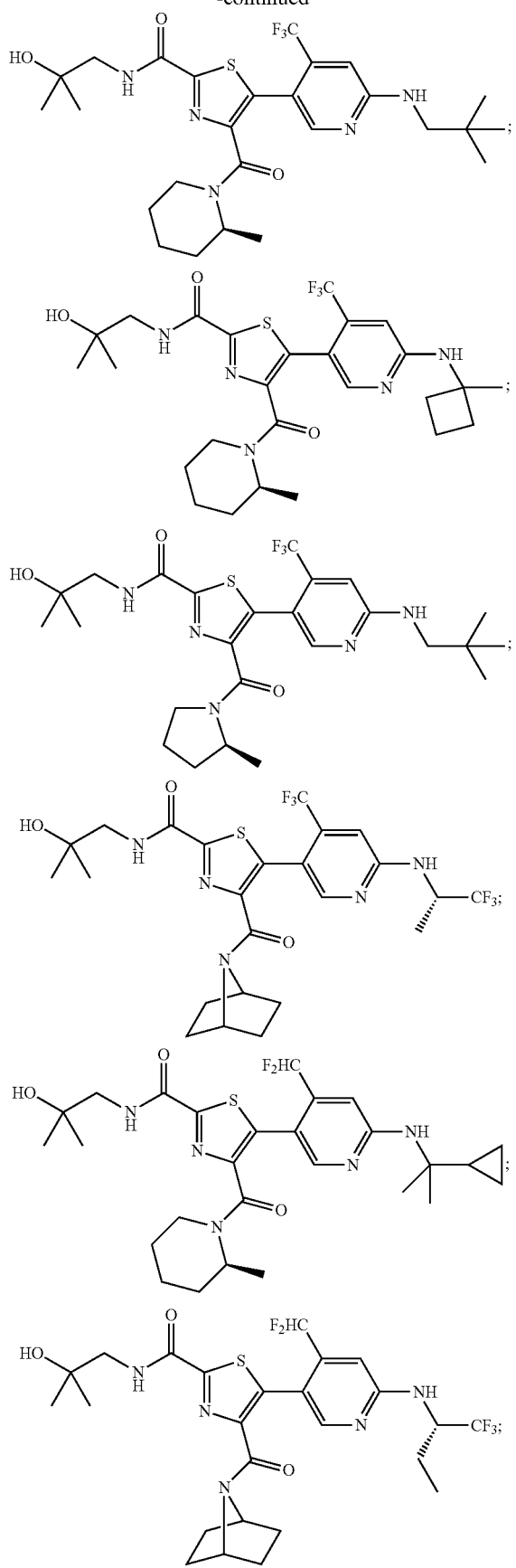
352
-continued
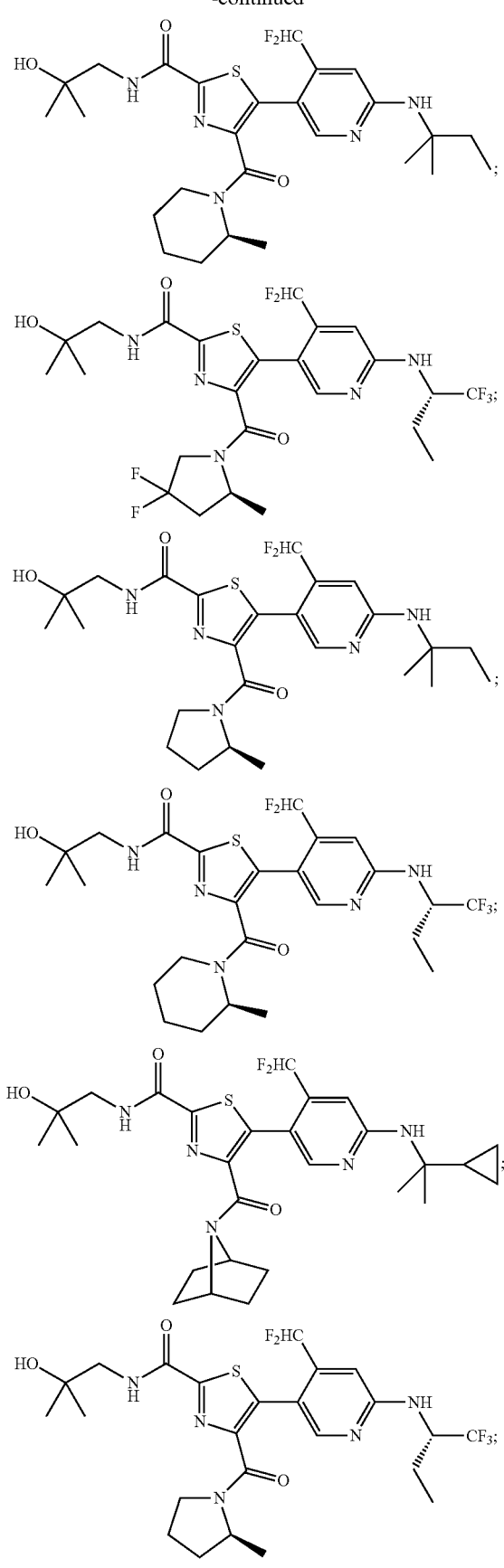

353
-continued
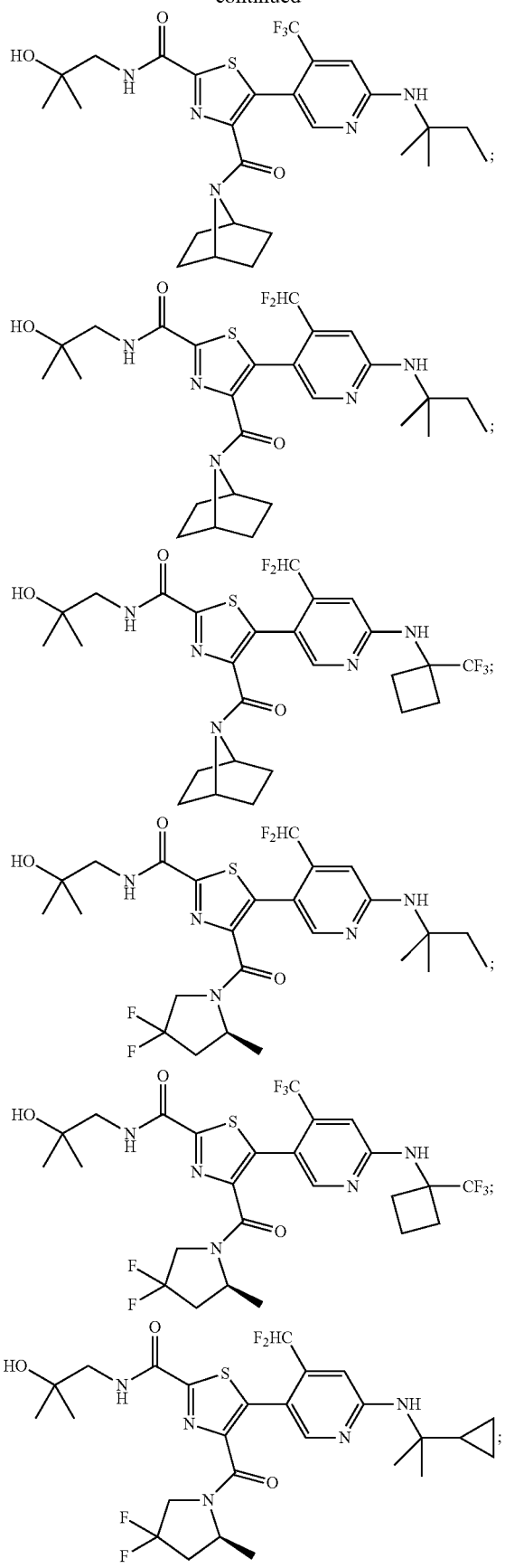
354
-continued
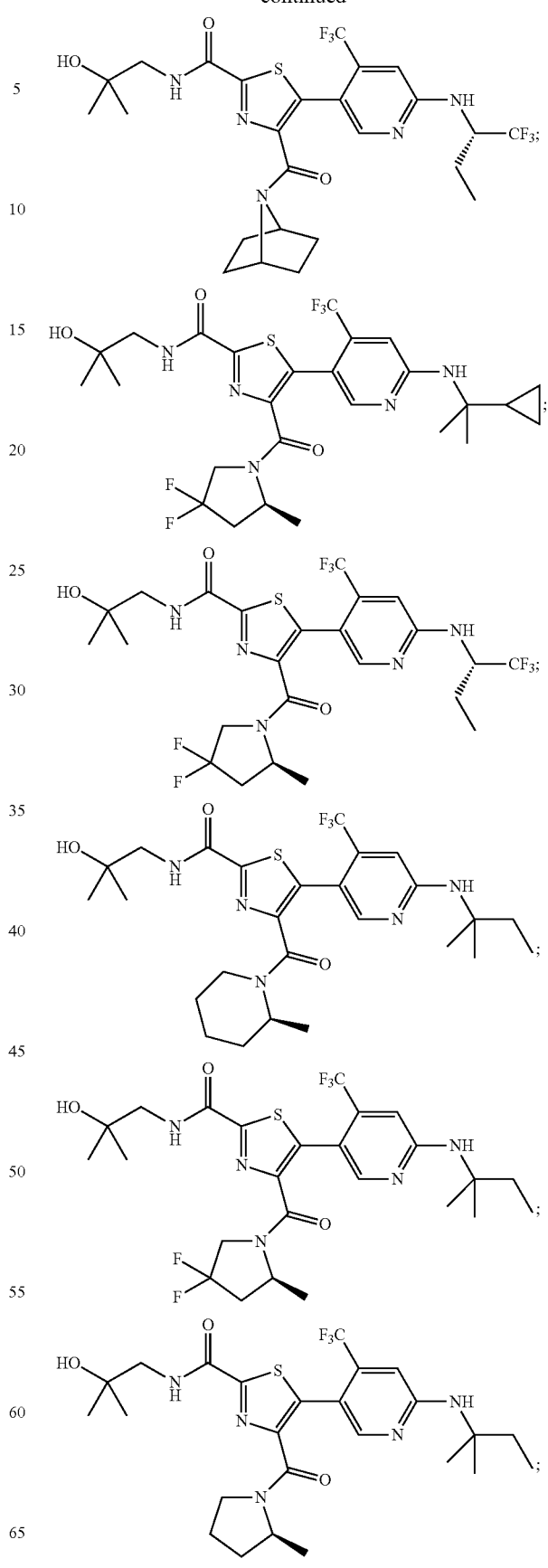

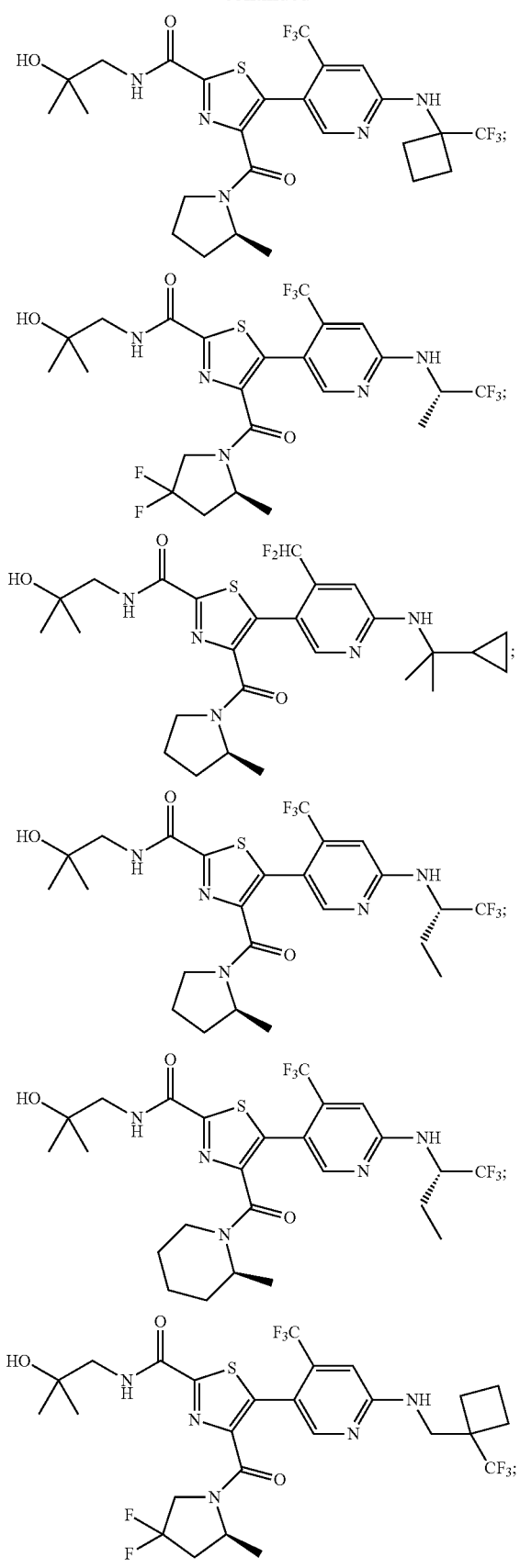
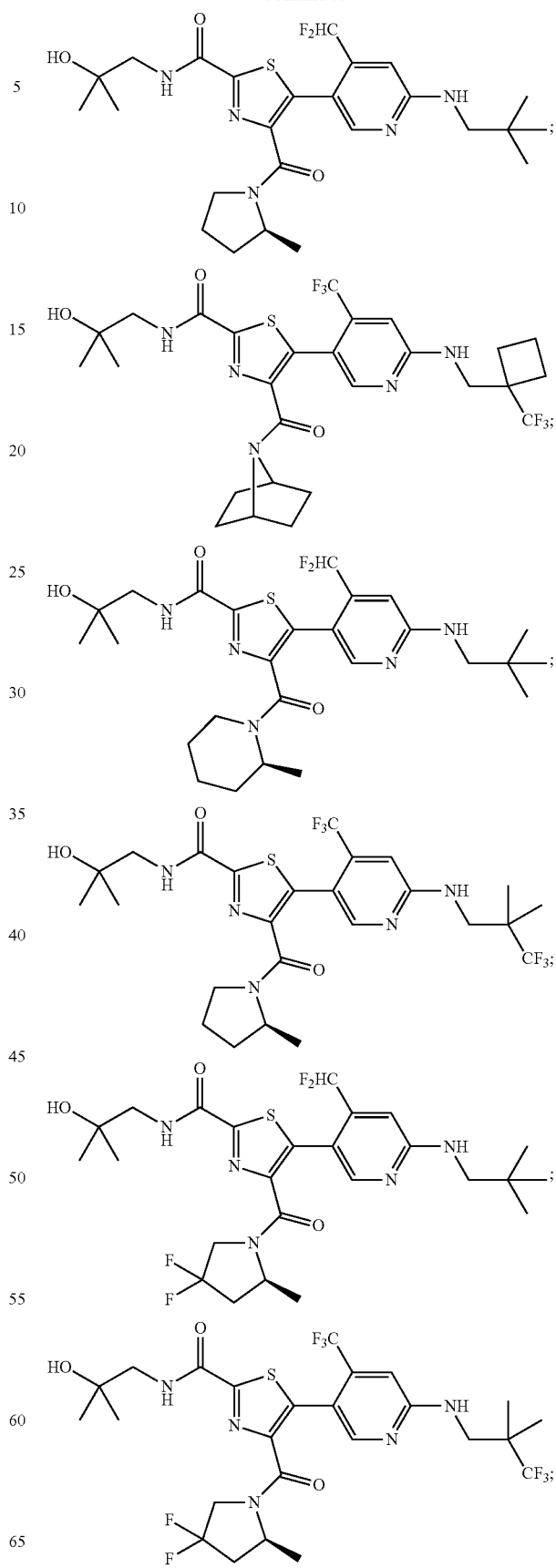

357
-continued
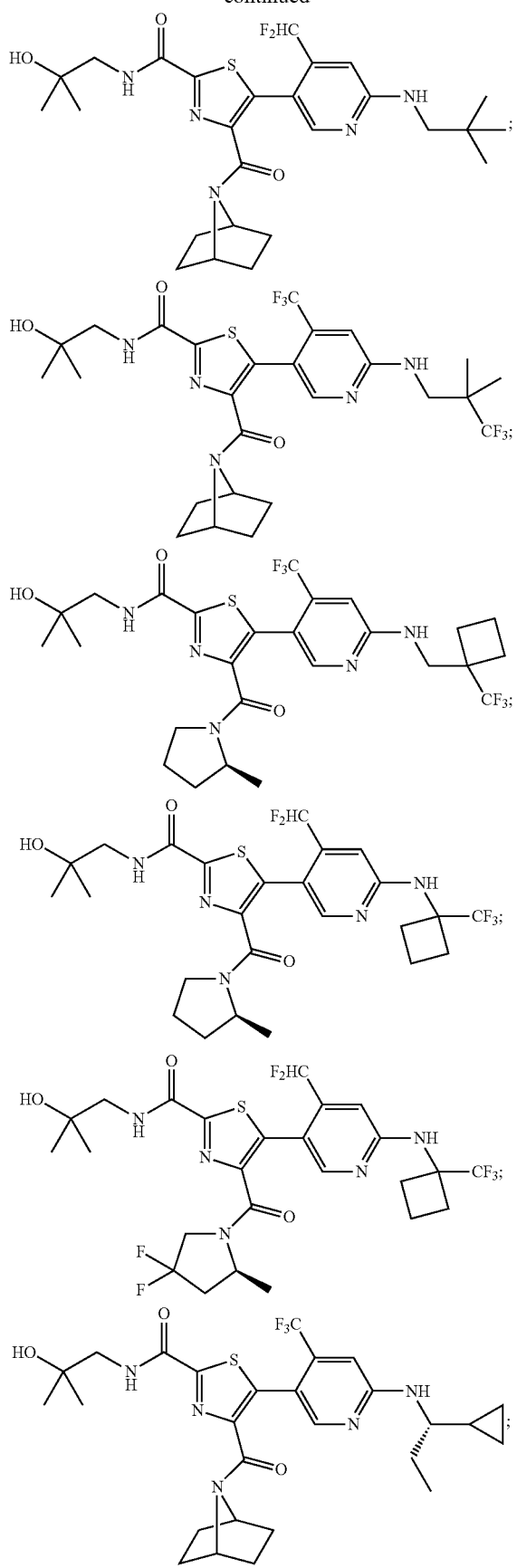
358
-continued
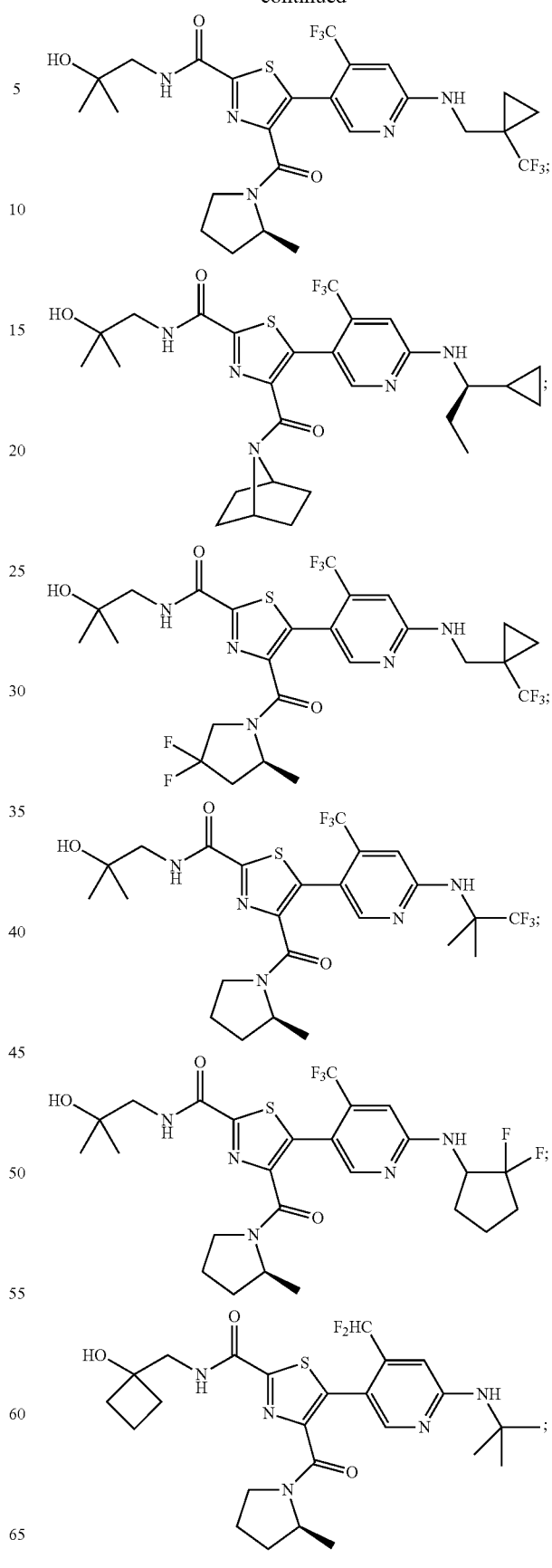

359
-continued
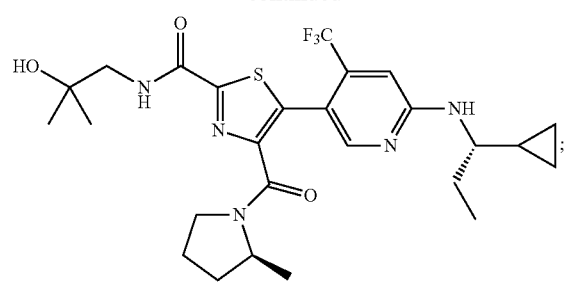
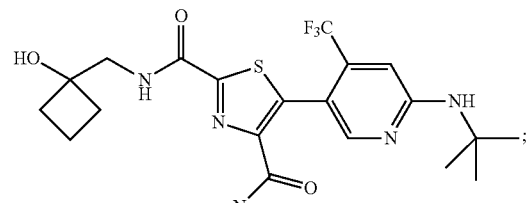
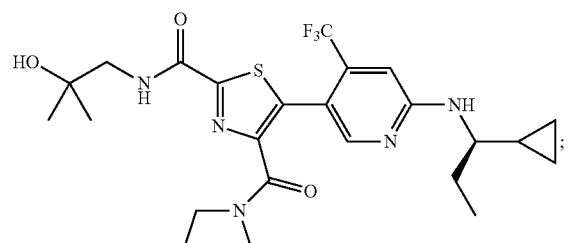
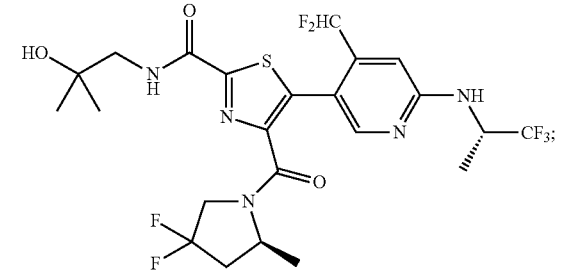
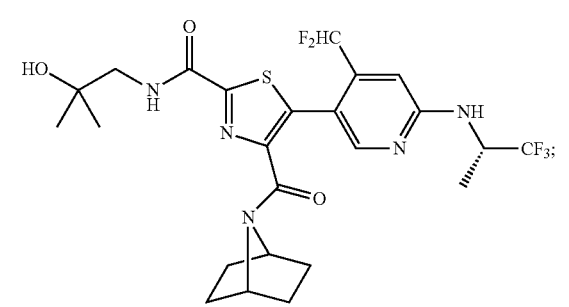
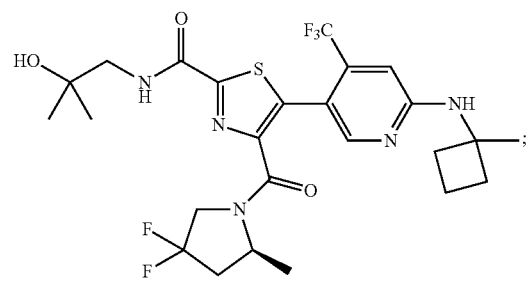
360
-continued
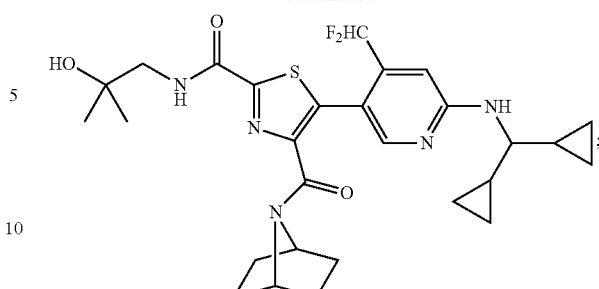
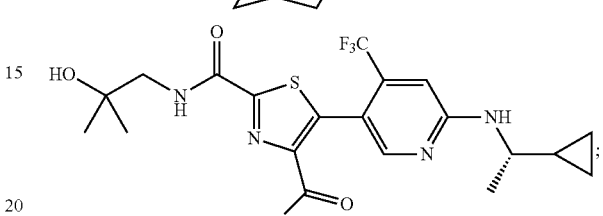
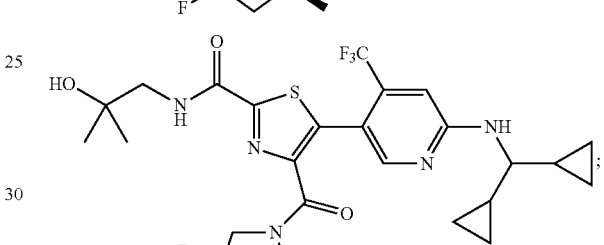
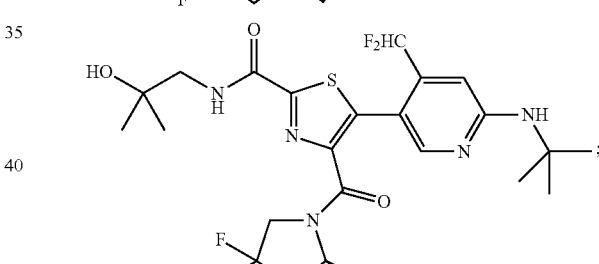
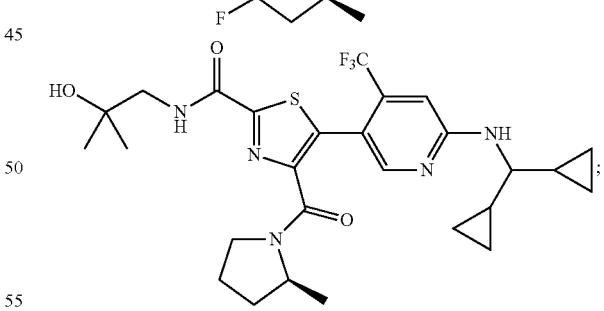
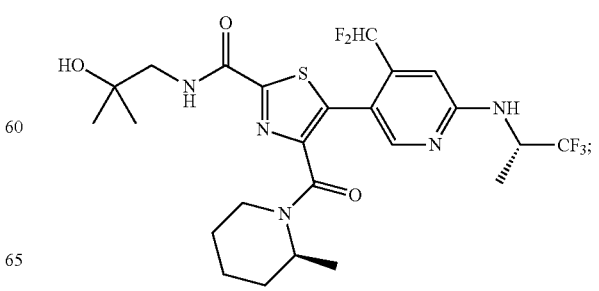

361
-continued
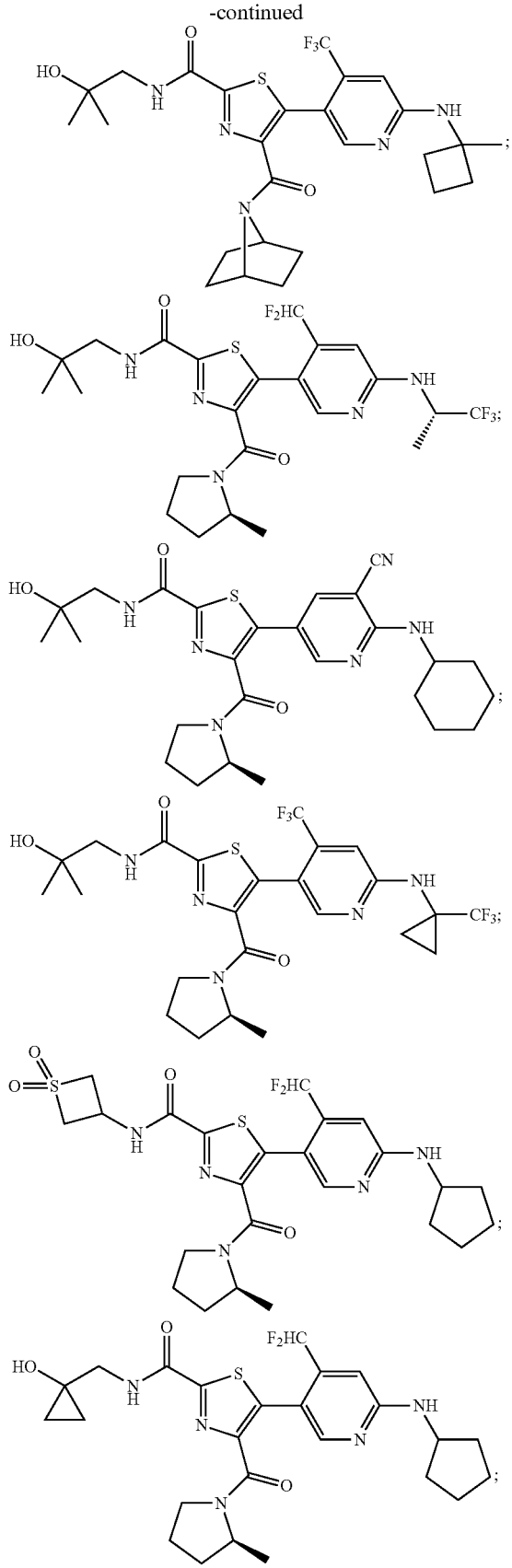
and pharmaceutically acceptable salts thereof.
362
Another embodiment of the invention is a compound selected from the group consisting of:
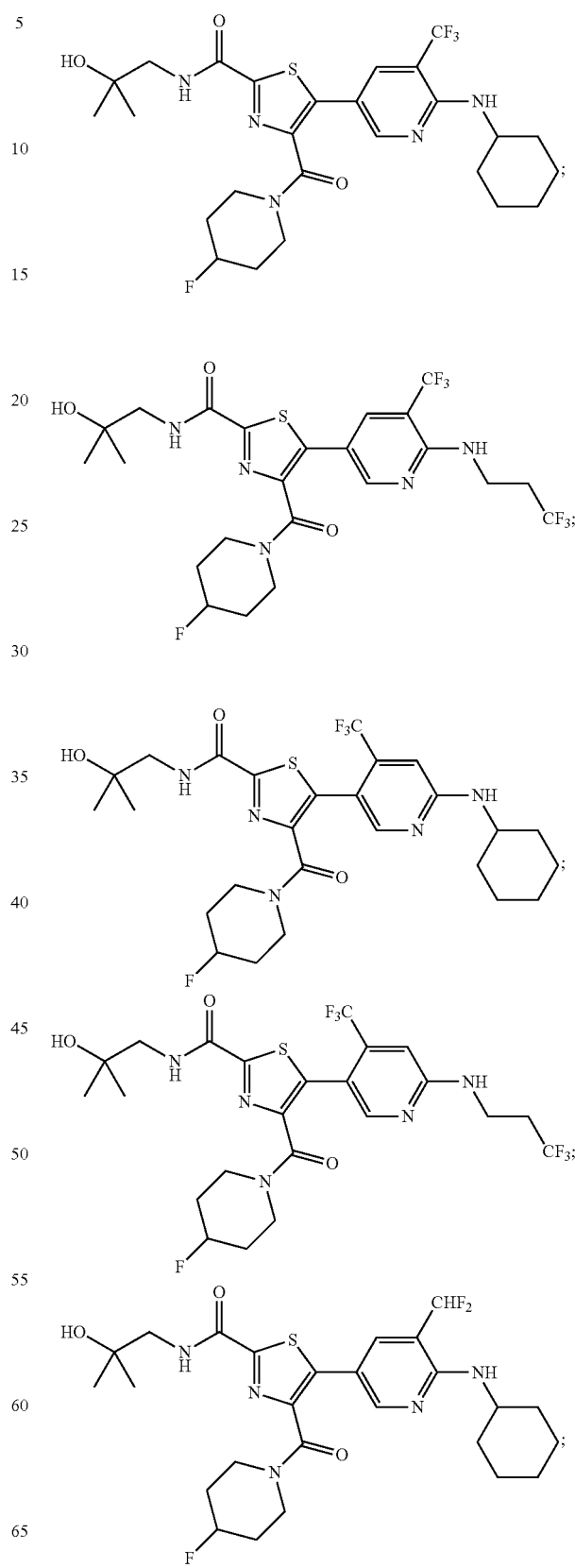

363
-continued
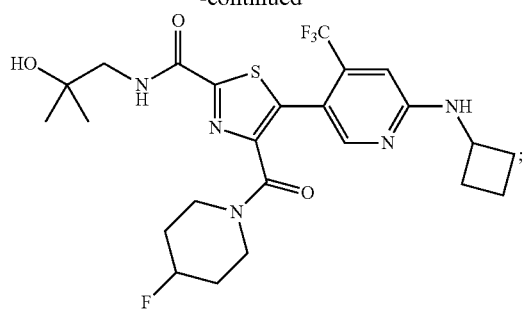
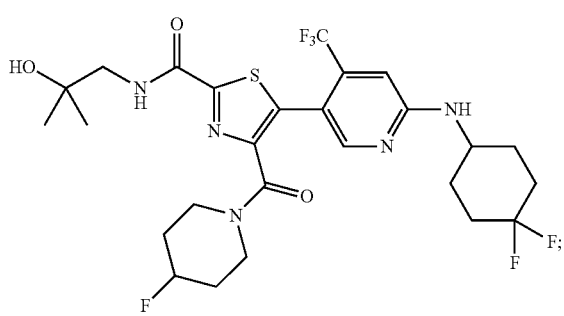
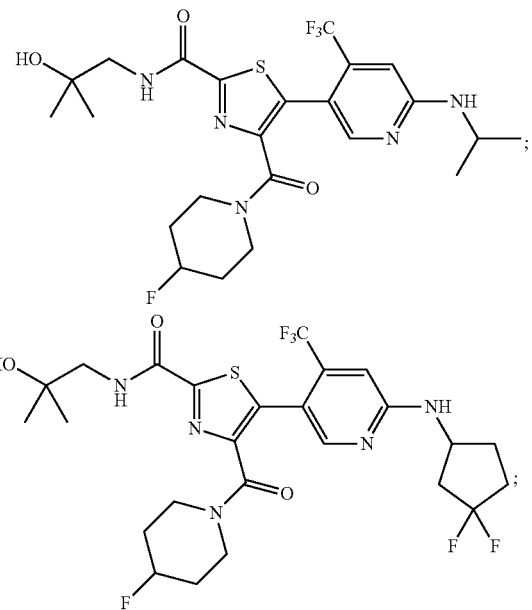
364
-continued
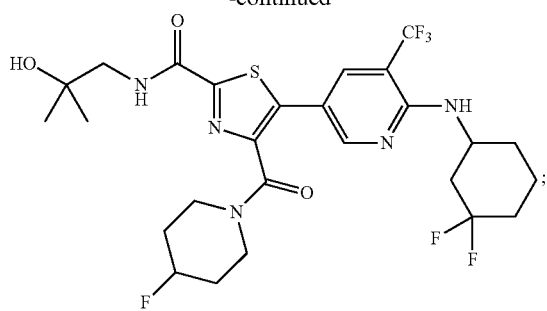

365
-continued
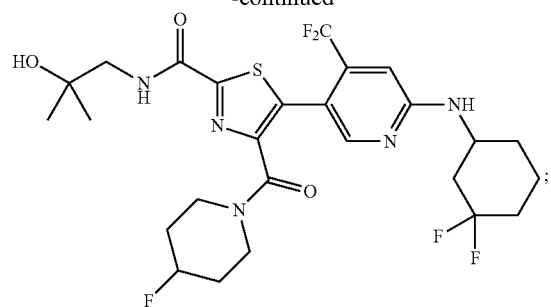
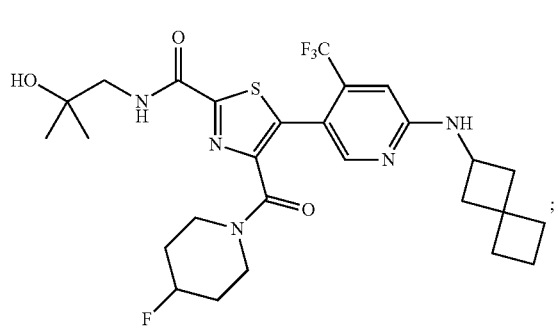
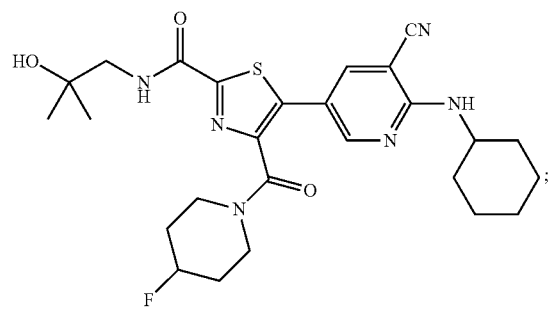
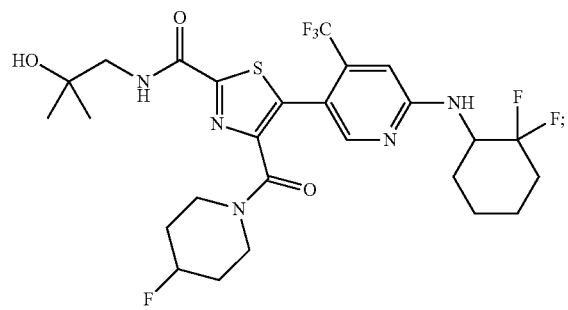
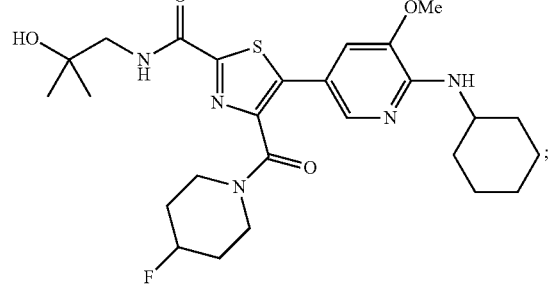
366
-continued
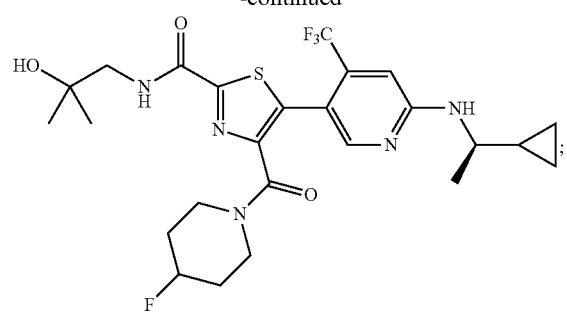
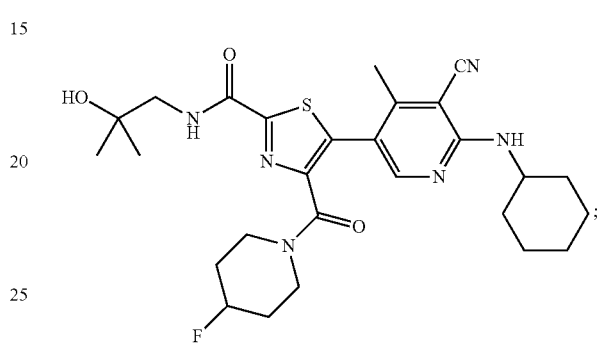
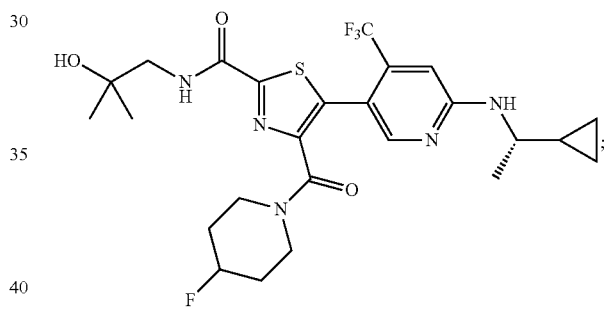
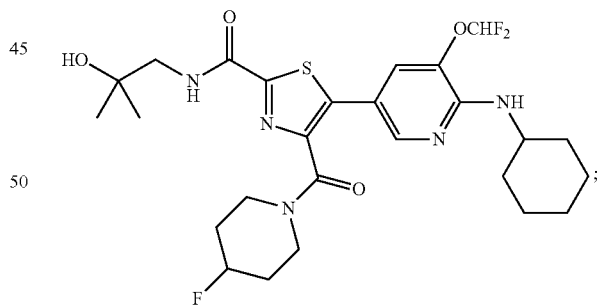
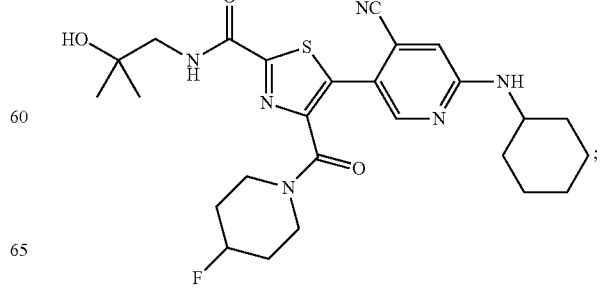

-continued

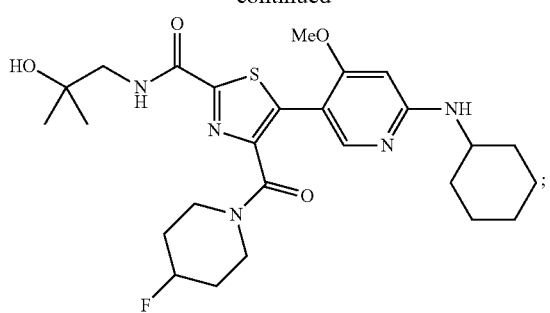

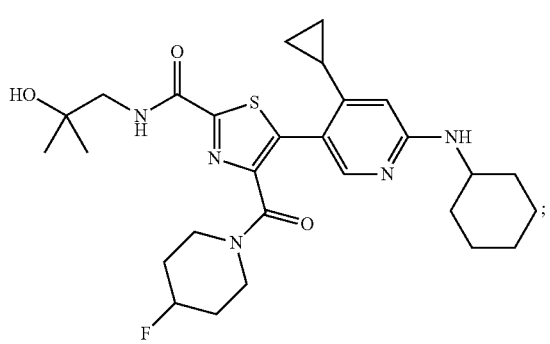

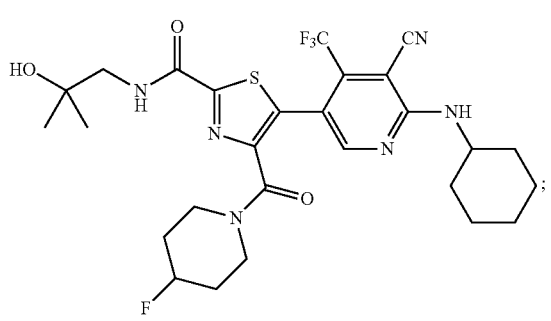

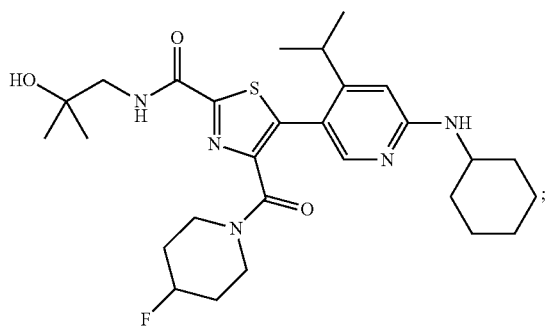

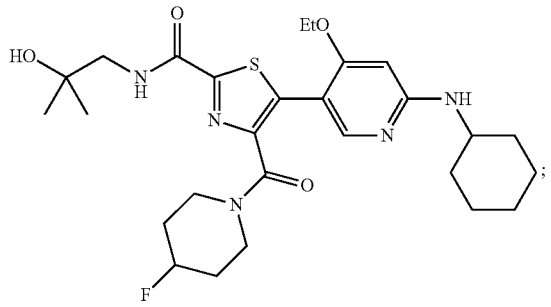

-continued

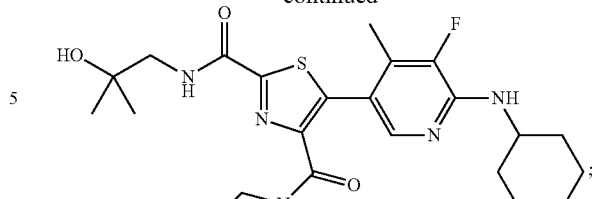

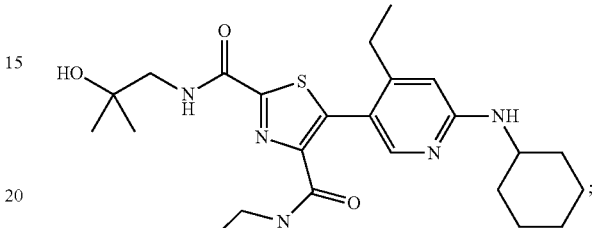

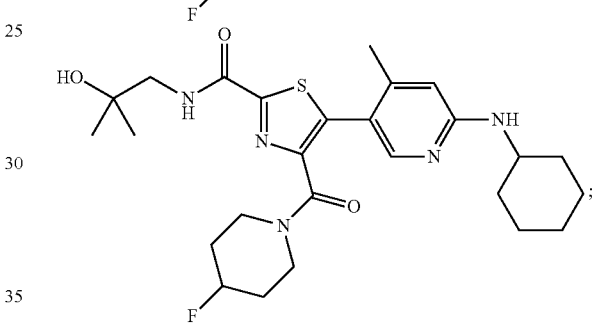

and pharmaceutically acceptable salts thereof.

Another embodiment of the invention comprises a compound of Formula I and a pharmaceutically acceptable carrier.

The present invention also provides a method for preventing, treating or ameliorating an RORγt mediated inflammatory syndrome, disorder or disease comprising administering to a subject in need thereof an effective amount of a compound of Formula I or a form, composition or medicament thereof.

The present invention provides a method of preventing, treating or ameliorating a syndrome, disorder or disease, wherein said syndrome, disorder or disease is selected from the group consisting of: ophthalmic disorders, uveitis, atherosclerosis, rheumatoid arthritis, psoriasis, psoriatic arthritis, atopic dermatitis, multiple sclerosis, Crohn's Disease, ulcerative colitis, ankylosing spondylitis, nephritis, organ allograft rejection, fibroid lung, systic fibrosis, renal insufficiency, diabetes and diabetic complications, diabetic nephropathy, diabetic retinopathy, diabetic retinitis, diabetic microangiopathy, tuberculosis, chronic obstructive pulmonary disease, sarcoidosis, invasive staphylococcia, inflammation after cataract surgery, allergic rhinitis, allergic conjunctivitis, chronic urticaria, systemic lupus erythematosus, asthma, allergic asthma, steroid resistant asthma, neutrophilic asthma, periodontal diseases, periodontis, gingivitis, gum disease, diastolic cardiomyopathies, cardiac infarction, myocarditis, chronic heart failure, angiostenosis, restenosis, reperfusion disorders, glomerulonephritis, solid tumors and cancers, chronic lymphocytic leukemia, chronic myelocytic leukemia, multiple myeloma, malignant myeloma, Hodgkin's disease, carcinomas of the bladder, breast, cervix, colon, lung, prostate, or stomach, depression and metabolic syndrome comprising administering to a subject in need thereof an effective amount of a compound of Formula I or a form, composition or medicament thereof.

The present invention provides a method of treating or ameliorating a syndrome, disorder or disease, wherein said syndrome, disorder or disease is selected from the group consisting of: rheumatoid arthritis, psoriasis, chronic obstructive pulmonary disorder, psoriatic arthritis, ankylosing spondylitis, Crohn's disease, and ulcerative colitis.

The present invention provides a method of treating or ameliorating a syndrome, disorder or disease, wherein said syndrome, disorder or disease is selected from the group consisting of: depression and metabolic syndrome.

The present invention provides a method of treating or ameliorating a syndrome, disorder or disease, wherein said syndrome, disorder or disease is selected from the group consisting of: rheumatoid arthritis, psoriasis, chronic obstructive pulmonary disorder, psoriatic arthritis, ankylosing spondylitis, Crohn's disease, and ulcerative colitis comprising administering to a subject in need thereof an effective amount of a compound of Formula I or a form, composition or medicament thereof.

The present invention provides a method of treating or ameliorating a syndrome, disorder or disease, wherein said syndrome, disorder or disease is selected from the group consisting of: inflammatory bowel diseases, rheumatoid arthritis, psoriasis, chronic obstructive pulmonary disorder, psoriatic arthritis, ankylosing spondylitis, neutrophilic asthma, steroid resistant asthma, multiple sclerosis, and systemic lupus erythematosus comprising administering to a subject in need thereof an effective amount of a compound of Formula I or a form, composition or medicament thereof.

The present invention provides a method of treating or ameliorating a syndrome, disorder or disease, wherein said syndrome, disorder or disease is selected from the group consisting of: inflammatory bowel diseases, rheumatoid arthritis, psoriasis, chronic obstructive pulmonary disorder, psoriatic arthritis, ankylosing spondylitis, neutrophilic asthma, steroid resistant asthma, multiple sclerosis, systemic lupus erythematosus, depression and metabolic syndrome comprising administering to a subject in need thereof an effective amount of a compound of Formula I or a form, composition or medicament thereof.

The present invention provides a method of treating or ameliorating a syndrome, disorder or disease, wherein said syndrome, disorder or disease is selected from the group consisting of: rheumatoid arthritis, and psoriasis comprising administering to a subject in need thereof an effective amount of a compound of Formula I or a form, composition or medicament thereof.

The present invention provides a method of treating or ameliorating a syndrome, disorder or disease, wherein said syndrome, disorder or disease is selected from the group consisting of: psoriatic arthritis and psoriasis comprising administering to a subject in need thereof an effective amount of a compound of Formula I or a form, composition or medicament thereof The present invention provides a method of treating or ameliorating a syndrome, disorder or disease, wherein said syndrome, disorder or disease is selected from the group consisting of: depression and metabolic syndrome comprising administering to a subject in need thereof an effective amount of a compound of Formula I or a form, composition or medicament thereof.

The present invention provides a method of treating or ameliorating a syndrome, disorder or disease, in a subject in need thereof comprising administering to the subject an effective amount of the compound of Formula I or composition or medicament thereof in a combination therapy with one or more anti-inflammatory agents, or immunosuppressive agents, wherein said syndrome, disorder or disease is selected from the group consisting of: rheumatoid arthritis, and psoriasis.

The present invention provides a method of treating or ameliorating a syndrome, disorder or disease, in a subject in need thereof comprising administering to the subject an effective amount of the compound of Formula I or composition or medicament thereof in a combination therapy with one or more anti-inflammatory agents, or immunosuppressive agents, wherein said syndrome, disorder or disease is selected from the group consisting of: psoriatic arthritis and psoriasis.

The present invention provides a method of treating or ameliorating a syndrome, disorder or disease, in a subject in need thereof comprising administering to the subject an effective amount of the compound of Formula I or composition or medicament thereof in a combination therapy with one or more anti-inflammatory agents, or immunosuppressive agents, wherein said syndrome, disorder or disease is selected from the group consisting of: depression and metabolic syndrome.

The present invention provides a method of treating or ameliorating a syndrome, disorder or disease, wherein said syndrome, disorder or disease is rheumatoid arthritis, comprising administering to a subject in need thereof an effective amount of a compound of Formula I or a form, composition or medicament thereof.

The present invention provides a method of treating or ameliorating a syndrome, disorder or disease, wherein said syndrome, disorder or disease is psoriasis comprising administering to a subject in need thereof an effective amount of a compound of Formula I or a form, composition or medicament thereof.

The present invention provides a method of treating or ameliorating a syndrome, disorder or disease, wherein said syndrome, disorder or disease is chronic obstructive pulmonary disorder comprising administering to a subject in need thereof an effective amount of a compound of Formula I or a form, composition or medicament thereof.

The present invention provides a method of treating or ameliorating a syndrome, disorder or disease, wherein said syndrome, disorder or disease is psoriatic arthritis comprising administering to a subject in need thereof an effective amount of a compound of Formula I or a form, composition or medicament thereof.

The present invention provides a method of treating or ameliorating a syndrome, disorder or disease, wherein said syndrome, disorder or disease is ankylosing spondylitis comprising administering to a subject in need thereof an effective amount of a compound of Formula I or a form, composition or medicament thereof.

The present invention provides a method of treating or ameliorating an inflammatory bowel disease, wherein said inflammatory bowel disease is Crohn's disease comprising administering to a subject in need thereof an effective amount of a compound of Formula I or a form, composition or medicament thereof.

The present invention provides a method of treating or ameliorating an inflammatory bowel disease, wherein said inflammatory bowel disease is ulcerative colitis comprising administering to a subject in need thereof an effective amount of a compound of Formula I or a form, composition or medicament thereof.

The present invention provides a method of treating or ameliorating a syndrome, disorder or disease, wherein said syndrome, disorder or disease is neutrophilic asthma comprising administering to a subject in need thereof an effective amount of a compound of Formula I or a form, composition or medicament thereof.

The present invention provides a method of treating or ameliorating a syndrome, disorder or disease, wherein said syndrome, disorder or disease is steroid resistant asthma comprising administering to a subject in need thereof an effective amount of a compound of Formula I or a form, composition or medicament thereof.

The present invention provides a method of treating or ameliorating a syndrome, disorder or disease, wherein said syndrome, disorder or disease is multiple sclerosis comprising administering to a subject in need thereof an effective amount of a compound of Formula I or a form, composition or medicament thereof.

The present invention provides a method of treating or ameliorating a syndrome, disorder or disease, wherein said syndrome, disorder or disease is systemic lupus erythematosus comprising administering to a subject in need thereof an effective amount of a compound of Formula I or a form, composition or medicament thereof.

The present invention provides a method of treating or ameliorating a syndrome, disorder or disease, wherein said syndrome, disorder or disease is depression comprising administering to a subject in need thereof an effective amount of a compound of Formula I or a form, composition or medicament thereof.

The present invention provides a method of treating or ameliorating a syndrome, disorder or disease, wherein said syndrome, disorder or disease is metabolic syndrome comprising administering to a subject in need thereof an effective amount of a compound of Formula I or a form, composition or medicament thereof.

The invention also relates to methods of modulating RORγt activity in a mammal by administration of an effective amount of at least one compound of Formula I.

Another embodiment of the invention is a method of inhibiting production of interleukin-17, comprising administering to a subject in need thereof an effective amount of a compound of Formula I.

Definitions

The term "administering" with respect to the methods of the invention, means a method for therapeutically or prophylactically preventing, treating or ameliorating a syndrome, disorder or disease as described herein by using a compound of Formula I or a form, composition or medicament thereof. Such methods include administering an effective amount of said compound, compound form, composition or medicament at different times during the course of a therapy or concurrently in a combination form. The methods of the invention are to be understood as embracing all known therapeutic treatment regimens.

The term "subject" refers to a patient, which may be an animal, typically a mammal, typically a human, which has been the object of treatment, observation or experiment and is at risk of (or susceptible to) developing a syndrome, disorder or disease that is associated with abberant RORγt expression or RORγt overexpression, or a patient with an inflammatory condition that accompanies syndromes, disorders or diseases associated with abberant RORγt expression or RORγt overexpression.

The term "effective amount" means that amount of active compound or pharmaceutical agent that elicits the biological or medicinal response in a tissue system, animal or human, that is being sought by a researcher, veterinarian, medical doctor, or other clinician, which includes preventing, treating or ameliorating the symptoms of a syndrome, disorder or disease being treated.

As used herein, the term "composition" is intended to encompass a product comprising the specified ingredients in the specified amounts, as well as any product which results, directly or indirectly, from combinations of the specified ingredients in the specified amounts.

The term "alkyl" refers to both linear and branched chain radicals of up to 12 carbon atoms, preferably up to 6 carbon atoms, unless otherwise indicated, and includes, but is not limited to, methyl, ethyl, propyl, isopropyl, butyl, isobutyl, sec-butyl, tert-butyl, pentyl, isopentyl, hexyl, isohexyl, heptyl, octyl, 2,2,4-trimethylpentyl, nonyl, decyl, undecyl and dodecyl. Any alkyl group may be optionally substituted with one $OCH_3$, one OH, or up to two fluorine atoms.

The term "$C_{(a-b)}$" (where a and b are integers referring to a designated number of carbon atoms) refers to an alkyl, alkenyl, alkynyl, alkoxy or cycloalkyl radical or to the alkyl portion of a radical in which alkyl appears as the prefix root containing from a to b carbon atoms inclusive. For example, $C_{(1-4)}$ denotes a radical containing 1, 2, 3 or 4 carbon atoms.

Pharmaceutically Acceptable Salts

Pharmaceutically acceptable acidic/anionic salts include, and are not limited to acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, glyceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, methylbromide, methylnitrate, methylsulfate, mucate, napsylate, nitrate, pamoate, pantothenate, phosphate/diphosphate, polygalacturonate, salicylate, stearate, subacetate, succinate, sulfate, tannate, tartrate, teoclate, tosylate and triethiodide. Organic or inorganic acids also include, and are not limited to, hydriodic, perchloric, sulfuric, phosphoric, propionic, glycolic, methanesulfonic, hydroxyethanesulfonic, oxalic, 2-naphthalenesulfonic, p-toluenesulfonic, cyclohexanesulfamic, saccharinic or trifluoroacetic acid.

Pharmaceutically acceptable basic/cationic salts include, and are not limited to aluminum, 2-amino-2-hydroxymethyl-propane-1,3-diol (also known as tris(hydroxymethyl)aminomethane, tromethane or "TRIS"), ammonia, benzathine, t-butylamine, calcium, calcium gluconate, calcium hydroxide, chloroprocaine, choline, choline bicarbonate, choline chloride, cyclohexylamine, diethanolamine, ethylenediamine, lithium, LiOMe, L-lysine, magnesium, meglumine, $NH_3$, $NH_4OH$, N-methyl-D-glucamine, piperidine, potassium, potassium-t-butoxide, potassium hydroxide (aqueous), procaine, quinine, sodium, sodium carbonate, sodium-2-ethylhexanoate, sodium hydroxide, triethanolamine, or zinc.

Methods of Use

The present invention is directed to a method for preventing, treating or ameliorating a RORγt mediated inflammatory syndrome, disorder or disease comprising administering to a subject in need thereof an effective amount of a compound of Formula I or a form, composition or medicament thereof.

Since RORγt is an N-terminal isoform of RORγ, it is recognized that compounds of the present invention which are modulators of RORγt are likely to be modulators of RORγ as well. Therefore the mechanistic description "RORγt modulators" is intended to encompass RORγ modulators as well.

When employed as RORγt modulators, the compounds of the invention may be administered in an effective amount within the dosage range of about 0.5 mg to about 10 g, preferably between about 0.5 mg to about 5 g, in single or divided daily doses. The dosage administered will be affected by factors such as the route of administration, the health, weight and age of the recipient, the frequency of the treatment and the presence of concurrent and unrelated treatments.

It is also apparent to one skilled in the art that the therapeutically effective dose for compounds of the present invention or a pharmaceutical composition thereof will vary according to the desired effect. Therefore, optimal dosages to be administered may be readily determined by one skilled in the art and will vary with the particular compound used, the mode of administration, the strength of the preparation, and the advancement of the disease condition. In addition, factors associated with the particular subject being treated, including subject age, weight, diet and time of administration, will result in the need to adjust the dose to an appropriate therapeutic level. The above dosages are thus exemplary of the average case. There can, of course, be individual instances where higher or lower dosage ranges are merited, and such are within the scope of this invention.

The compounds of Formula I may be formulated into pharmaceutical compositions comprising any known pharmaceutically acceptable carriers. Exemplary carriers include, but are not limited to, any suitable solvents, dispersion media, coatings, antibacterial and antifungal agents and isotonic agents. Exemplary excipients that may also be components of the formulation include fillers, binders, disintegrating agents and lubricants.

The pharmaceutically-acceptable salts of the compounds of Formula I include the conventional non-toxic salts or the quaternary ammonium salts which are formed from inorganic or organic acids or bases. Examples of such acid addition salts include acetate, adipate, benzoate, benzenesulfonate, citrate, camphorate, dodecylsulfate, hydrochloride, hydrobromide, lactate, maleate, methanesulfonate, nitrate, oxalate, pivalate, propionate, succinate, sulfate and tartrate. Base salts include ammonium salts, alkali metal salts such as sodium and potassium salts, alkaline earth metal salts such as calcium and magnesium salts, salts with organic bases such as dicyclohexylamino salts and salts with amino acids such as arginine. Also, the basic nitrogen-containing groups may be quaternized with, for example, alkyl halides.

The pharmaceutical compositions of the invention may be administered by any means that accomplish their intended purpose. Examples include administration by parenteral, subcutaneous, intravenous, intramuscular, intraperitoneal, transdermal, buccal or ocular routes. Alternatively or concurrently, administration may be by the oral route. Suitable formulations for parenteral administration include aqueous solutions of the active compounds in water-soluble form, for example, water-soluble salts, acidic solutions, alkaline solutions, dextrose-water solutions, isotonic carbohydrate solutions and cyclodextrin inclusion complexes.

The present invention also encompasses a method of making a pharmaceutical composition comprising mixing a pharmaceutically acceptable carrier with any of the compounds of the present invention. Additionally, the present invention includes pharmaceutical compositions made by mixing a pharmaceutically acceptable carrier with any of the compounds of the present invention.

Polymorphs and Solvates

Furthermore, the compounds of the present invention may have one or more polymorph or amorphous crystalline forms and as such are intended to be included in the scope of the invention. In addition, the compounds may form solvates, for example with water (i.e., hydrates) or common organic solvents. As used herein, the term "solvate" means a physical association of the compounds of the present invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. The term "solvate" is intended to encompass both solution-phase and isolatable solvates. Non-limiting examples of suitable solvates include ethanolates, methanolates, and the like.

It is intended that the present invention include within its scope polymorphs and solvates of the compounds of the present invention. Thus, in the methods of treatment of the present invention, the term "administering" shall encompass the means for treating, ameliorating or preventing a syndrome, disorder or disease described herein with the compounds of the present invention or a polymorph or solvate thereof, which would obviously be included within the scope of the invention albeit not specifically disclosed.

In another embodiment, the invention relates to a compound as described in Formula I for use as a medicament.

In another embodiment, the invention relates to the use of a compound as described in Formula I for the preparation of a medicament for the treatment of a disease associated with an elevated or aberrant RORγt activity.

The present invention includes within its scope prodrugs of the compounds of this invention. In general, such prodrugs will be functional derivatives of the compounds which are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs", Ed. H. Bundgaard, Elsevier, 1985.

Furthermore, it is intended that within the scope of the present invention, any element, in particular when mentioned in relation to a compound of Formula I, shall comprise all isotopes and isotopic mixtures of said element, either naturally occurring or synthetically produced, either with natural abundance or in an isotopically enriched form. For example, a reference to hydrogen includes within its scope $^1$H, $^2$H (D), and $^3$H (T). Similarly, references to carbon and oxygen include within their scope respectively $^{12}$C, $^{13}$C and $^{14}$C and $^{16}$O and $^{18}$O. The isotopes may be radioactive or non-radioactive. Radiolabelled compounds of Formula I may comprise a radioactive isotope selected from the group of $^3$H, $^{11}$C, $^{18}$F, $^{122}$I, $^{123}$I, $^{125}$I, $^{131}$I, $^{75}$Br, $^{76}$Br, $^{77}$Br and $^{82}$Br. Preferably, the radioactive isotope is selected from the group of $^3$H, $^{11}$C and $^{18}$F.

Some compounds of the present invention may exist as atropisomers. Atropisomers are stereoisomers resulting from hindered rotation about single bonds where the steric strain barrier to rotation is high enough to allow for the isolation of the conformers. It is to be understood that all such conformers and mixtures thereof are encompassed within the scope of the present invention.

Where the compounds according to this invention have at least one stereo center, they may accordingly exist as enantiomers or diastereomers. It is to be understood that all such isomers and mixtures thereof are encompassed within the scope of the present invention.

Where the processes for the preparation of the compounds according to the invention give rise to mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-D-tartaric acid and/or (+)-di-p-toluoyl-L-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral column vial HPLC or SFC. In some instances rotamers of compounds may exist which are observable by 1H NMR leading to complex multiplets and peak integration in the 1H NMR spectrum.

Chiral centers, of which the absolute configuration is known, are labelled by prefixes R and S, assigned by the standard sequence-rule procedure, and preceded when necessary by the appropriate locants. Chiral centers, of which the relative but not the absolute configuration is known, are labelled arbitrarily by prefixes R* and S*, preceded when necessary by the appropriate locants. These prefixes are assigned by the standard sequence-rule procedure on the arbitrary assumption that the center of chirality with the lowest locant has chirality R. When a compound contains chiral centers with known absolute configurations and a sterically unrelated set of chiral centers with known relative configurations but unknown absolute configurations, then R* and S* are used to designate the latter. (*Pure & Appl. Chem.* 45, 1976, 11-30).

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

Abbreviations

Herein and throughout the application, the following abbreviations may be used.

Ac acetyl
ACN acetonitrile
BINAP (±)-2,2'-bis(diphenylphosphino)-1,1'-binaphthalene
Boc tert-butyloxycarbonyl
br broad
bu butyl
Cy cyclohexyl
d doublet
dba dibenzylideneacetone
DBU 1,8-Diazabicyclo(5.4.0)undec-7-ene
DCE dichloroethane
DCM dichloromethane
DIPEA NN-diisopropylethylamine (Hünig's base)
DMA N,N-dimethylacetamide
DMF N,N-dimethylformamide
DMSO dimethyl sulfoxide
EDC 1-ethyl-3-(3-dimethylaminopropyl) carbodiimide
EtOAc ethyl acetate
ESI electrospray ionization
Et ethyl
FCC flash column chromatography
h hour(s)
HATU O-(7-azabenzotriazol-1-yl)-N,N,N',N'-tetramethyluronium hexafluorophosphate
HOBt 1-hydroxybenzotriazole
HPLC high pressure liquid chromatography
i-Pr or iPr isopropyl
Hz Hertz
LC liquid chromatography
LAH lithium aluminum hydride
m multiplet
M molar (moles/liter)
Me methyl
min minute(s)
MHz megahertz
μm micrometer
mm millimeter
MS mass spectrometry
N normal
NB S N-bromosuccinimide
nm nanometer
NMR nuclear magnetic resonance
Piv pivaloyl/pivalic (Me$_3$CO)
Pr propyl
PyBOP (benzotriazol-1-yloxy)tripyrrolidinophosphonium hexafluorophosphate
q quartet
rt room temperature
s singlet
SFC supercritical fluid chromatography
SPhos 2-Dicyclohexylphosphino-2',6'-dimethoxybiphenyl
t tertiary
t triplet
t-Bu tert-butyl
TB S tert-butyldimethylsilyl
TEA triethylamine
tert tertiary
TFA trifluoroacetic acid
THF tetrahydrofuran
THP tetrahydropyran
Ts tosyl
XantPhos 4,5-Bis(diphenylphosphino)-9,9-dimethylxanthene
XtalFluor-E® (Diethylamino)difluorosulfonium tetrafluoroborate General Schemes:

Compounds of Formula I in the present invention can be synthesized in accordance with the general synthetic methods known to those who are skilled in the art. The following reaction schemes are only meant to represent examples of the invention and are in no way meant to be a limit of the invention.

The compounds of the present invention can be prepared according to Schemes 1-3. Coupling of a 3-pyridyl group to the thiazole ring of compounds of Formula I can be accomplished by coupling the 5-bromopyridine building blocks C-I to the thiazole derivatives B-I in the presence of palladium catalysis, using appropriate ligands, solvents, additives and temperatures to form the 5-(3-pyridyl)-substituted thiazoles A-I (Scheme 1). Alternatively, 5-(3-pyridyl)-substituted thiazoles A-II can be prepared by the coupling of 5-bromopyridine building blocks C-I to thiazole esters B-III in the presence of palladium catalysis, using appropriate ligands, solvents, additives and temperatures. Subsequent ester hydrolysis, using reagents such as potassium tert-butoxide in solvents such as THF, and amide bond formation using reagents such as HATU and DIPEA in solvents such as DMF then provides 5-(3-pyridyl)-substituted thiazoles A-I. Alternatively, direct aminolysis of esters A-II with amines in solvents such as EtOH then affords 5-(3-pyridyl)-substituted thiazoles A-I. When employing hydrochloride salts of amines, direct aminolysis is achieved in suitable solvents such as EtOH in the presence of bases such as DIPEA. In some cases, hydrolysis of esters A-II using reagents such as DIPEA in solvents such as EtOH and water afforded the corresponding carboxylic acids, which were then converted to the corresponding acid chlorides using reagents such as oxallyl chloride and DMF in solvents such as DCM. Amide bond formation could then be achieved using amines in the presence of DIPEA in solvents such as DCM to afford substituted thiazoles A-I.

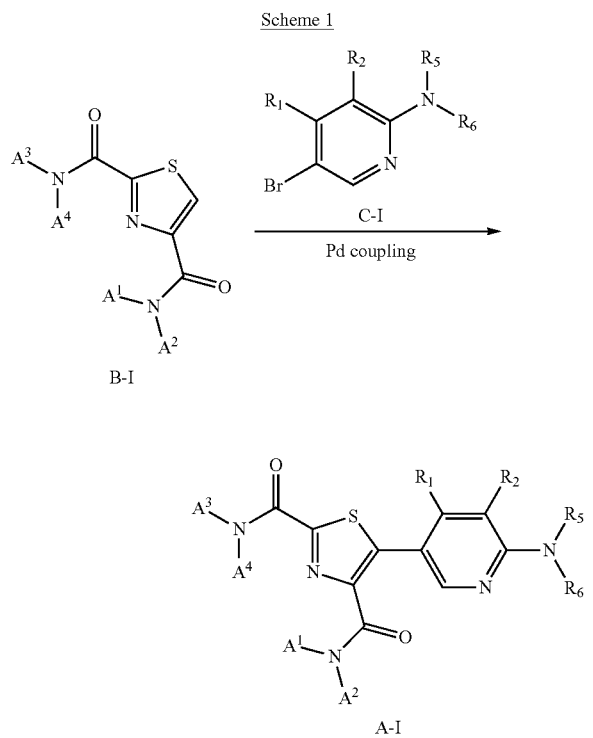

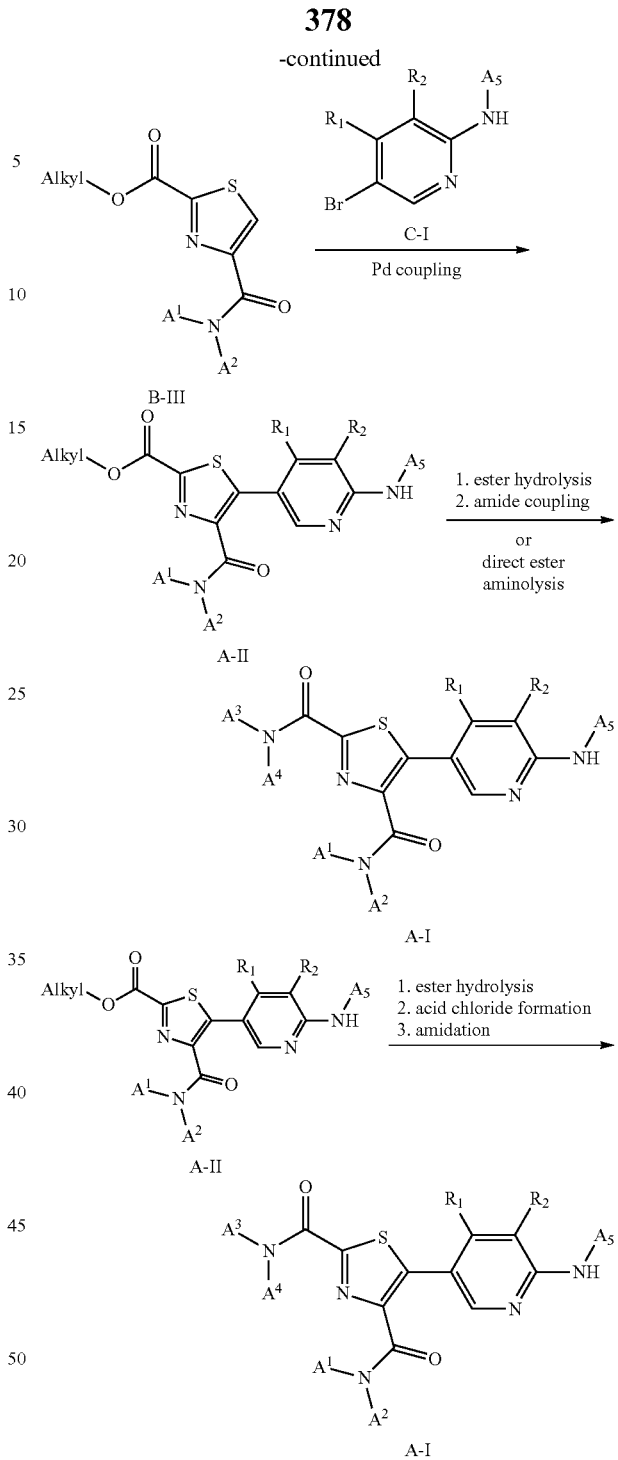

Preparation of the 2-amino-5-bromopyridines C-I are shown in Scheme 2. 2-Amino-5-bromopyridines C-I can be prepared by direct amination of 5-bromo-2-chloropyridines C-II with amines under microwave conditions. Alternatively, when employing hydrochloride salts of amines, direct amination is achieved in suitable solvents such as acetonitrile in the presence of bases such as DIPEA. Direct amination of 2-bromopyridines C-III with amines under microwave conditions affords intermediates C-IV. Alternatively, intermediates C-IV are prepared by direct amination of 2-chloropyridines C-V with hydrochloride salts of amines in suitable solvents such as acetonitrile in the presence of bases such as DIPEA, or by direct amination of 2-fluoropyridines C-VI with hydrochloride salts of amines in suitable solvents such as DMSO in the presence of bases such as NaHCO₃. In addition, 2-aminopyridines C-IV may be prepared by a palladium mediated amination of 2-bromopyridines C-III or 2-chloropyridines C-V using reagents such as Pd₂(dba)₃. Bromination using reagents such as NBS or bromine affords 2-amino-5-bromopyridines C-I.

ester B-IV from B-II using tert-butanol and TsCl in the presence of bases such as pyridine. Subsequent selective ester hydrolysis at the 2-position of the thiazole ring and amide bond formation then affords B-V. Alternatively B-V can be formed from B-IV by direct aminolysis with amines in appropriate solvents and temperatures. Subsequent ester hydrolysis using reagents such as TFA followed by amide bond formation then provides B-I.

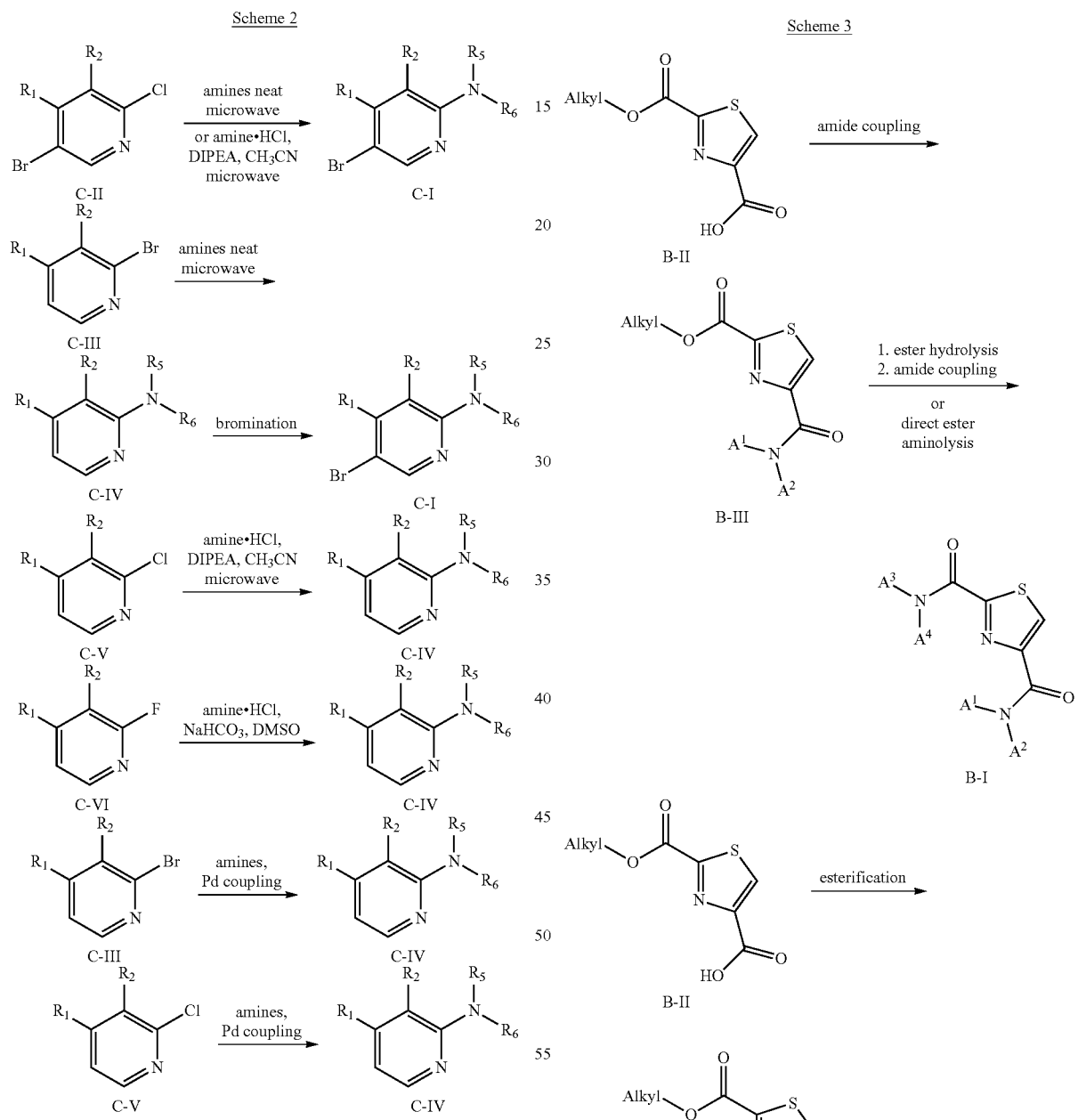

The preparation of thiazole derivatives B-I is shown in Scheme 3. B-I can be prepared starting from 2-(alkoxycarbonyl)thiazole-4-carboxylic acid B-II by a process involving standard methods for amide bond formation, ester hydrolysis and a second amide bond formation. Alternatively, intermediates B-III can undergo a direct aminolysis with amines in appropriate solvents and temperatures to afford B-I. Thiazoles B-I can also be prepared by formation of tert-butyl

381

-continued

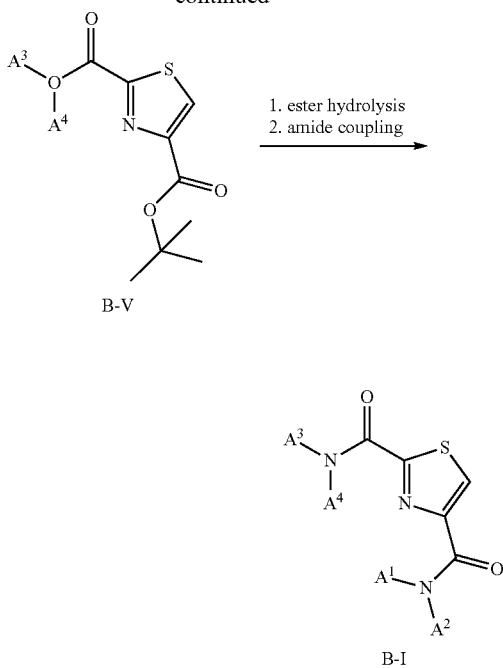

1. ester hydrolysis
2. amide coupling

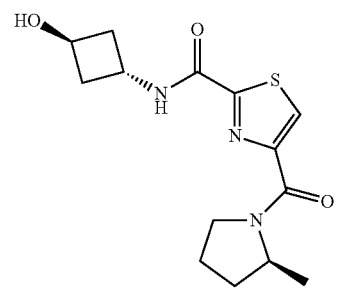

INTERMEDIATES

Compounds of the present invention can be prepared by methods known to those who are skilled in the art. The following examples are only meant to represent examples of the invention and are in no way meant to be a limit of the invention.

Intermediate 1

5-Bromo-N-cyclohexyl-3-(trifluoromethyl)pyridin-2-amine

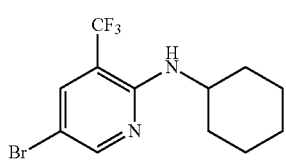 [SMILES: FC(F)(F)c1cc(Br)cnc1NC1CCCCC1]

A solution of 5-bromo-2-chloro-3-(trifluoromethyl)pyridine (250 mg, 0.960 mmol) and cyclohexanamine (571 mg, 5.76 mmol) in a CEM microwave vial was heated in a microwave at 140° C. for 4 h. The reaction mixture was cooled, poured into 1:1 saturated aqueous sodium bicarbonate/water solution and was extracted with ethyl acetate (2×). The combined organic extracts were dried over anhydrous Na₂SO₄, and concentrated to dryness. The residue was redissolved in DCM and purified by FCC (10% EtOAc/hexanes) to give the title compound.

382

Intermediate 2: Step A

N-((1r,3r)-3-Hydroxycyclobutyl)-4-((S)-2-methylpyrrolidine-1-carbonyl)thiazole-2-carboxamide

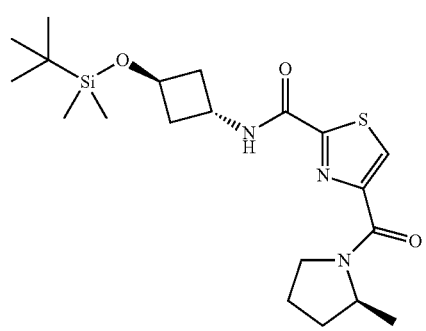 [SMILES: C[C@H]1CCCN1C(=O)c1csc(C(=O)N[C@H]2C[C@H](O[Si](C)(C)C(C)(C)C)C2)n1]

The title compound was prepared as described in Intermediate 73: Step C, using (1r,3r)-3-aminocyclobutanol in place of methyl 1-(aminomethyl)cyclobutanol.

Intermediate 2: Step B

N-((1r,3r)-3-((tert-Butyldimethylsilyl)oxy)cyclobutyl)-4-((S)-2-methylpyrrolidine-1-carbonyl)thiazole-2-carboxamide To a solution of N-((1r,3r)-3-hydroxycyclobutyl)-4-((S)-2-methylpyrrolidine-1-carbonyl)thiazole-2-carboxamide (300 mg, 1.0 mmol, Intermediate 2: Step A), TBSCl (220 mg, 1.5 mmol), and DCM (15 mL) was added imidazole (330 mg, 4.9 mmol) and this mixture was allowed to stir at rt for 16 hours. Water (20 mL) was then added to the reaction followed by extraction with DCM (30 mL×2). The combined organic extracts were dried over anhydrous sodium sulfate and concentrated to dryness. The residue was purified by FCC (0-5% DCM/MeOH) to give the title compound.

Intermediate 3

5-Bromo-N-cyclohexyl-4-(trifluoromethyl)pyridin-2-amine

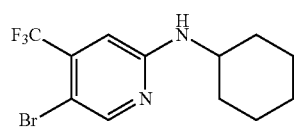 [SMILES: FC(F)(F)c1cc(NC2CCCCC2)ncc1Br]

The title compound was prepared as described in Intermediate 1, using 5-bromo-2-chloro-4-(trifluoromethyl)pyridine in place of 5-bromo-2-chloro-3-(trifluoromethyl)pyridine.

Intermediate 4

5-Bromo-N-cyclohexyl-3-(difluoromethyl)pyridin-2-amine

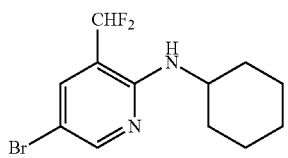 [SMILES: FC(F)c1cc(Br)cnc1NC1CCCCC1]

The title compound was prepared as described in Intermediate 1, using 5-bromo-2-chloro-3-(difluoromethyl)pyridine in place of 5-bromo-2-chloro-3-(trifluoromethyl)pyridine.

Intermediate 5

5-Bromo-3-(trifluoromethyl)-N-(3,3,3-trifluoropropyl)pyridin-2-amine

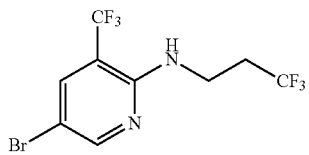 [SMILES: FC(F)(F)CCNc1ncc(Br)cc1C(F)(F)F]

The title compound was prepared as described in Intermediate 1, using 3,3,3-trifluoropropan-1-amine in place of cyclohexanamine.

Intermediate 6

5-Bromo-4-(trifluoromethyl)-N-(3,3,3-trifluoropropyl)pyridin-2-amine

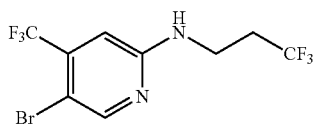

The title compound was prepared as described in Intermediate 1, using 3,3,3-trifluoropropan-1-amine in place of cyclohexanamine and 5-bromo-2-chloro-4-(trifluoromethyl)pyridine in place of 5-bromo-2-chloro-3-(trifluoromethyl)pyridine.

Intermediate 7

5-Bromo-N-cyclobutyl-4-(trifluoromethyl)pyridin-2-amine

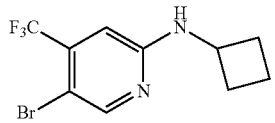 [SMILES: FC(F)(F)c1cc(NC2CCC2)ncc1Br]

The title compound was prepared as described in Intermediate 1, using cyclobutanamine in place of cyclohexanamine and 5-bromo-2-chloro-4-(trifluoromethyl)pyridine in place of 5-bromo-2-chloro-3-(trifluoromethyl)pyridine.

Intermediate 8

5-Bromo-N-cyclopentyl-4-(trifluoromethyl)pyridin-2-amine

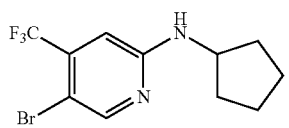 [SMILES: FC(F)(F)c1cc(NC2CCCC2)ncc1Br]

The title compound was prepared as described in Intermediate 1, using cyclopentanamine in place of cyclohexanamine and 5-bromo-2-chloro-4-(trifluoromethyl)pyridine in place of 5-bromo-2-chloro-3-(trifluoromethyl)pyridine.

Intermediate 9

5-Bromo-2-(cyclohexylamino)nicotinonitrile

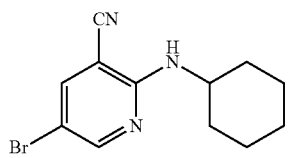 [SMILES: N#Cc1cc(Br)cnc1NC1CCCCC1]

The title compound was prepared as described in Intermediate 1, using 5-bromo-2-chloronicotinonitrile in place of 5-bromo-2-chloro-3-(trifluoromethyl)pyridine.

Intermediate 10

5-Bromo-N-cyclohexyl-3-methoxypyridin-2-amine

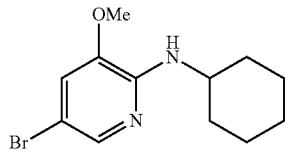 [SMILES: COc1cc(Br)cnc1NC1CCCCC1]

The title compound was prepared as described in Intermediate 1, using 5-bromo-2-chloro-3-methoxypyridine in place of 5-bromo-2-chloro-3-(trifluoromethyl)pyridine.

Intermediate 11

5-Bromo-N-isopropyl-4-(trifluoromethyl)pyridin-2-amine

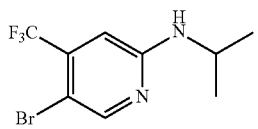

The title compound was prepared as described in Intermediate 1, using isopropylamine in place of cyclohexanamine and 5-bromo-2-chloro-4-(trifluoromethyl)pyridine in place of 5-bromo-2-chloro-3-(trifluoromethyl)pyridine.

Intermediate 12

5-Bromo-2-(cyclohexylamino)-4-methylnicotinonitrile

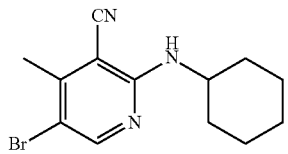 [SMILES: Cc1c(Br)cnc(NC2CCCCC2)c1C#N]

The title compound was prepared as described in Intermediate 1, using 5-bromo-2-chloro-4-methylnicotinonitrile in place of 5-bromo-2-chloro-3-(trifluoromethyl)pyridine.

Intermediate 13: Step A (S)-tert-Butyl 4,4-difluoro-2-methylpyrrolidine-1-carboxylate

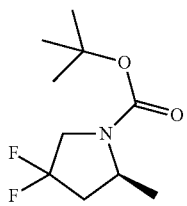

To a solution of triethylamine trihydrofluoride (0.82 mL, 5.0 mmol) and trimethylamine (0.35 mL, 2.5 mmol) in DCM (2 mL) at room temperature in an oven-dried microwave vial were successively added XtalFluor-E® (860 mg, 3.8 mmol) and (S)-1-Boc-2-methylpyrrolidin-4-one (500 mg in 1.9 mL DCE). The reaction was stirred at 80° C. for 90 min then was allowed to cool to room temperature and stirred at room temperature overnight. The reaction was next cooled to 0° C. and slowly quenched with saturated aqueous sodium bicarbonate and was stirred at room temperature for 15 minutes. The reaction was extracted with DCM (3×), dried over anhydrous magnesium sulfate, filtered over Celite®, and concentrated to dryness. The residue was purified by FCC (0-20% EtOAc/hexanes) to give the title compound as a brown oil.

Intermediate 13: Step B (S)-4,4-Difluoro-2-methylpyrrolidine hydrochloride

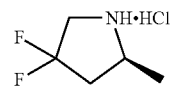

(S)-tert-Butyl 4,4-difluoro-2-methylpyrrolidine-1-carboxylate (790 mg, 3.6 mmol, Intermediate 13: Step A) was dissolved in HCl (4 M in 1,4-dioxane, 15 mL) and 1,4-dioxane (3.5 mL) at 0° C. and the resulting mixture was allowed to warm to rt and then was stirred at room temperature for 90 minutes. The reaction was concentrated to dryness to give the title compound as a light brown solid.

Intermediate 14

5-Bromo-2-(cyclohexylamino)isonicotinonitrile

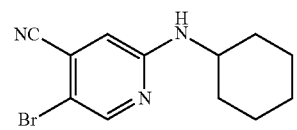 [SMILES: N#Cc1cc(NC2CCCCC2)ncc1Br]

The title compound was prepared as described in Intermediate 1, using 5-bromo-2-chloroisonicotinonitrile in place of 5-bromo-2-chloro-3-(trifluoromethyl)pyridine.

Intermediate 15

5-Bromo-N-cyclohexyl-4-(difluoromethyl)pyridin-2-amine

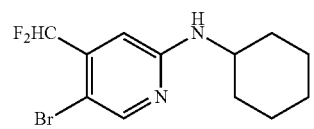 [SMILES: FC(F)c1cc(NC2CCCCC2)ncc1Br]

The title compound was prepared as described in Intermediate 1, using 5-bromo-2-chloro-4-(difluoromethyl)pyridine in place of 5-bromo-2-chloro-3-(trifluoromethyl)pyridine.

Intermediate 16

5-Bromo-N-cyclohexyl-3-(difluoromethoxy)pyridin-2-amine

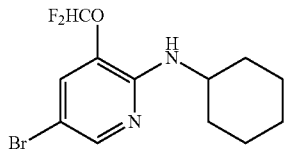 [SMILES: FC(F)Oc1cc(Br)cnc1NC1CCCCC1]

The title compound was prepared as described in Intermediate 1, using 5-bromo-2-chloro-3-(difluoromethoxy)pyridine in place of 5-bromo-2-chloro-3-(trifluoromethyl)pyridine.

Intermediate 17

(R)-5-Bromo-N-(1-cyclopropylethyl)-4-(trifluoromethyl)pyridin-2-amine

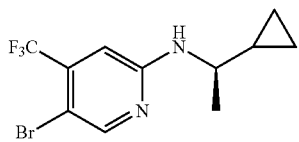 [SMILES: C[C@@H](Nc1cc(C(F)(F)F)c(Br)cn1)C1CC1]

The title compound was prepared as described in Intermediate 1, using (R)-1-cyclopropylethanamine in place of cyclohexanamine and 5-bromo-2-chloro-4-(trifluoromethyl)pyridine in place of 5-bromo-2-chloro-3-(trifluoromethyl)pyridine.

Intermediate 18

(S)-5-Bromo-N-(1-cyclopropylethyl)-4-(trifluoromethyl)pyridin-2-amine

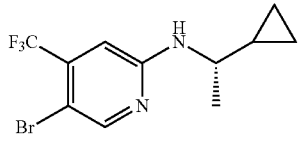 [SMILES: C[C@H](Nc1cc(C(F)(F)F)c(Br)cn1)C1CC1]

The title compound was prepared as described in Intermediate 1, using (S)-1-cyclopropylethanamine in place of cyclohexanamine and 5-bromo-2-chloro-4-(trifluoromethyl)pyridine in place of 5-bromo-2-chloro-3-(trifluoromethyl)pyridine.

Intermediate 19

5-Bromo-N-cyclopentyl-4-(difluoromethyl)pyridin-2-amine

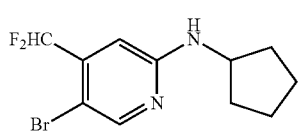 [SMILES: FC(F)c1cc(NC2CCCC2)ncc1Br]

The title compound was prepared as described in Intermediate 1, using cyclopentanamine in place of cyclohexanamine and 5-bromo-2-chloro-4-(difluoromethyl)pyridine in place of 5-bromo-2-chloro-3-(trifluoromethyl)pyridine.

Intermediate 20

(S)-5-Bromo-N-(1-cyclopropylethyl)-4-(difluoromethyl)pyridin-2-amine

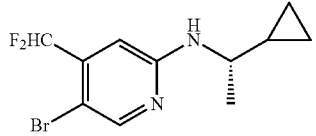 [SMILES: C[C@H](Nc1cc(C(F)F)c(Br)cn1)C1CC1]

The title compound was prepared as described in Intermediate 1, using (S)-1-cyclopropylethanamine in place of cyclohexanamine and 5-bromo-2-chloro-4-(difluoromethyl)pyridine in place of 5-bromo-2-chloro-3-(trifluoromethyl)pyridine.

Intermediate 21

(R)-5-Bromo-N-(1-cyclopropylethyl)-4-(difluoromethyl)pyridin-2-amine

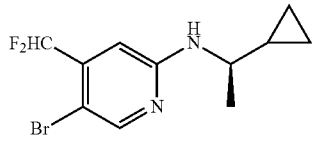 [SMILES: C[C@@H](Nc1cc(C(F)F)c(Br)cn1)C1CC1]

The title compound was prepared as described in Intermediate 1, using (R)-1-cyclopropylethanamine in place of cyclohexanamine and 5-bromo-2-chloro-4-(difluoromethyl)pyridine in place of 5-bromo-2-chloro-3-(trifluoromethyl)pyridine.

Intermediate 22

5-Bromo-N-neopentyl-4-(trifluoromethyl)pyridin-2-amine

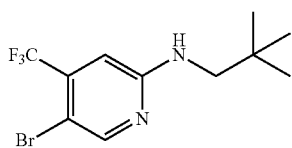 [SMILES: CC(C)(C)CNc1cc(C(F)(F)F)c(Br)cn1]

The title compound was prepared as described in Intermediate 1, using 5-bromo-2-chloro-4-(trifluoromethyl)pyrimidine in place of 5-bromo-2-chloro-3-(trifluoromethyl)pyridine and neopentylamine in place of cyclohexanamine.

Intermediate 23

5-Bromo-4-(difluoromethyl)-N-neopentylpyridin-2-amine

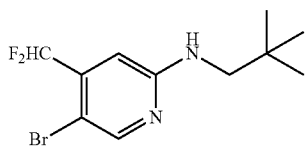 [SMILES: CC(C)(C)CNc1cc(C(F)F)c(Br)cn1]

The title compound was prepared as described in Intermediate 1, using 5-bromo-2-chloro-4-(difluoromethyl)pyridine in place of 5-bromo-2-chloro-3-(trifluoromethyl)pyridine and neopentylamine in place of cyclohexanamine.

Intermediate 24

5-Bromo-N-(1-cyclopropylpropyl)-4-(trifluoromethyl)pyridin-2-amine

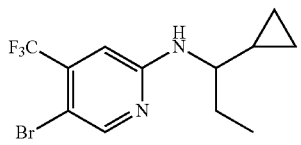 [SMILES: CCC(Nc1cc(C(F)(F)F)c(Br)cn1)C1CC1]

The title compound was prepared as described in Intermediate 1, using 5-bromo-2-chloro-4-(trifluoromethyl)pyridine in place of 5-bromo-2-chloro-3-(trifluoromethyl)pyridine and 1-cyclopropylpropan-1-amine in place of cyclohexanamine.

Intermediate 25

5-Bromo-N-(dicyclopropylmethyl)-4-(trifluoromethyl)pyridin-2-amine

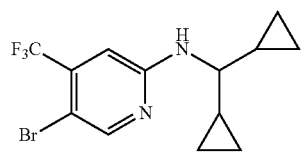 [SMILES: FC(F)(F)c1cc(NC(C2CC2)C2CC2)ncc1Br]

The title compound was prepared as described in Intermediate 1, using 5-bromo-2-chloro-4-(trifluoromethyl)pyridine in place of 5-bromo-2-chloro-3-(trifluoromethyl)pyridine and dicyclopropylmethanamine in place of cyclohexanamine.

Intermediate 26

5-Bromo-N-cyclohexyl-4-methoxypyridin-2-amine

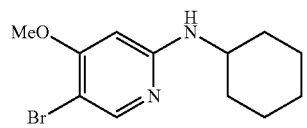 [SMILES: COc1cc(NC2CCCCC2)ncc1Br]

The title compound was prepared as described in Intermediate 1, using 5-bromo-2-chloro-4-(methoxy)pyridine in place of 5-bromo-2-chloro-3-(trifluoromethyl)pyridine.

Intermediate 27

5-Bromo-N-(3,3-difluorocyclohexyl)-3-(trifluoromethyl)pyridin-2-amine

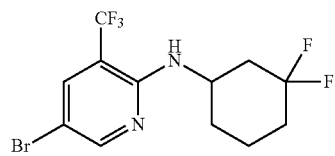 [SMILES: FC1(F)CCCC(Nc2ncc(Br)cc2C(F)(F)F)C1]

A solution of 5-bromo-2-chloro-3-(trifluoromethyl)pyridine (200 mg, 0.770 mmol), 3,3-difluorocyclohexanamine hydrochloride (395 mg, 2.30 mmol), DIPEA (0.53 mL, 3.1 mmol) and acetonitrile (2.0 mL) were combined in a CEM microwave vial and heated in a microwave at 140° C. for 4 h. The reaction mixture was cooled, poured into 1:1 saturated aqueous sodium bicarbonate/water solution and extracted with ethyl acetate (2×). The combined organic extracts were dried over anhydrous $Na_2SO_4$, and concentrated to dryness. The residue was purified by FCC (10% EtOAc/hexanes) to give the title compound.

Intermediate 28

5-Bromo-N-(3,3-difluorocyclobutyl)-3-(trifluoromethyl)pyridin-2-amine

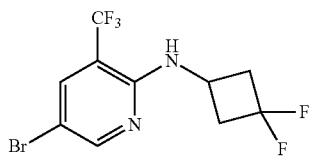 [SMILES: FC1(F)CC(Nc2ncc(Br)cc2C(F)(F)F)C1]

The title compound was prepared as described in Intermediate 27, using 3,3-difluorocyclobutanamine hydrochloride in place of 3,3-difluorocyclohexanamine hydrochloride.

Intermediate 29

5-Bromo-N-(4,4-difluorocyclohexyl)-4-(trifluoromethyl)pyridin-2-amine

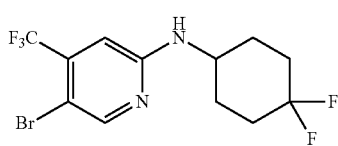 [SMILES: FC1(F)CCC(Nc2cc(C(F)(F)F)c(Br)cn2)CC1]

The title compound was prepared as described in Intermediate 27, using 4,4-difluorocyclohexanamine hydrochloride in place of 3,3-difluorocyclohexanamine hydrochloride and 5-bromo-2-chloro-4-(trifluoromethyl)pyridine in place of 5-bromo-2-chloro-3-(trifluoromethyl)pyridine.

Intermediate 30

5-Bromo-N-(3,3-difluorocyclopentyl)-4-(trifluoromethyl)pyridin-2-amine

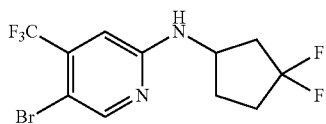 [SMILES: FC1(F)CCC(Nc2cc(C(F)(F)F)c(Br)cn2)C1]

The title compound was prepared as described in Intermediate 27, using 3,3-difluorocyclopentanamine hydrochloride in place of 3,3-difluorocyclohexanamine hydrochloride and 5-bromo-2-chloro-4-(trifluoromethyl)pyridine in place of 5-bromo-2-chloro-3-(trifluoromethyl)pyridine.

Intermediate 31

5-Bromo-N-(3,3-difluorocyclobutyl)-4-(trifluoromethyl)pyridin-2-amine

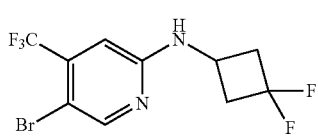 [SMILES: FC1(F)CC(Nc2cc(C(F)(F)F)c(Br)cn2)C1]

The title compound was prepared as described in Intermediate 27, using 3,3-difluorocyclobutanamine hydrochloride in place of 3,3-difluorocyclohexanamine hydrochloride and 5-bromo-2-chloro-4-(trifluoromethyl)pyridine in place of 5-bromo-2-chloro-3-(trifluoromethyl)pyridine.

Intermediate 32

5-Bromo-N-(6,6-difluorospiro[3.3]heptan-2-yl)-4-(trifluoromethyl)pyridin-2-amine

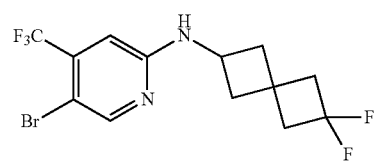 [SMILES: FC1(F)CC2(CC(Nc3cc(C(F)(F)F)c(Br)cn3)C2)C1]

The title compound was prepared as described in Intermediate 27, using 6,6-difluorospiro[3.3]heptan-2-amine hydrochloride in place of 3,3-difluorocyclohexanamine hydrochloride and 5-bromo-2-chloro-4-(trifluoromethyl)pyridine in place of 5-bromo-2-chloro-3-(trifluoromethyl)pyridine.

Intermediate 33

5-Bromo-N-(3,3-difluorocyclohexyl)-4-(trifluoromethyl)pyridin-2-amine

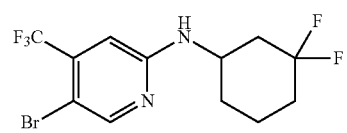 [SMILES: FC1(F)CCCC(Nc2cc(C(F)(F)F)c(Br)cn2)C1]

The title compound was prepared as described in Intermediate 27, using 5-bromo-2-chloro-4-(trifluoromethyl)pyridine in place of 5-bromo-2-chloro-3-(trifluoromethyl)pyridine.

Intermediate 34

5-Bromo-N-(spiro[3.3]heptan-2-yl)-4-(trifluoromethyl)pyridin-2-amine

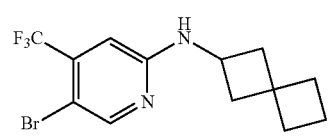 [SMILES: FC(F)(F)c1cc(NC2CC3(CCC3)C2)ncc1Br]

The title compound was prepared as described in Intermediate 27, using spiro[3.3]heptan-2-amine hydrochloride in place of 3,3-difluorocyclohexanamine hydrochloride and 5-bromo-2-chloro-4-(trifluoromethyl)pyridine in place of 5-bromo-2-chloro-3-(trifluoromethyl)pyridine.

Intermediate 35: Step A

N-Cyclohexyl-4-methylpyridin-2-amine

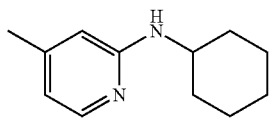

A mixture of 2-bromo-4-methylpyridine (500 mg, 2.91 mmol), cyclohexanamine (348 mg, 3.51 mmol), Pd$_2$(dba)$_3$ (28 mg, 0.030 mmol), BINAP (91 mg, 0.15 mmol), NaOt-Bu (563 mg, 5.86 mmol) and toluene (20 mL) in a 100 mL round bottom flask was heated to 100° C. for 4 h under a N$_2$ atmosphere. The crude reaction mixture was concentrated to dryness to give the title compound as a yellow solid which was used in the next step without further purification.

Intermediate 35: Step B

5-Bromo-N-cyclohexyl-4-methylpyridin-2-amine

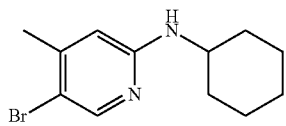

A mixture of N-cyclohexyl-4-methylpyridin-2-amine (200 mg, 1.05 mmol, Intermediate 35: Step A), NBS (185 mg, 1.04 mmol) and DCM (10 mL) in a round bottom flask was stirred at rt overnight. The mixture was concentrated, the residue was re-dissolved in DCM and purified by FCC (5% EtOAc/petroleum ether) to give the title compound as yellow solid.

Intermediate 36

5-Bromo-N-cyclohexyl-4-cyclopropylpyridin-2-amine

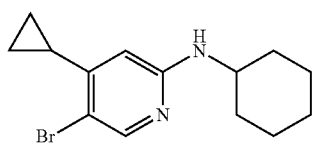 [SMILES: Brc1cnc(NC2CCCCC2)cc1C1CC1]

The title compound was prepared as described in Intermediate 35, using 2-bromo-4-cyclopropylpyridine in place of 2-bromo-4-methylpyridine in Step A.

Intermediate 37

5-Bromo-N-cyclohexyl-4-isopropylpyridin-2-amine

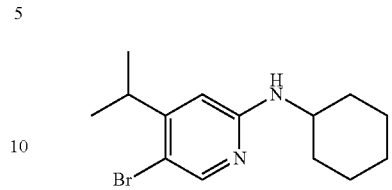

The title compound was prepared as described in Intermediate 35, using 2-bromo-4-isopropylpyridine in place of 2-bromo-4-methylpyridine in Step A.

Intermediate 38

5-Bromo-N-cyclohexyl-3-fluoro-4-methylpyridin-2-amine

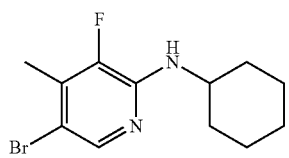 [SMILES: Cc1c(Br)cnc(NC2CCCCC2)c1F]

The title compound was prepared as described in Intermediate 35, using 2-bromo-3-fluoro-4-methylpyridine in place of 2-bromo-4-methylpyridine in Step A.

Intermediate 39: Step A

N-Cyclohexyl-4-ethoxypyridin-2-amine

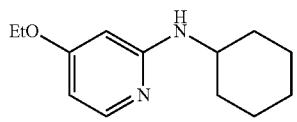 [SMILES: CCOc1ccnc(NC2CCCCC2)c1]

A mixture of 2-chloro-4-ethoxypyridine (200 mg, 1.3 mmol), cyclohexanamine (152 mg, 1.47 mmol), Pd$_2$(dba)$_3$ (12 mg, 0.013 mmol), BINAP (40 mg, 0.064 mmol), NaOt-Bu (244 mg, 2.53 mmol) and toluene (5 mL) in a 50 mL round bottom flask fitted with a reflux condenser was heated at 100° C. for 4 h under a N$_2$ atmosphere. The crude reaction mixture was concentrated to dryness to give the title compound as a red oil that was used in subsequent reactions without further purification.

Intermediate 39: Step B

5-Bromo-N-cyclohexyl-4-ethoxypyridin-2-amine

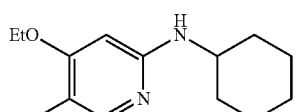

A mixture of N-cyclohexyl-4-ethoxypyridin-2-amine (154 mg, 0.676 mmol, Intermediate 39: Step A), NBS (123 mg, 0.676 mmol) and DCM (10 mL) in a 50 mL round bottom flask was stirred at rt overnight. The mixture was concentrated to dryness, the residue redissolved in DCM and purified by FCC (5% EtOAc/petroleum ether) to give the title compound as white solid.

Intermediate 40

5-Bromo-N-cyclohexyl-4-ethylpyridin-2-amine

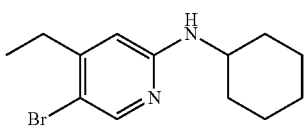 [SMILES: CCc1cc(NC2CCCCC2)ncc1Br]

The title compound was prepared as described in Intermediate 39, using 2-chloro-4-ethylpyridine in place of 2-chloro-4-ethoxypyridine in Step A.

Intermediate 41: Step A

N-(tert-Butyl)-4-(trifluoromethyl)pyridin-2-amine

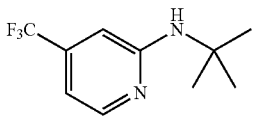

To an oven-dried vial under $N_2$ was added sodium tert-butoxide (1.40 g, 14.6 mmol), BINAP (427 mg, 0.690 mmol), and $Pd_2(dba)_3$ (312 mg, 0.340 mmol). To this mixture was then added a solution of tert-butylamine (1.00 g, 13.7 mmol) and 2-bromo-4-(trifluoromethyl)pyridine (1.50 g, 6.63 mmol) in THF (15.0 mL, THF was sparged with $N_2$ for 1 h before use). The vial was then capped and heated to 120° C. for 2 h. The reaction was poured into saturated aqueous sodium bicarbonate and then extracted with ethyl acetate (2×). The combined organic layers were dried over anhydrous sodium sulfate and concentrated to dryness, providing an orange oil that was used in the next step without further purification.

Intermediate 41: Step B

5-Bromo-N-(tert-butyl)-4-(trifluoromethyl)pyridin-2-amine

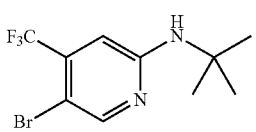 [SMILES: CC(C)(C)Nc1cc(C(F)(F)F)c(Br)cn1]

To a 300 mL round bottom flask under nitrogen was added N-(tert-butyl)-4-(trifluoromethyl)pyridin-2-amine (3.0 g, 14 mmol, Intermediate 41: Step A), NBS (1.9 g, 11 mmol) and DCM (100 mL). The reaction was stirred at rt for 18 h. then poured into saturated aqueous bicarbonate and extracted with ethyl acetate (2×). The combined organic layers were dried (sodium sulfate), filtered and concentrated to dryness. The crude residue was dissolved in DCM and purified by FCC (10% EtOAc/hexanes) to provide the title compound.

Intermediate 42

5-Bromo-4-(trifluoromethyl)-N-(1,1,1-trifluoropropan-2-yl)pyridin-2-amine

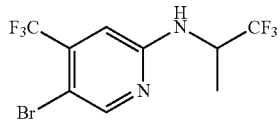 [SMILES: CC(Nc1cc(C(F)(F)F)c(Br)cn1)C(F)(F)F]

The title compound was prepared as described in Intermediate 41, using 1,1,1-trifluoropropan-2-amine in place of tert-butylamine in Step A.

Intermediate 43

(R)-5-Bromo-4-(trifluoromethyl)-N-(1,1,1-trifluoropropan-2-yl)pyridin-2-amine

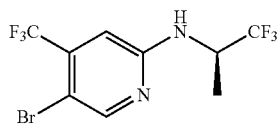

The title compound was prepared as described in Intermediate 41, using (R)-1,1,1-trifluoropropan-2-amine in place of tert-butylamine in Step A.

Intermediate 44

(S)-5-Bromo-4-(trifluoromethyl)-N-(1,1,1-trifluoropropan-2-yl)pyridin-2-amine

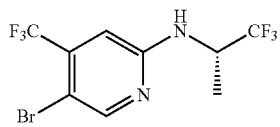 [SMILES: C[C@H](Nc1cc(C(F)(F)F)c(Br)cn1)C(F)(F)F]

The title compound was prepared as described in Intermediate 41, using (S)-1,1,1-trifluoropropan-2-amine in place of tert-butylamine in Step A.

Intermediate 45

5-Bromo-N-(2-cyclopropylpropan-2-yl)-4-(trifluoromethyl)pyridin-2-amine

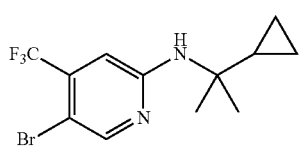 [SMILES: CC(C)(Nc1cc(C(F)(F)F)c(Br)cn1)C1CC1]

The title compound was prepared as described in Intermediate 41, using 2-cyclopropylpropan-2-amine in place of tert-butylamine in Step A.

Intermediate 46

5-Bromo-N-(1-methylcyclobutyl)-4-(trifluoromethyl)pyridin-2-amine

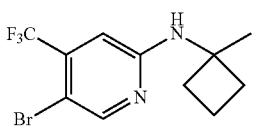

The title compound was prepared as described in Intermediate 41, using 1-methylcyclobutanamine hydrochloride in place of tert-butylamine in Step A.

Intermediate 47

5-Bromo-N-(2,2-difluorocyclohexyl)-4-(trifluoromethyl)pyridin-2-amine

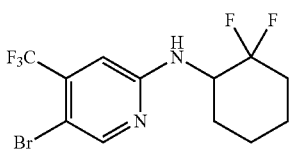

The title compound was prepared as described in Intermediate 41, using 2,2-difluorocyclohexanamine hydrochloride in place of tert-butylamine in Step A.

Intermediate 48

5-Bromo-N-(2-cyclopropylpropan-2-yl)-4-(difluoromethyl)pyridin-2-amine

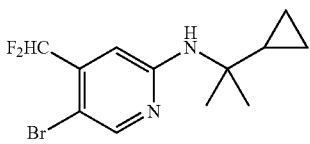 [SMILES: CC(C)(Nc1cc(C(F)F)c(Br)cn1)C1CC1]

The title compound was prepared as described in Intermediate 41, using 2-cyclopropylpropan-2-amine in place of tert-butylamine and 2-bromo-4-(difluoromethyl)pyridine in place of 2-bromo-4-(trifluoromethyl)pyridine in Step A.

Intermediate 49

(S)-5-Bromo-4-(difluoromethyl)-N-(1,1,1-trifluorobutan-2-yl)pyridin-2-amine

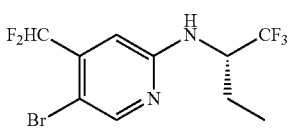 [SMILES: CC[C@H](Nc1cc(C(F)F)c(Br)cn1)C(F)(F)F]

The title compound was prepared as described in Intermediate 41, using (S)-1-trifluoromethyl-propylamine in place of tert-butylamine and 2-bromo-4-(difluoromethyl)pyridine in place of 2-bromo-4-(trifluoromethyl)pyridine in Step A.

Intermediate 50

5-Bromo-4-(difluoromethyl)-N-(tert-pentyl)pyridin-2-amine

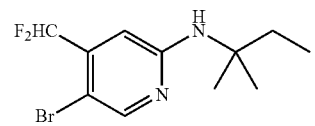 [SMILES: CCC(C)(C)Nc1cc(C(F)F)c(Br)cn1]

The title compound was prepared as described in Intermediate 41, using tert-amylamine in place of tert-butylamine and 2-bromo-4-(difluoromethyl)pyridine in place of 2-bromo-4-(trifluoromethyl)pyridine in Step A.

Intermediate 51

5-Bromo-N-(tert-pentyl)-4-(trifluoromethyl)pyridin-2-amine

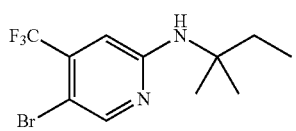 [SMILES: CCC(C)(C)Nc1cc(C(F)(F)F)c(Br)cn1]

The title compound was prepared as described in Intermediate 41, using tert-amylamine in place of tert-butylamine in Step A.

Intermediate 52

5-Bromo-4-(trifluoromethyl)-N-(1-(trifluoromethyl)cyclobutyl)pyridin-2-amine

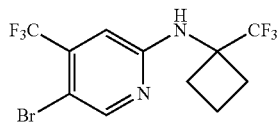

The title compound was prepared as described in Intermediate 41, using 1-(trifluoromethyl)cyclobutan-1-amine in place of tert-butylamine in Step A.

Intermediate 53

(S)-5-Bromo-N-(1,1,1-trifluorobutan-2-yl)-4-(trifluoromethyl)pyridin-2-amine

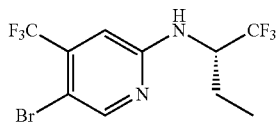

The title compound was prepared as described in Intermediate 41, using (S)-1-trifluoromethyl-propylamine in place of tert-butylamine in Step A.

Intermediate 54

5-Bromo-4-(trifluoromethyl)-N-((1-(trifluoromethyl)cyclobutyl)methyl)pyridin-2-amine

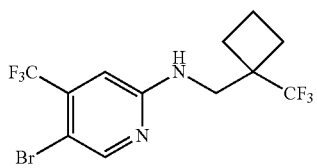 [SMILES: FC(F)(F)c1cc(NCC2(C(F)(F)F)CCC2)ncc1Br]

The title compound was prepared as described in Intermediate 41, using (1-(trifluoromethyl)cyclobutyl)methanamine in place of tert-butylamine in Step A.

Intermediate 55

5-Bromo-N-(3,3,3-trifluoro-2,2-dimethylpropyl)-4-(trifluoromethyl)pyridin-2-amine

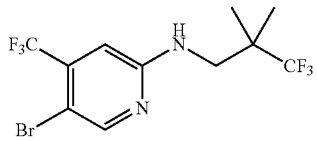

The title compound was prepared as described in Intermediate 41, using 3,3,3-trifluoro-2,2-dimethylpropan-1-amine in place of tert-butylamine in Step A.

Intermediate 56

5-Bromo-4-(difluoromethyl)-N-(1-(trifluoromethyl)cyclobutyl)pyridin-2-amine

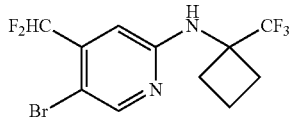 [SMILES: FC(F)c1cc(NC2(C(F)(F)F)CCC2)ncc1Br]

The title compound was prepared as described in Intermediate 41, using 1-(trifluoromethyl)cyclobutan-1-amine in place of tert-butylamine and 2-bromo-4-(difluoromethyl)pyridine in place of 2-bromo-4-(trifluoromethyl)pyridine in Step A.

Intermediate 57

5-Bromo-4-(trifluoromethyl)-N-((1-(trifluoromethyl)cyclopropyl)methyl)pyridin-2-amine

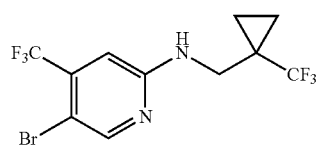 [SMILES: FC(F)(F)c1cc(NCC2(C(F)(F)F)CC2)ncc1Br]

The title compound was prepared as described in Intermediate 41, using (1-(trifluoromethyl)cyclopropyl)methanamine in place of tert-butylamine in Step A.

Intermediate 58

5-Bromo-N-(1,1,1-trifluoro-2-methylpropan-2-yl)-4-(trifluoromethyl)pyridin-2-amine

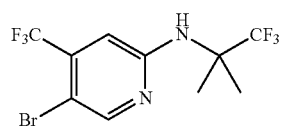

The title compound was prepared as described in Intermediate 41, using 1,1,1-trifluoro-2-methylpropan-2-amine in place of tert-butylamine in Step A.

Intermediate 59

5-Bromo-N-(tert-butyl)-4-(difluoromethyl)pyridin-2-amine

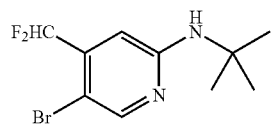

The title compound was prepared as described in Intermediate 41, using 2-bromo-4-(difluoromethyl)pyridine in place of 2-bromo-4-(trifluoromethyl)pyridine in Step A.

Intermediate 60

(S)-5-Bromo-4-(difluoromethyl)-N-(1,1,1-trifluoropropan-2-yl)pyridin-2-amine

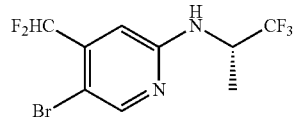 [SMILES: C[C@H](Nc1cc(C(F)F)c(Br)cn1)C(F)(F)F]

The title compound was prepared as described in Intermediate 41, using 2-bromo-4-(difluoromethyl)pyridine in place of 2-bromo-4-(trifluoromethyl)pyridine and (9-1,1,1-trifluoropropan-2-amine in place of tert-butylamine in Step A.

Intermediate 61: Step A 2-(Cyclohexylamino)-4-(trifluoromethyl)nicotinonitrile

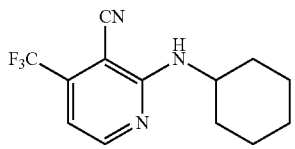 [SMILES: N#Cc1c(C(F)(F)F)ccnc1NC1CCCCC1]

A solution of 2-bromo-4-(trifluoromethyl)nicotinonitrile (250 mg, 0.996 mmol), cyclohexanamine (119 mg, 1.20 mmol), Pd$_2$(dba)$_3$ (10 mg, 0.011 mmol), BINAP (32 mg, 0.051 mmol), NaOt-Bu (193 mg, 2.00 mmol), and toluene (5 mL) in a 50 mL round bottom flask fitted with a reflux condenser was heated at 100° C. for 4 h under a N$_2$ atmosphere. The crude reaction mixture was concentrated to dryness to give the title compound which was used in the next step without purification.

Intermediate 61: Step B

5-Bromo-2-(cyclohexylamino)-4-(trifluoromethyl)nicotinonitrile

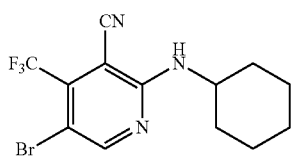 [SMILES: N#Cc1c(NC2CCCCC2)ncc(Br)c1C(F)(F)F]

A solution of 2-(cyclohexylamino)-4-(trifluoromethyl)nicotinonitrile (100 mg, 0.371 mmol, Intermediate 61: Step A), bromine (1 mL) and acetic acid (12 mL) was stirred at rt overnight in a 50 mL round bottom flask under N$_2$. The reaction mixture was poured into a solution of saturated aqueous Na$_2$S$_2$O$_3$ (10 mL), extracted with ethyl acetate (2×20 mL), dried over anhydrous MgSO$_4$, and concentrated to dryness. The residue was purified by FCC (5% EtOAc/petroleum ether) to give the title compound.

Intermediate 62: Step A

Ethyl (S)-5-(6-(cyclopentylamino)-4-(difluoromethyl)pyridin-3-yl)-4-(2-methylpyrrolidine-1-carbonyl)thiazole-2-carboxylate

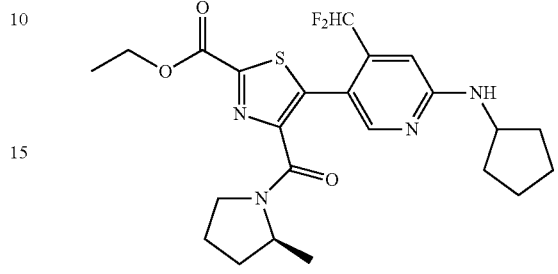

5-Bromo-N-cyclopentyl-4-(difluoromethyl) pyridin-2-amine (870 mg, 3.0 mmol, Intermediate 19), (S)-ethyl 4-(2-methylpyrrolidine-1-carbonyl)thiazole-2-carboxylate (720 mg, 2.7 mmol, Intermediate 73, Step A), Pd(OAc)$_2$ (67 mg, 0.30 mmol), PCy$_3$·HBF$_4$ (220 mg, 0.60 mmol), pivalic acid (122 mg, 1.20 mmol), K$_2$CO$_3$ (1.66 g, 12.0 mmol), and DMA (10 mL) were added to a 20 mL microwave tube under Ar. The resultant mixture was sparged with Ar for 5 minutes and then stirred at 120° C. in the microwave for 1 hour. The crude reaction was cooled to room temperature and concentrated to dryness to give the crude product. Purification by FCC (10-50% petroleum ether/EtOAc) then afforded the title compound as a white solid.

Intermediate 62: Step B

Potassium (S)-5-(6-(cyclopentylamino)-4-(difluoromethyl)pyridin-3-yl)-4-(2-methylpyrrolidine-1-carbonyl)thiazole-2-carboxylic acid

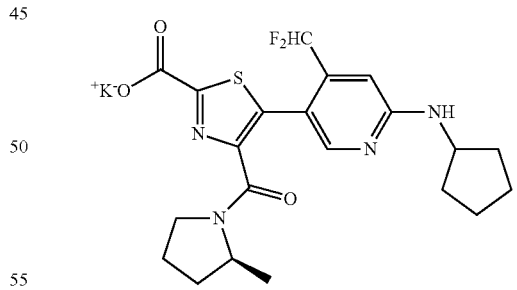

t-BuOK (140 mg, 1.2 mmol) was added to a mixture consisting of (5)-ethyl 5-(6-(cyclopentylamino)-4-(difluoromethyl)pyridin-3-yl)-4-(2-methylpyrrolidine-1-carbonyl)thiazole-2-carboxylate (540 mg, 1.1 mmol, Intermediate 62: Step A), H$_2$O (0.5 mL), and THF (2 mL) in a 25 mL round bottom flask. The resultant mixture was stirred at 60° C. for 2 hours before diluting with H$_2$O (20 mL) and extracting with dichloromethane (20 mL×2). The aqueous layer was frozen using dry ice/acetone and then lyophilized to dryness to afford the title compound as a white solid.

Intermediate 63: Step A 4-(Trifluoromethyl)-N-(1-(trifluoromethyl)cyclopropyl)pyridin-2-amine

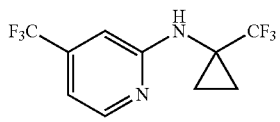 [SMILES: FC(F)(F)c1ccnc(NC2(C(F)(F)F)CC2)c1]

To an oven-dried vial under N₂ was added sodium tert-butoxide (357 mg, 3.70 mmol), BINAP (111 mg, 0.180 mmol) and Pd₂(dba)₃ (81 mg, 0.088 mmol). Then, a solution of 1-(trifluoromethyl)cyclopropanamine (464 mg, 3.60 mmol) and 2-bromo-4-(trifluoromethyl)pyridine (400 mg, 1.77 mmol) in THF (3.9 mL) was added and the resulting mixture was stirred at rt for 3.5 hours. The mixture was partitioned between saturated aqueous NaHCO₃ (30 mL) and EtOAc (30 mL), and the aqueous layer was further extracted with EtOAc (2×25 mL). The organic layers were combined, dried over anhydrous Na₂SO₄, filtered and concentrated to dryness to provide the title compound as a yellow-orange oil, which was used without further purification.

Intermediate 63: Step B

5-Bromo-4-(trifluoromethyl)-N-(1-(trifluoromethyl)cyclopropyl)pyridin-2-amine

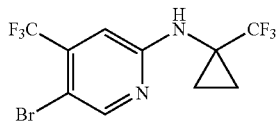

The title compound was prepared as described in Intermediate 41: Step B, using 4-(trifluoromethyl)-N-(1-(trifluoromethyl)cyclopropyl)pyridin-2-amine (Intermediate 63: Step A) in place of N-(tert-butyl)-4-(trifluoromethyl)pyridin-2-amine.

Intermediate 64: Step A

N-(2,2-Difluorocyclopentyl)-4-(trifluoromethyl)pyridin-2-amine

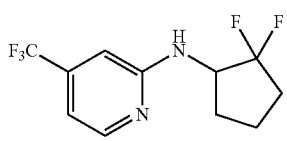 [SMILES: FC(F)(F)c1ccnc(NC2CCCC2(F)F)c1]

To an oven-dried vial under N₂ was added 2,2-difluorocyclopentan-1-amine.HCl (400 mg, 2.40 mmol) and NaHCO₃ (213 mg, 2.50 mmol). Then a mixture of 2-fluoro-4-(trifluoromethyl)pyridine (203 mg, 1.20 mmol) in DMSO (2 mL, sparged with nitrogen for 1 hour prior to addition) was added and the resulting mixture was stirred at 140° C. for 20 hours. The mixture was cooled to rt and partitioned between saturated aqueous NaHCO₃ (20 mL) and EtOAc (20 mL). The layers were separated and the aqueous layer further extracted with EtOAc (20 mL). The organic layers were combined, washed with water (2×15 mL), dried over anhydrous Na₂SO₄, filtered and concentrated to dryness to provide the title compound as a brown oil, which was taken on without further purification.

Intermediate 64: Step B

5-Bromo-N-(2,2-difluorocyclopentyl)-4-(trifluoromethyl)pyridin-2-amine

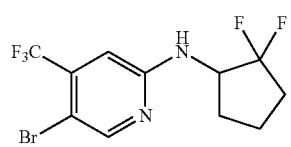 [SMILES: FC(F)(F)c1cc(NC2CCCC2(F)F)ncc1Br]

The title compound was prepared as described in Intermediate 41: Step B, using N-(2,2-difluorocyclopentyl)-4-(trifluoromethyl)pyridin-2-amine (Intermediate 64: Step A) in place of N-(tert-butyl)-4-(trifluoromethyl)pyridin-2-amine.

Intermediate 65: Step A 2-(Ethoxycarbonyl)thiazole-4-carboxylic acid

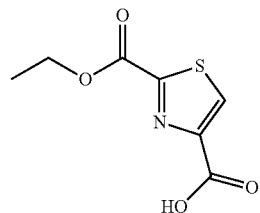

To a 3-neck, 200 mL round bottom flask under nitrogen was added 3-bromo-2-oxopropanoic acid (5 g, 30 mmol) and anhydrous 1,4-dioxane (50 mL). To this mixture was added ethyl 2-amino-2-thioxoacetate (4.1 g, 31 mmol) and the mixture heated at 50° C. for 1.5 h. The reaction was concentrated to dryness, the residue was dissolved in saturated aqueous NaHCO₃ (100 mL) and water (100 mL), and the aqueous solution extracted with ethyl acetate (4×100 mL). The aqueous layer was acidified to pH ~2 with concentrated HCl. After precipitate formation (~20 min) the aqueous mixture was extracted with ethyl acetate (3×100 mL). The combined organic layers were dried over anhydrous sodium sulfate and concentrated to dryness to give the title compound as a red solid, which was used in next step without further purification.

Intermediate 65: Step B

Ethyl 4-(4-fluoropiperidine-1-carbonyl)thiazole-2-carboxylate

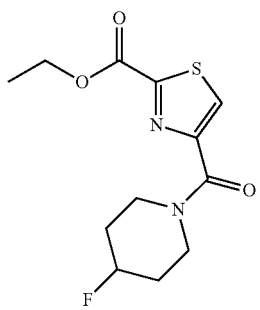 [SMILES: CCOC(=O)c1nc(C(=O)N2CCC(F)CC2)cs1]

To a 200 mL round bottom flask under N₂ was added 2-(ethoxycarbonyl)thiazole-4-carboxylic acid (2.5 g, 12 mmol, Intermediate 65: Step A) and DMF (65 mL). Once the acid was in solution, PyBOP (9.7 g, 19 mmol) and methylmorpholine (2.9 g, 29 mmol) were added. After 10 min. 4-fluoropiperidine (2.3 g, 16 mmol) was added and the reaction was allowed to stir overnight at rt. The reaction was then diluted with ethyl acetate, washed with saturated aqueous sodium bicarbonate (1×), water (2×), and brine (1×), dried over anhydrous Na₂SO₄, filtered and concentrated to dryness. The residue was dissolved in DCM and purified by FCC (0-80% EtOAc/hexanes) to give the title compound.

Intermediate 65: Step C 4-(4-Fluoropiperidine-1-carbonyl)-N-(2-hydroxy-2-methylpropyl)thiazole-2-carboxamide

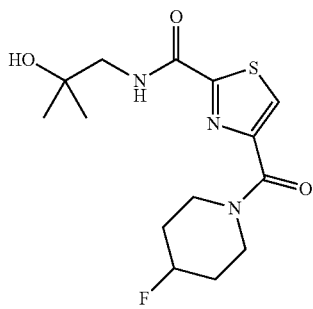 [SMILES: CC(C)(O)CNC(=O)c1nc(C(=O)N2CCC(F)CC2)cs1]

To a 100-mL round bottom flask was added ethyl 4-(4-fluoropiperidine-1-carbonyl)thiazole-2-carboxylate (0.76 g, 2.6 mmol, Intermediate 65: Step B) and toluene (13 mL). A solution of 1-amino-2-methylpropan-2-ol (473 mg, 5.31 mmol) in toluene (5 mL) was then added to the reaction mixture, followed by K₂CO₃ (0.73 g, 5.3 mmol). The reaction was heated to 90° C. and allowed to stir at that temperature for 18 h. The reaction was cooled, diluted with water, and extracted with ethyl acetate (3×). The combined organic layers were washed with water, followed by brine, then dried over anhydrous Na₂SO₄ and concentrated to dryness. The residue was dissolved in DCM and purified by FCC (0-80% EtOAc/hexanes) to give the title compound.

Intermediate 66: Step A 4-tert-Butyl 2-ethyl thiazole-2,4-dicarboxylate

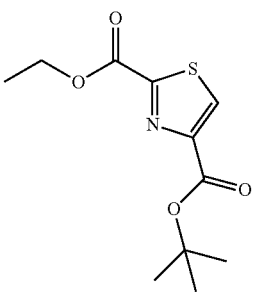 [SMILES: CCOC(=O)c1nc(C(=O)OC(C)(C)C)cs1]

A round bottom flask under N₂ containing 2-(ethoxycarbonyl)thiazole-4-carboxylic acid (2.0 g, 9.9 mmol, Intermediate 65: Step A), tert-BuOH (18 mL, 190 mmol), and pyridine (5 mL) was cooled to 0° C. in an ice bath, and then TsCl (4.4 g, 23 mmol) was added in one portion. The reaction was allowed to warm to rt gradually over 1 h and stirred for 18 h. The reaction was quenched by the addition of saturated aqueous potassium carbonate (100 mL) and water (100 mL) and the mixture stirred for 30 min. The mixture was then extracted with ether (3×100 mL) and the combined organic layers were washed with 5% saturated aqueous K₂CO₃ (2×100 mL) and 5% saturated aqueous K₂CO₃ in brine (1×100 mL). The combined organic layers were then dried over anhydrous Na₂SO₄, and concentrated to dryness. The residue was purified by FCC (0-80% EtOAc/hexanes) to give the title compound.

Intermediate 66: Step B tert-Butyl 2-((2-hydroxy-2-methylpropyl)carbamoyl)thiazole-4-carboxylate

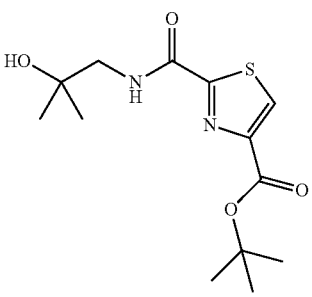 [SMILES: CC(C)(O)CNC(=O)c1nc(C(=O)OC(C)(C)C)cs1]

The title compound was prepared as described in Example 65, Step C, using 4-tert-butyl 2-ethyl thiazole-2,4-dicarboxylate (Intermediate 66: Step A) in place of ethyl 4-(4-fluoropiperidine-1-carbonyl)thiazole-2-carboxylate.

Intermediate 66: Step C 2-((2-Hydroxy-2-methylpropyl)carbamoyl)thiazole-4-carboxylic acid

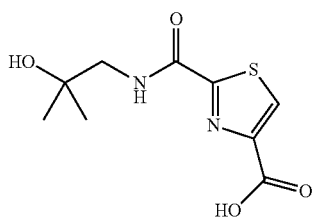 [SMILES: CC(C)(O)CNC(=O)c1nc(C(=O)O)cs1]

A solution of tert-butyl 2-((2-hydroxy-2-methylpropyl)carbamoyl)thiazole-4-carboxylate (1.0 g, 3.3 mmol, Intermediate 66: Step B) in 1:1 TFA:DCM (20 mL) was allowed to stand for 1 h. The reaction was concentrated to dryness and the residue was placed under high vacuum overnight to give the title compound, which was used in next step without purification.

Intermediate 66: Step D (S)—N-(2-Hydroxy-2-methylpropyl)-4-(2-methylpiperidine-1-carbonyl)thiazole-2-carboxamide

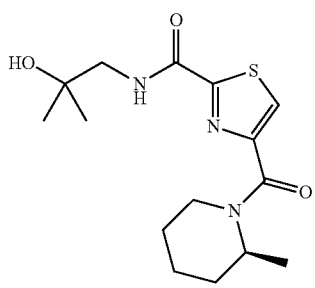 [SMILES: C[C@H]1CCCCN1C(=O)c1csc(C(=O)NCC(C)(C)O)n1]

To a 100 mL round bottom flask under nitrogen containing 2-((2-hydroxy-2-methylpropyl)carbamoyl)thiazole-4-carboxylic acid (806 mg, 3.30 mmol, Intermediate 66: Step C) was added, DMF (20 mL) followed by PyBOP (2.6 g, 5.0 mmol) and methylmorpholine (1.10 g, 10.9 mmol). After 10 min. (S)-2-methylpiperidine (491 mg, 4.90 mmol) was added and the reaction allowed to stir overnight at rt. The reaction was poured into ethyl acetate and washed with water (3×) and brine (1×). The organic layer was dried over anhydrous sodium sulfate and concentrated to dryness. The crude residue was dissolved in DCM and purified by FCC (0-50% EtOAc/hexanes) to provide the title compound.

Intermediate 67

(S)-4-(4,4-Difluoro-2-methylpyrrolidine-1-carbonyl)-N-(2-hydroxy-2-methylpropyl)thiazole-2-carboxamide

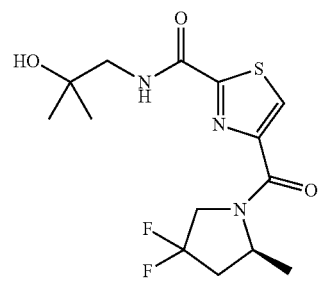 [SMILES: C[C@H]1CC(F)(F)CN1C(=O)c1csc(C(=O)NCC(C)(C)O)n1]

The title compound was prepared as described in Intermediate 66: Step D, using (S)-4,4-difluoro-2-methylpyrrolidine hydrochloride (Intermediate 13: Step B) in place of (S)-2-methylpiperidine.

Intermediate 68

(S)—N-(2-Hydroxy-2-methylpropyl)-4-(2-methylazetidine-1-carbonyl)thiazole-2-carboxamide

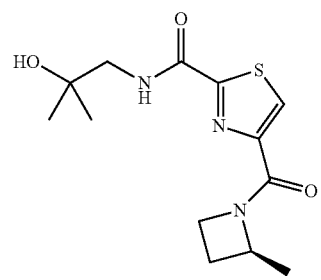 [SMILES: C[C@H]1CCN1C(=O)c1csc(C(=O)NCC(C)(C)O)n1]

The title compound was prepared as described in Intermediate 66: Step D, using (S)-2-methylazetidine hydrochloride in place of (S)-2-methylpiperidine.

Intermediate 69

(S)—N-2-Hydroxy-2-methylpropyl)-4-(2-methylpyrrolidine-1-carbonyl)thiazole-2-carboxamide

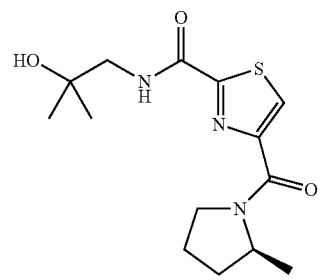 [SMILES: C[C@H]1CCCN1C(=O)c1csc(C(=O)NCC(C)(C)O)n1]

The title compound was prepared as described in Intermediate 66: Step D, using (S)-2-methylpyrrolidine in place of (S)-2-methylpiperidine.

Intermediate 70: Step A

Ethyl-4-((1s,4s)-7-azabicyclo[2.2.1]heptane-7-carbonyl)thiazole-2-carboxylate

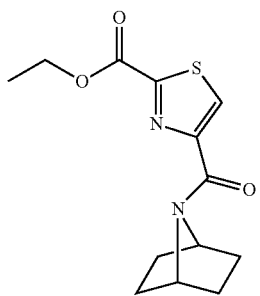 [SMILES: CCOC(=O)c1nc(C(=O)N2C3CCC2CC3)cs1]

In a 200 mL round bottom flask under N₂ was added 2-(ethoxycarbonyl)thiazole-4-carboxylic acid (6.0 g, 30 mmol, Intermediate 65, Step A) and methyl THP (70 mL). This mixture was cooled to 0° C. then (1s,4s)-7-azabicyclo[2.2.1]heptane was added (4.4 g, 33 mmol). Propyl phosphonic anhydride solution (>50% by wt. % in EtOAc) was then added (28 mL, 44 mmol) followed by addition of DIPEA (16 mL, 95 mmol). The mixture was allowed to warm to rt and stirred at rt for 18 h. The reaction was then poured into saturated aqueous sodium bicarbonate and extracted with ethyl acetate (4×). The combined organic layers were washed with brine (1×), dried over anhydrous sodium sulfate and concentrated to dryness to provide the title compound, which was used in next step without further purification.

Intermediate 70: Step B 4-((1s,4s)-7-Azabicyclo[2.2.1]heptane-7-carbonyl)-N-(2-hydroxy-2-methylpropyl)thiazole-2-carboxamide

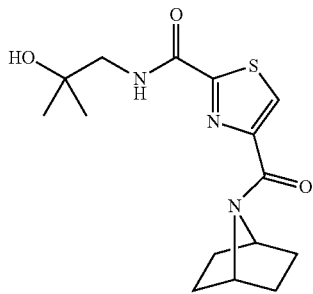 [SMILES: CC(C)(O)CNC(=O)c1nc(C(=O)N2C3CCC2CC3)cs1]

In a 2-neck 200 mL flask under N₂ was added ethyl-4-((1s,4s)-7-azabicyclo[2.2.1]heptane-7-carbonyl)thiazole-2-carboxylate (9.5 g, 34 mmol, Intermediate 70, Step A), 1-amino-2-methylpropan-2-ol (13.3 g, 149 mmol) and EtOH (100 mL), and the reaction was stirred at rt for 18 h. The reaction mixture was then poured into saturated aqueous sodium bicarbonate and extracted with EtOAc (5×). The combined organic layers were washed with brine (1×), dried over anhydrous sodium sulfate and concentrated to dryness. The crude residue was dissolved in DCM and purified by FCC (0-10% DCM/MeOH) to provide the title compound.

Intermediate 71

4-(4,4-Difluoropiperidine-1-carbonyl)-N-(3-hydroxy-3-methylbutyl)thiazole-2-carboxamide

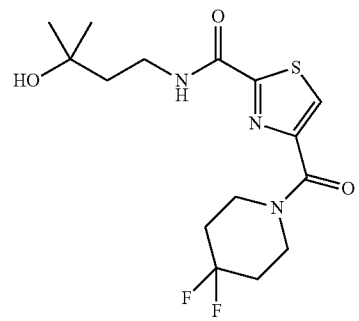 [SMILES: CC(C)(O)CCNC(=O)c1nc(C(=O)N2CCC(F)(F)CC2)cs1]

The title compound was prepared as described in Intermediate 70, using 4,4-difluoropiperidine in place of (1s,4s)-7-azabicyclo[2.2.1]heptane in step A and 4-amino-2-methylbutan-2-ol in place of 1-amino-2-methylpropan-2-ol in step B.

Intermediate 72: Step A 4-(tert-Butoxycarbonyl)thiazole-2-carboxylic acid

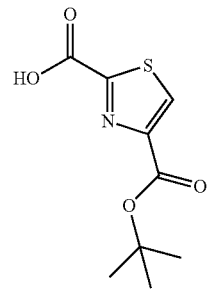

To a solution of 4-tert-butyl 2-ethyl thiazole-2,4-dicarboxylate (5.0 g, 19 mmol, Intermediate 66: Step A) in THF (50 mL) was added aqueous LiOH (21 mL, 1 M, 21 mmol) drop-wise over 2 min at rt and the resulting mixture was stirred at rt for 5 h. The reaction was concentrated to dryness and the residue was acidified with aqueous 1 M HCl to pH 6 and lyophilized to give the title compound as a white solid, which was used in the next step without further purification.

Intermediate 72: Step B tert-Butyl 2-((1,1-dioxidotetrahydro-2H-thiopyran-4-yl)carbamoyl)thiazole-4-carboxylate

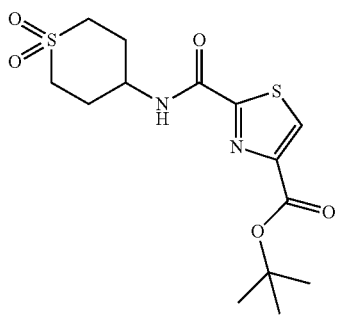 [SMILES: CC(C)(C)OC(=O)c1csc(C(=O)NC2CCS(=O)(=O)CC2)n1]

To a 250-mL round bottom flask under N₂ was added 4-(tert-butoxycarbonyl)thiazole-2-carboxylic acid (6.0 g, 20 mmol, Intermediate 72: Step A), 4-aminotetrahydro-2H-thiopyran-1,1-dioxide hydrochloride (4.4 g, 24 mmol), HATU (9.0 g, 24 mmol), DIPEA (7.7 g, 60 mmol) and DMF (30 mL). This mixture was allowed to stir at rt for 16 h followed by dilution with water (50 mL) and extraction with EtOAc (50 mL×3). The combined organic layers were washed with water (50 mL) and brine (50 mL), dried over anhydrous sodium sulfate, filtered, and concentrated to dryness. The residue was recrystallized from EtOAc (50 mL) to give the title compound as a white solid.

Intermediate 72: Step C 2-((1,1-Dioxidotetrahydro-2H-thiopyran-4-yl)carbamoyl)thiazole-4-carboxylic acid

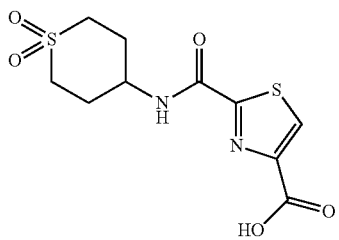 [SMILES: O=C(O)c1csc(C(=O)NC2CCS(=O)(=O)CC2)n1]

tert-Butyl 2-((1,1-dioxidotetrahydro-2H-thiopyran-4-yl)carbamoyl)thiazole-4-carboxylate (1.0 g, 2.8 mmol, Intermediate 72: Step B) was dissolved in 1:1 TFA:DCM (20 mL) and allowed to stand for 1 h. The reaction was concentrated to dryness and the residue placed on high vacuum overnight to give the title compound, which was used in the next step without purification.

Intermediate 72: Step D (S)—N-(1,1-Dioxidotetrahydro-2H-thiopyran-4-yl)-4-(2-methylpiperidine-1-carbonyl)thiazole-2-carboxamide

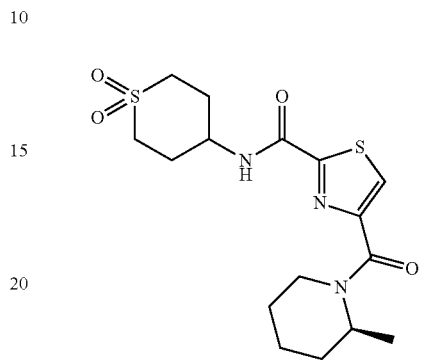

To a 100 mL round bottom flask, under N₂, containing 2-((1,1-dioxidotetrahydro-2H-thiopyran-4-yl)carbamoyl)thiazole-4-carboxylic acid (500 mg, 1.6 mmol, Intermediate 72: Step C) was added DMF (10 mL) followed by PyBOP (1.3 g, 2.5 mmol) and methylmorpholine (0.55 g, 5.4 mmol). After 10 min (S)-2-methylpiperidine (244 mg, 2.52 mmol) in DMF (5.0 mL) was added and the reaction was allowed to stir overnight at 50° C. The reaction was then poured into ethyl acetate and washed with water (3×) and brine (1×). The organic layer was dried over anhydrous sodium sulfate and concentrated to dryness. The crude residue was dissolved in DCM and purified by FCC (0-50% ethyl acetate/hexanes) to provide the title compound.

Intermediate 73: Step A

Ethyl (S)-4-(2-methylpyrrolidine-1-carbonyl)thiazole-2-carboxylate

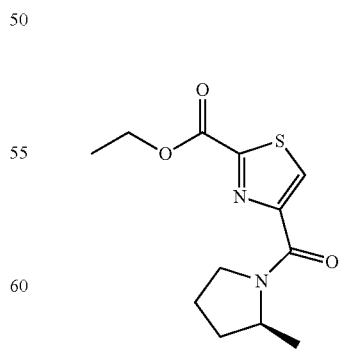

The title compound was prepared as described in Intermediate 65: Step B, using (9-2-methylpyrrolidine in place of 4-fluoropiperidine

Intermediate 73: Step B

Potassium (S)-4-(2-methylpyrrolidine-1-carbonyl)thiazole-2-carboxylate

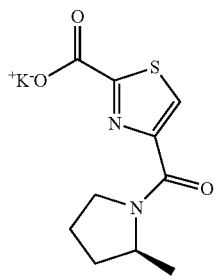

A solution of (9-ethyl 4-(2-methylpyrrolidine-1-carbonyl)thiazole-2-carboxylate (7.5 g, 28 mmol, Intermediate 73: Step A), potassium t-butoxide (3.44 g, 311 mmol), THF (160 mL), and H$_2$O (4 mL) was stirred at 60° C. for 2 hours. The reaction was diluted with H$_2$O (30 mL) and extracted with DCM (30 mL×2). The aqueous layer was collected and lyophilized to dryness to give the title compound as a yellow solid.

Intermediate 73: Step C (S)—N-((1-Hydroxycyclobutyl)methyl)-4-(2-methylpyrrolidine-1-carbonyl)thiazole-2-carboxamide

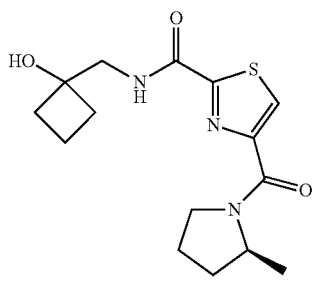 [SMILES: C[C@H]1CCCN1C(=O)c1csc(C(=O)NCC2(O)CCC2)n1]

To a 300 mL round bottom flask under N$_2$ was added EDC.HCl (4.9 g, 26 mmol), 1-(aminomethyl)cyclobutanol (1.3 g, 13 mmol), potassium (S)-4-(2-methylpyrrolidine-1-carbonyl)thiazole-2-carboxylate (3.6 g, 13 mmol, Intermediate 73: Step B), HOBt (3.5 g, 26 mmol), DIPEA (6.8 mL, 39 mmol) and THF (100 mL). The resultant mixture was stirred at room temperature for 16 hours before diluting with ethyl acetate (200 mL). This mixture was washed with H$_2$O (50 mL) and brine (30 mL), dried over anhydrous sodium sulfate, filtered, and concentrated to dryness to give the crude product, which was purified by preparative HPLC. The purified material was suspended in water (10 mL), the mixture frozen using dry ice/acetone, and then lyophilized to dryness to afford the title compound as a white solid.

Intermediate 74

4-((S)-2-Methylpyrrolidine-1-carbonyl)-N-((1r,3r)-3-(methylsulfonyl)cyclobutyl)thiazole-2-carboxamide

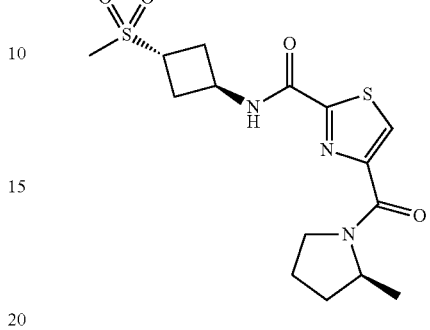

The title compound was prepared as described in Intermediate 73: Step C substituting (1r,3r)-3-(methylsulfonyl)cyclobutanamine in place of 1-(aminomethyl)cyclobutanol.

Intermediate 75

(S)—N-((3-Hydroxyoxetan-3-yl)methyl)-4-(2-methylpyrrolidine-1-carbonyl)thiazole-2-carboxamide

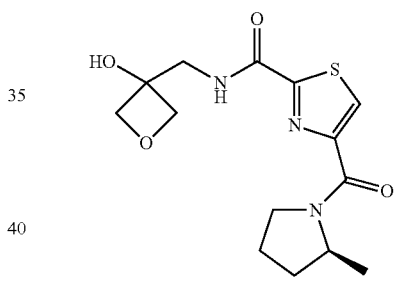

The title compound was prepared as described in Intermediate 73: Step C substituting 3-(aminomethyl)oxetan-3-ol in place of 1-(aminomethyl)cyclobutanol.

The following intermediates can be prepared by procedures described.

Intermediate 76: Step A

2-Methyl-2-((trimethylsilyl)oxy)propanenitrile

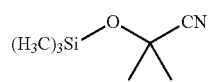

To a flask containing acetone (2 mL, 27.1 mmol), zinc iodide (173 mg, 0.54 mmol) and DCM (55 mL) is added trimethylsilyl cyanide (4.4 mL, 35.2 mmol), and the resulting mixture stirred at rt for 18 hours. The mixture is diluted with saturated aqueous NaHCO$_3$, the layers separated, and the aqueous layer further extracted with DCM. The organics are combined, dried over MgSO$_4$, filtered and concentrated to dryness to give the title compound.

Intermediate 76: Step B tert-Butyl (2-hydroxy-2-methylpropyl-1,1-d$_2$)carbamate

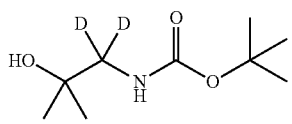

To a sealed tube containing borane-d$_3$ (7 mL, 7 mmol, 1 M in THF) is added 2-methyl-2-((trimethylsilyl)oxy)propanenitrile (1.3 g, 7 mmol, Intermediate 76: Step A) and the resulting solution is stirred at 65° C. for 15 hours. The mixture is allowed to cool to rt, then water is added until the evolution of H$_2$ ceases. The mixture is then warmed to 60° C. and the THF is removed under a stream of N$_2$. The solution is allowed to cool to rt, then aqueous 1 N HCl (3 mL) is added followed by concentrated HCl (1 mL) slowly. The resulting mixture is stirred at 60° C. for 6 hours, then cooled to rt, diluted with THF (8 mL) and neutralized with 10 M aqueous NaOH. Then, Boc-anhydride (1.5 mL, 7 mmol) is added and the reaction is stirred at rt for 15 hours. The mixture is diluted with EtOAc, the layers separated, and the aqueous layer further extracted with EtOAc. The combined organic layers are dried over anhydrous MgSO$_4$ and concentrated to dryness to provide the crude product. The crude material is purified by FCC (0-60% EtOAc/hexanes) to provide the title compound.

Intermediate 76: Step C

1-Amino-2-methylpropan-1,1-d$_2$-2-ol hydrochloride

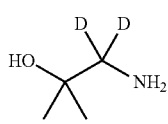

A mixture of tert-butyl (2-hydroxy-2-methylpropyl-1,1-d$_2$)carbamate (1.2 g, 6.4 mmol, Intermediate 76: Step B), TFA (5.9 mL, 76 mmol) and DCM (22 mL) is stirred at rt for 15 hours. The solution is concentrated to dryness then dissolved in DCM/MeOH. HCl (1.8 mL, 7.0 mmol, 4 M in 1,4-dioxane) is then added and the resulting solution is concentrated to dryness. The residue is suspended in EtOAc/hexane and stirred vigorously under a stream of N$_2$. The mixture is filtered and the solids rinsed with hexane. The solids are then dissolved in MeOH and concentrated to dryness to afford the title compound.

Intermediate 76: Step D (S)—N-(2-Hydroxy-2-methylpropyl-1,1-d$_2$)-4-(2-methylpyrrolidine-1-carbonyl)thiazole-2-carboxamide

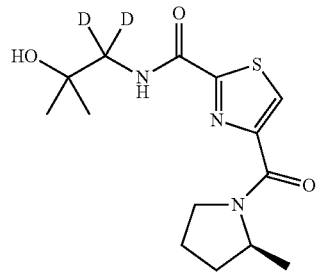 [SMILES: [2H]C([2H])(NC(=O)c1nc(C(=O)N2CCC[C@@H]2C)cs1)C(C)(C)O]

The title compound is prepared as described in Intermediate 70 using (S)-2-methylpyrrolidine in place of (1s,4s)-7-azabicyclo[2.2.1]heptane in Step A and 1-amino-2-methylpropan-1,1-d$_2$-2-ol hydrochloride (Intermediate 76: Step C) in place of 1-amino-2-methylpropan-2-ol in Step B.

Intermediate 77: Step A 2-(Methyl-d$_3$)-2-((trimethylsilyl)oxy)propanenitrile-3,3,3-d$_3$

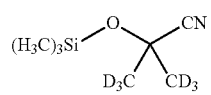

The title compound is prepared as described in Intermediate 76: Step A using acetone-d$_6$ in place of acetone.

Intermediate 77: Step B 2-(Aminomethyl)propan-1,1,1,3,3,3-d$_6$-2-ol hydrochloride

2-(Methyl-d$_3$)-2-((trimethylsilyl)oxy)propanenitrile-3,3,3-d$_3$ (11.64 g, 71.3 mmol, Intermediate 77: Step A) is added to a suspension of LAH (5.4 g, 142.5 mmol, 1 M in THF) in THF (150 mL) at 0-5° C. The resulting suspension is allowed to warm to rt overnight. The solution is then cooled to 0° C. and water (5.4 mL), 15% aqueous NaOH (5.4 mL) and water (16 mL) are added sequentially dropwise. The mixture is allowed to warm to rt over 20 minutes and then is filtered through Celite® and the filter cake washed with THF. The filtrate and wash are combined and concentrated to dryness. The residue is diluted with THF and then HCl (12.5 mL, 50 mmol, 4 M in 1,4-dioxane) is added and the resulting mixture is concentrated to dryness. EtOAc is added to the residue and the product solidified. The solids are

Intermediate 77: Step C (S)—N-(2-Hydroxy-2-(methyl-d₃)propyl-3,3,3-d₃)-4-(2-methylpyrrolidine-1-carbonyl)thiazole-2-carboxamide

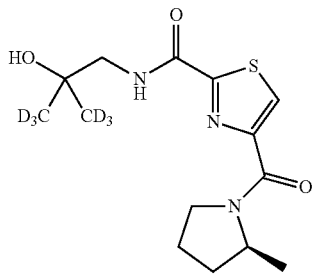 [SMILES: [2H]C([2H])([2H])C(O)(CNC(=O)c1nc(C(=O)N2CCC[C@@H]2C)cs1)C([2H])([2H])[2H]]

The title compound is prepared as described in Intermediate 70 using (S)-2-methylpyrrolidine in place of (1s,4s)-7-azabicyclo[2.2.1]heptane in Step A and 2-(aminomethyl)propan-1,1,1,3,3,3-d₆-2-ol hydrochloride (Intermediate 77: Step B) in place of 1-amino-2-methylpropan-2-ol in Step B.

Intermediate 78

(S)—N-((1-Hydroxycyclopropyl)methyl)-4-(2-methylpyrrolidine-1-carbonyl)thiazole-2-carboxamide

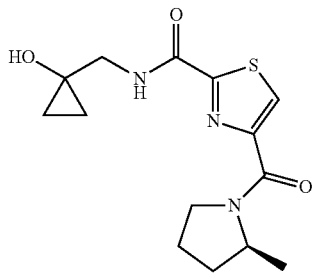 [SMILES: C[C@H]1CCCN1C(=O)c1csc(C(=O)NCC2(O)CC2)n1]

The title compound can be prepared as described in Intermediate 70 using (S)-2-methylpyrrolidine in place of (1s,4s)-7-azabicyclo[2.2.1]heptane in Step A and 1-(aminomethyl)cyclopropan-1-ol in place of 1-amino-2-methylpropan-2-ol in Step B.

Intermediate 79

(S)-4-(4,4-Difluoro-2-methylpyrrolidine-1-carbonyl)-N-(3-hydroxy-3-methylcyclobutyl)thiazole-2-carboxamide

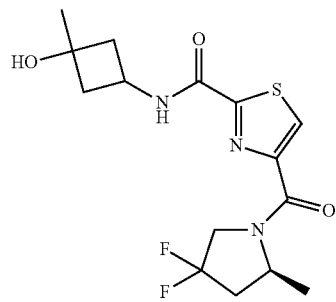 [SMILES: C[C@H]1CC(F)(F)CN1C(=O)c1csc(C(=O)NC2CC(C)(O)C2)n1]

The title compound can be prepared as described in Intermediate 70 using (S)-4,4-difluoro-2-methylpyrrolidine hydrochloride (Intermediate 13: Step B) in place of (1s,4s)-7-azabicyclo[2.2.1]heptane in Step A and 3-amino-1-methylcyclobutan-1-ol in place of 1-amino-2-methylpropan-2-ol in Step B.

Intermediate 80

(S)-4-(4,4-Difluoro-2-methylpyrrolidine-1-carbonyl)-N-(1,1-dioxidothietan-3-yl)thiazole-2-carboxamide

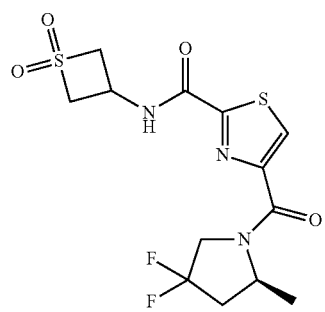 [SMILES: C[C@H]1CC(F)(F)CN1C(=O)c1csc(C(=O)NC2CS(=O)(=O)C2)n1]

The title compound can be prepared as described in Intermediate 70 using (S)-4,4-difluoro-2-methylpyrrolidine hydrochloride (Intermediate 13: Step B) in place of (1s,4s)-7-azabicyclo[2.2.1]heptane in Step A and 3-aminothietane 1,1-dioxide in place of 1-amino-2-methylpropan-2-ol in Step B.

Intermediate 81

(S)-4-(4,4-Difluoro-2-methylpyrrolidine-1-carbonyl)-N-(1-hydroxy-2-methylpropan-2-yl)thiazole-2-carboxamide

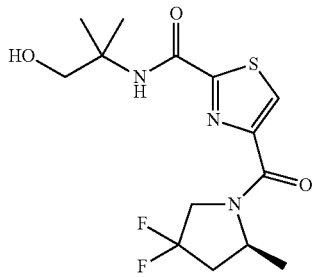 [SMILES: C[C@H]1CC(F)(F)CN1C(=O)c1csc(C(=O)NC(C)(C)CO)n1]

The title compound can be prepared as described in Intermediate 70 using (S)-4,4-difluoro-2-methylpyrrolidine hydrochloride (Intermediate 13: Step B) in place of (1s,4s)-7-azabicyclo[2.2.1]heptane in Step A and 2-amino-2-methylpropan-1-ol in place of 1-amino-2-methylpropan-2-ol in Step B.

Intermediate 82

(4-((1s,4s)-7-Azabicyclo[2.2.1]heptane-7-carbonyl)thiazol-2-yl)(3-hydroxy-3-methylazetidin-1-yl)methanone

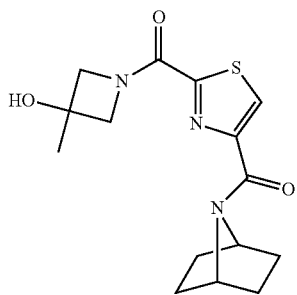 [SMILES: CC1(O)CN(C(=O)c2nc(C(=O)N3C4CCC3CC4)cs2)C1]

The title compound can be prepared as described in Intermediate 70 using 3-methylazetidin-3-ol in place of 1-amino-2-methylpropan-2-ol in Step B.

Intermediate 83

4-((1s,4s)-7-Azabicyclo[2.2.1]heptane-7-carbonyl)-N-(1-hydroxy-2-methylpropan-2-yl)-N-methylthiazole-2-carboxamide

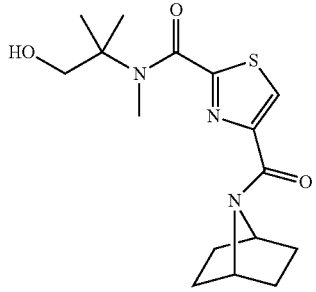 [SMILES: CN(C(=O)c1nc(C(=O)N2C3CCC2CC3)cs1)C(C)(C)CO]

The title compound can be prepared as described in Intermediate 70 using 2-methyl-2-(methylamino)propan-1-ol in place of 1-amino-2-methylpropan-2-ol in Step B.

Intermediate 84

4-((1s,4s)-7-Azabicyclo[2.2.1]heptane-7-carbonyl)-N-(2-hydroxy-2-methylpropyl)-N-methylthiazole-2-carboxamide

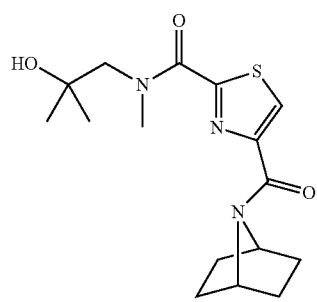 [SMILES: CN(CC(C)(C)O)C(=O)c1nc(C(=O)N2C3CCC2CC3)cs1]

The title compound can be prepared as described in Intermediate 70 using 2-methyl-1-(methylamino)propan-2-ol in place of 1-amino-2-methylpropan-2-ol in Step B.

Intermediate 85

N-(3-Hydroxy-3-methylbutan-2-yl)-N-methyl-4-((S)-2-methylpiperidine-1-carbonyl)thiazole-2-carboxamide

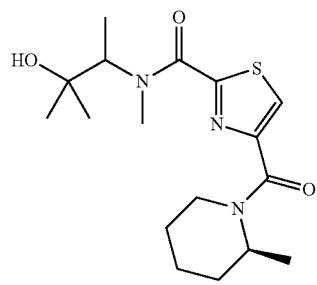 [SMILES: CC(N(C)C(=O)c1nc(C(=O)N2CCCC[C@@H]2C)cs1)C(C)(C)O]

The title compound can be prepared as described in Intermediate 70 using (S)-2-methylpiperidine in place of (1s,4s)-7-azabicyclo[2.2.1]heptane in Step A and 2-methyl-3-(methylamino)butan-2-ol in place of 1-amino-2-methylpropan-2-ol in Step B.

Intermediate 86

(S)-4-(2-Methylpiperidine-1-carbonyl)-N-(oxetan-3-yl)thiazole-2-carboxamide

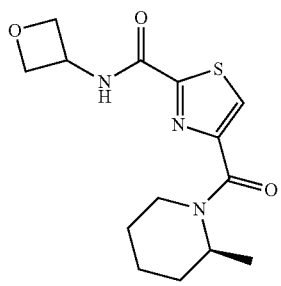 [SMILES: C[C@H]1CCCCN1C(=O)c1csc(C(=O)NC2COC2)n1]

The title compound can be prepared as described in Intermediate 70 using (S)-2-methylpiperidine in place of (1s,4s)-7-azabicyclo[2.2.1]heptane in Step A and oxetan-3-amine in place of 1-amino-2-methylpropan-2-ol in Step B.

Intermediate 87

(S)-(2-(2,2-Dioxido-2-thia-6-azaspiro[3.3]heptane-6-carbonyl)thiazol-4-yl)(2-methylpiperidin-1-yl)methanone

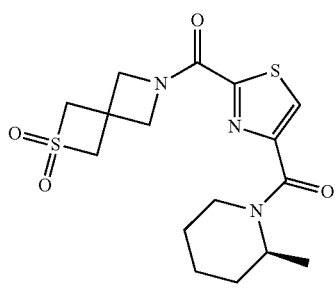 [SMILES: C[C@H]1CCCCN1C(=O)c1csc(C(=O)N2CC3(C2)CS(=O)(=O)C3)n1]

The title compound can be prepared as described in Intermediate 70 using (S)-2-methylpiperidine in place of (1s,4s)-7-azabicyclo[2.2.1]heptane in Step A and 2-thia-6-azaspiro[3.3]heptane 2,2-dioxide in place of 1-amino-2-methylpropan-2-ol in Step B.

Intermediate 88

(S)-(2-(1,1-Dioxidothiomorpholine-4-carbonyl)thiazol-4-yl)(2-methylpiperidin-1-yl)methanone

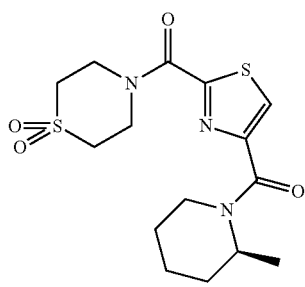 [SMILES: C[C@H]1CCCCN1C(=O)c1csc(C(=O)N2CCS(=O)(=O)CC2)n1]

The title compound can be prepared as described in Intermediate 70 using (S)-2-methylpiperidine in place of (1s,4s)-7-azabicyclo[2.2.1]heptane in Step A and thiomorpholine 1,1-dioxide in place of 1-amino-2-methylpropan-2-ol in Step B.

Intermediate 89

5-Bromo-N-(1-cyclobutylethyl)-4-(trifluoromethyl)pyridin-2-amine

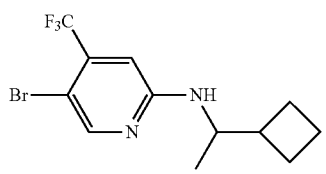 [SMILES: CC(Nc1cc(C(F)(F)F)c(Br)cn1)C1CCC1]

The title compound was prepared as described in Intermediate 41, using 1-cyclobutylethan-1-amine in place of tert-butylamine in Step A.

Intermediate 90

5-Bromo-N-(1-cyclopropylpropyl)-4-difluoromethyl)pyridin-2-amine

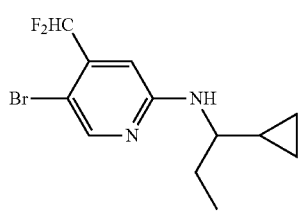 [SMILES: CCC(Nc1cc(C(F)F)c(Br)cn1)C1CC1]

The title compound was prepared as described in Intermediate 41, using 1-cyclopropylpropan-1-amine in place of tert-butylamine and 2-bromo-4-(difluoromethyl)pyridine in place of 2-bromo-4-(trifluoromethyl)pyridine in Step A.

Intermediate 91

5-Bromo-N-(1-methylcyclobutyl)-4-(difluoromethyl)pyridin-2-amine

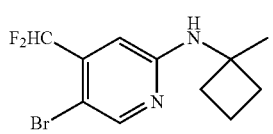 [SMILES: CC1(Nc2cc(C(F)F)c(Br)cn2)CCC1]

The title compound was prepared as described in Intermediate 41, using 1-methylcyclobutanamine hydrochloride in place of tert-butylamine and 2-bromo-4-(difluoromethyl)pyridine in place of 2-bromo-4-(trifluoromethyl)pyridine in Step A.

Intermediate 92

5-Bromo-N-(dicyclopropylmethyl)-4-(difluoromethyl)pyridin-2-amine

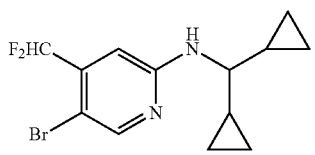 [SMILES: FC(F)c1cc(NC(C2CC2)C2CC2)ncc1Br]

The title compound was prepared as described in Intermediate 41, using dicyclopropylmethanamine in place of tert-butylamine and 2-bromo-4-(difluoromethyl)pyridine in place of 2-bromo-4-(trifluoromethyl)pyridine in Step A.

Intermediate 93

Ethyl (S)-4-(4,4-difluoro-2-methylpyrrolidine-1-carbonyl)-5-(6-((1-methylcyclobutyl)amino)-4-(trifluoromethyl)pyridin-3-yl)thiazole-2-carboxylate

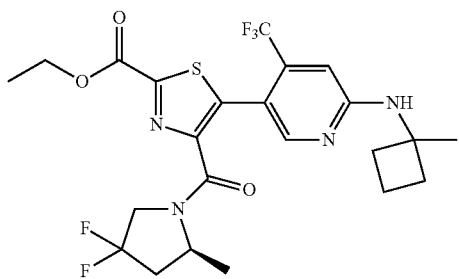 [SMILES: CCOC(=O)c1nc(C(=O)N2CC(F)(F)C[C@@H]2C)c(-c2cnc(NC3(C)CCC3)cc2C(F)(F)F)s1]

To a 300 mL screw cap pressure vessel under N₂ was added 5-bromo-N-(1-methylcyclobutyl)-4-(trifluoromethyl)pyridin-2-amine (6.5 g, 21.0 mmol, Intermediate 46), ethyl (S)-4-(4,4-difluoro-2-methylpyrrolidine-1-carbonyl)thiazole-2-carboxylate (4.3 g, 14.1 mmol, Intermediate 109: Step A), potassium carbonate (3.9 g, 28.2 mmol) and DMF (150 mL, purged with N₂ for 1 h). To this mixture was added bis(tri-t-butylphosphine)Pd (0), (1.4 g, 2.7 mmol) and the reaction capped and heated to 130° C. for 8 h. The reaction was then cooled to rt and poured into saturated aqueous bicarbonate. The aqueous layer was extracted with ethyl acetate (3×), then the combined organic layers were dried over anhydrous sodium sulfate and evaporated under reduced pressure. The crude residue was re-dissolved in DCM and purified by FCC (0-80% ethyl acetate/hexanes) to afford a tan colored foamy solid after removal of the solvent under reduced pressure.

Intermediate 94

Ethyl 5-(4-(difluoromethyl)-6-(((S)-1,1,1-trifluoropropan-2-yl)amino)pyridin-3-yl)-4-((S)-2-methylpyrrolidine-1-carbonyl)thiazole-2-carboxylate

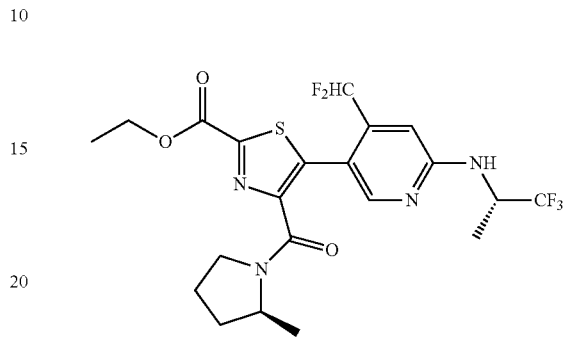

The title compound was prepared as described in Intermediate 93 substituting (S)-5-bromo-4-(difluoromethyl)-N-(1,1,1-trifluoropropan-2-yl)pyridin-2-amine (Intermediate 60) in place of 5-bromo-N-(1-methylcyclobutyl)-4-(trifluoromethyl)pyridin-2-amine and ethyl (S)-4-(2-methylpyrrolidine-1-carbonyl)thiazole-2-carboxylate (Intermediate 73: Step A) in place of ethyl (S)-4-(4,4-difluoro-2-methylpyrrolidine-1-carbonyl)thiazole-2-carboxylate.

Intermediate 95

Ethyl 4-((1s,4s)-7-azabicyclo[2.2.1]heptane-7-carbonyl)-5-(4-difluoromethyl)-6-((1-methylcyclobutyl)amino)pyridine-3-yl)thiazole-2-carboxylate

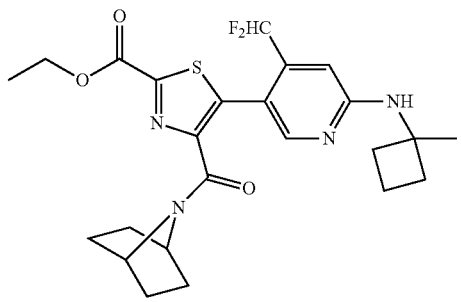 [SMILES: CCOC(=O)c1nc(C(=O)N2C3CCC2CC3)c(-c2cnc(NC3(C)CCC3)cc2C(F)F)s1]

The title compound was prepared as described in Intermediate 93 substituting 5-bromo-N-(1-methylcyclobutyl)-4-(difluoromethyl)pyridin-2-amine (Intermediate 91) in place of 5-bromo-N-(1-methylcyclobutyl)-4-(trifluoromethyl)pyridine-2-amine and ethyl 4-((1s,4s)-7-azabicyclo[2.2.1]heptane-7-carbonyl)thiazole-2-carboxylate (Intermediate 70: Step A) in place of ethyl (S)-4-(4,4-difluoro-2-methylpyrrolidine-1-carbonyl)thiazole-2-carboxylate.

Intermediate 96

Ethyl 4-((S)-4,4-difluoro-2-methylpyrrolidine-1-carbonyl)-5-(4-(difluoromethyl)-6-(((S)-1,1,1,-trifluoropropan-2-yl)amino)pyridine-3-yl)thiazole-2-carboxylate

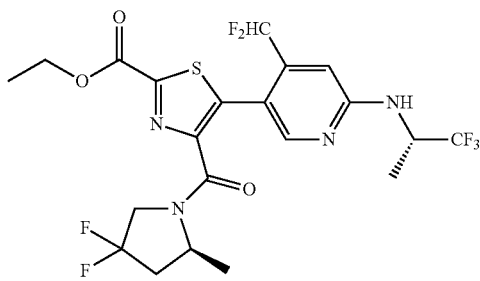 [SMILES: CCOC(=O)c1nc(C(=O)N2CC(F)(F)C[C@@H]2C)c(-c2cnc(N[C@@H](C)C(F)(F)F)cc2C(F)F)s1]

The title compound was prepared as described in Intermediate 93 substituting (S)-5-bromo-4-(difluoromethyl)-N-(1,1,1-trifluoropropan-2-yl)pyridin-2-amine (Intermediate 60) in place of 5-bromo-N-(1-methylcyclobutyl)-4-(trifluoromethyl)pyridin-2-amine.

Intermediate 97

Ethyl 5-(6-(((S)-1-cyclopropylethyl)amino)-4-(difluoromethyl)pyridine-3-yl)-4-(((S)-4,4-difluoro-2-methylpyrrolidine-1-carbonyl)thiazole-2-carboxylate

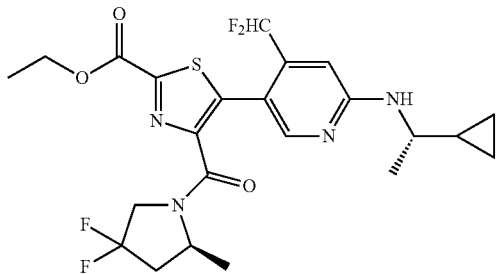 [SMILES: CCOC(=O)c1nc(C(=O)N2CC(F)(F)C[C@@H]2C)c(-c2cnc(N[C@@H](C)C3CC3)cc2C(F)F)s1]

The title compound was prepared as described in Intermediate 93 substituting (S)-5-bromo-N-(1-cyclopropylethyl)-4-(difluoromethyl)pyridin-2-amine (Intermediate 20) in place of 5-bromo-N-(1-methylcyclobutyl)-4-(trifluoromethyl)pyridin-2-amine.

Intermediate 98

Ethyl 5-(6-(((S)-1-cyclopropylethyl)amino)-4-(trifluoromethyl)pyridine-3-yl)-4-(((S)-4,4-difluoro-2-methylpyrrolidine-1-carbonyl)thiazole-2-carboxylate

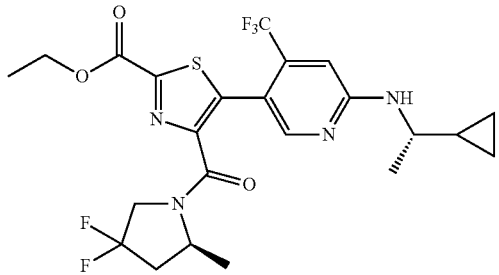 [SMILES: CCOC(=O)c1nc(C(=O)N2CC(F)(F)C[C@@H]2C)c(-c2cnc(N[C@@H](C)C3CC3)cc2C(F)(F)F)s1]

The title compound was prepared as described in Intermediate 93 substituting (S)-5-bromo-N-(1-cyclopropylethyl)-4-(trifluoromethyl)pyridin-2-amine (Intermediate 18) in place of 5-bromo-N-(1-methylcyclobutyl)-4-(trifluoromethyl)pyridin-2-amine.

Intermediate 99

Ethyl 4-((1s,4s)-7-azabicyclo[2.2.1]heptane-7-carbonyl)-5-(4-(difluoromethyl)-6-(((S)-1,1,1-trifluorobutan-2-yl)amino)pyridin-3-yl)thiazole-2-carboxylate

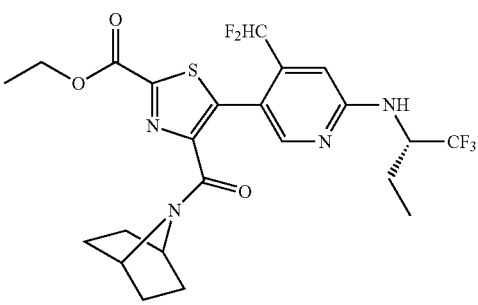 [SMILES: CCOC(=O)c1nc(C(=O)N2C3CCC2CC3)c(-c2cnc(N[C@@H](CC)C(F)(F)F)cc2C(F)F)s1]

The title compound was prepared as described in Example 77 substituting (S)-5-bromo-4-(difluoromethyl)-N-(1,1,1-trifluorobutan-2-yl)pyridin-2-amine (Intermediate 49) for 5-bromo-N-(1-methylcyclobutyl)-4-(trifluoromethyl)pyridin-2-amine and ethyl 4-((1s,4s)-7-azabicyclo[2.2.1]heptane-7-carbonyl)thiazole-2-carboxylate (Intermediate 70: Step A) for (S)—N-(2-hydroxy-2-methylpropyl)-4-(2-methylpyrrolidine-1-carbonyl)thiazole-2-carboxamide.

Intermediate 100

Ethyl 4-((1s,4s)-7-azabicyclo[2.2.1]heptane-7-carbonyl)-5-(6-(((S)-1,1,1-trifluorobutan-2-yl)amino)-4-(trifluoromethyl)pyridin-3-yl)thiazole-2-carboxylate

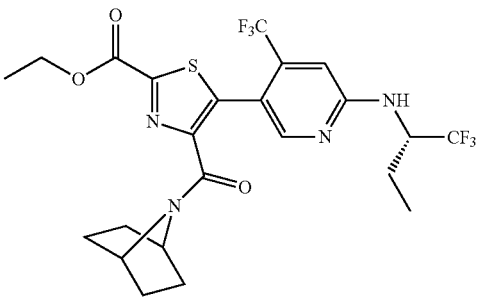 [SMILES: CCOC(=O)c1nc(C(=O)N2C3CCC2CC3)c(-c2cnc(N[C@@H](CC)C(F)(F)F)cc2C(F)(F)F)s1]

The title compound was prepared as described in Example 77 substituting (S)-5-bromo-N-(1,1,1-trifluorobutan-2-yl)-4-(trifluoromethyl)pyridin-2-amine (Intermediate 53) for 5-bromo-N-(1-methylcyclobutyl)-4-(trifluoromethyl)pyridin-2-amine and ethyl 4-((1s,4s)-7-azabicyclo[2.2.1]heptane-7-carbonyl)thiazole-2-carboxylate (Intermediate 70: Step A) for (5)-N-(2-hydroxy-2-methylpropyl)-4-(2-methylpyrrolidine-1-carbonyl)thiazole-2-carboxamide.

Intermediate 101: Step A (E/Z)-2-(2-((tert-Butyldimethylsilyl)oxy)vinyl)isoindoline-1,3-dione

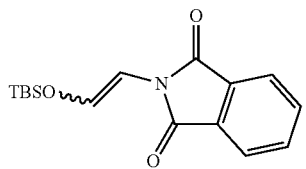 [SMILES: CC(C)(C)[Si](C)(C)OC=CN1C(=O)c2ccccc2C1=O]

To a 250 mL round-bottom flask was added N-(2-oxoethyl)phthalimide (6 g, 31.7 mmol), tert-butyldimethylsilyl trifluoromethanesulfonate (8.7 mL, 37.9 mmol) and DCM (100 mL). Then DBU (5.4 mL, 36.1 mmol) was added dropwise and the resulting yellow solution was stirred at rt for 1 hour. The solution was washed with 1 M aqueous $H_2SO_4$ (50 mL) and the aqueous layer was extracted with DCM (2×50 mL). The organic layers were combined, washed with water (50 mL), saturated aqueous $NaHCO_3$ (50 mL) and dried over anhydrous sodium sulfate. The mixture was filtered and concentrated to dryness. The crude residue was purified by FCC (0-5% EtOAc/Hexanes) to provide the title compounds as yellow oils.

Intermediate 101: Step B1

2-(((1S*,2R*)-2-((tert-Butyldimethylsilyl)oxy)cyclopropyl)isoindoline-1,3-dione

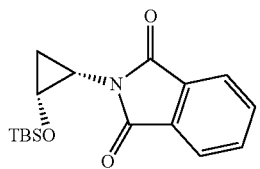 [SMILES: CC(C)(C)[Si](C)(C)O[C@@H]1C[C@@H]1N1C(=O)c2ccccc2C1=O]

To an oven-dried 500 mL round-bottom flask was added (Z)-2-(2-((tert-butyldimethylsilyl)oxy)vinyl)isoindoline-1,3-dione (4.28 g, 14.11 mmol, Intermediate 101: Step A) and dry benzene (71 mL) and the resulting solution was cooled to 0° C. in an ice-bath. Then, $Et_2Zn$ (212 mL, 212 mmol, 1 M in hexanes) was added followed by $CH_2I_2$ (17 mL, 212 mmol) and the mixture was allowed to slowly warm to rt and then stirred at rt for 21 hours. The mixture was partitioned between 1 N aqueous $H_2SO_4$ (100 mL) and hexanes (100 mL). The layers were separated and the organic layer was washed with water (100 mL) followed by saturated aqueous $NaHCO_3$ (100 mL) and then dried over anhydrous sodium sulfate. The mixture was filtered and concentrated to dryness. The crude residue was dissolved in DCM and purified by FCC (0-10% EtOAc/Hexanes) to provide the title compound.

Intermediate 101: Step B2

2-((1R*,2R*)-2-((tert-Butyldimethylsilyl)oxy)cyclopropyl)isoindoline-1,3-dione

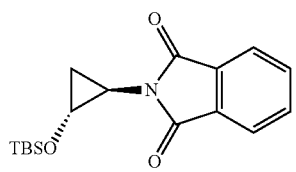 [SMILES: CC(C)(C)[Si](C)(C)O[C@@H]1C[C@H]1N1C(=O)c2ccccc2C1=O]

To an oven-dried 500 mL round-bottom flask was added (Z)-2-(2-((tert-butyldimethylsilyl)oxy)vinyl)isoindoline-1,3-dione (4.28 g, 14.11 mmol, Intermediate 101: Step A) and dry benzene (71 mL) and the resulting solution was cooled to 0° C. in an ice-bath. Then, $Et_2Zn$ (212 mL, 212 mmol, 1 M in hexanes) was added followed by $CH_2I_2$ (17 mL, 212 mmol) and the mixture was allowed to slowly warm to rt and then stirred at rt for 21 hours. The mixture was partitioned between 1 N aqueous $H_2SO_4$ (100 mL) and hexanes (100 mL). The layers were separated and the organic layer was washed with water (100 mL) followed by saturated aqueous $NaHCO_3$ (100 mL) and then dried over anhydrous sodium sulfate. The mixture was filtered and concentrated to dryness. The crude residue was dissolved in DCM and purified by FCC (0-10% EtOAc/Hexanes) to provide the title compound.

Intermediate 101: Step C trans-(1R*,2R*)-2-((tert-Butyldimethylsilyl)oxy)cyclopropan-1-amine

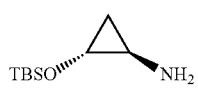

To a 200 mL round-bottom flask was added 2-((1R*,2R*)-2-((tert-butyldimethylsilyl)oxy)cyclopropyl)isoindoline-1,3-dione (4.53 g, 14.27 mmol, Intermediate 101: Step B2), DCM (55 mL) and EtOH (11 mL). Then, hydrazine hydrate (4.16 mL, 85.62 mmol) was added and the resulting solution was stirred at rt for 4 hours. The mixture was filtered through a pad of Celite® and the solution concentrated to dryness. The crude material was dissolved in DCM and washed with saturated aqueous $NaHCO_3$. The organic layer was dried over anhydrous sodium sulfate, filtered and concentrated to dryness to provide the title compound as a yellow oil.

Intermediate 101: Step D

N-((1R*,2R*)-2-((tert-Butyldimethylsilyl)oxy)cyclopropyl)-5-(4-(difluoromethyl)-6-(((S)-1,1,1-trifluoropropan-2-yl)amino)pyridin-3-yl)-4-((S)-2-methylpyrrolidine-1-carbonyl)thiazole-2-carboxamide

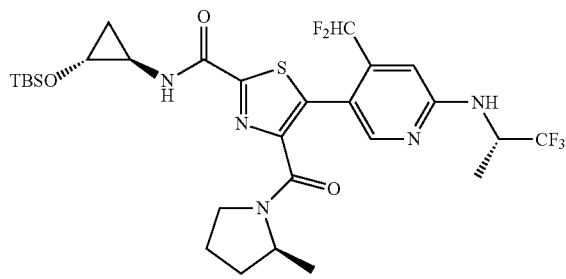 [SMILES: C[C@H](Nc1cc(C(F)F)c(-c2sc(C(=O)N[C@@H]3C[C@H]3O[Si](C)(C)C(C)(C)C)nc2C(=O)N2CCC[C@@H]2C)cn1)C(F)(F)F]

The title compound was prepared as described in Example 148 substituting trans-(1R*,2R*)-2-((tert-butyldimethylsilyl)oxy)cyclopropan-1-amine (Intermediate 101: Step C) for (R)-(−)-2-amino-1-propanol and ethyl 5-(4-(difluoromethyl)-6-(((S)-1,1,1-trifluoropropan-2-yl)amino)pyridin-3-yl)-4-((S)-2-methylpyrrolidine-1-carbonyl)thiazole-2-carboxylate (Intermediate 94) for ethyl (S)-5-(6-(tert-butylamino)-4-(difluoromethyl)pyridin-3-yl)-4-(2-methylpyrrolidine-1-carbonyl)thiazole-2-carboxylate.

Intermediate 101: Step E cis-(1S*,2R*)-2-((tert-Butyldimethylsilyl)oxy)cyclopropan-1-amine

The title compound was prepared as described for Intermediate 101: Step C substituting 2-((1S*,2R*)-2-((tert-butyldimethylsilyl)oxy)cyclopropyl)isoindoline-1,3-dione (Intermediate 101: Step B1) for 2-((1R*,2R*)-2-((tert-butyldimethylsilyl)oxy)cyclopropyl)isoindoline-1,3-dione.

Intermediate 101: Step F1

N-((1R*,2*S)-2-((tert-Butyldimethylsilyl)oxy)cyclopropyl)-5-(4-(difluoromethyl)-6-(((S)-1,1,1-trifluorobutan-2-yl)amino)pyridin-3-yl)-4-((S)-2-methylpyrrolidine-1-carbonyl)thiazole-2-carboxamide

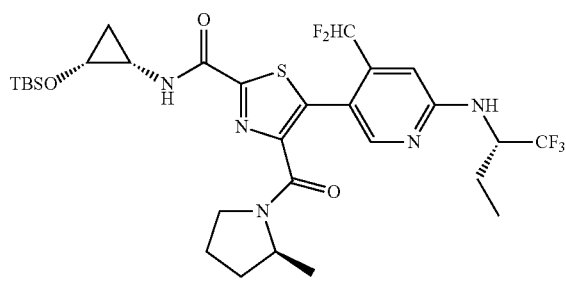 [SMILES: CC[C@H](Nc1cc(C(F)F)c(-c2sc(C(=O)N[C@H]3C[C@H]3O[Si](C)(C)C(C)(C)C)nc2C(=O)N2CCC[C@@H]2C)cn1)C(F)(F)F]

The title compound was prepared as described in Example 148 substituting cis-(1*S,2R*)-2-((tert-butyldimethylsilyl)oxy)cyclopropan-1-amine (Intermediate 101: Step E) for (R)-(−)-2-amino-1-propanol and ethyl 5-(4-(difluoromethyl)-6-(((S)-1,1,1-trifluorobutan-2-yl)amino)pyridin-3-yl)-4-((S)-2-methylpyrrolidine-1-carbonyl)thiazole-2-carboxylate (Intermediate 102) for ethyl (S)-5-(6-(tert-butylamino)-4-(difluoromethyl)pyridin-3-yl)-4-(2-methylpyrrolidine-1-carbonyl)thiazole-2-carboxylate. The pure diastereomer was isolated via SFC (Stationary phase: Whelk O1 (S,S), 5 µm, 250×21.1 mm, Mobile phase: 22% iPrOH+0.3% iPrNH2, 78% $CO_2$, first eluting enantiomer).

Intermediate 101: Step F2

N-((1S*,2R*)-2-((tert-Butyldimethylsilyl)oxy)cyclopropyl)-5-(4-(difluoromethyl)-6-(((S)-1,1,1-trifluoropropan-2-yl)amino)pyridin-3-yl)-4-((S)-2-methylpyrrolidine-1-carbonyl)thiazole-2-carboxamide

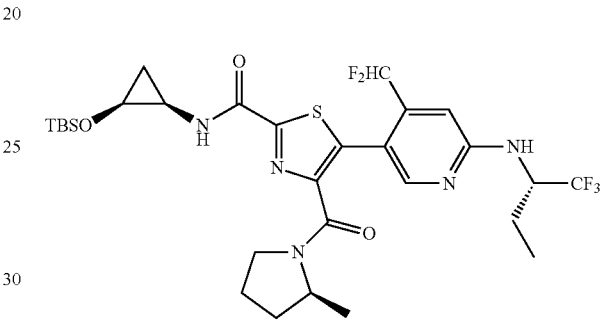

The title compound was prepared as described in Example 148 substituting cis-(1S*,2R*)-2-((tert-butyldimethylsilyl)oxy)cyclopropan-1-amine (Intermediate 101: Step E) for (R)-(−)-2-amino-1-propanol and ethyl 5-(4-(difluoromethyl)-6-(((S)-1,1,1-trifluorobutan-2-yl)amino)pyridin-3-yl)-4-((S)-2-methylpyrrolidine-1-carbonyl)thiazole-2-carboxylate (Intermediate 102) for ethyl (5)-5-(6-(tert-butylamino)-4-(difluoromethyl)pyridin-3-yl)-4-(2-methylpyrrolidine-1-carbonyl)thiazole-2-carboxylate. The pure diastereomer was isolated via SFC (Stationary phase: Whelk O1 (S,S), 5 µm, 250×21.1 mm, Mobile phase: 22% iPrOH+0.3% $iPrNH_2$, 78% $CO_2$, second eluting enantiomer).

Intermediate 101: Step G1

N-((1R*,2R*)-2-((tert-Butyldimethylsilyl)oxy)cyclopropyl)-5-(4-(difluoromethyl)-6-(((S)-1,1,1-trifluorobutan-2-yl)amino)pyridin-3-yl)-4-((S)-2-methylpyrrolidine-1-carbonyl)thiazole-2-carboxamide

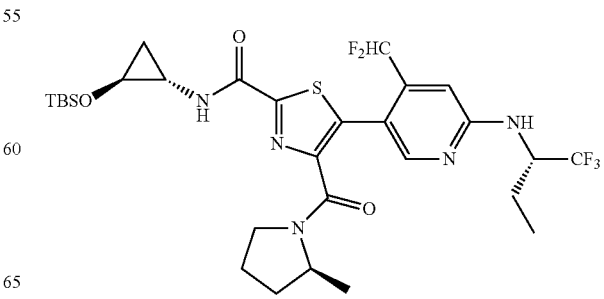

The title compound was prepared as described in Intermediate 101: Step D substituting ethyl 5-(4-(difluoromethyl)-6-(((S)-1,1,1-trifluorobutan-2-yl)amino)pyridin-3-yl)-4-((S)-2-methylpyrrolidine-1-carbonyl)thiazole-2-carboxylate (Intermediate 102) for ethyl 5-(4-(difluoromethyl)-6-(((S)-1,1,1-trifluoropropan-2-yl)amino)pyridin-3-yl)-4-((S)-2-methylpyrrolidine-1-carbonyl) thiazole-2-carboxylate. The pure diastereomer was isolated via SFC (Stationary phase: Chiralpak AD-H, 5 μm, 250×30 mm, Mobile phase: 7.5% iPrOH+0.3% iPrNH2, 92.5% CO$_2$, first eluting enantiomer).

Intermediate 101: Step G2

N-((1S*,2S*)-2-((tert-Butyldimethylsilyl)oxy)cyclopropyl)-5-(4-(difluoromethyl)-6-(((S)-1,1,1-trifluorobutan-2-yl)amino)pyridin-3-yl)-4-((S)-2-methylpyrrolidine-1-carbonyl)thiazole-2-carboxamide

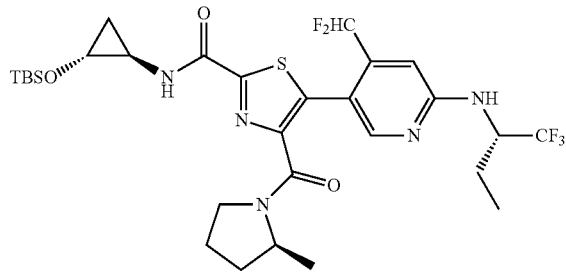 [SMILES: CC[C@H](Nc1cc(C(F)F)c(-c2sc(C(=O)N[C@@H]3C[C@H]3O[Si](C)(C)C(C)(C)C)nc2C(=O)N2CCC[C@@H]2C)cn1)C(F)(F)F]

The title compound was prepared as described in Intermediate 101: Step D substituting ethyl 5-(4-(difluoromethyl)-6-(((S)-1,1,1-trifluorobutan-2-yl)amino)pyridin-3-yl)-4-((S)-2-methylpyrrolidine-1-carbonyl)thiazole-2-carboxylate (Intermediate 102) for ethyl 5-(4-(difluoromethyl)-6-(((S)-1,1,1-trifluoropropan-2-yl)amino)pyridin-3-yl)-4-((S)-2-methylpyrrolidine-1-carbonyl) thiazole-2-carboxylate. The pure diastereomer was isolated via SFC (Stationary phase: Chiralpak AD-H, 5 μm, 250×30 mm, Mobile phase: 7.5% iPrOH+0.3% iPrNH$_2$, 92.5% CO$_2$, second eluting enantiomer).

Intermediate 102

Ethyl 5-(4-(difluoromethyl)-6-(((S)-1,1,1-trifluorobutan-2-yl)amino)pyridin-3-yl)-4-((S)-2-methylpyrrolidine-1-carbonyl)thiazole-2-carboxylate

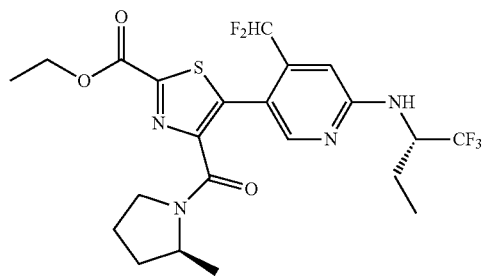 [SMILES: CCOC(=O)c1nc(C(=O)N2CCC[C@@H]2C)c(-c2cnc(N[C@@H](CC)C(F)(F)F)cc2C(F)F)s1]

The title compound was prepared as described in Example 77 substituting (S)-5-bromo-4-(difluoromethyl)-N-(1,1,1-trifluorobutan-2-yl)pyridin-2-amine (Intermediate 49) for 5-bromo-N-(1-methylcyclobutyl)-4-(trifluoromethyl)pyridin-2-amine and ethyl (S)-4-(2-methylpyrrolidine-1-carbonyl)thiazole-2-carboxylate (Intermediate 73: Step A) for (S)—N-(2-hydroxy-2-methylpropyl)-4-(2-methylpyrrolidine-1-carbonyl)thiazole-2-carboxamide.

Intermediate 103

Ethyl 4-(((S)-2-methylpyrrolidine-1-carbonyl)-5-(6-(((S)-1,1,1-trifluorobutan-2-yl)amino)-4-(trifluoromethyl)pyridin-3-yl)thiazole-2-carboxylate

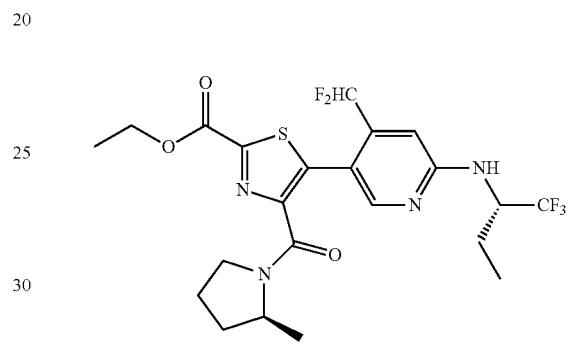

The title compound was prepared as described in Example 77 substituting (S)-5-bromo-N-(1,1,1-trifluorobutan-2-yl)-4-(trifluoromethyl)pyridin-2-amine (Intermediate 53) for 5-bromo-N-(1-methylcyclobutyl)-4-(trifluoromethyl)pyridin-2-amine and ethyl (S)-4-(2-methylpyrrolidine-1-carbonyl)thiazole-2-carboxylate (Intermediate 73: Step A) for (S)—N-(2-hydroxy-2-methylpropyl)-4-(2-methylpyrrolidine-1-carbonyl)thiazole-2-carboxamide.

Intermediate 104: Step A (R)-5-Bromo-4-(difluoromethyl)-N-(1,1,1-trifluorobutan-2-yl)pyridin-2-amine

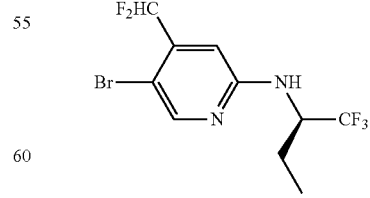

The title compound was prepared as described in Intermediate 41, using (R)-1,1,1-trifluoro-2-butylamine in place of tert-butylamine and 2-bromo-4-(difluoromethyl)pyridine in place of 2-bromo-4-(trifluoromethyl)pyridine in Step A.

Intermediate 104: Step B

Ethyl 5-(4-(difluoromethyl)-6-(((R)-1,1,1-trifluorobutan-2-yl)amino)pyridin-3-yl)-4-((S)-2-methylpyrrolidine-1-carbonyl)thiazole-2-carboxylate

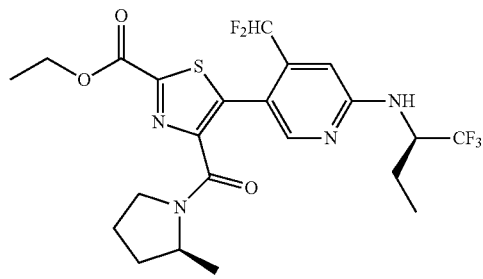 [SMILES: CCOC(=O)c1nc(C(=O)N2CCC[C@@H]2C)c(-c2cnc(N[C@H](CC)C(F)(F)F)cc2C(F)F)s1]

The title compound was prepared as described in Example 77 substituting (R)-5-bromo-4-(difluoromethyl)-N-(1,1,1-trifluorobutan-2-yl)pyridin-2-amine (Intermediate 104: Step A) for 5-bromo-N-(1-methylcyclobutyl)-4-(trifluoromethyl)pyridin-2-amine and ethyl (S)-4-(2-methylpyrrolidine-1-carbonyl)thiazole-2-carboxylate (Intermediate 73: Step A) for (S)—N-(2-hydroxy-2-methylpropyl)-4-(2-methylpyrrolidine-1-carbonyl)thiazole-2-carboxamide.

Intermediate 105 trans-N-((1R*,2R*)-2-((tert-Butyldimethylsilyl)oxy)cyclopropyl)-5-(4-(difluoromethyl)-6-(((S)-1,1,1-trifluoropropan-2-yl)amino)pyridin-3-yl)-4-((S)-2-methylpyrrolidine-1-carbonyl)thiazole-2-carboxamide

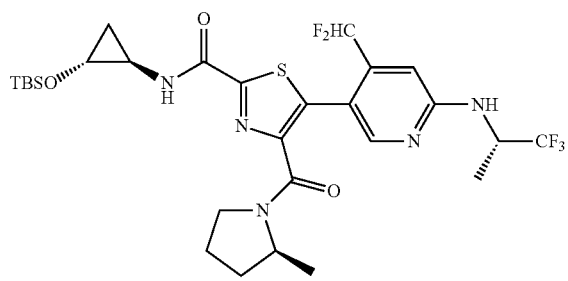 [SMILES: C[C@H](Nc1cc(C(F)F)c(-c2sc(C(=O)N[C@@H]3C[C@H]3O[Si](C)(C)C(C)(C)C)nc2C(=O)N2CCC[C@@H]2C)cn1)C(F)(F)F]

The title compound was prepared as described in Example 148 substituting trans-(1R*,2R*)-2-((tert-butyldimethylsilyl)oxy)cyclopropan-1-amine (Intermediate 101: Step C) for (R)-(−)-2-amino-1-propanol and ethyl 5-(4-(difluoromethyl)-6-(((S)-1,1,1-trifluoropropan-2-yl)amino)pyridin-3-yl)-4-((S)-2-methylpyrrolidine-1-carbonyl)thiazole-2-carboxylate (Intermediate 94) for ethyl (S)-5-(6-(tert-butylamino)-4-(difluoromethyl)pyridin-3-yl)-4-(2-methylpyrrolidine-1-carbonyl)thiazole-2-carboxylate.

Intermediate 106

Ethyl (S)-5-(6-(tert-butylamino)-4-(difluoromethyl)pyridin-3-yl)-4-(2-methylpyrrolidine-1-carbonyl)thiazole-2-carboxylate

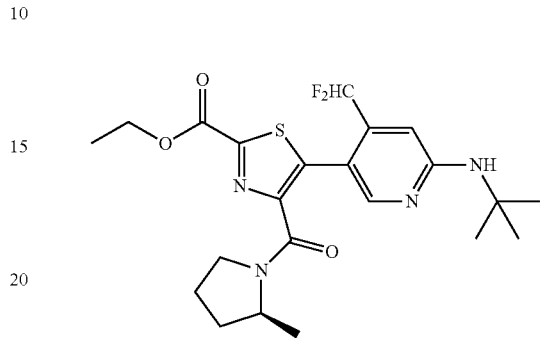

The title compound was prepared as described in Example 77 substituting 5-bromo-N-(tert-butyl)-4-(difluoromethyl)pyridin-2-amine (Intermediate 59) for 5-bromo-N-(1-methylcyclobutyl)-4-(trifluoromethyl)pyridin-2-amine and ethyl (S)-4-(2-methylpyrrolidine-1-carbonyl)thiazole-2-carboxylate (Intermediate 73: Step A) for (S)—N-(2-hydroxy-2-methylpropyl)-4-(2-methylpyrrolidine-1-carbonyl)thiazole-2-carboxamide.

Intermediate 107

Ethyl (S)-5-(6-(tert-butylamino)-4-(trifluoromethyl)pyridin-3-yl)-4-(2-methylpyrrolidine-1-carbonyl)thiazole-2-carboxylate

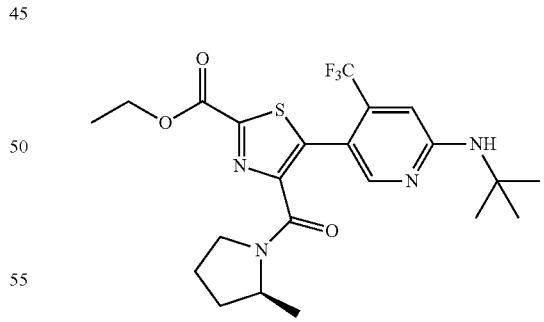

The title compound was prepared as described in Example 77 substituting 5-bromo-N-(tert-butyl)-4-(trifluoromethyl)pyridin-2-amine (Intermediate 41: Step B) for 5-bromo-N-(1-methylcyclobutyl)-4-(trifluoromethyl)pyridin-2-amine and ethyl (S)-4-(2-methylpyrrolidine-1-carbonyl)thiazole-2-carboxylate (Intermediate 73: Step A) for (S)—N-(2-hydroxy-2-methylpropyl)-4-(2-methylpyrrolidine-1-carbonyl)thiazole-2-carboxamide.

Intermediate 108: Step A

Ethyl (S)-4-(2-methylpiperidine-1-carbonyl)thiazole-2-carboxylate

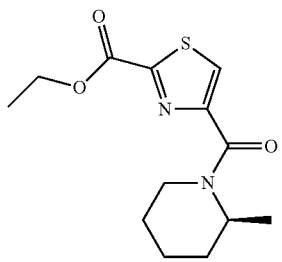 [SMILES: CCOC(=O)c1nc(C(=O)N2CCCC[C@@H]2C)cs1]

The title compound was prepared as described in Intermediate 70: Step A, using (S)-2-methylpiperidine in place of (1s,4s)-7-azabicyclo[2.2.1]heptane.

Intermediate 108: Step B

Ethyl 5-(4-(difluoromethyl)-6-(((S)-1,1,1-trifluorobutan-2-yl)amino)pyridin-3-yl)-4-((S)-2-methylpiperidine-1-carbonyl)thiazole-2-carboxylate

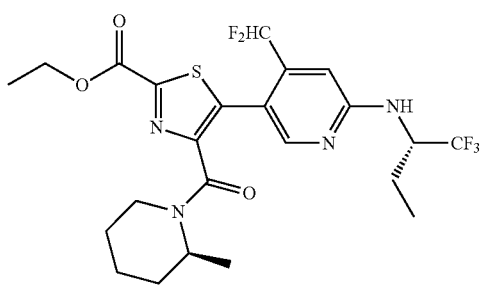 [SMILES: CCOC(=O)c1nc(C(=O)N2CCCC[C@@H]2C)c(-c2cnc(N[C@@H](CC)C(F)(F)F)cc2C(F)F)s1]

The title compound was prepared as described in Example 77 substituting (S)-5-bromo-4-(difluoromethyl)-N-(1,1,1-trifluorobutan-2-yl)pyridin-2-amine (Intermediate 49) for 5-bromo-N-(1-methylcyclobutyl)-4-(trifluoromethyl)pyridin-2-amine and ethyl (S)-4-(2-methylpiperidine-1-carbonyl)thiazole-2-carboxylate (Intermediate 108: Step A) for (S)—N-(2-hydroxy-2-methylpropyl)-4-(2-methylpyrrolidine-1-carbonyl)thiazole-2-carboxamide.

Intermediate 109: Step A

Ethyl (S)-4-(4,4-difluoro-2-methylpyrrolidine-1-carbonyl)thiazole-2-carboxylate

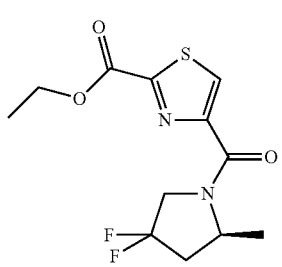 [SMILES: CCOC(=O)c1nc(C(=O)N2CC(F)(F)C[C@@H]2C)cs1]

The title compound was prepared as described in Intermediate 70: Step A, using (S)-4,4-difluoro-2-methylpyrrolidine hydrochloride (Intermediate 13: Step B) in place of (1s,4s)-7-azabicyclo[2.2.1]heptane.

Intermediate 109: Step B

Ethyl 4-((S)-4,4-difluoro-2-methylpyrrolidine-1-carbonyl)-5-(4-(difluoromethyl)-6-(((S)-1,1,1-trifluorobutan-2-yl)amino)pyridin-3-yl)thiazole-2-carboxylate

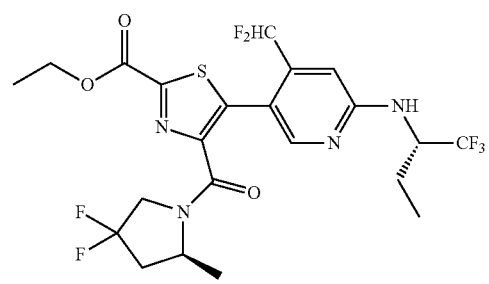 [SMILES: CCOC(=O)c1nc(C(=O)N2CC(F)(F)C[C@@H]2C)c(-c2cnc(N[C@@H](CC)C(F)(F)F)cc2C(F)F)s1]

The title compound was prepared as described in Example 77 substituting (S)-5-bromo-4-(difluoromethyl)-N-(1,1,1-trifluorobutan-2-yl)pyridin-2-amine (Intermediate 49) for 5-bromo-N-(1-methylcyclobutyl)-4-(trifluoromethyl)pyridin-2-amine and ethyl (S)-4-(4,4-difluoro-2-methylpyrrolidine-1-carbonyl)thiazole-2-carboxylate (Intermediate 109: Step A) for (S)—N-(2-hydroxy-2-methylpropyl)-4-(2-methylpyrrolidine-1-carbonyl)thiazole-2-carboxamide.

Intermediate 110

Ethyl (S)-5-(6-(tert-butylamino)-4-(difluoromethyl)pyridin-3-yl)-4-(4,4-difluoro-2-methylpyrrolidine-1-carbonyl)thiazole-2-carboxylate

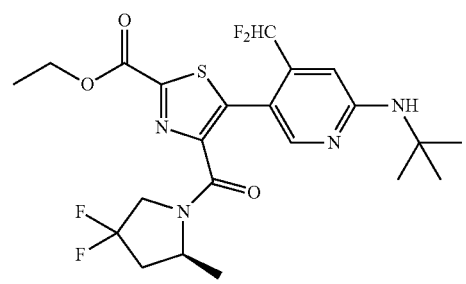 [SMILES: CCOC(=O)c1nc(C(=O)N2CC(F)(F)C[C@@H]2C)c(-c2cnc(NC(C)(C)C)cc2C(F)F)s1]

The title compound was prepared as described in Example 77 substituting 5-bromo-N-(tert-butyl)-4-(difluoromethyl)pyridin-2-amine (Intermediate 59) for 5-bromo-N-(1-methylcyclobutyl)-4-(trifluoromethyl)pyridin-2-amine and ethyl (S)-4-(4,4-difluoro-2-methylpyrrolidine-1-carbonyl)thiazole-2-carboxylate (Intermediate 109: Step A) for (S)—N-(2-hydroxy-2-methylpropyl)-4-(2-methylpyrrolidine-1-carbonyl)thiazole-2-carboxamide.

Intermediate 111

2-(Aminomethyl)-1,1,1,3,3,3-hexafluoropropan-2-ol

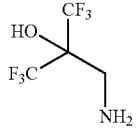

To a 25 mL round-bottom flask was added ammonium hydroxide solution (2.8 mL, 21.6 mmol, 30% in H$_2$O) and Et$_2$O (2.77 mL). Then, 2,2-bis(trifluoromethyl)oxirane (1 mL, 8.3 mmol) was added slowly and the resulting mixture stirred at rt for 3.5 hours. Et$_2$O (10 mL) was added and the layers were separated. The aqueous layer was extracted further with Et$_2$O (15 mL) and then the organic layers were combined, dried over anhydrous sodium sulfate, filtered and concentrated to dryness at low temperature to provide the title compound as a white solid.

Intermediate 112

5-Bromo-4-(difluoromethyl)-N-((1-(trifluoromethyl)cyclobutyl)methyl)pyridin-2-amine

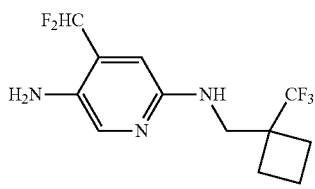 [SMILES: Nc1cnc(NCC2(C(F)(F)F)CCC2)cc1C(F)F]

The title compound was prepared as described in Intermediate 41, using [1-(trifluoromethyl)cyclobutyl]methanamine in place of tert-butylamine and 2-bromo-4-(difluoromethyl)pyridine in place of 2-bromo-4-(trifluoromethyl)pyridine in Step A.

Intermediate 113

5-Bromo-4-(difluoromethyl)-N-((1-(trifluoromethyl)cyclopropyl)methyl)pyridin-2-amine

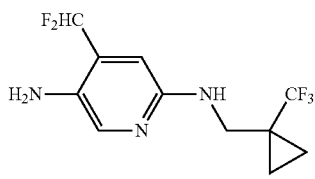 [SMILES: Nc1cnc(NCC2(C(F)(F)F)CC2)cc1C(F)F]

The title compound was prepared as described in Intermediate 41, using [1-(trifluoromethyl)cyclopropyl]methanamine HCl in place of tert-butylamine and 2-bromo-4-(difluoromethyl)pyridine in place of 2-bromo-4-(trifluoromethyl)pyridine in Step A.

Intermediate 114

5-Bromo-N-((1-methylcyclopropyl)methyl)-4-(trifluoromethyl)pyridin-2-amine

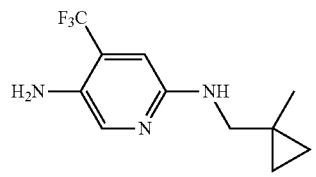 [SMILES: CC1(CNc2cc(C(F)(F)F)c(N)cn2)CC1]

The title compound was prepared as described in Intermediate 41, using (1-methylcyclopropyl)methanamine HCl in place of tert-butylamine in Step A.

Intermediate 115

(R)-5-Bromo-N-(1,1,1-trifluorobutan-2-yl)-4-(trifluoromethyl)pyridin-2-amine

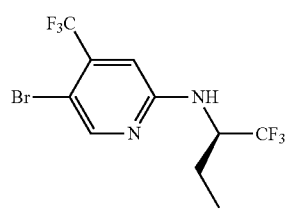 [SMILES: CC[C@@H](Nc1cc(C(F)(F)F)c(Br)cn1)C(F)(F)F]

The title compound was prepared as described in Intermediate 41, using (R)-1-trifluoromethyl-propylamine in place of tert-butylamine in Step A.

Intermediate 116

Ethyl 4-((1s,4s)-7-azabicyclo[2.2.1]heptane-7-carbonyl)-5-(4-(trifluoromethyl)-6-(((S)-1,1,1-trifluoropropan-2-yl)amino)pyridin-3-yl)thiazole-2-carboxylate

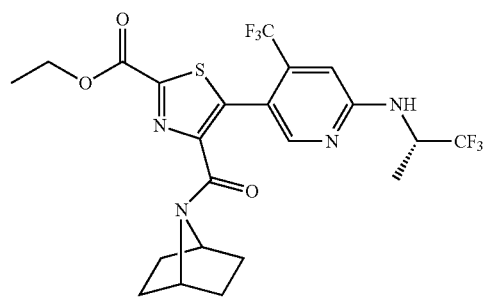 [SMILES: CCOC(=O)c1nc(C(=O)N2C3CCC2CC3)c(-c2cnc(N[C@@H](C)C(F)(F)F)cc2C(F)(F)F)s1]

The title compound was prepared as described in Intermediate 93 substituting (S)-5-bromo-4-(difluoromethyl)-N-(1,1,1-trifluoropropan-2-yl)pyridin-2-amine (Intermediate 60) in place of 5-bromo-N-(1-methylcyclobutyl)-4-(trifluoromethyl)pyridine-2-amine and ethyl 4-((2s,4s)-7-azabicyclo[2.2.1]heptane-7-carbonyl)thiazole-2-carboxylate (Intermediate 70: Step A) in place of ethyl (S)-4-(4,4-difluoro-2-methylpyrrolidine-1-carbonyl)thiazole-2-carboxylate.

Intermediate 117

Ethyl 4-((1s,4s)-7-azabicyclo[2.2.1]heptane-7-carbonyl)-5-(4-(difluoromethyl)-6-(((S)-1,1,1-trifluoropropan-2-yl)amino)pyridin-3-yl)thiazole-2-carboxylate

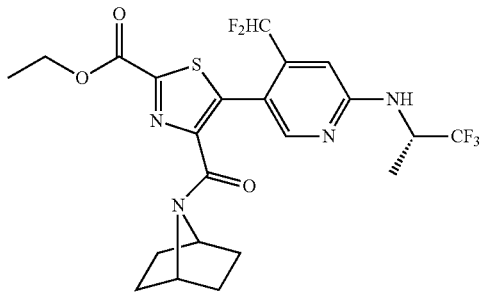 [SMILES: CCOC(=O)c1nc(C(=O)N2C3CCC2CC3)c(-c2cnc(N[C@@H](C)C(F)(F)F)cc2C(F)F)s1]

Ethyl 4-((1s,4s)-7-azabicyclo[2.2.1]heptane-7-carbonyl)thiazole-2-carboxylate (1.0 g, 3.6 mmol, Intermediate 70: Step A), (S)-5-bromo-4-(difluoromethyl)-N-(1,1,1-trifluoropropan-2-yl)pyridin-2-amine (1.25 g, 3.92 mmol, Intermediate 60), pivalic acid (146 mg, 1.43 mmol), $K_2CO_3$ (1.97 g, 14.3 mmol), 4A molecular sieves (2.0 g), and DMA (25 mL) were added to a 50 mL round-bottomed flask. The mixture was sparged with $N_2$ for 5 minutes and then treated with $Pd(OAc)_2$ (80 mg, 0.36 mmol), $PCy_3.HBF_4$ (260 mg, 0.707 mmol). The resultant mixture was sparged with $N_2$ for another 5 minutes and then stirred at 95° C. for 16 hours before cooling to room-temperature, quenching with water (50 mL), and extracting with ethyl acetate (50 mL×2). The combined organic extracts were dried over anhydrous $Na_2SO_4$, filtered, and concentrated to dryness under reduced pressure to afford the crude product, which was purified by preparative HPLC. The product was lyophilized from water to afford the title compound as a white solid.

Intermediate 118: Step A

N-(1-Cyclopropyl-2,2,2-trifluoroethyl)-4-(difluoromethyl)pyridin-2-amine

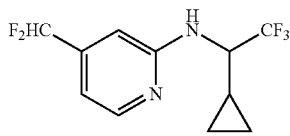 [SMILES: FC(F)c1ccnc(NC(C2CC2)C(F)(F)F)c1]

2-Bromo-4-(difluoromethyl)pyridine (500 mg, 2.40 mmol), and (S)-1-cyclopropyl-2,2,2-trifluoroethanamine (633 mg, 3.61 mmol), t-BuONa (693 mg, 7.22 mmol) were dissolved t-amyl-OH (10 mL). The resultant mixture was sparged with Ar for 5 min and then treated with SPhos-Pd-G3.DCM (103 mg, 0.119 mmol). The mixture was sparged with Ar for another 5 min and then stirred at 95° C. for 15 hours before quenching with water (20 mL) and extracting with ethyl acetate (30 mL×2). The combined organic extracts were dried over anhydrous $Na_2SO_4$, filtered, and concentrated to dryness under reduced pressure to give the crude product, which was purified by FCC (0-20% ethyl acetate/petroleum ether) to afford the title compound as a yellow oil.

Intermediate 118: Step B

5-Bromo-N-(1-cyclopropyl-2,2,2-trifluoroethyl)-4-(difluoromethyl)pyridin-2-amine

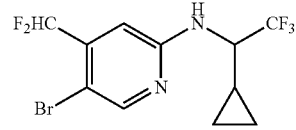

NBS (235 mg, 1.32 mmol) was added in portions to a solution consisting of N-(1-cyclopropyl-2,2,2-trifluoroethyl)-4-(difluoromethyl)pyridin-2-amine (440 mg, 1.65 mmol, Intermediate 118: Step A) and MeCN (30 mL). The resultant mixture was stirred at room temperature for 2 hours before quenching with water (20 mL) and extracting with ethyl acetate (50 mL×2). The combined organic extracts were dried over anhydrous $Na_2SO_4$, filtered, and concentrated to dryness under reduced pressure to give the crude product, which was purified by FCC (0-10% ethyl acetate/petroleum ether) to afford the title compound as a yellow oil.

Intermediate 119

(S)-5-Bromo-N-(1-cyclopropyl-2,2,2-trifluoroethyl)-4-(difluoromethyl)pyridin-2-amine

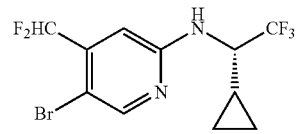 [SMILES: FC(F)c1cc(N[C@@H](C2CC2)C(F)(F)F)ncc1Br]

The title compound was prepared as described in Intermediate 118 substituting (S)-1-cyclopropyl-2,2,2-trifluoroethanamine for 1-cyclopropyl-2,2,2-trifluoroethanamine in Step A.

Intermediate 120

5-Bromo-4-(difluoromethyl)-N-(4,4,4-trifluoro-2-methylbutan-2-yl)pyridin-2-amine

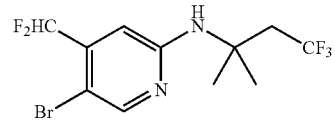 [SMILES: CC(C)(CC(F)(F)F)Nc1cc(C(F)F)c(Br)cn1]

The title compound was prepared as described in Intermediate 118 substituting 4,4,4-trifluoro-2-methylbutan-2-amine for 1-cyclopropyl-2,2,2-trifluoroethanamine in Step A.

Intermediate 121: Step A (R)-4-(Difluoromethyl)-N-(3-methylbutan-2-yl)pyridin-2-amine

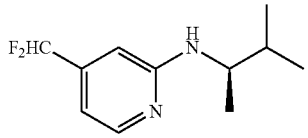

2-Chloro-4-(difluoromethyl)pyridine (2.0 g, 12 mmol) and (R)-3-methylbutan-2-amine (4.3 g, 49 mmol) were added to a 30 mL microwave tube. The resultant mixture was stirred while heating at 180° C. for 16 hours and at 200° C. for another 16 hours before cooling to room temperature and concentrating to dryness under reduced pressure to give the crude product, which was purified by FCC (0-10% ethyl acetate/petroleum ether) to afford the title compound as a yellow oil.

Intermediate 121: Step B (R)-5-Bromo-4-(difluoromethyl)-N-(3-methylbutan-2-yl)pyridin-2-amine

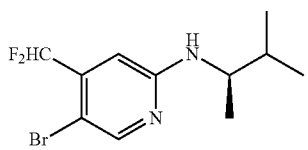 [SMILES: CC(C)[C@@H](C)Nc1cc(C(F)F)c(Br)cn1]

NBS (1.52 g, 8.54 mmol) was added in portions to a 0° C. (ice/water) solution consisting of (R)-4-(difluoromethyl)-N-(3-methylbutan-2-yl)pyridin-2-amine (1.83 g, 8.54 mmol, Intermediate 121: Step A) and dichloromethane (30 mL). The resultant mixture was stirred at 0° C. for 1 hour before pouring into water (30 mL) and extracting with dichloromethane (30 mL×3). The combined organic extracts were dried over anhydrous Na$_2$SO$_4$, filtered, and concentrated to dryness under reduced pressure to give the crude product, which was purified by FCC (0-10% ethyl acetate/petroleum ether) to afford the title compound as a yellow oil.

Intermediate 122

(R)-5-Bromo-4-(difluoromethyl)-N-(3,3-dimethylbutan-2-yl)pyridin-2-amine

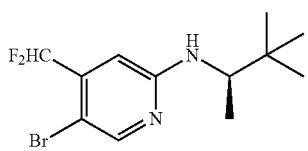 [SMILES: C[C@@H](Nc1cc(C(F)F)c(Br)cn1)C(C)(C)C]

The title compound was prepared as described in Intermediate 121 substituting (R)-3,3-dimethylbutan-2-amine for (R)-3-methylbutan-2-amine in Step A.

Intermediate 123

(S)-5-Bromo-4-(difluoromethyl)-N-(3,3-dimethylbutan-2-yl)pyridin-2-amine

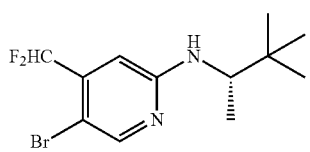 [SMILES: C[C@H](Nc1cc(C(F)F)c(Br)cn1)C(C)(C)C]

The title compound was prepared as described in Intermediate 121 substituting (S)-3,3-dimethylbutan-2-amine for (R)-3-methylbutan-2-amine in Step A.

Intermediate 124

(S)-5-Bromo-4-(difluoromethyl)-N-(3-methylbutan-2-yl)pyridin-2-amine

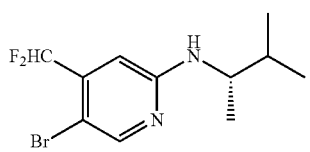 [SMILES: CC(C)[C@H](C)Nc1cc(C(F)F)c(Br)cn1]

The title compound was prepared as described in Intermediate 121 substituting (S)-3-methylbutan-2-amine for (R)-3-methylbutan-2-amine in Step A.

Intermediate 125

5-Bromo-N-(cyclobutylmethyl)-4-(difluoromethyl)pyridin-2-amine

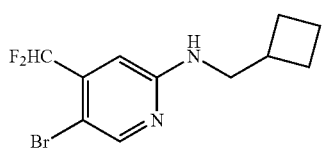 [SMILES: FC(F)c1cc(NCC2CCC2)ncc1Br]

The title compound was prepared as described in Intermediate 121 substituting cyclobutylmethanamine for (R)-3-methylbutan-2-amine in Step A.

Intermediate 126

(S)-5-(6-(tert-Butylamino)-4-(trifluoromethyl)pyridin-3-yl)-4-(2-methylpyrrolidine-1-carbonyl)thiazole-2-carboxylic acid

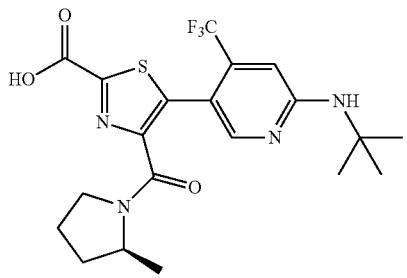 [SMILES: C[C@H]1CCCN1C(=O)c1nc(C(=O)O)sc1-c1cnc(NC(C)(C)C)cc1C(F)(F)F]

Ethyl (S)-5-(6-(tert-butylamino)-4-(trifluoromethyl)pyridin-3-yl)-4-(2-methylpyrrolidine-1-carbonyl)thiazole-2-carboxylate (1.01 g, 2.08 mmol, Intermediate 107) was diluted with EtOH and water (13 mL, 1:1 v/v) before DIPEA (1.1 mL, 6.3 mmol) was added, and the suspension was stirred at 80° C. for 3 h. After this time, the solution was allowed to cool and its pH was adjusted to pH 4 with 1.0 N aqueous HCl. The resulting mixture was extracted three times with EtOAc, and the organic layers were combined, dried with anhydrous MgSO₄, filtered, and concentrated to afford the title compound.

Intermediate 127: Step A (S)—N-(1-Cyclopropyl-2,2,2-trifluoroethyl)-4-(difluoromethyl)pyridin-2-amine

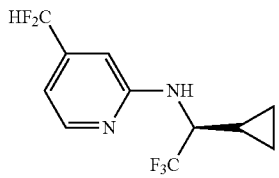

A mixture of 2-bromo-4-(difluoromethyl)pyridine (2.0 g, 9.6 mmol), (S)-1-cyclopropyl-2,2,2-trifluoroethanamine (2.2 g, 13 mmol), and NaOt-Bu (2.77 g, 28.9 mmol) in t-amyl alcohol (40 mL) was sparged with argon for 5 min before SPhos Pd G3 (250 mg, 0.289 mmol) was added, and the mixture was sparged with argon for another 5 min. The mixture was then stirred at 95° C. for 15 hours. After this time, the mixture was allowed to cool, diluted with water, and extracted twice with ethyl acetate. The organic layers were combined, dried over anhydrous Na₂SO₄, filtered, and concentrated. The residue was purified by FCC (0-5% EtOAc/petroleum ether) to afford the title compound.

Intermediate 127: Step B (S)-5-Bromo-N-(1-cyclopropyl-2,2,2-trifluoroethyl)-4-(difluoromethyl)pyridin-2-amine

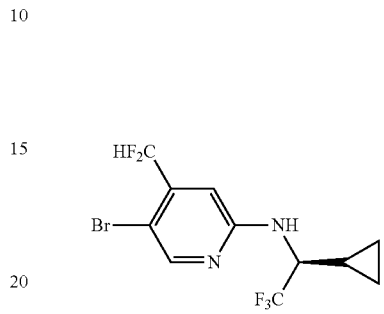

N-Bromosuccinimide (1.60 g, 8.99 mmol) was added in portions to a solution of (S)—N-(1-cyclopropyl-2,2,2-trifluoroethyl)-4-(difluoromethyl)pyridin-2-amine (2.40 g, 9.02 mmol, Intermediate 127: Step A) in MeCN (25 mL), and the resulting mixture was stirred at rt for 5 h. The mixture was diluted with water, and then extracted with twice with EtOAc. The organic layers were combined, dried over anhydrous Na₂SO₄, filtered, and concentrated. The residue was purified by FCC (2-20% EtOAc/petroleum ether) to afford the title compound.

Intermediate 128

Ethyl 5-(6-(((S)-1-cyclopropyl-2,2,2-trifluoroethyl)amino)-4-(difluoromethyl)pyridin-3-yl)-4-((S)-2-methylpyrrolidine-1-carbonyl)thiazole-2-carboxylate

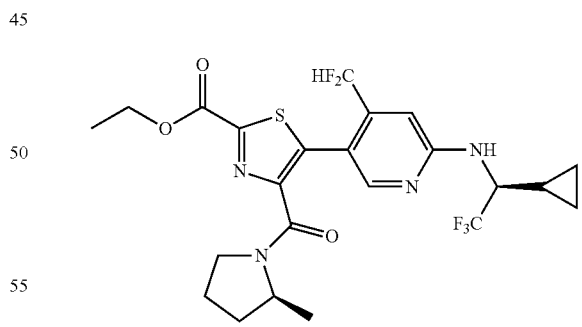

The title compound was prepared as described in Example 77, substituting (S)-5-bromo-N-(1-cyclopropyl-2,2,2-trifluoroethyl)-4-(difluoromethyl)pyridin-2-amine (Intermediate 127: Step B) and ethyl (S)-4-(2-methylpyrrolidine-1-carbonyl)thiazole-2-carboxylate (Intermediate 73: Step A) for 5-bromo-N-(1-methylcyclobutyl)-4-(trifluoromethyl)pyridin-2-amine and (S)—N-(2-hydroxy-2-methylpropyl)-4-(2-methylpyrrolidine-1-carbonyl)thiazole-2-carboxamide.

Intermediate 129

Ethyl 5-(6-(((S)-1-cyclopropyl-2,2,2-trifluoroethyl)amino)-4-(difluoromethyl)pyridin-3-yl)-4-((S)-4,4-difluoro-2-methylpyrrolidine-1-carbonyl)thiazole-2-carboxylate

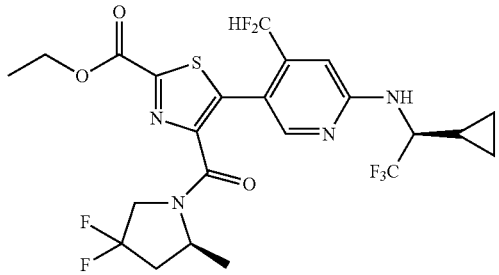

The title compound was prepared as described in Example 77, substituting (S)-5-bromo-N-(1-cyclopropyl-2,2,2-trifluoroethyl)-4-(difluoromethyl)pyridin-2-amine (Intermediate 127: Step B) and ethyl (S)-4-(4,4-difluoro-2-methylpyrrolidine-1-carbonyl)thiazole-2-carboxylate (Intermediate 109: Step A) for 5-bromo-N-(1-methylcyclobutyl)-4-(trifluoromethyl)pyridin-2-amine and (S)—N-(2-hydroxy-2-methylpropyl)-4-(2-methylpyrrolidine-1-carbonyl)thiazole-2-carboxamide.

Intermediate 130

Ethyl 4-((1s,4s)-7-azabicyclo[2.2.1]heptane-7-carbonyl)-5-(6-(((S)-1-cyclopropyl-2,2,2-trifluoroethyl)amino)-4-(difluoromethyl)pyridin-3-yl)thiazole-2-carboxylate

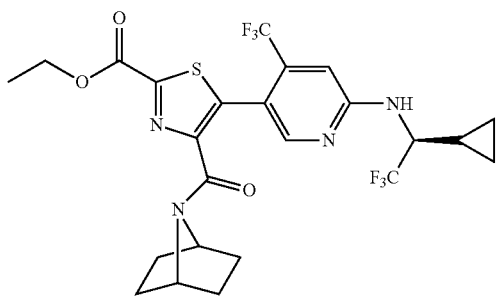 [SMILES: CCOC(=O)c1nc(C(=O)N2C3CCC2CC3)c(-c2cnc(N[C@@H](C3CC3)C(F)(F)F)cc2C(F)(F)F)s1]

The title compound was prepared as described in Example 77, substituting (S)-5-bromo-N-(1-cyclopropyl-2,2,2-trifluoroethyl)-4-(difluoromethyl)pyridin-2-amine (Intermediate 127: Step B) and ethyl 4-((1s,4s)-7-azabicyclo[2.2.1]heptane-7-carbonyl)thiazole-2-carboxylate (Intermediate 70: Step A) for 5-bromo-N-(1-methylcyclobutyl)-4-(trifluoromethyl)pyridin-2-amine and (S)-N-(2-hydroxy-2-methylpropyl)-4-(2-methylpyrrolidine-1-carbonyl)thiazole-2-carboxamide.

Intermediate 131

5-Bromo-4-(difluoromethyl)-N-(1-methylcyclobutyl)pyridin-2-amine

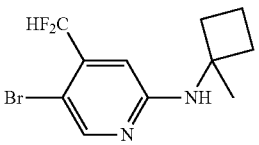

The title compound was prepared as described in Intermediate 127, substituting 1-methylcyclobutan-1-amine for (S)-1-cyclopropyl-2,2,2-trifluoroethanamine in Step A.

Intermediate 132

N—((R)-3-Hydroxy-3-methylbutan-2-yl)-4-((S)-2-methylpyrrolidine-1-carbonyl)thiazole-2-carboxamide

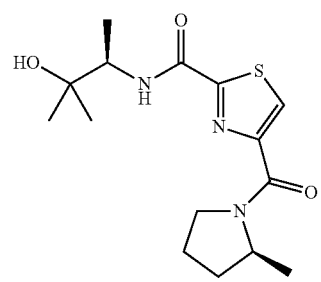 [SMILES: C[C@H]1CCCN1C(=O)c1csc(C(=O)N[C@H](C)C(C)(C)O)n1]

The title compound was prepared as described in Example 148, substituting ethyl (S)-4-(2-methylpyrrolidine-1-carbonyl)thiazole-2-carboxylate (Intermediate 73: Step A) and (R)-3-amino-2-methylbutan-2-ol for ethyl (S)-5-(6-(tert-butylamino)-4-(difluoromethyl)pyridin-3-yl)-4-(2-methylpyrrolidine-1-carbonyl)thiazole-2-carboxylate and (R)-(−)-2-amino-1-propanol.

Intermediate 133

Potassium (S)-5-(4-(difluoromethyl)-6-(((1-methylcyclobutyl)amino)pyridin-3-yl)-4-(2-methylpyrrolidine-1-carbonyl)thiazole-2-carboxylate

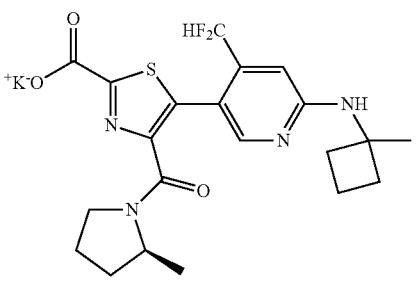

The title compound was prepared as described in Intermediate 62, substituting 5-bromo-4-(difluoromethyl)-N-(1- methylcyclobutyl)pyridin-2-amine (Intermediate 131) for 5-bromo-N-cyclopentyl-4-(difluoromethyl) pyridin-2-amine.

Intermediate 134

(S)—N-(1,1-Dioxidotetrahydro-2H-thiopyran-4-yl)-4-(2-methylpyrrolidine-1-carbonyl)thiazole-2-carboxamide

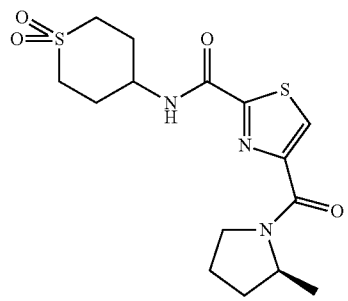 [SMILES: C[C@H]1CCCN1C(=O)c1csc(C(=O)NC2CCS(=O)(=O)CC2)n1]

The title compound was prepared as described in Intermediate 72, Step B, substituting potassium (S)-4-(2-methylpyrrolidine-1-carbonyl)thiazole-2-carboxylate (Intermediate 73: Step B) for 4-(tert-butoxycarbonyl)thiazole-2-carboxylic acid.

Intermediate 135

4-((S)-4,4-Difluoro-2-methylpyrrolidine-1-carbonyl)-N—((R)-3-hydroxy-3-methylbutan-2-yl)thiazole-2-carboxamide

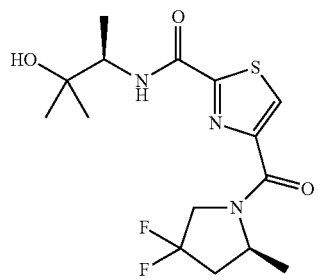 [SMILES: C[C@H]1CC(F)(F)CN1C(=O)c1csc(C(=O)N[C@H](C)C(C)(C)O)n1]

The title compound was prepared as described in Example 148, substituting ethyl (S)-4-(4,4-difluoro-2-methylpyrrolidine-1-carbonyl)thiazole-2-carboxylate (Intermediate 109: Step A) and (R)-3-amino-2-methylbutan-2-ol for ethyl (S)-5-(6-(tert-butylamino)-4-(difluoromethyl)pyridin-3-yl)-4-(2-methylpyrrolidine-1-carbonyl)thiazole-2-carboxylate and (R)-(−)-2-amino-1-propanol.

Intermediate 136

Ethyl (S)-4-(4,4-difluoro-2-methylpyrrolidine-1-carbonyl)-5-(4-(difluoromethyl)-6-((1-methylcyclobutyl)amino)pyridin-3-yl)thiazole-2-carboxylate

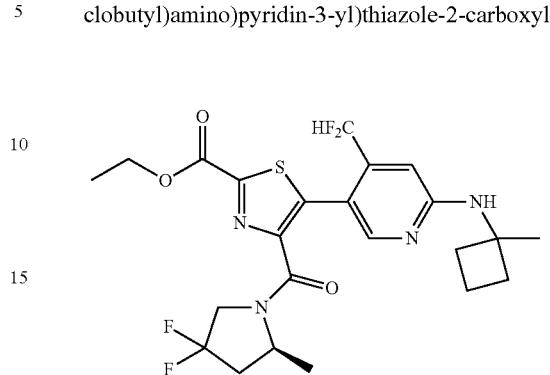

The title compound was prepared as described in Intermediate 62, Step A, substituting 5-bromo-4-(difluoromethyl)-N-(1-methylcyclobutyl)pyridin-2-amine (Intermediate 131) and ethyl (S)-4-(4,4-difluoro-2-methylpyrrolidine-1-carbonyl)thiazole-2-carboxylate (Intermediate 109: Step A) for 5-bromo-N-cyclopentyl-4-(difluoromethyl) pyridin-2-amine and (S)-ethyl 4-(2-methylpyrrolidine-1-carbonyl)thiazole-2-carboxylate.

Intermediate 137

(R)-5-Bromo-N-(1-cyclopropyl-2,2,2-trifluoroethyl)-4-(difluoromethyl)pyridin-2-amine

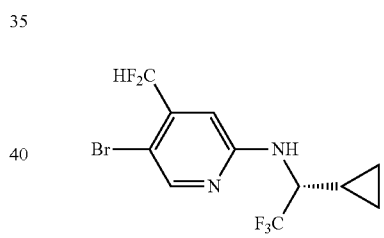

The title compound was prepared as described in Intermediate 127, substituting (R)-1-cyclopropyl-2,2,2-trifluoroethanamine for (S)-1-cyclopropyl-2,2,2-trifluoroethanamine in Step A.

Intermediate 138

(R)-5-Bromo-4-(difluoromethyl)-N-(1,1,1-trifluoropropan-2-yl)pyridin-2-amine

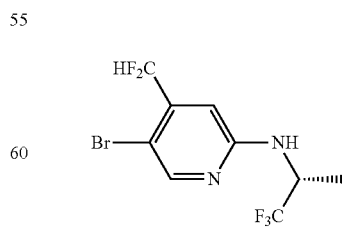

The title compound was prepared as described in Intermediate 127, substituting (R)-1,1,1-trifluoropropan-2-amine for (S)-1-cyclopropyl-2,2,2-trifluoroethanamine in Step A.

Intermediate 139

N—((S)-3-Hydroxy-3-methylbutan-2-yl)-4-((S)-2-methylpyrrolidine-1-carbonyl)thiazole-2-carboxamide

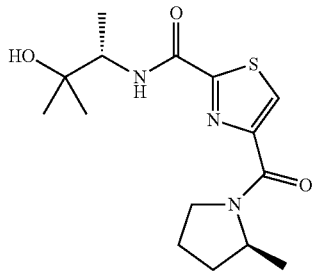 [SMILES: C[C@H](NC(=O)c1nc(C(=O)N2CCC[C@@H]2C)cs1)C(C)(C)O]

The title compound was prepared as described in Example 148, substituting ethyl (S)-4-(2-methylpyrrolidine-1-carbonyl)thiazole-2-carboxylate (Intermediate 73: Step A) and (S)-3-amino-2-methylbutan-2-ol for ethyl (S)-5-(6-(tert-butylamino)-4-(difluoromethyl)pyridin-3-yl)-4-(2-methylpyrrolidine-1-carbonyl)thiazole-2-carboxylate and (R)-(−)-2-amino-1-propanol.

Intermediate 140

4-((S)-4,4-Difluoro-2-methylpyrrolidine-1-carbonyl)-N—((S)-3-hydroxy-3-methylbutan-2-yl)thiazole-2-carboxamide

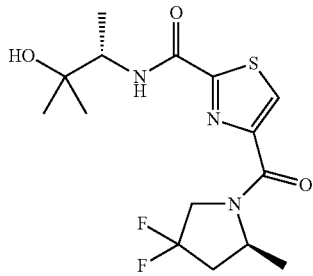 [SMILES: C[C@H](NC(=O)c1nc(C(=O)N2CC(F)(F)C[C@@H]2C)cs1)C(C)(C)O]

The title compound was prepared as described in Example 148, substituting ethyl (S)-4-(4,4-difluoro-2-methylpyrrolidine-1-carbonyl)thiazole-2-carboxylate (Intermediate 109: Step A) and (S)-3-amino-2-methylbutan-2-ol for ethyl (S)-5-(6-(tert-butylamino)-4-(difluoromethyl)pyridin-3-yl)-4-(2-methylpyrrolidine-1-carbonyl)thiazole-2-carboxylate and (R)-(−)-2-amino-1-propanol.

Intermediate 141

Potassium (S)-4-(4,4-difluoro-2-methylpyrrolidine-1-carbonyl)thiazole-2-carboxylate

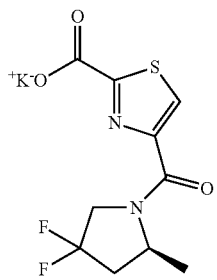

The title compound was prepared as described in Intermediate 73: Step B, substituting ethyl (S)-4-(4,4-difluoro-2-methylpyrrolidine-1-carbonyl)thiazole-2-carboxylate (Intermediate 109: Step A) for ethyl (S)-4-(2-methylpyrrolidine-1-carbonyl)thiazole-2-carboxylate.

Intermediate 142

(S)-4-(4,4-Difluoro-2-methylpyrrolidine-1-carbonyl)-N-(1,1-dioxidotetrahydro-2H-thiopyran-4-yl)thiazole-2-carboxamide

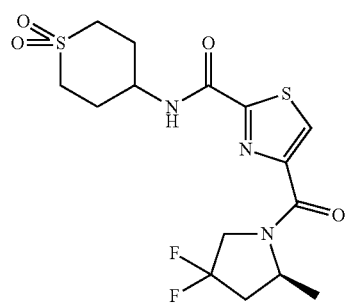 [SMILES: C[C@H]1CC(F)(F)CN1C(=O)c1csc(C(=O)NC2CCS(=O)(=O)CC2)n1]

The title compound was prepared as described in Intermediate 72: Step B, substituting potassium (S)-4-(4,4-difluoro-2-methylpyrrolidine-1-carbonyl)thiazole-2-carboxylate (Intermediate 141) for 4-(tert-butoxycarbonyl)thiazole-2-carboxylic acid.

Intermediate 143

4-((1s,4s)-7-Azabicyclo[2.2.1]heptane-7-carbonyl)-N—((R)-3-hydroxy-3-methylbutan-2-yl)thiazole-2-carboxamide

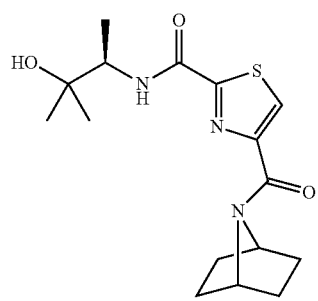 [SMILES: C[C@@H](NC(=O)c1nc(C(=O)N2C3CCC2CC3)cs1)C(C)(C)O]

The title compound was prepared as described in Example 148, substituting ethyl 4-((1s,4s)-7-azabicyclo[2.2.1]heptane-7-carbonyl)thiazole-2-carboxylate (Intermediate 70: Step A) and (R)-3-amino-2-methylbutan-2-ol for ethyl (S)-5-(6-(tert-butylamino)-4-(difluoromethyl)pyridin-3-yl)-4-(2-methylpyrrolidine-1-carbonyl)thiazole-2-carboxylate and (R)-(−)-2-amino-1-propanol.

Intermediate 144

Ethyl 4-((1s,4s)-7-Azabicyclo[2.2.1]heptane-7-carbonyl)-5-(4-(difluoromethyl)-6-((1-methylcyclobutyl)amino)pyridin-3-yl)thiazole-2-carboxylate

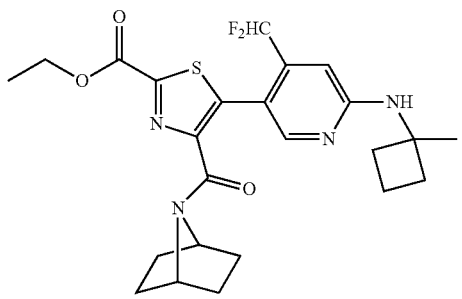 [SMILES: CCOC(=O)c1nc(C(=O)N2C3CCC2CC3)c(-c2cnc(NC3(C)CCC3)cc2C(F)F)s1]

The title compound was prepared as described in Intermediate 62: Step A, substituting 5-bromo-4-(difluoromethyl)-N-(1-methylcyclobutyl)pyridin-2-amine (Intermediate 131) and ethyl 4-((1s,4s)-7-azabicyclo[2.2.1]heptane-7-carbonyl)thiazole-2-carboxylate (Intermediate 70: Step A) for 5-bromo-N-cyclopentyl-4-(difluoromethyl)pyridin-2-amine and ethyl (S)-4-(2-methylpyrrolidine-1-carbonyl)thiazole-2-carboxylate.

Intermediate 145

Potassium 4-((1s,4s)-7-azabicyclo[2.2.1]heptane-7-carbonyl)-5-(4-(difluoromethyl)-6-((1-methylcyclobutyl)amino)pyridin-3-yl)thiazole-2-carboxylate

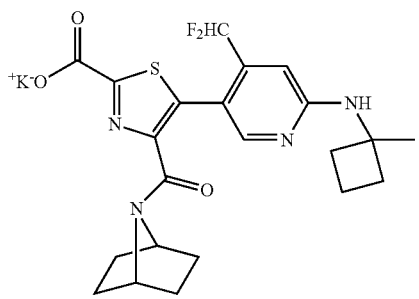

The title compound was prepared as described in Intermediate 73: Step B, substituting ethyl 4-((1s,4s)-7-azabicyclo[2.2.1]heptane-7-carbonyl)-5-(4-(difluoromethyl)-6-((1-methylcyclobutyl)amino)pyridin-3-yl)thiazole-2-carboxylate (Intermediate 144) for ethyl (S)-4-(2-methylpyrrolidine-1-carbonyl)thiazole-2-carboxylate.

Intermediate 146

Potassium 4-((1s,4s)-7-azabicyclo[2.2.1]heptane-7-carbonyl)thiazole-2-carboxylate

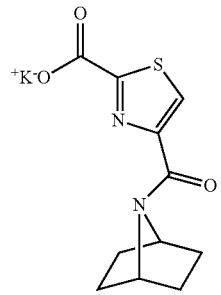

The title compound was prepared as described in Intermediate 73: Step B, substituting ethyl 4-((1s,4s)-7-azabicyclo[2.2.1]heptane-7-carbonyl)thiazole-2-carboxylate (Intermediate 70: Step A) for ethyl (S)-4-(2-methylpyrrolidine-1-carbonyl)thiazole-2-carboxylate.

Intermediate 147

4-((1s,4s)-7-Azabicyclo[2.2.1]heptane-7-carbonyl)-N-(1,1-dioxidotetrahydro-2H-thiopyran-4-yl)thiazole-2-carboxamide

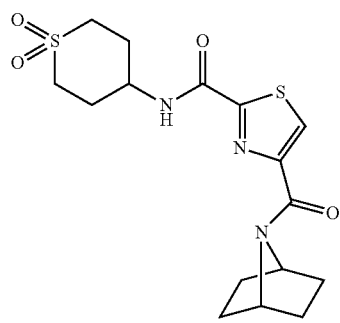 [SMILES: O=C(NC1CCS(=O)(=O)CC1)c1nc(C(=O)N2C3CCC2CC3)cs1]

The title compound was prepared as described in Intermediate 72: Step B, substituting potassium 4-((1s,4s)-7-azabicyclo[2.2.1]heptane-7-carbonyl)thiazole-2-carboxylate (Intermediate 146) for 4-(tert-butoxycarbonyl)thiazole-2-carboxylic acid.

Intermediate 148

Ethyl 5-(6-(((R)-1-cyclopropyl-2,2,2-trifluoroethyl)amino)-4-(difluoromethyl)pyridin-3-yl)-4-((S)-2-methylpyrrolidine-1-carbonyl)thiazole-2-carboxylate

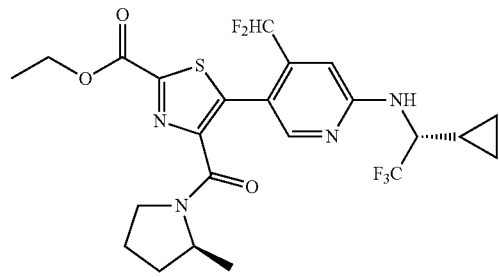 [SMILES: CCOC(=O)c1nc(C(=O)N2CCC[C@@H]2C)c(-c2cnc(N[C@H](C3CC3)C(F)(F)F)cc2C(F)F)s1]

The title compound was prepared as described in Intermediate 62: Step A, substituting (R)-5-bromo-N-(1-cyclopropyl-2,2,2-trifluoroethyl)-4-(difluoromethyl)pyridin-2-amine (Intermediate 137) and ethyl (S)-4-(2-methylpyrrolidine-1-carbonyl)thiazole-2-carboxylate (Intermediate 73: Step A) for 5-bromo-N-cyclopentyl-4-(difluoromethyl)pyridin-2-amine and ethyl (S)-4-(2-methylpyrrolidine-1-carbonyl)thiazole-2-carboxylate.

Intermediate 149

Ethyl 5-(4-(difluoromethyl)-6-(((R)-1,1,1-trifluoropropan-2-yl)amino)pyridin-3-yl)-4-((S)-2-methylpyrrolidine-1-carbonyl)thiazole-2-carboxylate

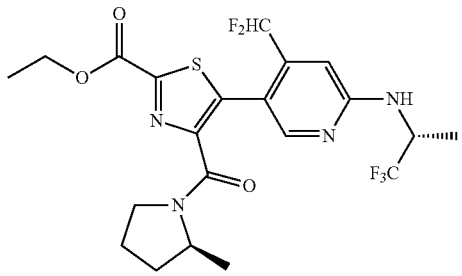 [SMILES: CCOC(=O)c1nc(C(=O)N2CCC[C@@H]2C)c(-c2cnc(N[C@H](C)C(F)(F)F)cc2C(F)F)s1]

The title compound was prepared as described in Intermediate 62: Step A, substituting (R)-5-bromo-4-(difluoromethyl)-N-(1,1,1-trifluoropropan-2-yl)pyridin-2-amine (Intermediate 138) and ethyl (S)-4-(2-methylpyrrolidine-1-carbonyl)thiazole-2-carboxylate (Intermediate 73: Step A) for 5-bromo-N-cyclopentyl-4-(difluoromethyl)pyridin-2-amine and ethyl (S)-4-(2-methylpyrrolidine-1-carbonyl)thiazole-2-carboxylate.

Intermediate 150

Ethyl (S)-4-(2-methylpyrrolidine-1-carbonyl)-5-(6-(neopentylamino)-4-(trifluoromethyl) pyridin-3-yl)thiazole-2-carboxylate

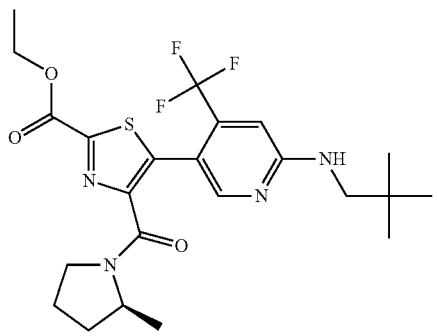 [SMILES: CCOC(=O)c1nc(C(=O)N2CCC[C@@H]2C)c(-c2cnc(NCC(C)(C)C)cc2C(F)(F)F)s1]

The title compound was prepared as described in Intermediate 93 substituting 5-bromo-N-neopentyl-4-(trifluoromethyl)pyridine-2-amine (Intermediate 73: Step A) in place of 5-bromo-N-(1-methylcyclobutyl)-4-(trifluoromethyl)pyridine-2-amine and ethyl (S)-4-(2-methylpyrrolidine-1-carbonyl)thiazole-2-carboxylate (Intermediate 22) in place of ethyl (S)-4-(4,4-difluoro-2-methylpyrrolidine-1-carbonyl)thiazole-2-carboxylate.

Intermediate 151

Ethyl (S)-5-(4-(difluoromethyl)-6-(neopentylamino)pyridin-3-yl)-4-(2-methylpyrrolidine-1-carbonyl)thiazole-2-carboxylate

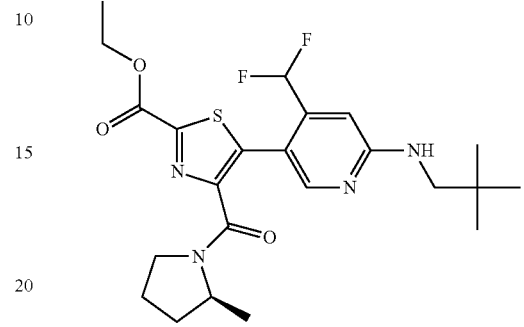

The title compound was prepared as described in Intermediate 93 substituting 5-bromo-4-(difluoromethyl)-N-neopentylpyridin-2-amine (Intermediate 73: Step A) in place of 5-bromo-N-(1-methylcyclobutyl)-4-(trifluoromethyl)pyridine-2-amine and ethyl (S)-4-(2-methylpyrrolidine-1-carbonyl)thiazole-2-carboxylate (Intermediate 23) in place of ethyl (S)-4-(4,4-difluoro-2-methylpyrrolidine-1-carbonyl)thiazole-2-carboxylate.

Intermediate 152

Ethyl 4-((1s,4s)-7-azabicyclo[2.2.1]heptane-7-carbonyl)-5-(4-(difluoromethyl)-6-(((S)-1,1,1-trifluoropropan-2-yl)amino)pyridin-3-yl)thiazole-2-carboxylate

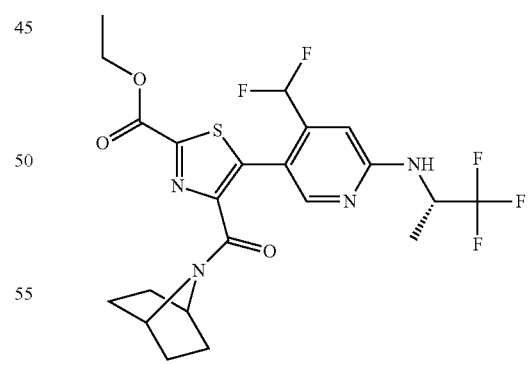

The title compound was prepared as described in Intermediate 93 substituting (S)-5-bromo-4-(difluoromethyl)-N-(1,1,1-trifluoropropan-2-yl)pyridin-2-amine (Intermediate 60) in place of 5-bromo-N-(1-methylcyclobutyl)-4-(trifluoromethyl)pyridine-2-amine and ethyl 4-((1s,4s)-7-azabicyclo[2.2.1]heptane-7-carbonyl)thiazole-2-carboxylate (Intermediate 70: Step A) in place of ethyl (S)-4-(4,4-difluoro-2-methylpyrrolidine-1-carbonyl)thiazole-2-carboxylate.

Intermediate 153

Potassium 4-((1s,4s)-7-azabicyclo[2.2.1]heptane-7-carbonyl)-5-(4-(difluoromethyl)-6-(((S)-1,1,1-trifluoropropan-2-yl)amino)pyridin-3-yl)thiazole-2-carboxylate

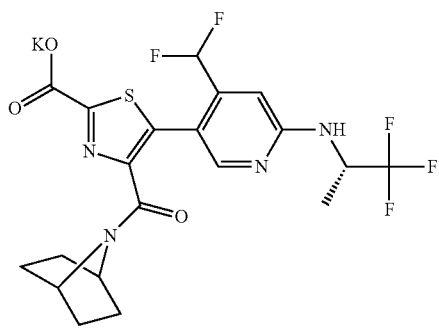

The title compound was prepared as described in Intermediate 62, Step B substituting ethyl 4-((1s,4s)-7-azabicyclo[2.2.1]heptane-7-carbonyl)-5-(4-(difluoromethyl)-6-(((S)-1,1,1-trifluoropropan-2-yl)amino)pyridin-3-yl)thiazole-2-carboxylate (Intermediate 152) for ethyl (S)-5-(6-(cyclopentylamino)-4-(difluoromethyl)pyridin-3-yl)-4-(2-methylpyrrolidine-1-carbonyl)thiazole-2-carboxylate (Intermediate 62, Step A).

Intermediate 154

Ethyl 4-((1s,4s)-7-azabicyclo[2.2.1]heptane-7-carbonyl)-5-(6-(tert-butylamino)-4-(difluoromethyl)pyridin-3-yl)thiazole-2-carboxylate

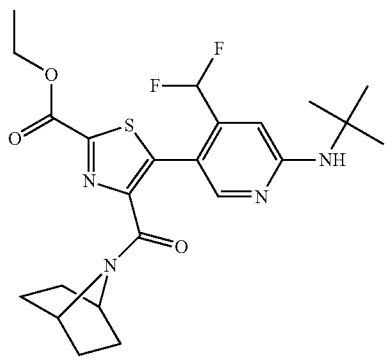 [SMILES: CCOC(=O)c1nc(C(=O)N2C3CCC2CC3)c(-c2cnc(NC(C)(C)C)cc2C(F)F)s1]

The title compound was prepared as described in Intermediate 93 substituting 5-bromo-N-(tert-butyl)-4-(difluoromethyl)pyridin-2-amine (Intermediate 59) in place of 5-bromo-N-(1-methylcyclobutyl)-4-(trifluoromethyl)pyridine-2-amine and ethyl 4-((1s,4s)-7-azabicyclo[2.2.1]heptane-7-carbonyl)thiazole-2-carboxylate (Intermediate 70: Step A) in place of ethyl (S)-4-(4,4-difluoro-2-methylpyrrolidine-1-carbonyl)thiazole-2-carboxylate.

Intermediate 155

Potassium 4-((1s,4s)-7-azabicyclo[2.2.1]heptane-7-carbonyl)-5-(6-(tert-butylamino)-4-(difluoromethyl)pyridin-3-yl)thiazole-2-carboxylate

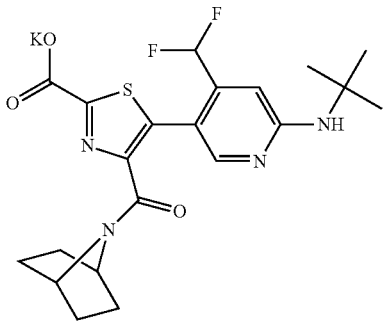

The title compound was prepared as described in Intermediate 62, Step B substituting ethyl 4-((1s,4s)-7-azabicyclo[2.2.1]heptane-7-carbonyl)-5-(6-(tert-butylamino)-4-(difluoromethyl)pyridin-3-yl)thiazole-2-carboxylate (Intermediate 154) for ethyl (S)-5-(6-(cyclopentylamino)-4-(difluoromethyl)pyridin-3-yl)-4-(2-methylpyrrolidine-1-carbonyl)thiazole-2-carboxylate (Intermediate 62, Step A).

Intermediate 156

Potassium (S)-5-(6-(tert-butylamino)-4-(difluoromethyl)pyridin-3-yl)-4-(2-methylpyrrolidine-1-carbonyl)thiazole-2-carboxylate

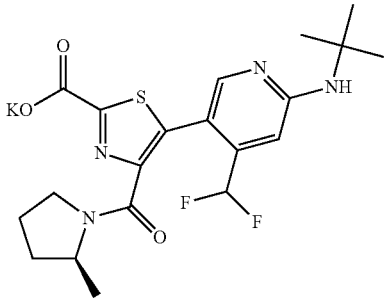

The title compound was prepared as described in Intermediate 62, Step B substituting ethyl (S)-5-(6-(tert-butylamino)-4-(difluoromethyl)pyridin-3-yl)-4-(2-methylpyrrolidine-1-carbonyl)thiazole-2-carboxylate (Intermediate 106) for ethyl (S)-5-(6-(cyclopentylamino)-4-(difluoromethyl)pyridin-3-yl)-4-(2-methylpyrrolidine-1-carbonyl)thiazole-2-carboxylate (Intermediate 62, Step A).

Intermediate 157

Potassium 4-((S)-4,4-difluoro-2-methylpyrrolidine-1-carbonyl)-5-(4-(difluoromethyl)-6-(((S)-1,1,1-trifluoropropan-2-yl)amino)pyridin-3-yl)thiazole-2-carboxylate

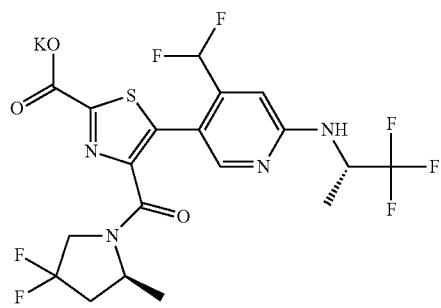

The title compound was prepared as described in Intermediate 62, Step B substituting ethyl 4-((S)-4,4-difluoro-2-methylpyrrolidine-1-carbonyl)-5-(4-(difluoromethyl)-6-(((S)-1,1,1,-trifluoropropan-2-yl)amino)pyridine-3-yl)thiazole-2-carboxylate (Intermediate 96) for ethyl (S)-5-(6-(cyclopentylamino)-4-(difluoromethyl)pyridin-3-yl)-4-(2-methylpyrrolidine-1-carbonyl)thiazole-2-carboxylate (Intermediate 62, Step A).

Intermediate 158

Ethyl 4-((S)-4,4-difluoro-2-methylpyrrolidine-1-carbonyl)-5-(4-(difluoromethyl)-6-(((S)-1,1,1-trifluorobutan-2-yl)amino)pyridin-3-yl)thiazole-2-carboxylate

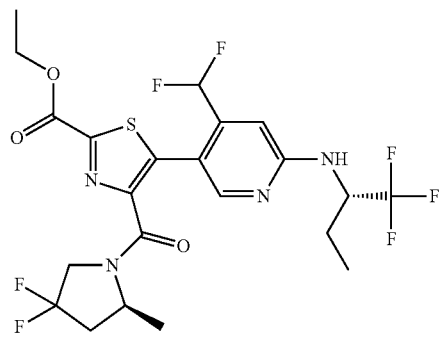 [SMILES: CCOC(=O)c1nc(C(=O)N2CC(F)(F)C[C@@H]2C)c(-c2cnc(N[C@@H](CC)C(F)(F)F)cc2C(F)F)s1]

The title compound was prepared as described in Intermediate 93 substituting (S)-5-bromo-4-(difluoromethyl)-N-(1,1,1-trifluorobutan-2-yl)pyridin-2-amine (Intermediate 49) in place of 5-bromo-N-(1-methylcyclobutyl)-4-(trifluoromethyl)pyridine-2-amine and ethyl (S)-4-(4,4-difluoro-2-methylpyrrolidine-1-carbonyl)thiazole-2-carboxylate (Intermediate 109: Step A) in place of ethyl (S)-4-(4,4-difluoro-2-methylpyrrolidine-1-carbonyl)thiazole-2-carboxylate.

Intermediate 159

Potassium 4-((S)-4,4-difluoro-2-methylpyrrolidine-1-carbonyl)-5-(4-(difluoromethyl)-6-(((S)-1,1,1-trifluorobutan-2-yl)amino)pyridin-3-yl)thiazole-2-carboxylate

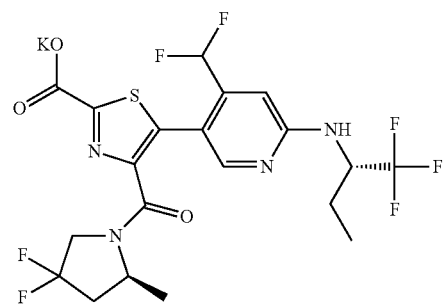

The title compound was prepared as described in Intermediate 62, Step B substituting ethyl 4-((S)-4,4-difluoro-2-methylpyrrolidine-1-carbonyl)-5-(4-(difluoromethyl)-6-(((S)-1,1,1-trifluorobutan-2-yl)amino)pyridin-3-yl)thiazole-2-carboxylate (Intermediate 158) for ethyl (S)-5-(6-(cyclopentylamino)-4-(difluoromethyl)pyridin-3-yl)-4-(2-methylpyrrolidine-1-carbonyl)thiazole-2-carboxylate (Intermediate 62, Step A).

Intermediate 160

Ethyl 4-((1s,4s)-7-azabicyclo[2.2.1]heptane-7-carbonyl)-5-(6-(tert-butylamino)-4-(difluoromethyl)pyridin-3-yl)thiazole-2-carboxylate

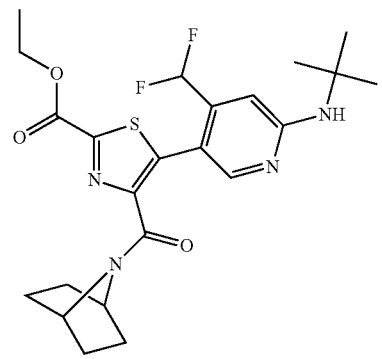 [SMILES: CCOC(=O)c1nc(C(=O)N2C3CCC2CC3)c(-c2cnc(NC(C)(C)C)cc2C(F)F)s1]

The title compound was prepared as described in Intermediate 93 substituting 5-bromo-N-(tert-butyl)-4-(difluoromethyl)pyridin-2-amine (Intermediate 59) in place of 5-bromo-N-(1-methylcyclobutyl)-4-(trifluoromethyl)pyridine-2-amine and ethyl 4-((1s,4s)-7-azabicyclo[2.2.1]heptane-7-carbonyl)thiazole-2-carboxylate (Intermediate 70: Step A) in place of ethyl (S)-4-(4,4-difluoro-2-methylpyrrolidine-1-carbonyl)thiazole-2-carboxylate.

Intermediate 161

Potassium 4-((1s,4s)-7-azabicyclo[2.2.1]heptane-7-carbonyl)-5-(6-(tert-butylamino)-4-(difluoromethyl)pyridin-3-yl)thiazole-2-carboxylate

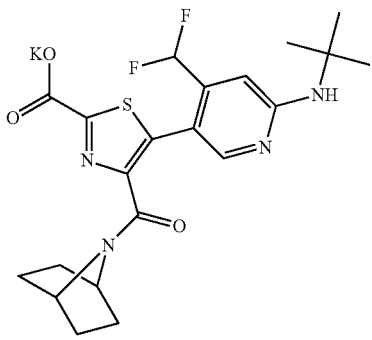

The title compound was prepared as described in Intermediate 62, Step B substituting ethyl 4-((1s,4s)-7-azabicyclo[2.2.1]heptane-7-carbonyl)-5-(6-(tert-butylamino)-4-(difluoromethyl)pyridin-3-yl)thiazole-2-carboxylate. (Intermediate 160) for ethyl (5)-5-(6-(cyclopentylamino)-4-(difluoromethyl)pyridin-3-yl)-4-(2-methylpyrrolidine-1-carbonyl)thiazole-2-carboxylate (Intermediate 62, Step A).

Intermediate 162

Potassium (S)-5-(6-(tert-butylamino)-4-(difluoromethyl)pyridin-3-yl)-4-(4,4-difluoro-2-methylpyrrolidine-1-carbonyl)thiazole-2-carboxylate

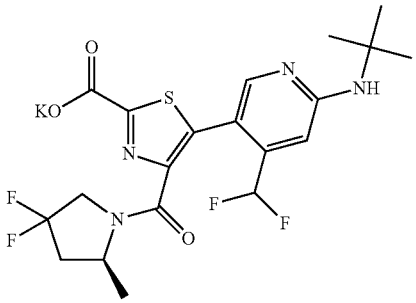

The title compound was prepared as described in Intermediate 62, Step B substituting ethyl (S)-5-(6-(tert-butylamino)-4-(difluoromethyl)pyridin-3-yl)-4-(4,4-difluoro-2-methylpyrrolidine-1-carbonyl)thiazole-2-carboxylate (Intermediate 110) for ethyl (S)-5-(6-(cyclopentylamino)-4-(difluoromethyl)pyridin-3-yl)-4-(2-methylpyrrolidine-1-carbonyl)thiazole-2-carboxylate (Intermediate 62, Step A).

Intermediate 163

Potassium (S)-5-(6-(tert-butylamino)-4-(difluoromethyl)pyridin-3-yl)-4-(2-methylpyrrolidine-1-carbonyl)thiazole-2-carboxylate

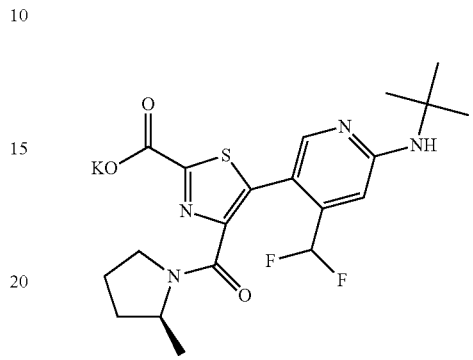

The title compound was prepared as described in Intermediate 62, Step B substituting ethyl (S)-5-(6-(tert-butylamino)-4-(difluoromethyl)pyridin-3-yl)-4-(2-methylpyrrolidine-1-carbonyl)thiazole-2-carboxylate (Intermediate 106) for ethyl (S)-5-(6-(cyclopentylamino)-4-(difluoromethyl)pyridin-3-yl)-4-(2-methylpyrrolidine-1-carbonyl)thiazole-2-carboxylate (Intermediate 62, Step A).

Intermediate 164

Potassium 4-((1s,4s)-7-azabicyclo[2.2.1]heptane-7-carbonyl)-5-(6-(((S)-1-cyclopropyl-2,2,2-trifluoroethyl)amino)-4-(difluoromethyl)pyridin-3-yl)thiazole-2-carboxylate

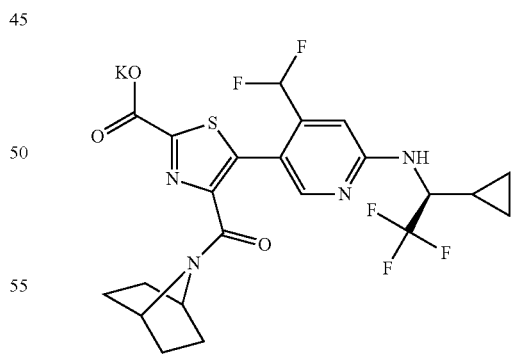

The title compound was prepared as described in Intermediate 62, Step B substituting ethyl 4-((1s,4s)-7-azabicyclo[2.2.1]heptane-7-carbonyl)-5-(6-(((S)-1-cyclopropyl-2,2,2-trifluoroethyl)amino)-4-(difluoromethyl)pyridin-3-yl)thiazole-2-carboxylate (Intermediate 130) for ethyl (S)-5-(6-(cyclopentylamino)-4-(difluoromethyl)pyridin-3-yl)-4-(2-methylpyrroldine-1-carbonyl)thiazole-2-carboxylate (Intermediate 62, Step A).

Intermediate 165

Potassium 4-((1s,4s)-7-azabicyclo[2.2.1]heptane-7-carbonyl)-5-(6-(((S)-1-cyclopropyl-2,2,2-trifluoroethyl)amino)-4-(difluoromethyl)pyridin-3-yl)thiazole-2-carboxylate

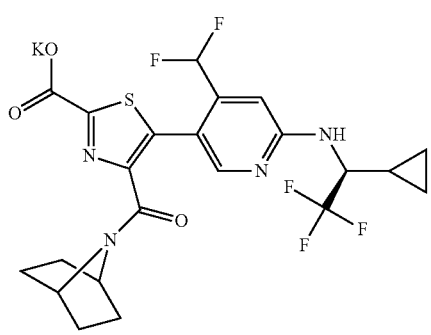

The title compound was prepared as described in Intermediate 62, Step B substituting 4-((1s,4s)-7-azabicyclo[2.2.1]heptane-7-carbonyl)-5-(6-(((S)-1-cyclopropyl-2,2,2-trifluoroethyl)amino)-4-(difluoromethyl)pyridin-3-yl) thiazole-2-carboxylate (Intermediate 130) for ethyl (S)-5-(6-(cyclopentylamino)-4-(difluoromethyl)pyridin-3-yl)-4-(2-methylpyrrolidine-1-carbonyl)thiazole-2-carboxylate (Intermediate 62, Step A).

Intermediate 166

(R)-4-((1s,4s)-7-Azabicyclo[2.2.1]heptane-7-carbonyl)-N-(3-hydroxy-3-methylbutan-2-yl)thiazole-2-carboxamide

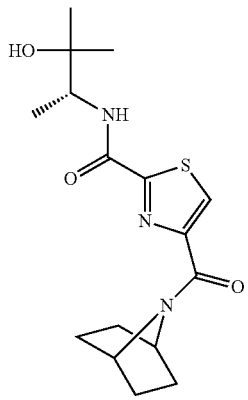 [SMILES: C[C@@H](NC(=O)c1nc(C(=O)N2C3CCC2CC3)cs1)C(C)(C)O]

The title compound was prepared as described in Example 148 substituting (R)-3-amino-2-methylbutan-2-ol for (R)-(−)-2-amino-1-propanol and ethyl 4-(7-azabicyclo[2.2.1]heptane-7-carbonyl)thiazole-2-carboxylate (Intermediate 70: Step A) for ethyl 4-((1s,4s)-7-azabicyclo[2.2.1]heptane-7-carbonyl)-5-(4-(trifluoromethyl)-6-(((S)-1,1,1-trifluoropropan-2-yl)amino)pyridin-3-yl)thiazole-2-carboxylate.

Intermediate 167

(S)-4-((1s,4s)-7-Azabicyclo[2.2.1]heptane-7-carbonyl)-N-(3-hydroxy-3-methylbutan-2-yl)thiazole-2-carboxamide

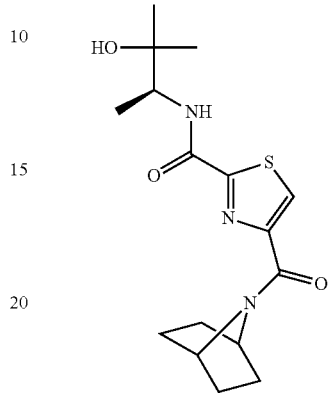

The title compound was prepared as described in Example 148 substituting (S)-3-amino-2-methylbutan-2-ol for (R)-(−)-2-amino-1-propanol and ethyl 4-((1s,4s)-7-azabicyclo[2.2.1]heptane-7-carbonyl)thiazole-2-carboxylate (Intermediate 70: Step A) for ethyl 4-((1R,4R)-7-azabicyclo[2.2.1]heptane-7-carbonyl)-5-(4-(trifluoromethyl)-6-(((S)-1,1,1-trifluoropropan-2-yl)amino)pyridin-3-yl)thiazole-2-carboxylate.

Example 1

5-(6-(Cyclohexylamino)-5-(trifluoromethyl)pyridin-3-yl)-4-(4-fluoropiperidine-1-carbonyl)-N-(2-hydroxy-2-methylpropyl)thiazole-2-carboxamide

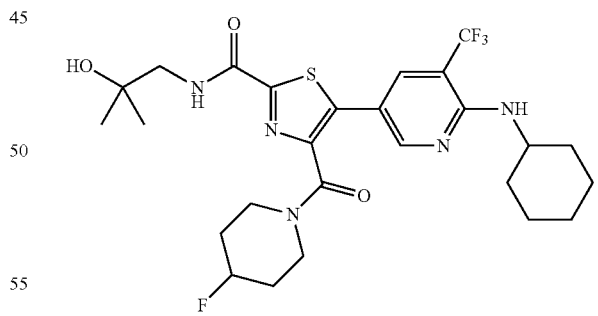

To an oven-dried vial under $N_2$ was added 5-bromo-N-cyclohexyl-3-(trifluoromethyl)pyridin-2-amine (100 mg, 0.3 mmol, Intermediate 1) and 4-(4-fluoropiperidine-1-carbonyl)-N-(2-hydroxy-2-methylpropyl)thiazole-2-carboxamide (130 mg, 0.40 mmol, Intermediate 65: Step C). To this mixture was added pivalic acid (16 mg, 0.21 mmol), KOAc (77 mg, 0.84 mmol), palladium(II) acetate (5.0 mg, 0.022 mmol), and 2-dicyclohexylphosphino-2',6'-di-i-propoxy-1,1'-biphenyl (19 mg, 0.044 mmol), in that order, followed by butyronitrile (2 mL) that was sparged with nitrogen for 90 minutes in a separate flask. The reaction was heated to 120° C. for 18 h. The reaction was cooled to room temperature, poured into a saturated aqueous sodium bicarbonate/water solution (1:1), and extracted with ethyl acetate (3×). The combined organic layers were dried over anhydrous sodium sulfate, and concentrated to dryness. The residue was purified by reverse phase HPLC to give the title compound. MS (ESI): mass calcd. for $C_{26}H_{33}F_4N_5O_3S$, 571.6; m/z found, 572.1[M+H]$^+$. $^1$H NMR (400 MHz, CDCl$_3$) δ 8.41 (d, J=2.4 Hz, 1H), 7.81 (dd, J=2.3, 0.9 Hz, 1H), 7.57-7.49 (m, 1H), 5.00 (d, J=7.5 Hz, 1H), 4.96-4.88 (m, 0.5H), 4.84-4.76 (m, 0.5H), 4.13-4.06 (m, 2H), 3.65-3.54 (m, 1H), 3.46 (d, J=6.3 Hz, 2H), 3.43-3.31 (m, 1H), 3.30-3.21 (m, 1H), 2.10-1.60 (m, 8H), 1.51-1.37 (m, 2H), 1.30 (s, 10.5H), 1.11-1.04 (m, 0.5H).

Example 2

(S)-5-(6-(Cyclopentylamino)-4-(difluoromethyl) pyridin-3-yl)-N-((1-hydroxycyclopropyl)methyl)-4-(2-methylpyrrolidine-1-carbonyl)thiazole-2-carboxamide

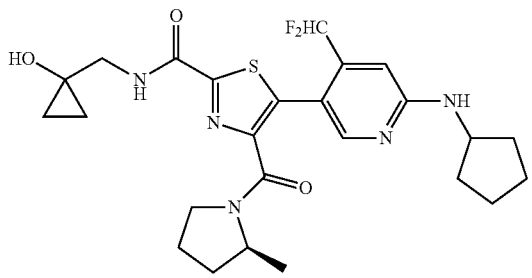 [SMILES: C[C@H]1CCCN1C(=O)c1nc(C(=O)NCC2(O)CC2)sc1-c1cnc(NC2CCCC2)cc1C(F)F]

EDC.HCl (327 mg, 1.71 mmol) was added to a mixture of 1-(aminomethyl)cyclopropanol (74 mg, 0.80 mmol), potassium (S)-5-(6-(cyclopentylamino)-4-(difluoromethyl)pyridin-3-yl)-4-(2-methylpyrrolidine-1-carbonyl)thiazole-2-carboxylate (400 mg, 0.80 mmol, Intermediate 62: Step B), HOBt (220 mg, 1.7 mmol), DIPEA (450 uL, 2.5 mmol), and THF (5 mL) in a 25 mL round bottom flask under N$_2$ at room temperature. The reaction mixture was stirred at room temperature for 16 hours. Saturated aqueous NH$_4$Cl (20 mL) was added to the reaction which was then extracted with ethyl acetate (20 mL×2). The combined organic extracts were washed with brine (10 mL), dried over anhydrous sodium sulfate and concentrated to dryness. The residue was purified by preparative HPLC to give the title compound as a pale yellow solid. MS (ESI): mass calcd. for $C_{25}H_{31}F_2N_5O_3S$, 519.6; m/z found, 520.2 [M+H]$^+$. $^1$H NMR (400 MHz, DMSO-d$_6$) δ 8.74-8.65 (m, 1H), 8.01 (s, 1H), 7.33 (d, J=7.0 Hz, 1H), 7.14-6.79 (m, 1H), 6.73 (s, 1H), 5.53 (s, 1H), 4.26-4.16 (m, 1H), 4.09-3.97 (m, 1H), 3.48-3.41 (m, 4H), 1.98-1.78 (m, 4H), 1.73-1.38 (m, 8H), 1.10 (d, J=6.5 Hz, 2H), 0.90 (d, J=6.5 Hz, 1H), 0.63-0.52 (m, 4H).

Example 3

5-(6-(Cyclohexylamino)-4-(trifluoromethyl)pyridin-3-yl)-4-(4-fluoropiperidine-1-carbonyl)-N-(2-hydroxy-2-methylpropyl)thiazole-2-carboxamide

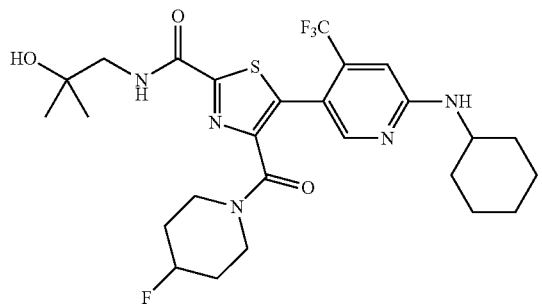 [SMILES: CC(C)(O)CNC(=O)c1nc(C(=O)N2CCC(F)CC2)c(-c2cnc(NC3CCCCC3)cc2C(F)(F)F)s1]

To an oven-dried vial under N$_2$ was added 5-bromo-N-cyclohexyl-4-(trifluoromethyl)pyridin-2-amine (242 mg, 0.75 mmol, Intermediate 3), 4-(4-fluoropiperidine-1-carbonyl)-N-(2-hydroxy-2-methylpropyl)thiazole-2-carboxamide (237 mg, 0.72 mmol, Intermediate 65: Step C), palladium pivalate (44 mg, 0.14 mmol), cesium carbonate (232 mg, 0.71 mmol) and DMF (10.0 mL). The reaction was capped and heated at 120° C. for 18 h. There was no product present by LC/MS after 18 h so an additional 0.2 eq. of palladium pivalate was added and the reaction heated for an additional 24 h at 120° C. The reaction was cooled, poured into a 1:1 mixture of saturated aqueous sodium bicarbonate/water and extracted with ethyl acetate (2×). The combined organic layers were dried over anhydrous sodium sulfate and concentrated to dryness. The residue was purified by reverse phase HPLC to give the title compound. MS (ESI): mass calcd. for $C_{26}H_{33}F_4N_5O_3S$, 571.6; m/z found, 572.2 [M+H]$^+$. $^1$H NMR (400 MHz, CDCl$_3$) δ 8.18 (s, 1H), 7.59-7.55 (m, 1H), 6.60 (s, 1H), 5.01-4.86 (m, 2H), 3.97-3.88 (m, 1H), 3.75-3.31 (m, 6H), 2.11-1.97 (m, 3H), 1.95-1.55 (m, 7H), 1.51-1.35 (m, 2H), 1.31 (s, 9H).

Example 4

(S)-5-(6-(Cyclohexylamino)-5-(trifluoromethyl)pyridin-3-yl)-N-(2-hydroxy-2-methylpropyl)-4-(2-methylpiperidine-1-carbonyl)thiazole-2-carboxamide

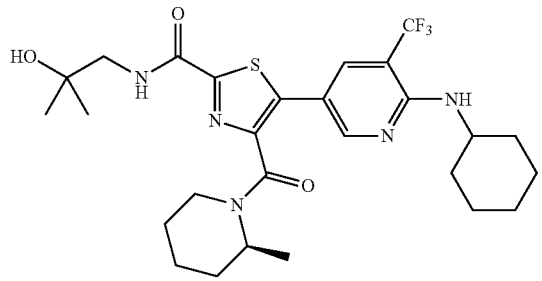 [SMILES: C[C@H]1CCCCN1C(=O)c1nc(C(=O)NCC(C)(C)O)sc1-c1cnc(NC2CCCCC2)c(C(F)(F)F)c1]

The title compound was prepared as described in Example 3 substituting 5-bromo-N-cyclohexyl-3-(trifluoromethyl) pyridin-2-amine (Intermediate 1) for 5-bromo-N-cyclohexyl-4-(trifluoromethyl)pyridin-2-amine and (S)—N-(2- hydroxy-2-methylpropyl)-4-(2-methylpiperidine-1-carbonyl)thiazole-2-carboxamide (Intermediate 66: Step D) for 4-(4-fluoropiperidine-1-carbonyl)-N-(2-hydroxy-2-methylpropyl)thiazole-2-carboxamide. MS (ESI): mass calcd. for $C_{27}H_{36}F_3N_5O_3S$, 567.7; m/z found, 568.2[M+H]$^+$. $^1$H NMR (400 MHz, CDCl$_3$) δ 8.42 (dd, J=12.1, 2.4 Hz, 1H), 7.81 (dd, J=20.5, 2.4 Hz, 1H), 7.62-7.51 (m, 1H), 5.02 (dd, J=29.2, 6.6 Hz, 2H), 4.62 (d, J=13.4 Hz, 0.5H), 4.12-4.04 (m, 1H), 3.77 (dd, J=9.3, 4.0 Hz, 0.5H), 3.46 (d, J=6.3 Hz, 2H), 3.25 (d, J=12.9 Hz, 1H), 3.07-2.80 (m, 1H), 2.14-1.98 (m, 3H), 1.81-1.35 (m, 8H), 1.33-1.03 (m, 14H).

Example 5

(S)-5-(6-(Cyclohexylamino)-4-(trifluoromethyl)pyridin-3-yl)-N-(2-hydroxy-2-methylpropyl)-4-(2-methylpiperidine-1-carbonyl)thiazole-2-carboxamide

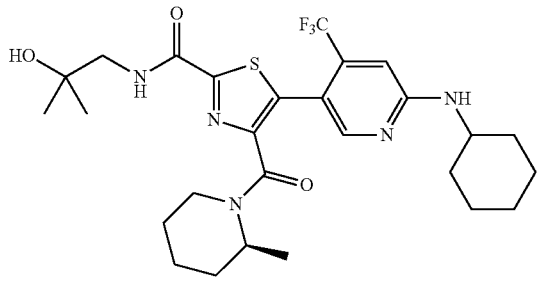 [SMILES: C[C@H]1CCCCN1C(=O)c1nc(C(=O)NCC(C)(C)O)sc1-c1cnc(NC2CCCCC2)cc1C(F)(F)F]

The title compound was prepared as described in Example 3 substituting (S)—N-(2-hydroxy-2-methylpropyl)-4-(2-methylpiperidine-1-carbonyl)thiazole-2-carboxamide (Intermediate 66: Step D) for 4-(4-fluoropiperidine-1-carbonyl)-N-(2-hydroxy-2-methylpropyl)thiazole-2-carboxamide. MS (ESI): mass calcd. for $C_{27}H_{36}F_3N_5O_3S$, 567.7; m/z found, 568.2 [M+H]$^+$. $^1$H NMR (400 MHz, CDCl$_3$) δ 8.20 (d, J=15.5 Hz, 1H), 7.59 (d, J=7.0 Hz, 1H), 6.60 (s, 1H), 4.91 (d, J=8.0 Hz, 1.5H), 4.49-4.45 (m, 0.4H), 3.95 (s, 0.4H), 3.67 (s, 1H), 3.47 (dd, J=6.3, 1.4 Hz, 2.6H), 2.98 (t, J=13.4 Hz, 0.6H), 2.82-2.76 (m, 0.6H), 2.11-1.95 (m, 3H), 1.82-1.74 (m, 2H), 1.71-1.35 (m, 7H), 1.35-1.07 (m, 14H).

Example 6

5-(6-(Cyclohexylamino)-5-(difluoromethyl)pyridin-3-yl)-4-(4-fluoropiperidine-1-carbonyl)-N-(2-hydroxy-2-methylpropyl)thiazole-2-carboxamide

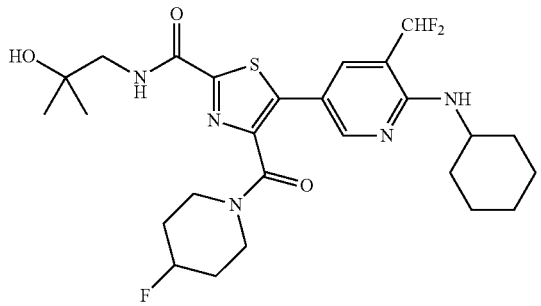

The title compound was prepared as described in Example 3 substituting 5-bromo-N-cyclohexyl-3-(difluoromethyl)pyridin-2-amine (Intermediate 4) for 5-bromo-N-cyclohexyl-4-(trifluoromethyl)pyridin-2-amine. MS (ESI): mass calcd. for $C_{26}H_{34}F_3N_5O_3S$, 553.6; m/z found, 554.2 [M+H]$^+$. $^1$H NMR (400 MHz, DMSO-d$_6$) δ 9.89 (s, 1H), 8.54 (d, J=7.6 Hz, 1H), 8.47 (d, J=2.5 Hz, 1H), 8.40-8.35 (m, 1H), 8.19 (d, J=2.5 Hz, 1H), 4.92 (s, 1H), 4.80 (s, 1H), 4.12 (s, 1H), 3.74-3.63 (m, 2H), 3.39-3.34 (m, 1H), 3.27 (d, J=6.3 Hz, 2H), 3.23-3.19 (m, 1H), 1.94-1.88 (m, 4H), 1.68 (s, 2H), 1.48-1.37 (m, 8H), 1.12 (s, 6H).

Example 7

4-(4-Fluoropiperidine-1-carbonyl)-N-(2-hydroxy-2-methylpropyl)-5-(5-(trifluoromethyl)-6-((3,3,3-trifluoropropyl)amino)pyridin-3-yl)thiazole-2-carboxamide

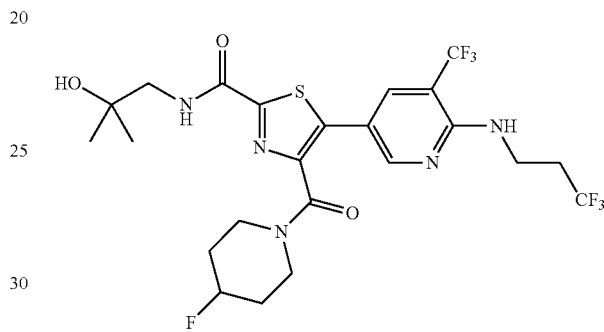

The title compound was prepared as described in Example 3 substituting 5-bromo-3-(trifluoromethyl)-N-(3,3,3-trifluoropropyl)pyridin-2-amine (Intermediate 5) for 5-bromo-N-cyclohexyl-4-(trifluoromethyl)pyridin-2-amine. MS (ESI): mass calcd. for $C_{23}H_{26}F_7N_5O_3S$, 585.5; m/z found, 585.9 [M+H]$^+$. $^1$H NMR (400 MHz, CDCl$_3$) δ 8.48-8.44 (m, 1H), 7.87 (dd, J=2.4, 0.9 Hz, 1H), 7.58-7.51 (m, 1H), 5.37 (s, 1H), 4.94-4.91 (m, 0.5H), 4.82-4.79 (m, 0.5H), 4.15-4.06 (m, 1H), 3.85 (q, J=6.3 Hz, 2H), 3.66-3.52 (m, 1H), 3.47 (d, J=6.3 Hz, 2H), 3.44-3.35 (m, 1H), 3.30-3.20 (m, 1H), 2.56-2.45 (m, 2H), 2.05-1.65 (m, 5H), 1.30 (s, 6H).

Example 8

4-(4-Fluoropiperidine-1-carbonyl)-N-(2-hydroxy-2-methylpropyl)-5-(4-(trifluoromethyl)-6-((3,3,3-trifluoropropyl)amino)pyridin-3-yl)thiazole-2-carboxamide

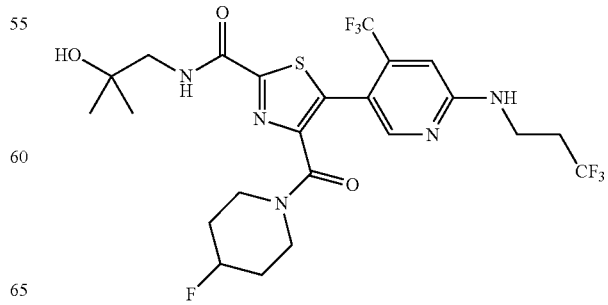

The title compound was prepared as described in Example 3 substituting 5-bromo-4-(trifluoromethyl)-N-(3,3,3-trifluoropropyl)pyridin-2-amine (Intermediate 6) for 5-bromo-N-cyclohexyl-4-(trifluoromethyl)pyridin-2-amine. MS (ESI): mass calcd. for $C_{23}H_{26}F_7N_5O_3S$, 585.5; m/z found, 585.9 [M+H]$^+$. $^1$H NMR (500 MHz, CDCl$_3$) δ 8.24 (s, 1H), 7.58-7.53 (m, 1H), 6.66 (s, 1H), 5.20 (t, J=6.1 Hz, 1H), 4.92-4.78 (m, 1H), 4.00-3.87 (m, 1H), 3.72 (q, J=6.4 Hz, 2H), 3.60-3.38 (m, 5H), 2.53-2.44 (m, 2H), 1.96-1.69 (m, 5H), 1.32 (s, 6H).

Example 9

5-(6-(Cyclobutylamino)-4-(trifluoromethyl)pyridin-3-yl)-4-(4-fluoropiperidine-1-carbonyl)-N-(2-hydroxy-2-methylpropyl)thiazole-2-carboxamide

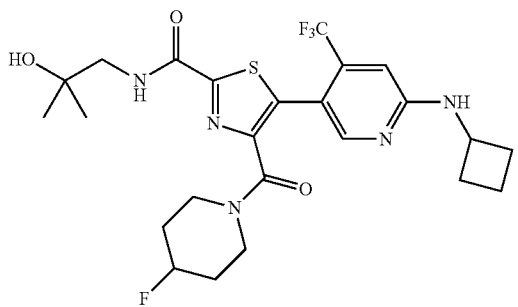 [SMILES: CC(C)(O)CNC(=O)c1nc(C(=O)N2CCC(F)CC2)c(-c2cnc(NC3CCC3)cc2C(F)(F)F)s1]

The title compound was prepared as described in Example 3 substituting 5-bromo-N-cyclobutyl-4-(trifluoromethyl)pyridin-2-amine (Intermediate 7) for 5-bromo-N-cyclohexyl-4-(trifluoromethyl)pyridin-2-amine. MS (ESI): mass calcd. for $C_{24}H_{29}F_4N_5O_3S$, 543.6; m/z found, 544.0 [M+H]$^+$. $^1$H NMR (400 MHz, CDCl$_3$) δ 8.19 (s, 1H), 7.58-7.52 (m, 1H), 6.56 (s, 1H), 5.23 (d, J=6.9 Hz, 1H), 4.83-4.74 (m, 1H), 4.22 (q, J=7.7 Hz, 1H), 3.92 (d, J=13.2 Hz, 1H), 3.60-3.34 (m, 5H), 2.54-2.38 (m, 2H), 2.02-1.63 (m, 9H), 1.31 (s, 6H).

Example 10

5-(6-(Cyclopentylamino)-4-(trifluoromethyl)pyridin-3-yl)-4-(4-fluoropiperidine-1-carbonyl)-N-(2-hydroxy-2-methylpropyl)thiazole-2-carboxamide

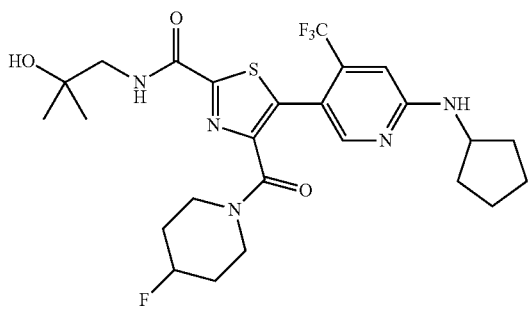 [SMILES: CC(C)(O)CNC(=O)c1nc(C(=O)N2CCC(F)CC2)c(-c2cnc(NC3CCCC3)cc2C(F)(F)F)s1]

The title compound was prepared as described in Example 3 substituting 5-bromo-N-cyclopentyl-4-(trifluoromethyl)pyridin-2-amine (Intermediate 8) for 5-bromo-N-cyclohexyl-4-(trifluoromethyl)pyridin-2-amine. MS (ESI): mass calcd. for $C_{25}H_{31}F_4N_5O_3S$, 557.6; m/z found, 558.2 [M+H]$^+$. $^1$H NMR (400 MHz, CDCl$_3$) δ 8.19 (s, 1H), 7.59-7.53 (m, 1H), 6.64 (s, 1H), 5.04 (d, J=6.9 Hz, 1H), 4.92-4.78 (m, 1H), 4.08 (q, J=6.4 Hz, 1H), 3.92 (d, J=13.0 Hz, 1H), 3.62-3.34 (m, 5H), 2.17-2.00 (m, 2H), 1.98-1.61 (m, 9H), 1.56-1.43 (m, 2H), 1.31 (s, 6H).

Example 11

(S)-5-(6-(Cyclohexylamino)-4-(trifluoromethyl)pyridin-3-yl)-4-(4,4-difluoro-2-methylpyrrolidine-1-carbonyl)-N-(2-hydroxy-2-methylpropyl)thiazole-2-carboxamide

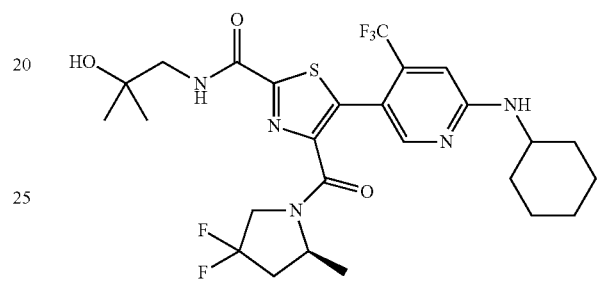

The title compound was prepared as described in Example 3 substituting (S)-4-(4,4-difluoro-2-methylpyrrolidine-1-carbonyl)-N-(2-hydroxy-2-methylpropyl)thiazole-2-carboxamide (Intermediate 67) for 4-(4-fluoropiperidine-1-carbonyl)-N-(2-hydroxy-2-methylpropyl)thiazole-2-carboxamide. MS (ESI): mass calcd. for $C_{26}H_{32}F_5N_5O_3S$, 589.6; m/z found, 590.3 [M+H]$^+$. $^1$H NMR (400 MHz, CDCl$_3$) δ 8.13 (s, 1H), 7.50 (d, J=7.7 Hz, 1H), 6.59 (s, 1H), 4.89 (d, J=7.9 Hz, 1H), 4.75-4.65 (m, 0.3H), 4.51-4.46 (m, 0.7H), 4.13-4.01 (m, 1H), 3.94-3.82 (m, 1H), 3.67 (s, 1H), 3.56-3.44 (m, 2H), 2.57-2.52 (m, 1H), 2.22-1.97 (m, 3H), 1.89 (s, 1H), 1.80-1.75 (m, 2H), 1.71-1.60 (m, 1H), 1.51-1.15 (m, 14H).

Example 12

4-(4-Fluoropiperidine-1-carbonyl)-N-(2-hydroxy-2-methylpropyl)-5-(6-(isopropylamino)-4-(trifluoromethyl)pyridin-3-yl)thiazole-2-carboxamide

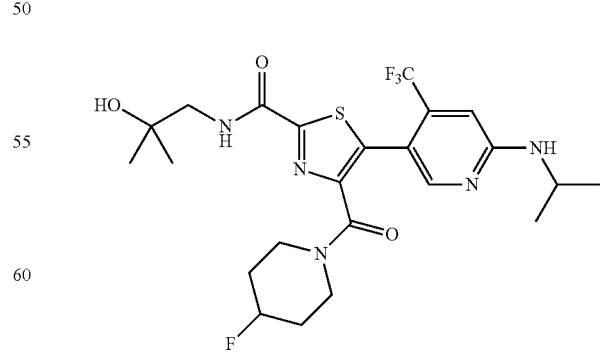

The title compound was prepared as described in Example 3 substituting 5-bromo-N-isopropyl-4-(trifluoromethyl)pyridin-2-amine (Intermediate 11) for 5-bromo-N-cyclohexyl-4-(trifluoromethyl)pyridin-2-amine. MS (ESI): mass calcd. for $C_{23}H_{29}F_4N_5O_3S$, 531.6; m/z found, 532.2 [M+H]+. 1H NMR (400 MHz, CDCl3) δ 8.20 (s, 1H), 7.58-7.53 (m, 1H), 6.61 (s, 1H), 4.95-4.74 (m, 2H), 4.09-3.86 (m, 2H), 3.60-3.34 (m, 5H), 1.96-1.63 (m, 5H), 1.38-1.19 (m, 12H).

Example 13

5-(6-((3,3-Difluorocyclohexyl)amino)-5-(trifluoromethyl)pyridin-3-yl)-4-(4-fluoropiperidine-1-carbonyl)-N-(2-hydroxy-2-methylpropyl)thiazole-2-carboxamide

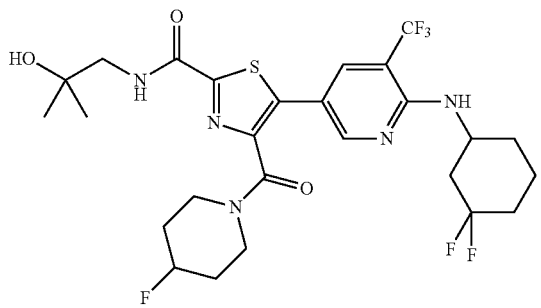 [SMILES: CC(C)(O)CNC(=O)c1nc(C(=O)N2CCC(F)CC2)c(-c2cnc(NC3CCCC(F)(F)C3)c(C(F)(F)F)c2)s1]

The title compound was prepared as described in Example 3 substituting 5-bromo-N-(3,3-difluorocyclohexyl)-3-(trifluoromethyl)pyridin-2-amine (Intermediate 27) for 5-bromo-N-cyclohexyl-4-(trifluoromethyl)pyridin-2-amine. MS (ESI): mass calcd. for $C_{26}H_{31}F_6N_5O_3S$, 607.6; m/z found, 608.3 [M+H]+. 1H NMR (500 MHz, CDCl3) δ 8.45-8.42 (m, 1H), 7.86-7.82 (m, 1H), 7.56-7.52 (m, 1H), 5.29 (s, 1H), 4.94-4.90 (m, 1H), 4.84-4.80 (m, 1H), 4.58-4.52 (m, 1H), 4.17-4.04 (m, 1H), 3.62-3.56 (m, 1H), 3.47 (d, J=6.3 Hz, 2H), 3.41-3.37 (m, 1H), 3.29-3.24 (m, 1H), 2.46-2.40 (m, 1H), 2.08-1.78 (m, 8H), 1.78-1.48 (m, 3H), 1.30 (s, 6H).

Example 14

5-(6-(Cyclohexylamino)-4-(difluoromethyl)pyridin-3-yl)-4-(4-fluoropiperidine-1-carbonyl)-N-(2-hydroxy-2-methylpropyl)thiazole-2-carboxamide

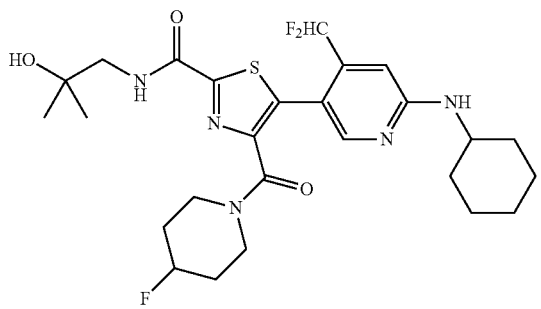

The title compound was prepared as described in Example 3 substituting 5-bromo-N-cyclohexyl-4-(difluoromethyl)pyridin-2-amine (Intermediate 15) for 5-bromo-N-cyclohexyl-4-(trifluoromethyl)pyridin-2-amine. MS (ESI): mass calcd. for $C_{26}H_{34}F_3N_5O_3S$, 553.6; m/z found, 554.3 [M+H]+. 1H NMR (500 MHz, CDCl3) δ 8.04 (s, 1H), 7.58-7.54 (m, 1H), 6.85-6.63 (m, 1H), 6.60 (s, 1H), 4.92-4.75 (m, 2H), 3.97-3.93 (m, 1H), 3.67 (br s, 1H), 3.57-3.31 (m, 5H), 2.06-2.01 (m, 2H), 1.95 (s, 1H), 1.92-1.62 (m, 7H), 1.49-1.36 (m, 2H), 1.31 (s, 9H).

Example 15

5-(6-(Cyclohexylamino)-4-(trifluoromethyl)pyridin-3-yl)-4-(4,4-difluoropiperidine-1-carbonyl)-N-(3-hydroxy-3-methylbutyl)thiazole-2-carboxamide

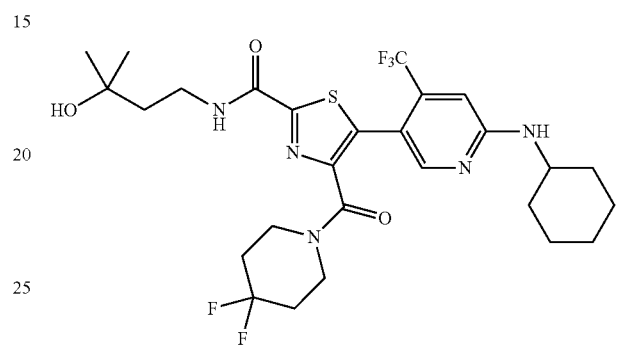

The title compound was prepared as described in Example 3 substituting 4-(4,4-difluoropiperidine-1-carbonyl)-N-(3-hydroxy-3-methylbutyl)thiazole-2-carboxamide (Intermediate 71) for 4-(4-fluoropiperidine-1-carbonyl)-N-(2-hydroxy-2-methylpropyl)thiazole-2-carboxamide. MS (ESI): mass calcd. for $C_{27}H_{34}F_5N_5O_3S$, 603.7; m/z found, 603.9 [M+H]+. 1H NMR (400 MHz, CDCl3) δ 8.17 (s, 1H), 7.97-7.93 (m, 1H), 6.59 (s, 1H), 4.92 (d, J=7.9 Hz, 1H), 3.77-3.74 (m, 2H), 3.66-3.62 (m, 3H), 3.54-3.51 (m, 2H), 2.09-1.86 (m, 6H), 1.83-1.76 (m, 4H), 1.69-1.63 (m, 1H), 1.55 (s, 1H), 1.51-1.36 (m, 2H), 1.33 (s, 6H), 1.31-1.17 (m, 3H).

Example 16

5-(6-((3,3-Difluorocyclobutyl)amino)-5-(trifluoromethyl)pyridin-3-yl)-4-(4-fluoropiperidine-1-carbonyl)-N-(2-hydroxy-2-methylpropyl)thiazole-2-carboxamide

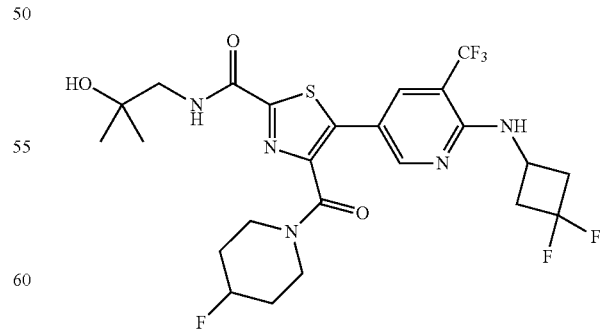

The title compound was prepared as described in Example 3 substituting 5-bromo-N-(3,3-difluorocyclobutyl)-3-(trifluoromethyl)pyridin-2-amine (Intermediate 28) for 5-bromo-N-cyclohexyl-4-(trifluoromethyl)pyridin-2-amine.

MS (ESI): mass calcd. for $C_{24}H_{27}F_6N_5O_3S$, 579.6; m/z found, 580.2 [M+H]$^+$. $^1$H NMR (500 MHz, CDCl$_3$) δ 8.23 (s, 1H), 7.57-7.53 (m, 1H), 6.61 (s, 1H), 5.35 (d, J=6.0 Hz, 1H), 4.97-4.87 (m, 1H), 4.93-4.91 (m, 0.5H), 4.83-4.81 (m, 0.5H), 4.24 (d, J=8.6 Hz, 1H), 3.99-3.86 (m, 1H), 3.60-3.41 (m, 5H), 3.14-3.06 (m, 2H), 2.61-2.44 (m, 2H), 1.95-1.73 (m, 4H), 1.32 (d, J=1.7 Hz, 6H).

Example 17

(S)-5-(6-(Cyclohexylamino)-4-(trifluoromethyl)pyridin-3-yl)-N-(1,1-dioxidotetrahydro-2H-thiopyran-4-yl)-4-(2-methylpiperidine-1-carbonyl)thiazole-2-carboxamide

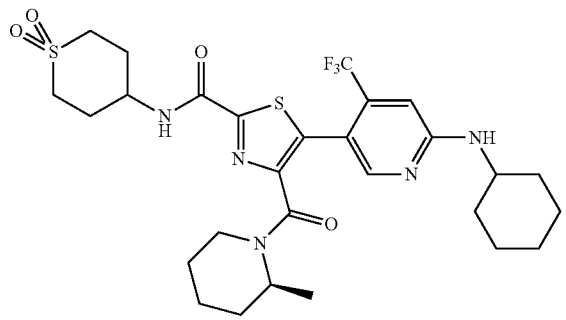 [SMILES: C[C@H]1CCCCN1C(=O)c1nc(C(=O)NC2CCS(=O)(=O)CC2)sc1-c1cnc(NC2CCCCC2)cc1C(F)(F)F]

The title compound was prepared as described in Example 3 substituting (S)—N-(1,1-dioxidotetrahydro-2H-thiopyran-4-yl)-4-(2-methylpiperidine-1-carbonyl)thiazole-2-carboxamide (Intermediate 72: Step D) for 4-(4-fluoropiperidine-1-carbonyl)-N-(2-hydroxy-2-methylpropyl)thiazole-2-carboxamide. MS (ESI): mass calcd. for $C_{28}H_{36}F_3N_5O_4S_2$, 627.8; m/z found, 628.2 [M+H]$^+$. $^1$H NMR (500 MHz, CDCl$_3$) δ 8.19 (d, J=20.1 Hz, 1H), 7.22 (dd, J=16.1, 7.9 Hz, 1H), 6.62 (s, 1H), 4.92 (d, J=8.0 Hz, 1.5H), 4.47 (d, J=13.6 Hz, 0.4H), 4.26-4.21 (m, 1H), 3.88 (s, 0.4H), 3.68 (s, 1H), 3.37 (d, J=13.2 Hz, 0.6H), 3.22-3.07 (m, 4H), 2.94 (t, J=13.3 Hz, 0.6H), 2.79 (t, J=13.3 Hz, 0.4H), 2.42 (dd, J=9.8, 5.4 Hz, 2H), 2.30 (s, 2H), 2.08-1.97 (m, 2H), 1.80-1.75 (m, 2H), 1.71-0.99 (m, 15H).

Example 18

5-(6-((4,4-Difluorocyclohexyl)amino)-4-(trifluoromethyl)pyridin-3-yl)-4-(4-fluoropiperidine-1-carbonyl)-N-(2-hydroxy-2-methylpropyl)thiazole-2-carboxamide

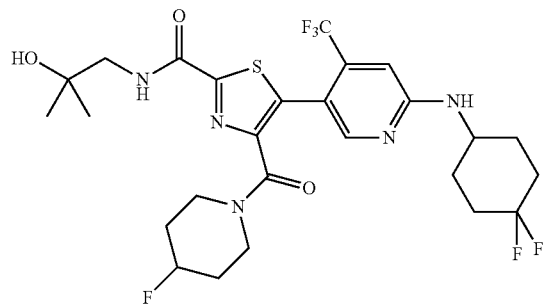 [SMILES: CC(C)(O)CNC(=O)c1nc(C(=O)N2CCC(F)CC2)c(-c2cnc(NC3CCC(F)(F)CC3)cc2C(F)(F)F)s1]

The title compound was prepared as described in Example 3 substituting 5-bromo-N-(4,4-difluorocyclohexyl)-4-(trifluoromethyl)pyridin-2-amine (Intermediate 29) for 5-bromo-N-cyclohexyl-4-(trifluoromethyl)pyridin-2-amine. MS (ESI): mass calcd. for $C_{26}H_{31}F_6N_5O_3S$, 607.6; m/z found, 608.1 [M+H]$^+$. $^1$H NMR (500 MHz, CDCl$_3$) δ 8.22 (s, 1H), 7.57-7.53 (m, 1H), 6.63 (s, 1H), 4.94-4.87 (m, 0.5H), 4.85-4.78 (t, J=7.7 Hz, 1.5H), 3.99-3.88 (m, 2H), 3.61-3.37 (m, 5H), 2.23-2.07 (m, 4H), 1.96-1.70 (m, 7H), 1.66-1.56 (q, J=14.3, 12.1 Hz, 2H), 1.32 (s, 6H).

Example 19

(S)-5-(6-(Cyclohexylamino)-4-(trifluoromethyl)pyridin-3-yl)-N-(2-hydroxy-2-methylpropyl)-4-(2-methylpyrrolidine-1-carbonyl)thiazole-2-carboxamide

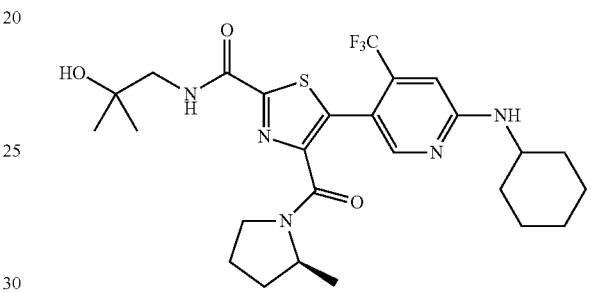

The title compound was prepared as described in Example 3 substituting (S)—N-(2-hydroxy-2-methylpropyl)-4-(2-methylpyrrolidine-1-carbonyl)thiazole-2-carboxamide (Intermediate 69) for 4-(4-fluoropiperidine-1-carbonyl)-N-(2-hydroxy-2-methylpropyl)thiazole-2-carboxamide. MS (ESI): mass calcd. for $C_{26}H_{34}F_3N_5O_3S$, 553.6; m/z found, 554.2 [M+H]$^+$. $^1$H NMR (500 MHz, CDCl$_3$) δ 8.17 (s, 1H), 7.59-7.52 (m, 1H), 6.58 (s, 1H), 4.88 (d, J=7.7 Hz, 1H), 4.33-4.17 (m, 1H), 3.72-3.36 (m, 5H), 2.10-1.97 (m, 4H), 1.97-1.82 (m, 2H), 1.81-1.70 (m, 3H), 1.68-1.62 (m, 2H), 1.61-1.49 (m, 1H), 1.47-1.37 (m, 2H), 1.35-1.17 (m, 9H), 1.11 (d, J=6.4 Hz, 1H).

Example 20

5-(6-((3,3-Difluorocyclopentyl)amino)-4-(trifluoromethyl)pyridin-3-yl)-4-(4-fluoropiperidine-1-carbonyl)-N-(2-hydroxy-2-methylpropyl)thiazole-2-carboxamide

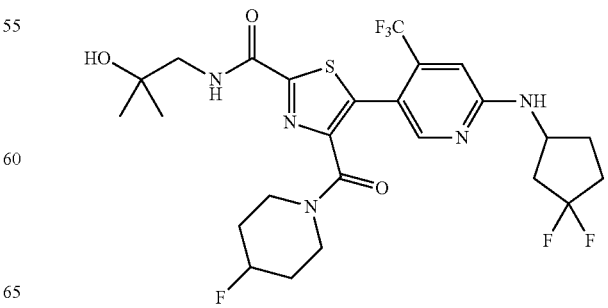

The title compound was prepared as described in Example 3 substituting 5-bromo-N-(3,3-difluorocyclopentyl)-4-(trifluoromethyl)pyridin-2-amine (Intermediate 30) for 5-bromo-N-cyclohexyl-4-(trifluoromethyl)pyridin-2-amine. MS (ESI): mass calcd. for $C_{25}H_{29}F_6N_5O_3S$, 593.6; m/z found, 594.2 [M+H]$^+$. $^1$H NMR (500 MHz, CDCl$_3$) δ 8.21 (s, 1H), 7.59-7.52 (m, 1H), 6.61 (s, 1H), 5.28 (d, J=7.1 Hz, 1H), 4.93-4.90 (m, 0.5H), 4.83-4.80 (m, 0.5H), 4.49-4.43 (m, 1H), 3.95-3.90 (m, 1H), 3.61-3.38 (m, 5H), 2.71-2.55 (m, 1H), 2.39-2.22 (m, 2H), 2.21-1.94 (m, 3H), 1.93-1.71 (m, 5H), 1.32 (s, 6H).

Example 21

5-(6-((3,3-Difluorocyclobutyl)amino)-4-(trifluoromethyl)pyridin-3-yl)-4-(4-fluoropiperidine-1-carbonyl)-N-(2-hydroxy-2-methylpropyl)thiazole-2-carboxamide

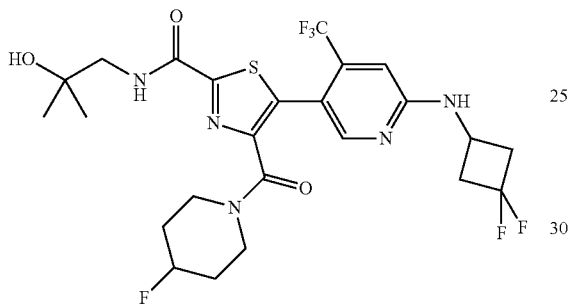

The title compound was prepared as described in Example 3 substituting 5-bromo-N-(3,3-difluorocyclobutyl)-4-(trifluoromethyl)pyridin-2-amine (Intermediate 31) for 5-bromo-N-cyclohexyl-4-(trifluoromethyl)pyridin-2-amine. MS (ESI): mass calcd. for $C_{24}H_{27}F_6N_5O_3S$, 579.6; m/z found, 580.0 [M+H]$^+$. $^1$H NMR (500 MHz, CDCl$_3$) δ 8.21 (s, 1H), 7.58-7.52 (m, 1H), 6.58 (s, 1H), 5.49 (d, J=6.0 Hz, 1H), 4.94-4.90 (m, 0.5H), 4.84-4.80 (m, 0.5H), 4.31-4.18 (m, 1H), 3.95-3.90 (m, 1H), 3.58-3.46 (m, 5H), 3.16-3.00 (m, 2H), 2.58-2.46 (m, 2H), 1.97-1.72 (m, 5H), 1.32 (s, 6H).

Example 22

5-(6-(((6,6-Difluorospiro[3.3]heptan-2-yl)amino)-4-(trifluoromethyl)pyridin-3-yl)-4-(4-fluoropiperidine-1-carbonyl)-N-(2-hydroxy-2-methylpropyl)thiazole-2-carboxamide

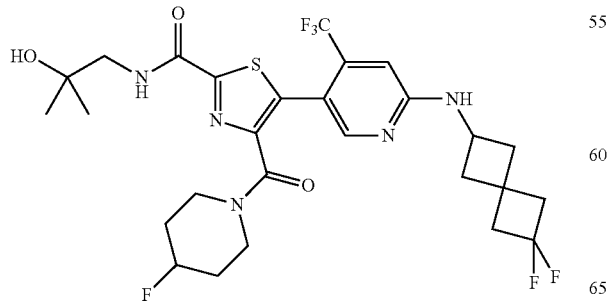

The title compound was prepared as described in Example 3 substituting 5-bromo-N-(6,6-difluorospiro[3.3]heptan-2-yl)-4-(trifluoromethyl)pyridin-2-amine (Intermediate 33) for 5-bromo-N-cyclohexyl-4-(trifluoromethyl)pyridin-2-amine. MS (ESI): mass calcd. for $C_{27}H_{31}F_6N_5O_3S$, 619.6; m/z found, 620.1 [M+H]$^+$. $^1$H NMR (400 MHz, CDCl$_3$) δ 8.20 (s, 1H), 7.58-7.51 (m, 1H), 6.56 (s, 1H), 5.14 (d, J=6.6 Hz, 1H), 4.94-4.89 (m, 0.5H), 4.82-4.78 (m, 0.5H), 4.26-4.20 (m, 1H), 3.94-3.88 (m, 1H), 3.60-3.37 (m, 5H), 2.77-2.51 (m, 6H), 2.12-2.04 (m, 2H), 1.90 (s, 5H), 1.32 (s, 6H).

Example 23

5-(6-((3,3-Difluorocyclohexyl)amino)-4-(trifluoromethyl)pyridin-3-yl)-4-(4-fluoropiperidine-1-carbonyl)-N-(2-hydroxy-2-methylpropyl)thiazole-2-carboxamide

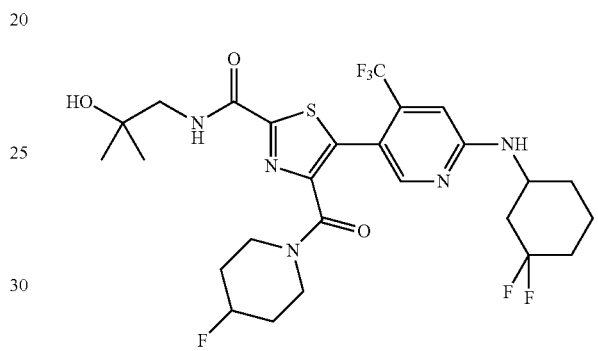

The title compound was prepared as described in Example 3 substituting 5-bromo-N-(3,3-difluorocyclohexyl)-4-(trifluoromethyl)pyridin-2-amine (Intermediate 32) for 5-bromo-N-cyclohexyl-4-(trifluoromethyl)pyridin-2-amine. MS (ESI): mass calcd. for $C_{26}H_{31}F_6N_5O_3S$, 607.6; m/z found, 608.1 [M+H]$^+$. $^1$H NMR (400 MHz, CDCl$_3$) δ 8.22 (s, 1H), 7.58-7.52 (m, 1H), 6.64 (s, 1H), 5.04 (d, J=8.1 Hz, 1H), 4.94-4.90 (m, 0.5H), 4.81-4.78 (m, 0.5H), 4.22 (s, 1H), 3.94-3.89 (m, 1H), 3.60-3.37 (m, 5H), 2.45-2.40 (m, 1H), 2.11-1.63 (m, 11H), 1.50-1.31 (m, 1H), 1.32 (s, 6H).

Example 24

4-(4-Fluoropiperidine-1-carbonyl)-N-(2-hydroxy-2-methylpropyl)-5-(6-(spiro[3.3]heptan-2-ylamino)-4-(trifluoromethyl)pyridin-3-yl)thiazole-2-carboxamide

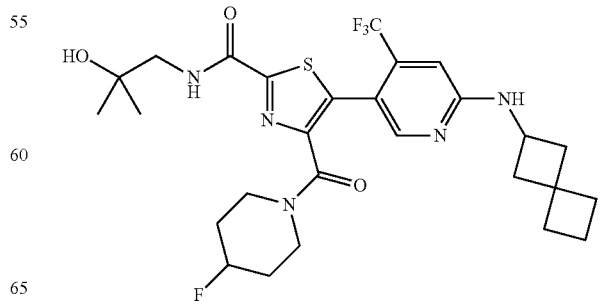

The title compound was prepared as described in Example 3 substituting 5-bromo-N-(spiro[3.3]heptan-2-yl)-4-(trifluoromethyl)pyridin-2-amine (Intermediate 34) for 5-bromo-N-cyclohexyl-4-(trifluoromethyl)pyridin-2-amine. MS (ESI): mass calcd. for $C_{27}H_{33}F_4N_5O_3S$, 583.7; m/z found, 584.1 [M+H]$^+$. $^1$H NMR (500 MHz, CDCl$_3$) δ 8.19 (s, 1H), 7.59-7.52 (m, 1H), 6.54 (s, 1H), 5.14 (d, J=6.6 Hz, 1H), 4.93-4.87 (m, 0.5H), 4.83-4.77 (m, 0.5H), 4.09-4.02 (m, 1H), 3.94-3.85 (m, 1H), 3.59-3.36 (m, 5H), 2.58-2.50 (m, 2H), 2.14-2.05 (m, 2H), 2.00-1.93 (m, 2H), 1.93-1.64 (m, 9H), 1.31 (s, 6H).

Example 25

(S)-5-(6-(Cyclohexylamino)-4-(trifluoromethyl)pyridin-3-yl)-N-(2-hydroxy-2-methylpropyl)-4-(2-methylazetidine-1-carbonyl)thiazole-2-carboxamide

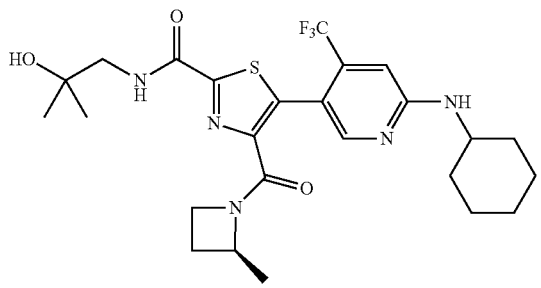 [SMILES: C[C@H]1CCN1C(=O)c1nc(C(=O)NCC(C)(C)O)sc1-c1cnc(NC2CCCCC2)cc1C(F)(F)F]

The title compound was prepared as described in Example 3 substituting (S)—N-(2-hydroxy-2-methylpropyl)-4-(2-methylazetidine-1-carbonyl)thiazole-2-carboxamide (Intermediate 68) for 4-(4-fluoropiperidine-1-carbonyl)-N-(2-hydroxy-2-methylpropyl)thiazole-2-carboxamide. MS (ESI): mass calcd. for $C_{25}H_{32}F_3N_5O_3S$, 539.6; m/z found, 540.1 [M+H]$^+$. $^1$H NMR (500 MHz, CDCl$_3$) δ 8.10 (d, J=7.6 Hz, 1H), 7.57-7.48 (m, 1H), 6.59 (s, 1H), 4.91-4.87 (m, 1.3H), 4.60-4.43 (m, 1.3H), 4.28-4.22 (m, 0.7H), 4.12-3.93 (m, 0.8H), 3.65 (s, 1H), 3.54-3.41 (m, 2H), 2.55-2.40 (m, 1H), 2.03 (d, J=11.7 Hz, 2H), 1.98-1.53 (m, 3H), 1.51-1.12 (m, 16H).

Example 26

5-(6-((2,2-Difluorocyclohexyl)amino)-4-(trifluoromethyl)pyridin-3-yl)-4-(4-fluoropiperidine-1-carbonyl)-N-(2-hydroxy-2-methylpropyl)thiazole-2-carboxamide

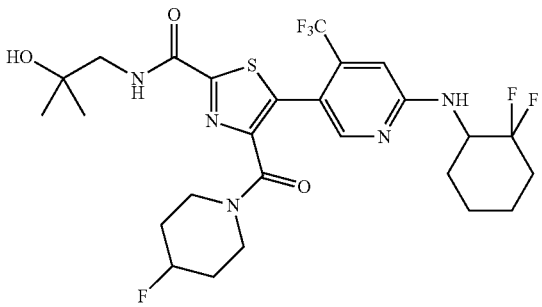 [SMILES: CC(C)(O)CNC(=O)c1nc(C(=O)N2CCC(F)CC2)c(-c2cnc(NC3CCCCC3(F)F)cc2C(F)(F)F)s1]

The title compound was prepared as described in Example 3 substituting 5-bromo-N-(2,2-difluorocyclohexyl)-4-(trifluoromethyl)pyridin-2-amine (Intermediate 47) for 5-bromo-N-cyclohexyl-4-(trifluoromethyl)pyridin-2-amine. MS (ESI): mass calcd. for $C_{26}H_{31}F_6N_5O_3S$, 607.6; m/z found, 608.1 [M+H]$^+$. $^1$H NMR (500 MHz, CDCl$_3$) δ 8.25-8.19 (m, 1H), 7.60-7.51 (m, 1H), 6.74 (s, 1H), 5.10 (t, J=8.3 Hz, 1H), 4.89 (s, 0.5H), 4.79 (s, 0.5H), 4.40 (s, 1H), 3.94 (t, J=15.1 Hz, 1H), 3.59-3.33 (m, 5H), 2.28-2.18 (m, 1H), 2.10 (s, 1H), 1.96 (s, 1H), 1.92-1.72 (m, 7H), 1.64-1.41 (m, 3H), 1.31 (s, 6H).

Example 27

(S)-5-(6-(Cyclopentylamino)-4-(trifluoromethyl)pyridin-3-yl)-N-(2-hydroxy-2-methylpropyl)-4-(2-methylpiperidine-1-carbonyl)thiazole-2-carboxamide

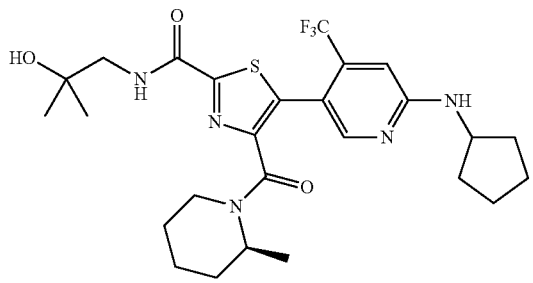 [SMILES: C[C@H]1CCCCN1C(=O)c1nc(C(=O)NCC(C)(C)O)sc1-c1cnc(NC2CCCC2)cc1C(F)(F)F]

The title compound was prepared as described in Example 3 substituting 5-bromo-N-cyclopentyl-4-(trifluoromethyl)pyridin-2-amine (Intermediate 8) for 5-bromo-N-cyclohexyl-4-(trifluoromethyl)pyridin-2-amine and (S)—N-(2-hydroxy-2-methylpropyl)-4-(2-methylpiperidine-1-carbonyl)thiazole-2-carboxamide (Intermediate 66: Step D) for 4-(4-fluoropiperidine-1-carbonyl)-N-(2-hydroxy-2-methylpropyl)thiazole-2-carboxamide. MS (ESI): mass calcd. for $C_{26}H_{34}F_3N_5O_3S$, 553.6; m/z found, 554.1 [M+H]$^+$. $^1$H NMR (500 MHz, CDCl$_3$) δ 8.21 (d, J=19.3 Hz, 1H), 7.60 (br s, 1H), 6.64 (s, 1H), 5.02 (d, J=7.0 Hz, 1H), 4.89 (s, 0.6H), 4.47 (d, J=13.9 Hz, 0.4H), 4.11-4.05 (m, 1H), 3.96 (s, 0.4H), 3.54-3.38 (m, 2.6H), 2.98 (t, J=13.3 Hz, 0.5H), 2.79 (t, J=13.3 Hz, 0.4H), 2.15-1.92 (m, 3H), 1.82-1.37 (m, 11H), 1.31 (s, 6H), 1.25-1.08 (m, 4H).

Example 28

(S)-5-(6-(Cyclopentylamino)-4-(trifluoromethyl)pyridin-3-yl)-N-(1,1-dioxidotetrahydro-2H-thiopyran-4-yl)-4-(2-methylpiperidine-1-carbonyl)thiazole-2-carboxamide

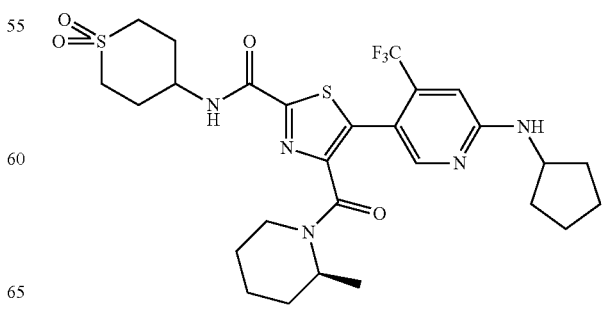

The title compound was prepared as described in Example 3 substituting 5-bromo-N-cyclopentyl-4-(trifluoromethyl)pyridin-2-amine (Intermediate 8) for 5-bromo-N-cyclohexyl-4-(trifluoromethyl)pyridin-2-amine and (S)—N-(1,1-dioxidotetrahydro-2H-thiopyran-4-yl)-4-(2-methylpiperidine-1-carbonyl)thiazole-2-carboxamide (Intermediate 72: Step D) for 4-(4-fluoropiperidine-1-carbonyl)-N-(2-hydroxy-2-methylpropyl)thiazole-2-carboxamide. MS (ESI): mass calcd. for $C_{27}H_{34}F_3N_5O_4S_2$, 613.7; m/z found, 614.1 [M+H]+. $^1$H NMR (500 MHz, CDCl$_3$) δ 8.26-8.15 (m, 1H), 7.25-7.16 (m, 1H), 6.65 (s, 1H), 5.04 (d, J=6.9 Hz, 1H), 4.90 (s, 0.6H), 4.47 (d, J=13.5 Hz, 0.4H), 4.27-4.20 (m, 1H), 4.15-4.05 (m, 1H), 3.88 (s, 0.4H), 3.37 (d, J=13.3 Hz, 0.6H), 3.23-3.06 (m, 4H), 2.95 (t, J=13.1 Hz, 0.6H), 2.79 (t, J=13.4 Hz, 0.4H), 2.46-2.38 (m, 2H), 2.35-2.24 (m, 2H), 2.13-2.04 (m, 2H), 1.82-1.03 (m, 15H).

Example 29

(R)-5-(6-((1-Cyclopropylethyl)amino)-4-(trifluoromethyl)pyridin-3-yl)-4-(4-fluoropiperidine-1-carbonyl)-N-(2-hydroxy-2-methylpropyl)thiazole-2-carboxamide

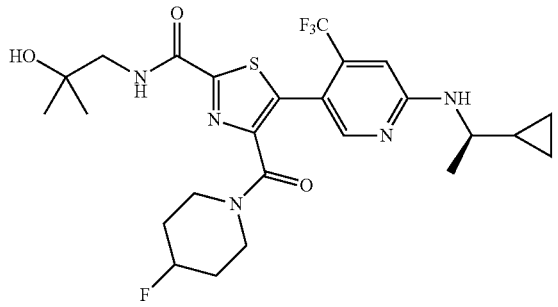 [SMILES: C[C@@H](Nc1cc(C(F)(F)F)c(-c2sc(C(=O)NCC(C)(C)O)nc2C(=O)N2CCC(F)CC2)cn1)C1CC1]

The title compound was prepared as described in Example 3 substituting (R)-5-bromo-N-(1-cyclopropylethyl)-4-(trifluoromethyl)pyridin-2-amine (Intermediate 17) for 5-bromo-N-cyclohexyl-4-(trifluoromethyl)pyridin-2-amine. MS (ESI): mass calcd. for $C_{25}H_{31}F_4N_5O_3S$, 557.6; m/z found, 558.2 [M+H]+. $^1$H NMR (500 MHz, CDCl$_3$) δ 8.18 (s, 1H), 7.60-7.52 (m, 1H), 6.62 (s, 1H), 5.02 (d, J=7.5 Hz, 1H), 4.93-4.85 (m, 0.5H), 4.84-4.75 (m, 0.5H), 3.92 (d, J=12.8 Hz, 1H), 3.58-3.37 (m, 6H), 1.96 (s, 1H), 1.92-1.63 (m, 4H), 1.38-1.22 (m, 9H), 0.98-0.90 (m, 1H), 0.58-0.50 (m, 2H), 0.37-0.33 (m, 1H), 0.30-0.27 (m, 1H).

Example 30

(S)-5-(6-((1-Cyclopropylethyl)amino)-4-(trifluoromethyl)pyridin-3-yl)-4-(4-fluoropiperidine-1-carbonyl)-N-(2-hydroxy-2-methylpropyl)thiazole-2-carboxamide

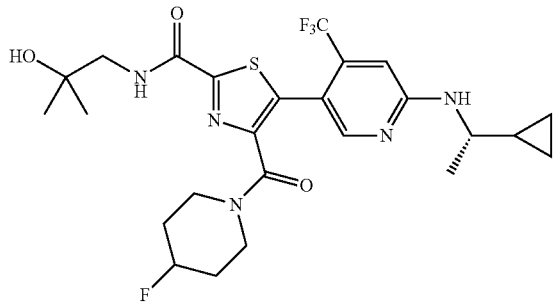 [SMILES: C[C@H](Nc1cc(C(F)(F)F)c(-c2sc(C(=O)NCC(C)(C)O)nc2C(=O)N2CCC(F)CC2)cn1)C1CC1]

The title compound was prepared as described in Example 3 substituting (S)-5-bromo-N-(1-cyclopropylethyl)-4-(trifluoromethyl)pyridin-2-amine (Intermediate 18) for 5-bromo-N-cyclohexyl-4-(trifluoromethyl)pyridin-2-amine. MS (ESI): mass calcd. for $C_{25}H_{31}F_4N_5O_3S$, 557.6; m/z found, 558.2 [M+H]+. $^1$H NMR (500 MHz, CDCl$_3$) δ 8.18 (s, 1H), 7.60-7.51 (m, 1H), 6.62 (s, 1H), 5.01 (d, J=7.5 Hz, 1H), 4.92-4.86 (m, 0.5H), 4.83-4.75 (m, 0.5H), 3.92 (d, J=13.2 Hz, 1H), 3.58-3.36 (m, 6H), 1.95 (s, 1H), 1.90-1.68 (m, 4H), 1.33-1.25 (m, 9H), 0.98-0.90 (m, 1H), 0.55-0.50 (m, 2H), 0.38-0.34 (m, 1H), 0.31-0.27 (m, 1H).

Example 31

5-(6-(((R*)-2,2-Difluorocyclohexyl)amino)-4-(trifluoromethyl)pyridin-3-yl)-N-(2-hydroxy-2-methylpropyl)-4-((S)-2-methylpiperidine-1-carbonyl)thiazole-2-carboxamide

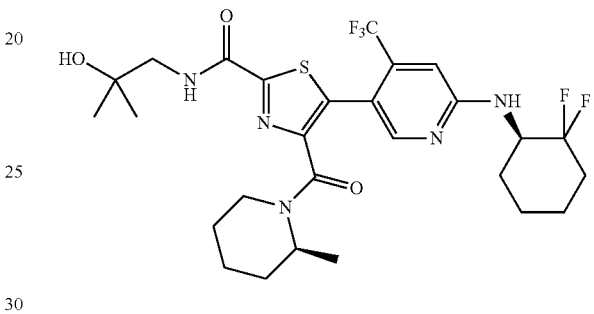

The title compound was prepared as described in Example 3 substituting 5-bromo-N-(2,2-difluorocyclohexyl)-4-(trifluoromethyl)pyridin-2-amine (Intermediate 47) for 5-bromo-N-cyclohexyl-4-(trifluoromethyl)pyridin-2-amine and (S)—N-(2-hydroxy-2-methylpropyl)-4-(2-methylpiperidine-1-carbonyl)thiazole-2-carboxamide (Intermediate 66: Step D) for 4-(4-fluoropiperidine-1-carbonyl)-N-(2-hydroxy-2-methylpropyl)thiazole-2-carboxamide. The pure diastereomer was isolated via SFC (Stationary phase: Chiralpak IC, 5 µm, 250×21 mm, Mobile phase: 12% EtOH+ 0.2% TEA, 88% CO$_2$, first eluting peak) monitoring elution at 254 nm. MS (ESI): mass calcd. for $C_{27}H_{34}F_5N_5O_3S$, 603.7; m/z found, 604.1 [M+H]+. $^1$H NMR (500 MHz, CDCl$_3$) δ 8.23 (d, J=22.5 Hz, 1H), 7.67-7.56 (m, 1H), 6.75 (s, 1H), 5.12 (d, J=9.1 Hz, 1H), 4.89 (br s, 0.5H), 4.49-4.38 (m, 1.5H), 3.93 (s, 0.5H), 3.55-3.36 (m, 2.5H), 2.95 (t, J=13.2 Hz, 0.5H), 2.85-2.69 (m, 0.5H), 2.33-2.16 (m, 1H), 2.14-0.99 (m, 23H).

Example 32

5-(6-(((S*)-2,2-Difluorocyclohexyl)amino)-4-(trifluoromethyl)pyridin-3-yl)-N-(2-hydroxy-2-methylpropyl)-4-((S)-2-methylpiperidine-1-carbonyl)thiazole-2-carboxamide

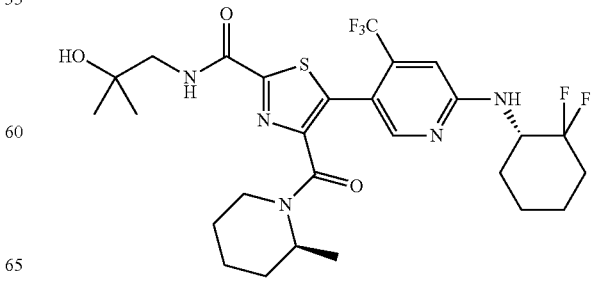

The title compound was prepared as described in Example 3 substituting 5-bromo-N-(2,2-difluorocyclohexyl)-4-(trifluoromethyl)pyridin-2-amine (Intermediate 47) for 5-bromo-N-cyclohexyl-4-(trifluoromethyl)pyridin-2-amine and (S)—N-(2-hydroxy-2-methylpropyl)-4-(2-methylpiperidine-1-carbonyl)thiazole-2-carboxamide (Intermediate 66: Step D) for 4-(4-fluoropiperidine-1-carbonyl)-N-(2-hydroxy-2-methylpropyl)thiazole-2-carboxamide. The pure diastereomer was isolated via SFC (Stationary phase: Chiralpak IC, 5 μm, 250×21 mm, Mobile phase: 12% EtOH+ 0.2% TEA, 88% $CO_2$, second eluting peak) monitoring elution at 254 nm. MS (ESI): mass calcd. for $C_{27}H_{34}F_5N_5O_3S$, 603.7; m/z found, 604.1 [M+H]$^+$. $^1$H NMR (500 MHz, CDCl$_3$) δ 8.23 (d, J=15.9 Hz, 1H), 7.66-7.58 (m, 1H), 6.74 (s, 1H), 5.22-5.13 (m, 1H), 4.87 (br s, 0.5H), 4.49-4.38 (m, 1.5H), 3.95 (s, 0.5H), 3.53-3.36 (m, 2.5H), 3.04-2.90 (m, 0.5H), 2.79 (t, J=13.2 Hz, 0.5H), 2.33-2.16 (m, 1H), 2.15-1.00 (m, 23H).

Example 33

N-(2-Hydroxy-2-methylpropyl)-4-((S)-2-methylpiperidine-1-carbonyl)-5-(4-(trifluoromethyl)-6-((1,1,1-trifluoropropan-2-yl)amino)pyridin-3-yl)thiazole-2-carboxamide

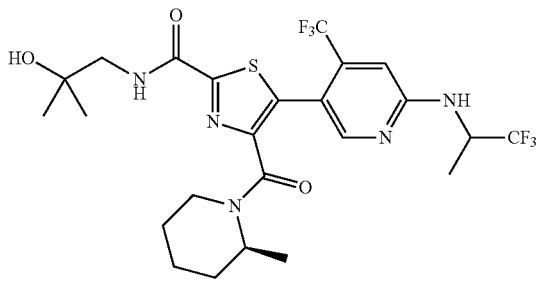 [SMILES: CC(Nc1cc(C(F)(F)F)c(-c2sc(C(=O)NCC(C)(C)O)nc2C(=O)N2CCCC[C@@H]2C)cn1)C(F)(F)F]

The title compound was prepared as described in Example 3 substituting 5-bromo-4-(trifluoromethyl)-N-(1,1,1-trifluoropropan-2-yl)pyridin-2-amine (Intermediate 42) for 5-bromo-N-cyclohexyl-4-(trifluoromethyl)pyridin-2-amine and (S)—N-(2-hydroxy-2-methylpropyl)-4-(2-methylpiperidine-1-carbonyl)thiazole-2-carboxamide (Intermediate 66: Step D) for 4-(4-fluoropiperidine-1-carbonyl)-N-(2-hydroxy-2-methylpropyl)thiazole-2-carboxamide. MS (ESI): mass calcd. for $C_{24}H_{29}F_6N_5O_3S$, 581.6; m/z found, 582.1 [M+H]$^+$. $^1$H NMR (500 MHz, CDCl$_3$) δ 8.32-8.19 (m, 1H), 7.65-7.55 (m, 1H), 6.80-6.69 (m, 1H), 5.18-4.79 (m, 2.6H), 4.45 (d, J=12.6 Hz, 0.4H), 4.00 (d, J=18.6 Hz, 0.4H), 3.55-3.40 (m, 2.6H), 3.03-2.95 (m, 0.5H), 2.81 (t, J=13.8 Hz, 0.5H), 2.12-1.92 (m, 1H), 1.74-1.01 (m, 18H).

Example 34

(S)-5-(6-(Cyclohexylamino)-4-(difluoromethyl)pyridin-3-yl)-N-(2-hydroxy-2-methylpropyl)-4-(2-methylpiperidine-1-carbonyl)thiazole-2-carboxamide

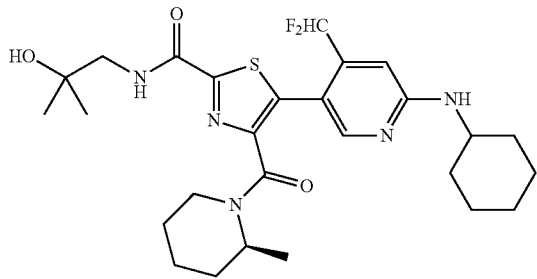 [SMILES: C[C@H]1CCCCN1C(=O)c1nc(C(=O)NCC(C)(C)O)sc1-c1cnc(NC2CCCCC2)cc1C(F)F]

The title compound was prepared as described in Example 3 substituting 5-bromo-N-cyclohexyl-4-(difluoromethyl)pyridin-2-amine (Intermediate 15) for 5-bromo-N-cyclohexyl-4-(trifluoromethyl)pyridin-2-amine and (5)-methyl 2,2-dimethyl-3-(4-(2-methylpiperidine-1-carbonyl)thiazole-2-carboxamido)propanoate (Intermediate 66: Step D) for 4-(4-fluoropiperidine-1-carbonyl)-N-(2-hydroxy-2-methylpropyl)thiazole-2-carboxamide. MS (ESI): mass calcd. for $C_{27}H_{37}F_2N_5O_3S$, 549.7; m/z found, 550.1 [M+H]$^+$. $^1$H NMR (500 MHz, CDCl$_3$) δ 10.25-10.00 (br s, 1H), 7.73 (d, J=9.0 Hz, 1H), 7.53 (s, 1H), 7.05-6.75 (m, 2H), 4.81 (s, 0.6H), 4.38 (d, J=13.5 Hz, 0.7H), 4.14 (s, 0.8H), 3.63 (d, J=13.6 Hz, 0.7H), 3.56-3.38 (m, 3H), 3.19 (t, J=13.0 Hz, 0.6H), 2.85 (t, J=12.7 Hz, 0.5H), 2.03 (d, J=11.7 Hz, 2H), 1.93-1.80 (m, 2H), 1.79-1.14 (m, 21H).

Example 35

5-(6-(((R*)-2,2-Difluorocyclohexyl)amino)-4-(trifluoromethyl)pyridin-3-yl)-N-(2-hydroxy-2-methylpropyl)-4-((S)-2-methylpyrrolidine-1-carbonyl)thiazole-2-carboxamide

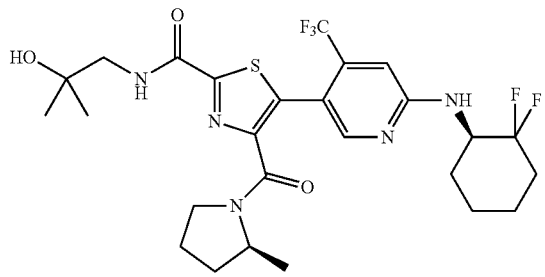 [SMILES: C[C@H]1CCCN1C(=O)c1nc(C(=O)NCC(C)(C)O)sc1-c1cnc(N[C@@H]2CCCCC2(F)F)cc1C(F)(F)F]

The title compound was prepared as described in Example 3 substituting 5-bromo-N-(2,2-difluorocyclohexyl)-4-(trifluoromethyl)pyridin-2-amine (Intermediate 47) for 5-bromo-N-cyclohexyl-4-(trifluoromethyl)pyridin-2-amine and (S)—N-(2-hydroxy-2-methylpropyl)-4-(2-methylpyrrolidine-1-carbonyl)thiazole-2-carboxamide (Intermediate 69) for 4-(4-fluoropiperidine-1-carbonyl)-N-(2-hydroxy-2-methylpropyl)thiazole-2-carboxamide. The pure diastereomer was isolated via chiral SFC (Stationary phase: Chiralpak IA, 5 μm, 250×21 mm, Mobile phase: 10% EtOH+ 0.2% TEA, 90% $CO_2$, first eluting peak) monitoring elution at 254 nm. MS (ESI): mass calcd. for $C_{26}H_{32}F_5N_5O_3S$, 589.6; m/z found, 590.1 [M+H]$^+$. $^1$H NMR (400 MHz, CDCl$_3$) δ 8.19 (s, 1H), 7.65-7.48 (m, 1H), 6.73 (d, J=2.8 Hz, 1H), 5.14 (dd, J=8.5, 5.1 Hz, 1H), 4.47-4.25 (m, 1H), 4.23-4.15 (m, 1H), 3.71-3.30 (m, 4.5H), 3.07 (s, 1.5H), 2.31-0.78 (m, 20H).

Example 36

5-(6-(((S*)-2,2-Difluorocyclohexyl)amino)-4-(trifluoromethyl)pyridin-3-yl)-N-(2-hydroxy-2-methylpropyl)-4-((S)-2-methylpyrrolidine-1-carbonyl)thiazole-2-carboxamide

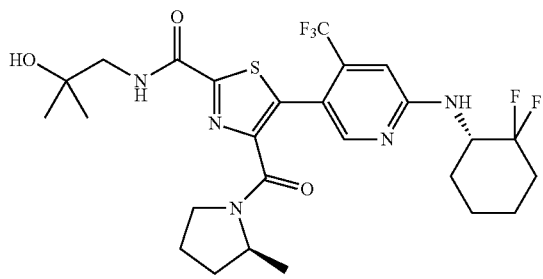 [SMILES: C[C@H]1CCCN1C(=O)c1nc(C(=O)NCC(C)(C)O)sc1-c1cnc(N[C@H]2CCCCC2(F)F)cc1C(F)(F)F]

The title compound was prepared as described in Example 3 substituting 5-bromo-N-(2,2-difluorocyclohexyl)-4-(trifluoromethyl)pyridin-2-amine (Intermediate 47) for 5-bromo-N-cyclohexyl-4-(trifluoromethyl)pyridin-2-amine and (S)—N-(2-hydroxy-2-methylpropyl)-4-(2-methylpyrrolidine-1-carbonyl)thiazole-2-carboxamide (Intermediate 69) for 4-(4-fluoropiperidine-1-carbonyl)-N-(2-hydroxy-2-methylpropyl)thiazole-2-carboxamide. The pure diastereomer was isolated via chiral SFC (Stationary phase: Chiralpak IA, 5 µm, 250×21 mm, Mobile phase: 10% EtOH+ 0.2% TEA, 90% CO$_2$, second eluting peak) monitoring elution at 254 nm. MS (ESI): mass calcd. for C$_{26}$H$_{32}$F$_5$N$_5$O$_3$S, 589.6; m/z found, 590.1 [M+H]$^+$. $^1$H NMR (400 MHz, CDCl$_3$) δ 8.19 (s, 1H), 7.65-7.48 (m, 1H), 6.72 (d, J=4.6 Hz, 1H), 5.16 (dd, J=19.2, 9.1 Hz, 1H), 4.47-4.25 (m, 1H), 4.23-4.15 (m, 1H), 3.67-3.29 (m, 4.5H), 3.08 (s, 1.5H), 2.36-0.73 (m, 20H).

Example 37

5-(6-(((S)-1-Cyclopropylethyl)amino)-4-(difluoromethyl)pyridin-3-yl)-N-(2-hydroxy-2-methylpropyl)-4-((S)-2-methylpiperidine-1-carbonyl)thiazole-2-carboxamide

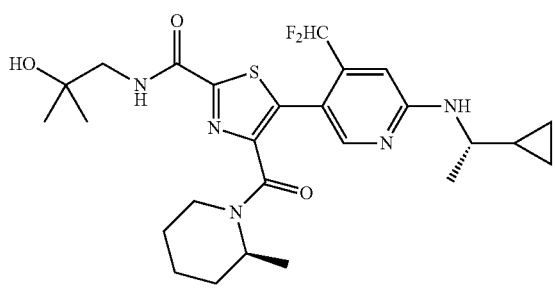

The title compound was prepared as described in Example 3 substituting (S)-5-bromo-N-(1-cyclopropylethyl)-4-(difluoromethyl)pyridin-2-amine (Intermediate 20) for 5-bromo-N-cyclohexyl-4-(trifluoromethyl)pyridin-2-amine and (S)—N-(2-hydroxy-2-methylpropyl)-4-(2-methylpiperidine-1-carbonyl)thiazole-2-carboxamide (Intermediate 66: Step D) for 4-(4-fluoropiperidine-1-carbonyl)-N-(2-hydroxy-2-methylpropyl)thiazole-2-carboxamide. MS (ESI): mass calcd. for C$_{26}$H$_{35}$F$_2$N$_5$O$_3$S, 535.7; m/z found, 536.1 [M+H]$^+$. $^1$H NMR (400 MHz, CDCl$_3$) δ 8.03 (s, 1H), 7.66-7.53 (m, 1H), 6.62 (s, 2H), 4.92 (d, J=7.6 Hz, 1.5H), 4.44 (d, J=13.2 Hz, 0.5H), 3.90 (s, 0.5H), 3.55-3.31 (m, 3.5H), 2.99 (t, J=13.1 Hz, 0.5H), 2.79 (t, J=13.0 Hz, 0.5H), 2.00 (d, J=27.5 Hz, 1H), 1.76-1.23 (m, 14H), 1.15 (dd, J=22.5, 7.0 Hz, 4H), 0.99-0.90 (m, 1H), 0.62-0.45 (m, 2H), 0.39-0.26 (m, 2H).

Example 38

(S)-5-(6-(Cyclopentylamino)-4-(trifluoromethyl)pyridin-3-yl)-N-(2-hydroxy-2-methylpropyl)-4-(2-methylpyrrolidine-1-carbonyl)thiazole-2-carboxamide

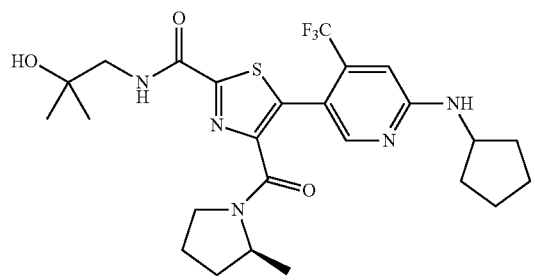 [SMILES: C[C@H]1CCCN1C(=O)c1nc(C(=O)NCC(C)(C)O)sc1-c1cnc(NC2CCCC2)cc1C(F)(F)F]

The title compound was prepared as described in Example 3 substituting 5-bromo-N-cyclopentyl-4-(trifluoromethyl)pyridin-2-amine (Intermediate 8) for 5-bromo-N-cyclohexyl-4-(trifluoromethyl)pyridin-2-amine and (S)—N-(2-hydroxy-2-methylpropyl)-4-(2-methylpyrrolidine-1-carbonyl)thiazole-2-carboxamide (Intermediate 69) for 4-(4-fluoropiperidine-1-carbonyl)-N-(2-hydroxy-2-methylpropyl)thiazole-2-carboxamide. MS (ESI): mass calcd. for C$_{25}$H$_{32}$F$_3$N$_5$O$_3$S, 539.6; m/z found, 540.1 [M+H]$^+$. $^1$H NMR (400 MHz, CDCl$_3$) δ 8.17 (s, 1H), 7.61-7.55 (m, 1H), 6.62 (s, 1H), 5.12-5.02 (m, 1H), 4.40-3.98 (m, 2H), 3.64-3.35 (m, 4H), 2.20-1.41 (m, 12H), 1.40-1.19 (m, 9H), 1.11 (d, J=6.4 Hz, 1H).

Example 39

5-(6-(((S)-1-Cyclopropylethyl)amino)-4-(trifluoromethyl)pyridin-3-yl)-N-(2-hydroxy-2-methylpropyl)-4-((S)-2-methylpiperidine-1-carbonyl)thiazole-2-carboxamide

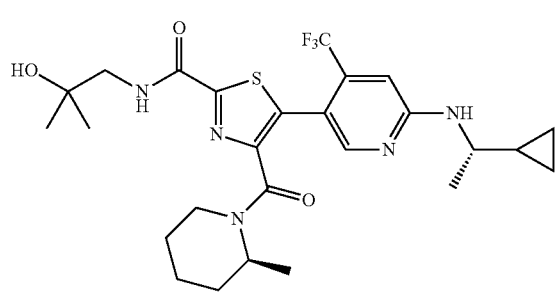 [SMILES: C[C@H](Nc1cc(C(F)(F)F)c(-c2sc(C(=O)NCC(C)(C)O)nc2C(=O)N2CCCC[C@@H]2C)cn1)C1CC1]

The title compound was prepared as described in Example 3 substituting (S)-5-bromo-N-(1-cyclopropylethyl)-4-(trifluoromethyl)pyridin-2-amine (Intermediate 18) for 5-bromo-N-cyclohexyl-4-(trifluoromethyl)pyridin-2-amine and (S)—N-(2-hydroxy-2-methylpropyl)-4-(2-methylpiperidine-1-carbonyl)thiazole-2-carboxamide (Intermediate 66: Step D) for 4-(4-fluoropiperidine-1-carbonyl)-N-(2-hydroxy-2-methylpropyl)thiazole-2-carboxamide. MS (ESI): mass calcd. for $C_{26}H_{34}F_3N_5O_3S$, 553.6; m/z found, 554.1 [M+H]$^+$. $^1$H NMR (400 MHz, CDCl$_3$) δ 8.19 (d, J=15.3 Hz, 1H), 7.60 (d, J=7.3 Hz, 1H), 6.62 (s, 1H), 5.00 (d, J=7.6 Hz, 1H), 4.89 (s, 0.6H), 4.47 (d, J=13.4 Hz, 0.4H), 3.96 (s, 0.4H), 3.57-3.32 (m, 3.6H), 2.98 (t, J=13.3 Hz, 0.6H), 2.79 (t, J=13.3 Hz, 0.4H), 2.10-2.01 (m, 1H), 1.79-1.05 (m, 18H), 0.99-0.90 (m, 1H), 0.64-0.43 (m, 2H), 0.43-0.22 (m, 2H).

Example 40

5-(6-(((S)-1-Cyclopropylethyl)amino)-4-(trifluoromethyl)pyridin-3-yl)-N-(2-hydroxy-2-methylpropyl)-4-((S)-2-methylpyrrolidine-1-carbonyl)thiazole-2-carboxamide

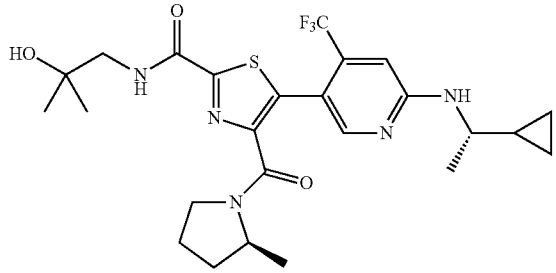 [SMILES: C[C@H](Nc1cc(C(F)(F)F)c(-c2sc(C(=O)NCC(C)(C)O)nc2C(=O)N2CCC[C@@H]2C)cn1)C1CC1]

The title compound was prepared as described in Example 3 substituting (S)-5-bromo-N-(1-cyclopropylethyl)-4-(trifluoromethyl)pyridin-2-amine (Intermediate 18) for 5-bromo-N-cyclohexyl-4-(trifluoromethyl)pyridin-2-amine and (S)—N-(2-hydroxy-2-methylpropyl)-4-(2-methylpyrrolidine-1-carbonyl)thiazole-2-carboxamide (Intermediate 69) for 4-(4-fluoropiperidine-1-carbonyl)-N-(2-hydroxy-2-methylpropyl)thiazole-2-carboxamide. MS (ESI): mass calcd. for $C_{25}H_{32}F_3N_5O_3S$, 539.6; m/z found, 540.1 [M+H]$^+$. $^1$H NMR (400 MHz, CDCl$_3$) δ 8.15 (d, J=2.0 Hz, 1H), 7.65-7.49 (m, 1H), 6.60 (s, 1H), 5.02-4.98 (m, 1H), 4.30-4.20 (m, 1H), 3.65-3.32 (m, 5H), 2.14-1.99 (m, 1.6H), 1.99-1.45 (m, 2.4H), 1.40-1.17 (m, 12H), 1.11 (d, J=6.4 Hz, 1H), 0.97-0.93 (m, 1H), 0.61-0.45 (m, 2H), 0.42-0.23 (m, 2H).

Example 41

(S)-5-(6-(Cyclopentylamino)-4-(difluoromethyl)pyridin-3-yl)-N-(2-hydroxy-2-methylpropyl)-4-(2-methylpiperidine-1-carbonyl)thiazole-2-carboxamide

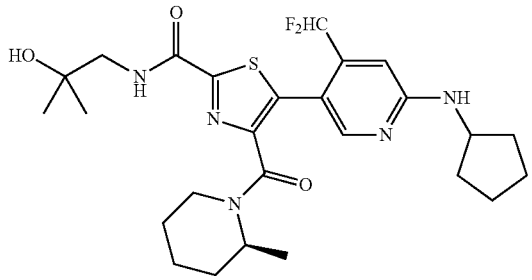

The title compound was prepared as described in Example 3 substituting 5-bromo-N-cyclopentyl-4-(difluoromethyl)pyridin-2-amine (Intermediate 19) for 5-bromo-N-cyclohexyl-4-(trifluoromethyl)pyridin-2-amine and (S)—N-(2-hydroxy-2-methylpropyl)-4-(2-methylpiperidine-1-carbonyl)thiazole-2-carboxamide (Intermediate 66: Step D) for 4-(4-fluoropiperidine-1-carbonyl)-N-(2-hydroxy-2-methylpropyl)thiazole-2-carboxamide. MS (ESI): mass calcd. for $C_{26}H_{35}F_2N_5O_3S$, 535.7; m/z found, 536.1 [M+H]$^+$. $^1$H NMR (500 MHz, CDCl$_3$) δ 8.05 (s, 1H), 7.68-7.54 (m, 1H), 6.81-6.64 (m, 2H), 4.97 (d, J=7.0 Hz, 1H), 4.89 (s, 0.5H), 4.44 (d, J=12.6 Hz, 0.5H), 4.10-4.06 (m, 1H), 3.90 (s, 0.5H), 3.50-3.44 (m, 2H), 3.37 (d, J=13.2 Hz, 0.5H), 3.05-2.92 (m, 0.5H), 2.79 (t, J=13.0 Hz, 0.5H), 2.21-1.98 (m, 3H), 1.86-1.38 (m, 11H), 1.30 (s, 6H), 1.21-1.09 (m, 4H).

Example 42

(S)-5-(6-(Cyclopentylamino)-4-(difluoromethyl)pyridin-3-yl)-N-(2-hydroxy-2-methylpropyl)-4-(2-methylpyrrolidine-1-carbonyl)thiazole-2-carboxamide

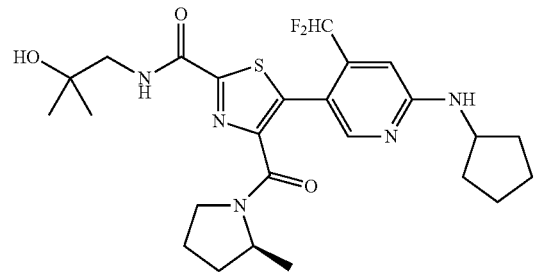 [SMILES: C[C@H]1CCCN1C(=O)c1nc(C(=O)NCC(C)(C)O)sc1-c1cnc(NC2CCCC2)cc1C(F)F]

The title compound was prepared as described in Example 3 substituting 5-bromo-N-cyclopentyl-4-(difluoromethyl)pyridin-2-amine (Intermediate 19) for 5-bromo-N-cyclohexyl-4-(trifluoromethyl)pyridin-2-amine and (S)—N-(2-hydroxy-2-methylpropyl)-4-(2-methylpyrrolidine-1-carbonyl)thiazole-2-carboxamide (Intermediate 69) for 4-(4-fluoropiperidine-1-carbonyl)-N-(2-hydroxy-2-methylpropyl)thiazole-2-carboxamide. MS (ESI): mass calcd. for $C_{25}H_{33}F_2N_5O_3S$, 521.6; m/z found, 522.1 [M+H]$^+$. $^1$H NMR (500 MHz, CDCl$_3$) δ 8.01 (d, J=19.2 Hz, 1H), 7.59-7.53 (m, 1H), 7.02-6.37 (m, 2H), 4.94 (t, J=7.0 Hz, 1H), 4.34-4.16 (m, 1H), 4.09-4.00 (m, 1H), 3.65-3.32 (m, 4H), 2.15-1.41 (m, 13H), 1.32 (d, J=1.6 Hz, 6H), 1.23 (d, J=6.3 Hz, 2H), 1.02 (d, J=6.4 Hz, 1H).

Example 43

5-(6-(((S)-1-Cyclopropylethyl)amino)-4-(difluoromethyl)pyridin-3-yl)-N-(2-hydroxy-2-methylpropyl)-4-((S)-2-methylpyrrolidine-1-carbonyl)thiazole-2-carboxamide

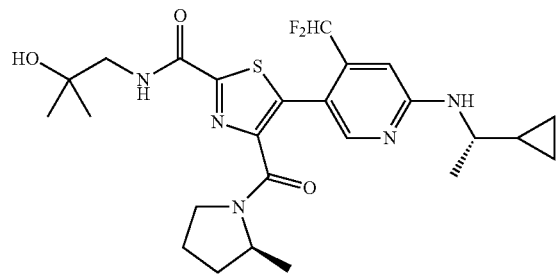 [SMILES: C[C@H](Nc1cc(C(F)F)c(-c2sc(C(=O)NCC(C)(C)O)nc2C(=O)N2CCC[C@@H]2C)cn1)C1CC1]

The title compound was prepared as described in Example 3 substituting (S)-5-bromo-N-(1-cyclopropylethyl)-4-(difluoromethyl)pyridin-2-amine (Intermediate 20) for 5-bromo-N-cyclohexyl-4-(trifluoromethyl)pyridin-2-amine and (S)—N-(2-hydroxy-2-methylpropyl)-4-(2-methylpyrrolidine-1-carbonyl)thiazole-2-carboxamide (Intermediate 69) for 4-(4-fluoropiperidine-1-carbonyl)-N-(2-hydroxy-2-methylpropyl)thiazole-2-carboxamide. MS (ESI): mass calcd. for $C_{25}H_{33}F_2N_5O_3S$, 521.6; m/z found, 522.1 $[M+H]^+$. $^1H$ NMR (500 MHz, $CDCl_3$) δ 7.99 (d, J=19.4 Hz, 1H), 7.59-7.53 (m, 1H), 7.00-6.57 (m, 2H), 4.93 (dd, J=7.4, 2.2 Hz, 1H), 4.34-4.15 (m, 1H), 3.65-3.33 (m, 5H), 2.13-1.50 (m, 5H), 1.38-1.20 (m, 11H), 1.06-0.88 (m, 2H), 0.60-0.45 (m, 2H), 0.40-0.23 (m, 2H).

Example 44

(S)-5-(6-(Cyclopentylamino)-4-(difluoromethyl)pyridin-3-yl)-4-(4,4-difluoro-2-methylpyrrolidine-1-carbonyl)-N-(2-hydroxy-2-methylpropyl)thiazole-2-carboxamide

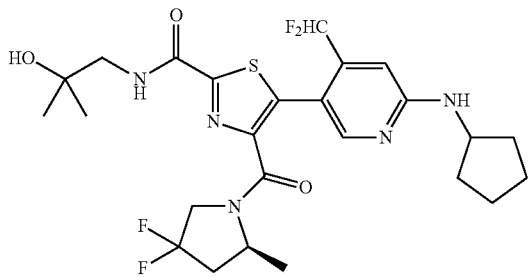 [SMILES: C[C@H]1CC(F)(F)CN1C(=O)c1nc(C(=O)NCC(C)(C)O)sc1-c1cnc(NC2CCCC2)cc1C(F)F]

The title compound was prepared as described in Example 3 substituting 5-bromo-N-cyclopentyl-4-(difluoromethyl)pyridin-2-amine (Intermediate 19) for 5-bromo-N-cyclohexyl-4-(trifluoromethyl)pyridin-2-amine and (S)-4-(4,4-difluoro-2-methylpyrrolidine-1-carbonyl)-N-(2-hydroxy-2-methylpropyl)thiazole-2-carboxamide (Intermediate 67) for 4-(4-fluoropiperidine-1-carbonyl)-N-(2-hydroxy-2-methylpropyl)thiazole-2-carboxamide. MS (ESI): mass calcd. for $C_{25}H_{31}F_4N_5O_3S$, 557.6; m/z found, 558.1 $[M+H]^+$. $^1H$ NMR (400 MHz, $CDCl_3$) δ 8.00 (d, J=9.2 Hz, 1H), 7.53-7.50 (m, 1H), 6.91-6.56 (m, 2H), 4.97 (d, J=6.9 Hz, 1H), 4.70-4.66 (m, 0.3H), 4.58-4.44 (m, 0.7H), 4.16-3.98 (m, 2H), 3.95-3.85 (m, 1H), 3.60-3.39 (m, 2H), 2.71-2.44 (m, 1H), 2.23-1.59 (m, 8H), 1.59-1.43 (m, 2H), 1.42-1.15 (m, 9H).

Example 45

N-(2-Hydroxy-2-methylpropyl)-4-((S)-2-methylpiperidine-1-carbonyl)-5-(4-(trifluoromethyl)-6-(((R)-1,1,1-trifluoropropan-2-yl)amino)pyridin-3-yl)thiazole-2-carboxamide

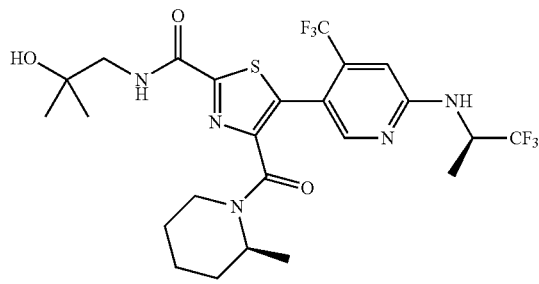 [SMILES: C[C@H]1CCCCN1C(=O)c1nc(C(=O)NCC(C)(C)O)sc1-c1cnc(N[C@H](C)C(F)(F)F)cc1C(F)(F)F]

The title compound was prepared as described in Example 3 substituting (R)-5-bromo-4-(trifluoromethyl)-N-(1,1,1-trifluoropropan-2-yl)pyridin-2-amine (Intermediate 43) for 5-bromo-N-cyclohexyl-4-(trifluoromethyl)pyridin-2-amine and (S)—N-(2-hydroxy-2-methylpropyl)-4-(2-methylpiperidine-1-carbonyl)thiazole-2-carboxamide (Intermediate 66: Step D) for 4-(4-fluoropiperidine-1-carbonyl)-N-(2-hydroxy-2-methylpropyl)thiazole-2-carboxamide. MS (ESI): mass calcd. for $C_{24}H_{29}F_6N_5O_3S$, 581.6; m/z found, 582.0 $[M+H]^+$. $^1H$ NMR (400 MHz, $CDCl_3$) δ 8.26 (d, J=5.6 Hz, 1H), 7.65-7.55 (m, 1H), 6.72 (d, J=13.6 Hz, 1H), 5.20-4.79 (m, 2.6H), 4.46 (d, J=13.3 Hz, 0.4H), 4.03 (s, 0.4H), 3.51-3.47 (m, 2.6H), 3.01 (t, J=13.3 Hz, 0.6H), 2.81 (t, J=13.2 Hz, 0.4H), 2.04-1.93 (m, 1H), 1.77-1.03 (m, 18H).

Example 46

4-((1s,4s)-7-Azabicyclo[2.2.1]heptane-7-carbonyl)-5-(6-(cyclopentylamino)-4-(difluoromethyl)pyridin-3-yl)-N-(2-hydroxy-2-methylpropyl)thiazole-2-carboxamide

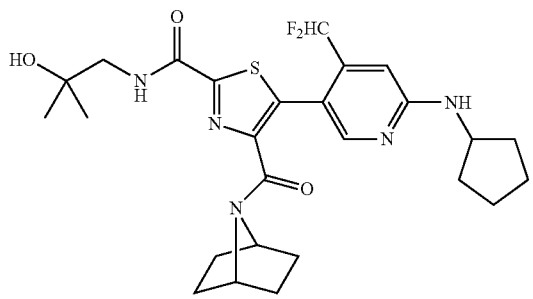 [SMILES: CC(C)(O)CNC(=O)c1nc(C(=O)N2C3CCC2CC3)c(-c2cnc(NC3CCCC3)cc2C(F)F)s1]

The title compound was prepared as described in Example 3 substituting 5-bromo-N-cyclopentyl-4-(difluoromethyl)pyridin-2-amine (Intermediate 19) for 5-bromo-N-cyclohexyl-4-(trifluoromethyl)pyridin-2-amine and 4-((1s,4s)-7-azabicyclo[2.2.1]heptane-7-carbonyl)-N-(2-hydroxy-2-methylpropyl)thiazole-2-carboxamide (Intermediate 70: Step B) for 4-(4-fluoropiperidine-1-carbonyl)-N-(2-hydroxy-2-methylpropyl)thiazole-2-carboxamide. MS (ESI): mass calcd. for $C_{26}H_{33}F_2N_5O_3S$, 533.6; m/z found, 534.1 $[M+H]^+$. $^1H$ NMR (400 MHz, $CDCl_3$) δ 8.03 (s, 1H), 7.63-7.56 (m, 1H), 6.91-6.64 (m, 2H), 4.97 (d, J=7.0 Hz, 1H), 4.68 (t, J=4.5 Hz, 1H), 4.28 (t, J=4.6 Hz, 1H), 4.07 (h, J=6.5 Hz, 1H), 3.48 (d, J=6.3 Hz, 2H), 2.17-2.00 (m, 3H), 1.86-1.38 (m, 14H), 1.32 (s, 6H).

Example 47

N-(2-Hydroxy-2-methylpropyl)-4-((S)-2-methylpiperidine-1-carbonyl)-5-(4-(trifluoromethyl)-6-(((S)-1,1,1-trifluoropropan-2-yl)amino)pyridin-3-yl)thiazole-2-carboxamide

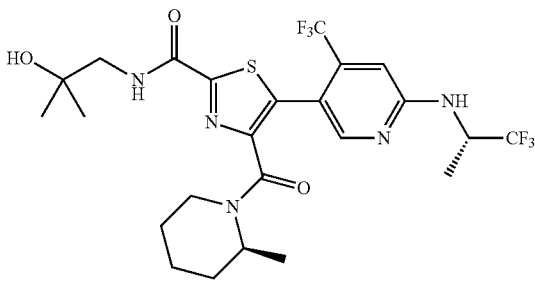

The title compound was prepared as described in Example 3 substituting (S)-5-bromo-4-(trifluoromethyl)-N-(1,1,1-trifluoropropan-2-yl)pyridin-2-amine (Intermediate 44) for 5-bromo-N-cyclohexyl-4-(trifluoromethyl)pyridin-2-amine and (S)—N-(2-hydroxy-2-methylpropyl)-4-(2-methylpiperidine-1-carbonyl)thiazole-2-carboxamide (Intermediate 66: Step D) for 4-(4-fluoropiperidine-1-carbonyl)-N-(2-hydroxy-2-methylpropyl)thiazole-2-carboxamide. MS (ESI): mass calcd. for $C_{24}H_{29}F_6N_5O_3S$, 581.6; m/z found, 582.0 [M+H]$^+$. $^1$H NMR (400 MHz, CDCl$_3$) δ 8.27 (d, J=16.3 Hz, 1H), 7.60 (d, J=6.4 Hz, 1H), 6.76 (s, 1H), 5.08-4.82 (m, 2.6H), 4.45 (d, J=13.6 Hz, 0.4H), 3.98 (s, 0.4H), 3.57-3.39 (m, 2.6H), 2.98 (t, J=13.2 Hz, 0.6H), 2.80 (t, J=13.2 Hz, 0.4H), 2.06-1.97 (m, 1H), 1.75-1.03 (m, 18H).

Example 48

5-(6-(((R)-1-Cyclopropylethyl)amino)-4-(trifluoromethyl)pyridin-3-yl)-N-(2-hydroxy-2-methylpropyl)-4-((S)-2-methylpyrrolidine-1-carbonyl)thiazole-2-carboxamide

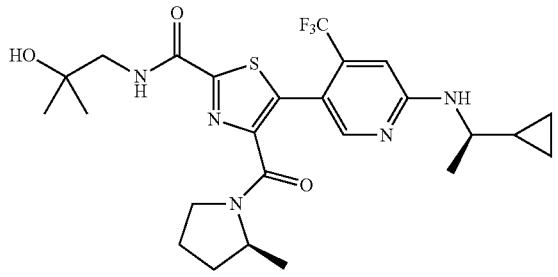 [SMILES: C[C@@H](Nc1cc(C(F)(F)F)c(-c2sc(C(=O)NCC(C)(C)O)nc2C(=O)N2CCC[C@@H]2C)cn1)C1CC1]

The title compound was prepared as described in Example 3 substituting (R)-5-bromo-N-(1-cyclopropylethyl)-4-(trifluoromethyl)pyridin-2-amine (Intermediate 17) for 5-bromo-N-cyclohexyl-4-(trifluoromethyl)pyridin-2-amine and (S)—N-(2-hydroxy-2-methylpropyl)-4-(2-methylpyrrolidine-1-carbonyl)thiazole-2-carboxamide (Intermediate 69) for 4-(4-fluoropiperidine-1-carbonyl)-N-(2-hydroxy-2-methylpropyl)thiazole-2-carboxamide. MS (ESI): mass calcd. for $C_{25}H_{32}F_3N_5O_3S$, 539.6; m/z found, 540.2 [M+H]$^+$. $^1$H NMR (400 MHz, CDCl$_3$) δ 8.17-8.14 (m, 1H), 7.60-7.52 (m, 1H), 6.61 (s, 1H), 4.97 (d, J=7.3 Hz, 1H), 4.37-4.16 (m, 1H), 3.67-3.31 (m, 5H), 2.13-1.47 (m, 4H), 1.38-1.20 (m, 12H), 1.11 (d, J=6.4 Hz, 1H), 0.98-0.90 (m, 1H), 0.62-0.44 (m, 2H), 0.36-0.27 (m, 2H).

Example 49

5-(6-(((S)-1-Cyclopropylethyl)amino)-4-(trifluoromethyl)pyridin-3-yl)-N-((1-hydroxycyclobutyl)methyl)-4-((S)-2-methylpyrrolidine-1-carbonyl)thiazole-2-carboxamide

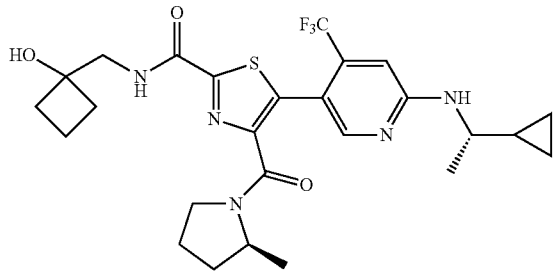 [SMILES: C[C@H](Nc1cc(C(F)(F)F)c(-c2sc(C(=O)NCC3(O)CCC3)nc2C(=O)N2CCC[C@@H]2C)cn1)C1CC1]

The title compound was prepared as described in Example 3 substituting (S)-5-bromo-N-(1-cyclopropylethyl)-4-(trifluoromethyl)pyridin-2-amine (Intermediate 18) for 5-bromo-N-cyclohexyl-4-(trifluoromethyl)pyridin-2-amine and (S)—N-((1-hydroxycyclobutyl)methyl)-4-(2-methylpyrrolidine-1-carbonyl)thiazole-2-carboxamide (Intermediate 73: Step C) for 4-(4-fluoropiperidine-1-carbonyl)-N-(2-hydroxy-2-methylpropyl)thiazole-2-carboxamide. MS (ESI): mass calcd. for $C_{26}H_{32}F_3N_5O_3S$, 551.6; m/z found, 552.0 [M+H]$^+$. $^1$H NMR (400 MHz, CDCl$_3$) δ 8.15 (s, 1H), 7.64-7.48 (m, 1H), 6.60 (s, 1H), 5.02-4.96 (m, 1H), 4.35-4.15 (m, 1H), 3.75-3.32 (m, 5H), 2.73-2.62 (m, 1H), 2.25-1.45 (m, 9H), 1.35-1.16 (m, 6.2H), 1.09 (d, J=6.5 Hz, 0.8H), 1.02-0.85 (m, 1H), 0.63-0.44 (m, 2H), 0.42-0.22 (m, 2H).

Example 50

5-(6-(((R)-1-Cyclopropylethyl)amino)-4-(difluoromethyl)pyridin-3-yl)-N-(2-hydroxy-2-methylpropyl)-4-((S)-2-methylpyrrolidine-1-carbonyl)thiazole-2-carboxamide

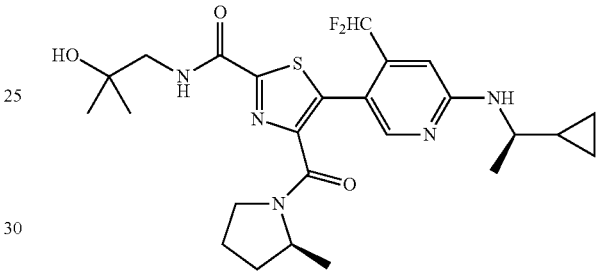

The title compound was prepared as described in Example 3 substituting (R)-5-bromo-N-(1-cyclopropylethyl)-4-(difluoromethyl)pyridin-2-amine (Intermediate 21) for 5-bromo-N-cyclohexyl-4-(trifluoromethyl)pyridin-2-amine and (S)—N-(2-hydroxy-2-methylpropyl)-4-(2-methylpyrrolidine-1-carbonyl)thiazole-2-carboxamide (Intermediate 69) for 4-(4-fluoropiperidine-1-carbonyl)-N-(2-hydroxy-2-methylpropyl)thiazole-2-carboxamide. MS (ESI): mass calcd. for $C_{25}H_{33}F_2N_5O_3S$, 521.6; m/z found, 522.1 [M+H]$^+$. $^1$H NMR (400 MHz, CDCl$_3$) δ 8.02-7.97 (m, 1H), 7.62-7.49 (m, 1H), 7.04-6.52 (m, 2H), 4.95-4.89 (m, 1H), 4.36-4.15 (m, 1H), 3.66-3.32 (m, 5H), 2.14-1.45 (m, 5H), 1.37-1.19 (m, 11H), 1.02 (d, J=6.4 Hz, 1H), 1.03-0.91 (m, 1H), 0.62-0.43 (m, 2H), 0.41-0.22 (m, 2H).

Example 51

4-((1s,4s)-7-Azabicyclo[2.2.1]heptane-7-carbonyl)-5-(6-(((S)-1-cyclopropylethyl)amino)-4-(trifluoromethyl)pyridin-3-yl)-N-(2-hydroxy-2-methylpropyl)thiazole-2-carboxamide

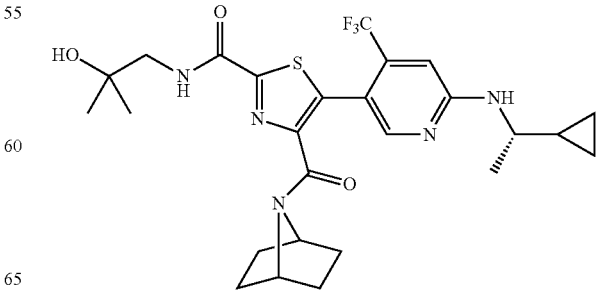

The title compound was prepared as described in Example 3 substituting (S)-5-bromo-N-(1-cyclopropylethyl)-4-(trifluoromethyl)pyridin-2-amine (Intermediate 18) for 5-bromo-N-cyclohexyl-4-(trifluoromethyl)pyridin-2-amine and 4-((1s,4s)-7-azabicyclo[2.2.1]heptane-7-carbonyl)-N-(2-hydroxy-2-methylpropyl)thiazole-2-carboxamide (Intermediate 70: Step B) for 4-(4-fluoropiperidine-1-carbonyl)-N-(2-hydroxy-2-methylpropyl)thiazole-2-carboxamide. MS (ESI): mass calcd. for $C_{26}H_{32}F_3N_5O_3S$, 551.6; m/z found, 552.2 [M+H]$^+$. $^1$H NMR (400 MHz, CDCl$_3$) δ 8.14 (s, 1H), 7.63-7.56 (m, 1H), 6.61 (s, 1H), 4.98 (d, J=7.5 Hz, 1H), 4.68 (s, 1H), 4.34 (s, 1H), 3.48 (d, J=6.3 Hz, 2H), 3.40 (p, J=7.0 Hz, 1H), 2.01 (s, 1H), 1.85-1.59 (s, 4H), 1.50-1.40 (m, 4H), 1.38-1.22 (m, 9H), 0.97-0.90 (m, 1H), 0.61-0.45 (m, 2H), 0.41-0.21 (m, 2H).

Example 52

(S)-5-(6-(tert-Butylamino)-4-(trifluoromethyl)pyridin-3-yl)-N-(2-hydroxy-2-methylpropyl)-4-(2-methylpyrrolidine-1-carbonyl)thiazole-2-carboxamide

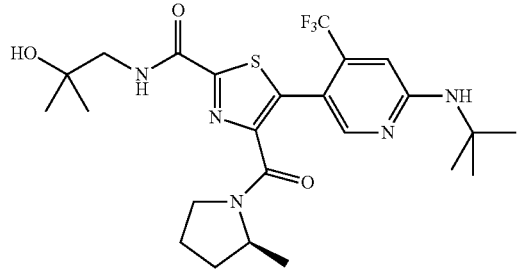 [SMILES: C[C@H]1CCCN1C(=O)c1nc(C(=O)NCC(C)(C)O)sc1-c1cnc(NC(C)(C)C)cc1C(F)(F)F]

The title compound was prepared as described in Example 3 substituting 5-bromo-N-(tert-butyl)-4-(trifluoromethyl)pyridin-2-amine (Intermediate 41: Step B) for 5-bromo-N-cyclohexyl-4-(trifluoromethyl)pyridin-2-amine and (S)—N-(2-hydroxy-2-methylpropyl)-4-(2-methylpyrrolidine-1-carbonyl)thiazole-2-carboxamide (Intermediate 69) for 4-(4-fluoropiperidine-1-carbonyl)-N-(2-hydroxy-2-methylpropyl)thiazole-2-carboxamide. MS (ESI): mass calcd. for $C_{24}H_{32}F_3N_5O_3S$, 527.6; m/z found, 528.2 [M+H]$^+$. $^1$H NMR (400 MHz, CDCl$_3$) δ 8.18 (s, 1H), 7.65-7.49 (m, 1H), 6.63 (s, 1H), 4.86 (s, 1H), 4.33-4.18 (m, 1H), 3.65-3.34 (m, 4H), 2.12-1.99 (m, 1.5H), 1.98-1.81 (m, 1.5H), 1.78-1.70 (m, 1H), 1.65-1.46 (s, 10H), 1.36-1.19 (m, 8H), 1.11 (d, J=6.4 Hz, 1H).

Example 53

4-((1s,4s)-7-Azabicyclo[2.2.1]heptane-7-carbonyl)-5-(6-(cyclopentylamino)-4-(trifluoromethyl)pyridin-3-yl)-N-(2-hydroxy-2-methylpropyl)thiazole-2-carboxamide

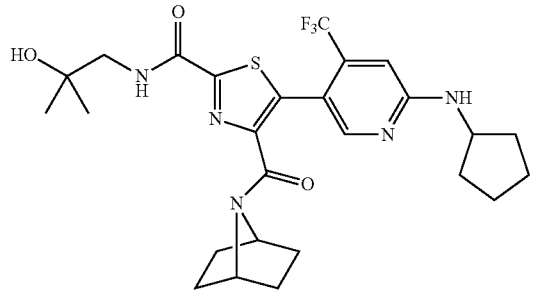 [SMILES: CC(C)(O)CNC(=O)c1nc(C(=O)N2C3CCC2CC3)c(-c2cnc(NC3CCCC3)cc2C(F)(F)F)s1]

The title compound was prepared as described in Example 3 substituting 5-bromo-N-cyclopentyl-4-(trifluoromethyl)pyridin-2-amine (Intermediate 8) for 5-bromo-N-cyclohexyl-4-(trifluoromethyl)pyridin-2-amine and 4-((1s,4s)-7-azabicyclo[2.2.1]heptane-7-carbonyl)-N-(2-hydroxy-2-methylpropyl)thiazole-2-carboxamide (Intermediate 70: Step B) for 4-(4-fluoropiperidine-1-carbonyl)-N-(2-hydroxy-2-methylpropyl)thiazole-2-carboxamide. MS (ESI): mass calcd. for $C_{26}H_{32}F_3N_5O_3S$, 551.6; m/z found, 552.2 [M+H]$^+$. $^1$H NMR (600 MHz, CDCl$_3$) δ 8.16 (s, 1H), 7.63-7.57 (m, 1H), 6.63 (s, 1H), 5.03 (d, J=6.8 Hz, 1H), 4.68 (s, 1H), 4.33 (d, J=5.2 Hz, 1H), 4.10-4.03 (m, 1H), 3.48 (d, J=6.3 Hz, 2H), 2.15-1.98 (m, 3H), 1.83-1.57 (m, 7H), 1.56-1.39 (m, 6H), 1.32 (s, 7H).

Example 54

N-(2-Hydroxy-2-methylpropyl)-4-((S)-2-methylpyrrolidine-1-carbonyl)-5-(4-(trifluoromethyl)-6-(((R)-1,1,1-trifluoropropan-2-yl)amino)pyridin-3-yl)thiazole-2-carboxamide

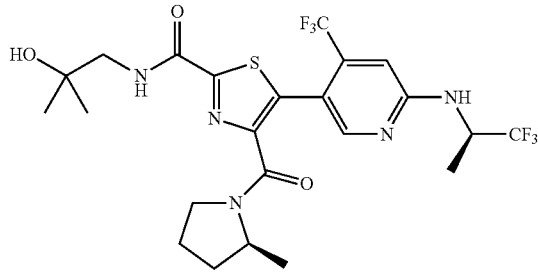 [SMILES: C[C@H]1CCCN1C(=O)c1nc(C(=O)NCC(C)(C)O)sc1-c1cnc(N[C@H](C)C(F)(F)F)cc1C(F)(F)F]

The title compound was prepared as described in Example 3 substituting (R)-5-bromo-4-(trifluoromethyl)-N-(1,1,1-trifluoropropan-2-yl)pyridin-2-amine (Intermediate 43) for 5-bromo-N-cyclohexyl-4-(trifluoromethyl)pyridin-2-amine and (S)—N-(2-hydroxy-2-methylpropyl)-4-(2-methylpyrrolidine-1-carbonyl)thiazole-2-carboxamide (Intermediate 69) for 4-(4-fluoropiperidine-1-carbonyl)-N-(2-hydroxy-2-methylpropyl)thiazole-2-carboxamide. MS (ESI): mass calcd. for $C_{23}H_{27}F_6N_5O_3S$, 567.6; m/z found, 568.1 [M+H]$^+$. $^1$H NMR (400 MHz, CDCl$_3$) δ 8.22-8.20 (m, 1H), 7.59-7.50 (m, 1H), 6.74-6.72 (m, 1H), 5.15-4.85 (m, 2H), 4.42-4.35 (m, 0.3H), 4.20-4.15 (m, 0.7H), 3.68-3.40 (m, 4H), 2.13-1.72 (m, 4H), 1.71-1.50 (m, 1H), 1.43-1.39 (m, 3H), 1.32 (s, 6H), 1.25-1.17 (m, 3H).

Example 55

4-((1s,4s)-7-Azabicyclo[2.2.1]heptane-7-carbonyl)-5-(6-(((S)-1-cyclopropylethyl)amino)-4-(difluoromethyl)pyridin-3-yl)-N-(2-hydroxy-2-methylpropyl)thiazole-2-carboxamide

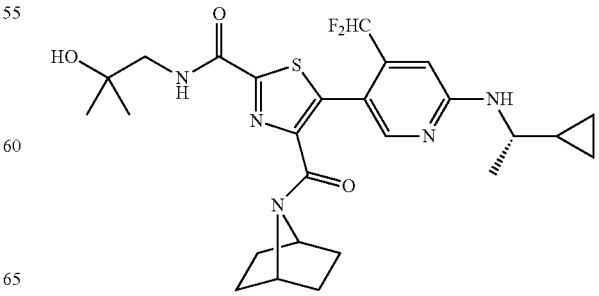

The title compound was prepared as described in Example 3 substituting (S)-5-bromo-N-(1-cyclopropylethyl)-4-(difluoromethyl)pyridin-2-amine (Intermediate 20) for 5-bromo-N-cyclohexyl-4-(trifluoromethyl)pyridin-2-amine and 4-((1s,4s)-7-azabicyclo[2.2.1]heptane-7-carbonyl)-N-(2-hydroxy-2-methylpropyl)thiazole-2-carboxamide (Intermediate 70: Step B) for 4-(4-fluoropiperidine-1-carbonyl)-N-(2-hydroxy-2-methylpropyl)thiazole-2-carboxamide. MS (ESI): mass calcd. for $C_{26}H_{33}F_2N_5O_3S$, 533.6; m/z found, 534.2 [M+H]$^+$. $^1$H NMR (400 MHz, CDCl$_3$) δ 8.01 (s, 1H), 7.63-7.56 (m, 1H), 6.91-6.62 (m, 2H), 4.92 (d, J=7.6 Hz, 1H), 4.68 (t, J=4.7 Hz, 1H), 4.28 (t, J=4.6 Hz, 1H), 3.48 (d, J=6.3 Hz, 2H), 3.45-3.35 (m, 1H), 2.02 (s, 1H), 1.83-1.72 (m, 2H), 1.65-1.55 (m, 2H), 1.49-1.40 (m, 4H), 1.36-1.22 (m, 9H), 0.97-0.91 (m, 1H), 0.62-0.43 (m, 2H), 0.40-0.21 (m, 2H).

Example 56

(S)-5-(6-((2-Cyclopropylpropan-2-yl)amino)-4-(trifluoromethyl)pyridin-3-yl)-N-(2-hydroxy-2-methylpropyl)-4-(2-methylpyrrolidine-1-carbonyl)thiazole-2-carboxamide

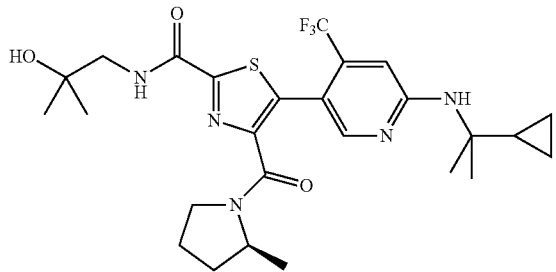 [SMILES: C[C@H]1CCCN1C(=O)c1nc(C(=O)NCC(C)(C)O)sc1-c1cnc(NC(C)(C)C2CC2)cc1C(F)(F)F]

The title compound was prepared as described in Example 3 substituting 5-bromo-N-(2-cyclopropylpropan-2-yl)-4-(trifluoromethyl)pyridin-2-amine (Intermediate 45) for 5-bromo-N-cyclohexyl-4-(trifluoromethyl)pyridin-2-amine and (S)—N-(2-hydroxy-2-methylpropyl)-4-(2-methylpyrrolidine-1-carbonyl)thiazole-2-carboxamide (Intermediate 69) for 4-(4-fluoropiperidine-1-carbonyl)-N-(2-hydroxy-2-methylpropyl)thiazole-2-carboxamide. MS (ESI): mass calcd. for $C_{26}H_{34}F_3N_5O_3S$, 553.6; m/z found, 554.2 [M+H]$^+$. $^1$H NMR (400 MHz, CDCl$_3$) δ 8.17 (s, 1H), 7.61-7.52 (m, 1H), 6.81-6.79 (m, 1H), 5.07 (s, 1H), 4.35-4.14 (m, 1H), 3.55-3.45 (m, 4H), 2.13-1.44 (m, 5H), 1.40-1.19 (m, 15.2H), 1.11 (d, J=6.6 Hz, 0.8H), 0.58-0.37 (m, 4H).

Example 57

5-(4-Cyano-6-(cyclohexylamino)pyridin-3-yl)-4-(4-fluoropiperidine-1-carbonyl)-N-(2-hydroxy-2-methylpropyl)thiazole-2-carboxamide

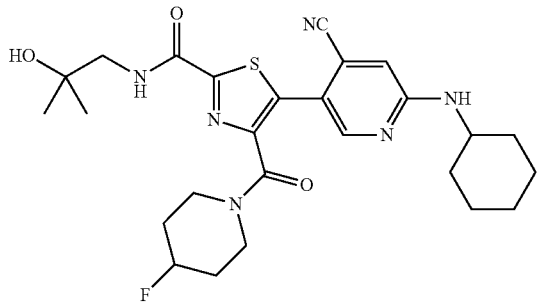 [SMILES: CC(C)(O)CNC(=O)c1nc(C(=O)N2CCC(F)CC2)c(-c2cnc(NC3CCCCC3)cc2C#N)s1]

To a 50 mL round-bottomed flask under N$_2$ was added 5-bromo-2-(cyclohexylamino)isonicotinonitrile (100 mg, 0.36 mmol, Intermediate 14), 4-(4-fluoropiperidine-1-carbonyl)-N-(2-hydroxy-2-methylpropyl)thiazole-2-carboxamide (130 mg, 0.40 mmol, Intermediate 65: Step C), hexakis(acetato)tripalladium (17 mg, 0.075 mmol), n-butyldi-1-adamantylphosphine (26 mg, 0.075 mmol), pivalic acid (15 mg, 0.15 mmol), K$_2$CO$_3$ (200 mg, 1.45 mmol) and DMA (5 mL) and the mixture was then stirred at 110° C. overnight. The reaction mixture was then diluted with water (5 mL) and extracted with ethyl acetate (3×5 mL). The combined organic phases were washed with saturated aqueous sodium chloride solution (3×10 mL), dried over anhydrous sodium sulfate and concentrated to dryness. The residue was purified by reverse-phase prep-HPLC to give the title compound as a yellow solid. MS (ESI): mass calcd. for $C_{26}H_{33}FN_6O_3S$, 528.6; m/z found, 529.2 [M+H]$^+$. $^1$H NMR (400 MHz, DMSO-d$_6$) δ 8.40-8.33 (m, 1H), 8.20 (s, 1H), 7.50 (d, J=7.7 Hz, 1H), 6.95 (s, 1H), 4.97-4.85 (m, 1H), 4.71 (s, 1H), 3.82-3.62 (m, 2H), 3.63-3.50 (m, 2H), 3.47-3.38 (m, 1H), 3.29 (d, J=6.2 Hz, 2H), 1.91-1.83 (m, 4H), 1.77-1.57 (m, 5H), 1.38-1.18 (m, 5H), 1.13 (s, 6H).

Example 58

5-(5-Cyano-6-(cyclohexylamino)pyridin-3-yl)-4-(4-fluoropiperidine-1-carbonyl)-N-(2-hydroxy-2-methylpropyl)thiazole-2-carboxamide

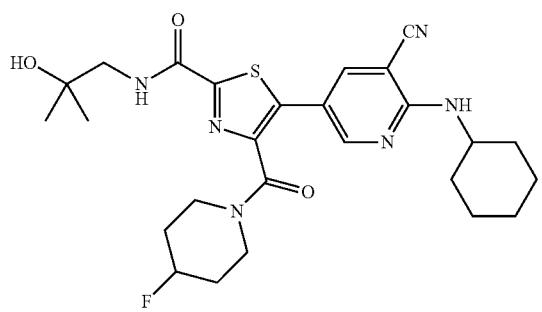 [SMILES: CC(C)(O)CNC(=O)c1nc(C(=O)N2CCC(F)CC2)c(-c2cnc(NC3CCCCC3)c(C#N)c2)s1]

The title compound was prepared as described in Example 57 substituting 5-bromo-2-(cyclohexylamino)nicotinonitrile (Intermediate 9) for 5-bromo-2-(cyclohexylamino)isonicotinonitrile. MS (ESI): mass calcd. for $C_{26}H_{33}FN_6O_3S$, 528.6; m/z found, 529.1 [M+H]$^+$. $^1$H NMR (400 MHz, DMSO-d$_6$) δ 8.42 (d, J=2.5 Hz, 1H), 8.40-8.33 (m, 1H), 8.05 (d, J=2.5 Hz, 1H), 7.31 (d, J=7.9 Hz, 1H), 4.94-4.82 (m, 1H), 4.69 (s, 1H), 4.07-3.93 (m, 1H), 3.79-3.69 (m, 1H), 3.66-3.57 (m, 1H), 3.31 (s, 1H), 3.28-3.27 (m, 2H), 3.24-3.14 (m, 1H), 1.99-1.79 (m, 3H), 1.79-1.59 (m, 5H), 1.51-1.23 (m, 5H), 1.18-1.08 (m, 7H).

Example 59

5-(6-(Cyclohexylamino)-5-methoxypyridin-3-yl)-4-(4-fluoropiperidine-1-carbonyl)-N-(2-hydroxy-2-methylpropyl)thiazole-2-carboxamide

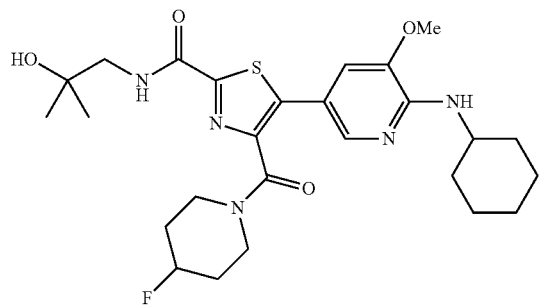 [SMILES: COc1cc(-c2sc(C(=O)NCC(C)(C)O)nc2C(=O)N2CCC(F)CC2)cnc1NC1CCCCC1]

The title compound was prepared as described in Example 57 substituting 5-bromo-N-cyclohexyl-3-methoxypyridin-2-amine (Intermediate 10) for 5-bromo-2-(cyclohexylamino)isonicotinonitrile. MS (ESI): mass calcd. for $C_{26}H_{36}FN_5O_4S$, 533.7; m/z found, 534.1 [M+H]$^+$. $^1$H NMR (400 MHz, DMSO-d$_6$) δ 8.38-8.32 (m, 1H), 7.82-7.75 (m, 1H), 7.08 (s, 1H), 6.39 (s, 1H), 4.91-4.79 (m, 1H), 3.89 (s, 1H), 3.84 (s, 3H), 3.81-3.71 (m, 1H), 3.70-3.59 (m, 1H), 3.40-3.27 (m, 4H), 3.20-3.09 (m, 1H), 1.86 (br s, 3H), 1.78-1.55 (m, 5H), 1.51-1.23 (m, 5H), 1.21-1.02 (m, 7H).

Example 60

5-(5-Cyano-6-(cyclohexylamino)-4-methylpyridin-3-yl)-4-(4-fluoropiperidine-1-carbonyl)-N-(2-hydroxy-2-methylpropyl)thiazole-2-carboxamide

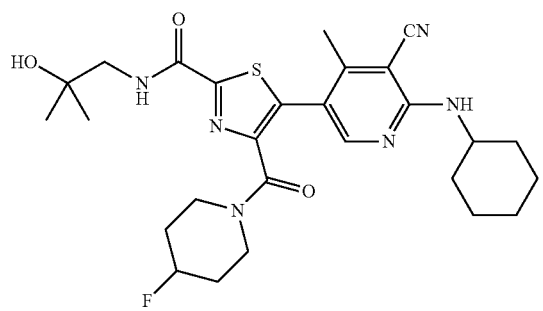 [SMILES: Cc1c(-c2sc(C(=O)NCC(C)(C)O)nc2C(=O)N2CCC(F)CC2)cnc(NC2CCCCC2)c1C#N]

The title compound was prepared as described in Example 57 substituting 5-bromo-2-chloro-4-methylnicotinonitrile (Intermediate 12) for 5-bromo-2-(cyclohexylamino)isonicotinonitrile. MS (ESI): mass calcd. for $C_{27}H_{35}FN_6O_3S$, 542.7; m/z found, 543.2 [M+H]$^+$. $^1$H NMR (400 MHz, DMSO-d$_6$) δ 8.44-8.38 (m, 1H), 8.16 (s, 1H), 6.99 (d, J=8.0 Hz, 1H), 4.97-4.77 (m, 1H), 4.70 (s, 1H), 4.07-3.91 (m, 1H), 3.65 (s, 1H), 3.53-3.43 (m, 2H), 3.29-3.28 (m, 3H), 2.28 (s, 3H), 1.84-1.71 (m, 6H), 1.66-1.36 (m, 5H), 1.34-1.24 (m, 2H), 1.20-1.06 (m, 7H).

Example 61

(S)-5-(6-(Cyclopentylamino)-4-(difluoromethyl)pyridin-3-yl)-N-(1,1-dioxidothietan-3-yl)-4-(2-methylpyrrolidine-1-carbonyl)thiazole-2-carboxamide

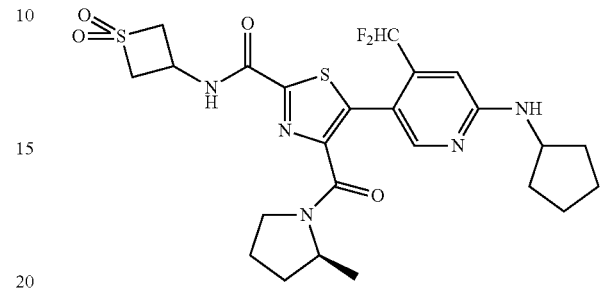

The title compound was prepared as described in Example 2 substituting 3-aminothietane 1,1-dioxide hydrochloride for 1-(aminomethyl)cyclopropanol. MS (ESI): mass calcd. for $C_{24}H_{29}F_2N_5O_4S_2$, 553.6; m/z found, 554.2 [M+H]$^+$. $^1$H NMR (400 MHz, CDCl$_3$) δ 8.06-7.97 (m, 1H), 7.85-7.74 (m, 1H), 7.02-6.73 (m, 1H), 6.66-6.62 (m, 1H), 5.05-4.97 (m, 1H), 4.95-4.81 (m, 1H), 4.70-4.55 (m, 2H), 4.28-4.02 (m, 4H), 3.64-3.29 (m, 2H), 2.12-1.89 (m, 4H), 1.84-1.65 (m, 5H), 1.58-1.44 (m, 3H), 1.25-1.18 (m, 2H), 1.00 (d, J=6.5 Hz, 1H).

Example 62

5-(6-(Cyclohexylamino)-5-(difluoromethoxy)pyridin-3-yl)-4-(4-fluoropiperidine-1-carbonyl)-N-(2-hydroxy-2-methylpropyl)thiazole-2-carboxamide

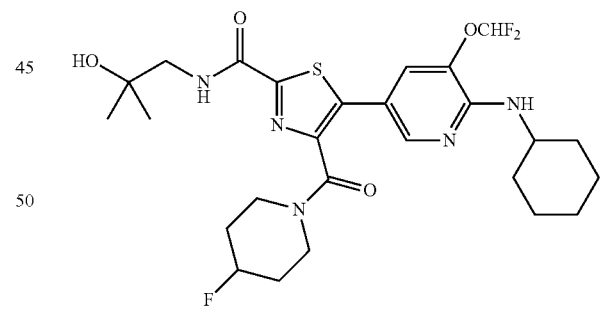

The title compound was prepared as described in Example 57 substituting 5-bromo-N-cyclohexyl-3-(difluoromethoxy)pyridin-2-amine (Intermediate 16) for 5-bromo-2-(cyclohexylamino)isonicotinonitrile. MS (ESI): mass calcd. for $C_{26}H_{34}F_3N_5O_4S$, 569.6; m/z found, 570.0 [M+H]$^+$. $^1$H NMR (400 MHz, DMSO-d$_6$) δ 8.41-8.33 (m, 1H), 8.10 (d, J=2.1 Hz, 1H), 7.40 (s, 1H), 7.34-6.98 (m, 1H), 6.63 (d, J=8.2 Hz, 1H), 4.91-4.80 (m, 1H), 4.69 (s, 1H), 3.94 (br s, 1H), 3.74 (br s, 1H), 3.68-3.58 (m, 1H), 3.28-3.27 (m, 3H), 3.19-3.11 (m, 1H), 1.95-1.80 (m, 3H), 1.78-1.56 (m, 6H), 1.47-1.23 (m, 5H), 1.11 (s, 6H).

Example 63

5-(6-(Cyclohexylamino)-4-methoxypyridin-3-yl)-4-(4-fluoropiperidine-1-carbonyl)-N-(2-hydroxy-2-methylpropyl)thiazole-2-carboxamide

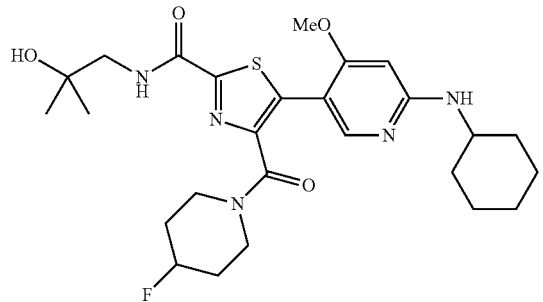 [SMILES: COc1cc(NC2CCCCC2)ncc1-c1sc(C(=O)NCC(C)(C)O)nc1C(=O)N1CCC(F)CC1]

The title compound was prepared as described in Example 57 substituting 5-bromo-N-cyclohexyl-4-methoxypyridin-2-amine (Intermediate 26) for 5-bromo-2-(cyclohexylamino)isonicotinonitrile. MS (ESI): mass calcd. for $C_{26}H_{36}FN_5O_4S$, 533.3; m/z: found, 534.1 [M+H]$^+$, $^1$H NMR (400 MHz, DMSO-d$_6$) δ 8.38-8.31 (m, 1H), 7.79 (d, J=1.9 Hz, 1H), 7.08 (s, 1H), 6.39 (s, 1H), 4.91-4.79 (m, 1H), 3.89 (s, 1H), 3.84 (s, 3H), 3.81-3.71 (m, 1H), 3.70-3.59 (m, 1H), 3.28-3.27 (m, 3H), 3.20-3.09 (m, 1H), 1.86 (br s, 3H), 1.78-1.55 (m, 5H), 1.51-1.23 (m, 5H), 1.21-1.02 (m, 7H).

Example 64

5-(6-(Cyclohexylamino)-4-cyclopropylpyridin-3-yl)-4-(4-fluoropiperidine-1-carbonyl)-N-(2-hydroxy-2-methylpropyl)thiazole-2-carboxamide

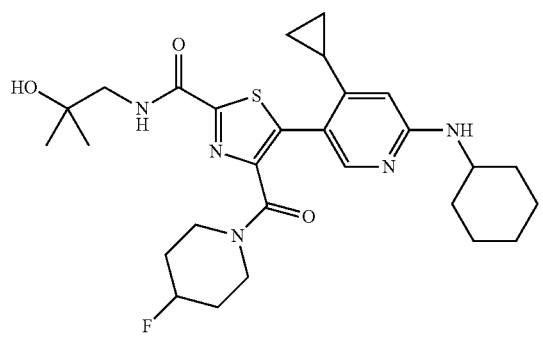 [SMILES: CC(C)(O)CNC(=O)c1nc(C(=O)N2CCC(F)CC2)c(-c2cnc(NC3CCCCC3)cc2C2CC2)s1]

The title compound was prepared as described in Example 57 substituting 5-bromo-N-cyclohexyl-4-cyclopropylpyridin-2-amine (Intermediate 36) for 5-bromo-2-(cyclohexylamino)isonicotinonitrile. MS (ESI): mass calcd. for $C_{28}H_{38}FN_5O_3S$, 543.2; m/z: found, 543.8 [M+H]$^+$. $^1$H NMR (400 MHz, DMSO-d$_6$) δ 8.38-8.31 (m, 1H), 7.82 (s, 1H), 6.65 (d, J=7.8 Hz, 1H), 6.06 (s, 1H), 4.92-4.63 (m, 2H), 3.78-3.63 (m, 2H), 3.56-3.44 (m, 1H), 3.28 (d, J=6.3 Hz, 2H), 3.22-3.12 (m, 1H), 1.88-1.85 (m, 2H), 1.80-1.65 (m, 4H), 1.58-1.50 (m, 3H), 1.38-1.24 (m, 3H), 1.23-1.13 (m, 3H), 1.13-1.11 (m, 7H), 0.96-0.88 (m, 2H), 0.72-0.64 (m, 2H).

Example 65

5-(6-(Cyclohexylamino)-4-isopropylpyridin-3-yl)-4-(4-fluoropiperidine-1-carbonyl)-N-(2-hydroxy-2-methylpropyl)thiazole-2-carboxamide

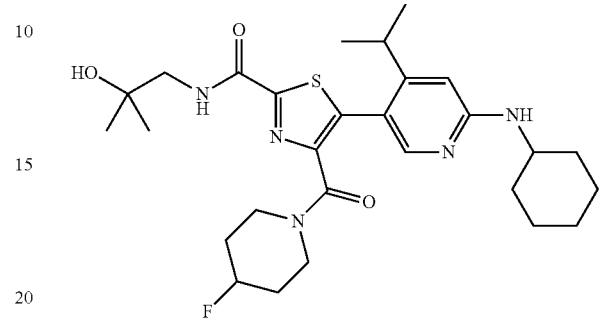

The title compound was prepared as described in Example 57 substituting 5-bromo-N-cyclohexyl-4-isopropylpyridin-2-amine (Intermediate 37) for 5-bromo-2-(cyclohexylamino)isonicotinonitrile. MS (ESI): mass calcd. for $C_{28}H_{40}FN_5O_3S$, 545.3; m/z found, 545.8 [M+H]$^+$. $^1$H NMR (400 MHz, DMSO-d$_6$) δ 8.38-8.32 (m, 1H), 7.83 (s, 1H), 6.72 (d, J=7.8 Hz, 1H), 6.47 (s, 1H), 4.89-4.77 (m, 1H), 4.75-4.65 (m, 1H), 3.72-3.65 (m, 2H), 3.51-3.17 (m, 5H), 2.89-2.82 (m, 1H), 1.90-1.87 (m, 2H), 1.73-1.69 (m, 3H), 1.60 (s, 3H), 1.48-1.26 (m, 3H), 1.25-1.15 (m, 3H), 1.14-1.11 (m, 6H), 1.10-1.07 (m, 6H).

Example 66

5-(6-(Cyclohexylamino)-5-fluoro-4-methylpyridin-3-yl)-4-(4-fluoropiperidine-1-carbonyl)-N-(2-hydroxy-2-methylpropyl)thiazole-2-carboxamide

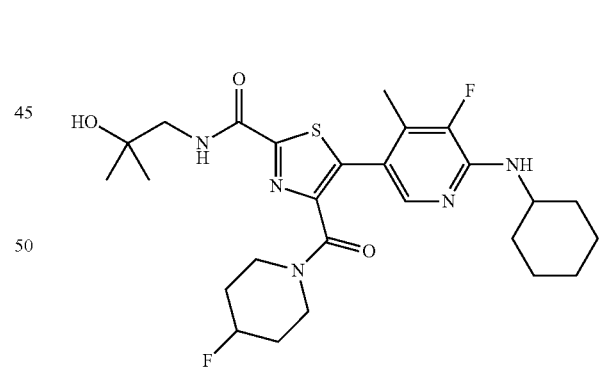

The title compound was prepared as described in Example 57 substituting 5-bromo-N-cyclohexyl-3-fluoro-4-methylpyridin-2-amine (Intermediate 38) for 5-bromo-2-(cyclohexylamino)isonicotinonitrile. MS (ESI): mass calcd. for $C_{26}H_{35}F_2N_5O_3S$, 535.2; m/z found, 535.8 [M+H]$^+$. $^1$H NMR (400 MHz, DMSO-d$_6$) δ 8.40-8.34 (m, 1H), 7.76 (s, 1H), 6.71 (d, J=6.9 Hz, 1H), 4.94-4.74 (m, 1H), 4.70 (s, 1H), 3.88 (d, 1H), 3.67 (s, 1H), 3.55-3.45 (m, 1H), 3.40-3.37 (m, 1H), 3.28 (d, J=6.3 Hz, 2H), 3.26-3.17 (m, 1H), 2.10 (d, J=2.2 Hz, 3H), 1.86 (s, 3H), 1.73 (s, 3H), 1.63-1.60 (m, 3H), 1.42 (s, 1H), 1.38-1.22 (m, 4H), 1.12 (s, 6H).

Example 67

5-(6-(Cyclohexylamino)-4-methylpyridin-3-yl)-4-(4-fluoropiperidine-1-carbonyl)-N-(2-hydroxy-2-methylpropyl)thiazole-2-carboxamide

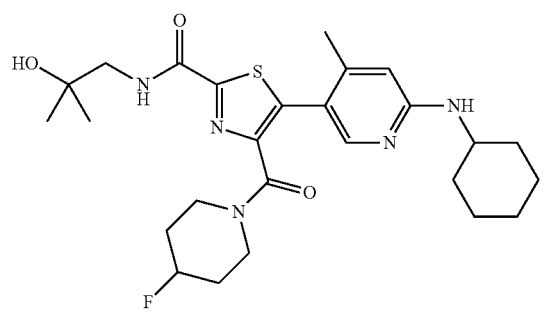 [SMILES: Cc1cc(NC2CCCCC2)ncc1-c1sc(C(=O)NCC(C)(C)O)nc1C(=O)N1CCC(F)CC1]

The title compound was prepared as described in Example 57 substituting 5-bromo-N-cyclohexyl-4-methylpyridin-2-amine (Intermediate 35: Step B) for 5-bromo-2-(cyclohexylamino)isonicotinonitrile. MS (ESI): mass calcd. for $C_{27}H_{37}FN_4O_3S$, 516.7; m/z found, 517.9 [M+H]$^+$. $^1$H NMR (400 MHz, DMSO-$d_6$) δ 8.41-8.34 (m, 1H), 7.84 (s, 1H), 6.74 (d, J=7.8 Hz, 1H), 6.39 (s, 1H), 4.90-4.72 (m, 1H), 3.75-3.13 (m, 9H), 2.13 (s, 3H), 1.90-1.87 (m, 2H), 1.82-1.66 (m, 3H), 1.66-1.50 (m, 3H), 1.36-1.27 (m, 3H), 1.25-1.14 (m, 3H), 1.12 (s, 6H).

Example 68

5-(5-Cyano-6-(cyclohexylamino)-4-(trifluoromethyl)pyridin-3-yl)-4-(4-fluoropiperidine-1-carbonyl)-N-(2-hydroxy-2-methylpropyl)thiazole-2-carboxamide

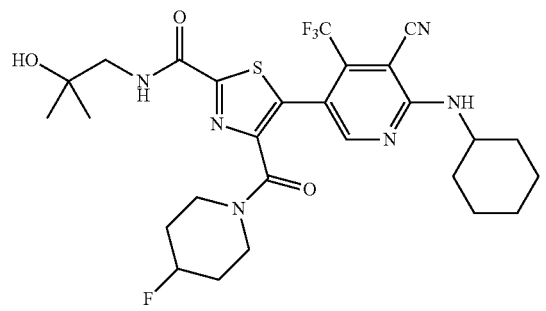 [SMILES: CC(C)(O)CNC(=O)c1nc(C(=O)N2CCC(F)CC2)c(-c2cnc(NC3CCCCC3)c(C#N)c2C(F)(F)F)s1]

The title compound was prepared as described in Example 57 substituting 5-bromo-2-(cyclohexylamino)-4-(trifluoromethyl)nicotinonitrile (Intermediate 61: Step B) for 5-bromo-2-(cyclohexylamino)isonicotinonitrile. MS (ESI): mass calcd. for $C_{27}H_{32}F_4N_6O_3S$, 596.6; m/z found, 597.2 [M+H]$^+$. $^1$H NMR (400 MHz, DMSO-$d_6$) δ 8.44 (s, 1H), 8.45-8.38 (m, 1H), 7.53 (d, J=7.9 Hz, 1H), 4.97-4.86 (m, 1H), 4.70 (s, 1H), 4.10-3.96 (m, 1H), 3.62-3.41 (m, 4H), 3.28 (d, J=6.2 Hz, 2H), 1.96-1.58 (m, 10H), 1.53-1.45 (m, 2H), 1.35-1.26 (m, 2H), 1.12 (s, 6H).

Example 69

5-(6-(Cyclohexylamino)-4-ethoxypyridin-3-yl)-4-(4-fluoropiperidine-1-carbonyl)-N-(2-hydroxy-2-methylpropyl)thiazole-2-carboxamide

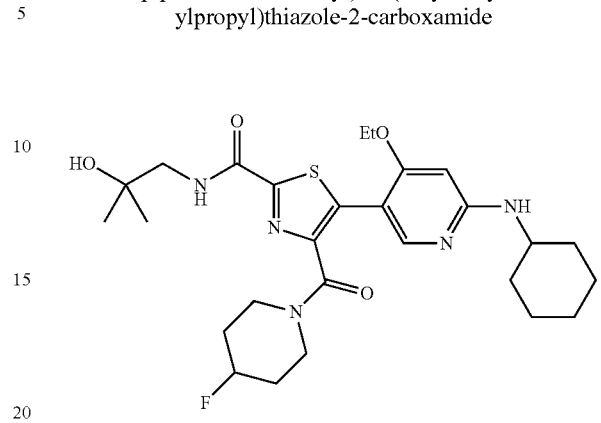

To a 50 mL round bottomed flask under N$_2$ was added 5-bromo-N-cyclohexyl-4-ethoxypyridin-2-amine (200 mg, 0.68 mmol, Intermediate 39: Step B), 4-(4-fluoropiperidine-1-carbonyl)-N-(2-hydroxy-2-methylpropyl)thiazole-2-carboxamide (250 mg, 0.75 mmol, Intermediate 65: Step C), hexakis(acetato)tripalladium (31 mg, 0.14 mmol), n-butyldi-1-adamantylphosphine (49 mg, 0.14 mmol), pivalic acid (28 mg, 0.27 mmol), K$_2$CO$_3$ (376 mg, 2.72 mmol) and DMA (5 mL). The mixture was then stirred at 110° C. for 6 h. The reaction mixture was diluted with water (10 mL) and the aqueous layer was extracted with ethyl acetate (3×20 mL). The combined organic layers were washed with saturated aqueous sodium chloride solution (20 mL), dried over anhydrous sodium sulfate and concentrated to dryness. The residue was purified by prep-HPLC to give the title compound as a yellow solid. MS (ESI): mass calcd. for $C_{27}H_{38}FN_5O_4S$, 547.3; m/z found, 547.8 [M+H]$^+$. $^1$H NMR (400 MHz, DMSO-$d_6$) δ 8.27-8.20 (m, 1H), 7.86 (s, 1H), 6.83 (d, J=7.6 Hz, 1H), 6.11 (s, 1H), 4.89-4.77 (m, 1H), 4.70 (s, 1H), 4.08 (q, J=6.9 Hz, 2H), 3.73 (s, 2H), 3.62-3.52 (m, 1H), 3.27-3.26 (m, 3H), 3.14-3.10 (m, 1H), 1.90-1.82 (m, 3H), 1.76-1.51 (m, 5H), 1.48-1.25 (m, 6H), 1.23-1.14 (m, 3H), 1.12 (s, 6H).

Example 70

5-(6-(cyclohexylamino)-4-ethylpyridin-3-yl)-4-(4-fluoropiperidine-1-carbonyl)-N-(2-hydroxy-2-methylpropyl)thiazole-2-carboxamide

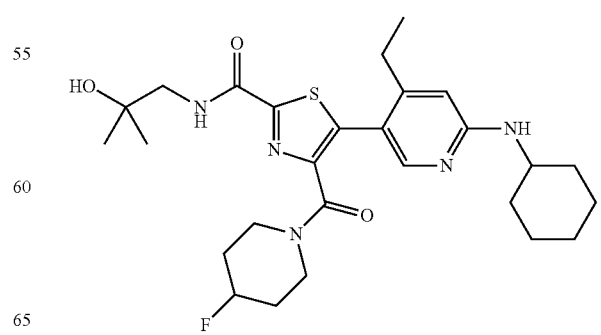

The title compound was prepared as described in Example 69 substituting 5-N-cyclohexyl-4-ethylpyridin-2-amine (Intermediate 40) for 5-bromo-N-cyclohexyl-4-ethoxypyridin-2-amine. MS (ESI) mass calcd for $C_{27}H_{38}FN_5O_3S$ 531.3 m/z:found 531.8 [M+H]+. 1H NMR (400 MHz, DMSO-d6) δ 8.35 (t, J=6.2 Hz, 1H), 7.83 (s, 1H), 6.78 (s, 1H), 6.43 (s, 1H), 4.88-4.76 (m, 1H), 4.70 (s, 1H), 3.81-3.60 (m, 2H), 3.54-3.44 (m, 1H), 3.34 (s, 1H), 3.28 (d, J=6.3 Hz, 2H), 3.23-3.13 (m, 1H), 2.50-2.43 (m, 2H), 1.90-1.88 (m, 2H), 1.79-1.69 (m, 3H), 1.60-1.57 (m, 3H), 1.36-1.27 (m, 3H), 1.23-1.15 (m, 3H), 1.12 (s, 6H), 1.06 (t, J=7.5 Hz, 3H).

Example 71

(S)-5-(6-(Cyclopentylamino)-4-(difluoromethyl)pyridin-3-yl)-N-((1-hydroxycyclobutyl)methyl)-4-(2-methylpyrrolidine-1-carbonyl)thiazole-2-carboxamide

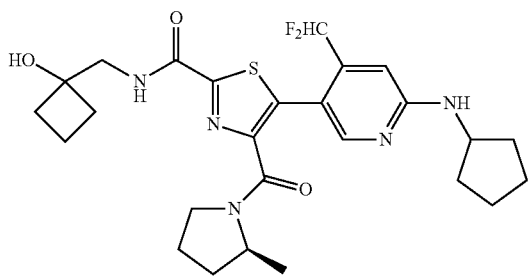 [SMILES: C[C@H]1CCCN1C(=O)c1nc(C(=O)NCC2(O)CCC2)sc1-c1cnc(NC2CCCC2)cc1C(F)F]

5-Bromo-N-cyclopentyl-4-(difluoromethyl) pyridin-2-amine (150 mg, 0.50 mmol, Intermediate 19), (S)—N-((1-hydroxycyclobutyl)methyl)-4-(2-methylpyrrolidine-1-carbonyl)thiazole-2-carboxamide (210 mg, 0.65 mmol, Intermediate 73, Step C), Pd(OAc)2 (11 mg, 0.049 mmol), PCy3.HBF4 (37 mg, 0.10 mmol), pivalic acid (20 mg, 0.20 mmol), K2CO3 (277 mg, 2.10 mmol), and DMAc (3 mL) were added to a 5 mL microwave tube. The resultant mixture was sparged with Ar for 5 minutes and then stirred at 120° C. in a microwave for 1 hour before cooling to room-temperature and pouring into ethyl acetate (20 mL). The resultant mixture was washed with H2O (10 mL×2), dried over anhydrous sodium sulfate and concentrated to dryness to give the crude product, which was purified by preparative HPLC. The purified product was suspended in water (10 mL), the mixture frozen using dry ice/acetone, and then lyophilized to dryness to afford the title compound as a white solid. MS (ESI): mass calcd. for $C_{26}H_{33}F_2N_5O_3S$ 533.2, m/z found 534.2 [M+H]+. 1H NMR (400 MHz, CDCl3-d) δ 8.06-7.95 (m, 1H), 7.65-7.49 (m, 1H), 7.04-6.72 (m, 1H), 6.69-6.61 (m, 1H), 5.06 (br. s., 1H), 4.33-4.16 (m, 1H), 4.12-4.01 (m, 1H), 3.76-3.53 (m, 3H), 3.49-3.35 (m, 1H), 2.77 (br. s., 1H), 2.23-2.01 (m, 7H), 1.99-1.85 (m, 2H), 1.80-1.69 (m, 6H), 1.58-1.44 (m, 3H), 1.27-1.18 (m, 2H), 1.04-0.96 (m, 1H).

Example 72

5-(6-(Cyclopentylamino)-4-(difluoromethyl)pyridin-3-yl)-4-((S)-2-methylpyrrolidine-1-carbonyl)-N-((1r,3r)-3-(methylsulfonyl)cyclobutyl)thiazole-2-carboxamide

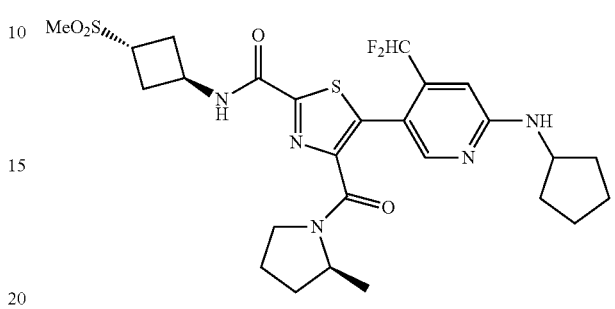

The title compound was prepared as described in Example 71 substituting 4-((S)-2-methylpyrrolidine-1-carbonyl)-N-((1r,3r)-3-(methylsulfonyl)cyclobutyl)thiazole-2-carboxamide (Intermediate 74) for (S)—N-((1-hydroxycyclobutyl)methyl)-4-(2-methylpyrrolidine-1-carbonyl)thiazole-2-carboxamide. MS (ESI): mass calcd. for $C_{26}H_{33}F_2N_5O_4S_2$, 581.7; m/z found, 582.2 [M+H]+. 1H NMR (400 MHz, DMSO-d6) δ 9.41-9.27 (m, 1H), 8.00 (s, 1H), 7.39-7.29 (m, 1H), 7.16-6.78 (m, 1H), 6.73 (s, 1H), 4.68-4.56 (m, 1H), 4.25-4.12 (m, 1H), 4.08-3.97 (m, 1H), 3.88-3.77 (d, J=5.0 Hz, 1H), 3.47-3.35 (m, 2H), 2.97 (s, 3H), 2.76-2.62 (m, 4H), 2.01-1.78 (m, 4H), 1.75-1.38 (m, 8H), 1.10 (d, J=6.0 Hz, 2H), 0.87 (d, J=6.5 Hz, 1H).

Example 73

(S)-5-(6-(Cyclopentylamino)-4-(difluoromethyl)pyridin-3-yl)-N-((3-hydroxyoxetan-3-yl)methyl)-4-(2-methylpyrrolidine-1-carbonyl)thiazole-2-carboxamide

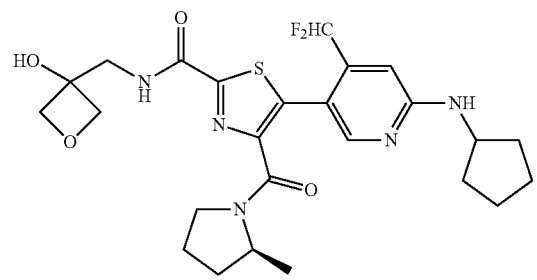 [SMILES: C[C@H]1CCCN1C(=O)c1nc(C(=O)NCC2(O)COC2)sc1-c1cnc(NC2CCCC2)cc1C(F)F]

The title compound was prepared as described in Example 71 substituting (S)—N-((3-hydroxyoxetan-3-yl)methyl)-4-(2-methylpyrrolidine-1-carbonyl)thiazole-2-carboxamide (Intermediate 75) for (S)—N-((1-hydroxycyclobutyl)methyl)-4-(2-methylpyrrolidine-1-carbonyl)thiazole-2-carboxamide. MS (ESI): mass calcd. for $C_{25}H_{31}F_2N_5O_4S$, 535.6; m/z found, 536.2 [M+H]+. 1H NMR (400 MHz, DMSO-d6) δ 8.94-8.81 (m, 1H), 8.01 (s, 1H), 7.34 (d, J=6.6 Hz, 1H), 7.16-6.78 (m, 1H), 6.73 (s, 1H), 5.98-5.88 (m, 1H), 4.55-4.36 (m, 4H), 4.26-3.97 (m, 2H), 3.70-3.42 (m, 4H), 2.01-1.40 (m, 12H), 1.10 (d, J=6.6 Hz, 2H), 0.90 (d, J=6.2 Hz, 1H).

Example 74

5-(6-(Cyclopentylamino)-4-(difluoromethyl)pyridin-3-yl)-N-((1r,3s)-3-hydroxycyclobutyl)-4-((S)-2-methylpyrrolidine-1-carbonyl)thiazole-2-carboxamide

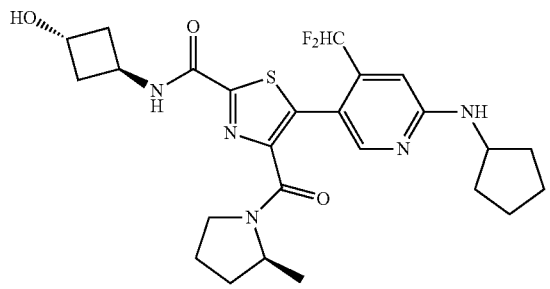 [SMILES: C[C@H]1CCCN1C(=O)c1nc(C(=O)N[C@H]2C[C@H](O)C2)sc1-c1cnc(NC2CCCC2)cc1C(F)F]

The title compound was prepared as described in Example 71 substituting N-((1r,3r)-3-((tert-butyldimethylsilyl)oxy)cyclobutyl)-4-((S)-2-methylpyrrolidine-1-carbonyl)thiazole-2-carboxamide (Intermediate 2: Step B) for (S)—N-((1-hydroxycyclobutyl)methyl)-4-(2-methylpyrrolidine-1-carbonyl)thiazole-2-carboxamide. MS (ESI): mass calcd. for $C_{25}H_{31}F_2N_5O_3S$, 519.6; m/z found, 520.2 [M+H]$^+$. $^1$H NMR (400 MHz, DMSO-d$_6$) δ 9.16-9.10 (m, 1H), 8.00 (s, 1H), 7.36-7.29 (m, 1H), 7.15-7.01 (m, 1H), 6.93-6.79 (m, 1H), 6.73 (s, 1H), 5.04-5.00 (m, 1H), 4.52-4.44 (m, 1H), 4.35-4.27 (m, 1H), 4.21-3.98 (m, 3H), 2.42-2.38 (m, 2H), 2.23-2.08 (m, 2H), 2.02-1.73 (m, 5H), 1.72-1.36 (m, 7H), 1.09 (d, J=6.5 Hz, 2H), 0.87 (d, J=6.0 Hz, 1H).

Example 75

(S)-5-(6-(Cyclohexylamino)-4-cyclopropylpyridin-3-yl)-N-(1,1-dioxidotetrahydro-2H-thiopyran-4-yl)-4-(2-methylpiperidine-1-carbonyl)thiazole-2-carboxamide

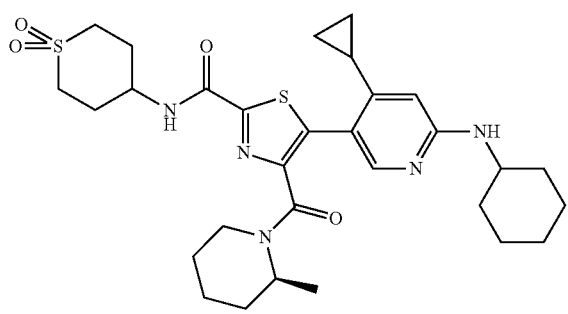 [SMILES: C[C@H]1CCCCN1C(=O)c1nc(C(=O)NC2CCS(=O)(=O)CC2)sc1-c1cnc(NC2CCCCC2)cc1C1CC1]

The title compound was prepared as described in Example 71 substituting (S)—N-(1,1-dioxidotetrahydro-2H-thiopyran-4-yl)-4-(2-methylpiperidine-1-carbonyl)thiazole-2-carboxamide (Intermediate 72: Step D) for (S)—N-((1-hydroxycyclobutyl)methyl)-4-(2-methylpyrrolidine-1-carbonyl)thiazole-2-carboxamide and 5-bromo-N-cyclohexyl-4-cyclopropylpyridin-2-amine (Intermediate 36) for 5-bromo-N-cyclopentyl-4-(difluoromethyl)pyridin-2-amine. MS (ESI): mass calcd. for $C_{30}H_{41}N_5O_4S_2$ 599.3, m/z found 600.2 [M+H]$^+$. $^1$H NMR (400 MHz, DMSO-d$_6$) δ 8.86-8.64 (m, 1H), 7.82 (s, 1H), 6.30 (d, J=7.5 Hz, 1H), 6.10 (s, 1H), 4.93-4.44 (m, 1H), 4.30-4.10 (m, 1H), 3.81-3.67 (m, 1H), 3.37-3.21 (m, 2H), 3.17-3.10 (m, 2H), 2.95-2.74 (m, 1H), 2.36-2.08 (m, 4H), 1.95-1.12 (m, 17H), 1.05 (d, J 7.0 Hz, 3H), 1.00-0.80 (m, 3H), 0.76-0.59 (m, 2H).

Example 76

(S)-5-(6-(Cyclohexylamino)-4-cyclopropylpyridin-3-yl)-N-(2-hydroxy-2-methylpropyl)-4-(2-methylpiperidine-1-carbonyl)thiazole-2-carboxamide

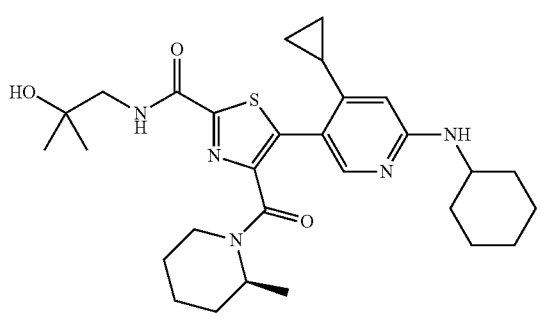 [SMILES: C[C@H]1CCCCN1C(=O)c1nc(C(=O)NCC(C)(C)O)sc1-c1cnc(NC2CCCCC2)cc1C1CC1]

The title compound was prepared as described in Example 71 substituting (S)—N-(2-hydroxy-2-methylpropyl)-4-(2-methylpiperidine-1-carbonyl)thiazole-2-carboxamide (Intermediate 66: Step D) for (S)—N-((1-hydroxycyclobutyl)methyl)-4-(2-methylpyrrolidine-1-carbonyl)thiazole-2-carboxamide and 5-bromo-N-cyclohexyl-4-cyclopropylpyridin-2-amine (Intermediate 36) for 5-bromo-N-cyclopentyl-4-(difluoromethyl)pyridin-2-amine. MS (ESI): mass calcd. for $C_{29}H_{41}N_5O_3S$ 539.3, m/z found 540.3 [M+H]$^+$. $^1$H NMR (400 MHz, DMSO-d$_6$) δ 8.13-8.01 (m, 1H), 7.83 (s, 1H), 6.34-6.26 (m, 1H), 6.10 (s, 1H), 4.48 (s, 1H), 3.79-3.68 (m, 1H), 3.31 (d, J=6.0 Hz, 2H), 2.90-2.81 (m, 1H), 2.06-1.53 (m, 9H), 1.48-1.19 (m, 10H), 1.16 (s, 6H), 1.07 (d, J=7.0 Hz, 3H), 0.95-0.86 (m, 2H), 0.74-0.63 (m, 2H).

Example 77

(S)—N-(2-Hydroxy-2-methylpropyl)-5-(6-((1-methylcyclobutyl)amino)-4-(trifluoromethyl)pyridin-3-yl)-4-(2-methylpyrrolidine-1-carbonyl)thiazole-2-carboxamide

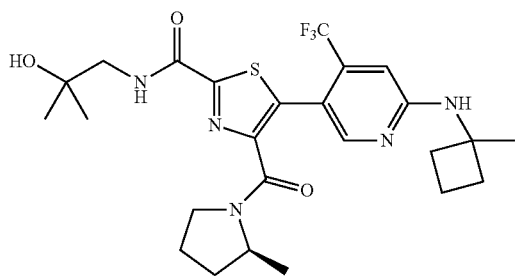 [SMILES: C[C@H]1CCCN1C(=O)c1nc(C(=O)NCC(C)(C)O)sc1-c1cnc(NC2(C)CCC2)cc1C(F)(F)F]

To an oven-dried vial under N$_2$ was added 5-bromo-N-(1-methylcyclobutyl)-4-(trifluoromethyl)pyridin-2-amine (90 mg, 0.29 mmol, Intermediate 46), (S)—N-(2-hydroxy- 2-methylpropyl)-4-(2-methylpyrrolidine-1-carbonyl)thiazole-2-carboxamide (91 mg, 0.29 mmol, Intermediate 69), bis(tri-tert-butylphosphine)palladium (0) (30 mg, 0.06 mmol), potassium carbonate (80 mg, 0.58 mmol) and DMF (2.0 mL, sparged with $N_2$ for 2 h). The vial was capped and heated at 130° C. for 24 h. The reaction was cooled, poured into saturated aqueous bicarbonate, and extracted with ethyl acetate (3×). The combined organic layers were dried over anhydrous sodium sulfate and concentrated to dryness. The crude residue was dissolved in 1:1 DMSO:MeOH and purified by reverse phase HPLC to provide the title compound. MS (ESI): mass calcd. for $C_{25}H_{32}F_3N_5O_3S$, 539.6; m/z found, 540.2 [M+H]$^+$. $^1$H NMR (600 MHz, CDCl$_3$) δ 8.17 (s, 1H), 7.60-7.50 (m, 1H), 6.50 (s, 1H), 5.21 (s, 1H), 4.35-4.27 (m, 0.3H), 4.25-4.16 (m, 0.7H), 3.65-3.37 (m, 4H), 2.30-2.25 (m, 2H), 2.19-1.83 (m, 8H), 1.77-1.73 (m, 1H), 1.65-1.51 (m, 2H), 1.36-1.18 (m, 9H), 1.11 (d, J=6.4 Hz, 1H).

Example 78

N-(2-Hydroxy-2-methylpropyl)-4-((S)-2-methylpyrrolidine-1-carbonyl)-5-(4-(trifluoromethyl)-6-(((S)-1,1,1-trifluoropropan-2-yl)amino)pyridin-3-yl)thiazole-2-carboxamide

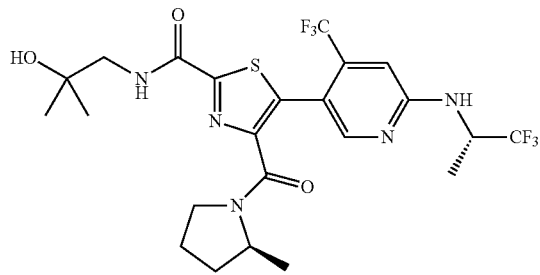 [SMILES: C[C@H](Nc1cc(C(F)(F)F)c(-c2sc(C(=O)NCC(C)(C)O)nc2C(=O)N2CCC[C@@H]2C)cn1)C(F)(F)F]

The title compound was prepared as described in Example 77 substituting (S)-5-bromo-4-(trifluoromethyl)-N-(1,1,1-trifluoropropan-2-yl)pyridin-2-amine (Intermediate 44) for 5-bromo-N-(1-methylcyclobutyl)-4-(trifluoromethyl)pyridin-2-amine. MS (ESI): mass calcd. for $C_{23}H_{27}F_6N_5O_3S$, 567.6; m/z found, 568.2 [M+H]$^+$. $^1$H NMR (400 MHz, CDCl$_3$) δ 8.20 (s, 1H), 7.62-7.50 (m, 1H), 6.68-6.64 (m, 1H), 5.55 (d, J=9.2 Hz, 0.7H), 5.32-5.30 (m, 0.3H), 5.07-4.88 (m, 1H), 4.59-4.50 (m, 0.2H), 4.19-4.14 (m, 0.8H), 3.74-3.36 (m, 4H), 2.17-1.47 (m, 4H), 1.45-1.21 (m, 12H), 1.09 (d, J=6.4 Hz, 1H).

Example 79

4-((1s,4s)-7-Azabicyclo[2.2.1]heptane-7-carbonyl)-5-(6-(tert-butylamino)-4-(trifluoromethyl)pyridin-3-yl)-N-(2-hydroxy-2-methylpropyl)thiazole-2-carboxamide

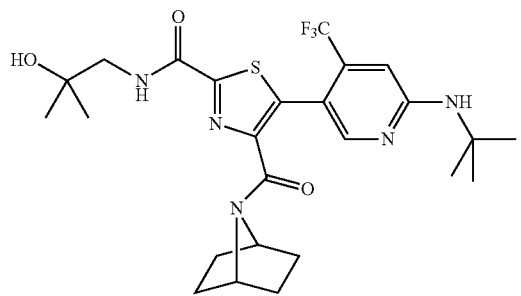 [SMILES: CC(C)(O)CNC(=O)c1nc(C(=O)N2C3CCC2CC3)c(-c2cnc(NC(C)(C)C)cc2C(F)(F)F)s1]

The title compound was prepared as described in Example 77 substituting 5-bromo-N-(tert-butyl)-4-(trifluoromethyl)pyridin-2-amine (Intermediate 41: Step B) for 5-bromo-N-(1-methylcyclobutyl)-4-(trifluoromethyl)pyridin-2-amine and 4-((1s,4s)-7-azabicyclo[2.2.1]heptane-7-carbonyl)-N-(2-hydroxy-2-methylpropyl)thiazole-2-carboxamide (Intermediate 70: Step B) for (S)—N-(2-hydroxy-2-methylpropyl)-4-(2-methylpyrrolidine-1-carbonyl)thiazole-2-carboxamide. MS (ESI): mass calcd. for $C_{25}H_{32}F_3N_5O_3S$, 539.2; m/z found, 539.9 [M+H]$^+$. $^1$H NMR (400 MHz, CDCl$_3$) δ 8.19-8.13 (s, 1H), 7.64-7.55 (m, 1H), 6.67-6.60 (s, 1H), 5.00-4.77 (m, 1H), 4.74-4.63 (m, 1H), 4.34-4.21 (m, 1H), 3.52-3.43 (d, J=6.4 Hz, 2H), 2.02-1.96 (m, 1H), 1.84-1.67 (m, 2H), 1.49-1.40 (m, 13H), 1.35-1.23 (m, 8H).

Example 80

(S)-5-(6-(tert-Butylamino)-4-(trifluoromethyl)pyridin-3-yl)-N-(2-hydroxy-2-methylpropyl)-4-(2-methylpiperidine-1-carbonyl)thiazole-2-carboxamide

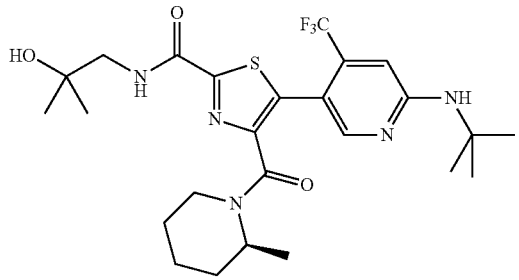 [SMILES: C[C@H]1CCCCN1C(=O)c1nc(C(=O)NCC(C)(C)O)sc1-c1cnc(NC(C)(C)C)cc1C(F)(F)F]

The title compound was prepared as described in Example 77 substituting 5-bromo-N-(tert-butyl)-4-(trifluoromethyl)pyridin-2-amine (Intermediate 41: Step B) for 5-bromo-N-(1-methylcyclobutyl)-4-(trifluoromethyl)pyridin-2-amine and (S)—N-(2-hydroxy-2-methylpropyl)-4-(2-methylpiperidine-1-carbonyl)thiazole-2-carboxamide (Intermediate 66: Step D) for (S)—N-(2-hydroxy-2-methylpropyl)-4-(2-methylpyrrolidine-1-carbonyl)thiazole-2-carboxamide. MS (ESI): mass calcd. for $C_{25}H_{34}F_3N_5O_3S$, 541.2; m/z found, 541.9 [M+H]$^+$. $^1$NMR (400 MHz, CDCl$_3$) δ 8.28-8.12 (m, 1H), 7.67-7.54 (m, 1H), 6.69-6.59 (s, 1H), 4.99-4.81 (m, 1.5H), 4.55-4.41 (m, 0.5H), 4.01-3.87 (m, 0.5H), 3.51-3.45 (dd, J=6.2, 1.3 Hz, 2H), 3.44-3.35 (m, 0.5H), 3.02-2.70 (m, 1H), 2.08-1.91 (m, 1H), 1.72-1.57 (m, 2H), 1.50-1.42 (s, 10H), 1.36-1.28 (m, 8H), 1.23-1.04 (m, 4H).

Example 81

(S)—N-(2-Hydroxy-2-methylpropyl)-5-(6-((1-methylcyclobutyl)amino)-4-(trifluoromethyl)pyridin-3-yl)-4-(2-methylpiperidine-1-carbonyl)thiazole-2-carboxamide

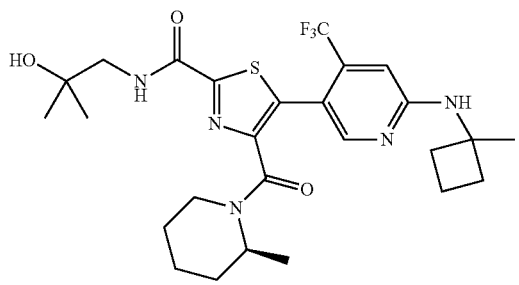 [SMILES: C[C@H]1CCCCN1C(=O)c1nc(C(=O)NCC(C)(C)O)sc1-c1cnc(NC2(C)CCC2)cc1C(F)(F)F]

The title compound was prepared as described in Example 77 substituting (S)—N-(2-hydroxy-2-methylpropyl)-4-(2-methylpiperidine-1-carbonyl)thiazole-2-carboxamide (Intermediate 66: Step D) for (S)—N-(2-hydroxy-2-methylpropyl)-4-(2-methylpyrrolidine-1-carbonyl)thiazole-2-carboxamide. MS (ESI): mass calcd. for $C_{26}H_{34}F_3N_5O_3S$, 553.6; m/z found, 554.3 [M+H]$^+$. $^1$H NMR (400 MHz, CDCl$_3$) δ 8.20 (d, J=15.7 Hz, 1H), 7.66-7.58 (m, 1H), 6.53 (s, 1H), 5.27 (br s, 1H), 4.89 (br s, 0.6H), 4.47 (d, J=13.3 Hz, 0.4H), 3.94 (br s, 0.4H), 3.55-3.36 (m, 2.6H), 3.00-2.75 (m, 1H), 2.35-2.06 (m, 5H), 2.02-1.87 (m, 2H), 1.74-1.04 (m, 18H).

Example 82

4-((1s,4s)-7-Azabicyclo[2.2.1]heptane-7-carbonyl)-N-(2-hydroxy-2-methylpropyl)-5-(4-(trifluoromethyl)-6-(((S)-1,1,1-trifluoropropan-2-yl)amino)pyridin-3-yl)thiazole-2-carboxamide

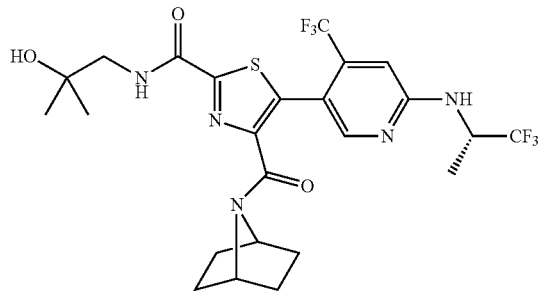

The title compound was prepared as described in Example 77 substituting (S)-5-bromo-4-(trifluoromethyl)-N-(1,1,1-trifluoropropan-2-yl)pyridin-2-amine (Intermediate 44) for 5-bromo-N-(1-methylcyclobutyl)-4-(trifluoromethyl)pyridin-2-amine and 4-((1s,4s)-7-azabicyclo[2.2.1]heptane-7-carbonyl)-N-(2-hydroxy-2-methylpropyl)thiazole-2-carboxamide (Intermediate 70: Step B) for (S)—N-(2-hydroxy-2-methylpropyl)-4-(2-methylpyrrolidine-1-carbonyl)thiazole-2-carboxamide. MS (ESI): mass calcd. for $C_{24}H_{27}F_6N_5O_3S$, 579.6; m/z found, 580.2 [M+H]$^+$. $^1$H NMR (400 MHz, CDCl$_3$) δ 8.18 (s, 1H), 7.62-7.55 (m, 1H), 6.69 (s, 1H), 5.37 (d, J=9.3 Hz, 1H), 5.03-4.88 (m, 1H), 4.67 (s, 1H), 4.49 (s, 1H), 3.55-3.45 (m, 2H), 2.03 (s, 1H), 1.65 (s, 3H), 1.56-1.23 (m, 14H).

Example 83

(S)-5-(6-(tert-Butylamino)-4-(trifluoromethyl)pyridin-3-yl)-4-(4,4-difluoro-2-methylpyrrolidine-1-carbonyl)-N-(2-hydroxy-2-methylpropyl)thiazole-2-carboxamide

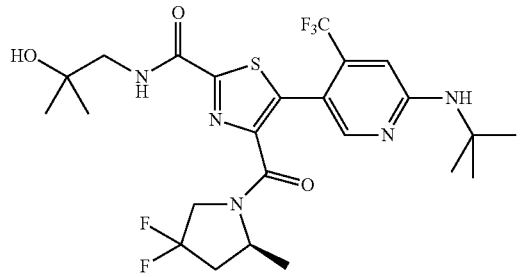 [SMILES: C[C@H]1CC(F)(F)CN1C(=O)c1nc(C(=O)NCC(C)(C)O)sc1-c1cnc(NC(C)(C)C)cc1C(F)(F)F]

The title compound was prepared as described in Example 77 substituting 5-bromo-N-(tert-butyl)-4-(trifluoromethyl)pyridin-2-amine (Intermediate 41: Step B) for 5-bromo-N-(1-methylcyclobutyl)-4-(trifluoromethyl)pyridin-2-amine and (S)-4-(4,4-difluoro-2-methylpyrrolidine-1-carbonyl)-N-(2-hydroxy-2-methylpropyl)thiazole-2-carboxamide (Intermediate 67) for (S)—N-(2-hydroxy-2-methylpropyl)-4-(2-methylpyrrolidine-1-carbonyl)thiazole-2-carboxamide. MS (ESI): mass calcd. for $C_{24}H_{30}F_5N_5O_3S$, 563.2; m/z found, 563.9 [M+H]$^+$. $^1$H NMR (400 MHz, CDCl$_3$) δ 8.20-8.10 (s, 1H), 7.57-7.42 (m, 1H), 6.68-6.60 (s, 1H), 5.01-4.39 (m, 2H), 4.20-3.71 (m, 2H), 3.60-3.37 (m, 2H), 2.68-2.42 (m, 1H), 2.22-1.97 (m, 1H), 1.92-1.73 (m, 1H), 1.49-1.44 (s, 9H), 1.39-1.27 (m, 9H).

Example 84

4-((1s,4s)-7-Azabicyclo[2.2.1]heptane-7-carbonyl)-N-(2-hydroxy-2-methylpropyl)-5-(6-(neopentylamino)-4-(trifluoromethyl)pyridin-3-yl)thiazole-2-carboxamide

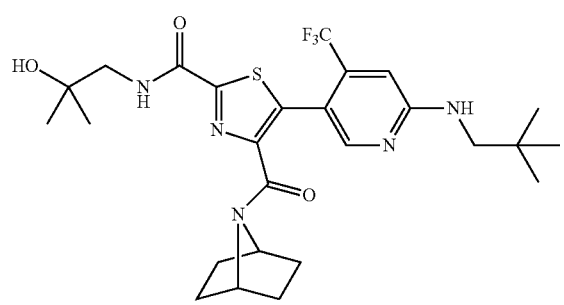 [SMILES: CC(C)(C)CNc1cc(C(F)(F)F)c(-c2sc(C(=O)NCC(C)(C)O)nc2C(=O)N2C3CCC2CC3)cn1]

The title compound was prepared as described for Example 77 substituting 4-((1s,4s)-7-azabicyclo[2.2.1]heptane-7-carbonyl)-N-(2-hydroxy-2-methylpropyl)thiazole-2-carboxamide (Intermediate 70: Step B) for (S)—N-(2-hydroxy-2-methylpropyl)-4-(2-methylpyrrolidine-1-carbonyl)thiazole-2-carboxamide and 5-bromo-N-neopentyl-4-(trifluoromethyl)pyridin-2-amine (Intermediate 22) for 5-bromo-N-(1-methylcyclobutyl)-4-(trifluoromethyl)pyridin-2-amine. MS (ESI): mass calcd. for $C_{26}H_{34}F_3N_5O_3S$, 553.6; m/z found, 554.2 [M+H]$^+$. $^1$H NMR (500 MHz, CDCl$_3$) δ 8.15 (s, 1H), 7.62-7.56 (m, 1H), 6.66 (s, 1H), 5.06-4.99 (m, 1H), 4.68 (s, 1H), 4.33 (s, 1H), 3.48 (d, J=6.3 Hz, 2H), 3.17 (d, J=6.1 Hz, 2H), 2.01 (s, 1H), 1.82-1.71 (m, 2H), 1.67-1.61 (m, 2H), 1.47-1.41 (m, 4H), 1.32 (s, 6H), 1.00 (s, 9H).

Example 85

(S)-4-(4,4-Difluoro-2-methylpyrrolidine-1-carbonyl)-N-(2-hydroxy-2-methylpropyl)-5-(6-(neopentylamino)-4-(trifluoromethyl)pyridin-3-yl)thiazole-2-carboxamide

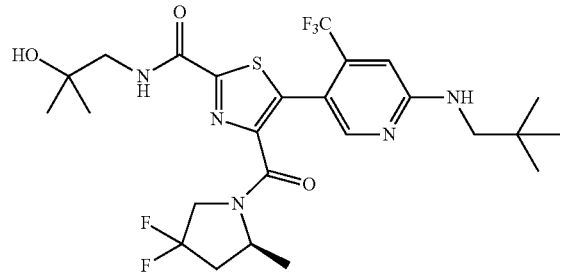 [SMILES: C[C@H]1CC(F)(F)CN1C(=O)c1nc(C(=O)NCC(C)(C)O)sc1-c1cnc(NCC(C)(C)C)cc1C(F)(F)F]

The title compound was prepared as described for Example 77 substituting (S)-4-(4,4-difluoro-2-methylpyrrolidine-1-carbonyl)-N-(2-hydroxy-2-methylpropyl)thiazole-2-carboxamide (Intermediate 67) for (S)—N-(2-hydroxy-2-methylpropyl)-4-(2-methylpyrrolidine-1-carbonyl)thiazole-2-carboxamide and 5-bromo-N-neopentyl-4-(trifluoromethyl)pyridin-2-amine (Intermediate 22) for 5-bromo-N-(1-methylcyclobutyl)-4-(trifluoromethyl)pyridin-2-amine. MS (ESI): mass calcd. for $C_{25}H_{32}F_5N_5O_3S$, 577.6; m/z found, 578.2 [M+H]$^+$. $^1$H NMR (500 MHz, CDCl$_3$) δ 8.13 (s, 1H), 7.54-7.46 (m, 1H), 6.66 (s, 1H), 5.08-5.00 (m, 1H), 4.73-4.45 (m, 1H), 4.14-3.81 (m, 2H), 3.56-3.42 (m, 2H), 3.20-3.11 (m, 2H), 2.62-2.50 (m, 1H), 2.17-2.00 (m, 1H), 1.93-1.80 (m, 1H), 1.37-1.28 (m, 9H), 1.01 (s, 9H).

Example 86

(S)—N-(2-Hydroxy-2-methylpropyl)-4-(2-methylpiperidine-1-carbonyl)-5-(6-(neopentylamino)-4-(trifluoromethyl)pyridin-3-yl)thiazole-2-carboxamide

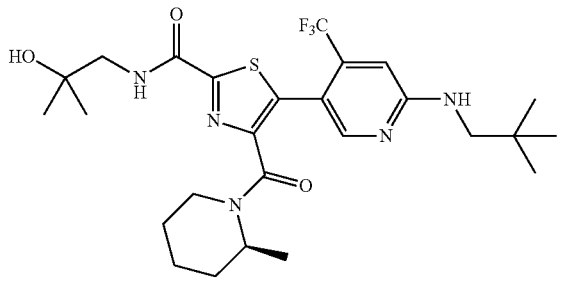 [SMILES: C[C@H]1CCCCN1C(=O)c1nc(C(=O)NCC(C)(C)O)sc1-c1cnc(NCC(C)(C)C)cc1C(F)(F)F]

The title compound was prepared as described for Example 77 substituting (S)—N-(2-hydroxy-2-methylpropyl)-4-(2-methylpiperidine-1-carbonyl)thiazole-2-carboxamide (Intermediate 66: Step D) for (S)—N-(2-hydroxy-2-methylpropyl)-4-(2-methylpyrrolidine-1-carbonyl)thiazole-2-carboxamide and 5-bromo-N-neopentyl-4-(trifluoromethyl)pyridin-2-amine (Intermediate 22) for 5-bromo-N-(1-methylcyclobutyl)-4-(trifluoromethyl)pyridin-2-amine. MS (ESI): mass calcd. for $C_{26}H_{36}F_3N_5O_3S$, 555.7; m/z found, 556.2 [M+H]$^+$. $^1$H NMR (500 MHz, CDCl$_3$) δ 8.25-8.15 (m, 1H), 7.63-7.55 (m, 1H), 6.67 (s, 1H), 5.08-5.01 (m, 1H), 4.93-3.41 (m, 4H), 3.22-3.13 (m, 2H), 3.02-2.74 (m, 1H), 2.08-1.96 (m, 1H), 1.69-1.62 (m, 1H), 1.57-1.50 (m, 2H), 1.44-1.35 (m, 1H), 1.31 (s, 6H), 1.20 (d, J=6.7 Hz, 1H), 1.12 (d, J=6.8 Hz, 2H), 1.00 (s, 9H), 1.59-1.58 (m, 2H).

Example 87

(S)—N-(2-Hydroxy-2-methylpropyl)-4-(2-methylpyrrolidine-1-carbonyl)-5-(6-(neopentylamino)-4-(trifluoromethyl)pyridin-3-yl)thiazole-2-carboxamide

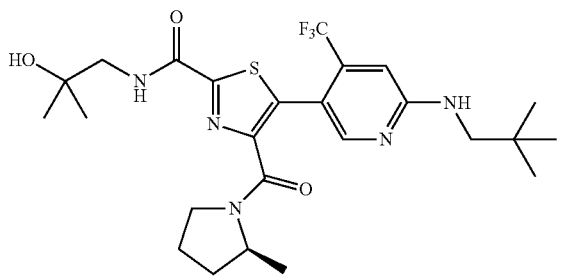 [SMILES: C[C@H]1CCCN1C(=O)c1nc(C(=O)NCC(C)(C)O)sc1-c1cnc(NCC(C)(C)C)cc1C(F)(F)F]

The title compound was prepared as described for Example 77 substituting 5-bromo-N-neopentyl-4-(trifluoromethyl)pyridin-2-amine (Intermediate 22) for 5-bromo-N-(1-methylcyclobutyl)-4-(trifluoromethyl)pyridin-2-amine. MS (ESI): mass calcd. for $C_{25}H_{34}F_3N_5O_3S$, 541.6; m/z found, 542.2 [M+H]$^+$. $^1$H NMR (500 MHz, CDCl$_3$) δ 8.15 (s, 1H), 7.64-7.54 (m, 1H), 6.67-6.62 (m, 1H), 5.25-5.11 (m, 1H), 4.36-4.16 (m, 1H), 3.58-3.39 (m, 4H), 3.23-3.09 (m, 2H), 2.27-2.15 (m, 1H), 2.09-2.05 (m, 1H), 1.95-1.88 (m, 1H), 1.78-1.75 (m, 1H), 1.58-1.48 (m, 1H), 1.32-1.29 (m, 6H), 1.25-1.23 (m, 2H), 1.10 (d, J=6.4 Hz, 1H), 1.01-0.98 (m, 9H).

Example 88

(S)-5-(6-((2-Cyclopropylpropan-2-yl)amino)-4-(difluoromethyl)pyridin-3-yl)-N-(2-hydroxy-2-methylpropyl)-4-(2-methylpiperidine-1-carbonyl)thiazole-2-carboxamide

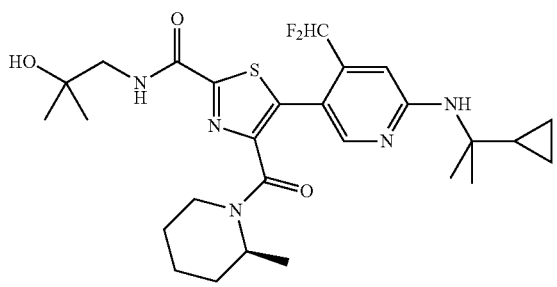 [SMILES: C[C@H]1CCCCN1C(=O)c1nc(C(=O)NCC(C)(C)O)sc1-c1cnc(NC(C)(C)C2CC2)cc1C(F)F]

The title compound was prepared as described for Example 77 using (S)—N-(2-hydroxy-2-methylpropyl)-4-(2-methylpiperidine-1-carbonyl)thiazole-2-carboxamide (Intermediate 66: Step D) for (S)—N-(2-hydroxy-2-methylpropyl)-4-(2-methylpyrrolidine-1-carbonyl)thiazole-2-carboxamide and 5-bromo-N-(2-cyclopropylpropan-2-yl)-4-(difluoromethyl)pyridin-2-amine (Intermediate 48) for 5-bromo-N-(1-methylcyclobutyl)-4-(trifluoromethyl)pyridin-2-amine. MS (ESI): mass calcd. for $C_{27}H_{37}F_2N_5O_3S$, 549.7; m/z found, 550.2 [M+H]$^+$. $^1$H NMR (500 MHz, CDCl$_3$) δ 8.05 (s, 1H), 7.73-7.60 (m, 1H), 6.91-6.60 (m, 2H), 5.08 (s, 1H), 4.93-4.38 (m, 1H), 3.91-3.31 (m, 3H), 2.96 (s, 2H), 2.89-2.86 (m, 2H), 2.48-2.38 (m, 1H), 1.70-1.59 (m, 1H), 1.57-1.40 (m, 3H), 1.31 (d, J=6.4 Hz, 12H), 1.17-1.09 (m, 3H), 0.53-0.46 (m, 2H), 0.44-0.39 (m, 2H).

Example 89

4-((1s,4s)-7-Azabicyclo[2.2.1]heptane-7-carbonyl)-5-(4-(difluoromethyl)-6-(((S)-1,1,1-trifluorobutan-2-yl)amino)pyridin-3-yl)-N-(2-hydroxy-2-methylpropyl)thiazole-2-carboxamide

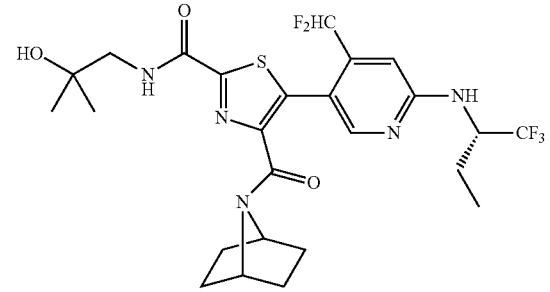 [SMILES: CC[C@H](Nc1cc(C(F)F)c(-c2sc(C(=O)NCC(C)(C)O)nc2C(=O)N2C3CCC2CC3)cn1)C(F)(F)F]

The title compound was prepared as described for Example 77 substituting 4-((1s,4s)-7-azabicyclo[2.2.1]heptane-7-carbonyl)-N-(2-hydroxy-2-methylpropyl)thiazole-2-carboxamide (Intermediate 70: Step B) for (S)—N-(2-hydroxy-2-methylpropyl)-4-(2-methylpyrrolidine-1-carbonyl)thiazole-2-carboxamide and (S)-5-bromo-4-(difluoromethyl)-N-(1,1,1-trifluorobutan-2-yl)pyridin-2-amine (Intermediate 49) for 5-bromo-N-(1-methylcyclobutyl)-4-(trifluoromethyl)pyridin-2-amine. MS (ESI): mass calcd. for $C_{25}H_{30}F_5N_5O_3S$, 575.6; m/z found, 576.2 [M+H]$^+$. $^1$H NMR (500 MHz, CDCl$_3$) δ 8.07-8.01 (m, 1H), 7.66-7.59 (m, 1H), 6.90-6.66 (m, 2H), 5.03 (d, J=9.8 Hz, 1H), 4.83-4.73 (m, 1H), 4.70-4.64 (m, 1H), 4.33-4.27 (m, 1H), 3.48 (d, J=6.2 Hz, 2H), 2.96-2.88 (m, 1H), 2.28 (s, 1H), 2.00-1.91 (m, 1H), 1.83-1.77 (m, 1H), 1.65-1.54 (m, 3H), 1.48-1.41 (m, 4H), 1.31 (s, 6H), 1.06-1.01 (m, 3H).

Example 90

4-((S)-4,4-Difluoro-2-methylpyrrolidine-1-carbonyl)-5-(4-(difluoromethyl)-6-(((S)-1,1,1-trifluorobutan-2-yl)amino)pyridin-3-yl)-N-(2-hydroxy-2-methylpropyl)thiazole-2-carboxamide

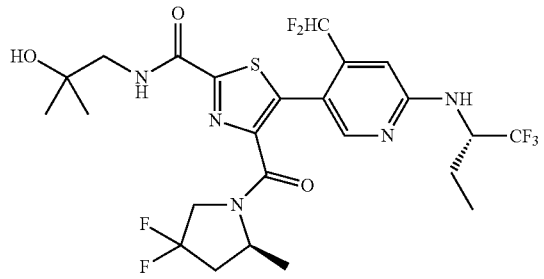 [SMILES: CC[C@H](Nc1cc(C(F)F)c(-c2sc(C(=O)NCC(C)(C)O)nc2C(=O)N2CC(F)(F)C[C@@H]2C)cn1)C(F)(F)F]

The title compound was prepared as described for Example 77 substituting (S)-4-(4,4-difluoro-2-methylpyrrolidine-1-carbonyl)-N-(2-hydroxy-2-methylpropyl)thiazole-2-carboxamide (Intermediate 67) for (S)—N-(2-hydroxy-2-methylpropyl)-4-(2-methylpyrrolidine-1-carbonyl)thiazole-2-carboxamide and (S)-5-bromo-4-(difluoromethyl)-N-(1,1,1-trifluorobutan-2-yl)pyridin-2-amine (Intermediate 49) for 5-bromo-N-(1-methylcyclobutyl)-4-(trifluoromethyl)pyridin-2-amine. MS (ESI): mass calcd. for $C_{24}H_{28}F_7N_5O_3S$, 599.6; m/z found, 600.2 [M+H]$^+$. $^1$H NMR (500 MHz, CDCl$_3$) δ 8.07-8.01 (m, 1H), 7.53-7.46 (m, 1H), 6.84-6.60 (m, 2H), 4.82-4.48 (m, 3H), 4.13-3.81 (m, 2H), 3.57-3.44 (m, 2H), 2.65-2.51 (m, 1H), 2.16-1.94 (m, 2H), 1.90-1.78 (m, 1H), 1.66-1.60 (m, 1H), 1.36 (d, J=6.4 Hz, 2H), 1.34-1.32 (m, 6H), 1.24 (d, J=6.5 Hz, 1H), 1.08-1.03 (m, 3H).

Example 91

5-(4-(Difluoromethyl)-6-(((S)-1,1,1-trifluorobutan-2-yl)amino)pyridin-3-yl)-N-(2-hydroxy-2-methylpropyl)-4-((S)-2-methylpiperidine-1-carbonyl)thiazole-2-carboxamide

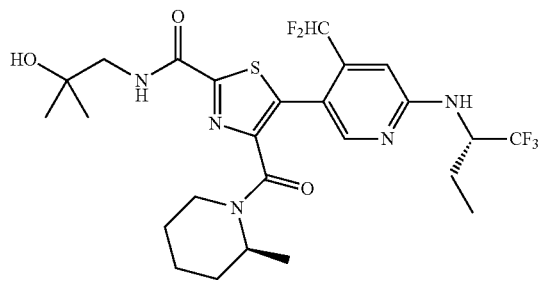 [SMILES: CC[C@H](Nc1cc(C(F)F)c(-c2sc(C(=O)NCC(C)(C)O)nc2C(=O)N2CCCC[C@@H]2C)cn1)C(F)(F)F]

The title compound was prepared as described for Example 77 substituting (S)—N-(2-hydroxy-2-methylpropyl)-4-(2-methylpiperidine-1-carbonyl)thiazole-2-carboxamide (Intermediate 66: Step D) for (S)—N-(2-hydroxy-2-methylpropyl)-4-(2-methylpyrrolidine-1-carbonyl)thiazole-2-carboxamide and (S)-5-bromo-4-(difluoromethyl)-N-(1,1,1-trifluorobutan-2-yl)pyridin-2-amine (Intermediate 49) for 5-bromo-N-(1-methylcyclobutyl)-4-(trifluoromethyl)pyridin-2-amine. MS (ESI): mass calcd. for $C_{25}H_{32}F_5N_5O_3S$, 577.6; m/z found, 578.2 [M+H]$^+$. $^1$H NMR (500 MHz, CDCl$_3$) δ 8.09 (s, 1H), 7.67-7.59 (m, 2H), 6.95-6.63 (m, 2H), 4.96 (d, J=9.8 Hz, 1H), 4.90-4.38 (m, 2H), 3.94-3.31 (m, 3H), 2.99-2.75 (m, 1H), 2.28-2.18 (m, 1H), 2.01-1.94 (m, 1H), 1.68-1.50 (m, 5H), 1.46-1.32 (m, 1H), 1.31 (s, 6H), 1.17 (d, J=6.9 Hz, 1H), 1.09 (d, J=7.1 Hz, 2H), 1.06-1.02 (m, 3H).

Example 92

5-(4-(Difluoromethyl)-6-(((S)-1,1,1-trifluorobutan-2-yl)amino)pyridin-3-yl)-N-(2-hydroxy-2-methylpropyl)-4-((S)-2-methylpyrrolidine-1-carbonyl)thiazole-2-carboxamide

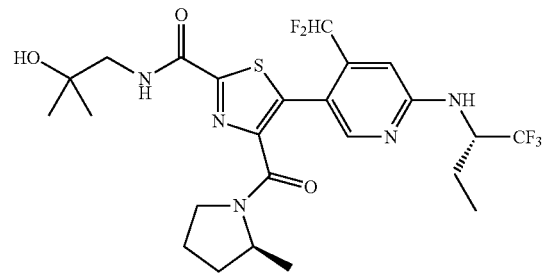 [SMILES: CC[C@H](Nc1cc(C(F)F)c(-c2sc(C(=O)NCC(C)(C)O)nc2C(=O)N2CCC[C@@H]2C)cn1)C(F)(F)F]

The title compound was prepared as described for Example 77 substituting (S)-5-bromo-4-(difluoromethyl)-N-(1,1,1-trifluorobutan-2-yl)pyridin-2-amine (Intermediate 49) for 5-bromo-N-(1-methylcyclobutyl)-4-(trifluoromethyl)pyridin-2-amine. MS (ESI): mass calcd. for $C_{24}H_{30}F_5N_5O_3S$, 563.6; m/z found, 564.2 [M+H]$^+$. $^1$H NMR (500 MHz, CDCl$_3$) δ 8.09-8.01 (m, 1H), 7.62-7.52 (m, 1H), 7.01-6.67 (m, 2H), 4.92-4.87 (m, 1H), 4.78 (s, 1H), 4.39-4.18 (m, 1H), 3.59-3.36 (m, 4H), 2.09-1.85 (m, 4H), 1.82-1.72 (m, 1H), 1.68-1.51 (m, 2H), 1.31 (s, 6H), 1.22 (d, J=6.3 Hz, 2H), 1.07-1.02 (m, 4H).

Example 93

4-((1s,4s)-7-Azabicyclo[2.2.1]heptane-7-carbonyl)-5-(4-(difluoromethyl)-6-(tert-pentylamino)pyridin-3-yl)-N-(2-hydroxy-2-methylpropyl)thiazole-2-carboxamide

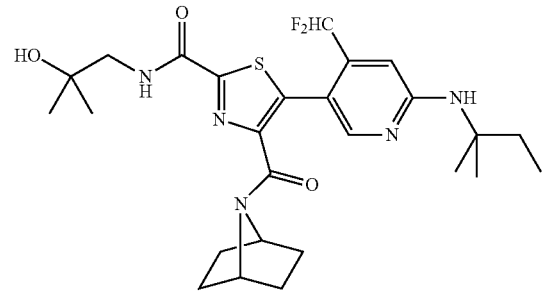 [SMILES: CCC(C)(C)Nc1cc(C(F)F)c(-c2sc(C(=O)NCC(C)(C)O)nc2C(=O)N2C3CCC2CC3)cn1]

The title compound was prepared as described for Example 77 substituting 4-((1s,4s)-7-azabicyclo[2.2.1]heptane-7-carbonyl)-N-(2-hydroxy-2-methylpropyl)thiazole-2-carboxamide (Intermediate 70: Step B) for (S)—N-(2-hydroxy-2-methylpropyl)-4-(2-methylpyrrolidine-1-carbonyl)thiazole-2-carboxamide and 5-bromo-4-(difluoromethyl)-N-(tert-pentyl)pyridin-2-amine (Intermediate 50) for 5-bromo-N-(1-methylcyclobutyl)-4-(trifluoromethyl)pyridin-2-amine. MS (ESI): mass calcd. for $C_{26}H_{35}F_2N_5O_3S$, 535.7; m/z found, 536.3 [M+H]$^+$. $^1$NMR (400 MHz, CDCl$_3$) δ 8.04-8.01 (m, 1H), 7.67-7.59 (m, 1H), 6.90-6.60 (m, 2H), 4.80-4.66 (m, 2H), 4.20-4.15 (m, 1H), 3.48 (d, J=6.3 Hz, 2H), 2.96 (s, 1H), 2.88 (s, 1H), 2.19 (s, 1H), 1.87-1.80 (m, 2H), 1.78-1.68 (m, 3H), 1.45-1.41 (m, 3H), 1.39 (s, 6H), 1.31 (s, 6H), 0.90-0.84 (m, 3H).

Example 94

(S)-4-(4,4-Difluoro-2-methylpyrrolidine-1-carbonyl)-5-(4-(difluoromethyl)-6-(tert-pentylamino)pyridin-3-yl)-N-(2-hydroxy-2-methylpropyl)thiazole-2-carboxamide

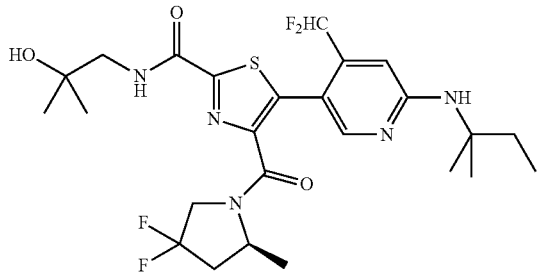 [SMILES: CCC(C)(C)Nc1cc(C(F)F)c(-c2sc(C(=O)NCC(C)(C)O)nc2C(=O)N2CC(F)(F)C[C@@H]2C)cn1]

The title compound was prepared as described for Example 77 substituting (S)-4-(4,4-difluoro-2-methylpyrrolidine-1-carbonyl)-N-(2-hydroxy-2-methylpropyl)thiazole-2-carboxamide (Intermediate 67) for (S)—N-(2-hydroxy-2-methylpropyl)-4-(2-methylpyrrolidine-1-carbonyl)thiazole-2-carboxamide and 5-bromo-4-(difluoromethyl)-N-(tert-pentyl)pyridin-2-amine (Intermediate 50) for 5-bromo-N-(1-methylcyclobutyl)-4-(trifluoromethyl)pyridin-2-amine. MS (ESI): mass calcd. for $C_{25}H_{33}F_4N_5O_3S$, 559.6; m/z found, 560.2 [M+H]$^+$. $^1$H NMR (500 MHz, CDCl$_3$) δ 8.04-7.96 (m, 2H), 7.60-7.49 (m, 1H), 6.81-6.56 (m, 2H), 4.80 (s, 1H), 4.68-4.50 (m, 1H), 4.11-3.82 (m, 2H), 3.56-3.42 (m, 2H), 2.96 (s, 3H), 2.90-2.86 (m, 3H), 2.60-2.50 (m, 1H), 2.13-2.04 (m, 1H), 1.86-1.81 (m, 2H), 1.40 (s, 6H), 1.36 (d, J=6.4 Hz, 2H), 1.21 (d, J=6.6 Hz, 1H), 0.92-0.86 (m, 3H).

Example 95

(S)-5-(4-(Difluoromethyl)-6-(tert-pentylamino)pyridin-3-yl)-N-(2-hydroxy-2-methylpropyl)-4-(2-methylpiperidine-1-carbonyl)thiazole-2-carboxamide

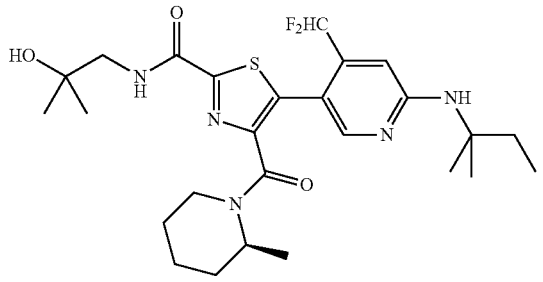 [SMILES: CCC(C)(C)Nc1cc(C(F)F)c(-c2sc(C(=O)NCC(C)(C)O)nc2C(=O)N2CCCC[C@@H]2C)cn1]

The title compound was prepared as described for Example 77 substituting (S)—N-(2-hydroxy-2-methylpropyl)-4-(2-methylpiperidine-1-carbonyl)thiazole-2-carboxamide (Intermediate 66: Step D) for (S)—N-(2-hydroxy-2-methylpropyl)-4-(2-methylpyrrolidine-1-carbonyl)thiazole-2-carboxamide and 5-bromo-4-(difluoromethyl)-N-(tert-pentyl)pyridin-2-amine (Intermediate 50) for 5-bromo-N-(1-methylcyclobutyl)-4-(trifluoromethyl)pyridin-2-amine. MS (ESI): mass calcd. for $C_{26}H_{37}F_2N_5O_3S$, 537.7; m/z found, 538.3 [M+H]$^+$. $^1$H NMR (500 MHz, CDCl$_3$) δ 8.07-8.01 (m, 1H), 7.65-7.54 (m, 1H), 6.90-6.61 (m, 2H), 4.94-4.42 (m, 2H), 3.90-3.29 (m, 3H), 3.00-2.71 (m, 2H), 2.04-1.92 (m, 1H), 1.88-1.81 (m, 2H), 1.70-1.59 (m, 1H), 1.55-1.46 (m, 2H), 1.40 (s, 6H), 1.31 (s, 6H), 1.17-1.09 (m, 3H), 0.90-0.84 (m, 3H).

Example 96

(S)-5-(4-(Difluoromethyl)-6-(tert-pentylamino)pyridin-3-yl)-N-(2-hydroxy-2-methylpropyl)-4-(2-methylpyrrolidine-1-carbonyl)thiazole-2-carboxamide

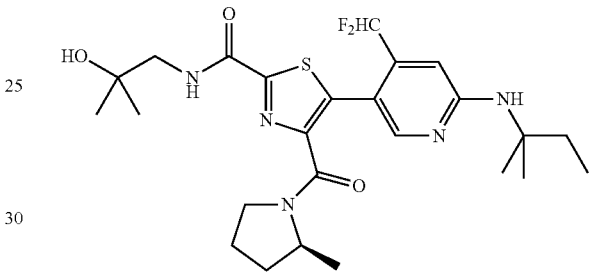

The title compound was prepared as described for Example 77 substituting 5-bromo-4-(difluoromethyl)-N-(tert-pentyl)pyridin-2-amine (Intermediate 50) for 5-bromo-N-(1-methylcyclobutyl)-4-(trifluoromethyl)pyridin-2-amine. MS (ESI): mass calcd. for $C_{25}H_{35}F_2N_5O_3S$, 523.6; m/z found, 524.2 [M+H]$^+$. $^1$H NMR (500 MHz, CDCl$_3$) δ 8.04-8.00 (m, 1H), 7.64-7.55 (m, 1H), 7.00-6.62 (m, 2H), 4.77 (s, 1H), 4.27-4.19 (m, 1H), 3.60-3.32 (m, 4H), 2.96 (s, 1H), 2.90-2.87 (m, 1H), 2.25-2.14 (m, 1H), 1.92-1.79 (m, 3H), 1.65-1.50 (m, 1H), 1.39 (s, 6H), 1.31 (s, 6H), 1.22 (d, J=6.3 Hz, 2H), 1.02 (d, J=6.4 Hz, 1H), 0.91-0.86 (m, 3H).

Example 97

4-((1s,4s)-7-Azabicyclo[2.2.1]heptane-7-carbonyl)-5-(6-((2-cyclopropylpropan-2-yl)amino)-4-(difluoromethyl)pyridin-3-yl)-N-(2-hydroxy-2-methylpropyl)thiazole-2-carboxamide

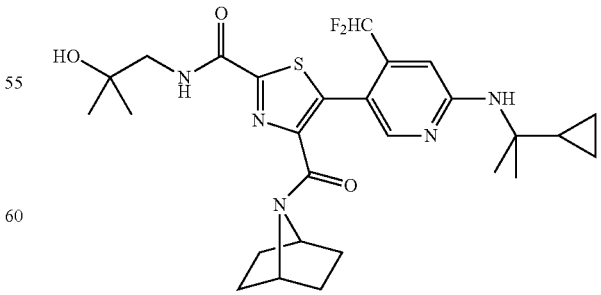

The title compound was prepared as described for Example 77 substituting 4-((1s,4s)-7-azabicyclo[2.2.1]heptane-7-carbonyl)-N-(2-hydroxy-2-methylpropyl)thiazole-2- carboxamide (Intermediate 70: Step B) for (S)—N-(2-hydroxy-2-methylpropyl)-4-(2-methylpyrrolidine-1-carbonyl)thiazole-2-carboxamide and 5-bromo-N-(2-cyclopropylpropan-2-yl)-4-(difluoromethyl)pyridin-2-amine (Intermediate 48) for 5-bromo-N-(1-methylcyclobutyl)-4-(trifluoromethyl)pyridin-2-amine. MS (ESI): mass calcd. for $C_{27}H_{35}F_2N_5O_3S$, 547.7; m/z found, 548.2 [M+H]$^+$. $^1$H NMR (400 MHz, CDCl$_3$) δ 8.03 (s, 1H), 7.64-7.57 (m, 1H), 6.91-6.61 (m, 2H), 5.02 (s, 1H), 4.73-4.65 (m, 1H), 4.25-4.18 (m, 1H), 3.48 (d, J=6.2 Hz, 2H), 2.09 (s, 1H), 1.81-1.72 (m, 2H), 1.60-1.51 (m, 2H), 1.48-1.39 (m, 4H), 1.33-1.30 (m, 12H), 1.29-1.24 (m, 1H), 0.53-0.45 (m, 2H), 0.45-0.39 (m, 2H).

Example 98

4-((1s,4s)-7-Azabicyclo[2.2.1]heptane-7-carbonyl)-N-(2-hydroxy-2-methylpropyl)-5-(6-(tert-pentylamino)-4-(trifluoromethyl)pyridin-3-yl)thiazole-2-carboxamide

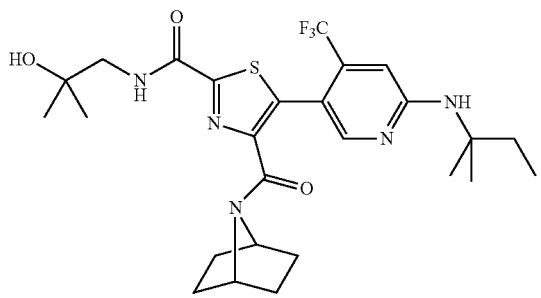 [SMILES: CCC(C)(C)Nc1cc(C(F)(F)F)c(-c2sc(C(=O)NCC(C)(C)O)nc2C(=O)N2C3CCC2CC3)cn1]

The title compound was prepared as described for Example 77 substituting 4-((1s,4s)-7-azabicyclo[2.2.1]heptane-7-carbonyl)-N-(2-hydroxy-2-methylpropyl)thiazole-2-carboxamide (Intermediate 70: Step B) for (S)—N-(2-hydroxy-2-methylpropyl)-4-(2-methylpyrrolidine-1-carbonyl)thiazole-2-carboxamide and 5-bromo-N-(tert-pentyl)-4-(trifluoromethyl)pyridin-2-amine (Intermediate 51) for 5-bromo-N-(1-methylcyclobutyl)-4-(trifluoromethyl)pyridin-2-amine. MS (ESI): mass calcd. for $C_{26}H_{34}F_3N_5O_3S$, 553.6; m/z found, 554.2 [M+H]$^+$. $^1$H NMR (500 MHz, CDCl$_3$) δ 8.14 (s, 1H), 7.67-7.59 (m, 1H), 6.65 (s, 1H), 4.82 (s, 1H), 4.69 (s, 1H), 4.21 (s, 1H), 3.48 (d, J=6.3 Hz, 2H), 2.97-2.87 (m, 1H), 2.22 (s, 1H), 1.87-1.81 (m, 2H), 1.79-1.72 (m, 2H), 1.57-1.48 (m, 2H), 1.44-1.41 (m, 3H), 1.39 (s, 6H), 1.31 (s, 6H), 0.89-0.85 (m, 3H).

Example 99

4-((1s,4s)-7-Azabicyclo[2.2.1]heptane-7-carbonyl)-N-(2-hydroxy-2-methylpropyl)-5-(4-(trifluoromethyl)-6-((1-(trifluoromethyl)cyclobutyl)amino)pyridin-3-yl)thiazole-2-carboxamide

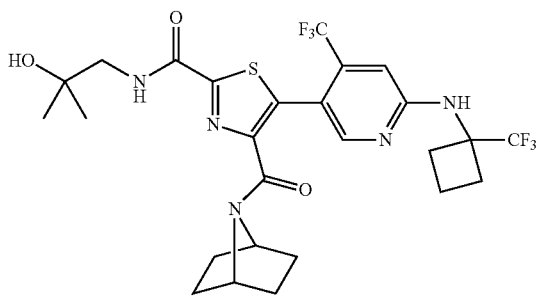 [SMILES: CC(C)(O)CNC(=O)c1nc(C(=O)N2C3CCC2CC3)c(-c2cnc(NC3(C(F)(F)F)CCC3)cc2C(F)(F)F)s1]

The title compound was prepared as described for Example 77 substituting 4-((1s,4s)-7-azabicyclo[2.2.1]heptane-7-carbonyl)-N-(2-hydroxy-2-methylpropyl)thiazole-2-carboxamide (Intermediate 70: Step B) for (S)—N-(2-hydroxy-2-methylpropyl)-4-(2-methylpyrrolidine-1-carbonyl)thiazole-2-carboxamide and 5-bromo-4-(trifluoromethyl)-N-(1-(trifluoromethyl)cyclobutyl)pyridin-2-amine (Intermediate 52) for 5-bromo-N-(1-methylcyclobutyl)-4-(trifluoromethyl)pyridin-2-amine. MS (ESI): mass calcd. for $C_{26}H_{29}F_6N_5O_3S$, 605.6; m/z found, 606.2 [M+H]$^+$. $^1$H NMR (400 MHz, CDCl$_3$) δ 8.22 (s, 1H), 7.63-7.55 (m, 1H), 6.64 (s, 1H), 5.33 (s, 1H), 4.72-4.32 (m, 2H), 3.49 (d, J=6.3 Hz, 2H), 2.70-2.40 (m, 4H), 2.14-2.01 (m, 3H), 1.82-1.64 (m, 4H), 1.49-1.42 (m, 4H), 1.32 (s, 6H).

Example 100

(S)-4-(4,4-Difluoro-2-methylpyrrolidine-1-carbonyl)-N-(2-hydroxy-2-methylpropyl)-5-(4-(trifluoromethyl)-6-((1-(trifluoromethyl)cyclobutyl)amino)pyridin-3-yl)thiazole-2-carboxamide

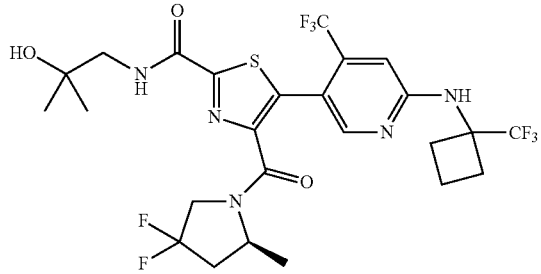 [SMILES: C[C@H]1CC(F)(F)CN1C(=O)c1nc(C(=O)NCC(C)(C)O)sc1-c1cnc(NC2(C(F)(F)F)CCC2)cc1C(F)(F)F]

The title compound was prepared as described in Example 77 substituting (S)-4-(4,4-difluoro-2-methylpyrrolidine-1-carbonyl)-N-(2-hydroxy-2-methylpropyl)thiazole-2-carboxamide (Intermediate 67) for (S)—N-(2-hydroxy-2-methylpropyl)-4-(2-methylpyrrolidine-1-carbonyl)thiazole-2-carboxamide and 5-bromo-4-(trifluoromethyl)-N-(1-(trifluoromethyl)cyclobutyl)pyridin-2-amine (Intermediate 52) for 5-bromo-N-(1-methylcyclobutyl)-4-(trifluoromethyl)pyridin-2-amine. MS (ESI): mass calcd. for $C_{25}H_{27}F_8N_5O_3S$, 629.6; m/z found, 630.1 [M+H]$^+$. $^1$H NMR (400 MHz, CDCl$_3$) δ 8.21 (s, 1H), 7.55-7.45 (m, 1H), 6.64 (s, 1H), 5.33-5.25 (m, 1H), 4.79-4.43 (m, 1H), 4.17-3.77 (m, 2H), 3.57-3.43 (m, 2H), 2.71-2.40 (m, 5H), 2.17-2.04 (m, 3H), 1.96-1.80 (m, 1H), 1.37 (d, J=6.4 Hz, 2H), 1.34-1.32 (m, 6H), 1.31-1.25 (m, 1H).

Example 101

4-((1s,4s)-7-Azabicyclo[2.2.1]heptane-7-carbonyl)-N-(2-hydroxy-2-methylpropyl)-5-(6-(((S)-1,1,1-trifluorobutan-2-yl)amino)-4-(trifluoromethyl)pyridin-3-yl)thiazole-2-carboxamide

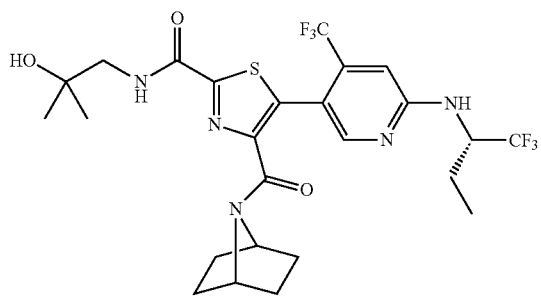 [SMILES: CC[C@H](Nc1cc(C(F)(F)F)c(-c2sc(C(=O)NCC(C)(C)O)nc2C(=O)N2C3CCC2CC3)cn1)C(F)(F)F]

The title compound was prepared as described in Example 77 substituting 4-((1s,4s)-7-azabicyclo[2.2.1]heptane-7-carbonyl)-N-(2-hydroxy-2-methylpropyl)thiazole-2-carboxamide (Intermediate 70: Step B) for (S)—N-(2-hydroxy-2-methylpropyl)-4-(2-methylpyrrolidine-1-carbonyl)thiazole-2-carboxamide and (S)-5-bromo-N-(1,1,1-trifluorobutan-2-yl)-4-(trifluoromethyl)pyridin-2-amine (Intermediate 53) for 5-bromo-N-(1-methylcyclobutyl)-4-(trifluoromethyl)pyridin-2-amine. MS (ESI): mass calcd. for $C_{25}H_{29}F_6N_5O_3S$, 593.6; m/z found, 594.2 [M+H]$^+$. $^1$H NMR (400 MHz, CDCl$_3$) δ 8.20 (s, 1H), 7.62-7.54 (m, 1H), 6.77 (s, 1H), 4.93-4.36 (m, 4H), 3.49 (d, J=6.3 Hz, 2H), 2.02-1.92 (m, 2H), 1.75 (br s, 2H), 1.67-1.59 (m, 3H), 1.49-1.41 (m, 4H), 1.32 (s, 6H), 1.07-1.01 (m, 3H).

Example 102

4-((S)-4,4-Difluoro-2-methylpyrrolidine-1-carbonyl)-N-(2-hydroxy-2-methylpropyl)-5-(6-(((S)-1,1,1-trifluorobutan-2-yl)amino)-4-(trifluoromethyl)pyridin-3-yl)thiazole-2-carboxamide

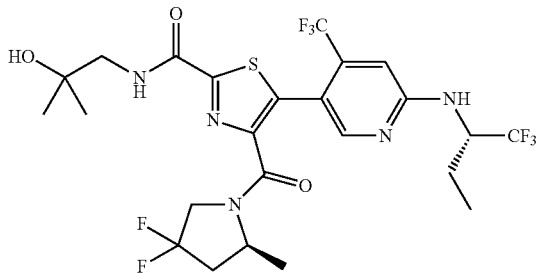 [SMILES: CC[C@H](Nc1cc(C(F)(F)F)c(-c2sc(C(=O)NCC(C)(C)O)nc2C(=O)N2CC(F)(F)C[C@@H]2C)cn1)C(F)(F)F]

The title compound was prepared as described in Example 77 substituting (S)-4-(4,4-difluoro-2-methylpyrrolidine-1-carbonyl)-N-(2-hydroxy-2-methylpropyl)thiazole-2-carboxamide (Intermediate 67) for (S)—N-(2-hydroxy-2-methylpropyl)-4-(2-methylpyrrolidine-1-carbonyl)thiazole-2-carboxamide and (S)-5-bromo-N-(1,1,1-trifluorobutan-2-yl)-4-(trifluoromethyl)pyridin-2-amine (Intermediate 53) for 5-bromo-N-(1-methylcyclobutyl)-4-(trifluoromethyl)pyridin-2-amine. MS (ESI): mass calcd. for $C_{24}H_{27}F_8N_5O_3S$, 617.6; m/z found, 618.1 [M+H]$^+$. $^1$H NMR (400 MHz, CDCl$_3$) δ 8.20 (s, 1H), 7.54-7.45 (m, 1H), 6.76 (s, 1H), 4.92-4.43 (m, 3H), 4.14-3.81 (m, 2H), 3.57-3.42 (m, 2H), 2.62-2.47 (m, 1H), 2.14-1.92 (m, 2H), 1.90-1.77 (m, 1H), 1.68-1.58 (m, 1H), 1.36 (d, J=6.3 Hz, 2H), 1.33 (d, J=3.5 Hz, 6H), 1.29 (d, J=6.6 Hz, 1H), 1.08-1.02 (m, 3H).

Example 103

(S)-4-(4,4-Difluoro-2-methylpyrrolidine-1-carbonyl)-N-(2-hydroxy-2-methylpropyl)-5-(6-(tert-pentylamino)-4-(trifluoromethyl)pyridin-3-yl)thiazole-2-carboxamide

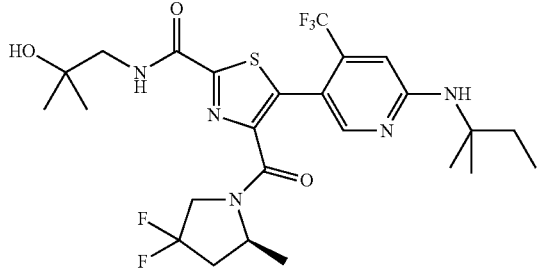 [SMILES: CCC(C)(C)Nc1cc(C(F)(F)F)c(-c2sc(C(=O)NCC(C)(C)O)nc2C(=O)N2CC(F)(F)C[C@@H]2C)cn1]

The title compound was prepared as described in Example 77 substituting (S)-4-(4,4-difluoro-2-methylpyrrolidine-1-carbonyl)-N-(2-hydroxy-2-methylpropyl)thiazole-2-carboxamide (Intermediate 67) for (S)—N-(2-hydroxy-2-methylpropyl)-4-(2-methylpyrrolidine-1-carbonyl)thiazole-2-carboxamide and 5-bromo-N-(tert-pentyl)-4-(trifluoromethyl)pyridin-2-amine (Intermediate 51) for 5-bromo-N-(1-methylcyclobutyl)-4-(trifluoromethyl)pyridin-2-amine. MS (ESI): mass calcd. for $C_{25}H_{32}F_5N_5O_3S$, 577.6; m/z found, 578.2 [M+H]$^+$. $^1$H NMR (400 MHz, CDCl$_3$) δ 8.12 (s, 1H), 7.55-7.46 (m, 1H), 6.64 (s, 1H), 4.79 (s, 1H), 4.68-4.46 (m, 1H), 4.15-3.78 (m, 2H), 3.56-3.43 (m, 2H), 2.62-2.46 (m, 1H), 2.15-1.99 (m, 1H), 1.96-1.78 (m, 3H), 1.40 (d, J=2.3 Hz, 6H), 1.36 (d, J=6.4 Hz, 2H), 1.33 (d, J=2.5 Hz, 6H), 1.29 (d, J=6.5 Hz, 1H), 0.92-0.86 (m, 3H).

Example 104

(S)—N-(2-Hydroxy-2-methylpropyl)-4-(2-methylpyrrolidine-1-carbonyl)-5-(4-(trifluoromethyl)-6-((1-(trifluoromethyl)cyclobutyl)amino)pyridin-3-yl)thiazole-2-carboxamide

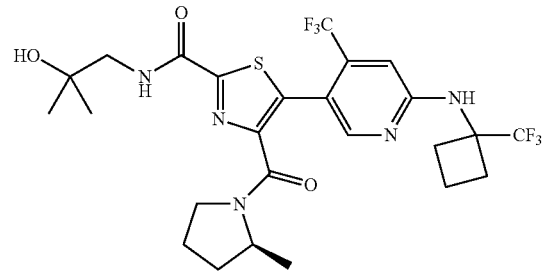 [SMILES: C[C@H]1CCCN1C(=O)c1nc(C(=O)NCC(C)(C)O)sc1-c1cnc(NC2(C(F)(F)F)CCC2)cc1C(F)(F)F]

The title compound was prepared as described in Example 77 substituting 5-bromo-4-(trifluoromethyl)-N-(1-(trifluoromethyl)cyclobutyl)pyridin-2-amine (Intermediate 52) for 5-bromo-N-(1-methylcyclobutyl)-4-(trifluoromethyl)pyridin-2-amine. MS (ESI): mass calcd. for $C_{25}H_{29}F_6N_5O_3S$, 593.6; m/z found, 594.2 [M+H]$^+$. $^1$H NMR (500 MHz, CDCl$_3$) δ 8.24 (s, 1H), 7.61-7.52 (m, 1H), 6.63 (s, 1H), 5.33 (s, 1H), 4.40-4.11 (m, 4H), 3.59-3.43 (m, 4H), 2.70-2.61 (m, 2H), 2.50-2.40 (m, 2H), 2.11-2.04 (m, 3H), 2.01-1.92 (m, 2H), 1.80-1.72 (m, 1H), 1.59-1.51 (m, 1H), 1.33-1.30 (m, 6H), 1.24 (d, J=6.3 Hz, 2H), 1.12 (d, J=6.4 Hz, 1H).

Example 105

(S)-5-(6-((2-Cyclopropylpropan-2-yl)amino)-4-(difluoromethyl)pyridin-3-yl)-N-(2-hydroxy-2-methylpropyl)-4-(2-methylpyrrolidine-1-carbonyl)thiazole-2-carboxamide

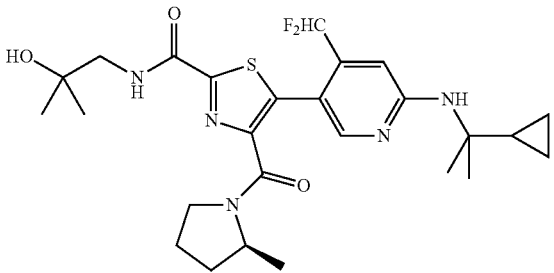 [SMILES: C[C@H]1CCCN1C(=O)c1nc(C(=O)NCC(C)(C)O)sc1-c1cnc(NC(C)(C)C2CC2)cc1C(F)F]

The title compound was prepared as described in Example 77 substituting 5-bromo-N-(2-cyclopropylpropan-2-yl)-4-

(difluoromethyl)pyridin-2-amine (Intermediate 48) for 5-bromo-N-(1-methylcyclobutyl)-4-(trifluoromethyl)pyridin-2-amine. MS (ESI): mass calcd. for $C_{26}H_{35}F_2N_5O_3S$, 535.7; m/z found, 536.2 [M+H]$^+$. $^1$H NMR (500 MHz, CDCl$_3$) δ 8.04-7.97 (m, 1H), 7.62-7.53 (m, 1H), 6.88-6.64 (m, 2H), 5.04 (s, 1H), 4.30-4.20 (m, 1H), 3.60-3.33 (m, 4H), 2.03-1.99 (m, 1H), 1.70-1.60 (m, 2H), 1.95-1.72 (m, 2H), 1.57-1.50 (m, 1H), 1.33-1.30 (m, 12H), 1.23 (d, J=6.3 Hz, 2H), 1.02 (d, J=6.4 Hz, 1H), 0.53-0.48 (m, 2H), 0.44-0.40 (m, 2H).

Example 106

(S)-5-(6-((2-Cyclopropylpropan-2-yl)amino)-4-(difluoromethyl)pyridin-3-yl)-4-(4,4-difluoro-2-methylpyrrolidine-1-carbonyl)-N-(2-hydroxy-2-methylpropyl)thiazole-2-carboxamide

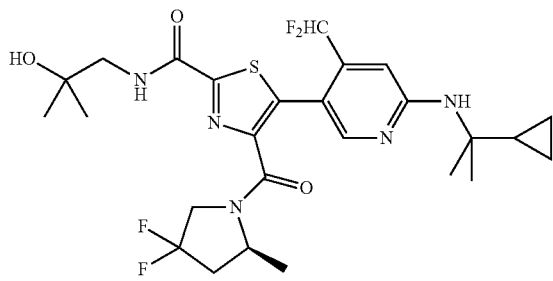 [SMILES: C[C@H]1CC(F)(F)CN1C(=O)c1nc(C(=O)NCC(C)(C)O)sc1-c1cnc(NC(C)(C)C2CC2)cc1C(F)F]

The title compound was prepared as described in Example 77 substituting (S)-4-(4,4-difluoro-2-methylpyrrolidine-1-carbonyl)-N-(2-hydroxy-2-methylpropyl)thiazole-2-carboxamide (Intermediate 67) for (S)—N-(2-hydroxy-2-methylpropyl)-4-(2-methylpyrrolidine-1-carbonyl)thiazole-2-carboxamide and 5-bromo-N-(2-cyclopropylpropan-2-yl)-4-(difluoromethyl)pyridin-2-amine (Intermediate 48) for 5-bromo-N-(1-methylcyclobutyl)-4-(trifluoromethyl)pyridin-2-amine. MS (ESI): mass calcd. for $C_{26}H_{33}F_4N_5O_3S$, 571.6; m/z found, 572.2 [M+H]$^+$. $^1$H NMR (500 MHz, CDCl$_3$) δ 8.01-7.96 (m, 1H), 7.57-7.49 (m, 1H), 6.81-6.56 (m, 2H), 5.06 (s, 1H), 4.69-4.48 (m, 1H), 4.09-3.80 (m, 2H), 3.55-3.50 (m, 1H), 3.48 (s, 4H), 3.47-3.41 (m, 1H), 2.61-2.49 (m, 1H), 2.06-1.99 (m, 1H), 1.36 (d, J=6.4 Hz, 2H), 1.32 (s, 9H), 1.22 (d, J=6.6 Hz, 1H), 1.17-1.13 (m, 1H), 0.53-0.48 (m, 2H), 0.44-0.40 (m, 2H).

Example 107

(S)-5-(6-((2-Cyclopropylpropan-2-yl)amino)-4-(trifluoromethyl)pyridin-3-yl)-4-(4,4-difluoro-2-methylpyrrolidine-1-carbonyl)-N-(2-hydroxy-2-methylpropyl)thiazole-2-carboxamide

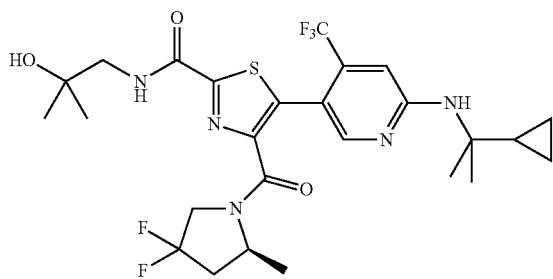 [SMILES: C[C@H]1CC(F)(F)CN1C(=O)c1nc(C(=O)NCC(C)(C)O)sc1-c1cnc(NC(C)(C)C2CC2)cc1C(F)(F)F]

The title compound was prepared as described in Example 77 substituting (S)-4-(4,4-difluoro-2-methylpyrrolidine-1-carbonyl)-N-(2-hydroxy-2-methylpropyl)thiazole-2-carboxamide (Intermediate 67) for (S)—N-(2-hydroxy-2-methylpropyl)-4-(2-methylpyrrolidine-1-carbonyl)thiazole-2-carboxamide and 5-bromo-N-(2-cyclopropylpropan-2-yl)-4-(trifluoromethyl)pyridin-2-amine (Intermediate 45) for 5-bromo-N-(1-methylcyclobutyl)-4-(trifluoromethyl)pyridin-2-amine. MS (ESI): mass calcd. for $C_{26}H_{32}F_5N_5O_3S$, 589.6; m/z found, 590.2 [M+H]$^+$. $^1$H NMR (500 MHz, CDCl$_3$) δ 8.13 (s, 1H), 7.55-7.47 (m, 1H), 6.80 (s, 1H), 5.10 (s, 1H), 4.70-4.45 (m, 1H), 4.14-3.78 (m, 2H), 3.56-3.43 (m, 2H), 2.60-2.47 (m, 1H), 2.18-2.00 (m, 1H), 1.94-1.79 (m, 1H), 1.36 (d, J=6.4 Hz, 2H), 1.34-1.31 (m, 12H), 1.30-1.25 (m, 2H), 0.54-0.47 (m, 2H), 0.44-0.38 (m, 2H).

Example 108

(S)—N-(2-Hydroxy-2-methylpropyl)-4-(2-methylpiperidine-1-carbonyl)-5-(6-(tert-pentylamino)-4-(trifluoromethyl)pyridin-3-yl)thiazole-2-carboxamide

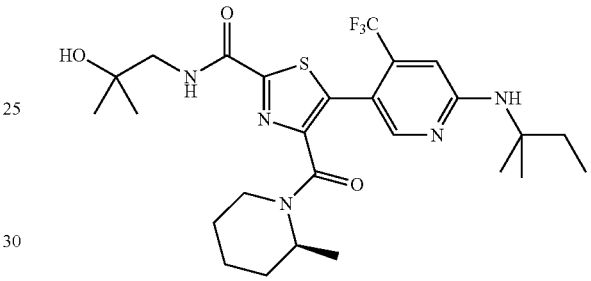

The title compound was prepared as described in Example 77 substituting (S)—N-(2-hydroxy-2-methylpropyl)-4-(2-methylpiperidine-1-carbonyl)thiazole-2-carboxamide (Intermediate 66: Step D) for (S)—N-(2-hydroxy-2-methylpropyl)-4-(2-methylpyrrolidine-1-carbonyl)thiazole-2-carboxamide and 5-bromo-N-(tert-pentyl)-4-(trifluoromethyl)pyridin-2-amine (Intermediate 51) for 5-bromo-N-(1-methylcyclobutyl)-4-(trifluoromethyl)pyridin-2-amine. MS (ESI): mass calcd. for $C_{26}H_{36}F_3N_5O_3S$, 555.7; m/z found, 556.2 [M+H]$^+$. $^1$H NMR (500 MHz, CDCl$_3$) δ 8.23-8.14 (m, 1H), 7.68-7.59 (m, 1H), 6.66 (s, 1H), 4.95-4.44 (m, 2H), 3.95-3.34 (m, 3H), 2.96-2.77 (m, 1H), 2.27-2.16 (m, 1H), 1.88-1.81 (m, 2H), 1.66-1.47 (m, 4H), 1.39 (s, 6H), 1.31 (s, 6H), 1.18-1.09 (m, 3H), 0.89-0.84 (m, 3H).

Example 109

(S)—N-(2-Hydroxy-2-methylpropyl)-4-(2-methylpyrrolidine-1-carbonyl)-5-(6-(tert-pentylamino)-4-(trifluoromethyl)pyridin-3-yl)thiazole-2-carboxamide

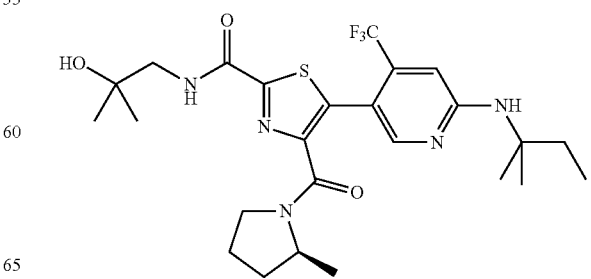

The title compound was prepared as described in Example 77 substituting 5-bromo-N-(tert-pentyl)-4-(trifluoromethyl)pyridin-2-amine (Intermediate 51) for 5-bromo-N-(1-methylcyclobutyl)-4-(trifluoromethyl)pyridin-2-amine. MS (ESI): mass calcd. for $C_{25}H_{34}F_3N_5O_3S$, 541.6; m/z found, 542.2 [M+H]$^+$. $^1$H NMR (500 MHz, CDCl$_3$) δ 8.17-8.14 (m, 1H), 7.65-7.52 (m, 1H), 6.64-6.61 (m, 1H), 4.79 (s, 1H), 4.27-4.17 (m, 1H), 3.60-3.36 (m, 4H), 2.13 (s, 1H), 2.08-2.02 (m, 1H), 1.91-1.72 (m, 4H), 1.56-1.48 (m, 1H), 1.41-1.38 (m, 6H), 1.31 (s, 6H), 1.23 (d, J=6.3 Hz, 2H), 1.10 (d, J=6.4 Hz, 1H), 0.90-0.86 (m, 3H).

Example 110

4-((S)-4,4-Difluoro-2-methylpyrrolidine-1-carbonyl)-N-(2-hydroxy-2-methylpropyl)-5-(4-(trifluoromethyl)-6-(((S)-1,1,1-trifluoropropan-2-yl)amino)pyridin-3-yl)thiazole-2-carboxamide

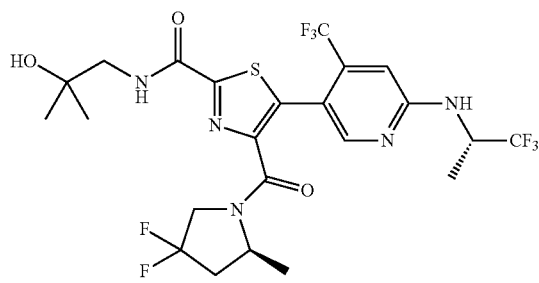 [SMILES: C[C@H](Nc1cc(C(F)(F)F)c(-c2sc(C(=O)NCC(C)(C)O)nc2C(=O)N2CC(F)(F)C[C@@H]2C)cn1)C(F)(F)F]

The title compound was prepared as described in Example 77 substituting (S)-4-(4,4-difluoro-2-methylpyrrolidine-1-carbonyl)-N-(2-hydroxy-2-methylpropyl)thiazole-2-carboxamide (Intermediate 67) for (S)—N-(2-hydroxy-2-methylpropyl)-4-(2-methylpyrrolidine-1-carbonyl)thiazole-2-carboxamide and (S)-5-bromo-4-(trifluoromethyl)-N-(1,1,1-trifluoropropan-2-yl)pyridin-2-amine (Intermediate 44) for 5-bromo-N-(1-methylcyclobutyl)-4-(trifluoromethyl)pyridin-2-amine. MS (ESI): mass calcd. for $C_{23}H_{25}F_8N_5O_3S$, 603.5; m/z found, 604.2 [M+H]$^+$. $^1$H NMR (500 MHz, CDCl$_3$) δ 8.17 (s, 1H), 7.57-7.48 (m, 1H), 6.73-6.65 (m, 1H), 5.58-5.32 (m, 1H), 5.02-4.91 (m, 1H), 4.49-3.80 (m, 3H), 3.58-3.43 (m, 2H), 2.66-2.49 (m, 1H), 2.21-2.04 (m, 2H), 1.40-1.36 (m, 5H), 1.33 (d, J=6.1 Hz, 6H), 1.29-1.26 (m, 1H).

Example 111

N-(2-Hydroxy-2-methylpropyl)-4-((S)-2-methylpyrrolidine-1-carbonyl)-5-(6-(((S)-1,1,1-trifluorobutan-2-yl)amino)-4-(trifluoromethyl)pyridin-3-yl)thiazole-2-carboxamide

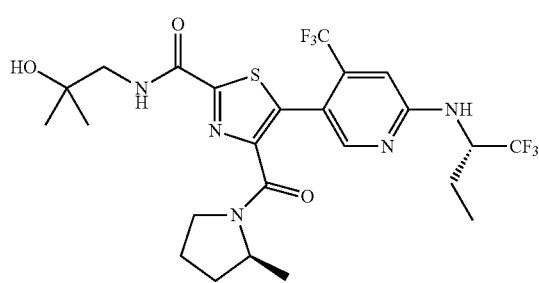 [SMILES: CC[C@H](Nc1cc(C(F)(F)F)c(-c2sc(C(=O)NCC(C)(C)O)nc2C(=O)N2CCC[C@@H]2C)cn1)C(F)(F)F]

The title compound was prepared as described in Example 77 substituting (S)-5-bromo-N-(1,1,1-trifluorobutan-2-yl)-4-(trifluoromethyl)pyridin-2-amine (Intermediate 53) for 5-bromo-N-(1-methylcyclobutyl)-4-(trifluoromethyl)pyridin-2-amine. MS (ESI): mass calcd. for $C_{24}H_{29}F_6N_5O_3S$, 581.6; m/z found, 582.2 [M+H]$^+$. $^1$H NMR (500 MHz, CDCl$_3$) δ 8.23-8.20 (m, 1H), 7.61-7.52 (m, 1H), 6.76-6.73 (m, 1H), 5.11-4.96 (m, 1H), 4.81 (s, 1H), 4.44-4.14 (m, 1H), 3.59-3.38 (m, 4H), 2.10-1.88 (m, 4H), 1.80-1.61 (m, 2H), 1.58-1.50 (m, 1H), 1.34-1.30 (m, 6H), 1.24 (d, J=6.3 Hz, 2H), 1.10 (d, J=6.4 Hz, 1H), 1.07-1.02 (m, 3H).

Example 112

N-(2-Hydroxy-2-methylpropyl)-4-((S)-2-methylpiperidine-1-carbonyl)-5-(6-(((S)-1,1,1-trifluorobutan-2-yl)amino)-4-(trifluoromethyl)pyridin-3-yl)thiazole-2-carboxamide

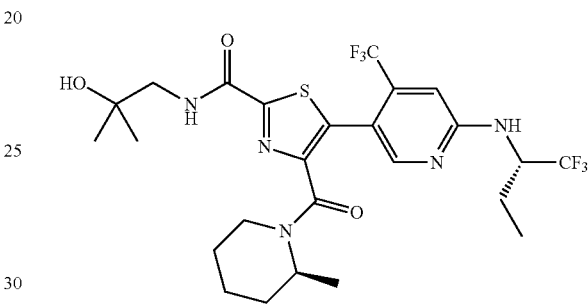

The title compound was prepared as described in Example 77 substituting (S)—N-(2-hydroxy-2-methylpropyl)-4-(2-methylpiperidine-1-carbonyl)thiazole-2-carboxamide (Intermediate 66: Step D) for (S)—N-(2-hydroxy-2-methylpropyl)-4-(2-methylpyrrolidine-1-carbonyl)thiazole-2-carboxamide and (S)-5-bromo-N-(1,1,1-trifluorobutan-2-yl)-4-(trifluoromethyl)pyridin-2-amine (Intermediate 53) for 5-bromo-N-(1-methylcyclobutyl)-4-(trifluoromethyl)pyridin-2-amine. MS (ESI): mass calcd. for $C_{25}H_{31}F_6N_5O_3S$, 595.6; m/z found, 596.2 [M+H]$^+$. $^1$H NMR (500 MHz, CDCl$_3$) δ 8.29-8.22 (m, 1H), 7.65-7.58 (m, 1H), 6.81 (s, 1H), 4.98-4.92 (m, 1H), 4.91-4.42 (m, 2H), 3.98-3.39 (m, 3H), 2.02-1.93 (m, 1H), 2.97-2.76 (m, 1H), 2.14-2.05 (m, 1H), 1.68-1.50 (m, 6H), 1.31 (s, 6H), 1.21-1.18 (m, 1H), 1.12-1.01 (m, 5H).

Example 113

(S)-5-(4-(Difluoromethyl)-6-(neopentylamino)pyridin-3-yl)-N-(2-hydroxy-2-methylpropyl)-4-(2-methylpyrrolidine-1-carbonyl)thiazole-2-carboxamide

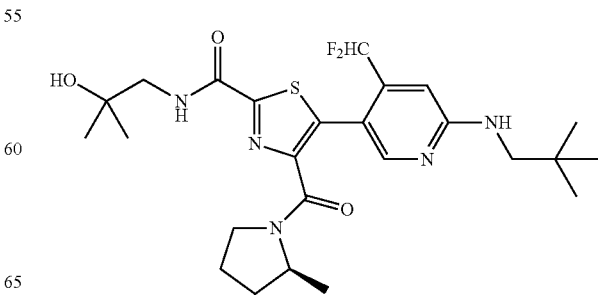

The title compound was prepared as described in Example 77 substituting 5-bromo-4-(difluoromethyl)-N-neopentylpyridin-2-amine (Intermediate 23) for 5-bromo-N-(1-methylcyclobutyl)-4-(trifluoromethyl)pyridin-2-amine. MS (ESI): mass calcd. for $C_{25}H_{35}F_2N_5O_3S$, 523.2; m/z found, 524.2 [M+H]$^+$. $^1$H NMR (500 MHz, CDCl$_3$) δ 8.03-7.97 (m, 1H), 7.64-7.53 (m, 1H), 6.99-6.65 (m, 2H), 5.05-4.95 (m, 1H), 4.32-4.17 (m, 1H), 3.60-3.35 (m, 4H), 3.19-3.12 (m, 2H), 2.31-2.17 (m, 1H), 2.06-1.88 (m, 2H), 1.78-1.72 (m, 1H), 1.65-1.50 (m, 1H), 1.31 (s, 6H), 1.22 (d, J=6.3 Hz, 2H), 1.02 (d, J=6.4 Hz, 1H), 1.01-0.98 (m, 9H).

Example 114

(S)-5-(4-(Difluoromethyl)-6-(neopentylamino)pyridin-3-yl)-N-(2-hydroxy-2-methylpropyl)-4-(2-methylpiperidine-1-carbonyl)thiazole-2-carboxamide

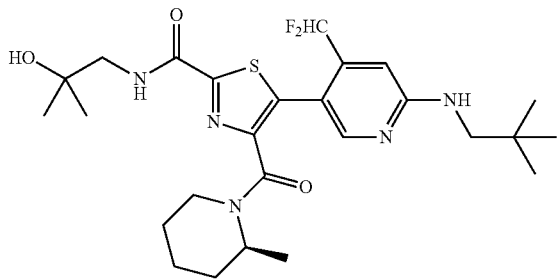

The title compound was prepared as described in Example 77 substituting (S)—N-(2-hydroxy-2-methylpropyl)-4-(2-methylpiperidine-1-carbonyl)thiazole-2-carboxamide (Intermediate 66: Step D) for (S)—N-(2-hydroxy-2-methylpropyl)-4-(2-methylpyrrolidine-1-carbonyl)thiazole-2-carboxamide and 5-bromo-4-(difluoromethyl)-N-neopentylpyridin-2-amine (Intermediate 23) for 5-bromo-N-(1-methylcyclobutyl)-4-(trifluoromethyl)pyridin-2-amine. MS (ESI): mass calcd. for $C_{26}H_{37}F_2N_5O_3S$, 537.3; m/z found, 538.3 [M+H]$^+$. $^1$H NMR (500 MHz, CDCl$_3$) δ 8.04 (s, 1H), 7.70-7.59 (m, 1H), 6.92-6.62 (m, 2H), 5.10-5.02 (m, 1H), 4.91-4.39 (m, 1H), 3.92-3.33 (m, 3H), 1.86 (s, 1H), 1.69-1.49 (m, 4H), 3.00-2.74 (m, 1H), 3.20-3.15 (m, 2H), 2.43-2.31 (m, 1H), 1.44-1.34 (m, 1H), 1.30 (s, 6H), 1.16 (d, J=6.8 Hz, 1H), 1.11 (d, J=7.0 Hz, 2H), 0.99 (s, 9H).

Example 115

(S)-4-(4,4-Difluoro-2-methylpyrrolidine-1-carbonyl)-5-(4-(difluoromethyl)-6-(neopentylamino)pyridin-3-yl)-N-(2-hydroxy-2-methylpropyl)thiazole-2-carboxamide

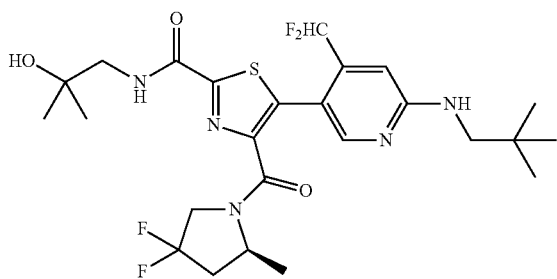

The title compound was prepared as described in Example 77 substituting (S)-4-(4,4-difluoro-2-methylpyrrolidine-1-carbonyl)-N-(2-hydroxy-2-methylpropyl)thiazole-2-carboxamide (Intermediate 67) for (S)—N-(2-hydroxy-2-methylpropyl)-4-(2-methylpyrrolidine-1-carbonyl)thiazole-2-carboxamide and 5-bromo-4-(difluoromethyl)-N-neopentylpyridin-2-amine (Intermediate 23) for 5-bromo-N-(1-methylcyclobutyl)-4-(trifluoromethyl)pyridin-2-amine. MS (ESI): mass calcd. for $C_{25}H_{33}F_4N_5O_3S$, 559.2; m/z found, 560.2 [M+H]$^+$. $^1$H NMR (500 MHz, CDCl$_3$) δ 8.03-7.96 (m, 1H), 7.57-7.47 (m, 1H), 6.89-6.57 (m, 2H), 5.03-4.95 (m, 1H), 4.69-4.46 (m, 1H), 4.11-3.81 (m, 2H), 3.56-3.42 (m, 2H), 3.16 (d, J=5.9 Hz, 2H), 2.61-2.49 (m, 1H), 2.18-1.96 (m, 2H), 1.36 (d, J=6.4 Hz, 2H), 1.34-1.31 (m, 6H), 1.22 (d, J=6.6 Hz, 1H), 1.00 (s, 9H).

Example 116

4-((1s,4s)-7-Azabicyclo[2.2.1]heptane-7-carbonyl)-5-(4-(difluoromethyl)-6-(neopentylamino)pyridin-3-yl)-N-(2-hydroxy-2-methylpropyl)thiazole-2-carboxamide

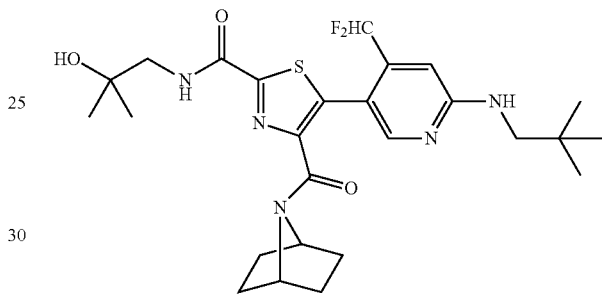

The title compound was prepared as described in Example 77 substituting 4-((1s,4s)-7-azabicyclo[2.2.1]heptane-7-carbonyl)-N-(2-hydroxy-2-methylpropyl)thiazole-2-carboxamide (Intermediate 70: Step B) for (S)—N-(2-hydroxy-2-methylpropyl)-4-(2-methylpyrrolidine-1-carbonyl)thiazole-2-carboxamide and 5-bromo-4-(difluoromethyl)-N-neopentylpyridin-2-amine (Intermediate 23) for 5-bromo-N-(1-methylcyclobutyl)-4-(trifluoromethyl)pyridin-2-amine. MS (ESI): mass calcd. for $C_{26}H_{35}F_2N_5O_3S$, 535.2; m/z found, 536.2 [M+H]$^+$. $^1$H NMR (500 MHz, CDCl$_3$) δ 8.02 (s, 1H), 7.78-7.63 (m, 1H), 6.87-6.63 (m, 2H), 5.21-5.04 (m, 1H), 4.70-4.63 (m, 1H), 4.25-4.17 (m, 1H), 3.49-3.46 (m, 2H), 3.19-3.14 (m, 2H), 2.06 (d, J=14.3 Hz, 1H), 1.80-1.71 (m, 2H), 1.59-1.51 (m, 2H), 1.47-1.39 (m, 4H), 1.30 (s, 6H), 0.99 (s, 9H).

Example 117

(S)—N-(2-Hydroxy-2-methylpropyl)-4-(2-methylpyrrolidine-1-carbonyl)-5-(4-(trifluoromethyl)-6-(((1-(trifluoromethyl)cyclobutyl)methyl)amino)pyridin-3-yl)thiazole-2-carboxamide

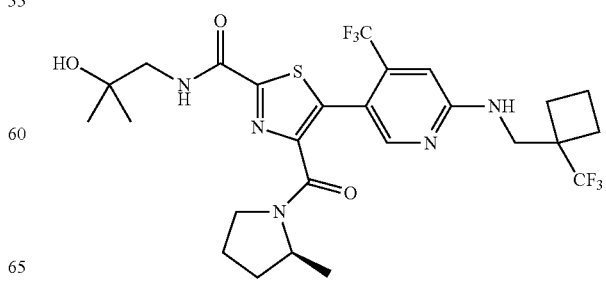

The title compound was prepared as described in Example 77 substituting 5-bromo-4-(trifluoromethyl)-N-((1-(trifluoromethyl)cyclobutyl)methyl)pyridin-2-amine (Intermediate 54) of 5-bromo-N-(1-methylcyclobutyl)-4-(trifluoromethyl)pyridin-2-amine. MS (ESI): mass calcd. for $C_{26}H_{31}F_6N_5O_3S$, 607.2; m/z found, 608.2 [M+H]$^+$. $^1$H NMR (500 MHz, CDCl$_3$) δ 8.24-8.19 (m, 1H), 7.60-7.50 (m, 1H), 6.70-6.66 (m, 1H), 5.10-4.97 (m, 1H), 4.38-4.16 (m, 1H), 3.92-3.77 (m, 2H), 3.58-3.40 (m, 4H), 2.37-2.29 (m, 2H), 2.09-1.99 (m, 4H), 1.98-1.96 (m, 1H), 1.94-1.73 (m, 2H), 1.56-1.51 (m, 1H), 1.33-1.30 (m, 6H), 1.24 (d, J=6.3 Hz, 2H), 1.12 (d, J=6.4 Hz, 1H).

Example 118

(S)-4-(4,4-Difluoro-2-methylpyrrolidine-1-carbonyl)-N-(2-hydroxy-2-methylpropyl)-5-(4-(trifluoromethyl)-6-(((1-(trifluoromethyl)cyclobutyl)methyl)amino)pyridin-3-yl)thiazole-2-carboxamide

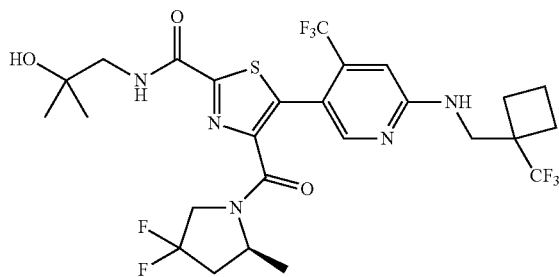 [SMILES: C[C@H]1CC(F)(F)CN1C(=O)c1nc(C(=O)NCC(C)(C)O)sc1-c1cnc(NCC2(C(F)(F)F)CCC2)cc1C(F)(F)F]

The title compound was prepared as described in Example 77 substituting (S)-4-(4,4-difluoro-2-methylpyrrolidine-1-carbonyl)-N-(2-hydroxy-2-methylpropyl)thiazole-2-carboxamide (Intermediate 67) for (S)—N-(2-hydroxy-2-methylpropyl)-4-(2-methylpyrrolidine-1-carbonyl)thiazole-2-carboxamide and 5-bromo-4-(trifluoromethyl)-N-((1-(trifluoromethyl)cyclobutyl)methyl)pyridin-2-amine (Intermediate 54) for 5-bromo-N-(1-methylcyclobutyl)-4-(trifluoromethyl)pyridin-2-amine. MS (ESI): mass calcd. for $C_{26}H_{29}F_8N_5O_3S$, 643.2; m/z found, 644.2 [M+H]$^+$. $^1$H NMR (500 MHz, CDCl$_3$) δ 8.19 (s, 1H), 7.54-7.46 (m, 1H), 6.70 (s, 1H), 5.06-4.99 (m, 1H), 4.78-4.44 (m, 1H), 4.15-3.78 (m, 4H), 3.56-3.44 (m, 2H), 2.61-2.49 (m, 1H), 2.38-2.30 (m, 2H), 2.12-1.96 (m, 5H), 1.90-1.76 (m, 1H), 1.37-1.29 (m, 9H).

Example 119

4-((1s,4s)-7-Azabicyclo[2.2.1]heptane-7-carbonyl)-N-(2-hydroxy-2-methylpropyl)-5-(4-(trifluoromethyl)-6-(((1-(trifluoromethyl)cyclobutyl)methyl)amino)pyridin-3-yl)thiazole-2-carboxamide

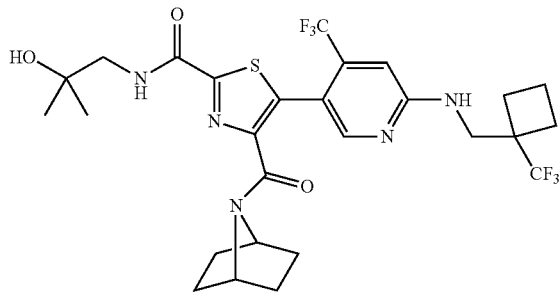 [SMILES: CC(C)(O)CNC(=O)c1nc(C(=O)N2C3CCC2CC3)c(-c2cnc(NCC3(C(F)(F)F)CCC3)cc2C(F)(F)F)s1]

The title compound was prepared as described in Example 77 substituting 4-((1s,4s)-7-azabicyclo[2.2.1]heptane-7-carbonyl)-N-(2-hydroxy-2-methylpropyl)thiazole-2-carboxamide (Intermediate 70: Step B) for (S)—N-(2-hydroxy-2-methylpropyl)-4-(2-methylpyrrolidine-1-carbonyl)thiazole-2-carboxamide and 5-bromo-4-(trifluoromethyl)-N-((1-(trifluoromethyl)cyclobutyl)methyl)pyridin-2-amine (Intermediate 54) for 5-bromo-N-(1-methylcyclobutyl)-4-(trifluoromethyl)pyridin-2-amine. MS (ESI): mass calcd. for $C_{27}H_{31}F_6N_5O_3S$, 619.2; m/z found, 620.2 [M+H]$^+$. $^1$H NMR (500 MHz, CDCl$_3$) δ 8.19 (s, 1H), 7.63-7.56 (m, 1H), 6.69 (s, 1H), 5.21-5.13 (m, 1H), 4.71-4.64 (m, 1H), 4.43-4.35 (m, 1H), 3.84 (d, J=6.1 Hz, 2H), 3.48 (d, J=6.3 Hz, 2H), 2.36-2.27 (m, 2H), 2.10 (s, 1H), 2.08-1.95 (m, 4H), 1.76 (br s, 2H), 1.70-1.65 (m, 2H), 1.48-1.41 (m, 4H), 1.32 (s, 6H).

Example 120

(S)—N-(2-Hydroxy-2-methylpropyl)-4-(2-methylpyrrolidine-1-carbonyl)-5-(6-((3,3,3-trifluoro-2,2-dimethylpropyl)amino)-4-(trifluoromethyl)pyridin-3-yl)thiazole-2-carboxamide

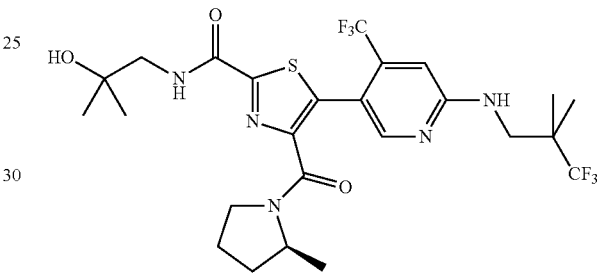

The title compound was prepared as described in Example 77 substituting 5-bromo-N-(3,3,3-trifluoro-2,2-dimethylpropyl)-4-(trifluoromethyl)pyridin-2-amine (Intermediate 55) for 5-bromo-N-(1-methylcyclobutyl)-4-(trifluoromethyl)pyridin-2-amine. MS (ESI): mass calcd. for $C_{25}H_{31}F_6N_5O_3S$, 595.2; m/z found, 596.2 [M+H]$^+$. $^1$H NMR (500 MHz, CDCl$_3$) δ 8.17 (s, 1H), 7.61-7.51 (m, 1H), 6.68-6.63 (m, 1H), 5.29-5.11 (m, 1H), 4.42-4.14 (m, 1H), 3.71-3.41 (m, 6H), 2.08-1.73 (m, 4H), 1.59-1.50 (m, 1H), 1.33-1.30 (m, 6H), 1.25 (d, J=6.3 Hz, 2H), 1.20-1.17 (m, 6H), 1.12 (d, J=6.4 Hz, 1H).

Example 121

(S)-4-(4,4-Difluoro-2-methylpyrrolidine-1-carbonyl)-N-(2-hydroxy-2-methylpropyl)-5-(6-((3,3,3-trifluoro-2,2-dimethylpropyl)amino)-4-(trifluoromethyl)pyridin-3-yl)thiazole-2-carboxamide

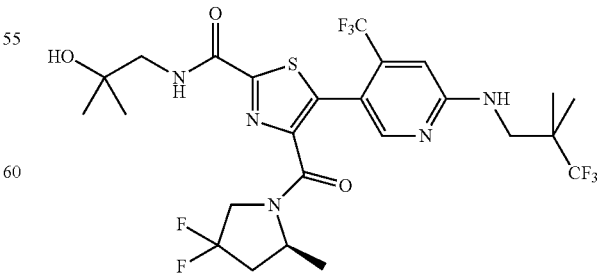

The title compound was prepared as described in Example 77 substituting (S)-4-(4,4-difluoro-2-methylpyrrolidine-1- carbonyl)-N-(2-hydroxy-2-methylpropyl)thiazole-2-carboxamide (Intermediate 67) for (S)—N-(2-hydroxy-2-methylpropyl)-4-(2-methylpyrrolidine-1-carbonyl)thiazole-2-carboxamide and 5-bromo-N-(3,3,3-trifluoro-2,2-dimethylpropyl)-4-(trifluoromethyl)pyridin-2-amine (Intermediate 55) for 5-bromo-N-(1-methylcyclobutyl)-4-(trifluoromethyl)pyridin-2-amine. MS (ESI): mass calcd. for $C_{25}H_{29}F_8N_5O_3S$, 631.2; m/z found, 632.2 [M+H]$^+$. $^1$H NMR (500 MHz, CDCl$_3$) δ 8.15 (s, 1H), 7.56-7.47 (m, 1H), 6.71-6.65 (m, 1H), 5.16-5.06 (m, 1H), 4.77-4.43 (m, 1H), 4.13-4.03 (m, 1H), 3.96-3.77 (m, 1H), 3.71-3.43 (m, 4H), 2.63-2.47 (m, 1H), 2.20-2.00 (m, 1H), 1.97-1.81 (m, 1H), 1.36 (d, J=6.4 Hz, 2H), 1.34-1.32 (m, 6H), 1.31-1.25 (m, 1H), 1.20 (s, 6H).

Example 122

4-((1s,4s)-7-Azabicyclo[2.2.1]heptane-7-carbonyl)-N-(2-hydroxy-2-methylpropyl)-5-(6-((3,3,3-trifluoro-2,2-dimethylpropyl)amino)-4-(trifluoromethyl)pyridin-3-yl)thiazole-2-carboxamide

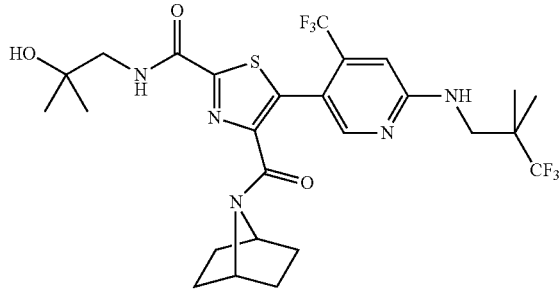 [SMILES: CC(C)(O)CNC(=O)c1nc(C(=O)N2C3CCC2CC3)c(-c2cnc(NCC(C)(C)C(F)(F)F)cc2C(F)(F)F)s1]

The title compound was prepared as described in Example 77 substituting 4-((1s,4s)-7-azabicyclo[2.2.1]heptane-7-carbonyl)-N-(2-hydroxy-2-methylpropyl)thiazole-2-carboxamide (Intermediate 70: Step B) for (S)—N-(2-hydroxy-2-methylpropyl)-4-(2-methylpyrrolidine-1-carbonyl)thiazole-2-carboxamide and 5-bromo-N-(3,3,3-trifluoro-2,2-dimethylpropyl)-4-(trifluoromethyl)pyridin-2-amine (Intermediate 55) for 5-bromo-N-(1-methylcyclobutyl)-4-(trifluoromethyl)pyridin-2-amine. MS (ESI): mass calcd. for $C_{26}H_{31}F_6N_5O_3S$, 607.2; m/z found, 608.2 [M+H]$^+$. $^1$H NMR (400 MHz, CDCl$_3$) δ 8.17 (s, 1H), 7.62-7.55 (m, 1H), 6.69 (s, 1H), 5.07 (t, J=6.5 Hz, 1H), 4.68 (s, 1H), 4.38 (s, 1H), 3.63 (d, J=6.4 Hz, 2H), 3.48 (d, J=6.3 Hz, 2H), 2.00 (s, 1H), 1.81-1.62 (m, 4H), 1.49-1.41 (m, 4H), 1.32 (s, 6H), 1.19 (s, 6H).

Example 123

(S)-5-(4-(Difluoromethyl)-6-((1-(trifluoromethyl)cyclobutyl)amino)pyridin-3-yl)-N-(2-hydroxy-2-methylpropyl)-4-(2-methylpyrrolidine-1-carbonyl)thiazole-2-carboxamide

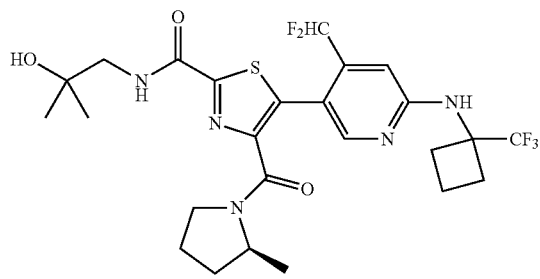 [SMILES: C[C@H]1CCCN1C(=O)c1nc(C(=O)NCC(C)(C)O)sc1-c1cnc(NC2(C(F)(F)F)CCC2)cc1C(F)F]

The title compound was prepared as described in Example 77 substituting 5-bromo-4-(difluoromethyl)-N-(1-(trifluoromethyl)cyclobutyl)pyridin-2-amine (Intermediate 56) for 5-bromo-N-(1-methylcyclobutyl)-4-(trifluoromethyl)pyridin-2-amine. MS (ESI): mass calcd. for $C_{25}H_{30}F_5N_5O_3S$, 575.2; m/z found, 576.2 [M+H]$^+$. $^1$H NMR (500 MHz, CDCl$_3$) δ 8.10-8.02 (m, 1H), 7.60-7.49 (m, 1H), 6.99-6.62 (m, 2H), 5.22 (s, 1H), 4.36-4.17 (m, 1H), 3.59-3.36 (m, 4H), 2.71-2.63 (m, 2H), 2.50-2.40 (m, 2H), 2.13-2.06 (m, 2H), 2.04-1.99 (m, 1H), 1.94-1.75 (m, 2H), 1.59-1.51 (m, 1H), 1.32 (s, 6H), 1.23 (d, J=6.3 Hz, 2H), 1.04 (d, J=6.4 Hz, 1H).

Example 124

(S)-4-(4,4-Difluoro-2-methylpyrrolidine-1-carbonyl)-5-(4-(difluoromethyl)-6-((1-(trifluoromethyl)cyclobutyl)amino)pyridin-3-yl)-N-(2-hydroxy-2-methylpropyl)thiazole-2-carboxamide

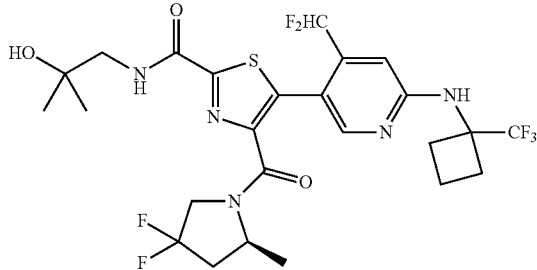 [SMILES: C[C@H]1CC(F)(F)CN1C(=O)c1nc(C(=O)NCC(C)(C)O)sc1-c1cnc(NC2(C(F)(F)F)CCC2)cc1C(F)F]

The title compound was prepared as described in Example 77 substituting (S)-4-(4,4-difluoro-2-methylpyrrolidine-1-carbonyl)-N-(2-hydroxy-2-methylpropyl)thiazole-2-carboxamide (Intermediate 67) for (S)—N-(2-hydroxy-2-methylpropyl)-4-(2-methylpyrrolidine-1-carbonyl)thiazole-2-carboxamide and 5-bromo-4-(difluoromethyl)-N-(1-(trifluoromethyl)cyclobutyl)pyridin-2-amine (Intermediate 56) for 5-bromo-N-(1-methylcyclobutyl)-4-(trifluoromethyl)pyridin-2-amine. MS (ESI): mass calcd. for $C_{25}H_{28}F_7N_5O_3S$, 611.2; m/z found, 612.2 [M+H]$^+$. $^1$H NMR (400 MHz, CDCl$_3$) δ 8.08-8.03 (m, 1H), 7.55-7.44 (m, 1H), 6.84-6.53 (m, 2H), 5.20 (s, 1H), 4.77-4.46 (m, 1H), 4.15-3.78 (m, 2H), 3.56-3.44 (m, 2H), 2.71-2.40 (m, 5H), 2.18-2.01 (m, 3H), 1.93-1.78 (m, 1H), 1.37 (d, J=6.4 Hz, 2H), 1.34-1.30 (m, 6H), 1.26-1.22 (m, 1H).

Example 125

(S)—N-(2-Hydroxy-2-methylpropyl)-4-(2-methylpyrrolidine-1-carbonyl)-5-(4-(trifluoromethyl)-6-((1-(trifluoromethyl)cyclopropyl)methyl)amino)pyridin-3-yl)thiazole-2-carboxamide

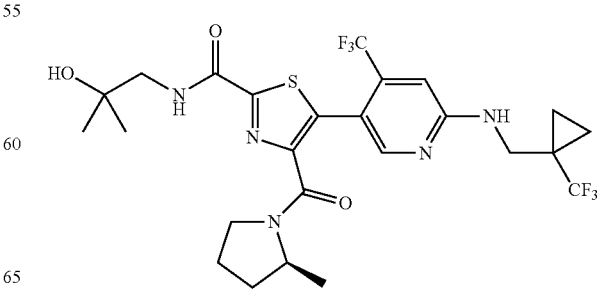

The title compound was prepared as described in Example 77 substituting 5-bromo-4-(trifluoromethyl)-N-((1-(trifluoromethyl)cyclopropyl)methyl)pyridin-2-amine (Intermediate 57) for 5-bromo-N-(1-methylcyclobutyl)-4-(trifluoromethyl)pyridin-2-amine. MS (ESI): mass calcd. for $C_{25}H_{29}F_6N_5O_3S$, 593.2; m/z found, 594.2 [M+H]$^+$. $^1$H NMR (400 MHz, CDCl$_3$) δ 8.17 (s, 1H), 7.62-7.51 (m, 1H), 6.67-6.63 (m, 1H), 5.31-5.17 (m, 1H), 4.40-4.14 (m, 1H), 3.75-3.41 (m, 6H), 2.08-1.73 (m, 4H), 1.59-1.50 (m, 1H), 1.32 (s, 6H), 1.24 (d, J=6.3 Hz, 2H), 1.12 (d, J=6.4 Hz, 1H), 1.07-1.01 (m, 2H), 0.90-0.84 (m, 2H).

Example 126

(S)-4-(4,4-Difluoro-2-methylpyrrolidine-1-carbonyl)-N-(2-hydroxy-2-methylpropyl)-5-(4-(trifluoromethyl)-6-(((1-(trifluoromethyl)cyclopropyl)methyl)amino)pyridin-3-yl)thiazole-2-carboxamide

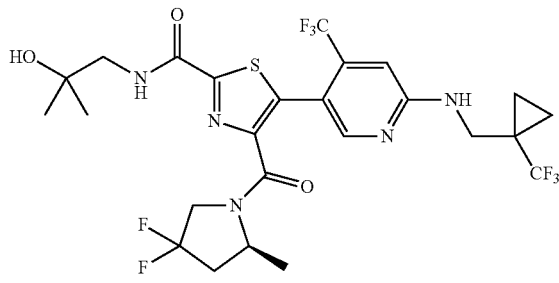 [SMILES: C[C@H]1CC(F)(F)CN1C(=O)c1nc(C(=O)NCC(C)(C)O)sc1-c1cnc(NCC2(C(F)(F)F)CC2)cc1C(F)(F)F]

The title compound was prepared as described in Example 77 substituting (S)-4-(4,4-difluoro-2-methylpyrrolidine-1-carbonyl)-N-(2-hydroxy-2-methylpropyl)thiazole-2-carboxamide (Intermediate 67) for (S)—N-(2-hydroxy-2-methylpropyl)-4-(2-methylpyrrolidine-1-carbonyl)thiazole-2-carboxamide and 5-bromo-4-(trifluoromethyl)-N-((1-(trifluoromethyl)cyclopropyl)methyl)pyridin-2-amine (Intermediate 57) for 5-bromo-N-(1-methylcyclobutyl)-4-(trifluoromethyl)pyridin-2-amine. MS (ESI): mass calcd. for $C_{25}H_{27}F_8N_5O_3S$, 629.2; m/z found, 630.1 [M+H]$^+$. $^1$H NMR (400 MHz, CDCl$_3$) δ 8.14 (s, 1H), 7.54-7.45 (m, 1H), 6.68 (s, 1H), 5.23-5.12 (m, 1H), 4.78-4.42 (m, 1H), 4.14-3.79 (m, 2H), 3.75-3.62 (m, 2H), 3.57-3.43 (m, 2H), 2.62-2.47 (m, 1H), 2.21-2.01 (m, 1H), 1.95-1.79 (m, 1H), 1.36 (d, J=6.3 Hz, 2H), 1.34-1.31 (m, 6H), 1.30 (d, J=6.2 Hz, 1H), 1.08-1.04 (m, 2H), 0.91-0.85 (m, 2H).

Example 127

5-(6-((2,2-Difluorocyclopentyl)amino)-4-(trifluoromethyl)pyridin-3-yl)-N-(2-hydroxy-2-methylpropyl)-4-((S)-2-methylpyrrolidine-1-carbonyl)thiazole-2-carboxamide

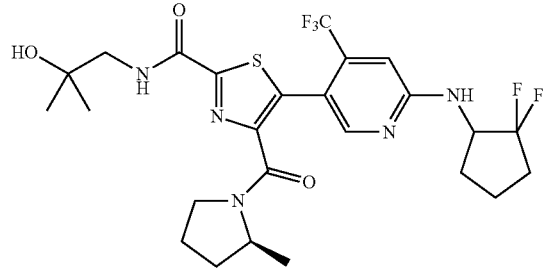 [SMILES: C[C@H]1CCCN1C(=O)c1nc(C(=O)NCC(C)(C)O)sc1-c1cnc(NC2CCCC2(F)F)cc1C(F)(F)F]

The title compound was prepared as described in Example 77 substituting 5-bromo-N-(2,2-difluorocyclopentyl)-4-(trifluoromethyl)pyridin-2-amine (Intermediate 64: Step B) for 5-bromo-N-(1-methylcyclobutyl)-4-(trifluoromethyl)pyridin-2-amine. MS (ESI): mass calcd. for $C_{25}H_{30}F_5N_5O_3S$, 575.2; m/z found, 576.2 [M+H]$^+$. $^1$H NMR (400 MHz, CDCl$_3$) δ 8.21 (s, 1H), 7.61-7.50 (m, 1H), 6.76-6.71 (m, 1H), 5.21-5.10 (m, 1H), 4.67-4.44 (m, 1H), 4.39-4.15 (m, 1H), 3.57-3.39 (m, 4H), 2.39-2.29 (m, 1H), 2.27-2.13 (m, 2H), 2.12-1.96 (m, 2H), 1.94-1.75 (m, 4H), 1.66-1.60 (m, 1H), 1.57-1.49 (m, 1H), 1.32 (s, 6H), 1.26-1.23 (m, 2H), 1.15-1.09 (m, 1H).

Example 128

5-(6-(((S*)-1-Cyclopropylpropyl)amino)-4-(trifluoromethyl)pyridin-3-yl)-N-(2-hydroxy-2-methylpropyl)-4-((S)-2-methylpyrrolidine-1-carbonyl)thiazole-2-carboxamide

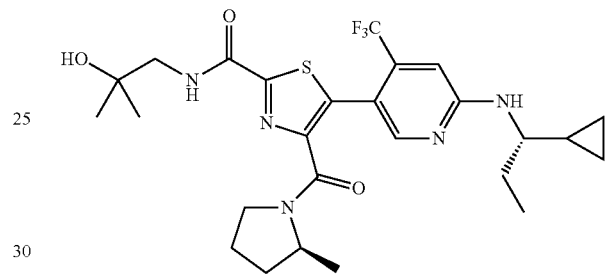

The title compound was prepared as described in Example 77 substituting 5-bromo-N-(1-cyclopropylpropyl)-4-(trifluoromethyl)pyridin-2-amine (Intermediate 24) for 5-bromo-N-(1-methylcyclobutyl)-4-(trifluoromethyl)pyridin-2-amine. A purification was performed via chiral SFC (Stationary phase: CHIRALPAK AD-H 5 μm 250×20 mm, Mobile phase: 90% CO$_2$, 10% MeOH (0.3% iPrNH$_2$), second eluting peak) to separate diastereomers. MS (ESI): mass calcd. for $C_{26}H_{34}F_3N_5O_3S$, 553.2; m/z found, 554.2 [M+H]$^+$. $^1$H NMR (400 MHz, CDCl$_3$) δ 8.13 (s, 1H), 7.65-7.51 (m, 1H), 6.60 (s, 1H), 4.96 (d, J=7.8 Hz, 1H), 4.33-4.15 (m, 1H), 3.67-3.33 (m, 5H), 3.32-3.18 (m, 1H), 2.14-1.48 (m, 5H), 1.38-1.21 (m, 9H), 1.12-1.07 (m, 1H), 1.06-0.81 (m, 4H), 0.64-0.52 (m, 1H), 0.50-0.42 (m, 1H), 0.37-0.25 (m, 2H).

Example 129

5-(6-(((R*)-1-Cyclopropylpropyl)amino)-4-(trifluoromethyl)pyridin-3-yl)-N-(2-hydroxy-2-methylpropyl)-4-((S)-2-methylpyrrolidine-1-carbonyl)thiazole-2-carboxamide

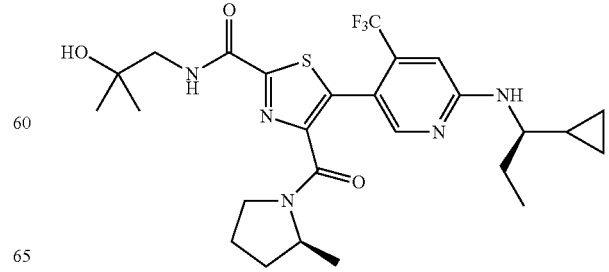

The title compound was prepared as described in Example 77 substituting 5-bromo-N-(1-cyclopropylpropyl)-4-(trifluoromethyl)pyridin-2-amine (Intermediate 24) for 5-bromo-N-(1-methylcyclobutyl)-4-(trifluoromethyl)pyridin-2-amine. A purification was performed via chiral SFC (Stationary phase: CHIRALPAK AD-H 5 μm 250×20 mm, Mobile phase: 90% $CO_2$, 10% MeOH (0.3% iPrNH$_2$), first eluting peak) to separate diastereomers. MS (ESI): mass calcd. for $C_{26}H_{34}F_3N_5O_3S$, 553.2; m/z found, 554.2 [M+H]$^+$. $^1$H NMR (400 MHz, CDCl$_3$) δ 8.14 (s, 1H), 7.63-7.52 (m, 1H), 6.60 (s, 1H), 4.90 (d, J=7.7 Hz, 1H), 4.34-4.14 (m, 1H), 3.67-3.18 (m, 5H), 3.32-3.18 (m, 1H), 2.13-1.48 (m, 5H), 1.37-1.17 (m, 9H), 1.13-0.79 (m, 5H), 0.62-0.41 (m, 2H), 0.38-0.24 (m, 2H).

Example 130

4-((1s,4s)-7-Azabicyclo[2.2.1]heptane-7-carbonyl)-5-(6-(((S*)-1-cyclopropyl)amino)-4-(trifluoromethyl)pyridin-3-yl)-N-(2-hydroxy-2-methylpropyl)thiazole-2-carboxamide

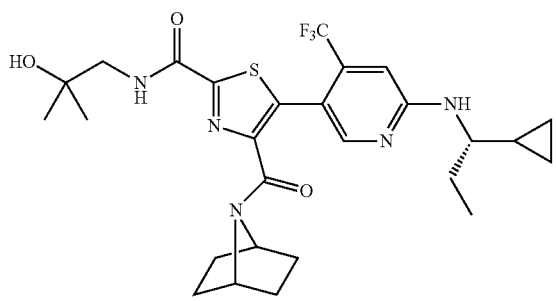 [SMILES: CC[C@H](Nc1cc(C(F)(F)F)c(-c2sc(C(=O)NCC(C)(C)O)nc2C(=O)N2C3CCC2CC3)cn1)C1CC1]

The title compound was prepared as described in Example 77 substituting 5-bromo-N-(1-cyclopropylpropyl)-4-(trifluoromethyl)pyridin-2-amine (Intermediate 24) for 5-bromo-N-(1-methylcyclobutyl)-4-(trifluoromethyl)pyridin-2-amine and 4-((1s,4s)-7-azabicyclo[2.2.1]heptane-7-carbonyl)-N-(2-hydroxy-2-methylpropyl)thiazole-2-carboxamide (Intermediate 31AC: Step B) for (S)—N-(2-hydroxy-2-methylpropyl)-4-(2-methylpyrrolidine-1-carbonyl)thiazole-2-carboxamide. A purification was performed via chiral SFC (Stationary phase: Chiralpak AS-H, 5 μm, 250×20 mm, Mobile phase: 0.5% isopropylamine, 75% $CO_2$, 25% MeOH, second eluting peak) to separate enantiomers. MS (ESI): mass calcd. for $C_{27}H_{34}F_3N_5O_3S$, 565.2; m/z found, 566.2 [M+H]$^+$. $^1$H NMR (400 MHz, CDCl$_3$) δ 8.12 (s, 1H), 7.61-7.57 (m, 1H), 6.61 (s, 1H), 4.90 (d, J=8.2 Hz, 1H), 4.68 (s, 1H), 4.30 (s, 1H), 3.48 (d, J=6.3 Hz, 2H), 3.29-3.22 (m, 1H), 1.95-1.52 (m, 5H), 1.46-1.38 (m, 4H), 1.32-1.18 (m, 7H), 1.11-0.84 (m, 5H), 0.62-0.51 (m, 1H), 0.51-0.42 (m, 1H), 0.37-0.23 (m, 2H).

Example 131

4-((1s,4s)-7-Azabicyclo[2.2.1]heptane-7-carbonyl)-5-(6-(((R*)-1-cyclopropyl)amino)-4-(trifluoromethyl)pyridin-3-yl)-N-(2-hydroxy-2-methylpropyl)thiazole-2-carboxamide

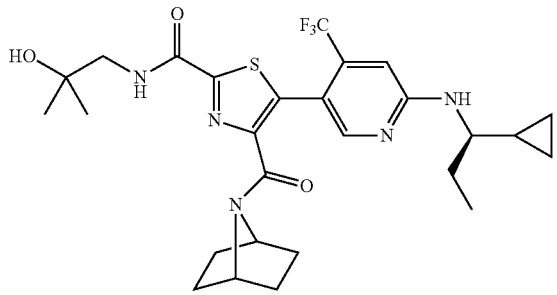 [SMILES: CC[C@@H](Nc1cc(C(F)(F)F)c(-c2sc(C(=O)NCC(C)(C)O)nc2C(=O)N2C3CCC2CC3)cn1)C1CC1]

The title compound was prepared as described in Example 77 substituting 5-bromo-N-(1-cyclopropylpropyl)-4-(trifluoromethyl)pyridin-2-amine (Intermediate 24) for 5-bromo-N-(1-methylcyclobutyl)-4-(trifluoromethyl)pyridin-2-amine and 4-((1s,4s)-7-azabicyclo[2.2.1]heptane-7-carbonyl)-N-(2-hydroxy-2-methylpropyl)thiazole-2-carboxamide (Intermediate 70: Step B) for (S)—N-(2-hydroxy-2-methylpropyl)-4-(2-methylpyrrolidine-1-carbonyl)thiazole-2-carboxamide. A purification was performed via chiral SFC (Stationary phase: Chiralpak AS-H, 5 μm, 250×20 mm, Mobile phase: 0.5% isopropylamine, 75% $CO_2$, 25% MeOH, first eluting peak) to separate enantiomers. MS (ESI): mass calcd. for $C_{27}H_{34}F_3N_5O_3S$, 565.2; m/z found, 566.2 [M+H]$^+$. $^1$H NMR (400 MHz, CDCl$_3$) δ 8.12 (s, 1H), 7.62-7.60 (m, 1H), 6.62 (s, 1H), 4.93 (d, J=8.2 Hz, 1H), 4.68 (s, 1H), 4.29 (s, 1H), 3.48 (d, J=6.3 Hz, 2H), 3.33-3.20 (m, 1H), 2.13-1.51 (m, 5H), 1.47-1.41 (m, 4H), 1.32-1.18 (m, 7H), 1.04-0.80 (m, 5H), 0.63-0.52 (m, 1H), 0.52-0.40 (m, 1H), 0.37-0.24 (m, 2H).

Example 132

(S)—N-(2-Hydroxy-2-methylpropyl)-4-(2-methylpyrrolidine-1-carbonyl)-5-(6-(((1,1,1-trifluoro-2-methylpropan-2-yl)amino)-4-(trifluoromethyl)pyridin-3-yl)thiazole-2-carboxamide

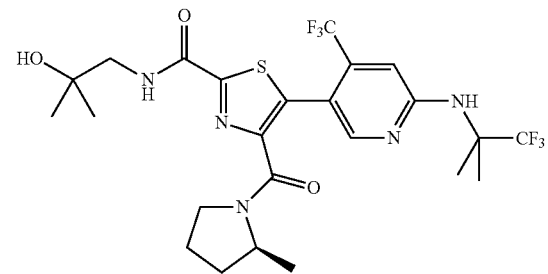 [SMILES: C[C@H]1CCCN1C(=O)c1nc(C(=O)NCC(C)(C)O)sc1-c1cnc(NC(C)(C)C(F)(F)F)cc1C(F)(F)F]

The title compound was prepared as described in Example 77 substituting 5-bromo-N-(1,1,1-trifluoro-2-methylpropan-2-yl)-4-(trifluoromethyl)pyridin-2-amine (Intermediate 58) for 5-bromo-N-(1-methylcyclobutyl)-4-(trifluoromethyl)pyridin-2-amine. MS (ESI): mass calcd. for $C_{24}H_{29}F_6N_5O_3S$, 581.6; m/z found, 582.2 [M+H]$^+$. $^1$H NMR (500 MHz, CDCl$_3$) δ 8.23-8.21 (m, 1H), 7.59-7.52 (m, 1H), 6.79 (s, 1H), 4.94-4.92 (m, 1H), 4.41-4.33 (m, 0.3H), 4.24-4.14 (m, 0.7H), 3.66-3.39 (m, 4H), 2.10-2.03 (m, 1H), 2.11-1.82 (m, 3H), 1.82-1.62 (m, 6H), 1.60-1.50 (m, 1H), 1.41-1.27 (m, 6H), 1.24 (d, J=6.3 Hz, 2.3H), 1.13 (d, J=6.4 Hz, 0.7H).

Example 133

(S)-5-(6-(tert-Butylamino)-4-(difluoromethyl)pyridin-3-yl)-N-((1-hydroxycyclobutyl)methyl)-4-(2-methylpyrrolidine-1-carbonyl)thiazole-2-carboxamide

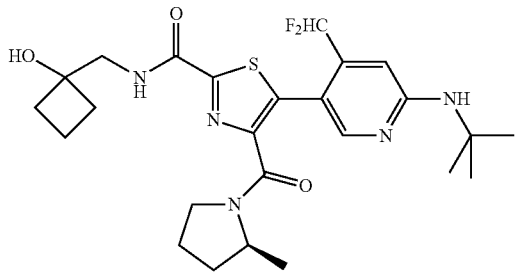 [SMILES: C[C@H]1CCCN1C(=O)c1nc(C(=O)NCC2(O)CCC2)sc1-c1cnc(NC(C)(C)C)cc1C(F)F]

The title compound was prepared as described in Example 77 substituting 5-bromo-N-(tert-butyl)-4-(difluoromethyl)pyridin-2-amine (Intermediate 59) for 5-bromo-N-(1-methylcyclobutyl)-4-(trifluoromethyl)pyridin-2-amine and (S)—N-((1-hydroxycyclobutyl)methyl)-4-(2-methylpyrrolidine-1-carbonyl)thiazole-2-carboxamide (Intermediate 73: Step C) for (S)—N-(2-hydroxy-2-methylpropyl)-4-(2-methylpyrrolidine-1-carbonyl)thiazole-2-carboxamide. MS (ESI): mass calcd. for $C_{25}H_{33}F_2N_5O_3S$, 521.6; m/z found, 522.2 [M+H]$^+$. $^1$H NMR (400 MHz, CDCl$_3$) δ 8.04-7.99 (m, 1H), 7.61-7.52 (m, 1H), 7.03-6.60 (m, 2H), 4.84 (s, 1H), 4.31-4.09 (m, 1.3H), 3.76-3.52 (m, 2.7H), 3.50-3.30 (m, 1H), 2.77-2.63 (m, 1H), 2.23-1.49 (m, 9H), 1.46 (s, 9H), 1.32-1.18 (m, 3H), 1.01 (d, J=6.4 Hz, 1H).

Example 134

(S)-5-(6-(tert-Butylamino)-4-(trifluoromethyl)pyridin-3-yl)-N-((1-hydroxycyclobutyl)methyl)-4-(2-methylpyrrolidine-1-carbonyl)thiazole-2-carboxamide

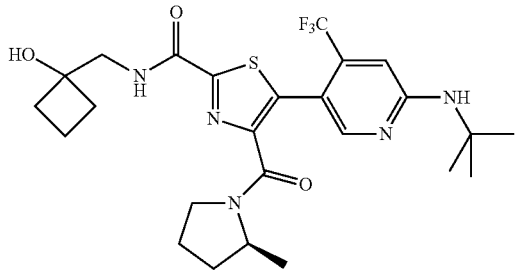 [SMILES: C[C@H]1CCCN1C(=O)c1nc(C(=O)NCC2(O)CCC2)sc1-c1cnc(NC(C)(C)C)cc1C(F)(F)F]

The title compound was prepared as described in Example 77 substituting 5-bromo-N-(tert-butyl)-4-(trifluoromethyl)pyridin-2-amine (Intermediate 41: Step B) for 5-bromo-N-(1-methylcyclobutyl)-4-(trifluoromethyl)pyridin-2-amine and (S)—N-((1-hydroxycyclobutyl)methyl)-4-(2-methylpyrrolidine-1-carbonyl)thiazole-2-carboxamide (Intermediate 73: Step C) for (S)—N-(2-hydroxy-2-methylpropyl)-4-(2-methylpyrrolidine-1-carbonyl)thiazole-2-carboxamide. MS (ESI): mass calcd. for $C_{25}H_{32}F_3N_5O_3S$, 539.6; m/z found, 540.2 [M+H]$^+$. $^1$H NMR (500 MHz, CDCl$_3$) δ 8.17 (s, 1H), 7.63-7.54 (m, 1H), 6.63 (s, 1H), 4.90 (s, 1H), 4.30-4.15 (m, 1H), 3.74-3.50 (m, 2.5H), 3.49-3.34 (m, 1.5H), 2.90-2.75 (m, 1H), 2.21-1.48 (m, 10H), 1.45 (s, 9H), 1.23 (d, J=6.3 Hz, 2.3H), 1.09 (d, J=6.4 Hz, 0.7H).

Example 135

4-((S)-4,4-Difluoro-2-methylpyrrolidine-1-carbonyl)-5-(4-difluoromethyl)-6-(((S)-1,1,1-trifluoropropan-2-yl)amino)pyridin-3-yl)-N-(2-hydroxy-2-methylpropyl)thiazole-2-carboxamide

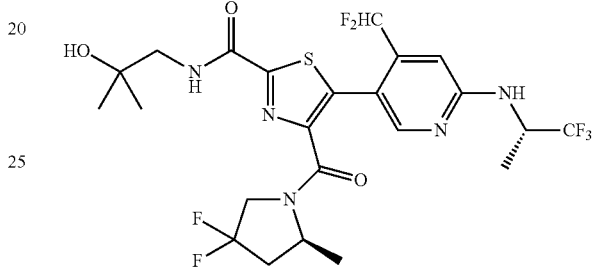

The title compound was prepared as described in Example 77 substituting (S)-5-bromo-4-(difluoromethyl)-N-(1,1,1-trifluoropropan-2-yl)pyridin-2-amine (Intermediate 60) for 5-bromo-N-(1-methylcyclobutyl)-4-(trifluoromethyl)pyridin-2-amine and (S)-4-(4,4-difluoro-2-methylpyrrolidine-1-carbonyl)-N-(2-hydroxy-2-methylpropyl)thiazole-2-carboxamide (Intermediate 67) for (S)—N-(2-hydroxy-2-methylpropyl)-4-(2-methylpyrrolidine-1-carbonyl)thiazole-2-carboxamide. MS (ESI): mass calcd. for $C_{23}H_{26}F_7N_5O_3S$, 585.5; m/z found, 586.1 [M+H]$^+$. $^1$H NMR (400 MHz, CDCl$_3$) δ 8.06 (d, J=13.1 Hz, 1H), 7.55-7.47 (m, 1H), 6.90-6.52 (m, 2H), 5.04-4.71 (m, 2.3H), 4.55-4.46 (m, 0.7H), 4.20-3.77 (m, 2H), 3.60-3.40 (m, 2H), 2.71-2.47 (m, 1H), 2.26-2.00 (m, 1H), 1.85 (d, J=35.4 Hz, 1H), 1.46-1.21 (m, 12H).

Example 136

4-((1s,4s)-7-Azabicyclo[2.2.1]heptane-7-carbonyl)-5-(4-difluoromethyl)-6-(((S)-1,1,1-trifluoropropan-2-yl)amino)pyridin-3-yl)-N-(2-hydroxy-2-methylpropyl)thiazole-2-carboxamide

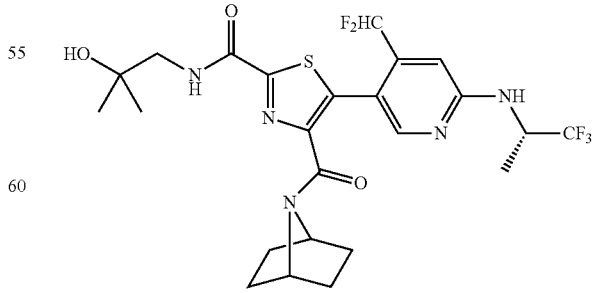

The title compound was prepared as described in Example 77 substituting (S)-5-bromo-4-(difluoromethyl)-N-(1,1,1- trifluoropropan-2-yl)pyridin-2-amine (Intermediate 60) for 5-bromo-N-(1-methylcyclobutyl)-4-(trifluoromethyl)pyridin-2-amine and 4-((1s,4s)-7-azabicyclo[2.2.1]heptane-7-carbonyl)-N-(2-hydroxy-2-methylpropyl)thiazole-2-carboxamide (Intermediate 70: Step B) for (S)—N-(2-hydroxy-2-methylpropyl)-4-(2-methylpyrrolidine-1-carbonyl)thiazole-2-carboxamide. MS (ESI): mass calcd. for $C_{24}H_{28}F_5N_5O_3S$, 561.6; m/z found, 562.1 [M+H]$^+$. $^1$H NMR (400 MHz, CDCl$_3$) δ 8.07 (s, 1H), 7.62-7.56 (m, 1H), 6.76 (d, J=12.2 Hz, 2H), 5.02-4.86 (m, 2H), 4.68 (t, J=4.7 Hz, 1H), 4.37 (t, J=4.6 Hz, 1H), 3.49 (d, J=6.2 Hz, 2H), 2.02 (s, 1H), 1.83-1.60 (m, 4H), 1.53-1.38 (m, 7H), 1.32 (s, 6H).

Example 137

4-((1s,4s)-7-Azabicyclo[2.2.1]heptane-7-carbonyl)-5-(6-((dicyclopropylmethyl)amino)-4-(trifluoromethyl)pyridin-3-yl)-N-(2-hydroxy-2-methypropyl)thiazole-2-carboxamide

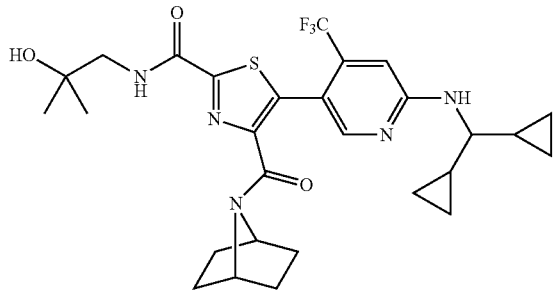 [SMILES: CC(C)(O)CNC(=O)c1nc(C(=O)N2C3CCC2CC3)c(-c2cnc(NC(C3CC3)C3CC3)cc2C(F)(F)F)s1]

The title compound was prepared as described in Example 77 substituting 5-bromo-N-(dicyclopropylmethyl)-4-(trifluoromethyl)pyridin-2-amine (Intermediate 25) for 5-bromo-N-(1-methylcyclobutyl)-4-(trifluoromethyl)pyridin-2-amine and 4-((1s,4s)-7-azabicyclo[2.2.1]heptane-7-carbonyl)-N-(2-hydroxy-2-methylpropyl)thiazole-2-carboxamide (Intermediate 70: Step B) for (S)—N-(2-hydroxy-2-methylpropyl)-4-(2-methylpyrrolidine-1-carbonyl)thiazole-2-carboxamide. MS (ESI): mass calcd. for $C_{28}H_{34}F_3N_5O_3S$, 577.7; m/z found, 578.2 [M+H]$^+$. $^1$H NMR (400 MHz, CDCl$_3$) δ 8.12 (s, 1H), 7.63-7.57 (m, 1H), 6.64 (s, 1H), 4.95 (d, J=8.0 Hz, 1H), 4.69 (s, 1H), 4.30 (s, 1H), 3.50-3.47 (m, 2H), 3.24 (q, J=7.5 Hz, 1H), 2.06-1.95 (m, 1H), 1.82-1.70 (m, 2H), 1.65-1.55 (m, 2H), 1.50-1.40 (m, 4H), 1.32 (s, 6H), 1.05-0.95 (m, 2H), 0.61-0.28 (m, 8H).

Example 138

(S)-5-(6-((Dicyclopropylmethyl)amino)-4-(trifluoromethyl)pyridin-3-yl)-4-(4,4-difluoro-2-methylpyrrolidine-1-carbonyl)-N-(2-hydroxy-2-methylpropyl)thiazole-2-carboxamide

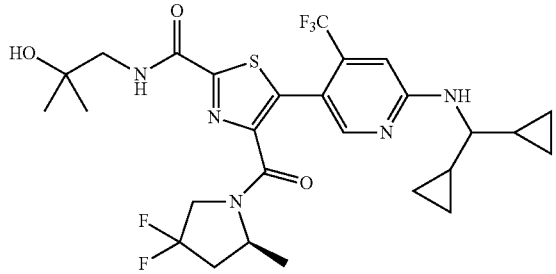 [SMILES: C[C@H]1CC(F)(F)CN1C(=O)c1nc(C(=O)NCC(C)(C)O)sc1-c1cnc(NC(C2CC2)C2CC2)cc1C(F)(F)F]

The title compound was prepared as described in Example 77 substituting 5-bromo-N-(dicyclopropylmethyl)-4-(trifluoromethyl)pyridin-2-amine (Intermediate 25) for 5-bromo-N-(1-methylcyclobutyl)-4-(trifluoromethyl)pyridin-2-amine and (S)-4-(4,4-difluoro-2-methylpyrrolidine-1-carbonyl)-N-(2-hydroxy-2-methylpropyl)thiazole-2-carboxamide (Intermediate 67) for (S)—N-(2-hydroxy-2-methylpropyl)-4-(2-methylpyrrolidine-1-carbonyl)thiazole-2-carboxamide. MS (ESI): mass calcd. for $C_{27}H_{32}F_5N_5O_3S$, 601.6; m/z found, 602.2 [M+H]$^+$. $^1$H NMR (400 MHz, CDCl$_3$) δ 8.10 (s, 1H), 7.49 (s, 1H), 6.64 (s, 1H), 4.96 (d, J=7.9 Hz, 1H), 4.72-4.64 (m, 0.3H), 4.52-4.45 (m, 0.7H), 4.20-3.79 (m, 2H), 3.56-3.44 (m, 2H), 3.23 (q, J=7.4 Hz, 1H), 2.65-2.45 (m, 1H), 2.23-1.98 (m, 1H), 1.90-1.80 (m, 1H), 1.43-1.21 (m, 9H), 1.05-0.95 (m, 2H), 0.61-0.28 (m, 8H).

Example 139

(S)-5-(6-((Dicyclopropylmethyl)amino)-4-(trifluoromethyl)pyridin-3-yl)-N-(2-hydroxy-2-methylpropyl)-4-(2-methylpyrrolidine-1-carbonyl)thiazole-2-carboxamide

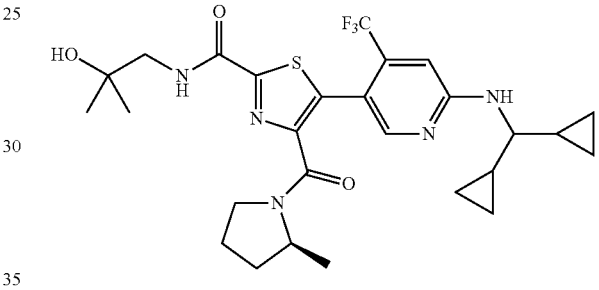

The title compound was prepared as described in Example 77 substituting 5-bromo-N-(dicyclopropylmethyl)-4-(trifluoromethyl)pyridin-2-amine (Intermediate 25) for 5-bromo-N-(1-methylcyclobutyl)-4-(trifluoromethyl)pyridin-2-amine. MS (ESI): mass calcd. for $C_{27}H_{34}F_3N_5O_3S$, 565.6; m/z found, 566.2 [M+H]$^+$. $^1$H NMR (400 MHz, CDCl$_3$) δ 8.13 (d, J=1.7 Hz, 1H), 7.59-7.54 (m, 1H), 6.63 (s, 1H), 4.95 (d, J=8.1 Hz, 1H), 4.32-4.17 (m, 1H), 3.68-3.34 (m, 4H), 3.26-3.19 (m, 1H), 2.13-1.68 (m, 4H), 1.63-1.47 (s, 1H), 1.32 (s, 6H), 1.24 (d, J=6.3 Hz, 2H), 1.11 (d, J=6.4 Hz, 1H), 1.06-0.93 (m, 2H), 0.64-0.27 (m, 8H).

Example 140

4-((1s,4s)-7-Azabicyclo[2.2.1]heptane-7-carbonyl)-N-(2-hydroxy-2-methylpropyl)-5-(6-((1-methylcyclobutyl)amino)-4-(trifluoromethyl)pyridin-3-yl)thiazole-2-carboxamide

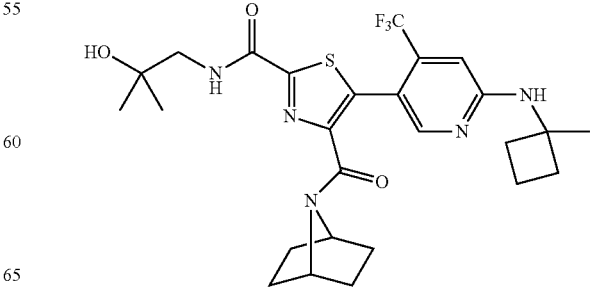

The title compound was prepared as described in Example 77 substituting 4-((1s,4s)-7-azabicyclo[2.2.1]heptane-7-carbonyl)-N-(2-hydroxy-2-methylpropyl)thiazole-2-carboxamide (Intermediate 70: Step B) for (S)—N-(2-hydroxy-2-methylpropyl)-4-(2-methylpyrrolidine-1-carbonyl)thiazole-2-carboxamide. MS (ESI): mass calcd. for $C_{26}H_{32}F_3N_5O_3S$, 551.6; m/z found, 552.2 [M+H]$^+$. $^1$H NMR (500 MHz, CDCl$_3$) δ 8.16 (s, 1H), 7.62-7.55 (m, 1H), 6.51 (s, 1H), 5.20 (s, 1H), 4.69 (s, 1H), 4.31 (s, 1H), 3.48 (d, J=6.3 Hz, 2H), 2.30-2.24 (m, 2H), 2.16-2.14 (m, 2H), 2.07-1.88 (m, 3H), 1.76 (s, 2H), 1.65-1.57 (m, 2H), 1.54 (s, 3H), 1.49-1.41 (m, 4H), 1.32 (s, 6H).

Example 141

(S)-4-(4,4-Difluoro-2-methylpyrrolidine-1-carbonyl)-N-(2-hydroxy-2-methylpropyl)-5-(6-((1-methylcyclobutyl)amino)-4-(trifluoromethyl)pyridin-3-yl)thiazole-2-carboxamide

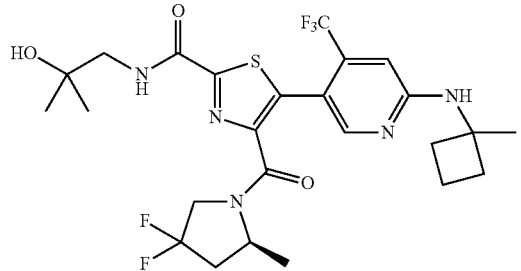 [SMILES: C[C@H]1CC(F)(F)CN1C(=O)c1nc(C(=O)NCC(C)(C)O)sc1-c1cnc(NC2(C)CCC2)cc1C(F)(F)F]

The title compound was prepared as described in Example 77 substituting (S)-4-(4,4-difluoro-2-methylpyrrolidine-1-carbonyl)-N-(2-hydroxy-2-methylpropyl)thiazole-2-carboxamide (Intermediate 67) for (S)—N-(2-hydroxy-2-methylpropyl)-4-(2-methylpyrrolidine-1-carbonyl)thiazole-2-carboxamide. MS (ESI): mass calcd. for $C_{25}H_{30}F_5N_5O_3S$, 575.6; m/z found, 576.2 [M+H]$^+$. $^1$H NMR (500 MHz, CDCl$_3$) δ 8.14 (s, 1H), 7.54-7.48 (m, 1H), 6.51 (s, 1H), 5.24 (s, 1H), 4.69-4.66 (m, 0.3H), 4.51-4.47 (m, 0.7H), 4.12-4.01 (m, 1H), 3.95-3.76 (m, 1H), 3.58-3.41 (m, 2H), 2.63-2.47 (m, 1H), 2.31-2.25 (m, 2H), 2.20-1.84 (m, 6H), 1.55 (s, 3H), 1.40-1.23 (m, 9H).

Example 142

5-(6-(((S)-1-Cyclopropylethyl)amino)-4-(trifluormethyl)pyridin-3-yl)-4-((S)-4,4-difluoro-2-methylpyrrolidine-1-carbonyl)-N-(2-hydroxy-2-methylpropyl)thiazole-2-carboxamide

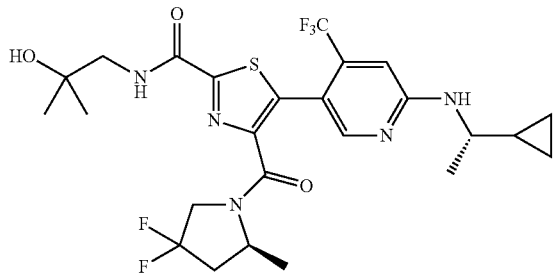

The title compound was prepared as described in Example 77 substituting (S)-5-bromo-N-(1-cyclopropylethyl)-4-(trifluoromethyl)pyridin-2-amine (Intermediate 18) for 5-bromo-N-(1-methylcyclobutyl)-4-(trifluoromethyl)pyridin-2-amine and (S)-4-(4,4-difluoro-2-methylpyrrolidine-1-carbonyl)-N-(2-hydroxy-2-methylpropyl)thiazole-2-carboxamide (Intermediate 67) for (S)—N-(2-hydroxy-2-methylpropyl)-4-(2-methylpyrrolidine-1-carbonyl)thiazole-2-carboxamide. MS (ESI): mass calcd. for $C_{25}H_{30}F_5N_5O_3S$, 575.6; m/z found, 576.2 [M+H]$^+$. $^1$H NMR (500 MHz, CDCl$_3$) δ 8.12 (s, 1H), 7.53-7.49 (m, 1H), 6.61 (s, 1H), 5.03 (d, J=7.4 Hz, 1H), 4.75-4.65 (m, 0.2H) 4.51-4.46 (m, 0.8H), 4.16-4.00 (m, 1H), 3.93-3.80 (m, 1H), 3.57-3.33 (m, 3H), 2.65-2.46 (m, 1H), 2.23-1.81 (m, 2H), 1.37-1.28 (m, 12H), 1.00-0.92 (m, 1H), 0.62-0.44 (m, 2H), 0.41-0.24 (m, 2H).

Example 143

(S)-5-(6-(tert-Butylamino)-4-(difluoromethyl)pyridin-3-yl)-4-(4,4-difluoro-2-methylpyrrolidine-1-carbonyl)-N-(2-hydroxy-2-methylpropyl)thiazole-2-carboxamide

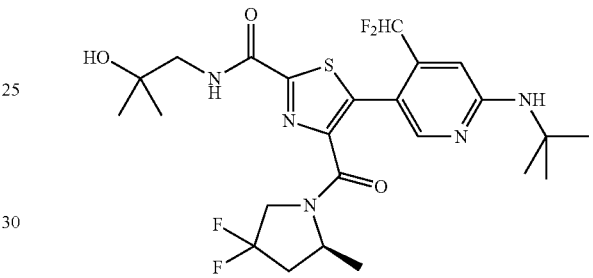

The title compound was prepared as described in Example 77 substituting 5-bromo-N-(tert-butyl)-4-(difluoromethyl)pyridin-2-amine (Intermediate 59) for 5-bromo-N-(1-methylcyclobutyl)-4-(trifluoromethyl)pyridin-2-amine and (S)-4-(4,4-difluoro-2-methylpyrrolidine-1-carbonyl)-N-(2-hydroxy-2-methylpropyl)thiazole-2-carboxamide (Intermediate 67) for (S)—N-(2-hydroxy-2-methylpropyl)-4-(2-methylpyrrolidine-1-carbonyl)thiazole-2-carboxamide. MS (ESI): mass calcd. for $C_{24}H_{31}F_4N_5O_3S$, 545.6; m/z found, 546.2 [M+H]$^+$. $^1$H NMR (500 MHz, CDCl$_3$) δ 8.02-7.99 (m, 1H), 7.52-7.48 (m, 1H), 6.90-6.34 (m, 2H), 4.85 (s, 1H), 4.72-4.61 (m, 0.3H), 4.58-4.46 (m, 0.7H), 4.09-4.00 (m, 1H), 3.92-3.85 (m, 1H), 3.55-3.43 (m, 2H), 2.60-2.53 (m, 1H), 2.15-2.05 (m, 1H), 1.90-1.82 (m, 1H), 1.46-1.44 (m, 10.5H), 1.41-1.17 (m, 7.5H).

Example 144

5-(4-Difluoromethyl)-6-(((S)-1,1,1-trifluoropropan-2-yl)amino)pyridin-3-yl)-N-(2-hydroxy-2-methylpropyl)-4-((S)-2-methylpiperidine-1-carbonyl)thiazole-2-carboxamide

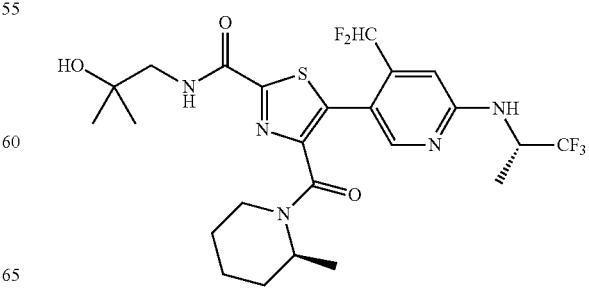

The title compound was prepared as described in Example 77 substituting (S)-5-bromo-4-(difluoromethyl)-N-(1,1,1-trifluoropropan-2-yl)pyridin-2-amine (Intermediate 60) for 5-bromo-N-(1-methylcyclobutyl)-4-(trifluoromethyl)pyridin-2-amine and (S)—N-(2-hydroxy-2-methylpropyl)-4-(2-methylpiperidine-1-carbonyl)thiazole-2-carboxamide (Intermediate 1AB, Step D) for (S)—N-(2-hydroxy-2-methylpropyl)-4-(2-methylpyrrolidine-1-carbonyl)thiazole-2-carboxamide. MS (ESI): mass calcd. for $C_{24}H_{30}F_5N_5O_3S$, 563.6; m/z found, 564.2 [M+H]$^+$. $^1$H NMR (500 MHz, CDCl$_3$) δ 8.10 (s, 1H), 7.63-7.56 (m, 1H), 6.96-6.62 (m, 2H), 5.03-4.83 (m, 2.5H), 4.43 (d, J=12.8 Hz, 0.5H), 3.95-3.87 (m, 0.5H), 3.50-3.46 (m, 2H), 3.38 (d, J=13.5 Hz, 0.5H), 3.06-2.90 (m, 0.5H), 2.82-2.77 (m, 0.5H), 2.14-1.97 (m, 1H), 1.73-1.49 (m, 3H), 1.45-1.41 (m, 4H), 1.31 (s, 7H), 1.20-1.10 (m, 4H).

Example 145

5-(4-(Difluoromethyl)-6-(((S)-1,1,1-trifluoropropan-2-yl)amino)pyridin-3-yl)-N-(2-hydroxy-2-methylpropyl)-4-((S)-2-methylpyrrolidine-1-carbonyl)thiazole-2-carboxamide

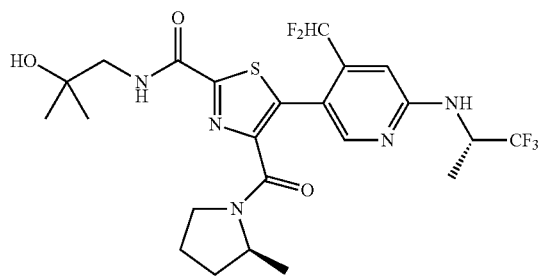

The title compound was prepared as described in Example 77 substituting (S)-5-bromo-4-(difluoromethyl)-N-(1,1,1-trifluoropropan-2-yl)pyridin-2-amine (Intermediate 60) for 5-bromo-N-(1-methylcyclobutyl)-4-(trifluoromethyl)pyridin-2-amine. MS (ESI): mass calcd. for $C_{23}H_{28}F_5N_5O_3S$, 549.6; m/z found, 550.2 [M+H]$^+$. $^1$H NMR (400 MHz, CDCl$_3$) δ 8.09 (s, 0.7H), 8.04 (s, 0.3H), 7.60-7.50 (m, 1H), 7.06-6.60 (m, 2H), 5.02-4.79 (m, 2H), 4.39-4.36 (m, 0.3H), 4.26-4.15 (m, 0.7H), 3.65-3.35 (m, 4H), 2.13-1.48 (m, 5H), 1.42 (d, J=6.8 Hz, 3H), 1.32 (s, 6H), 1.23 (d, J=6.3 Hz, 2H), 1.04 (d, J=6.4 Hz, 1H).

Example 146

(S)-5-(5-Cyano-6-(cyclohexylamino)pyridin-3-yl)-N-(2-hydroxy-2-methylpropyl)-4-(2-methylpyrrolidine-1-carbonyl)thiazole-2-carboxamide

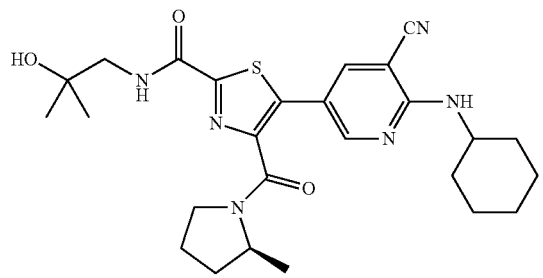 [SMILES: C[C@H]1CCCN1C(=O)c1nc(C(=O)NCC(C)(C)O)sc1-c1cnc(NC2CCCCC2)c(C#N)c1]

The title compound was prepared as described in Example 77 substituting 5-bromo-2-(cyclohexylamino)nicotinonitrile (Intermediate 9) for 5-bromo-N-(1-methylcyclobutyl)-4-(trifluoromethyl)pyridin-2-amine. MS (ESI) mass calcd for $C_{26}H_{34}N_6O_3S$ 510.2 m/z: found 511.2 [M+H]$^+$. $^1$H NMR (500 MHz, CDCl$_3$) δ 8.43 (d, J=2.5 Hz, 1H), 7.92-7.88 (m, 1H), 7.63-7.54 (m, 1H), 5.29-5.23 (m, 1H), 4.39-3.96 (m, 2H), 3.72-3.21 (m, 4H), 2.39-2.30 (m, 1H), 2.12-2.06 (m, 1H), 2.03-1.98 (m, 1H), 1.94-1.86 (m, 1H), 1.82-1.75 (m, 3H), 1.70-1.65 (m, 1H), 1.64-1.57 (m, 1H), 1.47-1.38 (m, 2H), 1.35 (d, J=6.4 Hz, 2H), 1.31-1.29 (m, 6H), 1.28-1.25 (m, 2H), 0.93 (d, J=6.4 Hz, 1H).

Example 147

(S)—N-(2-Hydroxy-2-methylpropyl)-4-(2-methylpyrrolidine-1-carbonyl)-5-(4-(trifluoromethyl)-6-((1-(trifluoromethyl)cyclopropyl)amino)pyridin-3-yl)thiazole-2-carboxamide

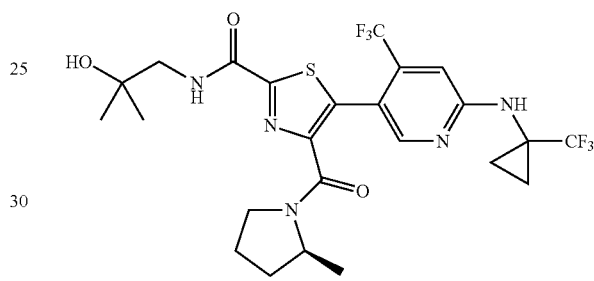

An oven-dried vial under N$_2$ was charged with (S)—N-(2-hydroxy-2-methylpropyl)-4-(2-methylpyrrolidine-1-carbonyl)thiazole-2-carboxamide (62 mg, 0.18 mmol, Intermediate 69), 5-bromo-4-(trifluoromethyl)-N-(1-(trifluoromethyl)cyclopropyl)pyridin-2-amine (84 mg, 0.18 mmol, Intermediate 63: Step B) K$_2$CO$_3$ (100 mg, 0.72 mmol), pivalic acid (7 mg, 0.07 mmol), di-(1-adamantyl)-n-butylphosphine (20 mg, 0.05 mmol) and Pd$_2$(dba)$_3$ (25 mg, 0.030 mmol). The vial was evacuated and backfilled with N$_2$ two times, then butyronitrile (1.1 mL, sparged with N$_2$ for 1 hour prior to addition) was added and the reaction was stirred at 100° C. for 22 hours. The reaction was cooled to rt, filtered through Celite, rinsing with EtOAc, and concentrated to dryness. The residue was re-subjected to the reaction conditions, by adding K$_2$CO$_3$ (100 mg, 0.72 mmol), pivalic acid (7.4 mg, 0.07 mmol), di-(1-adamantyl)-n-butylphosphine (20.4 mg, 0.05 mmol) and Pd$_2$(dba)$_3$ (25 mg, 0.03 mmol). The vial was evacuated and backfilled with N$_2$, then butyronitrile (1.1 mL, sparged with N$_2$ for 1 hour prior to addition) was added and the mixture stirred at 100° C. for 18 hours. The reaction was allowed to cool to rt, then quenched with water (15 mL) and extracted with EtOAc (15 mL). The aqueous layer was further extracted with EtOAc (20 mL), then the organics were combined, washed with brine, dried over anhydrous sodium sulfate and concentrated to dryness. The residue was purified by FCC (0-10% MeOH/DCM) followed by basic HPLC to provide the title compound as a light yellow oil. MS (ESI): mass calcd. for $C_{24}H_{27}F_6N_5O_3S$, 579.6; m/z found, 580.1 [M+H]$^+$. $^1$H NMR (500 MHz, CDCl$_3$) δ 8.26-8.23 (m, 1H), 7.60-7.50 (m, 1H), 7.43-7.34 (m, 1H), 6.99 (s, 1H), 6.99-6.94 (m, 1H), 5.71 (s, 1H), 4.42-4.15 (m, 1H), 3.59-3.45 (m, 3H), 2.09-2.02 (m, 1H), 1.96-1.92 (m, 1H), 1.80-1.73 (m, 1H), 1.58-

1.54 (m, 1H), 1.33-1.31 (m, 6H), 1.24 (d, J=6.3 Hz, 2H), 1.19-1.16 (m, 2H), 1.13 (d, J=6.5 Hz, 1H), 0.86-0.82 (m, 2H).

Example 148

5-(6-(tert-Butylamino)-4-(difluoromethyl)-3-pyridyl)-N-((1R)-2-hydroxy-1-methyl-ethyl)-4-((2S)-2-methylpyrrolidine-1-carbonyl)thiazole-2-carboxamide

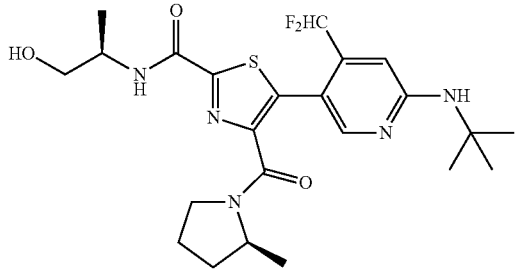 [SMILES: C[C@H](CO)NC(=O)c1nc(C(=O)N2CCC[C@@H]2C)c(-c2cnc(NC(C)(C)C)cc2C(F)F)s1]

To a microwave vial under $N_2$ was added ethyl (S)-5-(6-(tert-butylamino)-4-(difluoromethyl)pyridin-3-yl)-4-(2-methylpyrrolidine-1-carbonyl)thiazole-2-carboxylate (131 mg, 0.28 mmol, Intermediate 106), (R)-(−)-2-amino-1-propanol (105 mg, 1.4 mmol) and EtOH (1.33 mL), and the reaction was stirred at 100° C. for 18 h. The reaction mixture was cooled to rt and partitioned between EtOAc (20 mL) and saturated aqueous $NH_4Cl$ (20 mL). The layers were separated and the aqueous further extracted with EtOAc (2×15 mL). The organic layers were combined, dried over anhydrous sodium sulfate, filtered and concentrated to dryness. The crude residue was dissolved in DCM and purified by FCC (0-100% EtOAc/Hexanes) to provide the title compound as a yellow oil. MS (ESI): mass calcd. for $C_{23}H_{31}F_2N_5O_3S$, 495.6; m/z found, 496.1 [M+H]$^+$. $^1$H NMR (500 MHz, CDCl$_3$) δ 8.05-7.98 (m, 1H), 7.37-7.29 (m, 1H), 6.99-6.61 (m, 2H), 4.92-4.84 (s, 1H), 4.29-4.17 (m, 2H), 3.82-3.29 (m, 4H), 1.47-1.43 (m, 9H), 2.72-2.59 (s, 1H), 1.96-1.71 (m, 3H), 1.64-1.49 (m, 1H), 1.34-1.31 (d, J=6.8 Hz, 3H), 1.24-1.20 (d, J=6.3 Hz, 2H), 1.03-0.99 (d, J=6.4 Hz, 1H).

Example 149

[5-[6-(tert-Butylamino)-4-(difluoromethyl)-3-pyridyl]-2-(3-hydroxy-3-methyl-azetidine-1-carbonyl)thiazol-4-yl]-[(2S)-2-methylpyrrolidin-1-yl]methanone

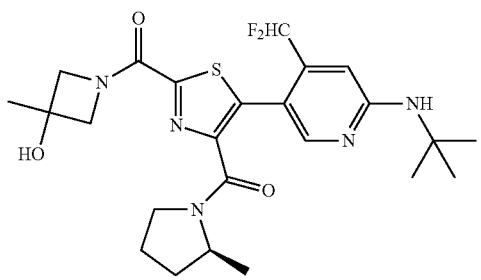 [SMILES: C[C@H]1CCCN1C(=O)c1nc(C(=O)N2CC(C)(O)C2)sc1-c1cnc(NC(C)(C)C)cc1C(F)F]

To a microwave vial under $N_2$ was added ethyl (S)-5-(6-(tert-butylamino)-4-(difluoromethyl)pyridin-3-yl)-4-(2-methylpyrrolidine-1-carbonyl)thiazole-2-carboxylate (131 mg, 0.28 mmol, Intermediate 106), 3-hydroxy-3-methylazetidine HCl (183 mg, 1.4 mmol), DIPEA (0.27 mL, 1.54 mmol) and EtOH (1.33 mL), and the reaction was stirred at 100° C. for 15 h. The reaction mixture was cooled to rt and partitioned between EtOAc (20 mL) and saturated aqueous $NH_4Cl$ (20 mL). The layers were separated and the aqueous further extracted with EtOAc (2×15 mL). The organic layers were combined, dried over anhydrous sodium sulfate, filtered and concentrated to dryness. The crude residue was dissolved in DCM and purified by FCC (0-100% EtOAc/Hexanes) to provide the title compound as a yellow oil. MS (ESI): mass calcd. for $C_{24}H_{31}F_2N_5O_3S$, 507.6; m/z found, 508.1 [M+H]$^+$. $^1$H NMR (500 MHz, CDCl$_3$) δ 8.02-7.93 (m, 1H), 6.95-6.58 (m, 2H), 4.92-4.86 (s, 1H), 4.63-4.49 (m, 2H), 4.43-4.16 (m, 1H), 4.16-4.09 (m, 3H), 3.60-3.22 (m, 3H), 2.09-2.03 (m, 2H), 1.97-1.72 (m, 3H), 1.55-1.49 (m, 1H), 1.47-1.41 (s, 9H), 1.24-1.18 (m, 2H), 1.01-0.90 (m, 1H).

Example 150

4-((1s,4s)-7-Azabicyclo[2.2.1]heptane-7-carbonyl)-N-((3R,4S)-4-hydroxytetrahydrofuran-3-yl)-5-(4-(trifluoromethyl)-6-(((1S)-2,2,2-trifluoro-1-methyl-ethyl)amino)-3-pyridyl)thiazole-2-carboxamide

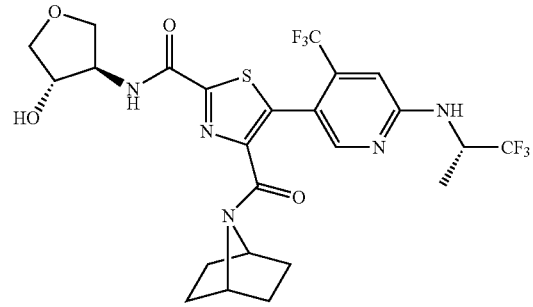 [SMILES: C[C@H](Nc1cc(C(F)(F)F)c(-c2sc(C(=O)N[C@@H]3COC[C@H]3O)nc2C(=O)N2C3CCC2CC3)cn1)C(F)(F)F]

The title compound was prepared as described in Example 148 substituting (3S,4R)-4-amino-tetrahydro-furan-3-ol for (R)-(−)-2-amino-1-propanol and ethyl 4-((1s,4s)-7-azabicyclo[2.2.1]heptane-7-carbonyl)-5-(4-(trifluoromethyl)-6-(((S)-1,1,1-trifluoropropan-2-yl)amino)pyridin-3-yl)thiazole-2-carboxylate (Intermediate 116) for ethyl (S)-5-(6-(tert-butylamino)-4-(difluoromethyl)pyridin-3-yl)-4-(2-methylpyrrolidine-1-carbonyl)thiazole-2-carboxylate. MS (ESI): mass calcd. for $C_{24}H_{25}F_6N_5O_4S$, 593.5; m/z found, 594.1 [M+H]$^+$. $^1$H NMR (400 MHz, CDCl$_3$) δ 8.21-8.16 (s, 1H), 7.35-7.28 (d, J=6.7 Hz, 1H), 6.74-6.67 (s, 1H), 5.39-5.32 (d, J=9.3 Hz, 1H), 5.02-4.92 (m, 1H), 4.72-4.63 (s, 1H), 4.49-4.27 (m, 3H), 4.25-4.14 (m, 2H), 3.87-3.74 (m, 2H), 3.31-3.26 (d, J=3.0 Hz, 1H), 1.80-1.69 (s, 2H), 1.68-1.53 (m, 2H), 1.51-1.42 (m, 4H), 1.42-1.38 (d, J=6.9 Hz, 3H).

Example 151

4-(1s,4s)-7-Azabicyclo[2.2.1]heptane-7-carbonyl)-5-(4-(difluoromethyl)-6-(((1S)-1-(trifluoromethyl)propyl)amino)-3-pyridyl)-N-((1S,3S)-3-hydroxycyclopentyl)thiazole-2-carboxamide

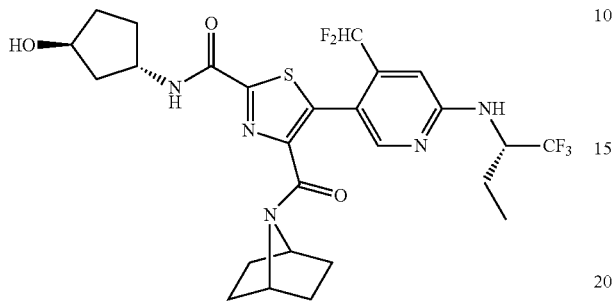

The title compound was prepared as described in Example 149 substituting (1S,3S)-3-aminocyclopentan-1-ol HCl for 3-hydroxy-3-methylazetidine HCl and ethyl 4-((1s,4s)-7-azabicyclo[2.2.1]heptane-7-carbonyl)-5-(4-(difluoromethyl)-6-(((S)-1,1,1-trifluorobutan-2-yl)amino)pyridin-3-yl)thiazole-2-carboxylate (Intermediate 99) for ethyl (S)-5-(6-(tert-butylamino)-4-(difluoromethyl)pyridin-3-yl)-4-(2-methylpyrrolidine-1-carbonyl)thiazole-2-carboxylate. MS (ESI): mass calcd. for $C_{26}H_{30}F_5N_5O_3S$, 587.6; m/z found, 588.1 [M+H]$^+$. $^1$H NMR (400 MHz, CDCl$_3$) δ 8.11-8.06 (s, 1H), 7.18-7.11 (d, J=7.8 Hz, 1H), 6.92-6.61 (m, 2H), 4.88-4.58 (m, 4H), 4.53-4.46 (m, 1H), 4.15-4.08 (m, 1H), 2.42-2.06 (m, 3H), 2.02-1.94 (m, 1H), 1.87-1.78 (m, 1H), 1.76-1.70 (m, 2H), 1.69-1.66 (s, 2H), 1.65-1.56 (m, 2H), 1.51-1.38 (m, 6H), 1.07-1.00 (m, 3H).

Example 152

4-(1s,4s)-7-Azabicyclo[2.2.1]heptane-7-carbonyl)-5-(4-(difluoromethyl)-6-(((1S)-1-(trifluoromethyl)propyl)amino)-3-pyridyl)-N-((1R,3R)-3-hydroxycyclopentyl)thiazole-2-carboxamide

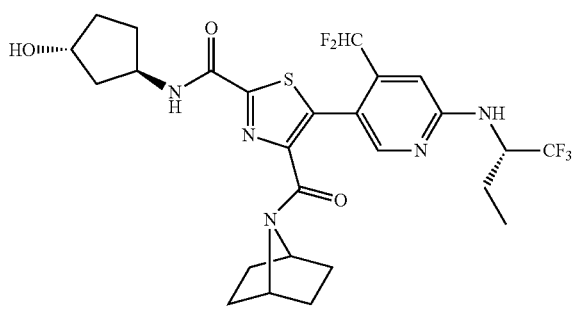 [SMILES: CC[C@H](Nc1cc(C(F)F)c(-c2sc(C(=O)N[C@@H]3CC[C@@H](O)C3)nc2C(=O)N2C3CCC2CC3)cn1)C(F)(F)F]

The title compound was prepared as described in Example 149 substituting (1R,3R)-3-aminocyclopentan-1-ol HCl for 3-hydroxy-3-methylazetidine HCl and ethyl 4-((1s,4s)-7-azabicyclo[2.2.1]heptane-7-carbonyl)-5-(4-(difluoromethyl)-6-(((S)-1,1,1-trifluorobutan-2-yl)amino)pyridin-3-yl)thiazole-2-carboxylate (Intermediate 99) for ethyl (S)-5-(6-(tert-butylamino)-4-(difluoromethyl)pyridin-3-yl)-4-(2-methylpyrrolidine-1-carbonyl)thiazole-2-carboxylate. MS (ESI): mass calcd. for $C_{26}H_{30}F_5N_5O_3S$, 587.6; m/z found, 588.1 [M+H]$^+$. $^1$H NMR (400 MHz, CDCl$_3$) δ 8.11-8.06 (s, 1H), 7.20-7.14 (d, J=7.8 Hz, 1H), 6.92-6.61 (m, 2H), 4.96-4.59 (m, 4H), 4.53-4.45 (m, 1H), 4.13-4.09 (m, 1H), 2.42-2.06 (m, 3H), 2.01-1.92 (m, 1H), 1.85-1.77 (m, 2H), 1.76-1.71 (m, 3H), 1.65-1.55 (m, 2H), 1.51-1.38 (m, 6H), 1.07-1.00 (m, 3H).

Example 153

4-(1s,4s)-7-Azabicyclo[2.2.1]heptane-7-carbonyl)-5-(4-(difluoromethyl)-6-(((1S)-1-(trifluoromethyl)propyl)amino)-3-pyridyl)-N-tetrahydropyran-4-yl-thiazole-2-carboxamide

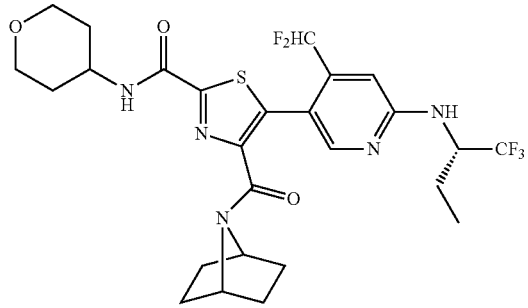 [SMILES: CC[C@H](Nc1cc(C(F)F)c(-c2sc(C(=O)NC3CCOCC3)nc2C(=O)N2C3CCC2CC3)cn1)C(F)(F)F]

The title compound was prepared as described in Example 148 substituting 4-aminotetrahydropyran for (R)-(−)-2-amino-1-propanol and ethyl 4-((1s,4s)-7-azabicyclo[2.2.1]heptane-7-carbonyl)-5-(4-(difluoromethyl)-6-(((S)-1,1,1-trifluorobutan-2-yl)amino)pyridin-3-yl)thiazole-2-carboxylate (Intermediate 99) for ethyl (S)-5-(6-(tert-butylamino)-4-(difluoromethyl)pyridin-3-yl)-4-(2-methylpyrrolidine-1-carbonyl)thiazole-2-carboxylate. MS (ESI): mass calcd. for $C_{26}H_{30}F_5N_5O_3S$, 587.6; m/z found, 588.1 [M+H]$^+$. $^1$H NMR (400 MHz, CDCl$_3$) δ 8.10-8.07 (s, 1H), 7.16-7.09 (d, J=8.3 Hz, 1H), 6.94-6.62 (m, 2H), 4.93-4.65 (m, 3H), 4.24-4.13 (m, 2H), 4.06-3.98 (m, 2H), 3.59-3.49 (m, 2H), 2.04-1.94 (m, 3H), 1.72-1.56 (m, 5H), 1.53-1.39 (m, 6H), 1.07-1.00 (m, 3H).

Example 154

4-(1s,4s)-7-Azabicyclo[2.2.1]heptane-7-carbonyl)-5-(4-(difluoromethyl)-6-(((1S)-1-(trifluoromethyl)propyl)amino)-3-pyridyl)-N-(1,1-dioxothian-4-yl)thiazole-2-carboxamide

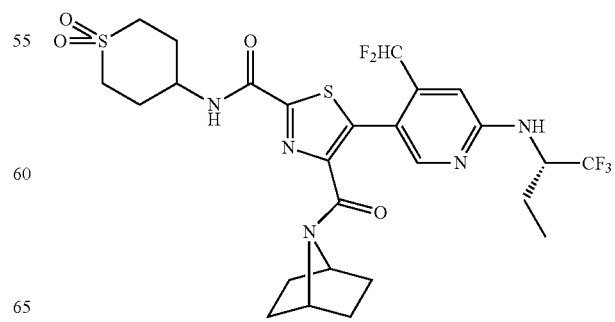

The title compound was prepared as described in Example 148 substituting 4-aminotetrahydro-2H-thiopyran 1,1-dioxide for (R)-(−)-2-amino-1-propanol and ethyl 4-((1s,4s)-7-azabicyclo[2.2.1]heptane-7-carbonyl)-5-(4-(difluoromethyl)-6-(((S)-1,1,1-trifluorobutan-2-yl)amino)pyridin-3-yl)thiazole-2-carboxylate (Intermediate 99) for ethyl (5)-5-(6-(tert-butylamino)-4-(difluoromethyl)pyridin-3-yl)-4-(2-methylpyrrolidine-1-carbonyl)thiazole-2-carboxylate. MS (ESI): mass calcd. for $C_{26}H_{30}F_5N_5O_4S_2$, 635.7; m/z found, 636.1 [M+H]$^+$. $^1$H NMR (400 MHz, CDCl$_3$) δ 8.11-8.06 (s, 1H), 7.68-7.54 (d, J=8.0 Hz, 1H), 6.91-6.60 (m, 2H), 4.86-4.61 (m, 2H), 4.32-4.18 (m, 1H), 4.08-3.99 (s, 1H), 1.57-1.54 (m, 3H), 3.22-3.12 (m, 4H), 2.48-2.25 (m, 4H), 2.00-1.94 (m, 1H), 1.66-1.59 (m, 1H), 1.49-1.36 (m, 6H), 1.06-1.00 (m, 3H).

Example 155

4-(1s,4s)-7-Azabicyclo[2.2.1]heptane-7-carbonyl)-N-((3R,4S)-4-hydroxytetrahydrofuran-3-yl)-5-(4-(trifluoromethyl)-6-(((1S)-1-(trifluoromethyl)propyl)amino)-3-pyridyl)thiazole-2-carboxamide

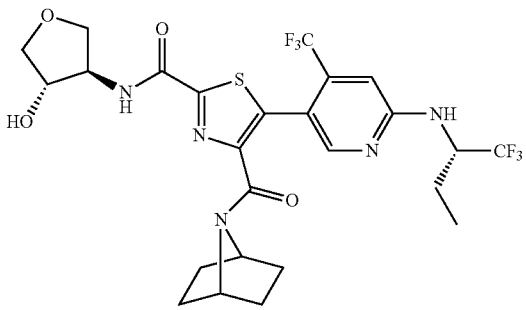 [SMILES: CC[C@H](Nc1cc(C(F)(F)F)c(-c2sc(C(=O)N[C@@H]3COC[C@H]3O)nc2C(=O)N2C3CCC2CC3)cn1)C(F)(F)F]

The title compound was prepared as described in Example 148 substituting (3S,4R)-4-amino-tetrahydro-furan-3-ol for (R)-(−)-2-amino-1-propanol and ethyl 4-((1R,4R)-7-azabicyclo[2.2.1]heptane-7-carbonyl)-5-(6-(((S)-1,1,1-trifluorobutan-2-yl)amino)-4-(trifluoromethyl)pyridin-3-yl)thiazole-2-carboxylate (Intermediate 100) for ethyl (S)-5-(6-(tert-butylamino)-4-(difluoromethyl)pyridin-3-yl)-4-(2-methylpyrrolidine-1-carbonyl)thiazole-2-carboxylate. MS (ESI): mass calcd. for $C_{25}H_{27}F_6N_5O_4S$, 607.6; m/z found, 608.1 [M+H]$^+$. $^1$H NMR (400 MHz, CDCl$_3$) δ 8.22-8.17 (s, 1H), 7.39-7.32 (d, J=6.7 Hz, 1H), 6.81-6.76 (s, 1H), 5.16-5.09 (d, J=9.8 Hz, 1H), 4.87-4.63 (m, 2H), 4.46-4.35 (m, 2H), 4.24-4.13 (m, 3H), 3.87-3.74 (m, 2H), 3.40-3.34 (s, 1H), 2.02-1.91 (m, 1H), 1.78-1.54 (m, 4H), 1.50-1.38 (m, 5H), 1.07-0.99 (m, 3H).

Example 156

4-(1s,4s)-7-Azabicyclo[2.2.1]heptane-7-carbonyl)-N-((3S,4R)-4-hydroxytetrahydrofuran-3-yl)-5-(4-(trifluoromethyl)-6-(((1S)-1-(trifluoromethyl)propyl)amino)-3-pyridyl)thiazole-2-carboxamide

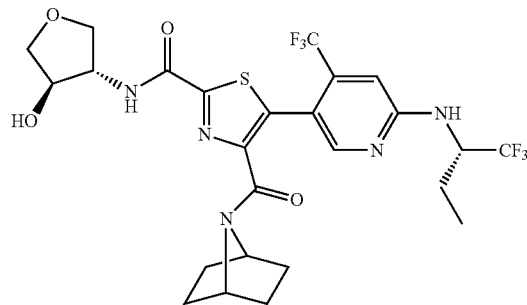 [SMILES: CC[C@H](Nc1cc(C(F)(F)F)c(-c2sc(C(=O)N[C@H]3COC[C@@H]3O)nc2C(=O)N2C3CCC2CC3)cn1)C(F)(F)F]

The title compound was prepared as described in Example 148 substituting (3R,4S)-4-amino-tetrahydro-furan-3-ol for (R)-(−)-2-amino-1-propanol and ethyl 4-((1s,4s)-7-azabicyclo[2.2.1]heptane-7-carbonyl)-5-(6-(((S)-1,1,1-trifluorobutan-2-yl)amino)-4-(trifluoromethyl)pyridin-3-yl)thiazole-2-carboxylate (Intermediate 100) for ethyl (5)-5-(6-(tert-butylamino)-4-(difluoromethyl)pyridin-3-yl)-4-(2-methylpyrrolidine-1-carbonyl)thiazole-2-carboxylate. MS (ESI): mass calcd. for $C_{25}H_{27}F_6N_5O_4S$, 607.6; m/z found, 608.1 [M+H]$^+$. $^1$H NMR (400 MHz, CDCl$_3$) δ 8.22-8.17 (s, 1H), 7.40-7.33 (d, J=6.7 Hz, 1H), 6.80-6.76 (s, 1H), 5.15-5.07 (d, J=9.7 Hz, 1H), 4.88-4.62 (m, 2H), 4.48-4.35 (m, 2H), 4.25-4.12 (m, 3H), 3.87-3.73 (m, 2H), 3.36-3.29 (s, 1H), 2.01-1.90 (m, 1H), 1.80-1.67 (m, 2H), 1.65-1.49 (m, 3H), 1.48-1.40 (m, 4H), 1.06-0.99 (m, 3H).

Example 157

5-(4-(Difluoromethyl)-6-(((S)-1,1,1-trifluoropropan-2-yl)amino)pyridin-3-yl)-N-((1R*,2R*)-2-hydroxycyclopropyl)-4-((S)-2-methylpyrrolidine-1-carbonyl)thiazole-2-carboxamide

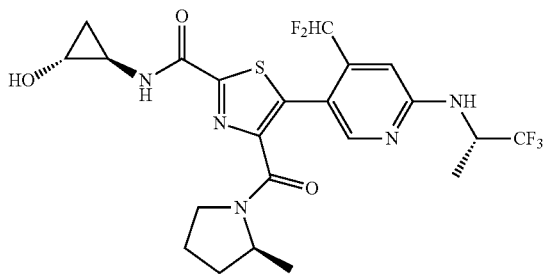

To a 25 mL round-bottom flask under N$_2$ was added N-((1R*,2R*)-2-((tert-butyldimethylsilyl)oxy)cyclopropyl)-5-(4-(difluoromethyl)-6-(((S)-1,1,1-trifluoropropan-2-yl)amino)pyridin-3-yl)-4-((S)-2-methylpyrrolidine-1-carbonyl)thiazole-2-carboxamide (377 mg, 0.55 mmol, Intermediate 101: Step D) and dry THF (3.1 mL). To this solution was added AcOH (47.4 µL, 0.83 mmol) followed by TBAF (0.83 mL, 0.83 mmol) and the resulting solution stirred at rt for 3 hours. The mixture was partitioned between brine (15 mL) and EtOAc (25 mL), and the organic phase was dried over anhydrous sodium sulfate, filtered and concentrated to dryness. The crude residue was purified by FCC 0-100% EtOAc/Hexanes) to provide a mixture of trans cyclopropyl isomers as a yellow oil. The pure diastereomer was isolated via SFC (Stationary phase: Chiralpak IC, 5 µm, 250×20 mm, Mobile phase: 20% EtOH+0.3% iPrNH$_2$, 80% CO$_2$, second eluting enantiomer). MS (ESI): mass calcd. for C$_{22}$H$_{24}$F$_5$N$_5$O$_3$S, 533.5; m/z found, 534.1 [M+H]$^+$. $^1$H NMR (400 MHz, CDCl$_3$) δ 8.10-8.01 (m, 1H), 7.21-7.10 (m, 1H), 7.01-6.59 (m, 2H), 4.98-4.88 (m, 2H), 4.29-4.15 (m, 1H), 3.65-3.31 (m, 3H), 2.93-2.86 (m, 1H), 2.09-1.99 (m, 1H), 1.95-1.71 (m, 2H), 1.58-1.49 (m, 1H), 1.43-1.38 (d, J=6.3 Hz, 3H), 1.30-1.23 (m, 2H), 1.22-1.19 (d, J=6.3 Hz, 2H), 1.02-0.96 (m, 2H).

Example 158

5-(4-(Difluoromethyl)-6-(((S)-1,1,1-trifluoropropan-2-yl)amino)pyridin-3-yl)-N-((1S*,2S*)-2-hydroxycyclopropyl)-4-((S)-2-methylpyrrolidine-1-carbonyl)thiazole-2-carboxamide

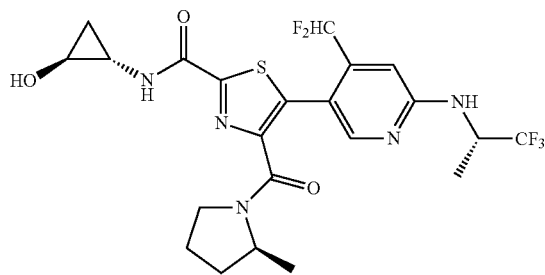 [SMILES: C[C@H](Nc1cc(C(F)F)c(-c2sc(C(=O)N[C@H]3C[C@@H]3O)nc2C(=O)N2CCC[C@@H]2C)cn1)C(F)(F)F]

The title compound was prepared as described in Example 157. The pure diastereomer was isolated via SFC (Stationary phase: Chiralpak IC, 5 µm, 250×20 mm, Mobile phase: 20% EtOH+0.3% iPrNH$_2$, 80% CO$_2$, first eluting enantiomer). MS (ESI): mass calcd. for C$_{22}$H$_{24}$F$_5$N$_5$O$_3$S, 533.5; m/z found, 534.1 [M+H]$^+$. $^1$H NMR (400 MHz, CDCl$_3$) δ 8.10-8.02 (m, 1H), 7.19-7.08 (m, 1H), 7.03-6.60 (m, 2H), 4.99-4.83 (m, 2H), 4.33-4.15 (m, 1H), 3.64-3.30 (m, 3H), 2.94-2.87 (m, 1H), 2.08-2.01 (m, 1H), 1.95-1.72 (m, 3H), 1.58-1.49 (m, 1H), 1.44-1.39 (d, J=6.7 Hz, 3H), 1.28-1.24 (m, 1H), 1.23-1.21 (m, 2H), 1.02-0.96 (m, 2H).

Example 159

5-(4-(Difluoromethyl)-6-(((S)-1,1,1-trifluoropropan-2-yl)amino)pyridin-3-yl)-N-((3R*,4R*)-4-hydroxytetrahydrofuran-3-yl)-4-((S)-2-methylpyrrolidine-1-carbonyl)thiazole-2-carboxamide

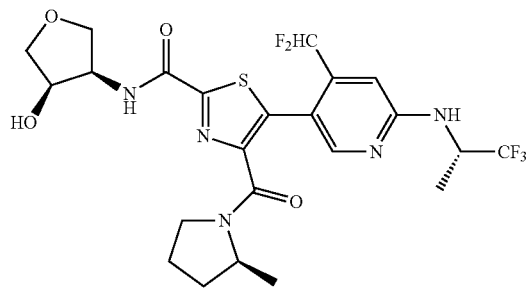 [SMILES: C[C@H](Nc1cc(C(F)F)c(-c2sc(C(=O)N[C@@H]3COC[C@@H]3O)nc2C(=O)N2CCC[C@@H]2C)cn1)C(F)(F)F]

The title compound was prepared as described in Example 149 substituting cis-4-aminotetrahydro-3-furanol HCl for 3-hydroxy-3-methylazetidine HCl and ethyl 5-(4-(difluoromethyl)-6-(((S)-1,1,1-trifluoropropan-2-yl)amino)pyridin-3-yl)-4-((S)-2-methylpyrrolidine-1-carbonyl)thiazole-2-carboxylate (Intermediate 94) for ethyl (S)-5-(6-(tert-butylamino)-4-(difluoromethyl)pyridin-3-yl)-4-(2-methylpyrrolidine-1-carbonyl)thiazole-2-carboxylate. The pure diastereomer was isolated via SFC (Stationary phase: Lux amylose 2, 5 µm, 250×21.2 mm, Mobile phase: 15% EtOH+0.3% iPrNH$_2$, 85% CO$_2$, second eluting enantiomer). MS (ESI): mass calcd. for C$_{23}$H$_{26}$F$_5$N$_5$O$_4$S, 563.5; m/z found, 564.1 [M+H]$^+$. $^1$H NMR (400 MHz, CDCl$_3$) δ 8.10-8.00 (m, 1H), 7.80-7.72 (m, 1H), 6.99-6.56 (m, 2H), 5.08-4.88 (m, 2H), 4.63-4.42 (m, 2H), 4.40-4.14 (m, 2H), 4.09-4.02 (dd, J=10.2, 4.5 Hz, 1H), 3.90-3.84 (m, 1H), 3.76-3.69 (m, 1H), 3.60-3.33 (m, 2H), 2.09-1.72 (m, 4H), 1.60-1.49 (m, 1H), 1.44-1.38 (d, J=6.8 Hz, 3H), 1.25-1.21 (d, J=6.3 Hz, 2H), 1.05-1.01 (d, J=6.4 Hz, 1H).

Example 160

5-(4-(Difluoromethyl)-6-(((S)-1,1,1-trifluoropropan-2-yl)amino)pyridin-3-yl)-N-((3S*,4S*)-4-hydroxytetrahydrofuran-3-yl)-4-((S)-2-methylpyrrolidine-1-carbonyl)thiazole-2-carboxamide

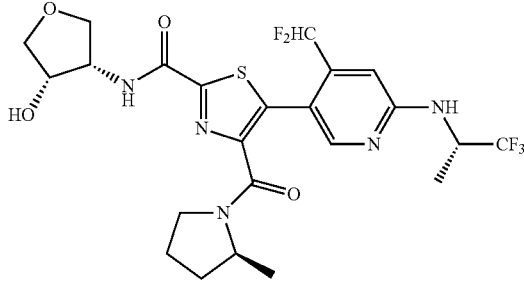 [SMILES: C[C@H](Nc1cc(C(F)F)c(-c2sc(C(=O)N[C@H]3COC[C@H]3O)nc2C(=O)N2CCC[C@@H]2C)cn1)C(F)(F)F]

The title compound was prepared as described in Example 159. The pure diastereomer was isolated via SFC (Stationary phase: Lux amylose 2, 5 µm, 250×21.2 mm, Mobile phase: 15% EtOH+0.3% iPrNH$_2$, 85% CO$_2$, first eluting enantiomer). MS (ESI): mass calcd. for C$_{23}$H$_{26}$F$_5$N$_5$O$_4$S, 563.5; m/z found, 564.1 [M+H]$^+$. $^1$H NMR (400 MHz, CDCl$_3$) δ 8.10-8.01 (m, 1H), 7.77-7.69 (d, J=7.9 Hz, 1H), 7.00-6.61 (m, 2H), 5.00-4.81 (m, 2H), 4.64-4.55 (m, 1H), 4.52-4.46 (m, 1H), 4.37-4.15 (m, 2H), 4.10-4.04 (dd, J=10.3, 4.5 Hz, 1H), 3.90-3.85 (m, 1H), 3.76-3.70 (m, 1H), 3.60-3.38 (m, 2H), 2.09-1.74 (m, 4H), 1.58-1.52 (m, 1H), 1.43-1.40 (d, J=6.8 Hz, 3H), 1.24-1.20 (d, J=6.3 Hz, 2H), 1.09-1.05 (d, J=6.4 Hz, 1H).

Example 161

5-(6-((1-Cyclobutylethyl)amino)-4-(trifluoromethyl)pyridine-3-yl)-4-((S)-4,4-difluoro-2-methylpyrrolidine-1-carbonyl)-N-(2-hydroxy-2-methylpropyl)thiazole-2-carboxamide

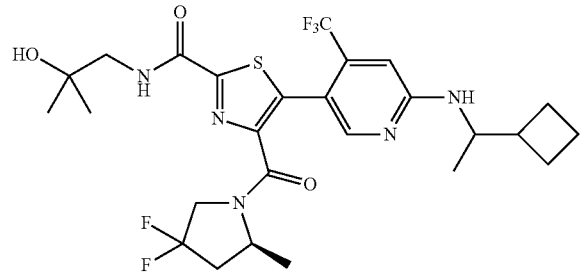 [SMILES: CC(Nc1cc(C(F)(F)F)c(-c2sc(C(=O)NCC(C)(C)O)nc2C(=O)N2CC(F)(F)C[C@@H]2C)cn1)C1CCC1]

547

The title compound was prepared as described in Example 77 substituting (S)-4-(4,4-difluoro-2-methylpyrrolidine-1-carbonyl)-N-(2-hydroxy-2-methylpropyl)thiazole-2-carboxamide (Intermediate 67) for (S)—N-(2-hydroxy-2-methylpropyl)-4-(2-methylpyrrolidine-1-carbonyl)thiazole-2-carboxamide and 5-bromo-N-(1-cyclobutylethyl)-4-(trifluoromethyl)pyridine-2-amine (Intermediate 89) for 5-bromo-N-(1-methylcyclobutyl)-4-(trifluoromethyl)pyridin-2-amine. MS (ESI): mass calcd. for $C_{26}H_{32}F_5N_5O_3S$, 589.2; m/z found, 590.2 [M+H]+. 1H NMR (500 MHz, CDCl3) δ 8.13 (s, 1H), 7.52-7.46 (m, 1H), 6.62 (s, 1H), 4.73 (d, J=8.3 Hz, 1.3H), 4.50-4.47 (m, 0.7H), 4.16-4.00 (m, 1H), 3.96-3.77 (m, 2H), 3.57-3.41 (m, 2H), 2.61-2.48 (m, 1H), 2.40-2.34 (m, 1H), 2.16-1.98 (m, 3H), 1.94-1.74 (m, 5H), 1.41-1.23 (m, 9H), 1.13 (dd, J=6.3, 2.3 Hz, 3H).

Example 162

5-(4-(Difluoromethyl)-6-(((S)-1,1,1-trifluorobutan-2-yl)amino)pyridin-3-yl)-N-((3R*,4R*)-4-hydroxytetrahydrofuran-3-yl)-4-((S)-2-methylpyrrolidine-1-carbonyl)thiazole-2-carboxamide

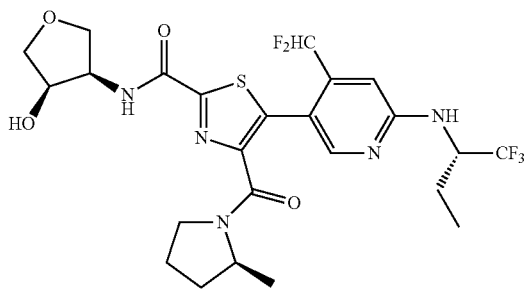 [SMILES: CC[C@H](Nc1cc(C(F)F)c(-c2sc(C(=O)N[C@@H]3COC[C@@H]3O)nc2C(=O)N2CCC[C@@H]2C)cn1)C(F)(F)F]

The title compound was prepared as described in Example 149 substituting cis-4-aminotetrahydro-3-furanol HCl for 3-hydroxy-3-methylazetidine HCl and ethyl 5-(4-(difluoromethyl)-6-(((S)-1,1,1-trifluorobutan-2-yl)amino)pyridin-3-yl)-4-((S)-2-methylpyrrolidine-1-carbonyl)thiazole-2-carboxylate (Intermediate 102) for ethyl (S)-5-(6-(tert-butylamino)-4-(difluoromethyl)pyridin-3-yl)-4-(2-methylpyrrolidine-1-carbonyl)thiazole-2-carboxylate. The pure diastereomer was isolated via SFC (Stationary phase: Lux amylose 2, 5 μm, 250×21.2 mm, Mobile phase: 15% EtOH+0.3% iPrNH2, 85% CO2, second eluting enantiomer). MS (ESI): mass calcd. for $C_{24}H_{28}F_5N_5O_4S$, 577.6; m/z found, 578.1 [M+H]+. 1H NMR (400 MHz, CDCl3) δ 8.08-7.99 (m, 1H), 7.82-7.74 (m, 1H), 7.01-6.59 (m, 2H), 5.03-4.95 (d, J=9.8 Hz, 1H), 4.85-4.68 (s, 1H), 4.62-4.41 (m, 2H), 4.39-3.83 (m, 4H), 3.75-3.70 (m, 1H), 3.58-3.32 (m, 2H), 2.09-2.01 (m, 1H), 1.99-1.87 (m, 2H), 1.80-1.72 (m, 1H), 1.66-1.50 (m, 2H), 1.23-1.20 (d, J=6.3 Hz, 2H), 1.08-0.99 (m, 4H).

Example 163

4-((1s,4s)-7-Azabicyclo[2.2.1]heptane-7-carbonyl)-5-(6-(((S*)-1-cyclopropyl)amino)-4-(difluoromethyl)pyridine-3-yl)-N-(2-hydroxy-2-methylpropyl)thiazole-2-carboxamide

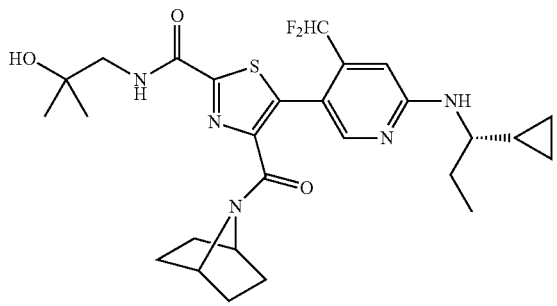 [SMILES: CC[C@H](Nc1cc(C(F)F)c(-c2sc(C(=O)NCC(C)(C)O)nc2C(=O)N2C3CCC2CC3)cn1)C1CC1]

The title compound was prepared as described in Example 77 substituting 4-((1s,4s)-7-azabicyclo[2.2.1]heptane-7-carbonyl)-N-(2-hydroxy-2-methylpropyl)thiazole-2-carboxamide (Intermediate 70) for (S)—N-(2-hydroxy-2-methylpropyl)-4-(2-methylpyrrolidine-1-carbonyl)thiazole-2-carboxamide and 5-bromo-N-(1-cyclopropylpropyl)-4-difluoromethyl)pyridine-2-amine (Intermediate 90) for 5-bromo-N-(1-methylcyclobutyl)-4-(trifluoromethyl)pyridin-2-amine. A purification was performed via chiral SFC (Stationary phase: Chiralpak AD-H, 5 μm, 250×30 mm, Mobile phase: 0.3% iPrNH2, 75% CO2, 25% EtOH/iPrOH (50/50), second eluting peak) to separate enantiomers. MS (ESI): mass calcd. for $C_{27}H_{35}F_2N_5O_3S$, 547.2; m/z found, 548.2 [M+H]+. 1H NMR (400 MHz, CDCl3) δ 8.00 (s, 1H), 7.61-7.57 (m, 1H), 6.91-6.61 (m, 2H), 4.84 (d, J=8.2 Hz, 1H), 4.72-4.66 (m, 1H), 4.27-4.23 (m, 1H), 3.48 (d, J=6.3 Hz, 2H), 3.30-3.23 (m, 1H), 1.87-1.37 (m, 10H), 1.32-1.26 (m, 7H), 1.06-0.83 (m, 4H), 0.61-0.51 (m, 1H), 0.51-0.40 (m, 1H), 0.37-0.24 (m, 2H).

Example 164

4-((1s,4s)-7-Azabicyclo[2.2.1]heptane-7-carbonyl)-5-(6-(((R*)-1-cyclopropyl)amino)-4-(difluoromethyl)pyridine-3-yl)-N-(2-hydroxy-2-methylpropyl)thiazole-2-carboxamide

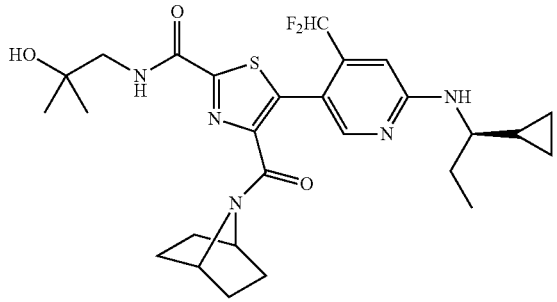 [SMILES: CC[C@@H](Nc1cc(C(F)F)c(-c2sc(C(=O)NCC(C)(C)O)nc2C(=O)N2C3CCC2CC3)cn1)C1CC1]

The title compound was prepared as described in Example 77 substituting 4-((1s,4s)-7-azabicyclo[2.2.1]heptane-7-carbonyl)-N-(2-hydroxy-2-methylpropyl)thiazole-2-carboxamide (Intermediate 70) for (S)—N-(2-hydroxy-2-methylpropyl)-4-(2-methylpyrrolidine-1-carbonyl)thiazole-2-carboxamide and 5-bromo-N-(1-cyclopropylpropyl)-4-difluoromethyl)pyridine-2-amine (Intermediate 90) for 5-bromo-N-(1-methylcyclobutyl)-4-(trifluoromethyl)pyridin-2-amine. A purification was performed via chiral SFC (Stationary phase: Chiralpak AD-H, 5 μm, 250×30 mm, Mobile phase: 0.3% iPrNH$_2$, 75% CO$_2$, 25% EtOH/iPrOH (50/50), first eluting peak) to separate enantiomers. MS (ESI): mass calcd. for C$_{27}$H$_{35}$F$_2$N$_5$O$_3$S, 547.2; m/z found, 548.2 [M+H]$^+$. $^1$H NMR (400 MHz, CDCl$_3$) δ 8.00 (s, 1H), 7.61-7.57 (m, 1H), 6.91-6.61 (m, 2H), 4.84 (d, J=8.2 Hz, 1H), 4.72-4.66 (m, 1H), 4.27-4.23 (m, 1H), 3.48 (d, J=6.3 Hz, 2H), 3.30-3.23 (m, 1H), 1.87-1.37 (m, 10H), 1.32-1.26 (m, 7H), 1.06-0.83 (m, 4H), 0.61-0.51 (m, 1H), 0.51-0.40 (m, 1H), 0.37-0.24 (m, 2H).

Example 165

5-(4-(Difluoromethyl)-6-(((S)-1,1,1-trifluorobutan-2-yl)amino)pyridin-3-yl)-N-((3S*,4S*)-4-hydroxytetrahydrofuran-3-yl)-4-((S)-2-methylpyrrolidine-1-carbonyl)thiazole-2-carboxamide

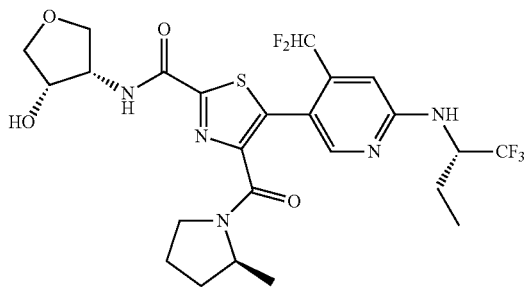 [SMILES: CC[C@H](Nc1cc(C(F)F)c(-c2sc(C(=O)N[C@H]3COC[C@H]3O)nc2C(=O)N2CCC[C@@H]2C)cn1)C(F)(F)F]

The title compound was prepared as described in Example 162. The pure diastereomer was isolated via SFC (Stationary phase: Lux amylose 2, 5 μm, 250×21.2 mm, Mobile phase: 15% EtOH+0.3% iPrNH$_2$, 85% CO$_2$, first eluting enantiomer). MS (ESI): mass calcd. for C$_{24}$H$_{28}$F$_5$N$_5$O$_4$S, 577.6; m/z found, 578.1 [M+H]$^+$. $^1$H NMR (400 MHz, CDCl$_3$) δ 8.08-7.99 (m, 1H), 7.83-7.76 (d, J=7.9 Hz, 1H), 6.98-6.60 (m, 2H), 5.03-4.96 (d, J=9.7 Hz, 1H), 4.84-4.70 (s, 1H), 4.61-4.42 (m, 2H), 4.28-4.13 (m, 2H), 4.08-4.02 (m, 1H), 3.89-3.83 (m, 1H), 3.74-3.70 (m, 1H), 3.58-3.38 (m, 2H), 2.10-1.49 (m, 7H), 1.21-1.17 (d, J=6.3 Hz, 2H), 1.08-1.01 (m, 4H).

Example 166

5-(6-(((S*)-1-Cyclopropyl)amino)-4-(difluoromethyl)pyridin-3-yl)-N-(2-hydroxy-2-methylpropyl)-4-((S)-2-methylpyrrolidine-1-carbonyl)thiazole-2-carboxamide

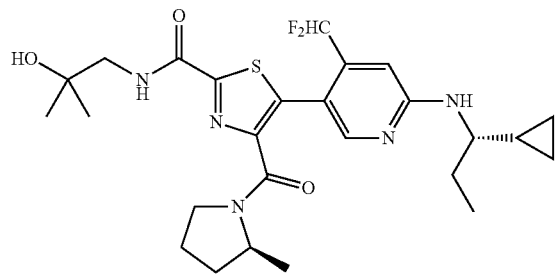 [SMILES: CC[C@H](Nc1cc(C(F)F)c(-c2sc(C(=O)NCC(C)(C)O)nc2C(=O)N2CCC[C@@H]2C)cn1)C1CC1]

The title compound was prepared as described in Example 77 substituting 5-bromo-N-(1-cyclopropylpropyl)-4-difluoromethyl)pyridine-2-amine (Intermediate 90) for 5-bromo-N-(1-methylcyclobutyl)-4-(trifluoromethyl)pyridin-2-amine. A purification was performed via chiral SFC (Stationary phase: Chiralpak AD-H, 5 μm, 250×30 mm, Mobile phase: 0.3% iPrNH$_2$, 82% CO$_2$, 18% iPrOH, second eluting peak) to separate enantiomers. MS (ESI): mass calcd. for C$_{27}$H$_{35}$F$_2$N$_5$O$_3$S, 535.2; m/z found, 536.2 [M+H]$^+$. $^1$H NMR (400 MHz, CDCl$_3$) δ 8.00-7.96 (m, 1H), 7.59-7.52 (m, 1H), 7.04-6.56 (m, 2H), 4.85 (d, J=8.2 Hz, 1H), 4.34-4.17 (m, 1H), 3.65-3.18 (m, 4H), 2.12-1.45 (m, 7H), 1.40-1.18 (m, 9H), 1.07-0.83 (m, 5H), 0.62-0.40 (m, 2H), 0.38-0.23 (m, 2H).

Example 167

5-(6-(((R*)-1-Cyclopropyl)amino)-4-(difluoromethyl)pyridin-3-yl)-N-(2-hydroxy-2-methylpropyl)-4-((S)-2-methylpyrrolidine-1-carbonyl)thiazole-2-carboxamide

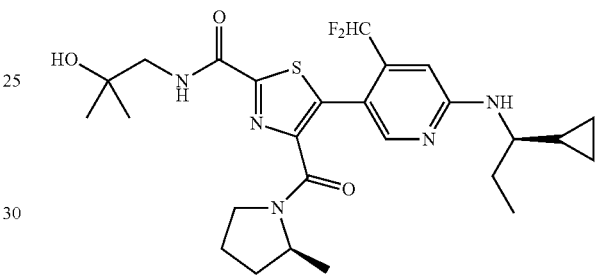

The title compound was prepared as described in Example 77 substituting 5-bromo-N-(1-cyclopropylpropyl)-4-difluoromethyl)pyridine-2-amine (Intermediate 90) for 5-bromo-N-(1-methylcyclobutyl)-4-(trifluoromethyl)pyridin-2-amine. A purification was performed via chiral SFC (Stationary phase: Chiralpak AD-H, 5 μm, 250×30 mm, Mobile phase: 0.3% iPrNH$_2$, 82% CO$_2$, 18% iPrOH, first eluting peak) to separate enantiomers. MS (ESI): mass calcd. for C$_{27}$H$_{35}$F$_2$N$_5$O$_3$S, 535.2; m/z found, 536.2 [M+H]$^+$. $^1$H NMR (400 MHz, CDCl$_3$) δ 8.02-7.96 (m, 1H), 7.64-7.50 (m, 1H), 7.03-6.58 (m, 2H), 4.87 (d, J=8.2 Hz, 1H), 4.35-4.16 (m, 1H), 3.65-3.18 (m, 4H), 2.16-1.49 (m, 7H), 1.40-1.16 (m, 9H), 1.07-0.80 (m, 5H), 0.61-0.52 (m, 1H), 0.52-0.42 (m, 1H), 0.38-0.24 (m, 2H).

Example 168

(S)-4-(4,4-Difluoro-2-methylpyrrolidine-1-carbonyl)-5-(4-difluoromethyl)-6-((1-methylcyclobutyl)amino)pyridin-3-yl)-N-(2-hydroxy-2-methylpropyl)thiazole-2-carboxamide

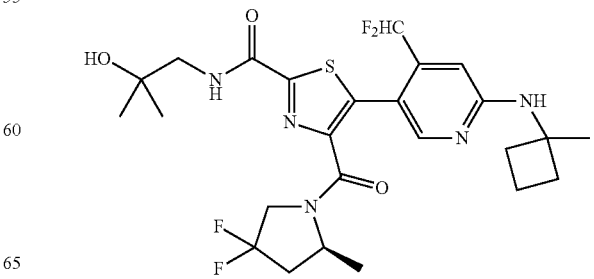

The title compound was prepared as described in Example 77 substituting (S)-4-(4,4-difluoro-2-methylpyrrolidine-1-carbonyl)-N-(2-hydroxy-2-methylpropyl)thiazole-2-carboxamide (Intermediate 67) for (S)—N-(2-hydroxy-2-methylpropyl)-4-(2-methylpyrrolidine-1-carbonyl)thiazole-2-carboxamide and 5-bromo-N-(1-methylcyclobutyl)-4-(difluoromethyl)pyridin-2-amine (Intermediate 91) for 5-bromo-N-(1-methylcyclobutyl)-4-(trifluoromethyl)pyridin-2-amine. MS (ESI): mass calcd. for $C_{25}H_{31}F_4N_5O_3S$, 557.2; m/z found, 558.2 [M+H]⁺. ¹H NMR (400 MHz, CDCl₃) δ 8.02-7.98 (m, 1H), 7.55-7.45 (m, 1H), 6.90-6.50 (m, 2H), 5.18 (s, 1H), 4.70-4.49 (m, 1H), 4.17-3.98 (m, 1H), 3.95-3.77 (m, 1H), 3.61-3.38 (m, 2H), 2.66-2.45 (m, 1H), 2.34-2.21 (m, 2H), 2.21-2.02 (m, 3H), 2.01-1.83 (m, 3H), 1.55 (s, 3H), 1.41-1.16 (m, 9H).

Example 169

4-((1s,4s)-7-Azabicyclo[2.2[1]heptane-7-carbonyl)-5-(4-(difluoromethyl)-6-((1-methylcyclobutyl)amino)pyridine-3-yl)-N-(2-hydroxy-2-methylpropyl))thiazole-2-carboxamide

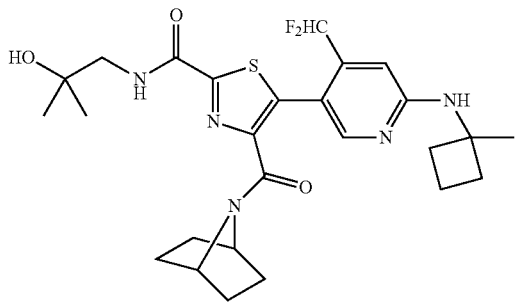 [SMILES: CC(C)(O)CNC(=O)c1nc(C(=O)N2C3CCC2CC3)c(-c2cnc(NC3(C)CCC3)cc2C(F)F)s1]

The title compound was prepared as described in Example 77 substituting 4-((1s,4s)-7-azabicyclo[2.2.1]heptane-7-carbonyl)-N-(2-hydroxy-2-methylpropyl)thiazole-2-carboxamide (Intermediate 70) for (S)—N-(2-hydroxy-2-methylpropyl)-4-(2-methylpyrrolidine-1-carbonyl)thiazole-2-carboxamide and 5-bromo-N-(1-methylcyclobutyl)-4-(difluoromethyl)pyridin-2-amine (Intermediate 91) for 5-bromo-N-(1-methylcyclobutyl)-4-(trifluoromethyl)pyridin-2-amine. MS (ESI): mass calcd. for $C_{26}H_{33}F_2N_5O_3S$, 533.2; m/z found, 534.2 [M+H]⁺. ¹H NMR (400 MHz, CDCl₃) δ 8.04-8.02 (m, 1H), 7.62-7.59 (m, 1H), 6.90-6.52 (m, 1H), 5.17 (s, 1H), 4.71-4.66 (m, 1H), 4.27-4.23 (m, 1H), 3.48 (d, J=6.3 Hz, 1H), 2.97-2.88 (m, 2H), 2.33-2.08 (m, 4H), 2.01-1.86 (m, 2H), 1.54 (s, 5H), 1.48-1.42 (m, 3H), 1.33-1.26 (m, 9H), 0.96-0.78 (m, 1H).

Example 170

N-((3R,4S)-4-Hydroxytetrahydrofuran-3-yl)-4-((2S)-2-methylpyrrolidine-1-carbonyl)-5-(4-(trifluoromethyl)-6-(((1S)-1-(trifluoromethyl)propyl)amino)-3-pyridyl)thiazole-2-carboxamide

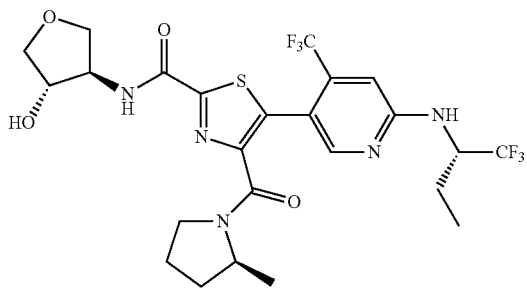 [SMILES: CC[C@H](Nc1cc(C(F)(F)F)c(-c2sc(C(=O)N[C@@H]3COC[C@H]3O)nc2C(=O)N2CCC[C@@H]2C)cn1)C(F)(F)F]

The title compound was prepared as described in Example 148 substituting ethyl 445)-2-methylpyrrolidine-1-carbonyl)-5-(6-(((S)-1,1,1-trifluorobutan-2-yl)amino)-4-(trifluoromethyl)pyridin-3-yl)thiazole-2-carboxylate (Intermediate 103) for ethyl (S)-5-(6-(tert-butylamino)-4-(difluoromethyl)pyridin-3-yl)-4-(2-methylpyrrolidine-1-carbonyl)thiazole-2-carboxylate and (3S,4R)-4-amino-tetrahydro-furan-3-ol for (R)-(−)-2-amino-1-propanol. MS (ESI): mass calcd. for $C_{24}H_{27}F_6N_5O_4S$, 595.6; m/z found, 596.1 [M+H]⁺. ¹H NMR (400 MHz, CDCl₃) δ 8.23-8.17 (s, 1H), 7.39-7.28 (m, 1H), 6.76-6.71 (m, 1H), 5.28-5.12 (m, 1H), 4.88-4.74 (m, 1H), 4.48-4.35 (m, 2H), 4.27-4.14 (m, 3H), 3.90-3.73 (m, 2H), 3.60-3.31 (m, 3H), 2.12-2.05 (m, 1H), 1.98-1.88 (m, 2H), 1.79-1.50 (m, 3H), 1.26-1.22 (d, J=6.3 Hz, 3H), 1.07-1.01 (m, 3H).

Example 171

4-((1s,4s)-7-Azabicyclo[2.2[1]heptane-7-carbonyl)-5-(6-(((S*)-1-cyclobutylethyl)amino)-4-(trifluoromethyl)pyridine-3-yl)-N-(2-hydroxy-2-methylpropyl)thiazole-2-carboxamide

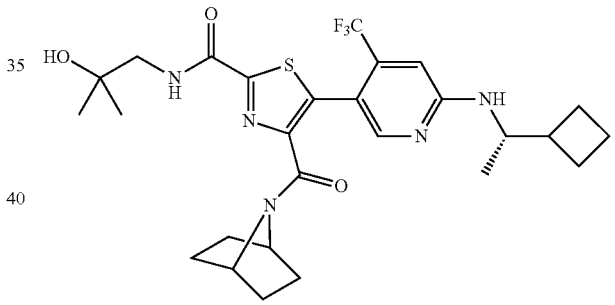

The title compound was prepared as described in Example 77 substituting 4-((1s,4s)-7-azabicyclo[2.2.1]heptane-7-carbonyl)-N-(2-hydroxy-2-methylpropyl)thiazole-2-carboxamide (Intermediate 70) for (S)—N-(2-hydroxy-2-methylpropyl)-4-(2-methylpyrrolidine-1-carbonyl)thiazole-2-carboxamide and 5-bromo-N-(1-cyclobutylethyl)-4-(trifluoromethyl)pyridine-2-amine (Intermediate 89) for 5-bromo-N-(1-methylcyclobutyl)-4-(trifluoromethyl)pyridin-2-amine. A purification was performed via chiral SFC (Stationary phase: Chiralpak IC, 5 μm, 250×20 mm, Mobile phase: 0.5% iPrNH₂, 85% CO₂, 15% MeOH, second eluting peak) to separate enantiomers. MS (ESI): mass calcd. for $C_{27}H_{34}F_3N_5O_3S$, 565.2; m/z found, 566.2 [M+H]⁺. ¹H NMR (500 MHz, CDCl₃) δ 8.14 (s, 1H), 7.64-7.60 (m, 1H), 6.62 (s, 1H), 4.82 (d, J=8.3 Hz, 1H), 4.68 (s, 1H), 4.32 (s, 1H), 3.89-3.81 (m, 1H), 3.48 (d, J=6.2 Hz, 2H), 2.62-2.29 (m, 3H), 2.10-1.97 (m, 2H), 1.94-1.70 (m, 5H), 1.48-1.41 (m, 4H), 1.32 (s, 6H), 1.25 (s, 1H), 1.20-1.15 (m, 1H), 1.12 (d, J=6.4 Hz, 3H).

Example 172

4-((1s,4s)-7-Azabicyclo[2.2.1]heptane-7-carbonyl)-5-(6-(((R*)-1-cyclobutylethyl)amino)-4-(trifluoromethyl)pyridine-3-yl)-N-(2-hydroxy-2-methylpropyl)thiazole-2-carboxamide

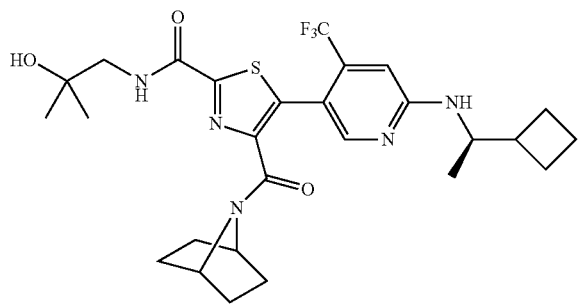 [SMILES: C[C@@H](Nc1cc(C(F)(F)F)c(-c2sc(C(=O)NCC(C)(C)O)nc2C(=O)N2C3CCC2CC3)cn1)C1CCC1]

The title compound was prepared as described in Example 77 substituting 4-((1s,4s)-7-azabicyclo[2.2.1]heptane-7-carbonyl)-N-(2-hydroxy-2-methylpropyl)thiazole-2-carboxamide (Intermediate 70) for (S)—N-(2-hydroxy-2-methylpropyl)-4-(2-methylpyrrolidine-1-carbonyl)thiazole-2-carboxamide and 5-bromo-N-(1-cyclobutylethyl)-4-(trifluoromethyl)pyridine-2-amine (Intermediate 89) for 5-bromo-N-(1-methylcyclobutyl)-4-(trifluoromethyl)pyridin-2-amine. A purification was performed via chiral SFC (Stationary phase: Chiralpak IC, 5 μm, 250×20 mm, Mobile phase: 0.5% iPrNH$_2$, 85% CO$_2$, 15% MeOH, first eluting peak) to separate enantiomers. MS (ESI): mass calcd. for C$_{27}$H$_{34}$F$_3$N$_5$O$_3$S, 565.2; m/z found, 566.2 [M+H]$^+$. $^1$H NMR (500 MHz, CDCl$_3$) δ 8.14 (s, 1H), 7.64-7.60 (m, 1H), 6.62 (s, 1H), 4.82 (d, J=8.3 Hz, 1H), 4.68 (s, 1H), 4.33 (s, 1H), 3.89-3.81 (m, 1H), 3.48 (d, J=6.3 Hz, 2H), 2.59 (s, 2H), 2.43-2.31 (m, 1H), 2.07-2.00 (m, 2H), 1.96-1.69 (m, 5H), 1.48-1.40 (m, 4H), 1.32 (s, 6H), 1.25 (s, 1H), 1.20-1.16 (m, 1H), 1.12 (d, J=6.4 Hz, 3H).

Example 173

(S)-5-(4-difluoromethyl)-6-((1-methylcyclobutyl)amino)pyridine-3-yl)-N-(2-hydroxy-2-methylpropyl)-4-(2-methylpyrrolidine-1-carbonyl)thiazole-2-carboxamide

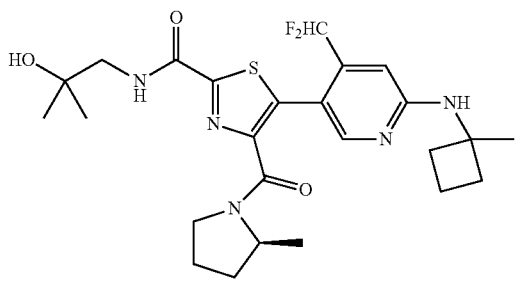 [SMILES: C[C@H]1CCCN1C(=O)c1nc(C(=O)NCC(C)(C)O)sc1-c1cnc(NC2(C)CCC2)cc1C(F)F]

The title compound was prepared as described in Example 77 substituting 5-bromo-N-(1-methylcyclobutyl)-4-(difluoromethyl)pyridine-2-amine (Intermediate 91) for 5-bromo-N-(1-methylcyclobutyl)-4-(trifluoromethyl)pyridin-2-amine. MS (ESI): mass calcd. for C$_{25}$H$_{33}$F$_2$N$_5$O$_3$S, 521.2; m/z found, 522.2 [M+H]$^+$. $^1$H NMR (400 MHz, CDCl$_3$) δ 8.03-7.99 (m, 1H), 7.61-7.53 (m, 1H), 7.01-6.50 (m, 2H), 5.20 (s, 1H), 4.36-4.17 (m, 1H), 3.64-3.30 (m, 4H), 2.35-1.83 (m, 10H), 1.83-1.49 (m, 4H), 1.31 (s, 6H), 1.28-1.20 (m, 2H), 1.02 (d, J=6.4 Hz, 1H).

Example 174

N-((3S,4R)-4-Hydroxytetrahydrofuran-3-yl)-4-((2S)-2-methylpyrrolidine-1-carbonyl)-5-(4-(trifluoromethyl)-6-(((1S)-1-(trifluoromethyl)propyl)amino)-3-pyridyl)thiazole-2-carboxamide

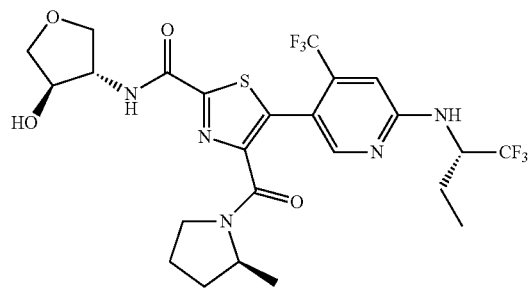 [SMILES: CC[C@H](Nc1cc(C(F)(F)F)c(-c2sc(C(=O)N[C@H]3COC[C@@H]3O)nc2C(=O)N2CCC[C@@H]2C)cn1)C(F)(F)F]

The title compound was prepared as described in Example 148 substituting ethyl 4-((S)-2-methylpyrrolidine-1-carbonyl)-5-(6-(((S)-1,1,1-trifluorobutan-2-yl)amino)-4-(trifluoromethyl)pyridin-3-yl)thiazole-2-carboxylate (Intermediate 103) for ethyl (S)-5-(6-(tert-butylamino)-4-(difluoromethyl)pyridin-3-yl)-4-(2-methylpyrrolidine-1-carbonyl)thiazole-2-carboxylate and (3R,4S)-4-amino-tetrahydro-furan-3-ol for (R)-(−)-2-amino-1-propanol. MS (ESI): mass calcd. for C$_{24}$H$_{27}$F$_6$N$_5$O$_4$S, 595.6; m/z found, 596.1 [M+H]$^+$. $^1$H NMR (400 MHz, CDCl$_3$) δ 8.22-8.16 (s, 1H), 6.79-6.75 (m, 1H), 4.87-4.76 (m, 1H), 4.41-4.31 (m, 2H), 4.26-4.14 (m, 3H), 3.91-3.84 (m, 1H), 3.77-3.72 (m, 1H), 3.60-3.31 (m, 2H), 2.13-2.06 (m, 1H), 1.98-1.87 (m, 2H), 1.79-1.70 (m, 1H), 1.64-1.50 (m, 2H), 1.26-1.23 (m, 3H), 1.09-0.99 (m, 4H).

Example 175

5-(6-(((S*)-1-Cyclobutylethyl)amino)-4-(trifluoromethyl)pyridine-3-yl)-N-(2-hydroxy-2-methylpropyl)-4-(((S)-2-methylpyrrolidine-1-carbonyl)thiazole-2-carboxamide

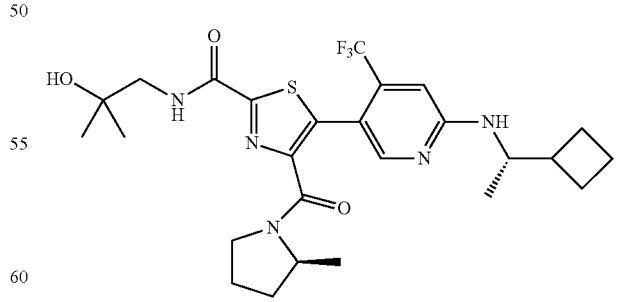

The title compound was prepared as described in Example 77 substituting 5-bromo-N-(1-cyclobutylethyl)-4-(trifluoromethyl)pyridine-2-amine (Intermediate 89) for 5-bromo-N-(1-methylcyclobutyl)-4-(trifluoromethyl)pyridin-2-amine. A purification was performed via chiral SFC (Stationary phase: Chiralpak IC, 5 μm, 250×20 mm, Mobile phase: 0.5% iPrNH$_2$, 85% CO$_2$, 15% MeOH/iPrOH (50/50), second eluting peak) to separate enantiomers. MS (ESI): mass calcd. for C$_{26}$H$_{34}$F$_3$N$_5$O$_3$S, 553.2; m/z found, 554.2 [M+H]$^+$. $^1$H NMR (400 MHz, CDCl$_3$) δ 8.16 (d, J=2.4 Hz, 1H), 7.63-7.50 (m, 1H), 6.61 (s, 1H), 4.76 (d, J=8.3 Hz, 1H), 4.33-4.17 (m, 1H), 3.87-3.77 (m, 1H), 3.61-3.37 (m, 4H), 2.45-2.29 (m, 1H), 2.14-1.70 (m, 6H), 1.66-1.50 (m, 1H), 1.39-1.18 (m, 11H), 1.15-1.08 (m, 4H), 0.93-0.78 (m, 1H).

Example 176

5-(6-(((R*)-1-Cyclobutylethyl)amino)-4-(trifluoromethyl)pyridine-3-yl)-N-(2-hydroxy-2-methylpropyl)-4-((S)-2-methylpyrrolidine-1-carbonyl)thiazole-2-carboxamide

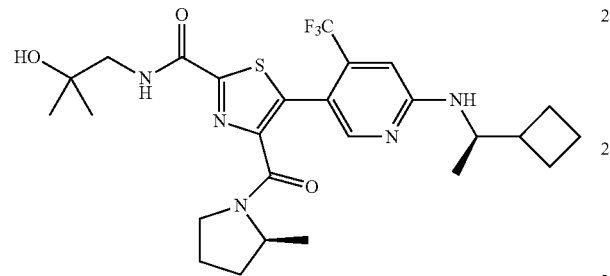

The title compound was prepared as described in Example 77 substituting 5-bromo-N-(1-cyclobutylethyl)-4-(trifluoromethyl)pyridine-2-amine (Intermediate 89) for 5-bromo-N-(1-methylcyclobutyl)-4-(trifluoromethyl)pyridin-2-amine. A purification was performed via chiral SFC (Stationary phase: Chiralpak IC, 5 μm, 250×20 mm, Mobile phase: 0.5% iPrNH$_2$, 85% CO$_2$, 15% MeOH/iPrOH (50/50), first eluting peak) to separate enantiomers. MS (ESI): mass calcd. for C$_{26}$H$_{34}$F$_3$N$_5$O$_3$S, 553.2; m/z found, 554.2 [M+H]$^+$. $^1$H NMR (400 MHz, CDCl$_3$) δ 8.16 (s, 1H), 7.64-7.49 (m, 1H), 6.61 (s, 1H), 4.74 (d, J=7.9 Hz, 1H), 4.34-4.15 (m, 1H), 3.92-3.76 (m, 1H), 3.65-3.36 (m, 4H), 2.42-2.34 (m, 1H), 2.13-1.45 (m, 7H), 1.43-1.19 (m, 11H), 1.18-1.06 (m, 4H), 0.90-0.82 (m, 1H).

Example 177

(S)-5-(6-((Dicyclopropylmethyl)amino)-4-(difluoromethyl)pyridine-3-yl)-4-(4,4-difluoro-2-methylpyrrolidine-1-carbonyl)-N-(2-hydroxy-2-methylpropyl)thiazole-2-carboxamide

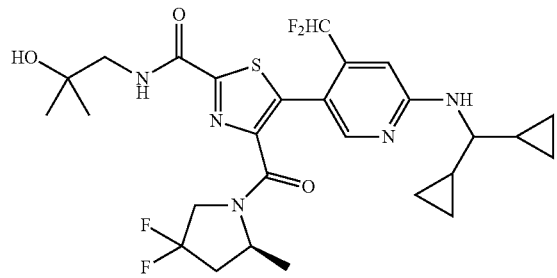 [SMILES: C[C@H]1CC(F)(F)CN1C(=O)c1nc(C(=O)NCC(C)(C)O)sc1-c1cnc(NC(C2CC2)C2CC2)cc1C(F)F]

The title compound was prepared as described in Example 77 substituting (S)-4-(4,4-difluoro-2-methylpyrrolidine-1-carbonyl)-N-(2-hydroxy-2-methylpropyl)thiazole-2-carboxamide (Intermediate 67) for (S)—N-(2-hydroxy-2-methylpropyl)-4-(2-methylpyrrolidine-1-carbonyl)thiazole-2-carboxamide and 5-bromo-N-(dicyclopropylmethyl)-4-(difluoromethyl)pyridin-2-amine (Intermediate 92) for 5-bromo-N-(1-methylcyclobutyl)-4-(trifluoromethyl)pyridin-2-amine. MS (ESI): mass calcd. for C$_{27}$H$_{33}$F$_4$N$_5$O$_3$S, 583.2; m/z found, 584.2 [M+H]$^+$. $^1$H NMR (400 MHz, CDCl$_3$) δ 7.96 (d, J=9.9 Hz, 1H), 7.55-7.45 (m, 1H), 6.95-6.32 (m, 2H), 4.90 (d, J=7.9 Hz, 1H), 4.73-4.44 (m, 1H), 4.15-3.98 (m, 1H), 3.97-3.76 (m, 1H), 3.59-3.38 (m, 2H), 3.28-3.15 (m, 1H), 2.65-2.49 (m, 1H), 2.24-1.79 (m, 2H), 1.43-1.17 (m, 9H), 1.05-0.95 (m, 2H), 0.63-0.21 (m, 8H).

Example 178

4-((1s,4s)-7-Azabicyclo[2.2.1]heptane-7-carbonyl)-5-(6-(((dicyclopropylmethyl)amino)-4-(difluoromethyl)pyridine-3-yl)-N-(2-hydroxy-2-methylpropyl)thiazole-2-carboxamide

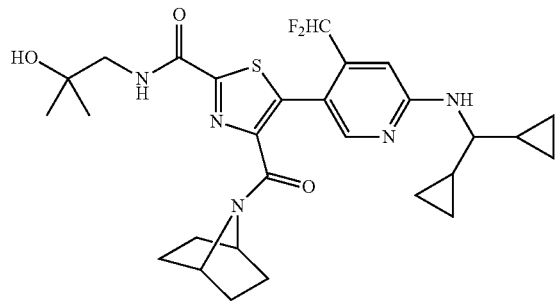 [SMILES: CC(C)(O)CNC(=O)c1nc(C(=O)N2C3CCC2CC3)c(-c2cnc(NC(C3CC3)C3CC3)cc2C(F)F)s1]

The title compound was prepared as described in Example 77 substituting 4-((1s,4s)-7-azabicyclo[2.2.1]heptane-7-carbonyl)-N-(2-hydroxy-2-methylpropyl)thiazole-2-carboxamide (Intermediate 70) for (S)—N-(2-hydroxy-2-methylpropyl)-4-(2-methylpyrrolidine-1-carbonyl)thiazole-2-carboxamide and 5-bromo-N-(dicyclopropylmethyl)-4-(difluoromethyl)pyridin-2-amine (Intermediate 92) for 5-bromo-N-(1-methylcyclobutyl)-4-(trifluoromethyl)pyridin-2-amine. MS (ESI): mass calcd. for C$_{28}$H$_{35}$F$_2$N$_5$O$_3$S, 559.2; m/z found, 560.2 [M+H]$^+$. $^1$NMR (500 MHz, CDCl$_3$) δ 7.99 (s, 1H), 7.61-7.58 (m, 1H), 6.88-6.63 (m, 2H), 4.88 (d, J=8.0 Hz, 1H), 4.71-4.68 (m, 1H), 4.25 (t, J=4.9 Hz, 1H), 3.48 (d, J=6.3 Hz, 2H), 3.24 (q, J=7.4 Hz, 1H), 2.03-2.00 (m, 1H), 1.81-1.72 (m, 2H), 1.67-1.52 (m, 2H), 1.50-1.39 (m, 4H), 1.32 (s, 6H), 1.07-0.95 (m, 2H), 0.59-0.29 (m, 8H).

Example 179

(S)-5-(6-((Dicyclopropylmethyl)amino)-4-(difluoromethyl)pyridine-3-yl)-N-(2-hydroxy-2-methylpropyl)-4-(2-methylpyrrolidine-1-carbonyl)thiazole-2-carboxamide

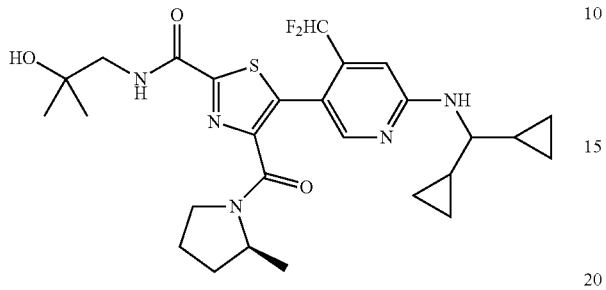

The title compound was prepared as described in Example 77 substituting 5-bromo-N-(dicyclopropylmethyl)-4-(difluoromethyl)pyridin-2-amine (Intermediate 92) for 5-bromo-N-(1-methylcyclobutyl)-4-(trifluoromethyl)pyridin-2-amine. MS (ESI): mass calcd. for $C_{27}H_{35}F_2N_5O_3S$, 547.2; m/z found, 548.2 [M+H]$^+$. $^1$H NMR (500 MHz, CDCl$_3$) δ 7.99-7.95 (m, 1H), 7.59-7.53 (m, 1H), 7.00-6.59 (m, 2H), 4.90-4.87 (m, 1H), 4.30-4.20 (m, 1H), 3.65-3.33 (m, 4H), 3.29-3.18 (m, 1H), 2.11-1.70 (m, 4H), 1.59-1.51 (m, 1H), 1.32 (d, J=1.6 Hz, 6H), 1.23 (d, J=6.3 Hz, 2H), 1.06-0.94 (m, 3H), 0.60-0.27 (m, 8H).

Example 180

(S)-5-(6-(tert-Butylamino)-4-(trifluoromethyl)pyridine-3-yl)-N-(2-hydroxy-2-(methyl-d$_3$)propyl-3,3,3-d$_3$)-4-(2-methylpyrrolidine-1-carbonyl)thiazole-2-carboxamide

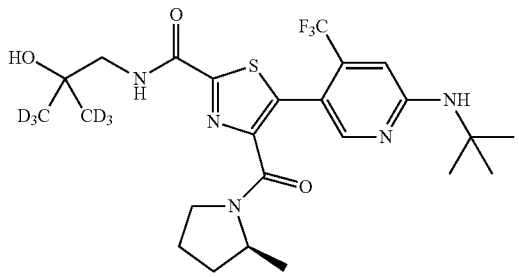 [SMILES: [2H]C([2H])([2H])C(O)(CNC(=O)c1nc(C(=O)N2CCC[C@@H]2C)c(-c2cnc(NC(C)(C)C)cc2C(F)(F)F)s1)C([2H])([2H])[2H]]

The title compound was prepared as described in Example 77 substituting (S)—N-(2-hydroxy-2-(methyl-d$_3$)propyl-3,3,3-d$_3$)-4-(2-methylpyrrolidine-1-carbonyl)thiazole-2-carboxamide (Intermediate 77) for (S)—N-(2-hydroxy-2-methylpropyl)-4-(2-methylpyrrolidine-1-carbonyl)thiazole-2-carboxamide and 5-bromo-N-(tert-butyl)-4-(trifluoromethyl)pyridin-2-amine (Intermediate 41) for 5-bromo-N-(1-methylcyclobutyl)-4-(trifluoromethyl)pyridin-2-amine. MS (ESI): mass calcd. for $C_{24}H_{26}D_6F_3N_5O_3S$, 533.2; m/z found, 534.2 [M+H]$^+$. $^1$H NMR (400 MHz, CDCl$_3$) δ 8.17 (s, 1H), 7.65-7.51 (m, 1H), 6.63 (s, 1H), 4.89 (s, 1H), 4.32-4.15 (m, 1H), 3.63-3.34 (m, 4H), 2.13-1.68 (m, 4H), 1.65-1.45 (m, 10H), 1.32-1.07 (m, 3H).

Example 181

(S)-5-(6-(tert-Butylamino)-4-(trifluoromethyl)pyridine-3-yl)-N-(2-hydroxy-2-methylpropyl-1,1-d$_2$)-4-(2-methylpyrrolidine-1-carbonyl)thiazole-2-carboxamide

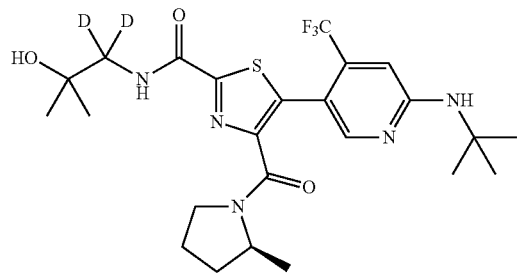 [SMILES: [2H]C([2H])(NC(=O)c1nc(C(=O)N2CCC[C@@H]2C)c(-c2cnc(NC(C)(C)C)cc2C(F)(F)F)s1)C(C)(C)O]

The title compound was prepared as described in Example 77 substituting (S)—N-(2-hydroxy-2-methylpropyl-1,1-d$_2$)-4-(2-methylpyrrolidine-1-carbonyl)thiazole-2-carboxamide (Intermediate 76) for (S)—N-(2-hydroxy-2-methylpropyl)-4-(2-methylpyrrolidine-1-carbonyl)thiazole-2-carboxamide and 5-bromo-N-(tert-butyl)-4-(trifluoromethyl)pyridin-2-amine (Intermediate 41) for 5-bromo-N-(1-methylcyclobutyl)-4-(trifluoromethyl)pyridin-2-amine. MS (ESI): mass calcd. for $C_{24}H_{30}D_2F_3N_5O_3S$, 529.2; m/z found, 530.2 [M+H]$^+$. $^1$H NMR (500 MHz, CDCl$_3$) δ 8.18 (s, 1H), 7.59-7.52 (m, 1H), 6.63 (s, 1H), 4.88 (s, 1H), 4.30-4.26 (m, 0.25H), 4.24-4.16 (m, 0.75H), 3.66-3.34 (m, 2H), 2.09-2.04 (m, 1H), 2.03-1.81 (m, 1H), 1.76-1.70 (m, 1H), 1.66-1.57 (m, 1H), 1.57-1.48 (m, 1H), 1.46 (s, 9H), 1.31 (s, 6H), 1.28-1.22 (m, 2.5H), 1.11 (d, J=6.4 Hz, 0.5H).

Example 182

4-((S)-4,4-Difluoro-2-methylpyrrolidine-1-carbonyl)-N-(cis-4-hydroxytetrahydrofuran-3-yl)-5-(6-((1-methylcyclobutyl)amino)-4-(trifluoromethyl)pyridine-3-yl)thiazole-2-carboxamide

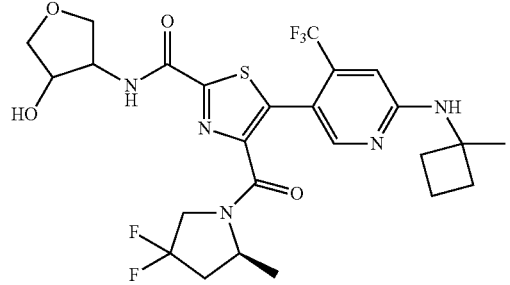 [SMILES: C[C@H]1CC(F)(F)CN1C(=O)c1nc(C(=O)NC2COCC2O)sc1-c1cnc(NC2(C)CCC2)cc1C(F)(F)F]

To a screw capped vial was added ethyl (S)-4-(4,4-difluoro-2-methylpyrrolidine-1-carbonyl)-5-(6-((1-methylcyclobutyl)amino)-4-(trifluoromethyl)pyridin-3-yl)thiazole-2-carboxylate (150 mg, 0.28 mmol, Intermediate 93), cis-4-aminotetrahydrofuran-3-ol hydrochloride (197 mg, 1.4 mmol), ethanol (3.0 mL) and DIPEA (0.24 mL, 1.4 mmol). The vial was capped and the reaction heated to 80° C. for 24 h. The solvent was removed under reduced pressure, crude residue re-dissolved in DCM and purified by FCC (0-100% ethyl acetate/DCM) to provide the title compound. MS (ESI): mass calcd. for C$_{25}$H$_{28}$F$_5$N$_5$O$_4$S, 589.2; m/z found, 590.2 [M+H]$^+$. $^1$H NMR (400 MHz, CDCl$_3$) δ 8.13 (s, 1H), 7.76-7.66 (m, 1H), 6.51 (s, 1H), 4.73-4.42 (m, 3H), 4.23-3.68 (m, 6H), 2.68-2.46 (m, 2H), 2.33-2.21 (m, 2H), 2.20-1.87 (m, 6H), 1.55 (s, 3H), 1.41-1.22 (m, 3H).

Example 183

4-((S)-4,4-Difluoro-2-methylpyrrolidine-1-carbonyl)-N-((3R*,4R*)-4-hydroxytetrahydrofuran-3-yl)-5-(6-((1-methylcyclobutyl)amino)-4-(trifluoromethyl)pyridine-3-yl)thiazole-2-carboxamide

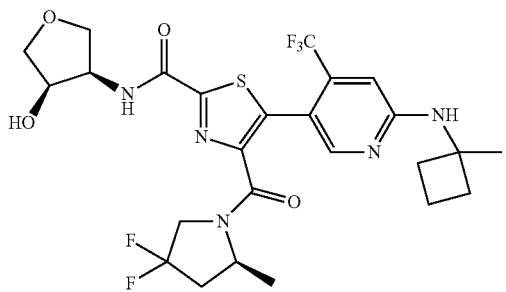 [SMILES: C[C@H]1CC(F)(F)CN1C(=O)c1nc(C(=O)N[C@@H]2COC[C@@H]2O)sc1-c1cnc(NC2(C)CCC2)cc1C(F)(F)F]

The title compound was isolated by purification of Example 182 by chiral SFC (Stationary phase: CHIRALPAK IC, 5 μm, 250×20 mm, Mobile phase: 85% CO$_2$, 15% methanol, 0.3% iPrNH$_2$). MS (ESI): mass calcd. for C$_{25}$H$_{28}$F$_5$N$_5$O$_4$S, 589.2; m/z found, 590.2 [M+H]$^+$. $^1$H NMR (600 MHz, CDCl$_3$) δ 8.14 (s, 1H), 7.76-7.71 (m, 1H), 6.51 (s, 1H), 5.23 (s, 1H), 4.69-4.56 (m, 1.2H), 4.55-4.45 (m, 1.8H), 4.20 (dd, J=8.9, 7.5 Hz, 1H), 4.15-4.01 (m, 2H), 3.94-3.86 (m, 1.8H), 3.85-3.70 (m, 1.2H), 2.60-2.50 (m, 1H), 2.31-2.25 (m, 2H), 2.19-2.02 (m, 3H), 2.01-1.89 (m, 2H), 1.55 (s, 3H), 1.36-1.30 (m, 3H), 1.22 (d, J=6.2 Hz, 0.3H), 1.09 (d, J=6.2 Hz, 0.7H).

Example 184

4-((S)-4,4-Difluoro-2-methylpyrrolidine-1-carbonyl)-N-((3S*,4S*)-4-hydroxytetrahydrofuran-3-yl)-5-(6-((1-methylcyclobutyl)amino)-4-(trifluoromethyl)pyridine-3-yl)thiazole-2-carboxamide

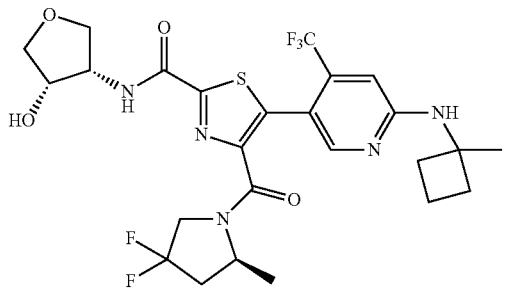 [SMILES: C[C@H]1CC(F)(F)CN1C(=O)c1nc(C(=O)N[C@H]2COC[C@H]2O)sc1-c1cnc(NC2(C)CCC2)cc1C(F)(F)F]

The title compound was isolated by purification of Example 182 by chiral SFC (Stationary phase: CHIRALPAK IC, 5 μm, 250×20 mm, Mobile phase: 85% CO$_2$, 15% methanol, 0.3% iPrNH$_2$). MS (ESI): mass calcd. for C$_{25}$H$_{28}$F$_5$N$_5$O$_4$S, 589.2; m/z found, 590.2 [M+H]$^+$. $^1$H NMR (600 MHz, CDCl$_3$) δ 8.14 (s, 1H), 7.76-7.71 (m, 1H), 6.51 (s, 1H), 5.23 (s, 1H), 4.69-4.56 (m, 1.2H), 4.55-4.45 (m, 1.8H), 4.20 (dd, J=8.9, 7.5 Hz, 1H), 4.15-4.01 (m, 2H), 3.94-3.86 (m, 1.8H), 3.85-3.70 (m, 1.2H), 2.60-2.50 (m, 1H), 2.31-2.25 (m, 2H), 2.19-2.02 (m, 3H), 2.01-1.89 (m, 2H), 1.55 (s, 3H), 1.36-1.30 (m, 3H), 1.22 (d, J=6.2 Hz, 0.3H), 1.09 (d, J=6.2 Hz, 0.7H).

Example 185

4-((S)-4,4-Difluoro-2-methylpyrrolidine-1-carbonyl)-N-((3S,4R)-4-hydroxytetrahydrofuran-3-yl)-5-(6-((1-methylcyclobutyl)amino)-4-(trifluoromethyl)pyridine-3-yl)thiazole-2-carboxamide

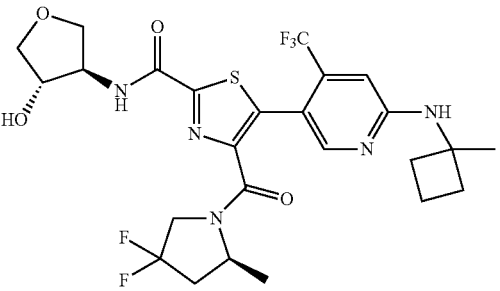 [SMILES: C[C@H]1CC(F)(F)CN1C(=O)c1nc(C(=O)N[C@@H]2COC[C@H]2O)sc1-c1cnc(NC2(C)CCC2)cc1C(F)(F)F]

The title compound was prepared as described in Example 189, using (3S,4R)-4-aminotetrahydrofuran-3-ol in place of (S)-3-amino-2-methylbutan-2-ol and ethyl (S)-4-(4,4-difluoro-2-methylpyrrolidine-1-carbonyl)-5-(6-((1-methylcyclobutyl)amino)-4-(trifluoromethyl)pyridin-3-yl)thiazole-2-carboxylate in place of ethyl 4-((1s,4s)-7-azabicyclo[2.2.1]heptane-7-carbonyl)-5-(4-(difluoromethyl)-6-((1-methylcyclobutyl)amino)pyridine-3-yl)thiazole-2-carboxylate. MS (ESI): mass calcd. for C$_{25}$H$_{28}$F$_5$N$_5$O$_4$S, 589.2; m/z found, 590.2 [M+H]$^+$. $^1$H NMR (400 MHz, CDCl$_3$) δ 8.14 (s, 1H), 7.26-7.19 (m, 1H), 6.51 (s, 1H), 5.29 (s, 1H), 4.63-4.34 (m, 3H), 4.28-3.70 (m, 6H), 3.20-3.10 (m, 1H), 2.64-2.46 (m, 1H), 2.34-2.21 (m, 2H), 2.20-1.87 (m, 5H), 1.55 (s, 3H), 1.38 (d, J=6.4 Hz, 2H), 1.29-1.18 (m, 1H).

Example 186

4-((S)-4,4-Difluoro-2-methylpyrrolidine-1-carbonyl)-N-((3R,4S)-4-hydroxytetrahydrofuran-3-yl)-5-(6-(((1-methylcyclobutyl)amino)-4-(trifluoromethyl)pyridine-3-yl)thiazole-2-carboxamide

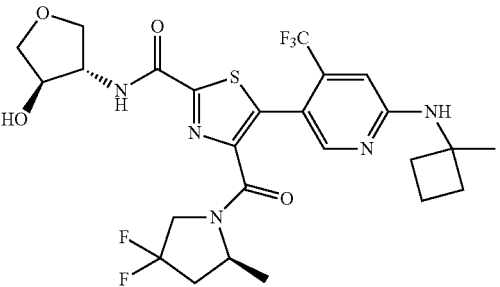 [SMILES: C[C@H]1CC(F)(F)CN1C(=O)c1nc(C(=O)N[C@H]2COC[C@@H]2O)sc1-c1cnc(NC2(C)CCC2)cc1C(F)(F)F]

The title compound was prepared as described in Example 189, using (3R,4S)-4-aminotetrahydrofuran-3-ol in place of (S)-3-amino-2-methylbutan-2-ol and ethyl (S)-4-(4,4-difluoro-2-methylpyrrolidine-1-carbonyl)-5-(6-((1-methylcyclobutyl)amino)-4-(trifluoromethyl)pyridin-3-yl)thiazole-2-carboxylate in place of ethyl 4-((1s,4s)-7-azabicyclo[2.2.1]heptane-7-carbonyl)-5-(4-(difluoromethyl)-6-((1-methylcyclobutyl)amino)pyridine-3-yl)thiazole-2-carboxylate. MS (ESI): mass calcd. for $C_{25}H_{28}F_5N_5O_4S$, 589.2; m/z found, 590.2 [M+H]$^+$. $^1$H NMR (400 MHz, CDCl$_3$) δ 8.14 (s, 1H), 7.26-7.19 (m, 1H), 6.51 (s, 1H), 5.29 (s, 1H), 4.63-4.34 (m, 3H), 4.28-3.70 (m, 6H), 3.20-3.10 (m, 1H), 2.64-2.46 (m, 1H), 2.34-2.21 (m, 2H), 2.20-1.87 (m, 5H), 1.55 (s, 3H), 1.38 (d, J=6.4 Hz, 2H), 1.29-1.18 (m, 1H).

Example 187

5-(4-(Difluoromethyl)-6-(((S)-1,1,1-trifluoropropan-2-yl)amino)pyridine-3-yl)-N-(1,1-dioxidotetrahydro-2H-thiopyran-4-yl)-4-((S)-2-methylpyrrolidine-1-carbonyl)thiazole-2-carboxamide

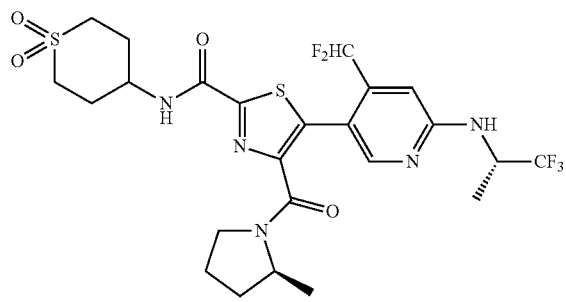 [SMILES: C[C@H](Nc1cc(C(F)F)c(-c2sc(C(=O)NC3CCS(=O)(=O)CC3)nc2C(=O)N2CCC[C@@H]2C)cn1)C(F)(F)F]

The title compound was prepared as described in Example 189, using 4-aminotetrahydro-2H-thiopyran-1,1-dioxide in place of (S)-3-amino-2-methylbutan-2-ol and ethyl 5-(4-(difluoromethyl)-6-(((S)-1,1,1-trifluoropropan-2-yl)amino)pyridine-3-yl)-4-((S)-2-methylpyrrolidine-1-carbonyl)thiazole-2-carboxylate (Intermediate 94) in place of ethyl 4-((1s,4s)-7-azabicyclo[2.2.1]heptane-7-carbonyl)-5-(4-(difluoromethyl)-6-((1-methylcyclobutyl)amino)pyridine-3-yl)thiazole-2-carboxylate. MS (ESI): mass calcd. for $C_{24}H_{28}F_5N_5O_4S_2$, 609.2; m/z found, 610.1 [M+H]$^+$. $^1$H NMR (400 MHz, CDCl$_3$) δ 8.10-8.04 (m, 1H), 7.22-6.61 (m, 3H), 5.02-4.82 (m, 2H), 4.30-4.17 (m, 2H), 3.64-3.52 (m, 0.7H), 3.49-3.28 (m, 1.3H), 3.27-3.07 (m, 4H), 2.51-2.23 (m, 4H), 2.13-1.72 (m, 3H), 1.60-1.52 (m, 1H), 1.42 (d, J=6.7 Hz, 3H), 1.25 (d, J=6.8 Hz, 2H), 1.01 (d, J=6.4 Hz, 1H).

Example 188

5-4-(Difluoromethyl)-6-(((S)-1,1,1-trifluoropropan-2-yl)amino)pyridine-3-yl)-N-((1r,3S)-3-hydroxycyclobutyl)-4-((S)-2-methylpyrrolidine-1-carbonyl)thiazole-2-carboxamide

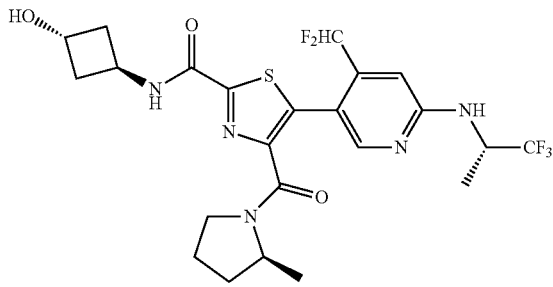 [SMILES: C[C@H](Nc1cc(C(F)F)c(-c2sc(C(=O)N[C@H]3C[C@H](O)C3)nc2C(=O)N2CCC[C@@H]2C)cn1)C(F)(F)F]

The title compound was prepared as described in Example 189, using (1r,3R)-3-aminocyclobutan-1-ol in place of (S)-3-amino-2-methylbutan-2-ol and ethyl 5-(4-(difluoromethyl)-6-(((S)-1,1,1-trifluoropropan-2-yl)amino)pyridine-3-yl)-4-((S)-2-methylpyrrolidine-1-carbonyl)thiazole-2-carboxylate (Intermediate 94) in place of ethyl 4-((1s,4s)-7-azabicyclo[2.2.1]heptane-7-carbonyl)-5-(4-(difluoromethyl)-6-((1-methylcyclobutyl)amino)pyridine-3-yl)thiazole-2-carboxylate. MS (ESI): mass calcd. for $C_{23}H_{26}F_5N_5O_3S$, 547.2; m/z found, 548.1 [M+H]$^+$. $^1$H NMR (400 MHz, CDCl$_3$) δ 8.10-8.03 (m, 1H), 7.35-7.22 (m, 1H), 7.05-6.60 (m, 2H), 5.01-4.84 (m, 2H), 4.72-4.54 (m, 2H), 4.30-4.08 (m, 1H), 3.63-3.52 (m, 0.7H), 3.49-3.29 (m, 1.3H), 2.52-2.40 (m, 4H), 2.13-1.48 (m, 4H), 1.42 (d, J=6.4 Hz, 3H), 1.30-1.18 (m, 3H), 1.01 (d, J=6.4 Hz, 1H).

Example 189

4-((1s,4s)-7-Azabicyclo[2.2.1]heptane-7-carbonyl)-5-(4-(difluoromethyl)-6-((1-methylcyclobutyl)amino)pyridine-3-yl)-N-4S-3-hydroxy-3-methylbutan-2-yl)thiazole-2-carboxamide

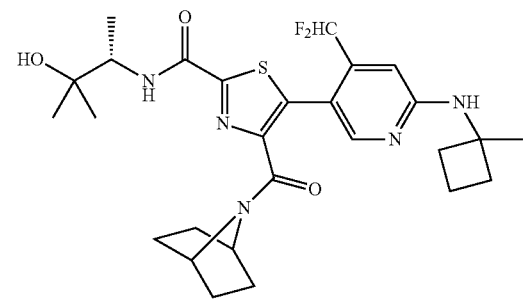 [SMILES: C[C@H](NC(=O)c1nc(C(=O)N2C3CCC2CC3)c(-c2cnc(NC3(C)CCC3)cc2C(F)F)s1)C(C)(C)O]

To a screw capped vial was added ethyl 4-((1s,4s)-7-azabicyclo[2.2.1]heptane-7-carbonyl)-5-(4-(difluoromethyl)-6-((1-methylcyclobutyl)amino)pyridine-3-yl)thiazole-2-carboxylate (100 mg, 0.20 mmol, Intermediate 95), (S)-3-amino-2-methylbutan-2-ol (105 mg, 1.0 mmol) and ethanol (2.0 mL). The vial was capped and the reaction heated to 80° C. for 24 h. The solvent was removed under reduced pressure, crude residue re-dissolved in DCM and purified by FCC (0-100% ethyl acetate/DCM) to provide the title compound. MS (ESI): mass calcd. for $C_{27}H_{35}F_2N_5O_3S$, 547.2; m/z found, 547.8 [M+H]$^+$. $^1$H NMR (400 MHz, CDCl$_3$) δ 8.04 (s, 1H), 7.43 (d, J=9.3 Hz, 1H), 6.52 (s, 2H), 5.14 (s, 1H), 4.69 (t, J=4.8 Hz, 1H), 4.22 (t, J=4.5 Hz, 1H), 4.16-4.03 (m, 1H), 2.30-2.22 (m, 2H), 2.17-2.10 (m, 2H), 1.99-1.87 (m, 3H), 1.85-1.69 (m, 2H), 1.55-1.53 (m, 4H), 1.49-1.38 (m, 5H), 1.34-1.22 (m, 9H).

Example 190

4-((S)-4,4-Difluoro-2-methylpyrrolidine-1-carbonyl)-5-(4-(difluoromethyl)-6-(((S-1,1,1-trifluoropropan-2-yl)amino)pyridin-3-yl)-N-((3S,4R)-4-hydroxytetrahydrofuran-3-yl)-thiazole-2-carboxamide

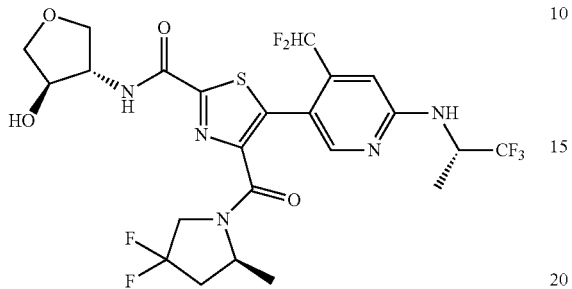

The title compound was prepared as described in Example 189, using (3R,3S)-4-aminotetrahydrofuran-3-ol in place of (S)-3-amino-2-methylbutan-2-ol and ethyl 4-((S)-4,4-difluoro-2-methylpyrrolidine-1-carbonyl)-5-(4-(difluoromethyl)-6-(((S)-1,1,1, -trifluoropropan-2-yl)amino)pyridine-3-yl)thiazole-2-carboxylate (Intermediate 96) in place of ethyl 4-((1s,4s)-7-azabicyclo[2.2.1]heptane-7-carbonyl)-5-(4-(difluoromethyl)-6-((1-methylcyclobutyl)amino)pyridine-3-yl)thiazole-2-carboxylate. MS (ESI): mass calcd. for $C_{23}H_{24}F_7N_5O_4S$, 599.1; m/z found, 600.1 [M+H]$^+$. $^1$H NMR (400 MHz, CDCl$_3$) δ 8.08-8.03 (m, 1H), 7.31-7.16 (m, 1H), 6.96-6.52 (m, 2H), 5.03-4.83 (m, 2H), 4.71-4.64 (m, 0.25H), 4.53-4.44 (m, 1.75H), 4.42-4.36 (m, 1H), 4.26-4.14 (m, 2H), 4.13-3.97 (m, 1H), 3.96-3.72 (m, 3H), 3.00 (s, 1H), 2.72-2.47 (m, 1H), 2.20-2.00 (m, 1H), 1.43-1.35 (m, 5.5H), 1.17 (d, J=6.5 Hz, 0.5H).

Example 191

4-((S)-4,4-Difluoro-2-methylpyrrolidine-1-carbonyl)-5-(4-(difluoromethyl)-6-(((S)-1,1,1-trifluoropropan-2-yl)amino)pyridine-3-yl)-N-((1r,3S)-3-hydroxycyclobutyl)thiazole-2-carboxamide

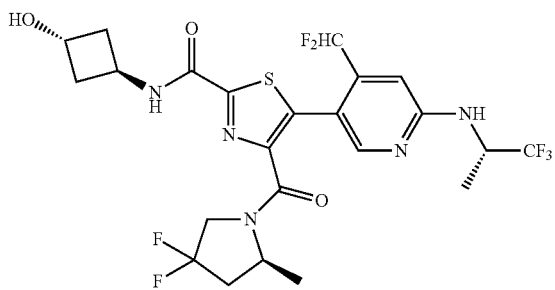 [SMILES: C[C@H](Nc1cc(C(F)F)c(-c2sc(C(=O)N[C@H]3C[C@H](O)C3)nc2C(=O)N2CC(F)(F)C[C@@H]2C)cn1)C(F)(F)F]

The title compound was prepared as described in Example 189, using (1r,3R)-3-aminocyclobutan-1-ol in place in place of (S)-3-amino-2-methylbutan-2-ol and ethyl 4-((S)-4,4-difluoro-2-methylpyrrolidine-1-carbonyl)-5-(4-(difluoromethyl)-6-(((S)-1,1,1,-trifluoropropan-2-yl)amino)pyridine-3-yl)thiazole-2-carboxylate (Intermediate 96) in place of ethyl 4-((1s,4s)-7-azabicyclo[2.2.1]heptane-7-carbonyl)-5-(4-(difluoromethyl)-6-((1-methylcyclobutyl)amino)pyridine-3-yl)thiazole-2-carboxylate. MS (ESI): mass calcd. for $C_{23}H_{24}F_7N_5O_3S$, 583.1; m/z found, 584.1 [M+H]$^+$. $^1$H NMR (500 MHz, CDCl$_3$) δ 8.08-8.04 (m, 1H), 7.21-7.16 (m, 1H), 6.92-6.55 (m, 2H), 5.00-4.90 (m, 1H), 4.82 (d, J=9.5 Hz, 1H), 4.73-4.57 (m, 2.3H), 4.54-4.46 (m, 0.7H), 4.08-3.98 (m, 1H), 3.92-3.78 (m, 1H), 2.65-2.40 (m, 5H), 2.23-2.02 (m, 1H), 1.84 (d, J=4.4 Hz, 1H), 1.42 (d, J=6.9 Hz, 3H), 1.36 (d, J=6.5 Hz, 2.3H), 1.31-1.15 (m, 0.7H).

Example 192

4-((S)-4,4-Difluoro-2-methylpyrrolidine-1-carbonyl)-5-(4-(difluoromethyl)-6-(((S)-1,1,1-trifluoropropan-2-yl)amino)pyridine-3-yl)-N-(1,1-dioxidothietan-3-yl)thiazole-2-carboxamide

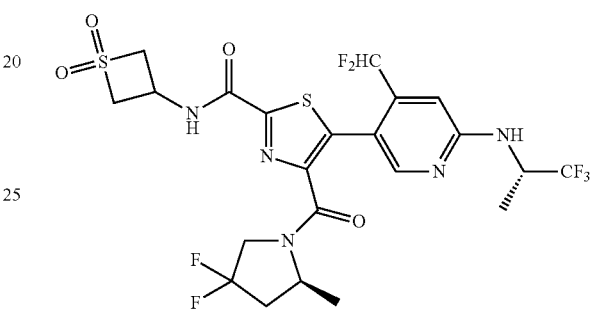

The title compound was prepared as described in Example 182, using 3-aminothietan-1,1-dioxide in place in place of (rac)-4-aminotetrahydrofuran-3-ol and ethyl 4-((S)-4,4-difluoro-2-methylpyrrolidine-1-carbonyl)-5-(4-(difluoromethyl)-6-(((S)-1,1,1,-trifluoropropan-2-yl)amino)pyridine-3-yl)thiazole-2-carboxylate (Intermediate 96) in place of ethyl (S)-4-(4,4-difluoro-2-methylpyrrolidine-1-carbonyl)-5-(6-((1-methylcyclobutyl)amino)-4-(trifluoromethyl)pyridin-3-yl)thiazole-2-carboxylate. MS (ESI): mass calcd. for $C_{22}H_{22}F_7N_5O_4S_2$, 617.1; m/z found, 618.0 [M+H]$^+$. $^1$H NMR (500 MHz, CDCl$_3$) δ 8.08-8.04 (m, 1H), 7.68-7.64 (m, 1H), 6.92-6.56 (m, 2H), 5.03-4.87 (m, 2H), 4.78 (d, J=9.6 Hz, 1H), 4.73-4.59 (m, 2.3H), 4.55-4.45 (m, 0.7H), 4.23-3.98 (m, 1H), 3.91-3.77 (m, 1H), 3.65 (s, 2H), 2.74-2.49 (m, 1H), 2.25-2.00 (m, 1H), 1.43-1.36 (m, 3H), 1.24 (d, J=17.1 Hz, 2.5H), 0.87 (dd, J=16.5, 9.8 Hz, 0.5H).

Example 193

5-(6-(((S)-1-Cyclopropylethyl)amino)-4-(difluoromethyl)pyridin-3-yl)-4-((S)-4,4-difluoro-2-methylpyrrolidine-1-carbonyl)-N—((S)-3-hydroxy-3-methylbutan-2-yl)thiazole-2-carboxamide

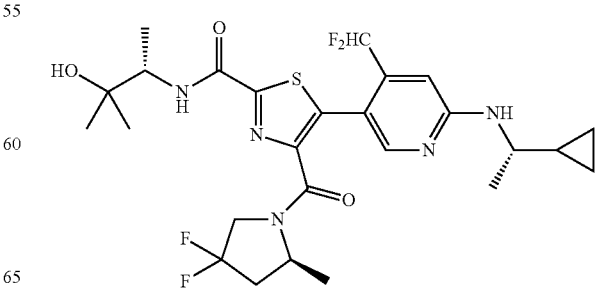

The title compound was prepared as described in Example 189, using ethyl 5-(6-(((S)-1-cyclopropylethyl)amino)-4-(difluoromethyl)pyridine-3-yl)-4-((S)-4,4-difluoro-2-methylpyrrolidine-1-carbonyl)thiazole-2-carboxylate (Intermediate 97) in place of ethyl 4-((1s,4s)-7-azabicyclo[2.2.1]heptane-7-carbonyl)-5-(4-(difluoromethyl)-6-((1-methylcyclobutyl)amino)pyridine-3-yl)thiazole-2-carboxylate. MS (ESI): mass calcd. for $C_{26}H_{33}F_4N_5O_3S$, 571.2; m/z found, 572.2 [M+H]$^+$. $^1$H NMR (400 MHz, CDCl$_3$) δ 7.99-7.97 (m, 1H), 7.40-7.33 (m, 1H), 6.93-6.53 (m, 2H), 4.94 (d, J=7.5 Hz, 1H), 4.72-4.66 (m, 0.3H), 4.58-4.45 (m, 0.7H), 4.17-3.98 (m, 2H), 3.96-3.77 (m, 1H), 3.41-3.35 (m, 1H), 2.69-2.45 (m, 1H), 2.23-1.99 (m, 1H), 1.87-1.81 (m, 1H), 1.44-1.18 (m, 15H), 1.03-0.80 (m, 1H), 0.61-0.45 (m, 2H), 0.41-0.22 (m, 2H).

Example 194

5-(6-(((S)-1-Cyclopropylethyl)amino)-4-(difluoromethyl)pyridine-3-yl)-4-((S)-4,4-difluoro-2-methylpyrrolidine-1-carbonyl)-N—((R)-3-hydroxy-3-methylbutan-2-yl)thiazole-2-carboxamide

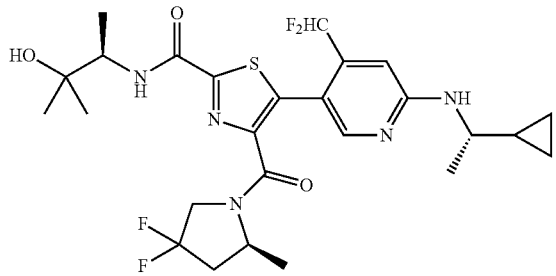 [SMILES: C[C@H](Nc1cc(C(F)F)c(-c2sc(C(=O)N[C@H](C)C(C)(C)O)nc2C(=O)N2CC(F)(F)C[C@@H]2C)cn1)C1CC1]

The title compound was prepared as described in Example 189, using (R)-3-amino-2-methylbutan-2-ol in place of (S)-3-amino-2-methylbutan-2-ol and ethyl 5-(6-(((S)-1-cyclopropylethyl)amino)-4-(difluoromethyl)pyridine-3-yl)-4-((S)-4,4-difluoro-2-methylpyrrolidine-1-carbonyl)thiazole-2-carboxylate (Intermediate 97) in place of ethyl 4-((1s,4s)-7-azabicyclo[2.2.1]heptane-7-carbonyl)-5-(4-(difluoromethyl)-6-((1-methylcyclobutyl)amino)pyridine-3-yl)thiazole-2-carboxylate. MS (ESI): mass calcd. for $C_{26}H_{33}F_4N_5O_3S$, 571.2; m/z found, 572.2 [M+H]$^+$. $^1$H NMR (400 MHz, CDCl$_3$) δ 7.99-7.97 (m, 1H), 7.40-7.33 (m, 1H), 6.93-6.53 (m, 2H), 4.94 (d, J=7.5 Hz, 1H), 4.72-4.66 (m, 0.3H), 4.58-4.45 (m, 0.7H), 4.17-3.98 (m, 2H), 3.96-3.77 (m, 1H), 3.41-3.35 (m, 1H), 2.69-2.45 (m, 1H), 2.23-1.99 (m, 1H), 1.87-1.81 (m, 1H), 1.44-1.18 (m, 15H), 1.03-0.80 (m, 1H), 0.61-0.45 (m, 2H), 0.41-0.22 (m, 2H).

Example 195

4-((S)-4,4-Difluoro-2-methylpyrrolidine-1-carbonyl)-N—((S)-3-hydroxy-3-methylbutan-2-yl)-5-(6-((1-methylcyclobutyl)amino)-4-(trifluoromethyl)pyridine-3-yl)thiazole-2-carboxamide

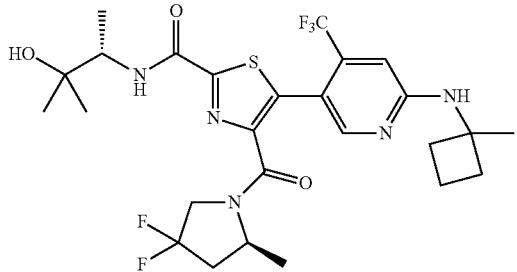 [SMILES: C[C@H](NC(=O)c1nc(C(=O)N2CC(F)(F)C[C@@H]2C)c(-c2cnc(NC3(C)CCC3)cc2C(F)(F)F)s1)C(C)(C)O]

The title compound was prepared as described in Example 189, using ethyl (S)-4-(4,4-difluoro-2-methylpyrrolidine-1-carbonyl)-5-(6-((1-methylcyclobutyl)amino)-4-(trifluoromethyl)pyridin-3-yl)thiazole-2-carboxylate in place of ethyl 4-((1s,4s)-7-azabicyclo[2.2.1]heptane-7-carbonyl)-5-(4-(difluoromethyl)-6-((1-methylcyclobutyl)amino)pyridine-3-yl)thiazole-2-carboxylate. MS (ESI): mass calcd. for $C_{26}H_{32}F_5N_5O_3S$, 589.2; m/z found, 590.2 [M+H]$^+$. $^1$H NMR (500 MHz, CDCl$_3$) δ 8.16-8.13 (m, 1H), 7.34 (d, J=9.2 Hz, 1H), 6.51 (s, 1H), 5.21 (s, 1H), 4.62-4.47 (m, 1H), 4.17-3.77 (m, 3H), 2.62-2.46 (m, 1H), 2.33-2.22 (m, 2H), 2.20-1.77 (m, 6H), 1.56 (s, 3H), 1.38-1.22 (m, 12H).

Example 196

4-((S)-4,4-Difluoro-2-methylpyrrolidine-1-carbonyl)-N—((R)-3-hydroxy-3-methylbutan-2-yl)-5-(6-((1-methhylcyclobutyl)amino)-4-(trifluoromethyl)pyridine-3-yl)thiazole-2-carboxamide

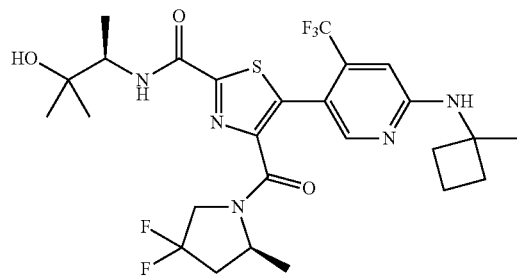 [SMILES: C[C@H]1CC(F)(F)CN1C(=O)c1nc(C(=O)N[C@H](C)C(C)(C)O)sc1-c1cnc(NC2(C)CCC2)cc1C(F)(F)F]

The title compound was prepared as described in Example 189, using (R)-3-amino-2-methylbutan-2-ol in place of (S)-3-amino-2-methylbutan-2-ol and ethyl (S)-4-(4,4-difluoro-2-methylpyrrolidine-1-carbonyl)-5-(6-((1-methylcyclobutyl)amino)-4-(trifluoromethyl)pyridin-3-yl)thiazole-2-carboxylate in place of ethyl 4-((1s,4s)-7-azabicyclo[2.2.1]heptane-7-carbonyl)-5-(4-(difluoromethyl)-6-((1-methylcyclobutyl)amino)pyridine-3-yl)thiazole-2-carboxylate. MS (ESI): mass calcd. for $C_{26}H_{32}F_5N_5O_3S$, 589.2; m/z found, 590.2 [M+H]$^+$. $^1$H NMR (500 MHz, CDCl$_3$) δ 8.14 (s, 1H), 7.36 (d, J=9.3 Hz, 1H), 6.51 (s, 1H), 5.21 (s, 1H), 4.70-4.64 (m, 0.3H), 4.55-4.44 (m, 0.7H), 4.18-3.96 (m, 2H), 3.95-3.74 (m, 1H), 2.64-2.46 (m, 1H), 2.34-2.22 (m, 2H), 2.21-2.01 (m, 3H), 2.00-1.76 (m, 3H), 1.56 (d, J=13.5 Hz, 3H), 1.41-1.19 (m, 12H).

Example 197

4-((S)-4,4-Difluoro-2-methylpyrrolidine-1-carbonyl)-N—((S)-3-hydroxy-3-methylbutan-2-yl)-5-(4-(trifluoromethyl)-6-(((S)-1,1,1-trifluoropropan-2-yl)amino)pyridine-3-yl)thiazole-2-carboxamide

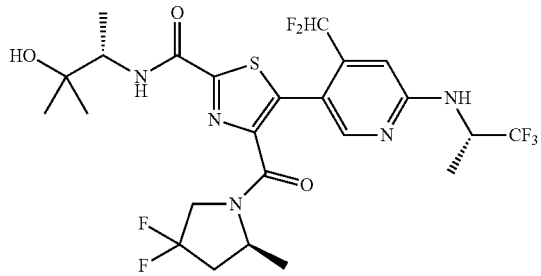 [SMILES: C[C@H](NC(=O)c1nc(C(=O)N2CC(F)(F)C[C@@H]2C)c(-c2cnc(N[C@@H](C)C(F)(F)F)cc2C(F)F)s1)C(C)(C)O]

The title compound was prepared as described in Example 189, using ethyl 4-((S)-4,4-difluoro-2-methylpyrrolidine-1-carbonyl)-5-(4-(difluoromethyl)-6-(((S)-1,1,1,-trifluoropropan-2-yl)amino)pyridine-3-yl)thiazole-2-carboxylate (Intermediate 96) in place of ethyl 4-((1s,4s)-7-azabicyclo[2.2.1]heptane-7-carbonyl)-5-(4-(difluoromethyl)-6-((1-methylcyclobutyl)amino)pyridine-3-yl)thiazole-2-carboxylate. MS (ESI): mass calcd. for $C_{24}H_{28}F_7N_5O_3S$, 599.2; m/z found, 600.2 [M+H]$^+$. $^1$H NMR (400 MHz, CDCl$_3$) δ 8.07-8.03 (m, 1H), 7.37-7.34 (m, 1H), 6.92-6.54 (m, 2H), 5.03-4.71 (m, 2.3H), 4.56-4.44 (m, 0.7H), 4.17-4.01 (m, 2.3H), 3.96-3.77 (m, 0.7H), 2.71-2.46 (m, 1H), 2.24-1.97 (m, 1H), 1.85-1.75 (m, 1H), 1.46-1.18 (m, 15H).

Example 198

4-((S)-4,4-Difluoro-2-methylpyrrolidine-1-carbonyl)-N—((R)-3-hydroxy-3-methylbutan-2-yl)-5-(4-(trifluoromethyl)-6-(((S)-1,1,1-trifluoropropan-2-yl)amino)pyridine-3-yl)thiazole-2-carboxamide

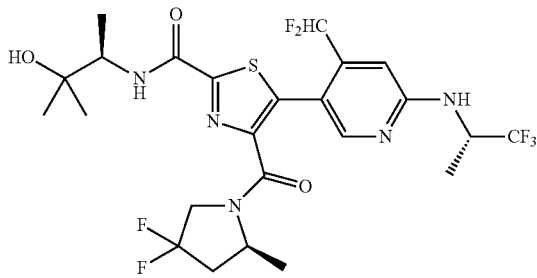 [SMILES: C[C@H](Nc1cc(C(F)F)c(-c2sc(C(=O)N[C@H](C)C(C)(C)O)nc2C(=O)N2CC(F)(F)C[C@@H]2C)cn1)C(F)(F)F]

The title compound was prepared as described in Example 189, using (R)-3-amino-2-methylbutan-2-ol in place of (S)-3-amino-2-methylbutan-2-ol and ethyl 4-((S)-4,4-difluoro-2-methylpyrrolidine-1-carbonyl)-5-(4-(difluoromethyl)-6-(((S)-1,1,1,-trifluoropropan-2-yl)amino)pyridine-3-yl)thiazole-2-carboxylate (Intermediate 96) in place of ethyl 4-((1s,4s)-7-azabicyclo[2.2.1]heptane-7-carbonyl)-5-(4-(difluoromethyl)-6-((1-methylcyclobutyl)amino)pyridine-3-yl)thiazole-2-carboxylate. MS (ESI): mass calcd. for $C_{24}H_{28}F_7N_5O_3S$, 599.2; m/z found, 600.2 [M+H]$^+$. $^1$H NMR (400 MHz, CDCl$_3$) δ 8.07-8.03 (m, 1H), 7.37-7.34 (m, 1H), 6.92-6.54 (m, 2H), 5.03-4.71 (m, 2.3H), 4.56-4.44 (m, 0.7H), 4.17-4.01 (m, 2.3H), 3.96-3.77 (m, 0.7H), 2.71-2.46 (m, 1H), 2.24-1.97 (m, 1H), 1.85-1.75 (m, 1H), 1.46-1.18 (m, 15H).

Example 199

5-(4-(Difluoromethyl)-6-(((S)-1,1,1-trifluoropropan-2-yl)amino)pyridine-3-yl)-N—((S)-3-hydroxy-3-methylburan-2-yl)-4-((S)-2-methylpyrrolidine-1-carbonyl)thiazole-2-carboxamide

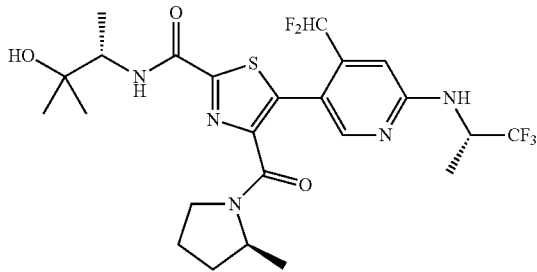 [SMILES: C[C@H](NC(=O)c1nc(C(=O)N2CCC[C@@H]2C)c(-c2cnc(N[C@@H](C)C(F)(F)F)cc2C(F)F)s1)C(C)(C)O]

The title compound was prepared as described in Example 189, using ethyl 5-(4-(difluoromethyl)-6-(((S)-1,1,1-trifluoropropan-2-yl)amino)pyridine-3-yl)-4-((S)-2-methylpyrrolidine-1-carbonyl)thiazole-2-carboxylate (Intermediate 94) in place of ethyl 4-((1s,4s)-7-azabicyclo[2.2.1]heptane-7-carbonyl)-5-(4-(difluoromethyl)-6-((1-methylcyclobutyl)amino)pyridine-3-yl)thiazole-2-carboxylate. MS (ESI): mass calcd. for $C_{24}H_{30}F_5N_5O_3S$, 563.2; m/z found, 564.2 [M+H]$^+$. $^1$H NMR (400 MHz, CDCl$_3$) δ 8.10-8.04 (m, 1H), 7.41-7.36 (m, 1H), 7.03-6.62 (m, 2H), 5.01-4.82 (m, 2H), 4.39-4.33 (m, 0.3H), 4.26-4.03 (m, 1.7H), 3.65-3.46 (m, 1.4H), 3.43-3.35 (m, 0.6H), 2.13-1.49 (m, 5H), 1.41 (d, J=6.7 Hz, 3H), 1.36-1.18 (m, 11H), 1.07 (d, J=6.4 Hz, 1H).

Example 200

5-(4-(Difluoromethyl)-6-(((S)-1,1,1-trifluoropropan-2-yl)amino)pyridine-3-yl)-N—((R)-3-hydroxy-3-methylburan-2-yl)-4-((S)-2-methylpyrrolidine-1-carbonyl)thiazole-2-carboxamide

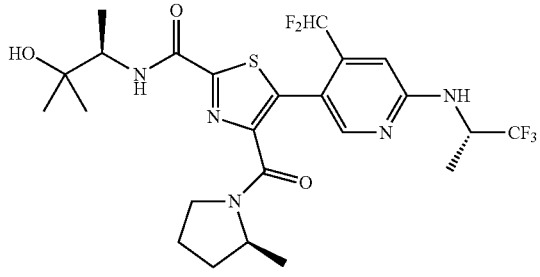 [SMILES: C[C@H](Nc1cc(C(F)F)c(-c2sc(C(=O)N[C@H](C)C(C)(C)O)nc2C(=O)N2CCC[C@@H]2C)cn1)C(F)(F)F]

The title compound was prepared as described in Example 189, using (R)-3-amino-2-methylbutan-2-ol in place of (S)-3-amino-2-methylbutan-2-ol and ethyl 5-(4-(difluoromethyl)-6-(((S)-1,1,1-trifluoropropan-2-yl)amino)pyridine-3-yl)-4-((S)-2-methylpyrrolidine-1-carbonyl)thiazole-2-carboxylate (Intermediate 94) in place of ethyl 4-((1s,4s)-7-azabicyclo[2.2.1]heptane-7-carbonyl)-5-(4-(difluoromethyl)-6-((1-methylcyclobutyl)amino)pyridine-3-yl)thiazole-2-carboxylate. MS (ESI): mass calcd. for $C_{24}H_{30}F_5N_5O_3S$, 563.2; m/z found, 564.2 [M+H]$^+$. $^1$H NMR (400 MHz, CDCl$_3$) δ 8.10-8.04 (m, 1H), 7.41-7.36 (m, 1H), 7.03-6.62 (m, 2H), 5.01-4.82 (m, 2H), 4.39-4.33 (m, 0.3H), 4.26-4.03 (m, 1.7H), 3.65-3.46 (m, 1.4H), 3.43-3.35 (m, 0.6H), 2.13-1.49 (m, 5H), 1.41 (d, J=6.7 Hz, 3H), 1.36-1.18 (m, 11H), 1.07 (d, J=6.4 Hz, 1H).

Example 201

5-(6-(((S)-1-Cyclopropylethyl)amino)-4-(trifluoromethyl)pyridine-3-yl)-4-((S)-4,4-difluoro-2-methylpyrrolidine-1-carbonyl)-N-((1R,2S)-2-hydroxycyclopentyl)thiazole-2-carboxamide

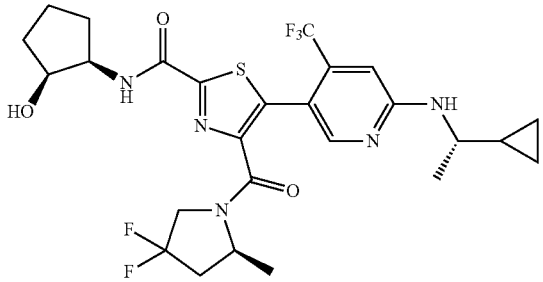 [SMILES: C[C@H](Nc1cc(C(F)(F)F)c(-c2sc(C(=O)N[C@@H]3CCC[C@@H]3O)nc2C(=O)N2CC(F)(F)C[C@@H]2C)cn1)C1CC1]

The title compound was prepared as described in Example 189, using (1S,2R)-2-aminocyclopentan-1-ol in place of (S)-3-amino-2-methylbutan-2-ol and ethyl 5-(6-(((S)-1-cyclopropylethyl)amino)-4-(trifluoromethyl)pyridine-3-yl)-4-((S)-4,4-difluoro-2-methylpyrrolidine-1-carbonyl)thiazole-2-carboxylate (Intermediate 98) in place of ethyl 4-((1s,4s)-7-azabicyclo[2.2.1]heptane-7-carbonyl)-5-(4-(difluoromethyl)-6-((1-methylcyclobutyl)amino)pyridine-3-yl)thiazole-2-carboxylate. MS (ESI): mass calcd. for $C_{26}H_{30}F_5N_5O_3S$, 587.2; m/z found, 588.2 [M+H]$^+$. $^1$H NMR (400 MHz, CDCl$_3$) δ 8.12 (s, 1H), 7.56 (dd, J=16.1, 8.1 Hz, 1H), 6.61 (s, 1H), 4.99 (d, J=7.4 Hz, 1H), 5.02-4.97 (m, 0.3H), 4.52-4.43 (m, 0.7H), 4.37-4.20 (m, 2H), 4.18-3.99 (m, 1H), 3.44-3.33 (m, 1H), 2.60-2.47 (m, 1H), 2.25-1.87 (m, 4H), 1.83-1.60 (m, 4H), 1.41-1.21 (m, 7H), 1.00-0.85 (m, 1H), 0.62-0.46 (m, 2H), 0.41-0.23 (m, 2H).

Example 202

5-(6-(((S)-1-Cyclopropylethyl)amino)-4-(trifluoromethyl)pyridine-3-yl)-4-((S)-4,4-difluoro-2-methylpyrrolidine-1-carbonyl)-N—((S)-3-hydroxy-3-methylbutan-2-yl)thiazole-2-carboxamide

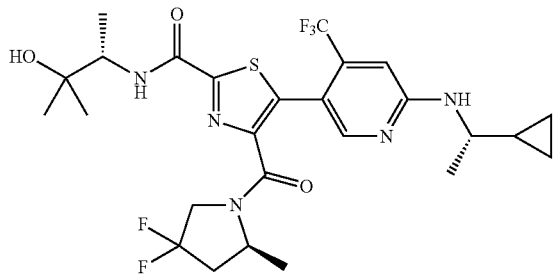 [SMILES: C[C@H](Nc1cc(C(F)(F)F)c(-c2sc(C(=O)N[C@@H](C)C(C)(C)O)nc2C(=O)N2CC(F)(F)C[C@@H]2C)cn1)C1CC1]

The title compound was prepared as described in Example 189, using ethyl 5-(6-(((S)-1-cyclopropylethyl)amino)-4-(trifluoromethyl)pyridine-3-yl)-4-((S)-4,4-difluoro-2-methylpyrrolidine-1-carbonyl)thiazole-2-carboxylate (Intermediate 98) in place of ethyl 4-((1s,4s)-7-azabicyclo[2.2.1]heptane-7-carbonyl)-5-(4-(difluoromethyl)-6-((1-methylcyclobutyl)amino)pyridine-3-yl)thiazole-2-carboxylate. MS (ESI): mass calcd. for $C_{26}H_{32}F_5N_5O_3S$, 589.2; m/z found, 590.1 [M+H]$^+$. $^1$H NMR (400 MHz, CDCl$_3$) δ 8.12 (s, 1H), 7.35 (d, J=9.3 Hz, 1H), 6.61 (s, 1H), 5.02 (d, J=7.5 Hz, 1H), 4.65-4.45 (m, 1H), 4.18-3.71 (m, 3H), 3.43-3.38 (m, 1H), 2.65-2.44 (m, 1H), 2.21-1.99 (m, 1H), 1.88-1.80 (m, 1H), 1.44-1.21 (m, 15H), 1.00-0.90 (m, 1H), 0.62-0.45 (m, 2H), 0.42-0.23 (m, 2H).

Example 203

5-(6-(((S)-1-Cyclopropylethyl)amino)-4-(trifluoromethyl)pyridine-3-yl)-4-((S)-4,4-difluoro-2-methylpyrrolidine-1-carbonyl)-N—((R)-3-hydroxy-3-methylbutan-2-yl)thiazole-2-carboxamide

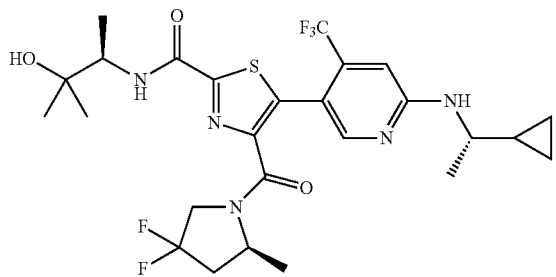 [SMILES: C[C@H](Nc1cc(C(F)(F)F)c(-c2sc(C(=O)N[C@H](C)C(C)(C)O)nc2C(=O)N2CC(F)(F)C[C@@H]2C)cn1)C1CC1]

The title compound was prepared as described in Example 189, using (R)-3-amino-2-methylbutan-2-ol in place of (S)-3-amino-2-methylbutan-2-ol and ethyl 5-(6-(((S)-1-cyclopropylethyl)amino)-4-(trifluoromethyl)pyridine-3-yl)-4-((S)-4,4-difluoro-2-methylpyrrolidine-1-carbonyl)thiazole-2-carboxylate (Intermediate 98) in place of ethyl 4-((1s,4s)-7-azabicyclo[2.2.1]heptane-7-carbonyl)-5-(4-(difluoromethyl)-6-((1-methylcyclobutyl)amino)pyridine-3-yl)thiazole-2-carboxylate. MS (ESI): mass calcd. for $C_{26}H_{32}F_5N_5O_3S$, 589.2; m/z found, 590.1 [M+H]$^+$. $^1$H NMR (400 MHz, CDCl$_3$) δ 8.12 (s, 1H), 7.37 (d, J=9.2 Hz, 1H), 6.61 (s, 1H), 5.02 (d, J=7.5 Hz, 1H), 4.75-4.65 (m, 0.3H), 4.53-4.44 (m, 0.7H), 4.19-3.73 (m, 3H), 3.45-3.35 (m, 1H), 2.66-2.44 (m, 1H), 2.25-1.80 (m, 2H), 1.47-1.18 (m, 14H), 1.06-0.75 (m, 2H), 0.63-0.45 (m, 2H), 0.43-0.22 (m, 2H).

Example 204

5-(4-(Difluoromethyl)-6-(((1R)-1-(trifluoromethyl)propyl)amino)-3-pyridyl)-N-((3R,4S)-4-hydroxytetrahydrofuran-3-yl)-4-((2S)-2-methylpyrrolidine-1-carbonyl)thiazole-2-carboxamide

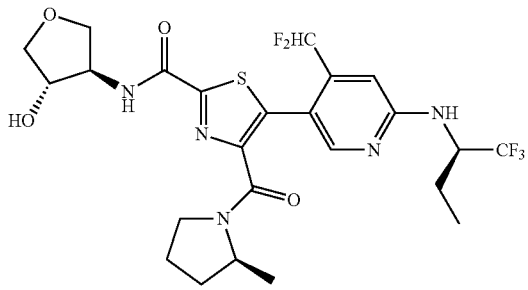 [SMILES: CC[C@@H](Nc1cc(C(F)F)c(-c2sc(C(=O)N[C@@H]3COC[C@H]3O)nc2C(=O)N2CCC[C@@H]2C)cn1)C(F)(F)F]

The title compound was prepared as described in Example 148 substituting ethyl 5-(4-(difluoromethyl)-6-(((R)-1,1,1-trifluorobutan-2-yl)amino)pyridin-3-yl)-4-((S)-2-methylpyrrolidine-1-carbonyl)thiazole-2-carboxylate (Intermediate 104: Step B) for ethyl (S)-5-(6-(tert-butylamino)-4-(difluoromethyl)pyridin-3-yl)-4-(2-methylpyrrolidine-1-carbonyl)thiazole-2-carboxylate and (3S,4R)-4-aminotetrahydro-furan-3-ol for (R)-(−)-2-amino-1-propanol. MS (ESI): mass calcd. for $C_{24}H_{28}F_5N_5O_4S$, 577.6; m/z found, 578.1 [M+H]$^+$. $^1$H NMR (400 MHz, CDCl$_3$) δ 8.10-8.01 (m, 1H), 7.37-7.27 (m, 1H), 7.02-6.64 (m, 2H), 4.92-4.71 (m, 2H), 4.49-4.36 (m, 2H), 4.24-4.13 (m, 3H), 3.89-3.73 (m, 2H), 3.62-3.32 (m, 3H), 2.04-1.90 (m, 3H), 1.83-1.50 (m, 3H), 1.23-1.18 (d, J=6.3 Hz, 2H), 1.08-1.00 (m, 4H).

Example 205

5-(4-(Difluoromethyl)-6-(((1R)-1-(trifluoromethyl)propyl)amino)-3-pyridyl)-N-((1r,3S)-3-hydroxycyclobutyl)-4-((2S)-2-methylpyrrolidine-1-carbonyl)thiazole-2-carboxamide

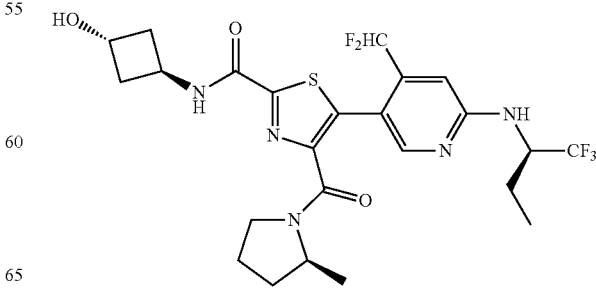

The title compound was prepared as described in Example 149 substituting ethyl 5-(4-(difluoromethyl)-6-(((R)-1,1,1-trifluorobutan-2-yl)amino)pyridin-3-yl)-4-((S)-2-methylpyrrolidine-1-carbonyl)thiazole-2-carboxylate (Intermediate 104: Step B) for ethyl (S)-5-(6-(tert-butylamino)-4-(difluoromethyl)pyridin-3-yl)-4-(2-methylpyrrolidine-1-carbonyl)thiazole-2-carboxylate and trans-3-aminocyclobutanol HCl for 3-hydroxy-3-methylazetidine HCl. MS (ESI): mass calcd. for $C_{24}H_{28}F_5N_5O_3S$, 561.6; m/z found, 562.1 [M+H]+. 1H NMR (400 MHz, CDCl3) δ 8.09-8.01 (m, 1H), 7.36-7.27 (m, 1H), 7.03-6.64 (m, 2H), 4.92-4.72 (m, 2H), 4.71-4.55 (m, 2H), 4.28-4.17 (m, 1H), 3.62-3.31 (m, 2H), 2.51-2.38 (m, 4H), 2.22-2.16 (d, J=4.2 Hz, 1H), 2.04-1.84 (m, 3H), 1.81-1.71 (m, 1H), 1.67-1.49 (m, 2H), 1.22-1.19 (d, J=6.3 Hz, 2H), 1.07-1.00 (m, 4H).

Example 206

5-(4-(Difluoromethyl)-6-(((1R)-1-(trifluoromethyl)propyl)amino)-3-pyridyl)-N-((1R)-2-hydroxy-1-methyl-ethyl)-4-((2S)-2-methylpyrrolidine-1-carbonyl)thiazole-2-carboxamide

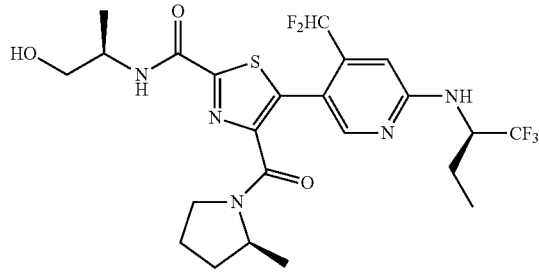 [SMILES: CC[C@@H](Nc1cc(C(F)F)c(-c2sc(C(=O)N[C@H](C)CO)nc2C(=O)N2CCC[C@@H]2C)cn1)C(F)(F)F]

The title compound was prepared as described in Example 148 substituting ethyl 5-(4-(difluoromethyl)-6-(((R)-1,1,1-trifluorobutan-2-yl)amino)pyridin-3-yl)-4-((S)-2-methylpyrrolidine-1-carbonyl)thiazole-2-carboxylate (Intermediate 104: Step B) for ethyl (S)-5-(6-(tert-butylamino)-4-(difluoromethyl)pyridin-3-yl)-4-(2-methylpyrrolidine-1-carbonyl)thiazole-2-carboxylate. MS (ESI): mass calcd. for $C_{23}H_{28}F_5N_5O_3S$, 549.6; m/z found, 550.1 [M+H]+. 1H NMR (400 MHz, CDCl3) δ 8.09-8.01 (m, 1H), 7.35-7.27 (m, 1H), 7.03-6.64 (m, 2H), 4.91-4.72 (m, 2H), 4.31-4.16 (m, 2H), 3.83-3.64 (m, 2H), 3.61-3.33 (m, 2H), 2.57-2.50 (m, 1H), 2.03-1.85 (m, 3H), 1.81-1.72 (m, 1H), 1.67-1.49 (m, 2H), 1.35-1.31 (d, J=6.8 Hz, 3H), 1.22-1.19 (d, J=6.3 Hz, 2H), 1.08-1.01 (m, 4H).

Example 207

5-(4-(Difluoromethyl)-6-(((1R)-1-(trifluoromethyl)propyl)amino)-3-pyridyl)-N-((3S,4R)-4-hydroxytetrahydrofuran-3-yl)-4-((2S)-2-methylpyrrolidine-1-carbonyl)thiazole-2-carboxamide

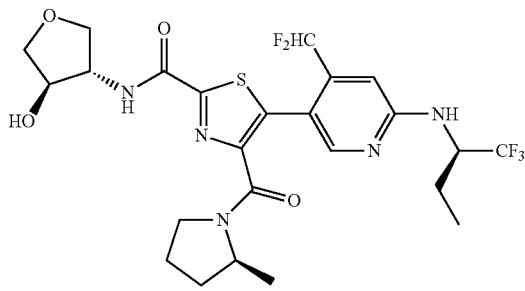 [SMILES: CC[C@@H](Nc1cc(C(F)F)c(-c2sc(C(=O)N[C@H]3COC[C@@H]3O)nc2C(=O)N2CCC[C@@H]2C)cn1)C(F)(F)F]

The title compound was prepared as described in Example 148 substituting ethyl 5-(4-(difluoromethyl)-6-(((R)-1,1,1-trifluorobutan-2-yl)amino)pyridin-3-yl)-4-((S)-2-methylpyrrolidine-1-carbonyl)thiazole-2-carboxylate (Intermediate 104: Step B) for ethyl (S)-5-(6-(tert-butylamino)-4-(difluoromethyl)pyridin-3-yl)-4-(2-methylpyrrolidine-1-carbonyl)thiazole-2-carboxylate and (3R,4S)-4-aminotetrahydro-furan-3-ol for (R)-(−)-2-amino-1-propanol. MS (ESI): mass calcd. for $C_{24}H_{28}F_5N_5O_4S$, 577.6; m/z found, 578.1 [M+H]+. 1H NMR (400 MHz, CDCl3) δ 8.09-8.00 (m, 1H), 7.36-7.27 (m, 1H), 7.05-6.65 (m, 2H), 4.91-4.70 (m, 2H), 4.47-4.36 (m, 2H), 4.28-4.13 (m, 3H), 3.90-3.73 (m, 2H), 3.63-3.30 (m, 3H), 2.04-1.90 (m, 3H), 1.81-1.52 (m, 3H), 1.24-1.21 (d, J=6.3 Hz, 2H), 1.08-1.02 (m, 3H), 1.01-0.97 (d, J=6.4 Hz, 1H).

Example 208

4-((1s,4s)-7-Azabicyclo[2.2.1]heptane-7-carbonyl)-5-(4-(difluoromethyl)-6-(((1S)-1-(trifluoromethyl)propyl)amino)-3-pyridyl)-N-((3R,4S)-4-hydroxytetrahydrofuran-3-yl)thiazole-2-carboxamide

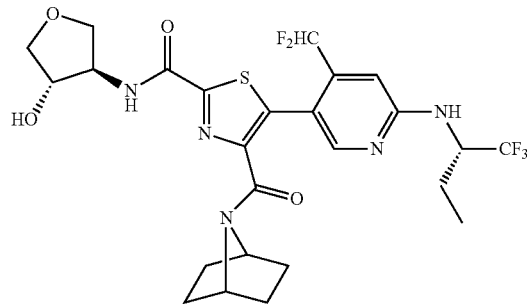 [SMILES: CC[C@H](Nc1cc(C(F)F)c(-c2sc(C(=O)N[C@@H]3COC[C@H]3O)nc2C(=O)N2C3CCC2CC3)cn1)C(F)(F)F]

The title compound was prepared as described in Example 148 substituting ethyl 4-((1s,4s)-7-azabicyclo[2.2.1]heptane-7-carbonyl)-5-(4-(difluoromethyl)-6-(((S)-1,1,1-trifluorobutan-2-yl)amino)pyridin-3-yl)thiazole-2-carboxylate (Intermediate 99) for ethyl (S)-5-(6-(tert-butylamino)-4-(difluoromethyl)pyridin-3-yl)-4-(2-methylpyrrolidine-1-carbonyl)thiazole-2-carboxylate and (3S,4R)-4-amino-tetrahydro-furan-3-ol for (R)-(−)-2-amino-1-propanol. MS (ESI): mass calcd. for $C_{25}H_{28}F_5N_5O_4S$, 589.6; m/z found, 590.1 [M+H]+. 1H NMR (500 MHz, CDCl3) δ 8.11-8.06 (s, 1H), 7.40-7.35 (d, J=6.8 Hz, 1H), 6.89-6.65 (m, 2H), 4.95-4.64 (m, 3H), 4.46-4.36 (m, 2H), 4.24-4.19 (m, 1H), 4.15-4.10 (m, 2H), 1.56-1.49 (m, 1H), 3.87-3.74 (m, 2H), 3.49-3.44 (d, J=3.1 Hz, 1H), 2.02-1.93 (m, 1H), 1.80-1.68 (m, 2H), 1.66-1.57 (m, 1H), 1.48-1.40 (m, 5H), 1.06-1.02 (m, 3H).

Example 209

4-((1s,4s)-7-Azabicyclo[2.2.1]heptane-7-carbonyl)-5-(4-(difluoromethyl)-6-(((1S)-1-(trifluoromethyl)propyl)amino)-3-pyridyl)-N-((3S,4R)-4-hydroxytetrahydrofuran-3-yl]thiazole-2-carboxamide

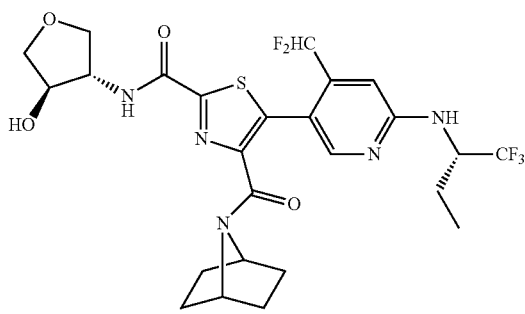

The title compound was prepared as described in Example 148 substituting ethyl 4-((1s,4s)-7-azabicyclo[2.2.1]heptane-7-carbonyl)-5-(4-(difluoromethyl)-6-(((S)-1,1,1-trifluorobutan-2-yl)amino)pyridin-3-yl)thiazole-2-carboxylate (Intermediate 99) for ethyl (S)-5-(6-(tert-butylamino)-4-(difluoromethyl)pyridin-3-yl)-4-(2-methylpyrrolidine-1-carbonyl)thiazole-2-carboxylate and (3R,4S)-4-amino-tetrahydro-furan-3-ol for (R)-(−)-2-amino-1-propanol. MS (ESI): mass calcd. for C$_{25}$H$_{28}$F$_{5}$N$_{5}$O$_{4}$S, 589.6; m/z found, 590.1 [M+H]$^+$. $^1$H NMR (500 MHz, CDCl$_3$) δ 8.10-8.06 (s, 1H), 7.41-7.36 (d, J=6.8 Hz, 1H), 6.89-6.65 (m, 2H), 4.95-4.64 (m, 3H), 4.48-4.36 (m, 2H), 4.24-4.19 (m, 1H), 4.15-4.10 (m, 2H), 3.87-3.74 (m, 2H), 3.51-3.46 (m, 1H), 2.02-1.94 (m, 1H), 1.80-1.68 (m, 2H), 1.66-1.57 (m, 1H), 1.52-1.38 (m, 6H), 1.07-1.01 (m, 3H).

Example 210

4-((1s,4s)-7-Azabicyclo[2.2.1]heptane-7-carbonyl)-5-(4-(difluoromethyl)-6-(((1S)-1-(trifluoromethyl)propyl)amino)-3-pyridyl)-N-((1S,2S)-2-hydroxycyclopentyl)thiazole-2-carboxamide

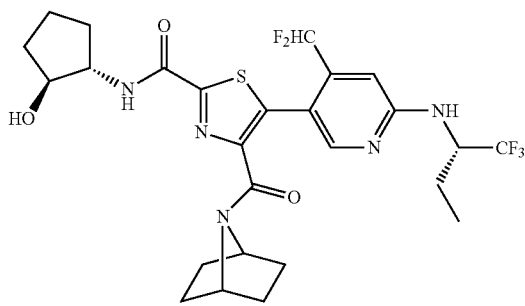 [SMILES: CC[C@H](Nc1cc(C(F)F)c(-c2sc(C(=O)N[C@H]3CCC[C@@H]3O)nc2C(=O)N2C3CCC2CC3)cn1)C(F)(F)F]

The title compound was prepared as described in Example 149 substituting ethyl 4-((1s,4s)-7-azabicyclo[2.2.1]heptane-7-carbonyl)-5-(4-(difluoromethyl)-6-(((S)-1,1,1-trifluorobutan-2-yl)amino)pyridin-3-yl)thiazole-2-carboxylate (Intermediate 99) for ethyl (S)-5-(6-(tert-butylamino)-4-(difluoromethyl)pyridin-3-yl)-4-(2-methylpyrrolidine-1-carbonyl)thiazole-2-carboxylate and (1S,2S)-trans-2-aminocyclopentanol HCl for 3-hydroxy-3-methylazetidine HCl. MS (ESI): mass calcd. for C$_{26}$H$_{30}$F$_{5}$N$_{5}$O$_{3}$S, 587.6; m/z found, 588.2 [M+H]$^+$. $^1$NMR (500 MHz, CDCl$_3$) δ 8.10-8.07 (s, 1H), 7.34-7.29 (d, J=5.3 Hz, 1H), 6.90-6.65 (m, 2H), 4.94-4.65 (m, 3H), 4.19-4.12 (m, 2H), 4.08-4.02 (m, 1H), 3.90-3.87 (m, 1H), 2.32-2.23 (m, 1H), 2.13-2.06 (m, 1H), 2.01-1.93 (m, 1H), 1.91-1.83 (m, 1H), 1.81-1.77 (m, 1H), 1.75-1.70 (m, 2H), 1.65-1.58 (m, 2H), 1.49-1.38 (m, 6H), 1.07-1.01 (m, 3H).

Example 211

5-(4-(Difluoromethyl)-6-(((S)-1,1,1-trifluorobutan-2-yl)amino)pyridin-3-yl)-N-((1R*,2S*)-2-hydroxycyclopropyl)-4-((S)-2-methylpyrrolidine-1-carbonyl)thiazole-2-carboxamide

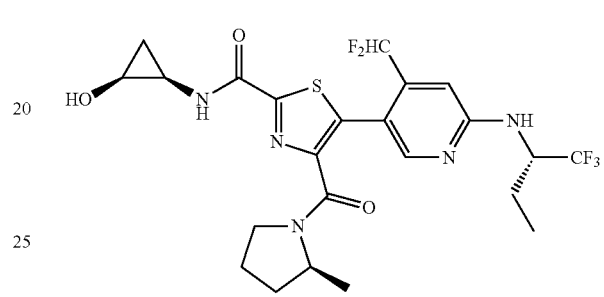

The title compound was prepared as described in Example 157 substituting N-((1R*,2S*)-2-((tert-butyldimethylsilyl)oxy)cyclopropyl)-5-(4-(difluoromethyl)-6-(((S)-1,1,1-trifluorobutan-2-yl)amino)pyridin-3-yl)-4-((S)-2-methylpyrrolidine-1-carbonyl)thiazole-2-carboxamide (Intermediate 101: Step F1) for N-((1R*,2R*)-2-((tert-butyldimethylsilyl)oxy)cyclopropyl)-5-(4-(difluoromethyl)-6-(((S)-1,1,1-trifluoropropan-2-yl)amino)pyridin-3-yl)-4-((S)-2-methylpyrrolidine-1-carbonyl)thiazole-2-carboxamide. MS (ESI): mass calcd. for C$_{23}$H$_{26}$F$_{5}$N$_{5}$O$_{3}$S, 547.5; m/z found, 548.1 [M+H]$^+$. $^1$H NMR (500 MHz, CDCl$_3$) δ 8.09-7.99 (m, 1H), 7.52-7.44 (m, 1H), 7.01-6.65 (m, 2H), 4.82-4.71 (m, 2H), 4.37-4.16 (m, 1H), 3.77-3.34 (m, 3H), 2.99-2.83 (m, 2H), 2.03-1.83 (m, 3H), 1.81-1.72 (m, 1H), 1.66-1.62 (m, 1H), 1.57-1.49 (m, 1H), 1.23-1.20 (d, J=6.3 Hz, 2H), 1.16-1.11 (m, 1H), 1.07-1.02 (m, 3H), 1.02-1.00 (d, J=6.4 Hz, 1H), 0.80-0.75 (m, 1H).

Example 212

5-(4-(Difluoromethyl)-6-(((S)-1,1,1-trifluorobutan-2-yl)amino)pyridin-3-yl)-N-((1S*,2R*)-2-hydroxycyclopropyl)-4-((S)-2-methylpyrrolidine-1-carbonyl)thiazole-2-carboxamide

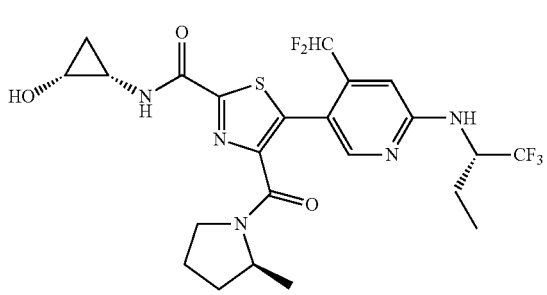 [SMILES: CC[C@H](Nc1cc(C(F)F)c(-c2sc(C(=O)N[C@H]3C[C@H]3O)nc2C(=O)N2CCC[C@@H]2C)cn1)C(F)(F)F]

The title compound was prepared as described in Example 157 substituting N-((1S*,2R*)-2-((tert-butyldimethylsilyl)oxy)cyclopropyl)-5-(4-(difluoromethyl)-6-(((S)-1,1,1-trifluoropropan-2-yl)amino)pyridin-3-yl)-4-((S)-2-methylpyrrolidine-1-carbonyl)thiazole-2-carboxamide (Intermediate 101: Step F$_2$) for N-((1R*,2R*)-2-((tert-butyldimethylsilyl)oxy)cyclopropyl)-5-(4-(difluoromethyl)-6-(((S)-1,1,1-trifluoropropan-2-yl)amino)pyridin-3-yl)-4-((S)-2-methylpyrrolidine-1-carbonyl)thiazole-2-carboxamide. MS (ESI): mass calcd. for $C_{23}H_{26}F_5N_5O_3S$, 547.5; m/z found, 548.1 [M+H]$^+$. $^1$H NMR (500 MHz, CDCl$_3$) δ 8.10-8.00 (m, 1H), 7.52-7.43 (m, 1H), 7.01-6.65 (m, 2H), 4.82-4.72 (m, 2H), 4.37-4.17 (m, 1H), 3.77-3.35 (m, 3H), 2.94-2.82 (m, 2H), 2.03-1.73 (m, 4H), 1.67-1.61 (m, 1H), 1.56-1.50 (m, 1H), 1.22-1.19 (d, J=6.3 Hz, 2H), 1.17-1.12 (m, 1H), 1.07-1.01 (m, 4H), 0.82-0.76 (m, 1H).

Example 213

5-(4-(Difluoromethyl)-6-(((S)-1,1,1-trifluorobutan-2-yl)amino)pyridin-3-yl)-N-((1R*,2R*)-2-hydroxycyclopropyl)-4-((S)-2-methylpyrrolidine-1-carbonyl)thiazole-2-carboxamide

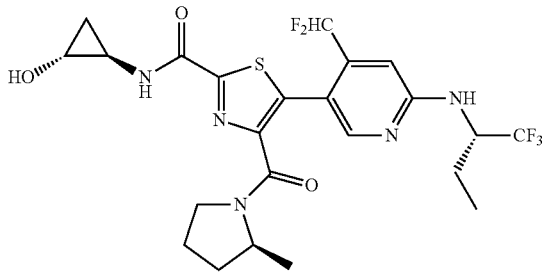 [SMILES: CC[C@H](Nc1cc(C(F)F)c(-c2sc(C(=O)N[C@@H]3C[C@H]3O)nc2C(=O)N2CCC[C@@H]2C)cn1)C(F)(F)F]

The title compound was prepared as described in Example 157 substituting N-((1R*,2R*)-2-((tert-butyldimethylsilyl)oxy)cyclopropyl)-5-(4-(difluoromethyl)-6-(((S)-1,1,1-trifluorobutan-2-yl)amino)pyridin-3-yl)-4-((S)-2-methylpyrrolidine-1-carbonyl)thiazole-2-carboxamide (Intermediate 101: Step G1) for N-((1R*,2R*)-2-((tert-butyldimethylsilyl)oxy)cyclopropyl)-5-(4-(difluoromethyl)-6-(((S)-1,1,1-trifluoropropan-2-yl)amino)pyridin-3-yl)-4-((S)-2-methylpyrrolidine-1-carbonyl)thiazole-2-carboxamide. MS (ESI): mass calcd. for $C_{23}H_{26}F_5N_5O_3S$, 547.5; m/z found, 548.1 [M+H]$^+$. $^1$H NMR (500 MHz, CDCl$_3$) δ 8.08-8.00 (m, 1H), 7.18-7.08 (m, 1H), 7.01-6.66 (m, 2H), 4.81-4.72 (m, 2H), 4.31-4.16 (m, 1H), 3.64-3.19 (m, 4H), 2.94-2.86 (m, 1H), 2.09-2.04 (m, 1H), 2.03-1.86 (m, 3H), 1.80-1.71 (m, 1H), 1.66-1.50 (m, 2H), 1.22-1.19 (d, J=6.3 Hz, 2H), 1.07-1.02 (m, 3H), 1.01-0.95 (m, 2H).

Example 214

5-(4-(Difluoromethyl)-6-(((S)-1,1,1-trifluorobutan-2-yl)amino)pyridin-3-yl)-N-((1S*,2S*)-2-hydroxycyclopropyl)-4-((S)-2-methylpyrrolidine-1-carbonyl)thiazole-2-carboxamide

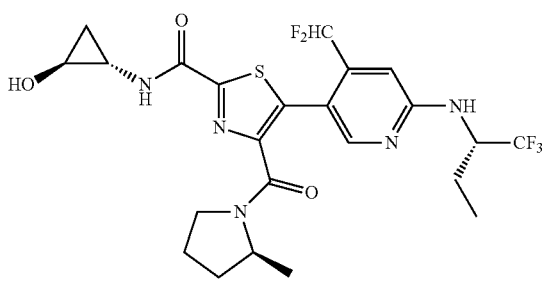 [SMILES: CC[C@H](Nc1cc(C(F)F)c(-c2sc(C(=O)N[C@H]3C[C@@H]3O)nc2C(=O)N2CCC[C@@H]2C)cn1)C(F)(F)F]

The title compound was prepared as described in Example 157 substituting N-((1S*,2S*)-2-((tert-butyldimethylsilyl)oxy)cyclopropyl)-5-(4-(difluoromethyl)-6-(((S)-1,1,1-trifluorobutan-2-yl)amino)pyridin-3-yl)-4-((S)-2-methylpyrrolidine-1-carbonyl)thiazole-2-carboxamide (Intermediate 101: Step G2) for N-((1R*,2R*)-2-((tert-butyldimethylsilyl)oxy)cyclopropyl)-5-(4-(difluoromethyl)-6-(((S)-1,1,1-trifluoropropan-2-yl)amino)pyridin-3-yl)-4-((S)-2-methylpyrrolidine-1-carbonyl)thiazole-2-carboxamide. MS (ESI): mass calcd. for $C_{23}H_{26}F_5N_5O_3S$, 547.5; m/z found, 548.1 [M+H]$^+$. $^1$H NMR (500 MHz, CDCl$_3$) δ 8.09-8.01 (m, 1H), 7.20-7.10 (m, 1H), 7.00-6.65 (m, 2H), 4.85-4.73 (m, 2H), 4.27-4.16 (m, 1H), 3.65-3.23 (m, 4H), 2.94-2.87 (m, 1H), 2.03-1.85 (m, 4H), 1.79-1.59 (m, 2H), 1.56-1.50 (m, 1H), 1.22-1.19 (d, J=6.3 Hz, 2H), 1.07-1.02 (m, 3H), 1.01-0.96 (m, 2H).

Example 215

5-(4-(Difluoromethyl)-6-(((1S)-2,2,2-trifluoro-1-methyl-ethyl)amino)-3-pyridyl)-N-((3R,4S)-4-hydroxytetrahydrofuran-3-yl)-4-((2S)-2-methylpyrrolidine-1-carbonyl)thiazole-2-carboxamide

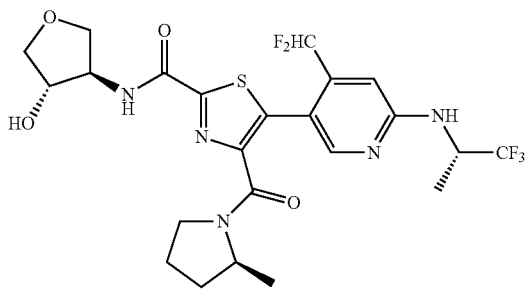

The title compound was prepared as described in Example 148 substituting (3S,4R)-4-amino-tetrahydro-furan-3-ol for (R)-(−)-2-amino-1-propanol and ethyl 5-(4-(difluoromethyl)-6-(((S)-1,1,1-trifluoropropan-2-yl)amino)pyridin-3-yl)-4-((S)-2-methylpyrrolidine-1-carbonyl)thiazole-2-carboxylate (Intermediate 94) for ethyl (S)-5-(6-(tert-butylamino)-4-(difluoromethyl)pyridin-3-yl)-4-(2-methylpyrrolidine-1-carbonyl)thiazole-2-carboxylate. MS (ESI): mass calcd. for $C_{23}H_{26}F_5N_5O_4S$, 563.5; m/z found, 564.1 [M+H]$^+$. $^1$H NMR (500 MHz, CDCl$_3$) δ 8.11-8.02 (m, 1H), 7.36-7.27 (m, 1H), 6.98-6.63 (m, 2H), 4.99-4.89 (m, 2H), 4.48-4.41 (m, 1H), 4.40-4.35 (m, 1H), 4.25-4.14 (m, 3H), 3.89-3.83 (m, 1H), 3.78-3.73 (m, 1H), 3.60-3.26 (m, 3H), 2.10-2.05 (m, 1H), 1.96-1.87 (m, 1H), 1.80-1.78 (m, 1H), 1.68-1.52 (m, 1H), 1.44-1.39 (d, J=6.3 Hz, 3H), 1.24-1.21 (d, J=6.3 Hz, 2H), 1.03-1.00 (d, J=6.4 Hz, 1H).

Example 216

5-(4-(Difluoromethyl)-6-(((S)-1,1,1-trifluorobutan-2-yl)amino)pyridin-3-yl)-N-((2R*,3R*)-3-hydroxybutan-2-yl)-4-((S)-2-methylpyrrolidine-1-carbonyl)thiazole-2-carboxamide

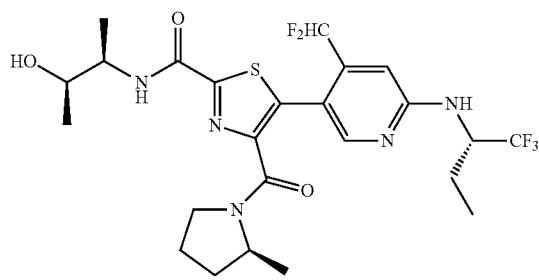 [SMILES: CC[C@H](Nc1cc(C(F)F)c(-c2sc(C(=O)N[C@H](C)[C@@H](C)O)nc2C(=O)N2CCC[C@@H]2C)cn1)C(F)(F)F]

The title compound was prepared as described in Example 148 substituting 3-aminobutan-2-ol for (R)-(−)-2-amino-1-propanol and ethyl 5-(4-(difluoromethyl)-6-(((S)-1,1,1-trifluorobutan-2-yl)amino)pyridin-3-yl)-4-((S)-2-methylpyrrolidine-1-carbonyl)thiazole-2-carboxylate (Intermediate 102) for ethyl (5)-5-(6-(tert-butylamino)-4-(difluoromethyl)pyridin-3-yl)-4-(2-methylpyrrolidine-1-carbonyl)thiazole-2-carboxylate. The pure diastereomer was isolated via SFC (Stationary phase: Chiralcel OD-H, 5 μm, 250×30 mm, Mobile phase: 14% iPrOH+0.3% iPrNH$_2$, 86% CO$_2$, first eluting diastereomer) followed by a second SFC (Stationary phase: Chiralpak AD-H, 5 μm, 250×30 mm, Mobile phase: 10% iPrOH+0.3% iPrNH$_2$, 90% CO$_2$, second eluting diastereomer). MS (ESI): mass calcd. for $C_{24}H_{30}F_5N_5O_3S$, 563.6; m/z found, 564.1 [M+H]$^+$. $^1$H NMR (400 MHz, CDCl$_3$) δ 8.10-8.00 (m, 1H), 7.40-7.32 (m, 1H), 7.07-6.66 (m, 2H), 4.85-4.67 (m, 2H), 4.32-3.98 (m, 3H), 3.60-3.34 (m, 2H), 2.08-1.97 (m, 2H), 1.93-1.86 (m, 1H), 1.80-1.72 (m, 1H), 1.65-1.60 (m, 1H), 1.56-1.50 (m, 1H), 1.28-1.20 (m, 9H), 1.08-1.02 (m, 4H).

Example 217

5-(4-(Difluoromethyl)-6-(((S)-1,1,1-trifluorobutan-2-yl)amino)pyridin-3-yl)-N-((2S*,3S*)-3-hydroxybutan-2-yl)-4-((S)-2-methylpyrrolidine-1-carbonyl)thiazole-2-carboxamide

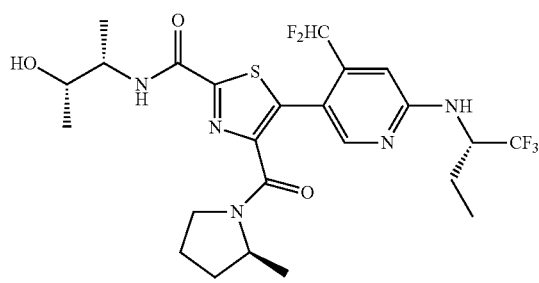 [SMILES: CC[C@H](Nc1cc(C(F)F)c(-c2sc(C(=O)N[C@@H](C)[C@H](C)O)nc2C(=O)N2CCC[C@@H]2C)cn1)C(F)(F)F]

The title compound was prepared as described in Example 148 substituting 3-aminobutan-2-ol for (R)-(−)-2-amino-1-propanol and ethyl 5-(4-(difluoromethyl)-6-(((S)-1,1,1-trifluorobutan-2-yl)amino)pyridin-3-yl)-4-((S)-2-methylpyrrolidine-1-carbonyl)thiazole-2-carboxylate (Intermediate 102) for ethyl (S)-5-(6-(tert-butylamino)-4-(difluoromethyl)pyridin-3-yl)-4-(2-methylpyrrolidine-1-carbonyl)thiazole-2-carboxylate. The pure diastereomer was isolated via SFC (Stationary phase: Chiralcel OD-H, 5 μm, 250×30 mm, Mobile phase: 14% i-PrOH+0.3% 1-PrNH$_2$, 86% CO$_2$, first eluting diastereomer) followed by a second SFC (Stationary phase: Chiralpak AD-H, 5 μm, 250×30 mm, Mobile phase: 10% iPrOH+0.3% iPrNH$_2$, 90% CO$_2$, first eluting diastereomer). MS (ESI): mass calcd. for $C_{24}H_{30}F_5N_5O_3S$, 563.6; m/z found, 564.1 [M+H]$^+$. $^1$H NMR (400 MHz, CDCl$_3$) δ 8.10-8.01 (m, 1H), 7.38-7.31 (m, 1H), 7.06-6.66 (m, 2H), 4.83-4.68 (m, 2H), 4.35-3.87 (m, 3H), 3.60-3.35 (m, 2H), 2.08-2.01 (m, 1H), 1.98-1.89 (m, 2H), 1.80-1.74 (m, 1H), 1.65-1.53 (m, 2H), 1.36-1.31 (d, J=6.8 Hz, 3H), 1.29-1.25 (d, J=6.3 Hz, 3H), 1.23-1.20 (m, 3H), 1.08-1.02 (m, 4H).

Example 218

5-(4-(Difluoromethyl)-6-(((S)-1,1,1-trifluorobutan-2-yl)amino)pyridin-3-yl)-N-((2R*,3S*)-3-hydroxybutan-2-yl)-4-((S)-2-methylpyrrolidine-1-carbonyl)thiazole-2-carboxamide

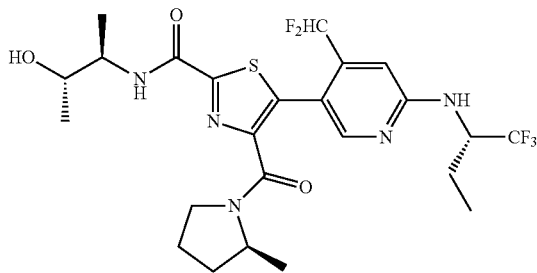 [SMILES: CC[C@H](Nc1cc(C(F)F)c(-c2sc(C(=O)N[C@H](C)[C@H](C)O)nc2C(=O)N2CCC[C@@H]2C)cn1)C(F)(F)F]

The title compound was prepared as described in Example 148 substituting 3-aminobutan-2-ol for (R)-(−)-2-amino-1-propanol and ethyl 5-(4-(difluoromethyl)-6-(((S)-1,1,1-trifluorobutan-2-yl)amino)pyridin-3-yl)-4-((S)-2-methylpyrrolidine-1-carbonyl)thiazole-2-carboxylate (Intermediate 102) for ethyl (S)-5-(6-(tert-butylamino)-4-(difluoromethyl)pyridin-3-yl)-4-(2-methylpyrrolidine-1-carbonyl)thiazole-2-carboxylate. The pure diastereomer was isolated via SFC (Stationary phase: Chiralcel OD-H, 5 μm, 250×30 mm, Mobile phase: 14% iPrOH+0.3% iPrNH$_2$, 86% CO$_2$, second eluting diastereomer) followed by a second SFC (Stationary phase: Chiralpak AD-H, 5 μm, 250×20 mm, Mobile phase: 15% i-PrOH+0.3% iPrNH$_2$, 85% CO$_2$). MS (ESI): mass calcd. for $C_{24}H_{30}F_5N_5O_3S$, 563.6; m/z found, 564.1 [M+H]$^+$. $^1$H NMR (500 MHz, CDCl$_3$) δ 8.09-8.01 (m, 1H), 7.39-7.30 (m, 1H), 7.03-6.68 (m, 2H), 4.83-4.65 (m, 2H), 4.30-3.99 (m, 3H), 3.61-3.33 (m, 2H), 2.07-1.75 (m, 4H), 1.65-1.61 (m, 1H), 1.54-1.50 (m, 1H), 1.29-1.24 (m, 6H), 1.22-1.20 (m, 3H), 1.08-1.02 (m, 4H).

Example 219

5-(4-(Difluoromethyl)-6-(((S)-1,1,1-trifluorobutan-2-yl)amino)pyridin-3-yl)-N-((2S*,3R*)-3-hydroxybutan-2-yl)-4-((S)-2-methylpyrrolidine-1-carbonyl)thiazole-2-carboxamide

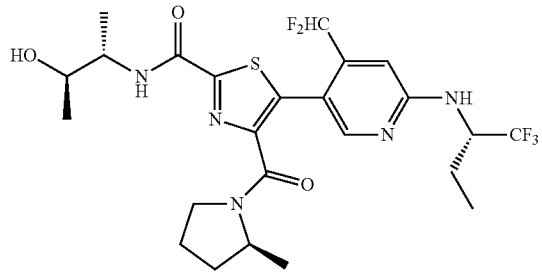 [SMILES: CC[C@H](Nc1cc(C(F)F)c(-c2sc(C(=O)N[C@@H](C)[C@@H](C)O)nc2C(=O)N2CCC[C@@H]2C)cn1)C(F)(F)F]

The title compound was prepared as described in Example 148 substituting 3-aminobutan-2-ol for (R)-(−)-2-amino-1-propanol and ethyl 5-(4-(difluoromethyl)-6-(((S)-1,1,1-trifluorobutan-2-yl)amino)pyridin-3-yl)-4-((S)-2-methylpyrrolidine-1-carbonyl)thiazole-2-carboxylate (Intermediate 102) for ethyl (S)-5-(6-(tert-butylamino)-4-(difluoromethyl)pyridin-3-yl)-4-(2-methylpyrrolidine-1-carbonyl)thiazole-2-carboxylate. The pure diastereomer was isolated via SFC (Stationary phase: Chiralcel OD-H, 5 µm, 250×30 mm, Mobile phase: 14% iPrOH+0.3% iPrNH$_2$, 86% CO$_2$, third eluting diastereomer). MS (ESI): mass calcd. for C$_{24}$H$_{30}$F$_5$N$_5$O$_3$S, 563.6; m/z found, 564.1 [M+H]$^+$. $^1$H NMR (400 MHz, CDCl$_3$) δ 8.10-8.01 (m, 1H), 7.37-7.29 (m, 1H), 7.07-6.66 (m, 2H), 4.84-4.65 (m, 2H), 4.33-3.86 (m, 3H), 3.62-3.33 (m, 2H), 2.08-1.75 (m, 5H), 1.67-1.62 (m, 1H), 1.36-1.32 (m, 3H), 1.30-1.25 (m, 4H), 1.24-1.21 (d, J=6.3 Hz, 2H), 1.08-1.02 (m, 4H).

Example 220

5-(4-(Difluoromethyl)-6-(((1S)-1-(trifluoromethyl)propyl)amino)-3-pyridyl)-N-((3R,4S)-4-hydroxytetrahydrofuran-3-yl)-4-((2S)-2-methylpyrrolidine-1-carbonyl)thiazole-2-carboxamide

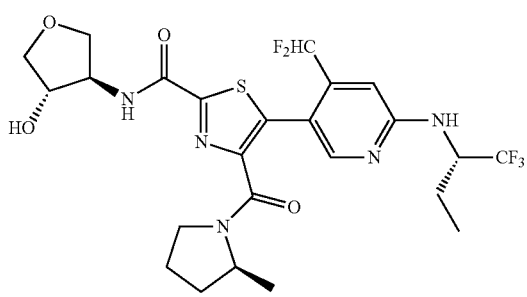 [SMILES: CC[C@H](Nc1cc(C(F)F)c(-c2sc(C(=O)N[C@@H]3COC[C@H]3O)nc2C(=O)N2CCC[C@@H]2C)cn1)C(F)(F)F]

The title compound was prepared as described in Example 148 substituting (3S,4R)-4-amino-tetrahydro-furan-3-ol for (R)-(−)-2-amino-1-propanol and ethyl 5-(4-(difluoromethyl)-6-(((S)-1,1,1-trifluorobutan-2-yl)amino)pyridin-3-yl)-4-((S)-2-methylpyrrolidine-1-carbonyl)thiazole-2-carboxylate (Intermediate 102) for ethyl (S)-5-(6-(tert-butylamino)-4-(difluoromethyl)pyridin-3-yl)-4-(2-methylpyrrolidine-1-carbonyl)thiazole-2-carboxylate. MS (ESI): mass calcd. for C$_{24}$H$_{28}$F$_5$N$_5$O$_4$S, 577.6; m/z found, 578.1 [M+H]$^+$. $^1$H NMR (400 MHz, CDCl$_3$) δ 8.10-8.02 (m, 1H), 7.39-7.28 (m, 1H), 7.04-6.63 (m, 2H), 4.96-4.89 (d, J=9.8 Hz, 1H), 4.84-4.71 (m, 1H), 4.48-4.35 (m, 2H), 4.25-4.14 (m, 3H), 3.91-3.74 (m, 2H), 3.60-3.30 (m, 3H), 2.10-1.92 (m, 3H), 1.83-1.71 (m, 1H), 1.67-1.50 (m, 2H), 1.23-1.20 (d, J=6.3 Hz, 2H), 1.07-1.02 (m, 3H), 1.02-0.98 (d, J=6.4 Hz, 1H).

Example 221

4-((1s,4s)-7-Azabicyclo[2.2.1]heptane-7-carbonyl)-5-(4-(difluoromethyl)-6-(((1S)-2,2,2-trifluoro-1-methyl-ethyl)amino)-3-pyridyl)-N-((1r,3S)-3-hydroxycyclobutyl)thiazole-2-carboxamide

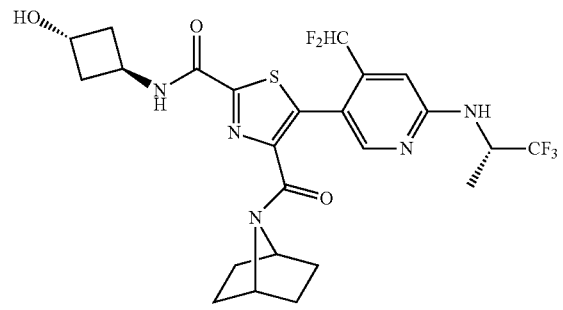 [SMILES: C[C@H](Nc1cc(C(F)F)c(-c2sc(C(=O)N[C@H]3C[C@H](O)C3)nc2C(=O)N2C3CCC2CC3)cn1)C(F)(F)F]

The title compound was prepared as described in Example 149 substituting trans-3-aminocyclobutanol HCl for 3-hydroxy-3-methylazetidine HCl and ethyl 4-((1R,4R)-7-azabicyclo[2.2.1]heptane-7-carbonyl)-5-(4-(difluoromethyl)-6-(((S)-1,1,1-trifluoropropan-2-yl)amino)pyridin-3-yl)thiazole-2-carboxylate (Intermediate 117) for ethyl (S)-5-(6-(tert-butylamino)-4-(difluoromethyl)pyridin-3-yl)-4-(2-methylpyrrolidine-1-carbonyl)thiazole-2-carboxylate. MS (ESI): mass calcd. for C$_{24}$H$_{26}$F$_5$N$_5$O$_3$S, 559.6; m/z found, 560.1 [M+H]$^+$. $^1$H NMR (400 MHz, CDCl$_3$) δ 8.10-8.07 (s, 1H), 7.37-7.31 (d, J=7.1 Hz, 1H), 6.91-6.60 (m, 2H), 5.01-4.90 (m, 2H), 4.70-4.56 (m, 3H), 4.21-4.16 (m, 1H), 2.51-2.39 (m, 4H), 2.21-2.16 (d, J=4.5 Hz, 1H), 1.79-1.69 (m, 3H), 1.51-1.39 (m, 8H).

Example 222

4-((1s,4s)-7-Azabicyclo[2.2.1]heptane-7-carbonyl)-5-(4-(difluoromethyl)-6-(((1S)-1-(trifluoromethyl)propyl)amino)-3-pyridyl)-N-((1r,3S)-3-hydroxycyclobutyl)thiazole-2-carboxamide

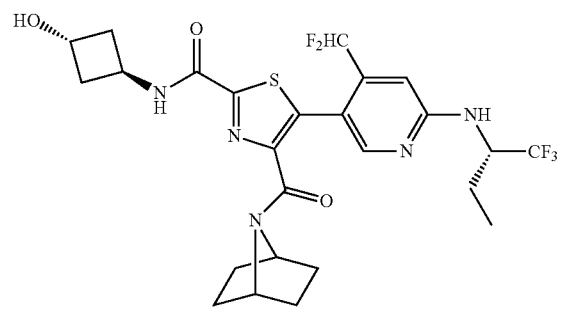 [SMILES: CC[C@H](Nc1cc(C(F)F)c(-c2sc(C(=O)N[C@H]3C[C@H](O)C3)nc2C(=O)N2C3CCC2CC3)cn1)C(F)(F)F]

The title compound was prepared as described in Example 149 substituting trans-3-aminocyclobutanol HCl for 3-hydroxy-3-methylazetidine HCl and ethyl 4-((1s,4s)-7-azabicyclo[2.2.1]heptane-7-carbonyl)-5-(4-(difluoromethyl)-6-(((S)-1,1,1-trifluorobutan-2-yl)amino)pyridin-3-yl)thiazole-2-carboxylate (Intermediate 99) for ethyl (S)-5-(6-(tert-butylamino)-4-(difluoromethyl)pyridin-3-yl)-4-(2-methylpyrrolidine-1-carbonyl)thiazole-2-carboxylate. MS (ESI): mass calcd. for $C_{25}H_{28}F_5N_5O_3S$, 573.6; m/z found, 574.1 [M+H]$^+$. $^1$H NMR (400 MHz, CDCl$_3$) δ 8.11-8.05 (s, 1H), 7.41-7.35 (d, J=7.2 Hz, 1H), 6.92-6.62 (m, 2H), 4.94-4.88 (m, 1H), 4.84-4.55 (m, 4H), 4.15-4.08 (m, 1H), 2.51-2.39 (m, 4H), 2.25-2.18 (m, 1H), 2.02-1.93 (m, 1H), 1.81-1.69 (m, 4H), 1.66-1.56 (m, 1H), 1.46-1.41 (m, 4H), 1.07-1.01 (m, 3H).

Example 223

5-(4-(Difluoromethyl)-6-(((S)-1,1,1-trifluoropropan-2-yl)amino)pyridin-3-yl)-N-((1S*,2S*)-2-hydroxycyclopropyl)-4-((S)-2-methylpyrrolidine-1-carbonyl)thiazole-2-carboxamide

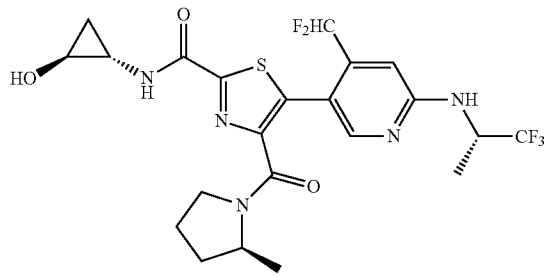 [SMILES: C[C@H](Nc1cc(C(F)F)c(-c2sc(C(=O)N[C@H]3C[C@@H]3O)nc2C(=O)N2CCC[C@@H]2C)cn1)C(F)(F)F]

The title compound was prepared as described in Example 157 substituting trans-N-((1R*,2R*)-2-((tert-butyl dim ethyl silyl)oxy)cyclopropyl)-5-(4-(difluoromethyl)-6-(((S)-1,1,1-trifluoropropan-2-yl)amino)pyridin-3-yl)-4-((S)-2-methylpyrrolidine-1-carbonyl)thiazole-2-carboxamide (Intermediate 105) for N-((1R*,2R*)-2-((tert-butyl dim ethyl silyl)oxy)cyclopropyl)-5-(4-(difluoromethyl)-6-(((S)-1,1,1-trifluoropropan-2-yl)amino)pyridin-3-yl)-4-((S)-2-methylpyrrolidine-1-carbonyl)thiazole-2-carboxamide. MS (ESI): mass calcd. for $C_{22}H_{24}F_5N_5O_3S$, 533.5; m/z found, 534.1 [M+H]$^+$. $^1$H NMR (500 MHz, CDCl$_3$) δ 8.10-8.02 (m, 1H), 7.19-7.09 (m, 1H), 6.98-6.63 (m, 2H), 4.99-4.87 (m, 2H), 4.31-4.16 (m, 1H), 3.64-3.28 (m, 4H), 2.94-2.86 (m, 1H), 2.08-2.04 (m, 1H), 1.96-1.87 (m, 1H), 1.79-1.50 (m, 2H), 1.43-1.40 (d, J=6.5 Hz, 3H), 1.27-1.26 (m, 1H), 1.23-1.20 (dd, J=6.3, 2.5 Hz, 2H), 1.02-0.96 (m, 2H).

Example 224

4-((1s,4s)-7-Azabicyclo[2.2.1]heptane-7-carbonyl)-5-(4-(difluoromethyl)-6-(((1S)-2,2,2-trifluoro-1-methyl-ethyl)amino)-3-pyridyl)-N-((1R,2R)-2-hydroxycyclopentyl)thiazole-2-carboxamide

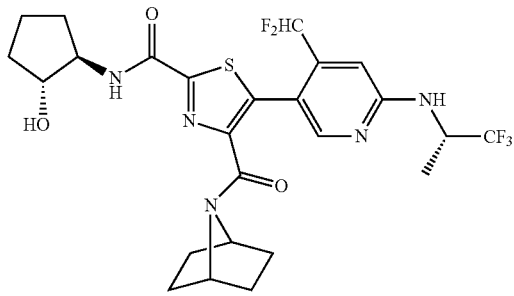 [SMILES: C[C@H](Nc1cc(C(F)F)c(-c2sc(C(=O)N[C@@H]3CCC[C@H]3O)nc2C(=O)N2C3CCC2CC3)cn1)C(F)(F)F]

The title compound was prepared as described in Example 149 substituting (1R,2R)-trans-2-aminocyclopentanol HCl for 3-hydroxy-3-methylazetidine HCl and ethyl 4-((1R,4R)-7-azabicyclo[2.2.1]heptane-7-carbonyl)-5-(4-(difluoromethyl)-6-(((S)-1,1,1-trifluoropropan-2-yl)amino)pyridin-3-yl)thiazole-2-carboxylate (Intermediate 117) for ethyl (S)-5-(6-(tert-butylamino)-4-(difluoromethyl)pyridin-3-yl)-4-(2-methylpyrrolidine-1-carbonyl)thiazole-2-carboxylate. MS (ESI): mass calcd. for $C_{25}H_{28}F_5N_5O_3S$, 573.6; m/z found, 574.1 [M+H]$^+$. $^1$H NMR (500 MHz, CDCl$_3$) δ 8.12-8.04 (s, 1H), 7.29-7.27 (m, 1H), 6.89-6.62 (m, 2H), 4.99-4.90 (m, 2H), 4.71-4.64 (m, 1H), 4.23-4.14 (m, 2H), 4.08-4.02 (m, 1H), 3.81-3.78 (m, 1H), 2.31-2.05 (m, 2H), 1.92-1.71 (m, 5H), 1.70-1.69 (s, 1H), 1.65-1.59 (m, 1H), 1.49-1.39 (m, 7H).

Example 225

4-((1s,4s)-7-Azabicyclo[2.2.1]heptane-7-carbonyl)-5-(4-(difluoromethyl)-6-(((1S)-1-(trifluoromethyl)propyl)amino)-3-pyridyl)-N-((1R,2R)-2-hydroxycyclopentyl)thiazole-2-carboxamide

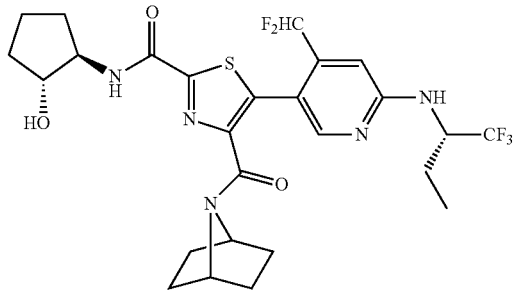 [SMILES: CC[C@H](Nc1cc(C(F)F)c(-c2sc(C(=O)N[C@@H]3CCC[C@H]3O)nc2C(=O)N2C3CCC2CC3)cn1)C(F)(F)F]

The title compound was prepared as described in Example 149 substituting (1R,2R)-trans-2-aminocyclopentanol HCl for 3-hydroxy-3-methylazetidine HCl and ethyl 4-((1s,4s)-7-azabicyclo[2.2.1]heptane-7-carbonyl)-5-(4-(difluoromethyl)-6-(((S)-1,1,1-trifluorobutan-2-yl)amino)pyridin-3-yl)thiazole-2-carboxylate (Intermediate 99) for ethyl (S)-5-(6-(tert-butylamino)-4-(difluoromethyl)pyridin-3-yl)-4-(2-methylpyrrolidine-1-carbonyl)thiazole-2-carboxylate. MS (ESI): mass calcd. for $C_{26}H_{30}F_5N_5O_3S$, 587.6; m/z found, 588.1 [M+H]$^+$. $^1$H NMR (500 MHz, CDCl$_3$) δ 8.11-8.06 (s, 1H), 7.31-7.27 (d, J=5.2 Hz, 1H), 6.90-6.64 (m, 2H), 4.89-4.64 (m, 3H), 4.19-4.02 (m, 3H), 3.82-3.78 (m, 1H), 2.31-2.06 (m, 2H), 2.01-1.84 (m, 2H), 1.80-1.73 (m, 4H), 1.66-1.57 (m, 2H), 1.48-1.38 (m, 5H), 1.07-1.01 (m, 3H).

Example 226

4-((1s,4s)-7-Azabicyclo[2.2.1]heptane-7-carbonyl)-5-(4-(difluoromethyl)-6-(((1S)-2,2,2-trifluoro-1-methyl-ethyl)amino)-3-pyridyl)-N-((1R)-2-hydroxy-1-methyl-ethyl)thiazole-2-carboxamide

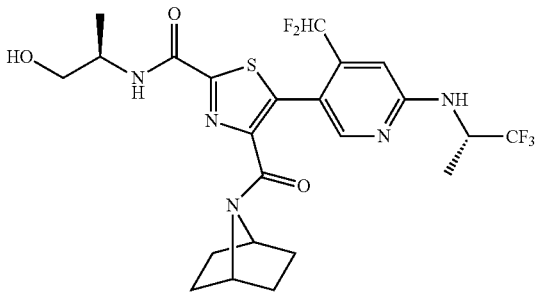 [SMILES: C[C@H](CO)NC(=O)c1nc(C(=O)N2C3CCC2CC3)c(-c2cnc(N[C@@H](C)C(F)(F)F)cc2C(F)F)s1]

The title compound was prepared as described in Example 148 substituting ethyl 4-((1s,4s)-7-azabicyclo[2.2.1]heptane-7-carbonyl)-5-(4-(difluoromethyl)-6-(((S)-1,1,1-trifluoropropan-2-yl)amino)pyridin-3-yl)thiazole-2-carboxylate (Intermediate 117) for ethyl (S)-5-(6-(tert-butylamino)-4-(difluoromethyl)pyridin-3-yl)-4-(2-methylpyrrolidine-1-carbonyl)thiazole-2-carboxylate. MS (ESI): mass calcd. for $C_{23}H_{26}F_5N_5O_3S$, 547.5; m/z found, 548.1 [M+H]$^+$. $^1$H NMR (500 MHz, CDCl$_3$) δ 8.11-8.05 (s, 1H), 7.38-7.32 (d, J=7.9 Hz, 1H), 6.88-6.62 (m, 2H), 5.01-4.90 (m, 2H), 4.70-4.64 (m, 1H), 4.31-4.21 (m, 2H), 1.63-1.53 (m, 2H), 3.83-3.65 (m, 2H), 2.56-2.46 (s, 1H), 1.81-1.72 (m, 2H), 1.48-1.43 (m, 4H), 1.43-1.39 (d, J=6.4 Hz, 3H), 1.35-1.30 (d, J=6.8 Hz, 3H).

Example 227

4-((1s,4s)-7-Azabicyclo[2.2.1]heptane-7-carbonyl)-5-(4-(difluoromethyl)-6-(((1S)-1-(trifluoromethyl)propyl)amino)-3-pyridyl)-N-((1R)-2-hydroxy-1-methyl-ethyl)thiazole-2-carboxamide

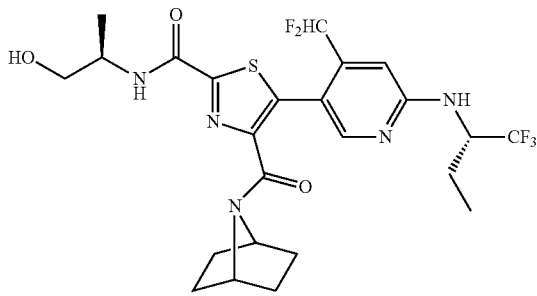 [SMILES: CC[C@H](Nc1cc(C(F)F)c(-c2sc(C(=O)N[C@H](C)CO)nc2C(=O)N2C3CCC2CC3)cn1)C(F)(F)F]

The title compound was prepared as described in Example 148 substituting ethyl 4-((1s,4s)-7-azabicyclo[2.2.1]heptane-7-carbonyl)-5-(4-(difluoromethyl)-6-(((S)-1,1,1-trifluorobutan-2-yl)amino)pyridin-3-yl)thiazole-2-carboxylate (Intermediate 99) for ethyl (S)-5-(6-(tert-butylamino)-4-(difluoromethyl)pyridin-3-yl)-4-(2-methylpyrrolidine-1-carbonyl)thiazole-2-carboxylate. MS (ESI): mass calcd. for $C_{24}H_{28}F_5N_5O_3S$, 561.6; m/z found, 562.1 [M+H]$^+$. $^1$H NMR (500 MHz, CDCl$_3$) δ 8.10-8.05 (s, 1H), 7.40-7.34 (d, J=7.9 Hz, 1H), 6.90-6.64 (m, 2H), 4.94-4.87 (d, J=9.8 Hz, 1H), 4.84-4.62 (m, 2H), 4.28-4.16 (m, 2H), 3.83-3.65 (m, 2H), 2.60-2.52 (s, 1H), 2.02-1.91 (m, 1H), 1.75-1.69 (m, 2H), 1.66-1.49 (m, 3H), 1.47-1.39 (m, 4H), 1.34-1.30 (d, J=6.8 Hz, 3H), 1.07-1.00 (m, 3H).

Example 228

4-((1s,4s)-7-Azabicyclo[2.2.1]heptane-7-carbonyl)-N-((3R*,4R*)-4-hydroxytetrahydrofuran-3-yl)-5-(4-(trifluoromethyl)-6-(((S)-1,1,1-trifluoropropan-2-yl)amino)pyridin-3-yl)thiazole-2-carboxamide

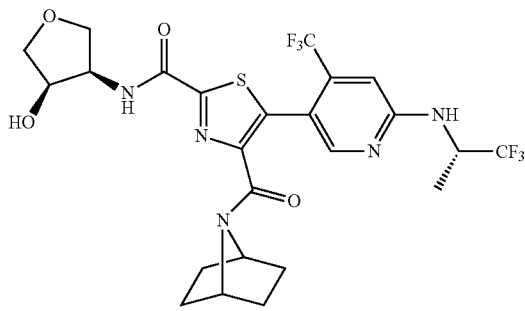 [SMILES: C[C@H](Nc1cc(C(F)(F)F)c(-c2sc(C(=O)N[C@@H]3COC[C@@H]3O)nc2C(=O)N2C3CCC2CC3)cn1)C(F)(F)F]

To a microwave vial under N$_2$ was added ethyl 4-((1s,4s)-7-azabicyclo[2.2.1]heptane-7-carbonyl)-5-(4-(trifluoromethyl)-6-(((S)-1,1,1-trifluoropropan-2-yl)amino)pyridin-3-yl)thiazole-2-carboxylate (178 mg, 0.33 mmol, Intermediate 116), cis-4-aminotetrahydro-3-furanol HCl (244 mg, 1.66 mmol), DIPEA (0.31 mL, 0.82 mmol) and EtOH (1.58 mL), and the reaction was stirred at 100° C. for 18 h. The reaction mixture was cooled to rt and partitioned between EtOAc (20 mL) and saturated aqueous NH$_4$Cl (20 mL). The layers were separated and the aqueous further extracted with EtOAc (2×15 mL). The organic layers were combined, dried over anhydrous sodium sulfate, filtered and concentrated to dryness. The crude residue was dissolved in DCM and purified by FCC (0-100% EtOAc/Hexanes) to provide the title compound. The pure diastereomer was isolated via SFC (Stationary phase: Chiralpak AD-H, 5 μm, 250×30 mm, Mobile phase: 25% iPrOH+0.3% iPrNH$_2$, 75% CO$_2$, second eluting enantiomer). MS (ESI): mass calcd. for $C_{24}H_{25}F_6N_5O_4S$, 593.5; m/z found, 594.2 [M+H]$^+$. $^1$H NMR (400 MHz, CDCl$_3$) δ 8.21-8.16 (s, 1H), 7.86-7.79 (d, J=7.8 Hz, 1H), 6.74-6.68 (s, 1H), 5.25-5.17 (d, J=9.3 Hz, 1H), 5.02-4.91 (m, 1H), 4.69-4.46 (m, 4H), 4.22-4.16 (m, 1H), 1.49-1.45 (m, 3H), 4.10-4.04 (m, 1H), 3.90-3.85 (m, 1H), 3.76-3.70 (m, 1H), 1.86-1.61 (m, 5H), 1.42-1.38 (m, 3H), 1.22-1.20 (d, J=6.1 Hz, 1H).

Example 229

5-(4-(Difluoromethyl)-6-(((1S)-1-(trifluoromethyl)propyl)amino)-3-pyridyl)-N-((1S,2S)-2-hydroxycyclopentyl)-4-((2S)-2-methylpyrrolidine-1-carbonyl)thiazole-2-carboxamide

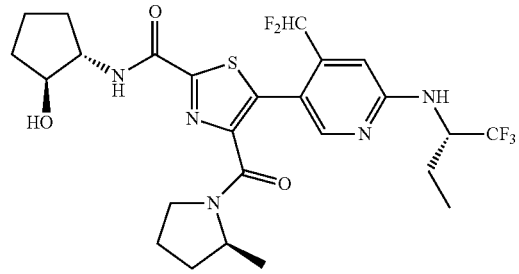 [SMILES: CC[C@H](Nc1cc(C(F)F)c(-c2sc(C(=O)N[C@H]3CCC[C@@H]3O)nc2C(=O)N2CCC[C@@H]2C)cn1)C(F)(F)F]

The title compound was prepared as described in Example 149 substituting (1S,2S)-trans-2-aminocyclopentanol HCl for 3-hydroxy-3-methylazetidine HCl and ethyl 5-(4-(difluoromethyl)-6-(((S)-1,1,1-trifluorobutan-2-yl)amino)pyridin-3-yl)-4-((S)-2-methylpyrrolidine-1-carbonyl)thiazole-2-carboxylate (Intermediate 102) for ethyl (S)-5-(6-(tert-butylamino)-4-(difluoromethyl)pyridin-3-yl)-4-(2-methylpyrrolidine-1-carbonyl)thiazole-2-carboxylate. MS (ESI): mass calcd. for $C_{25}H_{30}F_5N_5O_3S$, 575.6; m/z found, 576.1 [M+H]$^+$. $^1$H NMR (500 MHz, CDCl$_3$) δ 8.10-8.01 (m, 1H), 7.30-7.20 (m, 1H), 7.02-6.66 (m, 2H), 4.95-4.72 (m, 2H), 4.27-4.15 (m, 2H), 4.08-4.01 (m, 1H), 3.87-3.80 (s, 1H), 3.61-3.29 (m, 2H), 2.33-2.23 (m, 1H), 2.12-2.03 (m, 2H), 2.02-1.82 (m, 4H), 1.81-1.75 (m, 2H), 1.66-1.50 (m, 3H), 1.23-1.20 (d, J=6.3 Hz, 2H), 1.07-1.02 (m, 3H), 1.01-0.98 (d, J=6.4 Hz, 1H).

Example 230

5-(4-(Difluoromethyl)-6-(((1R)-1-(trifluoromethyl)propyl)amino)-3-pyridyl)-N-((1S)-2-hydroxy-1,2-dimethyl-propyl)-4-)(2S)-2-methylpyrrolidine-1-carbonyl)thiazole-2-carboxamide

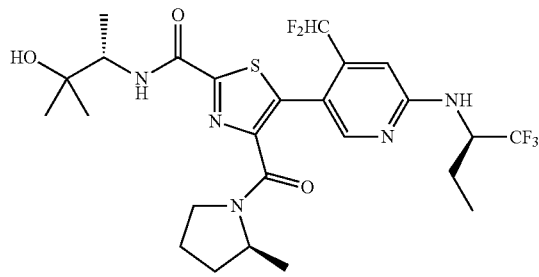 [SMILES: CC[C@@H](Nc1cc(C(F)F)c(-c2sc(C(=O)N[C@@H](C)C(C)(C)O)nc2C(=O)N2CCC[C@@H]2C)cn1)C(F)(F)F]

The title compound was prepared as described in Example 149 substituting ethyl 5-(4-(difluoromethyl)-6-(((R)-1,1,1-trifluorobutan-2-yl)amino)pyridin-3-yl)-4-((S)-2-methylpyrrolidine-1-carbonyl)thiazole-2-carboxylate (Intermediate 104: Step B) for ethyl (S)-5-(6-(tert-butylamino)-4-(difluoromethyl)pyridin-3-yl)-4-(2-methylpyrrolidine-1-carbonyl)thiazole-2-carboxylate and (S)-3-amino-2-methylbutan-2-ol HCl for 3-hydroxy-3-methylazetidine HCl. MS (ESI): mass calcd. for $C_{25}H_{32}F_5N_5O_3S$, 577.6; m/z found, 578.1 [M+H]$^+$. $^1$H NMR (500 MHz, CDCl$_3$) δ 8.09-8.00 (m, 1H), 7.43-7.35 (m, 1H), 7.01-6.67 (m, 2H), 4.91-4.83 (d, J=9.8 Hz, 1H), 4.82-4.72 (m, 1H), 4.28-4.08 (m, 2H), 3.63-3.37 (m, 2H), 2.02-1.85 (m, 3H), 1.83-1.73 (m, 1H), 1.66-1.50 (m, 2H), 1.32-1.28 (m, 9H), 1.27-1.23 (t, J=7.1 Hz, 1H), 1.23-1.18 (d, J=6.3 Hz, 2H), 1.10-1.07 (d, J=6.4 Hz, 1H), 1.07-1.02 (m, 3H).

Example 231

5-[4-(Difluoromethyl)-6-[[(1S)-1-(trifluoromethyl)propyl]amino]-3-pyridyl]-N-[(1R,2R)-2-hydroxycyclopentyl]-4-[(2S)-2-methylpyrrolidine-1-carbonyl]thiazole-2-carboxamide

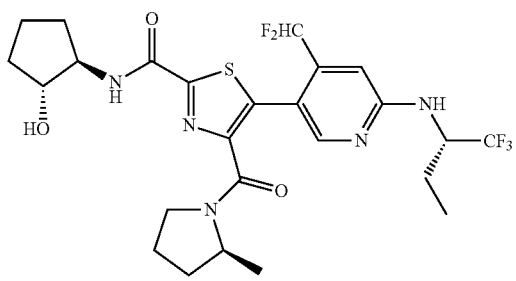 [SMILES: CC[C@H](Nc1cc(C(F)F)c(-c2sc(C(=O)N[C@@H]3CCC[C@H]3O)nc2C(=O)N2CCC[C@@H]2C)cn1)C(F)(F)F]

The title compound was prepared as described in Example 149 substituting (1R,2R)-trans-2-aminocyclopentanol HCl for 3-hydroxy-3-methylazetidine HCl and ethyl 5-(4-(difluoromethyl)-6-(((S)-1,1,1-trifluorobutan-2-yl)amino)pyridin-3-yl)-4-((S)-2-methylpyrrolidine-1-carbonyl)thiazole-2-carboxylate (Intermediate 102) for ethyl (S)-5-(6-(tert-butylamino)-4-(difluoromethyl)pyridin-3-yl)-4-(2-methylpyrrolidine-1-carbonyl)thiazole-2-carboxylate. MS (ESI): mass calcd. for $C_{25}H_{30}F_5N_5O_3S$, 575.6; m/z found, 576.1 [M+H]$^+$. $^1$H NMR (500 MHz, CDCl$_3$) δ 8.10-8.02 (m, 1H), 7.29-7.22 (m, 1H), 7.00-6.66 (m, 2H), 4.94-4.72 (m, 2H), 4.25-4.14 (m, 2H), 4.08-4.01 (m, 1H), 3.89-3.79 (s, 1H), 3.61-3.30 (m, 2H), 2.32-2.24 (m, 1H), 2.11-2.06 (m, 1H), 2.01-1.84 (m, 4H), 1.81-1.75 (m, 2H), 1.65-1.51 (m, 3H), 1.28-1.24 (t, J=7.1 Hz, 1H), 1.23-1.20 (d, J=6.3 Hz, 2H), 1.07-1.02 (m, 3H), 1.02-1.00 (d, J=6.4 Hz, 1H).

Example 232

5-(4-(Difluoromethyl)-6-(((S)-1,1,1-trifluorobutan-2-yl)amino)pyridin-3-yl)-N-(1,1-dioxidotetrahydro-2H-thiopyran-4-yl)-4-((S)-2-methylpyrrolidine-1-carbonyl)thiazole-2-carboxamide

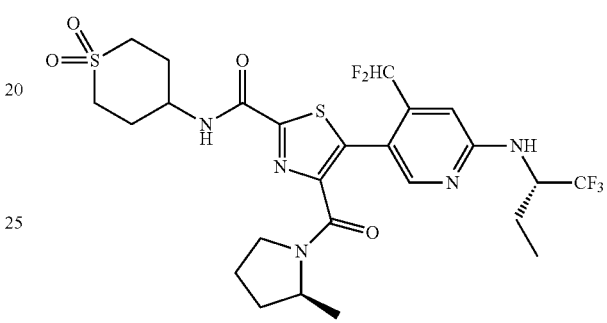

The title compound was prepared as described in Example 148 substituting 4-aminotetrahydro-2H-thiopyran 1,1-dioxide for (R)-(−)-2-amino-1-propanol and ethyl 5-(4-(difluoromethyl)-6-(((S)-1,1,1-trifluorobutan-2-yl)amino)pyridin-3-yl)-4-((S)-2-methylpyrrolidine-1-carbonyl)thiazole-2-carboxylate (Intermediate 102) for ethyl (S)-5-(6-(tert-butylamino)-4-(difluoromethyl)pyridin-3-yl)-4-(2-methylpyrrolidine-1-carbonyl)thiazole-2-carboxylate. MS (ESI): mass calcd. for $C_{25}H_{30}F_5N_5O_4S_2$, 623.7; m/z found, 624.1 [M+H]$^+$. $^1$H NMR (500 MHz, CDCl$_3$) δ 8.10-8.01 (m, 1H), 7.23-7.12 (m, 1H), 7.02-6.66 (m, 2H), 4.90-4.84 (m, 1H), 4.83-4.69 (m, 1H), 4.30-4.17 (m, 2H), 3.61-3.30 (m, 2H), 3.22-3.11 (m, 4H), 2.48-2.39 (m, 2H), 2.35-2.25 (m, 2H), 2.03-1.85 (m, 3H), 1.83-1.71 (m, 1H), 1.65-1.50 (m, 2H), 1.23-1.21 (d, J=6.3 Hz, 2H), 1.07-1.02 (m, 3H), 1.02-0.99 (d, J=6.4 Hz, 1H).

Example 233

5-[4-(Difluoromethyl)-6-[[(1S)-1-(trifluoromethyl)propyl]amino]-3-pyridyl]-N-((1r,3S)-3-hydroxycyclobutyl)-4-[(2S)-2-methylpyrrolidine-1-carbonyl]thiazole-2-carboxamide

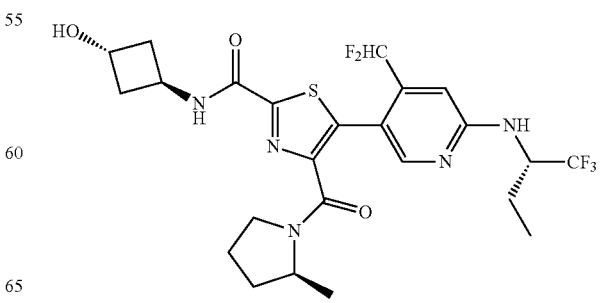

The title compound was prepared as described in Example 149 substituting trans-3-aminocyclobutanol HCl for 3-hydroxy-3-methylazetidine HCl and ethyl 5-(4-(difluoromethyl)-6-(((S)-1,1,1-trifluorobutan-2-yl)amino)pyridin-3-yl)-4-((S)-2-methylpyrrolidine-1-carbonyl)thiazole-2-carboxylate (Intermediate 102) for ethyl (S)-5-(6-(tert-butylamino)-4-(difluoromethyl)pyridin-3-yl)-4-(2-methylpyrrolidine-1-carbonyl)thiazole-2-carboxylate. MS (ESI): mass calcd. for $C_{24}H_{28}F_5N_5O_3S$, 561.6; m/z found, 562.2 [M+H]+. $^1$H NMR (500 MHz, CDCl$_3$) δ 8.10-8.00 (m, 1H), 7.36-7.27 (m, 1H), 7.01-6.66 (m, 2H), 4.91-4.85 (m, 1H), 4.84-4.70 (m, 1H), 4.70-4.56 (m, 2H), 4.26-4.17 (m, 1H), 3.60-3.31 (m, 2H), 2.50-2.39 (m, 4H), 2.17-2.09 (s, 1H), 2.04-1.84 (m, 3H), 1.80-1.71 (m, 1H), 1.64-1.50 (m, 2H), 1.23-1.19 (m, 2H), 1.07-0.99 (m, 4H).

Example 234

5-[4-(Difluoromethyl)-6-[[(1S)-1-(trifluoromethyl) propyl]amino]-3-pyridyl]-N-[(1R)-2-hydroxy-1-methyl-ethyl]-4-[(2S)-2-methylpyrrolidine-1-carbonyl]thiazole-2-carboxamide

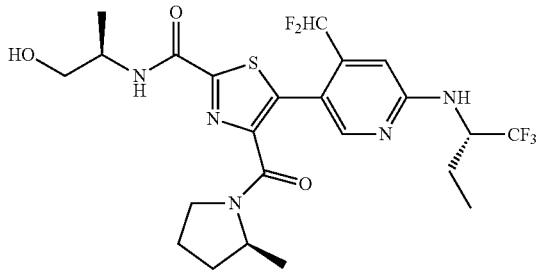 [SMILES: CC[C@H](Nc1cc(C(F)F)c(-c2sc(C(=O)N[C@H](C)CO)nc2C(=O)N2CCC[C@@H]2C)cn1)C(F)(F)F]

The title compound was prepared as described in Example 148 substituting ethyl 5-(4-(difluoromethyl)-6-(((S)-1,1,1-trifluorobutan-2-yl)amino)pyridin-3-yl)-4-((S)-2-methylpyrrolidine-1-carbonyl)thiazole-2-carboxylate (Intermediate 102) for ethyl (S)-5-(6-(tert-butylamino)-4-(difluoromethyl)pyridin-3-yl)-4-(2-methylpyrrolidine-1-carbonyl)thiazole-2-carboxylate. MS (ESI): mass calcd. for $C_{23}H_{28}F_5N_5O_3S$, 549.6; m/z found, 550.2 [M+H]+. $^1$H NMR (500 MHz, CDCl$_3$) δ 8.09-8.02 (m, 1H), 7.34-7.27 (m, 1H), 7.01-6.67 (m, 2H), 4.87-4.81 (m, 1H), 4.81-4.72 (m, 1H), 4.31-4.17 (m, 2H), 3.84-3.65 (m, 2H), 3.61-3.34 (m, 2H), 2.51-2.42 (m, 1H), 2.03-1.85 (m, 3H), 1.81-1.72 (m, 1H), 1.65-1.50 (m, 2H), 1.35-1.31 (d, J=6.8 Hz, 3H), 1.23-1.20 (dd, J=6.3, 4.3 Hz, 2H), 1.08-1.01 (m, 4H).

Example 235

5-(6-(tert-Butylamino)-4-(trifluoromethyl)pyridin-3-yl)-N-((2R*,3S*)-3-hydroxybutan-2-yl)-4-((S)-2-methylpyrrolidine-1-carbonyl)thiazole-2-carboxamide

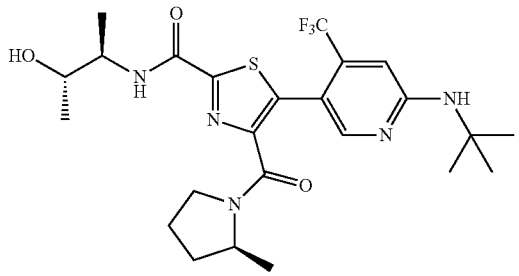 [SMILES: C[C@H](O)[C@@H](C)NC(=O)c1nc(C(=O)N2CCC[C@@H]2C)c(-c2cnc(NC(C)(C)C)cc2C(F)(F)F)s1]

The title compound was prepared as described in Example 148 substituting 3-aminobutan-2-ol for (R)-(−)-2-amino-1-propanol and ethyl (S)-5-(6-(tert-butylamino)-4-(trifluoromethyl)pyridin-3-yl)-4-(2-methylpyrrolidine-1-carbonyl)thiazole-2-carboxylate (Intermediate 107) for ethyl (S)-5-(6-(tert-butylamino)-4-(difluoromethyl)pyridin-3-yl)-4-(2-methylpyrrolidine-1-carbonyl)thiazole-2-carboxylate. The pure diastereomer was isolated via SFC (Stationary phase: Chiralcel OD-H, 5 μm, 250×30 mm, Mobile phase: 5% MeOH+0.3% iPrNH$_2$, 95% CO$_2$) followed by a second SFC (Stationary phase: Chiralpak AD-H, 5 μm, 250×20 mm, Mobile phase: 8% mixture of EtOH/iPrOH 50/50 v/v+0.3% iPrNH$_2$, 92% CO$_2$). MS (ESI): mass calcd. for $C_{24}H_{32}F_3N_5O_3S$, 527.6; m/z found, 528.2 [M+H]+. $^1$H NMR (500 MHz, CDCl$_3$) δ 8.19-8.16 (m, 1H), 7.39-7.32 (m, 1H), 6.64-6.60 (m, 1H), 4.87-4.83 (s, 1H), 4.23-4.14 (m, 2H), 4.05-3.97 (m, 1H), 3.61-3.35 (m, 2H), 2.09-2.02 (m, 1H), 1.47-1.44 (m, 9H), 1.91-1.85 (m, 1H), 1.77-1.71 (m, 1H), 1.54-1.51 (m, 1H), 1.28-1.26 (m, 3H), 1.25-1.23 (m, 5H), 1.22-1.20 (m, 1H), 1.12-1.09 (d, J=6.4 Hz, 1H).

Example 236

5-(6-(tert-Butylamino)-4-(trifluoromethyl)pyridin-3-yl)-N-((2S*,3S*)-3-hydroxybutan-2-yl)-4-((S)-2-methylpyrrolidine-1-carbonyl)thiazole-2-carboxamide

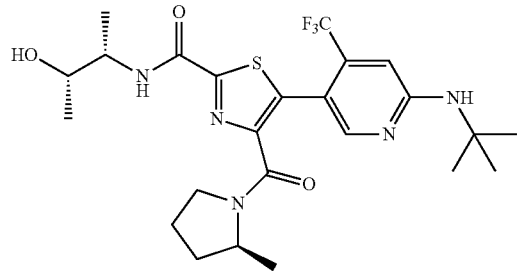 [SMILES: C[C@H](O)[C@H](C)NC(=O)c1nc(C(=O)N2CCC[C@@H]2C)c(-c2cnc(NC(C)(C)C)cc2C(F)(F)F)s1]

The title compound was prepared as described in Example 148 substituting 3-aminobutan-2-ol for (R)-(−)-2-amino-1-propanol and ethyl (S)-5-(6-(tert-butylamino)-4-(trifluoromethyl)pyridin-3-yl)-4-(2-methylpyrrolidine-1-carbonyl)thiazole-2-carboxylate (Intermediate 107) for ethyl (S)-5-(6-(tert-butylamino)-4-(difluoromethyl)pyridin-3-yl)-4-(2-methylpyrrolidine-1-carbonyl)thiazole-2-carboxylate. The pure diastereomer was isolated via SFC (Stationary phase: Chiralcel OD-H, 5 μm, 250×30 mm, Mobile phase: 5% MeOH+0.3% iPrNH$_2$, 95% CO$_2$) followed by a second SFC (Stationary phase: Chiralpak AD-H, 5 μm, 250×20 mm, Mobile phase: 8% mixture of EtOH/iPrOH 50/50 v/v+0.3% iPrNH$_2$, 92% CO$_2$). MS (ESI): mass calcd. for $C_{24}H_{32}F_3N_5O_3S$, 527.6; m/z found, 528.2 [M+H]+. $^1$H NMR (500 MHz, CDCl$_3$) δ 8.22-8.13 (s, 1H), 7.38-7.30 (m, 1H), 6.68-6.58 (s, 1H), 4.93-4.81 (m, 1H), 4.30-4.06 (m, 2H), 3.92-3.84 (m, 1H), 3.61-3.36 (m, 2H), 2.09-2.03 (m, 1H), 1.46-1.45 (m, 9H), 1.92-1.84 (m, 1H), 1.80-1.69 (m, 1H), 1.54-1.50 (m, 1H), 1.34-1.32 (d, J=6.8 Hz, 3H), 1.28-1.26 (m, 2H), 1.25-1.20 (m, 4H), 1.13-1.10 (d, J=6.4 Hz, 1H).

Example 237

5-(6-(tert-Butylamino)-4-(trifluoromethyl)pyridin-3-yl)-N-((2R*,3R*)-3-hydroxybutan-2-yl)-4-((S)-2-methylpyrrolidine-1-carbonyl)thiazole-2-carboxamide

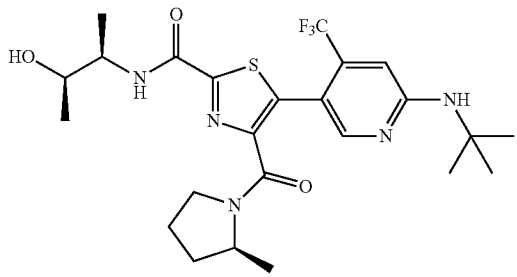 [SMILES: C[C@@H](O)[C@@H](C)NC(=O)c1nc(C(=O)N2CCC[C@@H]2C)c(-c2cnc(NC(C)(C)C)cc2C(F)(F)F)s1]

The title compound was prepared as described in Example 148 substituting 3-aminobutan-2-ol for (R)-(−)-2-amino-1-propanol and ethyl (S)-5-(6-(tert-butylamino)-4-(trifluoromethyl)pyridin-3-yl)-4-(2-methylpyrrolidine-1-carbonyl)thiazole-2-carboxylate (Intermediate 107) for ethyl (9-5-(6-(tert-butylamino)-4-(difluoromethyl)pyridin-3-yl)-4-(2-methylpyrrolidine-1-carbonyl)thiazole-2-carboxylate. The pure diastereomer was isolated via SFC (Stationary phase: Chiralcel OD-H, 5 μm, 250×30 mm, Mobile phase: 5% MeOH+0.3% iPrNH$_2$, 95% CO$_2$). MS (ESI): mass calcd. for C$_{24}$H$_{32}$F$_3$N$_5$O$_3$S, 527.6; m/z found, 528.2 [M+H]$^+$. $^1$H NMR (500 MHz, CDCl$_3$) δ 8.19-8.16 (s, 1H), 7.38-7.30 (m, 1H), 6.63-6.61 (m, 1H), 4.87-4.83 (s, 1H), 4.24-4.05 (m, 2H), 3.92-3.86 (m, 1H), 3.60-3.37 (m, 2H), 2.09-2.02 (m, 1H), 1.47-1.44 (m, 9H), 1.93-1.87 (m, 1H), 1.77-1.70 (m, 1H), 1.55-1.50 (m, 1H), 1.36-1.29 (d, J=6.8 Hz, 3H), 1.27-1.23 (m, 5H), 1.14-1.09 (m, 1H), 1.10-1.04 (d, J=6.3 Hz, 1H).

Example 238

5-(6-(tert-Butylamino)-4-(trifluoromethyl)pyridin-3-yl)-N-((2S*,3R*)-3-hydroxybutan-2-yl)-4-((S)-2-methylpyrrolidine-1-carbonyl)thiazole-2-carboxamide

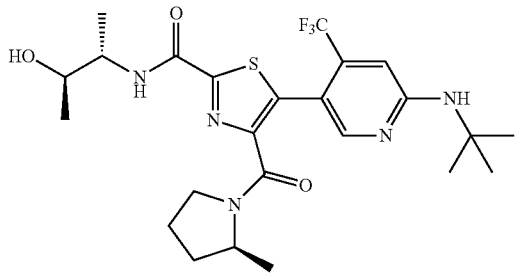 [SMILES: C[C@H](NC(=O)c1nc(C(=O)N2CCC[C@@H]2C)c(-c2cnc(NC(C)(C)C)cc2C(F)(F)F)s1)[C@@H](C)O]

The title compound was prepared as described in Example 148 substituting 3-aminobutan-2-ol for (R)-(−)-2-amino-1-propanol and ethyl (S)-5-(6-(tert-butylamino)-4-(trifluoromethyl)pyridin-3-yl)-4-(2-methylpyrrolidine-1-carbonyl)thiazole-2-carboxylate (Intermediate 107) for ethyl (9-5-(6-(tert-butylamino)-4-(difluoromethyl)pyridin-3-yl)-4-(2-methylpyrrolidine-1-carbonyl)thiazole-2-carboxylate. The pure diastereomer was isolated via SFC (Stationary phase: Chiralcel OD-H, 5 μm, 250×30 mm, Mobile phase: 5% MeOH+0.3% iPrNH$_2$, 95% CO$_2$). MS (ESI): mass calcd. for C$_{24}$H$_{32}$F$_3$N$_5$O$_3$S, 527.6; m/z found, 528.2 [M+H]$^+$. $^1$H NMR (500 MHz, CDCl$_3$) δ 8.19-8.16 (m, 1H), 7.40-7.31 (m, 1H), 6.64-6.61 (m, 1H), 4.87-4.83 (s, 1H), 4.25-4.14 (m, 2H), 4.05-3.97 (m, 1H), 3.76-3.36 (m, 3H), 2.09-2.02 (m, 1H), 1.47-1.44 (m, 9H), 1.92-1.85 (m, 1H), 1.79-1.69 (m, 1H), 1.53-1.51 (m, 1H), 1.28-1.26 (m, 3H), 1.25-1.23 (m, 4H), 1.12-1.09 (d, J=6.4 Hz, 1H), 1.09-1.06 (d, J=6.2 Hz, 1H).

Example 239

5-[4-(Difluoromethyl)-6-[[(1S)-1-(trifluoromethyl)propyl]amino]-3-pyridyl]-N-[(3S,4R)-4-hydroxytetrahydrofuran-3-yl]-4-[(2S)-2-methylpyrrolidine-1-carbonyl]thiazole-2-carboxamide

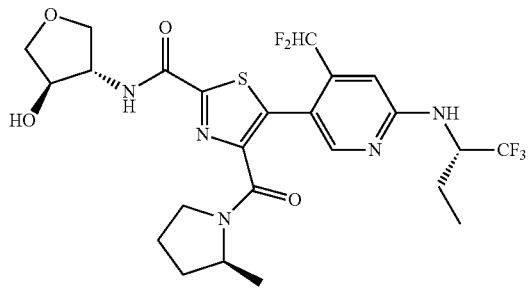 [SMILES: CC[C@H](Nc1cc(C(F)F)c(-c2sc(C(=O)N[C@H]3COC[C@@H]3O)nc2C(=O)N2CCC[C@@H]2C)cn1)C(F)(F)F]

The title compound was prepared as described in Example 148 substituting (3R,4S)-4-amino-tetrahydro-furan-3-ol for (R)-(−)-2-amino-1-propanol and ethyl 5-(4-(difluoromethyl)-6-(((S)-1,1,1-trifluorobutan-2-yl)amino)pyridin-3-yl)-4-((S)-2-methylpyrrolidine-1-carbonyl)thiazole-2-carboxylate (Intermediate 102) for ethyl (S)-5-(6-(tert-butylamino)-4-(difluoromethyl)pyridin-3-yl)-4-(2-methylpyrrolidine-1-carbonyl)thiazole-2-carboxylate. MS (ESI): mass calcd. for C$_{24}$H$_{28}$F$_5$N$_5$O$_4$S, 577.6; m/z found, 578.1 [M+H]$^+$. $^1$H NMR (500 MHz, CDCl$_3$) δ 8.09-8.01 (m, 1H), 7.37-7.27 (m, 1H), 7.03-6.67 (m, 2H), 4.93-4.85 (m, 1H), 4.82-4.71 (s, 1H), 4.47-4.36 (m, 2H), 4.30-4.09 (m, 3H), 3.89-3.74 (m, 2H), 3.62-3.29 (m, 3H), 2.04-1.88 (m, 3H), 1.81-1.52 (m, 3H), 1.24-1.21 (dd, J=6.3, 3.6 Hz, 2H), 1.08-1.02 (m, 3H), 1.00-0.97 (m, 1H).

Example 240

5-[4-(Difluoromethyl)-6-[[(1S)-1-(trifluoromethyl)propyl]amino]-3-pyridyl]-N-(1,1-dioxothietan-3-yl)-4-[(2S)-2-methylpyrrolidine-1-carbonyl]thiazole-2-carboxamide

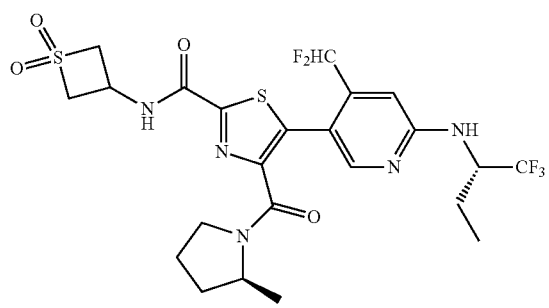 [SMILES: CC[C@H](Nc1cc(C(F)F)c(-c2sc(C(=O)NC3CS(=O)(=O)C3)nc2C(=O)N2CCC[C@@H]2C)cn1)C(F)(F)F]

The title compound was prepared as described in Example 149 substituting 3-aminothietane 1,1-dioxide HCl for 3-hydroxy-3-methylazetidine HCl and ethyl 5-(4-(difluoromethyl)-6-(((S)-1,1,1-trifluorobutan-2-yl)amino)pyridin-3-yl)-4-((S)-2-methylpyrrolidine-1-carbonyl)thiazole-2-carboxylate (Intermediate 102) for ethyl (S)-5-(6-(tert-butylamino)-4-(difluoromethyl)pyridin-3-yl)-4-(2-methylpyrrolidine-1-carbonyl)thiazole-2-carboxylate. MS (ESI): mass calcd. for $C_{23}H_{26}F_5N_5O_4S_2$, 595.6; m/z found, 596.0 [M+H]$^+$. $^1$H NMR (400 MHz, CDCl$_3$) δ 8.10-8.01 (m, 1H), 7.87-7.77 (m, 1H), 7.06-6.64 (m, 2H), 4.95-4.72 (m, 3H), 4.68-4.59 (m, 2H), 4.32-4.16 (m, 3H), 3.63-3.32 (m, 2H), 2.12-2.05 (m, 1H), 2.03-1.91 (m, 2H), 1.64-1.52 (m, 2H), 1.24-1.21 (m, 2H), 1.09-1.00 (m, 4H).

Example 241

5-[4-(Difluoromethyl)-6-[[(1S)-1-(trifluoromethyl)propyl]amino]-3-pyridyl]-N-[(1R)-2-hydroxy-1,2-dimethyl-propyl]-4-[(2S)-2-methylpiperidine-1-carbonyl]thiazole-2-carboxamide

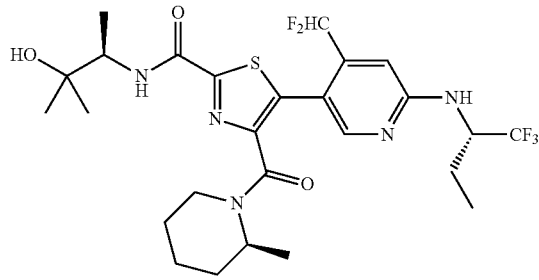 [SMILES: CC[C@H](Nc1cc(C(F)F)c(-c2sc(C(=O)N[C@H](C)C(C)(C)O)nc2C(=O)N2CCCC[C@@H]2C)cn1)C(F)(F)F]

The title compound was prepared as described in Example 148 substituting (R)-3-amino-2-methylbutan-2-ol for (R)-(−)-2-amino-1-propanol and ethyl 5-(4-(difluoromethyl)-6-(((S)-1,1,1-trifluorobutan-2-yl)amino)pyridin-3-yl)-4-((S)-2-methylpiperidine-1-carbonyl)thiazole-2-carboxylate (Intermediate 108: Step B) for ethyl (S)-5-(6-(tert-butylamino)-4-(difluoromethyl)pyridin-3-yl)-4-(2-methylpyrrolidine-1-carbonyl)thiazole-2-carboxylate. MS (ESI): mass calcd. for $C_{26}H_{34}F_5N_5O_3S$, 591.6; m/z found, 592.2 [M+H]$^+$. $^1$H NMR (600 MHz, CDCl$_3$) δ 8.11-8.08 (s, 1H), 7.45-7.38 (m, 1H), 6.94-6.65 (m, 2H), 4.93-4.40 (m, 3H), 4.11-4.05 (m, 1H), 3.94-3.31 (m, 1H), 3.00-2.75 (m, 1H), 2.09-1.94 (m, 2H), 1.67-1.48 (m, 5H), 1.44-1.33 (m, 1H), 1.31-1.27 (m, 9H), 1.19-1.08 (m, 3H), 1.06-1.02 (m, 3H).

Example 242

4-((1s,4s)-7-Azabicyclo[2.2.1]heptane-7-carbonyl)-5-[4-(difluoromethyl)-6-[[(1S)-1-(trifluoromethyl)propyl]amino]-3-pyridyl]-N-[(1R)-2-hydroxy-1,2-dimethyl-propyl]thiazole-2-carboxamide

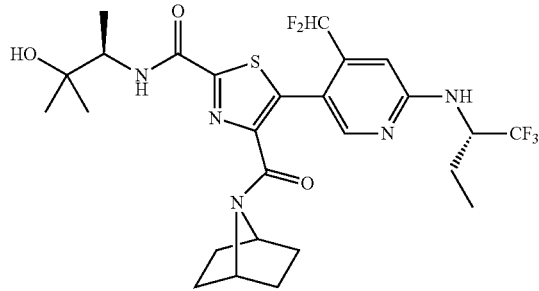 [SMILES: CC[C@H](Nc1cc(C(F)F)c(-c2sc(C(=O)N[C@H](C)C(C)(C)O)nc2C(=O)N2C3CCC2CC3)cn1)C(F)(F)F]

The title compound was prepared as described in Example 148 substituting (R)-3-amino-2-methylbutan-2-ol for (R)-(−)-2-amino-1-propanol and ethyl 4-((1s,4s)-7-azabicyclo[2.2.1]heptane-7-carbonyl)-5-(4-(difluoromethyl)-6-(((S)-1,1,1-trifluorobutan-2-yl)amino)pyridin-3-yl)thiazole-2-carboxylate (Intermediate 99) for ethyl (S)-5-(6-(tert-butylamino)-4-(difluoromethyl)pyridin-3-yl)-4-(2-methylpyrrolidine-1-carbonyl)thiazole-2-carboxylate. MS (ESI): mass calcd. for $C_{26}H_{32}F_5N_5O_3S$, 589.6; m/z found, 590.2 [M+H]$^+$. $^1$H NMR (600 MHz, CDCl$_3$) δ 8.09-8.04 (s, 1H), 7.46-7.41 (d, J=9.2 Hz, 1H), 6.90-6.68 (m, 2H), 4.87-4.25 (m, 4H), 4.11-4.05 (m, 1H), 2.00-1.94 (m, 2H), 1.81-1.71 (m, 2H), 1.64-1.52 (m, 3H), 1.48-1.42 (m, 4H), 1.32-1.30 (s, 3H), 1.30-1.28 (m, 6H), 1.06-1.02 (m, 3H).

Example 243

5-(6-(tert-Butylamino)-4-(trifluoromethyl)pyridin-3-yl)-N—((R*)-2,3-dihydroxy-3-methylbutyl)-4-((S)-2-methylpyrrolidine-1-carbonyl)thiazole-2-carboxamide

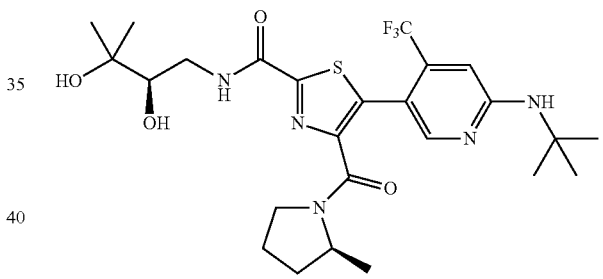

The title compound was prepared as described in Example 148 substituting 1-amino-3-methyl-2,3-butanediol for (R)-(−)-2-amino-1-propanol and ethyl (S)-5-(6-(tert-butylamino)-4-(trifluoromethyl)pyridin-3-yl)-4-(2-methylpyrrolidine-1-carbonyl)thiazole-2-carboxylate (Intermediate 107) for ethyl (S)-5-(6-(tert-butylamino)-4-(difluoromethyl)pyridin-3-yl)-4-(2-methylpyrrolidine-1-carbonyl)thiazole-2-carboxylate. The pure diastereomer was isolated via SFC (Stationary phase: Chiralpak AD-H, 5 μm, 250×30 mm, Mobile phase: 20% iPrOH/EtOH 50/50 v/v+0.5% iPrNH$_2$, 80% CO$_2$, second eluting enantiomer). MS (ESI): mass calcd. for $C_{25}H_{34}F_3N_5O_4S$, 557.6; m/z found, 558.2 [M+H]$^+$. $^1$H NMR (600 MHz, CDCl$_3$) δ 8.19-8.15 (m, 1H), 7.72-7.63 (m, 1H), 6.64-6.60 (m, 1H), 4.89-4.84 (s, 1H), 4.30-4.17 (m, 1H), 3.87-3.81 (m, 1H), 3.64-3.59 (m, 1H), 3.46-3.35 (m, 2H), 1.46-1.44 (m, 9H), 3.13-3.04 (m, 1H), 2.10-1.96 (m, 2H), 1.94-1.72 (m, 2H), 1.55-1.49 (m, 1H), 1.33-1.30 (s, 3H), 1.28-1.26 (s, 3H), 1.23-1.19 (m, 3H), 1.11-1.08 (d, J=6.4 Hz, 1H).

Example 244

5-(6-(tert-Butylamino)-4-(trifluoromethyl)pyridin-3-yl)-N—((S*)-2,3-dihydroxy-3-methylbutyl)-4-((S)-2-methylpyrrolidine-1-carbonyl)thiazole-2-carboxamide

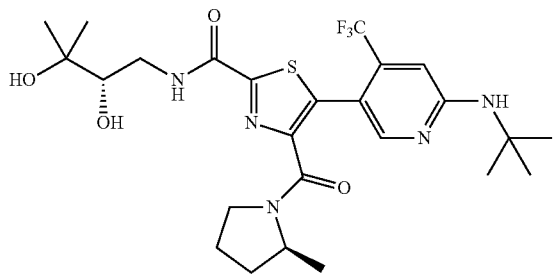 [SMILES: C[C@H]1CCCN1C(=O)c1nc(C(=O)NC[C@H](O)C(C)(C)O)sc1-c1cnc(NC(C)(C)C)cc1C(F)(F)F]

The title compound was prepared as described in Example 243. The pure diastereomer was isolated via SFC (Stationary phase: Chiralpak AD-H, 5 μm, 250×30 mm, Mobile phase: 20% iPrOH/EtOH 50/50 v/v+0.5% iPrNH$_2$, 80% CO$_2$, first eluting enantiomer). MS (ESI): mass calcd. for C$_{25}$H$_{34}$F$_3$N$_5$O$_4$S, 557.6; m/z found, 558.2 [M+H]$^+$. $^1$H NMR (600 MHz, CDCl$_3$) δ 8.18-8.15 (m, 1H), 7.74-7.63 (m, 1H), 6.66-6.59 (m, 1H), 4.92-4.84 (s, 1H), 1.47-1.44 (m, 9H), 4.37-4.17 (m, 1H), 3.88-3.82 (m, 1H), 3.65-3.60 (m, 1H), 3.51-3.46 (m, 1H), 3.42-3.32 (m, 2H), 2.08-2.01 (m, 1H), 1.95-1.87 (m, 1H), 1.77-1.70 (m, 1H), 1.64-1.50 (m, 2H), 1.32-1.29 (s, 3H), 1.27-1.26 (s, 3H), 1.24-1.20 (m, 3H), 1.10-1.06 (d, J=6.4 Hz, 1H).

Example 245

4-[(2S)-4,4-Difluoro-2-methyl-pyrrolidine-1-carbonyl]-5-[4-(difluoromethyl)-6-[[(1S)-1-(trifluoromethyl)propyl]amino]-3-pyridyl]-N-[(1R)-2-hydroxy-1,2-dimethyl-propyl]thiazole-2-carboxamide

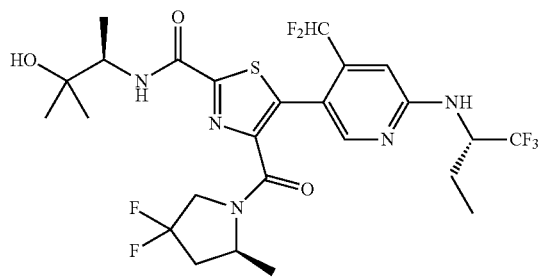 [SMILES: CC[C@H](Nc1cc(C(F)F)c(-c2sc(C(=O)N[C@H](C)C(C)(C)O)nc2C(=O)N2CC(F)(F)C[C@@H]2C)cn1)C(F)(F)F]

The title compound was prepared as described in Example 148 substituting (R)-3-amino-2-methylbutan-2-ol for (R)-(−)-2-amino-1-propanol and ethyl 4-((S)-4,4-difluoro-2-methylpyrrolidine-1-carbonyl)-5-(4-(difluoromethyl)-6-(((S)-1,1,1-trifluorobutan-2-yl)amino)pyridin-3-yl)thiazole-2-carboxylate (Intermediate 109: Step B) for ethyl (S)-5-(6-(tert-butylamino)-4-(difluoromethyl)pyridin-3-yl)-4-(2-methylpyrrolidine-1-carbonyl)thiazole-2-carboxylate. MS (ESI): mass calcd. for C$_{25}$H$_{30}$F$_7$N$_5$O$_3$S, 613.6; m/z found, 614.2 [M+H]$^+$. $^1$H NMR (400 MHz, CDCl$_3$) δ 8.07-8.00 (m, 1H), 7.42-7.34 (m, 1H), 6.94-6.56 (m, 2H), 4.88-4.46 (m, 3H), 4.11-3.77 (m, 3H), 2.66-2.47 (m, 1H), 2.21-2.05 (m, 1H), 2.02-1.94 (m, 1H), 1.93-1.84 (m, 1H), 1.65-1.56 (m, 1H), 1.38-1.34 (d, J=6.4 Hz, 2H), 1.33-1.29 (m, 9H), 1.27-1.25 (m, 1H), 1.08-1.02 (t, J=7.4 Hz, 3H).

Example 246

4-[(2S)-4,4-Difluoro-2-methyl-pyrrolidine-1-carbonyl]-5-[4-(difluoromethyl)-6-[[(1S)-1-(trifluoromethyl)propyl]amino]-3-pyridyl]-N-[(1S)-2-hydroxy-1,2-dimethyl-propyl]thiazole-2-carboxamide

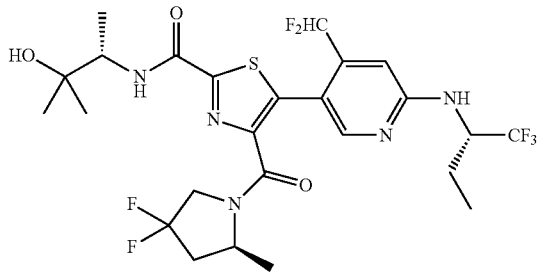 [SMILES: CC[C@H](Nc1cc(C(F)F)c(-c2sc(C(=O)N[C@@H](C)C(C)(C)O)nc2C(=O)N2CC(F)(F)C[C@@H]2C)cn1)C(F)(F)F]

The title compound was prepared as described in Example 148 substituting (S)-3-amino-2-methylbutan-2-ol for (R)-(−)-2-amino-1-propanol and ethyl 4-((S)-4,4-difluoro-2-methylpyrrolidine-1-carbonyl)-5-(4-(difluoromethyl)-6-(((S)-1,1,1-trifluorobutan-2-yl)amino)pyridin-3-yl)thiazole-2-carboxylate (Intermediate 109: Step B) for ethyl (S)-5-(6-(tert-butylamino)-4-(difluoromethyl)pyridin-3-yl)-4-(2-methylpyrrolidine-1-carbonyl)thiazole-2-carboxylate. MS (ESI): mass calcd. for C$_{25}$H$_{30}$F$_7$N$_5$O$_3$S, 613.6; m/z found, 614.2 [M+H]$^+$. $^1$H NMR (400 MHz, CDCl$_3$) δ 8.07-8.01 (m, 1H), 7.39-7.33 (d, J=9.2 Hz, 1H), 6.94-6.56 (m, 2H), 4.84-4.47 (m, 3H), 4.11-3.79 (m, 3H), 2.64-2.48 (m, 1H), 2.21-2.05 (m, 1H), 2.03-1.93 (m, 1H), 1.90-1.79 (m, 1H), 1.38-1.34 (d, J=6.4 Hz, 2H), 1.33-1.30 (m, 9H), 1.30-1.26 (m, 2H), 1.08-1.02 (t, J=7.4 Hz, 3H).

Example 247

5-[4-(Difluoromethyl)-6-[[(1S)-1-(trifluoromethyl)propyl]amino]-3-pyridyl]-N-[(1S)-2-hydroxy-1,2-dimethyl-propyl]-4-[(2S)-2-methylpiperidine-1-carbonyl]thiazole-2-carboxamide

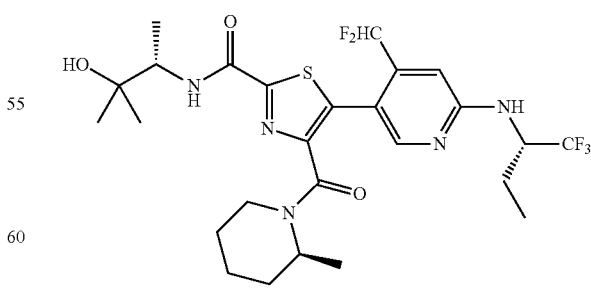

The title compound was prepared as described in Example 148 substituting (S)-3-amino-2-methylbutan-2-ol for (R)-(−)-2-amino-1-propanol and ethyl 5-(4-(difluoromethyl)-6-(((S)-1,1,1-trifluorobutan-2-yl)amino)pyridin-3-yl)-4-((S)-

2-methylpiperidine-1-carbonyl)thiazole-2-carboxylate (Intermediate 108: Step B) for ethyl (S)-5-(6-(tert-butylamino)-4-(difluoromethyl)pyridin-3-yl)-4-(2-methylpyrrolidine-1-carbonyl)thiazole-2-carboxylate. MS (ESI): mass calcd. for $C_{26}H_{34}F_5N_5O_3S$, 591.6; m/z found, 592.2 [M+H]$^+$. $^1$H NMR (400 MHz, CDCl$_3$) δ 8.12-8.07 (s, 1H), 7.47-7.40 (d, J=9.3 Hz, 1H), 6.98-6.60 (m, 2H), 4.94-4.40 (m, 3H), 4.12-4.05 (m, 1H), 3.94-3.31 (m, 1H), 2.99-2.74 (m, 1H), 2.12-2.05 (m, 1H), 2.02-1.93 (m, 1H), 1.68-1.39 (m, 6H), 1.31-1.27 (m, 9H), 1.21-1.18 (d, J=6.8 Hz, 1H), 1.12-1.01 (m, 5H).

Example 248

4-(1s,4s)-7-Azabicyclo[2.2.1]heptane-7-carbonyl)-5-[4-(difluoromethyl)-6-[[(1S)-1-(trifluoromethyl)propyl]amino]-3-pyridyl]-N-[(1S)-2-hydroxy-1,2-dimethyl-propyl]thiazole-2-carboxamide

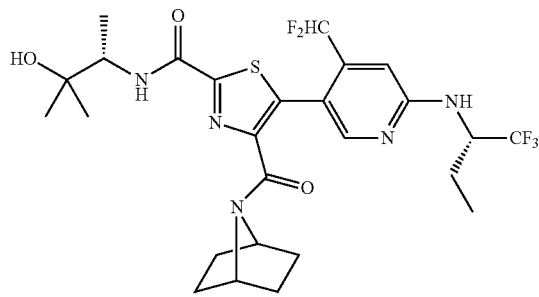 [SMILES: CC[C@H](Nc1cc(C(F)F)c(-c2sc(C(=O)N[C@@H](C)C(C)(C)O)nc2C(=O)N2C3CCC2CC3)cn1)C(F)(F)F]

The title compound was prepared as described in Example 148 substituting (S)-3-amino-2-methylbutan-2-ol for (R)-(−)-2-amino-1-propanol and ethyl 4-((1s,4s)-7-azabicyclo[2.2.1]heptane-7-carbonyl)-5-(4-(difluoromethyl)-6-(((S)-1,1,1-trifluorobutan-2-yl)amino)pyridin-3-yl)thiazole-2-carboxylate (Intermediate 99) for ethyl (S)-5-(6-(tert-butylamino)-4-(difluoromethyl)pyridin-3-yl)-4-(2-methylpyrrolidine-1-carbonyl)thiazole-2-carboxylate. MS (ESI): mass calcd. for $C_{26}H_{32}F_5N_5O_3S$, 589.6; m/z found, 590.2 [M+H]$^+$. $^1$H NMR (400 MHz, CDCl$_3$) δ 8.09-8.05 (s, 1H), 7.48-7.42 (d, J=9.2 Hz, 1H), 6.95-6.64 (m, 2H), 4.92-4.66 (m, 3H), 4.31-4.24 (m, 1H), 4.12-4.05 (m, 1H), 2.03-1.92 (m, 2H), 1.83-1.73 (m, 2H), 1.67-1.51 (m, 3H), 1.49-1.42 (m, 4H), 1.32-1.28 (m, 9H), 1.07-1.01 (m, 3H).

Example 249

[5-[6-(tert-Butylamino)-4-(trifluoromethyl)-3-pyridyl]-2-[3-(hydroxymethyl)azetidine-1-carbonyl]thiazol-4-yl]-[(2S)-2-methylpyrrolidin-1-yl]methanone

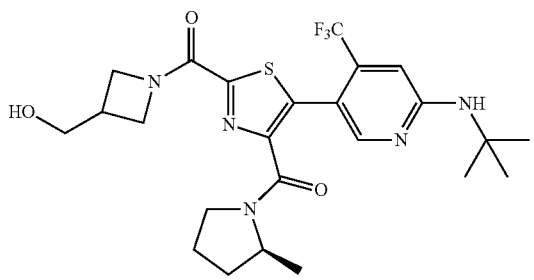 [SMILES: C[C@H]1CCCN1C(=O)c1nc(C(=O)N2CC(CO)C2)sc1-c1cnc(NC(C)(C)C)cc1C(F)(F)F]

The title compound was prepared as described in Example 148 substituting azetidin-3-ylmethanol for (R)-(−)-2-amino-1-propanol and ethyl (S)-5-(6-(tert-butylamino)-4-(trifluoromethyl)pyridin-3-yl)-4-(2-methylpyrrolidine-1-carbonyl)thiazole-2-carboxylate (Intermediate 107) for ethyl (S)-5-(6-(tert-butylamino)-4-(difluoromethyl)pyridin-3-yl)-4-(2-methylpyrrolidine-1-carbonyl)thiazole-2-carboxylate. MS (ESI): mass calcd. for $C_{24}H_{30}F_3N_5O_3S$, 525.6; m/z found, 526.1 [M+H]$^+$. $^1$H NMR (400 MHz, CDCl$_3$) δ 8.18-8.12 (m, 1H), 6.64-6.59 (m, 1H), 4.94-4.86 (s, 1H), 4.83-4.70 (m, 1H), 4.54-4.45 (m, 1H), 4.34-4.14 (m, 2H), 4.06-3.97 (m, 1H), 3.89-3.83 (m, 2H), 3.61-3.44 (m, 2H), 2.99-2.89 (m, 1H), 2.11-2.02 (m, 2H), 1.95-1.73 (m, 2H), 1.59-1.50 (m, 1H), 1.47-1.43 (s, 9H), 1.24-1.21 (m, 2H), 1.09-0.89 (m, 1H).

Example 250

[5-[6-(tert-Butylamino)-4-(trifluoromethyl)-3-pyridyl]-2-(3-hydroxyazetidine-1-carbonyl)thiazol-4-yl]-[(2S)-2-methylpyrrolidin-1-yl]methanone

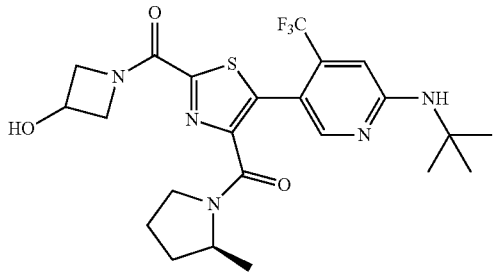 [SMILES: C[C@H]1CCCN1C(=O)c1nc(C(=O)N2CC(O)C2)sc1-c1cnc(NC(C)(C)C)cc1C(F)(F)F]

The title compound was prepared as described in Example 149 substituting 3-hydroxyazetidine HCl for 3-hydroxy-3-methylazetidine HCl and ethyl (S)-5-(6-(tert-butylamino)-4-(trifluoromethyl)pyridin-3-yl)-4-(2-methylpyrrolidine-1-carbonyl)thiazole-2-carboxylate (Intermediate 107) for ethyl (S)-5-(6-(tert-butylamino)-4-(difluoromethyl)pyridin-3-yl)-4-(2-methylpyrrolidine-1-carbonyl)thiazole-2-carboxylate. MS (ESI): mass calcd. for $C_{23}H_{28}F_3N_5O_3S$, 511.6; m/z found, 512.1 [M+H]$^+$. $^1$H NMR (400 MHz, CDCl$_3$) δ 8.17-8.11 (m, 1H), 6.65-6.59 (m, 1H), 4.99-4.85 (m, 2H), 4.79-4.69 (m, 1H), 4.55-4.43 (m, 2H), 4.23-4.14 (m, 1H), 4.11-4.05 (m, 1H), 3.61-3.43 (m, 2H), 3.34-3.24 (m, 1H), 2.10-2.02 (m, 1H), 1.97-1.74 (m, 2H), 1.61-1.48 (m, 1H), 1.48-1.41 (s, 9H), 1.24-1.20 (dd, J=6.3, 3.5 Hz, 2H), 1.08-0.90 (dd, J=8.5, 6.5 Hz, 1H).

Example 251

5-[6-(tert-Butylamino)-4-(trifluoromethyl)-3-pyridyl]-N-((1s,3R)-3-hydroxycyclobutyl)-4-[(2S)-2-methylpyrrolidine-1-carbonyl]thiazole-2-carboxamide

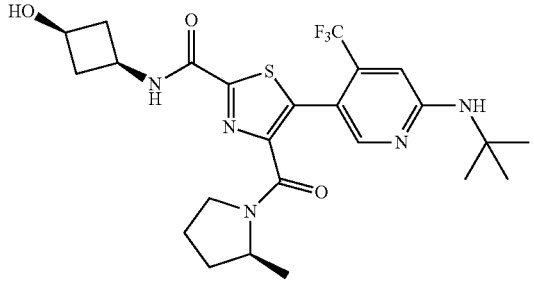 [SMILES: C[C@H]1CCCN1C(=O)c1nc(C(=O)N[C@H]2C[C@@H](O)C2)sc1-c1cnc(NC(C)(C)C)cc1C(F)(F)F]

The title compound was prepared as described in Example 149 substituting cis-3-amino-cyclobutanol HCl for 3-hydroxy-3-methylazetidine HCl and ethyl (S)-5-(6-(tert-butylamino)-4-(trifluoromethyl)pyridin-3-yl)-4-(2-methylpyrrolidine-1-carbonyl)thiazole-2-carboxylate (Intermediate 107) for ethyl (S)-5-(6-(tert-butylamino)-4-(difluoromethyl)pyridin-3-yl)-4-(2-methylpyrrolidine-1-carbonyl)thiazole-2-carboxylate. MS (ESI): mass calcd. for $C_{24}H_{30}F_3N_5O_3S$, 525.6; m/z found, 526.1 [M+H]$^+$. $^1$H NMR (400 MHz, CDCl$_3$) δ 8.20-8.13 (m, 1H), 7.42-7.28 (m, 1H), 6.66-6.61 (m, 1H), 4.98-4.91 (m, 1H), 4.24-4.09 (m, 3H), 3.63-3.32 (m, 2H), 2.95-2.84 (m, 2H), 1.47-1.41 (m, 9H), 2.52-2.45 (m, 1H), 2.09-2.05 (m, 1H), 2.04-2.00 (m, 1H), 1.94-1.70 (m, 3H), 1.57-1.48 (m, 1H), 1.25-1.22 (d, J=6.3 Hz, 2H), 1.10-1.03 (d, J=6.4 Hz, 1H).

Example 252

5-(4-(Difluoromethyl)-6-(((S)-1,1,1-trifluorobutan-2-yl)amino)pyridin-3-yl)-N-(cis-2-hydroxycyclopentyl)-4-((S)-2-methylpyrrolidine-1-carbonyl)thiazole-2-carboxamide

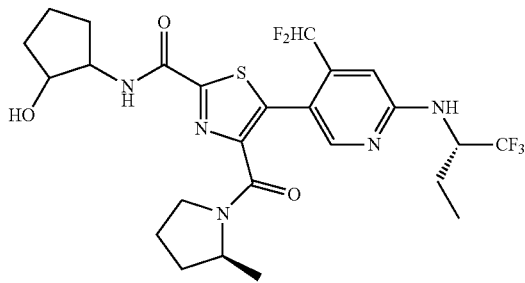 [SMILES: CC[C@H](Nc1cc(C(F)F)c(-c2sc(C(=O)NC3CCCC3O)nc2C(=O)N2CCC[C@@H]2C)cn1)C(F)(F)F]

The title compound was prepared as described in Example 149 substituting cis-2-amino-cyclopentanol HCl for 3-hydroxy-3-methylazetidine HCl and ethyl 5-(4-(difluoromethyl)-6-(((S)-1,1,1-trifluorobutan-2-yl)amino)pyridin-3-yl)-4-((S)-2-methylpyrrolidine-1-carbonyl)thiazole-2-carboxylate (Intermediate 102) for ethyl (S)-5-(6-(tert-butylamino)-4-(difluoromethyl)pyridin-3-yl)-4-(2-methylpyrrolidine-1-carbonyl)thiazole-2-carboxylate. MS (ESI): mass calcd. for $C_{25}H_{30}F_5N_5O_3S$, 575.6; m/z found, 576.1 [M+H]$^+$. $^1$H NMR (400 MHz, CDCl$_3$) δ 8.09-8.00 (m, 1H), 7.63-7.56 (m, 1H), 7.04-6.63 (m, 2H), 4.88-4.70 (m, 2H), 4.39-4.17 (m, 3H), 3.61-3.35 (m, 2H), 2.19-2.06 (m, 2H), 2.01-1.89 (m, 4H), 1.80-1.49 (m, 7H), 1.23-1.19 (m, 2H), 1.09-1.02 (m, 4H).

Example 253

5-[6-(tert-Butylamino)-4-(trifluoromethyl)-3-pyridyl]-N-(3-methyloxetan-3-yl)-4-[(2S)-2-methylpyrrolidine-1-carbonyl]thiazole-2-carboxamide

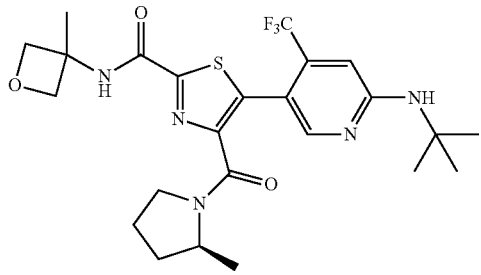 [SMILES: C[C@H]1CCCN1C(=O)c1nc(C(=O)NC2(C)COC2)sc1-c1cnc(NC(C)(C)C)cc1C(F)(F)F]

To a microwave vial under N$_2$ was added ethyl (S)-5-(6-(tert-butylamino)-4-(trifluoromethyl)pyridin-3-yl)-4-(2-methylpyrrolidine-1-carbonyl)thiazole-2-carboxylate (100 mg, 0.21 mmol, Intermediate 107), 3-methyl-3-oxetanamine (47.4 µL, 1.03 mmol) and EtOH (0.98 mL), and the reaction was stirred at 100° C. for 21 h. An additional aliquot of 3-methyl-3-oxetanamine (95 µL, 2.06 mmol) was added and the mixture stirred at 100° C. for 6 h. An additional aliquot of 3-methyl-3-oxetanamine (95 µL, 2.06 mmol) was added and the mixture stirred at 100° C. for 17 h. The reaction mixture was cooled to rt and partitioned between EtOAc (20 mL) and saturated aqueous NH$_4$Cl (20 mL). The layers were separated and the aqueous further extracted with EtOAc (2×15 mL). The organic layers were combined, dried over anhydrous sodium sulfate, filtered and concentrated to dryness. The crude residue was dissolved in DCM and purified by FCC (0-100% EtOAc/Hexanes) to provide the title compound. MS (ESI): mass calcd. for $C_{24}H_{30}F_3N_5O_3S$, 525.6; m/z found, 526.2 [M+H]$^+$. $^1$H NMR (400 MHz, CDCl$_3$) δ 8.19-8.11 (s, 1H), 7.55-7.43 (m, 1H), 6.65-6.59 (m, 1H), 5.06-4.97 (m, 1H), 4.95-4.88 (m, 2H), 4.58-4.51 (d, J=6.6 Hz, 2H), 4.24-4.13 (m, 1H), 3.60-3.31 (m, 2H), 2.08-1.99 (m, 1H), 1.93-1.82 (m, 2H), 1.77-1.70 (m, 3H), 1.56-1.45 (m, 1H), 1.45-1.41 (s, 9H), 1.22-1.19 (d, J=6.3 Hz, 2H), 1.07-1.02 (d, J=6.4 Hz, 1H).

Example 254

5-[6-(tert-Butylamino)-4-(trifluoromethyl)-3-pyridyl]-N-(1,1-dioxothian-4-yl)-4-[(2S)-2-methylpyrrolidine-1-carbonyl]thiazole-2-carboxamide

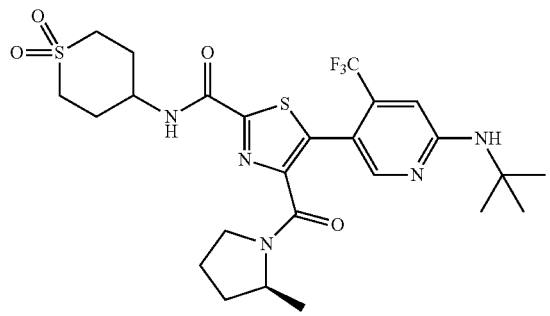 [SMILES: C[C@H]1CCCN1C(=O)c1nc(C(=O)NC2CCS(=O)(=O)CC2)sc1-c1cnc(NC(C)(C)C)cc1C(F)(F)F]

The title compound was prepared as described in Example 148 substituting 4-aminotetrahydro-2H-thiopyran 1,1-dioxide for (R)-(−)-2-amino-1-propanol and ethyl (S)-5-(6-(tert-butylamino)-4-(trifluoromethyl)pyridin-3-yl)-4-(2-methylpyrrolidine-1-carbonyl)thiazole-2-carboxylate (Intermediate 107) for ethyl (S)-5-(6-(tert-butylamino)-4-(difluoromethyl)pyridin-3-yl)-4-(2-methylpyrrolidine-1-carbonyl)thiazole-2-carboxylate. MS (ESI): mass calcd. for $C_{25}H_{32}F_3N_5O_4S_2$, 587.7; m/z found, 588.2 [M+H]$^+$. $^1$H NMR (400 MHz, CDCl$_3$) δ 8.15-8.06 (s, 1H), 7.41-7.33 (m, 1H), 6.66-6.58 (s, 1H), 5.12-5.05 (s, 1H), 4.29-4.11 (m, 2H), 3.60-3.27 (m, 2H), 3.18-3.08 (m, 4H), 2.44-2.34 (m, 2H), 2.32-2.19 (m, 2H), 2.11-2.02 (m, 1H), 1.91-1.65 (m, 2H), 1.54-1.45 (m, 1H), 1.44-1.38 (s, 9H), 1.21-1.18 (d, J=6.3 Hz, 2H), 1.06-1.00 (d, J=6.4 Hz, 1H).

Example 255

4-((1s,4s)-7-Azabicyclo[2.2.1]heptane-7-carbonyl)-N-((3S*,4S*)-4-hydroxytetrahydrofuran-3-yl)-5-(4-(trifluoromethyl)-6-(((S)-1,1,1-trifluoropropan-2-yl)amino)pyridin-3-yl)thiazole-2-carboxamide

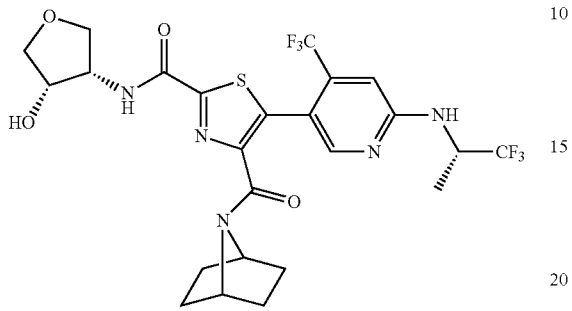

The title compound was prepared as described in Example 228. The pure diastereomer was isolated via SFC (Stationary phase: Chiralpak AD-H, 5 μm, 250×30 mm, Mobile phase: 25% iPrOH+0.3% iPrNH$_2$, 75% CO$_2$, first eluting enantiomer). MS (ESI): mass calcd. for C$_{24}$H$_{25}$F$_6$N$_5$O$_4$S, 593.5; m/z found, 594.2 [M+H]$^+$. $^1$H NMR (400 MHz, CDCl$_3$) δ 8.23-8.19 (s, 1H), 7.82-7.77 (d, J=7.8 Hz, 1H), 6.76-6.72 (s, 1H), 4.99-4.89 (m, 2H), 4.69-4.45 (m, 4H), 4.23-4.17 (m, 1H), 4.11-4.05 (dd, J=10.3, 4.4 Hz, 1H), 3.91-3.86 (m, 1H), 3.77-3.71 (m, 1H), 2.25-2.16 (m, 1H), 1.82-1.65 (m, 4H), 1.49-1.40 (m, 7H).

Example 256

5-[6-(tert-Butylamino)-4-(difluoromethyl)-3-pyridyl]-4-[(2S)-4,4-difluoro-2-methyl-pyrrolidine-1-carbonyl]-N-[(1R)-2-hydroxy-1,2-dimethyl-propyl]thiazole-2-carboxamide

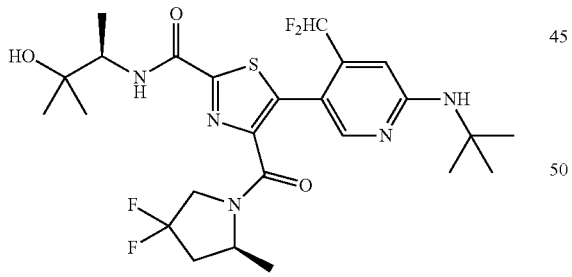

The title compound was prepared as described in Example 148 substituting (R)-3-amino-2-methylbutan-2-ol for (R)-(−)-2-amino-1-propanol and ethyl (S)-5-(6-(tert-butylamino)-4-(difluoromethyl)pyridin-3-yl)-4-(4,4-difluoro-2-methylpyrrolidine-1-carbonyl)thiazole-2-carboxylate (Intermediate 110) for ethyl (S)-5-(6-(tert-butylamino)-4-(difluoromethyl)pyridin-3-yl)-4-(2-methylpyrrolidine-1-carbonyl)thiazole-2-carboxylate. MS (ESI): mass calcd. for C$_{25}$H$_{33}$F$_4$N$_5$O$_3$S, 559.6; m/z found, 560.2 [M+H]$^+$. $^1$H NMR (400 MHz, CDCl$_3$) δ 8.03-7.97 (m, 1H), 7.41-7.34 (m, 1H), 6.90-6.53 (m, 2H), 4.90-4.84 (s, 1H), 4.71-4.47 (m, 1H), 4.11-3.81 (m, 3H), 1.48-1.44 (m, 9H), 2.65-2.46 (m, 1H), 2.11-2.05 (m, 1H), 1.99-1.89 (m, 1H), 1.70-1.60 (m, 1H), 1.38-1.34 (d, J=6.4 Hz, 2H), 1.33-1.29 (m, 9H).

Example 257

5-[6-(tert-Butylamino)-4-(difluoromethyl)-3-pyridyl]-4-[(2S)-4,4-difluoro-2-methyl-pyrrolidine-1-carbonyl]-N-[(1S)-2-hydroxy-1,2-dimethyl-propyl]thiazole-2-carboxamide

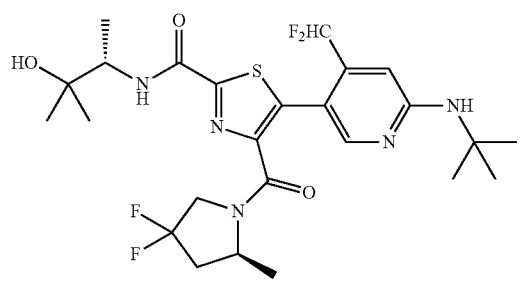 [SMILES: C[C@H](NC(=O)c1nc(C(=O)N2CC(F)(F)C[C@@H]2C)c(-c2cnc(NC(C)(C)C)cc2C(F)F)s1)C(C)(C)O]

The title compound was prepared as described in Example 148 substituting (S)-3-amino-2-methylbutan-2-ol for (R)-(−)-2-amino-1-propanol and ethyl (S)-5-(6-(tert-butylamino)-4-(difluoromethyl)pyridin-3-yl)-4-(4,4-difluoro-2-methylpyrrolidine-1-carbonyl)thiazole-2-carboxylate (Intermediate 110) for ethyl (S)-5-(6-(tert-butylamino)-4-(difluoromethyl)pyridin-3-yl)-4-(2-methylpyrrolidine-1-carbonyl)thiazole-2-carboxylate. MS (ESI): mass calcd. for C$_{25}$H$_{33}$F$_4$N$_5$O$_3$S, 559.6; m/z found, 560.2 [M+H]$^+$. $^1$H NMR (400 MHz, CDCl$_3$) δ 8.03-7.98 (m, 1H), 7.40-7.32 (d, J=9.2 Hz, 1H), 6.90-6.53 (m, 2H), 4.90-4.84 (s, 1H), 4.62-4.46 (m, 1H), 4.11-3.77 (m, 3H), 1.70-1.60 (m, 1H), 2.62-2.47 (m, 1H), 2.19-2.05 (m, 1H), 1.98-1.86 (m, 1H), 1.48-1.43 (s, 9H), 1.38-1.34 (d, J=6.5 Hz, 2H), 1.32-1.28 (m, 9H).

Example 258

5-[6-(tert-Butylamino)-4-(trifluoromethyl)-3-pyridyl]-N-((1r,3S)-3-hydroxycyclobutyl)-4-[(2S)-2-methylpyrrolidine-1-carbonyl]thiazole-2-carboxamide

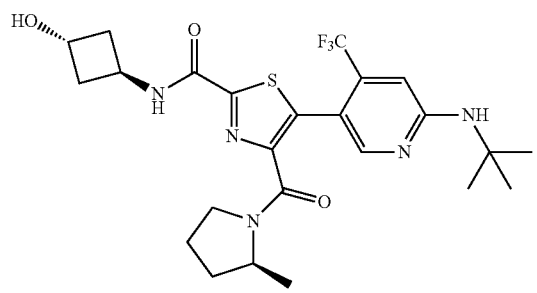 [SMILES: C[C@H]1CCCN1C(=O)c1nc(C(=O)N[C@H]2C[C@H](O)C2)sc1-c1cnc(NC(C)(C)C)cc1C(F)(F)F]

The title compound was prepared as described in Example 149 substituting trans-3-aminocyclobutanol HCl for 3-hydroxy-3-methylazetidine HCl and ethyl (S)-5-(6-(tert-butylamino)-4-(trifluoromethyl)pyridin-3-yl)-4-(2-methylpyrrolidine-1-carbonyl)thiazole-2-carboxylate (Intermediate 107) for ethyl (S)-5-(6-(tert-butylamino)-4-(difluoromethyl)pyridin-3-yl)-4-(2-methylpyrrolidine-1-carbonyl)thiazole-2-carboxylate. MS (ESI): mass calcd. for $C_{24}H_{30}F_3N_5O_3S$, 525.6; m/z found, 526.1 [M+H]+. 1H NMR (400 MHz, CDCl3) δ 8.20-8.14 (s, 1H), 7.38-7.28 (m, 1H), 6.65-6.60 (m, 1H), 4.96-4.91 (m, 1H), 4.71-4.55 (m, 2H), 4.24-4.10 (m, 1H), 3.64-3.33 (m, 2H), 2.51-2.39 (m, 4H), 2.18-2.13 (m, 1H), 2.10-1.70 (m, 3H), 1.57-1.49 (m, 1H), 1.47-1.42 (s, 9H), 1.25-1.22 (d, J=6.3 Hz, 2H), 1.09-1.03 (d, J=6.4 Hz, 1H).

Example 259

5-[6-(tert-Butylamino)-4-(trifluoromethyl)-3-pyridyl]-4-[(2S)-2-methylpyrrolidine-1-carbonyl]-N-(oxetan-3-yl)thiazole-2-carboxamide

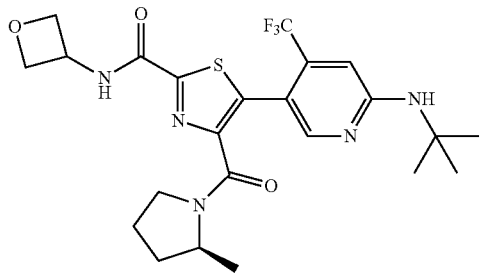 [SMILES: C[C@H]1CCCN1C(=O)c1nc(C(=O)NC2COC2)sc1-c1cnc(NC(C)(C)C)cc1C(F)(F)F]

The title compound was prepared as described in Example 148 substituting 3-oxetanamine for (R)-(−)-2-amino-1-propanol and ethyl (S)-5-(6-(tert-butylamino)-4-(trifluoromethyl)pyridin-3-yl)-4-(2-methylpyrrolidine-1-carbonyl)thiazole-2-carboxylate (Intermediate 107) for ethyl (S)-5-(6-(tert-butylamino)-4-(difluoromethyl)pyridin-3-yl)-4-(2-methylpyrrolidine-1-carbonyl)thiazole-2-carboxylate. MS (ESI): mass calcd. for $C_{23}H_{28}F_3N_5O_3S$, 511.6; m/z found, 512.1 [M+H]+. 1H NMR (400 MHz, CDCl3) δ 8.20-8.15 (s, 1H), 7.76-7.62 (m, 1H), 6.66-6.59 (m, 1H), 5.30-5.20 (m, 1H), 5.04-4.97 (m, 2H), 4.94-4.87 (s, 1H), 4.71-4.64 (m, 2H), 4.26-4.16 (m, 1H), 3.65-3.32 (m, 2H), 2.12-2.04 (m, 1H), 1.96-1.72 (m, 2H), 1.58-1.48 (m, 1H), 1.47-1.43 (s, 9H), 1.26-1.24 (d, J=6.4 Hz, 2H), 1.10-1.04 (d, J=6.4 Hz, 1H).

Example 260

5-[6-(tert-Butylamino)-4-(trifluoromethyl)-3-pyridyl]-N-(1,1-dioxothietan-3-yl)-4-[(2S)-2-methylpyrrolidine-1-carbonyl]thiazole-2-carboxamide

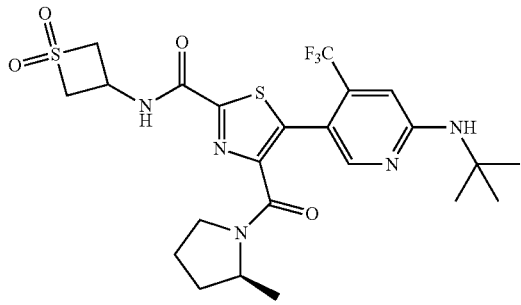 [SMILES: C[C@H]1CCCN1C(=O)c1nc(C(=O)NC2CS(=O)(=O)C2)sc1-c1cnc(NC(C)(C)C)cc1C(F)(F)F]

To a microwave vial under N2 was added ethyl (S)-5-(6-(tert-butylamino)-4-(trifluoromethyl)pyridin-3-yl)-4-(2-methylpyrrolidine-1-carbonyl)thiazole-2-carboxylate (100 mg, 0.21 mmol, Intermediate 107), 3-aminothietane 1,1-dioxide HCl (171 mg, 1.03 mmol), DIPEA (196 µL, 1.14 mmol) and EtOH (0.98 mL), and the reaction was stirred at 100° C. for 18 h. An additional aliquot of DIPEA (500 µL, 2.91 mmol) was added and the mixture stirred at 100° C. for 6 h. An additional aliquot of 3-aminothietane 1,1-dioxide HCl (171 mg, 1.03 mmol) was added and the mixture stirred at 100° C. for 17 h. The reaction mixture was cooled to rt and partitioned between EtOAc (20 mL) and saturated aqueous NH4Cl (20 mL). The layers were separated and the aqueous further extracted with EtOAc (2×15 mL). The organic layers were combined, dried over anhydrous sodium sulfate, filtered and concentrated to dryness. The crude residue was dissolved in DCM and purified by FCC (0-100% EtOAc/Hexanes) to provide the title compound. MS (ESI): mass calcd. for $C_{23}H_{28}F_3N_5O_4S_2$, 559.6; m/z found, 560.1 [M+H]+. 1H NMR (400 MHz, CDCl3) δ 8.19-8.12 (s, 1H), 7.99-7.91 (m, 1H), 6.67-6.60 (m, 1H), 4.95-4.91 (s, 1H), 4.91-4.83 (m, 1H), 4.65-4.54 (m, 2H), 4.25-4.15 (m, 3H), 3.66-3.31 (m, 2H), 2.11-2.03 (m, 1H), 1.96-1.71 (m, 2H), 1.59-1.50 (m, 1H), 1.49-1.43 (s, 9H), 1.26-1.24 (m, 2H), 1.11-1.05 (d, J=6.4 Hz, 1H).

Example 261

5-[6-(tert-Butylamino)-4-(trifluoromethyl)-3-pyridyl]-N-[3-(hydroxymethyl)oxetan-3-yl]-4-[(2S)-2-methylpyrrolidine-1-carbonyl]thiazole-2-carboxamide

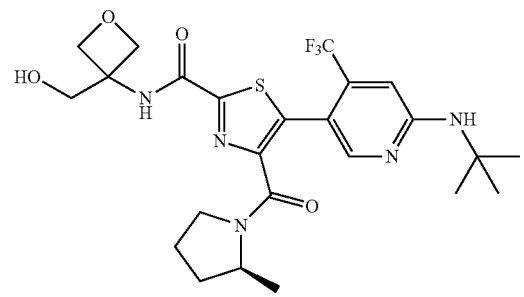 [SMILES: C[C@H]1CCCN1C(=O)c1nc(C(=O)NC2(CO)COC2)sc1-c1cnc(NC(C)(C)C)cc1C(F)(F)F]

The title compound was prepared as described in Example 148 substituting (3-aminooxetan-3-yl)methanol for (R)-(−)-2-amino-1-propanol and ethyl (S)-5-(6-(tert-butylamino)-4-(trifluoromethyl)pyridin-3-yl)-4-(2-methylpyrrolidine-1-carbonyl)thiazole-2-carboxylate (Intermediate 107) for ethyl (S)-5-(6-(tert-butylamino)-4-(difluoromethyl)pyridin-3-yl)-4-(2-methylpyrrolidine-1-carbonyl)thiazole-2-carboxylate. MS (ESI): mass calcd. for $C_{24}H_{30}F_3N_5O_4S$, 541.6; m/z found, 542.1 [M+H]+. 1H NMR (400 MHz, CDCl3) δ 8.17-8.14 (s, 1H), 7.84-7.74 (m, 1H), 6.65-6.61 (m, 1H), 4.98-4.93 (s, 1H), 4.91-4.85 (m, 2H), 4.69-4.65 (m, 2H), 4.22-4.14 (m, 3H), 1.77-1.73 (m, 1H), 3.57-3.20 (m, 3H), 2.10-2.04 (m, 1H), 1.91-1.85 (m, 1H), 1.56-1.47 (m, 1H), 1.47-1.44 (s, 9H), 1.24-1.21 (d, J=6.3 Hz, 2H), 1.09-1.05 (d, J=6.4 Hz, 1H).

Example 262

5-[6-(tert-Butylamino)-4-(trifluoromethyl)-3-pyridyl]-N-[1-(hydroxymethyl)cyclobutyl]-4-[(2S)-2-methylpyrrolidine-1-carbonyl]thiazole-2-carboxamide

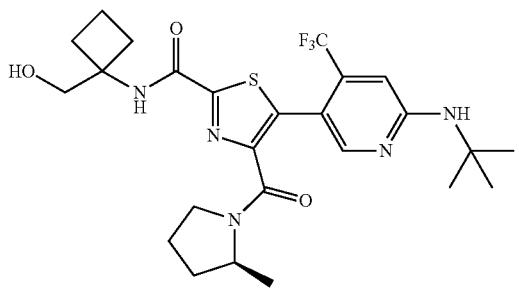 [SMILES: C[C@H]1CCCN1C(=O)c1nc(C(=O)NC2(CO)CCC2)sc1-c1cnc(NC(C)(C)C)cc1C(F)(F)F]

The title compound was prepared as described in Example 148 substituting (1-aminocyclobutyl)methanol for (R)-(−)-2-amino-1-propanol and ethyl (S)-5-(6-(tert-butylamino)-4-(trifluoromethyl)pyridin-3-yl)-4-(2-methylpyrrolidine-1-carbonyl)thiazole-2-carboxylate (Intermediate 107) for ethyl (S)-5-(6-(tert-butylamino)-4-(difluoromethyl)pyridin-3-yl)-4-(2-methylpyrrolidine-1-carbonyl)thiazole-2-carboxylate. MS (ESI): mass calcd. for $C_{25}H_{32}F_3N_5O_3S$, 539.6; m/z found, 540.2 [M+H]$^+$. $^1$H NMR (500 MHz, CDCl$_3$) δ 8.20-8.14 (s, 1H), 7.56-7.47 (m, 1H), 6.65-6.59 (m, 1H), 4.97-4.90 (s, 1H), 4.24-4.16 (m, 1H), 3.94-3.89 (d, J=5.8 Hz, 2H), 3.62-3.34 (m, 3H), 2.37-2.30 (m, 4H), 2.03-1.98 (m, 1H), 1.94-1.86 (m, 2H), 1.78-1.71 (m, 1H), 1.57-1.49 (m, 1H), 1.47-1.44 (s, 9H), 1.24-1.22 (d, J=6.3 Hz, 2H), 1.12-1.07 (d, J=6.4 Hz, 1H).

Example 263

5-[6-(tert-Butylamino)-4-(trifluoromethyl)-3-pyridyl]-N-[1-(hydroxymethyl)cyclopropyl]-4-[(2S)-2-methylpyrrolidine-1-carbonyl]thiazole-2-carboxamide

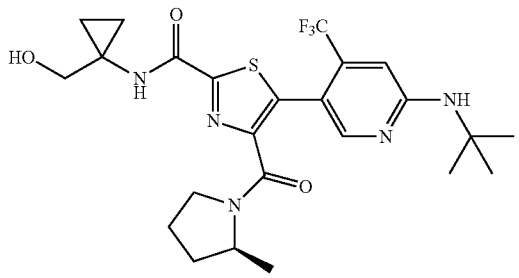 [SMILES: C[C@H]1CCCN1C(=O)c1nc(C(=O)NC2(CO)CC2)sc1-c1cnc(NC(C)(C)C)cc1C(F)(F)F]

The title compound was prepared as described in Example 148 substituting 1-amino-cyclopropanemethanol for (R)-(−)-2-amino-1-propanol and ethyl (S)-5-(6-(tert-butylamino)-4-(trifluoromethyl)pyridin-3-yl)-4-(2-methylpyrrolidine-1-carbonyl)thiazole-2-carboxylate (Intermediate 107) for ethyl (S)-5-(6-(tert-butylamino)-4-(difluoromethyl)pyridin-3-yl)-4-(2-methylpyrrolidine-1-carbonyl)thiazole-2-carboxylate. MS (ESI): mass calcd. for $C_{24}H_{30}F_3N_5O_3S$, 525.6; m/z found, 526.2 [M+H]$^+$. $^1$H NMR (500 MHz, CDCl$_3$) δ 8.18-8.14 (s, 1H), 7.70-7.58 (m, 1H), 6.66-6.61 (m, 1H), 4.97-4.91 (s, 1H), 4.23-4.15 (m, 1H), 3.77-3.69 (m, 2H), 3.60-3.32 (m, 3H), 2.09-2.05 (m, 1H), 1.93-1.85 (m, 1H), 1.77-1.73 (m, 1H), 1.55-1.48 (m, 1H), 1.47-1.44 (s, 9H), 1.24-1.21 (d, J=6.3 Hz, 2H), 1.06-1.03 (d, J=6.4 Hz, 1H), 1.03-1.00 (s, 4H).

Example 264

5-[6-(tert-Butylamino)-4-(difluoromethyl)-3-pyridyl]-4-[(2S)-2-methylpyrrolidine-1-carbonyl]-N-[3,3,3-trifluoro-2-hydroxy-2-(trifluoromethyl)propyl]thiazole-2-carboxamide

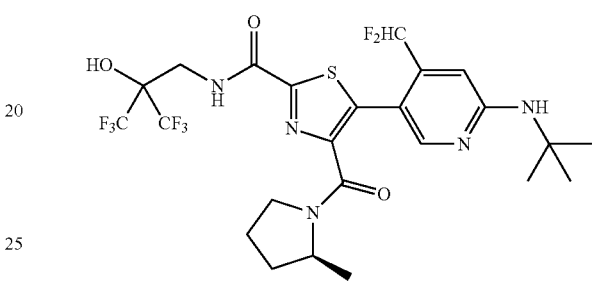

The title compound was prepared as described in Example 148 substituting 2-(aminomethyl)-1,1,1,3,3,3-hexafluoropropan-2-ol (Intermediate 111) for (R)-(−)-2-amino-1-propanol. MS (ESI): mass calcd. for $C_{24}H_{27}F_8N_5O_3S$, 617.6; m/z found, 618.1 [M+H]$^+$. $^1$H NMR (500 MHz, CDCl$_3$) δ 8.04-7.96 (m, 1H), 7.84-7.72 (m, 1H), 6.93-6.49 (m, 3H), 4.94-4.87 (s, 1H), 4.26-4.15 (m, 1H), 4.09-3.99 (m, 2H), 1.47-1.44 (m, 9H), 3.61-3.28 (m, 2H), 2.10-2.05 (m, 1H), 1.97-1.73 (m, 2H), 1.59-1.50 (m, 1H), 1.24-1.21 (d, J=6.3 Hz, 2H), 1.02-0.99 (d, J=6.4 Hz, 1H).

Example 265

5-[6-(tert-Butylamino)-4-(difluoromethyl)-3-pyridyl]-N-(2-hydroxy-2-methyl-propyl)-4-[(2S)-2-methylpyrrolidine-1-carbonyl]thiazole-2-carboxamide

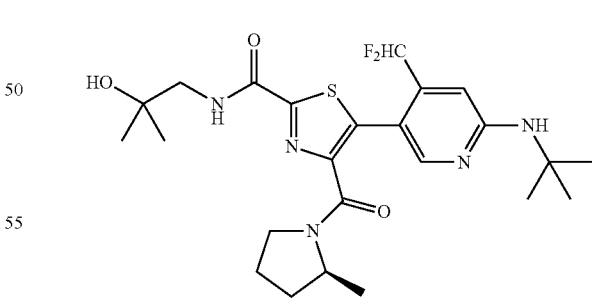

The title compound was prepared as described in Example 77 substituting 5-bromo-N-(tert-butyl)-4-(difluoromethyl)pyridin-2-amine (Intermediate 59) for 5-bromo-N-(1-methylcyclobutyl)-4-(trifluoromethyl)pyridin-2-amine. MS (ESI): mass calcd. for $C_{24}H_{33}F_2N_5O_3S$, 509.6; m/z found, 510.2 [M+H]$^+$. $^1$H NMR (400 MHz, CDCl$_3$) δ 8.05-7.98 (m, 1H), 7.66-7.54 (m, 1H), 7.00-6.61 (m, 2H), 4.89 (s, 1H), 4.30-4.18 (m, 1H), 3.60-3.32 (m, 4H), 2.97-2.87 (m, 1H), 1.47-1.44 (m, 9H), 2.36-2.22 (m, 1H), 1.93-1.85 (m, 1H), 1.79-1.49 (m, 2H), 1.31 (s, 6H), 1.23 (d, J=6.3 Hz, 2H), 1.02 (d, J=6.4 Hz, 1H).

Example 266

N-(1,1-Dideuterio-2-hydroxy-2-methyl-propyl)-5-[4-(difluoromethyl)-6-[[(1S)-1-(trifluoromethyl)propyl]amino]-3-pyridyl]-4-[(2S)-2-methylpyrrolidine-1-carbonyl]thiazole-2-carboxamide

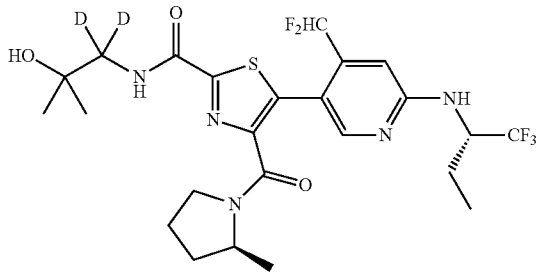 [SMILES: [2H]C([2H])(NC(=O)c1nc(C(=O)N2CCC[C@@H]2C)c(-c2cnc(N[C@@H](CC)C(F)(F)F)cc2C(F)F)s1)C(C)(C)O]

The title compound was prepared as described in Example 149 substituting 1-amino-2-methylpropan-1,1-d2-2-ol HCl (Intermediate 76: Step C) for 3-hydroxy-3-methylazetidine HCl and ethyl 5-(4-(difluoromethyl)-6-(((S)-1,1,1-trifluorobutan-2-yl)amino)pyridin-3-yl)-4-((S)-2-methylpyrrolidine-1-carbonyl)thiazole-2-carboxylate (Intermediate 102) for ethyl (S)-5-(6-(tert-butylamino)-4-(difluoromethyl)pyridin-3-yl)-4-(2-methylpyrrolidine-1-carbonyl)thiazole-2-carboxylate. MS (ESI): mass calcd. for $C_{24}H_{28}D2F_5N_5O_3S$, 565.6; m/z found, 566.2 [M+H]$^+$. $^1$H NMR (400 MHz, CDCl$_3$) δ 8.10-8.00 (m, 1H), 7.61-7.50 (m, 1H), 7.04-6.64 (m, 2H), 4.91-4.70 (m, 2H), 4.39-4.16 (m, 1H), 3.60-3.38 (m, 2H), 2.14-2.05 (m, 1H), 2.03-1.84 (m, 3H), 1.82-1.73 (m, 1H), 1.66-1.51 (m, 2H), 1.31 (s, 6H), 1.23-1.20 (m, 2H), 1.08-1.02 (m, 4H).

Example 267

5-[4-(Difluoromethyl)-6-[[(1S)-1-(trifluoromethyl)propyl]amino]-3-pyridyl]-N-[(1R)-2-hydroxy-1,2-dimethyl-propyl]-4-[(2S)-2-methylpyrrolidine-1-carbonyl]thiazole-2-carboxamide

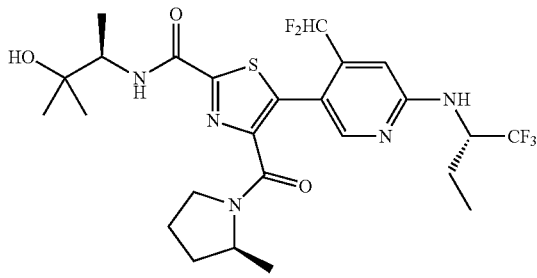 [SMILES: CC[C@H](Nc1cc(C(F)F)c(-c2sc(C(=O)N[C@H](C)C(C)(C)O)nc2C(=O)N2CCC[C@@H]2C)cn1)C(F)(F)F]

The title compound was prepared as described in Example 148 substituting (R)-3-amino-2-methylbutan-2-ol for (R)-(−)-2-amino-1-propanol and ethyl 5-(4-(difluoromethyl)-6-(((S)-1,1,1-trifluorobutan-2-yl)amino)pyridin-3-yl)-4-((S)-2-methylpyrrolidine-1-carbonyl)thiazole-2-carboxylate (Intermediate 102) for ethyl (S)-5-(6-(tert-butylamino)-4-(difluoromethyl)pyridin-3-yl)-4-(2-methylpyrrolidine-1-carbonyl)thiazole-2-carboxylate. MS (ESI): mass calcd. for $C_{25}H_{32}F_5N_5O_3S$, 577.6; m/z found, 578.2 [M+H]$^+$. $^1$H NMR (400 MHz, CDCl$_3$) δ 8.09-8.01 (m, 1H), 7.44-7.37 (m, 1H), 7.04-6.65 (m, 2H), 4.85-4.71 (m, 2H), 4.38-4.16 (m, 1H), 4.12-4.06 (m, 1H), 3.64-3.35 (m, 2H), 2.04-1.87 (m, 4H), 1.82-1.72 (m, 1H), 1.64-1.48 (m, 2H), 1.32-1.28 (m, 9H), 1.23-1.20 (m, 2H), 1.08-1.02 (m, 4H).

Example 268

[5-[6-(tert-Butylamino)-4-(trifluoromethyl)-3-pyridyl]-2-(3-hydroxy-3-methyl-azetidine-1-carbonyl)thiazol-4-yl]-[(2S)-2-methylpyrrolidin-1-yl]methanone

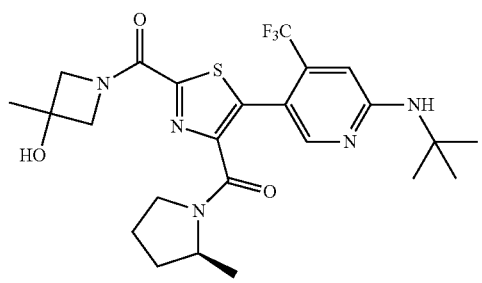 [SMILES: C[C@H]1CCCN1C(=O)c1nc(C(=O)N2CC(C)(O)C2)sc1-c1cnc(NC(C)(C)C)cc1C(F)(F)F]

The title compound was prepared as described in Example 149 substituting 3-hydroxy-3-methylazetidine HCl for 3-hydroxy-3-methylazetidine HCl and ethyl (S)-5-(6-(tert-butylamino)-4-(trifluoromethyl)pyridin-3-yl)-4-(2-methylpyrrolidine-1-carbonyl)thiazole-2-carboxylate (Intermediate 107) for ethyl (S)-5-(6-(tert-butylamino)-4-(difluoromethyl)pyridin-3-yl)-4-(2-methylpyrrolidine-1-carbonyl)thiazole-2-carboxylate. MS (ESI): mass calcd. for $C_{24}H_{30}F_3N_5O_3S$, 525.6; m/z found, 526.2 [M+H]$^+$. $^1$H NMR (400 MHz, CDCl$_3$) δ 8.18-8.12 (m, 1H), 6.64-6.60 (m, 1H), 4.97-4.90 (m, 1H), 4.65-4.52 (m, 2H), 4.22-4.09 (m, 3H), 3.61-3.42 (m, 2H), 2.95-2.84 (m, 1H), 2.11-2.04 (m, 1H), 1.97-1.72 (m, 2H), 1.61-1.57 (m, 3H), 1.57-1.50 (m, 1H), 1.45 (s, 9H), 1.24-1.20 (m, 2H), 1.09-1.00 (m, 1H).

Example 269

5-[6-(tert-Butylamino)-4-(difluoromethyl)-3-pyridyl]-N-[(1R)-2-hydroxy-1,2-dimethyl-propyl]-4-[(2S)-2-methylpyrrolidine-1-carbonyl]thiazole-2-carboxamide

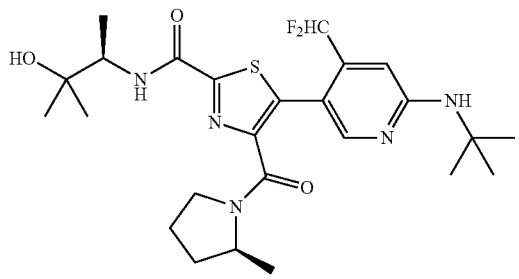 [SMILES: C[C@H]1CCCN1C(=O)c1nc(C(=O)N[C@H](C)C(C)(C)O)sc1-c1cnc(NC(C)(C)C)cc1C(F)F]

The title compound was prepared as described in Example 148 substituting (R)-3-amino-2-methylbutan-2-ol for (R)-

(−)-2-amino-1-propanol. MS (ESI): mass calcd. for $C_{25}H_{35}F_2N_5O_3S$, 523.6; m/z found, 524.2 [M+H]$^+$. $^1$H NMR (400 MHz, CDCl$_3$) δ 8.06-7.97 (m, 1H), 7.44-7.35 (m, 1H), 7.01-6.60 (m, 2H), 4.87 (s, 1H), 4.31-4.17 (m, 1H), 4.10-4.03 (m, 1H), 3.64-3.29 (m, 2H), 2.11-2.05 (m, 1H), 2.02-1.85 (m, 2H), 1.80-1.73 (m, 1H), 1.58-1.49 (m, 1H), 1.46 (s, 9H), 1.31-1.27 (m, 9H), 1.24-1.21 (m, 2H), 1.04 (d, J=6.4 Hz, 1H).

Example 270

5-[6-(tert-Butylamino)-4-(difluoromethyl)-3-pyridyl]-N-[(1S)-2-hydroxy-1,2-dimethyl-propyl]-4-[(2S)-2-methylpyrrolidine-1-carbonyl]thiazole-2-carboxamide

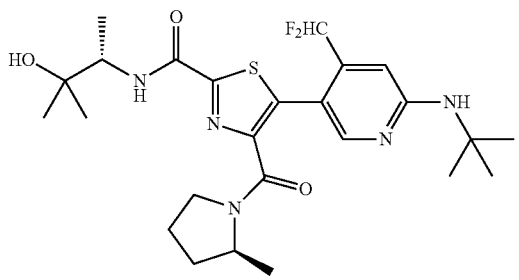 [SMILES: C[C@H](NC(=O)c1nc(C(=O)N2CCC[C@@H]2C)c(-c2cnc(NC(C)(C)C)cc2C(F)F)s1)C(C)(C)O]

The title compound was prepared as described in Example 148 substituting (S)-3-amino-2-methylbutan-2-ol for (R)-(−)-2-amino-1-propanol. MS (ESI): mass calcd. for $C_{25}H_{35}F_2N_5O_3S$, 523.6; m/z found, 524.2 [M+H]$^+$. $^1$H NMR (400 MHz, CDCl$_3$) δ 8.05-7.98 (m, 1H), 7.43-7.36 (m, 1H), 7.00-6.60 (m, 2H), 4.87 (s, 1H), 4.27-4.17 (m, 1H), 4.11-4.05 (m, 1H), 3.63-3.32 (m, 2H), 1.47-1.44 (m, 9H), 2.09-2.05 (m, 1H), 2.00-1.84 (m, 2H), 1.79-1.72 (m, 1H), 1.57-1.49 (m, 1H), 1.31-1.28 (m, 9H), 1.22 (d, J=6.3 Hz, 2H), 1.05 (d, J=6.4 Hz, 1H).

Example 271

5-[6-(tert-Butylamino)-4-(trifluoromethyl)-3-pyridyl]-4-[(2S)-2-methylpyrrolidine-1-carbonyl]-N-[3,3,3-trifluoro-2-hydroxy-2-(trifluoromethyl)propyl]thiazole-2-carboxamide

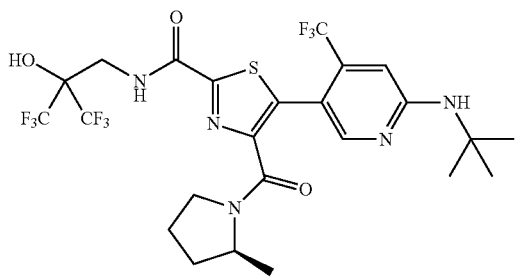 [SMILES: C[C@H]1CCCN1C(=O)c1nc(C(=O)NCC(O)(C(F)(F)F)C(F)(F)F)sc1-c1cnc(NC(C)(C)C)cc1C(F)(F)F]

The title compound was prepared as described in Example 148 substituting 2-(aminomethyl)-1,1,1,3,3,3-hexafluoropropan-2-ol (Intermediate 111) for (R)-(−)-2-amino-1-propanol and ethyl (S)-5-(6-(tert-butylamino)-4-(trifluoromethyl)pyridin-3-yl)-4-(2-methylpyrroldine-1-carbonyl)thiazole-2-carboxylate (Intermediate 107) for ethyl (S)-5-(6-(tert-butylamino)-4-(difluoromethyl)pyridin-3-yl)-4-(2-methylpyrrolidine-1-carbonyl)thiazole-2-carboxylate. MS (ESI): mass calcd. for $C_{24}H_{26}F_9N_5O_3S$, 635.5; m/z found, 636.1 [M+H]$^+$. $^1$H NMR (400 MHz, CDCl$_3$) δ 8.15-8.11 (m, 1H), 7.90-7.81 (m, 1H), 6.64 (s, 1H), 6.52 (s, 1H), 4.95 (s, 1H), 4.24-4.16 (m, 1H), 1.48-1.44 (m, 9H), 4.08-3.95 (m, 2H), 3.61-3.29 (m, 2H), 1.94-1.71 (m, 2H), 1.59-1.50 (m, 1H), 1.28-1.23 (m, 3H), 1.08 (d, J=6.4 Hz, 1H).

Example 272

5-[4-(Difluoromethyl)-6-[[(1S)-1-(trifluoromethyl)propyl]amino]-3-pyridyl]-N-[(1S)-2-hydroxy-1,2-dimethyl-propyl]-4-[(2S)-2-methylpyrrolidine-1-carbonyl]thiazole-2-carboxamide

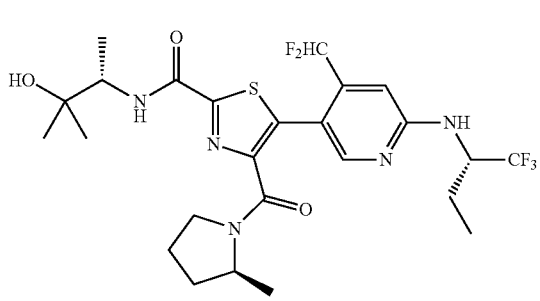 [SMILES: CC[C@H](Nc1cc(C(F)F)c(-c2sc(C(=O)N[C@@H](C)C(C)(C)O)nc2C(=O)N2CCC[C@@H]2C)cn1)C(F)(F)F]

The title compound was prepared as described in Example 148 substituting (S)-3-amino-2-methylbutan-2-ol for (R)-(−)-2-amino-1-propanol and ethyl 5-(4-(difluoromethyl)-6-(((S)-1,1,1-trifluorobutan-2-yl)amino)pyridin-3-yl)-4-((S)-2-methylpyrrolidine-1-carbonyl)thiazole-2-carboxylate (Intermediate 102) for ethyl (S)-5-(6-(tert-butylamino)-4-(difluoromethyl)pyridin-3-yl)-4-(2-methylpyrrolidine-1-carbonyl)thiazole-2-carboxylate. MS (ESI): mass calcd. for $C_{25}H_{32}F_5N_5O_3S$, 577.6; m/z found, 578.1 [M+H]$^+$. $^1$H NMR (400 MHz, CDCl$_3$) δ 8.10-8.00 (m, 1H), 7.45-7.34 (m, 1H), 7.04-6.64 (m, 2H), 4.88-4.71 (m, 2H), 4.30-4.06 (m, 2H), 3.64-3.34 (m, 2H), 2.04-1.84 (m, 4H), 1.83-1.71 (m, 1H), 1.64-1.50 (m, 2H), 1.33-1.27 (m, 9H), 1.24-1.19 (m, 2H), 1.10-1.01 (m, 4H).

Example 273

4-[(2S)-4,4-Difluoro-2-methyl-pyrrolidine-1-carbonyl]-5-[4-(difluoromethyl)-6-[[1-(trifluoromethyl)cyclobutyl]methylamino]-3-pyridyl]-N-(2-hydroxy-2-methyl-propyl)thiazole-2-carboxamide

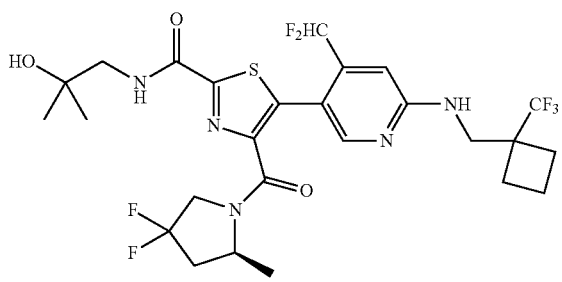 [SMILES: C[C@H]1CC(F)(F)CN1C(=O)c1nc(C(=O)NCC(C)(C)O)sc1-c1cnc(NCC2(C(F)(F)F)CCC2)cc1C(F)F]

The title compound was prepared as described in Example 77 substituting 5-bromo-4-(difluoromethyl)-N-((1-(trifluoromethyl)cyclobutyl)methyl)pyridin-2-amine (Intermediate 112) for 5-bromo-N-(1-methylcyclobutyl)-4-(trifluoromethyl)pyridin-2-amine and (S)-4-(4,4-difluoro-2-methylpyrrolidine-1-carbonyl)-N-(2-hydroxy-2-methylpropyl)thiazole-2-carboxamide (Intermediate 67) for (S)—N-(2-hydroxy-2-methylpropyl)-4-(2-methylpyrrolidine-1-carbonyl)thiazole-2-carboxamide. MS (ESI): mass calcd. for $C_{26}H_{30}F_7N_5O_3S$, 625.6; m/z found, 626.2 [M+H]$^+$. $^1$H NMR (400 MHz, CDCl$_3$) δ 8.07-8.02 (m, 1H), 7.58-7.47 (m, 1H), 6.93-6.53 (m, 2H), 5.04-4.93 (m, 1H), 4.77-4.45 (m, 1H), 4.14-3.86 (m, 2H), 3.86-3.80 (m, 2H), 3.58-3.41 (m, 2H), 2.64-2.48 (m, 1H), 2.40-2.29 (m, 2H), 2.15-1.96 (m, 6H), 1.36 (d, J=6.4 Hz, 2H), 1.35-1.31 (m, 6H), 1.23 (d, J=6.4 Hz, 1H).

The title compound was prepared as described in Example 77 substituting 5-bromo-4-(difluoromethyl)-N-((1-(trifluoromethyl)cyclopropyl)methyl)pyridin-2-amine (Intermediate 113) for 5-bromo-N-(1-methylcyclobutyl)-4-(trifluoromethyl)pyridin-2-amine and (S)-4-(4,4-difluoro-2-methylpyrrolidine-1-carbonyl)-N-(2-hydroxy-2-methylpropyl)thiazole-2-carboxamide (Intermediate 67) for (S)—N-(2-hydroxy-2-methylpropyl)-4-(2-methylpyrrolidine-1-carbonyl)thiazole-2-carboxamide. MS (ESI): mass calcd. for $C_{25}H_{28}F_7N_5O_3S$, 611.6; m/z found, 612.1 [M+H]$^+$. $^1$H NMR (500 MHz, CDCl$_3$) δ 8.01 (s, 1H), 7.55-7.45 (m, 1H), 6.88-6.55 (m, 2H), 5.11-5.05 (m, 1H), 4.74-4.46 (m, 1H), 4.11-3.80 (m, 2H), 3.68 (d, J=5.7 Hz, 2H), 3.56-3.40 (m, 2H), 2.65-2.48 (m, 1H), 2.19-2.06 (m, 1H), 1.98-1.86 (m, 1H), 1.36 (d, J=6.4 Hz, 2H), 1.34-1.31 (m, 6H), 1.23 (d, J=6.6 Hz, 1H), 1.09-1.03 (m, 2H), 0.90-0.84 (m, 2H).

Example 274

5-[4-(Difluoromethyl)-6-[[1-(trifluoromethyl)cyclobutyl]methylamino]-3-pyridyl]-N-(2-hydroxy-2-methyl-propyl)-4-[(2S)-2-methylpyrrolidine-1-carbonyl]thiazole-2-carboxamide

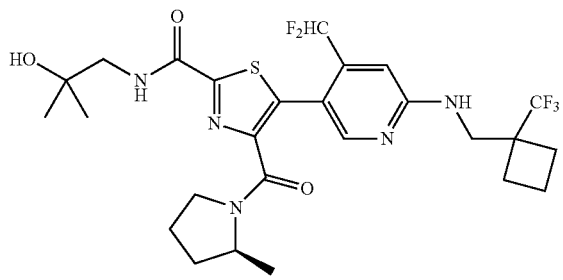 [SMILES: C[C@H]1CCCN1C(=O)c1nc(C(=O)NCC(C)(C)O)sc1-c1cnc(NCC2(C(F)(F)F)CCC2)cc1C(F)F]

Example 276

5-[4-(Difluoromethyl)-6-[[1-(trifluoromethyl)cyclopropyl]methylamino]-3-pyridyl]-N-(2-hydroxy-2-methyl-propyl)-4-[(2S)-2-methylpyrrolidine-1-carbonyl]thiazole-2-carboxamide

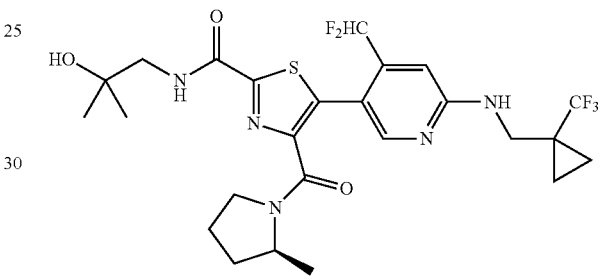

The title compound was prepared as described in Example 77 substituting 5-bromo-4-(difluoromethyl)-N-((1-(trifluoromethyl)cyclobutyl)methyl)pyridin-2-amine (Intermediate 112) for 5-bromo-N-(1-methylcyclobutyl)-4-(trifluoromethyl)pyridin-2-amine. MS (ESI): mass calcd. for $C_{26}H_{32}F_5N_5O_3S$, 589.6; m/z found, 590.2 [M+H]$^+$. $^1$H NMR (400 MHz, CDCl$_3$) δ 8.09-8.01 (m, 1H), 7.62-7.51 (m, 1H), 7.03-6.62 (m, 2H), 5.01-4.93 (m, 1H), 4.37-4.17 (m, 1H), 3.87-3.80 (m, 2H), 3.61-3.37 (m, 4H), 2.39-2.27 (m, 2H), 2.08-2.06 (m, 1H), 2.04-1.95 (m, 4H), 1.94-1.72 (m, 2H), 1.59-1.50 (m, 1H), 1.32 (s, 6H), 1.23 (d, J=6.3 Hz, 2H), 1.04 (d, J=6.4 Hz, 1H).

The title compound was prepared as described in Example 77 substituting 5-bromo-4-(difluoromethyl)-N-((1-(trifluoromethyl)cyclopropyl)methyl)pyridin-2-amine (Intermediate 113) for 5-bromo-N-(1-methylcyclobutyl)-4-(trifluoromethyl)pyridin-2-amine. MS (ESI): mass calcd. for $C_{25}H_{30}F_5N_5O_3S$, 575.6; m/z found, 576.2 [M+H]$^+$. $^1$H NMR (500 MHz, CDCl$_3$) δ 8.05-7.98 (m, 1H), 7.60-7.50 (m, 1H), 6.98-6.65 (m, 2H), 5.09-5.02 (m, 1H), 4.36-4.16 (m, 1H), 3.71-3.65 (m, 2H), 3.58-3.37 (m, 4H), 2.04-2.00 (m, 1H), 1.95-1.74 (m, 2H), 1.58-1.51 (m, 1H), 1.32 (s, 6H), 1.23 (d, J=6.3 Hz, 2H), 1.08-1.01 (m, 3H), 0.89-0.84 (m, 2H).

Example 275

4-[(2S)-4,4-Difluoro-2-methyl-pyrrolidine-1-carbonyl]-5-[4-(difluoromethyl)-6-[[1-(trifluoromethyl)cyclopropyl]methylamino]-3-pyridyl]-N-(2-hydroxy-2-methyl-propyl)thiazole-2-carboxamide

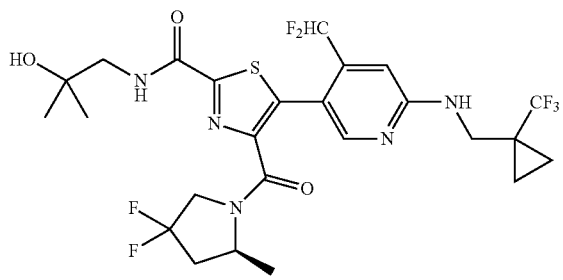 [SMILES: C[C@H]1CC(F)(F)CN1C(=O)c1nc(C(=O)NCC(C)(C)O)sc1-c1cnc(NCC2(C(F)(F)F)CC2)cc1C(F)F]

Example 277

4-[(2S)-4,4-Difluoro-2-methyl-pyrrolidine-1-carbonyl]-N-(2-hydroxy-2-methyl-propyl)-5-[6-[(1-methylcyclopropyl)methylamino]-4-(trifluoromethyl)-3-pyridyl]thiazole-2-carboxamide

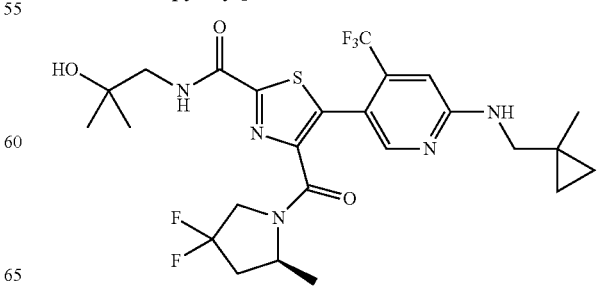

The title compound was prepared as described in Example 77 substituting 5-bromo-N-((1-methylcyclopropyl)methyl)-4-(trifluoromethyl)pyridin-2-amine (Intermediate 114) for 5-bromo-N-(1-methylcyclobutyl)-4-(trifluoromethyl)pyridin-2-amine and (S)-4-(4,4-difluoro-2-methylpyrrolidine-1-carbonyl)-N-(2-hydroxy-2-methylpropyl)thiazole-2-carboxamide (Intermediate 67) for (S)—N-(2-hydroxy-2-methylpropyl)-4-(2-methylpyrrolidine-1-carbonyl)thiazole-2-carboxamide. MS (ESI): mass calcd. for $C_{25}H_{30}F_5N_5O_3S$, 575.6; m/z found, 576.2 [M+H]⁺. ¹H NMR (500 MHz, CDCl₃) δ 8.14 (s, 1H), 7.56-7.45 (m, 1H), 6.65 (s, 1H), 5.13-5.05 (m, 1H), 4.75-4.43 (m, 1H), 4.14-3.75 (m, 2H), 3.56-3.42 (m, 2H), 3.20 (d, J=5.0 Hz, 2H), 2.62-2.48 (m, 1H), 2.19-2.01 (m, 1H), 1.98-1.83 (m, 1H), 1.36 (d, J=6.4 Hz, 2H), 1.34-1.31 (m, 6H), 1.31-1.27 (m, 1H), 1.16 (s, 3H), 0.51-0.47 (m, 2H), 0.42-0.38 (m, 2H).

Example 278

N-(2-Hydroxy-2-methyl-propyl)-5-[6-[(1-methylcyclopropyl)methylamino]-4-(trifluoromethyl)-3-pyridyl]-4-[(2S)-2-methylpyrrolidine-1-carbonyl]thiazole-2-carboxamide

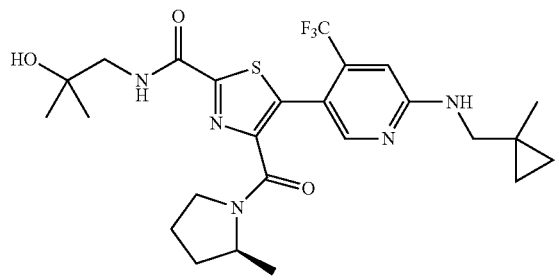 [SMILES: C[C@H]1CCCN1C(=O)c1nc(C(=O)NCC(C)(C)O)sc1-c1cnc(NCC2(C)CC2)cc1C(F)(F)F]

The title compound was prepared as described in Example 77 substituting 5-bromo-N-((1-methylcyclopropyl)methyl)-4-(trifluoromethyl)pyridin-2-amine (Intermediate 114) for 5-bromo-N-(1-methylcyclobutyl)-4-(trifluoromethyl)pyridin-2-amine. MS (ESI): mass calcd. for $C_{25}H_{32}F_3N_5O_3S$, 539.6; m/z found, 540.2 [M+H]⁺. ¹H NMR (500 MHz, CDCl₃) δ 8.17 (s, 1H), 7.62-7.53 (m, 1H), 6.66-6.59 (m, 1H), 5.17-5.05 (m, 1H), 4.36-4.14 (m, 1H), 3.61-3.40 (m, 4H), 3.24-3.15 (m, 2H), 2.11-1.86 (m, 3H), 1.80-1.69 (m, 1H), 1.58-1.49 (m, 1H), 1.34-1.28 (m, 6H), 1.25-1.23 (m, 2H), 1.16 (s, 3H), 1.13-1.09 (m, 1H), 0.51-0.46 (m, 2H), 0.41-0.35 (m, 2H).

Example 279

5-(6-(((S*)-2,2-Difluorocyclopentyl)amino)-4-(trifluoromethyl)pyridin-3-yl)-N-(2-hydroxy-2-methylpropyl)-4-((S)-2-methylpyrrolidine-1-carbonyl)thiazole-2-carboxamide

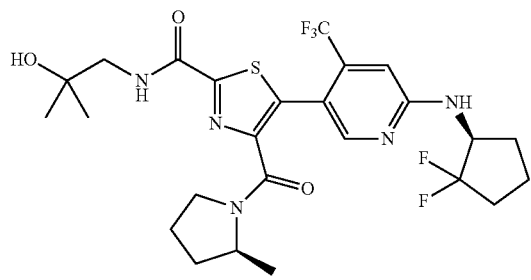 [SMILES: C[C@H]1CCCN1C(=O)c1nc(C(=O)NCC(C)(C)O)sc1-c1cnc(N[C@H]2CCCC2(F)F)cc1C(F)(F)F]

The title compound was prepared as described in Example 77 substituting 5-bromo-N-(2,2-difluorocyclopentyl)-4-(trifluoromethyl)pyridin-2-amine (Intermediate 64: Step B) for 5-bromo-N-(1-methylcyclobutyl)-4-(trifluoromethyl)pyridin-2-amine. The pure diastereomer was isolated via SFC (Stationary phase: Chiralpak AD-H, 5 μm, 250×20 mm, Mobile phase: 15% EtOH/iPrOH 50/50 v/v+0.3% iPrNH₂, 85% CO₂, second eluting enantiomer). MS (ESI): mass calcd. for $C_{25}H_{30}F_5N_5O_3S$, 575.6; m/z found, 576.2 [M+H]⁺. ¹H NMR (500 MHz, CDCl₃) δ 8.21 (s, 1H), 7.59-7.49 (m, 1H), 6.76 (s, 1H), 5.22-5.08 (m, 1H), 4.58-4.45 (m, 1H), 4.38-4.17 (m, 1H), 3.55-3.41 (m, 4H), 2.09-2.02 (m, 1H), 2.40-2.32 (m, 1H), 2.28-2.16 (m, 2H), 1.91-1.72 (m, 4H), 1.66-1.55 (m, 3H), 1.32 (s, 6H), 1.24 (d, J=6.3 Hz, 2H), 1.21-1.13 (m, 1H).

Example 280

5-(6-(((R*)-2,2-Difluorocyclopentyl)amino)-4-(trifluoromethyl)pyridin-3-yl)-N-(2-hydroxy-2-methylpropyl)-4-((S)-2-methylpyrrolidine-1-carbonyl)thiazole-2-carboxamide

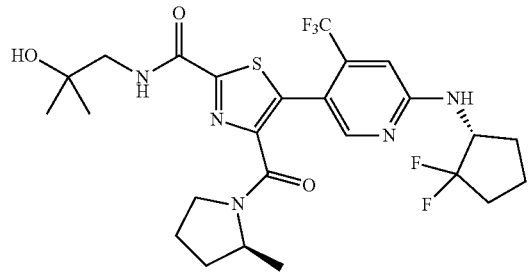 [SMILES: C[C@H]1CCCN1C(=O)c1nc(C(=O)NCC(C)(C)O)sc1-c1cnc(N[C@@H]2CCCC2(F)F)cc1C(F)(F)F]

The title compound was prepared as described in Example 279. The pure diastereomer was isolated via SFC (Stationary phase: Chiralpak AD-H, 5 μm, 250×20 mm, Mobile phase: 15% EtOH/iPrOH 50/50 v/v+0.3% iPrNH₂, 85% CO₂, first eluting enantiomer). MS (ESI): mass calcd. for $C_{25}H_{30}F_5N_5O_3S$, 575.6; m/z found, 576.2 [M+H]⁺. ¹H NMR (500 MHz, CDCl₃) δ 8.21 (s, 1H), 7.61-7.51 (m, 1H), 6.76-6.70 (m, 1H), 5.19-5.10 (m, 1H), 4.63-4.50 (m, 1H), 4.38-4.15 (m, 1H), 3.58-3.39 (m, 4H), 2.39-2.30 (m, 1H), 2.28-2.13 (m, 2H), 2.10-2.02 (m, 1H), 1.94-1.72 (m, 4H), 1.61-1.52 (m, 3H), 1.33-1.30 (m, 6H), 1.25 (d, J=6.2 Hz, 2H), 1.22-1.09 (m, 1H).

Example 281

5-[5-Cyano-6-(cyclohexylamino)-3-pyridyl]-N-(2-hydroxy-2-methyl-propyl)-4-[(2S)-2-methylpyrrolidine-1-carbonyl]thiazole-2-carboxamide

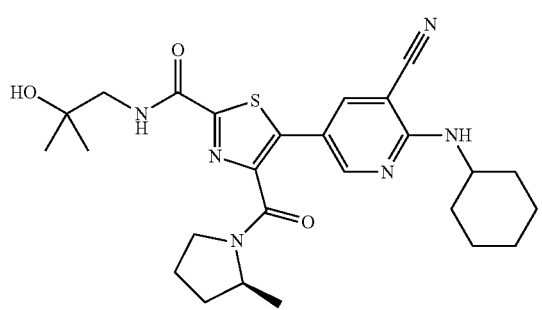 [SMILES: C[C@H]1CCCN1C(=O)c1nc(C(=O)NCC(C)(C)O)sc1-c1cnc(NC2CCCCC2)c(C#N)c1]

The title compound was prepared as described in Example 77 substituting 5-bromo-2-(cyclohexylamino)nicotinonitrile (Intermediate 9) for 5-bromo-N-(1-methylcyclobutyl)-4-(trifluoromethyl)pyridin-2-amine. MS (ESI): mass calcd. for $C_{26}H_{34}N_6O_3S$, 510.7; m/z found, 511.2 [M+H]$^+$. $^1$H NMR (500 MHz, CDCl$_3$) δ 8.43 (d, J=2.5 Hz, 1H), 7.92-7.88 (m, 1H), 7.63-7.54 (m, 1H), 5.29-5.23 (m, 1H), 4.39-3.96 (m, 2H), 3.72-3.21 (m, 4H), 2.39-2.30 (m, 1H), 2.12-2.06 (m, 1H), 2.03-1.98 (m, 1H), 1.94-1.86 (m, 1H), 1.82-1.75 (m, 3H), 1.70-1.65 (m, 1H), 1.64-1.57 (m, 1H), 1.47-1.38 (m, 2H), 1.35 (d, J=6.4 Hz, 2H), 1.31-1.29 (m, 6H), 1.28-1.25 (m, 2H), 0.93 (d, J=6.4 Hz, 1H).

Example 282

N-(2-Hydroxy-2-methyl-propyl)-4-[(2S)-2-methylpyrrolidine-1-carbonyl]-5-[4-(trifluoromethyl)-6-[[(1R)-1-(trifluoromethyl)propyl]amino]-3-pyridyl]thiazole-2-carboxamide

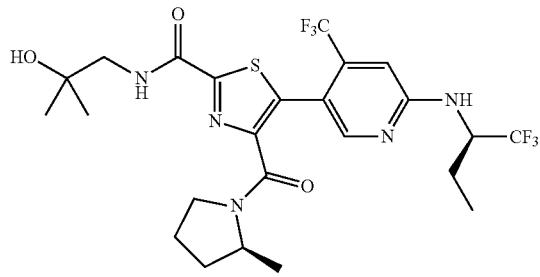 [SMILES: CC[C@@H](Nc1cc(C(F)(F)F)c(-c2sc(C(=O)NCC(C)(C)O)nc2C(=O)N2CCC[C@@H]2C)cn1)C(F)(F)F]

The title compound was prepared as described in Example 77 substituting (R)-5-bromo-N-(1,1,1-trifluorobutan-2-yl)-4-(trifluoromethyl)pyridin-2-amine (Intermediate 115) for 5-bromo-N-(1-methylcyclobutyl)-4-(trifluoromethyl)pyridin-2-amine. MS (ESI): mass calcd. for $C_{24}H_{29}F_6N_5O_3S$, 581.6; m/z found, 582.2 [M+H]$^+$. $^1$H NMR (500 MHz, CDCl$_3$) δ 8.24-8.19 (m, 1H), 7.62-7.52 (m, 1H), 6.79-6.74 (m, 1H), 4.92-4.84 (m, 1H), 4.78 (s, 1H), 4.40-4.16 (m, 1H), 3.59-3.43 (m, 4H), 2.07-1.90 (m, 4H), 1.81-1.72 (m, 1H), 1.67-1.63 (m, 1H), 1.58-1.51 (m, 1H), 1.32 (s, 6H), 1.23 (d, J=6.2 Hz, 2H), 1.15 (d, J=6.4 Hz, 1H), 1.08-1.01 (m, 3H).

Example 283

5-(4-(Difluoromethyl)-6-(((S)-1,1,1-trifluoropropan-2-yl)amino)pyridin-3-yl)-N-((1R,2R)-2-hydroxycyclopentyl)-4-((S)-2-methylpyrrolidine-1-carbonyl)thiazole-2-carboxamide

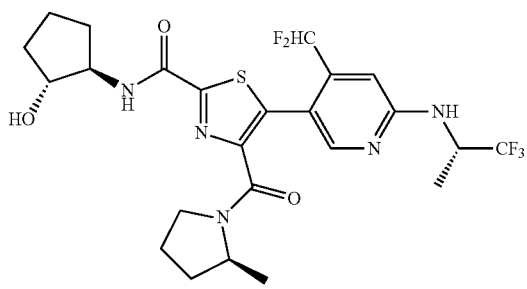 [SMILES: C[C@H](Nc1cc(C(F)F)c(-c2sc(C(=O)N[C@@H]3CCC[C@H]3O)nc2C(=O)N2CCC[C@@H]2C)cn1)C(F)(F)F]

The title compound was prepared as described in Example 149 substituting ethyl 5-(4-(difluoromethyl)-6-(((S)-1,1,1-trifluoropropan-2-yl)amino)pyridin-3-yl)-4-((S)-2-methylpyrrolidine-1-carbonyl)thiazole-2-carboxylate (Intermediate 94) for ethyl (S)-5-(6-(tert-butylamino)-4-(difluoromethyl)pyridin-3-yl)-4-(2-methylpyrrolidine-1-carbonyl)thiazole-2-carboxylate and (1R,2R)-trans-2-aminocyclopentanol HCl for 3-hydroxy-3-methylazetidine HCl. MS (ESI): mass calcd. for $C_{24}H_{28}F_5N_5O_3S$, 561.2; m/z found, 562.2 [M+H]$^+$. $^1$H NMR (500 MHz, CDCl$_3$) δ 8.12-8.04 (m, 1H), 7.25-7.18 (m, 1H), 7.00-6.66 (m, 2H), 5.00-4.89 (m, 1H), 4.83-4.76 (m, 1H), 4.27-4.13 (m, 2H), 4.08-4.01 (m, 1H), 3.78-3.73 (m, 1H), 3.62-3.31 (m, 2H), 2.32-2.24 (m, 1H), 2.15-1.69 (m, 7H), 1.67-1.50 (m, 2H), 1.42 (d, J=6.9 Hz, 3H), 1.25-1.00 (m, 3H).

Example 284

5-(4-(Difluoromethyl)-6-(((S)-1,1,1-trifluoropropan-2-yl)amino)pyridin-3-yl)-N—((R)-1-hydroxypropan-2-yl)-4-((S)-2-methylpyrrolidine-1-carbonyl)thiazole-2-carboxamide

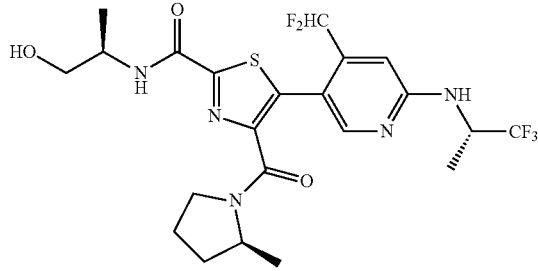 [SMILES: C[C@H](CO)NC(=O)c1nc(C(=O)N2CCC[C@@H]2C)c(-c2cnc(N[C@@H](C)C(F)(F)F)cc2C(F)F)s1]

The title compound was prepared as described in Example 148 substituting ethyl 5-(4-(difluoromethyl)-6-(((S)-1,1,1-trifluoropropan-2-yl)amino)pyridin-3-yl)-4-((S)-2-methylpyrrolidine-1-carbonyl)thiazole-2-carboxylate (Intermediate 94) for ethyl (S)-5-(6-(tert-butylamino)-4-(difluoromethyl)pyridin-3-yl)-4-(2-methylpyrrolidine-1-carbonyl)thiazole-2-carboxylate. MS (ESI): mass calcd. for $C_{22}H_{26}F_5N_5O_3S$, 535.2; m/z found, 536.2 [M+H]$^+$. $^1$H NMR (500 MHz, CDCl$_3$) δ 8.11-8.03 (m, 1H), 7.30-7.27 (m, 1H), 7.00-6.65 (m, 2H), 5.00-4.89 (m, 1H), 4.83-4.76 (m, 1H), 4.33-4.17 (m, 2H), 3.84-3.77 (m, 1H), 3.73-3.66 (m, 1H), 3.62-3.34 (m, 2H), 2.28-2.23 (m, 1H), 2.09-1.99 (m, 1H), 1.97-1.86 (m, 1H), 1.82-1.62 (m, 1H), 1.59-1.50 (m, 1H), 1.42 (d, J=6.9 Hz, 3H), 1.34 (d, J=6.9 Hz, 3H), 1.24-1.02 (m, 3H).

Example 285

5-(4-(Difluoromethyl)-6-(((S)-1,1,1-trifluoropropan-2-yl)amino)pyridin-3-yl)-N-((1S,2S)-2-hydroxycyclopentyl)-4-((S)-2-methylpyrrolidine-1-carbonyl)thiazole-2-carboxamide

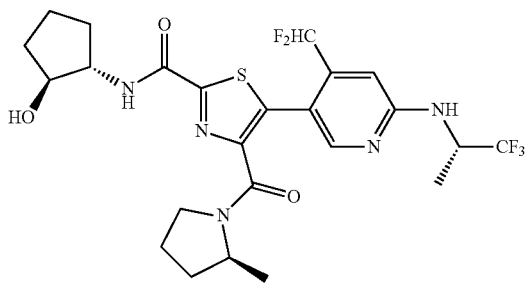 [SMILES: C[C@H](Nc1cc(C(F)F)c(-c2sc(C(=O)N[C@H]3CCC[C@@H]3O)nc2C(=O)N2CCC[C@@H]2C)cn1)C(F)(F)F]

The title compound was prepared as described in Example 149 substituting ethyl 5-(4-(difluoromethyl)-6-(((S)-1,1,1-trifluoropropan-2-yl)amino)pyridin-3-yl)-4-((S)-2-methylpyrrolidine-1-carbonyl)thiazole-2-carboxylate (Intermediate 94) for ethyl (S)-5-(6-(tert-butylamino)-4-(difluoromethyl)pyridin-3-yl)-4-(2-methylpyrrolidine-1-carbonyl)thiazole-2-carboxylate and (1S,2S)-2-aminocyclopentan-1-ol HCl for 3-hydroxy-3-methylazetidine HCl. MS (ESI): mass calcd. for $C_{24}H_{28}F_5N_5O_3S$, 561.2; m/z found, 562.2 [M+H]$^+$. $^1$H NMR (500 MHz, CDCl$_3$) δ 8.12-8.04 (m, 1H), 7.25-7.17 (m, 1H), 7.01-6.66 (m, 2H), 5.00-4.89 (m, 1H), 4.82-4.75 (m, 1H), 4.27-4.13 (m, 2H), 4.08-4.01 (m, 1H), 3.76 (d, J=2.1 Hz, 1H), 3.62-3.31 (m, 2H), 2.34-2.24 (m, 1H), 2.15-1.70 (m, 7H), 1.68-1.50 (m, 2H), 1.42 (d, J=6.9 Hz, 3H), 1.24-0.99 (m, 3H).

Example 286

5-(4-(Difluoromethyl)-6-(((S)-1,1,1-trifluoropropan-2-yl)amino)pyridin-3-yl)-N-(2-hydroxy-2-methylpropyl-1,1-d$_2$)-4-((S)-2-methylpyrrolidine-1-carbonyl)thiazole-2-carboxamide

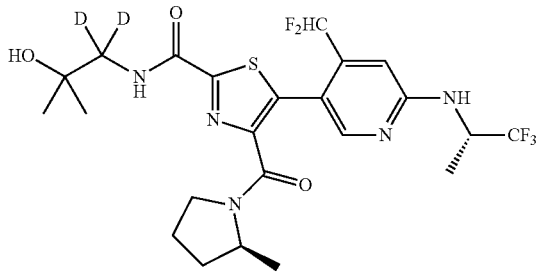 [SMILES: [2H]C([2H])(NC(=O)c1nc(C(=O)N2CCC[C@@H]2C)c(-c2cnc(N[C@@H](C)C(F)(F)F)cc2C(F)F)s1)C(C)(C)O]

The title compound was prepared as described in Example 149 substituting ethyl 5-(4-(difluoromethyl)-6-(((S)-1,1,1-trifluoropropan-2-yl)amino)pyridin-3-yl)-4-((S)-2-methylpyrrolidine-1-carbonyl)thiazole-2-carboxylate (Intermediate 94) for ethyl (S)-5-(6-(tert-butylamino)-4-(difluoromethyl)pyridin-3-yl)-4-(2-methylpyrrolidine-1-carbonyl)thiazole-2-carboxylate and 1-amino-2-methylpropan-1,1-d$_2$-2-ol HCl (Intermediate 76: Step C) for 3-hydroxy-3-methylazetidine HCl. MS (ESI): mass calcd. for $C_{23}H_{26}D2F_5N_5O_3S$, 551.2; m/z found, 552.3 [M+H]$^+$. $^1$H NMR (500 MHz, CDCl$_3$) δ 8.13-8.02 (m, 1H), 7.57-7.49 (m, 1H), 7.02-6.66 (m, 2H), 5.00-4.88 (m, 1H), 4.82-4.74 (m, 1H), 4.41-4.16 (m, 1H), 3.65-3.35 (m, 2H), 2.10-1.97 (m, 1H), 1.97-1.73 (m, 3H), 1.70-1.51 (m, 1H), 1.42 (d, J=6.9 Hz, 3H), 1.33-1.30 (m, 6H), 1.25-1.03 (m, 3H).

Example 287

5-(4-(Difluoromethyl)-6-(((S)-1,1,1-trifluoropropan-2-yl)amino)pyridin-3-yl)-4-((S)-2-methylpyrrolidine-1-carbonyl)-N-(tetrahydro-2H-pyran-4-yl)thiazole-2-carboxamide

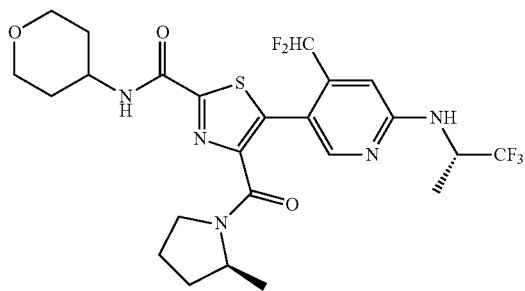 [SMILES: C[C@H](Nc1cc(C(F)F)c(-c2sc(C(=O)NC3CCOCC3)nc2C(=O)N2CCC[C@@H]2C)cn1)C(F)(F)F]

The title compound was prepared as described in Example 148 substituting ethyl 5-(4-(difluoromethyl)-6-(((S)-1,1,1-trifluoropropan-2-yl)amino)pyridin-3-yl)-4-((S)-2-methylpyrrolidine-1-carbonyl)thiazole-2-carboxylate (Intermediate 94) for ethyl (S)-5-(6-(tert-butylamino)-4-(difluoromethyl)pyridin-3-yl)-4-(2-methylpyrrolidine-1-carbonyl)thiazole-2-carboxylate and tetrahydro-2H-pyran-4-amine for (R)-(−)-2-amino-1-propanol. MS (ESI): mass calcd. for $C_{24}H_{28}F_5N_5O_3S$, 561.2; m/z found, 562.2 [M+H]$^+$. $^1$H NMR (500 MHz, CDCl$_3$) δ 8.11-8.03 (m, 1H), 7.10-6.98 (m, 1H), 6.91-6.66 (m, 2H), 5.01-4.89 (m, 1H), 4.80-4.75 (m, 1H), 4.29-4.13 (m, 2H), 4.02 (d, J=11.9 Hz, 2H), 3.63-3.32 (m, 4H), 2.10-1.98 (m, 3H), 1.96-1.71 (m, 2H), 1.70-1.60 (m, 2H), 1.58-1.50 (m, 1H), 1.44-1.39 (m, 3H), 1.24-1.01 (m, 3H).

Example 288

5-(4-(Difluoromethyl)-6-(((S)-1,1,1-trifluoropropan-2-yl)amino)pyridin-3-yl)-N-((1S,3S)-3-hydroxycyclopentyl)-4-((S)-2-methylpyrrolidine-1-carbonyl)thiazole-2-carboxamide

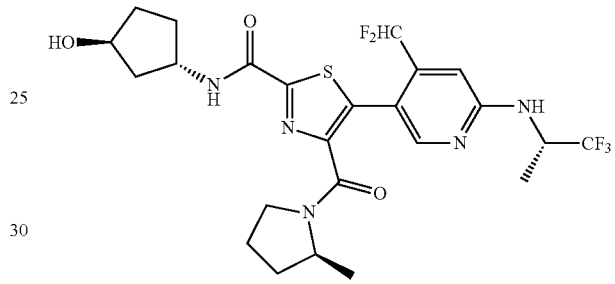

The title compound was prepared as described in Example 149 substituting ethyl 5-(4-(difluoromethyl)-6-(((S)-1,1,1-trifluoropropan-2-yl)amino)pyridin-3-yl)-4-((S)-2-methylpyrrolidine-1-carbonyl)thiazole-2-carboxylate (Intermediate 94) for ethyl (S)-5-(6-(tert-butylamino)-4-(difluoromethyl)pyridin-3-yl)-4-(2-methylpyrrolidine-1-carbonyl)thiazole-2-carboxylate and (1S,3S)-3-aminocyclopentan-1-ol HCl for 3-hydroxy-3-methylazetidine HCl. MS (ESI): mass calcd. for $C_{24}H_{28}F_5N_5O_3S$, 561.2; m/z found, 562.2 [M+H]$^+$. $^1$H NMR (400 MHz, CDCl$_3$) δ 8.12-8.02 (m, 1H), 7.15-6.62 (m, 3H), 5.01-4.88 (m, 1H), 4.85-4.79 (m, 1H), 4.70-4.58 (m, 1H), 4.55-4.46 (m, 1H), 4.29-4.15 (m, 1H), 3.61-3.29 (m, 2H), 2.44-2.32 (m, 1H), 2.25-1.53 (m, 9H), 1.51-1.48 (m, 1H), 1.42 (d, J=6.8 Hz, 3H), 1.24-0.98 (m, 3H).

Example 289

5-(4-(Difluoromethyl)-6-(((S)-1,1,1-trifluoropropan-2-yl)amino)pyridin-3-yl)-N-((1R,3R)-3-hydroxycyclopentyl)-4-((S)-2-methylpyrrolidine-1-carbonyl)thiazole-2-carboxamide

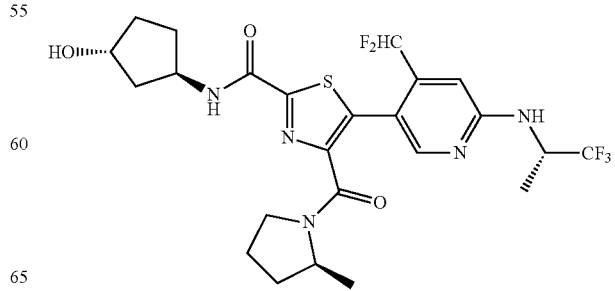

The title compound was prepared as described in Example 149 substituting ethyl 5-(4-(difluoromethyl)-6-(((S)-1,1,1-trifluoropropan-2-yl)amino)pyridin-3-yl)-4-((S)-2-methylpyrrolidine-1-carbonyl)thiazole-2-carboxylate (Intermediate 94) for ethyl (S)-5-(6-(tert-butylamino)-4-(difluoromethyl)pyridin-3-yl)-4-(2-methylpyrrolidine-1-carbonyl)thiazole-2-carboxylate and (1R,3R)-3-aminocyclopentan-1-ol HCl for 3-hydroxy-3-methylazetidine HCl. MS (ESI): mass calcd. for $C_{24}H_{28}F_5N_5O_3S$, 561.2; m/z found, 562.2 [M+H]$^+$. $^1$H NMR (400 MHz, CDCl$_3$) δ 8.13-8.00 (m, 1H), 7.15-6.61 (m, 3H), 5.01-4.90 (m, 1H), 4.90-4.80 (m, 1H), 4.70-4.58 (m, 1H), 4.54-4.46 (m, 1H), 4.28-4.15 (m, 1H), 3.60-3.30 (m, 2H), 2.43-2.32 (m, 1H), 2.25-1.48 (m, 10H), 1.42 (d, J=6.8 Hz, 3H), 1.25-0.98 (m, 3H).

Example 290

4-((1s,4s)-7-Azabicyclo[2.2.1]heptane-7-carbonyl)-5-(4-(difluoromethyl)-6-(((S)-1,1,1-trifluoropropan-2-yl)amino)pyridin-3-yl)-N-(-trans-2-hydroxycyclobutyl)thiazole-2-carboxamide

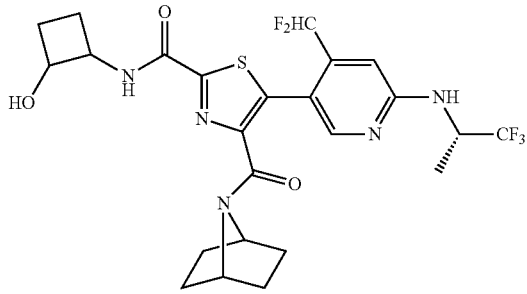 [SMILES: C[C@H](Nc1cc(C(F)F)c(-c2sc(C(=O)NC3CCC3O)nc2C(=O)N2C3CCC2CC3)cn1)C(F)(F)F]

The title compound was prepared as described in Example 149 substituting trans-2-aminocyclobutanol HCl for 3-hydroxy-3-methylazetidine HCl and ethyl 4-((1s,4s)-7-azabicyclo[2.2.1]heptane-7-carbonyl)-5-(4-(difluoromethyl)-6-(((S)-1,1,1-trifluoropropan-2-yl)amino)pyridin-3-yl)thiazole-2-carboxylate (Intermediate 117) for ethyl (S)-5-(6-(tert-butylamino)-4-(difluoromethyl)pyridin-3-yl)-4-(2-methylpyrrolidine-1-carbonyl)thiazole-2-carboxylate. MS (ESI): mass calcd. For $C_{24}H_{26}F_5N_5O_3S$, 559.2; m/z found, 560.2 [M+H]$^+$. $^1$H NMR (400 MHz, CDCl$_3$) δ 8.09 (s, 1H), 7.37 (d, J=4.8 Hz, 1H), 6.89-6.64 (m, 2H), 4.99-4.89 (m, 1H), 4.74 (d, J=9.5 Hz, 1H), 4.71-4.64 (m, 1H), 4.25-4.02 (m, 3H), 3.08 (dd, J=3.5, 1.3 Hz, 1H), 2.28-2.15 (m, 2H), 1.82-1.72 (m, 3H), 1.58-1.49 (m, 3H), 1.48-1.40 (m, 7H).

Example 291

4-((1s,4s)-7-Azabicyclo[2.2.1]heptane-7-carbonyl)-5-(4-(difluoromethyl)-6-(((S)-1,1,1-trifluoropropan-2-yl)amino)pyridin-3-yl)-N-((1R*,2R*)-2-hydroxycyclobutyl)thiazole-2-carboxamide

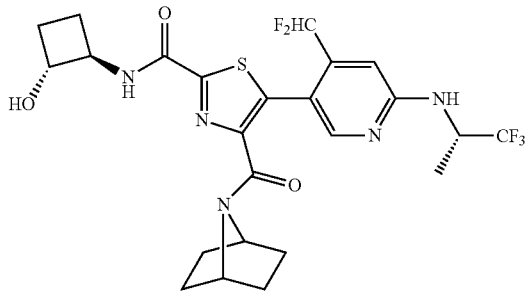 [SMILES: C[C@H](Nc1cc(C(F)F)c(-c2sc(C(=O)N[C@@H]3CC[C@H]3O)nc2C(=O)N2C3CCC2CC3)cn1)C(F)(F)F]

The title compound was prepared as described in Example 149 substituting trans-2-aminocyclobutanol HCl for 3-hydroxy-3-methylazetidine HCl and ethyl 4-((1s,4s)-7-azabicyclo[2.2.1]heptane-7-carbonyl)-5-(4-(difluoromethyl)-6-(((S)-1,1,1-trifluoropropan-2-yl)amino)pyridin-3-yl)thiazole-2-carboxylate (Intermediate 117) for ethyl (5)-5-(6-(tert-butylamino)-4-(difluoromethyl)pyridin-3-yl)-4-(2-methylpyrrolidine-1-carbonyl)thiazole-2-carboxylate followed by SFC purification (Stationary phase: Lux amylose 2, 5 μm, 250×21.1 mm, Mobile phase: 25% iPrOH+ 0.3% iPrNH$_2$, 75% CO$_2$) of Example 290. MS (ESI): mass calcd. for $C_{24}H_{26}F_5N_5O_3S$, 559.2; m/z found, 560.2 [M+H]$^+$. $^1$H NMR (400 MHz, CDCl$_3$) δ 8.09 (s, 1H), 7.39 (d, J=4.9 Hz, 1H), 6.93-6.62 (m, 2H), 5.01-4.90 (m, 1H), 4.81-4.74 (m, 1H), 4.71-4.65 (m, 1H), 4.25-4.01 (m, 3H), 3.13 (s, 1H), 2.29-2.14 (m, 2H), 1.84-1.71 (m, 3H), 1.55-1.50 (m, 3H), 1.49-1.40 (m, 7H).

Example 292

4-((1s,4s)-7-Azabicyclo[2.2.1]heptane-7-carbonyl)-5-(4-(difluoromethyl)-6-(((S)-1,1,1-trifluoropropan-2-yl)amino)pyridin-3-yl)-N-((1S*,2S*)-2-hydroxycyclobutyl)thiazole-2-carboxamide

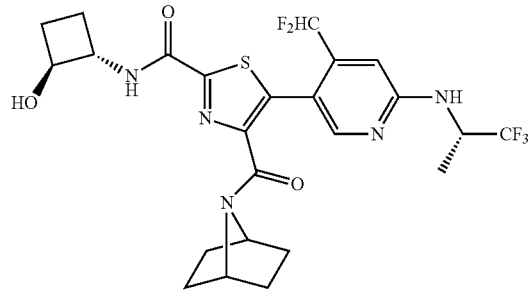 [SMILES: C[C@H](Nc1cc(C(F)F)c(-c2sc(C(=O)N[C@H]3CC[C@@H]3O)nc2C(=O)N2C3CCC2CC3)cn1)C(F)(F)F]

The title compound was prepared as described in Example 149 substituting trans-2-aminocyclobutanol HCl for 3-hydroxy-3-methylazetidine HCl and ethyl 4-((1s,4s)-7-azabicyclo[2.2.1]heptane-7-carbonyl)-5-(4-(difluoromethyl)-6-(((S)-1,1,1-trifluoropropan-2-yl)amino)pyridin-3-yl)thiazole-2-carboxylate (Intermediate 117) for ethyl (S)-5-(6-(tert-butylamino)-4-(difluoromethyl)pyridin-3-yl)-4-(2-methylpyrrolidine-1-carbonyl)thiazole-2-carboxylate followed by SFC purification (Stationary phase: Lux amylose 2, 5 μm, 250×21.1 mm, Mobile phase: 25% iPrOH+ 0.3% iPrNH$_2$, 75% CO$_2$) of Example 290. MS (ESI): mass calcd. for $C_{24}H_{26}F_5N_5O_3S$, 559.2; m/z found, 560.2 [M+H]$^+$. $^1$H NMR (400 MHz, CDCl$_3$) δ 8.09 (s, 1H), 7.39 (d, J=4.9 Hz, 1H), 6.92-6.61 (m, 2H), 5.02-4.89 (m, 1H), 4.83-4.77 (m, 1H), 4.70-4.64 (m, 1H), 4.27-4.01 (m, 3H), 3.16 (s, 1H), 2.29-2.14 (m, 2H), 1.83-1.70 (m, 3H), 1.57-1.50 (m, 3H), 1.50-1.40 (m, 7H).

Example 293

4-((1s,4s)-7-Azabicyclo[2.2.1]heptane-7-carbonyl)-5-(4-(difluoromethyl)-6-(((S)-1,1,1-trifluoropropan-2-yl)amino)pyridin-3-yl)-N-((1S,2S)-2-hydroxycyclopentyl)thiazole-2-carboxamide

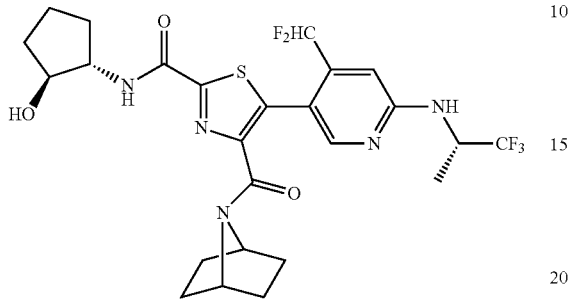

The title compound was prepared as described in Example 149 substituting (1S,2S)-2-aminocylclopentanol HCl for 3-hydroxy-3-methylazetidine HCl and ethyl 4-((1 s,4s)-7-azabicyclo[2.2.1]heptane-7-carbonyl)-5-(4-(difluoromethyl)-6-(((S)-1,1,1-trifluoropropan-2-yl)amino)pyridin-3-yl)thiazole-2-carboxylate (Intermediate 117) for ethyl (S)-5-(6-(tert-butylamino)-4-(difluoromethyl)pyridin-3-yl)-4-(2-methylpyrrolidine-1-carbonyl)thiazole-2-carboxylate. MS (ESI): mass calcd. for $C_{25}H_{28}F_5N_5O_3S$, 573.2; m/z found, 574.2 [M+H]$^+$. $^1$H NMR (500 MHz, CDCl$_3$) δ 8.09 (s, 1H), 7.27-7.24 (m, 1H), 6.89-6.64 (m, 2H), 4.99-4.90 (m, 1H), 4.79 (d, J=9.5 Hz, 1H), 4.71-4.64 (m, 1H), 4.24-4.00 (m, 3H), 3.74-3.69 (m, 1H), 2.32-2.24 (m, 1H), 2.14-2.05 (m, 1H), 1.94-1.69 (m, 5H), 1.66-1.49 (m, 3H), 1.48-1.39 (m, 7H).

Example 294

5-(6-((1-Cyclopropyl-2,2,2-trifluoroethyl)amino)-4-difluoromethyl)pyridine-3-yl)-N-(2-hydroxy-2-methylpropyl)-4-((S)-2-methylpyrrolidine-1-carbonyl)thiazole-2-carboxamide

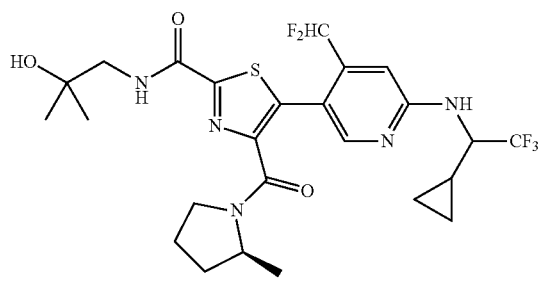 [SMILES: C[C@H]1CCCN1C(=O)c1nc(C(=O)NCC(C)(C)O)sc1-c1cnc(NC(C2CC2)C(F)(F)F)cc1C(F)F]

The title compound was prepared as described in Example 71, using 5-bromo-N-(1-cyclopropyl-2,2,2-trifluoroethyl)-4-(difluoromethyl)pyridin-2-amine (Intermediate 118, Step B) in place of 5-bromo-N-cyclopentyl-4-(difluoromethyl)pyridin-2-amine and (S)—N-(2-hydroxy-2-methylpropyl)-4-(2-methylpyrrolidine-1-carbonyl)thiazole-2-carboxamide (Intermediate 69) in place of (S)—N-((1-hydroxycyclobutyl)methyl)-4-(2-methylpyrrolidine-1-carbonyl)thiazole-2-carboxamide. MS (ESI): mass calcd. for $C_{25}H_{30}F_5N_5O_3S$ 575.2 m/z, found 576.0 [M+H]$^+$. $^1$H NMR (400 MHz, DMSO-d$_6$) δ 8.49-8.36 (m, 1H), 8.04 (s, 1H), 7.86 (d, J=9.0 Hz, 1H), 7.16-6.80 (m, 2H), 4.72-4.65 (m, 1H), 4.56-4.42 (m, 1H), 4.32-3.97 (m, 1H), 3.46-3.36 (m, 2H), 3.29-3.19 (m, 2H), 1.99-1.42 (m, 4H), 1.20-1.14 (m, 1H), 1.11 (s, 6H), 1.07 (d, J=6.2 Hz, 2H), 0.98-0.90 (m, 1H), 0.70-0.60 (m, 1H), 0.57-0.44 (m, 2H), 0.39-0.28 (m, 1H).

Example 295

5-(6-(((S)-1-Cyclopropyl-2,2,2-trifluoroethyl)amino)-4-difluoromethyl)pyridine-3-yl)-N-(2-hydroxy-2-methylpropyl)-4-((S)-2-methylpyrrolidine-1-carbonyl)thiazole-2-carboxamide

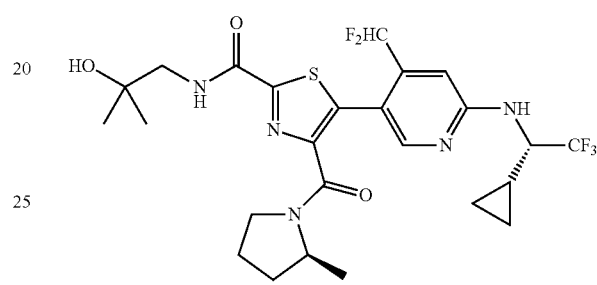

The title compound was prepared as described in Example 71, using (S)-5-bromo-N-(1-cyclopropyl-2,2,2-trifluoroethyl)-4-(difluoromethyl)pyridin-2-amine (Intermediate 119) in place of 5-bromo-N-cyclopentyl-4-(difluoromethyl)pyridin-2-amine and (S)—N-(2-hydroxy-2-methylpropyl)-4-(2-methylpyrrolidine-1-carbonyl)thiazole-2-carboxamide (Intermediate 69) in place of (S)—N-((1-hydroxycyclobutyl)methyl)-4-(2-methylpyrrolidine-1-carbonyl)thiazole-2-carboxamide. MS (ESI): mass calcd. for $C_{25}H_{30}F_5N_5O_3S$ 575.2 m/z, found 576.0 [M+H]$^+$. $^1$H NMR (400 MHz, DMSO-d$_6$) δ 8.50-8.36 (m, 1H), 8.03 (s, 1H), 7.86 (d, J=9.0 Hz, 1H), 7.22-6.82 (m, 2H), 4.73-4.64 (m, 1H), 4.57-4.42 (m, 1H), 4.32-3.96 (m, 1H), 3.44-3.36 (m, 2H), 3.29-3.18 (m, 2H), 2.02-1.40 (m, 4H), 1.20-1.03 (m, 9H), 0.94 (d, J=6.4 Hz, 1H), 0.70-0.59 (m, 1H), 0.58-0.43 (m, 2H), 0.40-0.26 (m, 1H).

Example 296

(S)-5-(4-Difluoromethyl)-6-((4,4,4-trifluoro-2-methylbutan-2-yl)amino)pyridine-3-yl)-N-(2-hydroxy-2-methylpropyl)-4-(2-methylpyrrolidine-1-carbonyl)thiazole-2-carboxamide

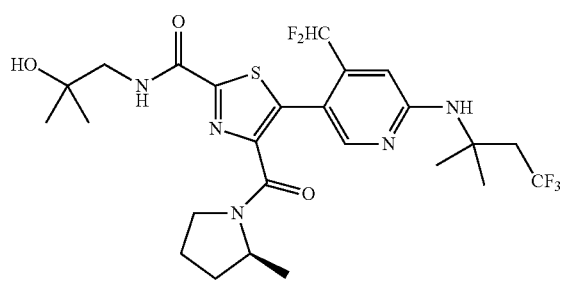 [SMILES: C[C@H]1CCCN1C(=O)c1nc(C(=O)NCC(C)(C)O)sc1-c1cnc(NC(C)(C)CC(F)(F)F)cc1C(F)F]

The title compound was prepared as described in Example 71, using 5-bromo-4-(difluoromethyl)-N-(4,4,4-trifluoro-2-methylbutan-2-yl)pyridin-2-amine (Intermediate 120) in place of 5-bromo-N-cyclopentyl-4-(difluoromethyl)pyridin-2-amine and (S)—N-(2-hydroxy-2-methylpropyl)-4-(2-methylpyrrolidine-1-carbonyl)thiazole-2-carboxamide (Intermediate 69) in place of (S)—N-((1-hydroxycyclobutyl)methyl)-4-(2-methylpyrrolidine-1-carbonyl)thiazole-2-carboxamide. MS (ESI): mass calcd. for $C_{25}H_{32}F_5N_5O_3S$ 577.2 m/z, found 578.0 [M+H]$^+$. $^1$H NMR (400 MHz, DMSO-$d_6$) δ 8.47-8.35 (m, 1H), 8.03-7.97 (m, 1H), 7.28-7.22 (m, 1H), 7.13-6.79 (m, 2H), 4.70-4.65 (m, 1H), 4.21-3.95 (m, 1H), 3.43-3.33 (m, 1H), 3.28-3.18 (m, 3H), 3.12-2.93 (m, 2H), 1.97-1.58 (m, 3H), 1.52-1.32 (m, 7H), 1.10 (s, 6H), 1.07-0.87 (m, 3H).

Example 297

5-(4-(Difluoromethyl)-6-(((R)-3-methylbutan-2-yl)amino)pyridine-3-yl)-N-(2-hydroxy-2-methylpropyl)-4-((S)-2-methylpyrrolidine-1-carbonyl)thiazole-2-carboxamide

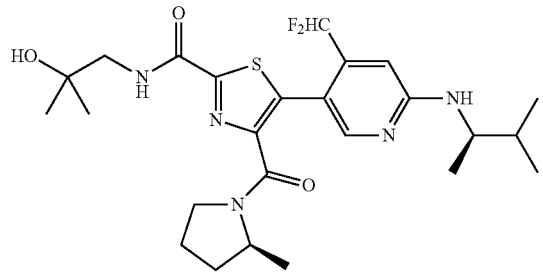 [SMILES: CC(C)[C@@H](C)Nc1cc(C(F)F)c(-c2sc(C(=O)NCC(C)(C)O)nc2C(=O)N2CCC[C@@H]2C)cn1]

The title compound was prepared as described in Example 71, using (R)-5-bromo-4-(difluoromethyl)-N-(3-methylbutan-2-yl)pyridin-2-amine (Intermediate 121) in place of 5-bromo-N-cyclopentyl-4-(difluoromethyl)pyridin-2-amine and (S)—N-(2-hydroxy-2-methylpropyl)-4-(2-methylpyrrolidine-1-carbonyl)thiazole-2-carboxamide (Intermediate 69) in place of (S)—N-((1-hydroxycyclobutyl)methyl)-4-(2-methylpyrrolidine-1-carbonyl)thiazole-2-carboxamide. MS (ESI): mass calcd. for $C_{25}H_{35}F_2N_5O_3S$ 523.2 m/z, found 524.1 [M+H]$^+$. $^1$H NMR (400 MHz, DMSO-$d_6$) δ 8.19-8.03 (m, 1H), 7.98 (s, 1H), 7.05-6.69 (m, 3H), 4.46 (s, 1H), 4.29-3.99 (m, 1H), 3.97-3.87 (m, 1H), 3.52-3.23 (m, 4H), 2.02-1.41 (m, 5H), 1.14 (s, 6H), 1.11-0.94 (m, 6H), 0.93-0.85 (m, 6H).

Example 298

5-(4-(Difluoromethyl)-6-(((R)-3,3-dimethylbutan-2-yl)amino)pyridin-3-yl)-N-(2-hydroxy-2-methylpropyl)-4-((S)-2-methylpyrrolidine-1-carbonyl)thiazole-2-carboxamide

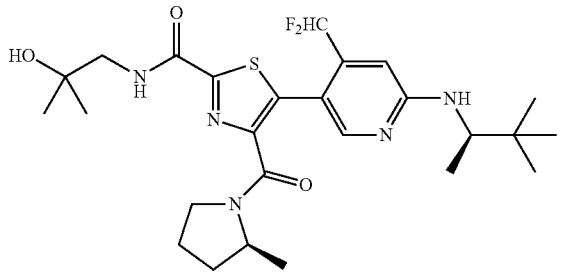 [SMILES: C[C@H]1CCCN1C(=O)c1nc(C(=O)NCC(C)(C)O)sc1-c1cnc(N[C@H](C)C(C)(C)C)cc1C(F)F]

The title compound was prepared as described in Example 71, using (R)-5-bromo-4-(difluoromethyl)-N-(3,3-dimethylbutan-2-yl)pyridin-2-amine (Intermediate 122) in place of 5-bromo-N-cyclopentyl-4-(difluoromethyl)pyridin-2-amine and (S)—N-(2-hydroxy-2-methylpropyl)-4-(2-methylpyrrolidine-1-carbonyl)thiazole-2-carboxamide (Intermediate 69) in place of (S)—N-((1-hydroxycyclobutyl)methyl)-4-(2-methylpyrrolidine-1-carbonyl)thiazole-2-carboxamide. MS (ESI): mass calcd. for $C_{26}H_{37}F_2N_5O_3S$ 537.3 m/z, found 538.0 [M+H]$^+$. $^1$H NMR (400 MHz, DMSO-$d_6$, t=80° C.) δ 8.19-8.02 (m, 1H), 7.97 (s, 1H), 7.07-6.64 (m, 3H), 4.45 (s, 1H), 4.22-3.99 (m, 2H), 3.48-3.23 (m, 4H), 2.02-1.35 (m, 4H), 1.14 (s, 6H), 1.11-0.94 (m, 6H), 0.92 (s, 9H).

Example 299

5-(4-(Difluoromethyl)-6-(((S)-3,3-dimethylbutan-2-yl)amino)pyridin-3-yl)-N-(2-hydroxy-2-methylpropyl)-4-((S)-2-methylpyrrolidine-1-carbonyl)thiazole-2-carboxamide

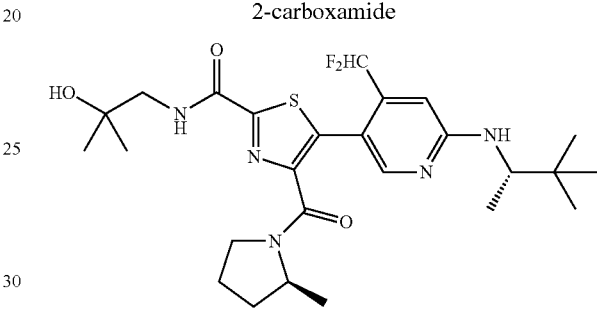

The title compound was prepared as described in Example 71, using (S)-5-bromo-4-(difluoromethyl)-N-(3,3-dimethylbutan-2-yl)pyridin-2-amine (Intermediate 123) in place of 5-bromo-N-cyclopentyl-4-(difluoromethyl)pyridin-2-amine and (S)—N-(2-hydroxy-2-methylpropyl)-4-(2-methylpyrrolidine-1-carbonyl)thiazole-2-carboxamide (Intermediate 69) in place of (S)—N-((1-hydroxycyclobutyl)methyl)-4-(2-methylpyrrolidine-1-carbonyl)thiazole-2-carboxamide. MS (ESI): mass calcd. for $C_{26}H_{37}F_2N_5O_3S$ 537.3 m/z, found 538.3 [M+H]$^+$. $^1$H NMR (400 MHz, DMSO-$d_6$) δ 8.42-8.31 (m, 1H), 7.94 (s, 1H), 7.12-6.76 (m, 3H), 4.68-4.63 (m, 1H), 4.20-3.95 (m, 2H), 3.43-3.32 (m, 1H), 3.29-3.19 (m, 3H), 2.00-1.38 (m, 4H), 1.16-0.96 (m, 12H), 0.89 (s, 9H).

Example 300

5-(4-(Difluoromethyl)-6-(((S)-3-methylbutan-2-yl)amino)pyridin-3-yl)-N-(2-hydroxy-2-methylpropyl)-4-((S)-2-methylpyrrolidine-1-carbonyl)thiazole-2-carboxamide

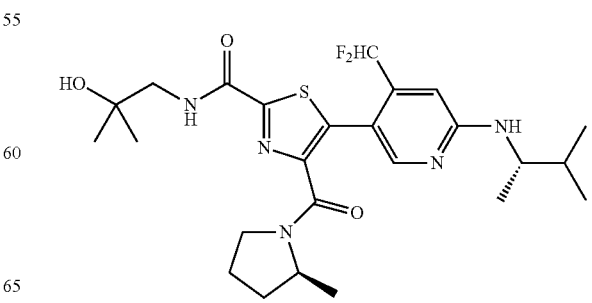

The title compound was prepared as described in Example 71, using (S)-5-bromo-4-(difluoromethyl)-N-(3-methylbutan-2-yl)pyridin-2-amine (Intermediate 124) in place of 5-bromo-N-cyclopentyl-4-(difluoromethyl)pyridin-2-amine and (S)—N-(2-hydroxy-2-methylpropyl)-4-(2-methylpyrrolidine-1-carbonyl)thiazole-2-carboxamide (Intermediate 69) in place of (S)—N-((1-hydroxycyclobutyl)methyl)-4-(2-methylpyrrolidine-1-carbonyl)thiazole-2-carboxamide. MS (ESI): mass calcd. for $C_{25}H_{35}F_2N_5O_3S$ 523.2 m/z, found 524.1 [M+H]+. $^1$H NMR (400 MHz, DMSO-$d_6$) δ 8.46-8.33 (m, 1H), 7.96 (s, 1H), 7.20-6.73 (m, 3H), 4.72-4.64 (m, 1H), 4.23-3.97 (m, 1H), 3.95-3.82 (m, 1H), 3.49-3.37 (m, 2H), 3.28-3.17 (m, 2H), 2.04-1.36 (m, 5H), 1.18-1.00 (m, 12H), 0.93-0.84 (m, 6H).

Example 301

(S)-5-(6-(((Cyclobutylmethyl)amino)-4-(difluoromethyl)pyridine-3-yl)-N-(2-hydroxy-2-methylpropyl)-4-(2-methylpyrrolidine-1-carbonyl)thiazole-2-carboxamide

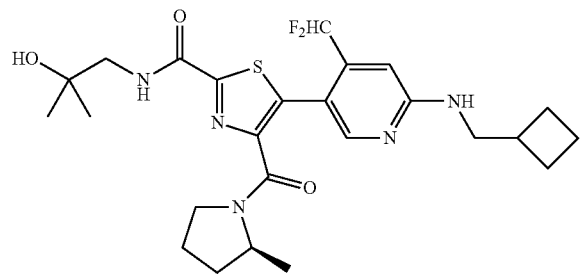 [SMILES: C[C@H]1CCCN1C(=O)c1nc(C(=O)NCC(C)(C)O)sc1-c1cnc(NCC2CCC2)cc1C(F)F]

The title compound was prepared as described in Example 71, using 5-bromo-N-(cyclobutylmethyl)-4-(difluoromethyl)pyridin-2-amine (Intermediate 125) in place of 5-bromo-N-cyclopentyl-4-(difluoromethyl)pyridin-2-amine and (S)—N-(2-hydroxy-2-methylpropyl)-4-(2-methylpyrrolidine-1-carbonyl)thiazole-2-carboxamide (Intermediate 69) in place of (S)—N-((1-hydroxycyclobutyl)methyl)-4-(2-methylpyrrolidine-1-carbonyl)thiazole-2-carboxamide. MS (ESI): mass calcd. for $C_{25}H_{33}F_2N_5O_3S$ 521.2 m/z, found 522.1 [M+H]+. $^1$H NMR (400 MHz, DMSO-$d_6$) δ 8.43-8.31 (m, 1H), 7.97 (s, 1H), 7.34-7.26 (m, 1H), 7.12-6.76 (m, 1H), 6.73 (s, 1H), 4.71-4.64 (m, 1H), 4.22-3.95 (m, 1H), 3.31-3.15 (m, 6H), 2.57-2.52 (m, 1H), 2.05-1.90 (m, 3H), 1.87-1.77 (m, 3H), 1.74-1.60 (m, 3H), 1.58-1.40 (m, 1H), 1.14-0.88 (m, 9H).

Example 302

(S)-5-(6-(tert-Butylamino)-4-(trifluoromethyl)pyridin-3-yl)-4-(2-methylpyrrolidine-1-carbonyl)-N-((5-oxo-4,5-dihydro-1H-1,2,4-triazol-3-yl)methyl)thiazole-2-carboxamide

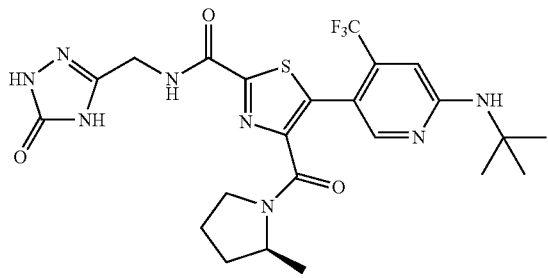 [SMILES: C[C@H]1CCCN1C(=O)c1nc(C(=O)NCc2n[nH]c(=O)[nH]2)sc1-c1cnc(NC(C)(C)C)cc1C(F)(F)F]

1,1'-Carbonyldiimidazole (14 mg, 0.087 mmol) was added to a solution of (S)-5-(6-(tert-butylamino)-4-(trifluoromethyl)pyridin-3-yl)-4-(2-methylpyrrolidine-1-carbonyl)thiazole-2-carboxylic acid (40 mg, 0.079 mmol, Intermediate 126) in DMF (0.3 mL), and the solution was maintained at rt for 1.5 h. After this time, 5-(aminomethyl)-2,4-dihydro-3H-1,2,4-triazol-3-one hydrochloride (14 mg, 0.095 mmol) and then DIPEA (0.016 mL, 0.095 mmol) were added, and the mixture was stirred at rt for 1 h. The mixture was then diluted with MeOH, filtered, and purified by preparative HPLC (XBridge $C_{18}$, MeCN/water, 0.05% TFA) to afford the title compound. MS (ESI): mass calcd. for $C_{23}H_{27}F_3N_8O_3S$, 552.2; m/z found, 552.8 [M+H]+. $^1$H NMR (400 MHz, DMSO-$d_6$, mixture of rotamers) δ 11.37-11.22 (m, 2H of both rotamers), 9.24 (t, J=6.1 Hz, 1H of major rotamer), 9.19 (t, J=6.2 Hz, 1H of minor rotamer), 8.05 (s, 1H of both rotamers), 7.22 (s, 1H of both rotamers), 6.94 (s, 1H of both rotamers), 4.50-4.40 (m, 1H of minor rotamer), 4.38-4.22 (m, 2H of both rotamers), 4.07-3.97 (m, 1H of major rotamer), 3.58-3.50 (m, 1H of both rotamers), 3.43-3.32 (m, 1H of both rotamers), 2.02-1.45 (m, 4H of both rotamers), 1.41 (s, 9H of both rotamers), 1.10 (d, J=6.3 Hz, 3H of major rotamer), 0.94 (d, J=6.4 Hz, 3H of minor rotamer).

Example 303

(S)—N-((1H-Tetrazol-5-yl)methyl)-5-(6-(tert-butylamino)-4-(trifluoromethyl)pyridin-3-yl)-4-(2-methylpyrrolidine-1-carbonyl)thiazole-2-carboxamide

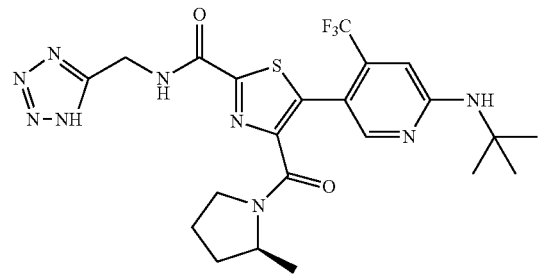 [SMILES: C[C@H]1CCCN1C(=O)c1nc(C(=O)NCc2nnn[nH]2)sc1-c1cnc(NC(C)(C)C)cc1C(F)(F)F]

The title compound was prepared as described in Example 302, substituting 1H-1,2,3,4-tetrazol-5-ylmethanamine for 5-(aminomethyl)-2,4-dihydro-3H-1,2,4-triazol-3-one hydrochloride. MS (ESI): mass calcd. for $C_{22}H_{26}F_3N_9O_2S$, 537.2; m/z found, 538.0 [M+H]+. $^1$H NMR (400 MHz, DMSO-$d_6$, tetrazole proton not observed) δ 9.60 (t, J=6.0 Hz, 1H of major rotamer), 9.55 (t, J=6.0 Hz, 1H of minor rotamer), 8.06 (s, 1H of major rotamer), 8.06 (s, 1H of minor rotamer), 7.23 (s, 1H of both rotamers), 6.95 (s, 1H of both rotamers), 4.86-4.74 (m, 2H of both rotamers), 4.44 (s, 1H of minor rotamer), 4.06-3.98 (m, 1H of major rotamer), 3.58-3.51 (m, 1H of major rotamer), 3.43-3.34 (m, 1H of both rotamers and 1H minor rotamer), 2.01-1.83 (m, 2H of both rotamers), 1.79-1.66 (m, 1H of both rotamers), 1.64-1.57 (m, 1H of minor rotamer), 1.54-1.46 (m, 1H of major rotamer), 1.41 (s, 9H of both rotamers), 1.10 (d, J=6.2 Hz, 3H of major rotamer), 0.95 (d, J=6.4 Hz, 3H of minor rotamer).

Example 304

5-(4-(Difluoromethyl)-6-(((R)-1,1,1-trifluoropropan-2-yl)amino)pyridin-3-yl)-N—((S)-3-hydroxy-3-methylbutan-2-yl)-4-((S)-2-methylpyrrolidine-1-carbonyl)thiazole-2-carboxamide

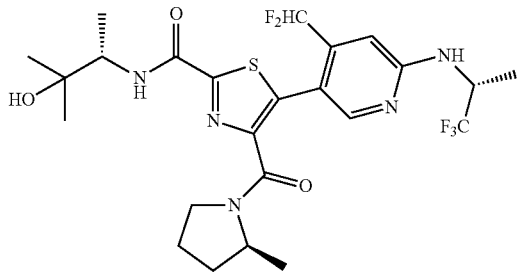 [SMILES: C[C@H](NC(=O)c1nc(C(=O)N2CCC[C@@H]2C)c(-c2cnc(N[C@H](C)C(F)(F)F)cc2C(F)F)s1)C(C)(C)O]

The title compound was prepared as described in Intermediate 62, Step A, substituting (R)-5-bromo-4-(difluoromethyl)-N-(1,1,1-trifluoropropan-2-yl)pyridin-2-amine (Intermediate 138) and N—((S)-3-hydroxy-3-methylbutan-2-yl)-4-((S)-2-methylpyrrolidine-1-carbonyl)thiazole-2-carboxamide (Intermediate 139) for 5-bromo-N-cyclopentyl-4-(difluoromethyl)pyridin-2-amine and ethyl (S)-4-(2-methylpyrrolidine-1-carbonyl)thiazole-2-carboxylate. MS (ESI): mass calcd. for $C_{24}H_{30}F_5N_5O_3S$ 563.2 m/z, found 564.0 [M+H]$^+$. $^1$H NMR (400 MHz, DMSO-d6, 80° C.) δ 8.09 (s, 1H), 7.92-7.80 (m, 1H), 7.55 (d, J=9.0 Hz, 1H), 7.10-6.77 (m, 2H), 5.02 (d, J=15.3 Hz, 1H), 4.49 (s, 1H), 4.19-3.87 (m, 2H), 3.47-3.33 (m, 2H), 2.05-1.81 (m, 2H), 1.77-1.42 (m, 2H), 1.36 (d, J=7.0 Hz, 3H), 1.22-1.17 (m, 6H), 1.15 (s, 3H), 1.13-1.08 (m, 2H), 1.07-1.00 (m, 1H).

Example 305

(S)-5-(6-(tert-Butylamino)-4-(trifluoromethyl)pyridin-3-yl)-4-(2-methylpyrrolidine-1-carbonyl)-N-((5-oxo-4,5-dihydro-1,3,4-oxadiazol-2-yl)methyl)thiazole-2-carboxamide

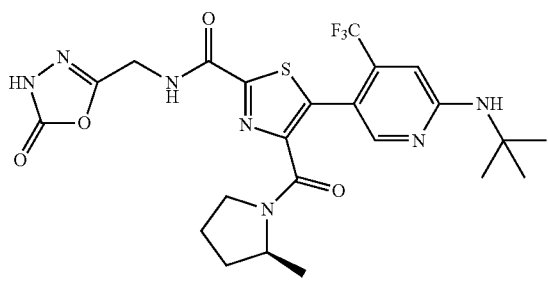 [SMILES: C[C@H]1CCCN1C(=O)c1nc(C(=O)NCc2n[nH]c(=O)o2)sc1-c1cnc(NC(C)(C)C)cc1C(F)(F)F]

The title compound was prepared as described in Example 302, substituting 5-(aminomethyl)-1,3,4-oxadiazol-2-(3H)-one hydrochloride for 5-(aminomethyl)-2,4-dihydro-3H-1,2,4-triazol-3-one hydrochloride. MS (ESI): mass calcd. for $C_{23}H_{26}F_3N_7O_4S$, 553.2; m/z found, 553.9 [M+H]$^+$. $^1$H NMR (400 MHz, CDCl$_3$, mixture of rotamers) δ 10.17 (br s, 1H of major rotamer), 10.05 (s, 1H of minor rotamer), 8.15 (s, 1H of both rotamers), 8.00 (t, J=6.2 Hz, 1H of major rotamer), 7.82 (t, J=6.2 Hz, 1H of minor rotamer), 6.651 (s, 1H of minor rotamer), 6.645 (s, 1H of major rotamer), 4.99 (s, 1H of minor rotamer), 4.97 (s, 1H of major rotamer), 4.67-4.52 (m, 2H of both rotamers), 4.27-4.18 (m, 1H of major rotamer), 4.18-4.10 (m, 1H of minor rotamer), 3.61-3.55 (m, 2H both of minor rotamer), 3.37-3.29 (m, 1H of major rotamer), 3.27-3.18 (m, 1H of major rotamer), 2.10-1.43 (m, 4H of both rotamers), 1.46 (s, 9H of both rotamers), 1.22 (d, J=6.2 Hz, 3H of major rotamer), 1.03 (d, J=6.4 Hz, 3H of minor rotamer).

Example 306

5-(4-(Difluoromethyl)-6-(((R)-1,1,1-trifluoropropan-2-yl)amino)pyridin-3-yl)-N—((R)-3-hydroxy-3-methylbutan-2-yl)-4-((S)-2-methylpyrrolidine-1-carbonyl)thiazole-2-carboxamide

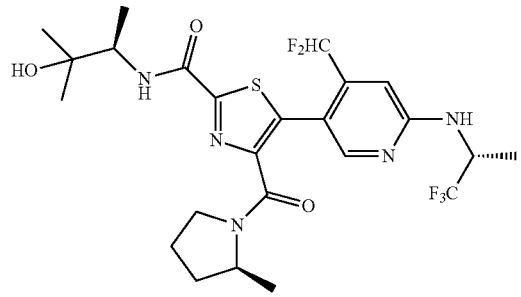 [SMILES: C[C@H]1CCCN1C(=O)c1nc(C(=O)N[C@H](C)C(C)(C)O)sc1-c1cnc(N[C@H](C)C(F)(F)F)cc1C(F)F]

The title compound was prepared as described in Intermediate 62, Step A, substituting (R)-5-bromo-4-(difluoromethyl)-N-(1,1,1-trifluoropropan-2-yl)pyridin-2-amine (Intermediate 138) and N—((R)-3-hydroxy-3-methylbutan-2-yl)-4-((S)-2-methylpyrrolidine-1-carbonyl)thiazole-2-carboxamide (Intermediate 132) for 5-bromo-N-cyclopentyl-4-(difluoromethyl)pyridin-2-amine and ethyl (S)-4-(2-methylpyrrolidine-1-carbonyl)thiazole-2-carboxylate. MS (ESI): mass calcd. for $C_{24}H_{30}F_5N_5O_3S$ 563.2, m/z found 564.0 [M+H]$^+$. $^1$H NMR (400 MHz, DMSO-d$_6$) δ 8.10 (d, J=9.5 Hz, 1H), 8.05 (s, 1H), 7.75 (d, J=8.8 Hz, 1H), 7.13-6.81 (m, 2H), 5.06-4.94 (m, 1H), 4.71 (br. s, 1H), 4.24-3.82 (m, 2H), 2.07-1.49 (m, 4H), 1.46-1.36 (m, 1H), 1.30 (d, J=6.8 Hz, 3H), 1.17-1.06 (m, 10H), 1.04 (d, J=6.4 Hz, 2H), 0.93 (d, J=6.4 Hz, 1H).

Example 307

(S)-5-(6-(tert-Butylamino)-4-(trifluoromethyl)pyridin-3-yl)-N-methyl-4-(2-methylpyrrolidine-1-carbonyl)thiazole-2-carboxamide

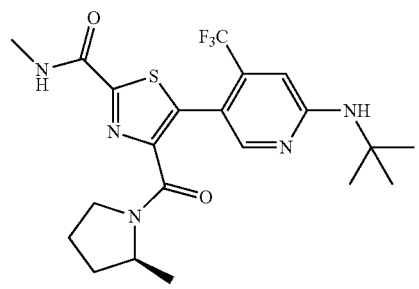 [SMILES: CNC(=O)c1nc(C(=O)N2CCC[C@@H]2C)c(-c2cnc(NC(C)(C)C)cc2C(F)(F)F)s1]

The title compound was prepared as described in Example 302, substituting aqueous methylamine (40% w/w, 5 equiv.) for 5-(aminomethyl)-2,4-dihydro-3H-1,2,4-triazol-3-one hydrochloride and omitting DIPEA. MS (ESI): mass calcd. for $C_{21}H_{26}F_3N_5O_2S$, 469.2; m/z found, 469.9 [M+H]$^+$. $^1$H NMR (500 MHz, CDCl$_3$, mixture of rotamers) δ 7.96 (s, 1H of major rotamer), 7.95 (s, 1H of minor rotamer), 7.14 (appar q, J=5.1 Hz, 1H of major rotamer), 7.13 (s, 1H of minor rotamer), 7.10 (s, 1H of major rotamer), 7.08-7.03 (m, 1H of minor rotamer), 6.02 (br s, NH), 4.68-4.61 (m, 1H of minor rotamer), 4.23-4.16 (m, 1H of major rotamer), 3.79-3.72 (m, 1H of major rotamer), 3.63-3.50 (m, 1H of both rotamers, 1H of minor rotamer), 3.10-3.04 (m, 3H of both rotamers), 2.12-2.04 (m, 1H of both rotamers), 2.03-1.77 (m, 2H of both rotamers), 1.75-1.68 (m, 1H of minor rotamer), 1.63-1.55 (m, 1H of major rotamer), 1.52 (s, 9H of both rotamers), 1.25 (d, J=6.2 Hz, 3H of major rotamer), 1.11 (d, J=6.4 Hz, 3H of minor rotamer).

Example 308

(S)-5-(6-(tert-Butylamino)-4-(trifluoromethyl)pyridin-3-yl)-4-(2-methylpyrrolidine-1-carbonyl)thiazole-2-carboxamide

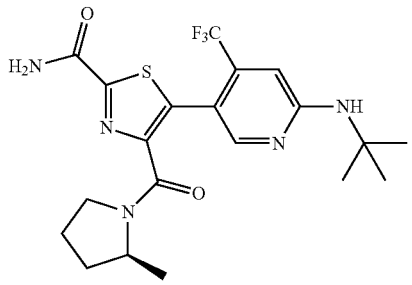 [SMILES: C[C@H]1CCCN1C(=O)c1nc(C(N)=O)sc1-c1cnc(NC(C)(C)C)cc1C(F)(F)F]

The title compound was prepared as described in Example 302, substituting aqueous ammonia (33% w/w, 5 equiv.) for 5-(aminomethyl)-2,4-dihydro-3H-1,2,4-triazol-3-one hydrochloride and omitting DIPEA. MS (ESI): mass calcd. for $C_{20}H_{24}F_3N_5O_2S$, 455.2; m/z found, 456.0 [M+H]$^+$. $^1$H NMR (500 MHz, CDCl$_3$, mixture of rotamers) δ 8.18 (s, 1H of both rotamers), 7.12 (s, 1H of major rotamer), 7.04 (s, 1H of minor rotamer), 6.64 (s, 1H of minor rotamer), 6.63 (s, 1H of major rotamer), 5.97 (s, 1H of minor rotamer), 5.93 (s, 1H of major rotamer), 4.95 (s, 1H of both rotamers), 4.34-4.27 (m, 1H of minor rotamer), 4.25-4.17 (m, 1H of major rotamer), 3.64-3.52 (m, 2H both of minor rotamers), 3.52-3.45 (m, 1H of major rotamer), 3.44-3.38 (m, 1H of major rotamer), 2.10-1.49 (m, 4H of both rotamers), 1.46 (s, 9H of both rotamers), 1.24 (d, J=6.3 Hz, 3H of major rotamer), 1.09 (d, J=6.4 Hz, 3H of minor rotamer).

Example 309

(S)-5-(6-(tert-Butylamino)-4-(trifluoromethyl)pyridin-3-yl)-N-ethyl-4-(2-methylpyrrolidine-1-carbonyl)thiazole-2-carboxamide

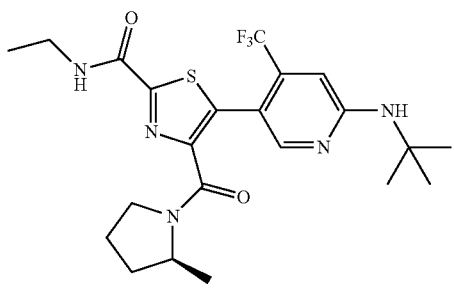 [SMILES: CCNC(=O)c1nc(C(=O)N2CCC[C@@H]2C)c(-c2cnc(NC(C)(C)C)cc2C(F)(F)F)s1]

The title compound was prepared as described in Example 302, substituting ethylamine (5 equiv.) for 5-(aminomethyl)-2,4-dihydro-3H-1,2,4-triazol-3-one hydrochloride and omitting DIPEA. MS (ESI): mass calcd. for $C_{22}H_{28}F_3N_5O_2S$, 483.2; m/z found, 484.0 [M+H]$^+$. $^1$H NMR (500 MHz, CDCl$_3$, mixture of rotamers) δ 7.98 (s, 1H of major rotamer), 7.96 (s, 1H of minor rotamer), 7.14 (t, J=6.0 Hz, 1H of major rotamer), 7.10 (s, 1H of minor rotamer), 7.07 (s, 1H of major rotamer), 7.05 (t, J=5.9 Hz, 1H of minor rotamer), 5.92 (br s, NH), 4.62-4.55 (m, 1H of minor rotamer), 4.23-4.16 (m, 1H of major rotamer), 3.75-3.68 (m, 1H of major rotamer), 3.63-3.47 (m, 3H of both rotamers, 1H of minor rotamer), 2.12-2.03 (m, 1H of both rotamers), 2.03-1.77 (m, 2H of both rotamers), 1.74-1.68 (m, 1H of minor rotamer), 1.62-1.55 (m, 1H of major rotamer), 1.52 (s, 9H of minor rotamer), 1.52 (s, 9H of major rotamer), 1.31 (t, J=7.3 Hz, 3H of both rotamers), 1.26 (d, J=6.2 Hz, 3H of major rotamer), 1.13 (d, J=6.4 Hz, 3H of minor rotamer).

Example 310

5-(6-(((S)-1-Cyclopropyl-2,2,2-trifluoroethyl)amino)-4-(difluoromethyl)pyridin-3-yl)-N-((1r,3S)-3-hydroxycyclobutyl)-4-((S)-2-methylpyrrolidine-1-carbonyl)thiazole-2-carboxamide

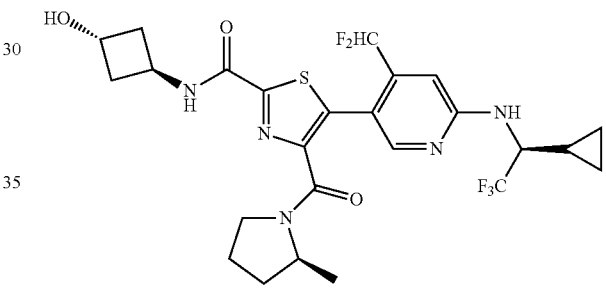

The title compound was prepared as described in Example 149, substituting ethyl 5-(6-(((S)-1-cyclopropyl-2,2,2-trifluoroethyl)amino)-4-(difluoromethyl)pyridin-3-yl)-4-((S)-2-methylpyrrolidine-1-carbonyl)thiazole-2-carboxylate (Intermediate 128) and trans-3-aminocyclobutanol HCl for ethyl (S)-5-(6-(tert-butylamino)-4-(difluoromethyl)pyridin-3-yl)-4-(2-methylpyrrolidine-1-carbonyl)thiazole-2-carboxylate and 3-hydroxy-3-methylazetidine HCl. MS (ESI): mass calcd. for $C_{25}H_{28}F_5N_5O_3S$, 573.2; m/z found, 574.2 [M+H]$^+$. $^1$H NMR (500 MHz, CDCl$_3$, mixture of rotamers) δ 8.85 (br s, 1H of minor rotamer), 8.58 (br s, 1H of major rotamer), 7.91 (s, 1H of major rotamer), 7.87 (s, 1H of minor rotamer), 7.24 (d, J=7.1 Hz, 1H of major rotamer), 7.19 (d, J=7.0 Hz, 1H of minor rotamer), 7.03-6.72 (m, CHF$_2$ of both rotamers), 6.94 (s, 1H of minor rotamer), 6.92 (s, 1H of major rotamer), 4.72-4.64 (m, 1H of both rotamers), 4.64-4.58 (m, 1H of both rotamers), 4.52-4.45 (m, 1H of minor rotamer), 4.24-4.17 (m, 1H of major rotamer), 3.72-3.55 (m, 2H of both rotamers plus 1H of minor rotamer), 3.49-3.43 (m, 1H of major rotamer), 3.26 (br s, OH), 2.55-2.41 (m, 4H of both rotamers), 2.15-2.05 (m, 1H of both rotamers), 2.05-1.89 (m, 1H of both rotamers plus 1H of minor rotamer), 1.89-1.79 (m, 1H of major rotamer), 1.75-1.68 (m, 1H of minor rotamer), 1.64-1.55 (m, 1H of major rotamer), 1.39-1.28 (m, 1H of both rotamers), 1.25 (d, J=6.3 Hz, 3H of major rotamer), 1.04 (d, J=6.4 Hz, 3H of minor rotamer), 0.88-0.80 (m, 1H of both rotamers), 0.79-0.70 (m, 1H of both rotamers), 0.65-0.58 (m, 1H of both rotamers), 0.46-0.39 (m, 1H of both rotamers).

Example 311

5-(6-(((S)-1-Cyclopropyl-2,2,2-trifluoroethyl)amino)-4-(difluoromethyl)pyridin-3-yl)-N—((R)-3-hydroxy-3-methylbutan-2-yl)-4-((S)-2-methylpyrrolidine-1-carbonyl)thiazole-2-carboxamide

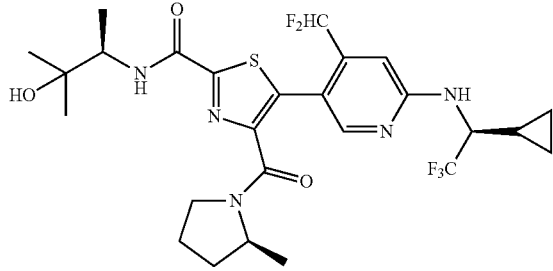 [SMILES: C[C@H]1CCCN1C(=O)c1nc(C(=O)N[C@H](C)C(C)(C)O)sc1-c1cnc(N[C@@H](C2CC2)C(F)(F)F)cc1C(F)F]

The title compound was prepared as described in Example 148, substituting ethyl 5-(6-(((S)-1-cyclopropyl-2,2,2-trifluoroethyl)amino)-4-(difluoromethyl)pyridin-3-yl)-4-((S)-2-methylpyrrolidine-1-carbonyl)thiazole-2-carboxylate (Intermediate 128) and (R)-3-amino-2-methylbutan-2-ol for ethyl (S)-5-(6-(tert-butylamino)-4-(difluoromethyl)pyridin-3-yl)-4-(2-methylpyrrolidine-1-carbonyl)thiazole-2-carboxylate and (R)-(−)-2-amino-1-propanol. MS (ESI): mass calcd. for $C_{26}H_{32}F_5N_5O_3S$, 589.2; m/z found, 590.2 [M+H]$^+$. $^1$H NMR (500 MHz, CDCl$_3$, mixture of rotamers) δ 9.45 (br s, 1H of minor rotamer), 9.16 (br s, 1H of major rotamer), 7.89 (s, 1H of major rotamer), 7.86 (s, 1H of minor rotamer), 7.43-7.36 (m, 1H of both rotamers), 7.00-6.72 (m, CHF$_2$ of both rotamers), 6.97 (s, 1H of minor rotamer), 6.96 (s, 1H of major rotamer), 4.80 (br s, OH), 4.65-4.57 (m, 1H of minor rotamer), 4.24-4.15 (m, 1H of major rotamer), 4.14-4.04 (m, 1H of both rotamers), 3.79-3.71 (m, 1H of major rotamer), 3.63-3.47 (m, 2H of both rotamers plus 1H of minor rotamer), 2.15-2.05 (m, 1H of both rotamers), 2.04-1.89 (m, 1H of both rotamers plus 1H of minor rotamer), 1.89-1.80 (m, 1H of major rotamer), 1.75-1.69 (m, 1H of minor rotamer), 1.64-1.56 (m, 1H of major rotamer), 1.41-1.33 (m, 1H of both rotamers), 1.33-1.29 (m, 9H of both rotamers), 1.26 (d, J=6.3 Hz, 3H of major rotamer), 1.11 (d, J=6.4 Hz, 3H of minor rotamer), 0.89-0.81 (m, 1H of both rotamers), 0.81-0.72 (m, 1H of both rotamers), 0.66-0.59 (m, 1H of both rotamers), 0.46-0.38 (m, 1H of both rotamers).

Example 312

5-(6-(((S)-1-Cyclopropyl-2,2,2-trifluoroethyl)amino)-4-(difluoromethyl)pyridin-3-yl)-N—((S)-3-hydroxy-3-methylbutan-2-yl)-4-((S)-2-methylpyrrolidine-1-carbonyl)thiazole-2-carboxamide

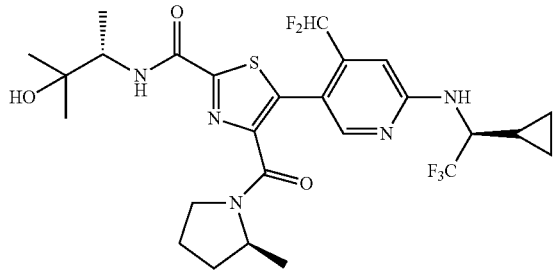 [SMILES: C[C@H](NC(=O)c1nc(C(=O)N2CCC[C@@H]2C)c(-c2cnc(N[C@@H](C3CC3)C(F)(F)F)cc2C(F)F)s1)C(C)(C)O]

The title compound was prepared as described in Example 148, substituting ethyl 5-(6-(((S)-1-cyclopropyl-2,2,2-trifluoroethyl)amino)-4-(difluoromethyl)pyridin-3-yl)-4-((S)-2-methylpyrrolidine-1-carbonyl)thiazole-2-carboxylate (Intermediate 128) and (S)-3-amino-2-methylbutan-2-ol for ethyl (S)-5-(6-(tert-butylamino)-4-(difluoromethyl)pyridin-3-yl)-4-(2-methylpyrrolidine-1-carbonyl)thiazole-2-carboxylate and (R)-(−)-2-amino-1-propanol. MS (ESI): mass calcd. for $C_{26}H_{32}F_5N_5O_3S$, 589.2; m/z found, 590.2 [M+H]$^+$. $^1$H NMR (500 MHz, CDCl$_3$, mixture of rotamers) δ 10.05 (br s, 1H of minor rotamer), 9.86 (br s, 1H of major rotamer), 7.92 (s, 1H of major rotamer), 7.91 (s, 1H of minor rotamer), 7.40 (d, J=9.1 Hz, 1H of both rotamers), 7.03 (s, 1H of minor rotamer), 7.02 (s, 1H of major rotamer), 6.98-6.72 (m, CHF$_2$ of both rotamers), 6.94 (br s, OH), 4.65-4.57 (m, 1H of minor rotamer), 4.23-4.16 (m, 1H of major rotamer), 4.14-4.07 (m, 1H of both rotamers), 3.86-3.80 (m, 1H of major rotamer), 3.63-3.52 (m, 1H of both rotamer plus 1H of minor rotamer), 3.46-3.35 (m, 1H of both rotamers), 2.16-2.06 (m, 1H of both rotamers), 2.06-1.92 (m, 1H of both rotamers plus 1H of minor rotamer), 1.92-1.82 (m, 1H of major rotamer), 1.77-1.71 (m, 1H of minor rotamer), 1.66-1.59 (m, 1H of major rotamer), 1.43-1.36 (m, 1H of both rotamers), 1.35-1.29 (m, 9H of both rotamers), 1.27 (d, J=6.3 Hz, 3H of major rotamer), 1.13 (d, J=6.4 Hz, 3H of minor rotamer), 0.91-0.84 (m, 1H of both rotamers), 0.83-0.75 (m, 1H of both rotamers), 0.68-0.60 (m, 1H of both rotamers), 0.47-0.40 (m, 1H of both rotamers).

Example 313

5-(6-(((S)-1-Cyclopropyl-2,2,2-trifluoroethyl)amino)-4-(difluoromethyl)pyridin-3-yl)-4-((S)-4,4-difluoro-2-methylpyrrolidine-1-carbonyl)-N—((S)-3-hydroxy-3-methylbutan-2-yl)thiazole-2-carboxamide

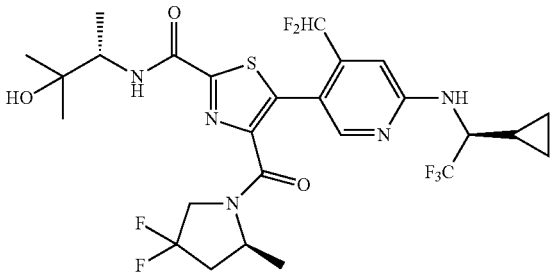 [SMILES: C[C@H](NC(=O)c1nc(C(=O)N2CC(F)(F)C[C@@H]2C)c(-c2cnc(N[C@@H](C3CC3)C(F)(F)F)cc2C(F)F)s1)C(C)(C)O]

The title compound was prepared as described in Example 148, substituting ethyl 5-(6-(((S)-1-cyclopropyl-2,2,2-trifluoroethyl)amino)-4-(difluoromethyl)pyridin-3-yl)-4-((S)-4,4-difluoro-2-methylpyrrolidine-1-carbonyl)thiazole-2-carboxylate (Intermediate 129) and (S)-3-amino-2-methylbutan-2-ol for ethyl (S)-5-(6-(tert-butylamino)-4-(difluoromethyl)pyridin-3-yl)-4-(2-methylpyrrolidine-1-carbonyl)thiazole-2-carboxylate and (R)-(−)-2-amino-1-propanol. MS (ESI): mass calcd. for $C_{26}H_{30}F_7N_5O_3S$, 625.2; m/z found, 626.2 [M+H]$^+$. $^1$H NMR (500 MHz, CDCl$_3$, mixture of rotamers) δ 8.16 (br s, 1H of both rotamers), 7.92 (s, 1H of major rotamer), 7.90 (s, 1H of minor rotamer), 7.35 (d, J=9.2 Hz, 1H of both rotamers), 6.92-6.63 (m, CHF$_2$ of both rotamers), 6.90 (s, 1H of minor rotamer), 6.89 (s, 1H of major rotamer), 4.84-4.75 (m, 1H of minor rotamer), 4.54-4.46 (m, 1H of major rotamer), 4.22-

4.05 (m, 2H of both rotamers), 4.05-3.95 (m, 1H of major rotamer), 3.88-3.78 (m, 1H of minor rotamer), 3.78-3.68 (m, 1H of both rotamers), 2.92 (br s, OH), 2.71-2.51 (m, 1H of both rotamers), 2.24-2.15 (m, 1H of minor rotamer), 2.11 (qd, J=13.9, 5.4 Hz, 1H of major rotamer), 1.38 (d, J=6.5 Hz, 3H of major rotamer), 1.35-1.24 (m, 10H of both rotamers plus 3H of minor rotamer), 0.86-0.79 (m, 1H of both rotamers), 0.77-0.69 (m, 1H of both rotamers), 0.65-0.57 (m, 1H of both rotamers), 0.46-0.38 (m, 1H of both rotamers).

Example 314

5-(6-(((S)-1-Cyclopropyl-2,2,2-trifluoroethyl) amino)-4-(difluoromethyl)pyridin-3-yl)-4-((S)-4,4-difluoro-2-methylpyrrolidine-1-carbonyl)-N—((R)-3-hydroxy-3-methylbutan-2-yl)thiazole-2-carboxamide

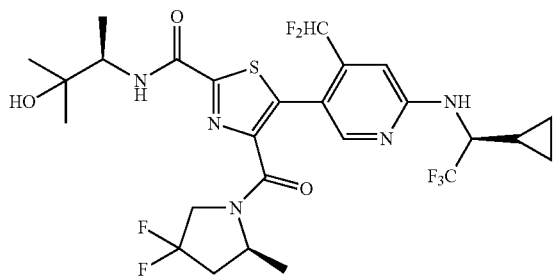 [SMILES: C[C@H]1CC(F)(F)CN1C(=O)c1nc(C(=O)N[C@H](C)C(C)(C)O)sc1-c1cnc(N[C@@H](C2CC2)C(F)(F)F)cc1C(F)F]

The title compound was prepared as described in Example 148, substituting ethyl 5-(6-(((S)-1-cyclopropyl-2,2,2-trifluoroethyl)amino)-4-(difluoromethyl)pyridin-3-yl)-4-((S)-4,4-difluoro-2-methylpyrrolidine-1-carbonyl)thiazole-2-carboxylate (Intermediate 129) and (R)-3-amino-2-methylbutan-2-ol for ethyl (S)-5-(6-(tert-butylamino)-4-(difluoromethyl)pyridin-3-yl)-4-(2-methylpyrrolidine-1-carbonyl)thiazole-2-carboxylate and (R)-(−)-2-amino-1-propanol. MS (ESI): mass calcd. for $C_{26}H_{30}F_7N_5O_3S$, 625.2; m/z found, 626.2 [M+H]$^+$. $^1$H NMR (500 MHz, CDCl$_3$, mixture of rotamers) δ 8.95 (br s, 1H of both rotamers), 7.92 (s, 1H of major rotamer), 7.90 (s, 1H of minor rotamer), 7.43-7.36 (m, 1H of both rotamers), 6.95 (s, 1H of minor rotamer), 6.94 (s, 1H of major rotamer), 6.91-6.63 (m, CHF$_2$ of both rotamers), 4.96-4.88 (m, 1H of minor rotamer), 4.54-4.45 (m, 1H of major rotamer), 4.28-4.17 (m, 1H of major rotamer), 4.13-3.97 (m, 2H of both rotamers), 3.89-3.79 (m, 1H of minor rotamer), 3.59 (br s, 1H of both rotamers), 3.37 (br s, OH), 2.72-2.51 (m, 1H of both rotamers), 2.21 (td, J=16.1, 15.3, 6.9 Hz, 1H of minor rotamer), 2.11 (qd, J=13.8, 5.1 Hz, 1H of major rotamer), 1.38 (d, J=6.4 Hz, 13H of both rotamers), 0.89-0.81 (m, 1H of both rotamers), 0.80-0.73 (m, 1H of both rotamers), 0.66-0.59 (m, 1H of both rotamers), 0.46-0.39 (m, 1H of both rotamers).

Example 315

5-(6-(((S)-1-Cyclopropyl-2,2,2-trifluoroethyl) amino)-4-(difluoromethyl)pyridin-3-yl)-4-((S)-4,4-difluoro-2-methylpyrrolidine-1-carbonyl)-N-((1r,3S)-3-hydroxycyclobutyl)thiazole-2-carboxamide

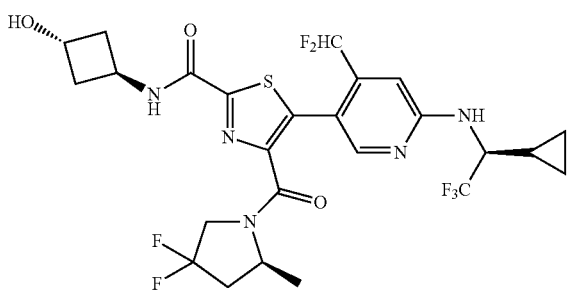 [SMILES: C[C@H]1CC(F)(F)CN1C(=O)c1nc(C(=O)N[C@H]2C[C@H](O)C2)sc1-c1cnc(N[C@@H](C2CC2)C(F)(F)F)cc1C(F)F]

The title compound was prepared as described in Example 149, substituting ethyl 5-(6-(((S)-1-cyclopropyl-2,2,2-trifluoroethyl)amino)-4-(difluoromethyl)pyridin-3-yl)-4-((S)-4,4-difluoro-2-methylpyrrolidine-1-carbonyl)thiazole-2-carboxylate (Intermediate 129) and trans-3-aminocyclobutanol HCl for ethyl (S)-5-(6-(tert-butylamino)-4-(difluoromethyl)pyridin-3-yl)-4-(2-methylpyrrolidine-1-carbonyl)thiazole-2-carboxylate and 3-hydroxy-3-methylazetidine HCl. MS (ESI): mass calcd. for $C_{25}H_{26}F_7N_5O_3S$, 609.2; m/z found, 610.2 [M+H]$^+$. $^1$H NMR (500 MHz, CDCl$_3$, mixture of rotamers) δ 9.05 (br s, 1H of both rotamers), 7.93 (s, 1H of major rotamer), 7.92 (s, 1H of minor rotamer), 7.20-7.13 (m, 1H of both rotamers), 6.96 (s, 1H of minor rotamer), 6.95 (s, 1H of major rotamer), 6.94-6.62 (m, CHF$_2$ of both rotamers), 4.86-4.41 (m, 4H of both rotamers), 4.27-4.16 (m, 1H of major rotamer), 4.10-3.92 (m, 1H of both rotamers), 3.90-3.80 (m, 1H of minor rotamer), 3.58 (br s, 1H of both rotamers), 2.80-2.54 (m, 1H of both rotamers), 2.54-2.41 (m, 4H of both rotamers), 2.26-2.06 (m, 1H of both rotamers), 1.38 (d, J=6.5 Hz, 3H of major rotamer), 1.38-1.31 (m, 1H of both rotamers), 1.23 (d, J=6.6 Hz, 3H of minor rotamer), 0.89-0.82 (m, 1H of both rotamers), 0.80-0.72 (m, 1H of both rotamers), 0.67-0.59 (m, 1H of both rotamers), 0.46-0.38 (m, 1H of both rotamers).

Example 316

4-((1s,4s)-7-Azabicyclo[2.2.1]heptane-7-carbonyl)-5-(6-(((S)-1-cyclopropyl-2,2,2-trifluoroethyl)amino)-4-(difluoromethyl)pyridin-3-yl)-N—((R)-3-hydroxy-3-methylbutan-2-yl)thiazole-2-carboxamide

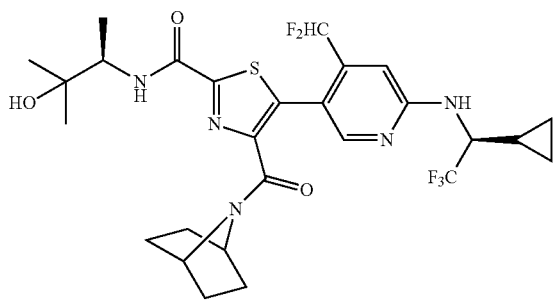 [SMILES: C[C@@H](NC(=O)c1nc(C(=O)N2C3CCC2CC3)c(-c2cnc(N[C@@H](C3CC3)C(F)(F)F)cc2C(F)F)s1)C(C)(C)O]

Example 317

4-((1s,4s)-7-Azabicyclo[2.2.1]heptane-7-carbonyl)-5-(6-(((S)-1-cyclopropyl-2,2,2-trifluoroethyl)amino)-4-(difluoromethyl)pyridin-3-yl)-N—((S)-3-hydroxy-3-methylbutan-2-yl)thiazole-2-carboxamide

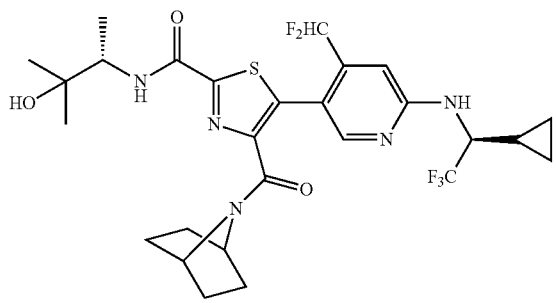 [SMILES: C[C@H](NC(=O)c1nc(C(=O)N2C3CCC2CC3)c(-c2cnc(N[C@@H](C3CC3)C(F)(F)F)cc2C(F)F)s1)C(C)(C)O]

The title compound was prepared as described in Example 148, substituting ethyl 4-((1s,4s)-7-azabicyclo[2.2.1]heptane-7-carbonyl)-5-(6-(((S)-1-cyclopropyl-2,2,2-trifluoroethyl)amino)-4-(difluoromethyl)pyridin-3-yl)thiazole-2-carboxylate (Intermediate 130) and (R)-3-amino-2-methylbutan-2-ol for ethyl (S)-5-(6-(tert-butylamino)-4-(difluoromethyl)pyridin-3-yl)-4-(2-methylpyrrolidine-1-carbonyl)thiazole-2-carboxylate and (R)-(−)-2-amino-1-propanol. MS (ESI): mass calcd. for $C_{27}H_{32}F_5N_5O_3S$, 601.2; m/z found, 602.2 [M+H]$^+$. $^1$H NMR (500 MHz, CDCl$_3$) δ 8.56 (s, 1H), 7.91 (br s, 1H), 7.44 (d, J=9.1 Hz, 1H), 6.92 (s, 1H), 6.83 (t, J=54.7 Hz, 1H), 4.68 (t, J=4.1 Hz, 1H), 4.62 (t, J=4.0 Hz, 1H), 4.08 (dq, J=9.1, 6.7 Hz, 1H), 3.85 (br s, 1H), 3.72-3.61 (m, 1H), 1.88-1.70 (m, 4H), 1.59-1.46 (m, 4H), 1.36-1.28 (m, 10H), 0.87-0.79 (m, 1H), 0.77-0.70 (m, 1H), 0.65-0.58 (m, 1H), 0.45-0.38 (m, 1H).

The title compound was prepared as described in Example 148, substituting ethyl 4-((1s,4s)-7-azabicyclo[2.2.1]heptane-7-carbonyl)-5-(6-(((S)-1-cyclopropyl-2,2,2-trifluoroethyl)amino)-4-(difluoromethyl)pyridin-3-yl)thiazole-2-carboxylate (Intermediate 130) and (S)-3-amino-2-methylbutan-2-ol for ethyl (S)-5-(6-(tert-butylamino)-4-(difluoromethyl)pyridin-3-yl)-4-(2-methylpyrrolidine-1-carbonyl)thiazole-2-carboxylate and (R)-(−)-2-amino-1-propanol. MS (ESI): mass calcd. for $C_{27}H_{32}F_5N_5O_3S$, 601.2; m/z found, 602.2 [M+H]$^+$. $^1$H NMR (500 MHz, CDCl$_3$) δ 8.65 (br s, 1H), 7.90 (s, 1H), 7.43 (d, J=9.1 Hz, 1H), 6.93 (s, 1H), 6.82 (t, J=54.7 Hz, 1H), 4.68 (t, J=4.1 Hz, 1H), 4.63 (t, J=4.3 Hz, 1H), 4.08 (dq, J=9.2, 6.8 Hz, 1H), 3.69-3.60 (m, 1H), 3.45 (br s, 1H), 1.88-1.72 (m, 4H), 1.58-1.47 (m, 4H), 1.37-1.27 (m, 10H), 0.87-0.80 (m, 1H), 0.78-0.70 (m, 1H), 0.65-0.58 (m, 1H), 0.45-0.39 (m, 1H).

Example 318

4-((1s,4s)-7-Azabicyclo[2.2.1]heptane-7-carbonyl)-5-(6-(((S)-1-cyclopropyl-2,2,2-trifluoroethyl)amino)-4-(difluoromethyl)pyridin-3-yl)-N-((1r,3S)-3-hydroxycyclobutyl)thiazole-2-carboxamide

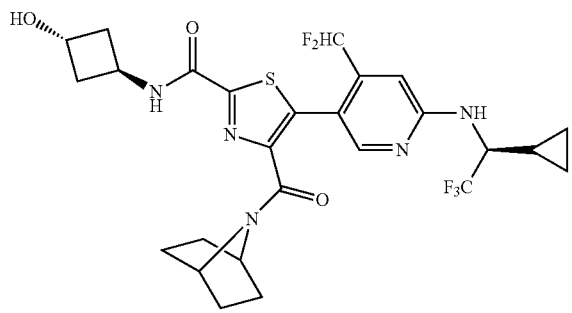 [SMILES: O=C(N[C@H]1C[C@H](O)C1)c1nc(C(=O)N2C3CCC2CC3)c(-c2cnc(N[C@@H](C3CC3)C(F)(F)F)cc2C(F)F)s1]

The title compound was prepared as described in Example 149, substituting ethyl 4-((1s,4s)-7-azabicyclo[2.2.1]heptane-7-carbonyl)-5-(6-(((S)-1-cyclopropyl-2,2,2-trifluoroethyl)amino)-4-(difluoromethyl)pyridin-3-yl)thiazole-2-carboxylate (Intermediate 130) and trans-3-aminocyclobutanol HCl for ethyl (S)-5-(6-(tert-butylamino)-4-(difluoromethyl)pyridin-3-yl)-4-(2-methylpyrrolidine-1-carbonyl)thiazole-2-carboxylate and 3-hydroxy-3-methylazetidine HCl. MS (ESI): mass calcd. for $C_{26}H_{28}F_5N_5O_3S$, 585.2; m/z found, 586.2 [M+H]$^+$. $^1$NMR (500 MHz, CDCl$_3$) δ 7.94 (s, 1H), 7.65 (br s, 1H), 7.25 (d, J=7.5 Hz, 1H), 6.88 (s, 1H), 6.80 (t, J=54.7 Hz, 1H), 4.71-4.64 (m, 2H), 4.64-4.58 (m, 1H), 4.46-4.40 (m, 1H), 3.89-3.78 (m, 1H), 3.06 (br s, 1H), 2.52-2.41 (m, 4H), 1.86-1.60 (m, 4H), 1.56-1.45 (m, 4H), 1.32-1.23 (m, 1H), 0.86-0.77 (m, 1H), 0.74-0.66 (m, 1H), 0.64-0.57 (m, 1H), 0.45-0.37 (m, 1H).

Example 319

5-(4-(Difluoromethyl)-6-(((R)-1,1,1-trifluoropropan-2-yl)amino)pyridin-3-yl)-N-((1r,3S)-3-hydroxycyclobutyl)-4-((S)-2-methylpyrrolidine-1-carbonyl)thiazole-2-carboxamide

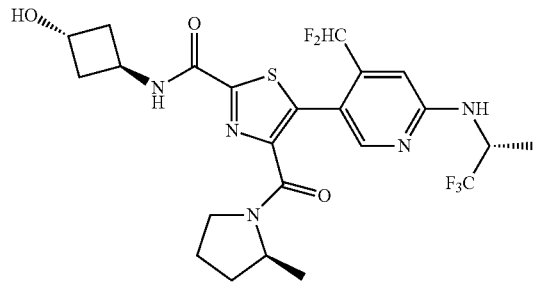 [SMILES: C[C@H]1CCCN1C(=O)c1nc(C(=O)N[C@H]2C[C@H](O)C2)sc1-c1cnc(N[C@H](C)C(F)(F)F)cc1C(F)F]

The title compound was prepared as described in Example 149, substituting ethyl 5-(4-(difluoromethyl)-6-(((R)-1,1,1-trifluoropropan-2-yl)amino)pyridin-3-yl)-4-((S)-2-methylpyrrolidine-1-carbonyl)thiazole-2-carboxylate (Intermediate 149) and trans-3-aminocyclobutanol HCl for ethyl (S)-5-(6-(tert-butylamino)-4-(difluoromethyl)pyridin-3-yl)-4-

(2-methylpyrrolidine-1-carbonyl)thiazole-2-carboxylate and 3-hydroxy-3-methylazetidine HCl. MS (ESI): mass calcd. for $C_{23}H_{26}F_5N_5O_3S$ 547.2, m/z found 548.0 [M+H]$^+$. $^1$H NMR (400 MHz, CDCl$_3$) δ 8.11-8.00 (m, 1H), 7.33 (d, J=7.3 Hz, 1H), 7.03-6.58 (m, 2H), 5.02-4.86 (m, 2H), 4.70-4.54 (m, 2H), 4.29-4.15 (m, 1H), 3.61-3.27 (m, 2H), 2.50-2.39 (m, 4H), 2.11-1.87 (m, 3H), 1.82-1.70 (m, 1H), 1.59-1.48 (m, 1H), 1.45-1.36 (m, 3H), 1.25-1.20 (m, 2H), 1.00 (d, J=6.2 Hz, 1H).

Example 320

5-(6-(((R)-1-Cyclopropyl-2,2,2-trifluoroethyl) amino)-4-(difluoromethyl)pyridin-3-yl)-N-((1r,3S)-3-hydroxycyclobutyl)-4-((S)-2-methylpyrrolidine-1-carbonyl)thiazole-2-carboxamide

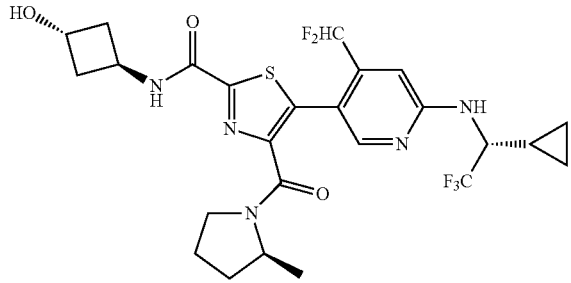 [SMILES: C[C@H]1CCCN1C(=O)c1nc(C(=O)N[C@H]2C[C@H](O)C2)sc1-c1cnc(N[C@H](C2CC2)C(F)(F)F)cc1C(F)F]

The title compound was prepared as described in Example 149, substituting ethyl 5-(6-(((R)-1-cyclopropyl-2,2,2-trifluoroethyl)amino)-4-(difluoromethyl)pyridin-3-yl)-4-((S)-2-methylpyrrolidine-1-carbonyl)thiazole-2-carboxylate (Intermediate 148) and trans-3-aminocyclobutanol HCl for ethyl (S)-5-(6-(tert-butylamino)-4-(difluoromethyl)pyridin-3-yl)-4-(2-methylpyrrolidine-1-carbonyl)thiazole-2-carboxylate and 3-hydroxy-3-methylazetidine HCl. MS (ESI): mass calcd. for $C_{25}H_{28}F_5N_5O_3S$ 573.2, m/z found 574.0 [M+H]$^+$. $^1$H NMR (400 MHz, DMSO-d$_6$) δ 8.06-7.98 (m, 1H), 7.37-7.28 (m, 1H), 7.06-6.62 (m, 2H), 5.01 (d, J=9.3 Hz, 1H), 4.73-4.54 (m, 2H), 4.41-4.15 (m, 2H), 3.62-3.28 (m, 2H), 2.55-2.36 (m, 4H), 2.19-1.70 (m, 4H), 1.59-1.48 (m, 1H), 1.32-1.19 (m, 2H), 1.18-1.06 (m, 1H), 1.00 (d, J=6.4 Hz, 1H), 0.82-0.69 (m, 1H), 0.64-0.51 (m, 2H), 0.47-0.34 (m, 1H).

Example 321

5-(4-(Difluoromethyl)-6-((1-methylcyclobutyl) amino)pyridin-3-yl)-N—((R)-3-hydroxy-3-methylbutan-2-yl)-4-((S)-2-methylpyrrolidine-1-carbonyl)thiazole-2-carboxamide

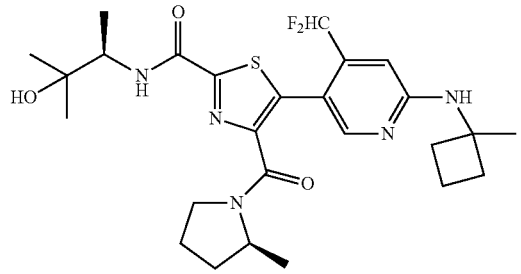 [SMILES: C[C@H]1CCCN1C(=O)c1nc(C(=O)N[C@H](C)C(C)(C)O)sc1-c1cnc(NC2(C)CCC2)cc1C(F)F]

The title compound was prepared as described in Intermediate 62: Step A, substituting 5-bromo-4-(difluoromethyl)-N-(1-methylcyclobutyl)pyridin-2-amine (Intermediate 131) and N—((R)-3-hydroxy-3-methylbutan-2-yl)-4-((S)-2-methylpyrrolidine-1-carbonyl)thiazole-2-carboxamide (Intermediate 132) for 5-bromo-N-cyclopentyl-4-(difluoromethyl)-pyridin-2-amine and (9-ethyl 4-(2-methylpyrrolidine-1-carbonyl)thiazole-2-carboxylate. MS (ESI): mass calcd. for $C_{26}H_{35}F_2N_5O_3S$ 535.2, m/z found 536.0 [M+H]$^+$. $^1$H NMR (500 MHz, DMSO-d$_6$) δ 8.13-8.01 (m, 1H), 7.96 (s, 1H), 7.45 (s, 1H), 7.11-6.77 (m, 1H), 6.67 (s, 1H), 4.73-4.66 (m, 1H), 4.04-3.84 (m, 2H), 3.29-3.18 (m, 2H), 2.28-2.18 (m, 2H), 2.05-1.90 (m, 3H), 1.85-1.74 (m, 3H), 1.68-1.55 (m, 1H), 1.50-1.40 (m, 4H), 1.15-1.04 (m, 11H), 0.93 (d, J=6.4 Hz, 1H).

Example 322

5-(4-(Difluoromethyl)-6-((1-methylcyclobutyl) amino)pyridin-3-yl)-N—((S)-3-hydroxy-3-methylbutan-2-yl)-4-((S)-2-methylpyrrolidine-1-carbonyl)thiazole-2-carboxamide

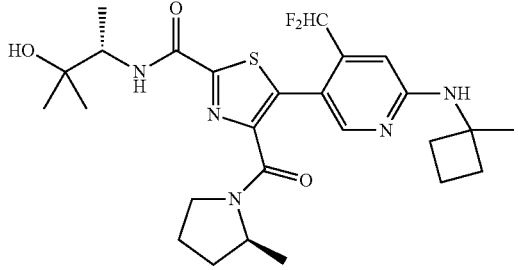 [SMILES: C[C@H](NC(=O)c1nc(C(=O)N2CCC[C@@H]2C)c(-c2cnc(NC3(C)CCC3)cc2C(F)F)s1)C(C)(C)O]

The title compound was prepared as described in Intermediate 62: Step A, substituting 5-bromo-4-(difluoromethyl)-N-(1-methylcyclobutyl)pyridin-2-amine (Intermediate 131) and N—((S)-3-hydroxy-3-methylbutan-2-yl)-4-((S)-2-methylpyrrolidine-1-carbonyl)thiazole-2-carboxamide (Intermediate 139) for 5-bromo-N-cyclopentyl-4-(difluoromethyl)-pyridin-2-amine and ethyl (S)-4-(2-methylpyrrolidine-1-carbonyl)thiazole-2-carboxylate. MS (ESI): mass calcd. for $C_{26}H_{35}F_2N_5O_3S$ 535.2, m/z found 536.0 [M+H]$^+$. $^1$H NMR (500 MHz, DMSO-d$_6$, 80° C.) δ 8.01 (s, 1H), 7.91-7.78 (m, 1H), 7.20 (s, 1H), 7.06-6.74 (m, 1H), 6.72 (s, 1H), 4.50 (br s, 1H), 4.16-4.01 (m, 1H), 3.98-3.85 (m, 1H), 3.52-3.26 (m, 2H), 2.36-2.27 (m, 2H), 2.07-1.67 (m, 7H), 1.55-1.45 (m, 4H), 1.23-1.17 (m, 6H), 1.16 (s, 3H), 1.14-1.09 (m, 2H), 1.06-0.99 (m, 1H).

Example 323

5-(4-(Difluoromethyl)-6-((1-methylcyclobutyl) amino)pyridin-3-yl)-N-((1r,3S)-3-hydroxycyclobutyl)-4-((S)-2-methylpyrrolidine-1-carbonyl) thiazole-2-carboxamide

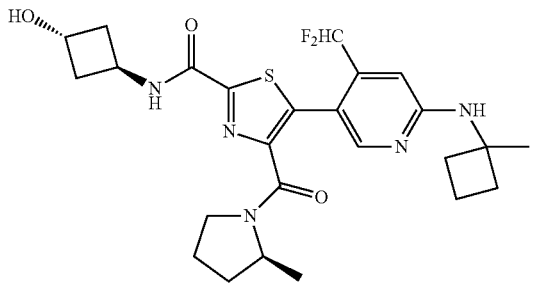 [SMILES: C[C@H]1CCCN1C(=O)c1nc(C(=O)N[C@H]2C[C@H](O)C2)sc1-c1cnc(NC2(C)CCC2)cc1C(F)F]

The title compound was prepared as described in Intermediate 72: Step B, substituting potassium (S)-5-(4-(difluoromethyl)-6-((1-methylcyclobutyl)amino)pyridin-3-yl)-4-(2-methylpyrrolidine-1-carbonyl)thiazole-2-carboxylate (Intermediate 133), trans-3-aminocyclobutanol HCl, and THF for 4-(tert-butoxycarbonyl)thiazole-2-carboxylic acid, 4-aminotetrahydro-2H-thiopyran-1,1-dioxide HCl, and DMF. MS (ESI): mass calcd. for $C_{25}H_{31}F_2N_5O_3S$ 519.2 m/z, found 520.0 [M+H]$^+$. $^1$H NMR (400 MHz, DMSO-d$_6$) δ 9.17-9.12 (m, 1H), 7.98 (s, 1H), 7.45 (s, 1H), 7.16-6.77 (m, 1H), 6.68 (s, 1H), 5.07-5.00 (m, 1H), 4.54-4.41 (m, 1H), 4.36-4.14 (m, 1H), 4.06-3.96 (m, 1H), 3.30-3.24 (m, 2H), 2.44-2.35 (m, 2H), 2.29-2.19 (m, 2H), 2.18-2.09 (m, 2H), 2.07-1.90 (m, 3H), 1.88-1.76 (m, 3H), 1.73-1.56 (m, 1H), 1.54-1.41 (m, 4H), 1.08 (d, J=6.2 Hz, 2H), 0.86 (d, J=6.4 Hz, 1H).

Example 324

(S)-5-(4-(Difluoromethyl)-6-((1-methylcyclobutyl)amino)pyridin-3-yl)-N-(1,1-dioxidotetrahydro-2H-thiopyran-4-yl)-4-(2-methylpyrrolidine-1-carbonyl)thiazole-2-carboxamide

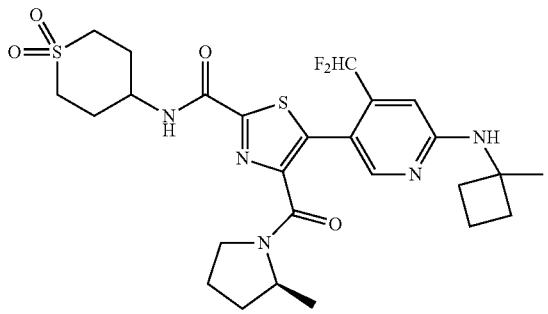 [SMILES: C[C@H]1CCCN1C(=O)c1nc(C(=O)NC2CCS(=O)(=O)CC2)sc1-c1cnc(NC2(C)CCC2)cc1C(F)F]

The title compound was prepared as described in Intermediate 62: Step A, substituting 5-bromo-4-(difluoromethyl)-N-(1-methylcyclobutyl)pyridin-2-amine (Intermediate 131) and (S)—N-(1,1-dioxidotetrahydro-2H-thiopyran-4-yl)-4-(2-methylpyrrolidine-1-carbonyl)thiazole-2-carboxamide (Intermediate 134) for 5-bromo-N-cyclopentyl-4-(difluoromethyl)pyridin-2-amine and ethyl (S)-4-(2-methylpyrrolidine-1-carbonyl)thiazole-2-carboxylate. MS (ESI): mass calcd. for $C_{26}H_{33}F_2N_5O_4S_2$ 581.2, m/z found 582.0 [M+H]$^+$. $^1$H NMR (400 MHz, DMSO-d$_6$) δ 9.04 (d, J=8.4 Hz, 1H), 7.96 (s, 1H), 7.45 (s, 1H), 7.13-6.75 (m, 1H), 6.67 (s, 1H), 4.26-4.13 (m, 2H), 4.04-3.95 (m, 1H), 3.31 (s, 3H), 3.11-3.02 (m, 2H), 2.29-2.13 (m, 4H), 2.12-1.90 (m, 5H), 1.87-1.74 (m, 3H), 1.69-1.59 (m, 1H), 1.54-1.37 (m, 4H), 1.06 (d, J=6.4 Hz, 2H), 0.85 (d, J=6.4 Hz, 1H).

Example 325

4-((S)-4,4-Difluoro-2-methylpyrrolidine-1-carbonyl)-5-(4-(difluoromethyl)-6-((1-methylcyclobutyl)amino)pyridin-3-yl)-N—((R)-3-hydroxy-3-methylbutan-2-yl)thiazole-2-carboxamide

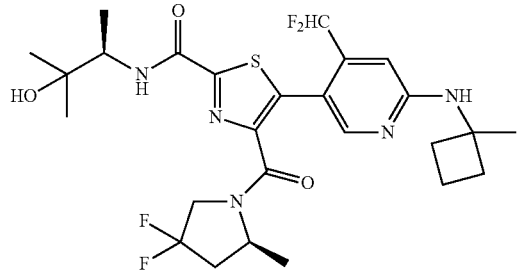 [SMILES: C[C@H]1CC(F)(F)CN1C(=O)c1nc(C(=O)N[C@H](C)C(C)(C)O)sc1-c1cnc(NC2(C)CCC2)cc1C(F)F]

The title compound was prepared as described in Intermediate 62: Step A, substituting 5-bromo-4-(difluoromethyl)-N-(1-methylcyclobutyl)pyridin-2-amine (Intermediate 131) and 4-((S)-4,4-difluoro-2-methylpyrrolidine-1-carbonyl)-N—((R)-3-hydroxy-3-methylbutan-2-yl)thiazole-2-carboxamide (Intermediate 135) for 5-bromo-N-cyclopentyl-4-(difluoromethyl)pyridin-2-amine and ethyl (S)-4-(2-methylpyrrolidine-1-carbonyl)thiazole-2-carboxylate. MS (ESI): mass calcd. for $C_{26}H_{33}F_4N_5O_3S$ 571.2 m/z, found 572.0 [M+H]$^1$. $^1$H NMR (500 MHz, DMSO-d$_6$) δ 8.16-8.02 (m, 1H), 7.98 (s, 1H), 7.47 (s, 1H), 7.07-6.74 (m, 1H), 6.70 (s, 1H), 4.80-4.71 (m, 1H), 4.61-4.24 (m, 1H), 4.02-3.80 (m, 3H), 2.65-2.53 (m, 2H), 2.30-2.21 (m, 2H), 2.09-1.97 (m, 2H), 1.91-1.75 (m, 2H), 1.49 (s, 3H), 1.24-1.20 (m, 3H), 1.18-1.11 (m, 9H)

Example 326

4-((S)-4,4-Difluoro-2-methylpyrrolidine-1-carbonyl)-5-(4-(difluoromethyl)-6-((1-methylcyclobutyl)amino)pyridin-3-yl)-N—((S)-3-hydroxy-3-methylbutan-2-yl)thiazole-2-carboxamide

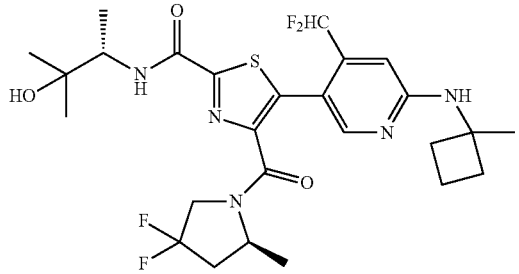 [SMILES: C[C@H](NC(=O)c1nc(C(=O)N2CC(F)(F)C[C@@H]2C)c(-c2cnc(NC3(C)CCC3)cc2C(F)F)s1)C(C)(C)O]

The title compound was prepared as described in Intermediate 62: Step A, substituting 5-bromo-4-(difluoromethyl)-N-(1-methylcyclobutyl)pyridin-2-amine (Intermediate 131) and 4-((S)-4,4-difluoro-2-methylpyrrolidine-1-carbonyl)-N—((S)-3-hydroxy-3-methylbutan-2-yl)thiazole-2-carboxamide (Intermediate 140) for 5-bromo-N-cyclopentyl-4-(difluoromethyl)pyridin-2-amine and ethyl (S)-4-(2-methylpyrrolidine-1-carbonyl)thiazole-2-carboxylate. MS (ESI): mass calcd. for $C_{26}H_{33}F_4N_5O_3S$ 571.2, m/z found 572.0 [M+H]$^+$. $^1$H NMR (400 MHz, DMSO-d$_6$) δ 8.10-8.01 (m, 1H), 8.01-7.95 (m, 1H), 7.47 (s, 1H), 7.07-6.76 (m, 1H), 6.69 (s, 1H), 4.76-4.68 (m, 1H), 4.50-4.25 (m, 1H), 4.03-3.76 (m, 3H), 2.65-2.54 (m, 2H), 2.31-2.20 (m, 2H), 2.08-1.97 (m, 2H), 1.88-1.77 (m, 2H), 1.49 (s, 3H), 1.22 (d, J=6.4 Hz, 3H), 1.18-1.08 (m, 9H).

Example 327

4-((S)-4,4-Difluoro-2-methylpyrrolidine-1-carbonyl)-5-(4-(difluoromethyl)-6-((1-methylcyclobutyl)amino)pyridin-3-yl)-N-((1r,3S)-3-hydroxycyclobutyl)thiazole-2-carboxamide

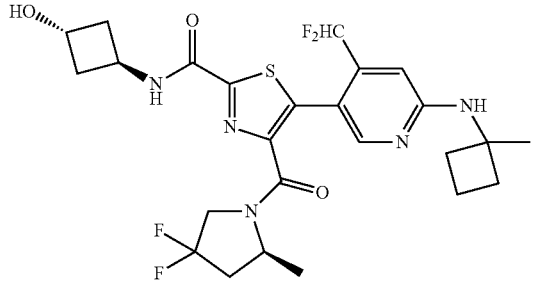 [SMILES: C[C@H]1CC(F)(F)CN1C(=O)c1nc(C(=O)N[C@H]2C[C@H](O)C2)sc1-c1cnc(NC2(C)CCC2)cc1C(F)F]

The title compound was prepared as described in Example 149, substituting ethyl (S)-4-(4,4-difluoro-2-methylpyrrolidine-1-carbonyl)-5-(4-(difluoromethyl)-6-((1-methylcyclobutyl)amino)pyridin-3-yl)thiazole-2-carboxylate (Intermediate 136) and trans-3-aminocyclobutanol HCl for ethyl (S)-5-(6-(tert-butylamino)-4-(difluoromethyl)pyridin-3-yl)-4-(2-methylpyrrolidine-1-carbonyl)thiazole-2-carboxylate and 3-hydroxy-3-methylazetidine HCl. MS (ESI): mass calcd. for $C_{25}H_{29}F_4N_5O_3S$ 555.2 m/z, found 556.0 [M+H]$^+$. $^1$H NMR (500 MHz, DMSO-d$_6$) δ 9.16-9.03 (m, 1H), 7.94 (s, 1H), 7.49-7.38 (m, 1H), 7.05-6.70 (m, 1H), 6.65 (s, 1H), 5.02 (d, J=5.1 Hz, 1H), 4.62-4.38 (m, 1H), 4.34-4.22 (m, 2H), 4.11-3.98 (m, 1H), 3.94-3.78 (m, 1H), 2.61-2.52 (m, 2H), 2.41-2.33 (m, 2H), 2.27-2.17 (m, 2H), 2.14-2.06 (m, 2H), 2.03-1.93 (m, 2H), 1.86-1.73 (m, 2H), 1.46 (s, 3H), 1.22-0.97 (m, 3H).

Example 328

(S)-4-(4,4-Difluoro-2-methylpyrrolidine-1-carbonyl)-5-(4-(difluoromethyl)-6-((1-methylcyclobutyl)amino)pyridin-3-yl)-N-(1,1-dioxidotetrahydro-2H-thiopyran-4-yl)thiazole-2-carboxamide

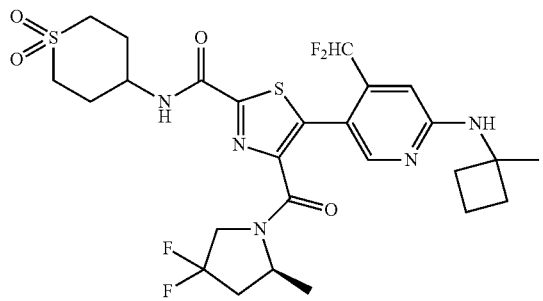 [SMILES: C[C@H]1CC(F)(F)CN1C(=O)c1nc(C(=O)NC2CCS(=O)(=O)CC2)sc1-c1cnc(NC2(C)CCC2)cc1C(F)F]

The title compound was prepared as described in Intermediate 62: Step A, substituting 5-bromo-4-(difluoromethyl)-N-(1-methylcyclobutyl)pyridin-2-amine (Intermediate 131) and (S)-4-(4,4-difluoro-2-methylpyrrolidine-1-carbonyl)-N-(1,1-dioxidotetrahydro-2H-thiopyran-4-yl)thiazole-2-carboxamide (Intermediate 142) for 5-bromo-N-cyclopentyl-4-(difluoromethyl)pyridin-2-amine and ethyl (S)-4-(2-methylpyrrolidine-1-carbonyl)thiazole-2-carboxylate. MS (ESI): mass calcd. for $C_{26}H_{31}F_4N_5O_4S_2$ 617.2 m/z, found 618.0 [M+H]$^+$. $^1$H NMR (500 MHz, DMSO-d$_6$, 80° C.) δ 8.82-8.65 (m, 1H), 8.00 (s, 1H), 7.20 (s, 1H), 7.04-6.66 (m, 2H), 4.67-3.82 (m, 4H), 3.39-3.24 (m, 2H), 3.19-3.13 (m, 2H), 2.69-2.53 (m, 2H), 2.38-2.23 (m, 4H), 2.20-2.13 (m, 2H), 2.10-2.01 (m, 1H), 1.94-1.78 (m, 2H), 1.52 (s, 3H), 1.33-1.07 (m, 3H).

Example 329

4-((1s,4s)-7-Azabicyclo[2.2.1]heptane-7-carbonyl)-5-(4-(difluoromethyl)-6-((1-methylcyclobutyl)amino)pyridin-3-yl)-N—((R)-3-hydroxy-3-methylbutan-2-yl)thiazole-2-carboxamide

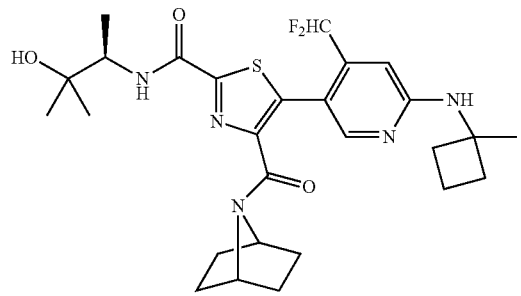 [SMILES: C[C@@H](NC(=O)c1nc(C(=O)N2C3CCC2CC3)c(-c2cnc(NC3(C)CCC3)cc2C(F)F)s1)C(C)(C)O]

The title compound was prepared as described in Intermediate 62: Step A, substituting 5-bromo-4-(difluoromethyl)-N-(1-methylcyclobutyl)pyridin-2-amine (Intermediate 131) and 4-((1s,4s)-7-azabicyclo[2.2.1]heptane-7-carbonyl)-N—((R)-3-hydroxy-3-methylbutan-2-yl)thiazole-2-carboxamide (Intermediate 143) for 5-bromo-N-cyclopentyl-4-(difluoromethyl)pyridin-2-amine and ethyl (S)-4-(2-methylpyrrolidine-1-carbonyl)thiazole-2-carboxylate. MS (ESI): mass calcd. for $C_{27}H_{35}F_2N_5O_3S$ 547.2, m/z found 548.0 [M+H]$^+$. $^1$H NMR (500 MHz, DMSO-d$_6$) δ 8.07 (d, J=9.5 Hz, 1H), 7.98 (s, 1H), 7.49 (s, 1H), 7.13-6.69 (m, 2H), 4.74 (s, 1H), 4.48 (br s 1H), 4.05 (br s 1H), 3.96-3.86 (m, 1H), 2.31-2.19 (m, 2H), 2.08-1.98 (m, 2H), 1.89-1.75 (m, 2H), 1.49 (s, 5H), 1.44-1.22 (m, 6H), 1.20-1.09 (m, 9H).

Example 330

4-((1s,4s)-7-Azabicyclo[2.2.1]heptane-7-carbonyl)-5-(4-(difluoromethyl)-6-((1-methylcyclobutyl)amino)pyridin-3-yl)-N-((1r,3R)-3-hydroxycyclobutyl)thiazole-2-carboxamide

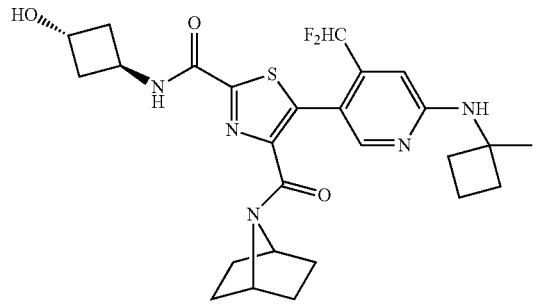 [SMILES: CC1(Nc2cc(C(F)F)c(-c3sc(C(=O)N[C@H]4C[C@H](O)C4)nc3C(=O)N3C4CCC3CC4)cn2)CCC1]

The title compound was prepared as described in Intermediate 72: Step B, substituting potassium 4-((1s,4s)-7-azabicyclo[2.2.1]heptane-7-carbonyl)-5-(4-(difluoromethyl)-6-((1-methylcyclobutyl)amino)pyridin-3-yl)thiazole-2-carboxylate (Intermediate 145), trans-3-aminocyclobutanol HCl, and THF for 4-(tert-butoxycarbonyl)thiazole-2-carboxylic acid, 4-aminotetrahydro-2H-thiopyran-1,1-dioxide HCl, and DMF. MS (ESI): mass calcd. for $C_{26}H_{31}F_2N_5O_3S$ 531.2 m/z, found 532.0 [M+H]$^+$. $^1$H NMR (500 MHz, DMSO-d$_6$) δ 9.14 (d, J=7.3 Hz, 1H), 7.94 (s, 1H), 7.46 (s, 1H), 7.11-6.79 (m, 1H), 6.68 (s, 1H), 5.00 (d, J=5.3 Hz, 1H), 4.50-4.38 (m, 2H), 4.32-4.21 (m, 1H), 3.97-3.87 (m, 1H), 2.40-2.32 (m, 2H), 2.26-2.15 (m, 2H), 2.14-2.06 (m, 2H), 2.04-1.95 (m, 2H), 1.84-1.74 (m, 2H), 1.48-1.24 (m, 9H), 1.22-1.08 (m, 2H).

Example 331

4-((1s,4s)-7-Azabicyclo[2.2.1]heptane-7-carbonyl)-5-(4-(difluoromethyl)-6-((1-methylcyclobutyl)amino)pyridin-3-yl)-N-(1,1-dioxidotetrahydro-2H-thiopyran-4-yl)thiazole-2-carboxamide

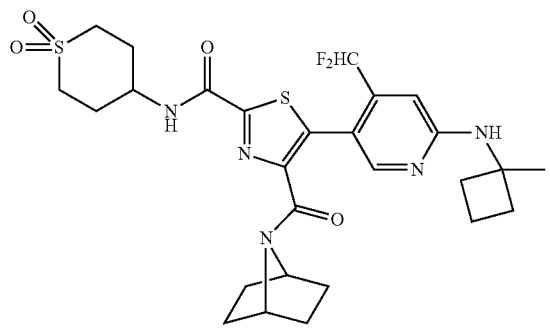 [SMILES: CC1(Nc2cc(C(F)F)c(-c3sc(C(=O)NC4CCS(=O)(=O)CC4)nc3C(=O)N3C4CCC3CC4)cn2)CCC1]

The title compound was prepared as described in Intermediate 62: Step A, substituting 5-bromo-4-(difluoromethyl)-N-(1-methylcyclobutyl)pyridin-2-amine (Intermediate 131) and 4-((1s,4s)-7-azabicyclo[2.2.1]heptane-7-carbonyl)-N-(1,1-dioxidotetrahydro-2H-thiopyran-4-yl)thiazole-2-carboxamide (Intermediate 147) for 5-bromo-N-cyclopentyl-4-(difluoromethyl)pyridin-2-amine and ethyl (S)-4-(2-methylpyrrolidine-1-carbonyl)thiazole-2-carboxylate. MS (ESI): mass calcd. for $C_{27}H_{33}F_2N_5O_4S_2$, 593.2, m/z found 594.2 [M+H]$^+$. $^1$H NMR (500 MHz, DMSO-d$_6$) δ 9.05 (d, J=8.6 Hz, 1H), 7.95 (s, 1H), 7.46 (s, 1H), 7.09-6.82 (m, 1H), 6.70 (s, 1H), 4.46-4.44 (m, 1H), 4.25-4.13 (m, 1H), 3.98-3.96 (m, 1H), 3.37-3.31 (m, 2H), 3.11-3.02 (m, 2H), 2.29-2.15 (m, 4H), 2.10-1.95 (m, 4H), 1.86-1.75 (m, 2H), 1.48-1.26 (m, 9H), 1.24-1.12 (m, 2H).

Example 332

5-(6-(((R)-1-Cyclopropyl-2,2,2-trifluoroethyl)amino)-4-(difluoromethyl)pyridin-3-yl)-N—((R)-3-hydroxy-3-methylbutan-2-yl)-4-((S)-2-methylpyrrolidine-1-carbonyl)thiazole-2-carboxamide

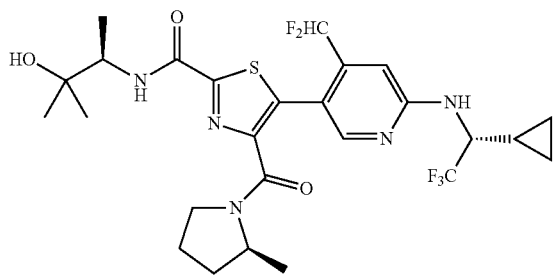 [SMILES: C[C@H]1CCCN1C(=O)c1nc(C(=O)N[C@H](C)C(C)(C)O)sc1-c1cnc(N[C@H](C2CC2)C(F)(F)F)cc1C(F)F]

The title compound was prepared as described in Intermediate 62: Step A, substituting (R)-5-bromo-N-(1-cyclopropyl-2,2,2-trifluoroethyl)-4-(difluoromethyl)pyridin-2-amine (Intermediate 137) and N—((R)-3-hydroxy-3-methylbutan-2-yl)-4-((S)-2-methylpyrrolidine-1-carbonyl)thiazole-2-carboxamide (Intermediate 132) for 5-bromo-N-cyclopentyl-4-(difluoromethyl)pyridin-2-amine and ethyl (S)-4-(2-methylpyrrolidine-1-carbonyl)thiazole-2-carboxylate. MS (ESI): mass calcd. for $C_{26}H_{32}F_5N_5O_3S$ 589.2, m/z found 590.0 [M+H]$^+$. $^1$H NMR (400 MHz, DMSO-d$_6$) δ 8.17-8.06 (m, 1H), 8.03 (s, 1H), 7.92-7.81 (m, 1H), 7.19-6.76 (m, 2H), 4.75-4.67 (m, 1H), 4.56-4.42 (m, 1H), 4.26-3.87 (m, 2H), 3.45-3.36 (m, 1H), 3.32-3.23 (m, 1H), 2.01-1.54 (m, 3H), 1.50-1.38 (m, 1H), 1.20-1.09 (m, 10H), 1.06 (d, J=6.4 Hz, 2H), 0.95 (d, J=6.4 Hz, 1H), 0.70-0.60 (m, 1H), 0.58-0.46 (m, 2H), 0.39-0.27 (m, 1H).

Example 333

5-(6-(((R)-1-Cyclopropyl-2,2,2-trifluoroethyl)amino)-4-(difluoromethyl)pyridin-3-yl)-N—((S)-3-hydroxy-3-methylbutan-2-yl)-4-((S)-2-methylpyrrolidine-1-carbonyl)thiazole-2-carboxamide

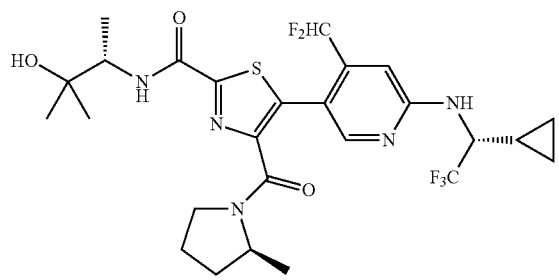 [SMILES: C[C@H](NC(=O)c1nc(C(=O)N2CCC[C@@H]2C)c(-c2cnc(N[C@H](C3CC3)C(F)(F)F)cc2C(F)F)s1)C(C)(C)O]

The title compound was prepared as described in Intermediate 62: Step A, substituting (R)-5-bromo-N-(1-cyclopropyl-2,2,2-trifluoroethyl)-4-(difluoromethyl)pyridin-2-amine (Intermediate 137) and N—((S)-3-hydroxy-3-methylbutan-2-yl)-4-((S)-2-methylpyrrolidine-1-carbonyl)thiazole-2-carboxamide (Intermediate 139) for 5-bromo-N-cyclopentyl-4-(difluoromethyl)pyridin-2-amine and ethyl (S)-4-(2-methylpyrrolidine-1-carbonyl)thiazole-2-carboxylate. MS (ESI): mass calcd. for $C_{26}H_{32}F_5N_5O_3S$ 589.2, m/z found 590.0 [M+H]$^+$. $^1$H NMR (400 MHz, DMSO-d6, 80° C.) δ 8.06 (s, 1H), 7.94-7.81 (m, 1H), 7.62 (d, J=8.5 Hz, 1H), 7.11-6.77 (m, 2H), 4.61-4.46 (m, 2H), 4.18-3.88 (m, 2H), 3.47-3.30 (m, 2H), 2.04-1.81 (m, 2H), 1.77-1.40 (m, 2H), 1.22-1.15 (m, 10H), 1.13-1.01 (m, 3H), 0.71-0.62 (m, 1H), 0.59-0.45 (m, 2H), 0.44-0.35 (m, 1H).

Example 334

5-[6-(2,2-Dimethylpropylamino)-4-(trifluoromethyl)-3-pyridyl]-N-[(1R)-2-hydroxy-1,2-dimethyl-propyl]-4-[(2S)-2-methylpyrrolidine-1-carbonyl]thiazole-2-carboxamide

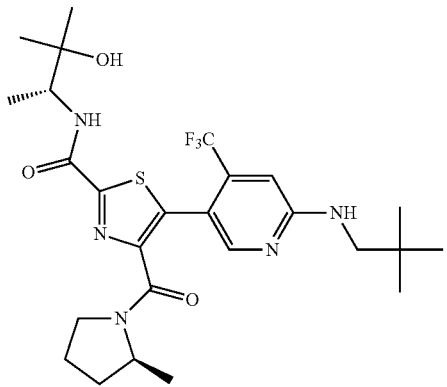 [SMILES: C[C@H]1CCCN1C(=O)c1nc(C(=O)N[C@H](C)C(C)(C)O)sc1-c1cnc(NCC(C)(C)C)cc1C(F)(F)F]

The title compound was prepared as described in Example 148 substituting (R)-3-amino-2-methylbutan-2-ol for (R)-(−)-2-amino-1-propanol and ethyl (S)-4-(2-methylpyrrolidine-1-carbonyl)-5-(6-(neopentylamino)-4-(trifluoromethyl)pyridin-3-yl)thiazole-2-carboxylate (Intermediate 150) for ethyl (S)-5-(6-(tert-butylamino)-4-(difluoromethyl)pyridin-3-yl)-4-(2-methylpyrrolidine-1-carbonyl)thiazole-2-carboxylate. MS (ESI): mass calcd. for $C_{26}H_{36}F_3N_5O_3S$, 555.7; m/z found, 556.3 [M+H]$^+$. $^1$H NMR (500 MHz, CDCl$_3$) δ 8.13 (s, 1H), 7.45 (d, J=9.3 Hz, 1H), 6.68-6.62 (m, 1H), 4.39-4.15 (m, 1H), 4.14-4.03 (m, 1H), 3.65-3.38 (m, 2H), 3.27-3.05 (m, 2H), 2.42-2.26 (m, 1H), 2.12-2.01 (m, 1H), 1.97-1.84 (m, 1H), 1.81-1.69 (m, 1H), 1.60-1.48 (m, 1H), 1.34-1.22 (m, 12H), 1.12 (d, J=6.4 Hz, 1H), 1.01-0.94 (m, 9H).

Example 335

5-[6-(tert-Butylamino)-4-(trifluoromethyl)-3-pyridyl]-N-[(1R)-2-hydroxy-1,2-dimethyl-propyl]-4-[(2S)-2-methylpyrrolidine-1-carbonyl]thiazole-2-carboxamide

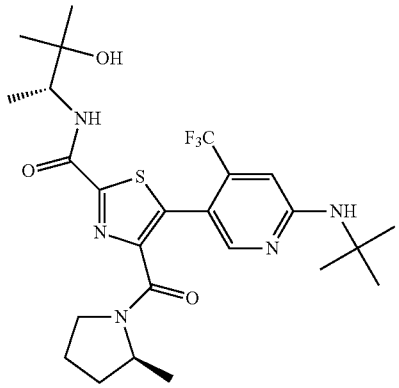 [SMILES: C[C@H]1CCCN1C(=O)c1nc(C(=O)N[C@H](C)C(C)(C)O)sc1-c1cnc(NC(C)(C)C)cc1C(F)(F)F]

The title compound was prepared as described in Example 148 substituting (R)-3-amino-2-methylbutan-2-ol for (R)-(−)-2-amino-1-propanol and ethyl (S)-5-(6-(tert-butylamino)-4-(trifluoromethyl)pyridin-3-yl)-4-(2-methylpyrrolidine-1-carbonyl)thiazole-2-carboxylate (Intermediate 107) for ethyl (S)-5-(6-(tert-butylamino)-4-(difluoromethyl)pyridin-3-yl)-4-(2-methylpyrrolidine-1-carbonyl)thiazole-2-carboxylate. MS (ESI): mass calcd. for $C_{25}H_{34}F_3N_5O_3S$, 541.6; m/z found, 542.2 [M+H]$^+$. $^1$H NMR (500 MHz, CDCl$_3$) δ 8.19-8.14 (m, 1H), 7.44 (d, J=9.2 Hz, 1H), 6.66-6.62 (m, 1H), 4.32-4.03 (m, 2H), 3.66-3.33 (m, 2H), 2.32-2.19 (m, 1H), 2.11-2.01 (m, 1H), 1.94-1.83 (m, 1H), 1.78-1.68 (m, 1H), 1.60-1.48 (m, 1H), 1.45 (s, 9H), 1.33-1.21 (m, 12H), 1.12 (d, J=6.3 Hz, 1H).

Example 336

5-[6-(tert-Butylamino)-4-(trifluoromethyl)-3-pyridyl]-N-[(1S)-2-hydroxy-1,2-dimethyl-propyl]-4-[(2S)-2-methylpyrrolidine-1-carbonyl]thiazole-2-carboxamide

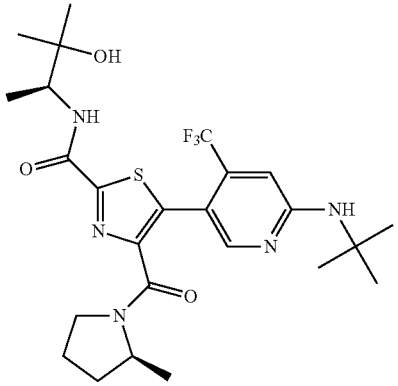 [SMILES: C[C@H](NC(=O)c1nc(C(=O)N2CCC[C@@H]2C)c(-c2cnc(NC(C)(C)C)cc2C(F)(F)F)s1)C(C)(C)O]

The title compound was prepared as described in Example 149 substituting (S)-3-amino-2-methylbutan-2-ol HCl for 3-hydroxy-3-methylazetidine HCl and ethyl (S)-5-(6-(tert-butylamino)-4-(trifluoromethyl)pyridin-3-yl)-4-(2-methylpyrrolidine-1-carbonyl)thiazole-2-carboxylate (Intermediate 107) for ethyl (S)-5-(6-(tert-butylamino)-4-(difluoromethyl)pyridin-3-yl)-4-(2-methylpyrrolidine-1-carbonyl)thiazole-2-carboxylate. MS (ESI): mass calcd. for $C_{25}H_{34}F_3N_5O_3S$, 541.6; m/z found, 542.3 [M+H]$^+$. $^1$H NMR (500 MHz, CDCl$_3$) δ 8.18-8.14 (s, 1H), 7.49-7.41 (dd, J=9.3, 3.5 Hz, 1H), 6.69-6.63 (s, 1H), 5.19-5.04 (m, 1H), 4.27-4.16 (m, 1H), 4.15-4.05 (m, 1H), 3.41-3.36 (m, 1H), 2.55-2.38 (m, 1H), 2.13-1.99 (m, 1H), 1.96-1.82 (m, 1H), 1.80-1.69 (m, 1H), 1.59-1.48 (m, 1H), 1.46-1.42 (s, 9H), 1.32-1.12 (m, 13H).

Example 337

5-[6-(tert-Butylamino)-4-(trifluoromethyl)-3-pyridyl]-N-(3-hydroxy-3-methyl-cyclobutyl)-4-[(2S)-2-methylpyrrolidine-1-carbonyl]thiazole-2-carboxamide

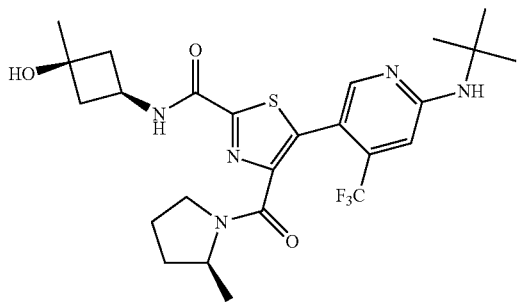 [SMILES: C[C@H]1CCCN1C(=O)c1nc(C(=O)N[C@H]2C[C@@](C)(O)C2)sc1-c1cnc(NC(C)(C)C)cc1C(F)(F)F]

The title compound was prepared as described in Example 149 substituting (1s,3s)-3-amino-1-methylcyclobutan-1-ol HCl for 3-hydroxy-3-methylazetidine HCl and ethyl (S)-5-(6-(tert-butylamino)-4-(trifluoromethyl)pyridin-3-yl)-4-(2-methylpyrrolidine-1-carbonyl)thiazole-2-carboxylate (Intermediate 107) for ethyl (S)-5-(6-(tert-butylamino)-4-(difluoromethyl)pyridin-3-yl)-4-(2-methylpyrrolidine-1-carbonyl)thiazole-2-carboxylate. MS (ESI): mass calcd. for $C_{25}H_{32}F_3N_5O_3S$, 539.6; m/z found, 540.3 [M+H]$^+$. $^1$H NMR (500 MHz, CDCl$_3$) δ 8.16 (s, 1H), 7.54 (d, J=8.0 Hz, 1H), 6.66-6.64 (m, 1H), 5.09 (s, 1H), 4.23-4.16 (m, 2H), 3.41-3.35 (m, 1H), 2.92 (br s, 1H), 2.63-2.58 (m, 2H), 2.27-2.20 (m, 2H), 2.09-2.02 (m, 1H), 1.93-1.86 (m, 1H), 1.76-1.70 (m, 1H), 1.58-1.49 (m, 1H), 1.45-1.42 (m, 11H), 1.26-1.22 (m, 2H).

Example 338

5-[6-(tert-Butylamino)-4-(trifluoromethyl)-3-pyridyl]-N-(3-hydroxy-3-methyl-butyl)-4-[(2S)-2-methylpyrrolidine-1-carbonyl]thiazole-2-carboxamide

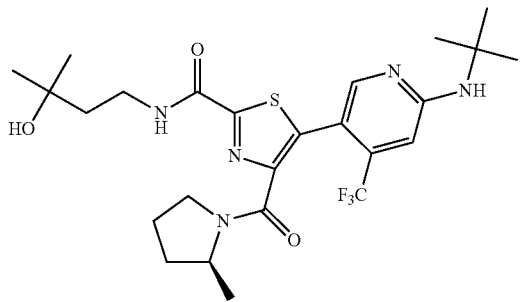 [SMILES: C[C@H]1CCCN1C(=O)c1nc(C(=O)NCCC(C)(C)O)sc1-c1cnc(NC(C)(C)C)cc1C(F)(F)F]

The title compound was prepared as described in Example 148 substituting 4-amino-2-methylbutan-2-ol for (R)-(−)-2-amino-1-propanol and ethyl (S)-5-(6-(tert-butylamino)-4-(trifluoromethyl)pyridin-3-yl)-4-(2-methylpyrrolidine-1-carbonyl)thiazole-2-carboxylate (Intermediate 107) for ethyl (S)-5-(6-(tert-butylamino)-4-(difluoromethyl)pyridin-3-yl)-4-(2-methylpyrrolidine-1-carbonyl)thiazole-2-carboxylate. MS (ESI): mass calcd. for $C_{25}H_{34}F_3N_5O_3S$, 541.6; m/z found, 542.2 [M+H]$^+$. $^1$H NMR (400 MHz, CDCl$_3$) δ 8.15 (s, 1H), 7.97-7.87 (m, 1H), 6.65 (s, 1H), 5.21-5.10 (m, 1H), 4.38-4.07 (m, 1H), 3.68-3.55 (m, 2H), 3.49-3.38 (m, 1H), 2.43-2.29 (m, 1H), 2.09-1.99 (m, 1H), 1.95-1.69 (m, 4H), 1.65-1.48 (m, 1H), 1.44 (s, 9H), 1.32-1.05 (m, 10H).

Example 339

5-[6-(tert-Butylamino)-4-(trifluoromethyl)-3-pyridyl]-N-(2-hydroxy-1,1-dimethyl-ethyl)-4-[(2S)-2-methylpyrrolidine-1-carbonyl]thiazole-2-carboxamide

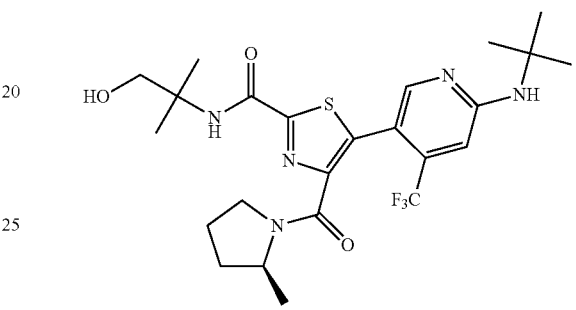

The title compound was prepared as described in Example 148 substituting 2-amino-2-methylpropan-1-ol for (R)-(−)-2-amino-1-propanol and ethyl (S)-5-(6-(tert-butylamino)-4-(trifluoromethyl)pyridin-3-yl)-4-(2-methylpyrrolidine-1-carbonyl)thiazole-2-carboxylate (Intermediate 107) for ethyl (S)-5-(6-(tert-butylamino)-4-(difluoromethyl)pyridin-3-yl)-4-(2-methylpyrrolidine-1-carbonyl)thiazole-2-carboxylate. MS (ESI): mass calcd. for $C_{24}H_{32}F_3N_5O_3S$, 527.6; m/z found, 528.2 [M+H]$^+$. $^1$H NMR (400 MHz, CDCl$_3$) δ 8.18-8.13 (m, 1H), 7.36-7.29 (m, 1H), 6.68-6.62 (m, 1H), 5.12-5.04 (m, 1H), 4.27-4.08 (m, 2H), 3.72 (d, J=5.7 Hz, 2H), 3.36 (t, J=6.8 Hz, 1H), 2.10-2.02 (m, 1H), 1.97-1.82 (m, 1H), 1.80-1.67 (m, 1H), 1.56-1.42 (m, 16H), 1.30-1.09 (m, 4H).

Example 340

5-[6-(tert-Butylamino)-4-(trifluoromethyl)-3-pyridyl]-N-(2-hydroxy-2-methyl-propyl)-N-methyl-4-[(2S)-2-methylpyrrolidine-1-carbonyl]thiazole-2-carboxamide

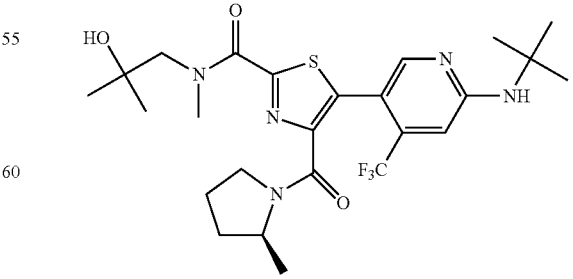

The title compound was prepared as described in Example 148 substituting 2-methyl-1-(methylamino)propan-2-ol for (R)-(−)-2-amino-1-propanol and ethyl (S)-5-(6-(tert-butylamino)-4-(trifluoromethyl)pyridin-3-yl)-4-(2-methylpyrrolidine-1-carbonyl)thiazole-2-carboxylate (Intermediate 107) for ethyl (S)-5-(6-(tert-butylamino)-4-(difluoromethyl)pyridin-3-yl)-4-(2-methylpyrrolidine-1-carbonyl)thiazole-2-carboxylate. MS (ESI): mass calcd. for $C_{25}H_{34}F_3N_5O_3S$, 541.6; m/z found, 542.2 [M+H]$^+$. $^1$H NMR (500 MHz, CDCl$_3$) δ 8.19-8.13 (m, 1H), 6.69-6.58 (m, 1H), 5.15-5.01 (m, 1H), 4.27-3.89 (m, 2H), 3.75-3.43 (m, 5H), 3.28 (s, 1H), 2.14-1.49 (m, 5H), 1.44 (s, 9H), 1.34-1.22 (m, 9H).

Example 341

5-[6-(tert-Butylamino)-4-(trifluoromethyl)-3-pyridyl]-N-[(1R)-1,2-dimethylpropyl]-4-[(2S)-2-methylpyrrolidine-1-carbonyl]thiazole-2-carboxamide

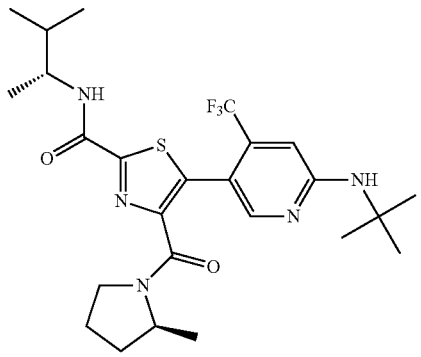 [SMILES: CC(C)[C@@H](C)NC(=O)c1nc(C(=O)N2CCC[C@@H]2C)c(-c2cnc(NC(C)(C)C)cc2C(F)(F)F)s1]

The title compound was prepared as described in Example 148 substituting (R)-3-methylbutan-2-amine for (R)-(−)-2-amino-1-propanol and ethyl (S)-5-(6-(tert-butylamino)-4-(trifluoromethyl)pyridin-3-yl)-4-(2-methylpyrrolidine-1-carbonyl)thiazole-2-carboxylate (Intermediate 107) for ethyl (S)-5-(6-(tert-butylamino)-4-(difluoromethyl)pyridin-3-yl)-4-(2-methylpyrrolidine-1-carbonyl)thiazole-2-carboxylate. MS (ESI): mass calcd. for $C_{25}H_{34}F_3N_5O_2S$, 525.6; m/z found, 526.2 [M+H]$^+$. $^1$H NMR (400 MHz, CDCl$_3$) δ 8.17 (s, 1H), 7.12-7.00 (m, 1H), 6.64 (s, 1H), 5.11-5.02 (m, 1H), 4.28-3.97 (m, 2H), 3.38 (t, J=6.7 Hz, 1H), 2.12-1.67 (m, 5H), 1.55-1.43 (m, 10H), 1.29-1.19 (m, 6H), 1.03-0.94 (m, 6H).

Example 342

5-[6-(tert-Butylamino)-4-(trifluoromethyl)-3-pyridyl]-N-(2-hydroxy-1,1,2-trimethyl-propyl)-4-[(2S)-2-methylpyrrolidine-1-carbonyl]thiazole-2-carboxamide

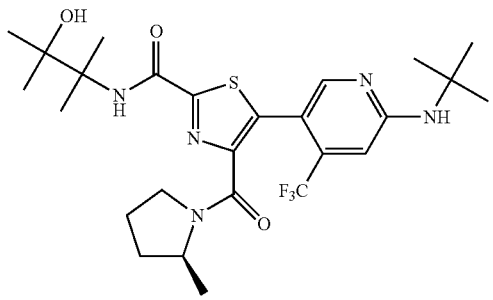 [SMILES: C[C@H]1CCCN1C(=O)c1nc(C(=O)NC(C)(C)C(C)(C)O)sc1-c1cnc(NC(C)(C)C)cc1C(F)(F)F]

The title compound was prepared as described in Example 148 substituting 3-amino-2,3-dimethylbutan-2-ol for (R)-(−)-2-amino-1-propanol and ethyl (S)-5-(6-(tert-butylamino)-4-(trifluoromethyl)pyridin-3-yl)-4-(2-methylpyrrolidine-1-carbonyl)thiazole-2-carboxylate (Intermediate 107) for ethyl (S)-5-(6-(tert-butylamino)-4-(difluoromethyl)pyridin-3-yl)-4-(2-methylpyrrolidine-1-carbonyl)thiazole-2-carboxylate. MS (ESI): mass calcd. for $C_{26}H_{36}F_3N_5O_3S$, 555.7; m/z found, 556.2 [M+H]$^+$. $^1$H NMR (400 MHz, CDCl$_3$) δ 8.17 (d, J=3.4 Hz, 1H), 7.54-7.43 (m, 1H), 6.63 (s, 1H), 5.00-4.63 (m, 2H), 4.34-4.14 (m, 1H), 3.42-3.33 (m, 1H), 2.12-2.02 (m, 1H), 1.93-1.83 (m, 1H), 1.78-1.67 (m, 2H), 1.51-1.43 (m, 16H), 1.29-1.21 (m, 9H).

Example 343

5-[4-(Difluoromethyl)-6-(2,2-dimethylpropylamino)-3-pyridyl]-N-[(1R)-2-hydroxy-1,2-dimethyl-propyl]-4-[(2S)-2-methylpyrrolidine-1-carbonyl]thiazole-2-carboxamide

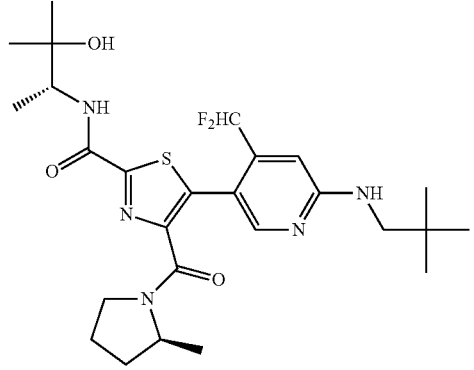 [SMILES: C[C@H]1CCCN1C(=O)c1nc(C(=O)N[C@H](C)C(C)(C)O)sc1-c1cnc(NCC(C)(C)C)cc1C(F)F]

The title compound was prepared as described in Example 148 substituting (R)-3-amino-2-methylbutan-2-ol for (R)-(−)-2-amino-1-propanol and ethyl (S)-5-(4-(difluoromethyl)-6-(neopentylamino)pyridin-3-yl)-4-(2-methylpyrrolidine-1-carbonyl)thiazole-2-carboxylate (Intermediate 151) for ethyl (S)-5-(6-(tert-butylamino)-4-(difluoromethyl)pyridin-3-yl)-4-(2-methylpyrrolidine-1-carbonyl)thiazole-2-carboxylate. MS (ESI): mass calcd. for $C_{26}H_{37}F_2N_5O_3S$, 537.7; m/z found, 538.2 [M+H]$^+$. $^1$H NMR (400 MHz, CDCl$_3$) δ 8.06-7.94 (m, 1H), 7.51-7.40 (m, 1H), 7.03-6.58 (m, 2H), 5.27-5.09 (m, 1H), 4.34-4.00 (m, 2H), 3.64-3.30 (m, 2H), 3.24-3.09 (m, 2H), 2.73-2.45 (m, 1H), 2.38-1.47 (m, 4H), 1.31-1.20 (m, 12H), 1.01-0.96 (m, 9H).

Example 344

5-[4-(Difluoromethyl)-6-(2,2-dimethylpropylamino)-3-pyridyl]-N-[(1S)-2-hydroxy-1,2-dimethyl-propyl]-4-[(2S)-2-methylpyrrolidine-1-carbonyl]thiazole-2-carboxamide

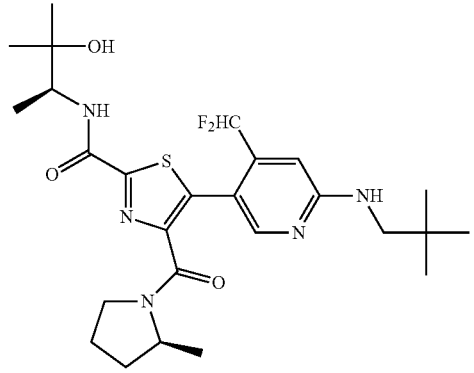 [SMILES: C[C@H](NC(=O)c1nc(C(=O)N2CCC[C@@H]2C)c(-c2cnc(NCC(C)(C)C)cc2C(F)F)s1)C(C)(C)O]

The title compound was prepared as described in Example 148 substituting (S)-3-amino-2-methylbutan-2-ol for (R)-(−)-2-amino-1-propanol and ethyl (S)-5-(4-(difluoromethyl)-6-(neopentylamino)pyridin-3-yl)-4-(2-methylpyrrolidine-1-carbonyl)thiazole-2-carboxylate (Intermediate 151) for ethyl (S)-5-(6-(tert-butylamino)-4-(difluoromethyl)pyridin-3-yl)-4-(2-methylpyrrolidine-1-carbonyl)thiazole-2-carboxylate. MS (ESI): mass calcd. for $C_{26}H_{37}F_2N_5O_3S$, 537.7; m/z found, 538.3 $[M+H]^+$. $^1H$ NMR (400 MHz, $CDCl_3$) δ 8.05-7.97 (m, 1H), 7.51-7.43 (m, 1H), 7.01-6.60 (m, 2H), 5.32-5.20 (m, 1H), 4.24-4.05 (m, 2H), 3.63-3.31 (m, 2H), 3.25-3.11 (m, 2H), 2.76 (s, 1H), 2.10-1.47 (m, 4H), 1.36-1.18 (m, 12H), 1.03-0.95 (m, 9H).

Example 345

5-[6-(tert-Butylamino)-4-(trifluoromethyl)-3-pyridyl]-N-[(2R)-2,3-dihydroxypropyl]-4-[(2S)-2-methylpyrrolidine-1-carbonyl]thiazole-2-carboxamide

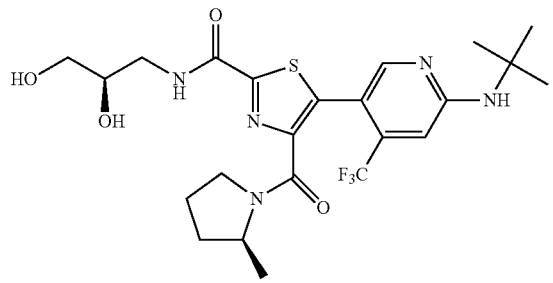 [SMILES: C[C@H]1CCCN1C(=O)c1nc(C(=O)NC[C@@H](O)CO)sc1-c1cnc(NC(C)(C)C)cc1C(F)(F)F]

The title compound was prepared as described in Example 148 substituting (R)-3-aminopropane-1,2-diol for (R)-(−)-2-amino-1-propanol and ethyl (S)-5-(6-(tert-butylamino)-4-(trifluoromethyl)pyridin-3-yl)-4-(2-methylpyrrolidine-1-carbonyl)thiazole-2-carboxylate (Intermediate 107) for ethyl (S)-5-(6-(tert-butylamino)-4-(difluoromethyl)pyridin-3-yl)-4-(2-methylpyrrolidine-1-carbonyl)thiazole-2-carboxylate. MS (ESI): mass calcd. for $C_{23}H_{30}F_3N_5O_4S$, 529.6; m/z found, 530.2 $[M+H]^+$. $^1H$ NMR (400 MHz, $CDCl_3$) δ 8.07 (s, 1H), 7.87-7.72 (m, 1H), 6.62-6.55 (m, 1H), 5.07-4.97 (m, 1H), 4.19-3.99 (m, 1H), 3.90-3.72 (m, 2H), 3.63-3.41 (m, 5H), 3.29 (t, J=6.5 Hz, 1H), 2.03-1.90 (m, 1H), 1.86-1.72 (m, 1H), 1.70-1.59 (m, 1H), 1.49-1.32 (m, 10H), 1.22-0.94 (m, 4H).

Example 346

5-[6-(tert-Butylamino)-4-(trifluoromethyl)-3-pyridyl]-N-[(1R)-2-hydroxy-1-methyl-ethyl]-4-[(2S)-2-methylpyrrolidine-1-carbonyl]thiazole-2-carboxamide

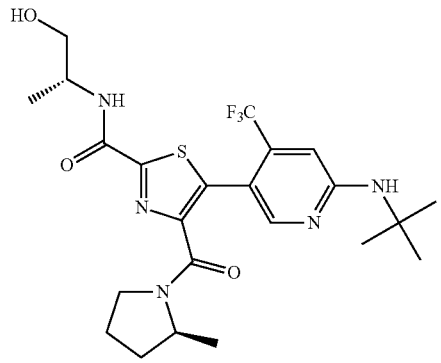 [SMILES: C[C@H](CO)NC(=O)c1nc(C(=O)N2CCC[C@@H]2C)c(-c2cnc(NC(C)(C)C)cc2C(F)(F)F)s1]

The title compound was prepared as described in Example 148 substituting ethyl (S)-5-(6-(tert-butylamino)-4-(trifluoromethyl)pyridin-3-yl)-4-(2-methylpyrrolidine-1-carbonyl)thiazole-2-carboxylate (Intermediate 107) for ethyl (S)-5-(6-(tert-butylamino)-4-(difluoromethyl)pyridin-3-yl)-4-(2-methylpyrrolidine-1-carbonyl)thiazole-2-carboxylate. MS (ESI): mass calcd. for $C_{23}H_{30}F_3N_5O_3S$, 513.6; m/z found, 514.2 $[M+H]^+$. $^1H$ NMR (400 MHz, $CDCl_3$) δ 8.20-8.12 (m, 1H), 7.47 (d, J=8.0 Hz, 1H), 6.66 (d, J=2.1 Hz, 1H), 5.21-5.10 (m, 1H), 4.31-4.07 (m, 2H), 3.81-3.60 (m, 2H), 3.41-3.27 (m, 2H), 2.11-1.99 (m, 1H), 1.96-1.80 (m, 1H), 1.79-1.67 (m, 1H), 1.58-1.41 (m, 10H), 1.37-1.07 (m, 7H).

Example 347

5-[6-(tert-Butylamino)-4-(trifluoromethyl)-3-pyridyl]-N-[cis-2-hydroxycyclopentyl]-4-[(2S)-2-methylpyrrolidine-1-carbonyl]thiazole-2-carboxamide

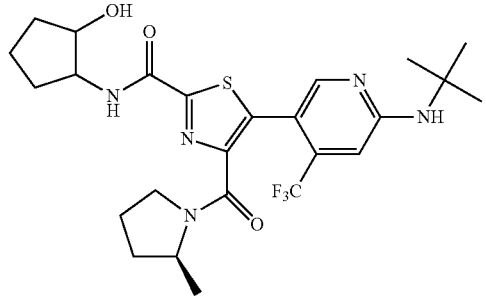 [SMILES: C[C@H]1CCCN1C(=O)c1nc(C(=O)NC2CCCC2O)sc1-c1cnc(NC(C)(C)C)cc1C(F)(F)F]

The title compound was prepared as described in Example 149 substituting cis-4-aminotetrahydrofuran-3-ol HCl for 3-hydroxy-3-methylazetidine HCl and ethyl (S)-5-(6-(tert-butylamino)-4-(trifluoromethyl)pyridin-3-yl)-4-(2-methylpyrrolidine-1-carbonyl)thiazole-2-carboxylate (Intermediate 107) for ethyl (S)-5-(6-(tert-butylamino)-4-(difluoromethyl)pyridin-3-yl)-4-(2-methylpyrrolidine-1-carbonyl)thiazole-2-carboxylate. MS (ESI): mass calcd. for $C_{25}H_{32}F_3N_5O_3S$, 539.6; m/z found, 540.2 $[M+H]^+$. $^1H$ NMR (400 MHz, $CDCl_3$) δ 8.20-8.10 (m, 1H), 7.79-7.65 (m, 1H), 6.66 (s, 1H), 5.19-5.06 (m, 1H), 4.30-4.11 (m, 3H), 3.63-3.33 (m, 2H), 2.21-2.00 (m, 2H), 1.98-1.83 (m, 3H), 1.83-1.67 (m, 3H), 1.67-1.58 (m, 1H), 1.57-1.40 (m, 10H), 1.32-1.05 (m, 4H).

Example 348

5-[6-(tert-Butylamino)-4-(trifluoromethyl)-3-pyridyl]-N-[(3S,4R)-4-hydroxytetrahydrofuran-3-yl]-4-[(2S)-2-methylpyrrolidine-1-carbonyl]thiazole-2-carboxamide

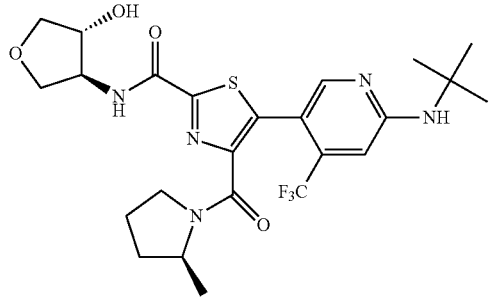 [SMILES: C[C@H]1CCCN1C(=O)c1nc(C(=O)N[C@H]2COC[C@@H]2O)sc1-c1cnc(NC(C)(C)C)cc1C(F)(F)F]

The title compound was prepared as described in Example 148 substituting (3R,4S)-4-aminotetrahydrofuran-3-ol for (R)-(−)-2-amino-1-propanol and ethyl (S)-5-(6-(tert-butylamino)-4-(trifluoromethyl)pyridin-3-yl)-4-(2-methylpyrrolidine-1-carbonyl)thiazole-2-carboxylate (Intermediate 107) for ethyl (S)-5-(6-(tert-butylamino)-4-(difluoromethyl)pyridin-3-yl)-4-(2-methylpyrrolidine-1-carbonyl)thiazole-2-carboxylate. MS (ESI): mass calcd. for $C_{24}H_{30}F_3N_5O_4S$, 541.6; m/z found, 542.2 [M+H]$^+$. $^1$H NMR (400 MHz, CD$_3$OD) δ 8.13-8.06 (m, 1H), 7.91 (s, 1H), 6.85 (s, 1H), 4.48-4.33 (m, 2H), 4.23-4.02 (m, 3H), 3.89-3.80 (m, 1H), 3.76-3.68 (m, 1H), 3.64-3.26 (m, 2H), 2.18-1.85 (m, 3H), 1.83-1.72 (m, 1H), 1.65-1.54 (m, 2H), 1.47 (s, 9H), 1.40-1.02 (m, 3H).

Example 349

[5-[6-(tert-Butylamino)-4-(trifluoromethyl)-3-pyridyl]-2-[(3R)-3-hydroxypyrrolidine-1-carbonyl]thiazol-4-yl]-[(2S)-2-methylpyrrolidin-1-yl]methanone

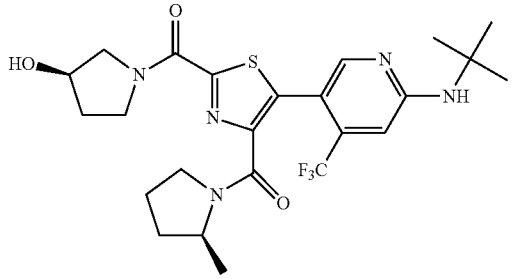 [SMILES: C[C@H]1CCCN1C(=O)c1nc(C(=O)N2CC[C@@H](O)C2)sc1-c1cnc(NC(C)(C)C)cc1C(F)(F)F]

The title compound was prepared as described in Example 148 substituting (R)-pyrrolidin-3-ol for (R)-(−)-2-amino-1-propanol and ethyl (S)-5-(6-(tert-butylamino)-4-(trifluoromethyl)pyridin-3-yl)-4-(2-methylpyrrolidine-1-carbonyl)thiazole-2-carboxylate (Intermediate 107) for ethyl (9-5-(6-(tert-butylamino)-4-(difluoromethyl)pyridin-3-yl)-4-(2-methylpyrrolidine-1-carbonyl)thiazole-2-carboxylate. MS (ESI): mass calcd. for $C_{24}H_{30}F_3N_5O_3S$, 525.6; m/z found, 526.2 [M+H]$^+$. $^1$H NMR (400 MHz, CDCl$_3$) δ 8.11-8.03 (m, 1H), 6.60-6.52 (m, 1H), 5.02-4.93 (m, 1H), 4.56-4.39 (m, 1H), 4.36-4.21 (m, 1H), 4.19-4.00 (m, 3H), 3.81-3.64 (m, 2H), 3.53-3.37 (m, 2H), 3.19-2.99 (s, 1H), 2.06-1.90 (m, 3H), 1.88-1.78 (m, 1H), 1.51-1.42 (m, 1H), 1.41-1.34 (s, 9H), 1.23-1.11 (m, 3H).

Example 350

[5-[6-(tert-Butylamino)-4-(trifluoromethyl)-3-pyridyl]-2-[(3S)-3-hydroxypyrrolidine-1-carbonyl]thiazol-4-yl]-[(2S)-2-methylpyrrolidin-1-yl]methanone

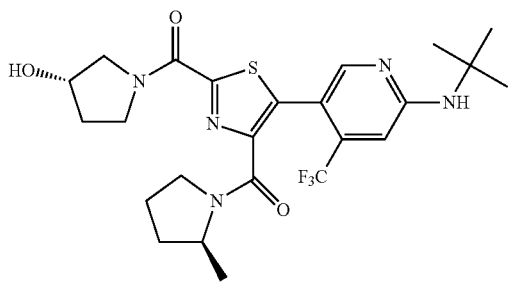 [SMILES: C[C@H]1CCCN1C(=O)c1nc(C(=O)N2CC[C@H](O)C2)sc1-c1cnc(NC(C)(C)C)cc1C(F)(F)F]

The title compound was prepared as described in Example 148 substituting (S)-pyrrolidin-3-ol for (R)-(−)-2-amino-1-propanol and ethyl (S)-5-(6-(tert-butylamino)-4-(trifluoromethyl)pyridin-3-yl)-4-(2-methylpyrrolidine-1-carbonyl)thiazole-2-carboxylate (Intermediate 107) for ethyl (S)-5-(6-(tert-butylamino)-4-(difluoromethyl)pyridin-3-yl)-4-(2-methylpyrrolidine-1-carbonyl)thiazole-2-carboxylate. MS (ESI): mass calcd. for $C_{24}H_{30}F_3N_5O_3S$, 525.6; m/z found, 526.2 [M+H]$^+$. $^1$H NMR (400 MHz, CDCl$_3$) δ 8.19-8.11 (m, 1H), 6.70-6.61 (m, 1H), 5.18-5.06 (s, 1H), 4.63-4.47 (m, 1H), 4.48-4.36 (m, 1H), 4.32-4.05 (m, 3H), 3.91-3.79 (m, 1H), 3.79-3.69 (m, 1H), 3.67-3.44 (m, 2H), 3.44-3.33 (m, 1H), 2.18-1.97 (m, 3H), 1.97-1.84 (m, 1H), 1.70-1.50 (m, 1H), 1.50-1.41 (s, 9H), 1.31-1.19 (m, 3H).

Example 351

5-[6-(tert-Butylamino)-4-(trifluoromethyl)-3-pyridyl]-N-[(1R,2R)-2-hydroxycyclopentyl]-4-[(2S)-2-methylpyrrolidine-1-carbonyl]thiazole-2-carboxamide

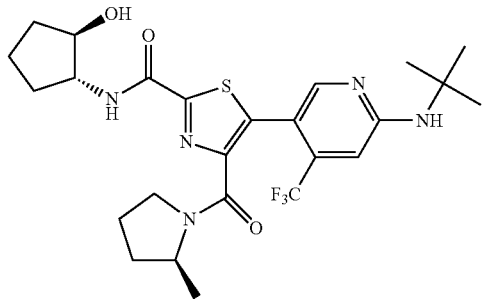 [SMILES: C[C@H]1CCCN1C(=O)c1nc(C(=O)N[C@@H]2CCC[C@H]2O)sc1-c1cnc(NC(C)(C)C)cc1C(F)(F)F]

The title compound was prepared as described in Example 149 substituting (1R,2R)-2-aminocyclopentan-1-ol HCl for 3-hydroxy-3-methylazetidine HCl and ethyl (S)-5-(6-(tert-butylamino)-4-(trifluoromethyl)pyridin-3-yl)-4-(2-methylpyrrolidine-1-carbonyl)thiazole-2-carboxylate (Intermediate 107) for ethyl (S)-5-(6-(tert-butylamino)-4-(difluoromethyl)pyridin-3-yl)-4-(2-methylpyrrolidine-1-carbonyl)thiazole-2-carboxylate. MS (ESI): mass calcd. for $C_{25}H_{32}F_3N_5O_3S$, 539.6; m/z found, 540.2 [M+H]$^+$. $^1$H NMR (400 MHz, CDCl$_3$) δ 8.23-8.15 (s, 1H), 7.40-7.33 (m, 1H), 6.70-6.64 (m, 1H), 5.14-5.01 (s, 1H), 4.30-4.00 (m, 4H), 3.41-3.34 (t, J=6.8 Hz, 1H), 2.37-2.22 (m, 1H), 2.16-2.02 (m, 2H), 1.97-1.85 (m, 2H), 1.82-1.70 (m, 3H), 1.70-1.61 (m, 1H), 1.59-1.42 (s, 10H), 1.29-1.06 (m, 4H).

Example 352

5-[6-(tert-Butylamino)-4-(trifluoromethyl)-3-pyridyl]-4-(2-methylpyrrolidine-1-carbonyl)-N-(3,3,3-trifluoro-2-hydroxy-propyl)thiazole-2-carboxamide

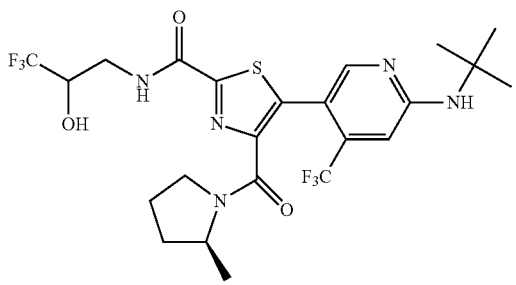 [SMILES: C[C@H]1CCCN1C(=O)c1nc(C(=O)NCC(O)C(F)(F)F)sc1-c1cnc(NC(C)(C)C)cc1C(F)(F)F]

The title compound was prepared as described in Example 148 substituting 3-amino-1,1,1-trifluoropropan-2-ol for (R)-(−)-2-amino-1-propanol and ethyl (S)-5-(6-(tert-butylamino)-4-(trifluoromethyl)pyridin-3-yl)-4-(2-methylpyrrolidine-1-carbonyl)thiazole-2-carboxylate (Intermediate 107) for ethyl (S)-5-(6-(tert-butylamino)-4-(difluoromethyl)pyridin-3-yl)-4-(2-methylpyrrolidine-1-carbonyl)thiazole-2-carboxylate. MS (ESI): mass calcd. for $C_{23}H_{27}F_6N_5O_3S$, 567.6; m/z found, 568.2 [M+H]$^+$. $^1$H NMR (400 MHz, CDCl$_3$) δ 8.23-8.17 (m, 1H), 7.75-7.60 (m, 1H), 6.72-6.64 (m, 1H), 5.00-4.90 (m, 1H), 4.29-4.20 (m, 2H), 4.20-4.12 (q, J=7.1 Hz, 1H), 4.05-3.95 (m, 1H), 3.68-3.57 (m, 1H), 3.47-3.36 (m, 1H), 2.12-2.07 (m, 1H), 2.01-1.87 (m, 1H), 1.84-1.73 (m, 1H), 1.67-1.60 (m, 2H), 1.54-1.47 (s, 9H), 1.34-1.07 (m, 3H).

Example 353

5-(6-(tert-Butylamino)-4-(trifluoromethyl)pyridin-3-yl)-4-((S)-2-methylpyrrolidine-1-carbonyl)-N—((S*)-3,3,3-trifluoro-2-hydroxypropyl)thiazole-2-carboxamide

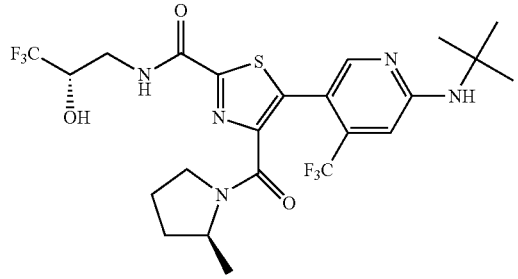 [SMILES: C[C@H]1CCCN1C(=O)c1nc(C(=O)NC[C@H](O)C(F)(F)F)sc1-c1cnc(NC(C)(C)C)cc1C(F)(F)F]

The title compound was prepared as described in Example 148 substituting 3-amino-1,1,1-trifluoropropan-2-ol for (R)-(−)-2-amino-1-propanol and ethyl (S)-5-(6-(tert-butylamino)-4-(trifluoromethyl)pyridin-3-yl)-4-(2-methylpyrrolidine-1-carbonyl)thiazole-2-carboxylate (Intermediate 107) for ethyl (S)-5-(6-(tert-butylamino)-4-(difluoromethyl)pyridin-3-yl)-4-(2-methylpyrrolidine-1-carbonyl)thiazole-2-carboxylate followed by SFC purification (Stationary phase: Chiralpak AD-H 5 μm 250×30 mm, Mobile phase: 90% CO$_2$, 10% i-PrOH (0.3% i-PrNH$_2$)). MS (ESI): mass calcd. for $C_{23}H_{27}F_6N_5O_3S$, 567.6; m/z found, 568.2 [M+H]$^+$. $^1$H NMR (400 MHz, CDCl$_3$) δ 8.05-7.99 (m, 1H), 7.76-7.62 (m, 1H), 6.62-6.54 (s, 1H), 5.08-4.97 (s, 1H), 4.14-3.82 (m, 3H), 3.51-3.20 (m, 3H), 2.02-1.90 (m, 1H), 1.88-1.75 (m, 1H), 1.71-1.59 (m, 1H), 1.49-1.31 (m, 10H), 1.18-0.91 (m, 4H).

Example 354

5-(6-(tert-Butylamino)-4-(trifluoromethyl)pyridin-3-yl)-4-((S)-2-methylpyrrolidine-1-carbonyl)-N—((R*)-3,3,3-trifluoro-2-hydroxypropyl)thiazole-2-carboxamide

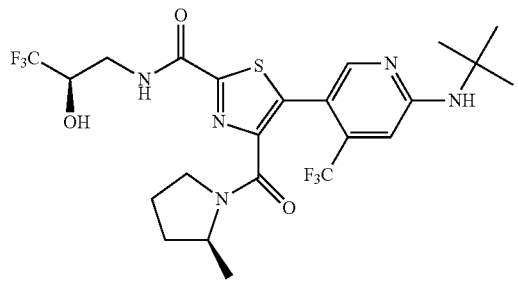 [SMILES: C[C@H]1CCCN1C(=O)c1nc(C(=O)NC[C@@H](O)C(F)(F)F)sc1-c1cnc(NC(C)(C)C)cc1C(F)(F)F]

The title compound was prepared as described in Example 148 substituting 3-amino-1,1,1-trifluoropropan-2-ol for (R)-(−)-2-amino-1-propanol and ethyl (S)-5-(6-(tert-butylamino)-4-(trifluoromethyl)pyridin-3-yl)-4-(2-methylpyrrolidine-1-carbonyl)thiazole-2-carboxylate (Intermediate 107) for ethyl (S)-5-(6-(tert-butylamino)-4-(difluoromethyl)pyridin-3-yl)-4-(2-methylpyrrolidine-1-carbonyl)thiazole-2-carboxylate followed by SFC purification (Stationary phase: Chiralpak AD-H 5 μm 250×30 mm, Mobile phase: 90% CO$_2$, 10% i-PrOH (0.3% i-PrNH$_2$)). MS (ESI): mass calcd. for $C_{23}H_{27}F_6N_5O_3S$, 567.6; m/z found, 568.2 [M+H]$^+$. $^1$H NMR (400 MHz, CDCl$_3$) δ 8.06-8.02 (m, 1H), 7.76-7.63 (m, 1H), 6.60-6.55 (m, 1H), 5.03-4.91 (m, 1H), 4.16-4.01 (m, 2H), 3.99-3.83 (m, 1H), 3.52-3.41 (m, 2H), 3.34-3.21 (m, 1H), 2.02-1.91 (m, 1H), 1.84-1.72 (m, 1H), 1.70-1.61 (m, 1H), 1.48-1.32 (m, 10H), 1.14-0.99 (m, 4H).

Example 355

N-(2-Amino-2-methyl-propyl)-5-[6-(tert-butylamino)-4-(trifluoromethyl)-3-pyridyl]-4-[(2S)-2-methylpyrrolidine-1-carbonyl]thiazole-2-carboxamide

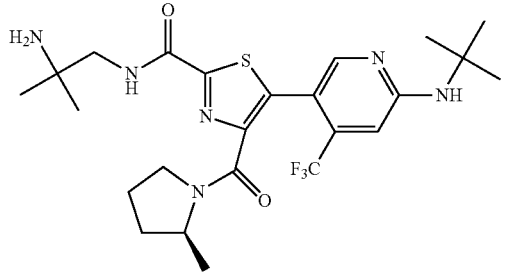 [SMILES: C[C@H]1CCCN1C(=O)c1nc(C(=O)NCC(C)(C)N)sc1-c1cnc(NC(C)(C)C)cc1C(F)(F)F]

The title compound was prepared as described in Example 148 substituting 2-methylpropane-1,2-diamine for (R)-(−)-2-amino-1-propanol and ethyl (S)-5-(6-(tert-butylamino)-4-(trifluoromethyl)pyridin-3-yl)-4-(2-methylpyrrolidine-1-carbonyl)thiazole-2-carboxylate (Intermediate 107) for ethyl (S)-5-(6-(tert-butylamino)-4-(difluoromethyl)pyridin-3-yl)-4-(2-methylpyrrolidine-1-carbonyl)thiazole-2-carboxylate. MS (ESI): mass calcd. for $C_{24}H_{33}F_3N_6O_2S$, 526.6; m/z found, 527.2 [M+H]$^+$. $^1$H NMR (400 MHz, CDCl$_3$) δ 8.22-8.15 (s, 1H), 7.72-7.62 (m, 1H), 6.69-6.62 (s, 1H), 5.12-5.01 (m, 1H), 4.37-4.08 (m, 1H), 3.67-3.27 (m, 4H), 2.13-2.01 (m, 1H), 2.00-1.85 (m, 1H), 1.83-1.69 (m, 1H), 1.60-1.40 (m, 11H), 1.30-1.10 (m, 10H).

Example 356

5-[6-(tert-Butylamino)-4-(trifluoromethyl)-3-pyridyl]-N-(1-methylazetidin-3-yl)-4-[(2S)-2-methylpyrrolidine-1-carbonyl]thiazole-2-carboxamide

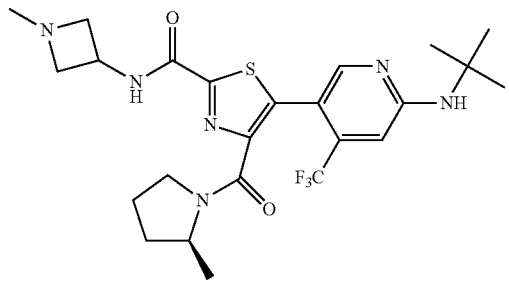 [SMILES: C[C@H]1CCCN1C(=O)c1nc(C(=O)NC2CN(C)C2)sc1-c1cnc(NC(C)(C)C)cc1C(F)(F)F]

The title compound was prepared as described in Example 148 substituting 1-methylazetidin-3-amine for (R)-(−)-2-amino-1-propanol and ethyl (S)-5-(6-(tert-butylamino)-4-(trifluoromethyl)pyridin-3-yl)-4-(2-methylpyrrolidine-1-carbonyl)thiazole-2-carboxylate (Intermediate 107) for ethyl (S)-5-(6-(tert-butylamino)-4-(difluoromethyl)pyridin-3-yl)-4-(2-methylpyrrolidine-1-carbonyl)thiazole-2-carboxylate. MS (ESI): mass calcd. for $C_{24}H_{31}F_3N_6O_2S$, 524.6; m/z found, 525.2 [M+H]$^+$. $^1$H NMR (400 MHz, CDCl$_3$) δ 8.14-8.07 (m, 1H), 7.54-7.39 (m, 1H), 6.58-6.52 (m, 1H), 4.91-4.80 (m, 1H), 4.69-4.54 (m, 1H), 4.21-4.07 (m, 1H), 3.70-3.57 (m, 2H), 3.43-3.24 (m, 2H), 3.09-2.95 (m, 1H), 2.34-2.25 (m, 3H), 2.06-1.93 (m, 1H), 1.90-1.77 (m, 2H), 1.70-1.63 (m, 1H), 1.53-1.32 (m, 10H), 1.19-0.97 (m, 3H).

Example 357

5-(6-(tert-Butylamino)-4-(trifluoromethyl)pyridin-3-yl)-4-((S)-2-methylpyrrolidine-1-carbonyl)-N-(3,3,3-trifluoro-2-hydroxy-2-methylpropyl)thiazole-2-carboxamide

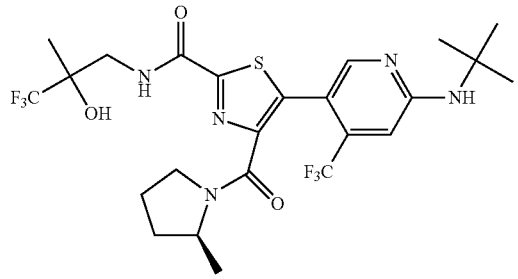 [SMILES: C[C@H]1CCCN1C(=O)c1nc(C(=O)NCC(C)(O)C(F)(F)F)sc1-c1cnc(NC(C)(C)C)cc1C(F)(F)F]

The title compound was prepared as described in Example 149 substituting 3-amino-1,1,1-trifluoro-2-methylpropan-2-ol HCl for 3-hydroxy-3-methylazetidine HCl and ethyl (S)-5-(6-(tert-butylamino)-4-(trifluoromethyl)pyridin-3-yl)-4-(2-methylpyrrolidine-1-carbonyl)thiazole-2-carboxylate (Intermediate 107) for ethyl (S)-5-(6-(tert-butylamino)-4-(difluoromethyl)pyridin-3-yl)-4-(2-methylpyrrolidine-1-carbonyl)thiazole-2-carboxylate. MS (ESI): mass calcd. for $C_{24}H_{29}F_6N_5O_3S$, 581.6; m/z found, 582.2 [M+H]$^+$. $^1$H NMR (500 MHz, CDCl$_3$) δ 8.21-8.16 (s, 1H), 7.67-7.54 (m, 1H), 6.67-6.63 (d, J=2.5 Hz, 1H), 4.94-4.88 (s, 1H), 4.28-4.18 (m, 1H), 4.18-4.09 (q, J=7.2 Hz, 1H), 3.87-3.69 (m, 2H), 1.63-1.58 (m, 2H), 3.47-3.37 (m, 1H), 2.12-2.03 (m, 2H), 1.97-1.85 (m, 1H), 1.82-1.72 (m, 1H), 1.50-1.46 (s, 9H), 1.46-1.44 (s, 3H), 1.28-1.23 (m, 2H).

Example 358

5-(6-(tert-Butylamino)-4-(trifluoromethyl)pyridin-3-yl)-4-((S)-2-methylpyrrolidine-1-carbonyl)-N—((S*)-3,3,3-trifluoro-2-hydroxy-2-methylpropyl)thiazole-2-carboxamide

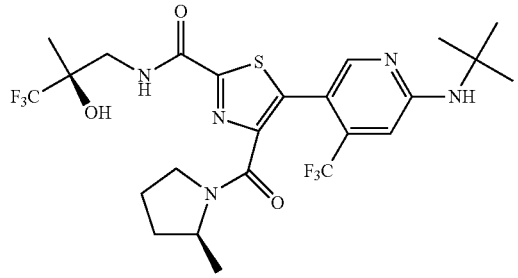 [SMILES: C[C@H]1CCCN1C(=O)c1nc(C(=O)NC[C@](C)(O)C(F)(F)F)sc1-c1cnc(NC(C)(C)C)cc1C(F)(F)F]

The title compound was prepared as described in Example 149 substituting 3-amino-1,1,1-trifluoro-2-methylpropan-2-ol HCl for 3-hydroxy-3-methylazetidine HCl and ethyl (S)-5-(6-(tert-butylamino)-4-(trifluoromethyl)pyridin-3-yl)-4-(2-methylpyrrolidine-1-carbonyl)thiazole-2-carboxylate (Intermediate 107) for ethyl (S)-5-(6-(tert-butylamino)-4-(difluoromethyl)pyridin-3-yl)-4-(2-methylpyrrolidine-1-carbonyl)thiazole-2-carboxylate followed by SFC purification (Stationary phase: CHIRALCEL OJ-H 5 μm 250×20 mm, Mobile phase: 90% CO$_2$, 10% mixture of ACN/MeOH 90/10 v/v). MS (ESI): mass calcd. for $C_{24}H_{29}F_6N_5O_3S$, 581.6; m/z found, 581.9 [M+H]$^+$. $^1$H NMR (400 MHz, CDCl$_3$) δ 8.18-8.11 (m, 1H), 7.76-7.66 (m, 1H), 6.69-6.61 (s, 1H), 5.09-4.99 (m, 1H), 4.60-4.27 (s, 1H), 4.25-4.10 (m, 1H), 3.85-3.62 (m, 2H), 3.62-3.30 (m, 2H), 2.13-1.99 (m, 1H), 1.97-1.80 (m, 2H), 1.79-1.67 (m, 1H), 1.64-1.36 (m, 12H), 1.31-1.04 (m, 3H).

Example 359

5-(6-(tert-Butylamino)-4-(trifluoromethyl)pyridin-3-yl)-4-((S)-2-methylpyrrolidine-1-carbonyl)-N—((R*)-3,3,3-trifluoro-2-hydroxy-2-methylpropyl)thiazole-2-carboxamide

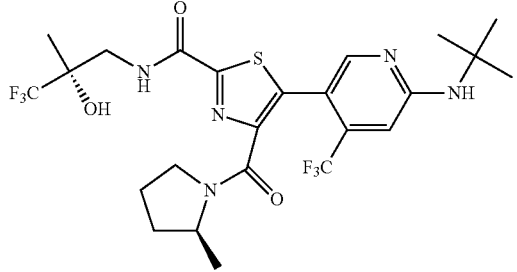

The title compound was prepared as described in Example 149 substituting 3-amino-1,1,1-trifluoro-2-methylpropan-2-ol HCl for 3-hydroxy-3-methylazetidine HCl and ethyl (S)-5-(6-(tert-butylamino)-4-(trifluoromethyl)pyridin-3-yl)-4-(2-methylpyrrolidine-1-carbonyl)thiazole-2-carboxylate (Intermediate 107) for ethyl (S)-5-(6-(tert-butylamino)-4-(difluoromethyl)pyridin-3-yl)-4-(2-methylpyrrolidine-1-carbonyl)thiazole-2-carboxylate followed by SFC purification (Stationary phase: CHIRALCEL OJ-H 5 μm 250×20 mm, Mobile phase: 90% CO$_2$, 10% mixture of ACN/MeOH 90/10 v/v). MS (ESI): mass calcd. for $C_{24}H_{29}F_6N_5O_3S$, 581.6; m/z found, 581.9 [M+H]$^+$. $^1$H NMR (400 MHz, CDCl$_3$) δ 8.18-8.08 (m, 1H), 7.83-7.66 (m, 1H), 6.70-6.59 (s, 1H), 5.11-5.01 (s, 1H), 4.78-4.48 (s, 1H), 4.31-4.10 (m, 1H), 3.86-3.72 (m, 1H), 3.72-3.59 (m, 1H), 3.60-3.28 (m, 2H), 2.12-1.98 (m, 1H), 1.98-1.80 (m, 1H), 1.80-1.66 (m, 1H), 1.66-1.35 (s, 13H), 1.25-1.04 (m, 3H).

Example 360

[5-[6-(tert-Butylamino)-4-(trifluoromethyl)-3-pyridyl]-2-[(1S,4S)-2-oxa-5-azabicyclo[2.2.1]heptane-5-carbonyl]thiazol-4-yl]-[(2S)-2-methylpyrrolidin-1-yl]methanone

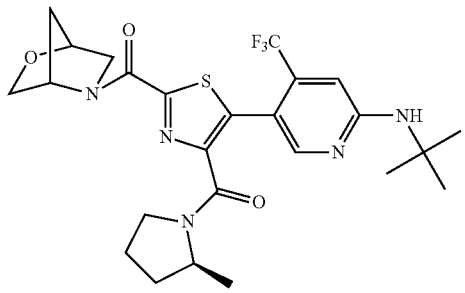 [SMILES: C[C@H]1CCCN1C(=O)c1nc(C(=O)N2CC3CC2CO3)sc1-c1cnc(NC(C)(C)C)cc1C(F)(F)F]

The title compound was prepared as described in Example 149 substituting (1S,4S)-2-oxa-5-azabicyclo[2.2.1]heptane HCl for 3-hydroxy-3-methylazetidine HCl and ethyl (S)-5-(6-(tert-butylamino)-4-(trifluoromethyl)pyridin-3-yl)-4-(2-methylpyrrolidine-1-carbonyl)thiazole-2-carboxylate (Intermediate 107) for ethyl (S)-5-(6-(tert-butylamino)-4-(difluoromethyl)pyridin-3-yl)-4-(2-methylpyrrolidine-1-carbonyl)thiazole-2-carboxylate. MS (ESI): mass calcd. for $C_{25}H_{30}F_3N_5O_3S$, 537.6; m/z found, 538.2 [M+H]$^+$. $^1$H NMR (500 MHz, CDCl$_3$) δ 8.17-8.13 (s, 1H), 6.65-6.59 (m, 1H), 5.00-4.93 (d, J=7.0 Hz, 1H), 4.76-4.70 (m, 1H), 4.24-4.08 (m, 2H), 4.05-3.88 (m, 3H), 3.72-3.62 (m, 1H), 3.51-3.42 (m, 2H), 2.12-1.86 (m, 5H), 1.82-1.71 (m, 1H), 1.48-1.42 (s, 9H), 1.29-1.20 (m, 3H).

Example 361

5-[6-(tert-Butylamino)-4-(trifluoromethyl)-3-pyridyl]-N-[(1S,3S)-3-hydroxycyclopentyl]-4-[(2S)-2-methylpyrrolidine-1-carbonyl]thiazole-2-carboxamide

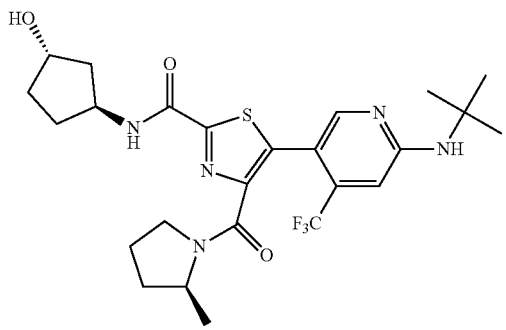 [SMILES: C[C@H]1CCCN1C(=O)c1nc(C(=O)N[C@H]2CC[C@H](O)C2)sc1-c1cnc(NC(C)(C)C)cc1C(F)(F)F]

The title compound was prepared as described in Example 149 substituting (1S,3S)-3-aminocyclopentan-1-ol HCl for 3-hydroxy-3-methylazetidine HCl and ethyl (S)-5-(6-(tert-butylamino)-4-(trifluoromethyl)pyridin-3-yl)-4-(2-methylpyrrolidine-1-carbonyl)thiazole-2-carboxylate (Intermediate 107) for ethyl (S)-5-(6-(tert-butylamino)-4-(difluoromethyl)pyridin-3-yl)-4-(2-methylpyrrolidine-1-carbonyl)thiazole-2-carboxylate. MS (ESI): mass calcd. for $C_{25}H_{32}F_3N_5O_3S$, 539.6; m/z found, 540.2 [M+H]$^+$. $^1$H NMR (500 MHz, CDCl$_3$) δ 8.19-8.15 (s, 1H), 7.21-7.09 (m, 1H), 6.67-6.61 (m, 1H), 5.03-4.95 (s, 1H), 4.70-4.57 (m, 1H), 4.53-4.44 (s, 1H), 4.25-4.08 (m, 1H), 3.64-3.50 (m, 1H), 3.38-3.31 (t, J=6.7 Hz, 1H), 2.43-2.29 (m, 1H), 2.25-2.00 (m, 3H), 1.99-1.92 (s, 1H), 1.92-1.79 (m, 2H), 1.77-1.66 (m, 2H), 1.66-1.56 (m, 1H), 1.55-1.48 (m, 1H), 1.48-1.42 (s, 9H), 1.28-1.20 (m, 3H).

Example 362

5-[6-(tert-Butylamino)-4-(trifluoromethyl)-3-pyridyl]-N-[(1S)-2-hydroxy-1-methyl-ethyl]-4-[(2S)-2-methylpyrrolidine-1-carbonyl]thiazole-2-carboxamide

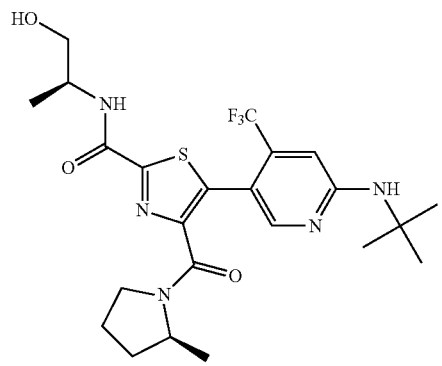 [SMILES: C[C@@H](CO)NC(=O)c1nc(C(=O)N2CCC[C@@H]2C)c(-c2cnc(NC(C)(C)C)cc2C(F)(F)F)s1]

The title compound was prepared as described in Example 148 substituting (S)-2-aminopropan-1-ol for (R)-(–)-2-amino-1-propanol and ethyl (S)-5-(6-(tert-butylamino)-4-(trifluoromethyl)pyridin-3-yl)-4-(2-methylpyrrolidine-1-carbonyl)thiazole-2-carboxylate (Intermediate 107) for ethyl (S)-5-(6-(tert-butylamino)-4-(difluoromethyl)pyridin-3-yl)-4-(2-methylpyrroldine-1-carbonyl)thiazole-2-carboxylate. MS (ESI): mass calcd. for $C_{23}H_{30}F_3N_5O_3S$, 513.6; m/z found, 514.2 [M+H]$^+$. $^1$H NMR (400 MHz, CDCl$_3$) δ 8.12-8.05 (s, 1H), 7.40-7.27 (m, 1H), 6.61-6.54 (m, 1H), 5.04-4.92 (m, 1H), 4.19-4.01 (m, 2H), 3.70-3.45 (m, 2H), 3.33-3.25 (dd, J=7.3, 5.2 Hz, 1H), 3.03-2.86 (m, 1H), 2.04-1.90 (m, 2H), 1.87-1.72 (m, 1H), 1.70-1.59 (m, 1H), 1.48-1.33 (s, 10H), 1.28-0.94 (m, 6H).

Example 363

5-[6-(tert-Butylamino)-4-(trifluoromethyl)-3-pyridyl]-N-[(2S)-2,3-dihydroxypropyl]-4-[(2S)-2-methylpyrrolidine-1-carbonyl]thiazole-2-carboxamide

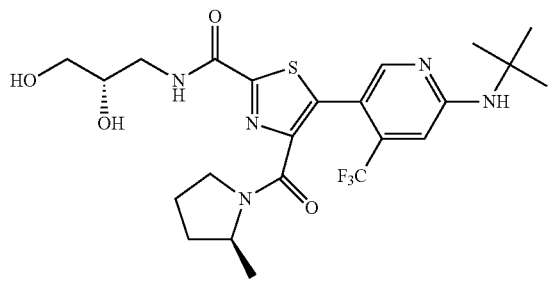 [SMILES: C[C@H]1CCCN1C(=O)c1nc(C(=O)NC[C@H](O)CO)sc1-c1cnc(NC(C)(C)C)cc1C(F)(F)F]

The title compound was prepared as described in Example 148 substituting (S)-3-aminopropane-1,2-diol for (R)-(−)-2-amino-1-propanol and ethyl (S)-5-(6-(tert-butylamino)-4-(trifluoromethyl)pyridin-3-yl)-4-(2-methylpyrrolidine-1-carbonyl)thiazole-2-carboxylate (Intermediate 107) for ethyl (S)-5-(6-(tert-butylamino)-4-(difluoromethyl)pyridin-3-yl)-4-(2-methylpyrroldine-1-carbonyl)thiazole-2-carboxylate. MS (ESI): mass calcd. for C$_{23}$H$_{30}$F$_3$N$_5$O$_4$S, 529.6; m/z found, 530.2 [M+H]$^+$. $^1$H NMR (500 MHz, CDCl$_3$) δ 8.18-8.12 (m, 1H), 7.94-7.81 (m, 1H), 6.69-6.61 (m, 1H), 5.18-5.10 (m, 1H), 4.30-4.08 (m, 1H), 3.95-3.86 (m, 2H), 3.69-3.58 (m, 4H), 3.55-3.49 (m, 1H), 3.41-3.33 (m, 1H), 2.08-2.00 (m, 1H), 1.94-1.81 (m, 1H), 1.76-1.68 (m, 1H), 1.54-1.40 (m, 10H), 1.27-1.02 (m, 4H).

Example 364

(5-(6-(tert-Butylamino)-4-(trifluoromethyl)pyridin-3-yl)-2-(3-hydroxy-3-methylpyrrolidine-1-carbonyl)thiazol-4-yl)((S)-2-methylpyrrolidin-1-yl)methanone

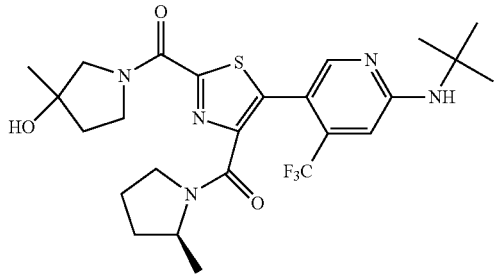

The title compound was prepared as described in Example 148 substituting 3-methylpyrrolidin-3-ol for (R)-(−)-2-amino-1-propanol and ethyl (S)-5-(6-(tert-butylamino)-4-(trifluoromethyl)pyridin-3-yl)-4-(2-methylpyrrolidine-1-carbonyl)thiazole-2-carboxylate (Intermediate 107) for ethyl (S)-5-(6-(tert-butylamino)-4-(difluoromethyl)pyridin-3-yl)-4-(2-methylpyrroldine-1-carbonyl)thiazole-2-carboxylate. MS (ESI): mass calcd. for C$_{25}$H$_{32}$F$_3$N$_5$O$_3$S, 539.6; m/z found, 540.2 [M+H]$^+$. $^1$H NMR (500 MHz, CDCl$_3$) δ 8.21-8.15 (m, 1H), 6.67-6.60 (m, 1H), 4.90-4.86 (s, 1H), 4.50-4.36 (m, 1H), 4.34-4.10 (m, 2H), 3.98-3.79 (m, 2H), 3.64-3.46 (m, 2H), 2.15-2.01 (m, 2H), 1.97-1.89 (m, 1H), 1.84-1.76 (m, 1H), 1.66-1.61 (s, 2H), 1.61-1.50 (m, 4H), 1.49-1.45 (s, 9H), 1.30-1.02 (m, 3H).

Example 365

(5-(6-(tert-Butylamino)-4-(trifluoromethyl)pyridin-3-yl)-2-((S*)-3-hydroxy-3-methylpyrrolidine-1-carbonyl)thiazol-4-yl)((S)-2-methylpyrrolidin-1-yl)methanone

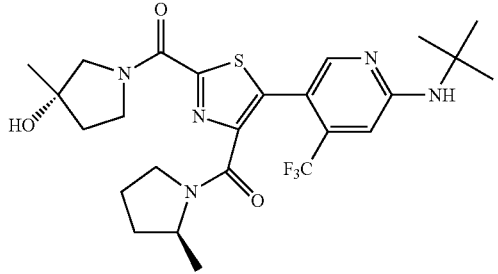 [SMILES: C[C@H]1CCCN1C(=O)c1nc(C(=O)N2CCC(C)(O)C2)sc1-c1cnc(NC(C)(C)C)cc1C(F)(F)F]

The title compound was prepared as described in Example 148 substituting 3-methylpyrrolidin-3-ol for (R)-(−)-2-amino-1-propanol and ethyl (S)-5-(6-(tert-butylamino)-4-(trifluoromethyl)pyridin-3-yl)-4-(2-methylpyrrolidine-1-carbonyl)thiazole-2-carboxylate (Intermediate 107) for ethyl (S)-5-(6-(tert-butylamino)-4-(difluoromethyl)pyridin-3-yl)-4-(2-methylpyrroldine-1-carbonyl)thiazole-2-carboxylate followed by SFC purification (Stationary phase: Lux Cellulose-2, 5 μm, 250×30 mm, Mobile phase: 50% CO$_2$, 50% mixture of ACN/MeOH 90/10 v/v). MS (ESI): mass calcd. for C$_{25}$H$_{32}$F$_3$N$_5$O$_3$S, 539.6; m/z found, 539.9 [M+H]$^+$. $^1$H NMR (400 MHz, CDCl$_3$) δ 8.19-8.11 (dd, J=3.2, 2.2 Hz, 1H), 6.68-6.58 (m, 1H), 5.10-4.98 (s, 1H), 4.58-4.24 (m, 1H), 4.25-4.11 (m, 1H), 3.92-3.75 (m, 2H), 3.62-3.43 (m, 2H), 2.81-2.55 (s, 1H), 2.17-1.81 (m, 5H), 1.79-1.55 (m, 1H), 1.52-1.38 (m, 13H), 1.26-1.01 (m, 3H).

Example 366

(5-(6-(tert-Butylamino)-4-(trifluoromethyl)pyridin-3-yl)-2-((R*)-3-hydroxy-3-methylpyrrolidine-1-carbonyl)thiazol-4-yl)-((S)-2-methylpyrrolidin-1-yl)methanone

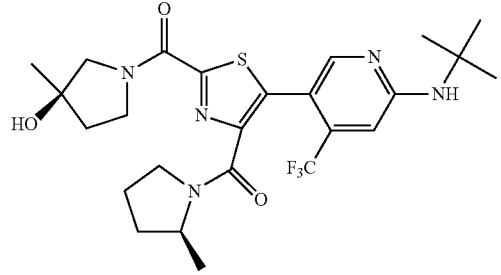 [SMILES: C[C@H]1CCCN1C(=O)c1nc(C(=O)N2CC[C@@](C)(O)C2)sc1-c1cnc(NC(C)(C)C)cc1C(F)(F)F]

The title compound was prepared as described in Example 148 substituting 3-methylpyrrolidin-3-ol for (R)-(−)-2-amino-1-propanol and ethyl (S)-5-(6-(tert-butylamino)-4-(trifluoromethyl)pyridin-3-yl)-4-(2-methylpyrrolidine-1-carbonyl)thiazole-2-carboxylate (Intermediate 107) for ethyl (S)-5-(6-(tert-butylamino)-4-(difluoromethyl)pyridin-3-yl)-4-(2-methylpyrroldine-1-carbonyl)thiazole-2-carboxylate followed by SFC purification (Stationary phase: Lux Cellulose-2, 5 μm, 250×30 mm, Mobile phase: 50% CO$_2$, 50% mixture of ACN/MeOH 90/10 v/v). MS (ESI): mass calcd. for C$_{25}$H$_{32}$F$_3$N$_5$O$_3$S, 539.6; m/z found, 539.9 [M+H]$^+$. $^1$H NMR (400 MHz, CDCl$_3$) δ 8.20-8.10 (t, J=3.3 Hz, 1H), 6.67-6.59 (d, J=2.9 Hz, 1H), 5.11-5.00 (d, J=3.0 Hz, 1H), 4.43-4.29 (m, 1H), 4.29-4.13 (m, 2H), 3.94-3.76 (m, 2H), 3.60-3.45 (m, 2H), 2.15-1.68 (m, 6H), 1.58-1.41 (m, 13H), 1.26-1.06 (m, 3H).

Example 367

5-[6-(tert-Buylamino)-4-(trifluoromethyl)-3-pyridyl]-N-[(1S,3R)-3-hydroxycyclopentyl]-4-[(2S)-2-methylpyrrolidine-1-carbonyl]thiazole-2-carboxamide

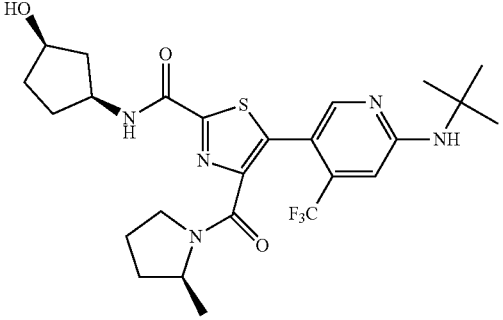 [SMILES: C[C@H]1CCCN1C(=O)c1nc(C(=O)N[C@H]2CC[C@@H](O)C2)sc1-c1cnc(NC(C)(C)C)cc1C(F)(F)F]

The title compound was prepared as described in Example 149 substituting (1R,3S)-3-aminocyclopentan-1-ol HCl for 3-hydroxy-3-methylazetidine HCl and ethyl (S)-5-(6-(tert-butylamino)-4-(trifluoromethyl)pyridin-3-yl)-4-(2-methylpyrrolidine-1-carbonyl)thiazole-2-carboxylate (Intermediate 107) for ethyl (S)-5-(6-(tert-butylamino)-4-(difluoromethyl)pyridin-3-yl)-4-(2-methylpyrrolidine-1-carbonyl)thiazole-2-carboxylate. MS (ESI): mass calcd. for $C_{25}H_{32}F_3N_5O_3S$, 539.6; m/z found, 540.2 [M+H]$^+$. $^1$H NMR (400 MHz, CDCl$_3$) δ 8.20-8.13 (m, 1H), 7.94-7.86 (m, 1H), 6.69-6.64 (m, 1H), 5.16-5.06 (m, 1H), 4.61-4.48 (m, 1H), 4.48-4.40 (s, 1H), 4.24-4.09 (m, 1H), 3.66-3.37 (m, 2H), 2.92-2.73 (m, 1H), 2.23-2.09 (m, 2H), 2.07-2.03 (s, 1H), 1.98-1.71 (m, 5H), 1.57-1.42 (m, 10H), 1.30-1.08 (m, 4H).

Example 368

[5-[6-(tert-Butylamino)-4-(trifluoromethyl)-3-pyridyl]-2-(6-oxa-2-azaspiro[3.3]heptane-2-carbonyl)thiazol-4-yl]-[(2S)-2-methylpyrrolidin-1-yl] methanone

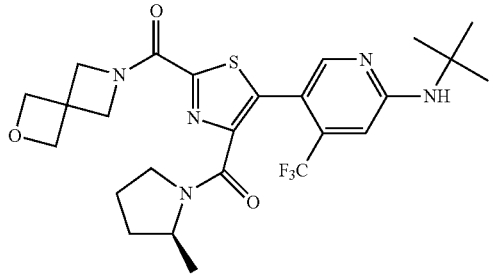 [SMILES: C[C@H]1CCCN1C(=O)c1nc(C(=O)N2CC3(COC3)C2)sc1-c1cnc(NC(C)(C)C)cc1C(F)(F)F]

The title compound was prepared as described in Example 149 substituting 2-oxa-6-azaspiro[3.3]heptane for 3-hydroxy-3-methylazetidine HCl and ethyl (S)-5-(6-(tert-butylamino)-4-(trifluoromethyl)pyridin-3-yl)-4-(2-methylpyrrolidine-1-carbonyl)thiazole-2-carboxylate (Intermediate 107) for ethyl (S)-5-(6-(tert-butylamino)-4-(difluoromethyl)pyridin-3-yl)-4-(2-methylpyrrolidine-1-carbonyl)thiazole-2-carboxylate. MS (ESI): mass calcd. for $C_{25}H_{30}F_3N_5O_3S$, 537.6; m/z found, 538.2 [M+H]$^+$. $^1$H NMR (500 MHz, CDCl$_3$) δ 8.19-8.11 (m, 1H), 6.67-6.58 (m, 1H), 5.01-4.80 (m, 7H), 4.44-4.34 (m, 2H), 4.25-4.08 (m, 1H), 3.65-3.44 (m, 2H), 2.14-2.03 (m, 1H), 2.03-1.90 (m, 1H), 1.84-1.74 (m, 1H), 1.62-1.53 (m, 1H), 1.51-1.40 (s, 9H), 1.29-1.02 (m, 3H).

Example 369

5-(6-(tert-Butylamino)-4-(trifluoromethyl)pyridin-3-yl)-N-(trans-2-hydroxycyclobutyl)-4-((S)-2-methylpyrrolidine-1-carbonyl)thiazole-2-carboxamide

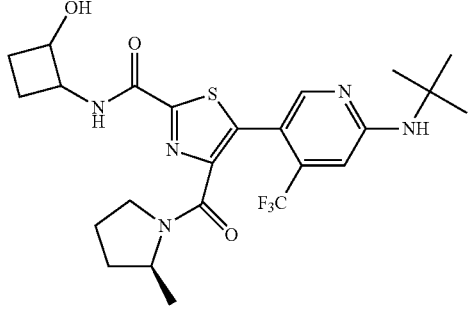 [SMILES: C[C@H]1CCCN1C(=O)c1nc(C(=O)NC2CCC2O)sc1-c1cnc(NC(C)(C)C)cc1C(F)(F)F]

The title compound was prepared as described in Example 149 substituting trans-2-aminocyclobutan-1-ol HCl for 3-hydroxy-3-methylazetidine HCl and ethyl (S)-5-(6-(tert-butylamino)-4-(trifluoromethyl)pyridin-3-yl)-4-(2-methylpyrrolidine-1-carbonyl)thiazole-2-carboxylate (Intermediate 107) for ethyl (S)-5-(6-(tert-butylamino)-4-(difluoromethyl)pyridin-3-yl)-4-(2-methylpyrrolidine-1-carbonyl)thiazole-2-carboxylate. MS (ESI): mass calcd. for $C_{24}H_{30}F_3N_5O_3S$, 525.6; m/z found, 526.2 [M+H]$^+$. $^1$H NMR (500 MHz, CDCl$_3$) δ 8.22-8.13 (s, 1H), 7.52-7.38 (m, 1H), 6.66-6.58 (m, 1H), 4.98-4.89 (s, 1H), 4.25-4.00 (m, 3H), 3.63-3.31 (m, 3H), 2.29-2.12 (m, 2H), 2.11-1.98 (m, 1H), 1.95-1.83 (m, 1H), 1.80-1.70 (m, 2H), 1.57-1.41 (m, 10H), 1.29-1.00 (m, 4H).

Example 370

5-(6-(tert-Butylamino)-4-(trifluoromethyl)pyridin-3-yl)-N-((1R*,2R*)-2-hydroxycyclobutyl)-4-((S)-2-methylpyrrolidine-1-carbonyl)thiazole-2-carboxamide

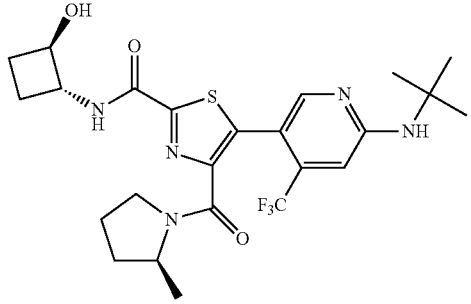 [SMILES: C[C@H]1CCCN1C(=O)c1nc(C(=O)N[C@@H]2CC[C@H]2O)sc1-c1cnc(NC(C)(C)C)cc1C(F)(F)F]

The title compound was prepared as described in Example 149 substituting trans-2-aminocyclobutan-1-ol HCl for 3-hydroxy-3-methylazetidine HCl and ethyl (S)-5-(6-(tert-butylamino)-4-(trifluoromethyl)pyridin-3-yl)-4-(2-methylpyrrolidine-1-carbonyl)thiazole-2-carboxylate (Intermediate 107) for ethyl (S)-5-(6-(tert-butylamino)-4-(difluoromethyl)pyridin-3-yl)-4-(2-methylpyrrolidine-1-carbonyl)thiazole-2-carboxylate followed by SFC purification (Stationary phase: CHIRALPAK AD-H, 5 μm, 250×20 mm, Mobile phase: 85% CO$_2$, 15% EtOH (0.3% i-PrNH$_2$)). MS (ESI): mass calcd. for $C_{24}H_{30}F_3N_5O_3S$, 525.6; m/z found, 525.9 [M+H]$^+$. $^1$H NMR (500 MHz, CDCl$_3$) δ 8.21-8.12 (s, 1H), 7.52-7.37 (m, 1H), 6.67-6.58 (m, 1H), 4.98-4.87 (m, 1H), 4.26-4.01 (m, 3H), 3.63-3.31 (m, 2H), 2.27-2.13 (m, 2H), 2.10-2.00 (m, 1H), 1.94-1.84 (m, 1H), 1.80-1.69 (m, 2H), 1.57-1.48 (m, 2H), 1.27-1.20 (m, 3H), 1.48-1.43 (m, 9H), 1.07-1.02 (d, J=6.4 Hz, 1H).

Example 371

5-(6-(tert-Butylamino)-4-(trifluoromethyl)pyridin-3-yl)-N-((1S*,2S*)-2-hydroxycyclobutyl)-4-((S)-2-methylpyrrolidine-1-carbonyl)thiazole-2-carboxamide

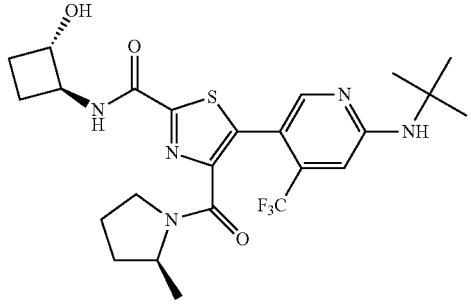 [SMILES: C[C@H]1CCCN1C(=O)c1nc(C(=O)N[C@H]2CC[C@@H]2O)sc1-c1cnc(NC(C)(C)C)cc1C(F)(F)F]

The title compound was prepared as described in Example 149 substituting trans-2-aminocyclobutan-1-ol HCl for 3-hydroxy-3-methylazetidine HCl and ethyl (S)-5-(6-(tert-butylamino)-4-(trifluoromethyl)pyridin-3-yl)-4-(2-methylpyrrolidine-1-carbonyl)thiazole-2-carboxylate (Intermediate 107) for ethyl (S)-5-(6-(tert-butylamino)-4-(difluoromethyl)pyridin-3-yl)-4-(2-methylpyrrolidine-1-carbonyl)thiazole-2-carboxylate followed by SFC purification (Stationary phase: CHIRALPAK AD-H, 5 μm, 250×20 mm, Mobile phase: 85% $CO_2$, 15% EtOH (0.3% i-PrNH$_2$)). MS (ESI): mass calcd. for $C_{24}H_{30}F_3N_5O_3S$, 525.6; m/z found, 525.9 [M+H]$^+$. $^1$H NMR (500 MHz, CDCl$_3$) δ 8.22-8.13 (s, 1H), 7.53-7.38 (m, 1H), 6.67-6.60 (m, 1H), 5.01-4.91 (s, 1H), 4.27-4.00 (m, 3H), 3.62-3.29 (m, 2H), 2.28-2.12 (m, 2H), 2.12-1.97 (m, 1H), 1.97-1.81 (m, 1H), 1.81-1.66 (m, 2H), 1.60-1.48 (m, 2H), 1.48-1.41 (s, 9H), 1.27-1.21 (m, 3H), 1.07-1.02 (d, J=6.4 Hz, 1H).

Example 372

[5-[6-(tert-Butylamino)-4-(trifluoromethyl)-3-pyridyl]-2-[(3R,4R)-3-fluoro-4-hydroxy-pyrrolidine-1-carbonyl]thiazol-4-yl]-[(2S)-2-methylpyrrolidin-1-yl]methanone

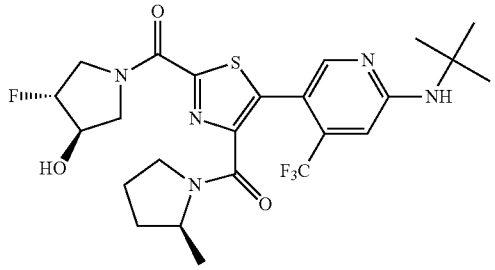 [SMILES: C[C@H]1CCCN1C(=O)c1nc(C(=O)N2C[C@@H](O)[C@H](F)C2)sc1-c1cnc(NC(C)(C)C)cc1C(F)(F)F]

The title compound was prepared as described in Example 149 substituting (3R,4R)-4-fluoropyrrolidin-3-ol HCl for 3-hydroxy-3-methylazetidine HCl and ethyl (S)-5-(6-(tert-butylamino)-4-(trifluoromethyl)pyridin-3-yl)-4-(2-methylpyrrolidine-1-carbonyl)thiazole-2-carboxylate (Intermediate 107) for ethyl (S)-5-(6-(tert-butylamino)-4-(difluoromethyl)pyridin-3-yl)-4-(2-methylpyrrolidine-1-carbonyl)thiazole-2-carboxylate. MS (ESI): mass calcd. for $C_{24}H_{29}F_4N_5O_3S$, 543.6; m/z found, 543.9 [M+H]$^+$. $^1$H NMR (400 MHz, CDCl$_3$) δ 8.17-8.08 (m, 1H), 6.70-6.62 (m, 1H), 5.15-4.88 (m, 2H), 4.63-4.31 (m, 3H), 4.24-4.10 (m, 2H), 4.05-3.78 (m, 2H), 1.81-1.70 (m, 1H), 3.62-3.39 (m, 2H), 2.13-2.00 (m, 1H), 1.99-1.83 (m, 1H), 1.49-1.41 (m, 10H), 1.28-1.18 (m, 3H).

Example 373

5-[6-(tert-Butylamino)-4-(trifluoromethyl)-3-pyridyl]-4-[(2S)-2-methylpyrrolidine-1-carbonyl]-N-[(3R)-tetrahydrofuran-3-yl]thiazole-2-carboxamide

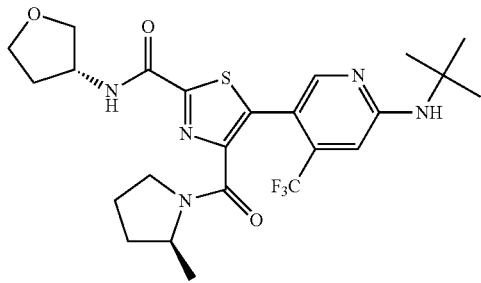 [SMILES: C[C@H]1CCCN1C(=O)c1nc(C(=O)N[C@@H]2CCOC2)sc1-c1cnc(NC(C)(C)C)cc1C(F)(F)F]

The title compound was prepared as described in Example 148 substituting (R)-tetrahydrofuran-3-amine for (R)-(−)-2-amino-1-propanol and ethyl (S)-5-(6-(tert-butylamino)-4-(trifluoromethyl)pyridin-3-yl)-4-(2-methylpyrrolidine-1-carbonyl)thiazole-2-carboxylate (Intermediate 107) for ethyl (S)-5-(6-(tert-butylamino)-4-(difluoromethyl)pyridin-3-yl)-4-(2-methylpyrrolidine-1-carbonyl)thiazole-2-carboxylate. MS (ESI): mass calcd. for $C_{24}H_{30}F_3N_5O_3S$, 525.6; m/z found, 525.9 [M+H]$^+$. $^1$H NMR (400 MHz, CDCl$_3$) δ 8.21-8.15 (s, 1H), 7.41-7.29 (m, 1H), 6.67-6.60 (m, 1H), 5.04-4.97 (m, 1H), 4.77-4.67 (m, 1H), 4.25-4.08 (m, 1H), 4.08-3.98 (m, 1H), 3.98-3.90 (m, 1H), 3.90-3.80 (m, 2H), 3.46-3.29 (m, 1H), 2.44-2.30 (m, 1H), 2.11-1.82 (m, 4H), 1.80-1.68 (m, 1H), 1.58-1.49 (m, 1H), 1.49-1.41 (s, 9H), 1.27-1.04 (m, 3H).

Example 374

5-[6-(tert-Butylamino)-4-(trifluoromethyl)-3-pyridyl]-4-[(2S)-2-methylpyrrolidine-1-carbonyl]-N-tetrahydropyran-4-yl-thiazole-2-carboxamide

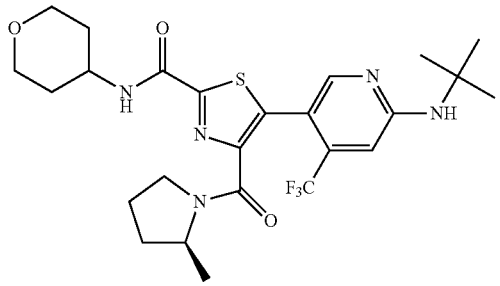 [SMILES: C[C@H]1CCCN1C(=O)c1nc(C(=O)NC2CCOCC2)sc1-c1cnc(NC(C)(C)C)cc1C(F)(F)F]

The title compound was prepared as described in Example 148 substituting tetrahydro-2H-pyran-4-amine for (R)-(−)-2-amino-1-propanol and ethyl (S)-5-(6-(tert-butylamino)-4-(trifluoromethyl)pyridin-3-yl)-4-(2-methylpyrrolidine-1-carbonyl)thiazole-2-carboxylate (Intermediate 107) for ethyl (S)-5-(6-(tert-butylamino)-4-(difluoromethyl)pyridin-3-yl)-4-(2-methylpyrrolidine-1-carbonyl)thiazole-2-carboxylate. MS (ESI): mass calcd. for $C_{25}H_{32}F_3N_5O_3S$, 539.6; m/z found, 539.9 [M+H]$^+$. $^1$H NMR (400 MHz, CDCl$_3$) δ 8.21-8.13 (s, 1H), 7.20-7.09 (m, 1H), 6.70-6.63 (m, 1H), 5.19-5.11 (m, 1H), 4.27-4.08 (m, 2H), 4.06-3.98 (m, 2H), 3.59-3.50 (m, 2H), 3.37-3.32 (m, 1H), 2.11-1.98 (m, 4H), 1.94-1.82 (m, 1H), 1.77-1.60 (m, 3H), 1.56-1.48 (m, 1H), 1.48-1.42 (s, 9H), 1.27-1.06 (m, 3H).

Example 375

5-(4-(Difluoromethyl)-6-(((S)-1,1,1-trifluorobutan-2-yl)amino)pyridin-3-yl)-N-(trans-2-hydroxycyclobutyl)-4-((S)-2-methylpyrrolidine-1-carbonyl)thiazole-2-carboxamide

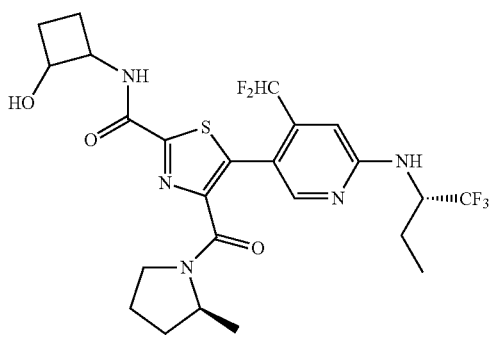 [SMILES: CC[C@H](Nc1cc(C(F)F)c(-c2sc(C(=O)NC3CCC3O)nc2C(=O)N2CCC[C@@H]2C)cn1)C(F)(F)F]

The title compound was prepared as described in Example 149 substituting trans-2-aminocyclobutan-1-ol HCl for 3-hydroxy-3-methylazetidine HCl and ethyl 5-(4-(difluoromethyl)-6-(((S)-1,1,1-trifluorobutan-2-yl)amino)pyridin-3-yl)-4-((S)-2-methylpyrrolidine-1-carbonyl)thiazole-2-carboxylate (Intermediate 102) for ethyl (S)-5-(6-(tert-butylamino)-4-(difluoromethyl)pyridin-3-yl)-4-(2-methylpyrrolidine-1-carbonyl)thiazole-2-carboxylate. MS (ESI): mass calcd. for $C_{24}H_{28}F_5N_5O_3S$, 561.6; m/z found, 561.9 [M+H]$^+$. $^1$H NMR (400 MHz, CDCl$_3$) δ 8.11-8.01 (m, 1H), 7.47-7.34 (m, 1H), 6.95-6.73 (m, 1H), 4.86-4.72 (m, 2H), 4.32-4.01 (m, 3H), 3.61-3.53 (dd, J=7.9, 6.1 Hz, 1H), 3.49-3.19 (m, 2H), 2.29-2.14 (m, 2H), 2.11-1.83 (m, 3H), 1.83-1.71 (m, 1H), 1.69-1.48 (m, 4H), 1.28-1.17 (m, 3H), 1.09-0.94 (m, 4H).

Example 376

5-(4-(Difluoromethyl)-6-(((S)-1,1,1-trifluorobutan-2-yl)amino)pyridin-3-yl)-N-((1R*,2R*)-2-hydroxycyclobutyl)-4-((S)-2-methylpyrrolidine-1-carbonyl)thiazole-2-carboxamide

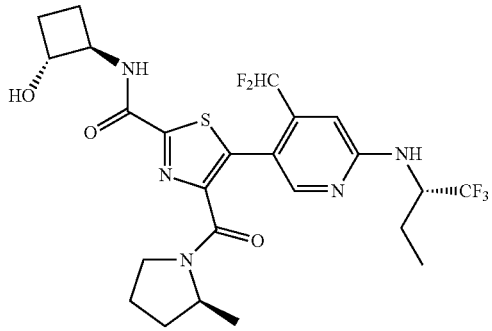 [SMILES: CC[C@H](Nc1cc(C(F)F)c(-c2sc(C(=O)N[C@@H]3CC[C@H]3O)nc2C(=O)N2CCC[C@@H]2C)cn1)C(F)(F)F]

The title compound was prepared as described in Example 149 substituting trans-2-aminocyclobutan-1-ol HCl for 3-hydroxy-3-methylazetidine HCl and ethyl 5-(4-(difluoromethyl)-6-(((S)-1,1,1-trifluorobutan-2-yl)amino)pyridin-3-yl)-4-((S)-2-methylpyrrolidine-1-carbonyl)thiazole-2-carboxylate (Intermediate 102) for ethyl (S)-5-(6-(tert-butylamino)-4-(difluoromethyl)pyridin-3-yl)-4-(2-methylpyrrolidine-1-carbonyl)thiazole-2-carboxylate followed by SFC purification (Stationary phase: Lux amylose 2, 5 µm, 250×21.2 mm, Mobile phase: 75% CO$_2$, 25% i-PrOH (0.3% i-PrNH$_2$)). MS (ESI): mass calcd. for $C_{24}H_{28}F_5N_5O_3S$, 561.6; m/z found, 561.9 [M+H]$^+$. $^1$H NMR (500 MHz, CDCl$_3$) δ 8.09-8.01 (m, 1H), 7.52-7.40 (m, 1H), 6.78-6.75 (m, 1H), 5.09-5.02 (m, 1H), 4.85-4.71 (s, 1H), 4.31-3.99 (m, 3H), 3.60-3.53 (m, 1H), 3.47-3.29 (m, 1H), 2.27-2.15 (m, 2H), 2.09-1.86 (m, 4H), 1.81-1.70 (m, 2H), 1.68-1.48 (m, 3H), 1.27-1.18 (m, 3H), 1.08-0.96 (m, 4H).

Example 377

5-(4-(Difluoromethyl)-6-(((S)-1,1,1-trifluorobutan-2-yl)amino)pyridin-3-yl)-N-((1S*,2S*)-2-hydroxycyclobutyl)-4-((S)-2-methylpyrrolidine-1-carbonyl)thiazole-2-carboxamide

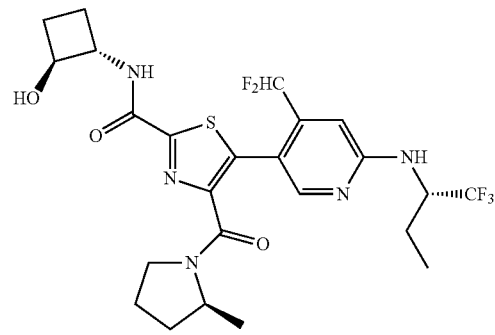 [SMILES: CC[C@H](Nc1cc(C(F)F)c(-c2sc(C(=O)N[C@H]3CC[C@@H]3O)nc2C(=O)N2CCC[C@@H]2C)cn1)C(F)(F)F]

The title compound was prepared as described in Example 149 substituting trans-2-aminocyclobutan-1-ol HCl for 3-hydroxy-3-methylazetidine HCl and ethyl 5-(4-(difluoromethyl)-6-(((S)-1,1,1-trifluorobutan-2-yl)amino)pyridin-3-yl)-4-((S)-2-methylpyrrolidine-1-carbonyl)thiazole-2-carboxylate (Intermediate 102) for ethyl (S)-5-(6-(tert-butylamino)-4-(difluoromethyl)pyridin-3-yl)-4-(2-methylpyrrolidine-1-carbonyl)thiazole-2-carboxylate followed by SFC purification (Stationary phase: Lux amylose 2, 5 µm, 250×21.2 mm, Mobile phase: 75% CO$_2$, 25% i-PrOH (0.3% i-PrNH$_2$)). MS (ESI): mass calcd. for $C_{24}H_{28}F_5N_5O_3S$, 561.6; m/z found, 561.9 [M+H]$^+$. $^1$H NMR (500 MHz, CDCl$_3$) δ 8.10-8.01 (m, 1H), 7.58-7.42 (m, 1H), 6.81-6.73 (m, 1H), 5.25-5.16 (m, 1H), 4.84-4.73 (s, 1H), 4.27-4.07 (m, 3H), 3.60-3.53 (m, 1H), 3.44-3.31 (m, 1H), 2.26-2.14 (m, 2H), 2.08-1.87 (m, 3H), 1.80-1.69 (m, 2H), 1.68-1.48 (m, 3H), 1.27-1.18 (m, 4H), 1.07-0.97 (m, 4H).

Example 378

[5-[4-(Difluoromethyl)-6-[[(1S)-1-(trifluoromethyl)propyl]amino]-3-pyridyl]-2-(8-oxa-3-azabicyclo[3.2.1]octane-3-carbonyl)thiazol-4-yl]-[(2S)-2-methylpyrrolidin-1-yl]methanone

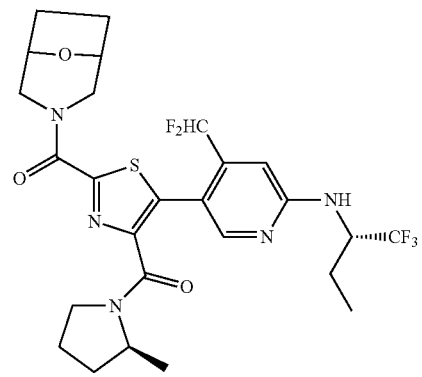 [SMILES: CC[C@H](Nc1cc(C(F)F)c(-c2sc(C(=O)N3CC4CCC(C3)O4)nc2C(=O)N2CCC[C@@H]2C)cn1)C(F)(F)F]

The title compound was prepared as described in Example 148 substituting 8-oxa-3-azabicyclo[3.2.1]octane for (R)-(−)-2-amino-1-propanol and ethyl 5-(4-(difluoromethyl)-6-(((S)-1,1,1-trifluorobutan-2-yl)amino)pyridin-3-yl)-4-((S)-2-methylpyrrolidine-1-carbonyl)thiazole-2-carboxylate (Intermediate 102) for ethyl (S)-5-(6-(tert-butylamino)-4-(difluoromethyl)pyridin-3-yl)-4-(2-methylpyrrolidine-1-carbonyl)thiazole-2-carboxylate. MS (ESI): mass calcd. for $C_{26}H_{30}F_5N_5O_3S$, 587.6; m/z found, 587.9 [M+H]$^+$. $^1$H NMR (500 MHz, CDCl$_3$) δ 8.07-8.02 (m, 1H), 7.28 (s, 1H), 6.81-6.72 (m, 1H), 5.20-5.05 (m, 2H), 4.77 (br s, 1H), 4.52-4.39 (m, 2H), 4.37-4.29 (m, 1H), 4.26-4.17 (m, 1H), 3.62-3.51 (m, 2H), 3.48-3.41 (m, 1H), 3.22 (br d, J=13.2 Hz, 1H), 2.20-1.81 (m, 8H), 1.84-1.77 (m, 1H), 1.68-1.53 (m, 2H), 1.29-1.20 (m, 2H), 1.06-0.98 (m, 3H).

Example 379

5-(4-(Difluoromethyl)-6-(((S)-1,1,1-trifluorobutan-2-yl)amino)pyridin-3-yl)-N-(cis-2-hydroxycyclobutyl)-4-((S)-2-methylpyrrolidine-1-carbonyl)thiazole-2-carboxamide

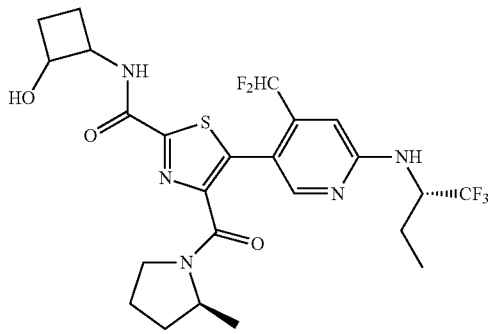 [SMILES: CC[C@H](Nc1cc(C(F)F)c(-c2sc(C(=O)NC3CCC3O)nc2C(=O)N2CCC[C@@H]2C)cn1)C(F)(F)F]

The title compound was prepared as described in Example 149 substituting cis-2-aminocyclobutan-1-ol HCl for 3-hydroxy-3-methylazetidine HCl and ethyl 5-(4-(difluoromethyl)-6-(((S)-1,1,1-trifluorobutan-2-yl)amino)pyridin-3-yl)-4-((S)-2-methylpyrrolidine-1-carbonyl)thiazole-2-carboxylate (Intermediate 102) for ethyl (S)-5-(6-(tert-butylamino)-4-(difluoromethyl)pyridin-3-yl)-4-(2-methylpyrrolidine-1-carbonyl)thiazole-2-carboxylate. MS (ESI): mass calcd. for $C_{24}H_{28}F_5N_5O_3S$, 561.6; m/z found, 561.9 [M+H]$^+$. $^1$H NMR (500 MHz, CDCl$_3$) δ 8.09-8.00 (m, 1H), 7.83-7.75 (m, 1H), 6.81-6.74 (m, 1H), 4.85-4.72 (m, 2H), 4.63-4.49 (m, 2H), 4.40-4.16 (m, 1H), 3.63-3.36 (m, 2H), 2.57-2.44 (m, 1H), 2.36-2.14 (m, 3H), 2.11-1.84 (m, 4H), 1.82-1.73 (m, 1H), 1.69-1.50 (m, 3H), 1.24-1.20 (m, 2H), 1.08-1.02 (m, 4H).

Example 380

5-(4-(Difluoromethyl)-6-(((S)-1,1,1-trifluorobutan-2-yl)amino)pyridin-3-yl)-N-((1S*,2R*)-2-hydroxycyclobutyl)-4-((S)-2-methylpyrrolidine-1-carbonyl)thiazole-2-carboxamide

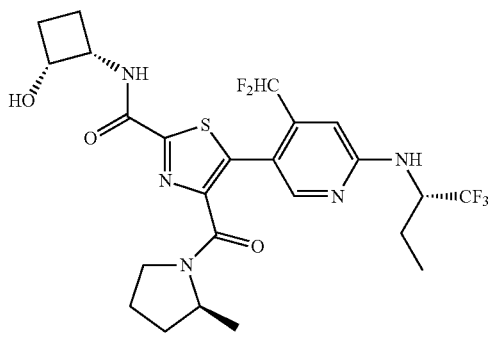 [SMILES: CC[C@H](Nc1cc(C(F)F)c(-c2sc(C(=O)N[C@H]3CC[C@H]3O)nc2C(=O)N2CCC[C@@H]2C)cn1)C(F)(F)F]

The title compound was prepared as described in Example 149 substituting cis-2-aminocyclobutan-1-ol HCl for 3-hydroxy-3-methylazetidine HCl and ethyl 5-(4-(difluoromethyl)-6-(((S)-1,1,1-trifluorobutan-2-yl)amino)pyridin-3-yl)-4-((S)-2-methylpyrrolidine-1-carbonyl)thiazole-2-carboxylate (Intermediate 102) for ethyl (S)-5-(6-(tert-butylamino)-4-(difluoromethyl)pyridin-3-yl)-4-(2-methylpyrrolidine-1-carbonyl)thiazole-2-carboxylate followed by SFC purification (Stationary phase: Chiralpak AS-H, 5 μm, 250×20 mm, Mobile phase: 90% CO$_2$, 10% MeOH (0.3% i-PrNH$_2$)). MS (ESI): mass calcd. for $C_{24}H_{28}F_5N_5O_3S$, 561.6; m/z found, 561.8 [M+H]$^+$. $^1$H NMR (500 MHz, CDCl$_3$) δ 8.09-7.99 (m, 1H), 7.98-7.90 (m, 1H), 6.82-6.72 (m, 1H), 5.40-5.27 (m, 1H), 4.86-4.71 (m, 1H), 4.60-4.47 (m, 2H), 4.36-4.08 (m, 1H), 3.63-3.30 (m, 3H), 2.32-2.12 (m, 3H), 2.08-1.83 (m, 4H), 1.81-1.71 (m, 1H), 1.68-1.57 (m, 1H), 1.28-1.13 (m, 4H), 1.10-0.96 (m, 4H).

Example 381

5-(4-(Difluoromethyl)-6-(((S)-1,1,1-trifluorobutan-2-yl)amino)pyridin-3-yl)-N-((1R*,2S*)-2-hydroxycyclobutyl)-4-((S)-2-methylpyrrolidine-1-carbonyl)thiazole-2-carboxamide

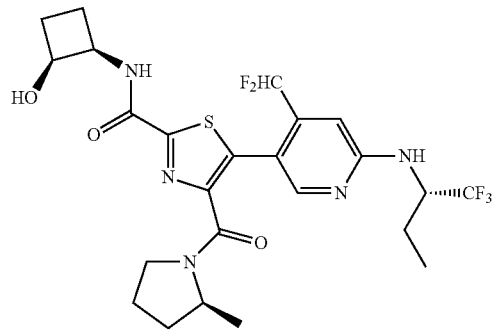 [SMILES: CC[C@H](Nc1cc(C(F)F)c(-c2sc(C(=O)N[C@@H]3CC[C@@H]3O)nc2C(=O)N2CCC[C@@H]2C)cn1)C(F)(F)F]

The title compound was prepared as described in Example 149 substituting cis-2-aminocyclobutan-1-ol HCl for 3-hydroxy-3-methylazetidine HCl and ethyl 5-(4-(difluoromethyl)-6-(((S)-1,1,1-trifluorobutan-2-yl)amino)pyridin-3-yl)-4-((S)-2-methylpyrrolidine-1-carbonyl)thiazole-2-carboxylate (Intermediate 102) for ethyl (S)-5-(6-(tert-butylamino)-4-(difluoromethyl)pyridin-3-yl)-4-(2-methylpyrrolidine-1-carbonyl)thiazole-2-carboxylate followed by SFC purification (Stationary phase: Chiralpak AS-H, 5 μm, 250×20 mm, Mobile phase: 90% CO$_2$, 10% MeOH (0.3% i-PrNH$_2$)). MS (ESI): mass calcd. for $C_{24}H_{28}F_5N_5O_3S$, 561.6; m/z found, 561.9 [M+H]$^+$. $^1$H NMR (500 MHz, CDCl$_3$) δ 8.09-8.00 (m, 1H), 7.99-7.91 (m, 1H), 6.86-6.71 (m, 1H), 5.51-5.37 (m, 1H), 4.86-4.72 (m, 1H), 4.58-4.46 (m, 2H), 4.40-4.08 (m, 1H), 3.72-3.30 (m, 3H), 2.34-2.11 (m, 2H), 2.09-1.83 (m, 4H), 1.81-1.70 (m, 1H), 1.70-1.57 (m, 1H), 1.57-1.47 (m, 1H), 1.28-1.13 (m, 4H), 1.10-0.96 (m, 4H).

Example 382

N-(1-Acetylazetidin-3-yl)-5-[4-(difluoromethyl)-6-[[(1S)-1-(trifluoromethyl)propyl]amino]-3-pyridyl]-4-[(2S)-2-methylpyrrolidine-1-carbonyl]thiazole-2-carboxamide

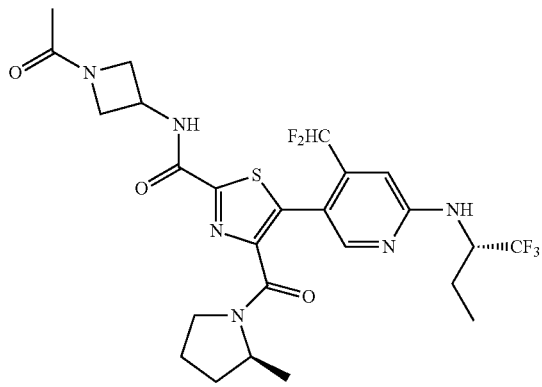 [SMILES: CC[C@H](Nc1cc(C(F)F)c(-c2sc(C(=O)NC3CN(C(C)=O)C3)nc2C(=O)N2CCC[C@@H]2C)cn1)C(F)(F)F]

The title compound was prepared as described in Example 149 substituting 1-(3-aminoazetidin-1-yl)ethan-1-one HCl for 3-hydroxy-3-methylazetidine HCl and ethyl 5-(4-(difluoromethyl)-6-(((S)-1,1,1-trifluorobutan-2-yl)amino)pyridin-3-yl)-4-((S)-2-methylpyrrolidine-1-carbonyl)thiazole-2-carboxylate (Intermediate 102) for ethyl (S)-5-(6-(tert-butylamino)-4-(difluoromethyl)pyridin-3-yl)-4-(2-methylpyrrolidine-1-carbonyl)thiazole-2-carboxylate. MS (ESI): mass calcd. for $C_{25}H_{29}F_5N_6O_3S$, 588.6; m/z found, 588.9 [M+H]$^+$. $^1$H NMR (500 MHz, CDCl$_3$) δ 8.10-8.00 (m, 1H), 7.74-7.62 (m, 1H), 6.93-6.65 (m, 2H), 5.25-5.15 (m, 1H), 4.92-4.74 (m, 2H), 4.57-4.51 (m, 1H), 4.46-4.38 (m, 1H), 4.26-3.99 (m, 3H), 3.61-3.31 (m, 2H), 2.10-1.93 (m, 3H), 1.93-1.90 (s, 3H), 1.82-1.73 (m, 1H), 1.68-1.51 (m, 2H), 1.26-1.17 (m, 2H), 1.08-0.96 (m, 4H).

Example 383

5-[4-(Difluoromethyl)-6-[[(1S)-1-(trifluoromethyl)propyl]amino]-3-pyridyl]-4-[(2S)-2-methylpyrrolidine-1-carbonyl]-N-(1-methylsulfonylazetidin-3-yl)thiazole-2-carboxamide

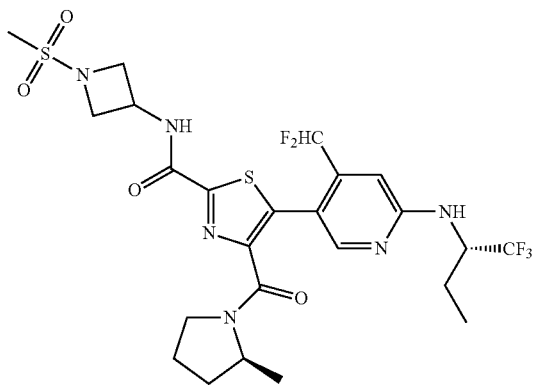 [SMILES: CC[C@H](Nc1cc(C(F)F)c(-c2sc(C(=O)NC3CN(S(C)(=O)=O)C3)nc2C(=O)N2CCC[C@@H]2C)cn1)C(F)(F)F]

The title compound was prepared as described in Example 148 substituting 1-(methylsulfonyl)azetidin-3-amine for (R)-(−)-2-amino-1-propanol and ethyl 5-(4-(difluoromethyl)-6-(((S)-1,1,1-trifluorobutan-2-yl)amino)pyridin-3-yl)-4-((S)-2-methylpyrrolidine-1-carbonyl)thiazole-2-carboxylate (Intermediate 102) for ethyl (S)-5-(6-(tert-butylamino)-4-(difluoromethyl)pyridin-3-yl)-4-(2-methylpyrrolidine-1-carbonyl)thiazole-2-carboxylate. MS (ESI): mass calcd. for $C_{24}H_{29}F_5N_6O_4S_2$, 624.8; m/z found, 624.8 [M+H]$^+$. $^1$H NMR (500 MHz, CDCl$_3$) δ 8.10-8.00 (m, 1H), 7.68-7.59 (m, 1H), 6.80-6.73 (m, 2H), 5.07-4.98 (m, 1H), 4.92-4.73 (m, 2H), 4.26-4.17 (m, 3H), 4.16-4.08 (m, 2H), 3.62-3.31 (m, 2H), 2.98-2.93 (m, 3H), 2.11-2.01 (m, 1H), 2.01-1.88 (m, 2H), 1.83-1.74 (m, 1H), 1.69-1.52 (m, 2H), 1.28-1.21 (m, 2H), 1.07-0.97 (m, 4H).

Example 384

[5-[4-(Difluoromethyl)-6-[[(1S)-1-(trifluoromethyl)propyl]amino]-3-pyridyl]-2-(6-oxa-2-azaspiro[3.3]heptane-2-carbonyl)thiazol-4-yl]-[(2S)-2-methylpyrrolidin-1-yl]methanone

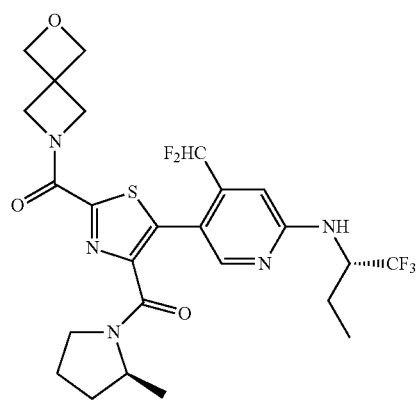 [SMILES: CC[C@H](Nc1cc(C(F)F)c(-c2sc(C(=O)N3CC4(COC4)C3)nc2C(=O)N2CCC[C@@H]2C)cn1)C(F)(F)F]

The title compound was prepared as described in Example 149 substituting 2-oxa-6-azaspiro[3.3]heptane hemioxalate for 3-hydroxy-3-methylazetidine HCl and ethyl 5-(4-(difluoromethyl)-6-(((S)-1,1,1-trifluorobutan-2-yl)amino)pyridin-3-yl)-4-((S)-2-methylpyrrolidine-1-carbonyl)thiazole-2-carboxylate (Intermediate 102) for ethyl (S)-5-(6-(tert-butylamino)-4-(difluoromethyl)pyridin-3-yl)-4-(2-methylpyrrolidine-1-carbonyl)thiazole-2-carboxylate. MS (ESI): mass calcd. for $C_{25}H_{28}F_5N_5O_3S$, 573.6; m/z found, 573.9 [M+H]$^+$. $^1$H NMR (500 MHz, CDCl$_3$) δ 8.06-7.98 (m, 1H), 6.78-6.73 (m, 1H), 5.11-5.03 (m, 1H), 4.91-4.73 (m, 7H), 4.42-4.37 (m, 2H), 4.26-4.18 (m, 1H), 3.62-3.44 (m, 2H), 2.13-2.03 (m, 1H), 2.00-1.92 (m, 2H), 1.90-1.75 (m, 2H), 1.71-1.54 (m, 2H), 1.28-1.22 (m, 2H), 1.06-0.97 (m, 4H).

Example 385

[5-[4-(Difluoromethyl)-6-[[(1S)-1-(trifluoromethyl)propyl]amino]-3-pyridyl]-2-(3-oxa-6-azaspiro[3.3]heptane-6-carbonyl)thiazol-4-yl]-[(2S)-2-methylpyrrolidin-1-yl]methanone

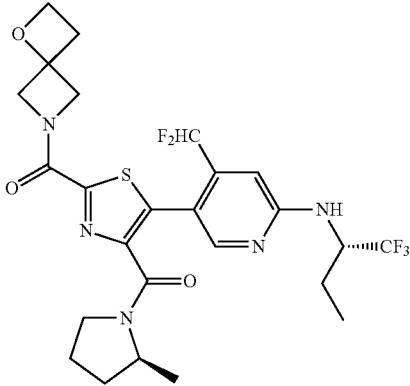 [SMILES: CC[C@H](Nc1cc(C(F)F)c(-c2sc(C(=O)N3CC4(CCO4)C3)nc2C(=O)N2CCC[C@@H]2C)cn1)C(F)(F)F]

The title compound was prepared as described in Example 149 substituting 1-oxa-6-azaspiro[3.3]heptane hemioxalate for 3-hydroxy-3-methylazetidine HCl and ethyl 5-(4-(difluoromethyl)-6-(((S)-1,1,1-trifluorobutan-2-yl)amino)pyridin-3-yl)-4-((S)-2-methylpyrrolidine-1-carbonyl)thiazole-2-carboxylate (Intermediate 102) for ethyl (S)-5-(6-(tert-butylamino)-4-(difluoromethyl)pyridin-3-yl)-4-(2-methylpyrrolidine-1-carbonyl)thiazole-2-carboxylate. MS (ESI): mass calcd. for $C_{25}H_{28}F_5N_5O_3S$, 573.6; m/z found, 573.9 [M+H]$^+$. $^1$H NMR (500 MHz, CDCl$_3$) δ 8.05-7.98 (m, 1H), 6.78-6.72 (m, 1H), 5.21-5.09 (m, 1H), 4.93-4.73 (m, 3H), 4.63-4.53 (m, 2H), 4.47-4.41 (m, 2H), 4.27-4.15 (m, 1H), 3.70-3.41 (m, 2H), 2.98-2.89 (m, 2H), 2.13-2.03 (m, 1H), 2.01-1.75 (m, 4H), 1.73-1.52 (m, 2H), 1.28-1.19 (m, 2H), 1.06-0.92 (m, 4H).

Example 386

5-(4-(Difluoromethyl)-6-(((S)-1,1,1-trifluoropropan-2-yl)amino)pyridin-3-yl)-N-(trans-2-hydroxycyclobutyl)-4-((S)-2-methylpyrrolidine-1-carbonyl)thiazole-2-carboxamide

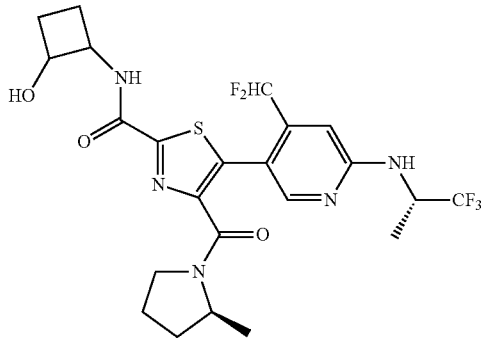

The title compound was prepared as described in Example 149 substituting trans-2-aminocyclobutan-1-ol HCl for 3-hydroxy-3-methylazetidine HCl and ethyl 5-(4-(difluoromethyl)-6-(((S)-1,1,1-trifluoropropan-2-yl)amino)pyridin-3-yl)-4-((S)-2-methylpyrrolidine-1-carbonyl)thiazole-2-carboxylate (Intermediate 94) for ethyl (S)-5-(6-(tert-butylamino)-4-(difluoromethyl)pyridin-3-yl)-4-(2-methylpyrrolidine-1-carbonyl)thiazole-2-carboxylate. MS (ESI): mass calcd. for $C_{23}H_{26}F_5N_5O_3S$, 547.5; m/z found, 547.9 [M+H]$^+$. $^1$H NMR (500 MHz, CDCl$_3$) δ 8.11-8.02 (m, 1H), 7.44-7.32 (m, 1H), 6.79-6.70 (m, 1H), 5.00-4.85 (m, 2H), 4.32-4.02 (m, 3H), 3.62-3.31 (m, 2H), 3.25-3.15 (m, 1H), 2.28-2.15 (m, 2H), 2.10-2.00 (m, 1H), 1.97-1.86 (m, 1H), 1.82-1.72 (m, 1H), 1.68-1.61 (m, 2H), 1.60-1.49 (m, 1H), 1.44-1.39 (m, 3H), 1.29-1.20 (m, 3H), 1.02-0.96 (m, 1H).

Example 387

5-(4-(Difluoromethyl)-6-(((S)-1,1,1-trifluoropropan-2-yl)amino)pyridin-3-yl)-N-(1R*,2R*)-2-hydroxycyclobutyl)-4-((S)-2-methylpyrrolidine-1-carbonyl)thiazole-2-carboxamide

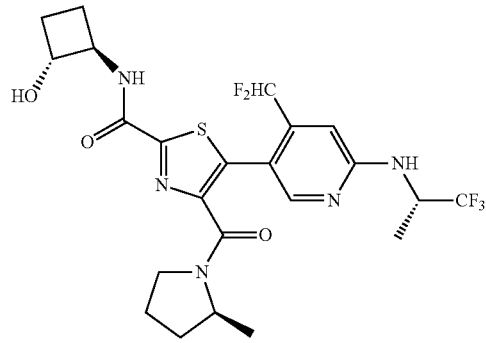 [SMILES: C[C@H](Nc1cc(C(F)F)c(-c2sc(C(=O)N[C@@H]3CC[C@H]3O)nc2C(=O)N2CCC[C@@H]2C)cn1)C(F)(F)F]

The title compound was prepared as described in Example 149 substituting trans-2-aminocyclobutan-1-ol HCl for 3-hydroxy-3-methylazetidine HCl and ethyl 5-(4-(difluoromethyl)-6-(((S)-1,1,1-trifluoropropan-2-yl)amino)pyridin-3-yl)-4-((S)-2-methylpyrrolidine-1-carbonyl)thiazole-2-carboxylate (Intermediate 94) for ethyl (S)-5-(6-(tert-butylamino)-4-(difluoromethyl)pyridin-3-yl)-4-(2-methylpyrrolidine-1-carbonyl)thiazole-2-carboxylate followed by SFC purification (Stationary phase: Lux amylose 2, 5 μm, 250×21.2 mm, Mobile phase: 75% CO$_2$, 25% i-PrOH). MS (ESI): mass calcd. for $C_{23}H_{26}F_5N_5O_3S$, 547.5; m/z found, 547.9 [M+H]$^+$. $^1$H NMR (500 MHz, CDCl$_3$) δ 8.11-8.00 (m, 1H), 7.49-7.36 (m, 1H), 6.77-6.68 (d, J=14.9 Hz, 1H), 5.23-5.11 (m, 1H), 5.02-4.87 (m, 1H), 4.35-4.12 (m, 2H), 4.13-4.03 (m, 1H), 3.61-3.53 (m, 1H), 3.53-3.43 (m, 1H), 3.41-3.30 (m, 1H), 2.27-2.14 (m, 2H), 2.10-1.98 (m, 1H), 1.98-1.83 (m, 2H), 1.82-1.71 (m, 2H), 1.68-1.49 (m, 2H), 1.44-1.36 (m, 3H), 1.26-1.21 (m, 2H), 1.01-0.95 (d, J=6.4 Hz, 1H).

Example 388

5-(4-(Difluoromethyl)-6-(((S)-1,1,1-trifluoropropan-2-yl)amino)pyridin-3-yl)-N-((1S*,2S*)-2-hydroxycyclobutyl)-4-((S)-2-methylpyrrolidine-1-carbonyl)thiazole-2-carboxamide

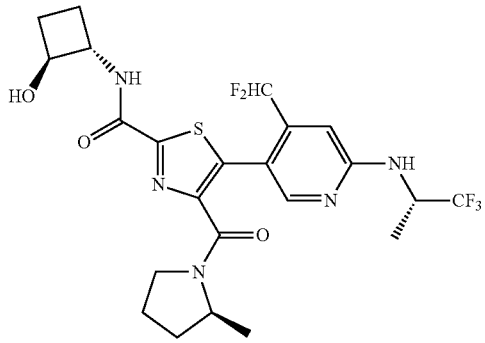 [SMILES: C[C@H](Nc1cc(C(F)F)c(-c2sc(C(=O)N[C@H]3CC[C@@H]3O)nc2C(=O)N2CCC[C@@H]2C)cn1)C(F)(F)F]

The title compound was prepared as described in Example 149 substituting trans-2-aminocyclobutan-1-ol HCl for 3-hydroxy-3-methylazetidine HCl and ethyl 5-(4-(difluoromethyl)-6-((S)-1,1,1-trifluoropropan-2-yl)amino)pyridin-3-yl)-4-((S)-2-methylpyrrolidine-1-carbonyl)thiazole-2-carboxylate (Intermediate 94) for ethyl (S)-5-(6-(tert-butylamino)-4-(difluoromethyl)pyridin-3-yl)-4-(2-methylpyrrolidine-1-carbonyl)thiazole-2-carboxylate followed by SFC purification (Stationary phase: Lux amylose 2, 5 μm, 250×21.2 mm, Mobile phase: 75% $CO_2$, 25% i-PrOH). MS (ESI): mass calcd. for $C_{23}H_{26}F_5N_5O_3S$, 547.5; m/z found, 547.8 [M+H]$^+$. $^1$H NMR (500 MHz, CDCl$_3$) δ 8.10-8.00 (m, 1H), 7.57-7.44 (m, 1H), 6.76-6.66 (m, 1H), 5.60-5.43 (m, 1H), 5.03-4.85 (m, 1H), 4.32-4.08 (m, 3H), 3.62-3.52 (m, 1H), 3.52-3.42 (m, 1H), 3.42-3.31 (m, 1H), 2.28-2.12 (m, 2H), 2.11-1.98 (m, 1H), 1.98-1.83 (m, 1H), 1.83-1.68 (m, 2H), 1.69-1.47 (m, 2H), 1.44-1.36 (m, 3H), 1.27-1.17 (m, 3H), 1.03-0.96 (m, 1H).

Example 389

5-(4-(Difluoromethyl)-6-(((S)-1,1,1-trifluoropropan-2-yl)amino)pyridin-3-yl)-N-(cis-2-hydroxycyclobutyl)-4-((S)-2-methylpyrrolidine-1-carbonyl)thiazole-2-carboxamide

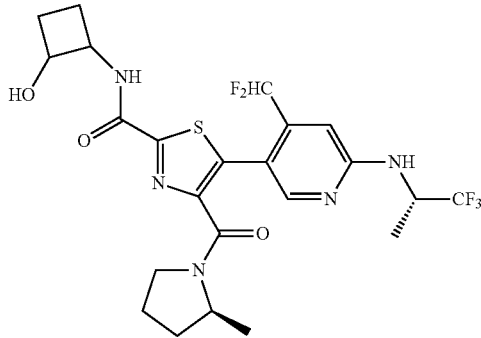 [SMILES: C[C@H](Nc1cc(C(F)F)c(-c2sc(C(=O)NC3CCC3O)nc2C(=O)N2CCC[C@@H]2C)cn1)C(F)(F)F]

The title compound was prepared as described in Example 149 substituting cis-2-aminocyclobutan-1-ol HCl for 3-hydroxy-3-methylazetidine HCl and ethyl 5-(4-(difluoromethyl)-6-((S)-1,1,1-trifluoropropan-2-yl)amino)pyridin-3-yl)-4-((S)-2-methylpyrrolidine-1-carbonyl)thiazole-2-carboxylate (Intermediate 94) for ethyl (S)-5-(6-(tert-butylamino)-4-(difluoromethyl)pyridin-3-yl)-4-(2-methylpyrrolidine-1-carbonyl)thiazole-2-carboxylate. MS (ESI): mass calcd. for $C_{23}H_{26}F_5N_5O_3S$, 547.5; m/z found, 547.9 [M+H]$^+$. $^1$H NMR (500 MHz, CDCl$_3$) δ 8.10-8.02 (m, 1H), 7.82-7.72 (m, 1H), 6.79-6.71 (m, 1H), 5.00-4.81 (m, 2H), 4.64-4.50 (m, 2H), 4.25-4.15 (m, 1H), 3.63-3.38 (m, 2H), 2.45-2.35 (m, 1H), 2.33-2.25 (m, 1H), 2.22-2.13 (m, 1H), 2.06-1.91 (m, 2H), 1.83-1.72 (m, 1H), 1.61-1.52 (m, 3H), 1.44-1.38 (d, J=6.7 Hz, 3H), 1.27-1.21 (m, 3H), 1.09-1.04 (m, 1H).

Example 390

5-(4-(Difluoromethyl)-6-(((S)-1,1,1-trifluoropropan-2-yl)amino)pyridin-3-yl)-N-((1S*,2R*)-2-hydroxycyclobutyl)-4-((S)-2-methylpyrrolidine-1-carbonyl)thiazole-2-carboxamide

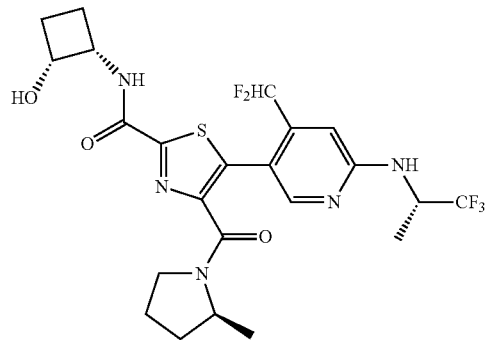 [SMILES: C[C@H](Nc1cc(C(F)F)c(-c2sc(C(=O)N[C@H]3CC[C@H]3O)nc2C(=O)N2CCC[C@@H]2C)cn1)C(F)(F)F]

The title compound was prepared as described in Example 149 substituting cis-2-aminocyclobutan-1-ol HCl for 3-hydroxy-3-methylazetidine HCl and ethyl 5-(4-(difluoromethyl)-6-(((S)-1,1,1-trifluoropropan-2-yl)amino)pyridin-3-yl)-4-((S)-2-methylpyrrolidine-1-carbonyl)thiazole-2-carboxylate (Intermediate 94) for ethyl (S)-5-(6-(tert-butylamino)-4-(difluoromethyl)pyridin-3-yl)-4-(2-methylpyrrolidine-1-carbonyl)thiazole-2-carboxylate followed by SFC purification (Stationary phase: Lux amylose 2, 5 μm, 250×21.2 mm, Mobile phase: 75% $CO_2$, 25% i-PrOH). MS (ESI): mass calcd. for $C_{23}H_{26}F_5N_5O_3S$, 547.5; m/z found, 547.9 [M+H]$^+$. $^1$H NMR (500 MHz, CDCl$_3$) δ 8.08-8.00 (m, 1H), 7.96-7.89 (d, J=6.7 Hz, 1H), 6.74-6.66 (m, 1H), 5.61-5.45 (m, 1H), 5.02-4.87 (m, 1H), 4.57-4.35 (m, 2H), 4.23-3.98 (m, 1H), 3.60-3.49 (m, 1H), 3.44-3.35 (m, 1H), 2.34-2.12 (m, 3H), 2.10-1.86 (m, 4H), 1.79-1.71 (m, 1H), 1.68-1.49 (m, 1H), 1.42-1.35 (m, 3H), 1.28-1.17 (m, 3H), 1.09-1.00 (d, J=6.4 Hz, 1H).

Example 391

5-(4-(Difluoromethyl)-6-(((S)-1,1,1-trifluoropropan-2-yl)amino)pyridin-3-yl)-N-((1R*,2S*)-2-hydroxycyclobutyl)-4-((S)-2-methylpyrrolidine-1-carbonyl)thiazole-2-carboxamide

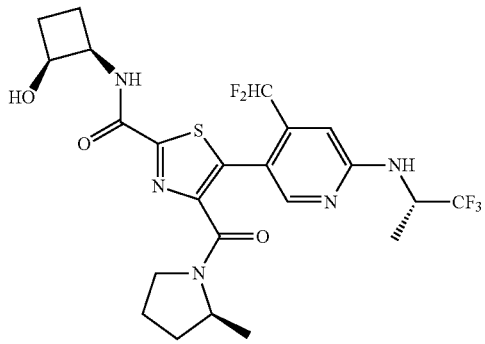 [SMILES: C[C@H](Nc1cc(C(F)F)c(-c2sc(C(=O)N[C@@H]3CC[C@@H]3O)nc2C(=O)N2CCC[C@@H]2C)cn1)C(F)(F)F]

The title compound was prepared as described in Example 149 substituting cis-2-aminocyclobutan-1-ol HCl for 3-hydroxy-3-methylazetidine HCl and ethyl 5-(4-(difluoromethyl)-6-(((S)-1,1,1-trifluoropropan-2-yl)amino)pyridin-3-yl)-4-((S)-2-methylpyrrolidine-1-carbonyl)thiazole-2-carboxylate (Intermediate 94) for ethyl (S)-5-(6-(tert-butylamino)-4-(difluoromethyl)pyridin-3-yl)-4-(2-methylpyrrolidine-1-carbonyl)thiazole-2-carboxylate followed by SFC purification (Stationary phase: Lux amylose 2, 5 μm, 250×21.2 mm, Mobile phase: 75% CO$_2$, 25% i-PrOH). MS (ESI): mass calcd. for C$_{23}$H$_{26}$F$_5$N$_5$O$_3$S, 547.5; m/z found, 547.9 [M+H]$^+$. $^1$H NMR (500 MHz, CDCl$_3$) δ 8.09-8.00 (m, 1H), 7.97-7.88 (m, 1H), 6.75-6.67 (m, 1H), 5.53-5.38 (m, 1H), 5.03-4.86 (m, 1H), 4.60-4.46 (m, 2H), 4.40-4.13 (m, 1H), 3.63-3.47 (m, 1H), 3.46-3.36 (m, 1H), 2.33-2.20 (m, 2H), 2.20-2.11 (m, 1H), 2.09-1.81 (m, 4H), 1.81-1.62 (m, 1H), 1.59-1.48 (m, 1H), 1.43-1.36 (m, 3H), 1.27-1.18 (m, 3H), 1.10-1.02 (d, J=6.4 Hz, 1H).

Example 392

[5-[4-(Difluoromethyl)-6-[[(1S)-1-(trifluoromethyl)propyl]amino]-3-pyridyl]-2-(6-oxa-3-azabicyclo[3.1.1]heptane-3-carbonyl)thiazol-4-yl]-[(2S)-2-methylpyrrolidin-1-yl]methanone

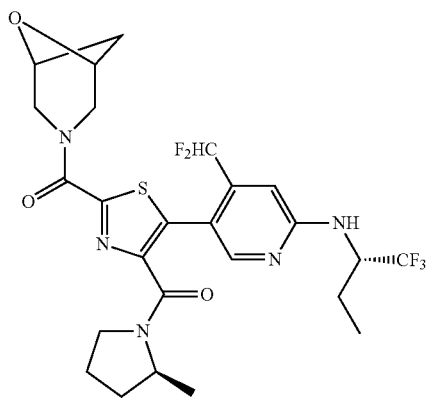 [SMILES: CC[C@H](Nc1cc(C(F)F)c(-c2sc(C(=O)N3CC4CC(C3)O4)nc2C(=O)N2CCC[C@@H]2C)cn1)C(F)(F)F]

The title compound was prepared as described in Example 149 substituting 6-oxa-3-azabicyclo[3.1.1]heptane TsOH for 3-hydroxy-3-methylazetidine HCl and ethyl 5-(4-(difluoromethyl)-6-(((S)-1,1,1-trifluorobutan-2-yl)amino)pyridin-3-yl)-4-((S)-2-methylpyrrolidine-1-carbonyl)thiazole-2-carboxylate (Intermediate 102) for ethyl (S)-5-(6-(tert-butylamino)-4-(difluoromethyl)pyridin-3-yl)-4-(2-methylpyrrolidine-1-carbonyl)thiazole-2-carboxylate. MS (ESI): mass calcd. for C$_{25}$H$_{28}$F$_5$N$_5$O$_3$S, 573.6; m/z found, 573.9 [M+H]$^+$. $^1$H NMR (600 MHz, CDCl$_3$) δ 8.09-8.00 (m, 1H), 6.81-6.74 (m, 1H), 5.54-5.42 (m, 1H), 4.85-4.59 (m, 4H), 4.44-4.33 (m, 1H), 4.32-4.17 (m, 1H), 4.16-4.04 (m, 1H), 3.94-3.86 (m, 1H), 3.66-3.55 (m, 1H), 3.54-3.42 (m, 1H), 3.36-3.27 (m, 1H), 2.11-2.02 (m, 1H), 2.00-1.84 (m, 4H), 1.83-1.74 (m, 1H), 1.71-1.52 (m, 2H), 1.29-1.19 (m, 2H), 1.08-0.93 (m, 4H).

Example 393

[5-[4-(Difluoromethyl)-6-[[(1S)-1-(trifluoromethyl)propyl]amino]-3-pyridyl]-2-(3-methylsulfonylazetidine-1-carbonyl)thiazol-4-yl]-[(2S)-2-methylpyrrolidin-1-yl]methanone

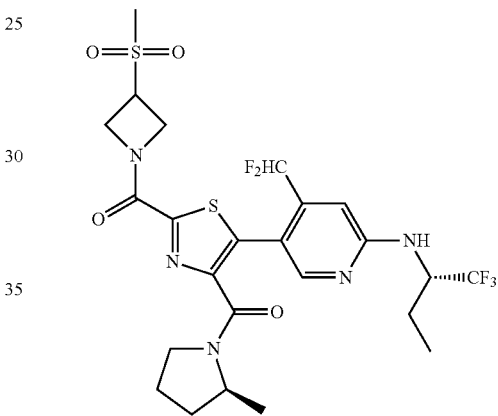

To a 25 mL round bottomed flask was added ethyl 5-(4-(difluoromethyl)-6-(((S)-1,1,1-trifluorobutan-2-yl)amino)pyridin-3-yl)-4-((S)-2-methylpyrrolidine-1-carbonyl)thiazole-2-carboxylate (0.25 g, 0.48 mmol, Intermediate 104: Step B), DIPEA (0.3 mL, 1.7 mmol), water (2 mL) and EtOH (2 mL) and the reaction was stirred at 80° C. for 2.5 h. The contents were cooled to room temperature and the pH was adjusted to approximately 4 with 1 M aqueous hydrochloric acid. The mixture was then extracted three times with ethyl acetate and the combined organic phases were dried over magnesium sulfate, filtered and concentrated under reduced pressure. The crude material was then taken up into DCM (5 mL), cooled to 0° C., then oxalyl chloride (60 μL, 0.67 mmol) and DMF (8 uL) were added under a nitrogen atmosphere. The reaction solution was stirred at 0° C. for 25 minutes, then warmed to room temperature and stirred for 45 minutes. The reaction solution was then concentrated under reduced pressure. The crude material was then re-dissolved in DCM (5 mL) then cooled to 0° C. under a nitrogen atmosphere followed by the addition of 3-methylsulfonylazetidine (78.7 mg, 0.58 mmol) and DIPEA (0.23 mL, 1.4 mmol). The contents were allowed to stir at 0° C. for 5 minutes then the contents were warmed to room temperature and stirred for 3 days. The reaction solution was then re-cooled to 0° C., quenched with a saturated aqueous ammonium chloride solution. The contents were transferred to a separatory funnel and extracted three times with ethyl acetate and the combined organic phases were dried over magnesium sulfate, filtered and concentrated under reduced pressure. The crude residue was dissolved in chloroform and purified by FCC (0-100% EtOAc/Hexanes) to provide the title compound. MS (ESI): mass calcd. for $C_{24}H_{28}F_5N_5O_4S_2$, 609.6; m/z found, 609.8 [M+H]$^+$. $^1$H NMR (500 MHz, CDCl$_3$) δ 8.07-7.99 (m, 1H), 6.80-6.71 (m, 1H), 5.22-5.14 (m, 1H), 5.11-4.94 (m, 2H), 4.85-4.72 (m, 1H), 4.59-4.49 (m, 2H), 4.23-4.09 (m, 2H), 3.61-3.49 (m, 1H), 3.47-3.39 (m, 1H), 2.99-2.93 (m, 3H), 2.12-2.01 (m, 1H), 2.00-1.89 (m, 2H), 1.86-1.74 (m, 1H), 1.69-1.49 (m, 2H), 1.27-1.16 (m, 3H), 1.07-0.94 (m, 4H).

Example 394

5-[4-(Difluoromethyl)-6-[[(1S)-1-(trifluoromethyl)propyl]amino]-3-pyridyl]-4-[(2S)-2-methylpyrrolidine-1-carbonyl]-N-tetrahydropyran-4-yl-thiazole-2-carboxamide

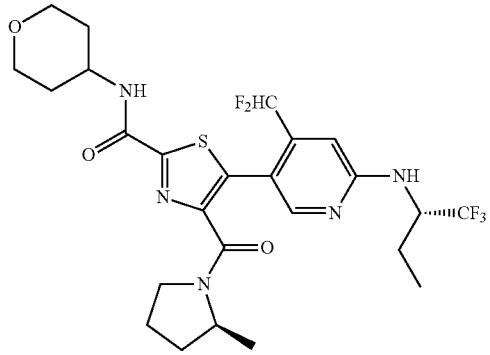 [SMILES: CC[C@H](Nc1cc(C(F)F)c(-c2sc(C(=O)NC3CCOCC3)nc2C(=O)N2CCC[C@@H]2C)cn1)C(F)(F)F]

The title compound was prepared as described in Example 148 substituting tetrahydro-2H-pyran-4-amine for (R)-(−)-2-amino-1-propanol and ethyl 5-(4-(difluoromethyl)-6-(((S)-1,1,1-trifluorobutan-2-yl)amino)pyridin-3-yl)-4-((S)-2-methylpyrrolidine-1-carbonyl)thiazole-2-carboxylate (Intermediate 102) for ethyl (S)-5-(6-(tert-butylamino)-4-(difluoromethyl)pyridin-3-yl)-4-(2-methylpyrrolidine-1-carbonyl)thiazole-2-carboxylate. MS (ESI): mass calcd. for $C_{25}H_{30}F_5N_5O_3S$, 575.6; m/z found, 575.9 [M+H]$^+$. $^1$H NMR (500 MHz, CDCl$_3$) δ 8.10-8.00 (m, 1H), 7.16-7.04 (m, 1H), 6.82-6.75 (m, 1H), 5.34-5.24 (m, 1H), 4.86-4.74 (m, 1H), 4.28-4.13 (m, 2H), 4.06-3.97 (m, 2H), 3.59-3.51 (m, 3H), 3.45-3.31 (m, 1H), 2.09-1.85 (m, 6H), 1.81-1.72 (m, 1H), 1.71-1.49 (m, 4H), 1.24-1.19 (m, 2H), 1.07-1.00 (m, 4H).

Example 395

[5-[4-(Difluoromethyl)-6-[[(1S)-1-(trifluoromethyl)propyl]amino]-3-pyridyl]-2-(morpholine-4-carbonyl)thiazol-4-yl]-[(2S)-2-methylpyrrolidin-1-yl]methanone

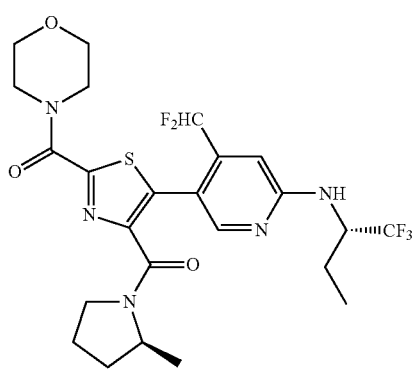 [SMILES: CC[C@H](Nc1cc(C(F)F)c(-c2sc(C(=O)N3CCOCC3)nc2C(=O)N2CCC[C@@H]2C)cn1)C(F)(F)F]

The title compound was prepared as described in Example 148 substituting morpholine for (R)-(−)-2-amino-1-propanol and ethyl 5-(4-(difluoromethyl)-6-(((S)-1,1,1-trifluorobutan-2-yl)amino)pyridin-3-yl)-4-((S)-2-methylpyrrolidine-1-carbonyl)thiazole-2-carboxylate (Intermediate 102) for ethyl (S)-5-(6-(tert-butylamino)-4-(difluoromethyl)pyridin-3-yl)-4-(2-methylpyrrolidine-1-carbonyl)thiazole-2-carboxylate. MS (ESI): mass calcd. for $C_{24}H_{28}F_5N_5O_3S$, 561.6; m/z found, 561.9 [M+H]$^+$. $^1$H NMR (500 MHz, CDCl$_3$) δ 8.08-8.00 (m, 1H), 6.80-6.72 (m, 1H), 5.23-5.11 (m, 1H), 4.84-4.71 (m, 1H), 4.52-4.27 (m, 2H), 4.25-4.16 (m, 1H), 3.89-3.74 (m, 6H), 3.64-3.39 (m, 2H), 2.10-2.01 (m, 1H), 2.01-1.83 (m, 3H), 1.82-1.73 (m, 1H), 1.69-1.50 (m, 2H), 1.23-1.20 (m, 2H), 1.06-0.99 (m, 4H).

Example 396

5-[6-(tert-Butylamino)-4-(difluoromethyl)-3-pyridyl]-N-[(1S,2S)-2-hydroxycyclopentyl]-4-[(2S)-2-methylpyrrolidine-1-carbonyl]thiazole-2-carboxamide

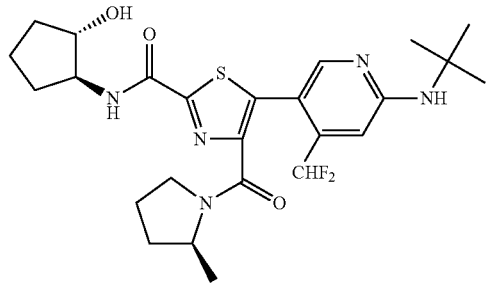 [SMILES: C[C@H]1CCCN1C(=O)c1nc(C(=O)N[C@H]2CCC[C@@H]2O)sc1-c1cnc(NC(C)(C)C)cc1C(F)F]

The title compound was prepared as described in Example 149 substituting (1S,2S)-2-aminocyclopentan-1-ol HCl for 3-hydroxy-3-methylazetidine HCl and ethyl (S)-5-(6-(tert-butylamino)-4-(difluoromethyl)pyridin-3-yl)-4-(2-methylpyrrolidine-1-carbonyl)thiazole-2-carboxylate (Intermediate 106) for ethyl (S)-5-(6-(tert-butylamino)-4-(difluoromethyl)pyridin-3-yl)-4-(2-methylpyrrolidine-1-carbonyl)thiazole-2-carboxylate. MS (ESI): mass calcd. for $C_{25}H_{33}F_2N_5O_3S$, 521.6; m/z found, 522.0 [M+H]$^+$. $^1$H NMR (500 MHz, CDCl$_3$) δ 8.09-7.99 (m, 1H), 7.35-7.23 (m, 1H), 6.75-6.62 (m, 1H), 5.01-4.92 (m, 1H), 4.26-4.11 (m, 2H), 4.09-4.00 (m, 1H), 4.00-3.92 (s, 1H), 3.63-3.51 (m, 1H), 3.38-3.27 (m, 1H), 2.33-2.21 (m, 1H), 2.13-1.98 (m, 2H), 1.99-1.81 (m, 3H), 1.81-1.69 (m, 3H), 1.67-1.57 (m, 1H), 1.57-1.48 (m, 1H), 1.48-1.43 (s, 9H), 1.24-1.18 (m, 2H), 1.03-0.96 (m, 1H).

Example 397

5-[6-(tert-Butylamino)-4-(difluoromethyl)-3-pyridyl]-N-[(1R,2R)-2-hydroxycyclopentyl]-4-[(2S)-2-methylpyrrolidine-1-carbonyl]thiazole-2-carboxamide

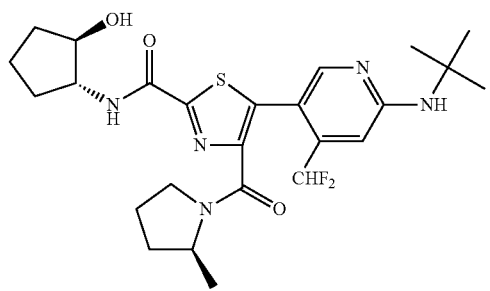 [SMILES: C[C@H]1CCCN1C(=O)c1nc(C(=O)N[C@@H]2CCC[C@H]2O)sc1-c1cnc(NC(C)(C)C)cc1C(F)F]

The title compound was prepared as described in Example 149 substituting (1R,2R)-2-aminocyclopentan-1-ol HCl for 3-hydroxy-3-methylazetidine HCl and ethyl (S)-5-(6-(tert-butylamino)-4-(difluoromethyl)pyridin-3-yl)-4-(2-methylpyrrolidine-1-carbonyl)thiazole-2-carboxylate (Intermediate 106) for ethyl (S)-5-(6-(tert-butylamino)-4-(difluoromethyl)pyridin-3-yl)-4-(2-methylpyrrolidine-1-carbonyl)thiazole-2-carboxylate. MS (ESI): mass calcd. for $C_{25}H_{33}F_2N_5O_3S$, 521.6; m/z found, 522.0 [M+H]$^+$. $^1$H NMR (500 MHz, CDCl$_3$) δ 8.09-7.97 (m, 1H), 7.36-7.25 (m, 1H), 6.74-6.62 (m, 1H), 5.03-4.93 (m, 1H), 4.26-4.10 (m, 2H), 4.10-4.01 (m, 1H), 4.02-3.95 (s, 1H), 3.61-3.52 (m, 1H), 3.38-3.27 (m, 1H), 2.32-2.21 (m, 1H), 2.13-2.00 (m, 2H), 1.98-1.81 (m, 3H), 1.81-1.67 (m, 3H), 1.67-1.57 (m, 1H), 1.57-1.48 (m, 1H), 1.48-1.42 (m, 9H), 1.24-1.19 (m, 2H), 1.03-0.96 (m, 1H).

Example 398

5-[4-(Difluoromethyl)-6-[[(1S)-1-(trifluoromethyl)propyl]amino]-3-pyridyl]-N-[(1S,3S)-3-hydroxycyclopentyl]-4-[(2S)-2-methylpyrrolidine-1-carbonyl]thiazole-2-carboxamide

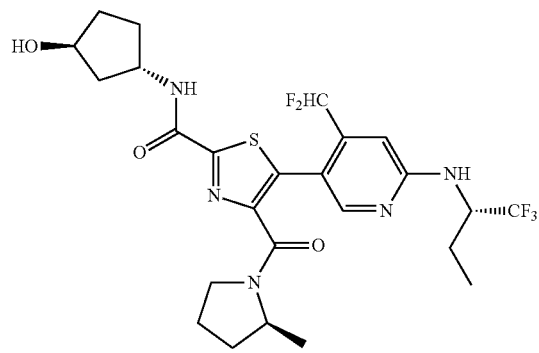 [SMILES: CC[C@H](Nc1cc(C(F)F)c(-c2sc(C(=O)N[C@H]3CC[C@H](O)C3)nc2C(=O)N2CCC[C@@H]2C)cn1)C(F)(F)F]

The title compound was prepared as described in Example 149 substituting (1S,3S)-3-aminocyclopentan-1-ol HCl for 3-hydroxy-3-methylazetidine HCl and ethyl 5-(4-(difluoromethyl)-6-(((S)-1,1,1-trifluorobutan-2-yl)amino)pyridin-3-yl)-4-((S)-2-methylpyrrolidine-1-carbonyl)thiazole-2-carboxylate (Intermediate 102) for ethyl (S)-5-(6-(tert-butylamino)-4-(difluoromethyl)pyridin-3-yl)-4-(2-methylpyrrolidine-1-carbonyl)thiazole-2-carboxylate. MS (ESI): mass calcd. for $C_{25}H_{30}F_5N_5O_3S$, 575.6; m/z found, 575.9 [M+H]$^+$. $^1$H NMR (500 MHz, CDCl$_3$) δ 8.09-8.00 (m, 1H), 7.22-7.08 (m, 1H), 6.82-6.74 (m, 1H), 5.19-5.09 (m, 1H), 4.84-4.73 (s, 1H), 4.69-4.58 (m, 1H), 4.53-4.44 (m, 1H), 4.26-4.15 (m, 1H), 3.62-3.51 (m, 1H), 3.42-3.28 (m, 1H), 2.42-2.31 (m, 1H), 2.23-2.01 (m, 4H), 2.01-1.67 (m, 6H), 1.67-1.47 (m, 3H), 1.29-1.18 (m, 2H), 1.07-0.96 (m, 4H).

Example 399

5-[4-(Difluoromethyl)-6-[[(1S)-1-(trifluoromethyl)propyl]amino]-3-pyridyl]-N-[(1R,3R)-3-hydroxycyclopentyl]-4-[(2S)-2-methylpyrrolidine-1-carbonyl]thiazole-2-carboxamide

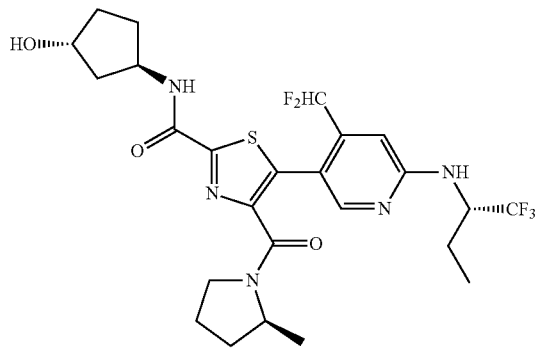 [SMILES: CC[C@H](Nc1cc(C(F)F)c(-c2sc(C(=O)N[C@@H]3CC[C@@H](O)C3)nc2C(=O)N2CCC[C@@H]2C)cn1)C(F)(F)F]

The title compound was prepared as described in Example 149 substituting (1R,3R)-3-aminocyclopentan-1-ol HCl for 3-hydroxy-3-methylazetidine HCl and ethyl 5-(4-(difluoromethyl)-6-(((S)-1,1,1-trifluorobutan-2-yl)amino)pyridin-3-yl)-4-((S)-2-methylpyrrolidine-1-carbonyl)thiazole-2-carboxylate (Intermediate 102) for ethyl (S)-5-(6-(tert-butylamino)-4-(difluoromethyl)pyridin-3-yl)-4-(2-methylpyrrolidine-1-carbonyl)thiazole-2-carboxylate. MS (ESI): mass calcd. for $C_{25}H_{30}F_5N_5O_3S$, 575.6; m/z found, 575.9 [M+H]$^+$. $^1$H NMR (500 MHz, CDCl$_3$) δ 8.09-8.00 (m, 1H), 7.22-7.11 (m, 1H), 6.83-6.73 (m, 1H), 5.23-5.16 (m, 1H), 4.86-4.72 (s, 1H), 4.69-4.58 (m, 1H), 4.53-4.44 (m, 1H), 4.26-4.09 (m, 1H), 3.61-3.52 (m, 1H), 3.42-3.27 (m, 1H), 2.42-2.30 (m, 1H), 2.27-2.15 (m, 2H), 2.15-2.01 (m, 2H), 2.01-1.67 (m, 6H), 1.67-1.47 (m, 3H), 1.29-1.18 (m, 2H), 1.07-0.97 (m, 4H).

Example 400

5-(6-(tert-Butylamino)-4-(difluoromethyl)pyridin-3-yl)-N-((1R,3S)-3-hydroxycyclobutyl)-4-((S)-2-methylpyrrolidine-1-carbonyl)thiazole-2-carboxamide

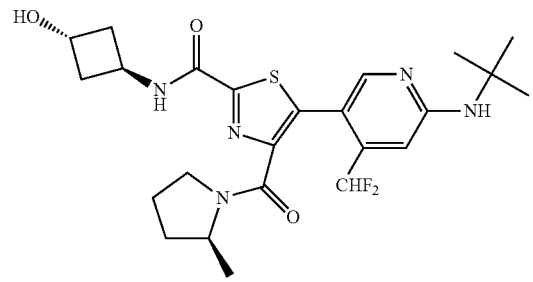 [SMILES: C[C@H]1CCCN1C(=O)c1nc(C(=O)N[C@H]2C[C@H](O)C2)sc1-c1cnc(NC(C)(C)C)cc1C(F)F]

The title compound was prepared as described in Example 149 substituting (1R,3R)-3-aminocyclobutan-1-ol HCl for 3-hydroxy-3-methylazetidine HCl and ethyl (S)-5-(6-(tert-butylamino)-4-(difluoromethyl)pyridin-3-yl)-4-(2-methylpyrrolidine-1-carbonyl)thiazole-2-carboxylate (Intermediate 106) for ethyl (S)-5-(6-(tert-butylamino)-4-(difluoromethyl)pyridin-3-yl)-4-(2-methylpyrrolidine-1- carbonyl)thiazole-2-carboxylate. MS (ESI): mass calcd. for $C_{24}H_{31}F_2N_5O_3S$, 507.6; m/z found, 507.9 [M+H]+. 1H NMR (400 MHz, CDCl3) δ 8.06-7.98 (m, 1H), 7.49-7.36 (m, 1H), 6.76-6.62 (m, 1H), 5.11-5.01 (s, 1H), 4.71-4.51 (m, 2H), 4.30-4.07 (m, 1H), 3.64-3.52 (m, 1H), 3.40-3.11 (m, 2H), 2.53-2.36 (m, 4H), 2.13-1.99 (m, 1H), 1.99-1.82 (m, 2H), 1.82-1.68 (m, 1H), 1.68-1.49 (m, 1H), 1.49-1.41 (d, J=9.1 Hz, 9H), 1.32-1.17 (m, 2H), 1.04-0.93 (d, J=6.4 Hz, 1H).

Example 401

5-[6-(tert-Butylamino)-4-(difluoromethyl)-3-pyridyl]-N-[(3S,4R)-4-hydroxytetrahydrofuran-3-yl]-4-[(2S)-2-methylpyrrolidine-1-carbonyl]thiazole-2-carboxamide

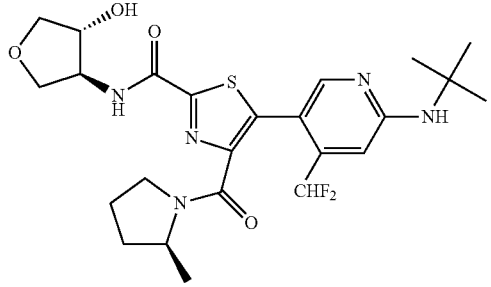 [SMILES: C[C@H]1CCCN1C(=O)c1nc(C(=O)N[C@H]2COC[C@@H]2O)sc1-c1cnc(NC(C)(C)C)cc1C(F)F]

The title compound was prepared as described in Example 148 substituting (3R,4S)-4-aminotetrahydrofuran-3-ol for (R)-(−)-2-amino-1-propanol and ethyl (S)-5-(6-(tert-butylamino)-4-(difluoromethyl)pyridin-3-yl)-4-(2-methylpyrrolidine-1-carbonyl)thiazole-2-carboxylate (Intermediate 106) for ethyl (S)-5-(6-(tert-butylamino)-4-(difluoromethyl)pyridin-3-yl)-4-(2-methylpyrrolidine-1-carbonyl)thiazole-2-carboxylate. MS (ESI): mass calcd. for $C_{24}H_{31}F_2N_5O_4S$, 523.6; m/z found, 523.9 [M+H]+. 1H NMR (400 MHz, CDCl3) δ 8.08-7.97 (m, 1H), 7.47-7.33 (m, 1H), 6.75-6.60 (m, 1H), 5.05-4.96 (d, J=2.1 Hz, 1H), 4.48-4.37 (m, 2H), 4.27-4.08 (m, 3H), 4.08-3.97 (s, 1H), 3.90-3.83 (m, 1H), 3.80-3.73 (m, 1H), 3.63-3.53 (m, 1H), 3.44-3.25 (m, 1H), 2.11-1.98 (m, 1H), 1.96-1.83 (m, 1H), 1.81-1.69 (m, 1H), 1.67-1.50 (m, 1H), 1.50-1.42 (s, 9H), 1.27-1.22 (m, 3H), 1.01-0.93 (d, J=6.4 Hz, 1H).

Example 402

5-[6-(tert-Butylamino)-4-(difluoromethyl)-3-pyridyl]-N-[(3R,4S)-4-hydroxytetrahydrofuran-3-yl]-4-[(2S)-2-methylpyrrolidine-1-carbonyl]thiazole-2-carboxamide

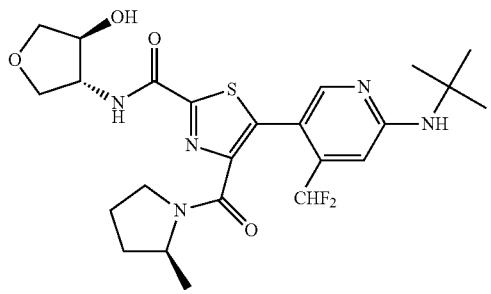 [SMILES: C[C@H]1CCCN1C(=O)c1nc(C(=O)N[C@@H]2COC[C@H]2O)sc1-c1cnc(NC(C)(C)C)cc1C(F)F]

The title compound was prepared as described in Example 148 substituting (3S,4R)-4-aminotetrahydrofuran-3-ol for (R)-(−)-2-amino-1-propanol and ethyl (S)-5-(6-(tert-butylamino)-4-(difluoromethyl)pyridin-3-yl)-4-(2-methylpyrrolidine-1-carbonyl)thiazole-2-carboxylate (Intermediate 106) for ethyl (S)-5-(6-(tert-butylamino)-4-(difluoromethyl)pyridin-3-yl)-4-(2-methylpyrrolidine-1-carbonyl)thiazole-2-carboxylate. MS (ESI): mass calcd. for $C_{24}H_{31}F_2N_5O_4S$, 523.6; m/z found, 523.9 [M+H]+. 1H NMR (400 MHz, CDCl3) δ 8.07-7.98 (m, 1H), 7.47-7.36 (m, 1H), 6.76-6.59 (m, 1H), 5.05-4.96 (s, 1H), 4.48-4.37 (m, 2H), 4.26-4.09 (m, 3H), 4.09-4.00 (s, 1H), 3.90-3.82 (m, 1H), 3.81-3.73 (m, 1H), 3.62-3.52 (m, 1H), 3.38-3.26 (m, 1H), 2.11-2.00 (m, 1H), 1.99-1.82 (m, 1H), 1.82-1.70 (m, 1H), 1.59-1.49 (m, 1H), 1.49-1.42 (m, 9H), 1.31-1.18 (m, 3H), 1.02-0.96 (d, J=6.4 Hz, 1H).

Example 403

5-(6-(tert-Butylamino)-4-(difluoromethyl)pyridin-3-yl)-N-(1R*,2R*)-2-hydroxycyclobutyl)-4-((S)-2-methylpyrrolidine-1-carbonyl)thiazole-2-carboxamide

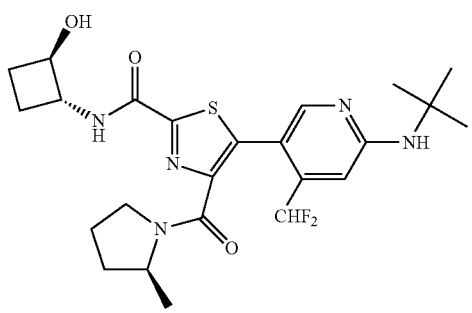 [SMILES: C[C@H]1CCCN1C(=O)c1nc(C(=O)N[C@@H]2CC[C@H]2O)sc1-c1cnc(NC(C)(C)C)cc1C(F)F]

The title compound was prepared as described in Example 149 substituting trans-2-aminocyclobutan-1-ol HCl for 3-hydroxy-3-methylazetidine HCl and ethyl (S)-5-(6-(tert-butylamino)-4-(difluoromethyl)pyridin-3-yl)-4-(2-methylpyrrolidine-1-carbonyl)thiazole-2-carboxylate (Intermediate 106) for ethyl (S)-5-(6-(tert-butylamino)-4-(difluoromethyl)pyridin-3-yl)-4-(2-methylpyrrolidine-1-carbonyl)thiazole-2-carboxylate followed by SFC purification (Stationary phase: Lux amylose 2, 5 μm, 250× 21.2 mm, Mobile phase: 65% $CO_2$, 35% i-PrOH (0.3% i-PrNH2)). MS (ESI): mass calcd. for $C_{24}H_{31}F_2N_5O_3S$, 507.6; m/z found, 507.9 [M+H]+. 1H NMR (400 MHz, CDCl3) δ 8.07-7.98 (m, 1H), 7.57-7.42 (m, 1H), 6.75-6.60 (m, 1H), 5.00-4.88 (s, 1H), 4.27-3.95 (m, 3H), 3.63-3.52 (m, 1H), 3.43-3.26 (m, 1H), 2.28-2.12 (m, 2H), 2.11-1.99 (m, 1H), 1.99-1.82 (m, 1H), 1.81-1.67 (m, 1H), 1.67-1.49 (m, 2H), 1.48-1.42 (s, 9H), 1.25-1.17 (m, 5H), 1.00-0.94 (d, J=6.4 Hz, 1H).

Example 404

5-(6-(tert-Butylamino)-4-(difluoromethyl)pyridin-3-yl)-N-((1S*,2S*)-2-hydroxycyclobutyl)-4-((S)-2-methylpyrrolidine-1-carbonyl)thiazole-2-carboxamide

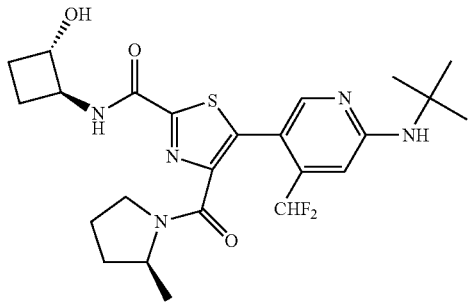 [SMILES: C[C@H]1CCCN1C(=O)c1nc(C(=O)N[C@H]2CC[C@@H]2O)sc1-c1cnc(NC(C)(C)C)cc1C(F)F]

The title compound was prepared as described in Example 149 substituting trans-2-aminocyclobutan-1-ol HCl for 3-hydroxy-3-methylazetidine HCl and ethyl (S)-5-(6-(tert-butylamino)-4-(difluoromethyl)pyridin-3-yl)-4-(2-methylpyrrolidine-1-carbonyl)thiazole-2-carboxylate (Intermediate 106) for ethyl (S)-5-(6-(tert-butylamino)-4-(difluoromethyl)pyridin-3-yl)-4-(2-methylpyrrolidine-1-carbonyl)thiazole-2-carboxylate followed by SFC purification (Stationary phase: Lux amylose 2, 5 µm, 250×21.2 mm, Mobile phase: 65% $CO_2$, 35% i-PrOH (0.3% i-$PrNH_2$)). MS (ESI): mass calcd. for $C_{24}H_{31}F_2N_5O_3S$, 507.6; m/z found, 508.0 $[M+H]^+$. $^1H$ NMR (400 MHz, $CDCl_3$) δ 8.08-7.97 (m, 1H), 7.57-7.42 (m, 1H), 6.78-6.59 (m, 1H), 4.99-4.89 (s, 1H), 4.28-4.03 (m, 3H), 3.62-3.52 (m, 1H), 3.42-3.29 (m, 1H), 2.28-2.11 (m, 2H), 2.11-1.99 (m, 1H), 1.96-1.83 (m, 2H), 1.81-1.68 (m, 2H), 1.59-1.49 (m, 2H), 1.49-1.41 (s, 9H), 1.28-1.17 (m, 3H), 1.01-0.95 (d, J=6.4 Hz, 1H).

Example 405

4-((1s,4s)-7-Azabicyclo[2.2.1]heptane-7-carbonyl)-5-(4-(difluoromethyl)-6-(((S)-1,1,1-trifluorobutan-2-yl)amino)pyridin-3-yl)-N-((1R*,2R*)-2-hydroxycyclobutyl)thiazole-2-carboxamide

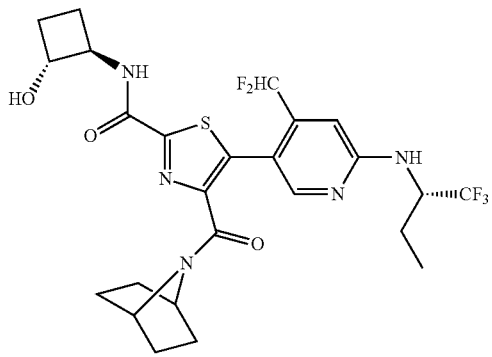 [SMILES: CC[C@H](Nc1cc(C(F)F)c(-c2sc(C(=O)N[C@@H]3CC[C@H]3O)nc2C(=O)N2C3CCC2CC3)cn1)C(F)(F)F]

The title compound was prepared as described in Example 149 substituting trans-2-aminocyclobutan-1-ol HCl for 3-hydroxy-3-methylazetidine HCl and ethyl 4-((1s,4s)-7-azabicyclo[2.2.1]heptane-7-carbonyl)-5-(4-(difluoromethyl)-6-(((S)-1,1,1-trifluorobutan-2-yl)amino)pyridin-3-yl)thiazole-2-carboxylate (Intermediate 99) for ethyl (S)-5-(6-(tert-butylamino)-4-(difluoromethyl)pyridin-3-yl)-4-(2-methylpyrrolidine-1-carbonyl)thiazole-2-carboxylate followed by SFC purification (Stationary phase: Lux amylose 2, 5 µm, 250×21.2 mm, Mobile phase: 70% $CO_2$, 30% i-PrOH (0.3% i-$PrNH_2$)). MS (ESI): mass calcd. for $C_{25}H_{28}F_5N_5O_3S$, 573.6; m/z found, 573.8 $[M+H]^+$. $^1H$ NMR (400 MHz, $CDCl_3$) δ 8.13-8.04 (s, 1H), 7.59-7.48 (d, J=5.4 Hz, 1H), 6.82-6.74 (m, 1H), 5.18-5.09 (d, J=9.7 Hz, 1H), 4.86-4.72 (m, 1H), 4.70-4.61 (m, 1H), 4.21-4.05 (m, 3H), 2.28-2.11 (m, 2H), 2.03-1.89 (m, 1H), 1.81-1.67 (m, 3H), 1.67-1.55 (m, 2H), 1.55-1.37 (m, 7H), 1.23-1.17 (m, 1H), 1.07-0.99 (m, 3H).

Example 406

4-((1s,4s)-7-Azabicyclo[2.2.1]heptane-7-carbonyl)-5-(4-(difluoromethyl)-6-(((S)-1,1,1-trifluorobutan-2-yl)amino)pyridin-3-yl)-N-((1S*,2S*)-2-hydroxycyclobutyl)thiazole-2-carboxamide

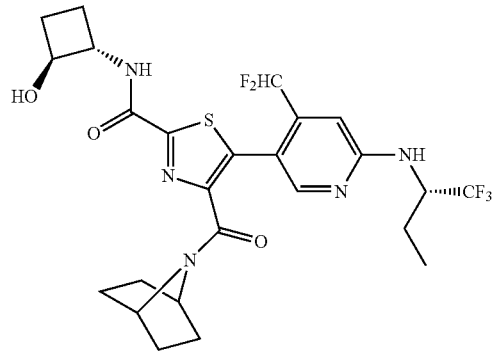 [SMILES: CC[C@H](Nc1cc(C(F)F)c(-c2sc(C(=O)N[C@H]3CC[C@@H]3O)nc2C(=O)N2C3CCC2CC3)cn1)C(F)(F)F]

The title compound was prepared as described in Example 149 substituting trans-2-aminocyclobutan-1-ol HCl for 3-hydroxy-3-methylazetidine HCl and ethyl 4-((1s,4s)-7-azabicyclo[2.2.1]heptane-7-carbonyl)-5-(4-(difluoromethyl)-6-(((S)-1,1,1-trifluorobutan-2-yl)amino)pyridin-3-yl)thiazole-2-carboxylate (Intermediate 99) for ethyl (S)-5-(6-(tert-butylamino)-4-(difluoromethyl)pyridin-3-yl)-4-(2-methylpyrrolidine-1-carbonyl)thiazole-2-carboxylate followed by SFC purification (Stationary phase: Lux amylose 2, 5 µm, 250×21.2 mm, Mobile phase: 70% $CO_2$, 30% i-PrOH (0.3% i-$PrNH_2$)). MS (ESI): mass calcd. for $C_{25}H_{28}F_5N_5O_3S$, 573.6; m/z found, 573.9 $[M+H]^+$. $^1H$ NMR (400 MHz, $CDCl_3$) δ 8.11-8.06 (s, 1H), 7.52-7.45 (d, J=5.2 Hz, 1H), 6.79-6.75 (m, 1H), 5.03-4.95 (d, J=9.7 Hz, 1H), 4.85-4.73 (m, 1H), 4.71-4.62 (m, 1H), 4.22-4.04 (m, 3H), 2.28-2.13 (m, 2H), 2.04-1.91 (m, 1H), 1.81-1.68 (m, 3H), 1.68-1.55 (m, 2H), 1.54-1.37 (m, 7H), 1.23-1.18 (m, 1H), 1.08-0.99 (m, 3H).

Example 407

5-[4-(Difluoromethyl)-6-[[(1S)-2,2,2-trifluoro-1-methyl-ethyl]amino]-3-pyridyl]-N-[(1S)-1-(hydroxymethyl)propyl]-4-[(2S)-2-methylpyrrolidine-1-carbonyl]thiazole-2-carboxamide

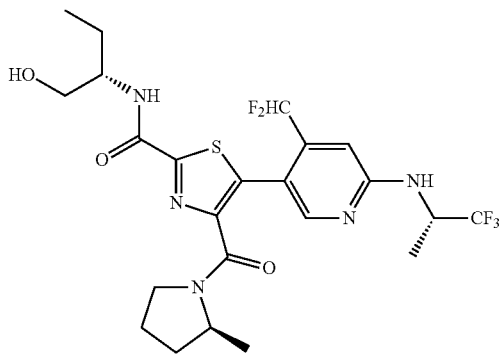 [SMILES: CC[C@@H](CO)NC(=O)c1nc(C(=O)N2CCC[C@@H]2C)c(-c2cnc(N[C@@H](C)C(F)(F)F)cc2C(F)F)s1]

The title compound was prepared as described in Example 148 substituting (S)-2-aminobutan-1-ol for (R)-(−)-2-amino-1-propanol and 5-(4-(difluoromethyl)-6-(((S)-1,1,1-trifluoropropan-2-yl)amino)pyridin-3-yl)-4-((S)-2-methylpyrrolidine-1-carbonyl)thiazole-2-carboxylate (Intermediate 94) for ethyl (S)-5-(6-(tert-butylamino)-4-(difluoromethyl)pyridin-3-yl)-4-(2-methylpyrrolidine-1-carbonyl)thiazole-2-carboxylate. MS (ESI): mass calcd. for $C_{23}H_{28}F_5N_5O_3S$, 549.6; m/z found, 549.9 [M+H]$^+$. $^1$H NMR (400 MHz, CDCl$_3$) δ 8.10-7.99 (m, 1H), 7.45-7.33 (m, 1H), 6.71 (s, 1H), 5.64-5.50 (m, 1H), 5.02-4.87 (m, 1H), 4.38-4.12 (m, 1H), 4.09-3.99 (m, 1H), 3.82-3.67 (m, 2H), 3.63-3.32 (m, 2H), 3.25-2.90 (m, 1H), 2.69-2.14 (m, 1H), 2.12-1.97 (m, 1H), 1.97-1.82 (m, 1H), 1.82-1.60 (m, 3H), 1.60-1.48 (m, 1H), 1.43-1.34 (m, 3H), 1.23 (d, J=6.3 Hz, 2H), 1.08-0.96 (m, 4H).

Example 408

5-[4-(Difluoromethyl)-6-[[(1S)-2,2,2-trifluoro-1-methyl-ethyl]amino]-3-pyridyl]-N-[(1R)-1-(hydroxymethyl)propyl]-4-[(2S)-2-methylpyrrolidine-1-carbonyl]thiazole-2-carboxamide

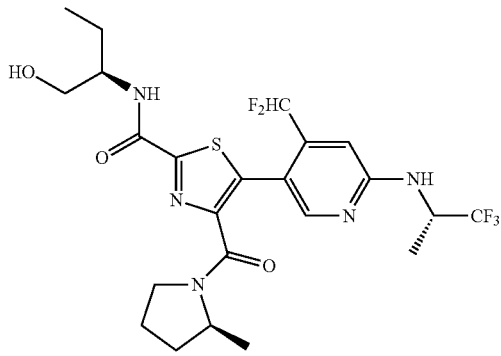 [SMILES: CC[C@H](CO)NC(=O)c1nc(C(=O)N2CCC[C@@H]2C)c(-c2cnc(N[C@@H](C)C(F)(F)F)cc2C(F)F)s1]

The title compound was prepared as described in Example 148 substituting (R)-2-aminobutan-1-ol for (R)-(−)-2-amino-1-propanol and 5-(4-(difluoromethyl)-6-(((S)-1,1,1-trifluoropropan-2-yl)amino)pyridin-3-yl)-4-((S)-2-methylpyrrolidine-1-carbonyl)thiazole-2-carboxylate (Intermediate 94) for ethyl (S)-5-(6-(tert-butylamino)-4-(difluoromethyl)pyridin-3-yl)-4-(2-methylpyrrolidine-1-carbonyl)thiazole-2-carboxylate. MS (ESI): mass calcd. for $C_{23}H_{28}F_5N_5O_3S$, 549.6; m/z found, 549.9 [M+H]$^+$. $^1$H NMR (400 MHz, CDCl$_3$) δ 8.08 (s, 1H), 7.42-7.30 (m, 1H), 6.71 (s, 1H), 5.54-5.40 (m, 1H), 5.03-4.86 (m, 1H), 4.32-4.14 (m, 1H), 4.10-3.99 (m, 1H), 3.84-3.68 (m, 2H), 3.64-3.33 (m, 2H), 3.08-2.85 (m, 1H), 2.43-2.11 (m, 1H), 2.11-1.83 (m, 2H), 1.83-1.61 (m, 3H), 1.59-1.48 (m, 1H), 1.43-1.37 (m, 3H), 1.25-1.20 (m, 2H), 1.02 (s, 4H), 1.09-0.98 (m, 4H).

Example 409

5-[4-(Difluoromethyl)-6-[[(1S)-2,2,2-trifluoro-1-methyl-ethyl]amino]-3-pyridyl]-4-[(2S)-2-methylpyrrolidine-1-carbonyl]-N-(1-methylsulfonylazetidin-3-yl)thiazole-2-carboxamide

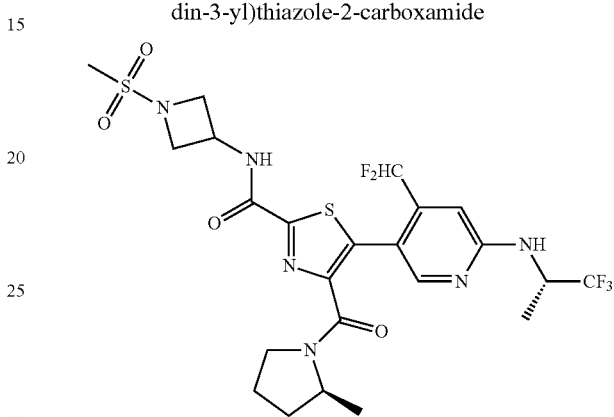

The title compound was prepared as described in Example 148 substituting 1-(methylsulfonyl)azetidin-3-amine for (R)-(−)-2-amino-1-propanol and ethyl 5-(4-(difluoromethyl)-6-(((S)-1,1,1-trifluoropropan-2-yl)amino)pyridin-3-yl)-4-((S)-2-methylpyrrolidine-1-carbonyl)thiazole-2-carboxylate (Intermediate 94) for ethyl (S)-5-(6-(tert-butylamino)-4-(difluoromethyl)pyridin-3-yl)-4-(2-methylpyrrolidine-1-carbonyl)thiazole-2-carboxylate. MS (ESI): mass calcd. for $C_{23}H_{27}F_5N_6O_4S_2$, 610.6; m/z found, 610.8 [M+H]$^+$. $^1$H NMR (400 MHz, CDCl$_3$) δ 8.09-8.07 (m, 1H), 7.66-7.54 (m, 1H), 6.77-6.68 (m, 1H), 5.19-5.06 (m, 1H), 5.03-4.82 (m, 2H), 4.36-4.17 (m, 3H), 4.18-4.08 (m, 2H), 3.63-3.48 (m, 1H), 3.44-3.30 (m, 1H), 2.96 (s, 3H), 2.05 (s, 1H), 2.00-1.88 (m, 1H), 1.86-1.72 (m, 1H), 1.72-1.47 (m, 2H), 1.47-1.37 (m, 3H), 1.26 (s, 2H), 1.04-0.95 (m, 1H).

Example 410

4-[(2S)-4,4-Difluoro-2-methyl-pyrrolidine-1-carbonyl]-5-[4-(difluoromethyl)-6-[[(1S)-2,2,2-trifluoro-1-methyl-ethyl]amino]-3-pyridyl]-N-[(1R,3R)-3-hydroxycyclopentyl]thiazole-2-carboxamide

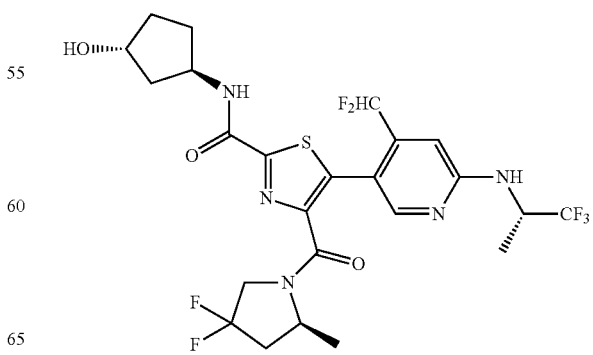

The title compound was prepared as described in Example 149 substituting (1R,3R)-3-aminocyclopentan-1-ol HCl for 3-hydroxy-3-methylazetidine HCl and ethyl 4-((S)-4,4-difluoro-2-methylpyrrolidine-1-carbonyl)-5-(4-(difluoromethyl)-6-(((S)-1,1,1-trifluoropropan-2-yl)amino)pyridin-3-yl)thiazole-2-carboxylate (Intermediate 96) for ethyl (S)-5-(6-(tert-butylamino)-4-(difluoromethyl)pyridin-3-yl)-4-(2-methylpyrrolidine-1-carbonyl)thiazole-2-carboxylate. MS (ESI): mass calcd. for $C_{24}H_{26}F_7N_5O_3S$, 597.6; m/z found, 597.8 [M+H]$^+$. $^1$H NMR (500 MHz, CDCl$_3$) δ 8.07-8.02 (m, 1H), 7.08-7.03 (m, 1H), 6.64 (br s, 1H), 5.20 (d, J=9.3 Hz, 1H), 4.95 (br dd, J=7.3, 15.8 Hz, 1H), 4.67-4.61 (m, 1H), 4.54-4.46 (m, 2H), 4.03 (br d, J=13.2 Hz, 1H), 3.89-3.81 (m, 1H), 2.61-2.52 (m, 1H), 2.43-2.35 (m, 1H), 2.24-2.08 (m, 5H), 1.96 (br s, 1H), 1.86-1.80 (m, 1H), 1.76-1.68 (m, 1H), 1.66-1.58 (m, 1H), 1.42-1.39 (m, 3H), 1.38-1.34 (m, 2H).

Example 411

4-((1s,4s)-7-Azabicyclo[2.2.1]heptane-7-carbonyl)-5-[4-(difluoromethyl)-6-[[(1S)-2,2,2-trifluoro-1-methyl-ethyl]amino]-3-pyridyl]-N-[(1S,3S)-3-hydroxycyclopentyl]thiazole-2-carboxamide

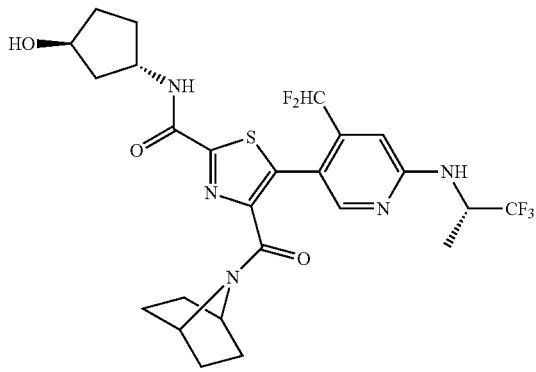 [SMILES: C[C@H](Nc1cc(C(F)F)c(-c2sc(C(=O)N[C@H]3CC[C@H](O)C3)nc2C(=O)N2C3CCC2CC3)cn1)C(F)(F)F]

The title compound was prepared as described in Intermediate 72: Step B, substituting potassium 4-((1s,4s)-7-azabicyclo[2.2.1]heptane-7-carbonyl)-5-(4-(difluoromethyl)-6-(((S)-1,1,1-trifluoropropan-2-yl)amino)pyridin-3-yl)thiazole-2-carboxylate (Intermediate 153) for 4-(tert-butoxycarbonyl)thiazole-2-carboxylic acid and (1S,3S)-3-aminocyclopentan-1-ol for 4-aminotetrahydro-2H-thiopyran-1,1-dioxide hydrochloride. MS (ESI): mass calcd. for $C_{25}H_{28}F_5N_5O_3S$, 573.6; m/z found, 574.0 [M+H]$^+$. $^1$H NMR (400 MHz, DMSO-d$_6$) δ 8.83 (d, J=8.2 Hz, 1H), 8.03 (s, 1H), 7.77 (d, J=8.8 Hz, 1H), 7.13-6.82 (m, 2H), 5.06-4.95 (m, 1H), 4.51 (d, J=3.5 Hz, 1H), 4.47-4.37 (m, 2H), 4.21-4.14 (m, 1H), 4.03-3.97 (m, 1H), 2.05-1.86 (m, 2H), 1.82-1.72 (m, 2H), 1.61-1.51 (m, 1H), 1.48-1.35 (m, 5H), 1.33-1.26 (m, 6H), 1.21-1.11 (m, 1H).

Example 412

5-[6-(tert-Butylamino)-4-(difluoromethyl)-3-pyridyl]-4-[(2S)-2-methylpyrrolidine-1-carbonyl]-N-tetrahydropyran-4-yl-thiazole-2-carboxamide

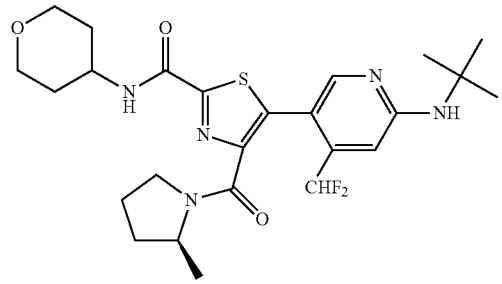 [SMILES: C[C@H]1CCCN1C(=O)c1nc(C(=O)NC2CCOCC2)sc1-c1cnc(NC(C)(C)C)cc1C(F)F]

The title compound was prepared as described in Example 148 substituting tetrahydro-2H-pyran-4-amine for (R)-(−)-2-amino-1-propanol and ethyl (S)-5-(6-(tert-butylamino)-4-(difluoromethyl)pyridin-3-yl)-4-(2-methylpyrrolidine-1-carbonyl)thiazole-2-carboxylate (Intermediate 106) for ethyl (S)-5-(6-(tert-butylamino)-4-(difluoromethyl)pyridin-3-yl)-4-(2-methylpyrrolidine-1-carbonyl)thiazole-2-carboxylate. MS (ESI): mass calcd. for $C_{25}H_{33}F_2N_5O_3S$, 521.6; m/z found, 522.0 [M+H]$^+$. $^1$H NMR (400 MHz, DMSO-d$_6$) δ 9.03-8.71 (m, 1H), 7.99-7.91 (m, 1H), 7.11-6.73 (m, 3H), 4.17-3.92 (m, 2H), 3.84 (d, J=10.8 Hz, 2H), 3.38-3.33 (m, 2H), 3.27-3.23 (m, 1H), 2.06-1.86 (m, 1H), 1.85-1.71 (m, 2H), 1.70-1.58 (m, 4H), 1.57-1.40 (m, 2H), 1.36 (s, 9H), 1.05 (d, J=6.4 Hz, 2H), 0.83 (d, J=6.4 Hz, 1H).

Example 413

4-((1s,4s)-7-Azabicyclo[2.2.1]heptane-7-carbonyl)-5-[6-(tert-butylamino)-4-(difluoromethyl)-3-pyridyl]-N-[(1S,3S)-3-hydroxycyclopentyl]thiazole-2-carboxamide

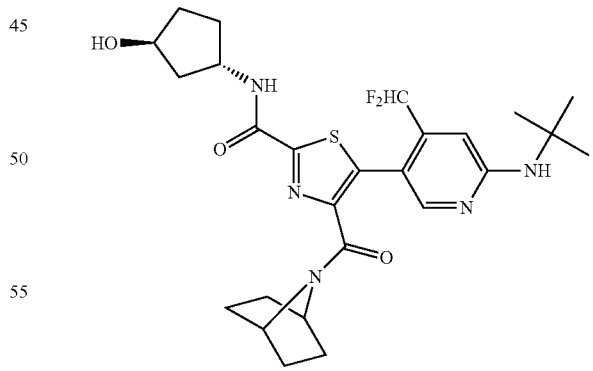

The title compound was prepared as described in Intermediate 72: Step B, substituting potassium 4-((1s,4s)-7-azabicyclo[2.2.1]heptane-7-carbonyl)-5-(6-(tert-butylamino)-4-(difluoromethyl)pyridin-3-yl)thiazole-2-carboxylate (Intermediate 155) for 4-(tert-butoxycarbonyl)thiazole-2-carboxylic acid and (1S,3S)-3-aminocyclopentan-1-ol for 4-aminotetrahydro-2H-thiopyran-1,1-dioxide hydrochloride. MS calcd.

for $C_{26}H_{33}F_2N_5O_3S$, 533.6; m/z found, 534.1 [M+H]$^+$. $^1$H NMR (400 MHz, DMSO-d$_6$) δ 8.83 (d, J=7.7 Hz, 1H), 7.94 (s, 1H), 7.13-6.73 (m, 3H), 4.60-4.38 (m, 3H), 4.24-4.14 (m, 1H), 3.99-3.84 (m, 1H), 2.03-1.89 (m, 2H), 1.82-1.71 (m, 2H), 1.63-1.51 (m, 1H), 1.44-1.24 (m, 16H), 1.22-1.09 (m, 2H).

Example 414

5-[6-(tert-Butylamino)-4-(difluoromethyl)-3-pyridyl]-N-[(1S,3S)-3-hydroxycyclopentyl]-4-[(2S)-2-methylpyrrolidine-1-carbonyl]thiazole-2-carboxamide

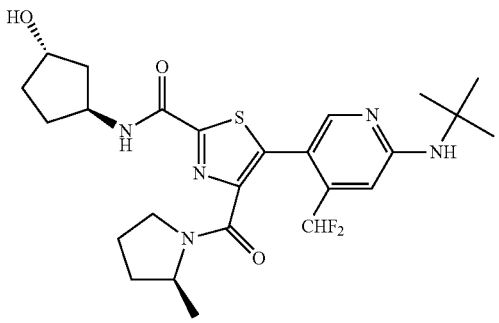 [SMILES: C[C@H]1CCCN1C(=O)c1nc(C(=O)N[C@H]2CC[C@H](O)C2)sc1-c1cnc(NC(C)(C)C)cc1C(F)F]

The title compound was prepared as described in Intermediate 72: Step B, substituting potassium (S)-5-(6-(tert-butylamino)-4-(difluoromethyl)pyridin-3-yl)-4-(2-methylpyrrolidine-1-carbonyl)thiazole-2-carboxylate (Intermediate 156) for 4-(tert-butoxycarbonyl)thiazole-2-carboxylic acid and (1S,3S)-3-aminocyclopentan-1-ol for 4-aminotetrahydro-2H-thiopyran-1,1-dioxide hydrochloride. MS (ESI): mass calcd. for $C_{25}H_{33}F_2N_5O_3S$, 521.6; m/z found, 522.0 [M+H]$^+$. $^1$H NMR (400 MHz, DMSO-d$_6$) δ 8.80 (d, J=8.2 Hz, 1H), 7.95 (s, 1H), 7.12-6.70 (m, 3H), 4.56-4.48 (m, 1H), 4.48-4.35 (m, 1H), 4.22-4.10 (m, 1H), 4.03-3.93 (m, 1H), 3.26-3.20 (m, 1H), 2.06-1.85 (m, 3H), 1.85-1.67 (m, 4H), 1.65-1.50 (m, 2H), 1.48-1.40 (m, 2H), 1.36 (s, 9H), 1.04 (d, J=6.2 Hz, 2H), 0.83 (d, J=6.4 Hz, 1H).

Example 415

4-[(2S)-4,4-Difluoro-2-methyl-pyrrolidine-1-carbonyl]-5-[6-(difluoromethyl)-6-[[(1S)-2,2,2-trifluoro-1-methyl-ethyl]amino]-3-pyridyl]-N-[(1S,3S)-3-hydroxycyclopentyl]thiazole-2-carboxamide

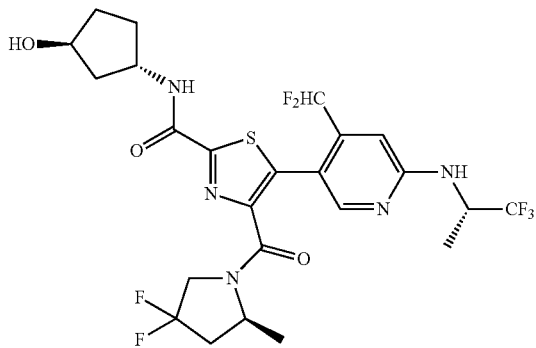 [SMILES: C[C@H](Nc1cc(C(F)F)c(-c2sc(C(=O)N[C@H]3CC[C@H](O)C3)nc2C(=O)N2CC(F)(F)C[C@@H]2C)cn1)C(F)(F)F]

The title compound was prepared as described in Intermediate 72: Step B, substituting potassium 4-((S)-4,4-difluoro-2-methylpyrrolidine-1-carbonyl)-5-(4-(difluoromethyl)-6-(((S)-1,1,1-trifluoropropan-2-yl)amino)pyridin-3-yl)thiazole-2-carboxylate (Intermediate 157) for 4-(tert-butoxycarbonyl)thiazole-2-carboxylic acid and (1S,3S)-3-aminocyclopentan-1-ol for 4-aminotetrahydro-2H-thiopyran-1,1-dioxide hydrochloride. MS (ESI): mass calcd. for $C_{24}H_{26}F_7N_5O_3S$, 597.6; m/z found, 597.9 [M+H]$^+$. $^1$H NMR (400 MHz, DMSO-d$_6$) δ 8.44 (br s, 1H), 8.08 (s, 1H), 7.54 (d, J=8.5 Hz, 1H), 7.05-6.73 (m, 2H), 5.09-4.97 (m, 1H), 4.51-4.42 (m, 1H), 4.33-4.23 (m, 2H), 4.12-3.88 (m, 2H), 2.69-2.54 (m, 1H), 2.21-1.78 (m, 6H), 1.70-1.47 (m, 2H), 1.36 (d, J=7.0 Hz, 3H), 1.22 (s, 3H).

Example 416

4-[(2S)-4,4-Difluoro-2-methyl-pyrrolidine-1-carbonyl]-5-[4-(difluoromethyl)-6-[[(1S)-1-(trifluoromethyl)propyl]amino]-3-pyridyl]-N-[(1S,3S)-3-hydroxycyclopentyl]thiazole-2-carboxamide

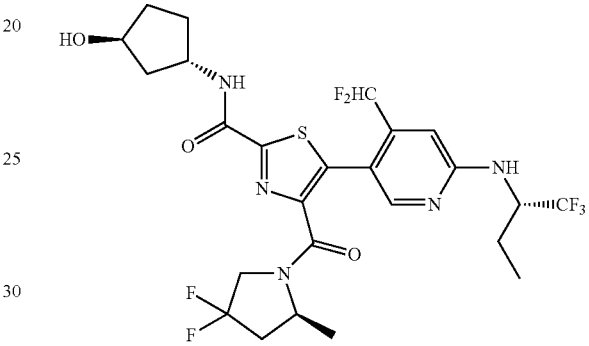

The title compound was prepared as described in Intermediate 72: Step B, substituting potassium 4-((S)-4,4-difluoro-2-methylpyrrolidine-1-carbonyl)-5-(4-(difluoromethyl)-6-(((S)-1,1,1-trifluorobutan-2-yl)amino)pyridin-3-yl)thiazole-2-carboxylate (Intermediate 159) for 4-(tert-butoxycarbonyl)thiazole-2-carboxylic acid and (1S,3S)-3-aminocyclopentan-1-ol for 4-aminotetrahydro-2H-thiopyran-1,1-dioxide hydrochloride. MS (ESI): mass calcd. for $C_{25}H_{28}F_7N_5O_3S$, 611.6; m/z found, 612.0 [M+H]$^+$. $^1$H NMR (400 MHz, DMSO-d$_6$) δ 8.84 (d, J=8.3 Hz, 1H), 8.06 (s, 1H), 7.75-7.65 (m, 1H), 7.12-6.75 (m, 2H), 4.91-4.79 (m, 1H), 4.56 (d, J=3.8 Hz, 1H), 4.52-4.41 (m, 1H), 4.38-3.80 (m, 4H), 2.68-2.54 (m, 2H), 2.26-1.74 (m, 6H), 1.67-1.43 (m, 3H), 1.26-1.15 (m, 2H), 1.06-1.02 (m, 1H), 0.95 (t, J=7.4 Hz, 3H).

Example 417

4-((1s,4s)-7-Azabicyclo[2.2.1]heptane-7-carbonyl)-5-[6-[[(1S)-1-cyclopropyl-2,2,2-trifluoro-ethyl]amino]-4-(difluoromethyl)-3-pyridyl]-N-[(3S,4R)-4-hydroxytetrahydrofuran-3-yl]thiazole-2-carboxamide

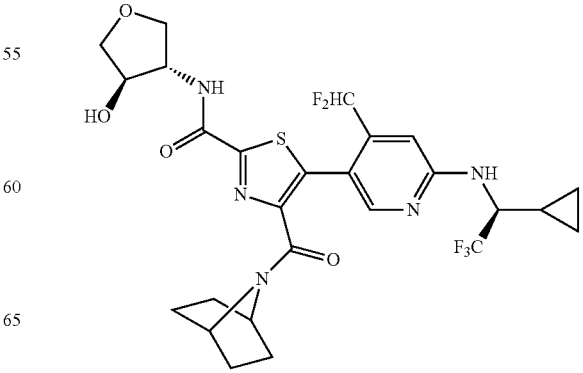

The title compound was prepared as described in Intermediate 72: Step B, substituting potassium 4-((1s,4s)-7-azabicyclo[2.2.1]heptane-7-carbonyl)-5-(6-(((S)-1-cyclopropyl-2,2,2-trifluoroethyl)amino)-4-(difluoromethyl)pyridin-3-yl)thiazole-2-carboxylate (Intermediate 165) for 4-(tert-butoxycarbonyl)thiazole-2-carboxylic acid and (3R,4S)-4-aminotetrahydrofuran-3-ol for 4-aminotetrahydro-2H-thiopyran-1,1-dioxide hydrochloride. MS (ESI): mass calcd. for $C_{26}H_{28}F_5N_5O_4S$, 601.6; m/z found, 601.9 [M+H]$^+$. $^1$H NMR (400 MHz, DMSO-d$_6$) δ 9.05-8.96 (m, 1H), 8.03 (s, 1H), 7.90 (d, J=9.0 Hz, 1H), 7.16-6.87 (m, 2H), 5.36-5.30 (m, 1H), 4.56-4.48 (m, 1H), 4.47-4.41 (m, 1H), 4.36-4.30 (m, 1H), 4.23-4.17 (m, 1H), 4.08-3.85 (m, 3H), 3.71-3.63 (m, 1H), 3.56-3.49 (m, 1H), 1.58-1.01 (m, 9H), 0.69-0.59 (m, 1H), 0.57-0.42 (m, 2H), 0.35-0.25 (m, 1H).

Example 418

4-[(2S)-4,4-Difluoro-2-methyl-pyrrolidine-1-carbonyl]-5-[4-(difluoromethyl)-6-[[(1S)-2,2,2-trifluoro-1-methyl-ethyl]amino]-3-pyridyl]-N-[(1S,2S)-2-hydroxycyclopentyl]thiazole-2-carboxamide

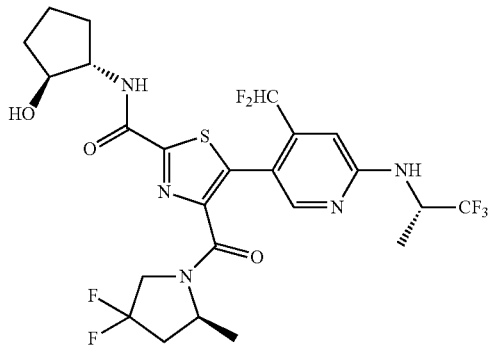 [SMILES: C[C@H](Nc1cc(C(F)F)c(-c2sc(C(=O)N[C@H]3CCC[C@@H]3O)nc2C(=O)N2CC(F)(F)C[C@@H]2C)cn1)C(F)(F)F]

The title compound was prepared as described in Intermediate 72: Step B, substituting potassium 4-((S)-4,4-difluoro-2-methylpyrrolidine-1-carbonyl)-5-(4-(difluoromethyl)-6-(((S)-1,1,1-trifluoropropan-2-yl)amino)pyridin-3-yl)thiazole-2-carboxylate (Intermediate 157) for 4-(tert-butoxycarbonyl)thiazole-2-carboxylic acid and (1S,2S)-2-aminocyclopentan-1-ol for 4-aminotetrahydro-2H-thiopyran-1,1-dioxide hydrochloride. MS (ESI): mass calcd. for $C_{24}H_{26}F_7N_5O_3S$, 597.6; m/z found, 598.0 [M+H]$^+$. $^1$H NMR (400 MHz, DMSO-d$_6$) δ 8.79-8.69 (m, 1H), 8.09 (s, 1H), 7.81-7.74 (m, 1H), 7.13-6.78 (m, 2H), 5.10-4.98 (m, 1H), 4.87-4.82 (m, 1H), 4.74-4.26 (m, 1H), 4.23-3.80 (m, 4H), 2.70-2.56 (m, 1H), 2.35-2.07 (m, 1H), 2.04-1.82 (m, 2H), 1.73-1.42 (m, 4H), 1.34 (d, J=7.0 Hz, 3H), 1.22 (d, J=6.3 Hz, 2H), 1.11-1.01 (m, 1H).

Example 419

4-[(2S)-4,4-Difluoro-2-methyl-pyrrolidine-1-carbonyl]-5-[4-(difluoromethyl)-6-[[(1S)-1-(trifluoromethyl)propyl]amino]-3-pyridyl]-N-[(1S,2S)-2-hydroxycyclopentyl]thiazole-2-carboxamide

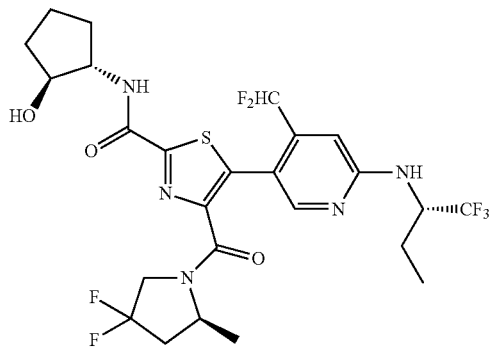 [SMILES: CC[C@H](Nc1cc(C(F)F)c(-c2sc(C(=O)N[C@H]3CCC[C@@H]3O)nc2C(=O)N2CC(F)(F)C[C@@H]2C)cn1)C(F)(F)F]

The title compound was prepared as described in Intermediate 72: Step B, substituting potassium 4-((S)-4,4-difluoro-2-methylpyrrolidine-1-carbonyl)-5-(4-(difluoromethyl)-6-(((S)-1,1,1-trifluorobutan-2-yl)amino)pyridin-3-yl)thiazole-2-carboxylate (Intermediate 159) for 4-(tert-butoxycarbonyl)thiazole-2-carboxylic acid and (1S,2S)-2-aminocyclopentan-1-ol for 4-aminotetrahydro-2H-thiopyran-1,1-dioxide hydrochloride. MS (ESI): mass calcd. for $C_{25}H_{28}F_7N_5O_3S$, 611.6; m/z found, 611.9 [M+H]$^+$. $^1$H NMR (400 MHz, DMSO-d$_6$) δ 8.77-8.68 (m, 1H), 8.03 (s, 1H), 7.74-7.63 (m, 1H), 7.10-6.74 (m, 1H), 4.89-4.76 (m, 2H), 4.89-4.76 (m, 2H), 4.36-4.22 (m, 1H), 4.18-4.01 (m, 2H), 4.00-3.78 (m, 2H), 2.65-2.52 (m, 1H), 2.24-2.02 (m, 1H), 2.00-1.90 (m, 1H), 1.89-1.75 (m, 1H), 1.70-1.50 (m, 4H), 1.49-1.38 (m, 1H), 1.25-1.14 (m, 2H), 1.05-0.98 (m, 1H), 0.97-0.85 (m, 3H).

Example 420

4-[(2S)-4,4-Difluoro-2-methyl-pyrrolidine-1-carbonyl]-5-[4-(difluoromethyl)-6-[[(1S)-2,2,2-trifluoro-1-methyl-ethyl]amino]-3-pyridyl]-N-[(1R,2R)-2-hydroxycyclopentyl]thiazole-2-carboxamide

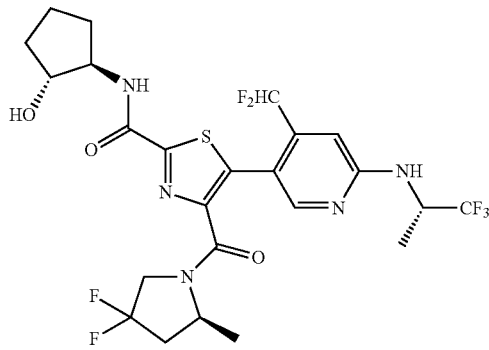 [SMILES: C[C@H](Nc1cc(C(F)F)c(-c2sc(C(=O)N[C@@H]3CCC[C@H]3O)nc2C(=O)N2CC(F)(F)C[C@@H]2C)cn1)C(F)(F)F]

The title compound was prepared as described in Intermediate 72: Step B, substituting potassium 4-((S)-4,4-difluoro-2-methylpyrrolidine-1-carbonyl)-5-(4-(difluoromethyl)-6-(((S)-1,1,1-trifluoropropan-2-yl)amino)pyridin-3-yl)thiazole-2-carboxylate (Intermediate 157) for 4-(tert-butoxycarbonyl)thiazole-2-carboxylic acid and (1R,2R)-2-aminocyclopentan-1-ol for 4-aminotetrahydro-2H-thiopyran-1,1-dioxide hydrochloride. MS (ESI): mass calcd. for $C_{24}H_{26}F_7N_5O_3S$, 597.6; m/z found, 597.9 [M+H]$^+$. $^1$H NMR (400 MHz, DMSO-d$_6$) δ 8.79-8.71 (m, 1H), 8.09 (s, 1H), 7.80-7.73 (m, 1H), 7.12-6.77 (m, 2H), 5.10-4.97 (m, 1H), 4.73-4.26 (m, 1H), 4.20-4.05 (m, 2H), 4.04-3.80 (m, 3H), 2.66-2.56 (m, 1H), 2.31-2.06 (m, 1H), 2.04-1.83 (m, 2H), 1.72-1.54 (m, 3H), 1.54-1.43 (m, 1H), 1.34 (d, J=6.5 Hz, 3H), 1.22 (d, J=6.0 Hz, 2H), 1.07 (d, J=6.0 Hz, 1H).

Example 421

4-[(2S)-4,4-Difluoro-2-methyl-pyrrolidine-1-carbonyl]-5-[4-(difluoromethyl)-6-[[(1S)-2,2,2-trifluoro-1-methyl-ethyl]amino]-3-pyridyl]-N-(1,1-dioxothian-4-yl)thiazole-2-carboxamide

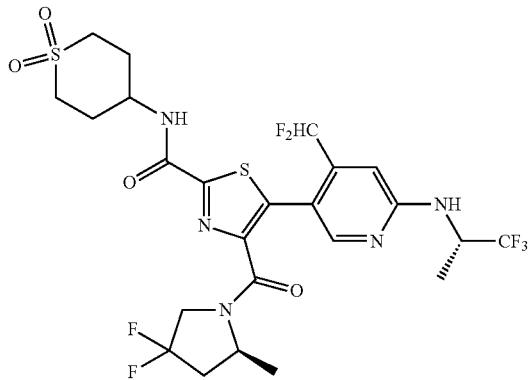 [SMILES: C[C@H](Nc1cc(C(F)F)c(-c2sc(C(=O)NC3CCS(=O)(=O)CC3)nc2C(=O)N2CC(F)(F)C[C@@H]2C)cn1)C(F)(F)F]

The title compound was prepared as described in Intermediate 72: Step B, substituting potassium 4-((S)-4,4-difluoro-2-methylpyrrolidine-1-carbonyl)-5-(4-(difluoromethyl)-6-(((S)-1,1,1-trifluoropropan-2-yl)amino)pyridin-3-yl)thiazole-2-carboxylate (Intermediate 157) for 4-(tert-butoxycarbonyl)thiazole-2-carboxylic acid. MS (ESI): mass calcd. for $C_{24}H_{26}F_7N_5O_4S_2$, 645.6; m/z found, 645.9 [M+H]$^+$. $^1$H NMR (400 MHz, DMSO-d$_6$) δ 9.01-8.93 (m, 1H), 8.04 (s, 1H), 7.78-7.70 (m, 1H), 7.08-6.73 (m, 2H), 5.07-4.61 (m, 1H), 4.34-4.07 (m, 3H), 4.00-3.72 (m, 1H), 3.40-3.36 (m, 1H), 3.12-3.00 (m, 2H), 2.62-2.51 (m, 1H), 2.28-2.14 (m, 3H), 2.13-2.00 (m, 3H), 1.30 (d, J=6.8 Hz, 3H), 1.18 (d, J=6.2 Hz, 2H), 1.02 (d, J=6.2 Hz, 1H).

Example 422

4-[(2S)-4,4-Difluoro-2-methyl-pyrrolidine-1-carbonyl]-5-[4-(difluoromethyl)-6-[[(1S)-1-(trifluoromethyl)propyl]amino]-3-pyridyl]-N-tetrahydropyran-4-yl-thiazole-2-carboxamide

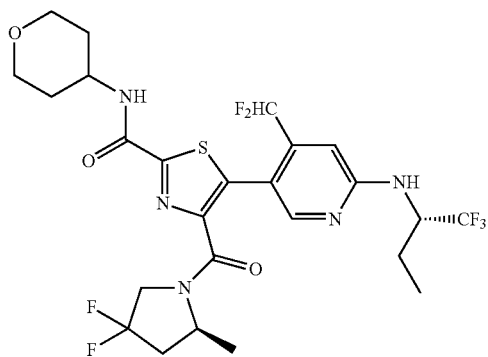 [SMILES: CC[C@H](Nc1cc(C(F)F)c(-c2sc(C(=O)NC3CCOCC3)nc2C(=O)N2CC(F)(F)C[C@@H]2C)cn1)C(F)(F)F]

The title compound was prepared as described in Example 148 substituting tetrahydro-2H-pyran-4-amine for (R)-(−)-2-amino-1-propanol and ethyl 4-((S)-4,4-difluoro-2-methylpyrrolidine-1-carbonyl)-5-(4-(difluoromethyl)-6-(((S)-1,1,1-trifluorobutan-2-yl)amino)pyridin-3-yl)thiazole-2-carboxylate (Intermediate 158) for ethyl (S)-5-(6-(tert-butylamino)-4-(difluoromethyl)pyridin-3-yl)-4-(2-methylpyrrolidine-1-carbonyl)thiazole-2-carboxylate. MS (ESI): mass calcd. for $C_{25}H_{28}F_7N_5O_3S$, 611.6; m/z found, 612.0 [M+H]$^+$. $^1$H NMR (400 MHz, DMSO-d$_6$) δ 8.90-8.84 (m, 1H), 8.07 (s, 1H), 7.75-7.68 (m, 1H), 7.13-6.79 (m, 2H), 4.94-4.61 (m, 1H), 4.36-4.26 (m, 1H), 4.19-3.78 (m, 5H), 3.43-3.38 (m, 2H), 2.65-2.55 (m, 1H), 2.30-2.06 (m, 1H), 1.88-1.57 (m, 6H), 1.21 (d, J=6.5 Hz, 2H), 1.05 (d, J=6.0 Hz, 1H), 0.96 (t, J=7.3 Hz, 3H).

Example 423

4-[(2S)-4,4-Difluoro-2-methyl-pyrrolidine-1-carbonyl]-5-[4-(difluoromethyl)-6-[[(1S)-1-(trifluoromethyl)propyl]amino]-3-pyridyl]-N-[(1R)-2-hydroxy-1-methyl-ethyl]thiazole-2-carboxamide

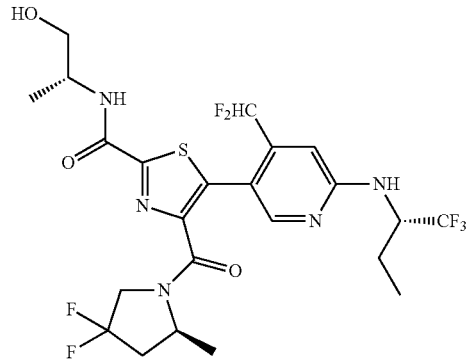 [SMILES: CC[C@H](Nc1cc(C(F)F)c(-c2sc(C(=O)N[C@H](C)CO)nc2C(=O)N2CC(F)(F)C[C@@H]2C)cn1)C(F)(F)F]

The title compound was prepared as described in Example 148 substituting ethyl 4-((S)-4,4-difluoro-2-methylpyrrolidine-1-carbonyl)-5-(4-(difluoromethyl)-6-(((S)-1,1,1-trifluorobutan-2-yl)amino)pyridin-3-yl)thiazole-2-carboxylate (Intermediate 158) for ethyl (S)-5-(6-(tert-butylamino)-4-(difluoromethyl)pyridin-3-yl)-4-(2-methylpyrrolidine-1-carbonyl)thiazole-2-carboxylate. MS (ESI): mass calcd. for $C_{23}H_{26}F_7N_5O_3S$, 585.5; m/z found, 586.0 [M+H]$^+$. $^1$H NMR (400 MHz, DMSO-d$_6$) δ 8.57-8.47 (m, 1H), 8.07 (s, 1H), 7.76-7.68 (m, 1H), 7.12-6.79 (m, 2H), 4.94-4.60 (m, 2H), 4.37-4.26 (m, 1H), 4.16-3.80 (m, 3H), 3.55-3.39 (m, 2H), 2.66-2.56 (m, 1H), 2.28-2.06 (m, 1H), 1.91-1.78 (m, 1H), 1.69-1.54 (m, 1H), 1.26-1.14 (m, 5H), 1.08 (d, J=6.5 Hz, 1H), 0.96 (t, J=7.3 Hz, 3H).

Example 424

4-[(2S)-4,4-Difluoro-2-methyl-pyrrolidine-1-carbonyl]-5-[4-(difluoromethyl)-6-[[(1S)-1-(trifluoromethyl)propyl]amino]-3-pyridyl]-N-[(1R,3R)-3-hydroxycyclopentyl]thiazole-2-carboxamide

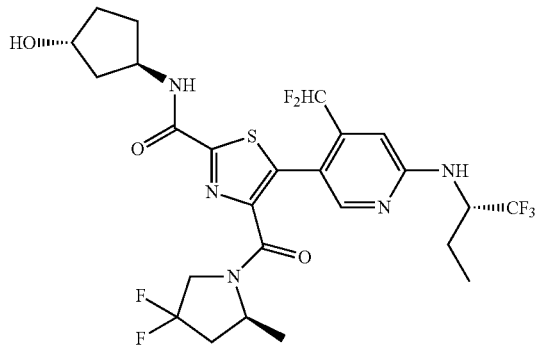 [SMILES: CC[C@H](Nc1cc(C(F)F)c(-c2sc(C(=O)N[C@@H]3CC[C@@H](O)C3)nc2C(=O)N2CC(F)(F)C[C@@H]2C)cn1)C(F)(F)F]

The title compound was prepared as described in Intermediate 72: Step B, substituting potassium 4-((S)-4,4-difluoro-2-methylpyrrolidine-1-carbonyl)-5-(4-(difluoromethyl)-6-(((S)-1,1,1-trifluorobutan-2-yl)amino)pyridin-3-yl)thiazole-2-carboxylate (Intermediate 159) for 4-(tert-butoxycarbonyl)thiazole-2-carboxylic acid and (1R,3R)-3-aminocyclopentan-1-ol for 4-aminotetrahydro-2H-thiopyran-1,1-dioxide hydrochloride. MS (ESI): mass calcd. for $C_{25}H_{28}F_7N_5O_3S$, 611.6; m/z found, 612.0 [M+H]$^+$. $^1$H NMR (400 MHz, DMSO-d$_6$) δ 8.80 (d, J=8.4 Hz, 1H), 8.01 (s, 1H), 7.70-7.63 (m, 1H), 7.07-6.72 (m, 2H), 4.88-4.73 (m, 1H), 4.67-4.49 (m, 1H), 4.48-4.36 (m, 1H), 4.30-4.21 (m, 1H), 4.21-4.13 (m, 1H), 4.13-3.98 (m, 1H), 3.95-3.73 (m, 1H), 2.59-2.50 (m, 1H), 2.24-1.85 (m, 3H), 1.84-1.69 (m, 3H), 1.64-1.38 (m, 3H), 1.15 (d, J=6.4 Hz, 2H), 0.99 (d, J=6.4 Hz, 1H), 0.90 (t, J=7.3 Hz, 3H).

Example 425

4-[(2S)-4,4-Difluoro-2-methyl-pyrrolidine-1-carbonyl]-5-[4-(difluoromethyl)-6-[[(1S)-1-(trifluoromethyl)propyl]amino]-3-pyridyl]-N-[(1R,2R)-2-hydroxycyclopentyl]thiazole-2-carboxamide

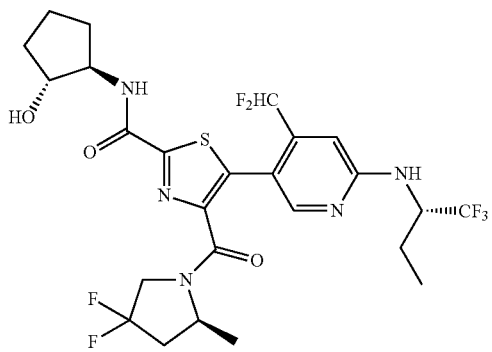 [SMILES: CC[C@H](Nc1cc(C(F)F)c(-c2sc(C(=O)N[C@@H]3CCC[C@H]3O)nc2C(=O)N2CC(F)(F)C[C@@H]2C)cn1)C(F)(F)F]

The title compound was prepared as described in Intermediate 72: Step B, substituting potassium 4-((S)-4,4-difluoro-2-methylpyrrolidine-1-carbonyl)-5-(4-(difluoromethyl)-6-(((S)-1,1,1-trifluorobutan-2-yl)amino)pyridin-3-yl)thiazole-2-carboxylate (Intermediate 159) for 4-(tert-butoxycarbonyl)thiazole-2-carboxylic acid and (1R,2R)-2-aminocyclopentan-1-ol for 4-aminotetrahydro-2H-thiopyran-1,1-dioxide hydrochloride. MS (ESI): mass calcd. for $C_{25}H_{28}F_7N_5O_3S$, 611.6; m/z found, 611.9 [M+H]$^+$. $^1$H NMR (400 MHz, DMSO-d$_6$) δ 8.77-8.70 (m, 1H), 8.01 (s, 1H), 7.70-7.63 (m, 1H), 7.07-6.73 (m, 2H), 4.86-4.55 (m, 2H), 4.30-4.21 (m, 1H), 4.13-3.99 (m, 2H), 3.98-3.76 (m, 2H), 2.59-2.51 (m, 1H), 2.24-2.00 (m, 1H), 1.98-1.73 (m, 3H), 1.67-1.48 (m, 4H), 1.47-1.36 (m, 1H), 1.15 (d, J=6.4 Hz, 2H), 1.00 (d, J=6.4 Hz, 1H), 0.90 (t, J=7.3 Hz, 3H).

Example 426

4-[(2S)-4,4-Difluoro-2-methyl-pyrrolidine-1-carbonyl]-5-[4-(difluoromethyl)-6-[[(1S)-1-(trifluoromethyl)propyl]amino]-3-pyridyl]-N-(1,1-dioxothian-4-yl)thiazole-2-carboxamide

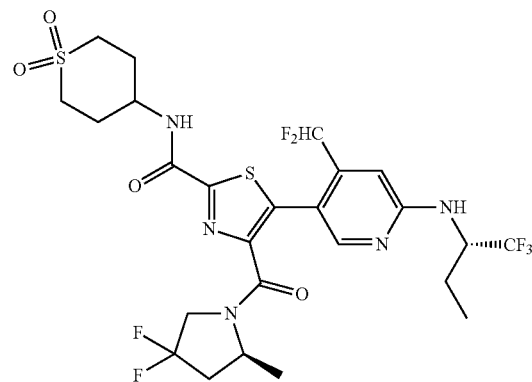 [SMILES: CC[C@H](Nc1cc(C(F)F)c(-c2sc(C(=O)NC3CCS(=O)(=O)CC3)nc2C(=O)N2CC(F)(F)C[C@@H]2C)cn1)C(F)(F)F]

The title compound was prepared as described in Intermediate 72: Step B, substituting potassium 4-((S)-4,4-difluoro-2-methylpyrrolidine-1-carbonyl)-5-(4-(difluoromethyl)-6-(((S)-1,1,1-trifluorobutan-2-yl)amino)pyridin-3-yl)thiazole-2-carboxylate (Intermediate 159) for 4-(tert-butoxycarbonyl)thiazole-2-carboxylic acid. MS (ESI): mass calcd. for $C_{25}H_{28}F_7N_5O_4S_2$, 659.6; m/z found, 659.9 [M+H]$^+$. $^1$H NMR (400 MHz, DMSO-d$_6$) δ 8.99-8.92 (m, 1H), 8.01 (s, 1H), 7.71-7.63 (m, 1H), 7.06-6.72 (m, 2H), 4.87-4.63 (m, 1H), 4.31-4.03 (m, 3H), 3.96-3.72 (m, 1H), 3.10-2.98 (m, 2H), 2.60-2.49 (m, 2H), 2.26-2.12 (m, 3H), 2.11-1.99 (m, 3H), 1.8-1.69 (m, 1H), 1.64-1.50 (m, 1H), 1.15 (d, J=6.4 Hz, 2H), 1.00 (d, J=6.4 Hz, 1H), 0.90 (t, J=7.3 Hz, 3H).

Example 427

4-((1s,4s)-7-Azabicyclo[2.2.1]heptane-7-carbonyl)-5-[6-(tert-butylamino)-4-(difluoromethyl)-3-pyridyl]-N-[(1R)-2-hydroxy-1-methyl-ethyl]thiazole-2-carboxamide

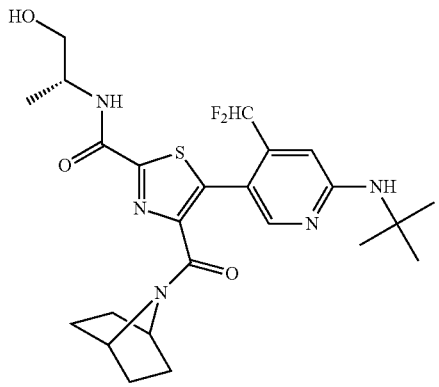 [SMILES: C[C@H](CO)NC(=O)c1nc(C(=O)N2C3CCC2CC3)c(-c2cnc(NC(C)(C)C)cc2C(F)F)s1]

The title compound was prepared as described in Example 148 substituting ethyl 4-((1s,4s)-7-azabicyclo[2.2.1]heptane-7-carbonyl)-5-(6-(tert-butylamino)-4-(difluoromethyl)pyridin-3-yl)thiazole-2-carboxylate (Intermediate 154) for ethyl 4-((1R,4R)-7-azabicyclo[2.2.1]heptane-7-carbonyl)-5-(4-(trifluoromethyl)-6-(((S)-1,1,1-trifluoropropan-2-yl)amino)pyridin-3-yl)thiazole-2-carboxylate. MS (ESI): mass calcd. for $C_{24}H_{31}F_2N_5O_3S$, 507.6; m/z found, 508.0 [M+H]⁺. ¹H NMR (400 MHz, DMSO-$d_6$) δ 8.46 (d, J=8.6 Hz, 1H), 7.95 (s, 1H), 7.09-6.76 (m, 3H), 4.83-4.77 (m, 1H), 4.49-4.38 (m, 1H), 4.04-3.89 (m, 2H), 3.50-3.35 (m, 2H), 1.50-1.24 (m, 15H), 1.20-1.07 (m, 5H).

Example 428

5-[6-(tert-Butylamino)-4-(difluoromethyl)-3-pyridyl]-4-[(2S)-4,4-difluoro-2-methyl-pyrrolidine-1-carbonyl]-N-[(1R)-2-hydroxy-1-methyl-ethyl]thiazole-2-carboxamide

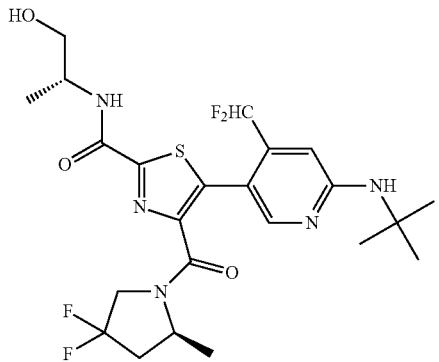 [SMILES: C[C@H](CO)NC(=O)c1nc(C(=O)N2CC(F)(F)C[C@@H]2C)c(-c2cnc(NC(C)(C)C)cc2C(F)F)s1]

The title compound was prepared as described in Example 148 substituting ethyl (S)-5-(6-(tert-butylamino)-4-(difluoromethyl)pyridin-3-yl)-4-(4,4-difluoro-2-methylpyrrolidine-1-carbonyl)thiazole-2-carboxylate (Intermediate 110) for ethyl (S)-5-(6-(tert-butylamino)-4-(difluoromethyl)pyridin-3-yl)-4-(2-methylpyrrolidine-1-carbonyl)thiazole-2-carboxylate. MS (ESI): mass calcd. for $C_{23}H_{29}F_4N_5O_3S$, 531.6; m/z found, 532.0 [M+H]⁺. ¹H NMR (400 MHz, DMSO-$d_6$) δ 8.57-8.47 (m, 1H), 7.99 (s, 1H), 7.11-6.73 (m, 3H), 4.90-4.82 (m, 1H), 4.62-4.26 (m, 1H), 4.09-3.78 (m, 3H), 3.54-3.40 (m, 2H), 2.66-2.55 (m, 1H), 2.30-2.06 (m, 1H), 1.40 (s, 9H), 1.21 (d, J=6.5 Hz, 2H), 1.17 (d, J=7.0 Hz, 3H), 1.06 (d, J=6.5 Hz, 1H).

Example 429

5-(6-(tert-Butylamino)-4-(difluoromethyl)pyridin-3-yl)-4-((S)-4,4-difluoro-2-methylpyrrolidine-1-carbonyl)-N-((1r,3S)-3-hydroxycyclobutyl)thiazole-2-carboxamide

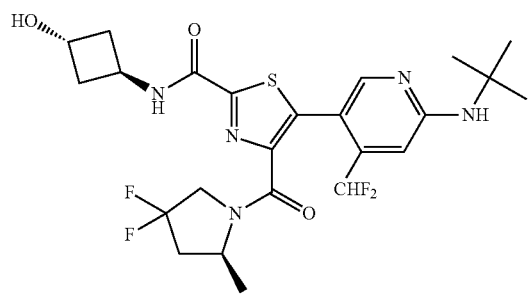 [SMILES: C[C@H]1CC(F)(F)CN1C(=O)c1nc(C(=O)N[C@H]2C[C@H](O)C2)sc1-c1cnc(NC(C)(C)C)cc1C(F)F]

The title compound was prepared as described in Example 148 substituting (1R,3R)-3-aminocyclobutan-1-ol for (R)-(−)-2-amino-1-propanol and ethyl (S)-5-(6-(tert-butylamino)-4-(difluoromethyl)pyridin-3-yl)-4-(4,4-difluoro-2-methylpyrrolidine-1-carbonyl)thiazole-2-carboxylate (Intermediate 110) for ethyl (S)-5-(6-(tert-butylamino)-4-(difluoromethyl)pyridin-3-yl)-4-(2-methylpyrrolidine-1-carbonyl)thiazole-2-carboxylate. MS (ESI): mass calcd. for $C_{24}H_{29}F_4N_5O_3S$, 543.6; m/z found, 544.0 [M+H]⁺. ¹H NMR (400 MHz, CDCl₃) δ 8.01-7.94 (m, 1H), 7.23-7.17 (m, 1H), 6.90-6.46 (m, 2H), 4.85 (s, 1H), 4.72-4.55 (m, 2H), 4.55-4.45 (m, 1H), 4.11-3.72 (m, 2H), 2.62-2.36 (m, 5H), 2.18-1.98 (m, 1H), 1.87 (s, 1H), 1.44 (s, 9H), 1.34 (d, J=6.0 Hz, 2H), 1.15 (d, J=6.4 Hz, 1H).

Example 430

4-((1s,4s)-7-Azabicyclo[2.2.1]heptane-7-carbonyl)-5-[6-(tert-butylamino)-4-(difluoromethyl)-3-pyridyl]-N-[(1R,3R)-3-hydroxycyclopentyl]thiazole-2-carboxamide

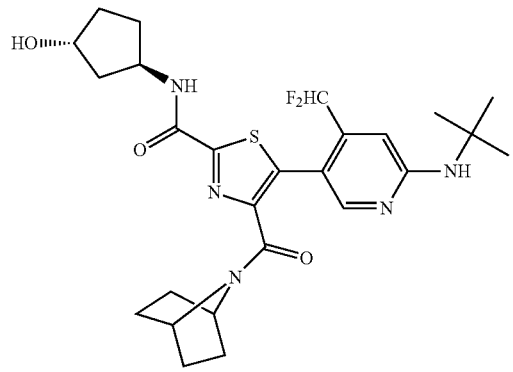 [SMILES: CC(C)(C)Nc1cc(C(F)F)c(-c2sc(C(=O)N[C@@H]3CC[C@@H](O)C3)nc2C(=O)N2C3CCC2CC3)cn1]

The title compound was prepared as described in Intermediate 72: Step B, substituting potassium 4-((1s,4s)-7-azabicyclo[2.2.1]heptane-7-carbonyl)-5-(6-(tert-butylamino)-4-(difluoromethyl)pyridin-3-yl)thiazole-2-carboxylate (Intermediate 161) for 4-(tert-butoxycarbonyl)thiazole-2-carboxylic acid and (1R,3R)-3-aminocyclopentan-1-ol for 4-aminotetrahydro-2H-thiopyran-1,1-dioxide hydrochloride. MS (ESI): mass calcd. for $C_{26}H_{33}F_2N_5O_3S$, 533.6; m/z found, 534.0 [M+H]$^+$. $^1$H NMR (400 MHz, DMSO-$d_6$) δ 8.82 (d, J=8.4 Hz, 1H), 7.94 (s, 1H), 7.11-6.74 (m, 3H), 4.53-4.37 (m, 3H), 4.21-4.13 (m, 1H), 3.95-3.86 (m, 1H), 2.05-1.85 (m, 2H), 1.83-1.69 (m, 2H), 1.62-1.49 (m, 1H), 1.49-1.23 (m, 16H), 1.21-1.06 (m, 2H).

Example 431

5-[6-(tert-Butylamino)-4-(difluoromethyl)-3-pyridyl]-4-[(2S)-4,4-difluoro-2-methyl-pyrrolidine-1-carbonyl]-N-(1,1-dioxothian-4-yl)thiazole-2-carboxamide

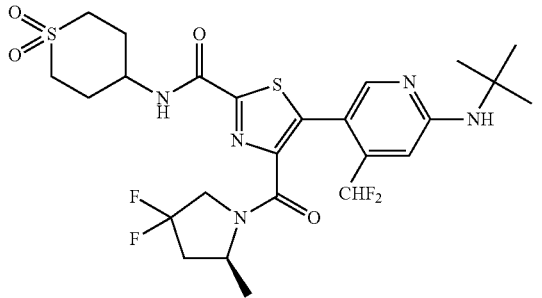 [SMILES: C[C@H]1CC(F)(F)CN1C(=O)c1nc(C(=O)NC2CCS(=O)(=O)CC2)sc1-c1cnc(NC(C)(C)C)cc1C(F)F]

The title compound was prepared as described in Intermediate 72: Step B, substituting potassium (S)-5-(6-(tert-butylamino)-4-(difluoromethyl)pyridin-3-yl)-4-(4,4-difluoro-2-methylpyrrolidine-1-carbonyl)thiazole-2-carboxylate (Intermediate 162) for 4-(tert-butoxycarbonyl)thiazole-2-carboxylic acid and. MS (ESI): mass calcd. for $C_{25}H_{31}F_4N_5O_4S_2$, 605.7; m/z found, 606.0 [M+H]$^+$. $^1$H NMR (400 MHz, DMSO-$d_6$) δ 9.04-8.97 (m, 1H), 7.99 (s, 1H), 7.11-6.72 (m, 3H), 4.72-4.17 (m, 2H), 4.16-4.01 (m, 1H), 4.00-3.79 (m, 1H), 3.43-3.37 (m, 2H), 3.16-3.04 (m, 2H), 2.66-2.55 (m, 1H), 2.31-2.03 (m, 5H), 1.40 (s, 9H), 1.22 (d, J=6.0 Hz, 2H), 1.04 (d, J=6.5 Hz, 1H).

Example 432

5-[6-(tert-Butylamino)-4-(difluoromethyl)-3-pyridyl]-N-[(1R,3R)-3-hydroxycyclopentyl]-4-[(2S)-2-methylpyrrolidine-1-carbonyl]thiazole-2-carboxamide

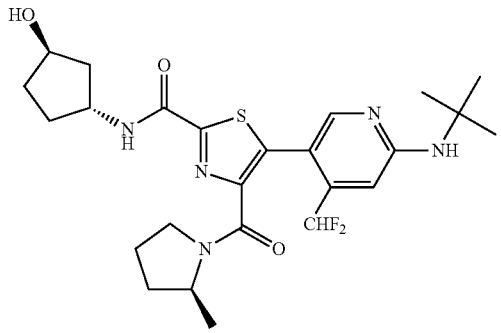 [SMILES: C[C@H]1CCCN1C(=O)c1nc(C(=O)N[C@@H]2CC[C@@H](O)C2)sc1-c1cnc(NC(C)(C)C)cc1C(F)F]

The title compound was prepared as described in Intermediate 72: Step B, substituting potassium (S)-5-(6-(tert-butylamino)-4-(difluoromethyl)pyridin-3-yl)-4-(2-methylpyrrolidine-1-carbonyl)thiazole-2-carboxylate (Intermediate 163) for 4-(tert-butoxycarbonyl)thiazole-2-carboxylic acid and (1R,3R)-3-aminocyclopentan-1-ol for 4-aminotetrahydro-2H-thiopyran-1,1-dioxide hydrochloride. MS (ESI): mass calcd. for $C_{25}H_{33}F_2N_5O_3S$, 521.6; m/z found, 522.0 [M+H]$^+$. $^1$H NMR (400 MHz, DMSO-$d_6$) δ 8.80 (d, J=8.4 Hz, 1H), 7.95 (s, 1H), 7.11-6.73 (m, 3H), 4.52-4.48 (m, 1H), 4.47-4.37 (m, 1H), 4.22-4.09 (m, 1H), 4.03-3.92 (m, 1H), 3.27-3.23 (m, 1H), 2.05-1.86 (m, 3H), 1.85-1.68 (m, 4H), 1.66-1.49 (m, 2H), 1.48-1.40 (m, 2H), 1.36 (s, 9H), 1.05 (d, J=6.2 Hz, 2H), 0.83 (d, J=6.4 Hz, 1H).

Example 433

4-((1s,4s)-7-Azabicyclo[2.2.1]heptane-7-carbonyl)-5-[6-(tert-butylamino)-4-(difluoromethyl)-3-pyridyl]-N-(1,1-dioxothian-4-yl)thiazole-2-carboxamide

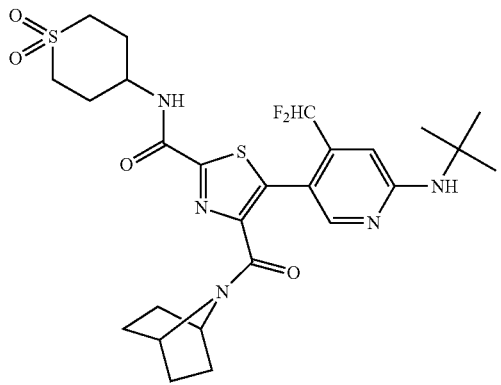 [SMILES: CC(C)(C)Nc1cc(C(F)F)c(-c2sc(C(=O)NC3CCS(=O)(=O)CC3)nc2C(=O)N2C3CCC2CC3)cn1]

The title compound was prepared as described in Intermediate 72: Step B, substituting potassium 4-((1s,4s)-7-azabicyclo[2.2.1]heptane-7-carbonyl)-5-(6-(tert-butylamino)-4-(difluoromethyl)pyridin-3-yl)thiazole-2-carboxylate (Intermediate 161) for 4-(tert-butoxycarbonyl)thiazole-2-carboxylic acid. MS (ESI): mass calcd. for $C_{26}H_{33}F_2N_5O_4S_2$, 581.7; m/z found, 582.0 [M+H]$^+$. $^1$H NMR (400 MHz, DMSO-$d_6$) δ 9.05 (d, J=8.4 Hz, 1H), 7.94 (s, 1H), 7.09-6.78 (m, 3H), 4.48-4.41 (m, 1H), 4.24-4.12 (m, 1H), 3.98-3.92 (m, 1H), 3.10-3.01 (m, 2H), 2.27-2.13 (m, 2H), 2.08-1.99 (m, 2H), 1.52-1.24 (m, 17H), 1.22-1.09 (m, 2H).

Example 434

4-((1s,4s)-7-Azabicyclo[2.2.1]heptane-7-carbonyl)-5-[6-(tert-butylamino)-4-(difluoromethyl)-3-pyridyl]-N-[(1R,2R)-2-hydroxycyclopentyl]thiazole-2-carboxamide

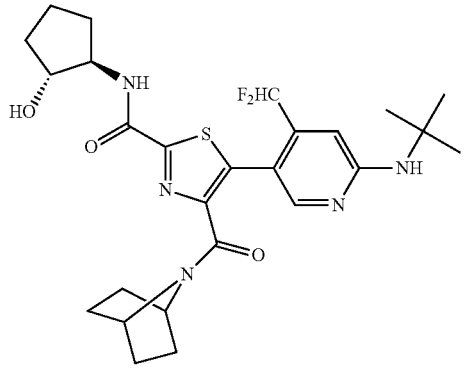 [SMILES: CC(C)(C)Nc1cc(C(F)F)c(-c2sc(C(=O)N[C@@H]3CCC[C@H]3O)nc2C(=O)N2C3CCC2CC3)cn1]

The title compound was prepared as described in Intermediate 72: Step B, substituting potassium 4-((1s,4s)-7-azabicyclo[2.2.1]heptane-7-carbonyl)-5-(6-(tert-butylamino)-4-(difluoromethyl)pyridin-3-yl)thiazole-2-carboxylate (Intermediate 161) for 4-(tert-butoxycarbonyl)thiazole-2-carboxylic acid and (1R,2R)-2-aminocyclopentan-1-ol for 4-aminotetrahydro-2H-thiopyran-1,1-dioxide hydrochloride. MS (ESI): mass calcd. for $C_{26}H_{33}F_2N_5O_3S$, 533.6; m/z found, 534.0 [M+H]$^+$. $^1$H NMR (400 MHz, CDCl$_3$) δ 8.07 (s, 1H), 7.35-7.31 (m, 1H), 6.89-6.60 (m, 2H), 4.86 (s, 1H), 4.70 (s, 1H), 4.20-4.14 (m, 1H), 4.08-3.99 (m, 2H), 2.33-2.22 (m, 1H), 2.16-2.05 (m, 1H), 1.94-1.57 (m, 8H), 1.50-1.24 (m, 14H).

Example 435

5-[6-(tert-Butylamino)-4-(difluoromethyl)-3-pyridyl]-N-(1,1-dioxothian-4-yl)-4-[(2S)-2-methylpyrrolidine-1-carbonyl]thiazole-2-carboxamide

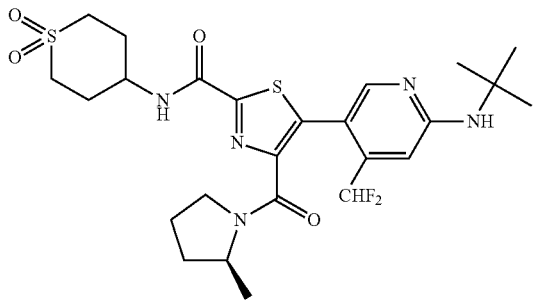 [SMILES: C[C@H]1CCCN1C(=O)c1nc(C(=O)NC2CCS(=O)(=O)CC2)sc1-c1cnc(NC(C)(C)C)cc1C(F)F]

The title compound was prepared as described in Intermediate 72: Step B, substituting potassium (S)-5-(6-(tert-butylamino)-4-(difluoromethyl)pyridin-3-yl)-4-(2-methylpyrrolidine-1-carbonyl)thiazole-2-carboxylate (Intermediate 163) for 4-(tert-butoxycarbonyl)thiazole-2-carboxylic acid. MS (ESI): mass calcd. for $C_{25}H_{33}F_2N_5O_4S_2$, 569.7; m/z found, 570.0 [M+H]$^+$. $^1$H NMR (400 MHz, DMSO-d$_6$) δ 9.08-9.02 (m, 1H), 7.98 (s, 1H), 7.13-6.77 (m, 3H), 4.28-4.15 (m, 1H), 4.07-3.97 (m, 1H), 3.33-3.29 (m, 3H), 3.14-3.03 (m, 2H), 2.30-2.15 (m, 2H), 2.13-2.02 (m, 2H), 2.00-1.72 (m, 3H), 1.71-1.52 (m, 1H), 1.50-1.43 (m, 1H), 1.39 (s, 9H), 1.08 (d, J=6.4 Hz, 2H), 0.87 (d, J=6.4 Hz, 1H).

Example 436

4-((1s,4s)-7-Azabicyclo[2.2.1]heptane-7-carbonyl)-5-[6-[[(1S)-1-cyclopropyl-2,2,2-trifluoro-ethyl]amino]-4-(difluoromethyl)-3-pyridyl]-N-(1,1-dioxothian-4-yl)thiazole-2-carboxamide

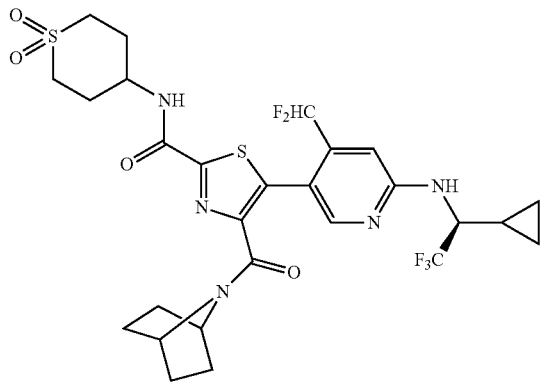 [SMILES: O=C(NC1CCS(=O)(=O)CC1)c1nc(C(=O)N2C3CCC2CC3)c(-c2cnc(N[C@@H](C3CC3)C(F)(F)F)cc2C(F)F)s1]

The title compound was prepared as described in Intermediate 72: Step B, substituting potassium 4-((1s,4s)-7-azabicyclo[2.2.1]heptane-7-carbonyl)-5-(6-(((S)-1-cyclopropyl-2,2,2-trifluoroethyl)amino)-4-(difluoromethyl)pyridin-3-yl)thiazole-2-carboxylate (Intermediate 164) for 4-(tert-butoxycarbonyl)thiazole-2-carboxylic acid. MS (ESI): mass calcd. for $C_{27}H_{30}F_5N_5O_4S_2$, 647.7; m/z found, 648.0 [M+H]$^+$. $^1$H NMR (400 MHz, DMSO-d$_6$) δ 9.10 (d, J=8.4 Hz, 1H), 8.02 (s, 1H), 7.89 (d, J=9.3 Hz, 1H), 7.16-6.87 (m, 2H), 4.56-4.42 (m, 2H), 4.28-4.16 (m, 1H), 4.06-4.00 (m, 1H), 3.41-3.36 (m, 1H), 3.14-3.04 (m, 2H), 2.30-2.17 (m, 2H), 2.11-2.03 (m, 2H), 1.53-1.28 (m, 7H), 1.27-1.08 (m, 3H), 0.69-0.59 (m, 1H), 0.57-0.44 (m, 2H), 0.36-0.24 (m, 1H).

Example 437

4-((1s,4s)-7-Azabicyclo[2.2.1]heptane-7-carbonyl)-5-[6-[[(1S)-1-cyclopropyl-2,2,2-trifluoro-ethyl]amino]-4-(difluoromethyl)-3-pyridyl]-N-[(1R,3R)-3-hydroxycyclopentyl]thiazole-2-carboxamide

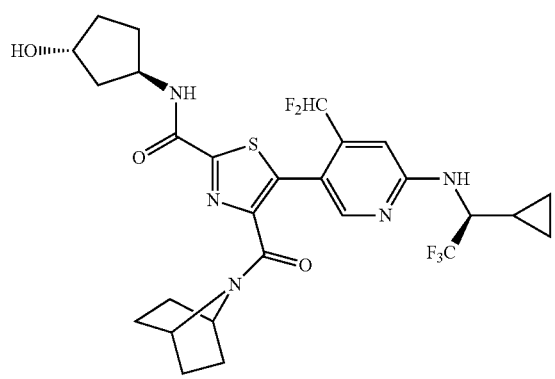 [SMILES: O=C(N[C@@H]1CC[C@@H](O)C1)c1nc(C(=O)N2C3CCC2CC3)c(-c2cnc(N[C@@H](C3CC3)C(F)(F)F)cc2C(F)F)s1]

The title compound was prepared as described in Intermediate 72: Step B, substituting potassium 4-((1s,4s)-7-azabicyclo[2.2.1]heptane-7-carbonyl)-5-(6-(((S)-1-cyclopropyl-2,2,2-trifluoroethyl)amino)-4-(difluoromethyl)pyridin-3-yl)thiazole-2-carboxylate (Intermediate 165) for 4-(tert-butoxycarbonyl)thiazole-2-carboxylic acid and (1R,3R)-3-aminocyclopentan-1-ol for 4-aminotetrahydro-2H-thiopyran-1,1-dioxide hydrochloride. MS (ESI): mass calcd. for $C_{27}H_{30}F_5N_5O_3S$, 599.6; m/z found, 600.0 [M+H]$^+$. $^1$H NMR (400 MHz, DMSO-d$_6$) δ 8.87 (d, J=8.2 Hz, 1H), 8.02 (s, 1H), 7.89 (d, J=9.3 Hz, 1H), 7.16-6.86 (m, 2H), 4.57-4.40 (m, 4H), 4.24-4.16 (m, 1H), 4.02-3.95 (m, 1H), 2.09-1.88 (m, 2H), 1.86-1.73 (m, 2H), 1.65-1.52 (m, 1H), 1.51-1.27 (m, 7H), 1.26-1.09 (m, 3H), 0.69-0.58 (m, 1H), 0.57-0.44 (m, 2H), 0.35-0.26 (m, 1H).

Example 438

4-((1s,4s)-7-Azabicyclo[2.2.1]heptane-7-carbonyl)-5-[4-(difluoromethyl)-6-[[(1S)-2,2,2-trifluoro-1-methyl-ethyl]amino]-3-pyridyl]-N-[(1R,3R)-3-hydroxycyclopentyl]thiazole-2-carboxamide

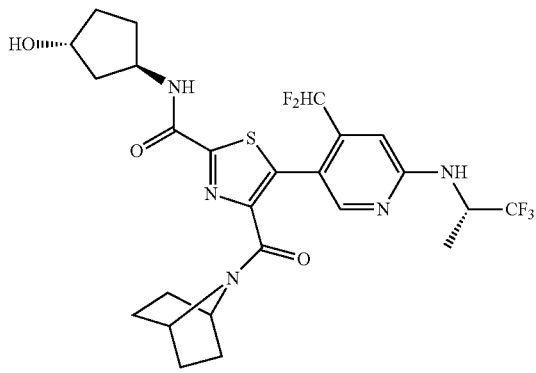 [SMILES: C[C@H](Nc1cc(C(F)F)c(-c2sc(C(=O)N[C@@H]3CC[C@@H](O)C3)nc2C(=O)N2C3CCC2CC3)cn1)C(F)(F)F]

The title compound was prepared as described in Intermediate 72: Step B, substituting potassium 4-((1 s,4s)-7-azabicyclo[2.2.1]heptane-7-carbonyl)-5-(4-(difluoromethyl)-6-(((S)-1,1,1-trifluoropropan-2-yl)amino)pyridin-3-yl)thiazole-2-carboxylate (Intermediate 153) for 4-(tert-butoxycarbonyl)thiazole-2-carboxylic acid and (1R,3R)-2-aminocyclopentan-1-ol for 4-aminotetrahydro-2H-thiopyran-1,1-dioxide hydrochloride. MS (ESI): mass calcd. for $C_{25}H_{28}F_5N_5O_3S$, 573.6; m/z found, 574.0 [M+H]$^+$. $^1$H NMR (400 MHz, DMSO-d$_6$) δ 8.82 (d, J=7.9 Hz, 1H), 8.03 (s, 1H), 7.78 (d, J=8.4 Hz, 1H), 7.13-6.80 (m, 2H), 5.08-4.93 (m, 1H), 4.56-4.37 (m, 3H), 4.18 (s, 1H), 4.00 (s, 1H), 2.04-1.85 (m, 2H), 1.83-1.71 (m, 2H), 1.60-1.12 (m, 13H).

Example 439

4-((1s,4s)-7-Azabicyclo[2.2.1]heptane-7-carbonyl)-5-[6-[[(1S)-1-cyclopropyl-2,2,2-trifluoro-ethyl]amino]-4-(difluoromethyl)-3-pyridyl]-N-[(1R,2R)-2-hydroxycyclopentyl]thiazole-2-carboxamide

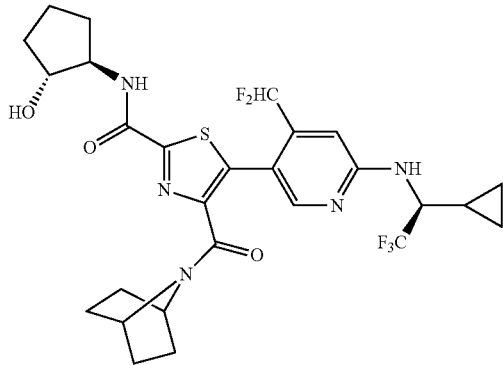 [SMILES: O=C(N[C@@H]1CCC[C@H]1O)c1nc(C(=O)N2C3CCC2CC3)c(-c2cnc(N[C@@H](C3CC3)C(F)(F)F)cc2C(F)F)s1]

The title compound was prepared as described in Intermediate 72: Step B, substituting potassium 4-((1s,4s)-7-azabicyclo[2.2.1]heptane-7-carbonyl)-5-(6-(((S)-1-cyclopropyl-2,2,2-trifluoroethyl)amino)-4-(difluoromethyl)pyridin-3-yl)thiazole-2-carboxylate (Intermediate 165) for 4-(tert-butoxycarbonyl)thiazole-2-carboxylic acid and (1R, 2R)-2-aminocyclopentan-1-ol for 4-aminotetrahydro-2H-thiopyran-1,1-dioxide hydrochloride. MS (ESI): mass calcd. for $C_{27}H_{30}F_5N_5O_3S$, 599.6; m/z found, 600.0 [M+H]$^+$. $^1$H NMR (400 MHz, DMSO-d$_6$) δ 8.78 (d, J=8.2 Hz, 1H), 8.03 (s, 1H), 7.89 (d, J=9.3 Hz, 1H), 7.17-6.87 (m, 2H), 4.83 (d, J=5.1 Hz, 1H), 4.57-4.42 (m, 2H), 4.10-3.95 (m, 3H), 2.00-1.80 (m, 2H), 1.69-1.53 (m, 3H), 1.52-1.28 (m, 7H), 1.27-1.07 (m, 3H), 0.69-0.58 (m, 1H), 0.57-0.44 (m, 2H), 0.37-0.26 (m, 1H).

Example 440

4-((1s,4s)-7-Azabicyclo[2.2.1]heptane-7-carbonyl)-5-[6-(tert-butylamino)-4-(difluoromethyl)-3-pyridyl]-N-[(1S,2S)-2-hydroxycyclopentyl]thiazole-2-carboxamide

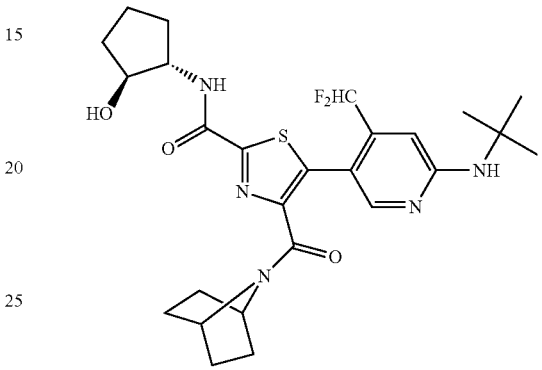

The title compound was prepared as described in Intermediate 72: Step B, substituting potassium 4-((1s,4s)-7-azabicyclo[2.2.1]heptane-7-carbonyl)-5-(6-(tert-butylamino)-4-(difluoromethyl)pyridin-3-yl)thiazole-2-carboxylate (Intermediate 155) for 4-(tert-butoxycarbonyl)thiazole-2-carboxylic acid and (1S,2S)-2-aminocyclopentan-1-ol for 4-aminotetrahydro-2H-thiopyran-1,1-dioxide hydrochloride. MS (ESI): mass calcd. for $C_{26}H_{33}F_2N_5O_3S$, 533.6; m/z found, 534.0 [M+H]$^+$. $^1$H NMR (400 MHz, DMSO-d$_6$) δ 8.72 (d, J=8.2 Hz, 1H), 7.95 (s, 1H), 7.09-6.77 (m, 3H), 4.79 (d, J=4.9 Hz, 1H), 4.47-4.41 (m, 1H), 4.06-3.89 (m, 3H), 1.97-1.77 (m, 2H), 1.66-1.50 (m, 3H), 1.47-1.23 (m, 16H), 1.21-1.07 (m, 2H).

Example 441

4-((1s,4s)-7-Azabicyclo[2.2.1]heptane-7-carbonyl)-5-[6-[[(1S)-1-cyclopropyl-2,2,2-trifluoro-ethyl]amino]-4-(difluoromethyl)-3-pyridyl]-N-[(1S,3S)-3-hydroxycyclopentyl]thiazole-2-carboxamide

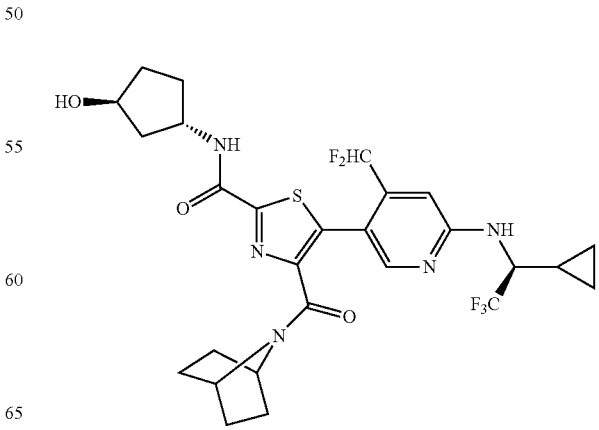

The title compound was prepared as described in Intermediate 72: Step B, substituting potassium 4-((1s,4s)-7-azabicyclo[2.2.1]heptane-7-carbonyl)-5-(6-(((S)-1-cyclopropyl-2,2,2-trifluoroethyl)amino)-4-(difluoromethyl)pyridin-3-yl)thiazole-2-carboxylate (Intermediate 165) for 4-(tert-butoxycarbonyl)thiazole-2-carboxylic acid and (1S,3S)-3-aminocyclopentan-1-ol for 4-aminotetrahydro-2H-thiopyran-1,1-dioxide hydrochloride. MS (ESI): mass calcd. for $C_{27}H_{30}F_5N_5O_3S$, 599.6; m/z found, 600.0 [M+H]+. 1H NMR (400 MHz, DMSO-$d_6$) δ 8.88 (d, J=8.4 Hz, 1H), 8.02 (s, 1H), 7.90 (d, J=9.0 Hz, 1H), 7.16-6.87 (m, 2H), 4.56-4.42 (m, 4H), 4.24-4.17 (m, 1H), 4.02-3.95 (m, 1H), 2.08-1.89 (m, 2H), 1.86-1.74 (m, 2H), 1.64-1.53 (m, 1H), 1.52-1.27 (m, 7H), 1.26-1.09 (m, 3H), 0.69-0.60 (m, 1H), 0.56-0.44 (m, 2H), 0.35-0.25 (m, 1H).

Example 442

4-((1s,4s)-7-Azabicyclo[2.2.1]heptane-7-carbonyl)-5-[6-[[(1S)-1-cyclopropyl-2,2,2-trifluoro-ethyl]amino]-4-(difluoromethyl)-3-pyridyl]-N-[(3R,4S)-4-hydroxytetrahydrofuran-3-yl]thiazole-2-carboxamide

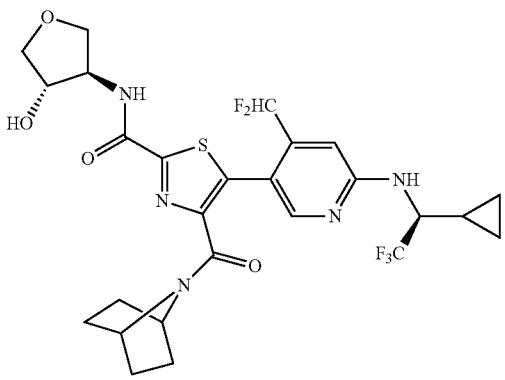 [SMILES: O=C(N[C@@H]1COC[C@H]1O)c1nc(C(=O)N2C3CCC2CC3)c(-c2cnc(N[C@@H](C3CC3)C(F)(F)F)cc2C(F)F)s1]

The title compound was prepared as described in Intermediate 72: Step B, substituting potassium 4-((1s,4s)-7-azabicyclo[2.2.1]heptane-7-carbonyl)-5-(6-(((S)-1-cyclopropyl-2,2,2-trifluoroethyl)amino)-4-(difluoromethyl)pyridin-3-yl)thiazole-2-carboxylate (Intermediate 165) for 4-(tert-butoxycarbonyl)thiazole-2-carboxylic acid and (3S,4R)-4-aminotetrahydrofuran-3-ol for 4-aminotetrahydro-2H-thiopyran-1,1-dioxide hydrochloride. MS (ESI): mass calcd. for $C_{26}H_{28}F_5N_5O_4S$, 601.6; m/z found, 602.0 [M+H]+. 1H NMR (400 MHz, DMSO-$d_6$) δ 9.06-8.98 (m, 1H), 8.03 (s, 1H), 7.90 (d, J=9.3 Hz, 1H), 7.17-6.87 (m, 2H), 5.33 (d, J=4.0 Hz, 1H), 4.58-4.42 (m, 2H), 4.36-4.31 (m, 1H), 4.21 (br s, 1H), 4.03-3.96 (m, 2H), 3.95-3.90 (m, 1H), 3.69-3.63 (m, 1H), 3.55-3.48 (m, 1H), 1.50-1.27 (m, 6H), 1.26-1.09 (m, 3H), 0.70-0.59 (m, 1H), 0.56-0.44 (m, 2H), 0.36-0.25 (m, 1H).

Example 443

4-((1s,4s)-7-Azabicyclo[2.2.1]heptane-7-carbonyl)-5-(6-(((S)-1-cyclopropyl-2,2,2-trifluoroethyl)amino)-4-(difluoromethyl)pyridin-3-yl)-N-((1R*,2R*)-2-hydroxycyclobutyl)thiazole-2-carboxamide

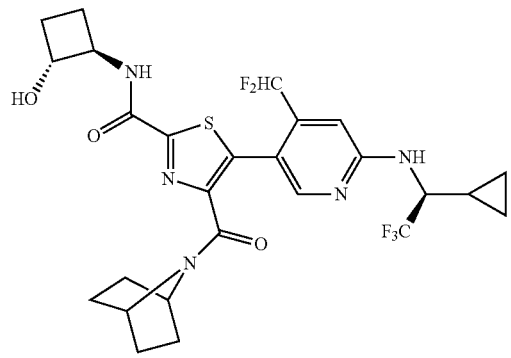 [SMILES: O=C(N[C@@H]1CC[C@H]1O)c1nc(C(=O)N2C3CCC2CC3)c(-c2cnc(N[C@@H](C3CC3)C(F)(F)F)cc2C(F)F)s1]

The title compound was prepared as described in Intermediate 72: Step B, substituting potassium 4-((1s,4s)-7-azabicyclo[2.2.1]heptane-7-carbonyl)-5-(6-(((S)-1-cyclopropyl-2,2,2-trifluoroethyl)amino)-4-(difluoromethyl)pyridin-3-yl)thiazole-2-carboxylate (Intermediate 165) for 4-(tert-butoxycarbonyl)thiazole-2-carboxylic acid and trans-2-aminocyclobutan-1-ol for 4-aminotetrahydro-2H-thiopyran-1,1-dioxide hydrochloride followed by SFC purification (Stationary phase: AY, 250×30 mm, 10 μm, (eluent:30% (v/v) supercritical $CO_2$ in EtOH and $H_2O$ with 0.1% $NH_3$). MS (ESI): mass calcd. for $C_{26}H_{28}F_5N_5O_3S$, 585.6; m/z found, 586.0 [M+H]+. 1H NMR (400 MHz, DMSO-$d_6$) δ 9.12 (d, J=7.7 Hz, 1H), 7.98 (s, 1H), 7.89 (d, J=9.0 Hz, 1H), 7.10-6.81 (m, 2H), 5.39 (d, J=6.8 Hz, 1H), 4.51-4.38 (m, 2H), 4.16-4.04 (m, 2H), 3.98-3.89 (m, 1H), 1.95-1.78 (m, 2H), 1.51-1.25 (m, 8H), 1.24-1.06 (m, 3H), 0.64-0.56 (m, 1H), 0.52-0.39 (m, 2H), 0.30-0.22 (m, 1H).

Example 444

4-((1s,4s)-7-Azabicyclo[2.2.1]heptane-7-carbonyl)-5-(6-(((S)-1-cyclopropyl-2,2,2-trifluoroethyl)amino)-4-(difluoromethyl)pyridin-3-yl)-N-((1S*,2S*)-2-hydroxycyclobutyl)thiazole-2-carboxamide

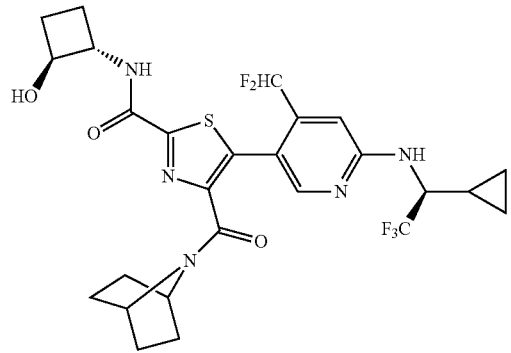 [SMILES: O=C(N[C@H]1CC[C@@H]1O)c1nc(C(=O)N2C3CCC2CC3)c(-c2cnc(N[C@@H](C3CC3)C(F)(F)F)cc2C(F)F)s1]

The title compound was prepared as described in Intermediate 72: Step B, substituting potassium 4-((1s,4s)-7-azabicyclo[2.2.1]heptane-7-carbonyl)-5-(6-(((S)-1-cyclopropyl-2,2,2-trifluoroethyl)amino)-4-(difluoromethyl)pyridin-3-yl)thiazole-2-carboxylate (Intermediate 165) for 4-(tert-butoxycarbonyl)thiazole-2-carboxylic acid and trans-2-aminocyclobutan-1-ol for 4-aminotetrahydro-2H-thiopyran-1,1-dioxide hydrochloride followed by SFC purification (Stationary phase: AY, 250×30 mm, 10 μm (eluent: 30% (v/v) supercritical CO$_2$ in EtOH and H$_2$O with 0.1% NH$_3$). MS (ESI): mass calcd. for C$_{26}$H$_{28}$F$_5$N$_5$O$_3$S, 585.6; m/z found, 586.0 [M+H]$^+$. $^1$H NMR (400 MHz, DMSO-d$_6$) δ 9.17-9.10 (m, 1H), 8.00 (s, 1H), 7.87 (d, J=9.3 Hz, 1H), 7.13-6.84 (m, 2H), 5.31-5.26 (m, 1H), 4.55-4.39 (m, 2H), 4.17-4.06 (m, 2H), 4.00-3.93 (m, 1H), 1.96-1.87 (m, 1H), 1.87-1.78 (m, 1H), 1.54-1.25 (m, 8H), 1.25-1.06 (m, 3H), 0.66-0.57 (m, 1H), 0.53-0.41 (m, 2H), 0.32-0.23 (m, 1H).

Example 445

4-((1s,4s)-7-Azabicyclo[2.2.1]heptane-7-carbonyl)-5-[4-(difluoromethyl)-6-[[(1S)-2,2,2-trifluoro-1-methyl-ethyl]amino]-3-pyridyl]-N-[(1R)-2-hydroxy-1,2-dimethyl-propyl]thiazole-2-carboxamide

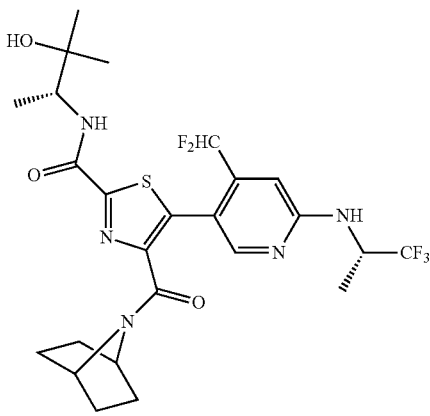 [SMILES: C[C@H](Nc1cc(C(F)F)c(-c2sc(C(=O)N[C@H](C)C(C)(C)O)nc2C(=O)N2C3CCC2CC3)cn1)C(F)(F)F]

The title compound was prepared as described in Example 3 substituting (S)-5-bromo-4-(difluoromethyl)-N-(1,1,1-trifluoropropan-2-yl)pyridin-2-amine (Intermediate 59) for 5-bromo-N-cyclohexyl-4-(trifluoromethyl)pyridin-2-amine and (R)-4-((1s,4s)-7-azabicyclo[2.2.1]heptane-7-carbonyl)-N-(3-hydroxy-3-methylbutan-2-yl)thiazole-2-carboxamide (Intermediate 166) for 4-(4-fluoropiperidine-1-carbonyl)-N-(2-hydroxy-2-methylpropyl)thiazole-2-carboxamide. MS (ESI): mass calcd. for C$_{25}$H$_{30}$F$_5$N$_5$O$_3$S, 575.6; m/z found, 576.0 [M+H]$^+$. $^1$H NMR (400 MHz, DMSO-d$_6$) δ 8.10-8.03 (m, 2H), 7.79 (d, J=8.8 Hz, 1H), 7.12-6.84 (m, 2H), 5.09-4.95 (m, 1H), 4.74 (s, 1H), 4.48-4.39 (m, 1H), 4.15-4.06 (m, 1H), 3.93-3.84 (m, 1H), 1.62-1.17 (m, 12H), 1.16-1.06 (m, 8H).

Example 446

4-((1s,4s)-7-Azabicyclo[2.2.1]heptane-7-carbonyl)-5-[4-(difluoromethyl)-6-[[(1S)-2,2,2-trifluoro-1-methyl-ethyl]amino]-3-pyridyl]-N-[(1S)-2-hydroxy-1,2-dimethyl-propyl]thiazole-2-carboxamide

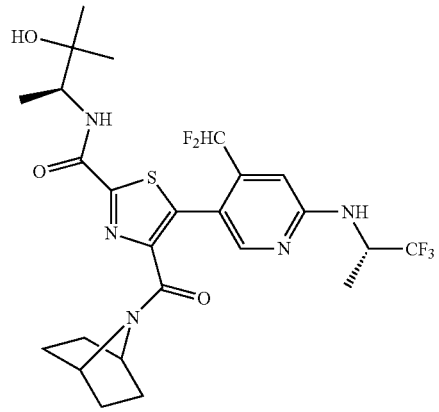 [SMILES: C[C@H](NC(=O)c1nc(C(=O)N2C3CCC2CC3)c(-c2cnc(N[C@@H](C)C(F)(F)F)cc2C(F)F)s1)C(C)(C)O]

The title compound was prepared as described in Example 3 substituting (S)-5-bromo-4-(difluoromethyl)-N-(1,1,1-trifluoropropan-2-yl)pyridin-2-amine (Intermediate 60) for 5-bromo-N-cyclohexyl-4-(trifluoromethyl)pyridin-2-amine and (S)-4-((1s,4s)-7-azabicyclo[2.2.1]heptane-7-carbonyl)-N-(3-hydroxy-3-methylbutan-2-yl)thiazole-2-carboxamide (Intermediate 167) for 4-(4-fluoropiperidine-1-carbonyl)-N-(2-hydroxy-2-methylpropyl)thiazole-2-carboxamide. MS (ESI): mass calcd. for C$_{25}$H$_{30}$F$_5$N$_5$O$_3$S, 575.6; m/z found, 576.0 [M+H]$^+$. $^1$H NMR (400 MHz, DMSO-d$_6$) δ 8.11-8.00 (m, 2H), 7.78 (d, J=9.0 Hz, 1H), 7.14-6.81 (m, 2H), 5.10-4.94 (m, 1H), 4.73 (s, 1H), 4.49-4.39 (m, 1H), 4.16-4.08 (m, 1H), 3.88 (s, 1H), 1.53-1.28 (m, 11H), 1.19-1.04 (m, 9H).

Example 447

4-[(2S)-4,4-Difluoro-2-methyl-pyrrolidine-1-carbonyl]-5-[4-(difluoromethyl)-6-[[(1S)-2,2,2-trifluoro-1-methyl-ethyl]amino]-3-pyridyl]-N-[(1R)-2-hydroxy-1-methyl-ethyl]thiazole-2-carboxamide

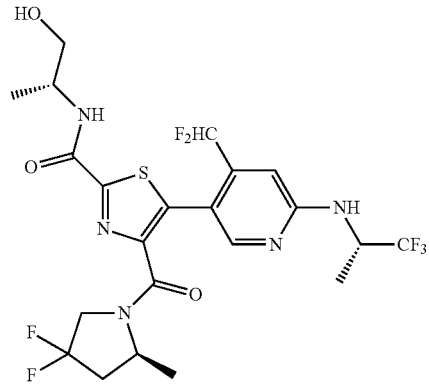 [SMILES: C[C@H](CO)NC(=O)c1nc(C(=O)N2CC(F)(F)C[C@@H]2C)c(-c2cnc(N[C@@H](C)C(F)(F)F)cc2C(F)F)s1]

The title compound was prepared as described in Example 148 substituting ethyl 4-((S)-4,4-difluoro-2-methylpyrrolidine-1-carbonyl)-5-(4-(difluoromethyl)-6-(((S)-1,1,1,-trifluoropropan-2-yl)amino)pyridine-3-yl)thiazole-2-carboxylate (Intermediate 96) for ethyl (S)-5-(6-(tert-butylamino)-

4-(difluoromethyl)pyrid6517in-3-yl)-4-(2-methylpyrrolidine-1-carbonyl)thiazole-2-carboxylate. MS (ESI): mass calcd. for $C_{22}H_{24}F_7N_5O_3S$, 571.5; m/z found, 571.9 [M+H]⁺. ¹H NMR (400 MHz, DMSO-$d_6$) δ 8.54-8.43 (m, 1H), 8.05 (s, 1H), 7.78-7.70 (m, 1H), 7.08-6.74 (m, 2H), 5.07-4.93 (m, 1H), 4.85-4.55 (m, 1H), 4.35-4.21 (m, 1H), 4.18-3.74 (m, 3H), 3.51-3.36 (m, 2H), 2.62-2.53 (m, 1H), 2.23-2.03 (m, 1H), 1.31 (d, J=6.8 Hz, 3H), 1.20-1.12 (m, 5H), 1.05 (d, J=6.2 Hz, 1H).

Example 448

4-[(2S)-4,4-Difluoro-2-methyl-pyrrolidine-1-carbonyl]-5-[4-(difluoromethyl)-6-[[(1S)-2,2,2-trifluoro-1-methyl-ethyl]amino]-3-pyridyl]-N-tetrahydropyran-4-yl-thiazole-2-carboxamide

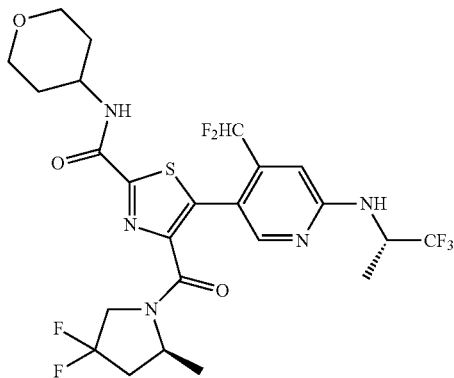 [SMILES: C[C@H](Nc1cc(C(F)F)c(-c2sc(C(=O)NC3CCOCC3)nc2C(=O)N2CC(F)(F)C[C@@H]2C)cn1)C(F)(F)F]

The title compound was prepared as described in Example 148 substituting tetrahydro-2H-pyran-4-amine for (R)-(−)-2-amino-1-propanol and ethyl 4-((S)-4,4-difluoro-2-methylpyrrolidine-1-carbonyl)-5-(4-(difluoromethyl)-6-(((S)-1,1,1,-trifluoropropan-2-yl)amino)pyridine-3-yl)thiazole-2-carboxylate (Intermediate 96) for ethyl (S)-5-(6-(tert-butylamino)-4-(difluoromethyl)pyridin-3-yl)-4-(2-methylpyrrolidine-1-carbonyl)thiazole-2-carboxylate. MS (ESI): mass calcd. for $C_{24}H_{26}F_7N_5O_3S$, 597.6; m/z found, 598.0 [M+H]⁺. ¹H NMR (400 MHz, DMSO-$d_6$) δ 8.86-8.80 (m, 1H), 8.05 (s, 1H), 7.78-7.71 (m, 1H), 7.10-6.73 (m, 2H), 5.06-4.58 (m, 1H), 4.33-4.20 (m, 1H), 4.17-3.76 (m, 5H), 3.40-3.34 (m, 2H), 2.62-2.53 (m, 1H), 2.26-2.02 (m, 1H), 1.79-1.63 (m, 4H), 1.31 (d, J=6.8 Hz, 3H), 1.18 (d, J=6.4 Hz, 2H), 1.02 (d, J=6.2 Hz, 1H).

Example 449

4-((S)-4,4-Difluoro-2-methylpyrrolidine-1-carbonyl)-5-(4-(difluoromethyl)-6-(((S)-1,1,1-trifluorobutan-2-yl)amino)pyridin-3-yl)-N-((1R,3S)-3-hydroxycyclobutyl)thiazole-2-carboxamide

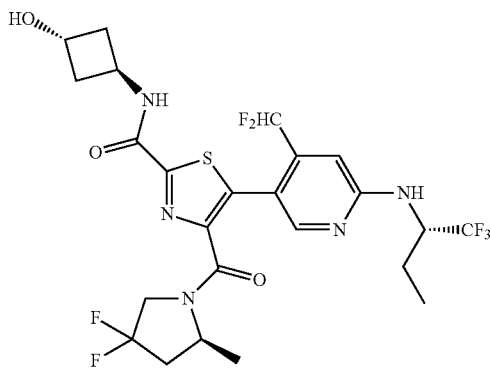 [SMILES: CC[C@H](Nc1cc(C(F)F)c(-c2sc(C(=O)N[C@H]3C[C@H](O)C3)nc2C(=O)N2CC(F)(F)C[C@@H]2C)cn1)C(F)(F)F]

The title compound was prepared as described in Example 148 substituting (1R,3R)-3-aminocyclobutan-1-ol for (R)-(−)-2-amino-1-propanol and ethyl 4-((S)-4,4-difluoro-2-methylpyrrolidine-1-carbonyl)-5-(4-(difluoromethyl)-6-(((S)-1,1,1-trifluorobutan-2-yl)amino)pyridin-3-yl)thiazole-2-carboxylate (Intermediate 158) for ethyl (S)-5-(6-(tert-butylamino)-4-(difluoromethyl)pyridin-3-yl)-4-(2-methylpyrrolidine-1-carbonyl)thiazole-2-carboxylate. MS (ESI): mass calcd. for $C_{24}H_{26}F_7N_5O_3S$, 597.6; m/z found, 597.9 [M+H]⁺. ¹H NMR (400 MHz, DMSO-$d_6$) δ 9.19-9.10 (m, 1H), 8.07 (s, 1H), 7.76-7.67 (m, 1H), 7.13-6.77 (m, 2H), 5.06 (d, J=5.0 Hz, 1H), 4.94-4.65 (m, 1H), 4.55-4.44 (m, 1H), 4.38-4.26 (m, 2H), 4.20-4.08 (m, 1H), 4.01-3.85 (m, 1H), 2.65-2.57 (m, 1H), 2.46-2.38 (m, 2H), 2.22-2.08 (m, 3H), 1.90-1.79 (m, 1H), 1.68-1.55 (m, 1H), 1.24-1.03 (m, 3H), 0.96 (d, J=7.3 Hz, 3H).

Example 450

5-[4-(Difluoromethyl)-6-[[(1S)-2,2,2-trifluoro-1-methyl-ethyl]amino]-3-pyridyl]-2-(3-methylsulfonylazetidine-1-carbonyl)thiazol-4-yl]-[(2S)-2-methylpyrrolidin-1-yl]methanone

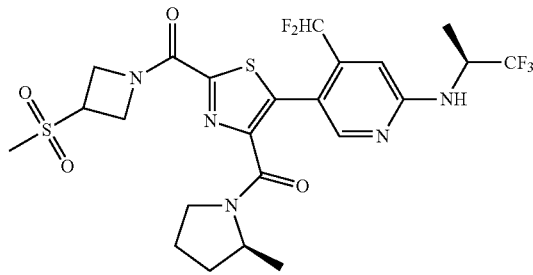 [SMILES: C[C@H](Nc1cc(C(F)F)c(-c2sc(C(=O)N3CC(S(C)(=O)=O)C3)nc2C(=O)N2CCC[C@@H]2C)cn1)C(F)(F)F]

The title compound was prepared as described in Example 393 substituting ethyl 5-(4-(difluoromethyl)-6-(((S)-1,1,1-trifluoropropan-2-yl)amino)pyridin-3-yl)-4-((S)-2-methylpyrrolidine-1-carbonyl)thiazole-2-carboxylate (Intermediate 94) for ethyl 5-(4-(difluoromethyl)-6-(((S)-1,1,1-trifluorobutan-2-yl)amino)pyridin-3-yl)-4-((S)-2-methylpyrrolidine-1-carbonyl)thiazole-2-carboxylate. MS (ESI): mass calcd. for $C_{23}H_{26}F_5N_5O_4S_2$, 595.1; m/z found, 595.8 [M+H]⁺. ¹H NMR (400 MHz, CDCl₃) δ 8.09-8.01 (m, 1H), 6.75-6.69 (m, 1H), 6.76-6.65 (m, 1H), 5.11-4.94 (m, 3H), 4.60-4.50 (m, 2H), 4.22-4.10 (m, 2H), 3.67-3.41 (m, 2H), 3.07-2.95 (m, 3H), 2.12-2.03 (m, 1H), 2.01-1.85 (m, 1H), 1.83-1.74 (m, 1H), 1.60-1.51 (m, 1H), 1.41 (d, J=6.8 Hz, 3H), 1.29-1.20 (m, 2H), 1.09-0.96 (m, 1H).

Example 451

4-(7-Azabicyclo[2.2.1]heptane-7-carbonyl)-5-[6-[[(1S)-1-cyclopropyl-2,2,2-trifluoro-ethyl]amino]-4-(difluoromethyl)-3-pyridyl]-N-[(1S,2S)-2-hydroxycyclopentyl]thiazole-2-carboxamide

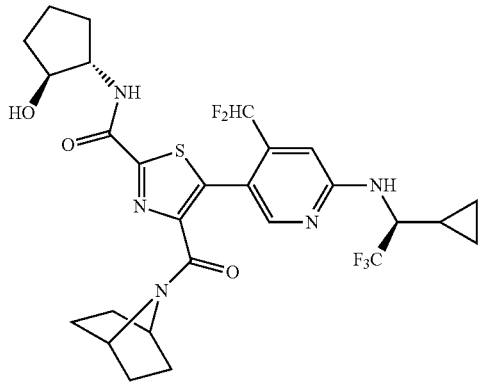 [SMILES: O=C(N[C@H]1CCC[C@@H]1O)c1nc(C(=O)N2C3CCC2CC3)c(-c2cnc(N[C@@H](C3CC3)C(F)(F)F)cc2C(F)F)s1]

The title compound was prepared as described in Intermediate 72: Step B, substituting potassium 4-((1R,4R)-7-azabicyclo[2.2.1]heptane-7-carbonyl)-5-(6-(((S)-1-cyclopropyl-2,2,2-trifluoroethyl)amino)-4-(difluoromethyl)pyridin-3-yl)thiazole-2-carboxylate (Intermediate 165) for 4-(tert-butoxycarbonyl)thiazole-2-carboxylic acid and (1S,2S)-2-aminocyclopentan-1-ol for 4-aminotetrahydro-2H-thiopyran-1,1-dioxide hydrochloride. MS (ESI): mass calcd. for $C_{27}H_{30}F_5N_5O_3S$, 599.6; m/z found, 600.0 [M+H]$^+$. $^1$H NMR (400 MHz, DMSO-d$_6$) δ 8.79 (d, J=8.3 Hz, 1H), 8.03 (s, 1H), 7.90 (d, J=9.0 Hz, 1H), 7.18-6.87 (m, 2H), 4.58-4.43 (m, 2H), 4.11-3.94 (m, 3H), 2.00-1.79 (m, 2H), 1.70-1.53 (m, 3H), 1.50-1.29 (m, 8H), 1.25-1.10 (m, 3H), 0.69-0.59 (m, 1H), 0.57-0.45 (m, 2H), 0.36-0.27 (m, 1H).

The following examples of the invention can be prepared by procedures described.

Example 452

N-(2-Hydroxy-2-(methyl-d$_3$)propyl-3,3,3-d$_3$)-4-((S)-2-methylpyrrolidine-1-carbonyl)-5-(6-(((S)-1,1,1-trifluorobutan-2-yl)amino)-4-(trifluoromethyl)pyridin-3-yl)thiazole-2-carboxamide

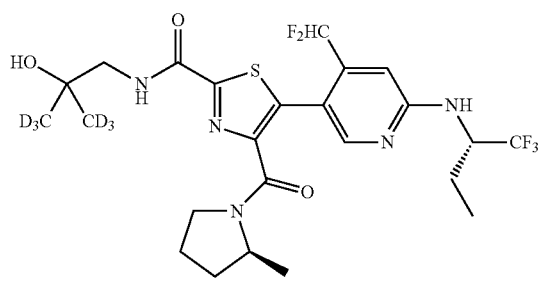 [SMILES: [2H]C([2H])([2H])C(O)(CNC(=O)c1nc(C(=O)N2CCC[C@@H]2C)c(-c2cnc(N[C@@H](CC)C(F)(F)F)cc2C(F)F)s1)C([2H])([2H])[2H]]

The title compound can be prepared as described in Example 77 substituting (S)-5-bromo-N-(1,1,1-trifluorobutan-2-yl)-4-(trifluoromethyl)pyridin-2-amine (Intermediate 53) for 5-bromo-N-(1-methylcyclobutyl)-4-(trifluoromethyl)pyridin-2-amine and (S)—N-(2-hydroxy-2-(methyl-d$_3$)propyl-3,3,3-d$_3$)-4-(2-methylpyrrolidine-1-carbonyl)thiazole-2-carboxamide (Intermediate 77: Step C) for (S)—N-(2-hydroxy-2-methylpropyl)-4-(2-methylpyrrolidine-1-carbonyl)thiazole-2-carboxamide.

Example 453

5-(6-(((S)-1-Cyclopropylpropyl)amino)-4-(trifluoromethyl)pyridin-3-yl)-N-((1-hydroxycyclopropyl)methyl)-4-((S)-2-methylpyrrolidine-1-carbonyl)thiazole-2-carboxamide

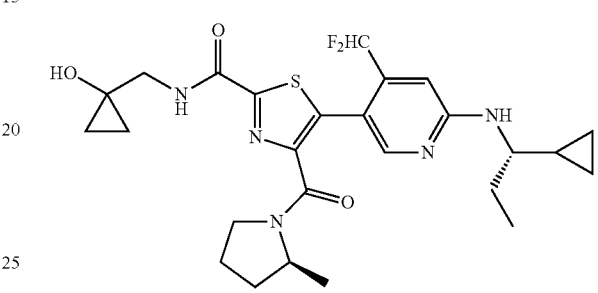

The title compound can be prepared as described in Example 77 substituting 5-bromo-N-(1-cyclopropylpropyl)-4-(trifluoromethyl)pyridin-2-amine (Intermediate 24) for 5-bromo-N-(1-methylcyclobutyl)-4-(trifluoromethyl)pyridin-2-amine and (S)—N-((1-hydroxycyclopropyl)methyl)-4-(2-methylpyrrolidine-1-carbonyl)thiazole-2-carboxamide (Intermediate 78) for (S)—N-(2-hydroxy-2-methylpropyl)-4-(2-methylpyrrolidine-1-carbonyl)thiazole-2-carboxamide.

Example 454

4-((S)-4,4-Difluoro-2-methylpyrrolidine-1-carbonyl)-N-(3-hydroxy-3-methylcyclobutyl)-5-(4-(trifluoromethyl)-6-(((S)-1,1,1-trifluoropropan-2-yl)amino)pyridin-3-yl)thiazole-2-carboxamide

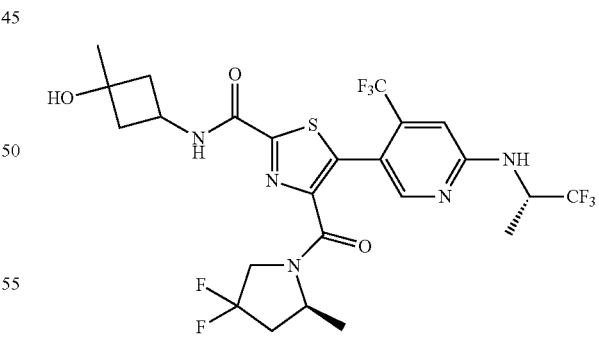

The title compound can be prepared as described in Example 77 substituting (S)-5-bromo-4-(trifluoromethyl)-N-(1,1,1-trifluoropropan-2-yl)pyridin-2-amine (Intermediate 44) for 5-bromo-N-(1-methylcyclobutyl)-4-(trifluoromethyl)pyridin-2-amine and (S)-4-(4,4-difluoro-2-methylpyrrolidine-1-carbonyl)-N-(3-hydroxy-3-methylcyclobutyl)thiazole-2-carboxamide (Intermediate 79) for (S)—N-(2-hydroxy-2-methylpropyl)-4-(2-methylpyrrolidine-1-carbonyl)thiazole-2-carboxamide.

Example 455

(S)-4-(4,4-Difluoro-2-methylpyrrolidine-1-carbonyl)-N-(1,1-dioxidothietan-3-yl)-5-(6-(neopentylamino)-4-(trifluoromethyl)pyridin-3-yl)thiazole-2-carboxamide

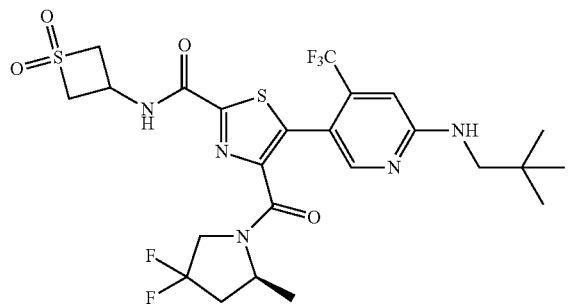 [SMILES: C[C@H]1CC(F)(F)CN1C(=O)c1nc(C(=O)NC2CS(=O)(=O)C2)sc1-c1cnc(NCC(C)(C)C)cc1C(F)(F)F]

The title compound can be prepared as described in Example 77 substituting 5-bromo-N-neopentyl-4-(trifluoromethyl)pyridin-2-amine (Intermediate 22) for 5-bromo-N-(1-methylcyclobutyl)-4-(trifluoromethyl)pyridin-2-amine and (S)-4-(4,4-difluoro-2-methylpyrrolidine-1-carbonyl)-N-(1,1-dioxidothietan-3-yl)thiazole-2-carboxamide (Intermediate 80) for (S)—N-(2-hydroxy-2-methylpropyl)-4-(2-methylpyrrolidine-1-carbonyl)thiazole-2-carboxamide.

Example 456

(S)-4-(4,4-Difluoro-2-methylpyrrolidine-1-carbonyl)-5-(4-(difluoromethyl)-6-(neopentylamino)pyridin-3-yl)-N-(1-hydroxy-2-methylpropan-2-yl)thiazole-2-carboxamide

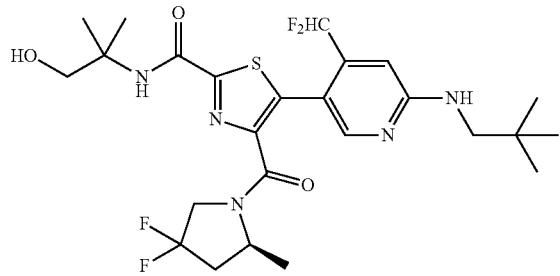 [SMILES: C[C@H]1CC(F)(F)CN1C(=O)c1nc(C(=O)NC(C)(C)CO)sc1-c1cnc(NCC(C)(C)C)cc1C(F)F]

The title compound can be prepared as described in Example 77 substituting 5-bromo-4-(difluoromethyl)-N-neopentylpyridin-2-amine (Intermediate 23) for 5-bromo-N-(1-methylcyclobutyl)-4-(trifluoromethyl)pyridine-2-amine and (S)-4-(4,4-difluoro-2-methylpyrrolidine-1-carbonyl)-N-(1-hydroxy-2-methylpropan-2-yl)thiazole-2-carboxamide (Intermediate 81) for (S)—N-(2-hydroxy-2-methylpropyl)-4-(2-methylpyrrolidine-1-carbonyl)thiazole-2-carboxamide.

Example 457

(4-((1s,4s)-7-Azabicyclo[2.2.1]heptane-7-carbonyl)-5-(4-(difluoromethyl)-6-(((S)-1,1,1-trifluoropropan-2-yl)amino)pyridin-3-yl)thiazol-2-yl)(3-hydroxy-3-methylazetidin-1-yl)methanone

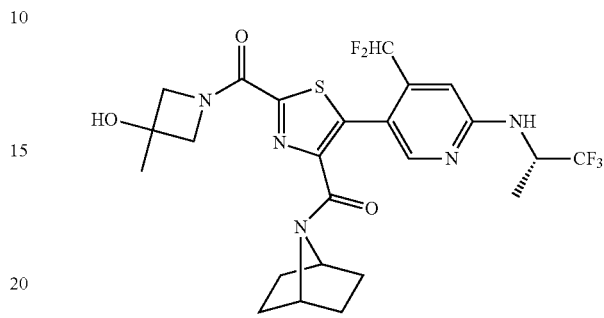

The title compound can be prepared as described in Example 77 substituting (S)-5-bromo-4-(difluoromethyl)-N-(1,1,1-trifluoropropan-2-yl)pyridin-2-amine (Intermediate 60) for 5-bromo-N-(1-methylcyclobutyl)-4-(trifluoromethyl)pyridin-2-amine and (4-((1s,4s)-7-azabicyclo[2.2.1]heptane-7-carbonyl)thiazol-2-yl)(3-hydroxy-3-methylazetidin-1-yl)methanone (Intermediate 82) for (S)—N-(2-hydroxy-2-methylpropyl)-4-(2-methylpyrrolidine-1-carbonyl)thiazole-2-carboxamide.

Example 458

4-((1s,4s)-7-Azabicyclo[2.2.1]heptane-7-carbonyl)-5-(4-(difluoromethyl)-6-(((S)-1,1,1-trifluorobutan-2-yl)amino)pyridin-3-yl)-N-(1-hydroxy-2-methylpropan-2-yl)-N-methylthiazole-2-carboxamide

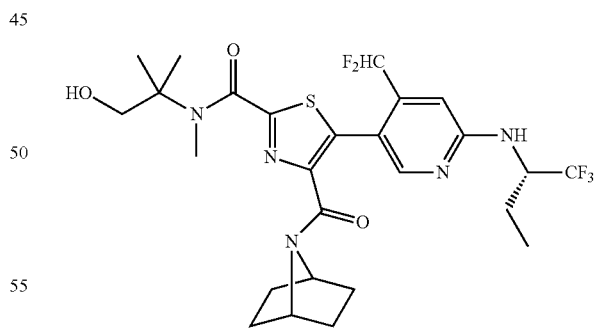

The title compound can be prepared as described in Example 77 substituting (S)-5-bromo-4-(difluoromethyl)-N-(1,1,1-trifluorobutan-2-yl)pyridin-2-amine (Intermediate 49) for 5-bromo-N-(1-methylcyclobutyl)-4-(trifluoromethyl)pyridin-2-amine and 4-((1s,4s)-7-azabicyclo[2.2.1]heptane-7-carbonyl)-N-(1-hydroxy-2-methylpropan-2-yl)-N-methylthiazole-2-carboxamide (Intermediate 83) for (S)—N-(2-hydroxy-2-methylpropyl)-4-(2-methylpyrrolidine-1-carbonyl)thiazole-2-carboxamide.

Example 459

4-((1s,4s)-7-Azabicyclo[2.2.1]heptane-7-carbonyl)-5-(6-(tert-butylamino)-4-(trifluoromethyl)pyridin-3-yl)-N-(2-hydroxy-2-methylpropyl)-N-methylthiazole-2-carboxamide

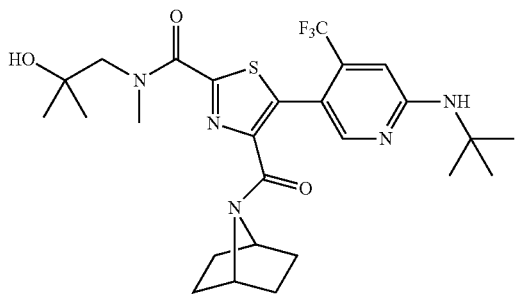 [SMILES: CN(CC(C)(C)O)C(=O)c1nc(C(=O)N2C3CCC2CC3)c(-c2cnc(NC(C)(C)C)cc2C(F)(F)F)s1]

The title compound can be prepared as described in Example 77 substituting 5-bromo-N-(tert-butyl)-4-(trifluoromethyl)pyridin-2-amine (Intermediate 41: Step B) for 5-bromo-N-(1-methylcyclobutyl)-4-(trifluoromethyl)pyridin-2-amine and 4-((1s,4s)-7-azabicyclo[2.2.1]heptane-7-carbonyl)-N-(2-hydroxy-2-methylpropyl)-N-methylthiazole-2-carboxamide (Intermediate 84) for (S)—N-(2-hydroxy-2-methylpropyl)-4-(2-methylpyrrolidine-1-carbonyl)thiazole-2-carboxamide.

Example 460

N-(3-Hydroxy-3-methylbutan-2-yl)-N-methyl-4-((S)-2-methylpiperidine-1-carbonyl)-5-(6-(((S)-1,1,1-trifluorobutan-2-yl)amino)-4-(trifluoromethyl)pyridin-3-yl)thiazole-2-carboxamide

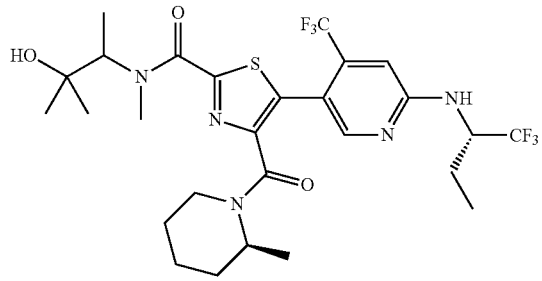 [SMILES: CC[C@H](Nc1cc(C(F)(F)F)c(-c2sc(C(=O)N(C)C(C)C(C)(C)O)nc2C(=O)N2CCCC[C@@H]2C)cn1)C(F)(F)F]

The title compound can be prepared as described in Example 77 substituting (S)-5-bromo-N-(1,1,1-trifluorobutan-2-yl)-4-(trifluoromethyl)pyridin-2-amine (Intermediate 53) for 5-bromo-N-(1-methylcyclobutyl)-4-(trifluoromethyl)pyridin-2-amine and N-(3-hydroxy-3-methylbutan-2-yl)-N-methyl-4-((S)-2-methylpiperidine-1-carbonyl)thiazole-2-carboxamide (Intermediate 85) for (S)—N-(2-hydroxy-2-methylpropyl)-4-(2-methylpyrrolidine-1-carbonyl)thiazole-2-carboxamide.

Example 461

5-(6-(((S)-1-Cyclopropylpropyl)amino)-4-(trifluoromethyl)pyridin-3-yl)-4-((S)-2-methylpiperidine-1-carbonyl)-N-(oxetan-3-yl)thiazole-2-carboxamide

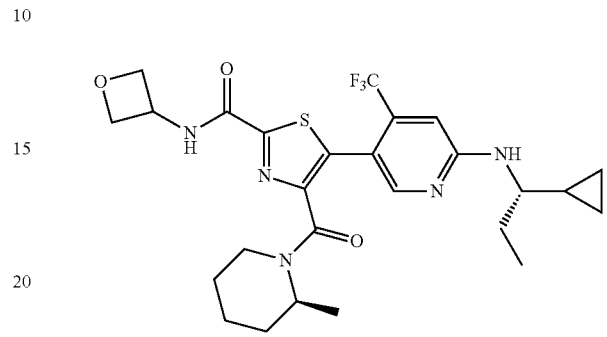

The title compound can be prepared as described in Example 77 substituting 5-bromo-N-(1-cyclopropylpropyl)-4-(trifluoromethyl)pyridin-2-amine (Intermediate 24) for 5-bromo-N-(1-methylcyclobutyl)-4-(trifluoromethyl)pyridin-2-amine and (S)-4-(2-methylpiperidine-1-carbonyl)-N-(oxetan-3-yl)thiazole-2-carboxamide (Intermediate 86) for (S)—N-(2-hydroxy-2-methylpropyl)-4-(2-methylpyrrolidine-1-carbonyl)thiazole-2-carboxamide.

Example 462

(2-(2,2-Dioxido-2-thia-6-azaspiro[3.3]heptane-6-carbonyl)-5-(4-(trifluoromethyl)-6-(((S)-1,1,1-trifluoropropan-2-yl)amino)pyridin-3-yl)thiazol-4-yl)((S)-2-methylpiperidin-1-yl)methanone

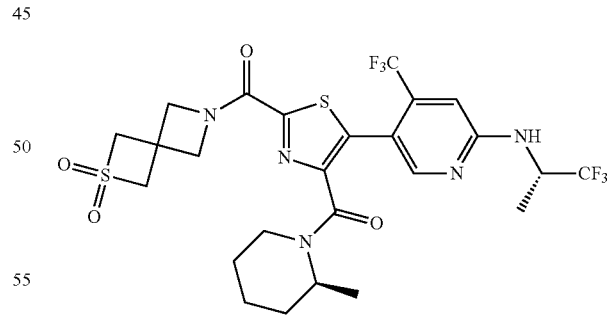

The title compound can be prepared as described in Example 77 substituting (S)-5-bromo-4-(trifluoromethyl)-N-(1,1,1-trifluoropropan-2-yl)pyridin-2-amine (Intermediate 44) for 5-bromo-N-(1-methylcyclobutyl)-4-(trifluoromethyl)pyridin-2-amine and (S)-(2-(2,2-dioxido-2-thia-6-azaspiro[3.3]heptane-6-carbonyl)thiazol-4-yl)(2-methylpiperidin-1-yl)methanone (Intermediate 87) for (S)—N-(2-hydroxy-2-methylpropyl)-4-(2-methylpyrrolidine-1-carbonyl)thiazole-2-carboxamide.

Example 463

(S)-(2-(1,1-Dioxidothiomorpholine-4-carbonyl)-5-(6-(neopentylamino)-4-(trifluoromethyl)pyridin-3-yl)thiazol-4-yl)(2-methylpiperidin-1-yl)methanone

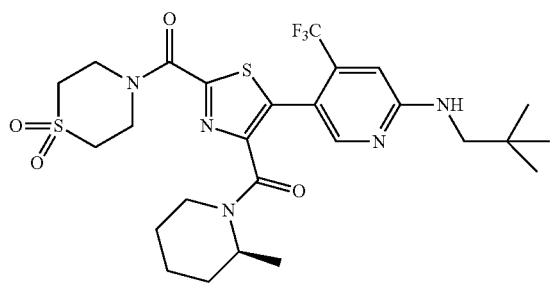 [SMILES: C[C@H]1CCCCN1C(=O)c1nc(C(=O)N2CCS(=O)(=O)CC2)sc1-c1cnc(NCC(C)(C)C)cc1C(F)(F)F]

The title compound can be prepared as described in Example 77 substituting 5-bromo-N-neopentyl-4-(trifluoromethyl)pyridin-2-amine (Intermediate 22) for 5-bromo-N-(1-methylcyclobutyl)-4-(trifluoromethyl)pyridin-2-amine and (S)-(2-(1,1-dioxidothiomorpholine-4-carbonyl)thiazol-4-yl)(2-methylpiperidin-1-yl)methanone (Intermediate 88) for (S)—N-(2-hydroxy-2-methylpropyl)-4-(2-methylpyrrolidine-1-carbonyl)thiazole-2-carboxamide.

In Vitro Biological Data

ThermoFluor® Assay

ThermoFluor® is a fluorescence based assay that estimates ligand binding affinities by measuring the effect of a ligand on protein thermal stability (Pantoliano, M. W., Petrella, E. C., Kwasnoski, J. D., Lobanov, V. S., Myslik, J., Graf, E., Carver, T., Asel, E., Springer, B. A., Lane, P., and Salemme, F. R. (2001) High-density miniaturized thermal shift assays as a general strategy for drug discovery. *J Biomol Screen* 6, 429-40, and Matulis, D., Kranz, J. K., Salemme, F. R., and Todd, M. J. (2005) Thermodynamic stability of carbonic anhydrase: measurements of binding affinity and stoichiometry using ThermoFluor. *Biochemistry* 44, 5258-66). This approach is applicable to a wide variety of systems, and rigorous in theoretical interpretation through quantitation of equilibrium binding constants ($K_D$).

In a ThermoFluor® experiment where protein stability is monitored as the temperature is steadily increased, an equilibrium binding ligand causes the midpoint of an unfolding transition ($T_m$) to occur at a higher temperature. The shift in the melting point described as a $\Delta T_m$ is proportional to the concentration and affinity of the ligand. The compound potency may be compared as a rank order of either $\Delta T_m$ values at a single compound concentration or in terms of $K_D$ values, estimated from concentration response curves.

RORγt ThermoFluor® Assay Construct

For the RORγt construct used in the ThermoFluor® assay, numbering for the nucleotide sequences was based on the reference sequence for human RORγt, transcript variant 2, NCBI Accession: NM_001001523.1 (SEQ ID NO:1). Nucleotides 850-1635 (SEQ ID NO:2) coding for the wild type human RORγt ligand binding domain (RORγt LBD) were cloned into the pHIS1 vector, a modified pET *E. coli* expression vector (Accelagen, San Diego), containing an in-frame N-terminal His-tag and a TurboTEV protease cleavage site (ENLYFQG, SEQ ID NO:3) upstream of the cloned insert sequence. The amino acid sequence for the RORγt construct used in the Thermofluor® assay is shown as SEQ ID NO:4.

ThermoFluor® experiments were carried out using instruments owned by Janssen Research and Discovery, L.L.C. through its acquisition of 3-Dimensional Pharmaceuticals, Inc. 1,8-ANS (Invitrogen) was used as a fluorescent dye. Protein and compound solutions are dispensed into black 384-well polypropylene PCR microplates (Abgene) and overlayed with silicone oil (1 µL, Fluka, type DC 200) to prevent evaporation.

Bar-coded assay plates are robotically loaded onto a thermostatically controlled PCR-type thermal block and then heated at a typical ramp-rate of 1° C./min for all experiments. Fluorescence was measured by continuous illumination with UV light (Hamamatsu LC6) supplied via fiber optic and filtered through a band-pass filter (380-400 nm; >6 OD cutoff). Fluorescence emission of the entire 384-well plate was detected by measuring light intensity using a CCD camera (Sensys, Roper Scientific) filtered to detect 500±25 nm, resulting in simultaneous and independent readings of all 384 wells. Images were collected at each temperature, and the sum of the pixel intensity in a given area of the assay plate was recorded versus temperature. Reference wells contained RORγt without compounds, and the assay conditions were as follows:

0.065 mg/mL RORγt
60 µM 1,8-ANS
100 mM Hepes, pH 7.0
10 mM NaCl
2.5 mM GSH
0.002% Tween-20

Project compounds were arranged in a pre-dosed mother plate (Greiner Bio-one) wherein compounds are serially diluted in 100% DMSO by 1:2 from a high concentration of 10 mM over 12 columns within a series (column 12 is a reference well containing DMSO, no compound). The compounds were robotically dispensed directly into assay plates (×=46 nL) using a Hummingbird capillary liquid handling instrument (Digilab). Following compound dispense, protein and dye in buffer was added to achieve the final assay volume of 3 µL, followed by 1 µL of silicone oil.

The binding affinity was estimated as described previously (Matulis, D., Kranz, J. K., Salemme, F. R., and Todd, M. J. (2005) Thermodynamic stability of carbonic anhydrase: measurements of binding affinity and stoichiometry using ThermoFluor®. *Biochemistry* 44, 5258-66) using the following thermodynamic parameters of protein unfolding:

Reference RORγt Tm: 47.8° C.
$\Delta H_{(Tm)}$=115 kcal/mol
$\Delta C_{p(Tm)}$=3 kcal/mol Cell Based Biological Data RORγt (Full-Length Human) Reporter Assay:

Three similar reporter assay protocols, shown below, have been used to test the functional activity of RORγt modulatory compounds on transcriptional activation driven by full-length human RORγt. All three provide similar data and can be used interchangeably.

Conditions A

Cells used in this assay were transiently co-transfected with three different plasmids, one expressing the GAL4-DNA binding domain (DBD)-RORγt fusion protein under control of a CMV promoter (NH2-Gal4-DBD:RORC-COOH in pCMV-BD, Stratagene #211342), and two reporter plasmids—the firefly luciferase reporter under control of a GAL4 promoter (pFR-Luc 2×GAL4) and Renilla luciferase reporter under control of CMV promoter (pRL-CMV, Promega # E2261). The full-length coding sequence was used for human RORγt, i.e., nucleotides 142-1635 of human RORγt, transcript variant 2, NCBI Accession:

NM_001001523.1 (SEQ ID NO:1). HEK293T cells were plated at 35000 per well in 96-well plate in medium of MEM with 8.6% FBS. After 18-22 hours incubation, the transfection was carried out by using a PEI solution with 170.5 ng total DNA/well (50 ng pCMV-BD-ROR plus 20 ng of pFR-Luc reporter and 0.5 ng of pRL-CMV reporter plus 100 ng Carrier DNA (Clontech #630440) for each well). 4-6 hours after transfection, cells were treated with compounds for overnight in the medium with final concentration of FBS 1.1% and DMSO 0.1%. After overnight (16 to 20 hours) incubation, media were removed and cells were lysed with 20 µL 1× Passive Lysis Buffer (Promega) for 10-15 minutes. Luminescence was measured using a BMG LUMIstar OPTIMA plate reader, after addition of 75 µL/well firefly luciferase buffer, followed by 75 µL/well Renilla luciferase buffer. To calculate the effect of compounds on RORγt activity, firefly values were normalized against values of DMSO only and values of reference compound at saturating concentration, then further normalized against Renilla signals. $IC_{50}$s were generated by plotting final Renilla normalized data against compound concentration and percent inhibition was calculated against DMSO control.

Conditions B

Cells used in this assay were transiently co-transfected with three different plasmids, one expressing the GAL4-DNA binding domain (DBD)-RORγt fusion protein under control of a CMV promoter (NH2-Gal4-DBD:RORC-COOH in pCMV-BD, Stratagene #211342), and two reporter plasmids—the firefly luciferase reporter under control of a GAL4 promoter (pFR-Luc 2×GAL4) and Renilla luciferase reporter under control of CMV promoter (pRL-CMV, Promega # E2261). The full-length coding sequence was used for human RORγt, i.e., nucleotides 142-1635 of human RORγt, transcript variant 2, NCBI Accession: NM_001001523.1 (SEQ ID NO:1). HEK293T cells were plated at 35,000 per well in 96-well plate in medium of DMEM with 10% FBS. After 18-22 hours incubation, the transfection was carried out by using a PEI solution with 170.5 ng total DNA/well (50 ng pCMV-BD-ROR plus 20 ng of pFR-Luc reporter and 0.5 ng of pRL-CMV reporter plus 100 ng Carrier DNA (Clontech #630440) for each well). 4-6 hours after transfection, cells were treated with compounds for overnight in the medium with final concentration of FBS 1.3% and DMSO 0.1%. After overnight (16 to 20 hours) incubation, media were removed and cells were lysed with 50 µL Glo Lysis Buffer (Promega) for 10-15 minutes followed by 10 minute incubation with 50 µL Dual Glo reagent (Promega) at room temperature. Firefly luciferase luminescence was measured using a BMG Pherastar plate reader. To each well, 50 µL Stop and Glo reagent was added and incubated for 10 minutes at room temperature. Renilla luminescence was measured using a BMG Pherastar plate reader. To calculate the effect of compounds on RORγt activity, firefly values were normalized against values of DMSO only and values of reference compound at saturating concentration, then further normalized against Renilla signals. IC50s were generated by plotting final Renilla normalized data against compound concentration and percent inhibition was calculated against DMSO control.

Conditions C

Cells used in this assay were transiently co-transfected with three different plasmids, one expressing the GAL4-DNA binding domain (DBD)-RORγt fusion protein under control of a CMV promoter ($NH_2$-Gal4-DBD:RORC-COOH in pCMV-BD, Stratagene #211342), and two reporter plasmids—the firefly luciferase reporter under control of a GAL4 promoter (pFR-Luc 2×GAL4) and Renilla luciferase reporter under control of CMV promoter (pRL-CMV, Promega # E2261). The full-length coding sequence was used for human RORγt, i.e., nucleotides 142-1635 of human RORγt, transcript variant 2, NCBI Accession: NM_001001523.1 (SEQ ID NO:1). HEK293T cells were plated at 8750 cells per well in 384-well plate in medium of DMEM with 10% FBS. After 18-22 hours incubation, the transfection was carried out by using a PEI solution with 42.6 ng total DNA/well (12.5 ng pCMV-BD-ROR plus 5 ng of pFR-Luc reporter and 0.125 ng of pRL-CMV reporter plus 25 ng Carrier DNA (Clontech #630440) for each well). 4-6 hours after transfection, cells were treated with compounds for overnight in the medium with final concentration of FBS 1.3% and DMSO 0.1%. After overnight (16 to 20 hours) incubation, media were removed and cells were lysed with 20 µL Glo Lysis Buffer (Promega) for 10-15 minutes followed by 10 minute incubation with 20 µL Dual Glo reagent (Promega) at room temperature. Firefly luciferase luminescence was measured using a BMG Pherastar plate reader. To each well, 20 µL Stop and Glo reagent was added and incubated for 10 minutes at room temperature. Renilla luminescence was measured using a BMG Pherastar plate reader. To calculate the effect of compounds on RORγt activity, firefly values were normalized against values of DMSO only and values of reference compound at saturating concentration, then further normalized against Renilla signals. $IC_{50}$s were generated by plotting final Renilla normalized data against compound concentration and percent inhibition was calculated against DMSO control.

Human Th17 Assay

The human Th17 assay tests the effect of RORγt modulatory compounds on IL-17 production by CD4 T cells under conditions which favor Th17 differentiation. Total $CD4^+$ T cells were isolated from the peripheral blood mononuclear cells (PBMC) of healthy donors using a $CD4^+$ T cell isolation kit II, following the manufacturer's instructions (Miltenyi Biotec). Cells were resuspended in a medium of RPMI-1640 supplemented with 10% fetal bovine serum, penicillin, streptomycin, glutamate, and β-mercaptoethanol and were added to 96-well plates at $1.5 \times 10^5$ per 100 µL per well. 50 µL of compound at titrated concentrations in DMSO were added into each well at final DMSO concentration at 0.2%. Cells were incubated for 1 hour, then 50 µL of Th17 cell differentiation medium was added to each well. The final concentrations of antibodies and cytokines (R&D Systems) in differentiation medium were: $3 \times 10^6$/mL anti-CD3/CD28 beads (prepared using human T cell activation/expansion kit, Miltenyi Biotec), 10 µg/mL anti-IL4, 10 µg/mL anti-IFNγ, 10 ng/mL IL1β, 10 ng/mL IL23, 50 ng/mL IL6, 3 ng/mL TGFβ and 20 U/mL IL2. Cells were cultured at 37° C. and 5% $CO_2$ for 3 days. Supernatants were collected and the accumulated IL-17 in culture was measured by using MULTI-SPOT® Cytokine Plate following manufacture's instruction (Meso Scale Discovery). The plate was read using Sector Imager 6000, and IL-17 concentration was extrapolated from the standard curve. The IC50s were determined by GraphPad.

TABLE 1

| Example # | ThermoFluor ® Assay, Kd (µM) | RORγt (FL) Reporter Assay A, IC$_{50}$ (µM) | RORγt (FL) Reporter Assay A, % inhibition @ 6 µM | RORγt (FL) Reporter Assay B or C, IC$_{50}$ (µM) | RORγt (FL) Reporter Assay B or C, % inhibition @ 6 µM | Human Th17 Assay, IC$_{50}$ (µM) |
|---|---|---|---|---|---|---|
| 1 | 0.035 | 0.079 | 100** | ND | ND | ND |
| 2 | 0.040 | ND | ND | 0.077 | 95* | ND |
| 3 | 0.0096 | 0.035 | 106** | ND | ND | 0.040 |
| 4 | 0.00098 | 0.0090 | 106 | ND | ND | ND |
| 5 | 0.00025 | 0.0090 | 104 | ND | ND | ND |
| 6 | ~0.010 | 0.16 | 110 | ND | ND | ND |
| 7 | 0.23 | 0.62 | 80 | ND | ND | ND |
| 8 | 0.12 | 0.34 | 95 | ND | ND | ND |
| 9 | 0.077 | 0.33 | 104 | ND | ND | ND |
| 10 | 0.0081 | 0.071 | 108 | ND | ND | ND |
| 11 | 0.0026 | 0.017 | 107** | ND | ND | ND |
| 12 | 0.063 | 0.85 | 92 | ND | ND | 0.19 |
| 13 | 0.037 | 0.10 | 99** | ND | ND | ND |
| 14 | 0.033 | 0.076 | 105 | ND | ND | ND |
| 15 | 0.0075 | 0.039 | 105** | ND | ND | ND |
| 16 | 0.13 | 0.47 | 105 | ND | ND | ND |
| 17 | 0.00015 | 0.0090 | 95** | ND | ND | ND |
| 18 | 0.080 | 0.62 | 106 | ND | ND | ND |
| 19 | 0.0044 | 0.032 | 99 | ND | ND | 0.040 |
| 20 | 0.052 | 0.20 | 110 | ND | ND | ND |
| 21 | 0.13 | 0.54 | 100 | ND | ND | ND |
| 22 | 0.44 | 0.91 | 84 | ND | ND | ND |
| 23 | 0.030 | 0.079 | 96 | ND | ND | ND |
| 24 | 0.020 | 0.097 | 107 | ND | ND | ND |
| 25 | 0.12 | ND | ND | 0.22 | 102.03 | ND |
| 26 | 0.0095 | ND | ND | 0.037 | 110.91 | ND |
| 27 | 0.00052 | ND | ND | 0.0084 | 106.29 | 0.016 |
| 28 | 0.00017 | ND | ND | 0.014 | 123.45 | ND |
| 29 | 0.022 | ND | ND | 0.022 | 104.84 | ND |
| 30 | 0.0028 | ND | ND | 0.020 | 103.81 | ND |
| 31 | 0.00015 | ND | ND | 0.0045 | 110.67 | ND |
| 32 | 0.00026 | ND | ND | 0.0022 | 108.97 | ND |
| 33 | 0.00043 | ND | ND | 0.0052 | 108.55 | ND |
| 34 | 0.00029 | ND | ND | 0.0069 | 105.12 | ND |
| 35 | 0.0039 | ND | ND | 0.020 | 113.8 | ND |
| 36 | 0.0017 | ND | ND | 0.016 | 116.32 | ND |
| 37 | 0.00065 | ND | ND | 0.014 | 92.175 | 0.052 |
| 38 | 0.0018 | ND | ND | 0.015 | 108.34 | 0.081 |
| 39 | 0.00012 | ND | ND | 0.013 | 104.57 | ND |
| 40 | 0.0028 | ND | ND | 0.013 | 102.02 | 0.056 |
| 41 | 0.00074 | ND | ND | 0.0076 | 103.11 | 0.043 |
| 42 | 0.0093 | ND | ND | 0.042 | 110.78 | ND |
| 43 | 0.0049 | ND | ND | 0.022 | 107.46 | ND |
| 44 | 0.0025 | ND | ND | 0.020 | 111.26 | ND |
| 45 | 0.00062 | ND | ND | 0.010 | 110.64 | ND |
| 46 | 0.0042 | ND | ND | 0.029 | 100* | ND |
| 47 | 0.00050 | ND | ND | 0.0054 | 96* | 0.0098 |
| 48 | 0.011 | ND | ND | 0.023 | 111* | ND |
| 49 | 0.0033 | ND | ND | 0.0076 | 99* | ND |
| 50 | 0.071 | ND | ND | 0.058 | 100* | ND |
| 51 | 0.0032 | ND | ND | 0.0048 | 101* | 0.021 |
| 52 | 0.0012 | ND | ND | 0.0088 | 106* | 0.010 |
| 53 | 0.0058 | ND | ND | 0.023 | 109* | ND |
| 54 | 0.012 | ND | ND | 0.046 | 109* | ND |
| 55 | 0.0079 | ND | ND | 0.031 | 92* | ND |
| 56 | 0.00034 | ND | ND | 0.0036 | 106* | ND |
| 57 | 0.079 | 0.078 | 106 | ND | ND | ND |
| 58 | 0.17 | 0.77 | 93 | ND | ND | ND |
| 59 | ND | 0.70 | 88 | ND | ND | ND |
| 60 | 0.16 | 0.43 | 90.333 | ND | ND | ND |
| 61 | 0.0070 | ND | ND | 0.013 | 103* | ND |
| 62 | 0.012 | 0.16 | 98 | ND | ND | ND |
| 63 | ND | 0.25 | 96 | ND | ND | ND |
| 64 | 0.017 | 0.063 | 96 | ND | ND | 0.22 |
| 65 | ND | 0.21 | 103 | ND | ND | ND |
| 66 | 0.041 | 0.15 | 85 | ND | ND | ND |
| 67 | 0.052 | 0.40 | 98 | ND | ND | ND |
| 68 | 0.37 | 1.1 | 70 | ND | ND | ND |
| 69 | 0.17 | 0.63 | 85 | ND | ND | ND |
| 70 | 0.036 | 0.13 | 108 | ND | ND | ND |
| 71 | 0.0037 | ND | ND | 0.013 | 111* | ND |
| 72 | 0.035 | ND | ND | 0.089 | 104* | ND |
| 73 | 0.011 | ND | ND | 0.074 | 104* | ND |
| 74 | 0.073 | ND | ND | 0.032 | 101* | ND |

TABLE 1-continued

| Example # | ThermoFluor ® Assay, Kd (μM) | RORγt (FL) Reporter Assay A, IC$_{50}$ (μM) | RORγt (FL) Reporter Assay A, % inhibition @ 6 μM | RORγt (FL) Reporter Assay B or C, IC$_{50}$ (μM) | RORγt (FL) Reporter Assay B or C, % inhibition @ 6 μM | Human Th17 Assay, IC$_{50}$ (μM) |
|---|---|---|---|---|---|---|
| 75 | −0.00023 | ND | ND | 0.0070 | 108** | 0.014 |
| 76 | −0.00034 | ND | ND | 0.0038 | 108.44 | 0.020 |
| 77 | 0.0013 | ND | ND | 0.017 | 108* | ND |
| 78 | 0.0032 | ND | ND | 0.049 | 110* | 0.014 |
| 79 | 0.0012 | ND | ND | 0.0083 | 111* | ND |
| 80 | 0.00019 | ND | ND | 0.0047 | 111* | ND |
| 81 | 0.00017 | ND | ND | 0.0093 | 105* | ND |
| 82 | 0.0048 | ND | ND | 0.079 | 117* | ND |
| 83 | 0.00055 | ND | ND | 0.0069 | 110*** | ND |
| 84 | 0.0012 | ND | ND | 0.018 | 136* | ND |
| 85 | 0.00053 | ND | ND | 0.027 | 128*** | ND |
| 86 | 0.00017 | ND | ND | 0.013 | 127* | 0.0028 |
| 87 | 0.0013 | ND | ND | 0.029 | 140* | 0.025 |
| 88 | 0.00019 | ND | ND | 0.010 | 138* | ND |
| 89 | 0.0052 | ND | ND | 0.024 | 100* | ND |
| 90 | 0.0014 | ND | ND | 0.11 | 86* | 0.076 |
| 91 | 0.00052 | ND | ND | 0.030 | 96* | 0.019 |
| 92 | 0.0034 | ND | ND | 0.071 | 106* | ND |
| 93 | 0.0011 | ND | ND | 0.010 | 121* | ND |
| 94 | 0.00036 | ND | ND | 0.012 | 115* | ND |
| 95 | 0.00015 | ND | ND | 0.0095 | 109* | ND |
| 96 | 0.0012 | ND | ND | 0.037 | 119* | ND |
| 97 | 0.0013 | ND | ND | 0.0036 | 111* | ND |
| 98 | 0.00041 | ND | ND | 0.0096 | 110* | ND |
| 99 | 0.00058 | ND | ND | 0.011 | 108* | ND |
| 100 | 0.00039 | ND | ND | 0.014 | 108* | ND |
| 101 | 0.0032 | ND | ND | 0.019 | 107* | ND |
| 102 | 0.00099 | ND | ND | 0.017 | 116* | ND |
| 103 | 0.00026 | ND | ND | 0.0039 | 110* | ND |
| 104 | 0.00064 | ND | ND | 0.025 | 110* | ND |
| 105 | 0.0020 | ND | ND | 0.015 | 116* | ND |
| 106 | 0.00079 | ND | ND | 0.022 | 117* | ND |
| 107 | 0.00026 | ND | ND | 0.011 | 111* | ND |
| 108 | 0.000070 | ND | ND | 0.047 | 104* | ND |
| 109 | 0.00053 | ND | ND | 0.018 | 124* | ND |
| 110 | 0.0022 | ND | ND | 0.026 | 112* | ND |
| 111 | 0.0018 | ND | ND | 0.029 | 106* | 0.017 |
| 112 | 0.00020 | ND | ND | 0.013 | 110* | ND |
| 113 | 0.0060 | ND | ND | 0.063 | 110* | ND |
| 114 | 0.00049 | ND | ND | 0.0097 | 117* | ND |
| 115 | 0.0019 | ND | ND | 0.028 | 115* | 0.022 |
| 116 | 0.0036 | ND | ND | 0.034 | 110* | 0.044 |
| 117 | 0.00078 | ND | ND | 0.0033 | 107* | ND |
| 118 | 0.00043 | ND | ND | 0.0071 | 109**** | ND |
| 119 | 0.0015 | ND | ND | 0.017 | 108* | ND |
| 120 | 0.0017 | ND | ND | 0.026 | 103* | ND |
| 121 | 0.00065 | ND | ND | 0.025 | 104* | ND |
| 122 | 0.0017 | ND | ND | 0.033 | 102* | 0.020 |
| 123 | 0.0019 | ND | ND | 0.013 | 105* | ND |
| 124 | 0.00052 | ND | ND | 0.021 | 108* | 0.0067 |
| 125 | 0.0024 | ND | ND | 0.059 | 100* | ND |
| 126 | 0.00085 | ND | ND | 0.069 | 98* | ND |
| 127 | 0.0062 | ND | ND | 0.11 | 114* | ND |
| 128 | 0.0026 | ND | ND | 0.023 | 107* | 0.018 |
| 129 | 0.0030 | ND | ND | 0.011 | 104* | ND |
| 130 | 0.0016 | ND | ND | 0.030 | 98*** | ND |
| 131 | 0.0014 | ND | ND | 0.030 | 107* | ND |
| 132 | 0.00041 | ND | ND | 0.014 | 112* | ND |
| 133 | 0.0045 | ND | ND | 0.028 | 105* | ND |
| 134 | 0.0012 | ND | ND | 0.014 | 108* | ND |
| 135 | 0.0035 | ND | ND | 0.039 | 100* | 0.044 |
| 136 | 0.016 | ND | ND | 0.79 | 109* | ND |
| 137 | 0.0011 | ND | ND | 0.012 | 97* | ND |
| 138 | 0.00062 | ND | ND | 0.012 | 100*** | ND |
| 139 | 0.0011 | ND | ND | 0.012 | 107* | ND |
| 140 | 0.0017 | ND | ND | 0.011 | 89* | 0.011 |
| 141 | 0.00068 | ND | ND | 0.023 | 100* | 0.0055 |
| 142 | 0.0014 | ND | ND | 0.027 | 109* | 0.019 |
| 143 | 0.0023 | ND | ND | 0.039 | 114* | ND |
| 144 | 0.0015 | ND | ND | 0.076 | 106* | 0.013 |
| 145 | 0.0077 | ND | ND | 0.074 | 76*** | ND |
| 146 | 0.21 | ND | ND | 0.83 | 98* | ND |
| 147 | 0.0094 | ND | ND | 0.12 | 94*** | ND |
| 148 | 0.0064 | ND | ND | 0.025 | 95* | ND |

TABLE 1-continued

| Example # | ThermoFluor ® Assay, Kd (µM) | RORγt (FL) Reporter Assay A, IC$_{50}$ (µM) | RORγt (FL) Reporter Assay A, % inhibition @ 6 µM | RORγt (FL) Reporter Assay B or C, IC$_{50}$ (µM) | RORγt (FL) Reporter Assay B or C, % inhibition @ 6 µM | Human Th17 Assay, IC$_{50}$ (µM) |
|---|---|---|---|---|---|---|
| 149 | 0.020 | ND | ND | 0.10 | 108* | ND |
| 150 | 0.0032 | ND | ND | 0.035 | 111* | ND |
| 151 | 0.00087 | ND | ND | 0.015 | 104* | ND |
| 152 | 0.00088 | ND | ND | 0.011 | 101.5 | ND |
| 153 | 0.0011 | ND | ND | 0.052 | 98* | ND |
| 154 | 0.0010 | ND | ND | 0.098 | 99* | ND |
| 155 | 0.0011 | ND | ND | 0.0058 | 103* | ND |
| 156 | 0.0010 | ND | ND | 0.044 | 102* | ND |
| 157 | 0.032 | ND | ND | 0.19 | 89* | ND |
| 158 | 0.017 | ND | ND | 0.31 | 96* | ND |
| 159 | 0.022 | ND | ND | 0.032 | 93*** | ND |
| 160 | 0.0087 | ND | ND | 0.41 | 101* | ND |
| 161 | 0.00078 | ND | ND | 0.020 | 106* | ND |
| 162 | 0.0095 | ND | ND | 0.031 | 104* | ND |
| 163 | 0.014 | ND | ND | 0.012 | 114* | ND |
| 164 | 0.0046 | ND | ND | 0.023 | 105* | ND |
| 165 | 0.0031 | ND | ND | 0.040 | 98* | ND |
| 166 | 0.0047 | ND | ND | 0.027 | 94* | ND |
| 167 | 0.0037 | ND | ND | 0.12 | 100* | ND |
| 168 | 0.0018 | ND | ND | 0.20 | 106* | ND |
| 169 | 0.0027 | ND | ND | 0.012 | 94* | 0.034 |
| 170 | 0.0019 | ND | ND | 0.024 | 101* | ND |
| 171 | 0.0040 | ND | ND | 0.016 | 108* | ND |
| 172 | 0.0012 | ND | ND | 0.039 | 102* | ND |
| 173 | 0.0058 | ND | ND | 0.055 | 95* | ND |
| 174 | 0.0014 | ND | ND | 0.025 | 106* | ND |
| 175 | 0.0058 | ND | ND | 0.044 | 119*** | ND |
| 176 | 0.0013 | ND | ND | 0.015 | 115*** | ND |
| 177 | 0.00097 | ND | ND | 0.0066 | 117* | ND |
| 178 | 0.0020 | ND | ND | 0.0055 | 102* | ND |
| 179 | 0.0022 | ND | ND | 0.018 | 105* | ND |
| 180 | 0.0018 | ND | ND | 0.020 | 113* | ND |
| 181 | 0.0011 | ND | ND | 0.0085 | 112* | ND |
| 182 | 0.00012 | ND | ND | 0.0081 | 99* | ND |
| 183 | 0.00022 | ND | ND | 0.034 | 76* | ND |
| 184 | 0.00070 | ND | ND | 0.049 | 92* | ND |
| 185 | 0.00023 | ND | ND | 0.015 | 101* | ND |
| 186 | 0.00018 | ND | ND | 0.016 | 98* | ND |
| 187 | 0.0068 | ND | ND | 0.14 | 85* | ND |
| 188 | 0.047 | ND | ND | 0.54 | 85* | ND |
| 189 | 0.0036 | ND | ND | 0.098 | 101* | ND |
| 190 | 0.0038 | ND | ND | 0.034 | 104* | ND |
| 191 | 0.018 | ND | ND | 0.032 | 98* | ND |
| 192 | 0.0028 | ND | ND | 0.037 | 101* | ND |
| 193 | 0.0026 | ND | ND | 0.032 | 82* | ND |
| 194 | 0.0047 | ND | ND | 0.088 | 85* | ND |
| 195 | 0.00043 | ND | ND | 0.033 | 85* | ND |
| 196 | 0.00064 | ND | ND | 0.027 | 109* | ND |
| 197 | 0.0017 | ND | ND | 0.066 | 91* | 0.030 |
| 198 | 0.0025 | ND | ND | 0.053 | 102* | ND |
| 199 | 0.0054 | ND | ND | 0.12 | 94* | 0.10 |
| 200 | 0.012 | ND | ND | 0.20 | 104* | ND |
| 201 | 0.00061 | ND | ND | 0.016 | 102* | ND |
| 202 | 0.0013 | ND | ND | 0.017 | 98* | ND |
| 203 | 0.0015 | ND | ND | 0.042 | 97* | ND |
| 204 | 0.0036 | ND | ND | 0.024 | 105* | ND |
| 205 | 0.0068 | ND | ND | 0.033 | 103* | ND |
| 206 | 0.0032 | ND | ND | 0.035 | 106*** | ND |
| 207 | 0.0026 | ND | ND | 0.019 | 103*** | ND |
| 208 | 0.0044 | ND | ND | 0.054 | 101* | ND |
| 209 | 0.0034 | ND | ND | 0.046 | 99* | ND |
| 210 | 0.00069 | ND | ND | 0.021 | 105* | ND |
| 211 | 0.0082 | ND | ND | 0.014 | 104* | ND |
| 212 | 0.013 | ND | ND | 0.30 | 104* | ND |
| 213 | 0.0061 | ND | ND | 0.019 | 103* | ND |
| 214 | 0.012 | ND | ND | 0.075 | 98* | ND |
| 215 | 0.012 | ND | ND | 0.10 | 107* | ND |
| 216 | 0.0041 | ND | ND | 0.0095 | 96* | ND |
| 217 | 0.0032 | ND | ND | 0.019 | 109* | ND |
| 218 | 0.0078 | ND | ND | 0.045 | 111* | ND |
| 219 | 0.0041 | ND | ND | 0.020 | 112* | ND |
| 220 | 0.0061 | ND | ND | 0.013 | 111***** | ND |
| 221 | 0.027 | ND | ND | 0.078 | 103* | ND |
| 222 | 0.010 | ND | ND | 0.012 | 113* | ND |

TABLE 1-continued

| Example # | ThermoFluor ® Assay, Kd (µM) | RORγt (FL) Reporter Assay A, IC$_{50}$ (µM) | RORγt (FL) Reporter Assay A, % inhibition @ 6 µM | RORγt (FL) Reporter Assay B or C, IC$_{50}$ (µM) | RORγt (FL) Reporter Assay B or C, % inhibition @ 6 µM | Human Th17 Assay, IC$_{50}$ (µM) |
|---|---|---|---|---|---|---|
| 223 | 0.033 | ND | ND | 0.10 | 112* | ND |
| 224 | 0.0027 | ND | ND | 0.026 | 112* | ND |
| 225 | 0.00095 | ND | ND | 0.0068 | 110* | ND |
| 226 | 0.014 | ND | ND | 0.14 | 94* | ND |
| 227 | 0.0046 | ND | ND | 0.014 | 95* | ND |
| 228 | 0.0023 | ND | ND | 0.095 | 91*** | ND |
| 229 | 0.00097 | ND | ND | 0.042 | 83* | ND |
| 230 | 0.0024 | ND | ND | 0.015 | 99* | ND |
| 231 | 0.0014 | ND | ND | 0.058 | 92* | ND |
| 232 | 0.0034 | ND | ND | 0.069 | 122* | ND |
| 233 | 0.010 | ND | ND | 0.022 | 124* | ND |
| 234 | 0.0052 | ND | ND | 0.042 | 116* | ND |
| 235 | 0.0012 | ND | ND | 0.034 | 106* | ND |
| 236 | 0.0016 | ND | ND | 0.047 | 122* | ND |
| 237 | 0.0023 | ND | ND | 0.031 | 101* | ND |
| 238 | 0.0055 | ND | ND | 0.029 | 92* | ND |
| 239 | 0.0054 | ND | ND | 0.019 | 105* | ND |
| 240 | 0.0025 | ND | ND | 0.057 | 107* | ND |
| 241 | 0.00059 | ND | ND | 0.024 | 103* | ND |
| 242 | 0.0028 | ND | ND | 0.015 | 86* | ND |
| 243 | 0.0073 | ND | ND | 0.0068 | 95* | 0.063 |
| 244 | 0.0062 | ND | ND | 0.0083 | 106* | ND |
| 245 | 0.0016 | ND | ND | 0.026 | 98* | ND |
| 246 | 0.0013 | ND | ND | 0.011 | 112*** | ND |
| 247 | 0.00028 | ND | ND | 0.023 | 100* | ND |
| 248 | 0.0034 | ND | ND | 0.016 | 102* | ND |
| 249 | 0.0081 | ND | ND | 0.024 | 103* | ND |
| 250 | 0.0081 | ND | ND | 0.028 | 106* | ND |
| 251 | 0.021 | ND | ND | 0.072 | 104* | ND |
| 252 | 0.0012 | ND | ND | 0.035 | 106* | ND |
| 253 | 0.0019 | ND | ND | 0.0077 | 108* | ND |
| 254 | 0.00025 | ND | ND | 0.016 | 107* | ND |
| 255 | 0.016 | ND | ND | 0.16 | 78*** | ND |
| 256 | 0.0017 | ND | ND | 0.020 | 123* | ND |
| 257 | 0.0018 | ND | ND | 0.031 | 98* | ND |
| 258 | 0.0035 | ND | ND | 0.065 | 110* | ND |
| 259 | 0.0030 | ND | ND | 0.025 | 101* | ND |
| 260 | 0.0007 | ND | ND | 0.014 | 112* | ND |
| 261 | 0.0026 | ND | ND | 0.023 | 104* | ND |
| 262 | 0.0016 | ND | ND | 0.020 | 104* | ND |
| 263 | 0.0011 | ND | ND | 0.0066 | 107* | ND |
| 264 | 0.0049 | ND | ND | 0.028 | 112* | ND |
| 265 | 0.0064 | ND | ND | 0.075 | 98* | ND |
| 266 | 0.0044 | ND | ND | 0.050 | 100* | ND |
| 267 | 0.0033 | ND | ND | 0.047 | 102* | ND |
| 268 | 0.0024 | ND | ND | 0.11 | 109* | ND |
| 269 | 0.0049 | ND | ND | 0.0082 | 101* | ND |
| 270 | 0.0035 | ND | ND | 0.0051 | 102* | ND |
| 271 | 0.0040 | ND | ND | 0.0057 | 106* | ND |
| 272 | 0.0021 | ND | ND | 0.018 | 105* | ND |
| 273 | 0.00051 | ND | ND | 0.0052 | 102* | ND |
| 274 | 0.00097 | ND | ND | 0.036 | 96* | ND |
| 275 | 0.0020 | ND | ND | 0.014 | 99* | ND |
| 276 | 0.0061 | ND | ND | 0.016 | 118*** | ND |
| 277 | 0.0024 | ND | ND | 0.011 | 113* | ND |
| 278 | 0.0074 | ND | ND | 0.040 | 100* | ND |
| 279 | 0.018 | ND | ND | 0.062 | 109*** | ND |
| 280 | 0.0049 | ND | ND | 0.016 | 110* | ND |
| 281 | 0.21 | ND | ND | 0.83 | 98* | ND |
| 282 | 0.0014 | ND | ND | 0.019 | 109* | ND |
| 283 | 0.0019 | ND | ND | 0.054 | 106* | ND |
| 284 | 0.0081 | ND | ND | 0.11 | 111* | ND |
| 285 | 0.0029 | ND | ND | 0.064 | 104* | ND |
| 286 | 0.011 | ND | ND | 0.14 | 104* | ND |
| 287 | 0.0043 | ND | ND | 0.034 | 109* | ND |
| 288 | 0.0044 | ND | ND | 0.029 | 103* | ND |
| 289 | 0.0038 | ND | ND | 0.069 | 99* | ND |
| 290 | 0.0063 | ND | ND | 0.0065 | 103* | ND |
| 291 | 0.0069 | ND | ND | 0.12 | 113* | ND |
| 292 | 0.0061 | ND | ND | 0.040 | 106* | ND |
| 293 | 0.0020 | ND | ND | 0.013 | 94* | ND |
| 294 | 0.0013 | ND | ND | 0.013 | 100* | ND |
| 295 | 0.0029 | ND | ND | 0.014 | 108* | ND |
| 296 | 0.00050 | ND | ND | 0.0071 | 108* | ND |

TABLE 1-continued

| Example # | ThermoFluor® Assay, Kd (μM) | RORγt (FL) Reporter Assay A, IC$_{50}$ (μM) | RORγt (FL) Reporter Assay A, % inhibition @ 6 μM | RORγt (FL) Reporter Assay B or C, IC$_{50}$ (μM) | RORγt (FL) Reporter Assay B or C, % inhibition @ 6 μM | Human Th17 Assay, IC$_{50}$ (μM) |
|---|---|---|---|---|---|---|
| 297 | 0.018 | ND | ND | 0.050 | 110* | ND |
| 298 | 0.0034 | ND | ND | 0.0077 | 99* | ND |
| 299 | 0.00091 | ND | ND | 0.011 | 103* | ND |
| 300 | 0.0016 | ND | ND | 0.029 | 100* | ND |
| 301 | 0.030 | ND | ND | 0.084 | 95* | ND |
| 302 | 0.049 | ND | ND | >3.0 | 86* | ND |
| 303 | 0.015 | ND | ND | 0.74 | 88* | ND |
| 304 | 0.0051 | ND | ND | 0.092 | 102* | ND |
| 305 | 0.0049 | ND | ND | 0.036 | 100* | 0.089 |
| 306 | 0.010 | ND | ND | 0.13 | 104* | ND |
| 307 | 0.043 | ND | ND | 0.15 | 102* | ND |
| 308 | 0.096 | ND | ND | 0.26 | 107* | ND |
| 309 | 0.016 | ND | ND | 0.013 | 95* | ND |
| 310 | 0.0087 | ND | ND | 0.036 | 92* | ND |
| 311 | 0.0037 | ND | ND | 0.040 | 107* | ND |
| 312 | 0.0022 | ND | ND | 0.027 | 106* | ND |
| 313 | 0.00074 | ND | ND | 0.036 | 106* | ND |
| 314 | 0.0014 | ND | ND | 0.035 | 101* | ND |
| 315 | 0.0029 | ND | ND | 0.015 | 99*** | ND |
| 316 | 0.0029 | ND | ND | 0.032 | 108* | ND |
| 317 | 0.0024 | ND | ND | 0.014 | 106* | ND |
| 318 | 0.0081 | ND | ND | 0.028 | 86* | 0.017 |
| 319 | 0.029 | ND | ND | 0.079 | 91* | ND |
| 320 | 0.0038 | ND | ND | 0.046 | 98* | ND |
| 321 | 0.0052 | ND | ND | 0.10 | 87* | ND |
| 322 | 0.0018 | ND | ND | 0.049 | 106* | ND |
| 323 | 0.0082 | ND | ND | 0.15 | 97*** | ND |
| 324 | 0.0024 | ND | ND | 0.038 | 93* | ND |
| 325 | 0.0012 | ND | ND | 0.12 | 96* | ND |
| 326 | 0.00071 | ND | ND | 0.097 | 90* | ND |
| 327 | 0.0020 | ND | ND | 0.011 | 93* | ND |
| 328 | 0.00031 | ND | ND | 0.051 | 87* | ND |
| 329 | 0.0017 | ND | ND | 0.038 | 89* | ND |
| 330 | 0.0042 | ND | ND | 0.016 | 93* | ND |
| 331 | 0.0015 | ND | ND | 0.023 | 81* | ND |
| 332 | 0.0015 | ND | ND | 0.089 | 107* | ND |
| 333 | 0.00078 | ND | ND | 0.030 | 98* | ND |
| 334 | 0.0014 | ND | ND | 0.007 | 106* | ND |
| 335 | 0.0013 | ND | ND | 0.040 | 102* | ND |
| 336 | 0.0011 | ND | ND | 0.0056 | 108* | 0.011 |
| 337 | 0.0029 | ND | ND | 0.013 | 105* | ND |
| 338 | 0.0039 | ND | ND | 0.0077 | 107* | ND |
| 339 | 0.00097 | ND | ND | 0.0029 | 109* | ND |
| 340 | 0.0053 | ND | ND | 0.011 | 111* | ND |
| 341 | 0.0040 | ND | ND | 0.0057 | 107* | ND |
| 342 | 0.0057 | ND | ND | 0.040 | 103* | ND |
| 343 | 0.0051 | ND | ND | 0.31 | 98* | ND |
| 344 | 0.0032 | ND | ND | 0.0053 | 53**** | ND |
| 345 | 0.016 | ND | ND | 0.063 | 111* | ND |
| 346 | 0.0014 | ND | ND | 0.013 | 112* | ND |
| 347 | 0.00038 | ND | ND | 0.0038 | 124* | ND |
| 348 | 0.00090 | ND | ND | 0.0031 | 105* | ND |
| 349 | 0.011 | ND | ND | 0.063 | 105* | ND |
| 350 | 0.0083 | ND | ND | 0.030 | 110* | ND |
| 351 | 0.00015 | ND | ND | 0.0080 | 92****** | ND |
| 352 | 0.0011 | ND | ND | 0.042 | 103* | ND |
| 353 | 0.0016 | ND | ND | 0.020 | 95* | ND |
| 354 | 0.00097 | ND | ND | 0.015 | 93* | ND |
| 355 | 0.022 | ND | ND | 0.17 | 98* | ND |
| 356 | 0.047 | ND | ND | 0.035 | 94* | ND |
| 357 | 0.0012 | ND | ND | 0.012 | 106* | ND |
| 358 | 0.0025 | ND | ND | 0.015 | 119* | ND |
| 359 | 0.0011 | ND | ND | 0.0076 | 125* | ND |
| 360 | 0.010 | ND | ND | 0.082 | 106* | ND |
| 361 | 0.00037 | ND | ND | 0.025 | 105* | ND |
| 362 | 0.0040 | ND | ND | 0.021 | 99* | ND |
| 363 | 0.013 | ND | ND | 0.13 | 111* | ND |
| 364 | 0.0079 | ND | ND | 0.039 | 111* | ND |
| 365 | 0.0081 | ND | ND | 0.052 | 92*** | ND |
| 366 | 0.010 | ND | ND | 0.063 | 97* | ND |
| 367 | 0.0021 | ND | ND | 0.021 | 99* | ND |
| 368 | 0.0017 | ND | ND | 0.0075 | 110* | ND |
| 369 | 0.00070 | ND | ND | 0.0066 | 106* | ND |
| 370 | 0.00069 | ND | ND | 0.010 | 96* | ND |

TABLE 1-continued

| Example # | ThermoFluor ® Assay, Kd (µM) | RORγt (FL) Reporter Assay A, IC$_{50}$ (µM) | RORγt (FL) Reporter Assay A, % inhibition @ 6 µM | RORγt (FL) Reporter Assay B or C, IC$_{50}$ (µM) | RORγt (FL) Reporter Assay B or C, % inhibition @ 6 µM | Human Th17 Assay, IC$_{50}$ (µM) |
|---|---|---|---|---|---|---|
| 371 | 0.00088 | ND | ND | 0.019 | 108* | ND |
| 372 | 0.0092 | ND | ND | 0.059 | 125* | ND |
| 373 | 0.0019 | ND | ND | 0.0046 | 122* | ND |
| 374 | 0.0016 | ND | ND | 0.0048 | 121* | ND |
| 375 | 0.0057 | ND | ND | 0.029 | 105* | ND |
| 376 | 0.0038 | ND | ND | 0.060 | 101* | ND |
| 377 | 0.0034 | ND | ND | 0.032 | 91* | ND |
| 378 | 0.018 | ND | ND | 0.079 | 109* | ND |
| 379 | 0.0024 | ND | ND | 0.055 | 101* | ND |
| 380 | 0.0016 | ND | ND | 0.018 | 108* | ND |
| 381 | 0.0067 | ND | ND | 0.012 | 107* | ND |
| 382 | 0.047 | ND | ND | 0.30 | 107* | ND |
| 383 | 0.0026 | ND | ND | 0.092 | 108* | ND |
| 384 | 0.0050 | ND | ND | 0.070 | 98* | ND |
| 385 | 0.10 | ND | ND | 0.35 | 95* | ND |
| 386 | 0.0094 | ND | ND | 0.072 | 99* | ND |
| 387 | 0.0099 | ND | ND | 0.13 | 102* | ND |
| 388 | 0.0086 | ND | ND | 0.085 | 103* | ND |
| 389 | 0.0077 | ND | ND | 0.14 | 90* | ND |
| 390 | 0.012 | ND | ND | 0.028 | 99* | ND |
| 391 | 0.0042 | ND | ND | 0.035 | 106* | ND |
| 392 | 0.044 | ND | ND | 0.13 | 102* | ND |
| 393 | 0.029 | ND | ND | 0.027 | 118* | ND |
| 394 | 0.0020 | ND | ND | 0.034 | 114* | ND |
| 395 | 0.040 | ND | ND | 0.034 | 103* | ND |
| 396 | 0.0011 | ND | ND | 0.021 | 96* | ND |
| 397 | 0.0012 | ND | ND | 0.0090 | 118* | ND |
| 398 | 0.0015 | ND | ND | 0.039 | 109* | ND |
| 399 | 0.0012 | ND | ND | 0.025 | 100* | ND |
| 400 | 0.013 | ND | ND | 0.056 | 84* | ND |
| 401 | 0.0043 | ND | ND | 0.038 | 102*** | ND |
| 402 | 0.0058 | ND | ND | 0.037 | 99* | ND |
| 403 | 0.0045 | ND | ND | 0.036 | 108* | ND |
| 404 | 0.0038 | ND | ND | 0.015 | 98***** | ND |
| 405 | 0.0020 | ND | ND | 0.11 | 95* | ND |
| 406 | 0.0027 | ND | ND | 0.081 | 92***** | ND |
| 407 | 0.015 | ND | ND | 0.12 | 100* | ND |
| 408 | 0.0038 | ND | ND | 0.073 | 83* | ND |
| 409 | 0.0063 | ND | ND | 0.036 | 103* | ND |
| 410 | 0.0011 | ND | ND | 0.018 | 97* | ND |
| 411 | 0.0036 | ND | ND | 0.11 | 100* | ND |
| 412 | 0.0034 | ND | ND | 0.037 | 127* | ND |
| 413 | 0.00082 | ND | ND | 0.020 | 133*** | ND |
| 414 | 0.0017 | ND | ND | 0.013 | 110* | ND |
| 415 | 0.0011 | ND | ND | 0.064 | 97* | ND |
| 416 | 0.00043 | ND | ND | 0.037 | 89*** | ND |
| 417 | 0.0024 | ND | ND | 0.028 | 94*** | ND |
| 418 | 0.00077 | ND | ND | 0.032 | 105* | ND |
| 419 | 0.00021 | ND | ND | 0.034 | 84* | ND |
| 420 | 0.00073 | ND | ND | 0.032 | 103* | ND |
| 421 | 0.0010 | ND | ND | 0.064 | 98*** | ND |
| 422 | 0.00062 | ND | ND | 0.023 | 101* | ND |
| 423 | 0.0011 | ND | ND | 0.038 | 103* | ND |
| 424 | 0.00023 | ND | ND | 0.063 | 98* | ND |
| 425 | 0.00018 | ND | ND | 0.050 | 103* | ND |
| 426 | 0.00037 | ND | ND | 0.079 | 96* | ND |
| 427 | 0.0030 | ND | ND | 0.0030 | 113* | ND |
| 428 | 0.0010 | ND | ND | 0.017 | 113* | ND |
| 429 | 0.0025 | ND | ND | 0.0095 | 113**** | ND |
| 430 | 0.00060 | ND | ND | 0.013 | 130*** | ND |
| 431 | 0.00036 | ND | ND | 0.020 | 107* | ND |
| 432 | 0.0013 | ND | ND | 0.011 | 122**** | ND |
| 433 | 0.0012 | ND | ND | 0.025 | 128* | ND |
| 434 | 0.00063 | ND | ND | 0.011 | 103* | ND |
| 435 | 0.0023 | ND | ND | 0.021 | 105* | ND |
| 436 | 0.0010 | ND | ND | 0.048 | 117*** | ND |
| 437 | 0.00044 | ND | ND | 0.016 | 90* | ND |
| 438 | 0.0040 | ND | ND | 0.083 | 99*** | ND |
| 439 | 0.00027 | ND | ND | 0.010 | 102* | ND |
| 440 | 0.00072 | ND | ND | 0.031 | 104* | ND |
| 441 | 0.00047 | ND | ND | 0.036 | 106* | ND |
| 442 | 0.0016 | ND | ND | 0.32 | 96*** | ND |
| 443 | 0.0022 | ND | ND | 0.016 | 107* | ND |
| 444 | 0.0023 | ND | ND | 0.0045 | 102* | ND |

TABLE 1-continued

| Example # | ThermoFluor ® Assay, Kd (µM) | RORγt (FL) Reporter Assay A, IC$_{50}$ (µM) | RORγt (FL) Reporter Assay A, % inhibition @ 6 µM | RORγt (FL) Reporter Assay B or C, IC$_{50}$ (µM) | RORγt (FL) Reporter Assay B or C, % inhibition @ 6 µM | Human Th17 Assay, IC$_{50}$ (µM) |
|---|---|---|---|---|---|---|
| 445 | 0.012 | ND | ND | 0.096 | 73* | ND |
| 446 | 0.013 | ND | ND | 0.18 | 108* | ND |
| 447 | 0.0021 | ND | ND | 0.075 | 89* | ND |
| 448 | 0.00080 | ND | ND | 0.028 | 99* | ND |
| 449 | 0.0021 | ND | ND | 0.021 | 108* | ND |
| 450 | 0.050 | ND | ND | 0.23 | 106* | ND |
| 451 | 0.00029 | ND | ND | 0.29 | 99* | ND |

ND: value not determined.
*% inhibition is shown at 3 µM compound concentration,
**% inhibition is shown at 2 µM compound concentration,
***% inhibition is shown at 1 µM compound concentration,
****% inhibition is shown at 0.33 µM compound concentration,
*****% inhibition is shown at 0.3 µM compound concentration,
******% inhibition is shown at 0.11 µM compound concentration.

Comparative Data

The 6-amino-pyridin-3-yl thiazole compounds of the present invention demonstrate unexpectedly superior RORγt modulator activity compared to 2-amino-pyridin-3-yl thiazole and 5-amino-pyridin-3-yl thiazole analogs, as shown in Table 2.

TABLE 2

| Example # | Structure | ThermoFluor ® Assay, Kd (µM) | RORγt (FL) Reporter Assay B or C, IC$_{50}$ (µM) |
|---|---|---|---|
| Comparator Example 1 | 2-amino-pyridin-4-yl core | 3.0 | >6 |
| Comparator Example 2 | 5-amino-pyridin-3-yl core | 5.8 | 3 |

TABLE 2-continued

| Example # | Structure | ThermoFluor ® Assay, Kd (μM) | RORγt (FL) Reporter Assay B or C, IC$_{50}$ (μM) |
|---|---|---|---|
| 146 | 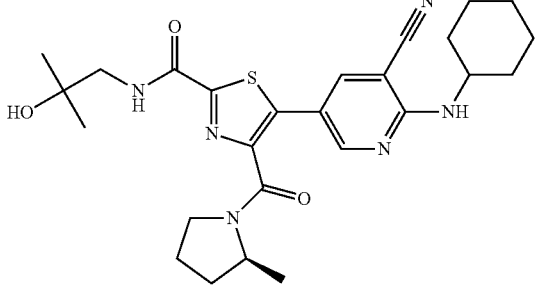 6-amino-pyridin-3-yl core | 0.21 | 0.83 |

Table 2 compares the inventive 6-amino-pyridin-3-yl thiazole compound of Example 146 to two analog compounds, Comparator Example 1, which is a 2-amino-pyridin-4-yl thiazole and Comparator Example 2, which is a 5-amino-pyridin-3-yl thiazole. The compound of the invention is surprisingly superior with 7.2 fold improvement in RORγt reporter assay activity compared to Comparator Example 1 and 3.6 fold improvement in RORγt reporter assay activity compared to Comparator Example 2. When comparing the same compounds in the Thermofluor® binding assay, the inventive compound, Example 146, is again surprisingly superior with 14 fold improvement in RORγt Thermofluor® binding assay activity compared to Comparator Example 1 and 27 fold improvement in RORγt Thermofluor® binding assay activity compared to Comparator Example 2.

In addition, the 6-amino-pyridin-3-yl thiazole compounds of the present invention demonstrate unexpectedly superior RORγt modulator activity compared to 6-sulfonamino analogs, as shown in Table 3.

TABLE 3

| Example # | Structure | ThermoFluor ® Assay, Kd (μM) | RORγt (FL) Reporter Assay A, IC$_{50}$ (μM) |
|---|---|---|---|
| Comparator Example 3 | 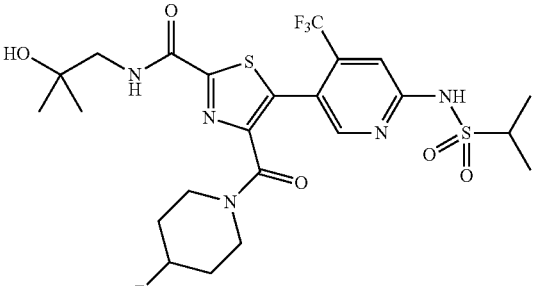 | 53 | >6 |
| 12 | 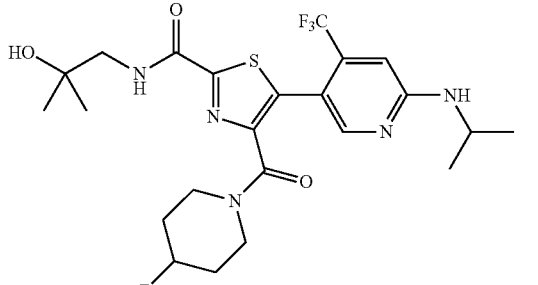 | 0.063 | 0.85 |

Thus, the compound of Example 12 demonstrated a desirable IC$_{50}$ of 0.85 μM. In contrast, the 6-sulfonamino analog demonstrated an IC$_{50}$ of greater than 6 μM, rendering it unsuitable for development as a therapeutic drug due to undesirable RORγt modulator activity. When comparing the same compounds in the Thermofluor® binding assay, the compound of Example 12 is again surprisingly superior with over 800 fold improvement in RORγt Thermofluor® binding assay activity compared to Comparator Example 3.

SYNTHESIS OF COMPARATOR COMPOUND EXAMPLES

Comparator Intermediate 1

4-Bromo-2-(cyclohexylamino)nicotinonitrile

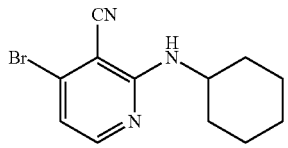 [SMILES: N#Cc1c(Br)ccnc1NC1CCCCC1]

To a vial was added 2,4-dibromo-nicotinonitrile (300 mg, 1.11 mmol) and cyclohexylamine (0.64 mL, 5.56 mmol) and the resulting mixture was stirred at rt for 5 minutes. The mixture was partitioned between saturated aqueous NaHCO$_3$ (10 mL), water (10 mL) and EtOAc (20 mL). The aqueous was further extracted with EtOAc (25 mL). The organics were combined, dried over anhydrous Na$_2$SO$_4$, filtered and concentrated to dryness. The residue was purified by FCC (EtOAc/hexanes=0/100 to 25/75) to provide the title compound as a white solid.

Comparator Intermediate 2

3-Bromo-5-(cyclohexylamino)isonicotinonitrile

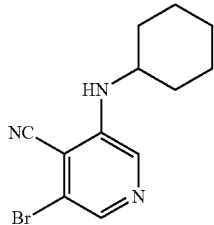 [SMILES: N#Cc1c(Br)cncc1NC1CCCCC1]

To a vial was added 3,5-dibromo-4-cyanopyridine (500 mg, 1.85 mmol), Pd(OAc)$_2$ (42 mg, 0.19 mmol), XantPhos (214 mg, 0.37 mmol), Cs$_2$CO$_3$ (1.51 g, 4.63 mmol) and cyclohexylamine (0.21 mL, 1.85 mmol). The vial was evacuated and backfilled with nitrogen twice, then 1,4-dioxane (7.1 mL) was added and the resulting mixture was stirred at 80° C. for 4.5 hours. The mixture was allowed to cool to rt, then was partitioned between water (25 mL) and EtOAc (40 mL). The aqueous was further extracted with EtOAc (40 mL), then the organics were combined, dried over anhydrous sodium sulfate, filtered and concentrated to dryness. The residue was purified by FCC (100% DCM) to provide the title compound as a cream-colored solid.

Comparator Intermediate 3

N-(5-Bromo-4-(trifluoromethyl)pyridin-2-yl)propane-2-sulfonamide

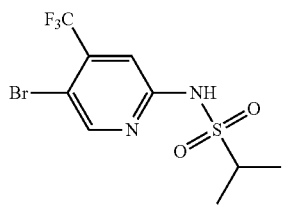 [SMILES: CC(C)S(=O)(=O)Nc1cc(C(F)(F)F)c(Br)cn1]

To a flask was added 5-bromo-4-(trifluoromethyl)pyridin-2-amine (0.52 g, 2.17 mmol), NaH (60% in mineral oil, 209 mg, 4.3 mmol) and DMF (8.7 mL). The mixture was cooled to 0° C. and stirred at that temperature for 20 minutes. Then, isopropylsulfonyl chloride (310 mg, 2.17 mmol) was added dropwise at 0° C. The mixture was allowed to warm to rt and stirred at that temperature for an additional two hours. The mixture was then poured into ice water (15 mL) and the precipitated solid was collected by filtration to provide the title compound as a yellow solid.

Comparator Example 1

(S)-5-(3-Cyano-2-(cyclohexylamino)pyridin-4-yl)-N-(2-hydroxy-2-methylpropyl)-4-(2-methylpyrrolidine-1-carbonyl)thiazole-2-carboxamide

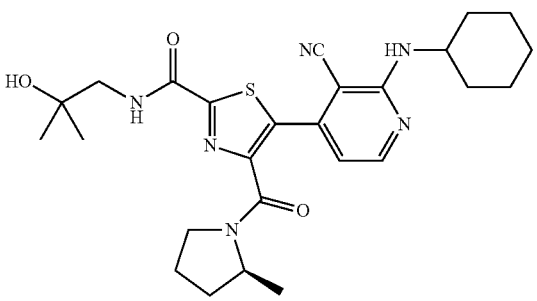 [SMILES: C[C@H]1CCCN1C(=O)c1nc(C(=O)NCC(C)(C)O)sc1-c1ccnc(NC2CCCCC2)c1C#N]

An oven-dried vial under nitrogen was charged with (S)—N-(2-hydroxy-2-methylpropyl)-4-(2-methylpyrrolidine-1-carbonyl)thiazole-2-carboxamide (46 mg, 0.15 mmol, Intermediate 69), 4-bromo-2-(cyclohexylamino)nicotinonitrile (41 mg, 0.15 mmol, Comparator Intermediate 1), K$_2$CO$_3$ (81 mg, 0.59 mmol), pivalic acid (6 mg, 0.059 mmol) and butyronitrile (0.91 mL, sparged with nitrogen for 1 hour prior to addition). The mixture was sparged with nitrogen for 30 minutes, then bis(tri-tert-butylphosphine) palladium(0) (7.5 mg, 0.015 mmol) was added and the mixture sparged with nitrogen for 2 minutes. The resulting mixture was stirred for 19 h at 100° C. The reaction mixture was then cooled to room temperature, diluted with water (15 mL), and the aqueous phase was extracted with EtOAc (2×20 mL). The combined organic layers were washed with brine (20 mL), dried over anhydrous Na$_2$SO$_4$, filtered and concentrated to dryness. The crude product was purified by basic HPLC to provide the title compound as a yellow amorphous solid. MS (ESI): mass calcd. for C$_{26}$H$_{34}$N$_6$O$_3$S, 510.7; m/z found, 511.1 [M+H]$^+$. $^1$H NMR (400 MHz, CDCl$_3$) δ 8.30-8.26 (m, 1H), 7.60-7.51 (m, 1H), 6.69-6.63

(m, 1H), 5.16-5.10 (m, 1H), 4.34-4.25 (m, 1H), 4.06-3.96 (m, 1H), 3.73-3.57 (m, 2H), 3.52-3.45 (m, 2H), 2.20-1.72 (m, 9H), 1.70-1.62 (m, 2H), 1.48-1.38 (m, 2H), 1.35-1.29 (m, 9H), 1.27-1.23 (m, 2H).

Comparator Example 2

(S)-5-(4-Cyano-5-(cyclohexylamino)pyridin-3-yl)-N-(2-hydroxy-2-methylpropyl)-4-(2-methylpyrrolidine-1-carbonyl)thiazole-2-carboxamide

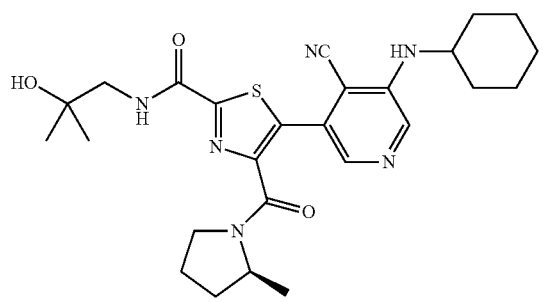 [SMILES: C[C@H]1CCCN1C(=O)c1nc(C(=O)NCC(C)(C)O)sc1-c1cncc(NC2CCCCC2)c1C#N]

The title compound was prepared as described in Comparator Example 1 using 3-bromo-5-(cyclohexylamino)isonicotinonitrile (Comparator Intermediate 2) in place of 4-bromo-2-(cyclohexylamino)nicotinonitrile. MS (ESI): mass calcd. for $C_{26}H_{34}N_6O_3S$, 510.7; m/z found, 511.1 [M+H]$^+$. $^1$H NMR (500 MHz, CDCl$_3$) δ 8.23 (s, 1H), 8.02-7.96 (m, 1H), 7.59-7.50 (m, 1H), 4.53-4.49 (m, 1H), 4.46-4.25 (m, 1H), 3.78-3.68 (m, 1H), 3.67-3.60 (m, 1H), 3.53-3.45 (m, 3H), 2.19-2.06 (m, 3H), 2.00-1.94 (m, 1H), 1.92 (s, 1H), 1.90-1.79 (m, 3H), 1.71-1.66 (m, 1H), 1.64-1.59 (m, 1H), 1.47-1.37 (m, 2H), 1.33-1.31 (m, 9H), 1.30-1.22 (m, 3H).

Comparator Example 3

4-(4-Fluoropiperidine-1-carbonyl)-N-(2-hydroxy-2-methylpropyl)-5-(6-((1-methylethyl)sulfonamido)-4-(trifluoromethyl)pyridin-3-yl)thiazole-2-carboxamide

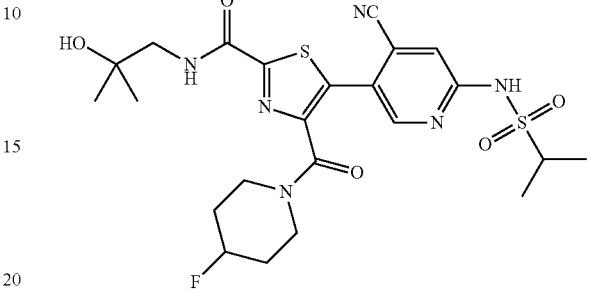

The title compound was prepared as described in Example 57 substituting N-(5-bromo-4-(trifluoromethyl)pyridin-2-yl)propane-2-sulfonamide (Comparator Intermediate for 5-bromo-2-(cyclohexylamino)isonicotinonitrile. MS (ESI): mass calcd. for $C_{23}H_{29}F_4N_5O_5S_2$, 595.2; m/z found, 596.2 [M+H]$^+$. $^1$H NMR (400 MHz, DMSO-d$_6$) δ 11.23 (s, 1H), 8.48 (s, 1H), 8.43 (t, J=6.1 Hz, 1H), 7.36 (s, 1H), 4.95-4.83 (m, 1H), 4.70 (s, 1H), 3.95-3.82 (m, 1H), 3.58-3.47 (m, 4H), 3.29 (d, J=6.3 Hz, 2H), 1.95-1.75 (m, 2H), 1.64 (br s, 2H), 1.32 (d, J=6.8 Hz, 6H), 1.13 (s, 6H).

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

All documents cited herein are incorporated by reference.

We claim:

1. A compound of Formula I:

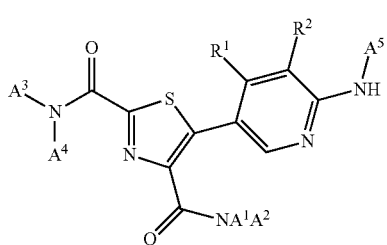

Formula I wherein
R¹ is H, —C$_{(1-3)}$alkyl, —CHF$_2$, —CF$_3$, —CN, —OCH$_3$, —OCH$_2$CH$_3$, cyclopropyl, OCF$_3$, or OCHF$_2$;
R² is H, F, —CHF$_2$, —CF$_3$, —CN, —OCH$_3$, —OCHF$_2$, or OCF$_3$; provided that R² may not be H if R¹ is H;
A¹ and A² are taken together with their attached nitrogen to form a ring selected from the group consisting of

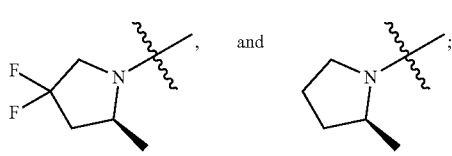

A³ is H, —C$_{(1-6)}$alkyl,

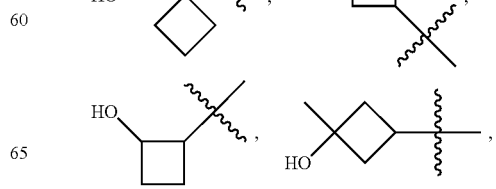

—SO$_2$CH(CH$_3$)$_2$, —SO$_2$CH$_3$,

747

-continued

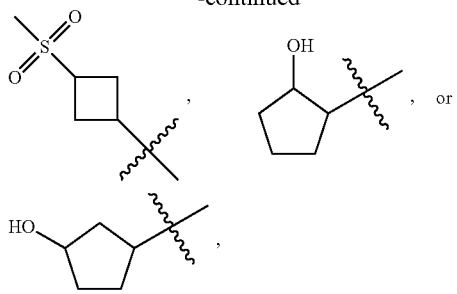

wherein said —C$_{(1-6)}$alkyl is optionally substituted with one —NH$_2$ group, one or two —OH groups, and may be additionally substituted with up to six fluorine atoms;
A$^4$ is —H, or —CH$_3$;
A$^5$ is —C$_{(4-6)}$cycloalkyl, —C$_{(1-6)}$alkyl,

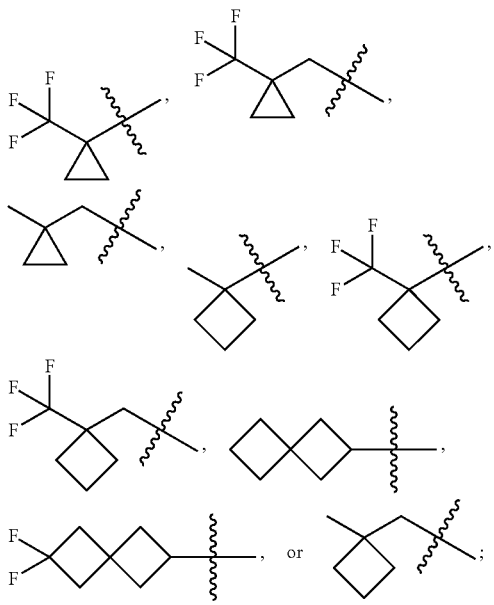

wherein said —C$_{(1-6)}$alkyl and —C$_{(4-6)}$cycloalkyl are optionally substituted with up to three fluorine atoms; and said —C$_{(1-6)}$alkyl is independently optionally substituted with one cyclobutyl, or up to two cyclopropyl groups;
and a pharmaceutically acceptable salt thereof.

2. The compound of claim 1 wherein:
A$^5$ is —C$_{(3-6)}$alkyl,

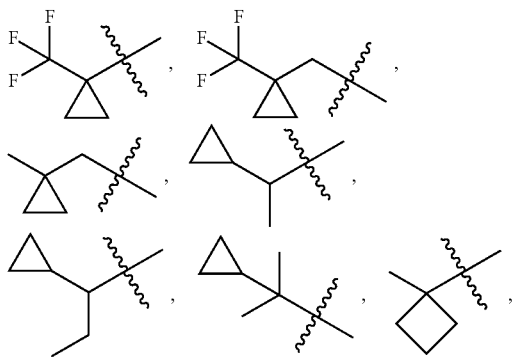

748

-continued

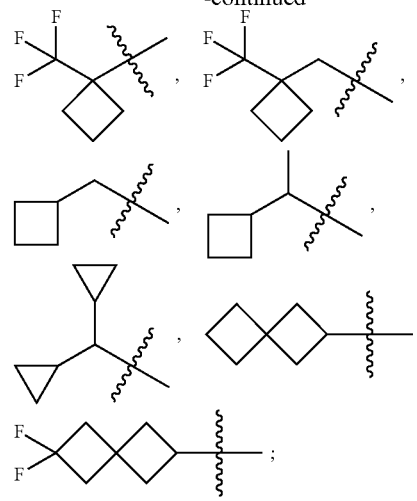

wherein said —C$_{(3-6)}$alkyl and —C$_{(4-6)}$cycloalkyl are optionally substituted with up to three fluorine atoms;
and a pharmaceutically acceptable salt thereof.

3. The compound of claim 2 wherein:
R$^1$ is H, —C$_{(1-3)}$alkyl, —CHF$_2$, —CF$_3$, —CN, —OCH$_3$, —OCH$_2$CH$_3$, or cyclopropyl;
R$^2$ is H, F, —CHF$_2$, —CF$_3$, —CN, —OCH$_3$, or —OCHF$_2$; provided that R$^2$ may not be H if R$^1$ is H;
and a pharmaceutically acceptable salt thereof.

4. The compound of claim 3 selected from the group consisting of:

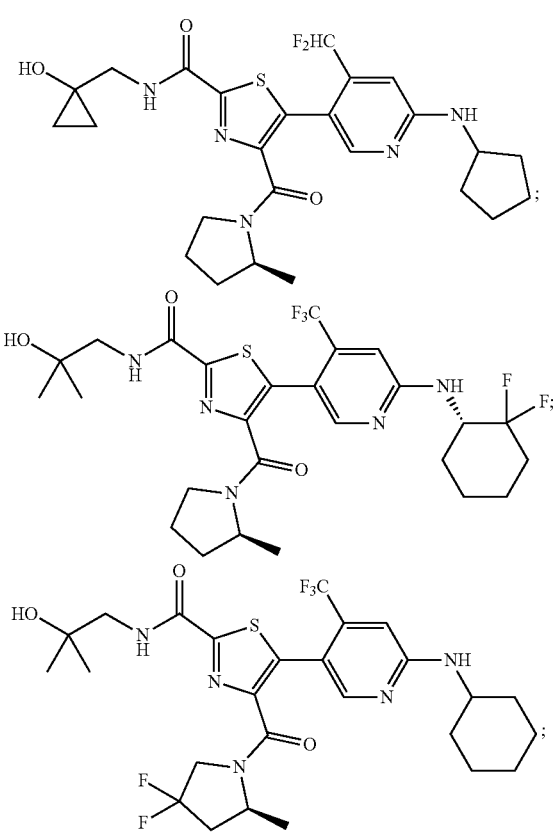

749
-continued
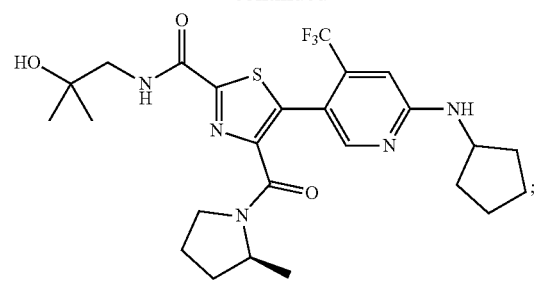
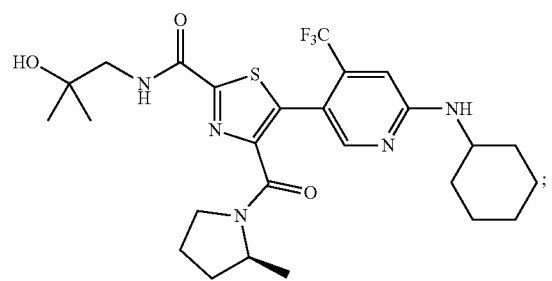
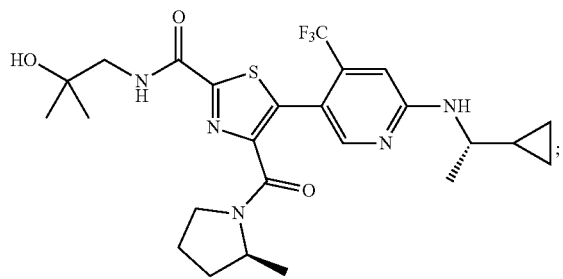
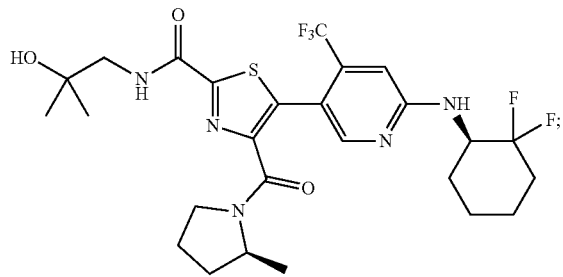
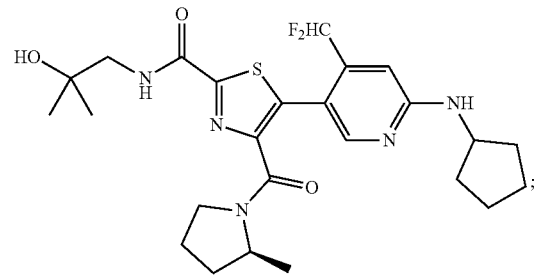
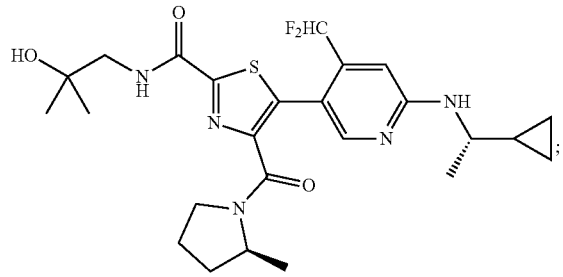
750
-continued
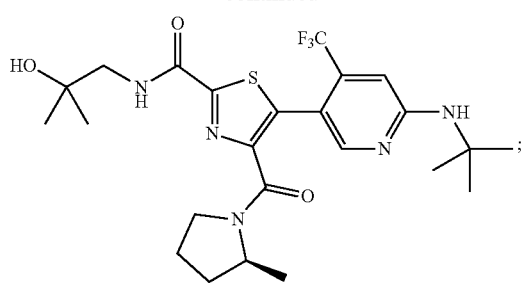
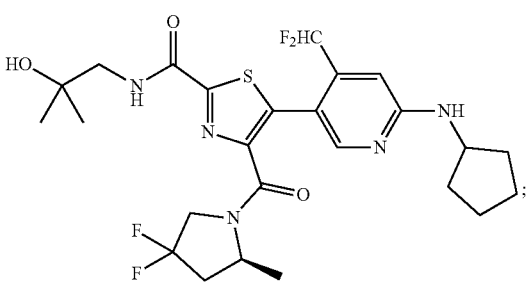
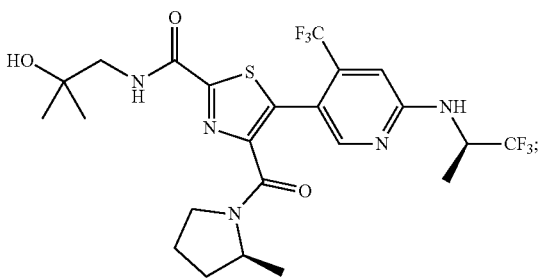
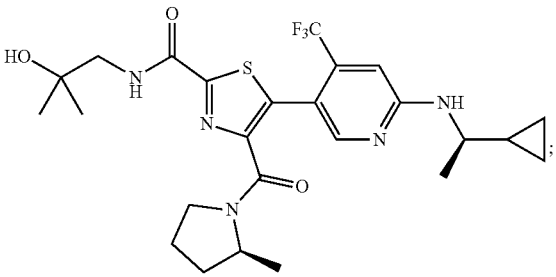
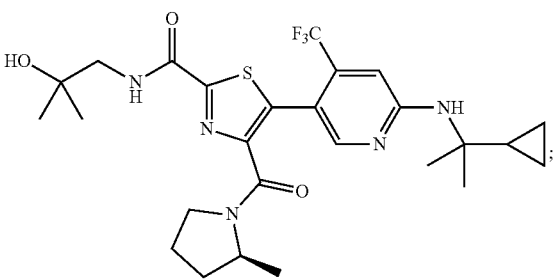
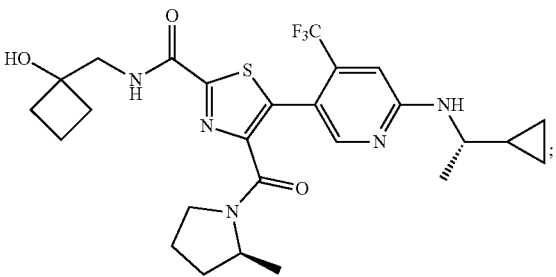

751
-continued
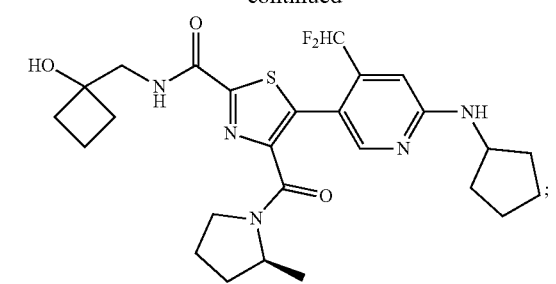
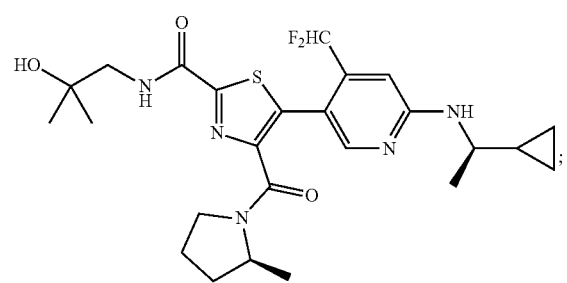
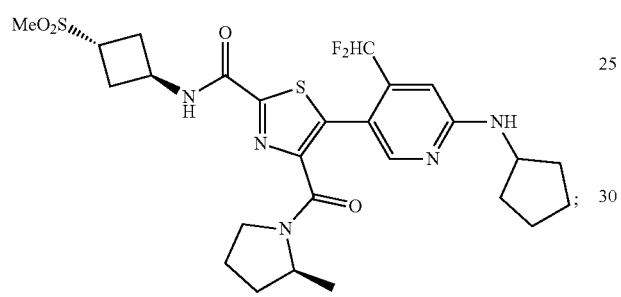
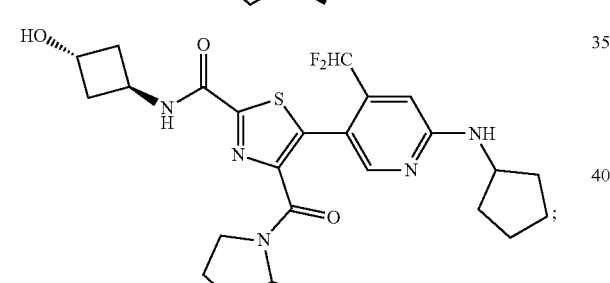
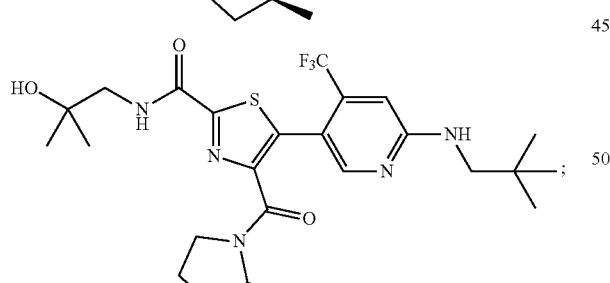
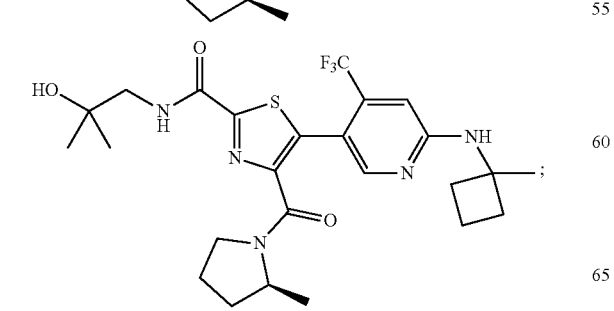
752
-continued
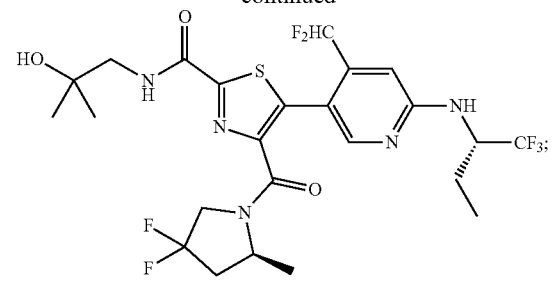
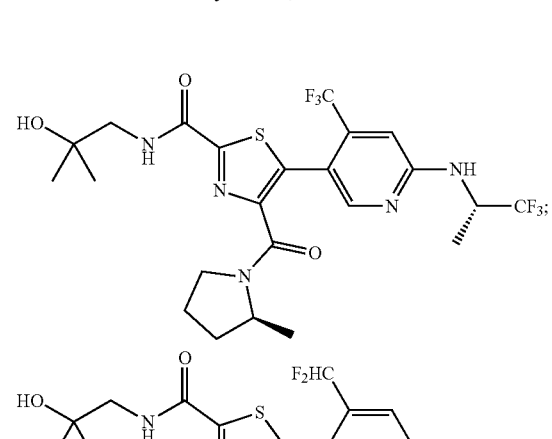
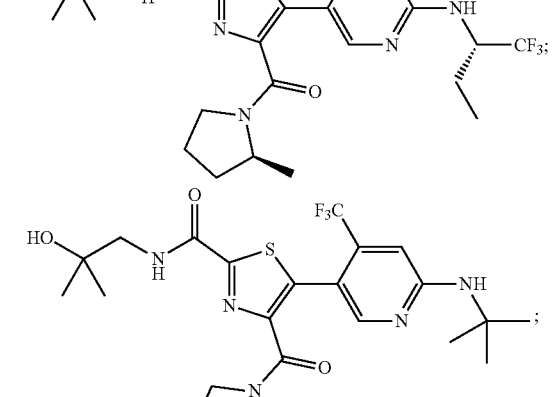
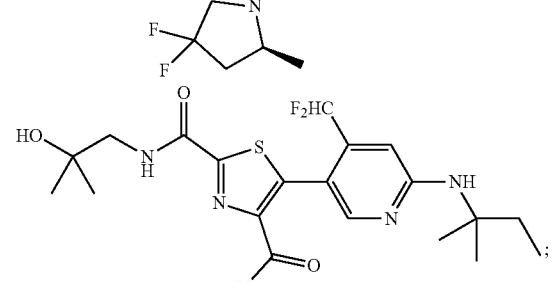
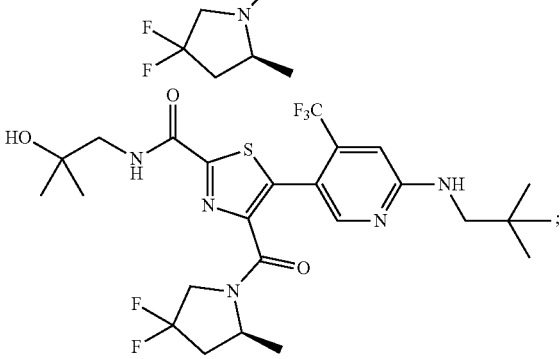

753
-continued
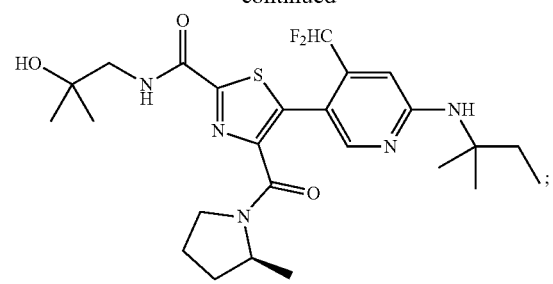
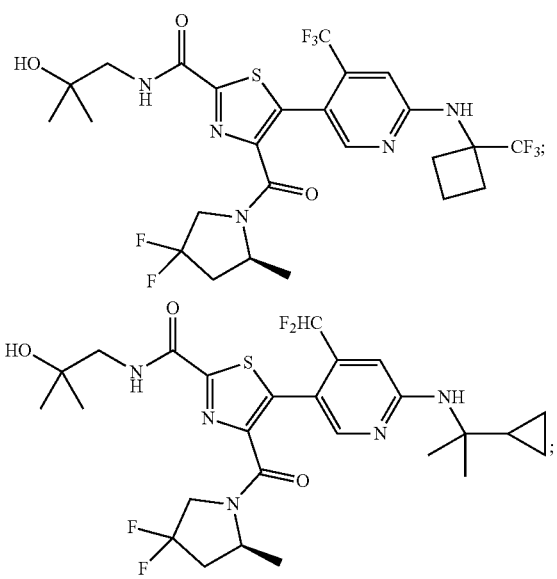
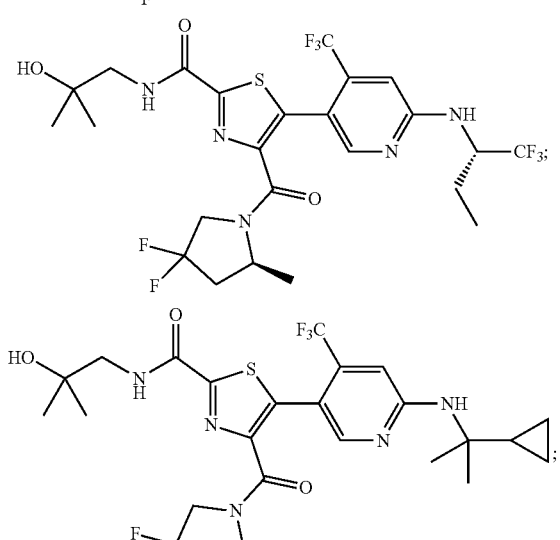
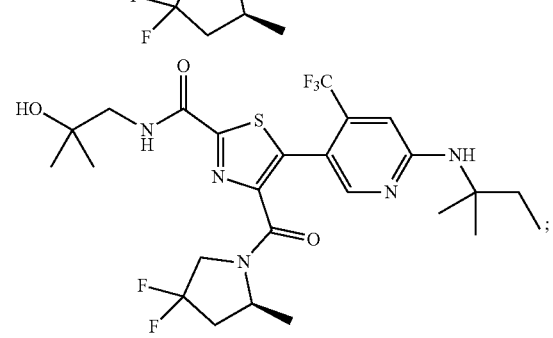
754
-continued
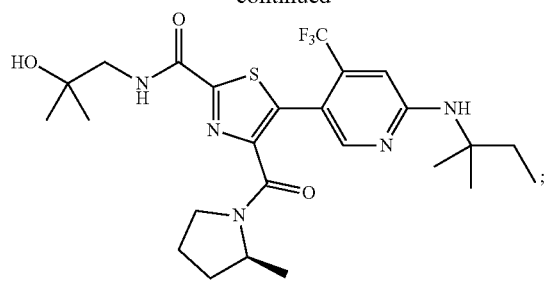
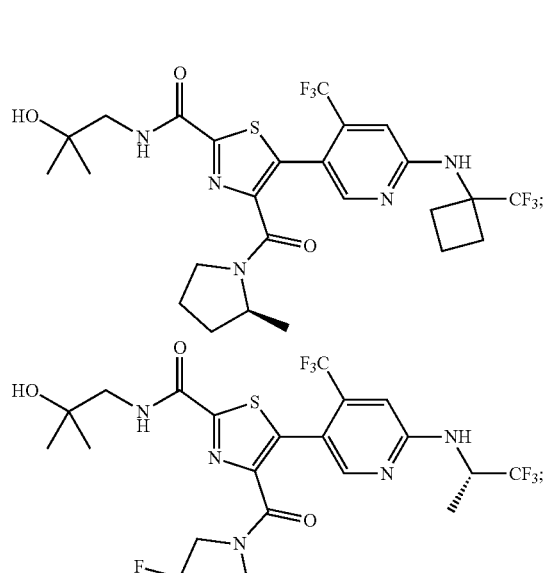
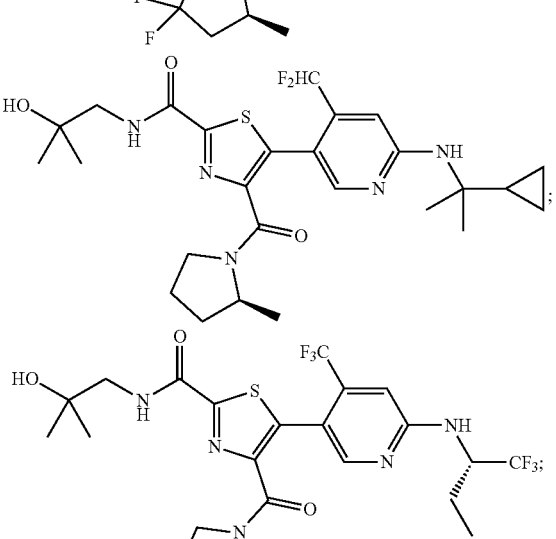
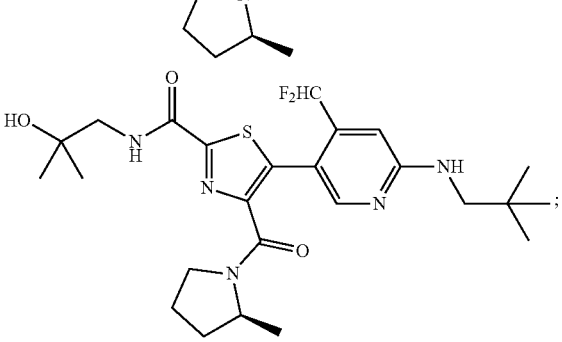

755
-continued
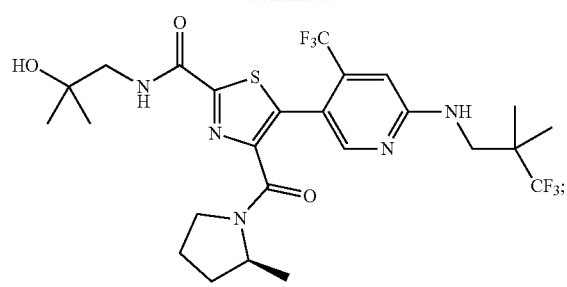
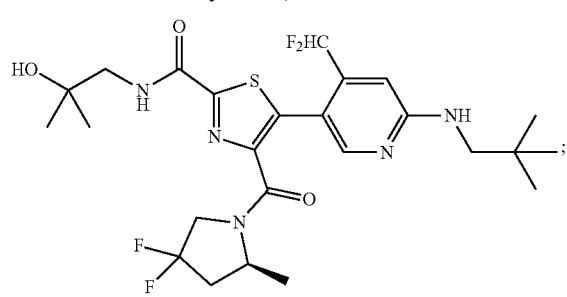
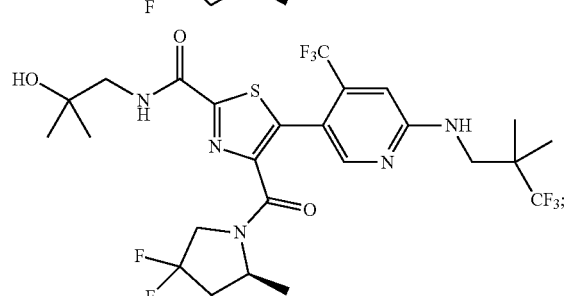
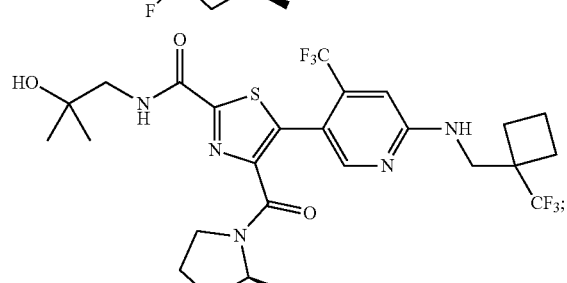
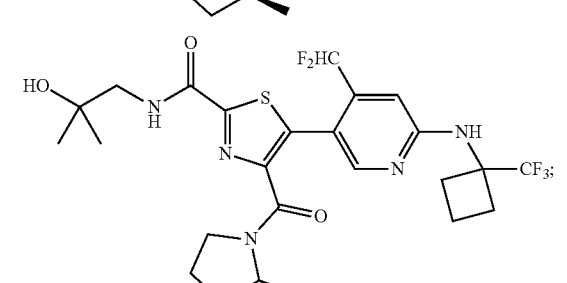
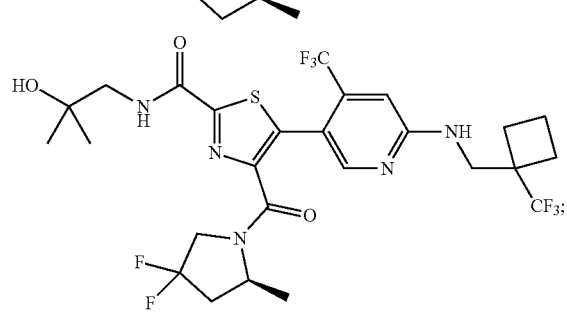
756
-continued
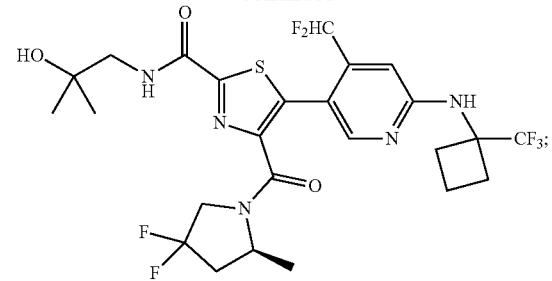
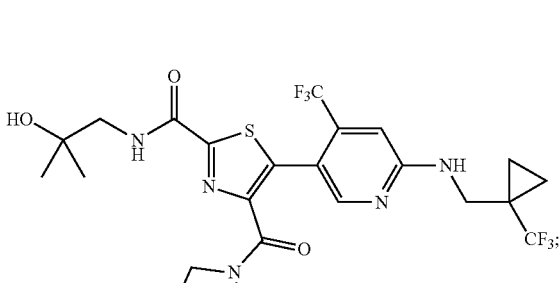
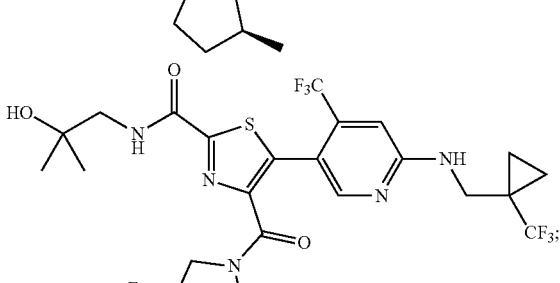
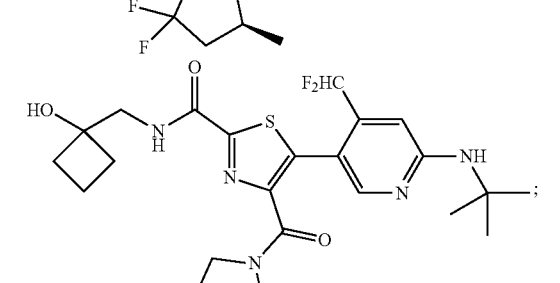
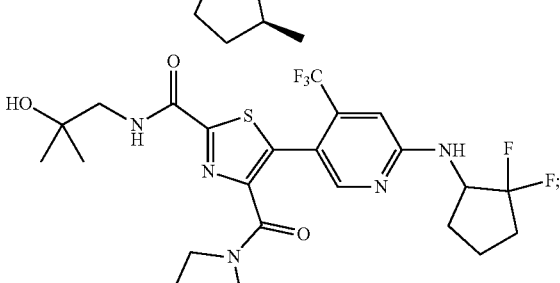
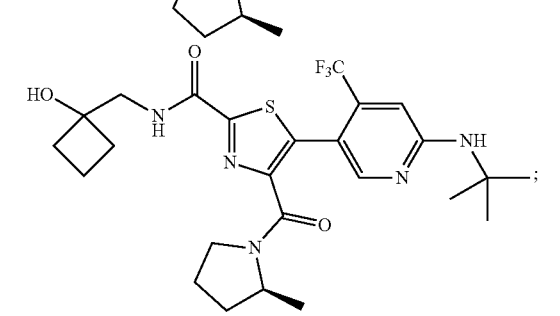

757
-continued
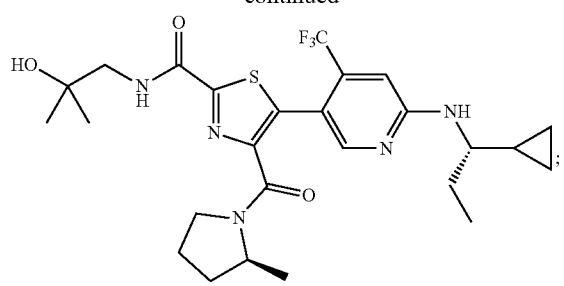
758
-continued
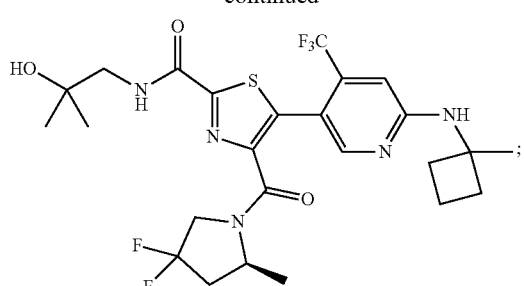
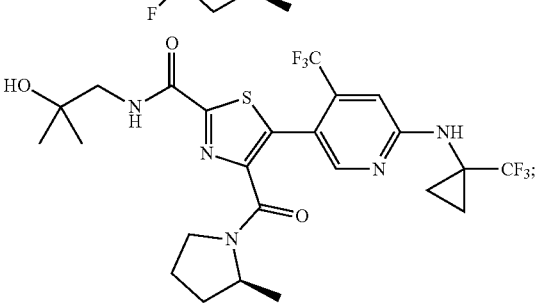
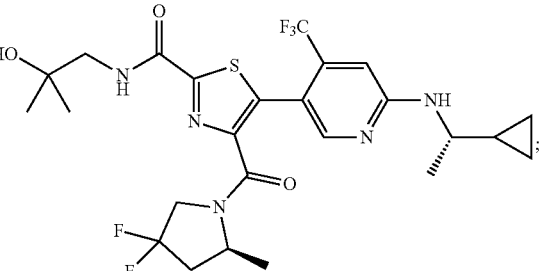
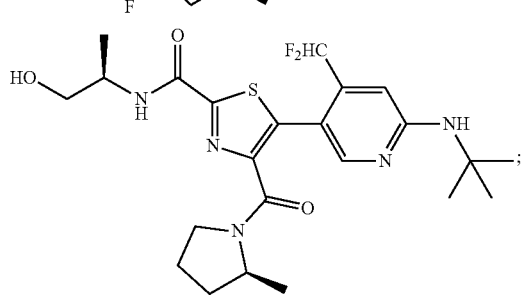
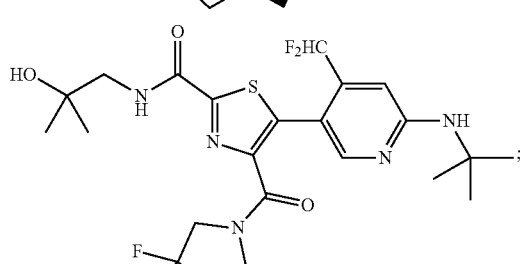
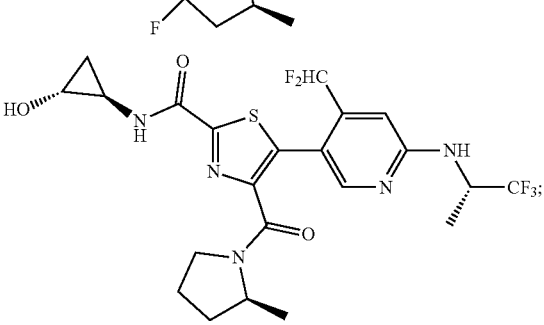

759
-continued
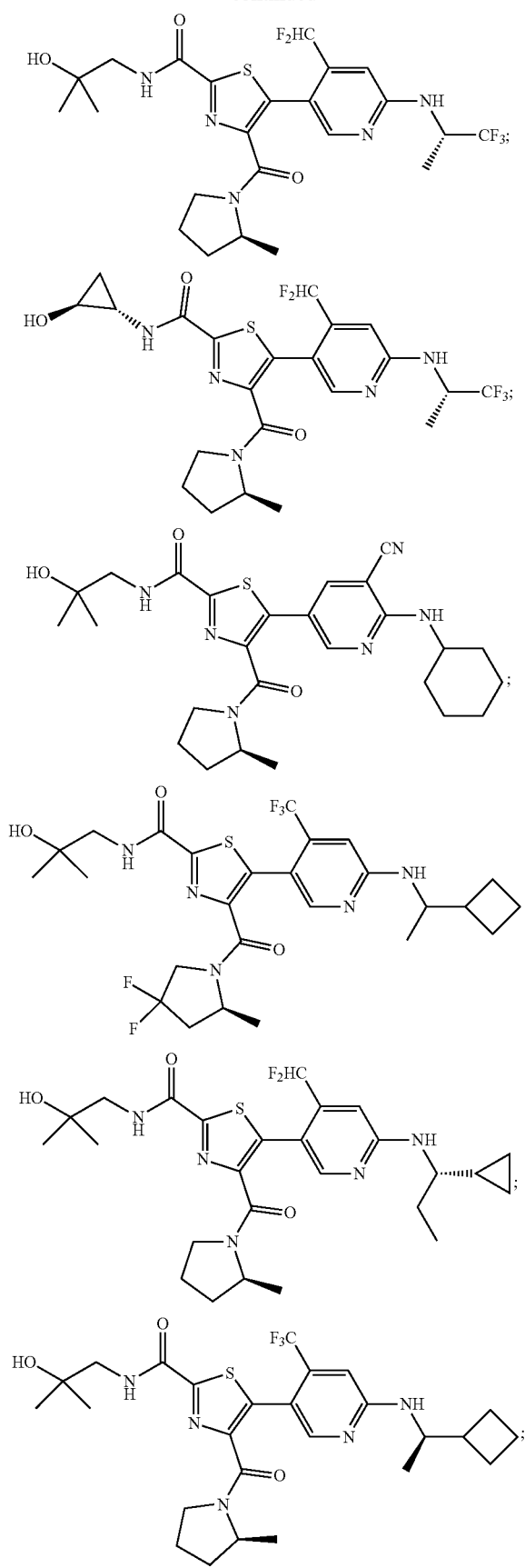
760
-continued
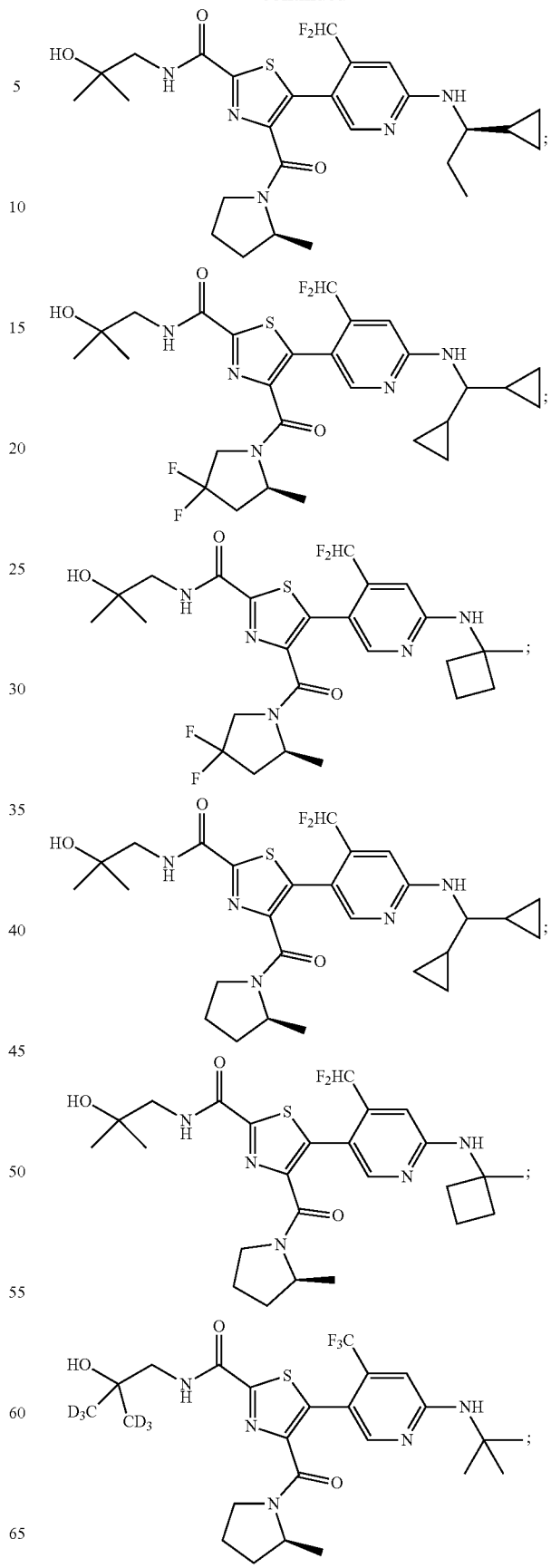

761
-continued
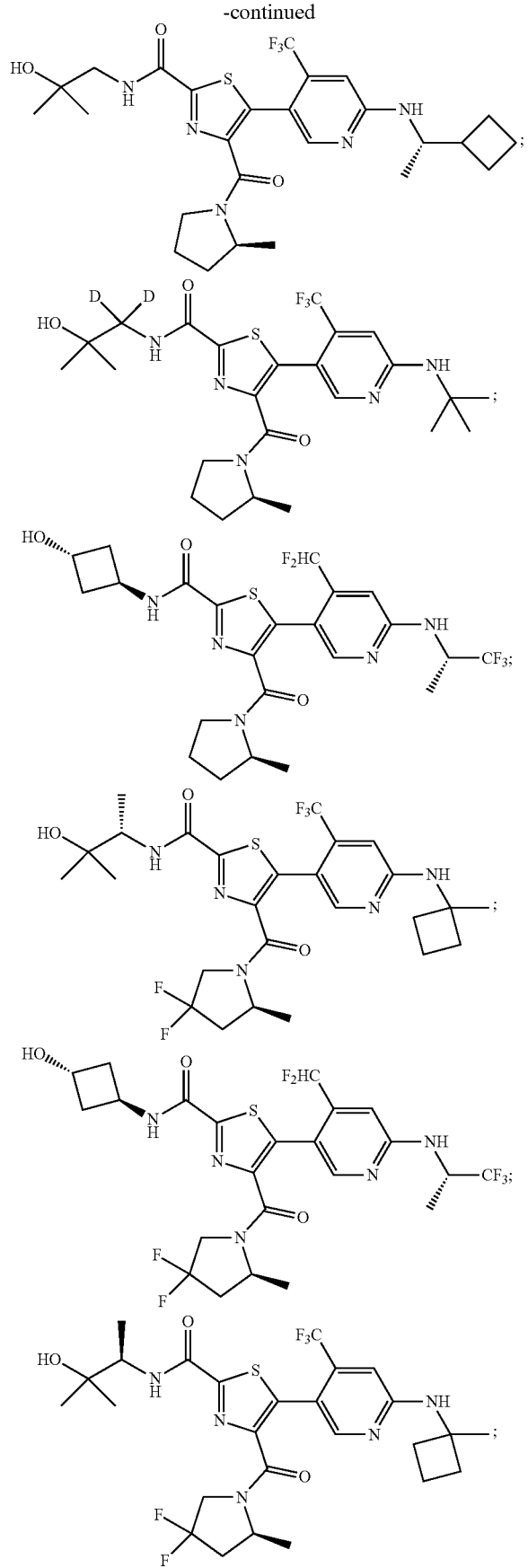
762
-continued
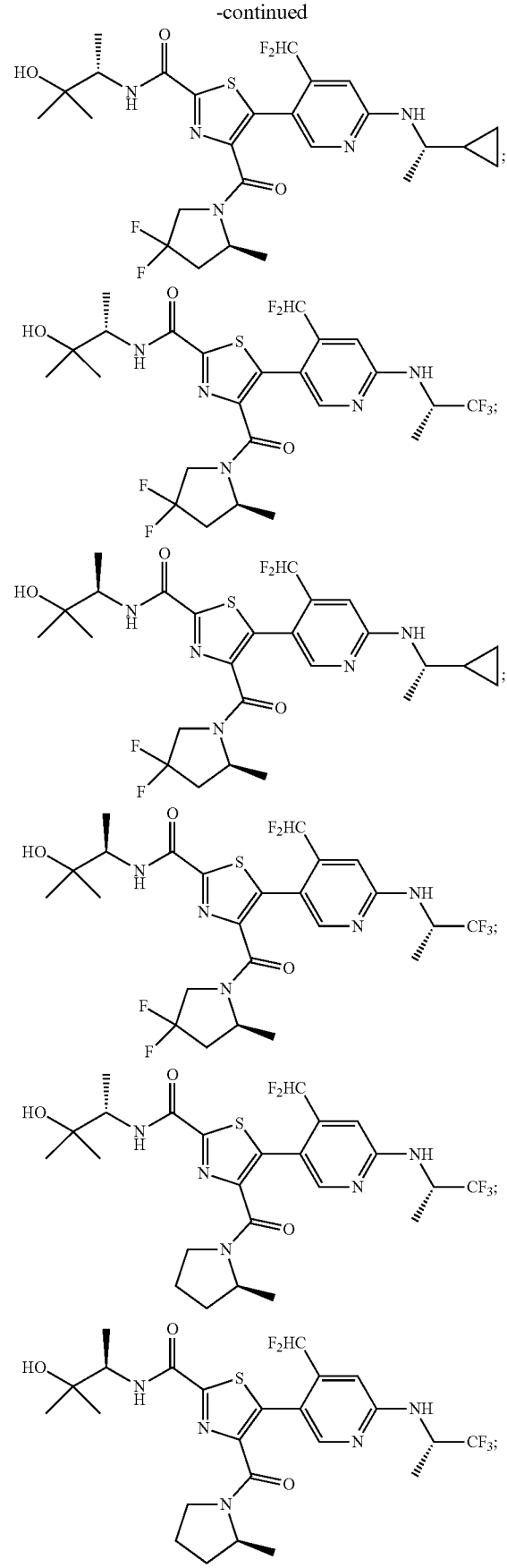

763
-continued
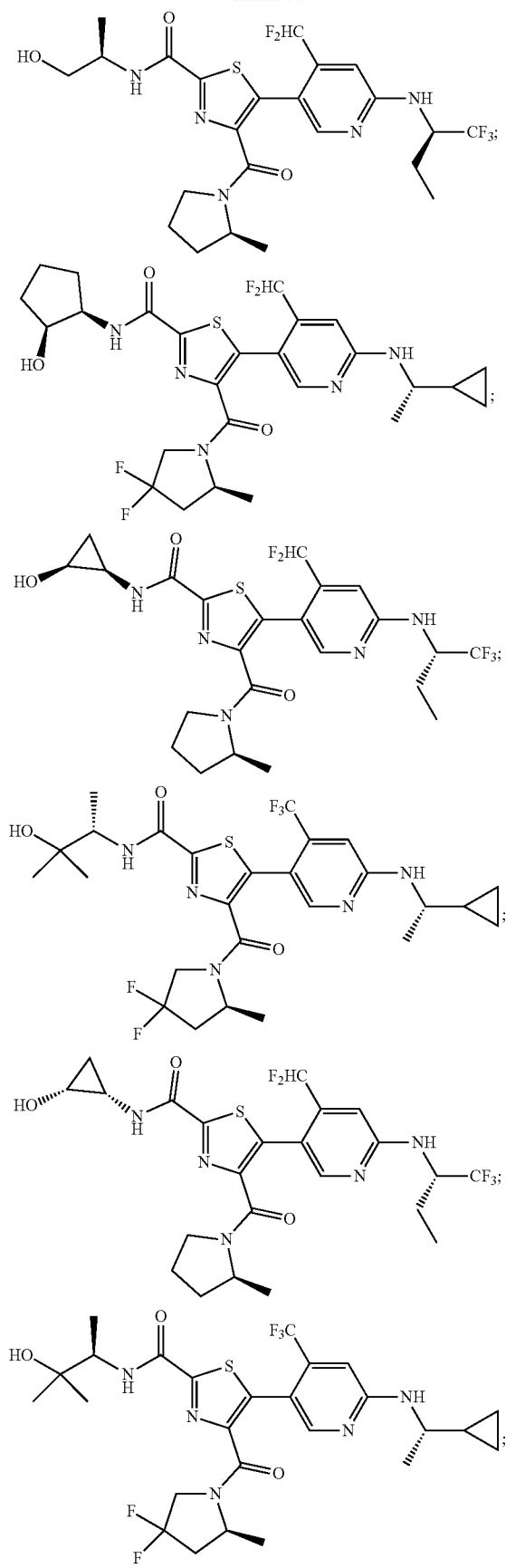
764
-continued
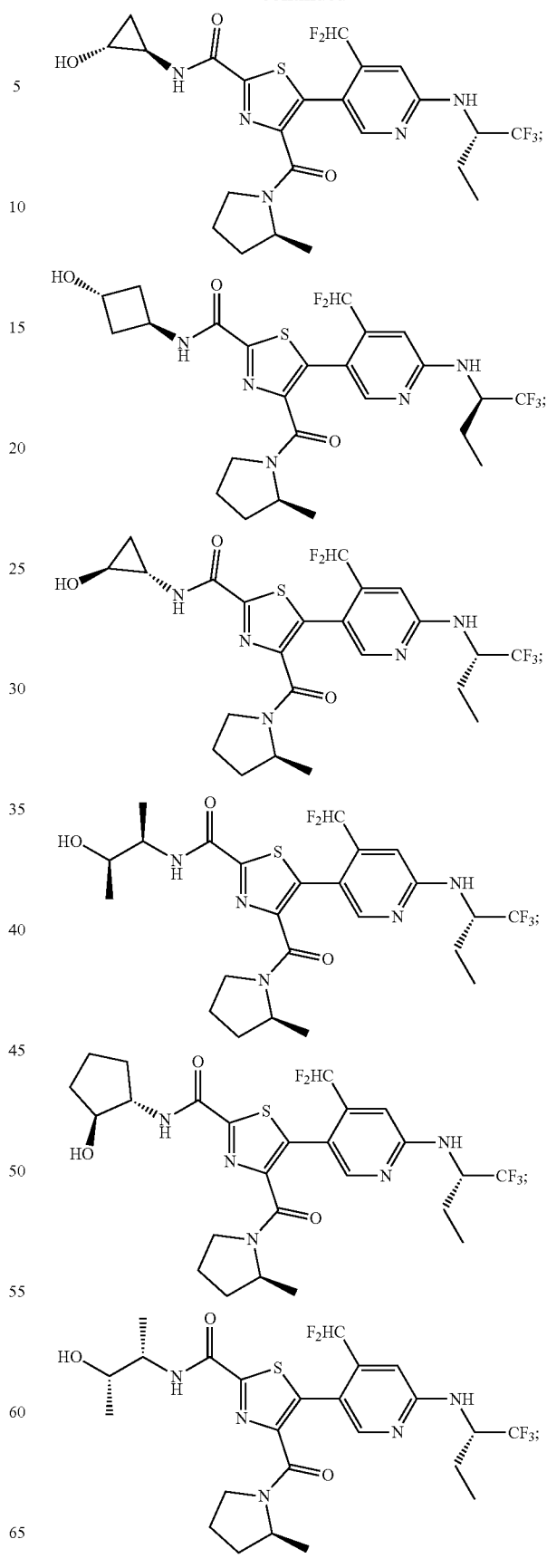

765
-continued
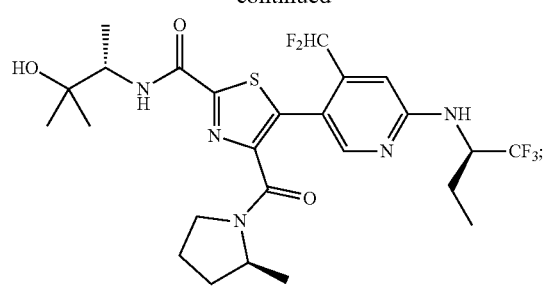
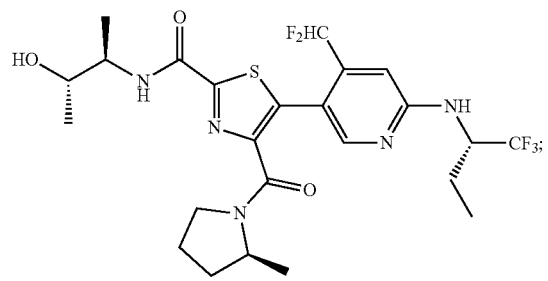
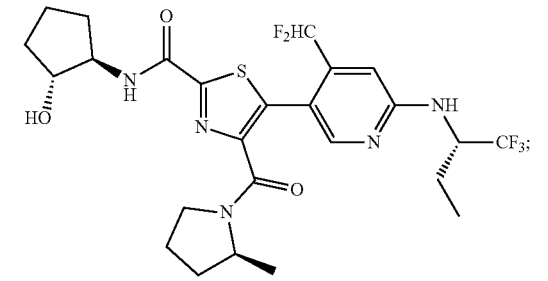
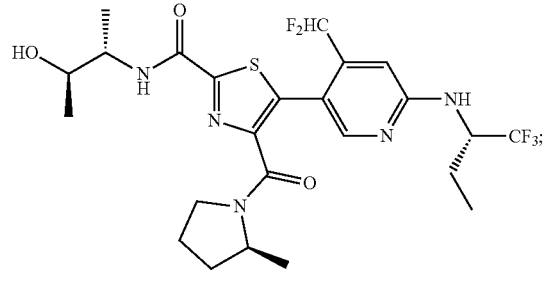
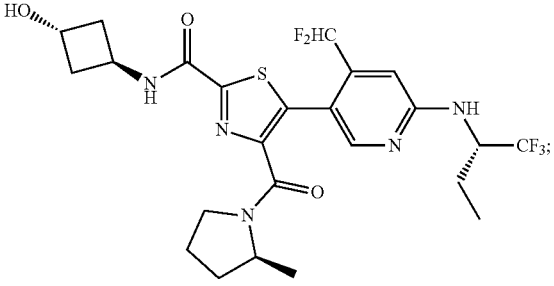
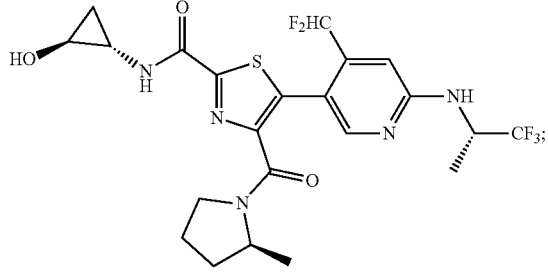
766
-continued
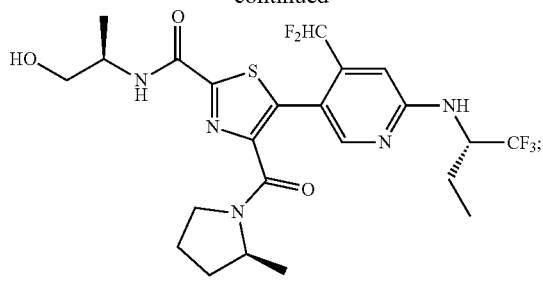
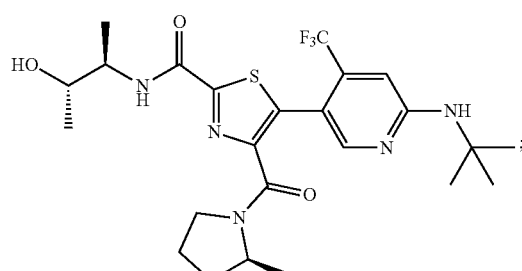
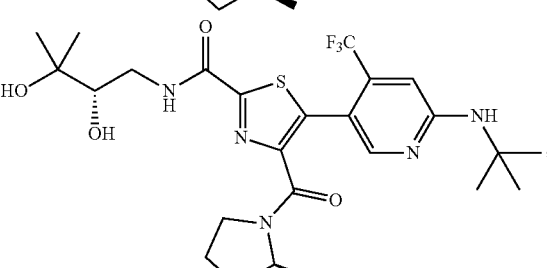
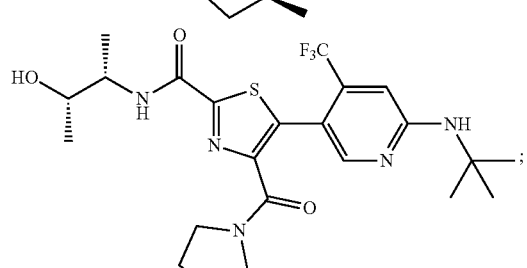
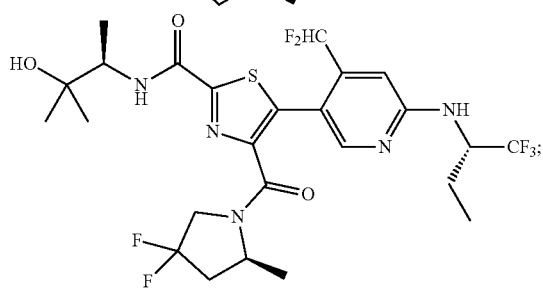
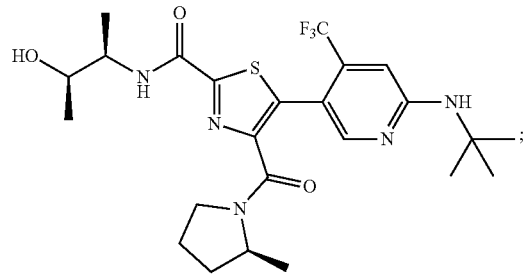

767
-continued
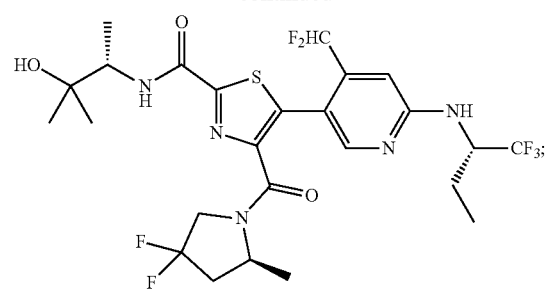
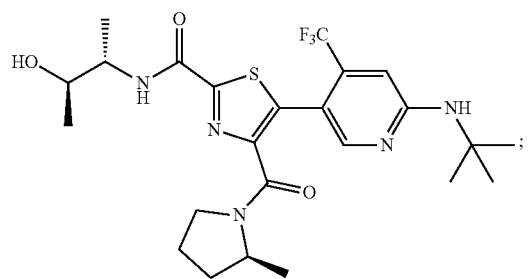
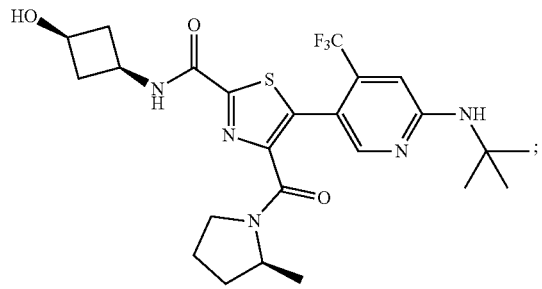
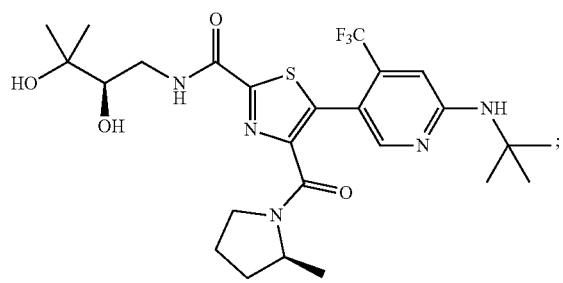
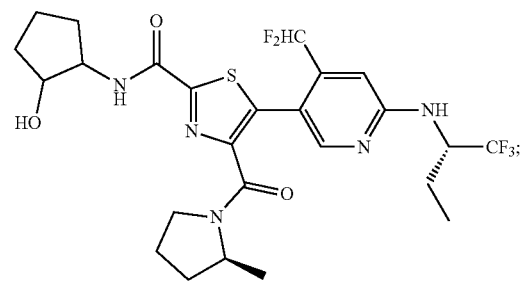
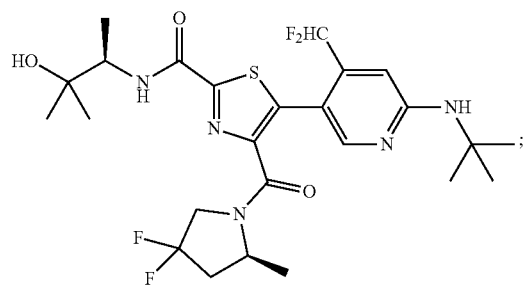
768
-continued
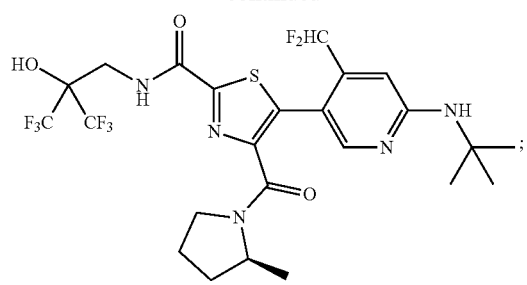
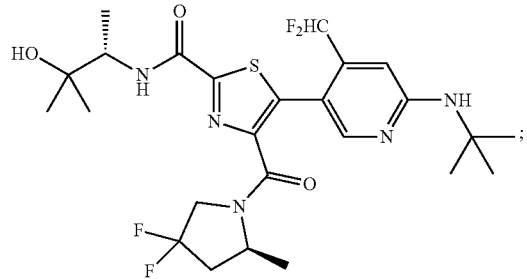
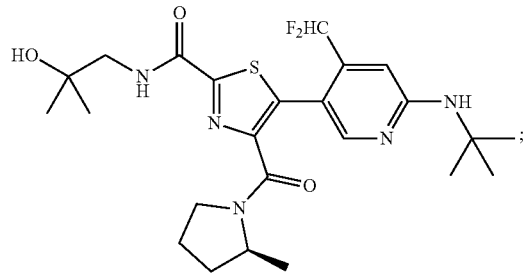
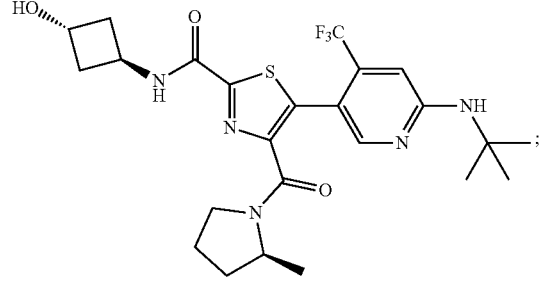
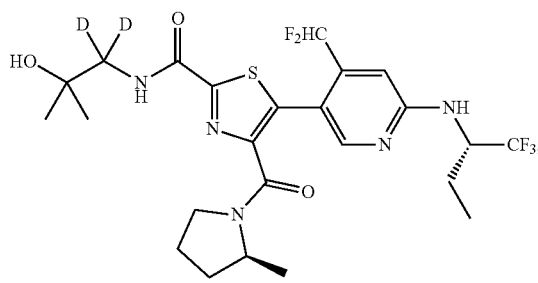
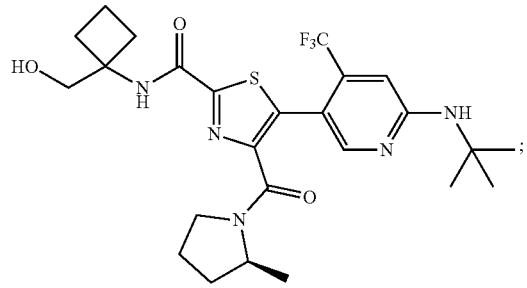

769
-continued
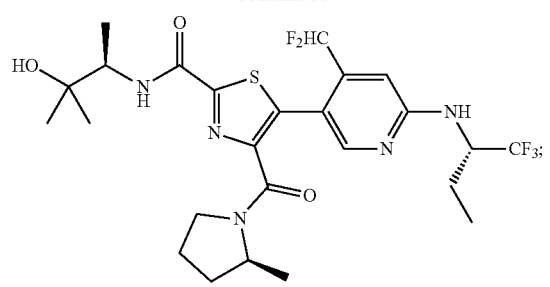
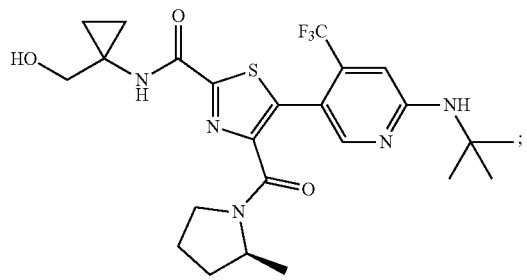
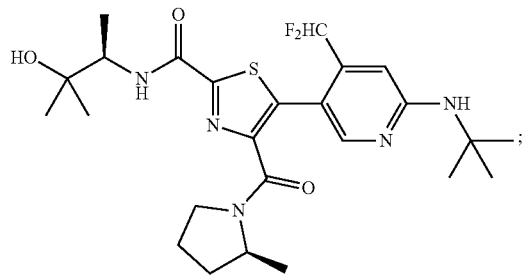
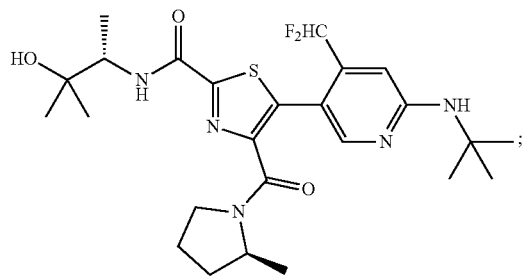
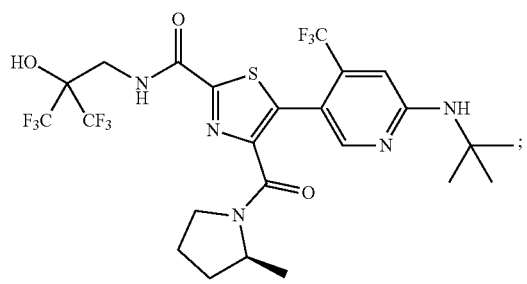
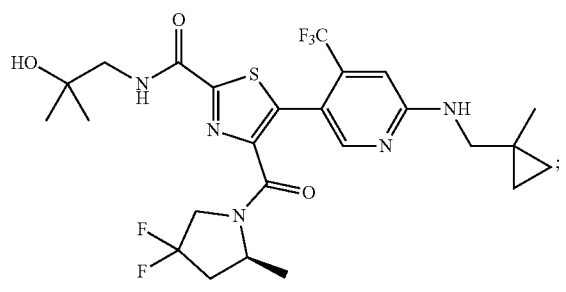
770
-continued
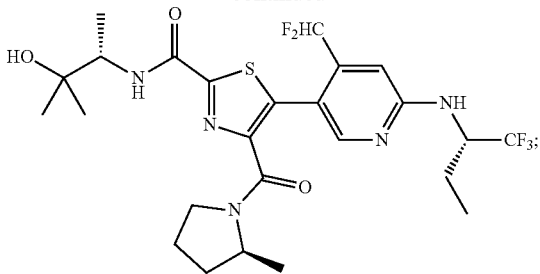
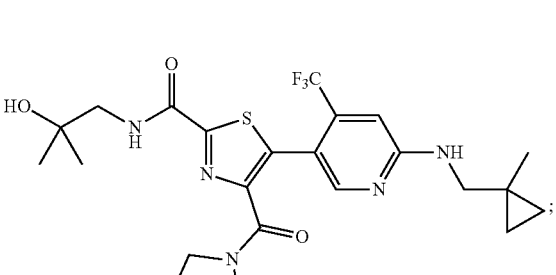
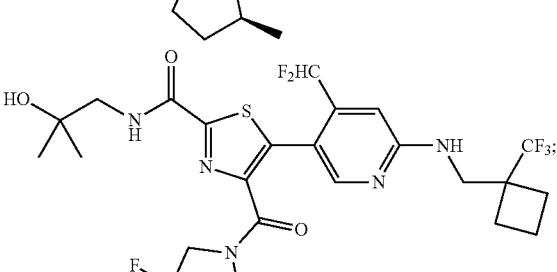
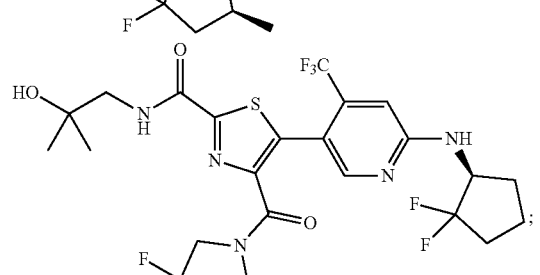
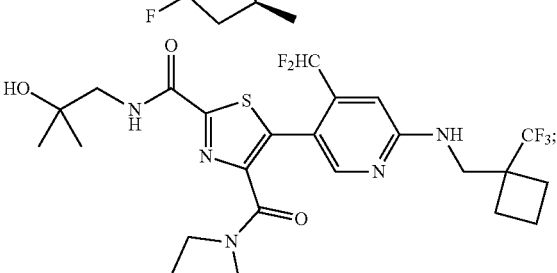
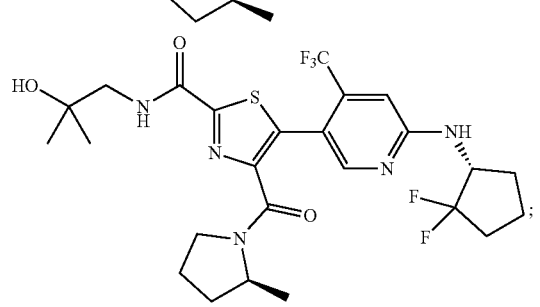

771
-continued
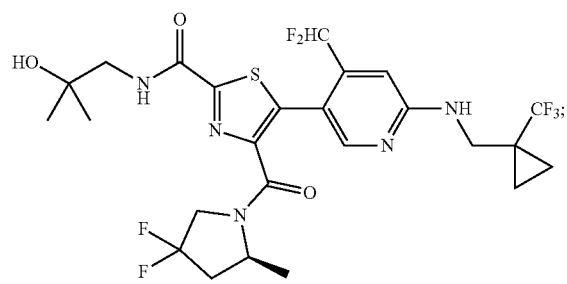
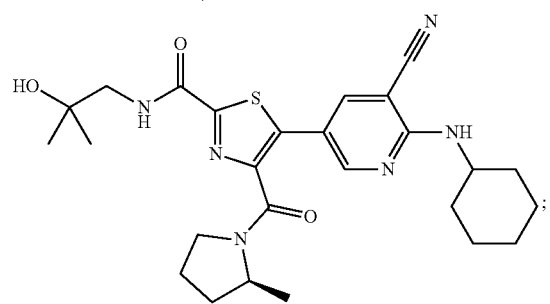
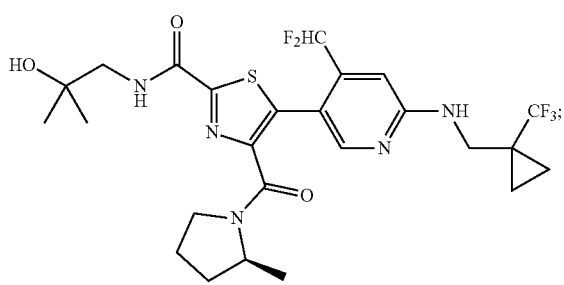
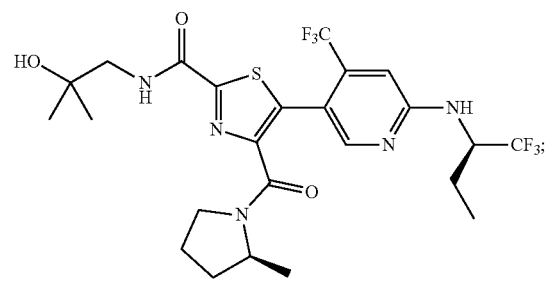
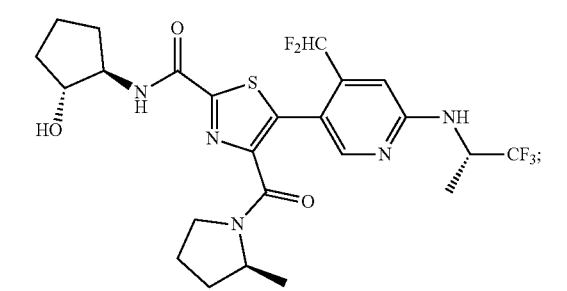
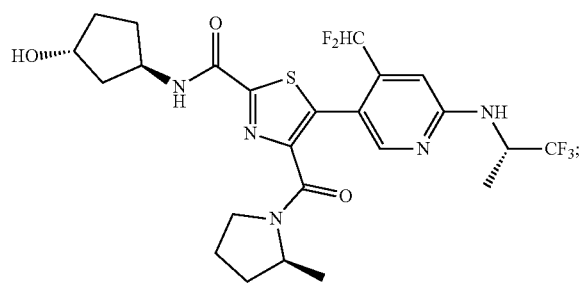
772
-continued
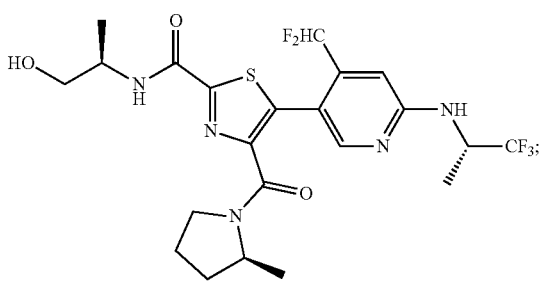
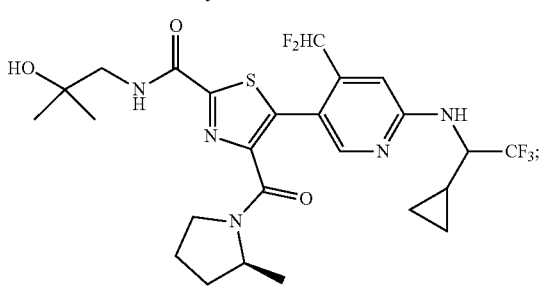
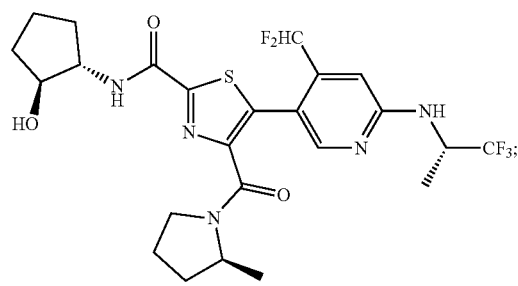
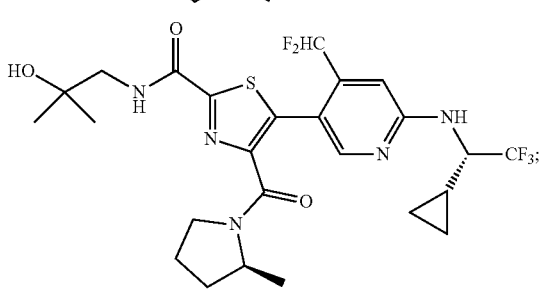
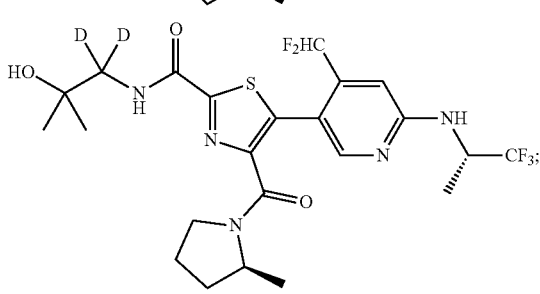
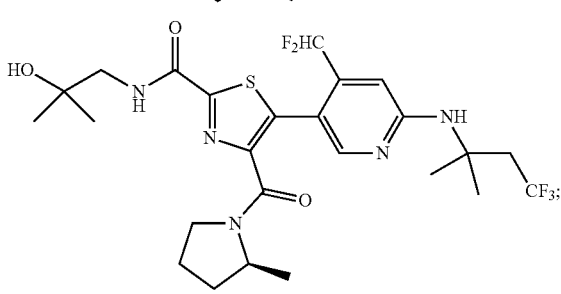

773
-continued
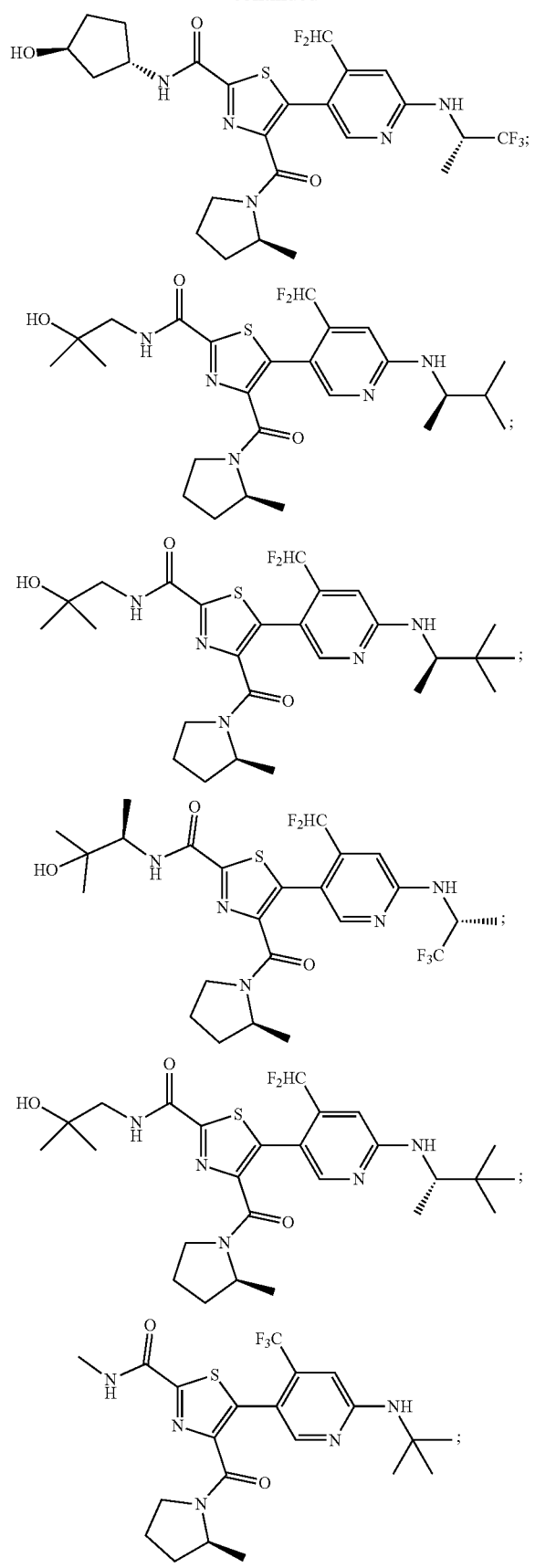
774
-continued
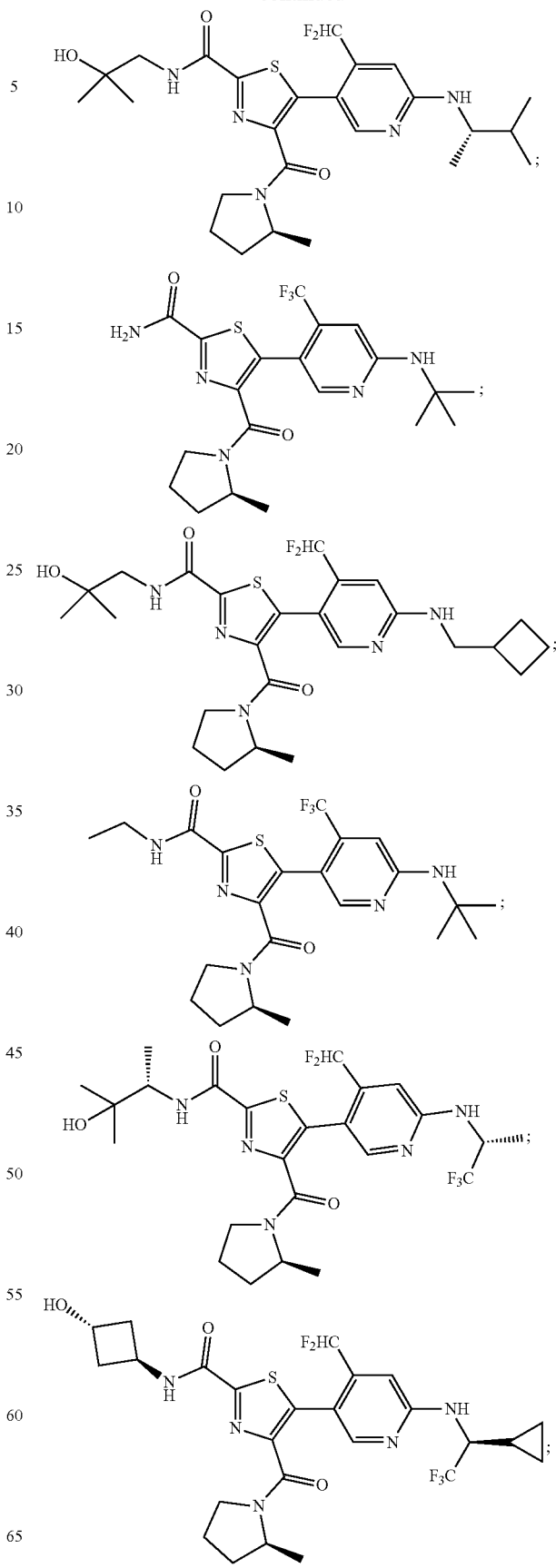

775
-continued
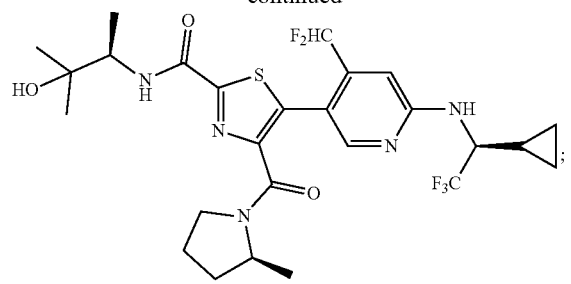
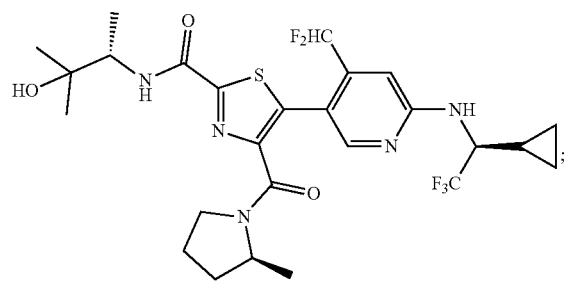
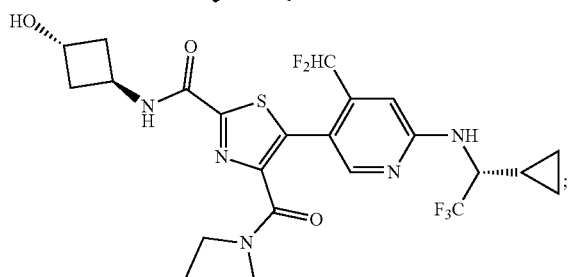
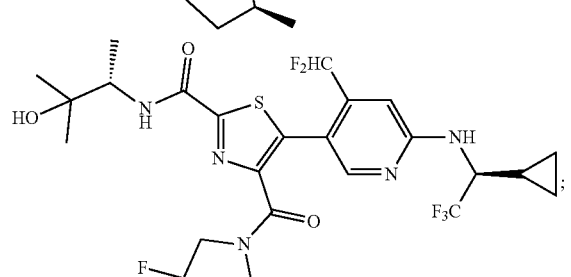
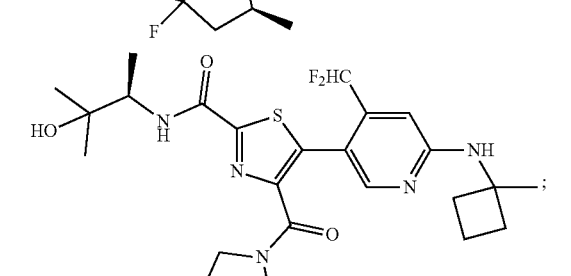
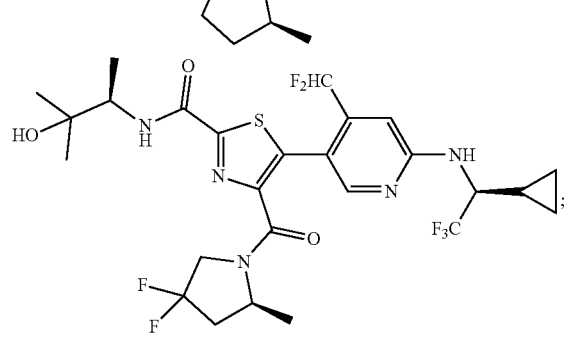
776
-continued
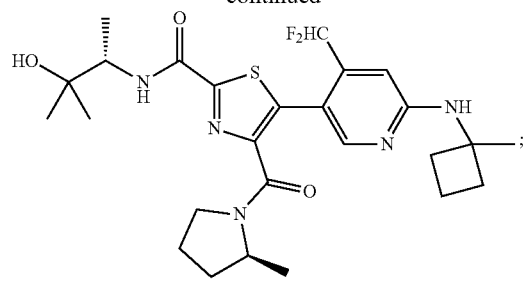
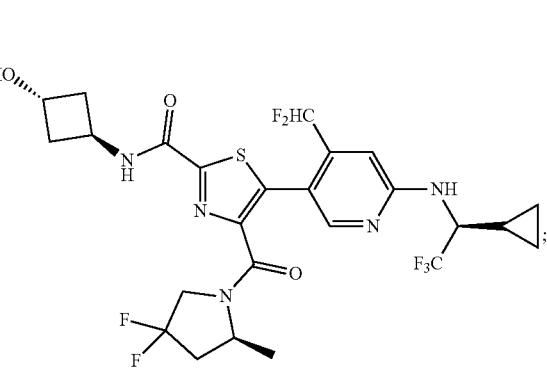
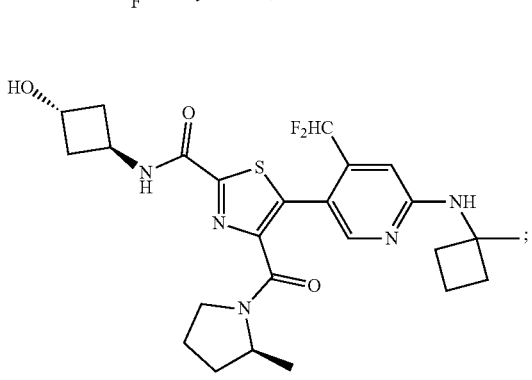
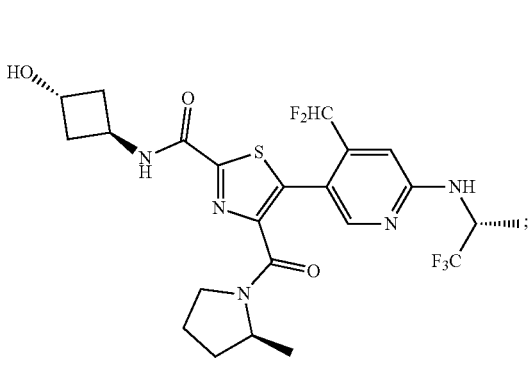
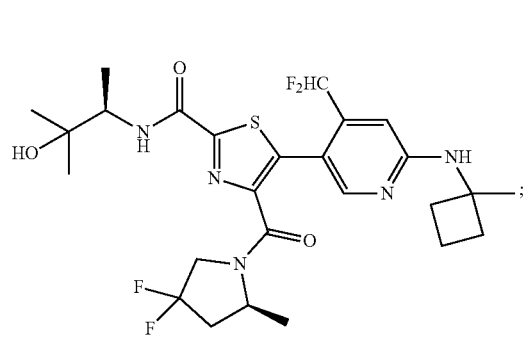

777
-continued
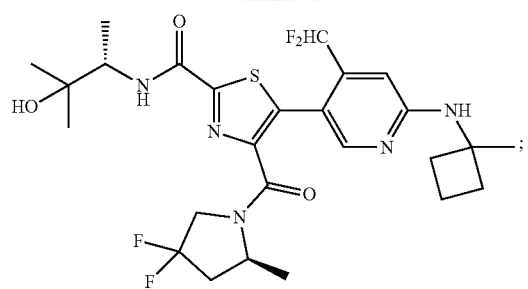
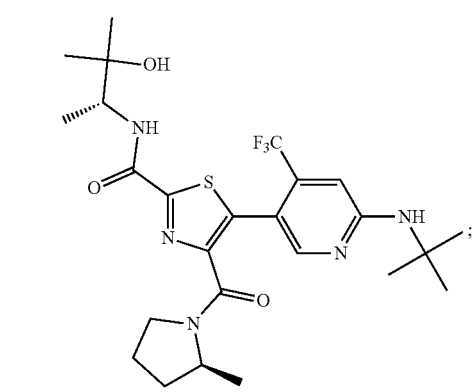
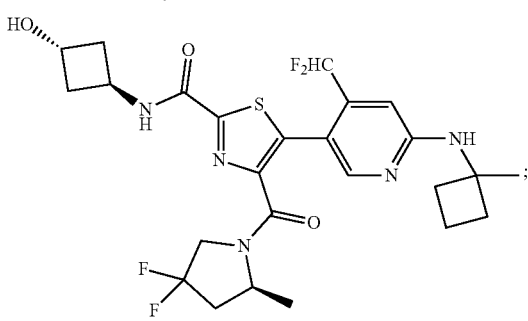
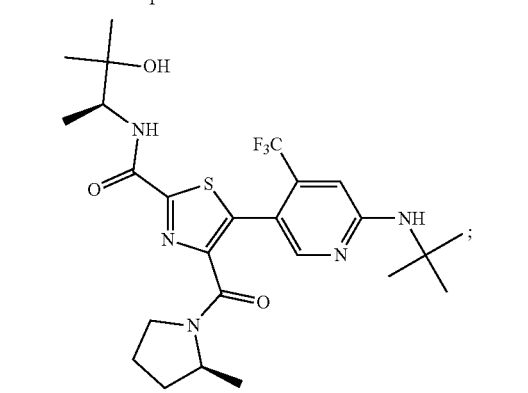
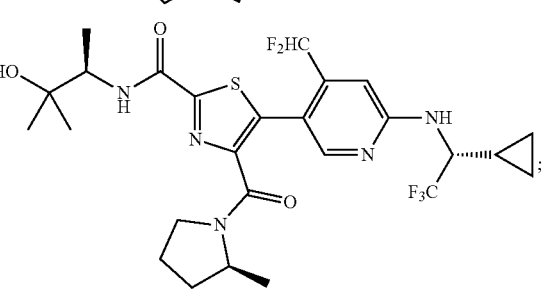
778
-continued
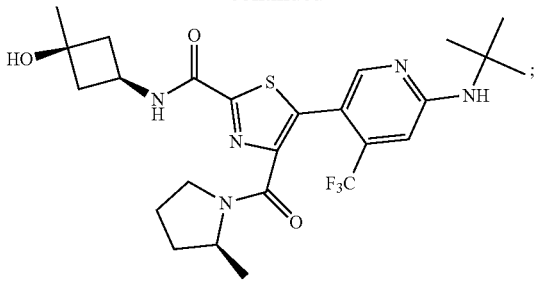
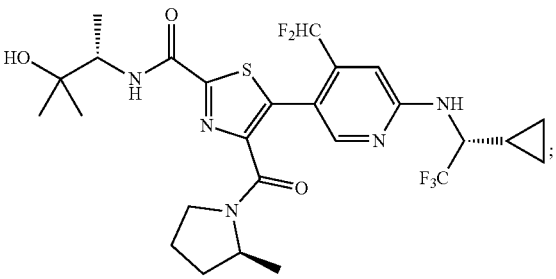
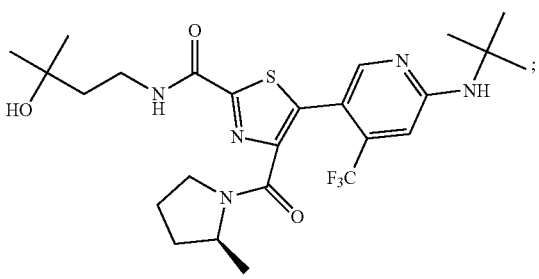
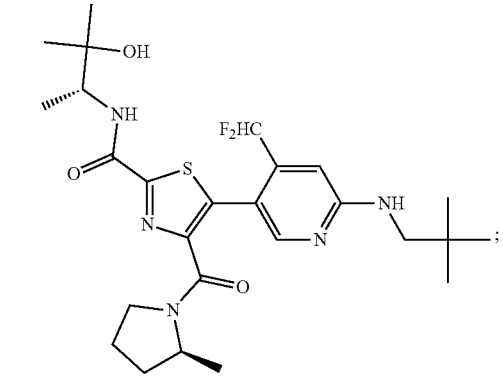
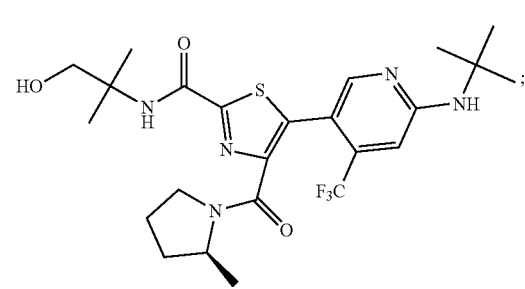

779
-continued
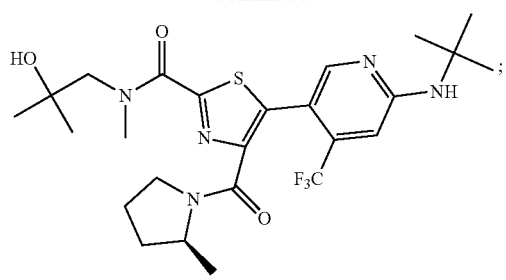
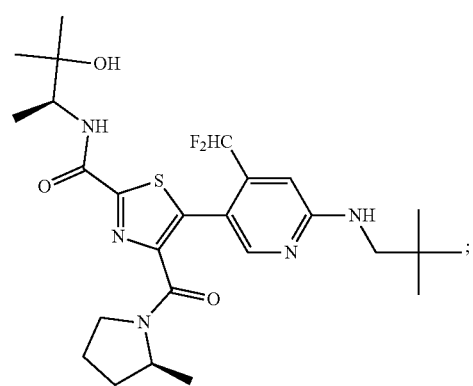
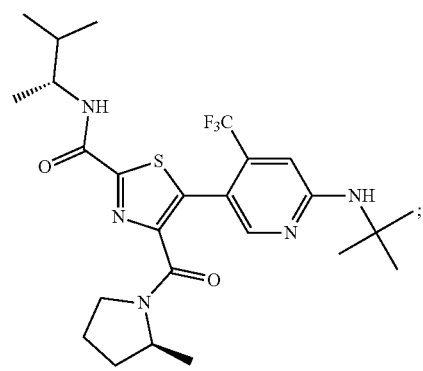
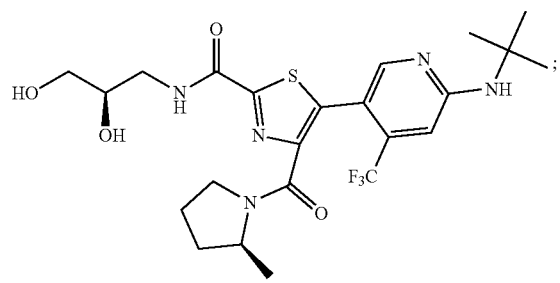
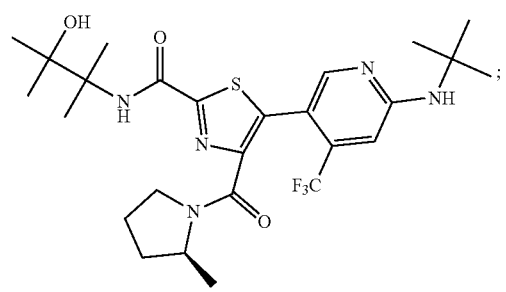
780
-continued
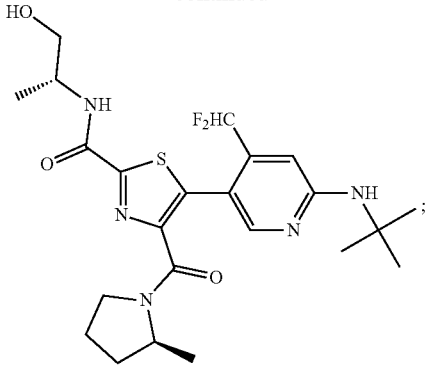
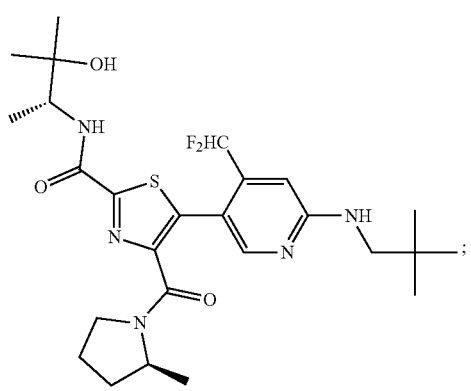
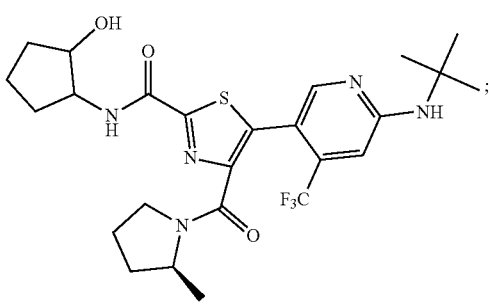
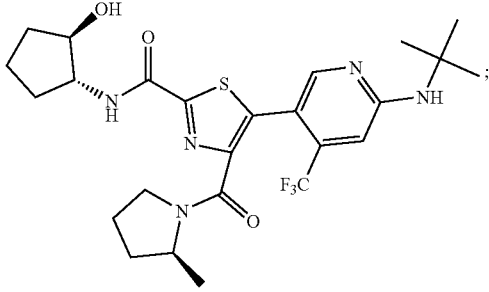
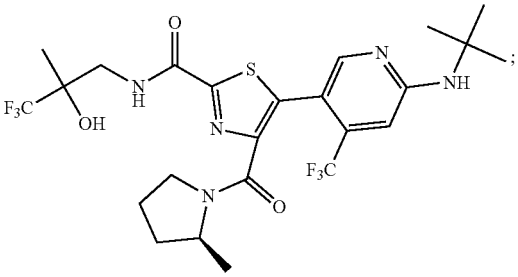

781
-continued
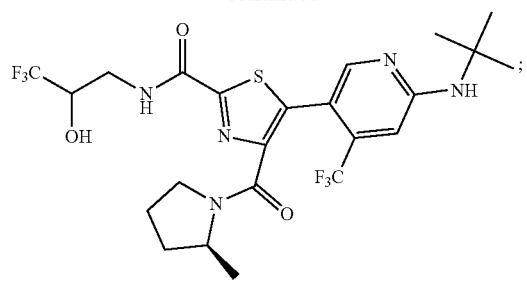
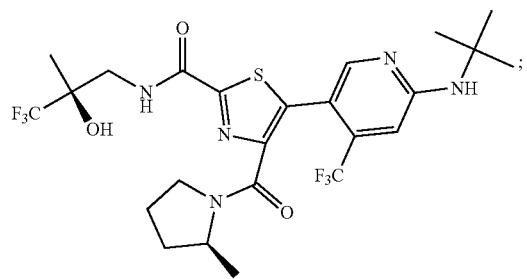
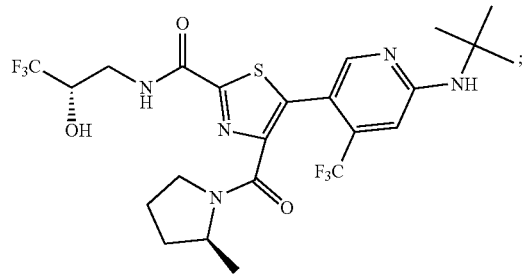
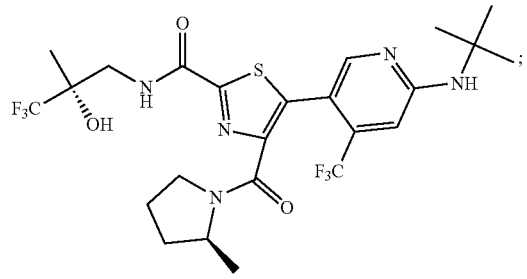
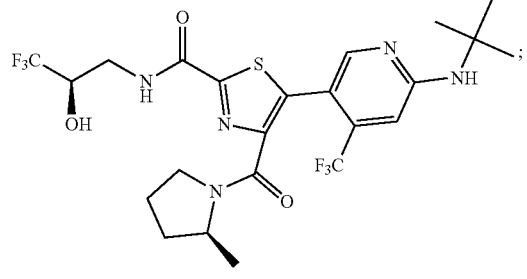
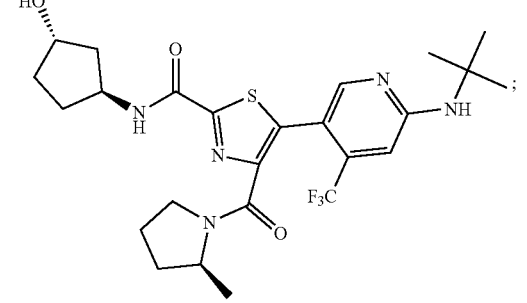
782
-continued
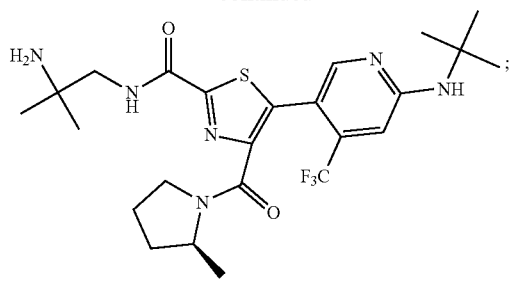
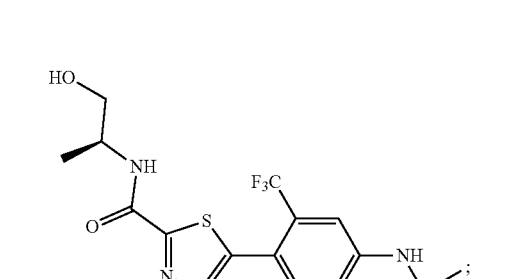
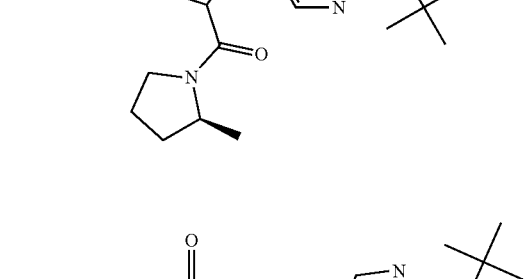
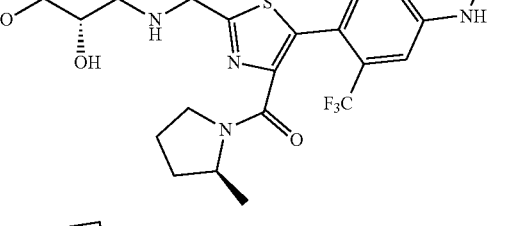
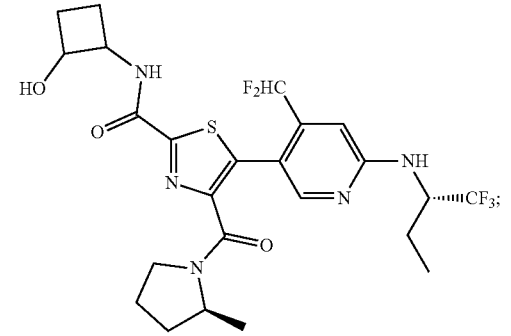
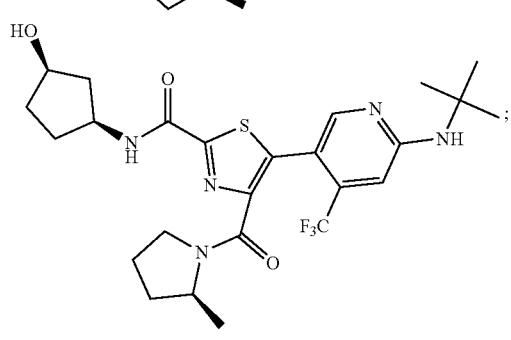

783 -continued
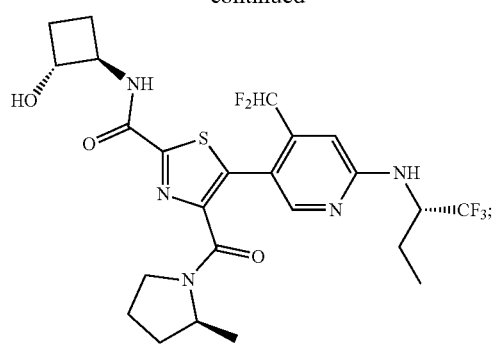
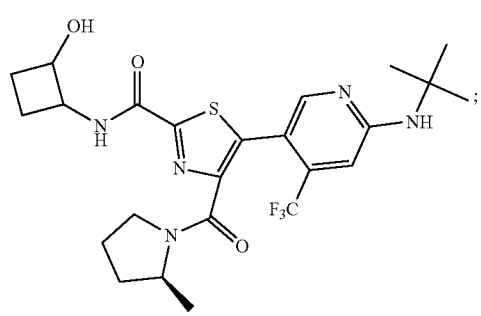
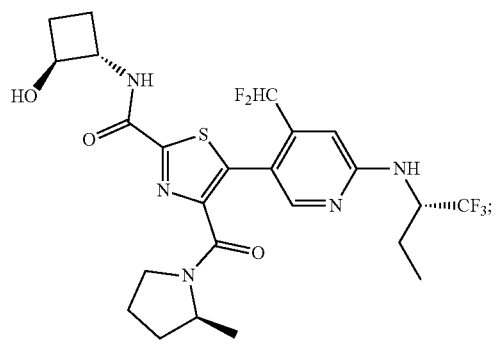
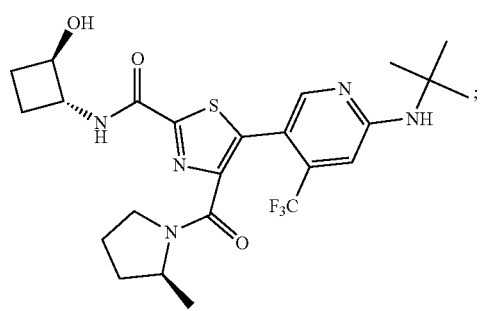
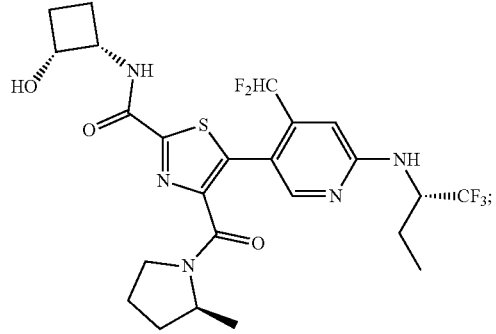
784 -continued
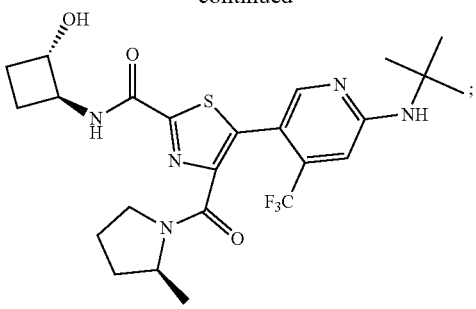
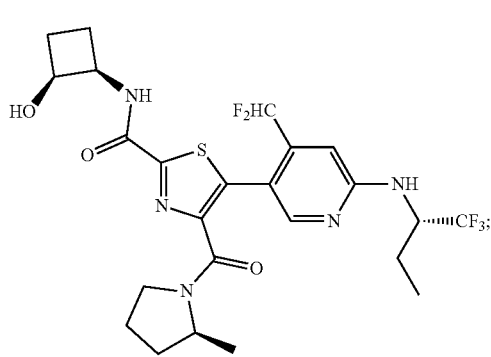
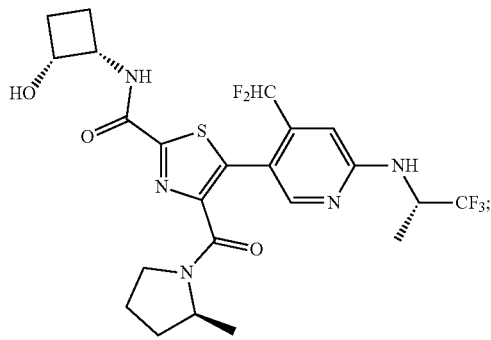
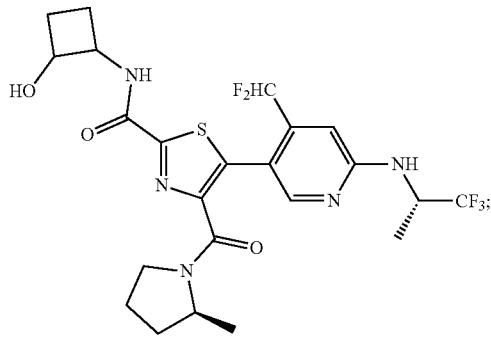
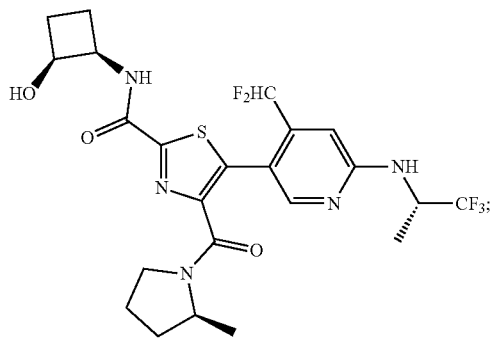

785
-continued
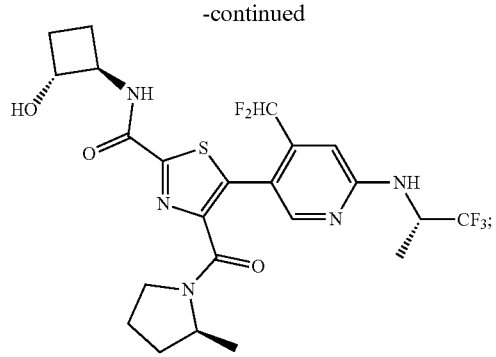
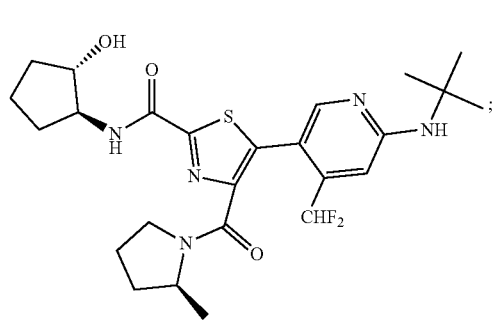
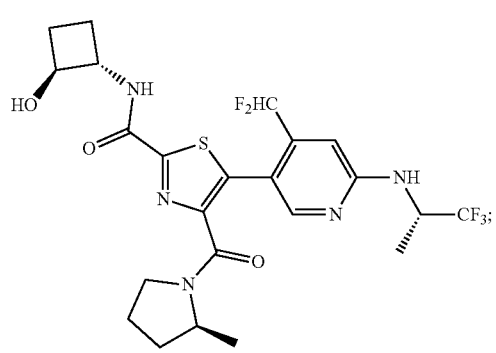
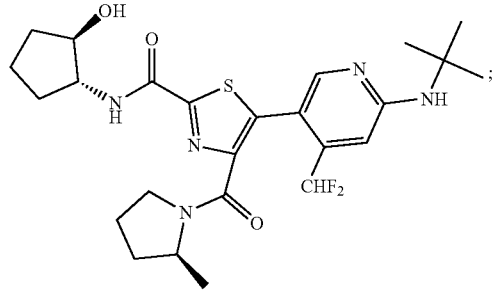
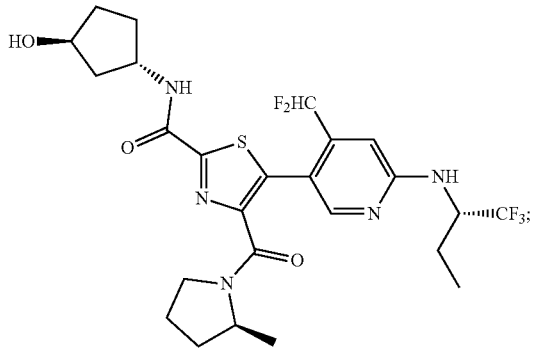
786
-continued
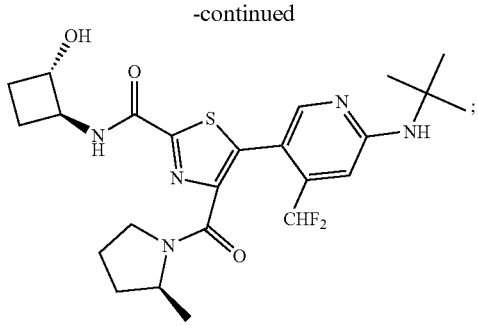
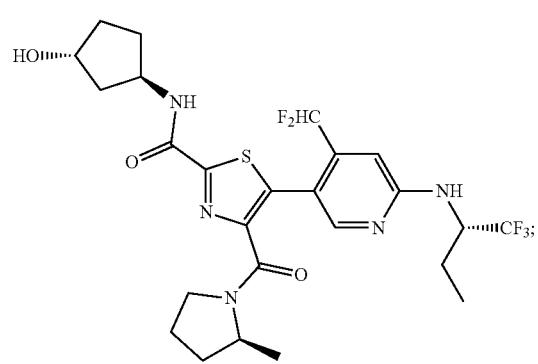
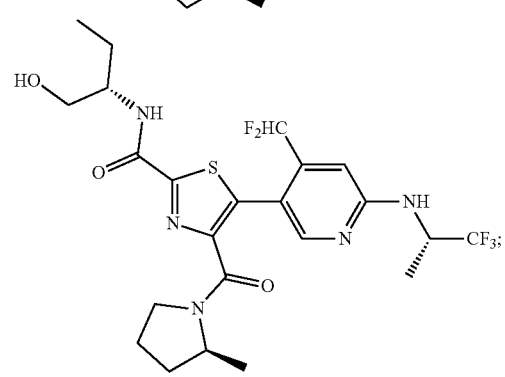
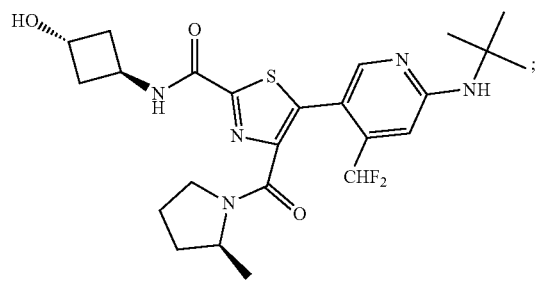
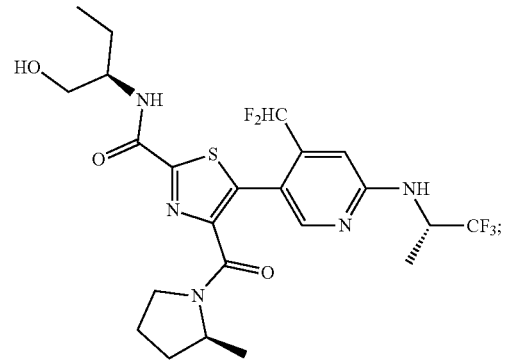

787
-continued
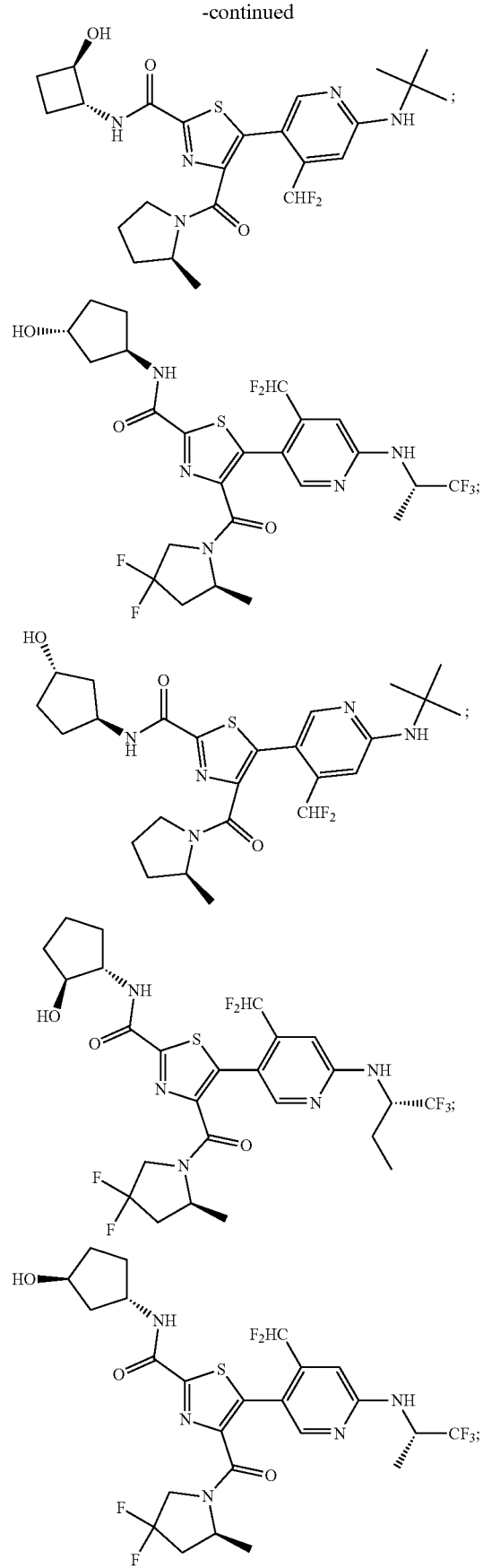
788
-continued
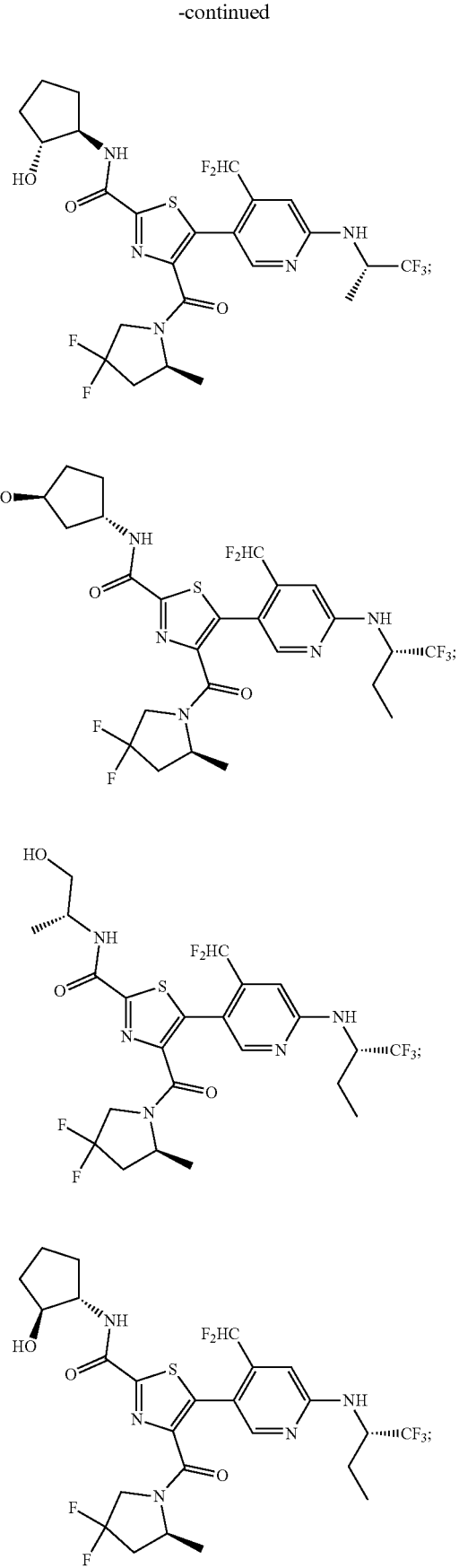

789
-continued
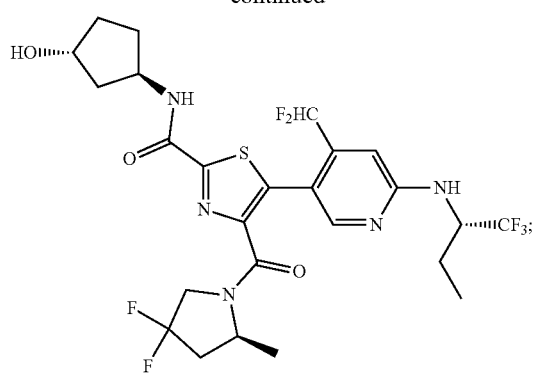
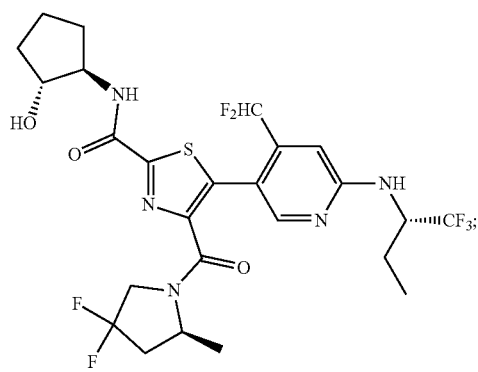
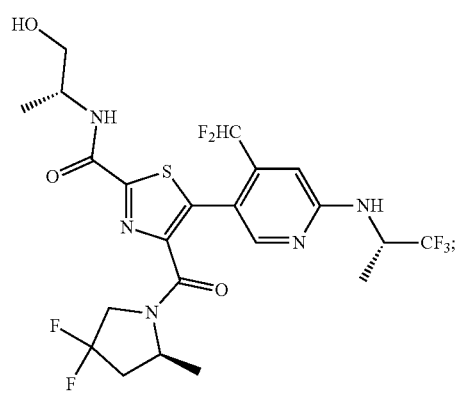
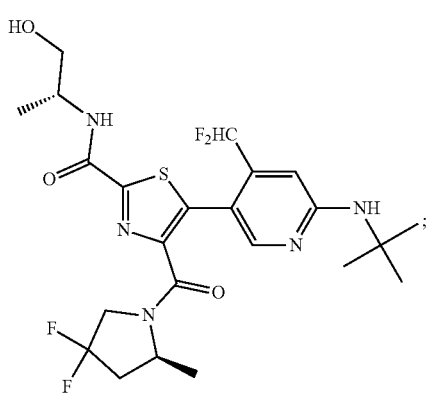
790
-continued
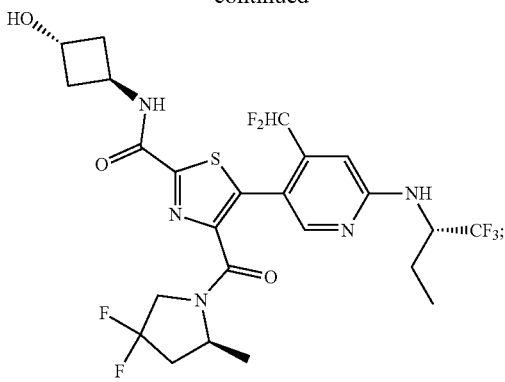
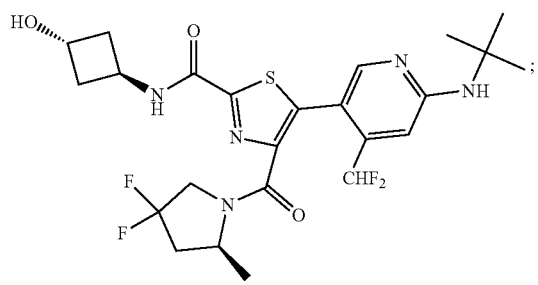
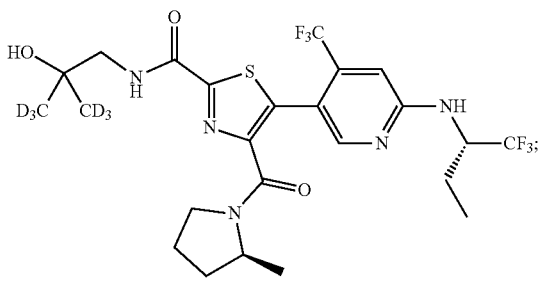
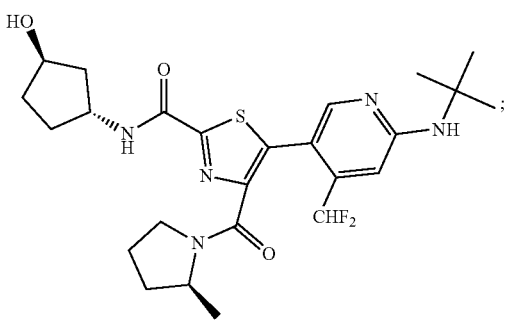
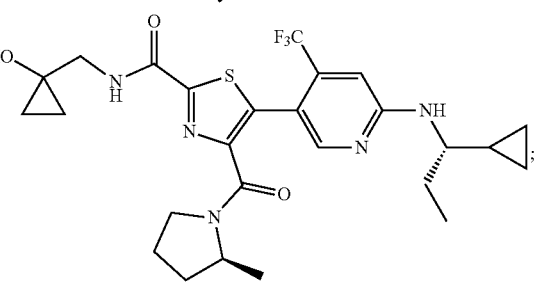

791

-continued

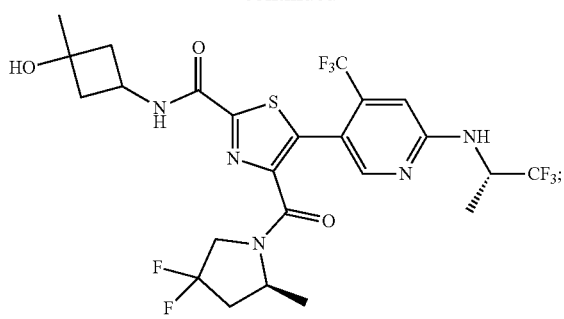

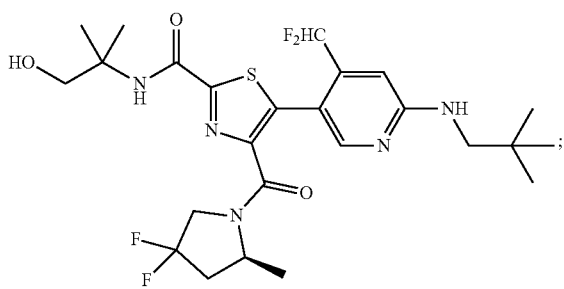

and a pharmaceutically acceptable salt thereof.

5. The compound of claim 3 selected from the group consisting of:

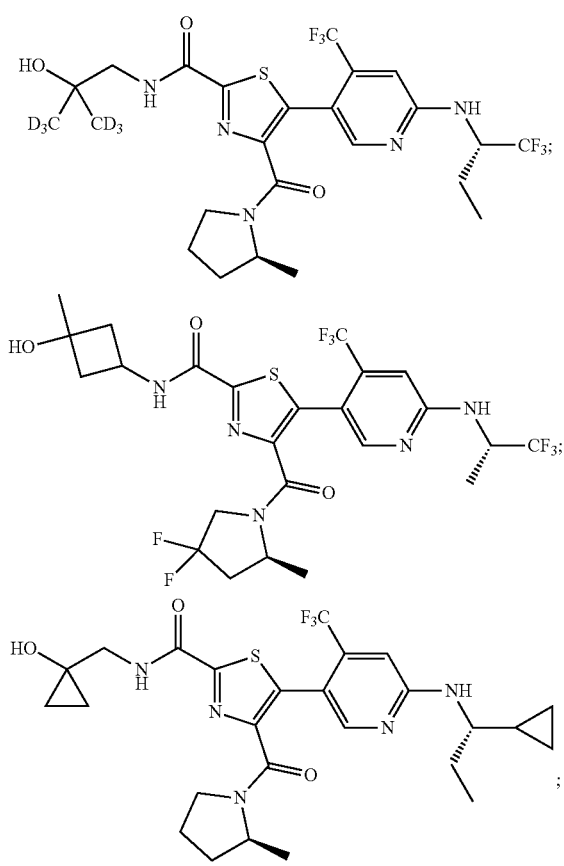

792

-continued

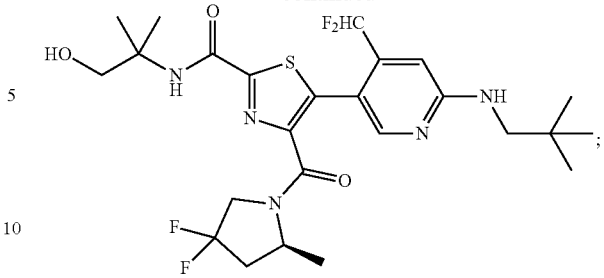

and a pharmaceutically acceptable salt thereof.

6. A pharmaceutical composition, comprising a compound of claim 1 and a pharmaceutically acceptable carrier.

7. A method for treating or ameliorating a RORγt mediated inflammatory syndrome, disorder or disease selected from the group consisting of: inflammatory bowel diseases, rheumatoid arthritis, psoriasis, chronic obstructive pulmonary disorder, psoriatic arthritis, ankylosing spondylitis, neutrophilic asthma, steroid resistant asthma, multiple sclerosis, and systemic lupus erythematosus, comprising administering to a subject in need thereof an effective amount of a compound of claim 1.

8. A method for treating or ameliorating a RORγt mediated inflammatory syndrome, disorder or disease selected from the group consisting of: depression and metabolic syndrome, comprising administering to a subject in need thereof an effective amount of a compound of claim 1.

9. The method of claim 7, wherein the disease is psoriasis.

10. The method of claim 7, wherein the disease is rheumatoid arthritis.

11. The method of claim 7, wherein the inflammatory bowel disease is ulcerative colitis.

12. The method of claim 7, wherein the inflammatory bowel disease is Crohn's disease.

13. The method of claim 7, wherein the disease is multiple sclerosis.

14. The method of claim 7, wherein the disease is neutrophilic asthma.

15. The method of claim 7, wherein the disease is steroid resistant asthma.

16. The method of claim 7, wherein the disease is psoriatic arthritis.

17. The method of claim 7, wherein the disease is ankylosing spondylitis.

18. The method of claim 7, wherein the disease is systemic lupus erythematosus.

19. The method of claim 7, wherein the disease is chronic obstructive pulmonary disorder.

20. The method of claim 8, wherein the disease is depression.

21. The method of claim 8, wherein the disease is metabolic syndrome.

22. A method of inhibiting production of interleukin-17, comprising administering to a subject in need thereof an effective amount of a compound of claim 1.

23. The compound of claim 4 selected from the group consisting of:

793
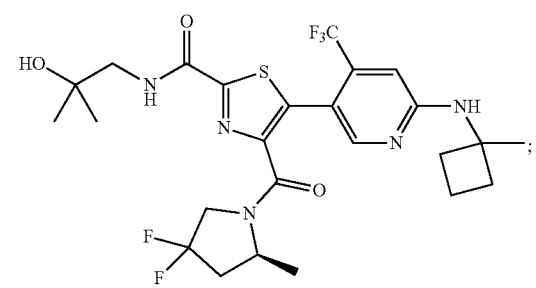
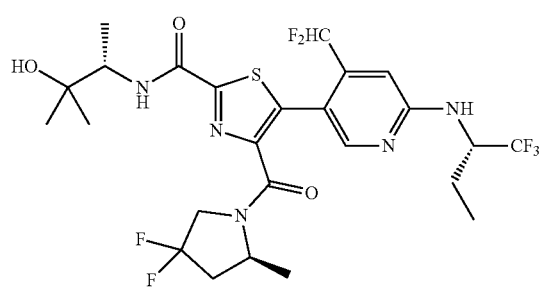
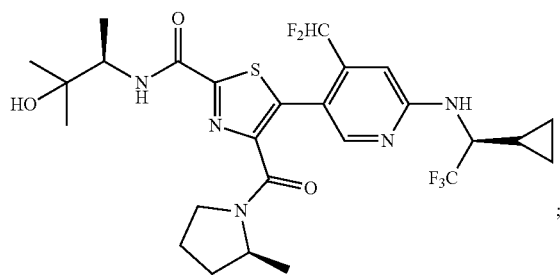
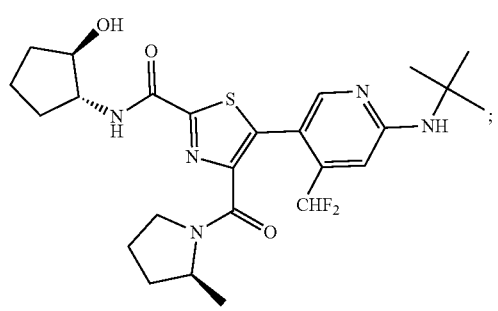
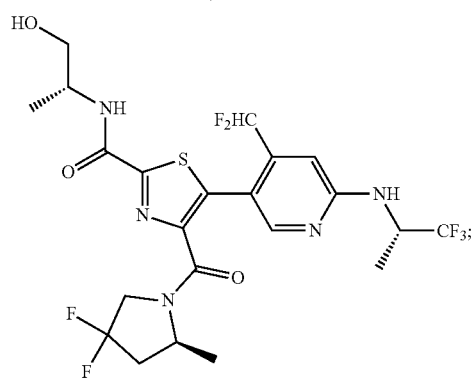
794
-continued
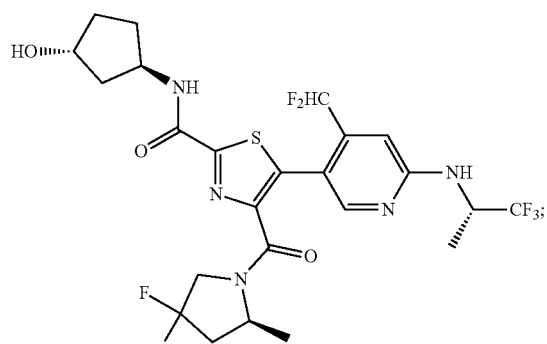
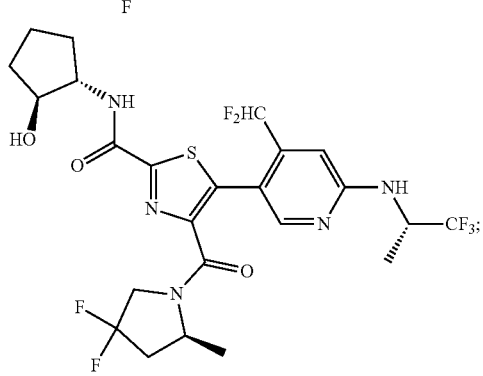
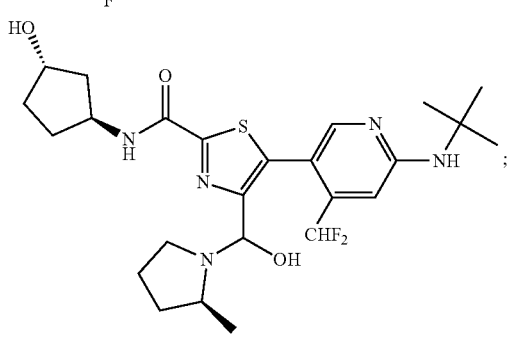
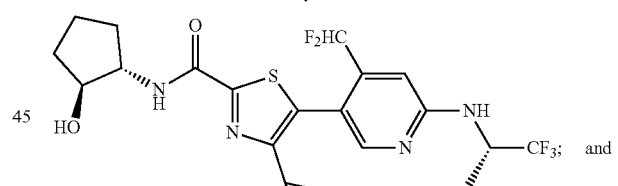
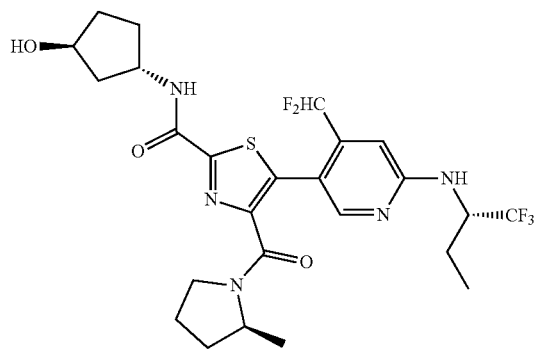
and a pharmaceutically acceptable salt thereof.

24. The compound of claim 23 that is:

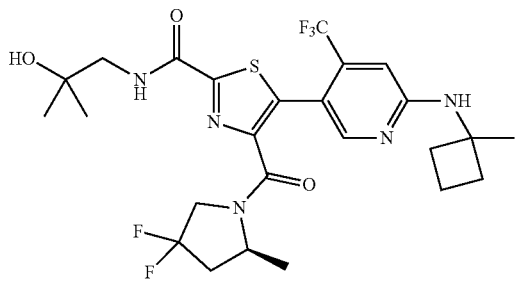 [SMILES: C[C@H]1CC(F)(F)CN1C(=O)c1nc(C(=O)NCC(C)(C)O)sc1-c1cnc(NC2(C)CCC2)cc1C(F)(F)F]

and a pharmaceutically acceptable salt thereof.

25. The compound of claim 23 that is:

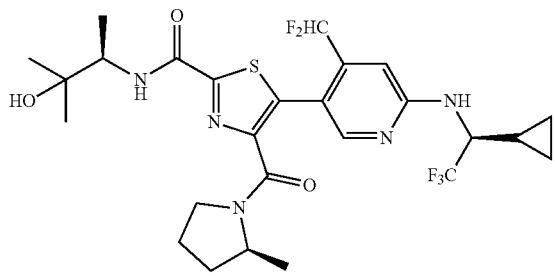 [SMILES: C[C@H]1CCCN1C(=O)c1nc(C(=O)N[C@H](C)C(C)(C)O)sc1-c1cnc(N[C@@H](C2CC2)C(F)(F)F)cc1C(F)F]

and a pharmaceutically acceptable salt thereof.

26. The compound of claim 23 that is:

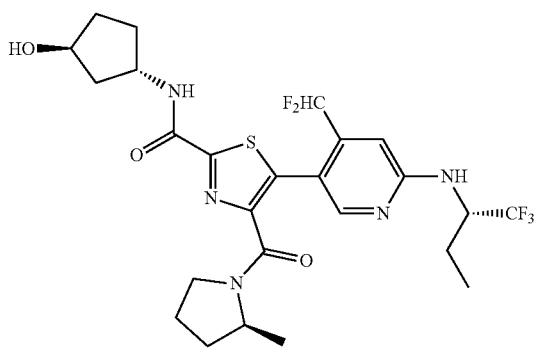 [SMILES: CC[C@H](Nc1cc(C(F)F)c(-c2sc(C(=O)N[C@H]3CC[C@H](O)C3)nc2C(=O)N2CCC[C@@H]2C)cn1)C(F)(F)F]

and a pharmaceutically acceptable salt thereof.

27. The compound of claim 23 that is:

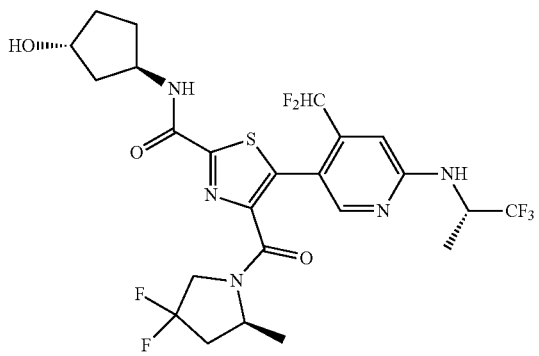 [SMILES: C[C@H](Nc1cc(C(F)F)c(-c2sc(C(=O)N[C@@H]3CC[C@@H](O)C3)nc2C(=O)N2CC(F)(F)C[C@@H]2C)cn1)C(F)(F)F]

and a pharmaceutically acceptable salt thereof.

28. The compound of claim 23 that is:

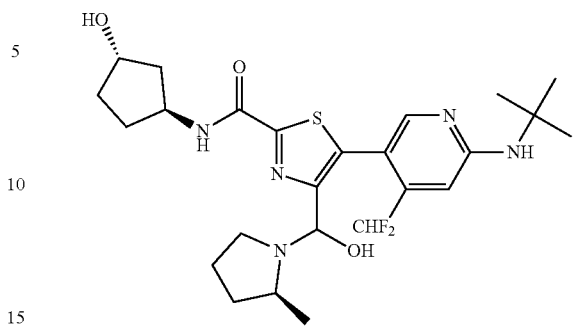

and a pharmaceutically acceptable salt thereof.

29. The compound of claim 23 that is:

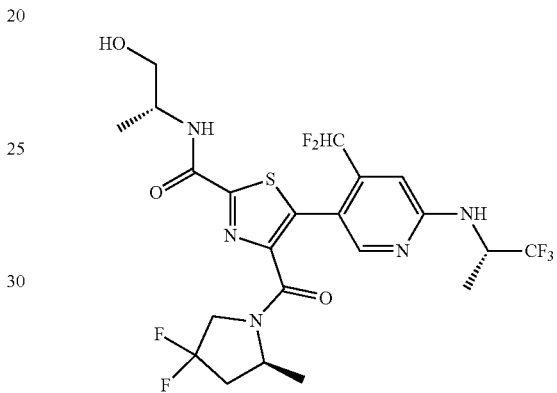

and a pharmaceutically acceptable salt thereof.

30. A pharmaceutical composition, comprising a compound of claim 23 and a pharmaceutically acceptable carrier.

31. A method for treating or ameliorating a RORγt mediated inflammatory syndrome, disorder or disease selected from the group consisting of: inflammatory bowel diseases, rheumatoid arthritis, psoriasis, chronic obstructive pulmonary disorder, psoriatic arthritis, ankylosing spondylitis, neutrophilic asthma, steroid resistant asthma, multiple sclerosis, and systemic lupus erythematosus, comprising administering to a subject in need thereof an effective amount of a compound of claim 23.

32. A method for treating or ameliorating a RORγt mediated inflammatory syndrome, disorder or disease selected from the group consisting of: depression and metabolic syndrome, comprising administering to a subject in need thereof an effective amount of a compound of claim 23.

33. The method of claim 31, wherein the disease is psoriasis.

34. The method of claim 31, wherein the disease is rheumatoid arthritis.

35. The method of claim 31, wherein the inflammatory bowel disease is ulcerative colitis.

36. The method of claim 31, wherein the inflammatory bowel disease is Crohn's disease.

37. The method of claim 31, wherein the disease is multiple sclerosis.

38. The method of claim 31, wherein the disease is neutrophilic asthma.

39. The method of claim 31, wherein the disease is steroid resistant asthma.

40. The method of claim 31, wherein the disease is psoriatic arthritis.

41. The method of claim 31, wherein the disease is ankylosing spondylitis.

42. The method of claim 31, wherein the disease is systemic lupus erythematosus.

43. The method of claim 31, wherein the disease is chronic obstructive pulmonary disorder.

44. The method of claim 32, wherein the disease is depression.

45. The method of claim 32, wherein the disease is metabolic syndrome.

\* \* \* \* \*

SEQUENCE LISTING

```
<160> NUMBER OF SEQ ID NOS: 4

<210> SEQ ID NO 1
<211> LENGTH: 3054
<212> TYPE: DNA
<213> ORGANISM: Homo sapiens

<400> SEQUENCE: 1
agagagctag gtgcagagct tcaggctgag gcgctgctga gagggcctcg ccccgcctct      60
gccgccagct gcaccccact cctggaccac cccctgctga gaaggacagg gagccaaggc     120
cggcagagcc aaggctcagt catgagaaca caaattgaag tgatcccttg caaaatctgt     180
ggggacaagt cgtctgggat ccactacggg gttatcacct gtgaggggtg caagggcttc     240
ttccgccgga gccagcgctg taacgcggcc tactcctgca cccgtcagca gaactgcccc     300
atcgaccgca ccagccgaaa ccgatgccag cactgccgcc tgcagaaatg cctggcgctg     360
ggcatgtccc gagatgctgt caagttcggc cgcatgtcca agaagcagag ggacagcctg     420
catgcagaag tgcagaaaca gctgcagcag cggcaacagc agcaacagga accagtggtc     480
aagacccctc cagcagggc ccaaggagca gataccctca cctacacctt ggggctccca     540
gacgggcagc tgcccctggg ctcctcgcct gacctgcctg aggcttctgc ctgtcccct      600
```

-continued

```
ggcctcctga aagcctcagg ctctgggccc tcatattcca caacttggc caaggcaggg     660 ctcaatgggg cctcatgcca ccttgaatac agccctgagc ggggcaaggc tgagggcaga    720
gagagcttct atagcacagg cagccagctg acccctgacc gatgtggact tcgttttgag    780
gaacacaggc atcctgggct tggggaactg ggacagggcc cagacagcta cggcagcccc    840
agtttccgca gcacaccgga ggcaccctat gcctccctga cagagataga gcacctggtg    900
cagagcgtct gcaagtccta cagggagaca tgccagctgc ggctggagga cctgctgcgg    960
cagcgctcca acatcttctc ccgggaggaa gtgactggct accagaggaa gtccatgtgg    1020
gagatgtggg aacggtgtgc ccaccacctc accgaggcca ttcagtacgt ggtggagttc    1080
gccaagaggc tctcaggctt tatggagctc tgccagaatg accagattgt gcttctcaaa    1140
gcaggagcaa tggaagtggt gctggttagg atgtgcccgg cctacaatgc tgacaaccgc    1200
acggtctttt ttgaaggcaa atacggtggc atggagctgt tccgagcctt gggctgcagc    1260
gagctcatca gctccatctt tgacttctcc cactccctaa gtgccttgca cttttccgag    1320
gatgagattg ccctctacac agcccttgtt ctcatcaatg cccatcggcc agggctccaa    1380
gagaaaagga aagtagaaca gctgcagtac aatctggagc tggccttttca tcatcatctc   1440 tgcaagactc atcgccaaag catcctggca agctgccac ccaaggggaa gcttcggagc     1500
ctgtgtagcc agcatgtgga aaggctgcag atcttccagc acctccaccc catcgtggtc    1560
caagccgctt ccctccact ctacaaggag ctcttcagca ctgaaaccga gtcacctgtg     1620
gggctgtcca agtgacctgg aagagggact ccttgcctct ccctatggcc tgctggccca    1680
cctccctgga ccccgttcca ccctcaccct tttcctttcc catgaaccct ggagggtggt    1740
ccccaccagc tctttggaag tgagcagatg ctgcggctgg cttctgtca gcaggccggc     1800 ctggcagtgg gacaatcgcc agagggtggg gctggcagaa caccatctcc agcctcagct    1860
ttgacctgtc tcatttccca tattccttca cacccagctt ctggaaggca tggggtggct    1920
gggatttaag gacttctggg ggaccaagac atcctcaaga aaacagggc atccagggct     1980 ccctggatga atagaatgca attcattcag aagctcagaa gctaagaata agcctttgaa    2040
atacctcatt gcatttccct ttgggcttcg gcttggggag atggatcaag ctcagagact    2100
ggcagtgaga gcccagaagg acctgtataa aatgaatctg gagctttaca ttttctgcct    2160
ctgccttcct cccagctcag caaggaagta tttgggcacc ctacccttta cctggggtct    2220
aaccaaaaat ggatgggatg aggatgagag gctggagata attgttttat gggatttggg    2280
tgtgggacta gggtacaatg aaggccaaga gcatctcaga catagagtta aaactcaaac    2340
ctcttatgtg cactttaaag atagacttta ggggctggca caaatctgat cagagacaca    2400
tatccataca caggtgaaac acatacagac tcaacagcaa tcatgcagtt ccagagacac    2460
atgaacctga cacaatctct cttatccttg aggccacagc ttggaggagc ctagaggcct    2520
caggggaaag tcccaatcct gagggaccct cccaaacatt tccatggtgc tccagtccac    2580
tgatcttggg tctggggtga tccaaatacc accccagctc cagctgtctt ctaccactag    2640
aagacccaag agaagcagaa gtcgctcgca ctggtcagtc ggaaggcaag atcagatcct    2700
ggaggacttt cctggcctgc ccgccagccc tgctcttgtt gtggagaagg aagcagatgt    2760
gatcacatca ccccgtcatt gggcaccgct gactccagca tggaggacac cagggagcag    2820
ggcctgggcc tgtttcccca gctgtgatct tgcccagaac ctctcttggc ttcataaaca    2880
gctgtgaacc ctcccctgag ggattaacag caatgatggg cagtcgtgga gttggggggg    2940
ttgggggtgg gattgtgtcc tctaagggga cgggttcatc tgagtaaaca taaacccccaa   3000
```

```
cttgtgccat tctttataaa atgattttaa aggcaaaaaa aaaaaaaaaa aaaa    3054
```

<210> SEQ ID NO 2
<211> LENGTH: 786
<212> TYPE: DNA
<213> ORGANISM: Homo sapiens

<400> SEQUENCE: 2

```
agcacaccgg aggcacccta tgcctccctg acagagatag agcacctggt gcagagcgtc    60
tgcaagtcct acagggagac atgccagctg cggctggagg acctgctgcg gcagcgctcc   120
aacatcttct cccgggagga agtgactggc taccagagga agtccatgtg ggagatgtgg   180
gaacggtgtg cccaccacct caccgaggcc attcagtacg tggtggagtt cgccaagagg   240
ctctcaggct ttatggagct ctgccagaat gaccagattg tgcttctcaa agcaggagca   300
atggaagtgg tgctggttag gatgtgccgg gcctacaatg ctgacaaccg cacggtcttt   360
tttgaaggca atacggtgg catggagctg ttccgagcct tgggctgcag cgagctcatc   420
agctccatct ttgacttctc ccactcccta agtgccttgc acttttccga ggatgagatt   480
gccctctaca cagcccttgt tctcatcaat gccatcggc cagggctcca agagaaaagg   540
aaagtagaac agctgcagta caatctggag ctggcctttc atcatcatct ctgcaagact   600
catcgccaaa gcatcctggc aaagctgcca cccaagggga agcttcggag cctgtgtagc   660
cagcatgtgg aaaggctgca gatcttccag cacctccacc ccatcgtggt ccaagccgct   720
ttccctccac tctacaagga gctcttcagc actgaaaccg agtcacctgt ggggctgtcc   780
aagtga                                                              786
```

<210> SEQ ID NO 3
<211> LENGTH: 7
<212> TYPE: PRT
<213> ORGANISM: Artificial Sequence
<220> FEATURE:
<223> OTHER INFORMATION: Description of Artificial Sequence: Synthetic
      TurboTEV protease cleavage site peptide

<400> SEQUENCE: 3

```
Glu Asn Leu Tyr Phe Gln Gly
1               5
```

<210> SEQ ID NO 4
<211> LENGTH: 283
<212> TYPE: PRT
<213> ORGANISM: Artificial Sequence
<220> FEATURE:
<223> OTHER INFORMATION: Description of Artificial Sequence: Synthetic
      Construct polypeptide used in the Thermofluor assay

<400> SEQUENCE: 4

```
Met Ala His His His His His His Ala Gly Gly Ala Glu Asn Leu Tyr
1               5                   10                  15

Phe Gln Gly Ala Met Asp Ser Thr Pro Glu Ala Pro Tyr Ala Ser Leu
            20                  25                  30

Thr Glu Ile Glu His Leu Val Gln Ser Val Cys Lys Ser Tyr Arg Glu
        35                  40                  45

Thr Cys Gln Leu Arg Leu Glu Asp Leu Leu Arg Gln Arg Ser Asn Ile
    50                  55                  60

Phe Ser Arg Glu Glu Val Thr Gly Tyr Gln Arg Lys Ser Met Trp Glu
65                  70                  75                  80
```

-continued

```
Met Trp Glu Arg Cys Ala His His Leu Thr Glu Ala Ile Gln Tyr Val
                85                  90                  95
Val Glu Phe Ala Lys Arg Leu Ser Gly Phe Met Glu Leu Cys Gln Asn
            100                 105                 110
Asp Gln Ile Val Leu Leu Lys Ala Gly Ala Met Glu Val Val Leu Val
        115                 120                 125
Arg Met Cys Arg Ala Tyr Asn Ala Asp Asn Arg Thr Val Phe Phe Glu
    130                 135                 140
Gly Lys Tyr Gly Gly Met Glu Leu Phe Arg Ala Leu Gly Cys Ser Glu
145                 150                 155                 160
Leu Ile Ser Ser Ile Phe Asp Phe Ser His Ser Leu Ser Ala Leu His
                165                 170                 175
Phe Ser Glu Asp Glu Ile Ala Leu Tyr Thr Ala Leu Val Leu Ile Asn
            180                 185                 190
Ala His Arg Pro Gly Leu Gln Glu Lys Arg Lys Val Glu Gln Leu Gln
        195                 200                 205
Tyr Asn Leu Glu Leu Ala Phe His His His Leu Cys Lys Thr His Arg
    210                 215                 220
Gln Ser Ile Leu Ala Lys Leu Pro Pro Lys Gly Lys Leu Arg Ser Leu
225                 230                 235                 240
Cys Ser Gln His Val Glu Arg Leu Gln Ile Phe Gln His Leu His Pro
                245                 250                 255
Ile Val Val Gln Ala Ala Phe Pro Pro Leu Tyr Lys Glu Leu Phe Ser
            260                 265                 270
Thr Glu Thr Glu Ser Pro Val Gly Leu Ser Lys
        275                 280
```